US00RE47334E

(19) United States
(12) Reissued Patent
Aciro et al.

(10) Patent Number: US RE47,334 E
(45) Date of Reissued Patent: Apr. 2, 2019

(54) MACROCYCLIC INHIBITORS OF FLAVIVIRIDAE VIRUSES

(71) Applicants: Gilead Sciences, Inc., Foster City, CA (US); Cypralis Limited, Cambridge (GB)

(72) Inventors: Caroline Aciro, Bottisham (GB); Victoria Alexandra Steadman, Stansted (GB); Simon Neil Pettit, Colchester (GB); Karine G. Poullennec, Chelmsford (GB); Linos Lazarides, London (GB); David Kenneth Dean, Ware (GB); Neil Andrew Dunbar, Chelmsford (GB); Adrian John Highton, Chelmsford (GB); Andrew John Keats, Chelmsford (GB); Dustin Scott Siegel, San Carlos, CA (US); Kapil Kumar Karki, Foster City, CA (US); Adam James Schrier, Redwood City, CA (US); Petr Jansa, San Mateo, CA (US); Richard Mackman, Millbrae, CA (US); Jean Yves Chiva, Chelmsford (GB)

(73) Assignees: Gilead Sciences, Inc., Foster, CA (US); Cypralis Limited, Cambridge (GB)

(21) Appl. No.: 15/715,080

(22) Filed: Sep. 25, 2017

Related U.S. Patent Documents

Reissue of:

(64) Patent No.: 9,145,441
Issued: Sep. 29, 2015
Appl. No.: 13/913,259
Filed: Jun. 7, 2013

U.S. Applications:

(60) Provisional application No. 61/657,550, filed on Jun. 8, 2012.

(51) Int. Cl.

| | |
|---|---|
| ***A61K 38/21*** | (2006.01) |
| ***C07D 498/18*** | (2006.01) |
| ***A61K 38/12*** | (2006.01) |
| ***A61K 45/06*** | (2006.01) |
| ***C07K 5/062*** | (2006.01) |
| ***C07D 487/18*** | (2006.01) |
| ***C07K 5/06*** | (2006.01) |
| ***C07K 5/068*** | (2006.01) |
| ***C07K 5/078*** | (2006.01) |

(52) U.S. Cl.
CPC ..... *C07K 5/06052* (2013.01); *A61K 38/12* (2013.01); *A61K 45/06* (2013.01); *C07D 487/18* (2013.01); *C07D 498/18* (2013.01); *C07K 5/06086* (2013.01); *C07K 5/06139* (2013.01); *C07K 5/06191* (2013.01); *A61K 38/21* (2013.01)

(58) Field of Classification Search
CPC ..... C07K 5/06052; C07K 5/06139; C07K 5/06191; C07K 5/06086; A61K 45/06; A61K 38/12; A61K 38/21; C07D 498/18; C07D 487/18
See application file for complete search history.

(56) References Cited

U.S. PATENT DOCUMENTS

| | | | |
|---|---|---|---|
| 7,625,881 | B2 | 12/2009 | Kalla et al. |
| 8,513,184 | B2 | 8/2013 | Appleby et al. |
| 8,933,015 | B2 | 1/2015 | Appleby et al. |
| 9,062,092 | B2 | 6/2015 | Steadman et al. |
| 9,090,653 | B2 | 7/2015 | Aciro et al. |
| 9,145,441 | B2 | 9/2015 | Aciro et al. |
| 9,512,175 | B2 | 12/2016 | Aciro et al. |
| 9,873,716 | B2 | 1/2018 | Aciro et al. |
| 2004/0209895 | A1 | 10/2004 | Luecking et al. |
| 2015/0274774 | A1 | 10/2015 | Aciro et al. |
| 2015/0361132 | A1 | 12/2015 | Aciro et al. |
| 2016/0220633 | A1 | 8/2016 | Aciro et al. |
| 2017/0190734 | A1 | 7/2017 | Aciro et al. |
| 2017/0190737 | A1 | 7/2017 | Aciro et al. |

FOREIGN PATENT DOCUMENTS

| | | |
|---|---|---|
| CN | 1193979 | 9/1998 |
| CN | 101242842 | 8/2008 |
| KR | 10-2008-0033274 | 4/2008 |
| WO | WO-1997/02285 | 1/1997 |
| WO | WO-1998/007743 | 2/1998 |
| WO | WO-2004/039833 | 5/2004 |
| WO | WO-2006/138507 | 12/2006 |
| WO | WO-2009/064975 | 5/2009 |
| WO | WO-2009/088256 | 7/2009 |
| WO | WO-2010/036551 | 4/2010 |
| WO | WO-2010/072742 | 7/2010 |
| WO | WO-2011/088345 | 7/2011 |
| WO | WO-2011/098808 | 8/2011 |
| WO | WO-2011/144924 | 11/2011 |
| WO | WO-2012/040040 | 3/2012 |

(Continued)

OTHER PUBLICATIONS

Cabrejas et al., "Macrolide Analogues of the Novel Immunosuppressant Sanglifehrin: New Application of the Ring-Closing Metathesis Reaction." Angew. Chem. Int. Ed. 1999, 38, No. 16, pp. 2443-2446.

(Continued)

*Primary Examiner* — Alan D Diamond
(74) *Attorney, Agent, or Firm* — Sheppard Mullin Richter & Hampton LLP

(57) ABSTRACT

Provided are compounds of Formula I:

Formula I and pharmaceutically acceptable salts and esters thereof. The compounds, compositions, and methods provided are useful for the treatment of virus infections, particularly hepatitis C infections.

30 Claims, No Drawings

(56) References Cited

FOREIGN PATENT DOCUMENTS

| | | |
|---|---|---|
| WO | WO-2012/078915 | 6/2012 |
| WO | WO-2013/183035 | 12/2013 |
| WO | WO-2013/185090 | 12/2013 |
| WO | WO-2013/185093 | 12/2013 |
| WO | WO-2013/185103 | 12/2013 |

OTHER PUBLICATIONS

Cannon, Chapter 19 in Burger's Medicinal Chemistry and Drug Discovery, Fifth Edition, vol. I: Priniciples and Practice, Wiley-Interscience, 1995, pp. 783-802.
CDC's Response to Zika, U.S. Department of Health and Human Services, Centers for Disease Control and Prevention, CS265799A, Aug. 12, 2016.
Communication pursuant to Article 94(3) EPC in European Application No. 13730439.0 dated Jan. 18, 2016, 3 pages.
Communication pursuant to Article 94(3) EPC for 11805697.7 dated Apr. 3, 2014, 4 pages.
Communication pursuant to Article 94(3) EPC in European Application No. 13729240.5 dated Dec. 17, 2015, 5 pages.
Communication pursuant to Rules 161(1) and 162 EPC in European Application No. 11805697.7 dated Jul. 31, 2013, 2 pages.
Communication pursuant to Rules 161(1) and 162 EPC in European Application No. 13729240.5 dated Mar. 6, 2015, 2 pages.
Communication pursuant to Rules 161(1) and 162 EPC in European Application No. 13730439.0 dated Jan. 23, 2015, 2 pages.
Communication pursuant to Rules 161(1) and 162 EPC in European Application No. 13731203.9 dated Mar. 6, 2015, 2 pages.
Examination Report for Australian Application 2011338262 dated Dec. 8, 2015, 3 pages.
Examination Report for New Zealand Application No. 612159, dated Mar. 18, 2014, 2 pages.
Examination Report for NZ Appl. No. 703040 dated Jun. 20, 2016, 7 pages.
Examination Report for Pakistan Application 368/2013 dated Apr. 6, 2016, 1 page.
Examination Report in Australia Application No. 2011338262 dated Nov. 14, 2016, 2 pages.
Examination Report in Australia Application No. 2013270670 dated Oct. 17, 2016, 3 pages.
Examination Report in Australia Application No. 2013270672 dated Nov. 2, 2016, 2 pages.
Examination Report in Australia Application No. 2013271413 dated Oct. 17, 2016, 2 pages.
Examination Report in New Zealand Application No. 703040 dated Nov. 11, 2015, 5 pages.
Examination Report in New Zealand Application No. 703062 dated May 3, 2016, 2 pages.
Examination Report in New Zealand Application No. 703062 dated Oct. 12, 2015, 3 pages.
Examination Report in New Zealand Application No. 703066 dated Nov. 19, 2015, 3 pages.
Examination Report in New Zealand Application No. 722900 dated Jun. 12, 2017, 3 pages.
Examination Report in New Zealand Application No. 724503 dated Dec. 7, 2016, 6 pages.
Examination Report in New Zealand Application No. 724503 dated Jun. 1, 2017, 3 pages.
Examination Report in New Zealand Application No. 724503 dated Mar. 2, 2017, 3 pages.
Examination Report in New Zealand Application No. 724616 dated Aug. 10, 2017, 3 pages.
Examination Report in New Zealand Application No. 724616 dated Jun. 2, 2017, 3 pages.
Examination Report in Pakistani Patent Application No. 890/2011 dated Aug. 28, 2015, 1 page.
Final Rejection in U.S. Appl. No. 13/913,259 dated Mar. 24, 2015.
First Office Action for Chinese Application 201180066396.4 dated Aug. 12, 2014, 10 pages, English translation.
International Preliminary Report on Patentability in International Application No. PCT/US2011/064009 dated Jun. 12, 2013, 6 pages.
International Preliminary Report on Patentability in International Application No. PCT/US2013/044809 dated Dec. 9, 2014, 6 pages.
International Preliminary Report on Patentability in International Application No. PCT/US2013/044812 dated Dec. 9, 2014, 7 pages.
International Preliminary Report on Patentability in International Application No. PCT/US2013/044826 dated Dec. 9, 2014, 7 pages.
International Search Report and Written Opinion for International Application No. PCT/US2011/064009 dated Feb. 8, 2012, 8 pages.
International Search Report and Written Opinion for PCT/US2013/044809 dated Sep. 16, 2013, 8 pages.
International Search Report and Written Opinion in International Application No. PCT/US2013/044812 dated Jul. 22, 2013, 10 pages.
International Search Report and Written Opinion in International Application No. PCT/US2013/044826 dated Jul. 31, 2013, 10 pages.
Leyssen et al., "Perspectives for the Treatment of Infections with Flaviviridae." Clinical Microbiology Reviews, Jan. 2000, p. 67-82.
Non-Final Office Action for U.S. Appl. No. 14/821,458 dated Mar. 10, 2016, 12 pages.
Non-Final Rejection for U.S. Appl. No. 14/719,242 dated Jun. 6, 2016, 17 pages.
Non-Final Rejection in U.S. Appl. No. 13/913,184 dated Sep. 12, 2014.
Non-Final Rejection in U.S. Appl. No. 13/913,259 dated Aug. 29, 2014.
Non-Final Rejection in U.S. Appl. No. 13/913,288 dated Aug. 28, 2014.
Non-Final Rejection in U.S. Appl. No. 14/740,680 dated Jun. 16, 2016, 15 pages.
Non-Final Rejection in U.S. Appl. No. 14/740,680 dated Mar. 15, 2017, 8 pages.
Non-Final Rejection in U.S. Appl. No. 15/094,777 dated Oct. 5, 2016, 10 pages.
Notice 65 in Panama Application No. 90454-01 dated Feb. 26, 2015, 2 pages.
Notification No. 12473/SHTT-SC2 in Vietnam Application No. 1-2014-04389 dated Apr. 22, 2015, 1 page.
Office Action and Search Report in Chinese Application No. 201380039194.X dated Nov. 18, 2015, 20 pages, with English translation.
Office Action and Search Report in Chinese Application No. 201380035449.5 dated Nov. 2, 2016, 8 pages.
Office Action and Search Report in Chinese Application No. 201380040628.8 dated Aug. 31, 2016, 6 pages.
Office Action and Search Report in Taiwan Application No. 102120164 dated Sep. 13, 2016, 6 pages.
Office Action for Chinese Application 201380040628.8 dated Dec. 29, 2015, 22 pages, with English translation.
Office Action for Chinese Application No. 201180066396.4 dated Apr. 1, 2015, 8 pages, with English translation.
Office Action for CN Appl. No. 201380039194.X dated Aug. 1, 2016, with English translation, 10 pages.
Office Action for Eurasian Application 201492188 dated Apr. 7, 2016, 7 pages, with English translation.
Office Action for Eurasian Application 201492205/28 dated May 6, 2016, 5 pages, with English translation.
Office Action for IL Appl. No. 236005 dated Jul. 6, 2016, with English translation, 4 pages.
Office Action for Israel Application No. 226739 dated May 4, 2015, 8 pages, with English translation.
Office Action for Taiwan Application No. 100145540 dated May 28, 2015, 13 pages, with English translation.
Office Action in Chile Application No. 3337-2014 dated Feb. 1, 2017, 8 pages.
Office Action in Chinese Application No. 201380035449.5 dated Jul. 17, 2017, 6 pages.
Office Action in Chinese Application No. 201380039194.X dated Jan. 4, 2017, 13 pages.

(56) References Cited

OTHER PUBLICATIONS

Office Action in Chinese Application No. 201380040628.8 dated Feb. 13, 2017, 7 pages.
Office Action in Eurasian Application No. 201492188 dated Jun. 17, 2016, 2 pages.
Office Action in European Application No. 13729240.5 dated Oct. 7, 2016, 5 pages.
Office Action in Japanese Application No. 2015-516258 dated Mar. 21, 2017, 5 pages.
Office Action in Taiwan Application No. 102120164 dated Apr. 28, 2017, 2 pages.
Office Action in Ukraine Application No. a2014 13748 dated Mar. 28, 2017, 4 pages.
Office Action in Ukraine Application No. a2014 13748 dated May 12, 2017, 1 page.
Official Action for Eurasian Application No. 201390822/28 dated Aug. 22, 2014, 4 pages, with English translation.
Official Action for Eurasian Application No. 201390822/28 dated May 22, 2015, 5 pages, with English translation.
Official Action for Eurasian Application No. 201390822/28 dated Dec. 14, 2015, 2 pages, with English translation.
Official Action for Mexican Application MX/a/2013/0064 75 dated May 13, 2015, with English translation, 4 pages.
Official Action for Thai Application 1401007328 dated Mar. 18, 2016, 2 pages, with English translation.
Official Action in dated Japanese Application No. 2015-516260 dated Mar. 21, 2017, 4 pages.
Official Action in Eurasian Application No. 201492205 dated Aug. 3, 2017, 1 page.
Official Action in Eurasian Application No. 201492205 dated Jan. 30, 2017, 3 pages.
Official Action in Eurasian Application No. 201492209 dated Jan. 7, 2016, 5 pages.
Official Action in Japanese Application No. 2015-516257 dated Mar. 21, 2017, 3 pages.
Official Notification in Israel Application No. 226739 dated Aug. 25, 2016, 2 pages.
Official Notification in Israel Application No. 236006 dated Jul. 26, 2017, 2 pages.
Penultimate Official Action in Japanese Application No. 2015-516258 dated Aug. 14, 2017, 3 pages.
Second Office Action for Chinese Application 201180066396.4 dated Jan. 7, 2015, 9 pages, with English translation.
Sedrani, et al., "Sanglifehrin-Cyclophilin Interaction:? Degradation Work, Synthetic Macrocyclic Analogues, X-ray Crystal Structure, and Binding Data," J. Am. Chem. Soc., 2003, 125 (13), pp. 3849-3859.
Smythe et al., " Design and Synthesis of a Biologically Active Antibody Mimic Based on an Antibody-Antigen Crystal Structure." J. Am. Chem. Soc., 1994, 116 (7), pp. 2725-2733.
Substantive Examination Report for Philippines Application No. 1/2014/502739 dated Feb. 22, 2016, 2 pages, English translation.
Supplementary Examination Report for Application No. 11201408047X dated Oct. 28, 2015, 3 pages.
Supplementary Examination Written Opinion in Singapore Application No. 11201408045U dated Feb. 21, 2017, 4 pages.
Supplementary Examination Written Opinion in Singapore Application No. 11201408064P dated Feb. 21, 2017, 3 pages.
Technical Report for Bolivian Application SP-0404-2011 dated Mar. 3, 2015, 19 pages, with English translation.
Uretsky, Antiviral drug, Gale Encyclopedia of Children's Health: Infancy through Adolescence, 2006, Encyclopedia.com.
Wagner, et al., "Synthesis of Macrolide Analogues of Sanglifehrin by RCM: Unique Reactivity of a Ruthenium Carbene Complex Bearing and Imidazol-2-ylidene Ligand," J. Org. Chem., 2000, 65:26, 9255-9260.
Examination Report for India Application No. 5657/DELNP/2013 dated Feb. 16, 2018. (6 pages).
Examination Report for Indian Application No. 2657/MUMNP/2014 dated Feb. 28, 2018. (6 pages).
Examiner Requisition for Canada Application No. 2819824 dated Jan. 5, 2018. (5 pages).
Examiner's Requisition for Canadian Application No. 2819824 dated Aug. 16, 2018. (3 pages).
First Examination Report for India Application No. 2658/MUMNP/2014 dated Feb. 28, 2018. (6 pages).
Further Examination Report for New Zealand Application No. 722900 dated Sep. 1, 2017. (3 pages).
Non-Final Office Action for U.S. Appl. No. 15/423,469 dated Apr. 18, 2018. (7 pages).
Non-Final Office Action for U.S. Appl. No. 15/465,492 dated Apr. 11, 2018. (13 pages).
Notice of Preliminary Rejection for Korean Application No. 10-2013-7017607 dated May 23, 2018. (6 pages).
Office Action for Mexican Application No. MX/a/2014/014766 dated Aug. 16, 2018. (1 page).
Official Action for El Salvador Application No. 2014004869 dated Oct. 31, 2017. (5 pages).
Official Action for Mexican Application No. MX/a/2014/014765 dated Feb. 16, 2018. (2 pages).
Official Action for Mexican Application No. MX/a/2014/014766 dated Feb. 23, 2018. (1 page).
Official Notification for Israel Application No. 236005 dated Oct. 17, 2017. (2 pages).
Official Notification for Israel Application No. 236006 dated Jan. 28, 2018. (2 pages).
Third Office Action for Chinese Application No. 201380035449.5 dated Feb. 12, 2018. (6 pages).
U.S. Appl. No. 13/913,184 Non-Final Rejection mailed Sep. 12, 2014.
U.S. Appl. No. 13/913,288 Non-Final Rejection mailed Aug. 28, 2014.

MACROCYCLIC INHIBITORS OF FLAVIVIRIDAE VIRUSES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims the benefit under 35 U.S.C. § 119(e) to U.S. Provisional Application Ser. No. 61/657,550, filed on Jun. 8, 2012, the entirety of which is incorporated herein by reference.

FIELD

The present application provides novel compounds inhibiting viruses, compositions containing such compounds, and therapeutic methods comprising the administration of such compounds.

BACKGROUND

RNA viruses comprising the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., J. Med. Chem. 2005, 48, 1-20; Maradpour, D., et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene 1985, 40, 1-8; Martell, et al., J. Virol. 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit. Therefore, there is a need to develop more effective anti-HCV therapies.

The macrocycle sanglifehrin and derivatives are immunomodulatory and bind peptidyl-prolyl cis/trans isomerase (PPIase) cyclophilins in a unique manner (WO 97/02285; WO 98/07743; J. Am. Chem. Soc 2003, 125, 3849-3859; J. Org. Chem. 2000, 65, 9255-9260; Angew. Chem. Int. Ed. 1999, 38, 2443-2446). The cyclophilins are peptidyl-prolyl cis/trans isomerases (PPIase) that regulate protein folding in vivo and inhibit hepatitis C virus (Lin et al., WO2006/138507). However, none of the sanglifehrins or their derivatives has become available for human anti-viral therapy. Therefore, there is a continuing need to develop macrocyclic sanglifehrins with anti-Flaviviridae virus activity and particularly anti-HCV activity.

SUMMARY

In one embodiment, there is provided a compound represented by Formula I:

Formula I

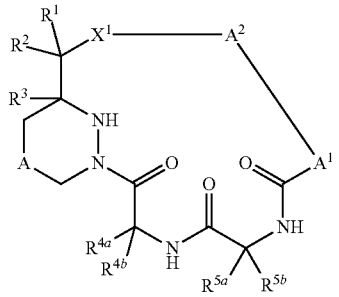

or a pharmaceutically acceptable salt, isotope, stereoisomer, mixture of stereoisomers, tautomer, ester or prodrug thereof, wherein:

A is a bond, —O—, —S(O)$_n$—, —NH—, —N((C$_1$-C$_4$)alkyl)- or (C$_1$-C$_2$)alkylene;

A$^1$ is —CR$^9$=CR$^9$—,

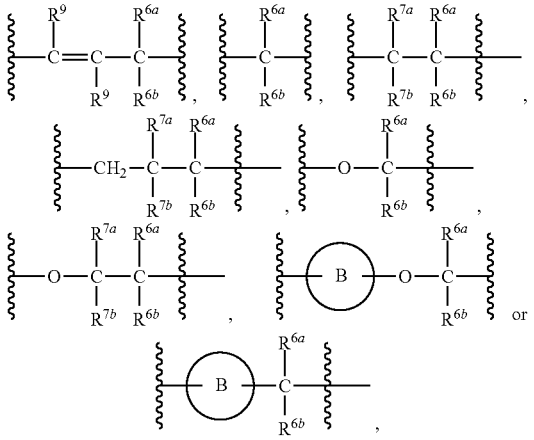

wherein B is arylene, heteroarylene, cycloalkylene or heterocycloalkylene;

A$^2$ is —CH(R$^8$)-arylene, —CH(R$^8$)-heteroarylene, —CH(R$^8$)-heterocycloalkylene, —CH(R$^8$)-cycloalkylene, arylene, heteroarylene or cycloalkylene, wherein $A^2$ is optionally substituted with one or more substituents selected from the group consisting of oxo, —$OR^9$, —$SR^9$, —$S(O)R^9$, —$S(O)_2R^9$, —$N(R^9)_2$, halo, halo($C_1$-$C_4$)alkyl, ($C_1$-$C_4$)alkoxy($C_1$-$C_4$)alkyl, halo($C_1$-$C_4$)alkoxy, cyano and ($C_1$-$C_8$)alkyl;

$X^1$ is a bond, —O—, —NH—, —N(($C_1$-$C_4$)alkyl)- or heterocycloalkylene;

$R^1$ and $R^2$ are independently H, ($C_1$-$C_4$)alkyl, ($C_2$-$C_4$)alkenyl, ($C_2$-$C_4$)alkynyl, halo, cyano or ($C_1$-$C_4$)alkanoyl; or $R^1$ and $R^2$, when taken together with the carbon to which they are both attached, form —C(═O)—, —C(═S)— or —C(═N($C_1$-$C_4$)alkyl)-;

$R^3$ is H or ($C_1$-$C_4$)alkyl which is optionally substituted with halo, cyano, hydroxy or ($C_1$-$C_4$)alkoxy;

$R^{4a}$ and $R^{4b}$ are independently H, ($C_1$-$C_8$)alkyl, aryl, aryl($C_1$-$C_4$)alkyl, heterocycloalkyl, heterocycloalkyl($C_1$-$C_4$)alkyl, cycloalkyl or cycloalkyl($C_1$-$C_4$)alkyl, wherein each of $R^{4a}$ and $R^{4b}$ is optionally substituted with one or more substituent selected from the group consisting of cyano, ($C_1$-$C_8$)alkoxy, —COOH, —C(O)O—($C_1$-$C_8$)alkyl, halo, hydroxyl, amino, mono($C_1$-$C_8$)alkylamino, di($C_1$-$C_8$)alkylamino, —C(O)-mono($C_1$-$C_8$)alkylamino, —C(O)-di($C_1$-$C_8$)alkylamino, —C(O)-heterocycloalkyl, heterocycloalkyl, aryl and heteroaryl, wherein each substituent is optionally substituted with one or more halo, heterocycloalkyl or aryl;

$R^{5a}$ and $R^{5b}$ are independently H, ($C_1$-$C_8$)alkyl, ($C_2$-$C_8$)alkenyl, ($C_2$-$C_8$)alkynyl, ($C_1$-$C_8$)alkoxy, aryl, heterocycloalkyl, cycloalkyl, aryl($C_1$-$C_4$)alkyl, cycloalkyl($C_1$-$C_4$)alkyl or heterocycloalkyl($C_1$-$C_4$)alkyl, wherein $R^{5a}$ and $R^{5b}$ are independently optionally substituted with one or more substituent selected from the group consisting of —$N_3$, cyano, —COOH, halo, hydroxyl, amino, mono($C_1$-$C_8$)alkylamino, di($C_1$-$C_8$)alkylamino, aryl and heteroaryl, or $R^{5a}$ and $R^{5b}$ together form a spirocycle having Formula (a):

(a)

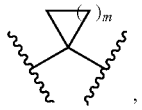

wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, —C(O)O—($C_1$-$C_8$)alkyl, —C(O)-di($C_1$-$C_8$)alkylamino, —C(O)—($C_1$-$C_8$)alkyl, —C(O)-heterocycloalkyl, —$S(O)_2R^{10}$, —$OSi(R^{10})_3$, ($C_1$-$C_4$)alkyl, cyano($C_1$-$C_4$)alkyl, halo($C_1$-$C_4$)alkyl, ($C_1$-$C_4$)alkoxy, ($C_1$-$C_8$)alkanoyl and aryl($C_1$-$C_4$)alkyl;

$R^{6a}$, $R^{6b}$, $R^{7a}$ and $R^{7b}$ are independently H, hydroxyl, cyano, ($C_1$-$C_8$)alkyl, ($C_2$-$C_8$)alkenyl, ($C_2$-$C_8$)alkynyl, ($C_1$-$C_8$)alkoxy, —$CH_2CH_2CR^9$(═N($C_1$-$C_4$)alkoxy), aryl, heterocycloalkyl, cycloalkyl, —$SR^9$, —$S(O)R^9$, —$S(O)_2R^9$ or —$N(R^9)_2$, wherein each of $R^{6a}$, $R^{6b}$, $R^{7a}$ and $R^{7b}$ is optionally substituted with one or more substituent selected from the group consisting of halo, hydroxyl, cyano, ($C_1$-$C_4$)alkyl, ($C_1$-$C_8$)alkoxy, aryl, cycloalkyl, heterocycloalkyl, mono($C_1$-$C_8$)alkylamino, di($C_1$-$C_8$)alkylamino, —$NHS(O)R^9$, —$NHC(O)R^9$, —OC(O)—($C_1$-$C_8$)alkyl —C(O)O—($C_1$-$C_8$)alkyl and ($C_1$-$C_8$)alkanoyl, wherein each —OC(O)—($C_1$-$C_8$)alkyl or ($C_1$-$C_8$)alkoxy is optionally substituted with one or more amino, —OC(O)O—($C_1$-$C_8$)alkyl or —$Si(R^{10})_3$; or $R^{6a}$ and $R^{6b}$ together form a spirocycle having Formula (a);

each $R^8$ is independently H, ($C_1$-$C_4$)alkyl, halo($C_1$-$C_4$)alkyl, ($C_2$-$C_4$)alkenyl, ($C_2$-$C_4$)alkynyl, aryl, heteroaryl, heterocycloalkyl or cycloalkyl, wherein $R^8$ is optionally substituted with —OR, —$N(R^9)_2$, —$CON(R^9)_2$ or cyano;

each $R^9$ is independently H, ($C_1$-$C_4$)alkyl, ($C_2$-$C_4$)alkenyl or ($C_2$-$C_4$)alkynyl;

each $R^{10}$ is independently H, ($C_1$-$C_4$)alkyl, ($C_2$-$C_4$)alkenyl, ($C_2$-$C_4$)alkynyl, cycloalkyl($C_1$-$C_4$)alkyl or aryl, wherein $R^{10}$ is optionally substituted with one or more halo;

each n is independently 0, 1 or 2; and m is 1, 2, 3, 4 or 5.

In another embodiment, there is provided a pharmaceutical composition comprising a compound of Formula I or a pharmaceutically acceptable salt, ester or prodrug thereof and one or more pharmaceutically acceptable carriers or excipients. In one aspect of the embodiment, the pharmaceutical composition further comprises one or more additional therapeutic agents.

In yet another embodiment, a method for treating Flaviviridae viral infection is provided comprising administering a therapeutically effective amount of a compound of Formula I or a pharmaceutically acceptable salt, ester or prodrug thereof to a mammal in need thereof. In one aspect of the embodiment, the treatment results in the reduction of the in viral load or clearance of viral RNA in a patient.

In yet another embodiment, a method for treating Coronaviridae viral infection is provided comprising administering a therapeutically effective amount of a compound of Formula I or a pharmaceutically acceptable salt, ester or prodrug thereof to a mammal in need thereof. In one aspect of the embodiment, the treatment results in the reduction of the in viral load or clearance of viral RNA in a patient.

DETAILED DESCRIPTION

Definitions

Unless stated otherwise, the following terms and phrases as used herein are intended to have the following meanings:

"Alkanoyl" is RC(O)—; "alkanoyloxy" is RC(O)O—; and "alkanoylamino" is RC(O)NR'—; where R is an alkyl group as defined herein, and R' is hydrogen or alkyl.

"Alkenyl" refers to a straight or branched hydrocarbyl group with at least one site of unsaturation, i.e., a carbon-carbon, $sp^2$ double bond. In some embodiments, alkenyl is a $C_2$-$C_{20}$ alkenyl group, a $C_2$-$C_{10}$ alkenyl group or a $C_2$-$C_6$ alkenyl group. Examples of alkenyl group include, but are not limited to, vinyl (—CH═$CH_2$), allyl (—$CH_2$CH═$CH_2$), cyclopentenyl (—$C_5H_7$), and 5-hexenyl (—$CH_2CH_2CH_2CH_2$CH═$CH_2$).

"Alkenylene" refers to an unsaturated, branched or straight chain or cyclic hydrocarbon radical having two monovalent radical centers derived by the removal of two hydrogen atoms from the same or two different carbon atoms of a parent alkene. For example, an alkenylene group can have 2 to 20 carbon atoms, 2 to 10 carbon atoms, or 2 to 6 carbon atoms. Typical alkenylene radicals include, but are not limited to, 1,2-ethenylene (—CH═CH—).

"Alkoxy" is RO— where R is alkyl, as defined herein. Non-limiting examples of alkoxy groups include methoxy, ethoxy and propoxy.

"Alkyl" refers to a straight or branched chain hydrocarbyl group. In an embodiment, alkyl has from 1 to 20 carbon atoms (i.e., $C_1$-$C_{20}$ alkyl). In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Examples of alkylene radicals include, but are not limited to, methylene (—$CH_2$—), ethylene (—$CH_2CH_2$—), propylene (—$CH_2CH_2CH_2$—) and butylene (—$CH_2CH_2CH_2CH_2$—).

"Alkynyl" refers to a hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne) or 2 to 6 carbon atoms (i.e., $C_2$-$C_6$ alkynyl). Examples of alkynyl groups include, but are not limited to, acetylenic (—C≡CH) and propargyl (—$CH_2$C≡CH).

"Alkylamino" refers to an amino group substituted with one or more alkyl groups. "Mono(alkyl)amino" or "(alkyl) amino" is RNH—, and "di(alkyl)amino" or "$(alkyl)_2$amino" is $R_2N$—, where each of the R groups is alkyl as defined herein and are the same or different. Examples of alkylamino groups include, but are not limited to, methylamino, ethylamino, propylamino, butylamino, dimethylamino, diethylamino and methylethylamino.

"Amino" refers to —$NH_2$.

"Alkoxyalkyl" refers to an alkyl moiety substituted with an alkoxy group.

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 2 to 20 carbon atoms, 2 to 10 carbon atoms, or 2 to 6 carbon atoms. Typical alkynylene radicals include, but are not limited to, acetylene (—C≡C—), propargylene (—$CH_2$C≡C—), and 4-pentynylene (—$CH_2CH_2CH_2$C≡C—).

"Aryl" refers to any monocyclic or bicyclic carbon ring of up to 7 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" refers to an alkyl as defined herein substituted with an aryl radical.

"Arylene" refers to an aryl as defined above having two monovalent radical centers derived by the removal of two hydrogen atoms from two different carbon atoms of a parent aryl.

Typical arylene radicals include, but are not limited to, phenylene, e.g.,

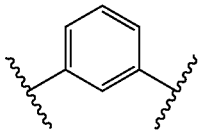

and naphthylene, e.g.,

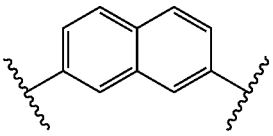

"Arylalkylene" refers to an arylalkyl as defined above having two monovalent radical centers derived by the removal of one hydrogen atom from the aryl radical and the other hydrogen removed from the alkyl radical of the group.

"Azidoalkyl" refers to an alkyl moiety substituted with an azide (—$N_3$) group.

"Cyanoalkyl" refers to an alkyl moiety substituted with a cyano (—CN) group.

"Cycloalkyl" refers to a hydrocarbyl group containing at least one saturated or partially unsaturated ring structure, and attached via a ring carbon. Cycloalkyl groups include hydrocarbon mono-, bi-, and poly-cyclic rings, whether fused, bridged, or spiro. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkylalkyl" refers to an alkyl moiety substituted with a cycloalkyl group. Examples of cycloalkylalkyl groups include cyclopropylmethyl, cyclobutylmethyl, cyclopentylethyl and cyclohexylmethyl.

"Cycloalkylene" refers to a cycloalkyl, as defined herein, having two monovalent radical centers derived by the removal of two hydrogen atoms from the same or two different carbon atoms of a parent cycloalkyl. Examples of cycloalkylene include, but are not limited to, cyclopropylene, cyclobutylene, cyclopentylene and cyclohexylene.

"Dialkylaminoalkyl" refers to an alkyl moiety substituted with a dialkylamino group, wherein dialkylamino is as defined herein.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

"Halo" refers to chloro (—Cl), bromo (—Br), fluoro (—F) or iodo (—I).

"Haloalkoxy" refers to alkoxy, as defined herein, substituted with one or more halo radicals.

"Haloalkoxyalkyl" refers to an alkyl moiety substituted with a haloalkoxy group, as defined herein.

"Haloalkyl" refers to an alkyl group, in which one or more hydrogen atoms of the alkyl group is replaced with a halogen atom. Examples of haloalkyl groups include, but are not limited to, —$CF_3$, —$CHF_2$, —$CFH_2$ and —$CH_2CF_3$.

"Heterocycloalkyl" refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached through a carbon atom or through a heteroatom, and when a substituent is present, the substituent can be on a carbon atom or a heteroatom of the heterocycloalkyl. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl and N-oxides thereof.

"Heterocycloalkylene" refers to a heterocycloalkyl, as defined above, having two monovalent radical centers derived by the removal of two hydrogen atoms from the same or two different carbon atoms of a parent heterocycloalkyl group.

"Heterocycloalkylalkyl" refers to an alkyl group, as defined herein, in which a hydrogen atom has been replaced with a heterocycloalkyl group.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thionaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylalkyl" refers to an alkyl group, as defined herein, in which a hydrogen atom has been replaced with a heteroaryl group.

"Heteroarylene" refers to a heteroaryl, as defined above, having two monovalent radical centers derived by the removal of two hydrogen atoms from the same or two different carbon atoms of a parent heteraryl group. Non-limiting examples of heteroarylene groups are:

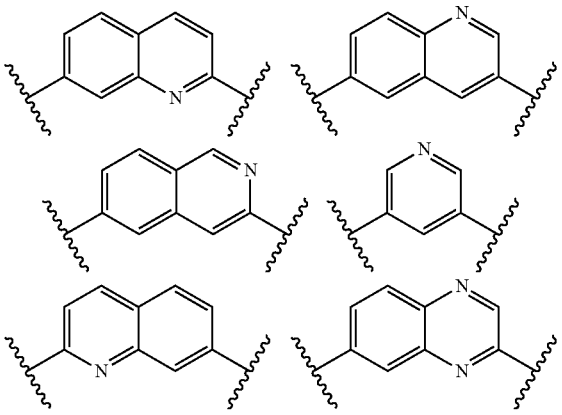

-continued

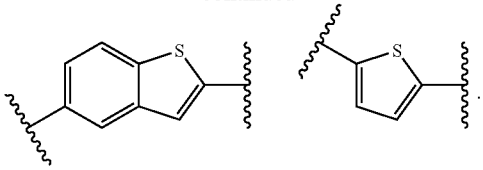

"Hydroxyalkoxy" refers to an alkoxy, as defined herein, substituted with a hydroxyl group (—OH). An example of hydroxyalkoxy is hydroxyethoxy.

"Hydroxyalkyl" refers to an alkyl group substituted with at least one hydroxy group. Examples of hydroxyalkyl groups include, but are not limited to, hydroxymethyl, hydroxyethyl, hydroxypropyl and hydroxybutyl.

"Prodrug" refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The term "optionally substituted" refers to a moiety wherein all substituents are hydrogen or wherein one or more of the hydrogens of the moiety are replaced by non-hydrogen substituents. Multiple substitutions on the same atom are also permitted where chemically feasible (e.g., a dioxo substitution to provide —$S(O)_2$—, geminal substituents, spiro cycloalkyl or heterocycloalkyl rings, etc.). In some embodiments, "one or more" substituents is from one to three substituents.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

A compound of a given formula (e.g. the compound of Formula I) is intended to encompass the compounds of the disclosure, and the pharmaceutically acceptable salts, stereoisomers, mixture of stereoisomers or tautomers of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space. Stereoisomers include enantiomers and diastereomers.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers or "tautomers". Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

"Pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically acceptable carrier" refers to a diluent, adjuvant, excipient, or carrier, or other ingredient which is pharmaceutically acceptable and with which a compound of the invention is administered.

"Pharmaceutically acceptable salt" refers to a salt which may enhance desired pharmacological activity. Examples of pharmaceutically acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

Any formula or structure given herein, including any compound provided herein, is also intended to represent unlabeled forms as well as isotopically labeled forms of the compounds. An "isotope" may have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium) $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included a compound provided herein in which from 1 to n hydrogens attached to a carbon atom is/are replaced by deuterium, in which n is the number of hydrogens in the molecule. Such compounds exhibit increased resistance to metabolism and are thus useful for increasing the half life of any compound provided herein when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound provided herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

Compounds

The present application provides a compound represented by Formula I:

Formula I

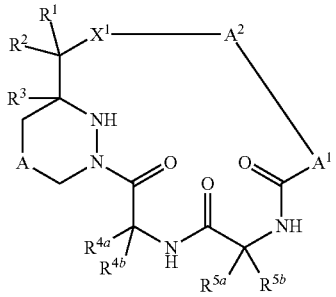

or a pharmaceutically acceptable salt, isotope, stereoisomer, mixture of stereoisomers, tautomer, ester or prodrug thereof, wherein:

A is a bond, —O—, —S(O)$_n$—, —NH—, —N((C$_1$-C$_4$)alkyl)- or (C$_1$-C$_2$)alkylene;

A$^1$ is —CR$^9$═CR$^9$—,

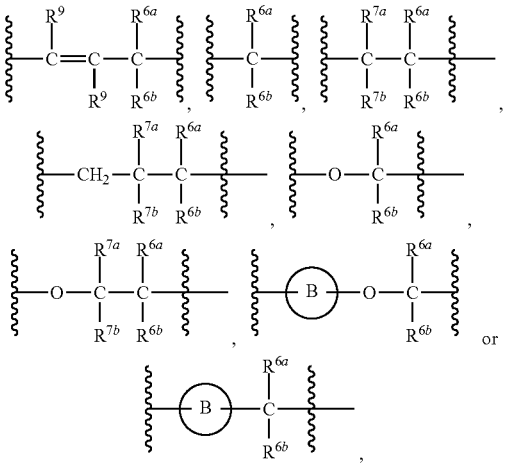

wherein B is arylene, heteroarylene, cycloalkylene or heterocycloalkylene;

A$^2$ is —CH(R$^8$)-arylene, —CH(R$^8$)-heteroarylene, —CH(R$^8$)-heterocycloalkylene, —CH(R$^8$)-cycloalkylene, arylene, heteroarylene or cycloalkylene, wherein A$^2$ is optionally substituted with one or more substituents selected from the group consisting of oxo, —OR$^9$, —SR$^9$, —S(O)R$^9$, —S(O)$_2$R$^9$, —N(R$^9$)$_2$, halo, halo(C$_1$-C$_4$)alkyl, (C$_1$-C$_4$)alkoxy(C$_1$-C$_4$)alkyl, halo(C$_1$-C$_4$)alkoxy, cyano and (C$_1$-C$_8$)alkyl;

X$^1$ is a bond, —O—, —NH—, —N((C$_1$-C$_4$)alkyl)- or heterocycloalkylene;

R$^1$ and R$^2$ are independently H, (C$_1$-C$_4$)alkyl, (C$_2$-C$_4$)alkenyl, (C$_2$-C$_4$)alkynyl, halo, cyano or (C$_1$-C$_4$)alkanoyl; or R$^1$ and R$^2$, when taken together with the carbon to which they are both attached, form —C(═O)—, —C(═S)— or —C(═N(C$_1$-C$_4$)alkyl)-;

R$^3$ is H or (C$_1$-C$_4$)alkyl which is optionally substituted with halo, cyano, hydroxy or (C$_1$-C$_4$)alkoxy;

R$^{4a}$ and R$^{4b}$ are independently H, (C$_1$-C$_8$)alkyl, aryl, aryl(C$_1$-C$_4$)alkyl, heterocycloalkyl, heterocycloalkyl(C$_1$-C$_4$)alkyl, cycloalkyl or cycloalkyl(C$_1$-C$_4$)alkyl, wherein each of R$^{4a}$ and R$^{4b}$ is optionally substituted with one or more substituent selected from the group consisting of cyano, (C$_1$-C$_8$)alkoxy, —COOH, —C(O)O—(C$_1$-C$_8$)alkyl, halo, hydroxyl, amino, mono(C$_1$-C$_8$)alkylamino, di(C$_1$-C$_8$)alkylamino, —C(O)-mono(C$_1$-C$_8$)alkylamino, —C(O)-di(C$_1$-C$_8$)alkylamino, —C(O)-heterocycloalkyl, heterocycloalkyl, aryl and heteroaryl, wherein each substituent is optionally substituted with one or more halo, heterocycloalkyl or aryl;

R$^{5a}$ and R$^{5b}$ are independently H, (C$_1$-C$_8$)alkyl, (C$_2$-C$_8$)alkenyl, (C$_2$-C$_8$)alkynyl, (C$_1$-C$_8$)alkoxy, aryl, heterocycloalkyl, cycloalkyl, aryl(C$_1$-C$_4$)alkyl, cycloalkyl(C$_1$-C$_4$)alkyl or heterocycloalkyl(C$_1$-C$_4$)alkyl, wherein R$^{5a}$ and R$^{5b}$ are independently optionally substituted with one or more substituent selected from the group consisting of —N$_3$, cyano, —COOH, halo, hydroxyl, amino, mono(C$_1$-C$_8$)alkylamino, di(C$_1$-C$_8$)alkylamino, aryl and heteroaryl, or R$^{5a}$ and R$^{5b}$ together form a spirocycle having Formula (a):

(a)

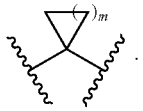

wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —NH$_2$, —C(O)O—(C$_1$-C$_8$)alkyl, —C(O)-di(C$_1$-C$_8$)alkylamino, —C(O)—(C$_1$-C$_8$)alkyl, —C(O)-heterocycloalkyl, —S(O)$_2$R$^{10}$, —OSi(R$^{10}$)$_3$, (C$_1$-C$_4$)alkyl, cyano(C$_1$-C$_4$)alkyl, halo(C$_1$-C$_4$)alkyl, (C$_1$-C$_4$)alkoxy, (C$_1$-C$_8$)alkanoyl and aryl(C$_1$-C$_4$)alkyl;

R$^{6a}$, R$^{6b}$, R$^{7a}$ and R$^{7b}$ are independently H, hydroxyl, cyano, (C$_1$-C$_8$)alkyl, (C$_2$-C$_8$)alkenyl, (C$_2$-C$_8$)alkynyl, (C$_1$-C$_8$)alkoxy, —CH$_2$CH$_2$CR$^9$(═N(C$_1$-C$_4$)alkoxy), aryl, heterocycloalkyl, cycloalkyl, cycloalkyl, —SR$^9$, —S(O)R$^9$, —S(O)$_2$R$^9$ or —N(R$^9$)$_2$, wherein each of R$^{6a}$, R$^{6b}$, R$^{7a}$ and R$^{7b}$ is optionally substituted with one or more substituent selected from the group consisting of halo, hydroxyl, cyano, (C$_1$-C$_4$)alkyl, (C$_1$-C$_8$)alkoxy, aryl, cycloalkyl, heterocycloalkyl, mono(C$_1$-C$_8$)alkylamino, di(C$_1$-C$_8$)alkylamino, —NHS(O)R$^9$, —NHC(O)R$^9$, —OC(O)—(C$_1$-C$_8$)alkyl —C(O)O—(C$_1$-C$_8$)alkyl and (C$_1$-C$_8$)alkanoyl, wherein each —OC(O)—(C$_1$-C$_8$)alkyl or (C$_1$-C$_8$)alkoxy is optionally substituted with one or more amino, —OC(O)O—(C$_1$-C$_8$)alkyl or —Si(R$^{10}$)$_3$; or R$^{6a}$ and R$^{6b}$ together form a spirocycle having Formula (a);

each R$^8$ is independently H, (C$_1$-C$_4$)alkyl, halo(C$_1$-C$_4$)alkyl, (C$_2$-C$_4$)alkenyl, (C$_2$-C$_4$)alkynyl, aryl, heteroaryl, heterocycloalkyl or cycloalkyl, wherein R$^8$ is optionally substituted with —OR, —N(R$^9$)$_2$, —CON(R$^9$)$_2$ or cyano;

each R$^9$ is independently H, (C$_1$-C$_4$)alkyl, (C$_2$-C$_4$)alkenyl or (C$_2$-C$_4$)alkynyl;

each R$^{10}$ is independently H, (C$_1$-C$_4$)alkyl, (C$_2$-C$_4$)alkenyl, (C$_2$-C$_4$)alkynyl, cycloalkyl(C$_1$-C$_4$)alkyl or aryl, wherein R$^{10}$ is optionally substituted with one or more halo;

each n is independently 0, 1 or 2; and m is 1, 2, 3, 4 or 5.

In one embodiment, A is methylene.

In one embodiment, A$^1$ is ethenylene, propenylene, ethylene, propylene, oxypropylene, oxypropenylene, pyrazolylene, phenylene or pyrimidinylene.

In one embodiment, $A^1$ is

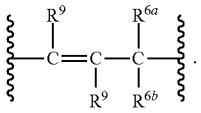

In one embodiment, $A^2$ is —CH($R^8$)-arylene or —CH($R^8$)-heteroarylene.

In one embodiment, $A^2$ is —CH($R^8$)-quinolinylene, —CH($R^8$)-isoquinolinylene, —CH($R^8$)-naphthyridinylene, —CH($R^8$)-cinnolinylene, —CH($R^8$)-quinoxalinylene, —CH($R^8$)-phenylene or —CH($R^8$)-halophenylene.

In one embodiment, $A^2$ is

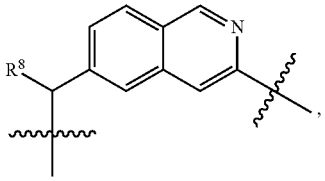

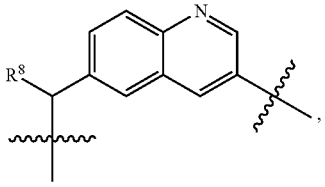

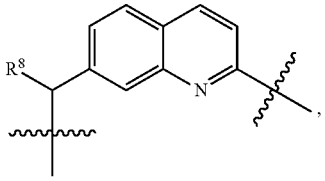

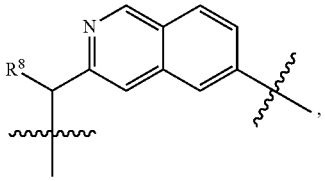

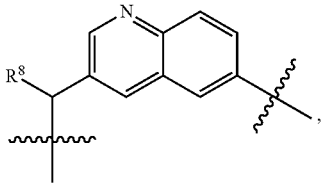

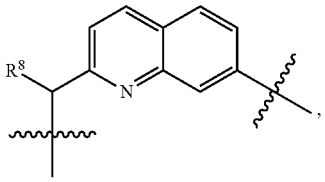

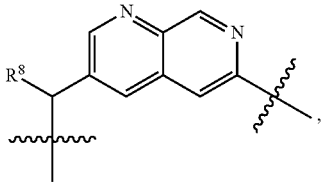

-continued

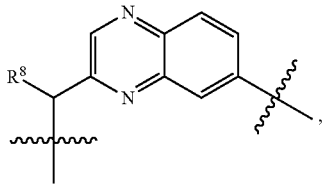

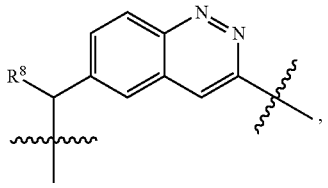

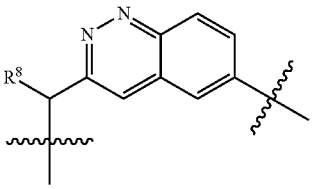

or

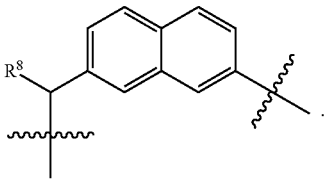

In one embodiment, $X^1$ is —O— or —NH—.

In one embodiment, $R^1$ and $R^2$, when taken together with the carbon to which they are both attached, form —C(═O)—.

In one embodiment, $R^3$ is H.

In one embodiment, $R^{6a}$ is H and $R^{6b}$ is H or ($C_1$-$C_4$)alkyl, or $R^{6a}$ and $R^{6b}$ together form a spirocycle having Formula (a).

In one embodiment, $R^{6a}$ and $R^{6b}$ form

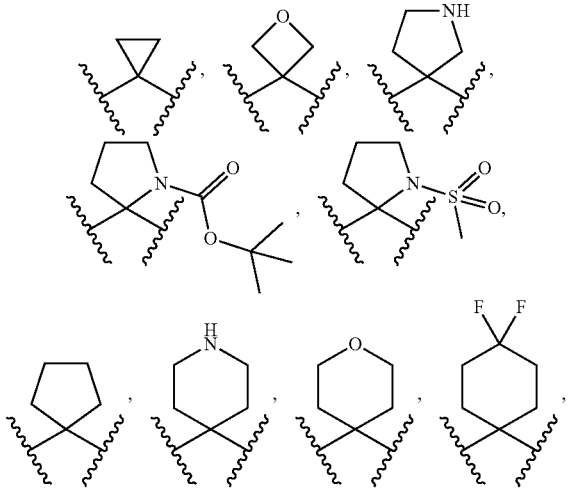

-continued

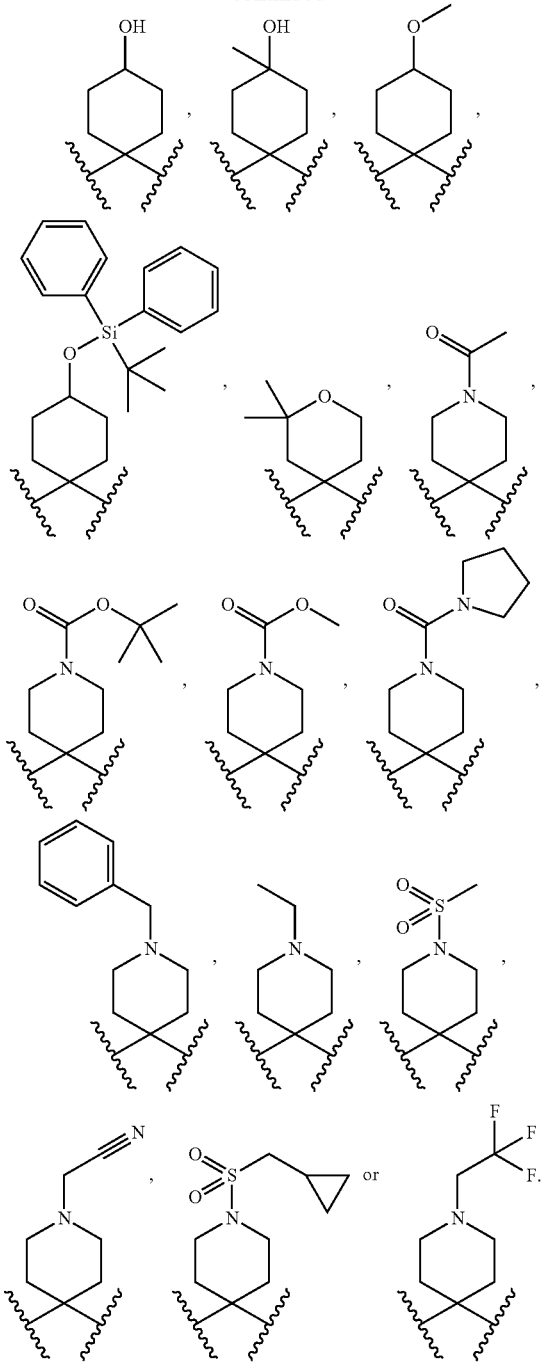

In one embodiment, $R^3$ is H; $R^{5a}$ is H; $R^{5b}$ is H, $(C_1-C_8)$alkyl, hydroxy$(C_1-C_8)$alkyl, $(C_2-C_8)$alkenyl, $(C_2-C_8)$alkynyl, azido$(C_1-C_8)$alkyl, aryl, cycloalkyl, aryl$(C_1-C_4)$alkyl, cycloalkyl$(C_1-C_4)$alkyl, heterocycloalkyl$(C_1-C_4)$alkyl or arylheterocycloalkyl$(C_1-C_4)$alkyl; $R^{6a}$ is H; and $R^{6b}$ is H, $(C_1-C_4)$alkyl or hydroxy$(C_1-C_4)$alkyl.

In one embodiment, $X^1$ is —O— or —NH—; $R^1$ and $R^2$, when taken together with the carbon to which they are both attached, form —C(═O)—; $R^3$ is H; $R^{4a}$ is H; $R^{4b}$ is methyl; $R^{5a}$ is H and $R^{5b}$ is iso-propyl, propenyl or propynyl; and $R^8$ is methyl.

In some embodiments, the present case is directed to compounds of Formula I:

Formula I

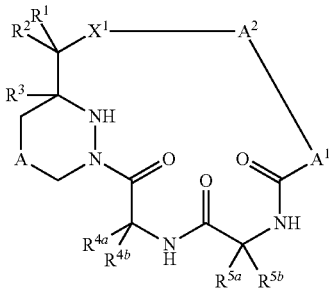

or a pharmaceutically acceptable salt, ester or prodrug thereof, wherein

A is a bond, —O—, —S(O)$_n$—, —NH—, —N((C$_1$-C$_4$)alkyl)- or $(C_1-C_2)$alkylene;

$A^1$ is —CR$^9$═CR$^9$—,

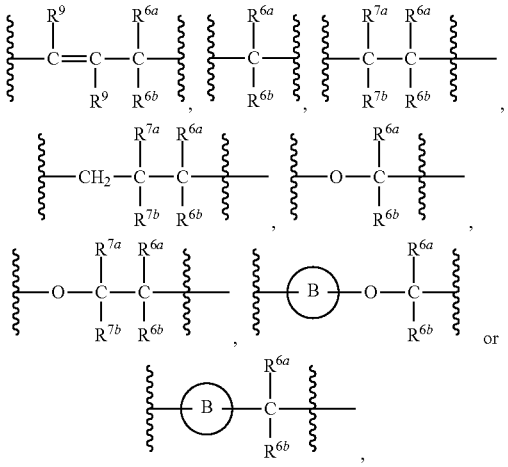

wherein B is arylene, heteroarylene, cycloalkylene or heterocycloalkylene;

$A^2$ is —CH(R$^8$)-arylene, —CH(R$^8$)-heteroarylene, —CH(R$^8$)-heterocycloalkylene, —CH(R$^8$)-cycloalkylene, arylene or cycloalkylene, wherein $A^2$ is optionally substituted with one or more substituents selected from OR$^9$, —SR$^9$, —S(O)R$^9$, —S(O)$_2$R$^9$, —N(R$^9$)$_2$, halo, halo$(C_1-C_4)$alkyl, halo$(C_1-C_4)$alkoxy, cyano and $(C_1-C_8)$alkyl;

$X^1$ is bond, —O—, —NH—, —N((C$_1$-C$_4$)alkyl)- or heterocycloalkylene;

$R^1$ and $R^2$ are independently H, $(C_1-C_4)$alkyl, $(C_2-C_4)$alkenyl, $(C_2-C_4)$alkynyl, halo, cyano or $(C_1-C_4)$alkanoyl; or $R^1$ and $R^2$, when taken together with the carbon to which they are both attached, form —C(═O)—, —C(═S)— or —C(═N(C$_1$-C$_4$)alkyl)-;

$R^3$ is H or $(C_1-C_4)$alkyl which is optionally substituted with halo, cyano, hydroxy or alkoxy;

$R^{4a}$ and $R^{4b}$ are independently H, $(C_1-C_8)$alkyl, aryl, aryl$(C_1-C_4)$alkyl, heterocycloalkyl, heterocycloalkyl$(C_1-C_4)$alkyl, cycloalkyl or cycloalkyl$(C_1-C_4)$alkyl, wherein each of $R^{4a}$ and $R^{4b}$ is optionally substituted with one or more substituent selected from cyano, —COOH, halo, hydroxyl, amino, mono$(C_1-C_8)$alkylamino, di$(C_1-C_8)$alkylamino, aryl and heteroaryl;

$R^{5a}$ and $R^{5b}$ are independently H, $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl($C_1$-$C_4$)alkyl, cycloalkyl($C_1$-$C_4$)alkyl or heterocycloalkyl($C_1$-$C_4$)alkyl, wherein $R^5$ is optionally substituted with one or more substituent selected from —$N_3$, cyano, —COOH, halo, hydroxyl, amino, mono($C_1$-$C_8$)alkylamino, di($C_1$-$C_8$)alkylamino, aryl and heteroaryl, or $R^{5a}$ and $R^{5b}$ together form a spirocycle having Formula (a):

(a)

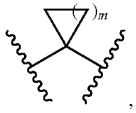

wherein a carbon ring atom of Formula (a) is optionally substituted with one or more heteroatom selected from SO, $SO_2$, O and N, and wherein a carbon ring atom of Formula (a) optionally has one or more substituents selected from halo, hydroxyl, —$NH_2$, ($C_1$-$C_4$)alkyl and ($C_1$-$C_4$)alkoxy;

$R^{6a}$, $R^{6b}$, $R^{7a}$ and $R^{7b}$ are independently H, hydroxyl, ($C_1$-$C_8$)alkyl, ($C_2$-$C_8$)alkenyl, ($C_2$-$C_8$)alkynyl, ($C_1$-$C_8$)alkoxy, —$CH_2CH_2CR^9$(=N($C_1$-$C_4$)alkoxy), aryl, heterocycloalkyl, cycloalkyl, —$SR^9$, —$S(O)R^9$, —$S(O)_2R^9$ or —$N(R^9)_2$, wherein each of $R^{6a}$, $R^{6b}$, $R^{7a}$ and $R^{7b}$ is optionally substituted with one or more substituent selected from halo, hydroxyl, cyano, ($C_1$-$C_4$)alkyl, ($C_1$-$C_8$)alkoxy, aryl, cycloalkyl, heterocycloalkyl, mono($C_1$-$C_8$)alkylamino, di($C_1$-$C_8$)alkylamino, —$NHS(O)R^9$, —$NHC(O)R^9$ and ($C_1$-$C_8$)alkanoyl; or $R^{6a}$ and $R^{6b}$ together form a spirocycle having Formula (a);

each $R^8$ is independently H, ($C_1$-$C_4$)alkyl, halo($C_1$-$C_4$)alkyl, ($C_2$-$C_4$)alkenyl, ($C_2$-$C_4$)alkynyl, aryl, heteroaryl, heterocycloalkyl or cycloalkyl, wherein $R^8$ is optionally substituted with —OR, —$N(R^9)_2$, —$CON(R^9)_2$, or cyano;

each $R^9$ is independently H, ($C_1$-$C_4$)alkyl, ($C_2$-$C_4$)alkenyl or ($C_2$-$C_4$)alkynyl;

each n is independently 0, 1 or 2; and m is 1, 2, 3, 4 or 5.

In one aspect of the embodiment, $A^1$ is ethenylene, propenylene, ethylene, propylene, oxypropylene, oxypropenylene, pyrazolylene, phenylene or pyrimidinylene.

In another aspect of the embodiment, $A^2$ is —CH($R^8$)-quinolinylene, —CH($R^8$)-isoquinolinylene, —CH($R^8$)-naphthyridinylene, —CH($R^8$)-cinnolinylene, —CH($R^8$)-quinoxalinylene, —CH($R^8$)-phenylene or —CH($R^8$)-halophenylene. In various aspects of the embodiment, $A^2$ is selected from

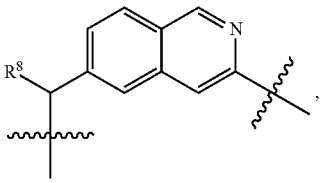

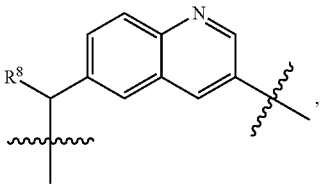

-continued

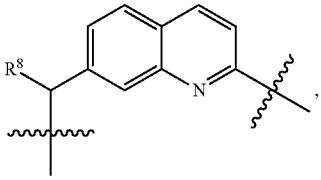

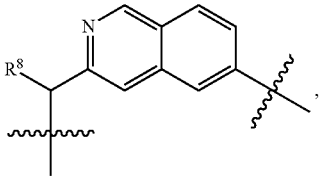

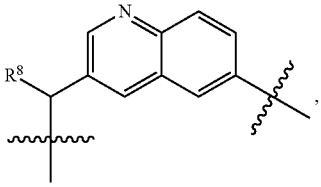

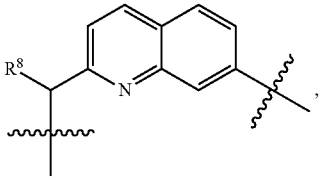

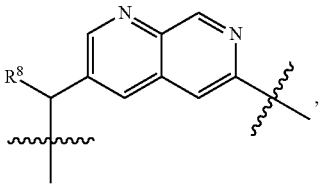

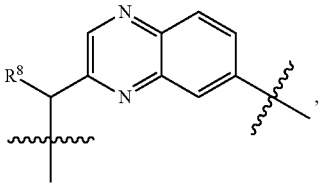

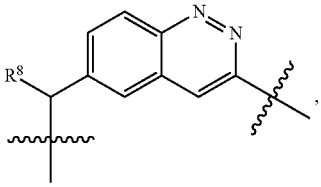

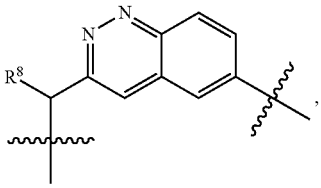

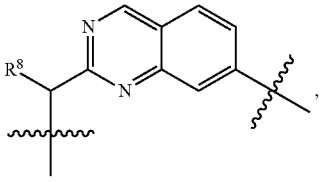

-continued

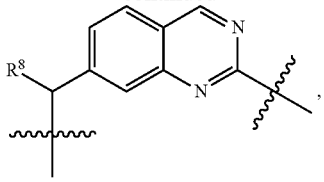

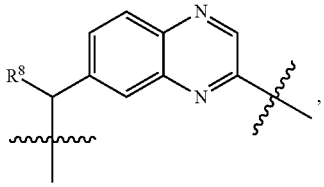

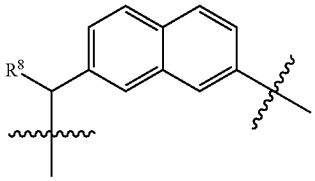

and

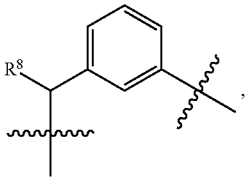

wherein the left bond of $A^5$ linker is attached to $X^1$.

In another aspect of the embodiment, $X^1$ is —O— or —NH—; $R^1$ and $R^2$, when taken together with the carbon to which they are both attached, form —C(═O)—; $R^3$ is H; $R^{4a}$ is H; $R^{4b}$ is methyl; $R^5$ is iso-propyl, propenyl or propynyl; and $R^8$ is methyl.

In another aspect of the embodiment, $R^{6a}$ is H and $R^{6b}$ is H or $(C_1\text{-}C_4)$alkyl, or $R^{6a}$ and $R^{6b}$ together form a spirocycle having Formula (a).

In one embodiment, provided is a compound of Formula II:

Formula II

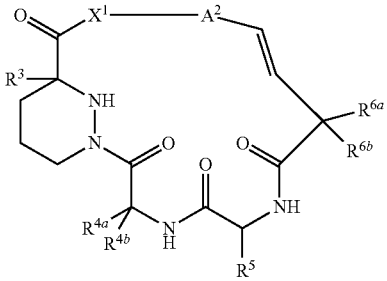

or a pharmaceutically acceptable salt, isotope, stereoisomer, mixture of stereoisomers, tautomer, ester or prodrug thereof, wherein:

$A^2$ is —CH($R^8$)-arylene, —CH($R^8$)-heteroarylene, —CH($R^8$)-heterocycloalkylene, —CH($R^8$)-cycloalkylene or cycloalkylene;

X' is a bond, —O—, —NH, —N($CH_3$)—,

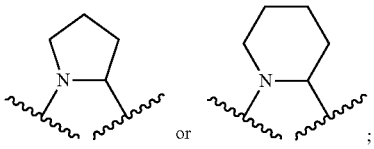

$R^3$ is H or $(C_1\text{-}C_4)$alkyl;

$R^{4a}$ and $R^{4b}$ are independently H, $(C_1\text{-}C_8)$alkyl, aryl, aryl$(C_1\text{-}C_4)$alkyl, heterocycloalkyl, heterocycloalkyl$(C_1\text{-}C_4)$alkyl, cycloalkyl or cycloalkyl$(C_1\text{-}C_4)$alkyl, wherein each of $R^{4a}$ and $R^{4b}$ is optionally substituted with one or more substituent selected from the group consisting of cyano, $(C_1\text{-}C_8)$alkoxy, —COOH, —C(O)O—$(C_1\text{-}C_8)$alkyl, halo, hydroxyl, amino, mono$(C_1\text{-}C_8)$alkylamino, di$(C_1\text{-}C_8)$alkylamino, —C(O)-mono$(C_1\text{-}C_8)$alkylamino, —C(O)-di$(C_1\text{-}C_8)$alkylamino, —C(O)-heterocycloalkyl, heterocycloalkyl, aryl and heteroaryl, wherein each substituent is optionally substituted with one or more halo, heterocycloalkyl or aryl;

$R^5$ is $(C_1\text{-}C_8)$alkyl, $(C_2\text{-}C_8)$alkenyl, $(C_2\text{-}C_8)$alkynyl, $(C_1\text{-}C_8)$alkoxy, aryl, heterocycloalkyl, cycloalkyl, aryl$(C_1\text{-}C_4)$alkyl, cycloalkyl$(C_1\text{-}C_4)$alkyl or heterocycloalkyl$(C_1\text{-}C_4)$alkyl, wherein $R^5$ is optionally substituted with one or more substituent selected from —$N_3$, cyano, —COOH, halo, hydroxyl, amino, mono$(C_1\text{-}C_8)$alkylamino, di$(C_1\text{-}C_8)$alkylamino, aryl and heteroaryl, $R^{6a}$ and $R^{6b}$ are independently H, hydroxyl, cyano, $(C_1\text{-}C_8)$alkyl, $(C_2\text{-}C_8)$alkenyl, $(C_2\text{-}C_8)$alkynyl, $(C_1\text{-}C_8)$alkoxy, —$CH_2CH_2CR^9$(═N$(C_1\text{-}C_4)$alkoxy), aryl, heterocycloalkyl, cycloalkyl, cycloalkyl, —$SR^9$, —S(O)$R^9$, —S(O)$_2R^9$ or —N$(R^9)_2$, wherein each of $R^{6a}$ and $R^{6b}$ is optionally substituted with one or more substituent selected from the group consisting of halo, hydroxyl, cyano, $(C_1\text{-}C_4)$alkyl, $(C_1\text{-}C_8)$alkoxy, aryl, cycloalkyl, heterocycloalkyl, mono$(C_1\text{-}C_8)$alkylamino, di$(C_1\text{-}C_8)$alkylamino, —NHS(O)$R^9$, —NHC(O)$R^9$, —OC(O)—$(C_1\text{-}C_8)$alkyl —C(O)O—$(C_1\text{-}C_8)$alkyl and $(C_1\text{-}C_8)$alkanoyl, wherein each —OC(O)—$(C_1\text{-}C_8)$alkyl or $(C_1\text{-}C_8)$alkoxy is optionally substituted with one or more amino, —OC(O)O—$(C_1\text{-}C_8)$alkyl or —Si$(R^{10})_3$; or $R^{6a}$ and $R^{6b}$ together form a spirocycle having Formula (a);

(a)

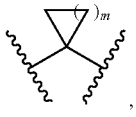

wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, —C(O)O—$(C_1\text{-}C_8)$alkyl, —C(O)-di$(C_1\text{-}C_8)$alkylamino, —C(O)—$(C_1\text{-}C_8)$alkyl, —C(O)-heterocycloalkyl, —S(O)$_2R^{10}$, —OSi$(R^{10})_3$, $(C_1\text{-}C_4)$alkyl, cyano$(C_1\text{-}C_4)$alkyl, halo$(C_1\text{-}C_4)$alkyl, $(C_1\text{-}C_4)$alkoxy, $(C_1\text{-}C_8)$alkanoyl and aryl$(C_1\text{-}C_4)$alkyl; and $R^8$ is H or $(C_1\text{-}C_4)$alkyl;

each $R^9$ is independently H, $(C_1\text{-}C_4)$alkyl, $(C_2\text{-}C_4)$alkenyl or $(C_2\text{-}C_4)$alkynyl; and each $R^{10}$ is independently H, $(C_1-C_4)$alkyl, $(C_2-C_4)$alkenyl, $(C_2-C_4)$alkynyl, cycloalkyl$(C_1-C_4)$alkyl or aryl, wherein $R^{10}$ is optionally substituted with one or more halo.

In another embodiment, there is provided a compound of Formula II:

Formula II

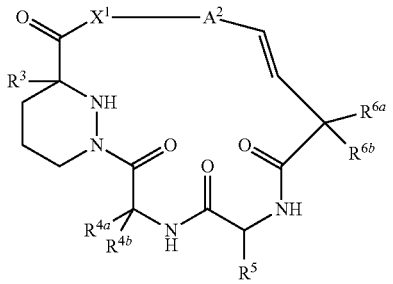

or a pharmaceutically acceptable salt, isotope, stereoisomer, mixture of stereoisomers, tautomer, ester or prodrug thereof, wherein:

$A^2$ is —CH($R^8$)-arylene, —CH($R^8$)-heteroarylene, —CH($R^8$)-heterocycloalkylene, —CH($R^8$)-cycloalkylene or cycloalkylene;

$X^1$ is bond, —O—, —NH, —N($CH_3$)—,

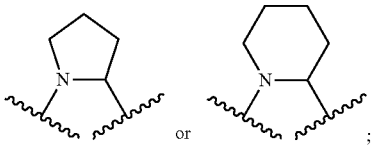

$R^3$ is H or $(C_1-C_4)$alkyl which is optionally substituted with halo, cyano, hydroxy or $(C_1-C_4)$alkoxy;

$R^{4a}$ and $R^{4b}$ are independently H, $(C_1-C_4)$alkoxy, halo$(C_1-C_4)$alkoxy or $(C_1-C_8)$alkyl;

$R^5$ is H, $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl$(C_1-C_4)$alkyl, cycloalkyl$(C_1-C_4)$alkyl or heterocycloalkyl$(C_1-C_4)$alkyl, wherein $R^5$ is optionally substituted with one or more substituent selected from —$N_3$, halo, hydroxyl, di$(C_1-C_8)$alkylamino, aryl or heteroaryl;

$R^{6a}$ and $R^{6b}$ are independently H, —OH, $(C_1-C_4)$alkoxy, halo$(C_1-C_4)$alkoxy or $(C_1-C_8)$alkyl, wherein each of $R^{6a}$ and $R^{6b}$ is optionally substituted with one or more substituent selected from halo, hydroxyl, $(C_1-C_4)$alkyl, aryl, cycloalkyl, heterocycloalkyl, di$(C_1-C_8)$alkylamino and $(C_1-C_8)$alkanoyl; or $R^{6a}$ and $R^{6b}$ together form

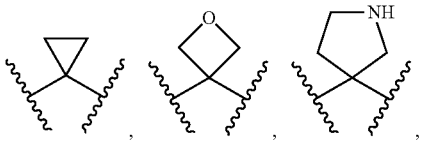

-continued

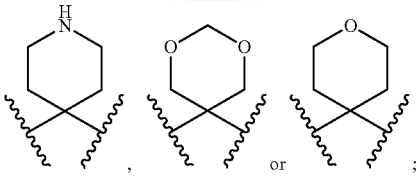

and $R^8$ is H or $(C_1-C_4)$alkyl.

In yet another embodiment, provided is a compound of Formula IIa:

Formula IIa

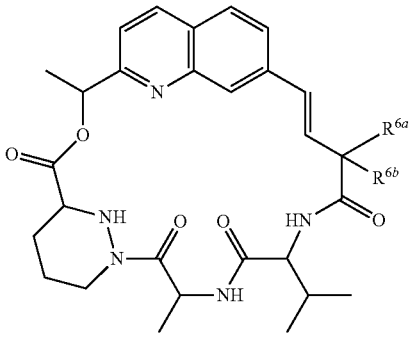

or a pharmaceutically acceptable salt, isotope, stereoisomer, mixture of stereoisomers, tautomer, ester or prodrug thereof, wherein:

$R^{6a}$ and $R^{6b}$ are independently H, hydroxyl, cyano, $(C_1-C_8)$alkyl, $(C_2-C_8)$alkenyl, $(C_2-C_8)$alkynyl, $(C_1-C_8)$alkoxy, —$CH_2CH_2CR^9$(=N$(C_1-C_4)$alkoxy), aryl, heterocycloalkyl, cycloalkyl, —$SR^9$, —S(O)$R^9$, —S(O)$_2R^9$ or —N($R^9$)$_2$, wherein each of $R^{6a}$ and $R^{6b}$ is optionally substituted with one or more substituent selected from the group consisting of halo, hydroxyl, cyano, $(C_1-C_4)$alkyl, $(C_1-C_8)$alkoxy, aryl, cycloalkyl, heterocycloalkyl, mono$(C_1-C_8)$alkylamino, di$(C_1-C_8)$alkylamino, —NHS(O)$R^9$, —NHC(O)$R^9$, —OC(O)—$(C_1-C_8)$alkyl —C(O)O—$(C_1-C_8)$alkyl and $(C_1-C_8)$alkanoyl, wherein each —OC(O)—$(C_1-C_8)$alkyl or $(C_1-C_8)$alkoxy is optionally substituted with one or more amino, —OC(O)O—$(C_1-C_8)$alkyl or —Si($R^{10}$)$_3$ or $R^{6a}$ and $R^{6b}$ together form a spirocycle having Formula (a);

(a)

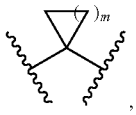

wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, —C(O)O—$(C_1-C_8)$alkyl, —C(O)-di$(C_1-C_8)$alkylamino, —C(O)—$(C_1-C_8)$alkyl, —C(O)-heterocycloalkyl, —S(O)$_2R^{10}$, —OSi($R^{10}$)$_3$, $(C_1-C_4)$alkyl, cyano$(C_1-C_4)$alkyl, halo$(C_1-C_4)$alkyl, $(C_1-C_4)$alkoxy, $(C_1-C_8)$alkanoyl and aryl$(C_1-C_4)$alkyl;

each $R^9$ is independently H, $(C_1\text{-}C_4)$alkyl, $(C_2\text{-}C_4)$alkenyl or $(C_2\text{-}C_4)$alkynyl; and each $R^{10}$ is independently H, $(C_1\text{-}C_4)$alkyl, $(C_2\text{-}C_4)$alkenyl, $(C_2\text{-}C_4)$alkynyl, cycloalkyl$(C_1\text{-}C_4)$alkyl or aryl, wherein $R^{10}$ is optionally substituted with one or more halo.

In various aspects embodiment, $A^2$ is

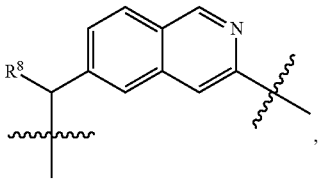

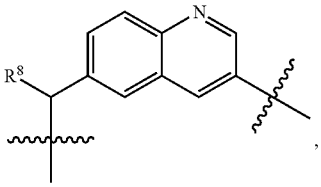

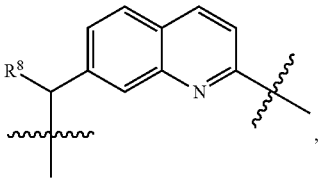

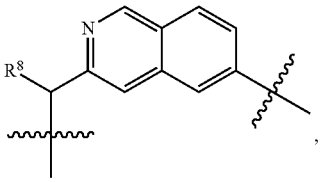

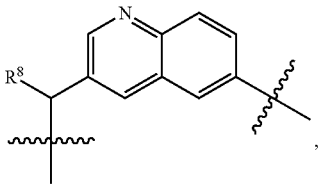

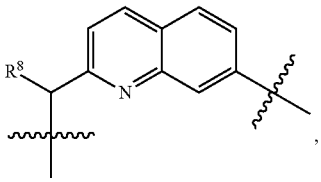

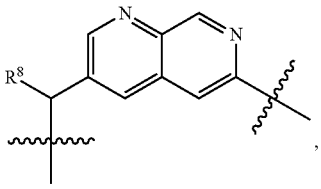

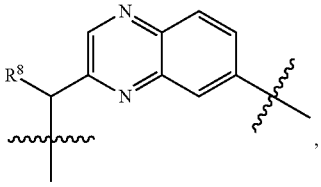

-continued

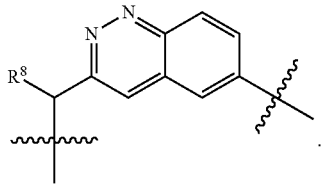

In one aspect of the embodiment, $R^3$ is H; $R^5$ is H, $(C_1\text{-}C_8)$alkyl, hydroxy$(C_1\text{-}C_8)$alkyl, aryl, cycloalkyl, aryl$(C_1\text{-}C_4)$alkyl or cycloalkyl$(C_1\text{-}C_4)$alkyl; and $R^{6a}$ and $R^{6b}$ are H. Non-limiting examples of such compounds include the following compounds and pharmaceutically acceptable salts thereof:

Formula (II-a)

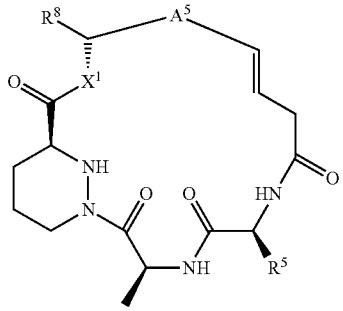

| Compound No. | $A^5$ | $X^1$ | $R^5$ | $R^8$ |
|---|---|---|---|---|
| a-1 | 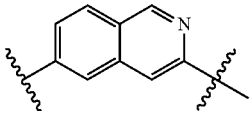 | —O— | —$CH_2$(OH) | Methyl |
| a-2 | | —O— | —CH(OH)$CH_3$ | Methyl |
| a-3 | | —O— | Cyclohexyl | Methyl |
| a-4 | | —O— | Benzyl | Methyl |
| a-5 | | —O— | Phenylethyl | Methyl |
| a-6 | | —O— | Propyl | —$CF_3$ |
| a-7 | | —O— | Iso-propyl | Methyl |
| a-8 | | —O— | Propyl | Methyl |
| a-9 | | —NH— | —$CH_2$(OH) | Methyl |
| a-10 | | —NH— | —CH(OH)$CH_3$ | Methyl |
| a-11 | | —NH— | Cyclohexyl | Methyl |
| a-12 | | —NH— | Benzyl | Methyl |
| a-13 | | —NH— | Phenylethyl | Methyl |
| a-14 | | —NH— | Propyl | —$CF_3$ |
| a-15 | | —NH— | Iso-propyl | Methyl |
| a-16 | | —NH— | Propyl | Methyl |
| a-17 | 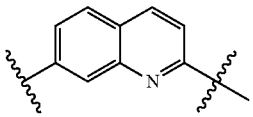 | —O— | Iso-propyl | Methyl |
| a-18 | | —NH— | Iso-propyl | Methyl |
| a-19 | 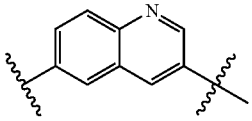 | —O— | Iso-propyl | Methyl |
| a-20 | | —NH— | Iso-propyl | Methyl |
| a-21 | 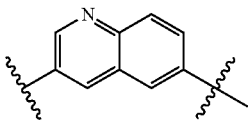 | —O— | Iso-propyl | Methyl |
| a-22 | | —NH— | Iso-propyl | Methyl |

-continued

Formula (II-a)

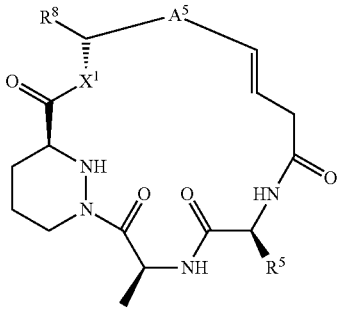

| Compound No. | $A^5$ | $X^1$ | $R^5$ | $R^8$ |
|---|---|---|---|---|
| a-23 | 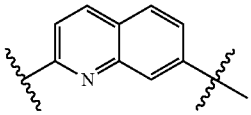 | —O— | Iso-propyl | Methyl |
| a-24 | | —NH— | Iso-propyl | Methyl |
| a-25 | 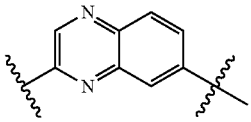 | —O— | Iso-propyl | Methyl |
| a-26 | | —NH— | Iso-propyl | Methyl |

-continued

Formula (II-a)

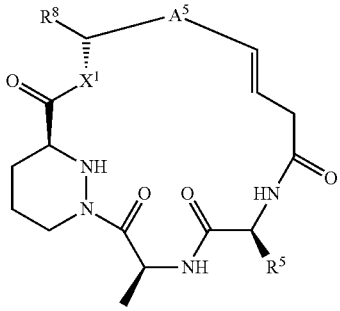

| Compound No. | $A^5$ | $X^1$ | $R^5$ | $R^8$ |
|---|---|---|---|---|
| a-27 | 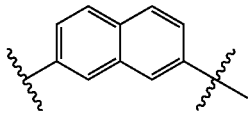 | —O— | Iso-propyl | Methyl |
| a-28 | | —NH— | Iso-propyl | Methyl |

In another aspect of the embodiment, $R^3$ is H; $R^5$ is H, $(C_1\text{-}C_8)$alkyl, hydroxy$(C_1\text{-}C_8)$alkyl, $(C_2\text{-}C_8)$alkenyl, $(C_2\text{-}C_8)$alkynyl, azido$(C_1\text{-}C_8)$alkyl, aryl, aryl$(C_1\text{-}C_4)$alkyl, cycloalkyl$(C_1\text{-}C_4)$alkyl, heterocycloalkyl$(C_1\text{-}C_4)$alkyl or arylheterocycloalkyl$(C_1\text{-}C_4)$alkyl; $R^{6a}$ is H; and $R^{6b}$ is $(C_1\text{-}C_4)$alkyl or hydroxy$(C_1\text{-}C_4)$alkyl. Non-limiting examples of such compounds include the following compounds and pharmaceutically acceptable salts thereof:

Formula (II-b)

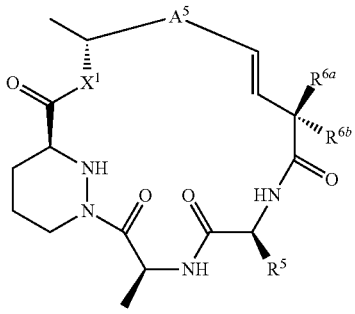

| Compound No. | $A^5$ | $X^1$ | $R^5$ | $R^{6a}$ | $R^{6b}$ |
|---|---|---|---|---|---|
| b-1 | 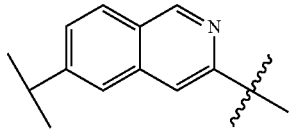 | —O— | Iso-propyl | Methyl | H |
| b-2 | | —O— | Iso-propyl | H | Methyl |
| b-3 | | —O— | Iso-propyl | Ethyl | H |
| b-4 | | —O— | Iso-propyl | —CH(OH)$CH_3$ | H |
| b-5 | | —NH— | Iso-propyl | Methyl | H |
| b-6 | | —NH— | Iso-propyl | H | Methyl |
| b-7 | | —NH— | Iso-propyl | Ethyl | H |
| b-8 | | —NH— | Iso-propyl | —CH(OH)$CH_3$ | H |
| b-9 | 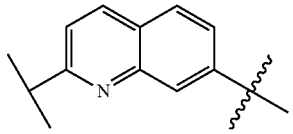 | —O— | Iso-propyl | Methyl | H |
| b-10 | | —O— | Iso-propyl | H | Methyl |
| b-11 | | —O— | Iso-propyl | Ethyl | H |
| b-12 | | —O— | Iso-propyl | —CH(OH)$CH_3$ | H |
| b-13 | | —NH— | Iso-propyl | Methyl | H |
| b-14 | | —NH— | Iso-propyl | H | Methyl |
| b-15 | | —NH— | Iso-propyl | Ethyl | H |
| b-16 | | —NH— | Iso-propyl | —CH(OH)$CH_3$ | H |

Also included are compounds having the following formulae:

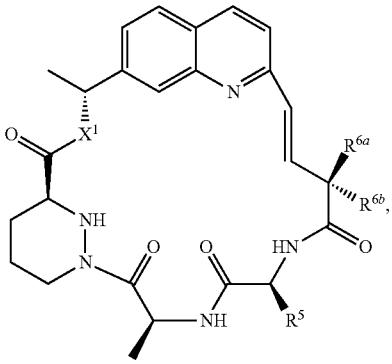

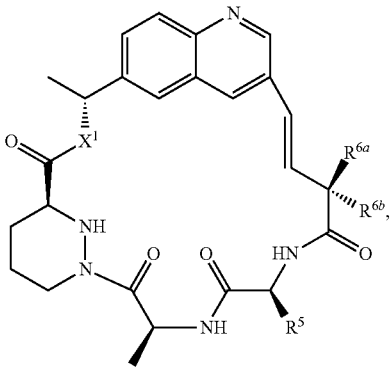

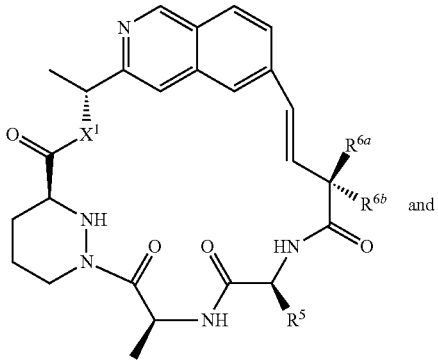

and

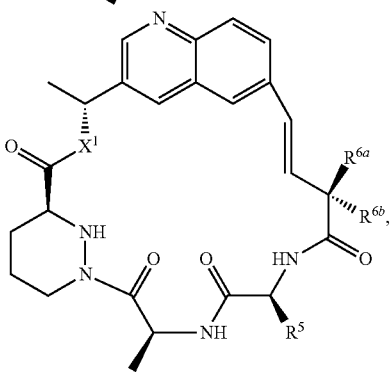

wherein the compounds of the formulae above have the same combination or pattern of substituents given in the table for Compounds b-1 to b-8.

In another aspect of the embodiment, $R^3$ is H; $R^5$ is H, $(C_1\text{-}C_8)$alkyl, hydroxy$(C_1\text{-}C_8)$alkyl, $(C_2\text{-}C_8)$alkenyl, $(C_2\text{-}C_8)$alkynyl, azido$(C_1\text{-}C_8)$alkyl, aryl, aryl$(C_1\text{-}C_4)$alkyl, cycloalkyl$(C_1\text{-}C_4)$alkyl, heterocycloalkyl$(C_1\text{-}C_4)$alkyl or heteroarylheterocycloalkyl$(C_1\text{-}C_4)$alkyl; and both $R^{6a}$ and $R^{6b}$ are methyl. In an aspect of this embodiment, $R^5$ is

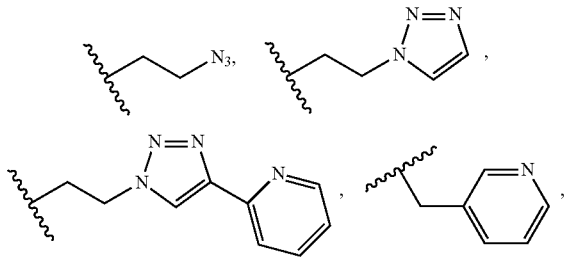

—$CH_2CH{=}CH_2$ or —$CH_2C{\equiv}CH$. Non-limiting examples of such compounds include the following compounds and pharmaceutically acceptable salts thereof:

Formula (II-c)

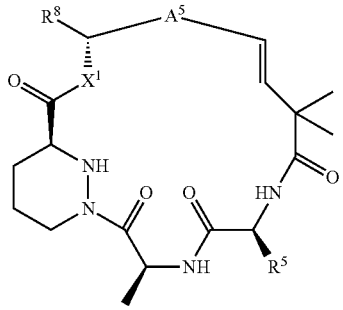

| Cmpd No. | $X^1$ | $R^5$ |
|---|---|---|
| Compounds c-1 to c-14: | | |
| $A^5$ = | 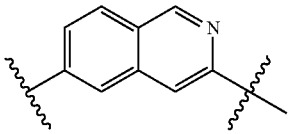 | |
| c-1 | —O— | Iso-propyl |
| c-2 | —O— | —$CH_2CH_2N_3$ |
| c-3 | —O— | 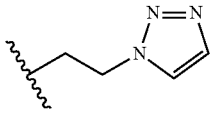 |
| c-4 | —O— | 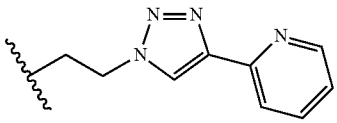 |
| c-5 | —O— | 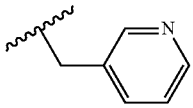 |
| c-6 | —O— | —$CH_2CH{=}CH_2$ |
| c-7 | —O— | —$CH_2C{=}CH$ |
| c-8 | —NH— | Iso-propyl |
| c-9 | —NH— | —$CH_2CH_2N_3$ |

-continued
Formula (II-c)
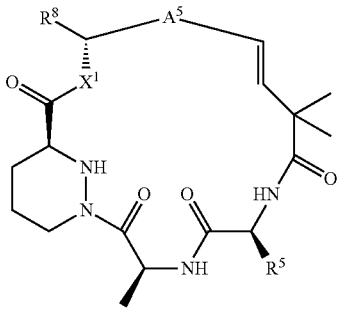
| Cmpd No. | $X^1$ | $R^5$ |
|---|---|---|
| c-10 | —NH— | 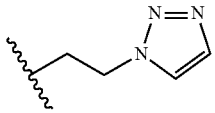 |
| c-11 | —NH— | 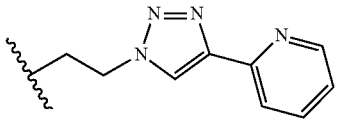 |
| c-12 | —NH— | 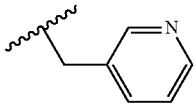 |
| c-13 | —NH— | —$CH_2CH{=}CH_2$ |
| c-14 | —NH— | —$CH_2C{\equiv}CH$ |
Compounds c-15 to c-28:
$A^5$ = 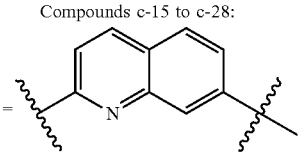
| | | |
|---|---|---|
| c-15 | —O— | Iso-propyl |
| c-16 | —O— | —$CH_2CH_2N_3$ |
| c-17 | —O— | 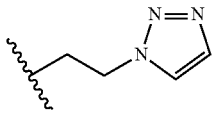 |
| c-18 | —O— | 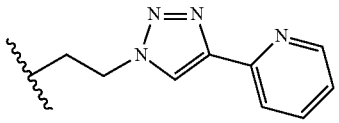 |
| c-19 | —O— | 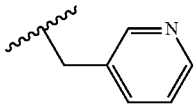 |
| c-20 | —O— | —$CH_2CH{=}CH_2$ |
| c-21 | —O— | —$CH_2C{\equiv}CH$ |
-continued
Formula (II-c)
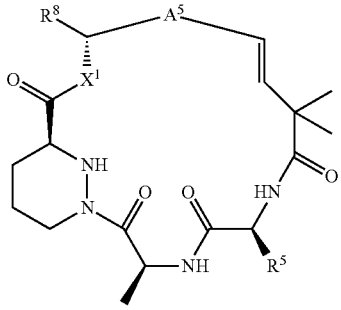
| Cmpd No. | $X^1$ | $R^5$ |
|---|---|---|
| c-22 | —NH— | Iso-propyl |
| c-23 | —NH— | —$CH_2CH_2N_3$ |
| c-24 | —NH— | 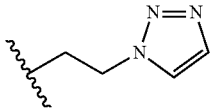 |
| c-25 | —NH— | 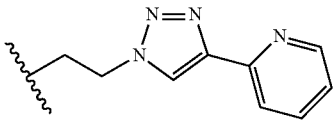 |
| c-26 | —NH— | 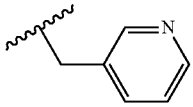 |
| c-27 | —NH— | —$CH_2CH{=}CH_2$ |
| c-28 | —NH— | —$CH_2C{\equiv}CH$ |
Also included are compounds having the following formulae:
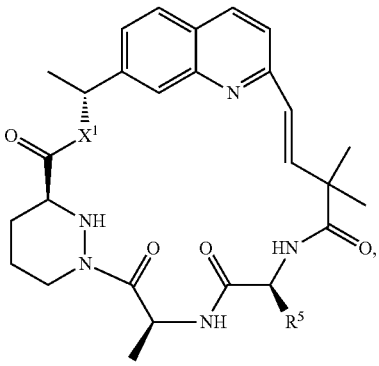

-continued

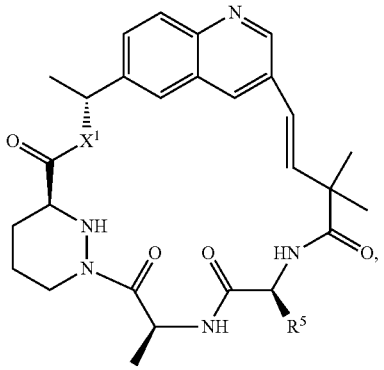

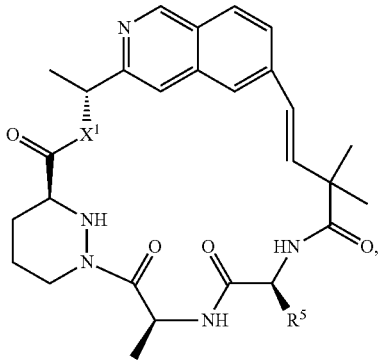

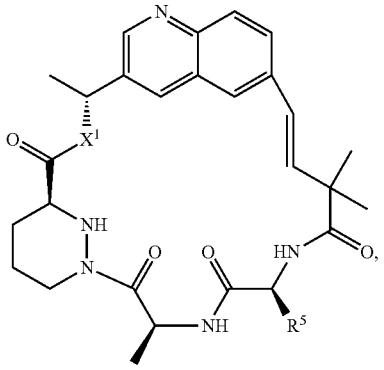

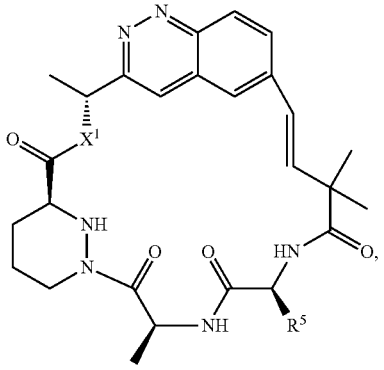

-continued

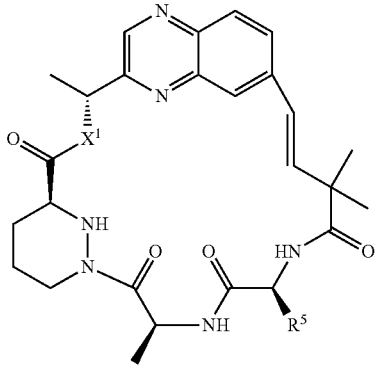

and

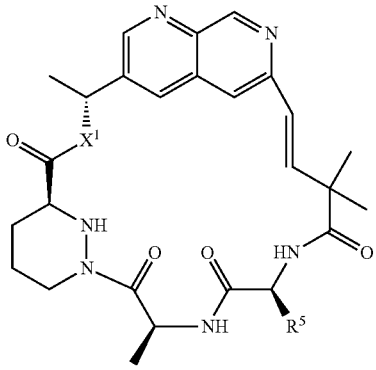

wherein the compounds of the formulae above have the same combination or pattern of substituents given in the table for Compounds c-1 to c-14.

In another aspect of the embodiment, $R^3$ is H; $R^5$ is H, $(C_1\text{-}C_8)$alkyl, hydroxy$(C_1\text{-}C_8)$alkyl, $(C_2\text{-}C_8)$alkenyl, $(C_2\text{-}C_8)$alkynyl, azido$(C_1\text{-}C_8)$alkyl, aryl, aryl$(C_1\text{-}C_4)$alkyl, cycloalkyl$(C_1\text{-}C_4)$alkyl, heterocycloalkyl$(C_1\text{-}C_4)$alkyl or heteroarylheterocycloalkyl$(C_1\text{-}C_4)$alkyl; and both $R^{6a}$ and $R^{6b}$ are hydroxymethyl. Non-limiting examples of such compounds include the following compounds and pharmaceutically acceptable salts thereof:

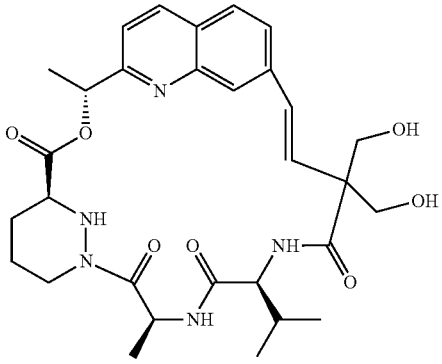

and

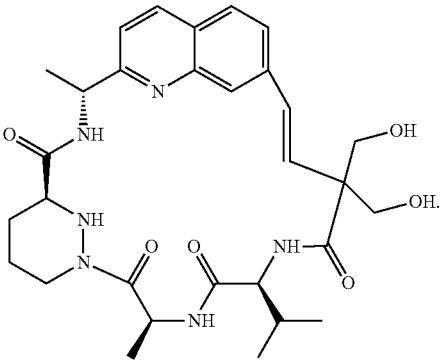

In another aspect of the embodiment, $R^3$ is H; and $R^{6a}$ and $R^{6b}$ form a spirocycle selected from

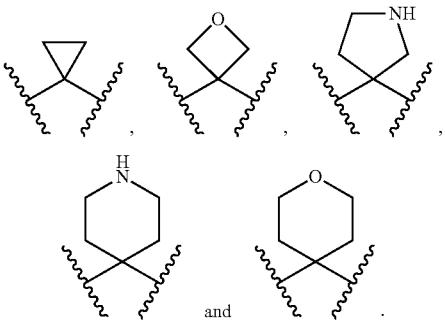

Non-limiting examples of such compounds include the following compounds and pharmaceutically acceptable salts thereof:

Formula (II-d)

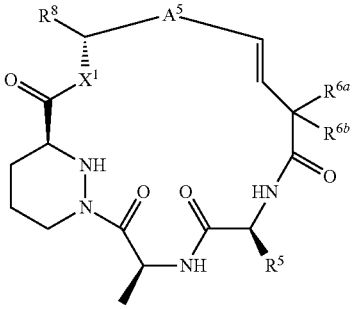

| Compound No. | $A^5$ | $X^1$ | $R^{6a}$ and $R^{6b}$ |
|---|---|---|---|
| d-1<br>d-2 | 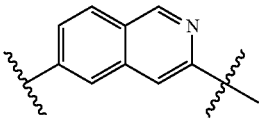 | —O—<br>—NH— | 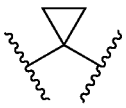 |
| d-3<br>d-4 | | —O—<br>—NH— | 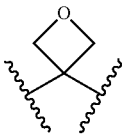 |
| d-5<br>d-6 | | —O—<br>—NH— | 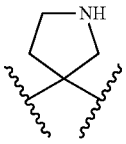 |
| d-7<br>d-8 | | —O—<br>—NH— | 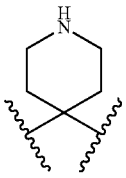 |

-continued

Formula (II-d)

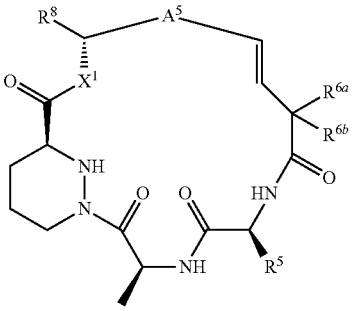

| Compound No. | $A^5$ | $X^1$ | $R^{6a}$ and $R^{6b}$ |
|---|---|---|---|
| d-9<br>d-10 | | —O—<br>—NH— | 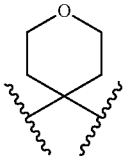 |
| d-11<br>d-12 | 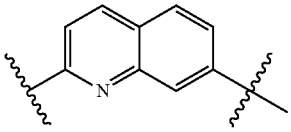 | —O—<br>—NH— | 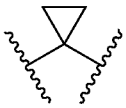 |
| d-13<br>d-14 | | —O—<br>—NH— | 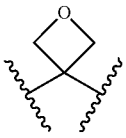 |
| d-15<br>d-16 | | —O—<br>—NH— | 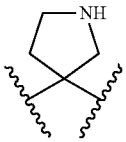 |
| d-17<br>d-18 | | —O—<br>—NH— | 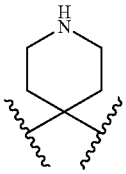 |
| d-19<br>d-20 | | —O—<br>—NH— | 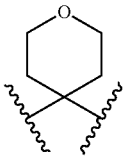 |

In yet another embodiment, there is provided a compound of Formula III:

Formula III

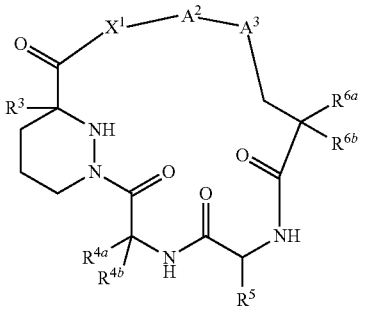

or a pharmaceutically acceptable salt, isotope, stereoisomer, mixture of stereoisomers, tautomer, ester or prodrug thereof, wherein $A^2$ is —CH($R^8$)-arylene, —CH($R^8$)-heteroarylene, —CH($R^8$)-heterocycloalkylene, —CH($R^8$)-cycloalkylene or cycloalkylene;

$A^3$ is —$CH_2$— or —O—;

$X^1$ is —O—, —N($CH_3$)— or —NH—;

$R^3$ is H or ($C_1$-$C_4$)alkyl;

$R^{4a}$ is H;

$R^{4b}$ is H, ($C_1$-$C_4$)alkoxy, halo($C_1$-$C_4$)alkoxy or ($C_1$-$C_8$)alkyl;

$R^5$ is H, ($C_1$-$C_8$)alkyl, hydroxy($C_1$-$C_8$)alkyl, ($C_2$-$C_8$)alkenyl, ($C_2$-$C_8$)alkynyl, azido($C_1$-$C_8$)alkyl, cycloalkyl, aryl($C_1$-$C_4$)alkyl, cycloalkyl($C_1$-$C_4$)alkyl, heterocycloalkyl($C_1$-$C_4$)alkyl or heteroarylheteroaryl($C_1$-$C_4$)alkyl;

$R^{6a}$ and $R^{6b}$ are independently H, —OH, ($C_1$-$C_4$)alkoxy, halo($C_1$-$C_4$)alkoxy or ($C_1$-$C_8$)alkyl, wherein each of $R^{6a}$ and $R^{6b}$ is optionally substituted with one or more substituent selected from halo, ($C_1$-$C_4$)alkyl, aryl, cycloalkyl, heterocycloalkyl, di($C_1$-$C_8$)alkylamino and ($C_1$-$C_8$)alkanoyl; or $R^{6a}$ and $R^{6b}$ together form

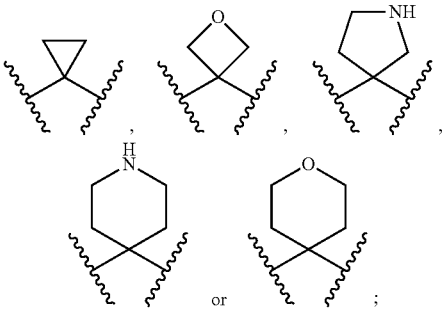

and $R^8$ is H or ($C_1$-$C_4$)alkyl.

In one aspect of the embodiment, $A^2$ is

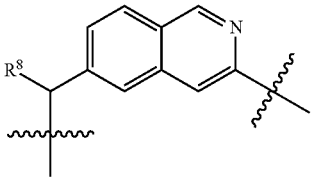

-continued

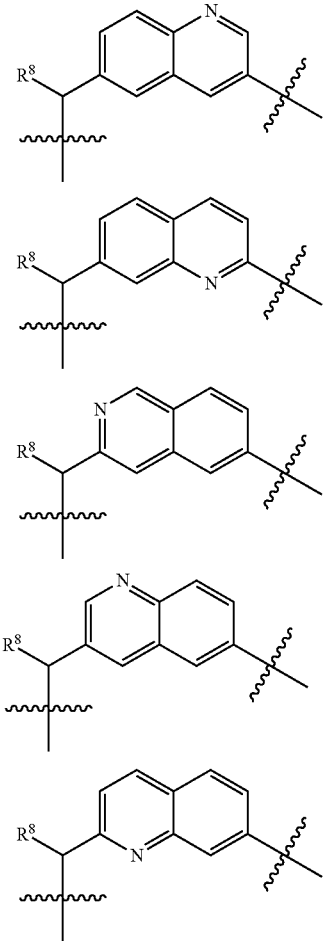

In one aspect of the embodiment, $R^3$ is H; and $A^3$ is —$CH_2$—. Non-limiting examples of such compounds include the following compounds and pharmaceutically acceptable salts thereof:

Formula (III-e)

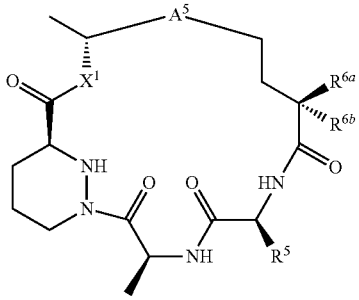

| Compound No. | $A^5$ | $X^1$ | $R^5$ | $R^{6a}$ | $R^{6b}$ |
|---|---|---|---|---|---|
| e-1 | 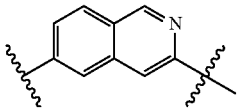 | —O— | Isopropyl | H | H |
| e-2 | | —O— | | | |
| e-3 | | —O— | Isopropyl | Methyl | H |
| | | | Isopropyl | Methyl | Methyl |

-continued

Formula (III-e)

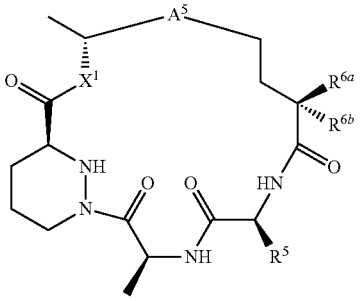

| Compound No. | $A^5$ | $X^1$ | $R^5$ | $R^{6a}$ | $R^{6b}$ |
|---|---|---|---|---|---|
| e-4 | | —O— | Iso-propyl | 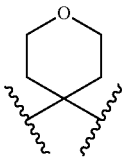 | |
| e-5 | | —NH— | Iso-propyl | H | H |
| e-6 | | —NH— | Iso-propyl | Methyl | H |
| e-7 | | —NH— | Iso-propyl | Methyl | Methyl |
| e-8 | | —NH— | Iso-propyl | 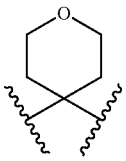 | |
| e-9 | 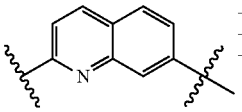 | —O— | Iso-propyl | H | H |
| e-10 | | —O— | | | |
| e-11 | | —O— | Iso-propyl | Methyl | H |
| | | | Iso-propyl | Methyl | Methyl |
| e-12 | | —O— | Iso-propyl | 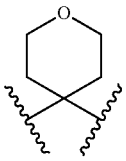 | |
| e-13 | | —NH— | Iso-propyl | H | H |
| e-14 | | —NH— | Iso-propyl | Methyl | H |
| e-15 | | —NH— | Iso-propyl | Methyl | Methyl |
| e-16 | | —NH— | Iso-propyl | 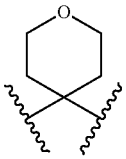 | |

Also included are compounds having the following formulae:

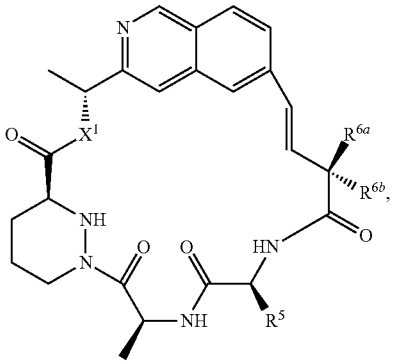

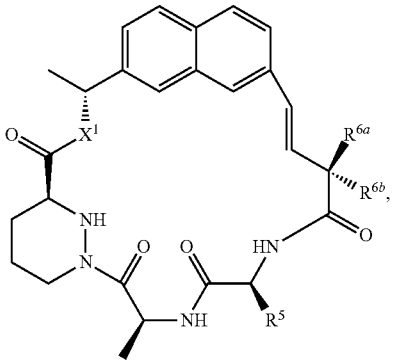

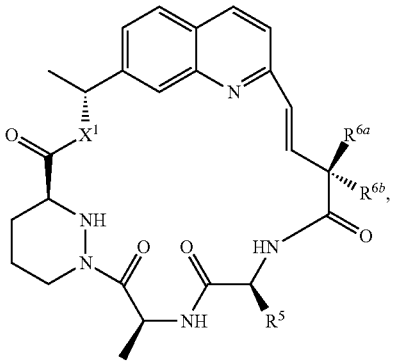

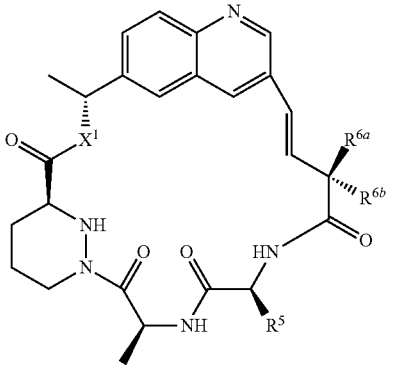

and

-continued
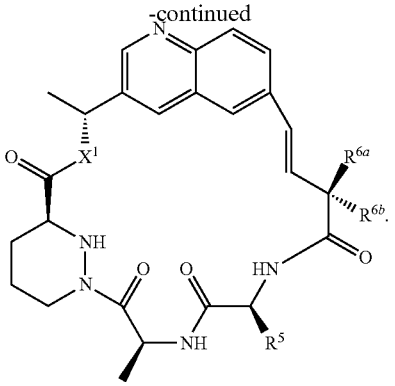
wherein the compounds of the formulae above have the same combination or pattern of substituents given in the table for Compounds e-1 to e-8.
In another aspect of the embodiment, $R^3$ is H; and $A^3$ is —O—. Non-limiting examples of such compounds include the following compounds and pharmaceutically acceptable salts thereof:
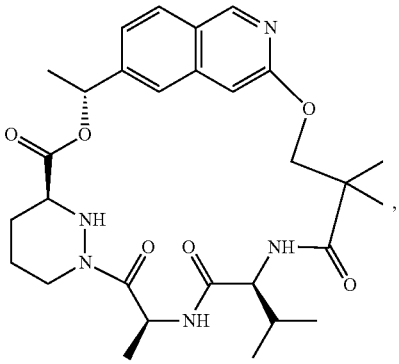
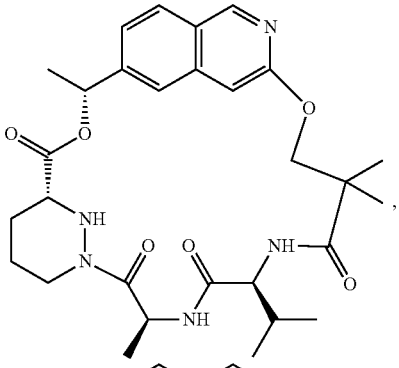
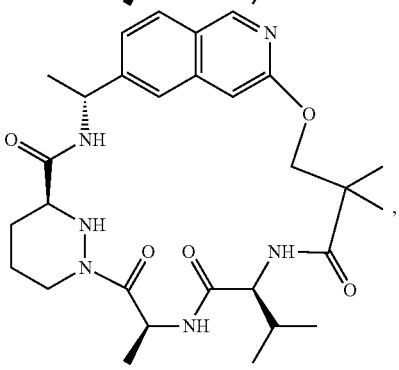
-continued
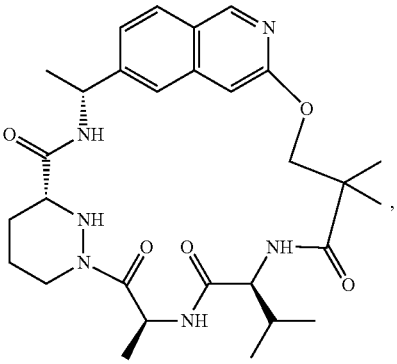
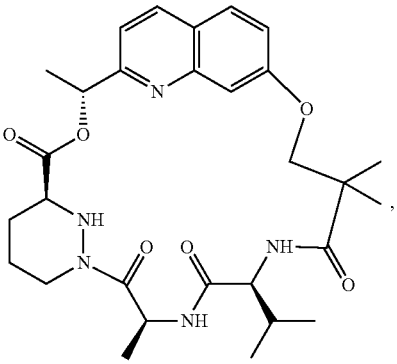
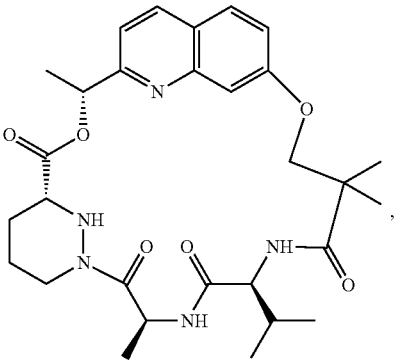
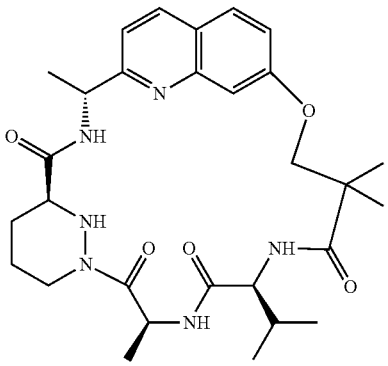
and -continued

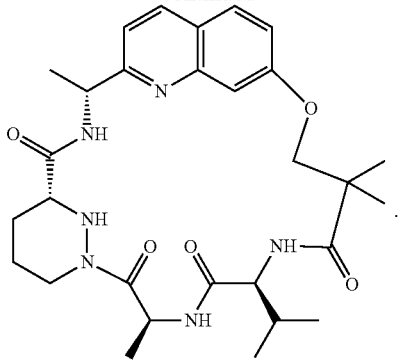

In yet another embodiment, there is provided a compound of Formula IV:

Formula IV

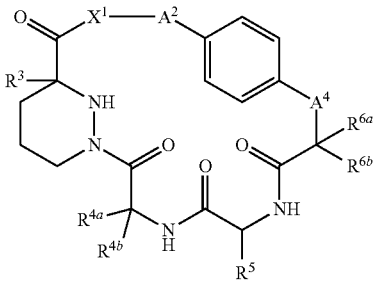

or a pharmaceutically acceptable salt, isotope, stereoisomer, mixture of stereoisomers, tautomer, ester or prodrug thereof, wherein $A^2$ is —CH($R^8$)-arylene, —CH($R^8$)-heteroarylene, —CH($R^8$)-heterocycloalkylene, —CH($R^8$)-cycloalkylene or cycloalkylene;

$A^4$ is bond or —O—.

$X^1$ is —O—, —N($CH_3$)— or —NH—;

$R^3$ is H or ($C_1$-$C_4$)alkyl;

$R^{4a}$ is H;

$R^{4b}$ is H, ($C_1$-$C_4$)alkoxy, halo($C_1$-$C_4$)alkoxy or ($C_1$-$C_8$)alkyl;

$R^5$ is H, ($C_1$-$C_8$)alkyl, hydroxy($C_1$-$C_8$)alkyl, ($C_2$-$C_8$)alkenyl, ($C_2$-$C_8$)alkynyl, azido($C_1$-$C_8$)alkyl, cycloalkyl, aryl($C_1$-$C_4$)alkyl, cycloalkyl($C_1$-$C_4$)alkyl, heterocycloalkyl($C_1$-$C_4$)alkyl or heteroarylheteroaryl($C_1$-$C_4$)alkyl;

$R^{6a}$ and $R^{6b}$ are independently H, —OH, ($C_1$-$C_4$)alkoxy, halo($C_1$-$C_4$)alkoxy or ($C_1$-$C_8$)alkyl, wherein each of $R^{6a}$ and $R^{6b}$ is optionally substituted with one or more substituent selected from halo, ($C_1$-$C_4$)alkyl, aryl, cycloalkyl, heterocycloalkyl, di($C_1$-$C_8$)alkylamino and ($C_1$-$C_8$)alkanoyl; and $R^8$ is H or ($C_1$-$C_4$)alkyl.

In one aspect of the embodiment, $A^2$ is —CH($R^8$)-arylene or —CH($R^8$)-heteroarylene; $R^3$ is H; and $A^4$ is —O—. Non-limiting examples of such compounds include the following compounds and pharmaceutically acceptable salts thereof:

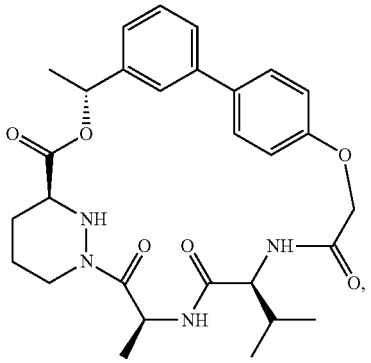

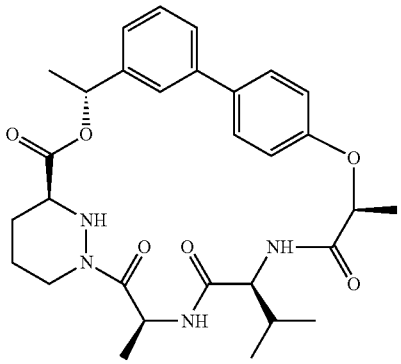

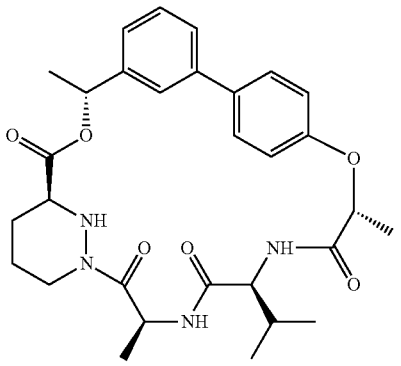

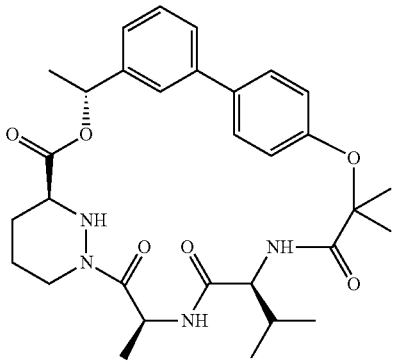

-continued

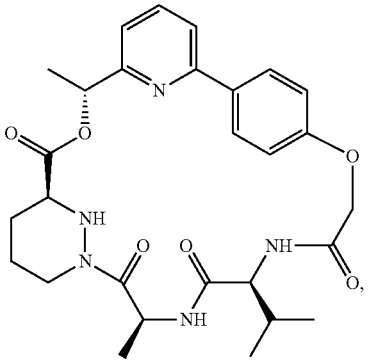

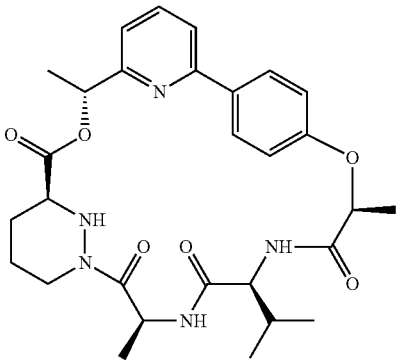

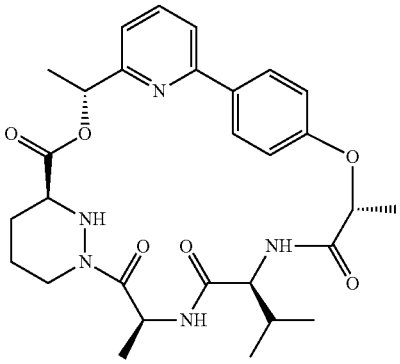

and

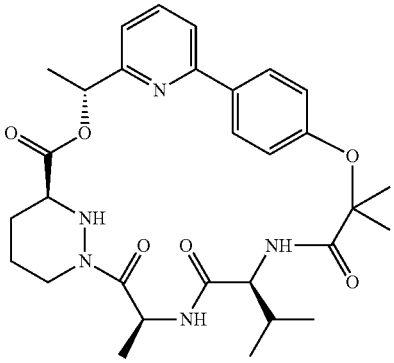

In another aspect of the embodiment, $A^2$ is —CH($R^8$)-arylene or —CH($R^8$)-heteroarylene; $R^3$ is H; and $A^4$ is bond. Non-limiting examples of such compounds include the following compounds and pharmaceutically acceptable salts thereof:

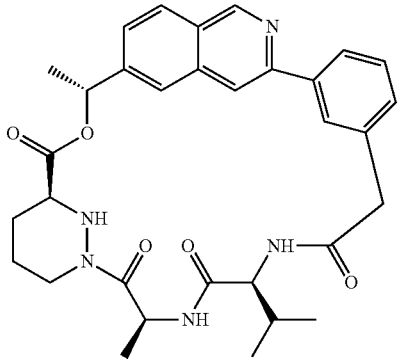

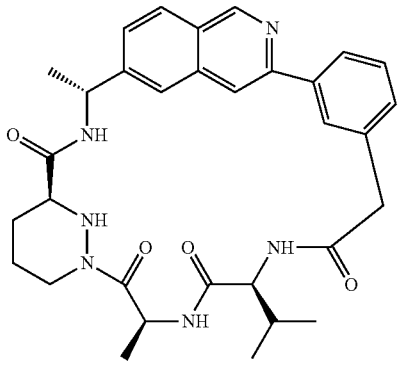

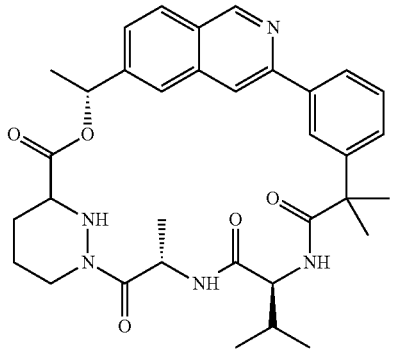

and

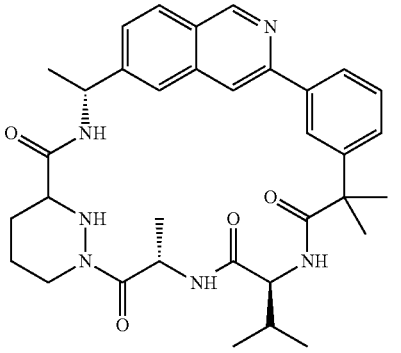

In yet another aspect of the embodiment, $A^1$ is ethenylene; $A^2$ is —CH($R^8$)-arylene, arylene, —CH($R^8$)-heteroarylene, —CH($R^8$)-heterocycloalkylene, —CH($R^8$)-cycloalkylene or cycloalkylene; $X^1$ is —O—, —NH— or —N(($C_1$-$C_4$)

alkyl)-. Non-limiting examples of such compounds include the following compounds and pharmaceutically acceptable salts thereof:

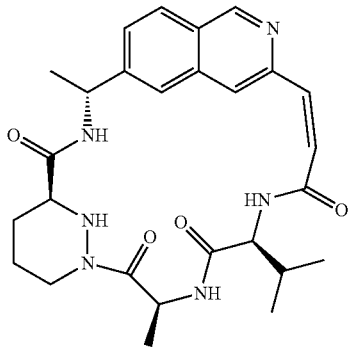

and

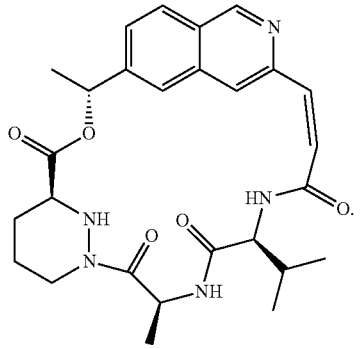

One skilled in the art will recognize that substituents and other moieties of the compounds of the generic formulae herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

Preparation of Macrocyclic Compounds

A compound of the present invention such as those of Formulae (I) and (II) can be prepared according to the schemes described below, but it shall be appreciated that modifications of the illustrated process or other process can also be used. As illustrated in Scheme 1, the macrocyclic compounds M (Q is NH) are synthesized from the five key components A-E by combining them together in sequence with the appropriate use of protecting groups ($PG_1$-$PG_8$) by one skilled in the art. The hashed lines numbered 1-5, hereby referred to as Connection 1, Connection 2, etc., respectively, are the 5 connections for combining Components A-E. The order in which the specific connections occur, can vary, and are dependent on the choice of protecting groups and chemistry required. Typically Connections 3, 4 or 5 are used as the final macrocyclization step.

Scheme 1

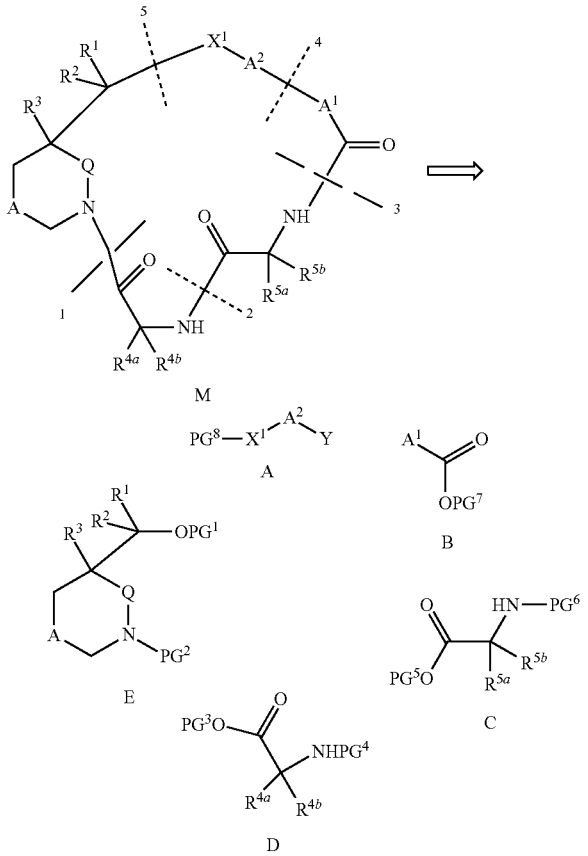

$PG^x$ = protecting group as needed

Illustratively, Connections 1 through 5 can be performed as described below:

Connections 1, 2 and 3 are amide bonds. The connections are made between the respective acid and amine using standard peptide coupling agents (EDC/HOBT, DCC, PyBOP, PyBROP, HATU, HBTU, COMU, etc) known to one skilled in the art. The acid and amine coupling partners are combined with the coupling agent in an organic solvent, e.g., DMF, dichloromethane, acetonitrile, etc., in the presence of a base, e.g., DIPEA, triethylamine, etc., at room temperature or slightly elevated temperature. When any of these three steps are chosen as the final macrocyclization step, most typically Connection 3, then macrolactamization conditions are preferred. Suitable macrolactamization procedures include, but are not limited to, those found in Davies, J. S. J. Peptide Sci. 2003, 9, 471-501.

Connection 4 is typically a carbon-carbon bond or a heteroatom-carbon bond where the heteroatom is O, S or N. When Connection 4 is a carbon-carbon bond, then standard carbon-carbon bond forming procedures, typically involving metal mediated cross coupling reactions, are preferred. Preferably, the carbon-carbon bond is formed using a Heck-type coupling reaction between a sp2 halide group and a terminal alkene, a Suzuki coupling between a sp2 halide group and a vinyl or aryl boronate, or ring closing metathesis (RCM) between two alkenes. Stille reactions can also be performed between a vinyl stannane and an aryl or vinyl halide as described in Nicolaou et al. Journal of American Chemical Society 2000, 122, 3830. In each of the examples above, the aryl or vinyl halide group can also be an aryl or vinyl triflate.

For example, when Y in A is an alkene, preferably —CH=$CH_2$, and $A^1$ in B contains a terminal alkene or Me-CH=CH—, then a cross metathesis reaction is performed. The two components are mixed in solvent, e.g., acetonitrile or toluene, and a metathesis catalyst, e.g., Grubbs I, Grubbs II, Hoyveda-Grubbs I, Hoyveda-Grubbs II, etc., is added followed by heating. If this connection is used to close the macrocyclic ring, RCM conditions are preferred (e.g., more dilute conditions to avoid dimerization). For relevant RCM conditions and examples see Sedrani et al. Journal of American Chemical Society 2003, 125, 3849 and Nicolaou et al. Journal of American Chemical Society 2000, 122, 3830. A typical RCM procedure includes heating (either conventionally or by microwave) of the acyclic precursor in a solvent such as toluene, or 1,2-dichloroethane, in the presence of a RCM catalyst, e.g., Grubbs I, Grubbs II, Hoyveda-Grubbs I, or Hoyveda-Grubbs II.

Alternatively, when Connection 4 is made via a Heck coupling reaction, the vinyl or aryl halide, or the triflate A and the alkene component B are mixed in a polar solvent, e.g., acetonitrile or toluene, in the presence of a Palladium (II) catalyst, e.g., Palladium$(OAc)_2$, a phosphine ligand, e.g., P(o-toluene)$_3$ or P(t-butyl)$_3$, etc., and a base, e.g., triethylamine. The reaction mixture is heated either conventionally or in a microwave reactor.

Alternatively, when Connection 4 is made via a Suzuki coupling reaction, the vinyl or aryl halide or the triflate A and the vinyl or aryl boronate B are mixed in a suitable solvent, e.g., cyclopentyl methyl ether, toluene, DMF, DME, etc., in the presence of a Palladium catalyst (e.g., Palladium(II)$Cl_2$ (p-$NMe_2Ph)_2$ and $K_3PO_4$ or tetrakis(triphenylphosphine) palladium(0), and a base, such as potassium carbonate. The reaction mixture is heated either conventionally or in a microwave reactor. It is also possible in such a coupling reaction to reverse the reactive functionalities on the two starting materials, such that A is an aryl or vinyl boronate and B contains a vinyl or aryl halide or triflate.

Alternatively, Connection 4 can be a carbon-oxygen bond, and in this case typical alkylation or nucleophilic aromatic substitution conditions can be used between a hydroxyl group and an alkyl halide, or aryl (or heteroaryl) halide. The hydroxyl reagent is mixed with the alkyl or heteroaryl halide (preferably an iodide or bromide), in an inert solvent, e.g., CPME, DMF, THF, etc., in the presence of a base, e.g., cesium carbonate, cesium hydroxide, sodium hydride, NaHMDS, etc., and the reaction is heated.

Alternatively, Connection 4 can be a carbon-nitrogen bond, and in this case typical alkylation, nucleophilic aromatic substitution or Buchwald conditions can be used between an amine group and an alkyl halide or heteroaryl halide. For example, the amine and the alkyl or heteroaryl halide are mixed and heated in an inert solvent, e.g., CPME, in the presence of a base, e.g., cesium carbonate, sodium hydride, etc. An alternative procedure for the carbon-nitrogen connection is to perform a reductive amination between an amine and a carbonyl compound. Typically the amine and aldehyde or ketone are mixed in an inert solvent, e.g., dioxane and treated after a period of time with sodium acetoxy borohydride or alternative reducing agent.

Connection 5 is typically an amide ($X^1$=—NH or substituted N), or ester ($X^1$=O) bond. When forming the amide bond, standard coupling procedures described for Connections 1-3 can be used. Often, this is the final step in closing the macrocycle. As such macrolactamization coupling procedures are more effective. Suitable macrolactamization procedures include, but are not limited to, those found in the following reference: Davies, J. S. J. Peptide Sci. 2003, 9, 471-501.

When forming the ester bond coupling reagents (e.g., EDC, DCC, PyBOP, HATU, COMU) can be used, or when this is the final step in formation of the macrocycle, macrolactonization procedures are preferred (e.g., Shiina, Yamaguchi). An example method for the macrolactonization step can be found in Journal of American Chemical Society 2002, 124, 4257 Paquette et al. or Chemical Reviews 2006, 106(3), 911-939. Typically, the acid and alcohol are mixed in a polar solvent, e.g., DMF, acetonitrile, etc., in the presence of the coupling agent and a base, e.g., DIPEA, DMAP.

Connection 5 can also be an ether bond where $R^1$ and $R^2$ are both hydrogen or alkyl groups. In this example the carbon-oxygen bond forming procedures described above for Connection 4 are used to connect the 2 components. Connection 5 can also be an amine bond where $R^1$ and $R^2$ are both hydrogen or alkyl groups and the procedures for connecting the amine and carbonyl components are also described above with respect to Connection 4.

The following general schemes provide general examples and sequences for constructing the macrocyclic compound M from the common precursors A-E.

Scheme 2: Use of RCM method for Connection 4

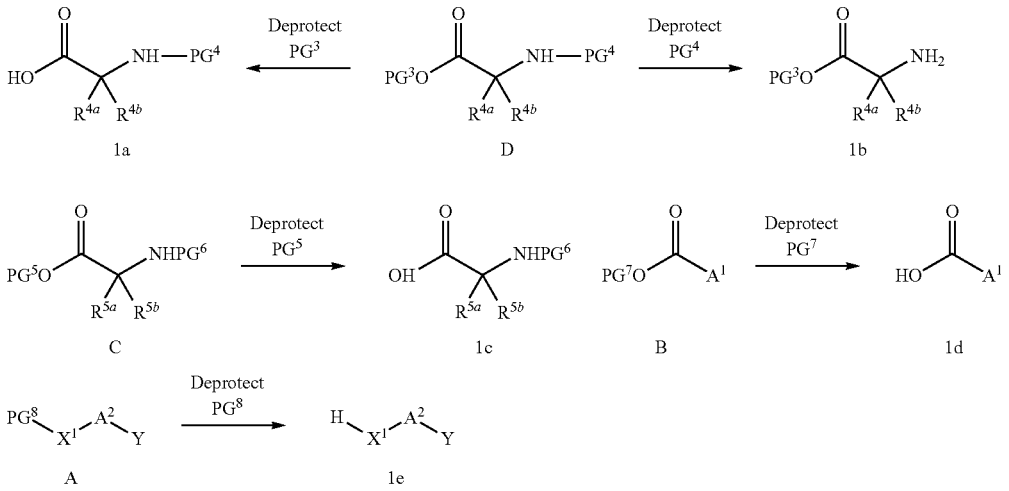

-continued

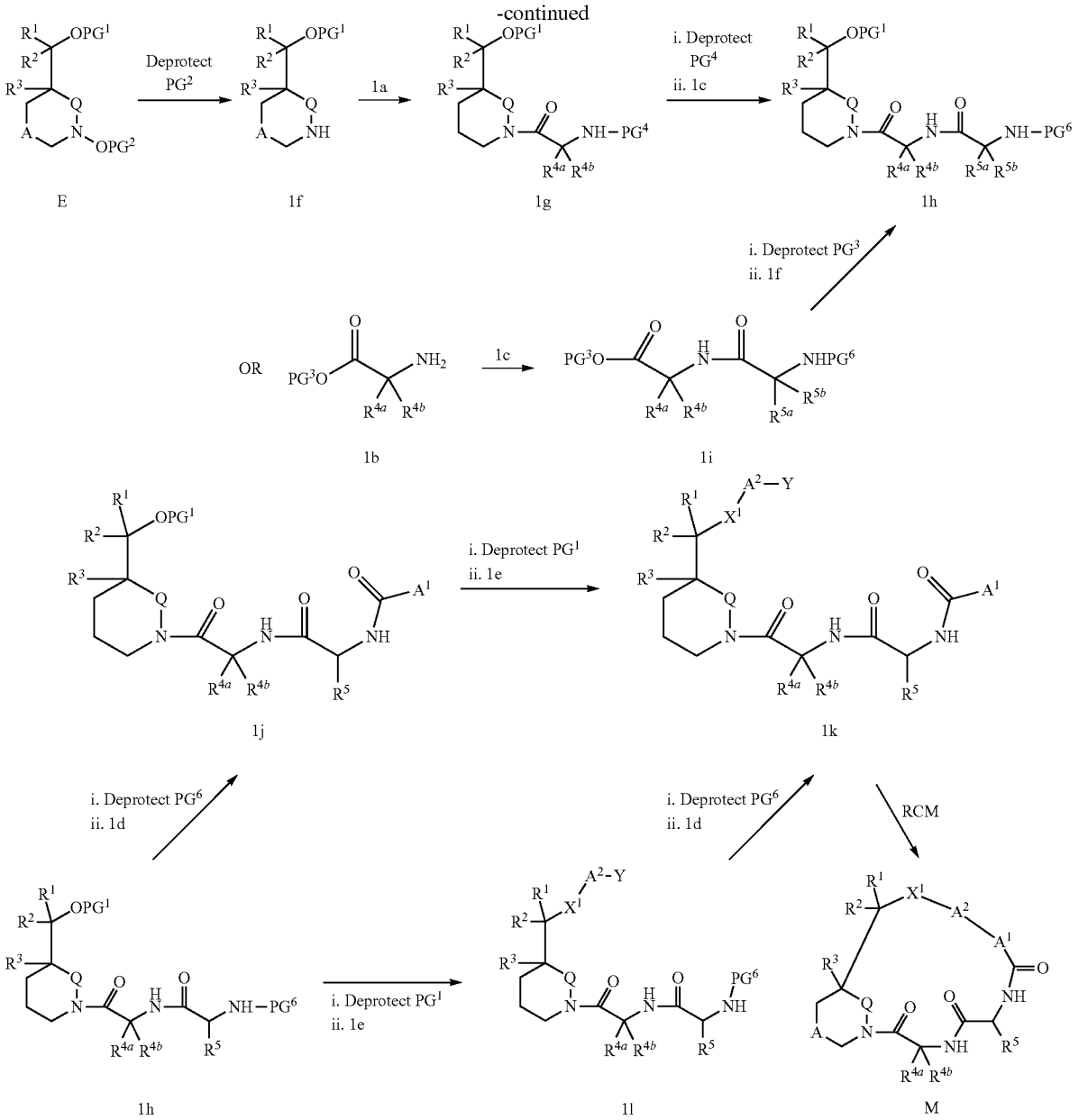

Compounds A-E are first deprotected ($PG^2$-$PG^8$) using conditions described in Greene and Wuts, Protective Groups in Organic Synthesis, John Wiley and Sons, Inc. (herein "Greene and Wuts") to provide Compounds 1a-1f.

In many cases, the optimal protecting groups and their deprotection methods are as follows. For Compound E the typical protecting group $PG^1$ for the acid (when $R^1$ and $R^2$ are C═O) is a methyl or trichloroethyl ester. The methyl and trichloroethyl esters can be removed by base, e.g., LiOH in a polar solvent, aqueous THF, etc. The trichloroethyl ester can also be removed by treatment with zinc and ammonium acetate in a polar solvent, e.g., THF. Typically, $PG^2$ and $PG^4$ are acid labile groups, e.g., BOC and are deprotected using HCl in dioxane, or TMSOTf in dioxane, dichloromethane. Typically, $PG^3$ and $PG^5$ are ester groups, removed by treatment with alkali metal hydroxide in aqueous THF or dioxane. Typically $PG^6$ is an acid labile group, e.g., BOC for amine and removed as described for $PG^2$; or silyl ether for a hydroxyl group and removed by treatment with HF•pyridine or TBAF in an organic solvent, e.g., dichloromethane. Typically $PG^8$ is an amine protecting group, e.g., BOC and removed as described for $PG^2$ or a silyl ether of a hydroxyl group removed as described for $PG^6$, or an acetate protecting group removed by treatment with alkali metal hydroxide in aqueous THF or dioxane.

Compound 1f is then coupled to acid 1a using the conditions described above for Connection 1 to produce compound 1 g. Compound 1 g is then deprotected using conditions described in Greene and Wuts and coupled to 1c to provide 1 h using the conditions described above for Connection 2. An alternative sequence for generating 1 h is first coupling amine 1b to acid 1c using conditions as described for Connection 2 above, to form 1i; deprotection of the protecting group $PG^3$ in 1i using conditions described in Greene and Wuts, and finally coupling with amine 1f using conditions described for Connection 1 above forms 1h.

Compound 1 h is deprotected at $PG^6$ using conditions described in Greene and Wuts and is then coupled to 1d using the conditions described above for Connection 3 to form 1j. Protecting group $PG^1$ in Compound 1j is then removed using conditions described in Greene and Wuts, and the acid is then coupled to 1e using conditions described for Connection 5 to form the acyclic intermediate 1k. An alternative sequence to 1k is first, deprotection of $PG^1$ and then coupling to 1e as described for Connection 5; and then deprotection of $PG^6$ as described in Greene and Wuts, followed by coupling to 1d using the conditions described for Connection 3 to form 1k. Acyclic intermediate 1k is then subjected to the RCM as described above for Connection 4 to form the macrocycle M.

Scheme 3: Macrolactamization/Macrolactonization Connection 5

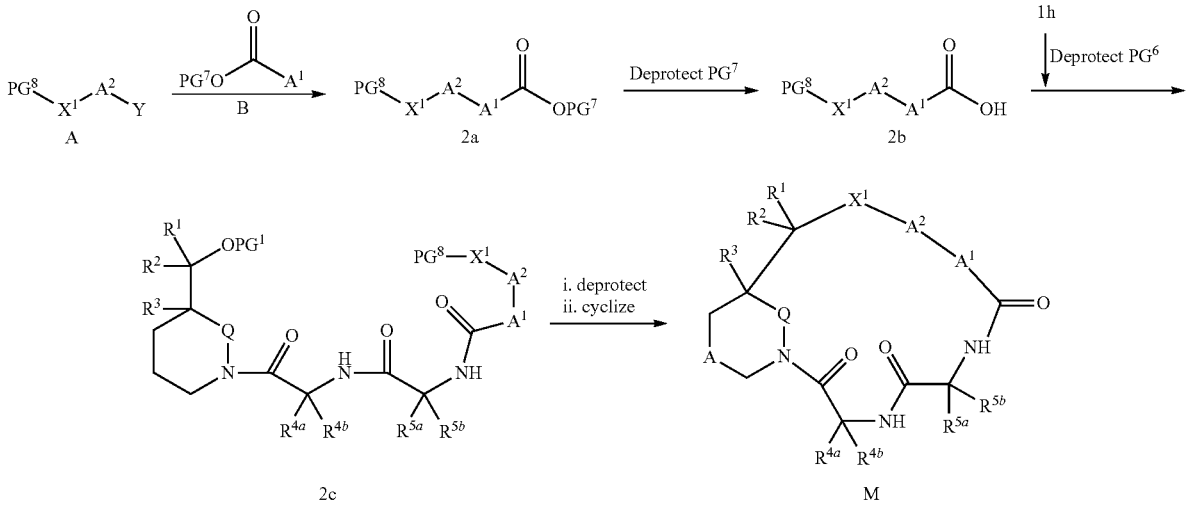

Compound A is coupled to Compound B using the conditions described above for Connection 4 to generate 2a. Compound 2a is then deprotected at $PG^7$ as described in Greene and Wuts to generate acid 2b. Acid 2b is then coupled to the deprotected product of 1 h (prepared from 1 h by deprotection of $PG^6$ described in Greene and Wuts) to generate the precursor 2c. Deprotection of 2c is carried out using conditions described in Greene and Wuts, and then the product is cyclized using the conditions described above for macrolactamization or macrolactonization in Connection 5, to provide Compound M.

Scheme 4: Macrolactamization/Macrolactonization Connection 5

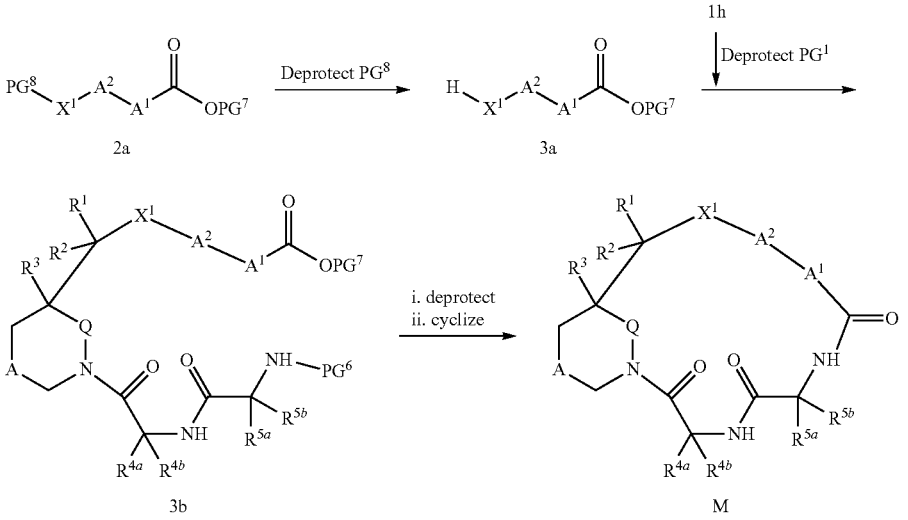

Compound 2a is deprotected at $PG^8$ as described in Greene and Wuts and above in Connection 5 to generate 3a which is then coupled, using conditions described above for Connection 5, to the deprotected product of 1 h (prepared from 1 h by deprotection of $PG^1$ described in Greene and Wuts) to generate the precursor 3b. Deprotection of 3b is carried out using conditions described in Greene and Wuts, and then cyclized using the conditions described above for macrolactamization or macrolactonization in Connection 3, to provide Compound M.

Scheme 5: Further transformation of macrocyclic compounds M to M1-M5

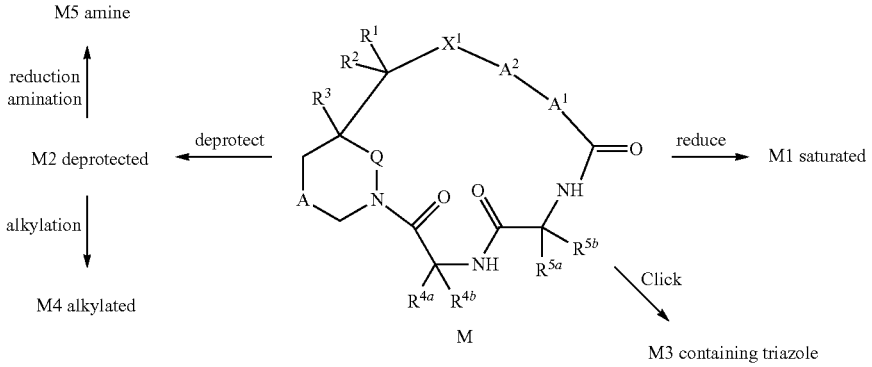

The final macrocycle M from the schemes above often contains protecting groups on side-chains that require further removal to generate the final compound M. For example, when M contains a C═C as a result of RCM, Compound M is mixed in a solvent such as ethanol, methanol, etc., in the presence of palladium on carbon catalyst under an atmosphere of hydrogen gas to provide reduced Compound M1. Protecting groups on the $R^{4a}$, $R^{4b}$, $R^{5a}$, $R^{5b}$, $A^1$, $A^2$ and/or $X^1$ are removed using conditions described in Greene and Wuts to generate Compound M2. Click chemistry can be used to provide triazole M3. Such a transformation is performed by treating the alkyne or azide in M, in solvent (e.g., DMF) with an alkyne or azide as appropriate in the presence of CuI to form M3.

Deprotected compound M2 can be further transformed to additional macrocycle M, for example, treatment of M2 containing a hydroxyl group with an alkyl halide in the presence of base, e.g., cesium carbonate, in solvent, e.g., DMF, acetonitrile, etc., forms alkylated product M4. M2 containing a ketone group is treated in solvent (e.g., DMF, methanol, etc) with an amine followed by the addition of sodium acetoxyborohydride to form amine product M5.

Scheme 6: Preparation of acids or esters B

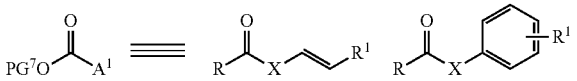

B

R = $OPG^7$ or OH
X = varied
$R^1$ = H or methyl, $B(pinn)_2$

R = $OPG^7$ or OH
X = varied
$R^1$ = halide, (pinn)

Many B components containing an acid or ester with a terminal alkene or Me-CH═C— or vinyl/aryl boronate groups are commercially available or described in the literature and these can be used in the above schemes directly. In addition, the following schemes below are examples of methods that can be used to generate additional B components.

Scheme 7: Preparation of acids or esters B

1

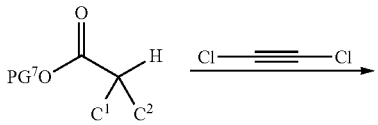

$C^1$ and $C^2$ = alkyl, or cycloalkyl, etc.
$PG^7$ = typically, t-butyl, methyl, or ethyl

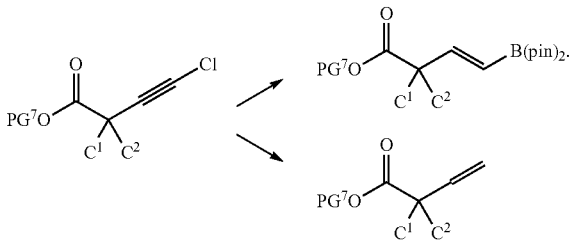

2

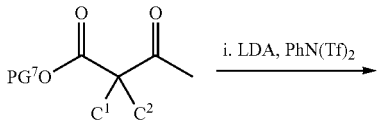

$C^1$ and $C^2$ = alkyl, or cycloalkyl, etc.
$PG^7$ = typically, t-butyl, methyl, or ethyl -continued

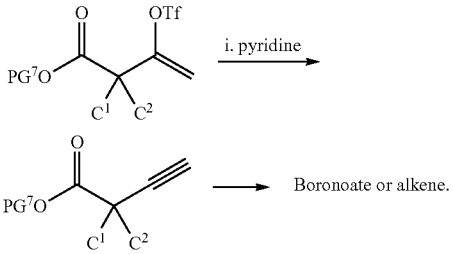

3

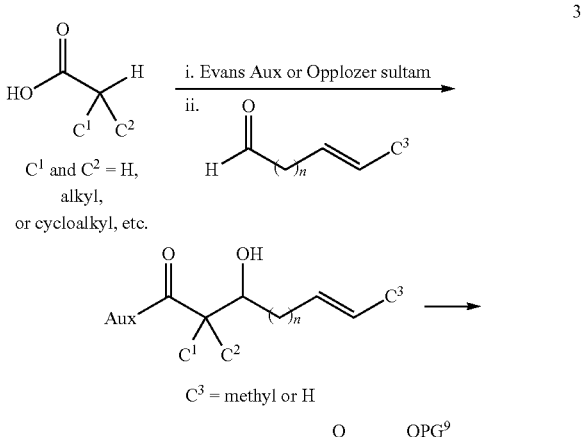

4

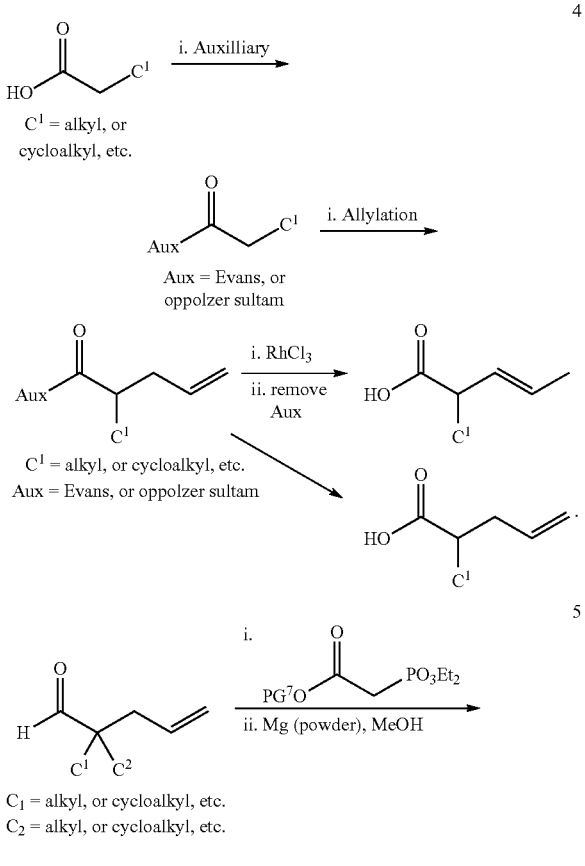

-continued

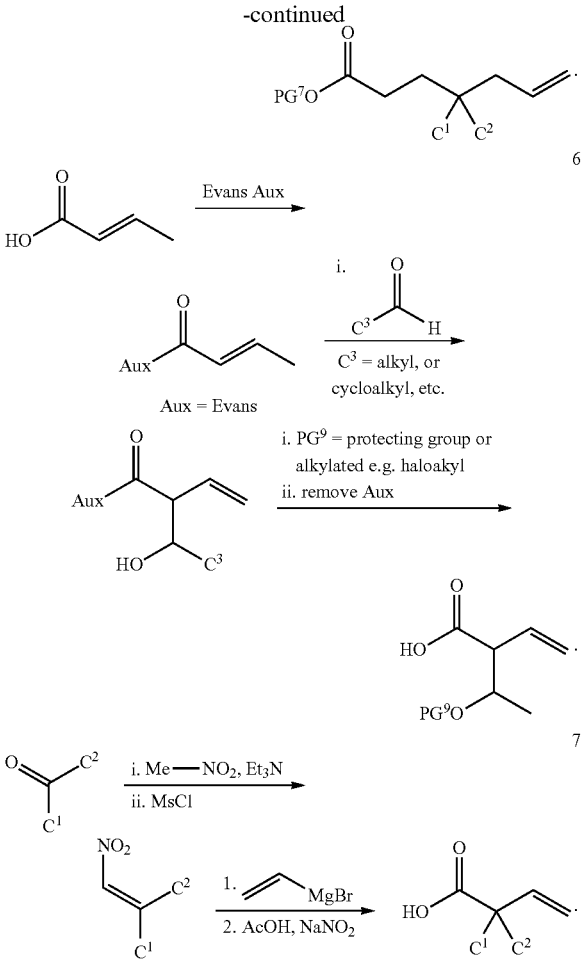

6

7

In Scheme 7, part 1, a protected acid is treated with a strong deprotonating base, e.g., LDA in an inert solvent, e.g., THF at −78° C. and HMPA. A pre-cooled solution of dichloroacetylene (prepared by treatment of trichloroethene with potassium hydride and MeOH (catalytic) in THF) is then added to generate the chloro acetylene product. This product is then reduced, for example, by treatment with Cu in acetic acid and THF to generate the alkyne which is then further reduced to the alkene, for example, by treatment of an alcoholic solution of the alkyne with a poisoned palladium reducing agent (e.g., Lindlar) in the presence of hydrogen gas. Alternatively the alkyne is treated with $Cp_2ZrHCl$ in dichloromethane in the presence of pinnacolborane to form the vinyl boronate.

In Scheme 7, part 2, a beta-keto ester with alpha substitution is converted to the vinyl triflate, for example by treating a THF solution of the beta-keto ester with a base, e.g., LDA in THF at −78° C., followed by addition of $PhN(Tf)_2$. The triflate product is then treated with pyridine at elevated temperature to form the alkyne. The alkyne is then treated as described above in Example 1 to generate the alkene or vinyl boronate products.

In Scheme 7, part 3, a chiral aldol reaction is used. An acyl group is first attached to a chiral auxiliary, e.g., Evans, Oppolzer sultam (see JACS 1990, 112, p 2767) using standard amide bond formation conditions described for Connection 1-3. The Oppolzer auxiliary product is treated with the aldehyde of choice, TBDMSOTf and base, e.g., triethylamine in anhydrous solvent, e.g., dichloromethane.

The Evans auxiliary is treated with base, e.g., LDA, KHMDS, DIPEA in organic solvent, e.g., THF at −78° C. and the aldehyde of choice in the presence of a Lewis acid, e.g., $TiCl_4$, $SnCl_4$, $BF_3OEt_2$. Protection of the resulting alcohol from the aldol reaction is performed as described in Greene and Wuts, or alternatively alkylation with an alkyl halide or Meerwein's reagent, i.e., treatment with trimethyloxonium tetrafluoroborate in an inert solvent, e.g., dichloromethane is performed. The auxiliary is then removed using standard alkali metal hydroxide removal conditions, e.g., LiOH in THF, or LiOH and hydrogen peroxide in THF to provide the free acid product.

In Scheme 7, part 4, an Evans auxiliary is allylated with an allyl halide as described in Synlett 2002, 12, 2039-2040. The product is then isomerized by treatment with $RhCl_3$ in ethanol and then the auxiliary removed by base and peroxide, e.g., LiOH and $H_2O_2$ in THF/Water. Alternatively the auxiliary is directly removed by LiOH and $H_2O_2$ in THF/Water to provide the terminal alkene.

In Scheme 7, part 5, a Horner Wadsworth Emmons reaction is used on an aldehyde (containing a terminal alkene) to generate the alpha-beta unsaturated ester which is then selectively reduced to the ester. For example the phosphonate is treated with base, e.g., sodium hydride in THF at low temperature, followed by addition of the aldehyde and warming to generate the unsaturated ester. The product is reduced by treatment with magnesium powder in methanol.

In Scheme 7, part 6, an alpha-beta unsaturated acid or is converted to the unsaturated Evans auxiliary (see Organic Letters 2007, 9, p 1635) and is treated with an aldehyde to generate the corresponding alkene product. The hydroxyl group is then protected using methods described in Greene and Wuts and then the auxiliary is removed by treatment with base and peroxide, e.g., LiOH and $H_2O_2$ in THF/Water. The hydroxyl can also be alkylated as described above for the aldol in Scheme 7, part 3.

In Scheme 7, part 7, a ketone is transformed via the nitro olefin as described in Angew. Chem. Int. Ed. 2006, 45 (46), 7736. The nitro olefin ihylsilyl chloride. The nitro alkyl product after addition of the vinyl group is then converted to the acid by treating with sodium nitrite and acetic acid in an inert polar solvent, e.g., DMSO.

Several types of A (or A1 as shown) are available commercially or described in the literature where $X^1$═O or NH and Y is a halide or alkene. The schemes below describe additional general methods for generating A1.

Scheme 8: Preparation of A

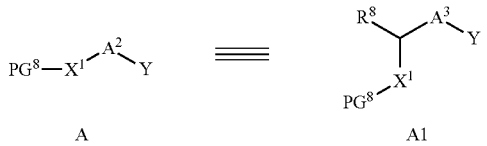

A — A1

$X^1$ = O, NH, N(alkyl), or substituted N, etc.
Y = halogen, alkene, or O-alkylene $A^3$ = aryl, heteroayl, or biaryl, etc.
$X^1$ = O, NH, or NR
Y = halogen, alkene, or O-alkylene
$R^8$ = H, lower alkyl, or haloalkyl

1

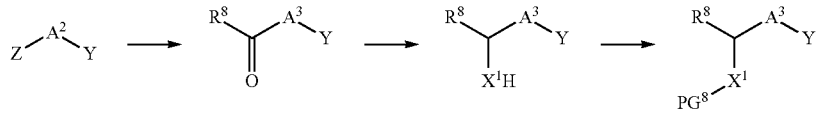

6a — 6b — 6c — A1

6c: $X^1$ = O
A1: $X^1$ = O $A^2$ = aryl, biaryl, heteroayl, or alkene
Z = acid, aldehyde, halogen, or OH
Y = I, Br, or Cl

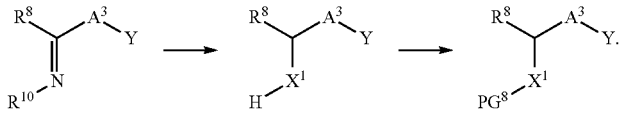

6d — 6e — A1

6e: $X^1$ = NH
A1: $X^1$ = NH

When Y = Halogen in A1

2

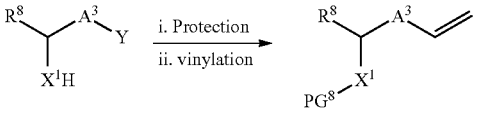

6c or 6e
Y = Halogen

A1

-continued

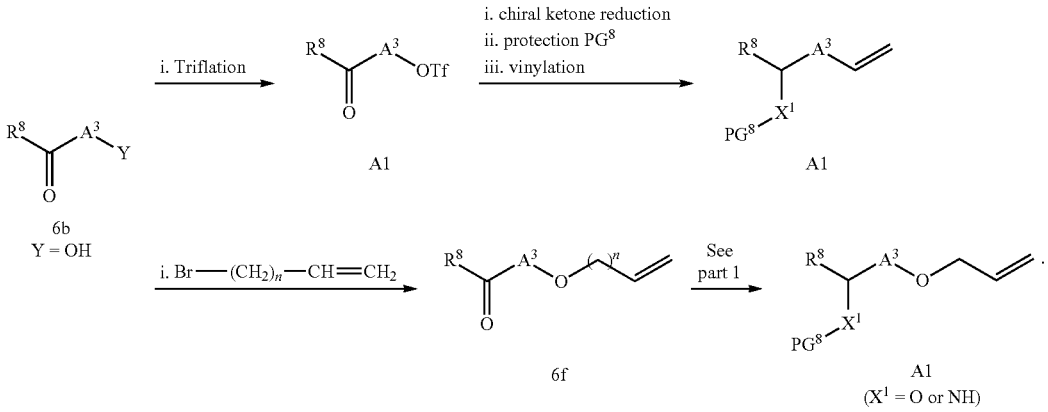

When Y = alkene in A1

In Scheme 8, part 1 (Y is a halogen in A1); the starting Compound 6a is typically a commercially available aromatic compound, that contains halogen Y and a group Z that can be transformed to the ketone 6b. Typical Z groups are halide, acid, aldehyde.

For example, when Z is an acid, 6a is treated with a coupling agent, e.g., HATU, EDC in the presence of a base, e.g., DIPEA and the Weinreb amine (Me-NH-OMe) to form the Weinreb amide. The amide is then treated with a nucleophile, e.g., TMS-$CF_3$ to form the $CF_3$ substituted ketone 6b or with a Grignard agent, e.g., MeMgBr in a solvent, e.g., THF at −78° C. to form the methyl ketone 6b.

When Z is a halogen, then the initial conversion, if required, to a more reactive halogen is performed by treatment with NaI and acetyl chloride in an inert solvent, e.g., acetonitrile. The halogen is then transformed to the ketone by a Stille reaction with an ethoxyvinyl stannane. The halide is treated in an inert solvent, e.g., toluene, with the stannane and a palladium (II) catalyst, e.g., $PdCl_2(PPh_3)_2$, followed by treatment of the product with 2M HCl to afford ketone 6b. In some cases the formation of an alkyl lithium reagent from the halide group can be performed by using nBuLi at −78° C. in THF and adding N-methoxy-N-methyl amide to afford the ketone 6b (e.g., N-methoxy-N-methylacetamide affords the $R^8$ is methyl in ketone 6b). A final method to generate the ketone 6b is through a vinyl group. 6a is treated with a vinyltrifluoroborate in the presence of a palladium catalyst, e.g., $PdCl_2$(dppf) and then the vinyl product is subsequently ozonolysed in a polar solvent, e.g., methanol at low temperature to give an aldehyde. The aldehyde is then reacted with a nucleophile, e.g., TSM-$CF_3$ or a Grignard reagent, e.g., MeMgBr to afford a secondary alcohol product. The secondary alcohol is then oxidized with Dess Martin Periodinane to give the desired ketone 6b or can be used as A1 itself.

Chiral alcohol ($X^1$ is O) and amine ($X^1$ is NH) A1 are generated using Chiral reduction methods on the ketone 6b. Chiral alcohol 6c is formed from 6b using one of the numerous chiral reduction methods available in the literature. Typically, dichloro(p-cumene)ruthenium(II) dimer and (1R,2R)-(−)-N-p-tosyl-1,2-diphenylethylenediamine are combined in water, and sodium formate and 6b is added in a water miscible solvent such as tetrahydrofuran. The reaction is then stirred at a temperature between ambient and reflux to produce 6c where $X^1$ is O. Alternatively, a chiral CBS reduction can be performed in an inert solvent, e.g., THF at low temperature to also afford the chiral alcohol 6c. Protection of the OH in 6c is performed using methods described in Greene and Wuts, typically a TBS ether or acetyl group are used to provide A1 ($X^1$ is O).

Alternatively, to prepare chiral A1 ($X^1$ is NH), ketone 6b is first converted to a chiral imine ($R^{10}$ is chiral group) and then reduced using a variety of methods described in the literature. For example, a chiral sulfinamide is reacted with the ketone 6b to afford a chiral sulfinimine 6d, which is then reduced with a suitable reducing agent, typically $NaBH_4$, or selectride, or a Noyori type reduction as described for the chiral alcohol above, with dichloro(p-cumene)ruthenium(II) dimer and (1R,2R)-(−)-N-p-tosyl-1,2-diphenylethylenediamine. The sulfinamide auxiliary is then removed by treatment with mineral acid, preferably HCl in a suitable organic solvent such as methanol, to afford 6e where $X^1$ is NH. Protection of the NH group can then be performed as described in Greene and Wuts to generate A1 ($X^1$ is NH).

In part 2 of Scheme 8, the synthesis of compound A1 where Y is —CH=$CH_2$, a precursor for metathesis and cross coupling reactions are illustrated.

For example, Compound 6c or 6e generated in Scheme 8, part 1 is first optionally protected on $X^1$ using a suitable protecting group as described in Greene and Wuts, and then a vinyl group is introduced by a suitable cross coupling method onto the aryl or sp2 halide. For example, a transition metal mediated coupling with a vinyl stannane or vinyl tetrafluoroborate using a suitable palladium catalyst, e.g., $PdCl_2(dppf)_2$ or $PdCl_2(PPh_3)_2$ in a suitable organic solvent, e.g., acetonitrile, dichloromethane, etc., with either thermal or microwave heating affords alkene A1.

Another typical method that can be used to introduce a vinyl group is starting from the ketone 6b where Y is OH. Initially, triflation of the alcohol is performed by treatment with $Tf_2O$ in the presence of a base, e.g., pyridine. The ketone group is then reduced with a Noyori reduction, or as described above through the sulfonamide, to provide the chiral alcohol or amine. The chiral alcohol or amine is then protected as described in Greene and Wuts, and then the triflate is reacted with a vinyl cross coupling reagent, e.g., vinyl stannane in a Stille coupling, or a vinyltrifluoroborate as described above to introduce the alkene. A further example of alkene generation using 6b ketone is via introduction of an allyl group. Thus, 6b where Y is OH is treated in an inert solvent in the presence of a suitable base, e.g., alkali metal carbonate, preferably potassium carbonate with allyl bromide to form 6f. Compound 6f is then similar to ketone 6b and is therefore able to be transformed as described above in part 1 to Compound A1 where $X^1$ is O or NH with protecting group $PG^8$.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Combination Therapy

The compounds of the present invention may be combined with one or more active agents. Non-limiting examples of suitable active agents to be combined include one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds to be combined are selected from the group consisting of:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon;

2) ribavirin and its analogs, e.g., ribavirin (Rebetol, Copegus), and taribavirin (Viramidine);

3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227);

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, PSI-7851, BCX-4678, valopicitabine (NM-283), GS-6620 and MK-0608;

7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190;

8) HCV NS5A inhibitors, e.g., AZD-2836 (A-831), AZD-7295 (A-689), and BMS-790052;

9) TLR-7 agonists, e.g., imiquimod, 852A, GS-9524, ANA-773, ANA-975, AZD-8848 (DSP-3025), PF-04878691, and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin;

13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOc-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib);

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride; and 18) endothelin antagonists, e.g. bosentan and ambrisentan.

In yet another embodiment, the present application provides a combination therapy comprising a composition of the present invention and a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV, and combinations thereof.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, Mb-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, Mb-210, racivir (±-FTC), D-d4FC, emtricitabine, phosphazide, fozivudine tidoxil, fosalvudine tidoxil, apricitibine amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SPO1A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCc-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-ANA 971, NOc-205, tarvacin, EHC-18, and NIM811, 19) pharmacokinetic enhancers, e.g., BAS-100, SPI-452, PF-4194477, TMC-41629, GS-9350, GS-9585, and roxythromycin, 20)RNAse H inhibitors, e.g., ODN-93 and ODN-112, 21) other anti-HIV agents, e.g., VGc-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In a specific aspect of this embodiment, the additional therapeutic agent is selected from ribavirin, telaprevir, boceprevir and sofosbuvir (GS-7977 (formerly PSI-7977)).

A combination therapy described herein may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

One or more compounds of the disclosure are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this disclosure is that they are orally bioavailable and can be dosed orally.

Method for Treating Viral Infection

The present application provides a method for treating a Flaviviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

Also provided is a method for treating a Coronaviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

In one embodiment, the method of inhibiting or treating a disease comprises administering to an animal a composition comprising an effective amount of one or more compounds of the invention or a pharmaceutically acceptable salt, isotope, stereoisomer, mixture of stereoisomers, tautomer, ester or prodrug thereof, and a pharmaceutically acceptable carrier. The composition to be administered may further contain a secondary therapeutic agent as described above.

A method of the present application is particularly suitable for use with humans, but may be used with other animals, particularly mammals, such as, for example, non-human primates, companion animals, farm animals, laboratory animals, and wild and zoo animals.

A method of the present application is particularly useful to treat diseases caused directly or indirectly by Flaviviridae virus since the compounds of the present invention have inhibitory activity against those viruses. In some embodiments, therefore, a method of the present invention is used in inhibiting or treating diseases caused by a Hepatitis C virus. In some embodiments, therefore, a method of the present invention is used in inhibiting or treating diseases caused by a Hepatitis B virus. In an aspect, such a method is applied to a patient with a disease caused by the viral infection such as dengue fever, yellow fever, hepatitis C, Japanese encephalitis, Kyasanur forest disease, Murray valley encephalitis, St. Louis encephalitis, tick-borne encephalitis or West Nile encephalitis.

In some embodiments, a sustained virologic response is achieved at about 12 weeks, at about 10 weeks, at about 8 weeks, at about 6 weekes, or at about 4 weeks, or at about 4 months, or at about 5 months, or at about 6 months, or at about 1 year, or at about 2 years.

A method of the present application is also particularly useful to treat diseases caused directly or indirectly by Coronaviridae virus since the compounds of the present invention have inhibitory activity against those viruses. In some embodiments, therefore, a method of the present invention is used in inhibiting or treating diseases caused by a SARS coronarirus. In an aspect, such a method is applied to a patient with a disease caused by the viral infection such as severe acute respiratory syndrome (SARS), cancer, inflammation, obesity, acquired immune deficiency syndrome (AIDS), or cirrhosis.

In another aspect, the compounds disclosed herein can be used for treating cancer. In yet another aspect, the compounds disclosed herein can be used for immunomodulation. In some embodiments, therefore, a method of the present invention comprises adjusting an immune response to a desired level, as in immunopotentiation, immunosuppression, or induction of immunologic tolerance.

In some embodiments, the compound is administered for about 12 weeks. In further embodiments, the compound is administered for about 12 weeks or less, for about 10 weeks or less, for about 8 weeks or less, for about 6 weeks or less, or for about 4 weeks or less. The compound may be administered once daily, twice daily, once every other day, two times a week, three times a week, four times a week, or five times a week.

EXAMPLES

The following examples are merely illustrative, and do not limit this disclosure in any way. For Examples 1 to 120, unless otherwise stated, preparative HPLC was performed on a Gilson HPLC system, using an Agilent Eclipse XDB/C18 7 micron, 250×21.2 mm semi-preparative column and an acetonitrile/water mobile phase at a flow rate of 20 mL/min.

For Examples 121 to 175, unless otherwise stated, preparative HPLC was performed on a Shimadzu HPLC system, using a 21.2×250 mm 10 micron C18 Phenomenex Gemini semi-preparative column and acetonitrile/water mobile phase at a flow rate of 20 mL/min.

List of Abbreviations and Acronyms

| Abbreviation | Meaning |
|---|---|
| ° C. | Degrees Celsius |
| di-tBuXPhos | 2-Di-tert-Butylphosphino-3,4,5,6-tetramethyl-2',4',6'-triisopropyl-1,1'-biphenyl |
| 2,6-lut. | 2,6-lutidine |
| MNBA | 2-Methyl-6-nitrobenzoic anhydride |
| 4AMS | 4 Angstrom molecular sieves |
| Ac | Acetyl |
| ACN | acetonitrile |
| app | Apparent |

-continued

| Abbreviation | Meaning |
|---|---|
| Aq | Aqueous |
| BINAP | (2,2'-bis(diphenylphosphino)-1,1'-binaphthyl) |
| Bn | Benzyl |
| Boc | tert-Butoxycarbonyl |
| Boc-Val-OH | (S)-2-tert-butoxycarbonylamino-3-methyl-butyric acid |
| BOP | Benzotriazole-1-yl-oxy-tris-(dimethylamino)-phosphonium hexafluorophosphate |
| Br | Broad |
| Bu | Butyl |
| cat | Catalytic |
| CBS | Corey Bakshi Shibata |
| CDMT | 2-chloro-4,6-dimethoxy-1,3,5-triazine |
| cm | Centimeter |
| cod | cyclooctadiene |
| COMU | (1-Cyano-2-ethoxy-2-oxoethylidenaminooxy)dimethylamino-morpholino-carbenium hexafluorophosphate |
| CP/Cp | Cyclopentyl |
| CPME | Cyclopentyl methyl ether |
| CSA | Camphorsulfonic acid |
| Cy/cHex | Cyclohexyl |
| d | Doublet |
| DAST | Diethylaminosulfur trifluoride |
| dba | dibenzylideneacetone |
| DBU | 1,8-Diazabicyclo[5.4.0]undec-7-ene |
| DCC | N,N'-dicyclohexylcarbodiimide |
| DCE | Dichloroethane |
| DCM | Dichloromethane |
| dd | Doublet of doublet |
| ddd | Doublet of doublet of doublet |
| ddt | Doublet of doublet of triplet |
| DIAD | Diisopropyl azodicarboxylate |
| DIPEA | N,N-Diisopropylethylamine |
| DMAP | 4-Dimethylaminopyridine |
| DME | 1,2-dimethoxyethane |
| DMF | Dimethylformamide |
| DMSO | Dimethylsulfoxide |
| dppf | 1,1'-bis(diphenylphosphino)ferrocene |
| dq | Doublet of quartet |
| dt | Doublet of triplet |
| dtd | Doublet of triplet of doublet |
| EA | Ethyl acetate |
| EDC | 1-Ethyl-3-(3-dimethylaminopropyl)carbodiimide |
| Equiv/eq | Equivalents |
| Et | Ethyl |
| g | Grams |
| HATU | (Dimethylamino)-N,N-dimethyl(2H-[1,2,3]triazolo[4,5-b]pyridin-3-yloxy)methaniminium hexafluorophosphate |
| HBTU | 2-(1 H-benzotriazole-1 -yl)-1,1,3,3-tetramethyluronium hexafluorophosphate |
| HDMS | Hexamethyldisilazane |
| HEX | hexane |
| HMPA | hexamethylphosphoramide |
| HOAc/AcOH | Acetic acid |
| HOBT | Hydroxybenzotriazole |
| HPLC | High-performance liquid chromatography |
| hrs/h | Hours |
| Hz | Hertz |
| $IC_{50}$ | The half maximal inhibitory concentration |
| Im | imidazole |
| i-Pr/iPr | Isopropyl |
| iPr2NEt | N,N-diisopropylethylamine |
| J | Coupling constant |
| Kg | Kilogram |
| KHMDS | potassium bis(trimethylsilyl)amide |
| LCMS | Liquid chromatography-mass spectrometry |
| LDA | Lithium diisopropylamide |
| LiHMDS | lithium bis(trimethylsilyl)amide |
| M | Molar |
| m | Multiplet |
| m/z | mass-to-charge ratio |
| M+ | Mass Peak |
| m-CPBA | meta-Chloroperoxybenzoic acid |
| Me | Methyl |
| mg | Milligram |
| MHz | Megahertz |
| min | Minute |
| mL | Milliliter |

-continued

| Abbreviation | Meaning |
|---|---|
| mM | Millimolar |
| mm | Millimeter |
| mmol | Millimole |
| mol | Mole |
| Ms | Methanesulfonyl |
| MW | Microwave |
| N | Normal |
| nM | Nanomolar |
| NaHMDS | sodium bis(trimethylsilyl)amide |
| NMM | N-methylmorpholine |
| NMR | Nuclear magnetic resonance |
| nPr | n-Propyl |
| o-Tol | o-Tolyl |
| Ph | Phenyl |
| Pin | Pinacolato |
| Piv | Pivaloyl |
| pTSA | p-Toluenesulfonic acid |
| Py/pyr | Pyridine |
| PyAOP | 7-azabenzotriazol-1-yloxy)tripyrrolidinophosphonium hexafluorophosphate |
| PyBop | benzotriazol-1-yl-oxytripyrrolidinophosphonium hexafluorophosphate |
| q | Quartet |
| quant | Quantitative |
| rac | Racemic |
| Rf | Retention factor |
| RT/rt/r.t. | Room temperature |
| s | Singlet |
| sat. | Saturated |
| SEMCl | 2-Trimethylsilylethyoxymethyl chloride |
| t | Triplet |
| TBAF | Tetra-n-butylammonium fluoride |
| TBDMS/TBS | tert-Butyldimethylsilyl |
| TBDPS | terf-Butyldiphenylsilyl |
| t-Bu | tert-butyl |
| td | Triplet of doublets |
| TEA | Triethylamine |
| Tf | Trifluoromethanesulfonyl |
| TFA | Trifluoroacetic acid |
| THF | Tetrahydrofuran |
| TLC | Thin layer chromatography |
| TMEDA | tetramethylenediamine |
| TMS | Trimethylsilyl |
| Tr/tr | Retention time |
| Ts | Tosyl |
| tt | Triplet of triplet |
| UV | Ultraviolet |
| wt. | weight |
| δ | Chemical shift |
| μL | Microliter |
| μM | Micromolar |
| μmol | Micromole |

Example 1

(E)-(2R,5S,11S,14S,17R,18R)-18-Hydroxy-14-isopropyl-2,11,17-trimethyl-3,9,12,15,28-pentaazatricyclo[21.3.1.1*5,9*]octacosa-1(26),21,23(27),24-tetraene-4,10,13,16-tetraone: Compound 1

Compound 1a

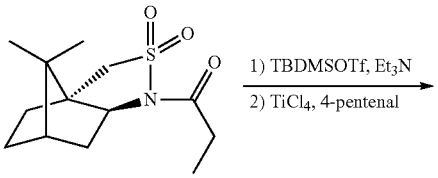

-continued

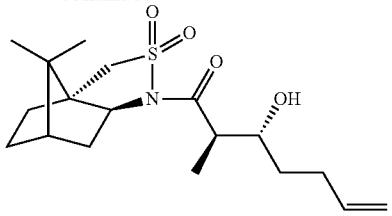

A solution of 1-((1R,5S)-10,10-dimethyl-3,3-dioxo-3lambda*6*-thia-4-aza-tricyclo[5.2.1.0*1,5*]dec-4-yl)-propan-1-one (3.95 g, 14.55 mmol) in toluene (50 mL) was prepared, then evaporated to dryness. This process was repeated and the resulting white solid was dissolved in anhydrous dichloromethane (16 mL). A small quantity of calcium hydride was added before adding tert-butyldimethylsilyl trifluoromethanesulfonate (3.83 mL, 14.5 mmol) and anhydrous triethylamine (2.33 mL, 16.7 mmol). The reaction mixture was stirred at RT ("RT") under a nitrogen atmosphere for 15 hours ("h"). The resulting solution was evaporated to yield a thick paste, which was re-dissolved in anhydrous dichloromethane (15 mL) and added dropwise to a stirred solution of 4-pentenal (2.69 g, 32.0 mmol) and titanium tetrachloride (1 M in dichloromethane, 32 mL, 32 mmol) in anhydrous dichloromethane (20 mL) at −78° C., under a nitrogen atmosphere. The reaction was stirred at −78° C. for 30 minutes ("min") before diluting with saturated aqueous ammonium chloride solution (100 mL). The layers were separated and the aqueous layer was extracted with dichloromethane (2×50 mL). The combined extract was dried over sodium sulfate, filtered and evaporated to give a brown gum. This was purified by silica gel chromatography using iso-hexanes/ethyl acetate 4:1 to yield the title compound (3.09 g, 60%) as a colorless gum.

Compound 1b

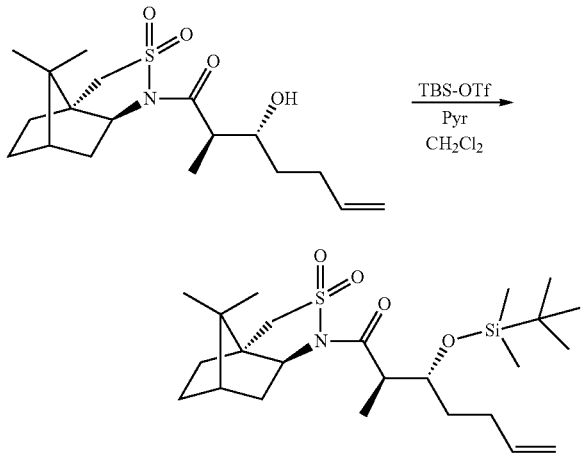

A solution of 1a (12.0 g, 0.034 mol) in anhydrous dichloromethane (520 mL) was cooled to 0° C., before adding pyridine (5.5 mL, 0.068 mol) then tert-butyldimethylsilyl trifluoromethanesulfonate (9 mL, 0.039 mol). The reaction mixture was stirred at 0° C. for 15 min then allowed to warm to RT and stirred for a further 1.5 h. The reaction mixture was washed with saturated sodium bicarbonate (400 mL). The aqueous wash was back-extracted with dichloromethane (200 mL). The organic layers were combined and washed with dilute brine (200 mL) and 2 M hydrochloric acid (200 mL). The solution was dried over sodium sulfate, filtered and evaporated to give the title product (15.29 g, 96%) as a white solid.

Compound 1c

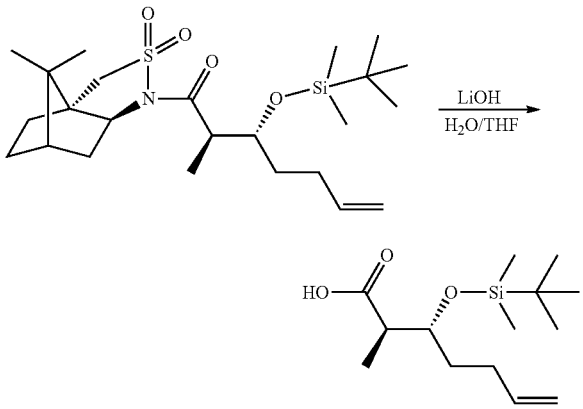

A solution of 1b (15.29 g, 0.0325 mol) in tetrahydrofuran (300 mL) was prepared and a 2 M aqueous solution of lithium hydroxide (120 mL) was added. The stirred mixture was heated to 60° C. for 15 h. The reaction was diluted with 2 M hydrochloric acid (250 mL). The layers were separated and the aqueous was extracted with ethyl acetate (2×200 mL). The organic layers were combined, dried over sodium sulfate, filtered and evaporated to give a cream solid (16.7 g). The solid was purified by silica gel chromatography using 3:7 ethyl acetate/iso-hexanes to yield the title product (7.18 g, 81%) as a colorless gum.

Compound 1d

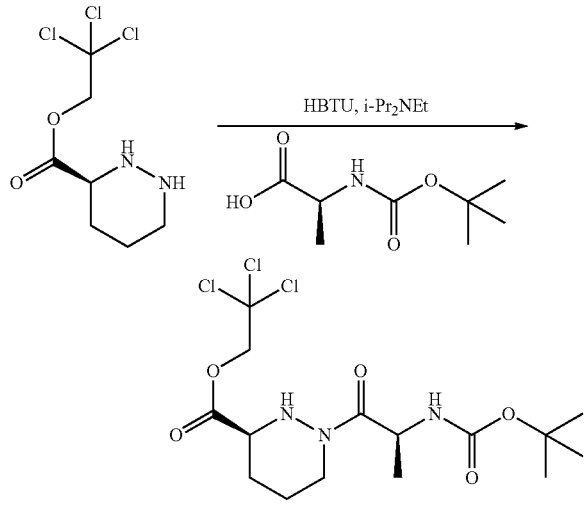

A solution of (S)-2-tert-butoxycarbonylamino-propionic acid (3.28 g, 17.32 mmol) in acetonitrile (160 mL) was cooled to 0° C. before addition of N,N-diisopropylethylamine (12 mL, 69.3 mmol) then 2-(1H-benzotriazole-1-yl)-1,1,3,3-tetramethyluronium hexafluorophosphate (6.57 g, 17.32 mmol). The reaction mixture was stirred at 0° C. for 20 min and a solution of (S)-hexahydropyridazine-3-carboxylic acid 2,2,2-trichloroethyl ester trifluoroacetic acid salt (preparation described in Angew. Chem. Int. Ed. Engl. 1999, 38, 2443, 6.49 g, 17.3 mmol) in acetonitrile (80 mL) was added. The reaction was allowed to warm to RT and was stirred for 15 h. The reaction mixture was evaporated then re-dissolved in ethyl acetate (150 mL). The solution was washed with brine (150 mL). The brine was back extracted with ethyl acetate (50 mL). The organic layers were combined, dried over sodium sulfate, filtered and evaporated to give a dark oil. The oil was purified by silica gel chromatography using iso-hexanes/ethyl acetate 1:1 to yield the title compound (6.88 g, 92%) as a colorless gum.

Compound 1e

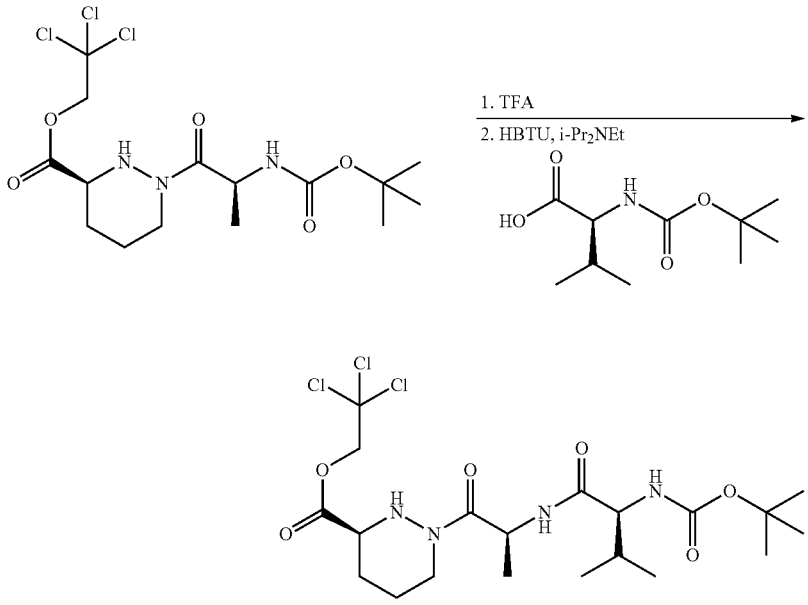

A solution of 1d (6.88 g, 15.9 mmol) in dichloromethane (200 mL) was prepared and trifluoroacetic acid (50 mL) was added. The reaction mixture was stirred at RT for 2 h. TLC showed the reaction to be complete. The solution was evaporated to give a brown oil. This was azeotroped with toluene (50 mL) and the resultant oil was dried under vacuum to give (S)-1-((S)-2-amino-propionyl)-hexahydro-pyridazine-3-carboxylic acid 2,2,2-trichloro-ethyl ester trifluoroacetic acid salt (7.8 g) as a brown gum. A solution of ((S)-1-carbamoyl-2-methylpropyl)-carbamic acid tert-butyl ester in acetonitrile (300 mL) was cooled to 0° C. before adding N,N-diisopropylethylamine (13.8 mL, 79.7 mmol) and 2-(1H-benzotriazole-1-yl)-1,1,3,3-tetramethyluronium hexafluorophosphate (6.33 g, 16.7 mmol). The reaction was stirred at 0° C. for 15 min before adding a solution of the (S)-1-((S)-2-amino-propionyl)-hexahydro-pyridazine-3-carboxylic acid 2,2,2-trichloro-ethyl ester trifluoroacetic acid salt (ca. 15.9 mmol) in acetonitrile (85 mL). The reaction was stirred at 0° C. for a further 20 min then allowed to warm to RT and stirred for 15 h. The reaction mixture was evaporated then re-dissolved in ethyl acetate (250 mL). The solution was washed with water (150 mL) then dried over sodium sulfate, filtered and evaporated to give a red oil. This was purified by silica gel chromatography using iso-hexanes/ethyl acetate 7:3 then iso-hexanes/ethyl acetate 1:1 to yield the title compound (8.2 g, 92%) as a pale orange amorphous solid.

Compound 1f

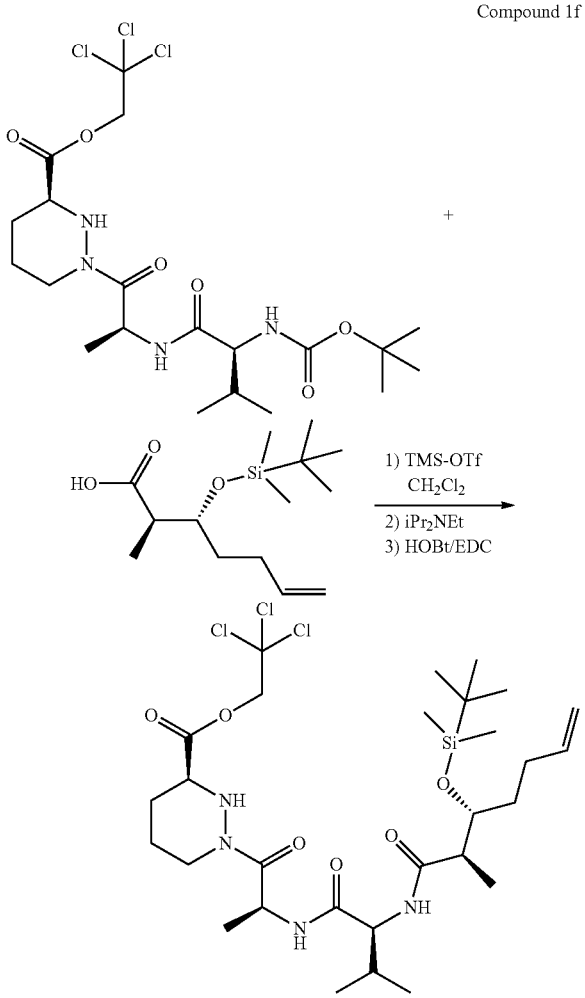

A solution of 1e (10.0 g, 18.5 mmol) in anhydrous dichloromethane (200 mL) was prepared and trimethylsilyl trifluoromethanesulfonate (5 mL, 27.75 mmol) was added. The reaction mixture was stirred at RT for 2 h, then N,N-diisopropylethylamine (13.2 mL, 75.8 mmol) was added and the reaction mixture was evaporated to dryness. The residue was re-dissolved in acetonitrile (200 mL) and a solution of (2R,3R)-3-(tert-butyl-dimethyl-silanyloxy)-2-methyl-hept-6-enoic acid (5.04 g, 18.5 mmol) in acetonitrile (60 mL) was added followed by 1-ethyl-3-(3-dimethylaminopropyl)carbodiimide (5.0 g, 26.4 mmol) and 1-hydroxybenzotriazole (4.4 g, 26.4 mmol). The reaction mixture was stirred at RT for 15 h. It was evaporated to give a thick yellow oil. The oil was purified by silica gel chromatography using 1:1 ethyl acetate/iso-hexanes then 3:2 ethyl acetate/iso-hexanes to yield the title product (8.75 g, 69%) as a white solid.

Compound 1g

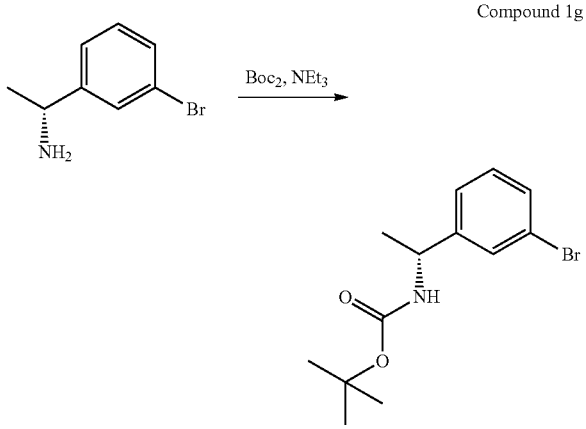

A solution of (R)-bromo-α-methylbenzylamine (1.023 g, 5.112 mmol) in dichloromethane (20 mL) was subsequently treated with triethylamine (720 μL, 5.112 mmol) and di-tert-butyl dicarbonate (1.784 g, 8.179 mmol). After overnight stirring at RT, the volatiles were removed in vacuo and the residue was purified by silica gel chromatography using a 50 g Isolute cartridge eluted with a continuous gradient of iso-hexanes/diethyl ether 1:0 to 4:1 to afford the title compound (1.552 g, 100%) as a white solid.

Compound 1h

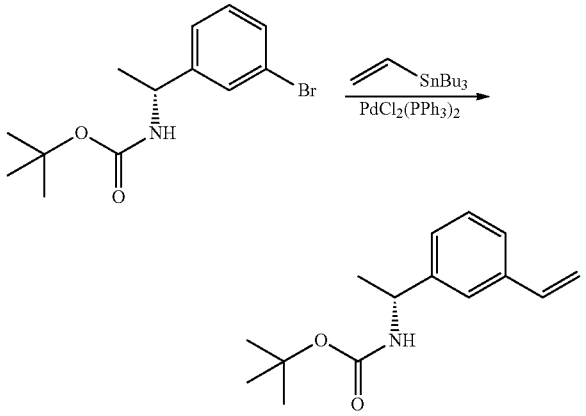

A solution of 1 g (10.26 g, 0.0342 mol.) and tributyl (vinyl)tin (32.5 g, 30 mL, 0.103 mol.) in toluene (175 mL) was purged with nitrogen for 30 min before addition of bis(triphenylphosphine) palladium (II) dichloride (2.38 g, 0.0034 mol.). The stirred mixture was heated to 60° C. for 16 h before cooling to RT. The reaction mixture was filtered through hyflo-supercel then evaporated to give a dark coloured oil. The oil was purified by silica gel chromatography using iso-hexanes/ethyl acetate 19:1 to yield the title compound (6.95 g, 82%) as a yellow oil.

Compound 1i

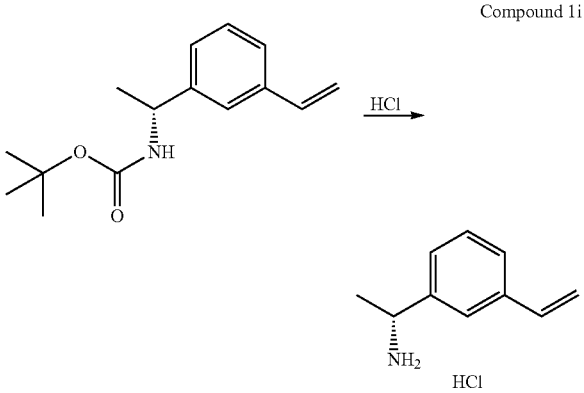

A solution of 1 h (6.95 g, 28.1 mmol.) in 1,4-dioxane (30 mL) was prepared and a solution of hydrogen chloride in 1,4 dioxane (4 M, 60 mL) was added. The reaction mixture was stirred at RT for 2 h then evaporated to dryness. The resultant solid was re-dissolved in toluene and evaporated. The solid was triturated with diethyl ether, which was removed by decanting. The solid was then dried under vacuum to give the title compound (4.96 g, 96%) as an off-white solid.

Compound 1j

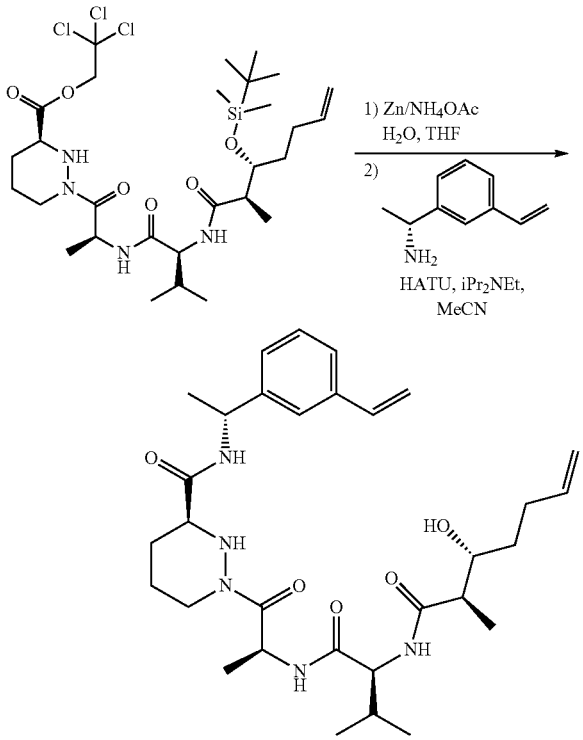

A solution of if (8.75 g, 12.75 mmol) in tetrahydrofuran (350 mL) was prepared and zinc powder (8.44 g, 127.5 mmol) was added followed by a 1 M aqueous solution of ammonium acetate (90 mL, 90 mmol). The reaction mixture was vigorously stirred for 16 h then filtered through hyflo-supercel. The solution was cooled over an ice bath before addition of aqueous ammonium chloride solution (350 mL). It was allowed to re-cool before acidifying to pH 1 by addition of 2 M hydrochloric acid. The layers were separated and the aqueous was extracted with ethyl acetate (2×250 mL). The organic layers were combined, dried over sodium sulfate filtered and evaporated to give a white solid. The solid was azeotroped with toluene (3×200 mL) then dried under vacuum to give a white solid (6.16 g), which was dissolved in acetonitrile (400 mL) before adding 1i (2.34 g, 12.75 mmol) followed by N,N-diisopropylethylamine (8.9 mL, 51 mmol) and 2-(1H-7-azabenzotriazol-1-yl)-1,1,3,3-tetramethyl uronium hexafluorophosphate methanaminium (6.8 g, 17.85 mmol). The reaction mixture was stirred at RT for 16 h and then evaporated to give a brown gum. The gum was purified by silica gel chromatography using ethyl acetate then 1:4 acetone/ethyl acetate to yield the title compound (5.51 g, 76%) as a cream solid.

Compound 1k

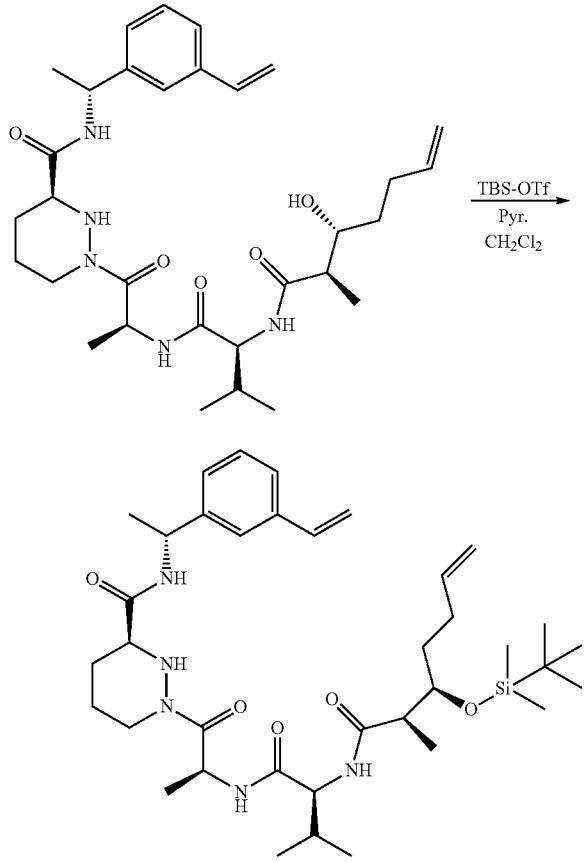

A solution of 1j (0.50 g, 0.88 mmol) in anhydrous dichloromethane (20 mL) was cooled over an ice bath, before adding pyridine (92 μL, 1.14 mmol) and tert-butyldimethylsilyl trifluoromethanesulfonate (242 μL, 1.05 mmol). The reaction mixture was stirred at 0° C. for 15 min, then allowed to warm to RT and stirred for 1 hour. The reaction mixture was evaporated and the residue was purified by silica gel chromatography using ethyl acetate to yield the title product (477 mg, 80%) as a white solid.

Compound 11

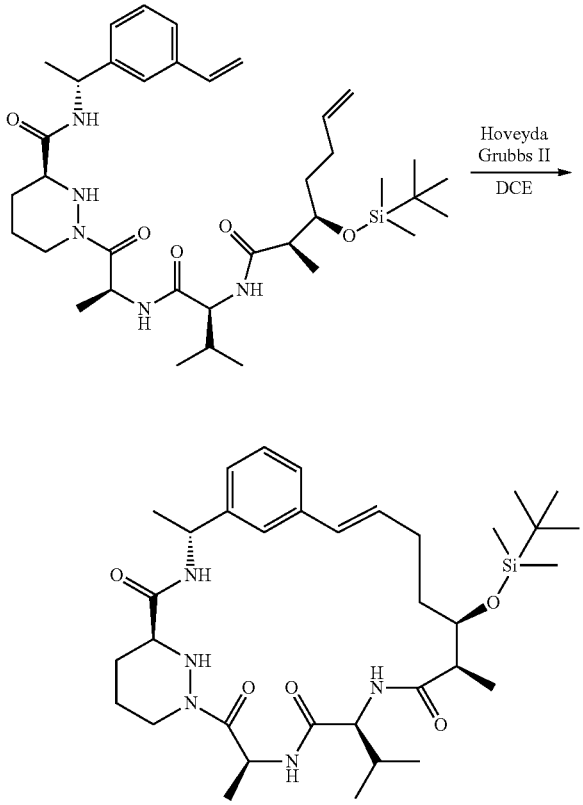

A solution of 1k (477 mg, 0.7 mmol) in 1,2-dichloroethane (250 mL) was prepared and Hoveyda-Grubbs $2^{nd}$ generation catalyst (43 mg, 0.07 mmol) was added. The stirred reaction mixture was heated to 80° C. for 1 hour. The reaction mixture was cooled to RT before adding silica gel. The mixture was stirred for 10 min then evaporated and the residue was purified by silica gel chromatography using ethyl acetate to yield the title product (198 mg, 43%) as a white solid.

Compound 1

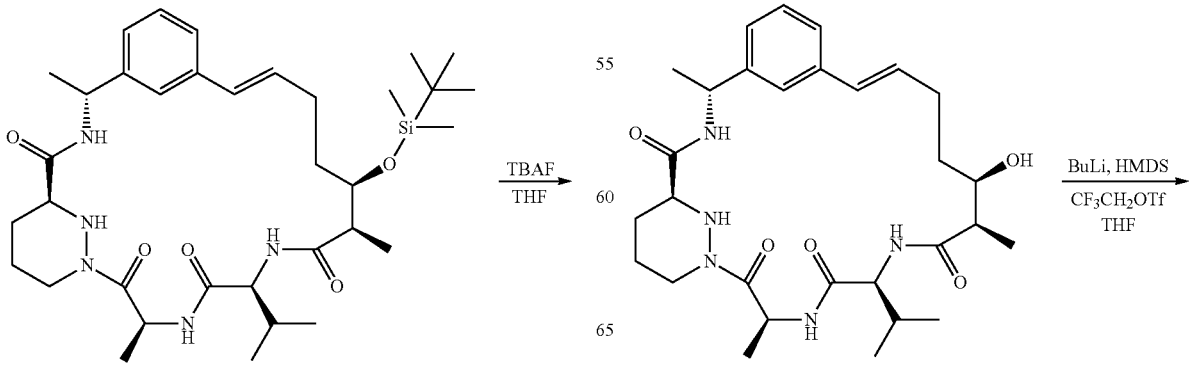

-continued

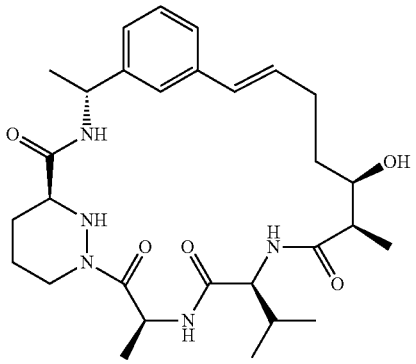

A solution of 11 (198 mg, 0.3 mmol) in tetrahydrofuran (20 mL) was cooled over an ice bath before adding a 1 M solution of tetrabutylammonium fluoride in tetrahydrofuran (1.5 mL, 1.5 mmol). The reaction was allowed to warm to RT and was stirred for 1 hour. The reaction mixture was treated with saturated aqueous sodium bicarbonate solution (20 mL) and extracted with ethyl acetate (2×20 mL). The extract was dried over sodium sulfate, filtered and evaporated. The residue was purified by silica gel chromatography using 1:9 acetone/ethyl acetate to yield the title product (150 mg, 92%) as a white solid. $^1$H NMR (300 MHz, $d_6$-DMSO) δ 0.83 (d, J=6.5 Hz, 3H), 0.85 (d, J=6.5 Hz, 3H), 1.12-1.21 (m, 4H), 1.28 (d, J=7.1 Hz, 3H), 1.36 (d, J=6.9 Hz, 3H), 1.40-1.90 (m, 7H), 1.92-2.08 (m, 1H), 2.19-2.34 (m, 2H), 2.67-2.80 (m, 1H), 3.56-3.65 (m, 1H), 3.99-4.12 (m, 1H), 4.22 (br d, J=12.2 Hz, 1H), 4.75 (d, J=11.8 Hz, 1H), 4.87-4.99 (m, 1H), 5.12-5.24 (m, 1H), 5.40 (d, J=4.5 Hz, 1H), 6.14-6.33 (m, 2H), 7.10-7.35 (m, 5H), 7.88 (d, J=8.3 Hz, 1H), 8.55 (d, J=8.3 Hz, 1H). LCMS (m/z) 542.3 [M+H], Tr=1.87 min.

Example 2

(E)-(2R,5S,11S,14S,17R,18R)-14-Isopropyl-2,11,17-trimethyl-18-(2,2,2-trifluoro-ethoxy)-3,9,12,15,28-pentaaza-tricyclo[21.3.1.1*5,9*]octacosa-1(26),21,23(27),24-tetraene-4,10,13,16-tetraone: Compound 2

Compound 2

-continued

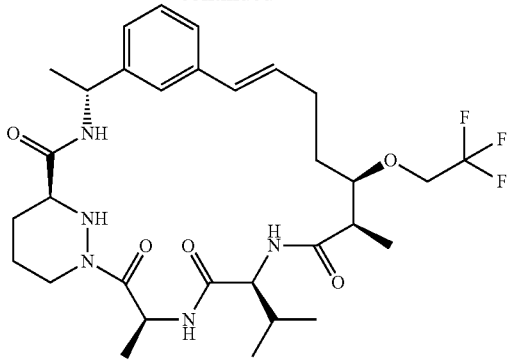

A solution of hexamethyldisilazane (235 μL, 1.13 mmol) in anhydrous tetrahydrofuran (4 mL) was cooled to −10° C. before adding a 2.5 M solution of n-butyllithium (380 μL, 0.94 mmol). The stirred mixture was warmed to 0° C. for 10 min before cooling to −78° C. A solution of Compound 1 (102 mg, 0.188 mmol) in anhydrous dimethylformamide (1.5 mL) and anhydrous tetrahydrofuran (1.5 mL) was added dropwise over 2 min followed by the addition of 2,2,2-trifluoroethyl trifluoromethanesulfonate (135 μL, 0.94 mmol). The reaction mixture was stirred at −78° C. under a nitrogen atmosphere then allowed to gradually warm to RT. The reaction mixture was quenched with the addition of a saturated aqueous solution of ammonium chloride (15 mL). The mixture was extracted with ethyl acetate (2×15 mL). The extract was dried over sodium sulfate, filtered and evaporated. The residue was purified by silica gel chromatography using 1:9 acetone/ethyl acetate to give a colorless gum (65 mg). The gum was further purified by reverse phase chromatography, using a 10 g C18 cartridge eluted with 2:3 acetonitrile/water. The partially evaporated fractions were extracted with ethyl acetate (2×15 mL). The extract was dried over sodium sulfate, filtered and evaporated to yield the title product (17 mg, 30%) as a white solid. $^1$H NMR (300 MHz, $CDCl_3$) 0.92 (d, J=6.7 Hz, 3H), 0.96 (d, J=6.9 Hz, 3H), 1.32 (d, J=7.1 Hz, 3H), 1.39 (d, J=7.1 Hz, 3H), 1.50 (d, J=6.7 Hz, 3H), 1.74-1.85 (m, 1H), 1.86-2.08 (m, 3H), 2.10-2.40 (m, 3H), 2.57-2.78 (m, 2H), 3.19-3.31 (m, 1H), 3.49 (app t, J=6.7 Hz, 1H), 3.58-3.79 (m, 4H), 3.81-4.18 (m, 2H), 4.49 (br d, J=12.3 Hz, 1H), 5.03-5.17 (m, 1H), 5.32-5.47 (m, 1H), 6.14-6.30 (m, 1H), 6.37-6.72 (m, 4H), 7.06-7.30 (m, 4H). LCMS (m/z) 624.3 [M+H], Tr=2.57 min.

Example 3

(2R,5S,11S,14S,17R,18R)-18-Hydroxy-14-isopropyl-2,11,17-trimethyl-3,9,12,15,28-pentaaza-tricyclo[21.3.1.1*5,9*]octacosa-1(26),23(27),24-triene-4,10,13,16-tetraone: Compound 3

Compound 3

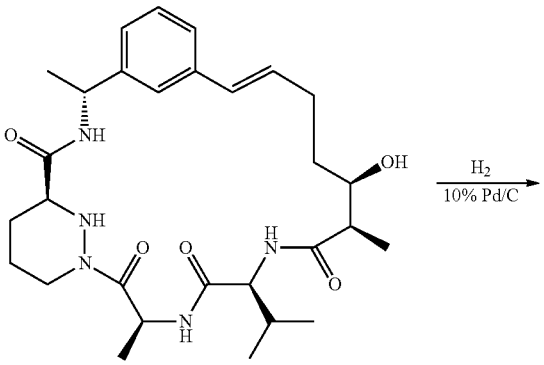

-continued

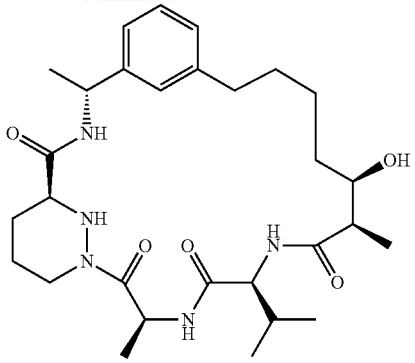

A solution of Compound 1 (100 mg, 0.184 mmol) in methanol (5 mL) was prepared and 10% palladium on carbon (5 mg) was added. The stirred mixture was placed under a hydrogen atmosphere for 1.5 h. The reaction mixture was filtered through hyflo-supercel then through a 0.2 μm filter before evaporating to give the title compound (95 mg, 95%) as a white solid. $^1$H NMR (300 MHz, $CDCl_3$) 0.93 (d, J=7.1 Hz, 3H), 0.96 (d, J=7.1 Hz, 3H), 1.32 (d, J=6.7 Hz, 3H), 1.37-2.16 (m, 12H), 1.54 (d, J=6.9 Hz, 3H), 2.34-2.46 (m, 1H), 2.52-2.75 (m, 3H), 3.16-3.27 (m, 1H), 3.43-3.62 (m, 3H), 3.74 (d, J=11.8 Hz, 1H), 3.98-4.06 (m, 1H), 4.50 (d, J=13.2 Hz, 1H), 5.11-5.36 (m, 2H), 6.39-6.50 (m, 2H), 7.70 (d, J=8.5 Hz, 1H), 7.06-7.28 (m, 4H). LCMS (m/z) 544.3 [M+H], Tr=1.91 min.

Example 4

Compound 4

Compound 4a

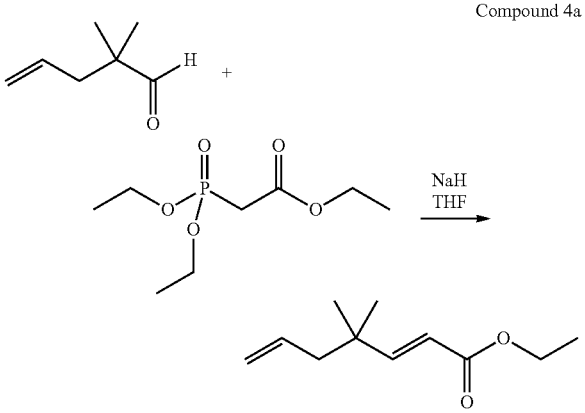

To a suspension of sodium hydride (60% in mineral oil, 783 mg, 19.6 mmol) in dry tetrahydrofuran at 0° C., under nitrogen was added dropwise triethyl phosphonoacetate (3.38 mL, 19.6 mmol). The white suspension was stirred for 1 h where it became a solution, then 2,2-dimethyl-4-pentenal (2.42 mL, 17.8 mmol) was slowly added and the resulting green/yellow solution was stirred at 0° C. and allowed to warm to RT. After 72 h ethanol (1 mL) was added to the solution, followed by water (100 mL) and the organics were extracted with diethyl ether (2×200 mL). The combined organics were washed with water (200 mL), dried over magnesium sulfate, filtered and concentrated in vacuo to give a crude residue. This was purified by silica gel chromatography, using iso-hexanes (144 mL), then iso-hexanes/diethyl ether 50:50 (72 mL), then diethyl ether (48 mL) to give the title compound (3.20 g, 99%) as an oil.

Compound 4b

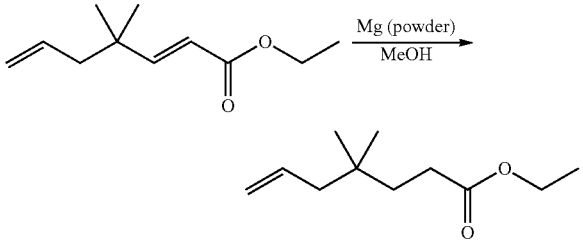

To 4a (3.20 g, 17.5 mmol) in dry methanol at RT, under nitrogen was slowly added magnesium powder (1.28 g, 52.7 mmol) while monitoring the temperature rise. After the addition was complete the mixture was stirred at RT overnight. After this time, to the reaction was added additional magnesium powder (852 mg, 35.1 mmol) and the reaction mixture stirred for 2 h. The mixture was neutralised from pH 10 to pH 7 with 2 M hydrochloric acid and then concentrated in vacuo to give a residue. The residue was suspended in ethyl acetate (300 mL) and water (500 mL) and the layers separated. The aqueous phase was then re-extracted with ethyl acetate (200 mL) and the combined organics were dried over magnesium sulfate, filtered and concentrated in vacuo to give the title compound (1.96 g, 61%) as a colorless oil.

Compound 4c

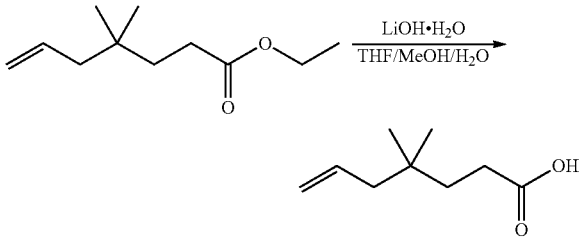

To 4b (2.02 g, 11.0 mmol) in a mixture of tetrahydrofuran (35 mL), methanol (9 mL) and water (9 mL) at RT, was added lithium hydroxide monohydrate (1.38 g, 32.9 mmol) and the mixture was stirred at RT for 1 h. After this time additional lithium hydroxide monohydrate (460 mg, 11.0 mmol) was added and the reaction mixture stirred for 1 h. After this time more lithium hydroxide monohydrate (460 mg, 11.0 mmol) was added and the reaction mixture stirred for 30 min. The reaction mixture was then concentrated in vacuo and the residue diluted with water (200 mL) and the organics extracted with diethyl ether (3×50 mL). The aqueous phase was acidified from pH 14 to pH 1 with 2 M hydrochloric acid and the organics extracted with ethyl acetate (3×50 mL). The combined ethyl acetate organics were then dried over sodium sulfate, filtered and concentrated in vacuo to give the desired product (1.03 g, 60%) as an oil.

Compound 4d

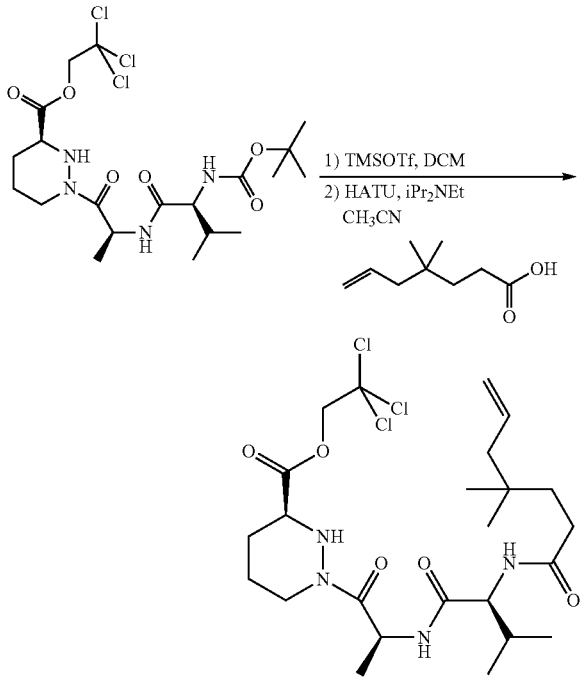

A solution of 1e (1.06 g, 2.00 mmol) in dichloromethane (10 mL) was cooled in an ice-water bath under nitrogen. Trimethylsilyl trifluoromethanesulfonate (0.591 mL, 4.00 mmol) was added dropwise, and the resulting solution was stirred for 1.5 h. The reaction was quenched with N,N-diisopropylethylamine (1.4 mL, 8.00 mmol) and the reaction mixture was concentrated in vacuo to give (S)-1-[(S)-2-((S)-2-amino-3-methyl-butyrylamino)-propionyl]-hexahydro-pyridazine-3-carboxylic acid 2,2,2-trichloro-ethyl ester as a white solid which was used without further purification. To (S)-1-[(S)-2-((S)-2-amino-3-methyl-butyrylamino)-propionyl]-hexahydro-pyridazine-3-carboxylic acid 2,2,2-trichloro-ethyl ester generated in the previous step was added a solution of 4,4-dimethyl-hept-6-enoic acid (343 mg, 2.20 mmol) in acetonitrile (70 mL). To this mixture was added N,N-diisopropylethylamine (1.4 mL, 8.03 mmol) and the reaction cooled in an ice-water bath before the addition of 2-(1H-7-azabenzotriazol-1-yl)-1,1,3,3-tetramethyluronium hexafluorophosphate methanaminium (1.07 g, 2.80 mmol). The yellow solution was then stirred and allowed to warm to RT overnight. The reaction mixture was quenched with 2 M hydrochloric acid (40 mL) and concentrated in vacuo. To the residue was added water (200 mL) and the organics were extracted with ethyl acetate (3×150 mL). The combined organics were then washed with brine (100 mL) and sodium hydrogen carbonate (200 mL). The organics were then dried over magnesium sulfate, filtered and concentrated in vacuo to give a crude yellow oil (2.27 g). This was purified by silica gel chromatography using iso-hexanes/ethyl acetate 90:10 (300 mL) then iso-hexanes/acetone 50:50 (300 mL) then iso-hexanes/acetone 0:100 to give the title compound (1.10 g, 97%) as a colorless oil.

Compound 4e

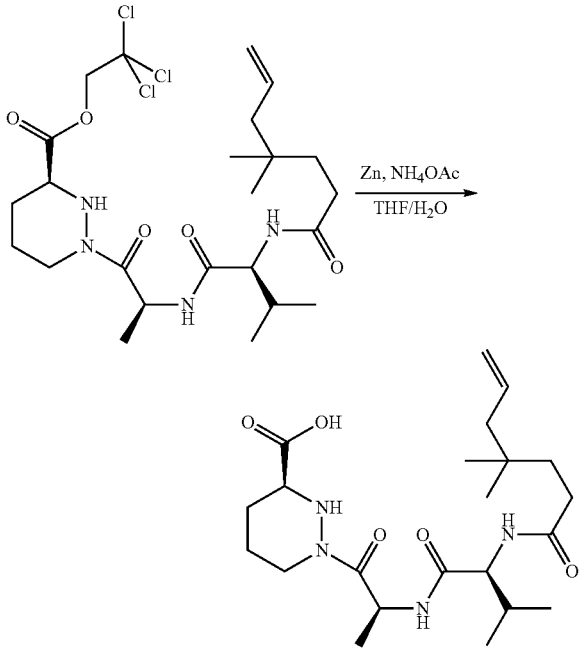

A solution of 4d (1.10 g, 1.94 mmol) in tetrahydrofuran (40 mL) was prepared and zinc powder (2.79 g, 42.6 mmol) was added followed by a solution of ammonium acetate (2.24 g, 29.0 mmol) in water (10 mL). The reaction mixture was stirred at RT for 24 h. Saturated aqueous potassium hydrogen sulphate (pH 2, 30 mL) and ethyl acetate (50 mL) were added and the suspension filtered through hyflo-supercel washing through with ethyl acetate. The layers were separated. And the aqueous phase was extracted with ethyl acetate (3×100 mL). The combined organic layers were washed with brine (250 mL), dried over sodium sulfate, filtered and evaporated to give a colorless gum. The residue was azeotroped with toluene (3×100 mL) to give the title compound (816 mg, 96%) as a white solid.

Compound 4f

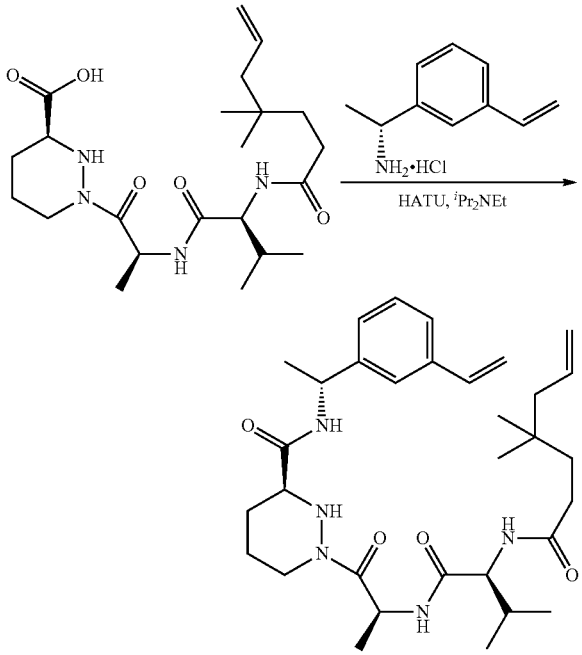

4e (439 mg, 1.00 mmol) was suspended in acetonitrile (35 mL) and (R)-1-(3-vinyl-phenyl)-ethylamine hydrochloride (202 mg, 1.10 mmol) was added followed by N,N-diisopropylethylamine (700 μL, 5.00 mmol) and the mixture cooled in an ice-water bath before addition of 2-(1H-7-azabenzotriazol-1-yl)-1,1,3,3-tetramethyluronium hexafluorophosphate methanaminium (532 mg, 1.40 mmol). The reaction mixture was stirred and allowed to warm to RT over 72 h. To the reaction mixture was added 2 M hydrochloric acid (20 mL) and the mixture concentrated in vacuo to give a residue. The aqueous layer was extracted with ethyl acetate (3×100 mL) and the combined ethyl acetate layers were washed with brine followed by sodium hydrogen carbonate (100 mL) then dried over sodium sulfate, filtered and concentrated in vacuo to give a crude residue. The residue was purified by silica gel chromatography using isohexanes/ethyl acetate 50:50 then neat ethyl acetate to give the title compound (402 mg, 71%).

Compound 4

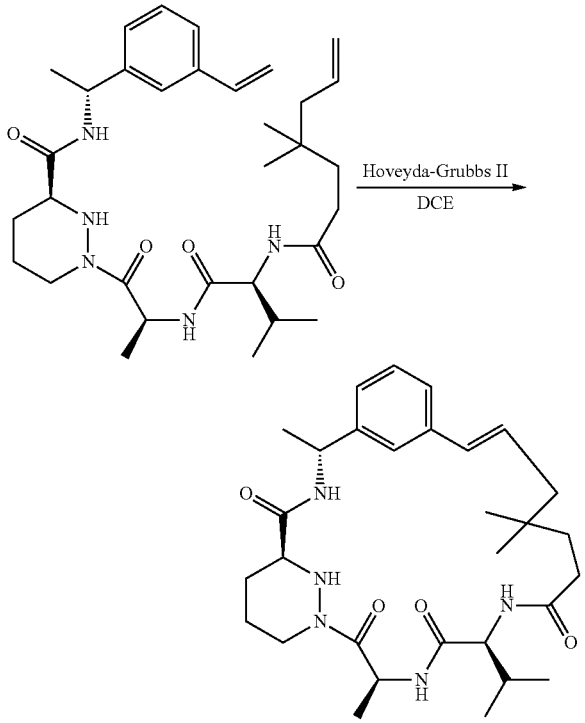

To a solution of 4f (402 mg, 0.71 mmol) in 1,2-dichloroethane (210 mL) was added Hoveyda-Grubbs 2$^{nd}$ generation catalyst (45 mg, 0.07 mmol) and the reaction mixture heated at 80° C. for 1 h. After this time the mixture was allowed to cool to RT and concentrated in vacuo. The residue was purified by silica gel chromatography using a gradient of ethyl acetate to ethyl acetate/acetone 75:25. Impure product (240 mg) was collected which was further purified by silica gel chromatography using ethyl acetate. After repurification, product (43 mg) was collected containing minor impurities. The impurities were removed via trituration from diethyl ether to give the title compound (30 mg, 8%) as a white solid. $^1$H NMR (300 MHz, $CD_3OD$) 0.89 (d, J=6.7 Hz, 3H), 0.92 (d, J=6.7 Hz, 3H), 0.96 (s, 3H), 0.97 (s, 3H), 1.35 (d, J=6.9 Hz, 3H), 1.50 (d, J=7.1 Hz, 3H), 1.59-1.83 (m, 3H), 1.85-2.00 (m, 3H), 2.09 (d, J=7.1 Hz, 2H), 2.15-2.25 (m, 1H), 2.31-2.44 (m, 1H), 2.78 (td, J=2.7, 12.7 Hz, 1H), 3.40-3.72 (m, 2H), 4.05-4.17 (m, 1H), 4.34 (br d, J=13.2 Hz, 1H), 5.05 (q, J=7.1 Hz, 1H), 5.35 (q, J=7.1 Hz, 1H), 6.19-6.32 (m, 1H), 6.37 (d, J=15.8 Hz, 1H), 7.15 (d, J=7.6 Hz, 1H), 7.21-7.29 (m, 2H), 7.37 (d, J=7.8 Hz, 1H). LCMS (m/z) 540.3 [M+H], Tr=2.41 min.

Example 5

Compound 5

Compound 5a

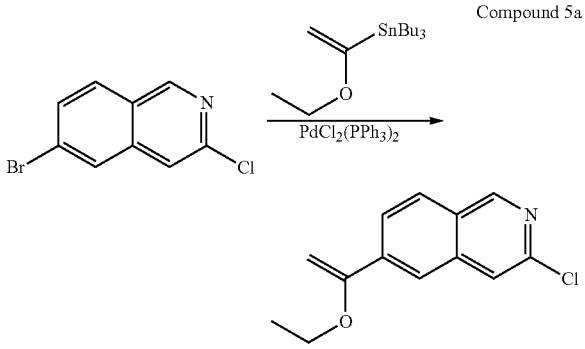

A solution of 6-bromo-3-chloro-isoquinoline (8.0 g, 33 mmol) and tributyl-(1-ethoxyvinyl)-tin (14.88 g, 14 mL, 41.2 mmol) in toluene (100 mL) was degassed with nitrogen for 30 min. Bis(triphenylphosphine)palladium(II) dichloride (1.16 g, 1.65 mmol, 5 mol %) was added and the reaction mixture was heated at 60° C. for 20 h. The reaction mixture was cooled to RT, the mixture was filtered and the filtrate was evaporated. The residue was purified by silica gel chromatography using a gradient of iso-hexanes/ethyl acetate 20:1 to 10:1 to afford the title compound (7.1 g, 92%) as a yellow solid.

Compound 5b

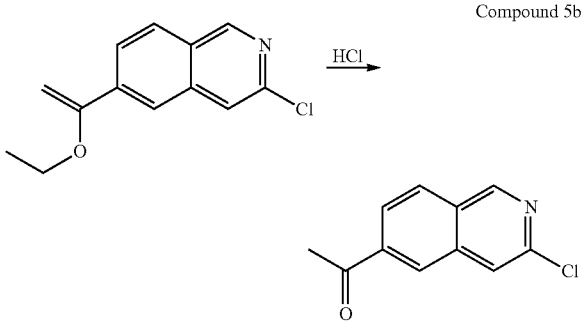

A solution of 5a (7.1 g, 30 mmol) in 1,4-dioxane (60 mL) and 2 M hydrochloric acid (30 mL) was stirred at RT for 30 min. The majority of the solvent was evaporated and the residue was partitioned between ethyl acetate and water. The organic extracts were combined, washed with water and brine, dried over sodium sulfate, filtered and evaporated. The residue was triturated with 5% ether in iso-hexanes and the resulting solid was collected and dried to afford the title compound (6.0 g, 97%) as a white solid.

Compound 5c

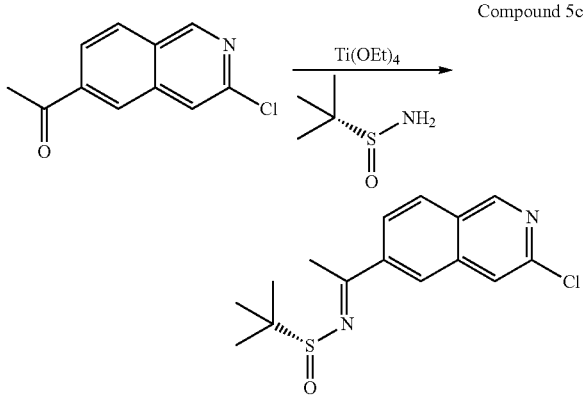

A solution of 5b (1.72 g, 8.3 mmol) in tetrahydrofuran (40 mL) was stirred under nitrogen. Titanium (IV) ethoxide (3.8 g, 3.45 mL, 16.6 mmol, tech. grade) was added followed by (R)-(+)-2-methyl-propanesulfinimide (1.11 g, 9.2 mmol) and the reaction mixture was stirred at 60° C. under nitrogen for 18 h. Additional (R)-(+)-2-methyl-propanesulfinimide (190 mg, 1.67 mmol) was added and the reaction mixture was stirred at 65° C. for further 2 h. The reaction mixture was cooled to RT and ethyl acetate and brine were added. The suspension was filtered through Celite and the filter pad was washed with ethyl acetate. The ethyl acetate layer was separated, washed with brine, dried over sodium sulfate, filtered and evaporated. The residue was purified by silica gel chromatography using a gradient of iso-hexanes/ethyl acetate 7:3 to 3:7 to afford the title compound (2.2 g, 86%) as a yellow solid.

Compound 5d

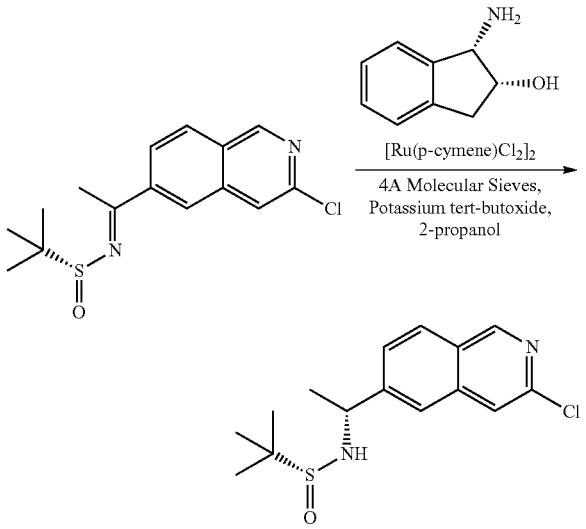

A mixture of (1S,2R)-(−)-cis-1-amino-2-indanol (60 mg, 0.4 mmol), dichloro (p-cymene) ruthenium(II) dimer (122 mg, 0.2 mmol) and powdered 4 Å molecular sieves (2 g) was suspended in anhydrous 2-propanol (9 mL) and stirred under nitrogen. The suspension was heated at 90° C. for 20 min. The reaction mixture was cooled to 40° C. and a solution of 5c (1.23 g, 4 mmol) in 2-propanol (28 mL) was added followed by a solution of potassium tert-butoxide (122 mg, 1.1 mmol) in 2-propanol (10 mL). The reaction mixture was stirred for 2 h at 40° C. and then allowed to cool. The mixture was poured directly onto a silica gel cartridge and eluted with ethyl acetate to give, after evaporation, the title compound (1.19 g, 96%) as a brown gum.

Compound 5e

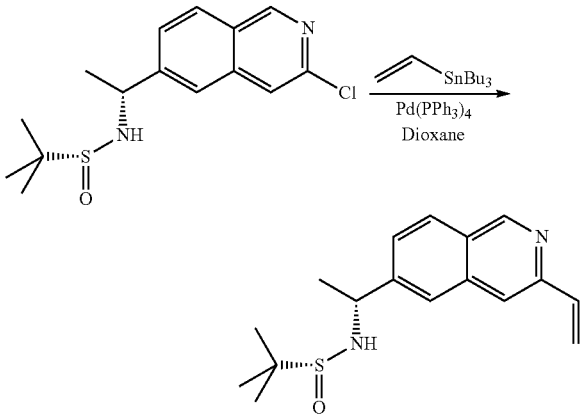

A mixture of 5d (0.66 g, 2.11 mmol), tributyl(vinyl)tin (1.85 mL, 6.35 mmol) and palladium tetrakis(triphenylphosphine) (488 mg, 0.42 mmol) in 1,4-dioxane (10.5 mL) was capped in a microwave vial. The reaction mixture was irradiated and stirred at 160° C. for 40 min in a microwave reactor. A second reaction was carried under identical scale and conditions and the reaction mixtures combined and evaporated. The residue was purified by silica gel chromatography using a gradient of 1:3 to 1:0 ethyl acetate/iso-hexanes to afford the title compound (1 g) as a brown gum. $^1$H NMR (300 MHz, $CDCl_3$) δ 1.27 (s, 9H), 1.62 (d, J=7.7 Hz, 3H), 3.53 (br s, 1H), 4.69-4.77 (m, 1H), 5.51 (dd, J=10.7, 1.3 Hz, 1H), 6.39 (dd, J=17.4, 1.3 Hz, 1H), 6.95 (dd, J=17.2, 10.7 Hz, 1H), 7.55-7.58 (m, 2H), 7.75 (s, 1H), 7.95 (d, J=8.3 Hz, 1H), 9.20 (s, 1H). LCMS (m/z) 303.0 [M+H], Tr=1.48 min.

Compound 5f

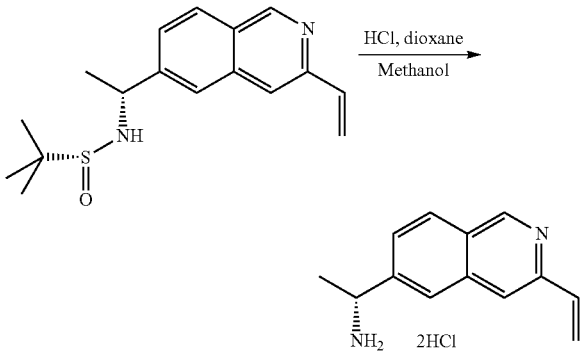

5e was suspended in 4 M hydrochloric acid in 1,4-dioxane (17 mL, 68 mmol) and methanol was added (34 mL). The reaction mixture was stirred for 90 min and then evaporated. The residue was passed through a SCX cartridge eluting with methanol and then methanolic ammonia. The basic fraction was collected and evaporated to give the title compound (530 mg, 63% over 2 steps) as a beige solid.

Compound 5g

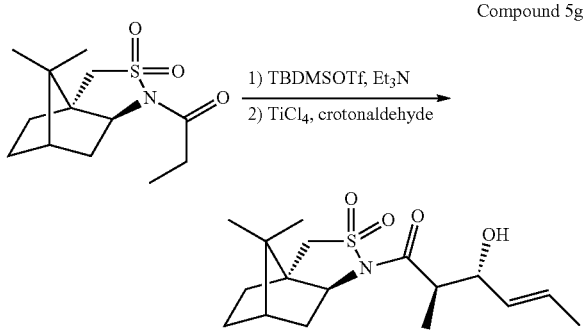

A solution of 1-((1R,5S)-10,10-dimethyl-3,3-dioxo-3lambda*6*-thia-4-aza-tricyclo[5.2.1.0*1,5*]dec-4-yl)-propan-1-one (6.0 g, 22.1 mmol) in anhydrous dichloromethane (24 mL) was prepared and tert-butyldimethylsilyl trifluoromethanesulfonate (5.0 mL, 22.1 mmol) was added, followed by anhydrous triethylamine (3.54 mL, 25.4 mmol). The reaction mixture was stirred at RT under a nitrogen atmosphere for 15 h. This gave a dark solution that was evaporated to give an oil. The oil was dissolved in anhydrous dichloromethane (22 mL) and the solution was added dropwise to a solution of crotonaldehyde (3.66 mL, 44.2 mmol) and titanium tetrachloride (1 M in dichloromethane, 44.2 mL, 44.2 mmol) in dichloromethane (22 mL) at −78° C. under a nitrogen atmosphere. The reaction mixture was stirred at −78° C. for 1 hour, before addition of ammonium chloride solution (30 mL). The stirred mixture was allowed to warm to RT before separating the layers. The aqueous layer was extracted with dichloromethane (2×25 mL). The organic layers were combined, dried over sodium sulfate, filtered and evaporated to give a brown oil. The oil was purified by silica gel chromatography using iso-hexanes/ethyl acetate 4:1 to yield the title compound (6.7 g, 89%) as a colorless solid.

Compound 5h

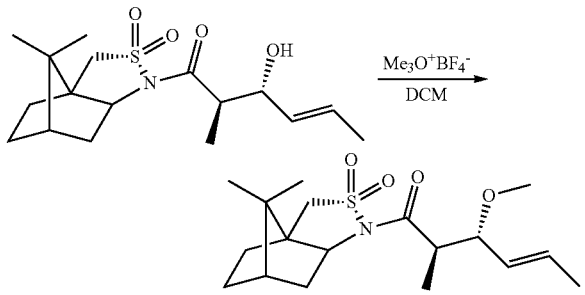

A solution of 5 g (4.15 g, 12.1 mmol) in anhydrous dichloromethane (80 mL) was prepared and 1,8-bis(dimethylamino)naphthalene (7.78 g, 36.3 mmol) was added followed by trimethyloxonium tetrafluoroborate (3.6 g, 24.2 mmol). The reaction mixture was stirred at RT for 3 h. The reaction mixture was treated with methanol (3 mL) and stirred for 5 min before adding hydrochloric acid (2 M, 200 mL) and ethyl acetate (250 mL). The mixture was filtered to remove an insoluble solid and the layers were separated. The aqueous layer was extracted with ethyl acetate (2×100 mL). The organic layers were combined and washed with brine, dried over sodium sulfate, filtered and evaporated to give the title compound (4.80 g, 100%) as a pale brown solid.

Compound 5i

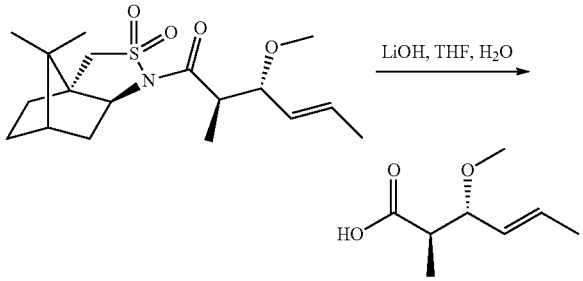

A solution of lithium hydroxide in water (2 M, 50 mL, 100 mmol) was added to a stirred solution of 5 h (4.80 g, 12.1 mmol) in tetrahydrofuran (130 mL). The reaction mixture was heated to 60° C. for 15 h. The reaction mixture was cooled to RT, before partially evaporating and adding hydrochloric acid (2 M, 150 mL). The mixture was extracted with ethyl acetate (3×50 mL). The extract was dried over sodium sulfate, filtered and evaporated to give a brown oil (3.5 g). The oil was purified by silica gel chromatography using iso-hexanes/diethyl ether 1:1 to give the title compound (1.132 g, 59%) as a colorless oil.

Compound 5j

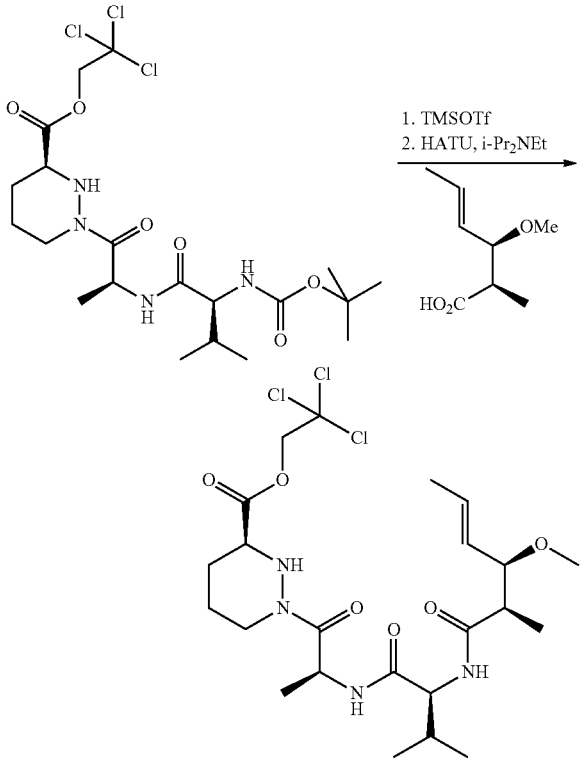

A cooled (0° C.) solution of (S)-1-[(S)-2-((S)-2-tert-butoxycarbonylamino-3-methyl-butyrylamino)-propionyl]-hexahydro-pyridazine-3-carboxylic acid 2,2,2-trichloroethyl ester (2.174 g, 4.088 mmol) in anhydrous dichloromethane (50 mL) was treated with trimethylsilyl trifluoromethanesulfonate (1.2 mL, 6.814 mmol). After 1 h at 0° C., the reaction mixture was treated with N,N-diisopropylethylamine (2.4 mL, 13.628 mmol) and the volatiles were removed in vacuo to afford the corresponding amine as a yellow foam. To this amine was added 5i (539.0 mg, 3.407 mmol), N,N-diisopropylethylamine (2.4 mL, 13.628 mmol) and acetonitrile (50 mL). The reaction mixture was cooled to 0° C. and treated with 2-(1H-7-azabenzotriazol-1-yl)-1,1,3,3-tetramethyl uronium hexafluorophosphate methanaminium (1.814 g, 4.770 mmol). After overnight stirring at RT the reaction was quenched with 1 M hydrochloric acid (100 mL). The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:4 to afford the title compound (2.193 g, 93%) as a light yellow solid.

Compound 5k

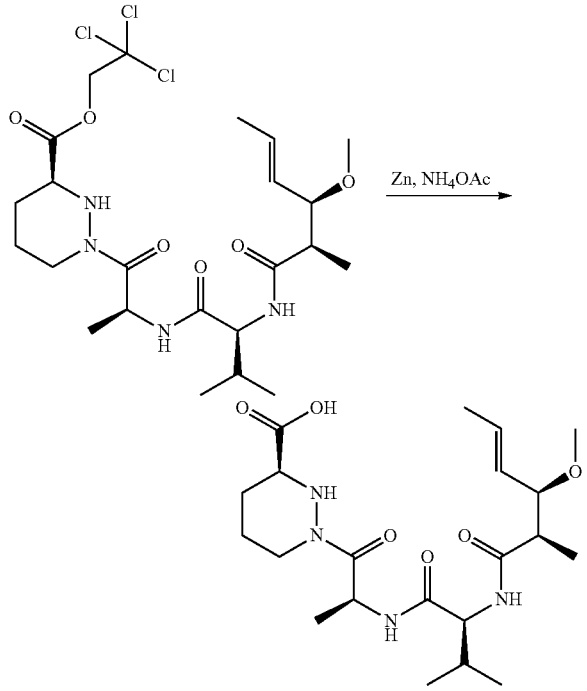

A solution of 5j (763.4 mg, 1.335 mmol) in tetrahydrofuran (25 mL) was subsequently treated with zinc powder (1.920 g, 29.365 mmol) and a solution of ammonium acetate (1.543 g, 20.025 mmol) in water (5 mL). After overnight stirring the reaction was filtered through Celite and quenched with 2 M hydrochloric acid. The aqueous layer was extracted with ethyl acetate (2×). The organics were combined, dried over sodium sulfate, filtered and the volatiles were removed in vacuo. Residual acetic acid was azeotroped off with toluene to provide the title compound (566.4 mg, 96%) as a light orange solid.

Compound 5l

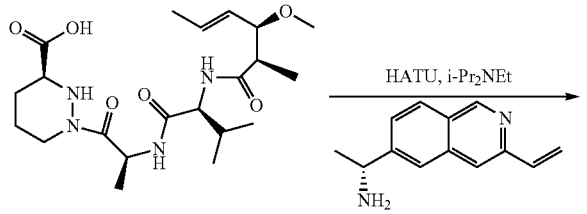

-continued

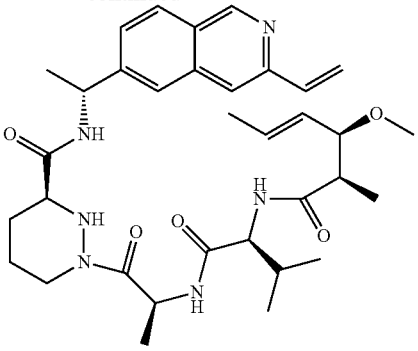

A solution of 5k (246 mg, 0.6 mmol), (R)-1-(3-vinyl-isoquinolin-6-yl)-ethylamine dihydrochloride (162 mg, 0.6 mmol) and N,N-diisopropylethylamine (387 mg, 0.52 mL, 3 mmol) in acetonitrile (20 mL) was stirred at RT under nitrogen. 2-(1H-7-azabenzotriazol-1-yl)-1,1,3,3-tetramethyl uronium hexafluorophosphate methanaminium (320 mg, 0.84 mmol) was added and the reaction mixture was stirred at RT for 4 h. The solvent was evaporated. The residue was diluted with ethyl acetate and saturated sodium hydrogen carbonate solution. A small amount of methanol (5 mL) was added to the suspension to give two clear layers. The organic layer was separated, washed with water and brine, dried over anhydrous sodium sulfate, filtered and evaporated. The residue was purified by silica gel chromatography using methanol/dichloromethane 1:20. The residue was triturated with ether and the resulting solid was collected, washed with ether and dried to afford the title compound (238 mg, 64%) as a pale brown solid.

Compound 5

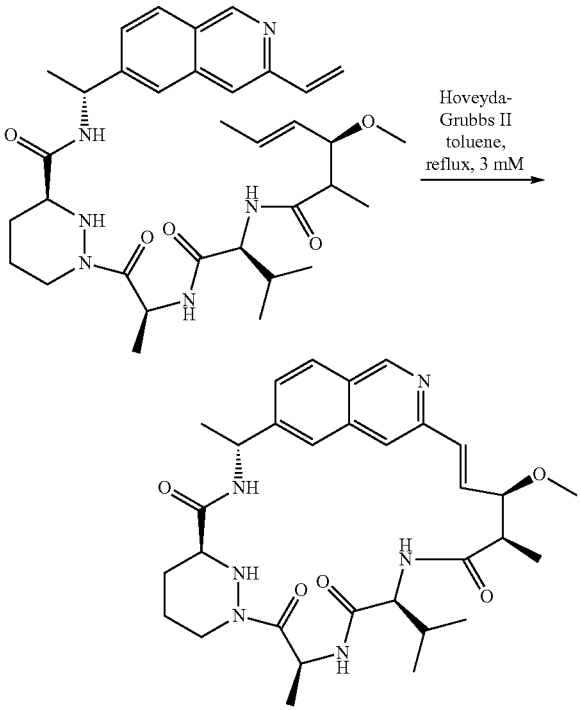

A solution of 5l (91 mg, 0.15 mmol) in toluene (45 mL) was stirred at RT under nitrogen. Hoveyda-Grubbs $2^{nd}$ generation catalyst (10 mg, 0.015 mmol) was added and the reaction mixture was heated at reflux under nitrogen for 2 h. Additional Hoveyda-Grubbs $2^{nd}$ generation catalyst (10 mg, 0.015 mmol) was added and the reaction mixture was heated at reflux under nitrogen for 6 h. The reaction mixture was cooled to RT, silica gel was added and the reaction mixture was evaporated. The residue was purified by silica gel chromatography using a gradient of ethyl acetate/acetone 20:1 to 5:2. The residue was triturated with ether and the resulting solid was collected, washed with ether/iso-hexanes (1:1) and dried to afford the title compound (23 mg, 26%) as a white solid. $^1$H NMR (300 MHz, $CDCl_3$) δ 0.99 (d, J=6.7 Hz, 3H), 1.04 (d, J=6.7 Hz, 3H), 1.44 (d, J=7.4 Hz, 3H), 1.53 (d, J=6.9 Hz, 3H), 1.61 (d, J=6.9 Hz, 3H), 1.68-2.20 (m, 5H), 2.62-2.74 (m, 2H), 3.35-3.43 (m, 1H), 3.44 (s, 3H), 3.72 (d, J=12.5 Hz, 1H), 3.88-3.92 (m, 2H), 4.23 (dd, J=8.9, 6.0 Hz, 1H), 4.55-4.60 (m, 1H), 5.30-5.37 (m, 1H), 5.80-5.90 (m, 1H), 6.38 (d, J=8.9 Hz, 1H), 6.43 (d, J=7.6 Hz, 1H), 6.93 (d, J=16.3 Hz, 1H), 7.24 (dd, J=16.3, 8.7 Hz, 1H), 7.45 (d, J=8.7 Hz, 1H), 7.56 (d, J=8.5 Hz, 1H), 7.69 (s, 1H), 7.93 (d, J=8.5 Hz, 1H), 9.17 (s, 1H). LCMS (m/z) 579.3 [M+H], Tr=1.40 min.

Example 6

Compound 6

Compound 6

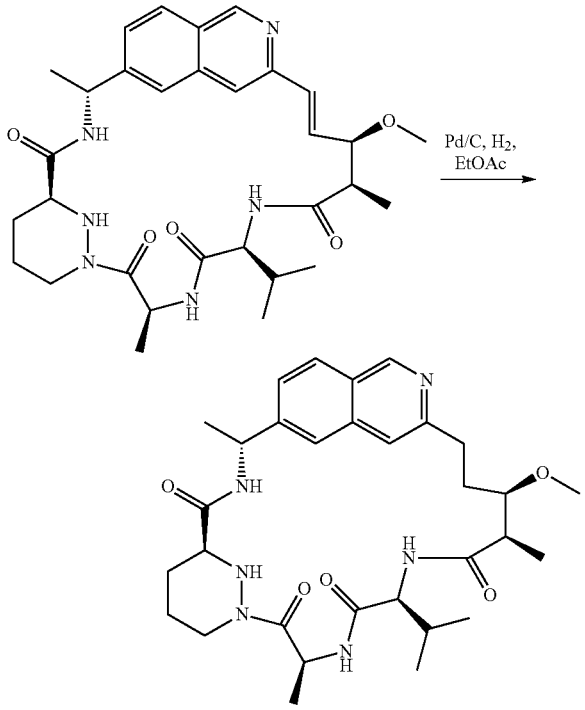

A solution of Compound 5 (11 mg, 0.019 mmol) in ethyl acetate (10 mL) containing 10% palladium on carbon (10 mg) was hydrogenated at RT and pressure for 3 h. The reaction mixture was filtered through filter aid and the filter pad was washed with ethyl acetate. The filtrate was evaporated and the residue was purified by silica gel chromatography using a gradient of ethyl acetate/acetone 10:1 to 2:1. The residue was triturated with ethyl acetate/ether (1:5) to afford the title compound (2.0 mg, 18%) as a white solid. $^1$H NMR (300 MHz, $CDCl_3$) δ 0.93 (d, J=6.7 Hz, 3H), 0.98 (d, J=6.7 Hz, 3H), 1.39 (d, J=6.9 Hz, 3H), 1.55-2.70 (m, 8H), 1.95-2.50 (m, 5H), 2.64-2.73 (m, 2H), 2.95-3.08 (m, 2H), 3.35-3.42 (m, 2H), 3.53 (s, 3H), 3.61 (d, J=12.1 Hz, 1H), 4.06-4.11 (m, 1H), 4.50-4.57 (m, 1H), 5.25-5.32 (m, 1H), 5.64-5.70 (m, 1H), 6.39 (d, J=8.3 Hz, 1H), 6.47-6.51 (m, 1H), 7.21-7.28 (m, 1H), 7.41 (d, J=8.8 Hz, 1H), 7.62 (s, 1H), 7.69 (s, 1H), 7.92 (d, J=8.8 Hz, 1H), 9.15 (s, 1H). LCMS (m/z) 581.3 [M+H], Tr=1.38 min.

Example 7

Compound 7

Compound 7a

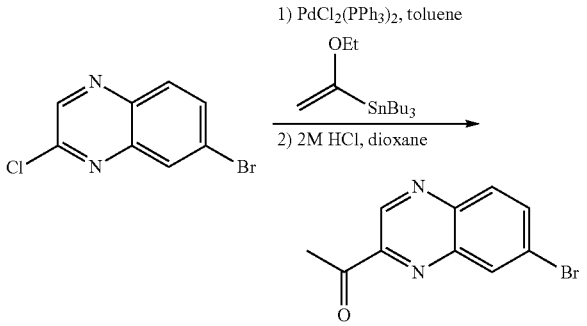

A mixture of 7-bromo-2-chloro-quinoxaline (1.46 g, 6.00 mmol) and tributyl(1-ethoxyvinyl)tin (2.71 g, 2.54 mL, 7.50 mmol) in toluene (21 mL) was degassed for 20 min. Bis (triphenylphosphine)palladium(II) dichloride (427 mg, 0.60 mmol) was added and the reaction mixture stirred under nitrogen and heated at 80° C. for 19 h before allowing to cool. The volatiles were evaporated and the residue suspended in 1,4-dioxane (15 mL), 2 M aqueous hydrochloric acid (15 mL) was added and the reaction mixture stirred for 45 min and then evaporated to remove the volatiles. The residue was diluted with water and extracted with ethyl acetate (2×) and the combined organic extracts were washed with brine, dried over magnesium sulfate, filtered and evaporated. The product was purified by chromatography using silica gel doped with 10% w/w potassium carbonate eluting using a gradient of iso-hexanes/ethyl acetate 1:0 to 9:1 to afford the title compound (836 mg, 56%) as a yellow solid.

Compound 7b

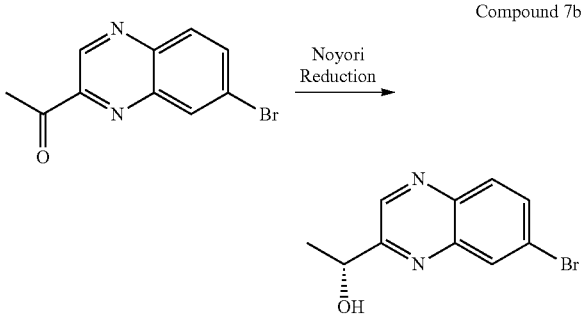

Dichloro (p-cymene) ruthenium(II) dimer (12 mg, 0.019 mmol) and (1R,2R)-(−)-N-p-tosyl-1,2-diphenylethylenediamine (17 mg, 0.045 mmol) were suspended in degassed water (7.5 mL) and the mixture was degassed with nitrogen for 15 min. The mixture was stirred at 70° C. under nitrogen for 90 min. The resulting turbid orange mixture was allowed to cool to RT. Solid 7a (948 mg, 3.78 mmol) followed by degassed tetrahydrofuran (7.5 mL) and sodium formate (1.29 g, 18.9 mmol) were added and the reaction mixture was degassed with nitrogen for 5 min. The reaction mixture was vigorously stirred at 40° C. for 3 h and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ethyl acetate 2:1 to afford the title compound (814 mg, 85%) as a purple solid.

Compound 7c

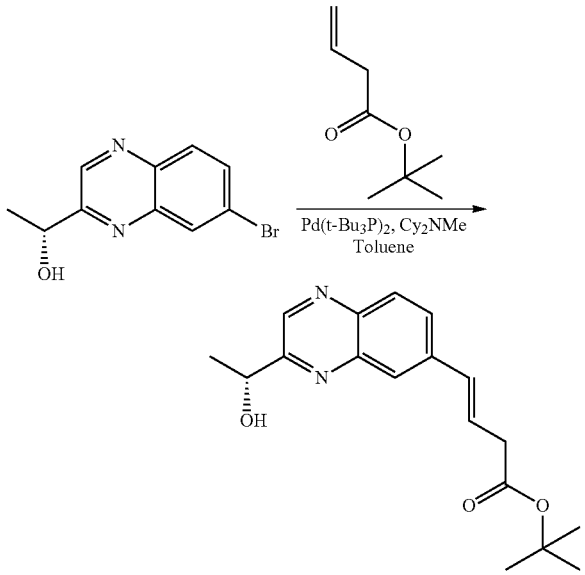

To a mixture of 7b (490 mg, 1.94 mmol), N,N-dicyclohexylmethylamine (416 mg, 457 μL, 2.13 mmol) and tert-butyl 3-butenoate (648 mg, 739 μL, 4.56 mmol) in toluene (19 mL) was added bis(tri-tert-butylphosphine)palladium(0) (41 mg, 0.080 mmol) under nitrogen and the reaction mixture stirred and heated under reflux for 5 h then allowed to cool. The mixture was evaporated and then purified by silica gel chromatography using a gradient of iso-hexanes/ethyl acetate 4:1 to 3:2 to afford the title compound (367 mg, 60%) as a yellow oil.

Compound 7d

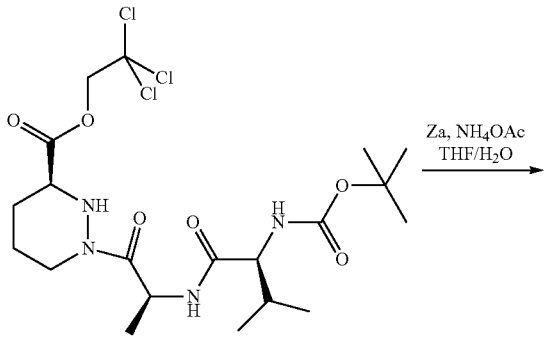

-continued

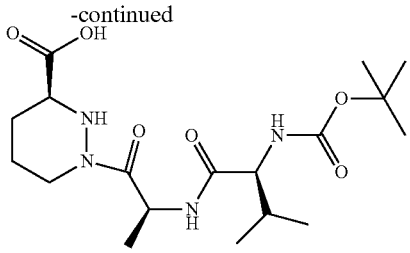

A solution of 1e (804 mg, 1.51 mmol) in tetrahydrofuran (37.7 mL) was prepared and zinc powder (2.18 g, 33.3 mmol) was added followed by a solution of ammonium acetate (1.75 g, 22.7 mmol) in water (9.4 mL). The reaction mixture was stirred at RT for 72 h. The reaction was filtered through hyflo-supercel washing through with ethyl acetate and saturated aqueous potassium hydrogen sulfate. The mixture was treated with 1 M hydrochloric acid (3 mL) and the layers were separated. The aqueous layer was extracted with ethyl acetate (2×100 mL). The organic layers were combined, washed with brine, filtered and evaporated to give a colorless gum. The residue was azeotroped with toluene (3×200 mL) to give the title compound (605 mg, quantitative yield) as a white solid.

To a stirred solution of 7d (456 mg, 1.14 mmol) and (E)-4-[3-((R)-1-hydroxy-ethyl)-quinoxalin-6-yl]-but-3-enoic acid tert-butyl ester (358 mg, 1.14 mmol) in dichloromethane (22 mL) was added 1-hydroxybenzotriazole containing approx. 20% water (270 mg, 1.60 mmol) followed by 4-dimethylaminopyridine (139 mg, 1.14 mmol) and N-(3-dimethylaminopropyl)-N'-ethylcarbodiimide hydrochloride (306 mg, 1.60 mmol). The reaction was stirred for 18 h and then diluted with dichloromethane, washed with saturated ammonium chloride solution (2×), dried over sodium sulfate, filtered and evaporated. The residue was purified by silica gel chromatography using a gradient of iso-hexanes/ethyl acetate 3:1 to 0:1 to afford the title compound (335 mg, 45%) as a white foam.

Compound 7

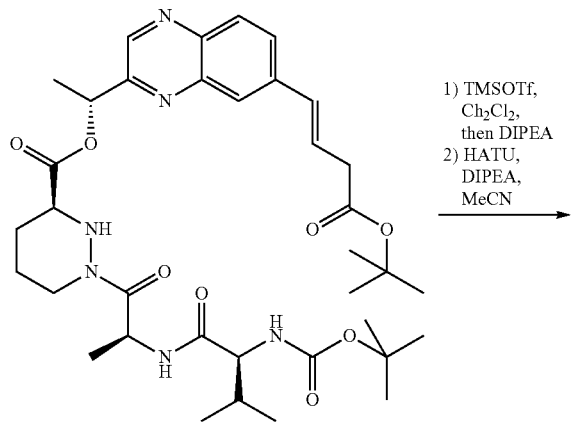

Compound 7e

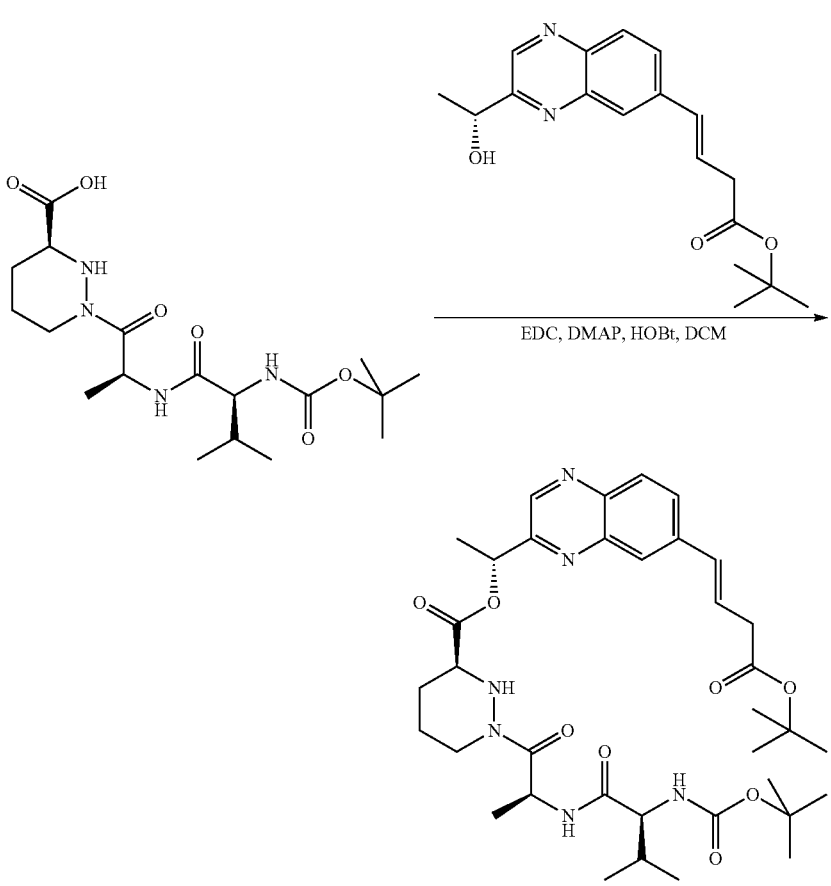

-continued

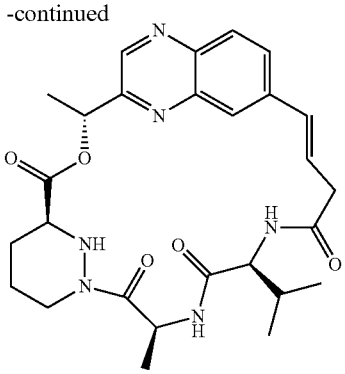

To a stirred solution of 7e (309 mg, 0.444 mmol) in dichloromethane (4.5 mL) at 0° C. under nitrogen was added trimethylsilyl trifluoromethanesulfonate (346 mg, 359 μL, 1.56 mmol) and the reaction mixture was allowed to warm to RT over 2.5 h. N,N-diisopropylethylamine (164 mg, 221 μL, 1.27 mmol) was added and the reaction mixture stirred for a further 10 min, evaporated and then suspended in acetonitrile (45 mL). The stirred mixture was cooled to 0° C. and 2-(1H-7-azabenzotriazol-1-yl)-1,1,3,3-tetramethyl uronium hexafluorophosphate methanaminium (236 mg, 0.622 mmol) and N,N-diisopropylethylamine (229 mg, 309 μL, 1.77 mmol) were added. After 90 min the reaction was quenched with a saturated ammonium chloride solution and the mixture evaporated to remove organic volatiles. The residue was diluted with dichloromethane and the organic layer separated and washed with saturated sodium bicarbonate (2×) and brine then dried over sodium sulfate, filtered and evaporated. The residue was purified by silica gel chromatography eluting with a gradient of ethyl acetate/acetone 1:0 to 9:1. The residue was further purified by reverse phase preparative HPLC using acetonitrile/water 3:7 to afford the title compound (7.6 mg, 3% over 2 steps) as a white solid. $^1$H NMR (300 MHz, $CD_3OD$) δ 1.00 (d, J=6.7 Hz, 3H), 1.01 (d, J=6.7 Hz, 3H), 1.62 (d, J=7.1 Hz, 3H), 1.66-1.75 (m, 2H), 1.77 (d, J=6.9 Hz, 3H), 1.91-2.05 (m, 3H), 2.72-2.82 (m, 1H), 2.98-3.08 (m, 1H), 3.38-3.41 (m, 1H), 3.78-3.84 (m, 1H), 4.25 (d, J=10.5 Hz, 1H), 4.41 (br d, J=11.3 Hz, 1H), 5.68 (q, J=7.1 Hz, 1H), 6.09 (q, J=6.9 Hz, 1H), 6.47 (d, J=16.3 Hz, 1H), 6.55-6.63 (m, 1H), 7.68 (s, 1H), 7.99 (s, 2H), 8.84 (s, 1H). LCMS (m/z) 523.2 [M+H], Tr=1.75 min.

Examples 8 and 9

Compounds 8 and 9

Compound 8a

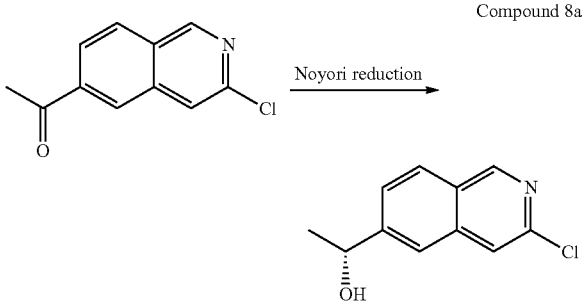

Dichloro (p-cymene) ruthenium(II) dimer (3 mg, 0.005 mmol) and (1R,2R)-(−)-N-p-tosyl-1,2-diphenylethylenediamine (4.4 mg, 0.012 mmol) were suspended in degassed water (2 mL) and the mixture was degassed with nitrogen for 15 min. The mixture was stirred at 70° C. under nitrogen for 90 min. The resulting yellow solution was cooled to RT. 1-(3-Chloro-isoquinolin-6-yl)-ethanone (206 mg, 1 mmol), sodium formate (340 mg, 5 mmol) and degassed tetrahydrofuran (1 mL) were added and the reaction mixture was degassed with nitrogen for 5 min. The reaction mixture was vigorously stirred at 40° C. for 2.5 h. The reaction mixture was cooled to RT and was extracted with ethyl acetate. The organic layer was separated, washed with water and brine, dried over sodium sulfate, filtered and evaporated. The residue was purified by silica gel chromatography using a gradient of iso-hexanes/ethyl acetate 4:1 to 2:1 to afford the title compound (193 mg, 92%) as a white solid.

Compound 8b

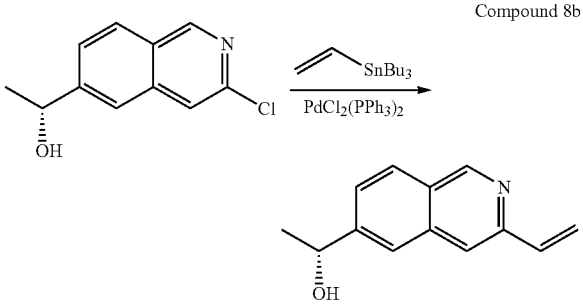

1,4-Dioxane (5 mL) was degassed with nitrogen, 8a (208 mg, 1 mmol), tributyl(vinyl)tin (951 mg, 0.9 mL, 3 mmol) and bis(triphenylphosphine)palladium(II) dichloride (70 mg, 0.1 mmol) were added and the reaction mixture was heated at 150° C. in a microwave reactor for 1 h. Additional tributyl(vinyl)tin (0.3 mL, 1 mmol) and bis(triphenylphosphine)palladium(II) dichloride (70 mg, 0.1 mmol) were added and the reaction mixture was heated at 150° C. in a microwave reactor for 1 h. The reaction mixture was cooled to RT and the mixture was filtered through filter aid and the filter pad was washed with ethyl acetate. The filtrate was evaporated and the residue was purified by silica gel chromatography using a gradient of iso-hexanes/ethyl acetate 4:1 to 2:1 followed by silica gel chromatography using iso-hexanes/ethyl acetate 3:1 to afford the title compound (100 mg, 50%) as a white solid.

Compound 8c

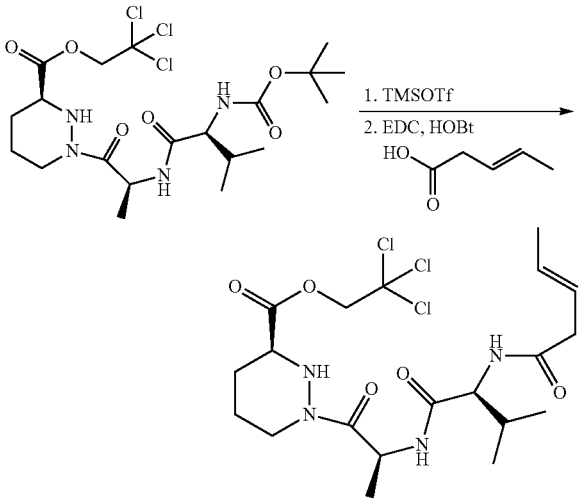

A solution of 1e (10.6 g, 20 mmol) in dichloromethane (300 mL) was stirred at 0° C. under nitrogen. Trimethylsilyl trifluoromethanesulfonate (6.66 g, 5.4 mL, 30 mmol) was added dropwise and the reaction mixture was stirred at 0° C.

for 1 h. Cold saturated sodium hydrogen carbonate solution (200 mL) was added and the reaction mixture was stirred at 0° C. for 15 min. The organic layer was separated, washed with saturated sodium hydrogen carbonate solution and brine, dried over sodium sulfate, filtered and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (20 mmol), which was used crude in the next step. A solution of (S)-1-[(S)-2-((S)-2-amino-3-methyl-butyrylamino)-propionyl]-hexahydro-pyridazine-3-carboxylic acid 2,2,2-trichloro-ethyl ester (20 mmol) in acetonitrile (240 mL) was stirred at 0° C. under nitrogen. (E)-Pent-3-enoic acid (2.20 g, 2.2 mL, 22 mmol) and 1-hydroxybenzotriazole hydrate (3.82 g, 20 mmol, wetted with not less than 20 wt. % water) and N-(3-dimethylaminopropyl)-N'-ethylcarbodiimide hydrochloride (5.38 g, 28 mmol) was added and the reaction mixture was stirred at 0° C. for 15 min and then at RT for 20 h. The solvent was evaporated and the residue was partitioned between ethyl acetate and water. The organic extracts were combined, washed with water and brine, dried over anhydrous sodium sulfate, filtered and evaporated. The residue was purified by silica gel chromatography using iso-hexanes/ethyl acetate 3:1 to neat ethyl acetate to afford the title compound (9.0 g, 88%) as a white solid.

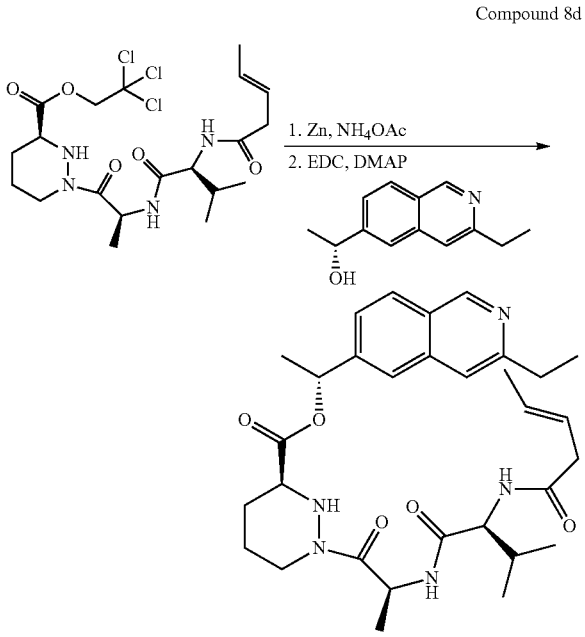

A solution of 8c (9.0 g, 17.5 mmol) in tetrahydrofuran (300 mL) was stirred at RT under nitrogen. Zinc powder (25.0 g, 385 mmol) was added followed by a solution of ammonium acetate (20.2 g, 263 mmol) in water (200 mL). The reaction mixture was stirred at RT under nitrogen for 18 h. The reaction mixture was filtered through Celite and the filter pad was washed with water (100 mL) and ethyl acetate (200 mL). The organic layer was separated and the solvent was evaporated to ca. 100 mL and the solution was extracted with water (100 mL). The aqueous layers were combined, saturated ammonium chloride solution (150 mL) was added and the solution was acidified to pH 1 with 2 M aqueous hydrochloric acid. The solution was extracted with ethyl acetate and the organic extracts were combined, washed with brine, dried over anhydrous magnesium sulfate, filtered and evaporated. The residue was co-evaporated with toluene (3×) to afford (S)-1-{(S)-2-[(S)-3-methyl-2-((E)-pent-3-enoylamino)-butyrylamino]-propionyl}-hexahydro-pyridazine-3-carboxylic acid (5.7 g, 85%) as a white solid which was used in the next reaction. A solution of (S)-1-{(S)-2-[(S)-3-methyl-2-((E)-pent-3-enoylamino)-butyrylamino]-propionyl}-hexahydro-pyridazine-3-carboxylic acid (5.16 g, 13.5 mmol) in dichloromethane (280 mL) and tetrahydrofuran (20 mL) was stirred at RT under nitrogen. (R)-1-(3-Vinyl-isoquinolin-6-yl)-ethanol (2.69 g, 13.5 mmol) was added followed by N-(3-dimethylaminopropyl)-N'-ethylcarbodiimide hydrochloride (3.63 g, 18.9 mmol) and 4-(dimethylamino)pyridine (1.64 g, 13.5 mmol) and the reaction mixture was stirred at RT for 6 h. Dichloromethane (200 mL) was added and the solution was washed with aqueous citric acid solution (pH 2-3). The organic layer was separated, washed with water and brine, dried over anhydrous sodium sulfate, filtered and evaporated. The residue was purified by silica gel chromatography using a gradient of iso-hexanes/ethyl acetate 3:1 to neat ethyl acetate followed by silica gel chromatography using iso-hexanes/ethyl acetate 1:8 to afford the title compound (3.91 g, 51%) as a white solid.

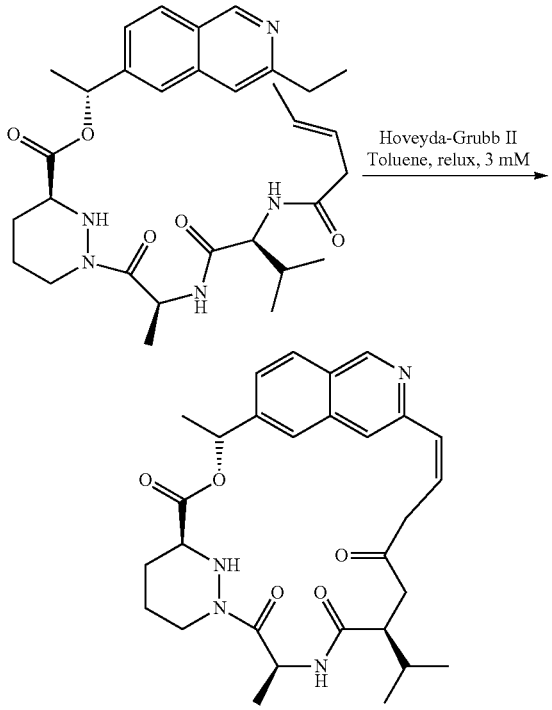

Example 8

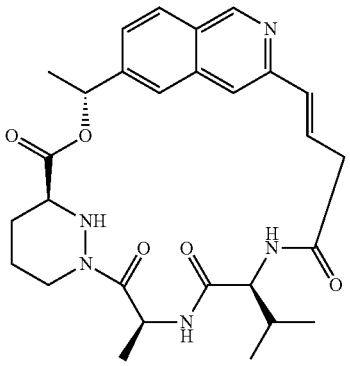

Example 9

A solution of 8d (1.13 g, 2 mmol) in toluene (600 mL) was stirred at RT under nitrogen for 15 min. Hoveyda-Grubbs $2^{nd}$ generation catalyst (125 mg, 0.2 mmol) was added and the reaction mixture was heated at reflux under nitrogen for 30 min. Additional Hoveyda-Grubbs $2^{nd}$ generation catalyst (125 mg, 0.2 mmol) was added and the reaction mixture was heated at reflux for 30 min. The reaction mixture was cooled to RT. The majority of the solvent was evaporated, silica gel was added and the solvent was evaporated. The residue was purified by silica gel chromatography using a gradient of ethyl acetate/acetone 9:1 to 3:2 followed by silica gel chromatography using ethyl acetate/methanol 40:1. The residue was triturated with ethyl acetate/ether (1:4) and the resulting solid was collected, washed with ethyl acetate/ether (1:4) and dried to afford a ~10:1 mixture of Compound 9 and Compound 8, as a pale brown solid (245 mg). A sample of the mixture was purified by reverse phase preparative HPLC to afford Compound 8 (4 mg) as a white solid. $^1$H NMR (300 MHz, $CD_3OD$) δ 1.01 (d, J=6.5 Hz, 3H), 1.02 (d, J=6.5 Hz, 3H), 1.37 (d, J=7.1 Hz, 3H), 1.65 (d, J=6.5 Hz, 3H), 1.70-2.15 (m, 5H), 2.95-3.05 (m, 1H), 3.70-3.76 (m, 1H), 4.03-4.10 (m, 2H), 4.12 (d, J=8.3 Hz, 1H), 5.64 (q, J=7.1 Hz, 1H), 6.10-6.20 (m, 2H), 6.98 (d, J=11.3 Hz, 1H), 7.65 (d, J=8.5 Hz, 1H), 7.93 (s, 1H), 8.05-8.10 (m, 2H), 9.21 (s, 1H). LCMS (m/z) 522.3 [M+H], Tr=1.25 min.

Compound 9, $^1$H NMR (300 MHz, $CDCl_3$) δ 0.97 (d, J=6.9 Hz, 3H), 0.99 (d, J=6.7 Hz, 3H), 1.53 (d, J=6.9 Hz, 3H), 1.71 (d, J=6.9 Hz, 3H), 1.75-2.70 (m, 6H), 3.20-3.40 (m, 2H), 3.63-3.77 (m, 2H), 4.23-4.29 (m, 1H), 4.53-5.57 (m, 1H), 5.65-5.76 (m, 1H), 6.04 (q, J=6.7 Hz, 1H), 6.38-6.53 (m, 3H), 6.72 (d, J=16.3 Hz, 1H), 7.39 (d, J=8.3 Hz, 1H), 7.55 (s, 1H), 7.72 (s, 1H), 7.92 (d, J=8.3 Hz, 1H), 9.13 (s, 1H). LCMS (m/z) 522.0 [M+H], Tr=1.40 min.

Example 10

Compound 10

Compound 10a

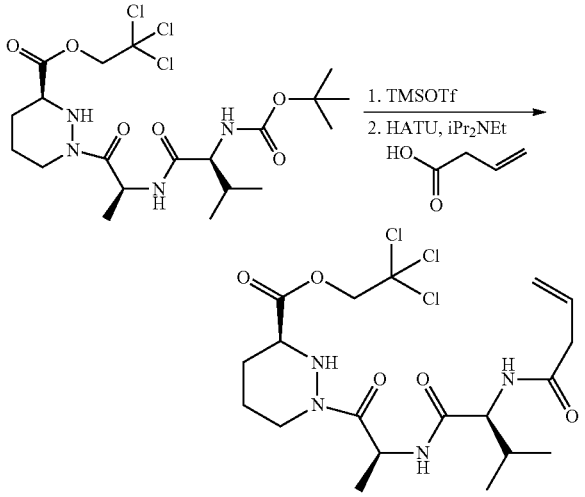

10a was prepared in the same manner as 4d using 3-butenoic acid instead of 4,4-dimethyl-hept-6-enoic acid in 66% yield.

Compound 10b

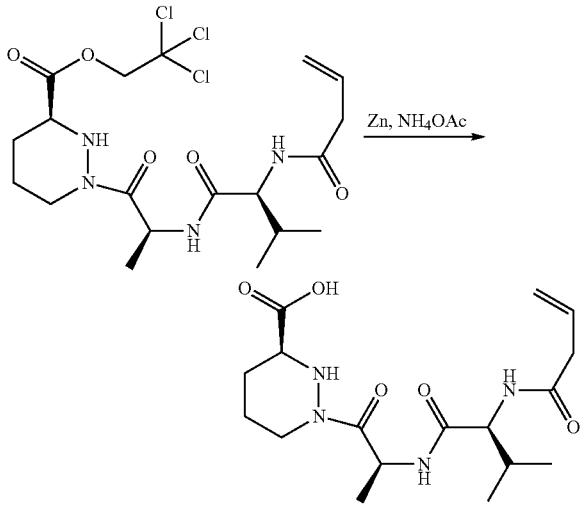

10b was prepared in the same manner as 4e using (S)-1-[(S)-2-((S)-2-but-3-enoylamino-3-methyl-butyrylamino)-propionyl]-hexahydro-pyridazine-3-carboxylic acid 2,2,2-trichloro-ethyl ester instead of (S)-1-{(S)-2-[(S)-2-(4,4-dimethyl-hept-6-enoyloxy)-3-methyl-butyrylamino]-propionyl}-hexahydro-pyridazine-3-carboxylic acid 2,2,2-trichloro-ethyl ester in 84% yield.

Compound 10c

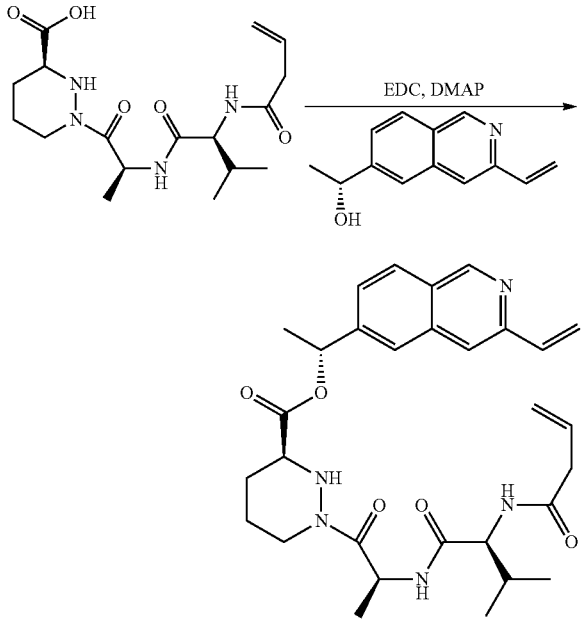

10c was prepared in the same manner as 8d using (S)-1-[(S)-2-((S)-2-but-3-enoylamino-3-methyl-butyrylamino)-propionyl]-hexahydro-pyridazine-3-carboxylic acid instead of (S)-1-{(S)-2-[(S)-3-methyl-2-((E)-pent-3-enoylamino) butyrylamino]-propionyl}-hexahydro-pyridazine-3-carboxylic acid in 84% yield.

Compound 9

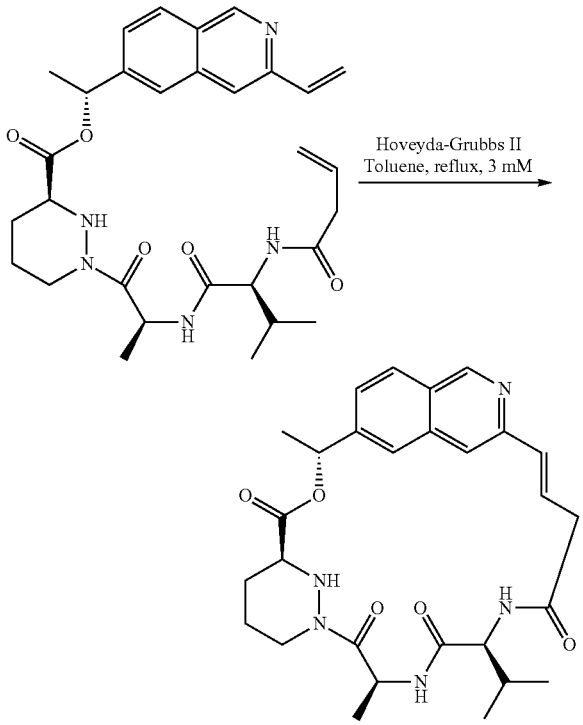

Compound 9 was prepared in the same manner as Compound 5 using (S)-1-[(S)-2-((S)-2-but-3-enoylamino-3-methyl-butyrylamino)-propionyl]-hexahydro-pyridazine-3-carboxylic acid (R)-1-(3-vinyl-isoquinolin-6-yl)-ethyl ester instead of (S)-1-{(S)-2-[(S)-2-((E)-(2R,3R)-3-methoxy-2-methyl-hex-4-enoylamino)-3-methyl-butyrylamino]-propionyl}-hexahydro-pyridazine-3-carboxylic acid [(R)-1-(3-vinyl-isoquinolin-6-yl)-ethyl]-amide in 9% yield.

Compound 10

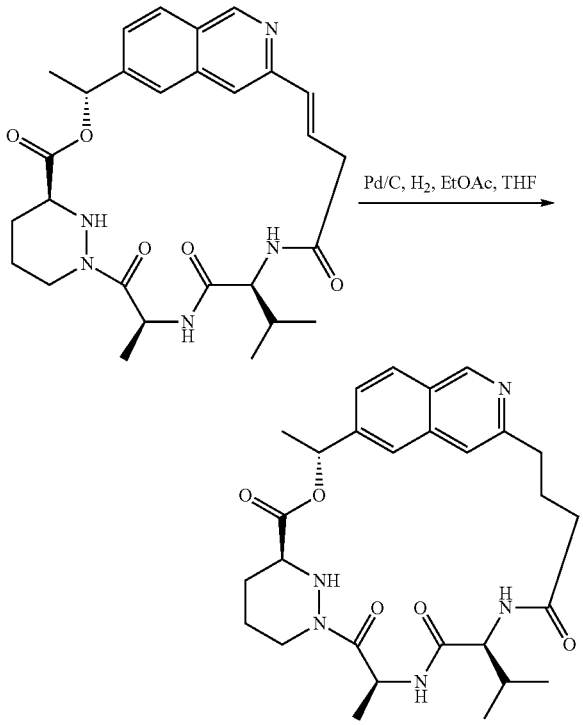

A solution of Compound 9 (16 mg, 0.03 mmol) in ethyl acetate (5 mL) and tetrahydrofuran (2 mL) containing 10% palladium on carbon (15 mg) was hydrogenated at RT and pressure for 3 h. The reaction mixture was filtered through filter aid and the filter pad was washed with ethyl acetate. The filtrate was evaporated and the residue was triturated with ether (2×2 mL) and the resulting solid was dried to afford the title compound (7.6 mg, 48%) as an off-white solid. $^1$H NMR (300 MHz, $CDCl_3$) δ 0.90 (d, J=6.7 Hz, 3H), 0.95 (d, J=6.5 Hz, 3H), 1.50 (d, J=7.1 Hz, 3H), 1.68 (d, J=6.5 Hz, 3H), 1.60-2.40 (m, 9H), 2.70-3.10 (m, 3H), 3.68-3.75 (m, 1H), 3.90 (d, J=11.8 Hz, 1H), 4.32-4.37 (m, 1H), 4.44-4.49 (m, 1H), 5.83-5.92 (m, 1H), 6.05-6.11 (m, 2H), 6.33 (d, J=7.8 Hz, 1H), 7.34 (s, 1H), 7.36 (d, J=8.3 Hz, 1H), 7.80 (s, 1H), 7.93 (d, J=8.3 Hz, 1H), 9.17 (s, 1H). LCMS (m/z) 524.3 [M+H], Tr=0.59 min.

Examples 11 and 12

Compounds 11 and 12

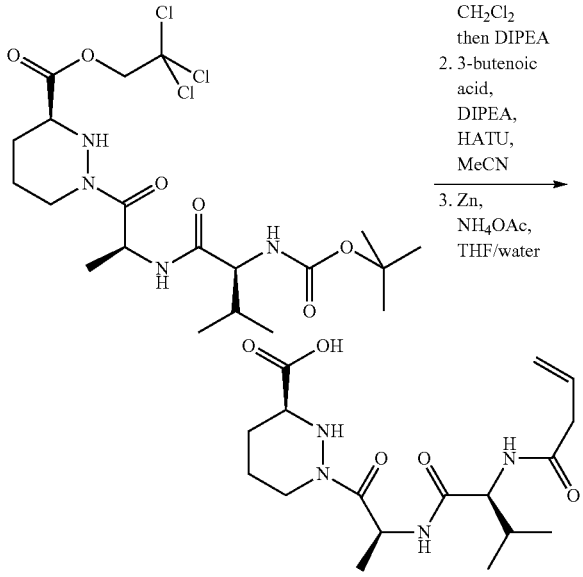

Compound 11a

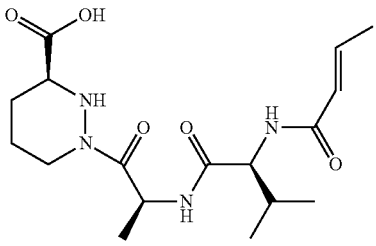

Compound 12b

To a stirred solution of 1e (10.6 g, 20.0 mmol) in dichloromethane (400 mL), at 0° C. under nitrogen, was added trimethylsilyl trifluoromethanesulfonate (6.67 g, 5.43 mL, 30.0 mmol) and the reaction mixture stirred at 0° C. for 2 h. N,N-Diisopropylethylamine (10.3 g, 13.9 mL, 80.0 mmol) was added and the mixture allowed to warm to ambient temperature. The volatiles were evaporated and the residue suspended in acetonitrile (250 mL). The stirred mixture was cooled to 0° C. under a blanket of nitrogen and then N,N-diisopropylethylamine (10.3 g, 13.9 mL, 80 mmol) and 3-butenoic acid (1.89 g, 1.86 mL, 4.40 mmol) added, followed by 2-(1H-7-azabenzotriazol-1-yl)-1,1,3,3-tetramethyl uronium hexafluorophosphate methanaminium (10.6 g, 28.0 mmol), portionwise. The reaction mixture was allowed to warm to ambient temperature and stirred for 18 h before evaporating. The residue was diluted with ethyl acetate and then washed successively with saturated sodium bicarbonate solution, water, 2 M hydrochloric acid, water then brine, dried over magnesium sulfate, filtered and evaporated. The residue was purified by silica gel chromatography using a gradient of iso-hexanes/ethyl acetate 1:1 to 0:1 to afford a ~1:1 mixture of (S)-1-[(S)-2-((S)-2-but-3-enoylamino-3-methyl-butyrylamino)-propionyl]-hexahydro-pyridazine-3-carboxylic acid 2,2,2-trichloro-ethyl ester and (S)-1-{(S)-2-[(S)-2-((E)-but-2-enoylamino)-3-methyl-butyrylamino]-propionyl}-hexahydro-pyridazine-3-carboxylic acid 2,2,2-trichloro-ethyl ester as an orange foam (7.23 g, 72%).

To a stirred solution of a mixture of (S)-1-[(S)-2-((S)-2-but-3-enoylamino-3-methyl-butyrylamino)-propionyl]-hexahydro-pyridazine-3-carboxylic acid 2,2,2-trichloro-ethyl ester and (S)-1-{(S)-2-[(S)-2-((E)-but-2-enoylamino)-3-methyl-butyrylamino]-propionyl}-hexahydro-pyridazine-3-carboxylic acid 2,2,2-trichloro-ethyl ester (~1:1, 0.99 g, 2.00 mmol) in tetrahydrofuran (40 mL) was added zinc powder (2.86 g, 44.0 mmol) and a solution of ammonium acetate (2.31 g, 30.0 mmol) in water (25 mL). The reaction mixture was allowed to warm to ambient temperature and stirred for 18 h, then diluted with ethyl acetate and the mixture filtered. From the filtrate the aqueous layer was separated and diluted with an equal amount of saturated ammonium chloride solution and then acidified to pH 1 with 2 M hydrochloric acid. The aqueous layer was extracted with ethyl acetate (2×) and the combined organic layers washed with brine, dried over magnesium sulfate, filtered and evaporated. The residue was azeotroped with toluene (3×) to give a mixture of the title compounds (~1:1, 466 mg, 63%) as a yellow foam.

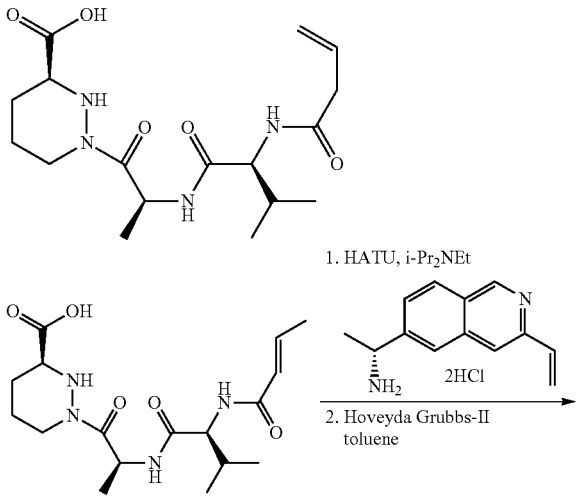

-continued

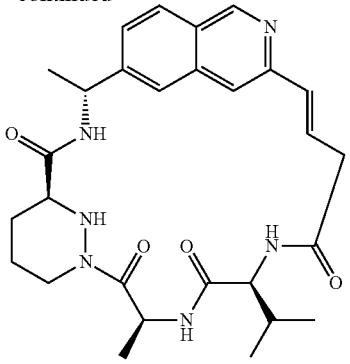

Compound 11

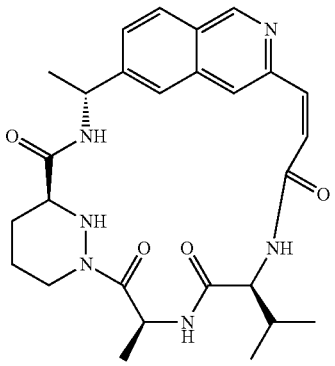

Compound 12

A mixture of 11a and 12b (~1:1, 250 mg, 0.68 mmol) in acetonitrile (20 mL) was stirred at RT under nitrogen. (R)-1-(3-vinyl-isoquinolin-6-yl)-ethylamine dihydrochloride (136 mg, 0.5 mmol) and N,N-diisopropylethylamine (323 mg, 0.44 mL, 2.5 mmol) was added followed by 2-(1H-7-azabenzotriazol-1-yl)-1,1,3,3-tetramethyl uronium hexafluorophosphate methanaminium (266 mg, 0.7 mmol) and the reaction mixture was stirred at RT for 18 h. The solvent was evaporated. The residue was diluted with ethyl acetate and the solution was washed with saturated sodium hydrogen carbonate solution, water and brine. The organic extract was dried over anhydrous magnesium sulfate, filtered and evaporated. The residue was purified by silica gel chromatography using a gradient of ethyl acetate to methanol/ethyl acetate 1:5 to afford a ~1:1 mixture of (S)-1-[(S)-2-((S)-2-but-3-enoylamino-3-methyl-butyrylamino)-propionyl]-hexahydro-pyridazine-3-carboxylic acid [(R)-1-(3-vinyl-isoquinolin-6-yl)-ethyl]-amide and (S)-1-{(S)-2-[(S)-2-((E)-but-2-enoylamino)-3-methyl-butyrylamino]-propionyl}-hexahydro-pyridazine-3-carboxylic acid [(R)-1-(3-vinyl-isoquinolin-6-yl)-ethyl]-amide as a white solid (153 mg, 56%) which was used in the next step without further purification.

A solution of a mixture of (S)-1-[(S)-2-((S)-2-but-3-enoylamino-3-methyl-butyrylamino)-propionyl]-hexahydro-pyridazine-3-carboxylic acid [(R)-1-(3-vinyl-isoquinolin-6-yl)ethyl]-amide and (S)-1-{(S)-2-[(S)-2-((E)-but-2-enoylamino)-3-methyl-butyrylamino]-propionyl}-hexahydro-pyridazine-3-carboxylic acid [(R)-1-(3-vinyl-isoquinolin-6-yl)-ethyl]-amide (~1:1, 150 mg, 0.27 mmol) in toluene (70 mL) was stirred at RT under nitrogen.

Hoveyda-Grubbs $2^{nd}$ generation catalyst (17 mg, 0.027 mmol) was added and the reaction mixture was heated at reflux under nitrogen for 90 min. Additional Hoveyda-Grubbs $2^{nd}$ generation catalyst (17 mg, 0.027 mmol) was added and the reaction mixture was heated at reflux under nitrogen for 90 min. The reaction mixture was cooled to RT, silica gel was added and the solvent was evaporated. The residue was purified by silica gel chromatography using a gradient of ethyl acetate to ethyl acetate/acetone 1:1. The residue was further purified by preparative thin layer chromatography using methanol/ethyl acetate 1:4 followed by silica gel chromatography using dichloromethane/methanol 20:1 to give the title compounds. Compound 11 (1.3 mg, 1%) as a white solid: $^1$H NMR (300 MHz, $CD_3OD$) δ 1.01 (d, J=6.7 Hz, 3H), 1.02 (d, J=6.7 Hz, 3H), 1.61 (d, J=7.1 Hz, 3H), 1.66 (d, J=7.1 Hz, 3H), 1.80-2.05 (m, 5H), 2.71-2.82 (m, 1H), 2.99-3.05 (m, 1H), 3.32-3.43 (m, 1H), 3.64-3.75 (m, 1H), 4.27 (d, J=10.1 Hz, 1H), 4.40-4.53 (m, 2H), 5.12 (q, J=7.1 Hz, 1H), 5.62 (q, J=7.1 Hz, 1H), 6.47-6.56 (m, 1H), 6.62 (d, J=15.8 Hz, 1H), 7.43 (s, 1H), 7.61 (dd, J=8.5, 1.6 Hz 1H), 7.74 (s, 1H), 8.05 (d, J=8.5 Hz, 1H), 9.13 (s, 1H). LCMS (m/z) 521.3 [M+H], Tr=0.97 min.

Compound 12 (1.7 mg, 1.2%) as a white solid: $^1$H NMR (300 MHz, $CD_3OD$) δ 0.98 (d, J=6.7 Hz, 3H), 1.03 (d, J=6.7 Hz, 3H), 1.47 (d, J=7.1 Hz, 3H), 1.60 (d, J=6.9 Hz, 3H), 1.65-2.16 (m, 5H), 2.81-2.89 (m, 1H), 3.61-3.69 (m, 1H), 4.04 (d, J=6.9 Hz, 1H), 4.30-4.36 (m, 1H), 4.75 (d, J=11.6 Hz, 1H), 5.23 (q, J=7.1 Hz, 1H), 5.90 (q, J=6.9 Hz, 1H), 6.36 (d, J=13.1 Hz, 1H), 6.92 (d, J=13.1 Hz, 1H), 7.65 (d, J=8.5 Hz 1H), 7.88 (s, 1H), 8.05 (d, J=8.5 Hz 1H), 8.46 (s, 1H), 9.16 (s, 1H). LCMS (m/z) 507.2 [M+H], Tr=0.95 min.

Example 13

Compound 13

Compound 13a

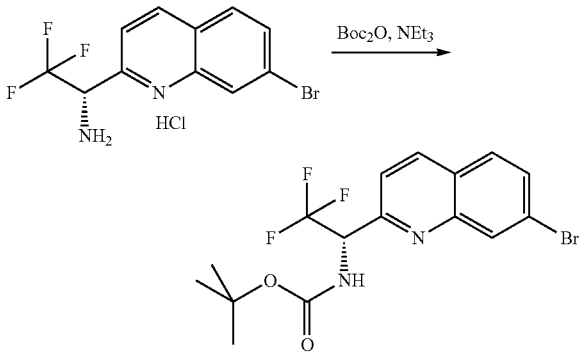

A suspension of (S)-1-(7-bromo-quinolin-2-yl)-2,2,2-trifluoro-ethylamine hydrochloride (Asiba Pharmatech, Edison, N.J., USA, 397 mg, 1.16 mmol) in dichloromethane (10 mL) was cooled using an ice bath. Triethylamine (985 μL, 3.48 mmol) was added and the reaction was stirred until a homogenous solution was observed. Di-tert-butyl dicarbonate (380 mg, 1.74 mmol) in dichloromethane (5 mL) was then added and the reaction was left to stir overnight. Di-tert-butyl dicarbonate (127 mg, 0.58 mmol) was added and the reaction was stirred for a further 6 h. Di-tert-butyl dicarbonate (253 mg, 1.16 mmol) was added along with 4 Å molecular sieves and the reaction was left to stir overnight. The reaction was washed with water and brine and the organics were dried over anhydrous sodium sulfate, filtered and concentrated. The residue was purified by silica gel chromatography using a stepwise gradient from 1:0 to 7:3 iso-hexanes/ethyl acetate to afford the title compound (343 mg, 73%) as an orange solid.

Compound 13b

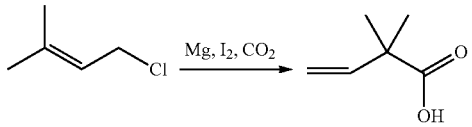

To a 3-necked flask, fitted with stirrer bar and thermometer, under an atmosphere of nitrogen and containing magnesium turnings (3.02 g, 0.124 mol) was added anhydrous tetrahydrofuran (105 mL). A single crystal of iodine was added to the reaction followed by 1-chloro-3-methyl-but-2-ene (2 mL, 17.75 mmol). The reaction was stirred for 20 min until all color had left the solution. 1-chloro-3-methyl-but-2-ene (5.57 mL, 49.45 mmol) was added. A gradual temperature increase was observed until the reaction had reached reflux. The reaction was left to stir for 1 hour, allowing the reaction to return to RT. The reaction was then transferred via cannula to a flask containing solid carbon dioxide (50 g). The reaction was then stirred for 2 h. A cooling ice bath was added and the reaction was quenched with 2 M hydrochloric acid. The reaction mixture was then extracted with diethyl ether. The organics were then dried over anhydrous sodium sulfate, filtered and concentrated. The residue was purified by silica gel chromatography using a stepwise gradient from 1:0 to 9:1 iso-hexanes/ethyl acetate to afford the title compound (2.69 g, 35%) as a pale yellow oil. $^1$H NMR (300 MHz, $CDCl_3$) δ 1.35 (s, 6H), 5.10-5.21 (m, 2H), 6.07 (dd, J=17.6, 10.5 Hz, 1H).

Compound 13c

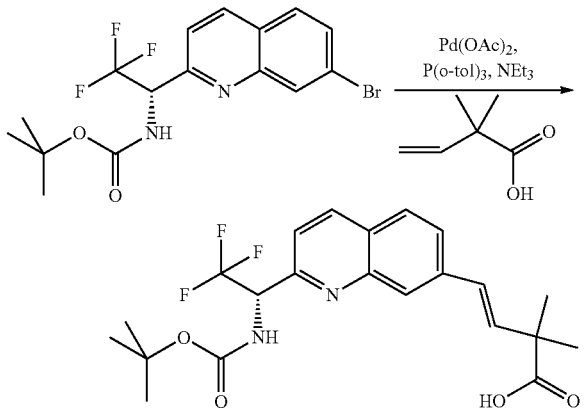

13a (343 mg, 0.846 mmol) and 13b (106 mg, 0.931 mmol) were placed in a microwave vessel and dissolved in acetonitrile (3 mL). Palladium(II) acetate (19 mg, 0.0846 mmol), tri(o-tolyl)phosphine (51 mg, 0.169 mmol) and triethylamine (236 μL, 1.69 mmol) were added and the vessel was sealed before being irradiated in the microwave for 30 min, using fixed hold time, on high absorption at 100° C. The solvent was removed and the residue was taken up in a mixture of water and ethyl acetate. The phases were separated and the aqueous was extracted with ethyl acetate. The combined organics were then dried over anhydrous sodium sulfate, filtered and concentrated. The residue was purified by silica gel chromatography using a stepwise gradient of iso-hexanes/ethyl acetate from 1:0 to 6:4. The isolated material was subjected to a second purification using the same conditions to afford the title compound (142 mg, 38%) as a pale yellow oil.

Compound 13d

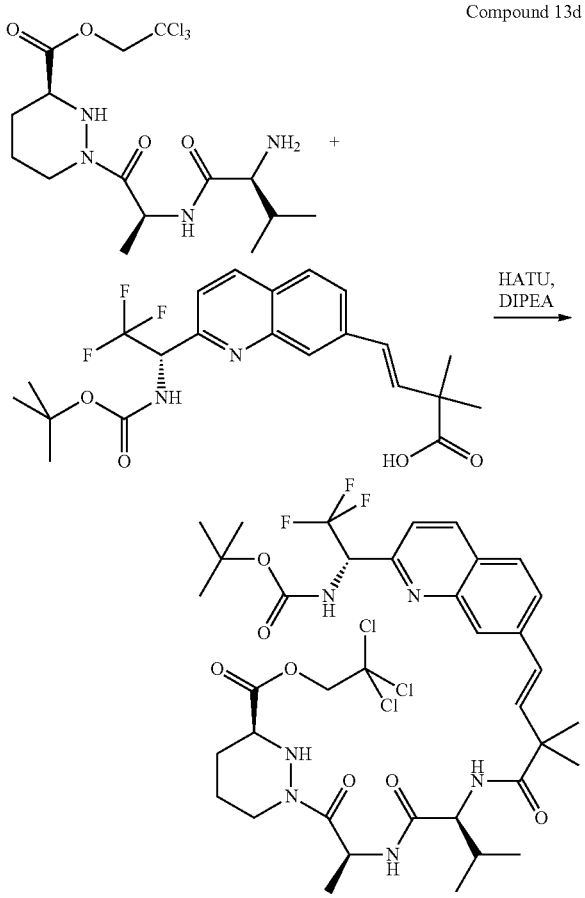

(S)-1-[(S)-2-((S)-2-Amino-3-methyl-butyrylamino)-propionyl]-hexahydro-pyridazine-3-carboxylic acid ethyl ester (210 mg, 0.486 mmol) and 13c (142 mg, 0.324 mmol) were dissolved in N,N-dimethylformamide (5 mL), under an atmosphere of nitrogen, and cooled using an ice bath. 2-(1H-7-azabenzotriazol-1-yl)-1,1,3,3-tetramethyl uronium hexafluorophosphate methanaminium (203 mg, 0.535 mmol) and N,N-diisopropylethylamine (423 μL, 2.43 mmol) were then added and the reaction was allowed to slowly warm to RT and left to stir overnight. The reaction was diluted with water and extracted with ethyl acetate. The combined organics were dried over anhydrous sodium sulfate, filtered and concentrated. The residue was purified by silica gel chromatography using a stepwise gradient of iso-hexanes/ethyl acetate from 1:0 to 0:1 to afford the product contaminated with residual solvent. Toluene was added and the solution was concentrated to afford the title compound (79 mg, 29%) as an orange solid.

Compound 13e

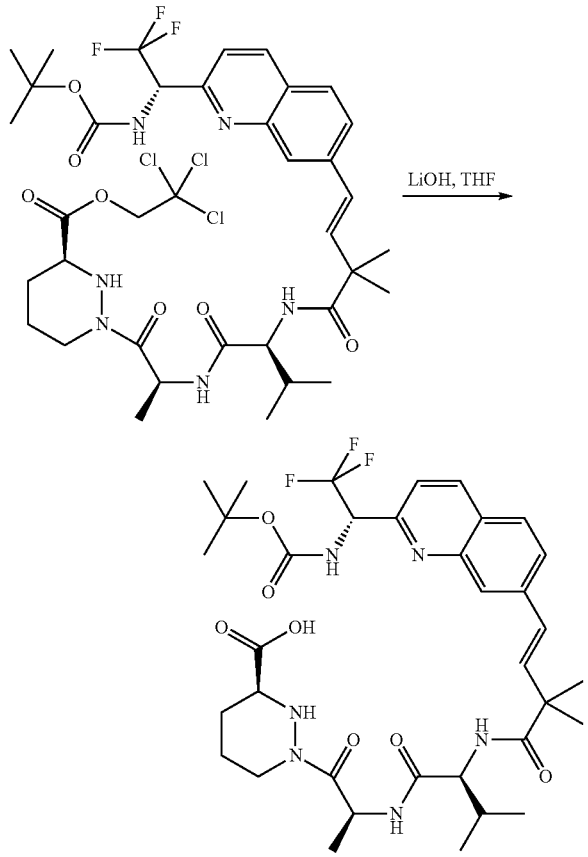

13d (79 mg, 0.0925 mmol) was dissolved in tetrahydrofuran (2 mL) and cooled using an ice bath. Methanol (1 mL) and water (1 mL) were then added followed by lithium hydroxide monohydrate (15 mg, 0.37 mmol). The reaction was then left to stir for 1 hour. 1 M hydrochloric acid was added until the solution was pH 2. The solvent was removed and the resultant solid was sequentially azeotroped with methanol, then acetonitrile and finally toluene to afford the title compound (67 mg, 100%) as a yellow solid.

Compound 13f

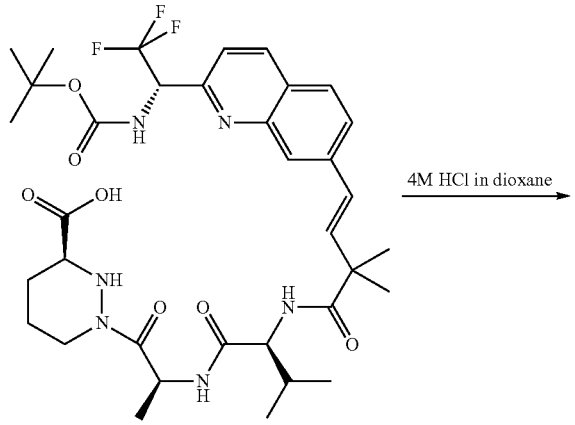

-continued

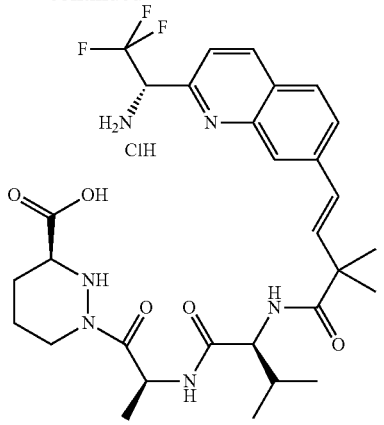

13e (66 mg, 0.0916 mmol) was dissolved in 4 M hydrochloric acid in 1,4-dioxane (2 mL) and left to stir for 30 min. The solvent was removed and the resultant solid was triturated with diethyl ether and dried to afford the title compound (50 mg, 83%) as a pale yellow solid.

Compound 13

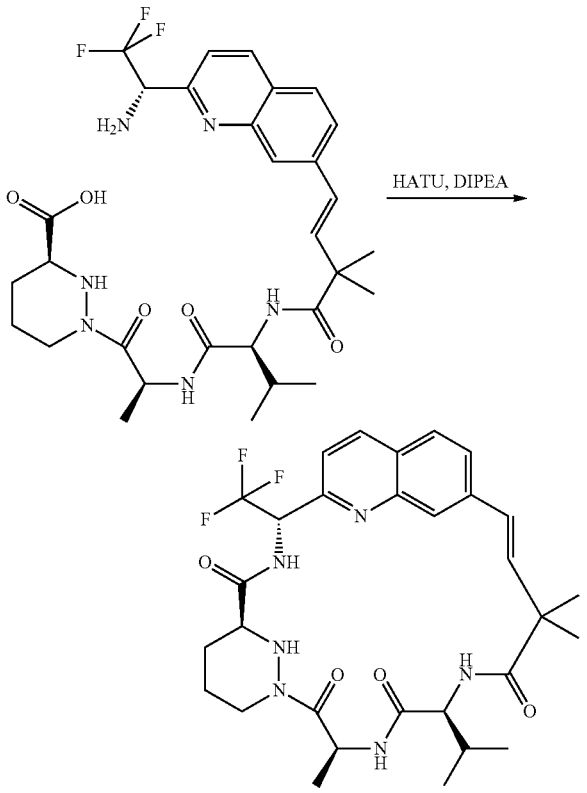

13f (50 mg, 0.0761 mmol) was dissolved in dichloromethane (76 mL), under an atmosphere of nitrogen and cooled using an ice bath. 2-(1H-7-Azabenzotriazol-1-yl)-1,1,3,3-tetramethyl uronium hexafluorophosphate methanaminium (58 mg, 0.152 mmol) and N,N-diisopropylethylamine (53 μL, 0.304 mmol) were then added and the reaction was allowed to slowly warm to RT and left to stir overnight. The solvent was removed and the residue was purified by silica gel chromatography using 7:3 iso-hexanes/acetone. The residue was re-purified by silica gel chromatography using a stepwise gradient of iso-hexanes/acetone from 1:0 to 1:1. The residue was then eluted through an HPLC system fitted with a Phenomenex Gemini 10μ 110A, 250×21.2 mm column using a continuous gradient of acetonitrile/water from 1:4 to 1:0 flow at 20 mL/min to afford the title compound (7 mg, 15%) as a solid. $^1$H NMR (300 MHz, $CDCl_3$) δ 086-1.08 (m, 6H), 1.25-1.54 (m, 8H), 1.57-1.81 (m, 5H), 1.88-2.00 (m, 1H), 2.37-2.80 (m, 1H), 3.32-3.65 (m, 1H), 3.69-3.97 (m, 1H), 4.22-4.39 (m, 1H), 4.50-4.68 (m, 1H), 5.74-6.05 (m, 2H), 6.22-6.39 (m, 1H), 6.44-6.54 (m, 1H), 6.63-6.76 (m, 1H), 7.45 (app t, J=8.5 Hz, 1H), 7.56 (app t, J=7.6 Hz, 1H), 7.81 (d, J=8.3 Hz, 1H), 8.19 (s, 1H), 8.76-9.09 (m, 1H). LCMS (m/z) 603.1 [M+H], Tr=2.59 min.

Example 14

Compound 14

Compound 14a

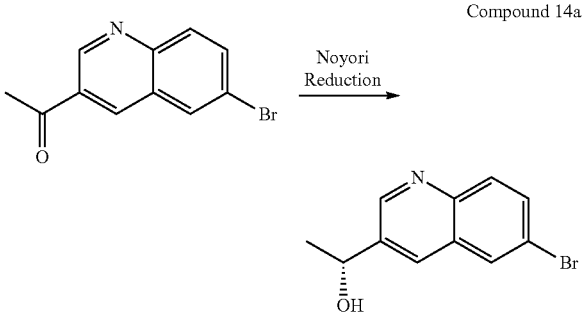

Dichloro (p-cymene) ruthenium(II) dimer (24 mg, 0.040 mmol) and (1R,2R)-(−)-N-p-tosyl-1,2-diphenylethylenediamine (35 mg, 0.096 mmol) were suspended in degassed water (16 mL) and the mixture was degassed with nitrogen for 15 min. The mixture was stirred at 70° C. under nitrogen for 90 min. The resulting turbid orange mixture was allowed to cool to RT. Solid 1-(6-bromo-quinolin-3-yl)-ethanone (prepared as in WO2011/063233, 1.92 g, 7.68 mmol) followed by degassed tetrahydrofuran (16 mL) and sodium formate (2.72 g, 40 mmol) were added and the reaction mixture was degassed with nitrogen for 5 min, further degassed tetrahydrofuran (5 mL) was added and the mixture degassed for another minute. The reaction mixture was vigorously stirred at 40° C. for 21 h and allowed to cool. It was then diluted with ethyl acetate and the mixture washed with water then brine, dried over magnesium sulfate, filtered and evaporated. The residue was purified by silica gel chromatography using a gradient of iso-hexanes/ethyl acetate 7:3 to 0:1 to afford the title compound (1.65 g, 85%) as a brown solid.

Compound 14b

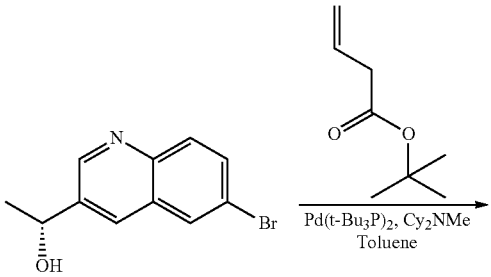

-continued

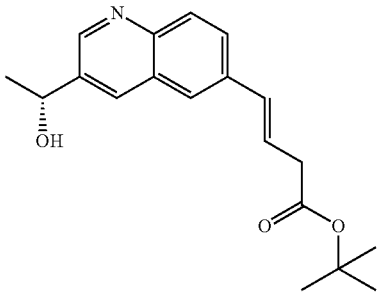

To a mixture of 14a (356 mg, 1.41 mmol), N,N-dicyclohexylmethylamine (275 mg, 301 μL, 1.41 mmol) and tert-butyl 3-butenoate (470 mg, 537 μL, 3.31 mmol) in toluene (14 mL) was added bis(tri-tert-butylphosphine)palladium(0) (30 mg, 0.058 mmol) under nitrogen and the reaction mixture stirred and heated under reflux for 90 min then allowed to cool. The mixture was evaporated and then purified by silica gel chromatography using a gradient of iso-hexanes/ethyl acetate 4:1 to 2:3 to afford the title compound as a yellow oil (144 mg, 33%).

To a stirred solution of (S)-1-[(S)-2-((S)-2-tert-butoxycarbonylamino-3-methyl-butyrylamino)-propionyl]-hexahydro-pyridazine-3-carboxylic acid (189 mg, 0.473 mmol) and 14b (148 mg, 0.473 mmol) in dichloromethane (10 mL) was added 1-hydroxybenzotriazole containing approx. 20% water (89 mg, 0.662 mmol) followed by 4-dimethylaminopyridine (58 mg, 0.473 mmol) then N-(3-dimethylaminopropyl)-N'-ethylcarbodiimide hydrochloride (127 mg, 0.662 mmol). The reaction was stirred for 62 h and then diluted with dichloromethane, washed with saturated ammonium chloride solution (2×) and brine, dried over magnesium sulfate, filtered and evaporated. Purified by silica gel chromatography using a gradient of iso-hexanes/ethyl acetate 3:1 to 2:3 afforded the title compound (126 mg, 38%) as a white foam.

Compound 14c

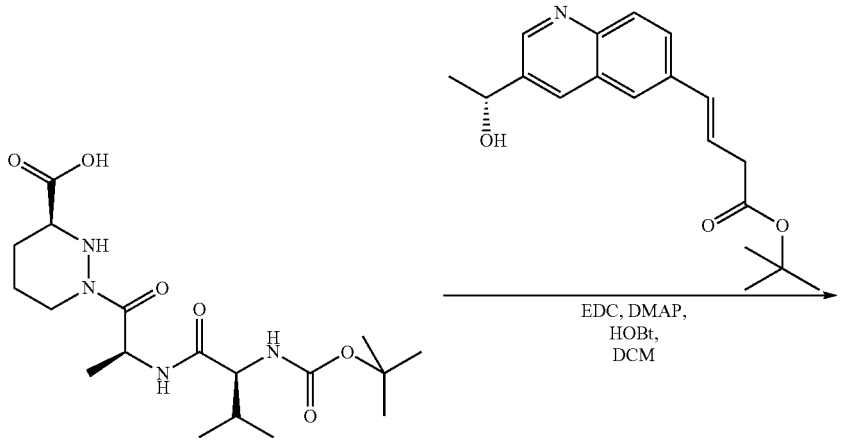

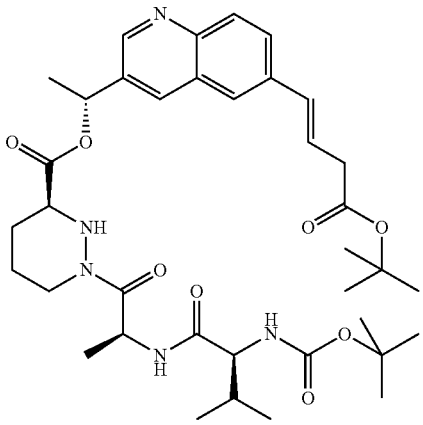

-continued

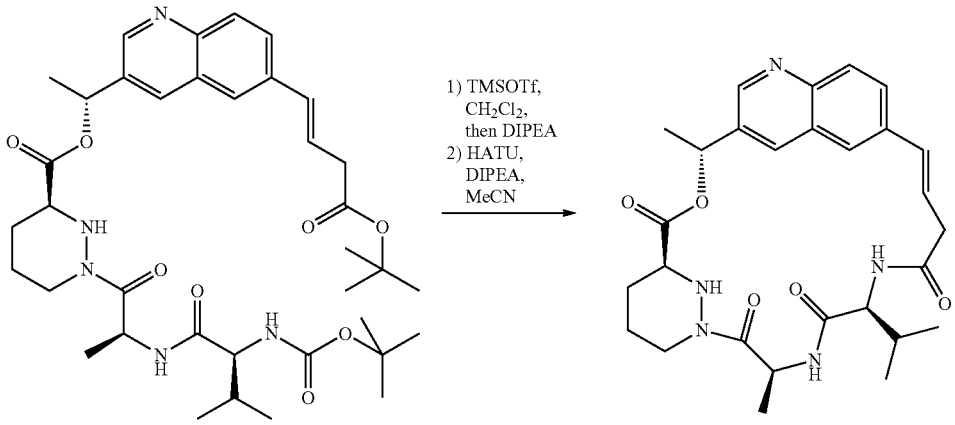

Compound 14

To a stirred solution of 14c (126 mg, 0.181 mmol) in dichloromethane (1.8 mL) at 0° C. under nitrogen was added trimethylsilyl trifluoromethanesulfonate (141 mg, 147 μL, 0.635 mmol) and the reaction mixture was allowed to warm to ambient temperature over 1.75 h. Further trimethylsilyl trifluoromethanesulfonate (20 mg, 21 μL, 0.091 mmol) was added and the reaction mixture was stirred for a further 15 min before the addition of N,N-diisopropylethylamine (164 221 μL, 1.27 mmol). After a further 10 min of stirring the reaction mixture was evaporated and then suspended in acetonitrile (18.1 mL). The stirred mixture was cooled to 0° C. and then 2-(1H-7-azabenzotriazol-1-yl)-1,1,3,3-tetramethyl uronium hexafluorophosphate methanaminium (96 mg, 0.253 mmol) and N,N-diisopropylethylamine (94 mg, 126 μL, 0.724 mmol) were added. After 45 min the reaction was quenched with saturated ammonium chloride solution (10 mL) and the mixture evaporated to remove organic volatiles. The residue was diluted with dichloromethane and the aqueous layer separated and extracted with dichloromethane. The organic extracts were washed with saturated sodium bicarbonate, water and then brine, dried over sodium sulfate, filtered and evaporated. The residue was purified by silica gel chromatography eluting with ethyl acetate/acetone 9:1 then by preparative reverse phase HPLC using a gradient of acetonitrile/water 3:7 to 1:1 to afford the title compound (6.5 mg, 7% over 2 steps) as a white solid. $^1$H NMR (300 MHz, $CD_3OD$) δ 1.00 (d, J=6.7 Hz, 3H), 1.03 (d, J=6.7 Hz, 3H), 1.61 (d, J=7.1 Hz, 3H), 1.75 (d, J=6.7 Hz, 3H), 1.91-2.01 (m, 3H), 2.68-2.79 (m, 1H), 3.00 (dd, J=14.5, 3.6 Hz, 1H), 3.35-3.42 (m, 1H), 3.73-3.82 (m, 1H), 4.29 (d, J=9.6 Hz, 1H), 4.41 (d, J=12.9 Hz, 1H), 4.70 (d, J=12.3 Hz, 1H), 5.47 (q, J=7.3 Hz, 1H), 6.15 (q, J=6.6 Hz, 1H), 6.30-6.40 (m, 1H), 6.63 (d, J=16.1 Hz, 1H), 7.55 (s, 1H), 7.82 (dd, J=8.7, 1.5 Hz, 1H), 7.95 (d, J=8.7 Hz, 1H), 8.21 (s, 1H), 8.79 (d, J=1.8 Hz, 1H). LCMS (m/z) 522.2 [M+H], Tr=1.60 min.

Example 15

Compound 15

Compound 15a

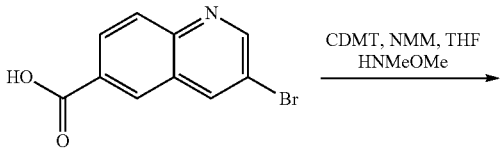

-continued

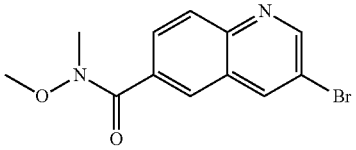

To a stirred mixture of 3-bromo-quinoline-6-carboxylic acid (prepared as in WO2011/090935, 1.94 g, 7.70 mmol) in tetrahydrofuran (77 mL) was added 2-chloro-4,6-dimethoxy-1,3,5-triazine (2.03 g, 11.5 mmol) and N-methylmorpholine (2.34 g, 2.54 mL, 23.1 mmol). The reaction mixture was stirred for 90 min and then N,O-dimethylhydroxylamine hydrochloride (751 mg, 7.70 mmol) added in one portion. The reaction mixture was stirred for a further 17 h and further N,O-dimethylhydroxylamine hydrochloride (375 mg, 3.85 mmol) was added and then after 5 h a further portion (175 mg, 1.80 mmol). The reaction mixture was stirred for a further hour and then diluted with dichloromethane, washed with water and then saturated ammonium chloride solution. The organic layer was dried over sodium sulfate, filtered and evaporated. The residue was purified by silica gel chromatography eluting with a gradient of isohexanes/ethyl acetate 4:1 to 7:3 to afford the title compound (1.43 g, 66%) as an off-white solid.

Compound 15b

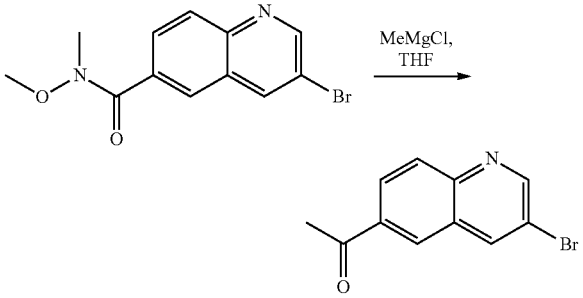

To a stirred solution of methyl magnesium chloride (3 M in tetrahydrofuran, 4.85 mL, 14.5 mmol) in tetrahydrofuran (10 mL) under nitrogen was added a solution of 15a (1.43 g, 4.85 mmol) in tetrahydrofuran (20 mL). The reaction mixture was stirred for 1 hour and then quenched with saturated ammonium chloride solution. The mixture was diluted with diethyl ether and water, the organic layer separated and washed with further water and the combined aqueous washes back-extracted with diethyl ether. The combined organic extracts were dried over magnesium sulfate, filtered and evaporated. The residue was purified by silica gel chromatography eluting with iso-hexanes/ethyl acetate 4:1 to afford the title compound as a white solid which was taken directly into the next step.

Compound 15c

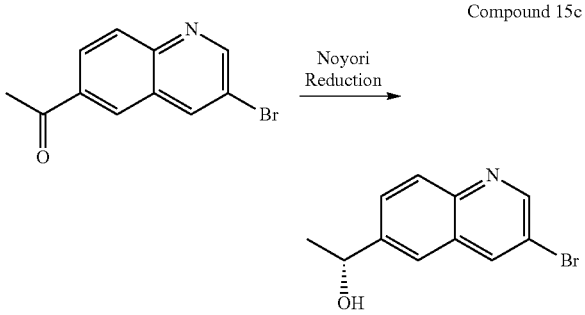

Dichloro (p-cymene) ruthenium(II) dimer (9 mg, 0.015 mmol) and (1R,2R)-(−)-N-p-tosyl-1,2-diphenylethylenediamine (14 mg, 0.037 mmol) were suspended in degassed water (9 mL) and the mixture was degassed with nitrogen for 15 min. The mixture was stirred at 70° C. under nitrogen for 90 min. The resulting turbid orange mixture was allowed to cool to RT. Solid 1-(3-bromo-quinolin-6-yl)-ethanone (771 mg, 3.08 mmol) and sodium formate (2.72 g, 40 mmol) followed by degassed tetrahydrofuran (4.5 mL) were added and the reaction mixture was degassed with nitrogen for 5 min. The reaction mixture was vigorously stirred at 40° C. for 3 h and allowed to cool. It was then diluted with ethyl acetate and the mixture washed with water then brine, dried over sodium sulfate, filtered and evaporated. The residue was purified by silica gel chromatography using a gradient of iso-hexanes/ethyl acetate 3:2 to 1:1 to afford the title compound (616 mg, 79%) as a grey solid.

Compound 15d

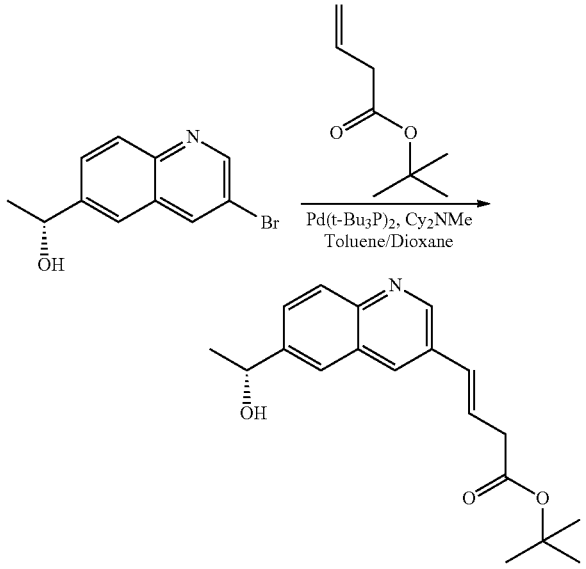

To a solution of 15c (560 mg, 2.22 mmol) in toluene (20 mL) and 1,4-dioxane (5 mL) was added N,N-dicyclohexylmethylamine (740 μL, 3.46 mmol) and tert-butyl 3-butenoate (741 mg, 844 μL, 5.22 mmol) was added bis(tri-tert-butylphosphine)palladium(0) (68 mg, 0.13 mmol) under nitrogen and the reaction mixture stirred and heated under reflux for 6 h then allowed to cool. The mixture was evaporated and then purified by silica gel chromatography using a gradient of iso-hexanes/ethyl acetate 4:1 to 0:1 to give a yellow gum. The gum was suspended in ethyl acetate and washed with saturated ammonium chloride solution (2×) followed by water then brine, dried over sodium sulfate, filtered and evaporated to afford the title compound (300 mg, 43%) as a yellow oil.

Compound 15e

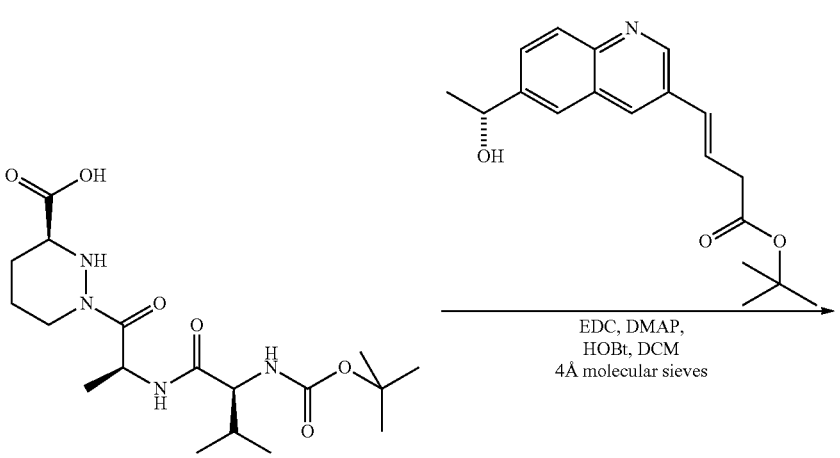

-continued

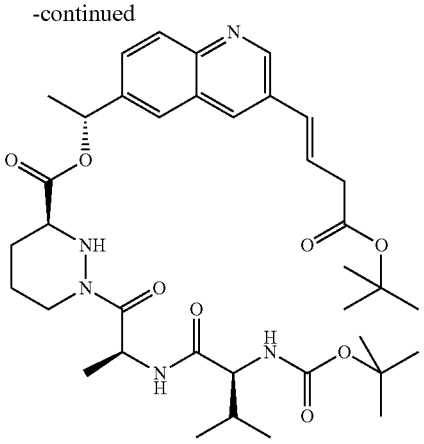

To a stirred slurry of (S)-1-[(S)-2-((S)-2-tert-butoxycarbonylamino-3-methyl-butyrylamino)-propionyl]-hexahydro-pyridazine-3-carboxylic acid (325 mg, 0.812 mmol), 15d (231 mg, 0.738 mmol) and powdered 4 Å molecular sieves in dichloromethane (16 mL) was added N-(3-dimethylaminopropyl)-N'-ethylcarbodiimide hydrochloride (198 mg, 1.03 mmol), 1-hydroxybenzotriazole hydrate containing approx. 20% water (174 mg, 1.03 mmol) followed by 4-dimethylaminopyridine (90 mg, 0.738 mmol). The reaction was stirred under nitrogen for 16 h and then filtered and the solid washed with dichloromethane. The filtrate was washed with saturated ammonium chloride solution (2×) and water, dried over sodium sulfate, filtered and evaporated. The residue was purified by silica gel chromatography using a gradient of iso-hexanes/ethyl acetate 1:1 to 0:1 to afford the title compound (307 mg, 60%) as a yellow foam.

Compound 15

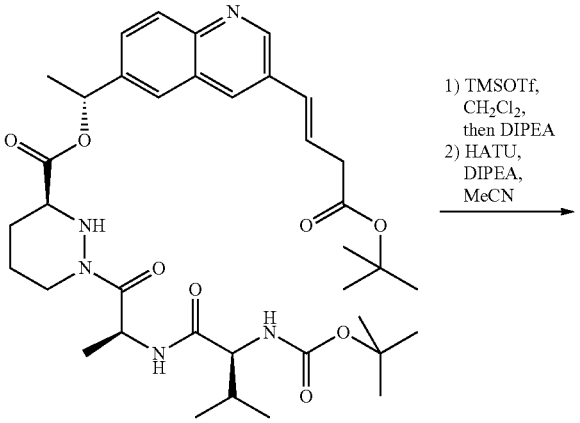

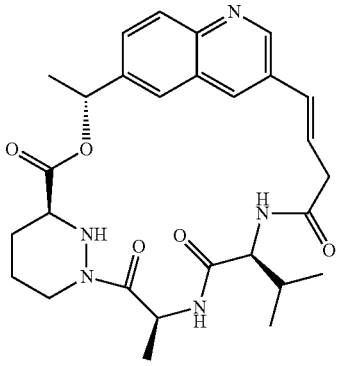

To a stirred solution of 15e (150 mg, 0.216 mmol) in dichloromethane (2 mL) at 0° C. under nitrogen was added trimethylsilyl trifluoromethanesulfonate (168 mg, 174 μL, 0.755 mmol) dropwise and the reaction mixture was allowed to warm to ambient temperature over 2.25 h. N,N-Diisopropylethylamine (195 mg, 263 μL, 1.51 mmol) was added and the reaction mixture stirred for a further 10 min, evaporated and then suspended in acetonitrile (21.6 mL). The stirred mixture was cooled to 0° C. and then 2-(1H-7-azabenzotriazol-1-yl)-1,1,3,3-tetramethyl uronium hexafluorophosphate methanaminium (115 mg, 0.320 mmol) and N,N-diisopropylethylamine (111 mg, 150 μL, 0.864 mmol) were added. After 1 h the reaction was quenched with saturated ammonium chloride solution and the mixture evaporated to remove organic volatiles. The residue was diluted with dichloromethane and the organic layer separated and washed with saturated ammonium chloride (2×) and brine then dried over sodium sulfate, filtered and evaporated. The residue was purified by preparative reverse phase HPLC using a gradient of acetonitrile/water 3:7 to 11:9 to afford the title compound (4.6 mg, 4% over 2 steps) as an off-white solid. $^1$H NMR (300 MHz, $CD_3OD$) δ 1.01 (app t, J=6.7 Hz, 6H), 1.62 (d, J=7.1 Hz, 3H), 1.70 (d, J=6.7 Hz, 3H), 1.75-1.85 (m, 1H), 1.91-2.05 (m, 3H), 2.70-2.80 (m, 1H), 2.98-3.06 (m, 1H), 3.36-3.45 (m, 1H), 3.74-3.84 (m, 1H), 4.26 (d, J=10.5 Hz, 1H), 4.42 (br d, J=12.3 Hz, 4.72-4.78 (m, 1H), 5.55 (q, J=7.1 Hz, 1H), 6.09 (q, J=6.5 Hz, 1H), 6.38-6.41 (m, 1H), 6.71 (d, J=16.1 Hz, 1H), 7.68 (dd, J=8.9, 1.9 Hz, 1H), 7.88-8.01 (m, 3H), 8.86 (d, J=2.0 Hz, 1H). LCMS (m/z) 522.3 [M+H], Tr=1.64 min.

Example 16

Compound 16

Compound 16a

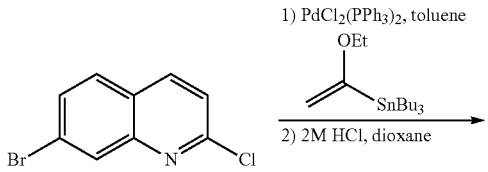

-continued

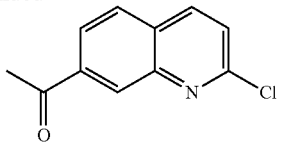

A mixture of 7-bromo-2-chloro-quinoline (1.05 g, 4.32 mmol) and tributyl(1-ethoxyvinyl)tin (1.95 g, 1.83 mL, 5.40 mmol) in toluene (21 mL) was degassed for 20 min. Bis (triphenylphosphine)palladium(II) dichloride (302 mg, 0.432 mmol) was added and the reaction mixture stirred under nitrogen and heated at 80° C. for 24 h before allowing to cool. The volatiles were evaporated and the residue suspended in 1,4-dioxane (10 mL) and 2 M aqueous hydrochloric acid (5 mL) was added and the reaction mixture stirred for 30 min and then evaporated to remove organics. The residue was diluted with ethyl acetate and water and the organic layer washed with brine, dried over sodium sulfate, filtered and evaporated. The product was purified on silica gel doped with 10% w/w potassium carbonate eluting using a gradient of iso-hexanes/ethyl acetate 9:1 to 4:1 to afford the title compound (422 mg, 48%) as a yellow solid.

Compound 16b

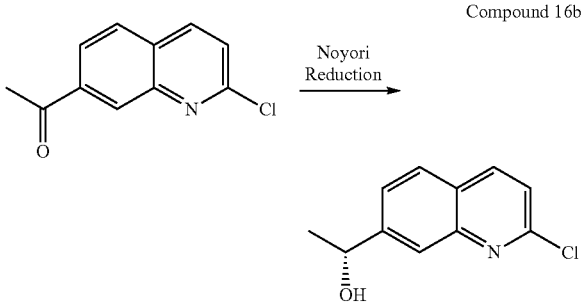

Dichloro(p-cymene)ruthenium(II) dimer (8.5 mg, 0.014 mmol) and (1R,2R)-(−)-N-p-tosyl-1,2-diphenylethylenediamine (12.1 mg, 0.033 mmol) were suspended in degassed water (5.5 mL) and the mixture was degassed with nitrogen for 20 min. The mixture was stirred at 70° C. under nitrogen for 90 min. The resulting turbid orange mixture was allowed to cool to RT. Solid 16a (571 mg, 2.78 mmol) and sodium formate (945 mg, 13.9 mmol) followed by degassed tetrahydrofuran (5.5 mL) were added and the reaction mixture was degassed with nitrogen for 5 min. The reaction mixture was vigorously stirred at 40° C. for 4 h and allowed to cool. It was then diluted with ethyl acetate and the mixture washed with water and the aqueous layer back-extracted with ethyl acetate. The combined organic extracts were washed with brine, dried over sodium sulfate, filtered and evaporated. The residue was purified by silica gel chromatography using a gradient of iso-hexanes/ethyl acetate 4:1 to 7:3 to afford the title compound (413 mg, 72%) as a beige solid.

Compound 16c

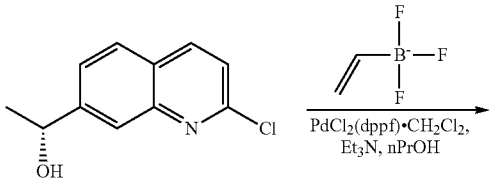

-continued

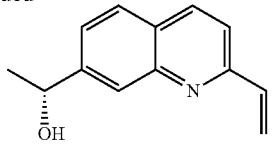

To a mixture of 16b (360 mg, 1.73 mmol), potassium vinyltrifluoroborate (279 mg, 2.08 mmol) and [1,1'-bis(diphenylphosphino)ferrocene]dichloropalladium(II), complex with dichloromethane (27 mg, 0.033 mmol) in dry n-propanol (27 mL) was added triethylamine (175 mg, 241 μL, 1.73 mmol) and the system evacuated and purged with nitrogen (3×). The reaction mixture was stirred and heated at reflux for 3 h before being allowed to cool. The mixture was poured into water and extracted with diethyl ether (2×) and the combined organic extracts dried over magnesium sulfate, filtered and evaporated. The residue was purified by silica gel chromatography using a gradient of iso-hexanes/ethyl acetate 7:3 to 3:2 to afford the title compound (270 mg, 78%) as a white solid.

Compound 16d

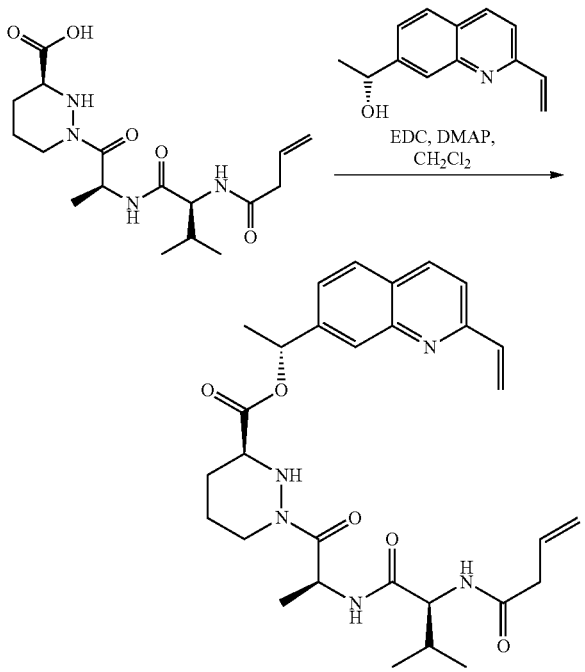

To a stirred mixture of 16c (100 mg, 0.500 mmol) and (S)-1-[(S)-2-((S)-2-but-3-enoylamino-3-methyl-butyrylamino)-propionyl]-hexahydro-pyridazine-3-carboxylic acid (203 mg, 0.550 mmol) in dichloromethane (10 mL) under nitrogen was added N-(3-dimethylaminopropyl)-N'-ethylcarbodiimide hydrochloride (134 mg, 0.700 mmol) and 4-dimethylaminopyridine (61 mg, 0.500 mmol). The reaction mixture was stirred for 16 h and then diluted with dichloromethane, washed successively with citric acid solution, water then brine, dried over sodium sulfate, filtered and evaporated. The residue was purified by silica gel chromatography using a gradient of iso-hexanes/ethyl acetate 1:1 to 0:1 to afford the title compound (103 mg, 38%) as a brown solid.

Compound 16

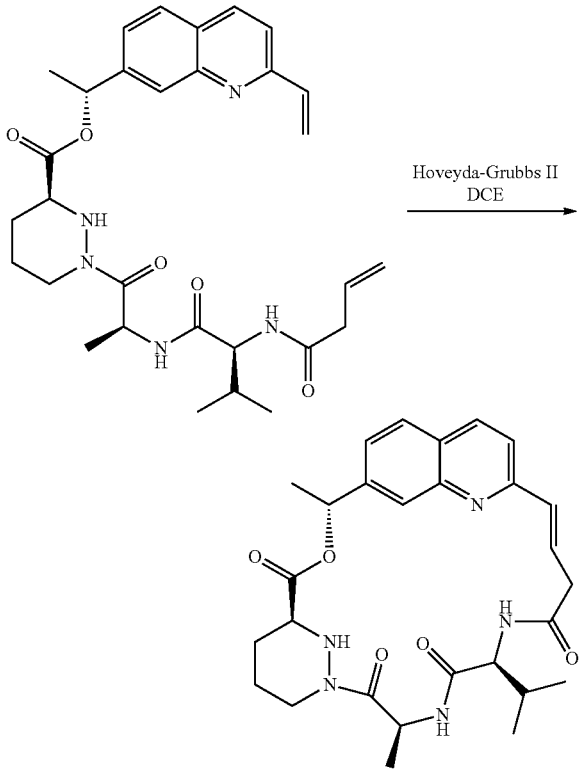

16d (60 mg, 0.109 mmol) and Hoveyda-Grubbs 2$^{nd}$ generation catalyst (20.5 mg, 0.0328 mmol) was suspended in 1,2-dichloroethane (6 mL) and the mixture heated in a microwave reactor at 100° C. for 1 h. The resulting mixture was combined with an identical reaction carried out using (10 mg, 0.0182) of the (S)-1-[(S)-2-((S)-2-but-3-enoylamino-3-methyl-butyrylamino)-propionyl]-hexahydro-pyridazine-3-carboxylic acid (R)-1-(2-vinyl-quinolin-7-yl) ethyl ester. The volatiles were evaporated and the residue purified by silica gel chromatography using a gradient of ethyl acetate/acetone 1:0 to 4:1 to give a brown gum. This was further purified by preparative thin layer chromatography using iso-hexanes/ethyl acetate 1:3 to afford the title compound (1.8 mg, 3%) as a white solid. $^1$H NMR (300 MHz, $CDCl_3$) δ 0.84-1.02 (m, 6H), 1.26 (app s, 3H), 1.67-1.72 (m, 3H), 1.83-1.96 (m, 1H), 2.00-2.08 (m, 1H), 2.63-2.74 (m, 1H), 3.24 (d, J=4.5 Hz, 1H), 3.50 (d, J=7.6 Hz, 1H), 4.21 (app t, J=10.3 Hz, 1H), 4.53-4.61 (m, 1H), 5.55 (app t, J=7.3 1H), 6.04-6.11 (m, 2H), 6.32 (d, J=7.8 Hz, 1H), 6.62 (d, J=16.3 Hz, 1H), 6.72-6.80 (m, 1H), 7.29-7.33 (m, 1H), 7.45 (d, J=8.5 Hz, 1H), 7.72 (d, J=8.3 Hz, 1H), 7.97-8.02 (m, 1H). LCMS (m/z) 552.2 [M+H], Tr=1.86 min.

Example 17

Compound 17

Compound 17a

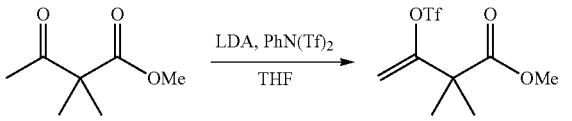

Under argon, a solution of diisopropylamine (2.51 g, 24.8 mmol) in tetrahydrofuran (150 mL) was cooled in an ice water bath. A solution of n-butyllithum in hexanes (2.5 M, 9.7 mL, 24 mmol) was added dropwise over 2 min, and the resulting solution was stirred for 10 additional min. The solution was then cooled to −78° C. in a $CO_2$:acetone bath, and methyl 2,2-dimethyl-3-oxobutanoate (3.2 g, 22 mmol) was added dropwise over 30 s. The solution was stirred for an additional 15 min, and N-phenyl-bis(trifluoromethanesulfonimide) (8.4 g, 23.5 mmol) was added as a solution in tetrahydrofuran (20 mL) via cannula over 5 min, washing with an additional portion of tetrahydrofuran (10 mL). The resulting solution was stirred for 10 min and was removed from the cold bath. After stirring an additional 1 h, the reaction mixture was concentrated in vacuo and diluted with diethyl ether (150 mL). The organic phase was washed with 1 M aqueous sodium hydroxide (1×100 mL, 1×30 mL), dried over anhydrous magnesium sulfate, filtered, and concentrated to afford the title compound (6.2 g, 100%) as an amber liquid that was used without further purification.

Compound 17b

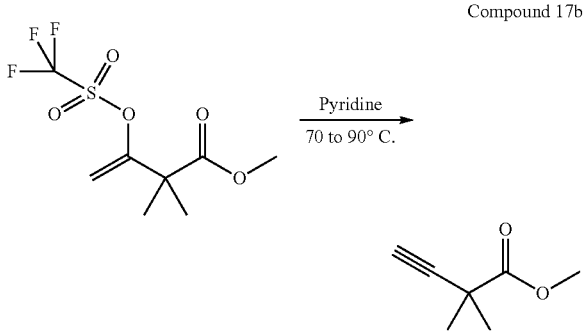

A solution of 17a (6.2 g, 22 mmol) in anhydrous pyridine (11 mL, 140 mmol) was heated to 70° C. After 18.5 h, the temperature was increased to 90° C. After stirring for a total of 72 h, the reaction mixture was partitioned between a stirred mixture of diethyl ether (100 mL) and 3 M aqueous hydrochloric acid (100 mL). The phases were separated, and the organic layer was washed with saturated aqueous sodium bicarbonate (75 mL), dried over magnesium sulfate, filtered, and concentrated to afford the title compound (2.7 g, 97%) as a slightly brown liquid that was used without further purification.

Compound 17c

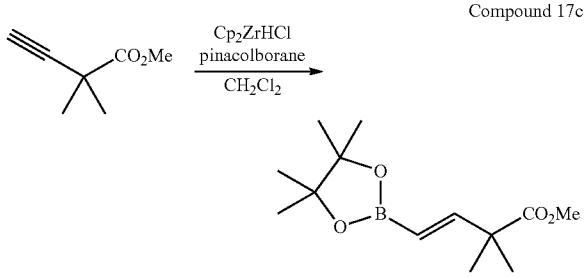

Under argon, bis(cyclopentadienyl)zirconium chloride hydride (290 mg, 1.1 mmol) was cooled in an ice water bath. A solution of 17b (1.4 g, 11.1 mmol) and pinacolborane (2.4 mL, 16.5 mmol) in dichloromethane (3 mL) was added by cannula, washing with an additional portion of dichloromethane (2 mL). The resulting mixture was removed from the cold bath and was stirred for 72 h at RT. The reaction was then diluted with ethyl acetate (50 mL), quenched with dropwise water (5 mL), and was further diluted with water (50 mL). The organic and aqueous phases were separated, and the aqueous phase was extracted with ethyl acetate (30 mL). The combined organic phases were dried over anhydrous sodium sulfate, filtered, and concentrated to afford a crude residue that was purified by silica gel chromatography (5 to 15% ethyl acetate in iso-hexanes) to afford the title compound (1.6 g, 57%) as a colorless oil that crystallized on standing at −15° C.

Compound 17d

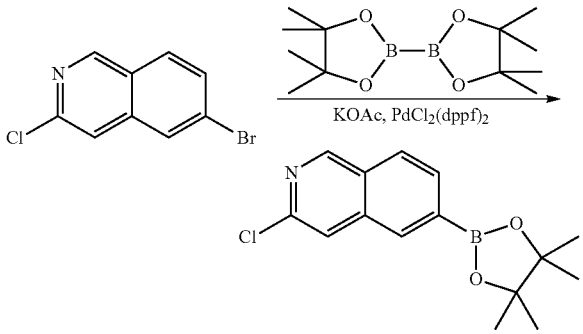

A mixture of 6-bromo-3-chloro-isoquinoline (485 mg, 2.0 mmol), bis(pinacolato)diboron (560 mg, 2.2 mmol), potassium acetate (392 mg, 4.0 mmol) and [1,1'-bis(diphenylphosphino)ferrocene]dichloropalladium(II), complex with dichloromethane (82 mg, 0.1 mmol) in 1,4-dioxane (4 mL) was heated at 160° C. in a microwave for 1 hour. The reaction mixture was filtered through Celite and the filter pad was washed with ethyl acetate. The filtrate was evaporated and the residue was purified by silica gel chromatography using a gradient of dichloromethane to dichloromethane/methanol 9:1 to afford the title compound (545 mg, 94%).

Compound 17e

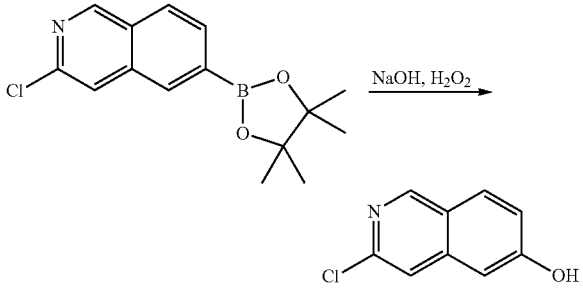

A solution of 17d (1.74 g, 6.0 mmol) in tetrahydrofuran (45 mL) was stirred at 0° C. under nitrogen. Sodium hydroxide solution (2 M, 9 mL, 18 mmol) and hydrogen peroxide (30%, 2.5 24 mmol) were added dropwise. The reaction mixture was stirred at 0° C. for 30 min. Water (30 mL) was added and the solution was acidified to pH 1 with 2 M hydrochloric acid. Sodium metabisulfite solution (1 M) was added and the mixture was extracted with ethyl acetate. The organic extracts were combined, washed with water and brine. The organic solution was filtered through a hydrophobic frit and the filtrate was evaporated to afford the title compound (662 mg, 61%) as an off-white solid.

Compound 17f

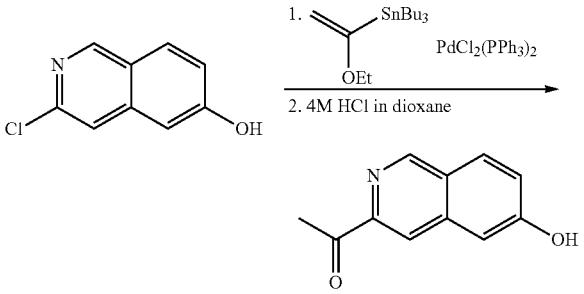

To a solution of 17e (1.25 g, 7.07 mmol) and tributyl-(1-ethoxy-vinyl)-tin (5.09 g, 4.77 mL, 14.1 mmol) in 1,4-dioxane (15 mL) was added bis(triphenylphosphine)palladium(II) dichloride (992 mg, 1.41 mmol) and the reaction mixture was heated at 160° C. in a microwave for 30 min. The reaction mixture was filtered through Celite and the filter pad was washed with ethyl acetate. The filtrate was evaporated and the residue was purified by silica gel chromatography using a gradient of iso-hexanes/ethyl acetate 9:1 to 3:1 to afford 3-(1-ethoxy-vinyl)-isoquinolin-6-ol (670 mg) as a gum which was used crude in the next step. 3-(1-Ethoxy-vinyl)-isoquinolin-6-ol (670 mg) was suspended in 1,4-dioxane (4 mL) and 4 M hydrogen chloride in 1,4-dioxane (8 mL) was added and the reaction mixture was stirred at RT for 30 min. The solvent was evaporated to afford the title compound (584 mg, 44% over 2 steps) as a white solid.

Compound 17g

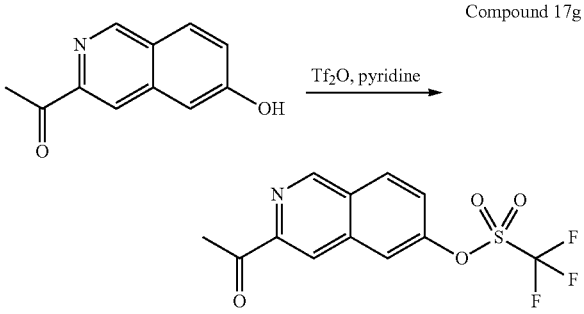

A solution of 17f (384 mg, 2.05 mmol) and pyridine (0.51 mL, 6.16 mmol) in dichloromethane (30 mL) was stirred in a salt-ice bath for 5 min. Trifluoromethanesulfonic anhydride (0.415 mL, 2.46 mmol) was added dropwise and the mixture was warmed to RT over 20 min. Additional trifluoromethanesulfonic anhydride (0.1 mL, 0.6 mmol) was added and the reaction mixture was stirred at RT for 10 min. Saturated ammonium chloride solution was added and the mixture was extracted with dichloromethane. The organic extracts were combined, dried over sodium sulfate, filtered and evaporated. The residue was purified by silica gel chromatography using iso-hexanes/ethyl acetate 19:1 to afford the title compound (300 mg, 44%) as a white solid.

Compound 17h

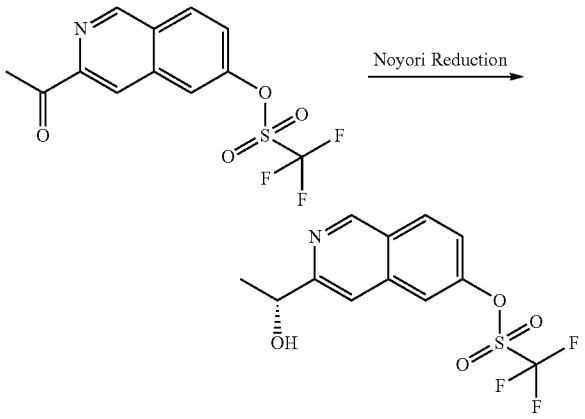

To dichloro (p-cymene) ruthenium (II) dimer (2 mg, 0.003 mmol) in water (2 mL) at RT was added (1R,2R)-(−)-N-p-tosyl-1,2-diphenylethylenediamine (3 mg, 0.008 mmol). The system was degassed for 15 min and then heated to 70° C. for 1.5 h. The reaction was cooled and a solution of 17 g (224 mg, 0.70 mmol) in degassed anhydrous tetrahydrofuran (1 mL) was added followed by sodium formate (237 mg, 3.50 mmol). The system was degassed for 2 min and then heated at 40° C. for 1 hour. After cooling to RT, water was added and the water was extracted with dichloromethane (2×). The combined organic layers were dried through a hydrophobic frit and concentrated in vacuo. The product was purified by silica gel chromatography using iso-hexanes/ethyl acetate 1:1 to afford the title compound (220 mg, 97%) as a brown oil.

Compound 17i

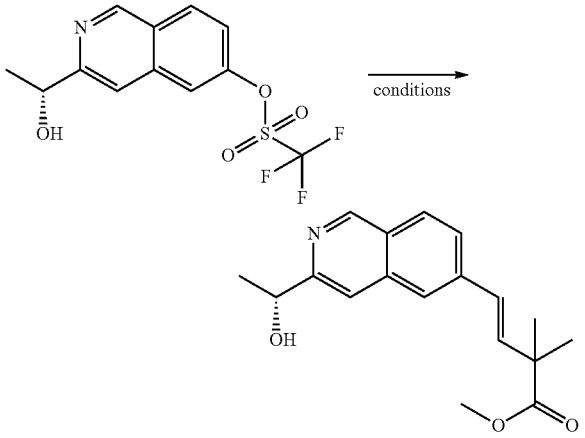

A round bottom flask was charged with 17 h (100 mg, 0.31 mmol), (E)-2,2-dimethyl-4-(4,4,5,5-tetramethyl-[1,3,2]dioxaborolan-2-yl)-but-3-enoic acid methyl ester (91 mg, 0.36 mmol), bis[(dicyclohexyl)(4-dimethylaminophenyl)phosphine]palladium(II) chloride (13 mg, 0.02 mmol), potassium phosphate tribasic (198 mg, 0.93 mmol) and lithium chloride (40 mg, 0.93 mmol). The system was flushed with nitrogen and cyclopentyl methyl ether (1 mL) and water (0.5 mL) were added. The reaction was heated for 1 hour at 90° C. and then cooled to RT. Ethyl acetate was added and the solution was washed with water. The organic layer was dried over magnesium sulfate, filtered and concentrated in vacuo. The residue was purified by silica gel chromatography using iso-hexanes/ethyl acetate 1:2 to give the title compound (70 mg, 75%) as a yellow oil.

Compound 17j

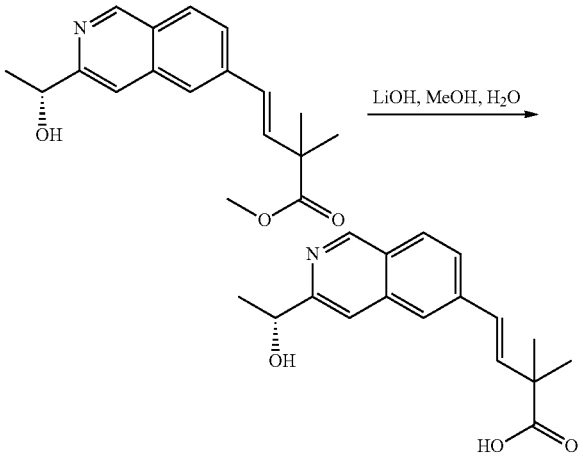

To 17i (140 mg, 0.47 mmol) in tetrahydrofuran (1 mL), methanol (0.5 mL) and water (0.5 mL) was added lithium hydroxide monohydrate (39 mg, 0.93 mmol) at RT. The reaction was stirred for 3 h and quenched by adding 2 M aqueous hydrochloric acid (0.5 mL). The reaction was concentrated in vacuo, followed by co-evaporation from methanol and then toluene. The ensuing yellow solid was used crude.

Compound 17k

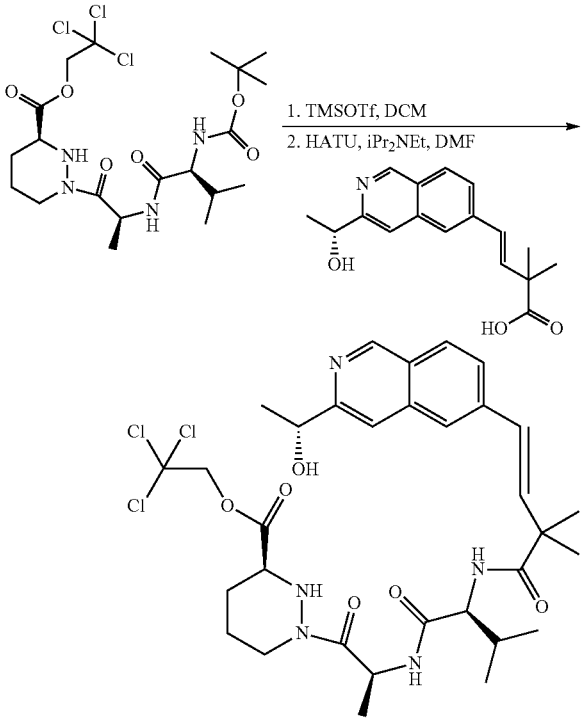

To 1e (250 mg, 0.47 mmol) in anhydrous dichloromethane (5 mL) at 0° C. and under an atmosphere of nitrogen, was added trimethylsilyl trifluoromethanesulfonate (128 μL, 0.70 mmol). The reaction mixture was stirred at 0° C. for 2 h before adding N,N-diisopropylethylamine (252 μL, 1.41 mmol) and then concentrated in vacuo, and co-evaporated with toluene to afford (S)-1-[(S)-2-((S)-2-amino-3-methyl-butyrylamino)-propionyl]-hexahydro-pyridazine-3-carboxylic acid 2,2,2-trichloro-ethyl ester as a white solid. To 17j (134 mg, 0.47 mmol) in anhydrous N,N-dimethylformamide (2 mL) at RT and under an atmosphere of nitrogen was added N,N-diisopropylethylamine (420 μL, 2.35 mmol) and 2-(1H-7-azabenzotriazol-1-yl)-1,1,3,3-tetramethyl uronium hexafluorophosphate methanaminium (250 mg, 0.66 mmol). The solution was stirred at RT for 3 min before adding a solution of (S)-1-[(S)-2-((S)-2-amino-3-methyl-butyrylamino)-propionyl]hexahydro-pyridazine-3-carboxylic acid 2,2,2-trichloro-ethyl ester in anhydrous N,N-dimethylformamide (2 mL). The reaction was stirred for 16 h. The reaction was quenched with water and extracted with ethyl acetate (2×). The combined organic layers were dried over sodium sulfate, filtered and concentrated in vacuo. The residue was purified by silica gel chromatography using iso-hexanes/acetone 1:1 to give the title compound (220 mg, 67% over 3 steps) as an off white solid.

Compound 17

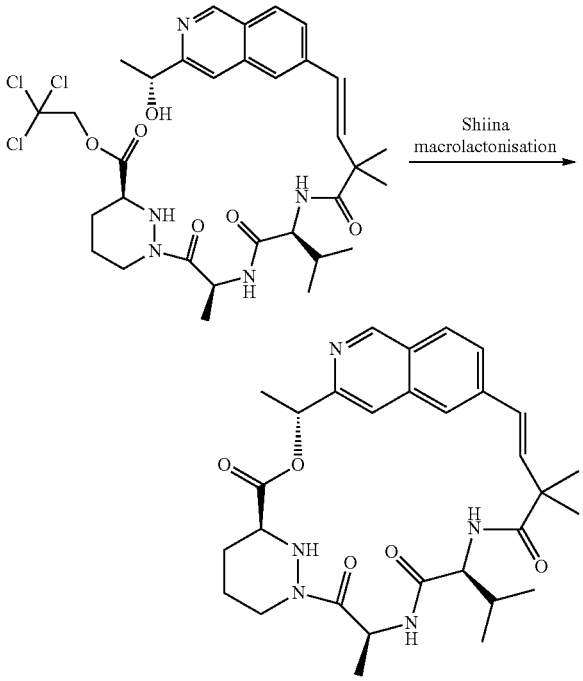

To 17k (220 mg, 0.31 mmol) in tetrahydrofuran (3 mL), methanol (1.5 mL) and water (1.5 mL) was added lithium hydroxide monohydrate (53 mg, 1.26 mmol) at RT. The reaction was stirred for 1.25 h and quenched by adding 2 M aqueous hydrochloric acid (0.64 mL). The reaction was concentrated in vacuo, followed by co-evaporation from methanol (2×) and then acetonitrile (6×). The resulting residue was dissolved in anhydrous N,N-dimethylformamide (4 mL), and added via syringe pump over 2 h to a suspension of 2-methyl-6-nitrobenzoic anhydride (271 mg, 0.79 mmol), 4-dimethylaminopyridine (288 mg, 2.36 mmol) and powdered 4 Å molecular sieves (3 g) in 1,2-dichloroethane (103 mL) at 50° C. Following the addition the reaction was stirred at 50° C. for 3 h, cooled to RT and filtered through Celite. The filtrate was concentrated to ⅓ of its volume, diluted with dichloromethane and washed with water (2×). The organic layer was dried through a hydrophobic frit and concentrated in vacuo. The residue was purified by silica gel chromatography using iso-hexanes/acetone 1:1 to give an off white solid. The solid was triturated twice with diethyl ether and vacuum dried for 16 h to afford the title compound (65 mg, 38% over 2 steps) as a white powder. $^1$H NMR (300 MHz, $CDCl_3$) 0.93 (d, J=6.7 Hz, 3H), 0.99 (d, J=6.7 Hz, 3H), 1.41 (s, 3H), 1.51 (s, 3H), 1.61 (d, J=7.1 Hz, 3H), 1.76 (d, J=6.7 Hz, 3H), 1.76 (m, 1H), 1.78-2.03 (m, 3H), 2.07-2.17 (m, 1H), 2.62-2.76 (m, 3.62-3.79 (m, 2H), 4.21-4.31 (m, 1H), 4.52-4.62 (m, 1H), 5.82-6.01 (m, 1H), 6.13 (q, J=6.7 Hz, 1H), 6.27 (d, J=16.1 Hz, 1H), 6.30-6.41 (m, 2H), 6.64 (d, J=16.1 Hz, 1H), 7.53 (d, J=8.5 Hz, 1H), 7.71 (s, 1H), 7.82 (s, 1H), 7.90 (d, J=8.5 Hz, 1H), 9.16 (s, 1H). LCMS (m/z) 549.9 [M+H], Tr=5.21 min.

Example 18

Compound 18

Compound 18

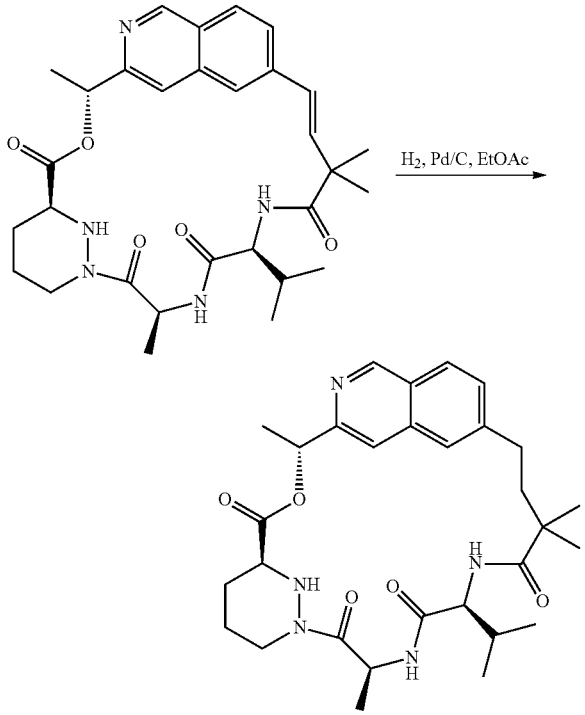

To Compound 17 (40 mg, 0.073 mmol) in ethyl acetate (10 mL) was added 10% palladium on carbon (30 mg) at RT. The system was purged with hydrogen and stirred vigorously for 16 h. The suspension was filtered through Celite and the filtrate concentrated in vacuo. The residue was purified by silica gel chromatography using iso-hexanes/acetone 1:1 to afford Compound 18 (8 mg, 20%) as a white solid. $^1$H NMR (300 MHz, $CDCl_3$) 0.92 (d, J=6.5 Hz, 3H), 1.00 (d, J=6.5 Hz, 3H), 1.27 (s, 3H), 1.31 (s, 3H), 1.48 (d, J=7.1 Hz, 3H), 1.64-1.79 (m, 1H), 1.75 (d, J=6.7 Hz, 3H), 1.80-2.12 (m, 5H), 2.45 (td, J=12.7, 3.6 Hz, 1H), 2.68-2.93 (m, 2H), 3.62-3.78 (m, 2H), 3.86 (d, J=12.0 Hz, 1H), 4.37 (app t, J=8.3 Hz, 1H), 4.50-4.61 1H), 5.87-6.00 (m, 1H), 6.18 (q, J=6.7 Hz, 1H), 6.38 (d, J=8.7 Hz, 1H), 6.58 (d, J=8.3 Hz, 1H), 7.36 (d, J=8.5 Hz, 1H), 7.42 (s, 1H), 7.64 (s, 1H), 7.83 (d, J=8.5 Hz, 1H), 9.14 (s, 1H). LCMS (m/z) 552.2 [M+H], Tr=5.11 min.

Example 19

Compound 19

Compound 19a

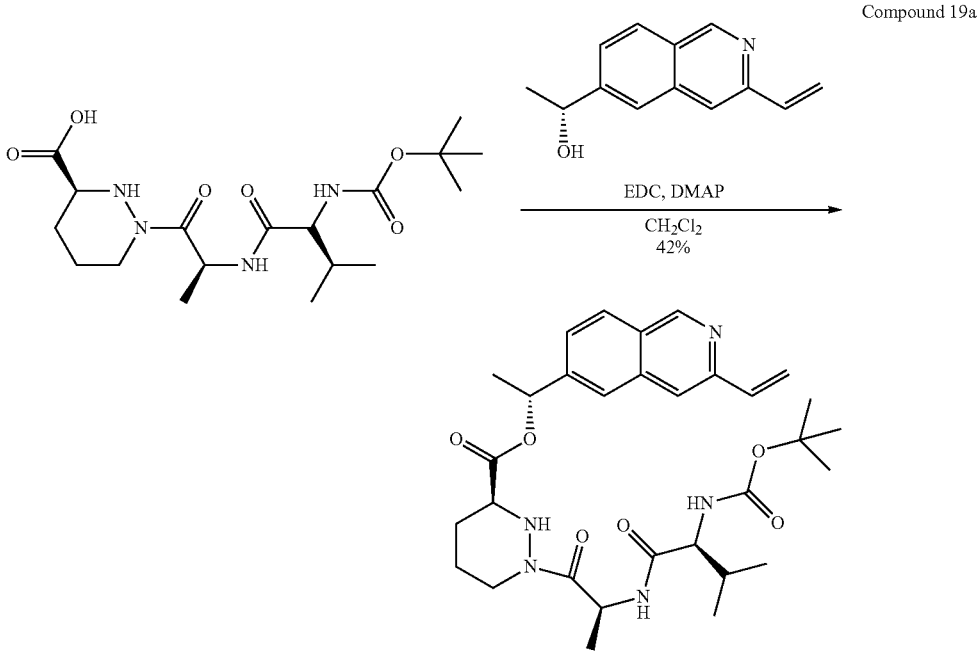

To a solution of (S)-1-[(S)-2-((S)-2-tert-butoxycarbonylamino-3-methyl-butyrylamino)-propionyl]-hexahydropyridazine-3-carboxylic acid (339 mg, 0.920 mmol) and (R)-1-(3-vinyl-isoquinolin-6-yl)-ethanol (183 mg, 0.920 mmol) in dichloromethane (4.6 mL) were added N-(3-dimethylaminopropyl)-N'-ethylcarbodiimide hydrochloride (211 mg, 1.10 mmol) and 4-dimethylaminopyridine (56.2 mg, 0.46 mmol) at 23° C. under an argon atmosphere. After 21 h, the reaction mixture was purified directly by silica gel flash column chromatography to afford the title compound (224 mg, 42%) as a light tan solid.

Compound 19b

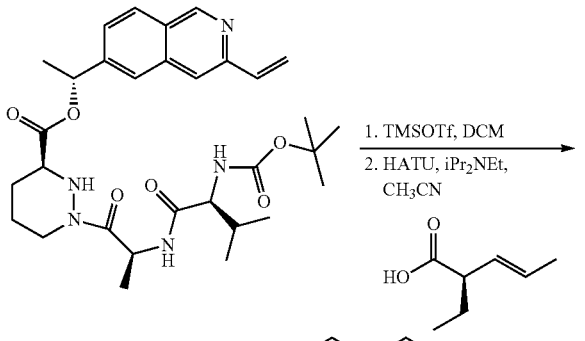

To 19a (800 mg, 1.38 mmol) in anhydrous dichloromethane (12 mL) at 0° C. and under an atmosphere of nitrogen, was added trimethylsilyl trifluoromethanesulfonate (374 μL, 2.07 mmol). The reaction mixture was stirred at 0° C. for 2 h before adding N,N-diisopropylethylamine (480 2.75 mmol) and then concentrated in vacuo to afford a white solid. To the solid was added a solution of (E)-(R)-2-ethyl-pent-3-enoic acid (188 mg, 1.65 mmol) in anhydrous acetonitrile (12 mL) followed by N,N-diisopropylethylamine (240 μL, 1.38 mmol) and 2-(1H-7-azabenzotriazol-1-yl)-1,1,3,3-tetramethyl uranium hexafluorophosphate methanaminium (733 mg, 1.93 mmol). The reaction was stirred at RT for 3 h and concentrated in vacuo. The residue was purified by silica gel chromatography using iso-hexanes/ethyl acetate 1:2 then 1:5 to give the title compound (250 mg, 74% over 2 steps) as a viscous yellow oil.

Compound 19

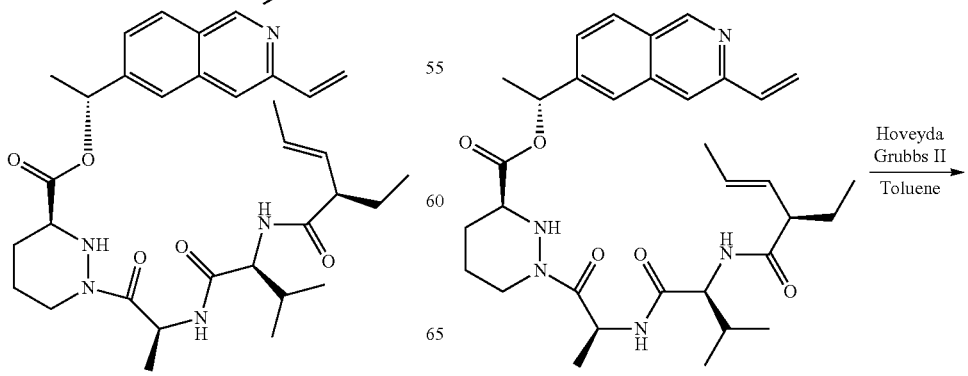

-continued

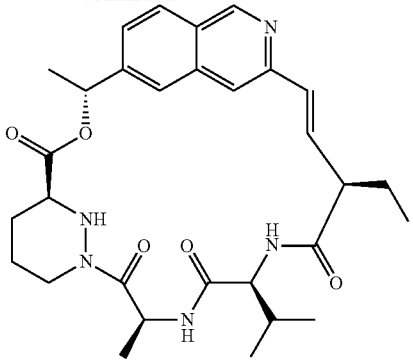

To 19b (200 mg, 0.34 mmol) in anhydrous toluene (113 mL) at 70° C. and under an atmosphere of nitrogen, was added Hoveyda-Grubbs 2$^{nd}$ generation catalyst (42 mg, 0.07 mmol). The reaction was heated at 120° C. for 2 h after which an additional amount of the Hoveyda-Grubbs 2$^{nd}$ generation catalyst (30 mg, 0.05 mmol) was added. Following a further 2 h at 120° C. the reaction was cooled to RT and potassium isocyanoacetate (83 mg) in methanol (2 mL) was added. The reaction was stirred for 1 hour, silica added and then concentrated in vacuo. The residue was purified by silica gel chromatography using ethyl acetate/acetone 3:1 to afford a brown solid. This was purified further by reverse phase preparative HPLC to give the title compound (2.2 mg, 1%) as a white solid. $^1$H NMR (300 MHz, $CD_3OD$) 0.97 (d, J=6.5 Hz, 3H), 1.02 (d, J=6.5 Hz, 3H), 1.11 (t, J=7.4 Hz, 3H), 1.64 (d, J=7.1 Hz, 3H), 1.70 (d, J=6.7 Hz, 3H), 1.71-2.06 (m, 7H), 2.66-2.82 (m, 1H), 3.13-3.22 (m, 1H), 3.75-3.85 (m, 1H), 4.30-4.48 (m, 2H), 5.51-5.67 (m, 1H), 6.07 (q, J=6.3 Hz, 1H), 6.48-6.57 (m, 1H), 6.61 (d, J=16.5 Hz, 1H), 7.47 (s, 1H), 7.58 (d, J=8.7 Hz, 1H), 7.89 (s, 1H), 8.07 (d, J=8.7 Hz, 1H), 9.15 (s, 1H). LCMS (m/z) 550.2 [M+H], Tr=1.67 min.

Example 20

Compound 20

Compound 20a

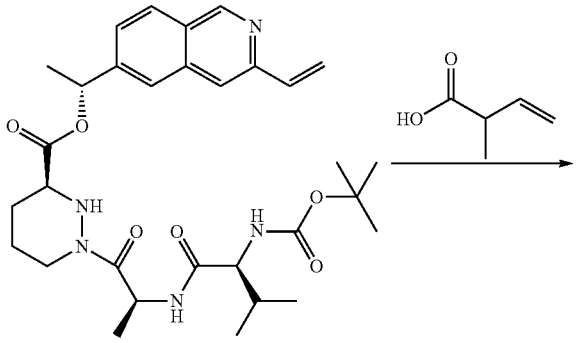

-continued

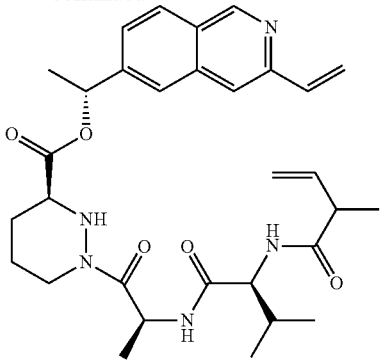

To 19a (390 mg, 0.67 mmol) in anhydrous dichloromethane (7 mL) at 0° C. and under an atmosphere of nitrogen, was added trimethylsilyl trifluoromethanesulfonate (182 μL, 1.01 mmol). The reaction mixture was stirred at 0° C. for 1 hour before quenching with a saturated aqueous solution of sodium hydrogen carbonate and extracting with ethyl acetate (2×). The organic layers were dried over sodium sulfate, filtered and concentrated in vacuo to afford a white solid. The solid was dissolved in anhydrous acetonitrile (4 mL) and 2-methyl-but-3-enoic acid (81 mg, 0.81 mmol), N-(3-dimethylaminopropyl)-N'-ethylcarbodiimide hydrochloride (184 mg, 0.94 mmol) and 1-hydroxybenzotriazole monohydrate (103 mg, 0.67 mmol) were added. The reaction was stirred at RT for 16 h and concentrated in vacuo. The residue was purified by silica gel chromatography using isohexanes/ethyl acetate 1:1 then 1:3 to give the title compound (259 mg, 69%) as a clear viscous oil.

Compound 20

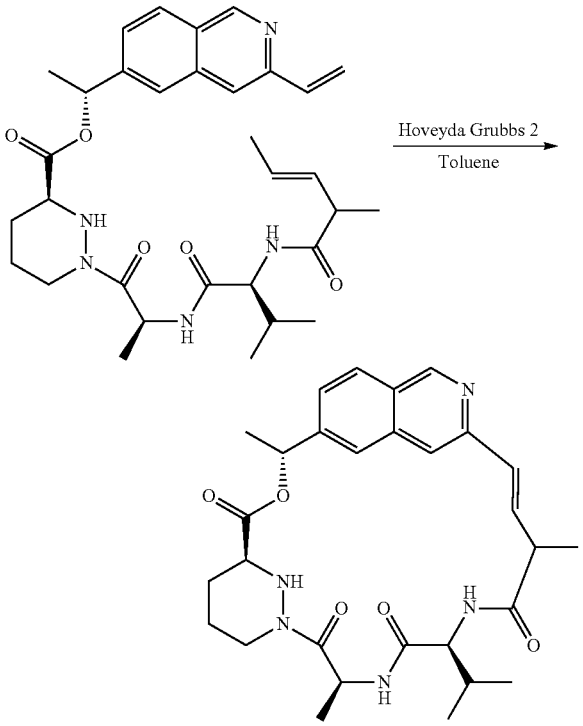

To 20a (250 mg, 0.44 mmol) in degassed anhydrous toluene (148 mL) was added 2,6-dichlorobenzoquinone (8 mg, 0.04 mmol). The mixture was heated to 105° C. and a solution of Hoveyda-Grubbs 2$^{nd}$ generation catalyst (83 mg, 0.13 mmol) in anhydrous toluene (20 mL), was added via syringe pump over 2 h. An additional amount of Hoveyda-Grubbs 2$^{nd}$ generation catalyst (28 mg) was added and the reaction heated to reflux for 1 h. The reaction was cooled to RT, silica gel was added and concentrated in vacuo. The residue was purified by silica gel chromatography using ethyl acetate/acetone 1:0 then 3:1 to afford an oil. This was triturated with diethyl ether and a few drops of ethyl acetate to afford a brown solid which was further purified by preparative TLC using ethyl acetate/acetone 5/1 to give the title compound (9 mg, 1%) as an off-white solid. $^1$H NMR (300 MHz, $CDCl_3$) 0.97 (d, J=6.7 Hz, 3H), 1.01 (d, J=6.7 Hz, 3H), 1.38 (d, J=6.7 Hz, 3H), 1.62 (d, J=7.1 Hz, 3H), 1.70 (d, J=6.9 Hz, 3H), 1.72-1.82 (m, 2H), 1.91-2.01 (m, 2H), 2.03-2.12 (m, 1H), 2.62-2.74 (m, 1H), 3.35 (app t, J=7.4 Hz, 1H), 3.59 (d, J=12.5 Hz, 1H), 3.65-3.77 (m, 1H), 4.26 (app t, J=8.9 Hz, 1H), 4.51-4.60 (m, 1H), 5.68-5.79 (m, 1H), 6.06 (q, J=6.7 Hz, 1H), 6.16 (d, J=9.2 Hz, 1H), 6.27 (d, J=9.2 Hz, 1H), 6.40 (dd, J=16.0, 7.8 Hz, 1H), 6.71 (d, J=16.0 Hz, 1H), 7.39 (dd, J=8.5, 1.3 Hz, 1H), 7.58 (s, 1H), 7.74 (s, 1H), 7.93 (d, J=8.5 Hz, 1H), 9.16 (s, 1H). LCMS (m/z) 536.2 [M+H], Tr=1.63 min.

Example 21

Compound 21

Compound 21a

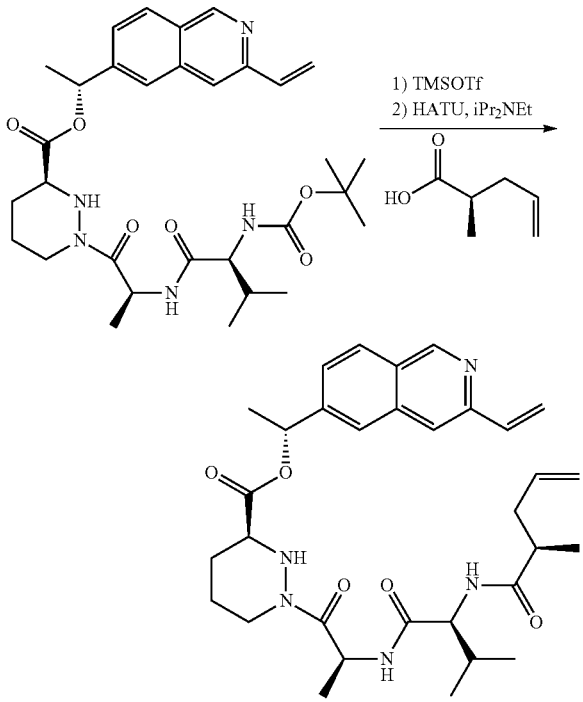

21a was prepared in the same manner as 20a replacing 2-methyl-but-3-enoic acid with (R)-2-methyl-pent-4-enoic acid (prepared as described in Synlett 2002, No 12, 2039-2040, 82 mg, 0.72 mmol), to afford the title compound (280 mg, 67%) as a white foam.

Compound 21

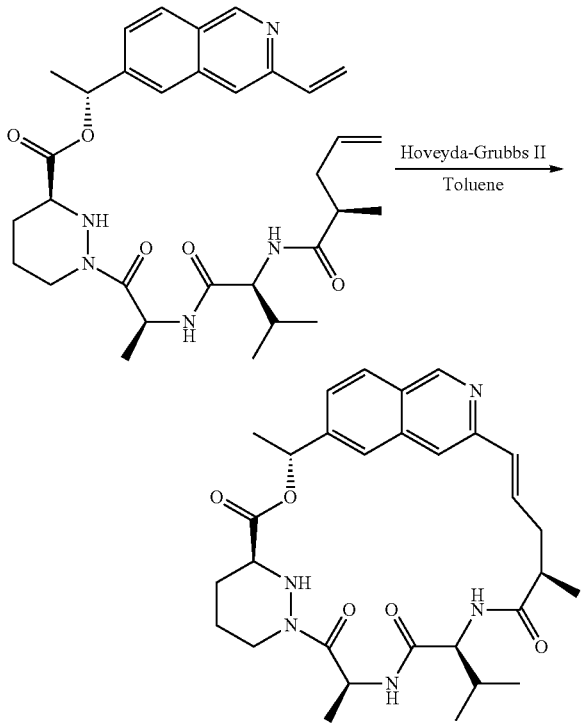

To 21a (250 mg, 0.43 mmol) in anhydrous toluene (144 mL) at RT and under an atmosphere of nitrogen, was added Hoveyda-Grubbs 2$^{nd}$ generation catalyst (54 mg, 0.09 mmol). The reaction was heated at 120° C. for 2 h after which an additional amount of the Hoveyda-Grubbs 2$^{nd}$ generation catalyst (25 mg, 0.04 mmol) was added. Following a further 1 h at 120° C. the reaction was cooled to RT and concentrated in vacuo. The residue was purified by silica gel chromatography using ethyl acetate/acetone 1:0 then 3:1 to afford a brown solid. This was triturated with diethyl ether/ethyl acetate 3:1 to give the title compound (50 mg, 22%) as an off-white solid. $^1$H NMR (300 MHz, $CDCl_3$) 0.91 (d, J=6.7 Hz, 3H), 0.99 (d, J=6.7 Hz, 3H), 1.29 (d, J=7.1 Hz, 3H), 1.59 (d, J=6.7 Hz, 3H), 1.67 (d, J=6.5 Hz, 3H), 1.70-1.84 (m, 1H), 1.92-2.15 (m, 4H), 2.33-2.48 (m, 1H), 2.63-2.98 (m, 3H), 3.53 (d, J=12.2 Hz, 1H), 3.60-3.72 (m, 1H), 4.42 (dd, J=6.7, 2.2 Hz, 1H), 4.52-4.61 (m, 1H), 5.62-5.74 (m, 1H), 6.11 (q, J=6.7 Hz, 1H), 6.16 (q, J=8.9 Hz, 1H), 6.42 (d, J=8.5 Hz, 1H), 6.53-6.66 (m, 1H), 6.75 (d, J=16.1 Hz, 1H), 7.37 (dd, J=8.7, 1.0 Hz, 1H), 7.80-7.96 (m, 3H), 9.16 (s, 1H). LCMS (m/z) 550.3 [M+H], Tr=1.50 min.

Example 22

Compound 22

Compound 22a

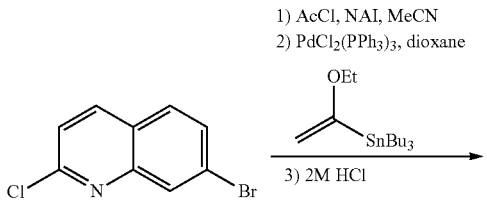

-continued

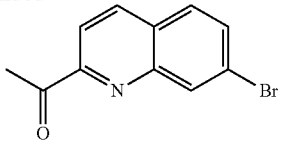

To a stirred slurry of 7-bromo-2-chloro-quinoline (8.10 g, 33.4 mmol) and sodium iodide (50.0 g, 334 mmol) in acetonitrile (27 mL) was slowly added acetyl chloride (3.56 mL, 50.0 mmol). The flask was stoppered and sealed and heated at 80° C. for 3 h before being allowed to cool. The mixture was treated sequentially with 10% w/w aqueous potassium carbonate solution (80 mL), 5% w/w aqueous sodium sulfite solution (80 mL) and saturated aqueous sodium thiosulfate solution (80 mL) and the mixture extracted with dichloromethane (2×). The combined organic extracts were dried over sodium sulfate, filtered and evaporated to give a crude 7-bromo-2-iodo-quinoline. To the quinoline was added tributyl(1-ethoxyvinyl)tin (13.6 mL, 40.1 mmol), 1,4-dioxane (67 mL) and bis(triphenylphosphine)palladium(II) dichloride (2.37 g, 3.34 mmol) and the reaction mixture heated at 100° C. for 5 h before allowing to cool. 2 M Aqueous hydrochloric acid (67 mL) was added and the reaction stirred for 1 h. The mixture was filtered and the solids washed with ethyl acetate and the filtrate evaporated to remove organics. The residue was extracted with ethyl acetate (3×) and the combined organic extracts were dried over sodium sulfate, filtered and evaporated. The product was purified on silica gel doped with 10% w/w potassium carbonate eluting with a gradient of 0 to 6% ethyl acetate in iso-hexanes to afford the title compound (5.5 g, 66%) as a white solid.

Compound 22b

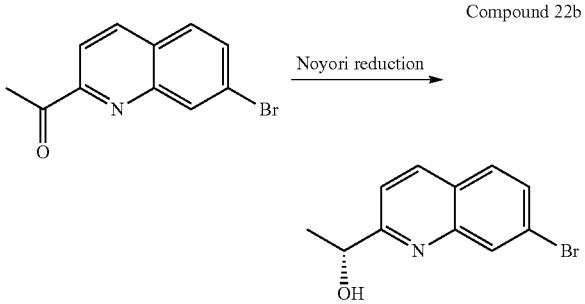

Dichloro (p-cymene) ruthenium(II) dimer (61 mg, 0.100 mmol) and (1R,2R)-(−)-N-p-tosyl-1,2-diphenylethylenediamine (88 mg, 0.012 mmol) was suspended in degassed water (40 mL) and the mixture was degassed with nitrogen for 5 min. The mixture was stirred at 70° C. under nitrogen for 90 min. The resulting turbid orange mixture was allowed to cool to RT. 22a (5.00 g, 20 mmol) in degassed tetrahydrofuran (40 mL) was added followed by sodium formate (6.8 g, 100 mmol) and the reaction mixture was degassed with nitrogen for 5 min. The reaction mixture was vigorously stirred at 40° C. for 4 h and allowed to cool. It was then diluted with ethyl acetate and water and the organic layer was separated, washed with water and brine, dried over sodium sulfate, filtered and evaporated. The residue was purified by silica gel chromatography using a gradient of 0% to 30% ethyl acetate in iso-hexanes to afford the title compound (4.96 g, 98%) as an off-white solid.

Compound 22c

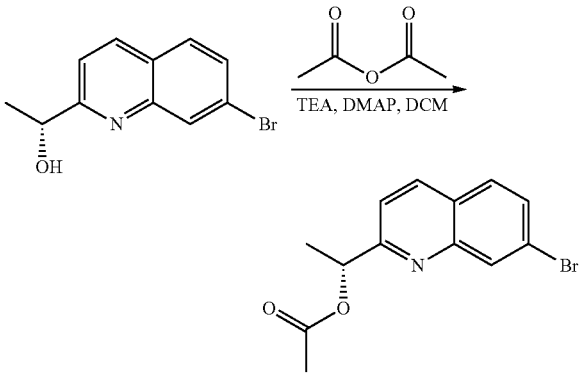

To a solution of 22b (1.00 g, 3.97 mmol) and triethylamine (1.65 mL, 11.9 mmol) in anhydrous dichloromethane at 0° C., was added acetic anhydride (0.75 mL, 7.93 mmol) and 4-(dimethylamino)pyridine (24 mg, 0.197 mmol). The reaction mixture was stirred and allowed to warm to RT. After 1.5 h water (100 mL) was added and the layers separated. The aqueous phase was re-extracted with dichloromethane (2×100 mL) and the combined organics were washed with brine (100 mL), dried over magnesium sulfate, filtered and concentrated in vacuo to give a crude residue. This was purified by silica gel chromatography using iso-hexanes (66 mL) then iso-hexanes/ethyl acetate 95:5 (300 mL), then iso-hexanes/ethyl acetate 9:1 (1066 mL) to yield the title compound (1.16 g, 99%) as a colorless oil.

Compound 22d

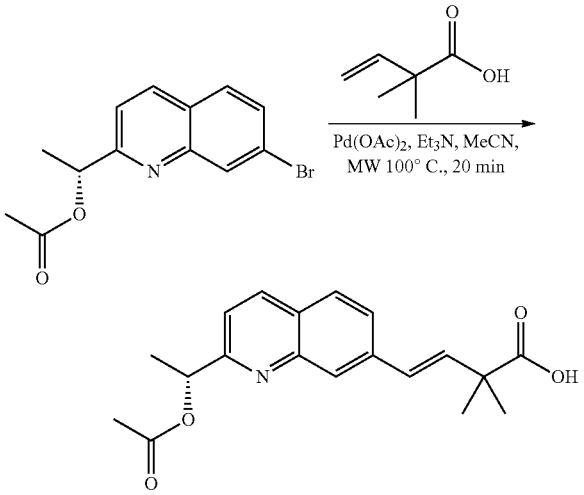

To a solution of 22c (1.16 g, 3.95 mmol) in anhydrous acetonitrile was added palladium(II) acetate (89 mg, 0.395 mmol), 2,2-dimethyl-but-3-enoic acid (496 mg, 4.35 mmol), tri(o-tolyl)phosphine (241 mg, 0.790 mmol) and triethylamine (1.09 mL, 7.90 mmol) then the mixture was heated in the microwave at 100° C. for 20 min. The reaction mixture was concentrated in vacuo then water (200 mL) was added and the organics extracted with ethyl acetate (2×50 mL). The combined organics were dried over sodium sulfate, filtered and concentrated in vacuo to give a crude residue. This was purified by silica gel chromatography using iso-hexanes/ ethyl acetate 95:5 (300 mL), then iso-hexanes/ethyl acetate 9:1 (1066 mL) then iso-hexanes/ethyl acetate 3:1 (1066 mL) to yield the title compound (792 mg, 61%) as a white solid.

Compound 22e

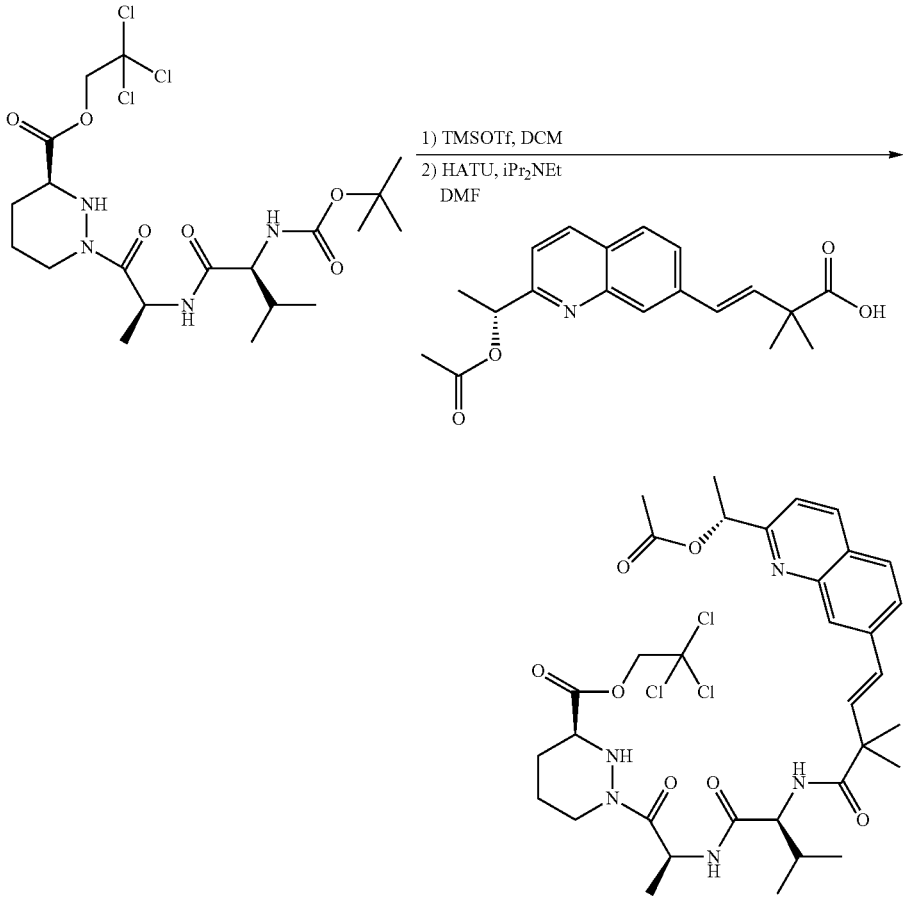

A solution of 1e (1.29 g, 2.42 mmol) in dichloromethane (12 mL) was cooled in an ice-water bath under nitrogen. Trimethylsilyl trifluoromethanesulfonate (0.715 mL, 4.84 mmol) was added dropwise, and the resulting solution was stirred for 1 h. The reaction was quenched with N,N-diisopropylethylamine (1.69 mL, 9.68 mmol) and the reaction mixture was concentrated in vacuo to give (S)-1-[(S)-2-((S)-2-amino-3-methyl-butyrylamino)-propionyl]-hexahydro-pyridazine-3-carboxylic acid 2,2,2-trichloro-ethyl ester as a white solid which was used without further purification. To a solution of 22d (792 mg, 2.42 mmol) in N,N-dimethylformamide (10 mL) at 0° C. under nitrogen was added N,N-diisopropylethylamine (2.11 mL, 12.1 mmol) and 2-(1H-7-azabenzotriazol-1-yl)-1,1,3,3-tetramethyl uronium hexafluorophosphate methanaminium (1.01 g, 2.66 mmol). The resulting mixture was stirred at RT for 15 min then re-cooled to 0° C. and (S)-1-[(S)-2-((S)-2-amino-3-methyl-butyrylamino)-propionyl]-hexahydro-pyridazine-3-carboxylic acid 2,2,2-trichloro-ethyl ester generated in the previous step, was added as a solution in N,N-dimethylformamide (10.7 mL). The reaction mixture was then allowed to warm to RT with stirring. After 1 h the mixture was diluted with ethyl acetate (100 mL) and water (100 mL). The phases were separated and the aqueous was extracted with ethyl acetate (100 mL). The combined organics were washed with brine (100 mL), dried over magnesium sulfate, filtered and concentrated in vacuo to give a crude residue. This was purified by silica gel chromatography using iso-hexanes/acetone 95:5 (1000 mL) then iso-hexanes/acetone 9:1 (1 L) then iso-hexanes/acetone 85:15 (1 L) then iso-hexanes/acetone 3:1 (1 L) then iso-hexanes/acetone 7:3 (1 L) to yield the title compound (1.11 g, 62%) as a colorless solid.

Compound 22f

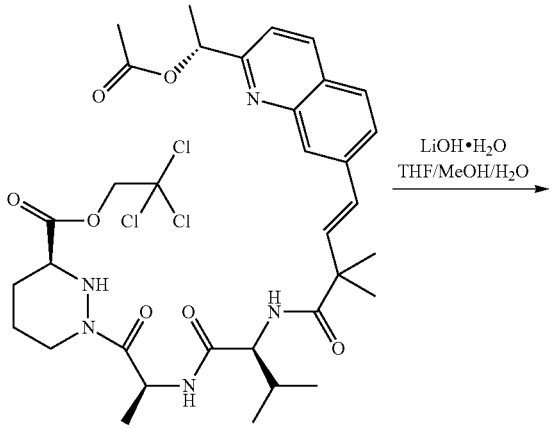

-continued

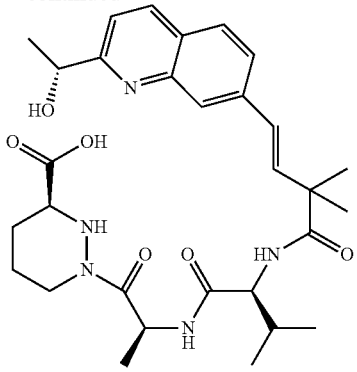

A solution of 22e (1.11 g, 1.50 mmol) in tetrahydrofuran (14.7 mL) was cooled in an ice-water bath and methanol (7.4 mL), water (7.4 mL), and lithium hydroxide monohydrate (252 mg, 6.0 mmol) were then added. The mixture was stirred for 1 h in the ice-water bath and then quenched with aqueous 1 M hydrochloric acid (6 mL, 6.0 mmol). The resulting solution was concentrated in vacuo, and the crude product was concentrated from methanol (4×250 mL) then acetonitrile (4×250 mL) and toluene (5×250 mL). The solid isolated was then left on the freeze dryer overnight to afford the title compound (853 mg, quantitative yield) as a white solid.

Compound 22

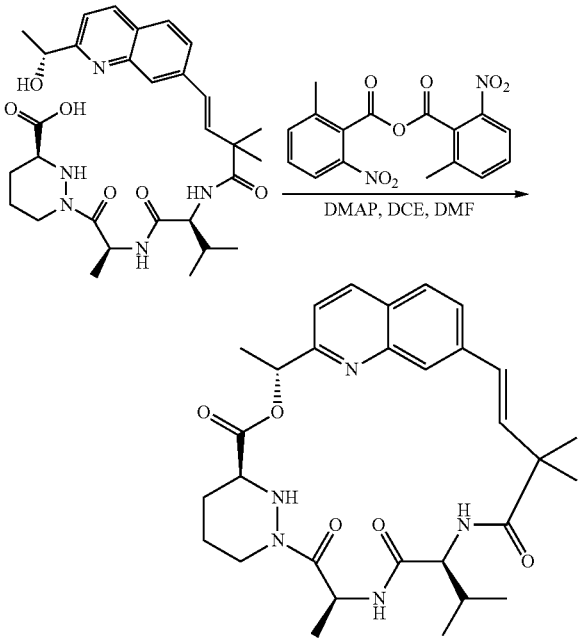

Under nitrogen, 2-methyl-6-nitrobenzoic anhydride (2.59 g, 7.51 mmol) and 4-(dimethylamino)pyridine (1.38 g, 11.3 mmol) were dissolved in 1,2-dichloroethane (500 mL) and the resulting solution was heated to 50° C. The crude seco-acid from the previous step, 22f (853 mg, 1.50 mmol) was dissolved in N,N-dimethylformamide (19 mL) and added to the reaction mixture dropwise via syringe pump over 6 h. After the addition was complete, the syringe pump was then rinsed with additional N,N-dimethylformamide (3 mL) and the reaction mixture was stirred at 50° C. for 40 min. After this time the mixture was concentrated to give a residue. This was purified by silica gel chromatography using iso-hexanes (66 mL), then iso-hexanes/acetone 4:1 (726 mL), then iso-hexanes/acetone 7:3 (726 mL), then iso-hexanes/acetone 3:2 (726 mL). This initial column gave impure product (1.10 g) which contained N,N-dimethylformamide. To this was added brine (200 mL) and the organics extracted with ethyl acetate (2×100 mL). The combined organics were dried over magnesium sulfate, filtered and concentrated in vacuo to give impure product (900 mg) which does not contain N,N-dimethylformamide. This residue was purified by a second silica gel chromatography using iso-hexanes/acetone 95:5 (6 L), then iso-hexanes/acetone 93:7 (1.5 L), then iso-hexanes/acetone 88:12 (3 L), then iso-hexanes/acetone 82:16 until all the product eluted from the column. Two batches of the desired product in 87% purity (batch A) and 77% purity (batch B) were isolated. Batch A was triturated twice with 100% diethyl ether to give the title compound (241 mg) in approximately 90-95% purity. Purification of Batch B by preparative reverse phase HPLC gave the title compound (181 mg) in approximately >95% purity. Batch A and B were combined to give the title compound (422 mg, 51%) as a white solid. $^1$H NMR (500 MHz, $CD_3OD$) 0.94 (app t, J=6.7 Hz, 6H), 1.34 (s, 3H), 1.48 (s, 3H), 1.58 (d, J=7.3 Hz, 3H), 1.62-1.75 (m, 5H), 1.82-1.91 (m, 1H), 1.92-2.03 (m, 2H), 2.66-2.78 (m, 1H), 3.78 (app d, J=8.5 Hz, 1H), 4.25-4.33 (m, 1H), 4.34-4.43 (m, 1H), 5.71 (q, J=7.3 Hz, 1H), 5.89 (q, J=6.7 Hz, 1H), 6.24 (d, J=16.0 Hz, 1H), 6.46 (d, J=16.0 Hz, 1H), 7.27 (br d, J=9.8 Hz, 1H), 7.38 (d, J=8.6 Hz, 1H), 7.60 (s, 1H), 7.75 (ABq, $\Delta\delta_{AB}$=0.03, $J_{AB}$=8.54 Hz, 2H), 8.18 (d, J=7.9 Hz, 1H). LCMS (m/z) 550.1 [M+H], Tr=2.24 min.

Example 23

Compound 23

Compound 23a

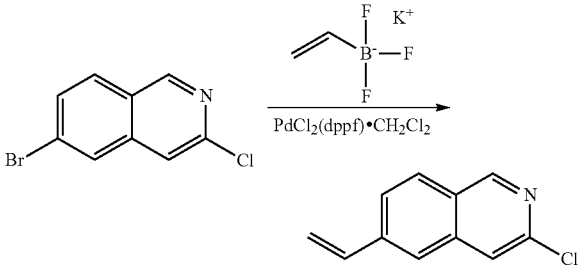

A solution of 6-bromo-3-chloro-isoquinoline (2.0 g, 8.25 mmol) in n-propanol (90 mL) was prepared and potassium vinyltrifluoroborate (1.11 g, 8.25 mmol) was added. The solution was purged with nitrogen for 10 min before addition of [1,1'-bis(diphenylphosphino)ferrocene]dichloropalladium(II), complex with dichloromethane (128 mg, 0.157 mmol) and triethylamine (1.15 mL, 8.25 mmol). The reaction mixture was then purged with nitrogen for a further 3 min before heating to reflux for 1 h. The reaction mixture was then allowed to cool to RT and water was added. The organics were then extracted with diethyl ether (3×150 mL). The combined organics were dried over magnesium sulfate, filtered and concentrated in vacuo to give a crude residue.

This was purified by silica gel chromatography, using isohexanes/diethyl ether 9:1 to give the title compound (1.26 g, 80%) as an oil.

Compound 23b

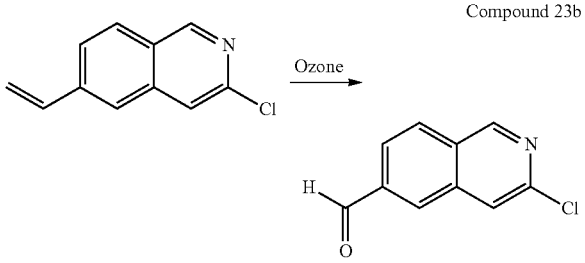

A suspension of 23a (1.24 g, 6.54 mmol) in methanol (125 mL) and dichloromethane (125 mL) was cooled to −78° C. The reaction was ozonised until a blue colour persisted (in approximately 15 min), then nitrogen was bubbled through the reaction mixture for 15 min to purge the ozone. The reaction was then treated with solid sodium bicarbonate (549 mg, 6.54 mmol) and dimethyl sulfide (1.31 mL, 1.31 mmol). The mixture was allowed to warm to RT and after 3 h the reaction mixture was concentrated in vacuo. Water (200 mL) was added to the residue and the aqueous layer extracted with dichloromethane (3×200 mL). The combined organics were dried over magnesium sulfate, filtered and concentrated in vacuo to give the title compound (1.02 g, 81%) as an oil.

Compound 23c

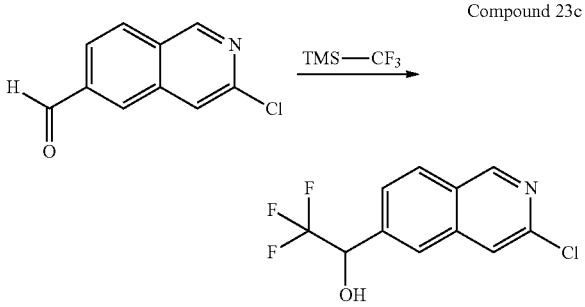

To a solution of 23b (1.02 g, 5.32 mmol) in tetrahydrofuran (10 mL) at 0° C. was added trimethyl(trifluoromethyl) silane solution (3.19 mL, 2 M in tetrahydrofuran, 6.38 mmol) followed by tetrabutylammonium fluoride solution (0.053 mL, 1 M in tetrahydrofuran, 0.053 mmol) and the resulting solution was stirred at 0° C. for 1.5 h. The reaction mixture was then allowed to warm to RT and 2 M hydrochloric acid (10 mL) was added and the mixture stirred for 10 min before addition of water (200 mL). The aqueous layer was then extracted with ethyl acetate (3×100 mL). The organics were combined, dried over sodium sulfate, filtered and concentrated to give the title compound (1.30 g, 93%) as a solid.

Compound 23d

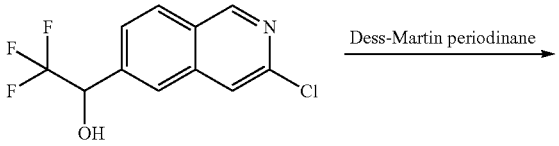

-continued

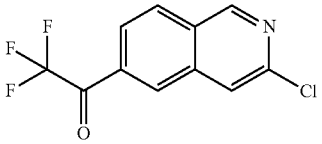

To a solution of 23c (1.30 g, 4.97 mmol) in dichloromethane (14.7 mL) at 0° C. was added Dess-Martin periodinane solution (14.7 mL, 15% in dichloromethane, 6.96 mmol) and the reaction mixture was stirred and allowed to warm to RT. 1 M Aqueous sodium metabisulfite (100 mL) was added and the reaction mixture was stirred for 15 min. To this mixture was added saturated aqueous sodium bicarbonate solution (100 mL) and the aqueous layer was extracted with dichloromethane (3×100 mL). The combined organics were washed with saturated aqueous sodium bicarbonate solution (200 mL) followed by brine (100 mL), dried over magnesium sulfate, filtered and concentrated in vacuo to give the title compound (1.0 g, 78%) as a solid.

Compound 23e

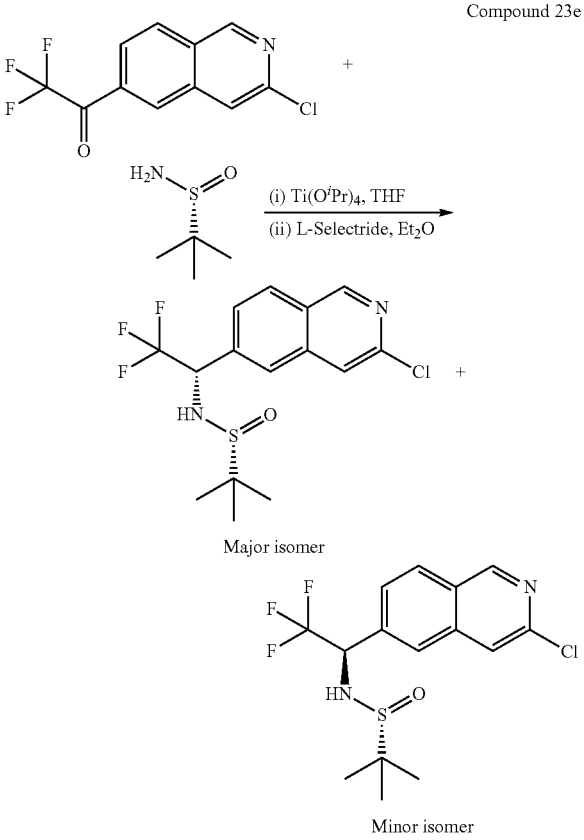

A mixture of 23d (686 mg, 2.64 mmol), (R)-2-methyl-2-propanesulfinamide (400 mg, 3.30 mmol) and titanium(IV) isopropoxide (1.95 mL, 6.60 mmol) in tetrahydrofuran (27.4 mL) was heated at reflux for 16 h then allowed to cool to RT. The reaction mixture was concentrated in vacuo and redissolved in diethyl ether (27.4 mL) then cooled to −78° C. To this mixture was added L-Selectride® solution (7.93 mL, 1.0 M in tetrahydrofuran, 7.93 mmol) and the reaction mixture stirred at −78° C. for 1 h. Brine (30 mL) was then added and the mixture allowed to warm to RT. More brine (200 mL) and ethyl acetate (300 mL) were added and the layers separated. The aqueous phase was re-extracted with dichloromethane (500 mL). The combined organics were dried over sodium sulfate, filtered and concentrated in vacuo to give a crude residue. This was purified by silica gel chromatography, using gradient elution of dichloromethane to dichloromethane/methanol 99:1 to give the title compound (553 mg, 57% yield, 94% d.e.).

Compound 23f

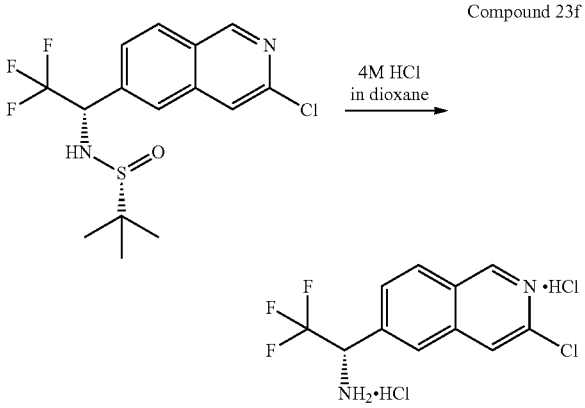

To a solution of 23e (553 mg, 1.52 mmol) in methanol (10 mL) was added 4 M hydrochloric acid solution in 1,4-dioxane (1.52 mL, 6.06 mmol) and the reaction mixture was stirred at RT for 30 min. Additional 4 M hydrochloric acid solution in 1,4-dioxane (1.52 mL, 6.06 mmol) was added and the reaction mixture stirred at RT for 30 min then concentrated in vacuo to give the title compound (507 mg, quantitative yield).

Compound 23g

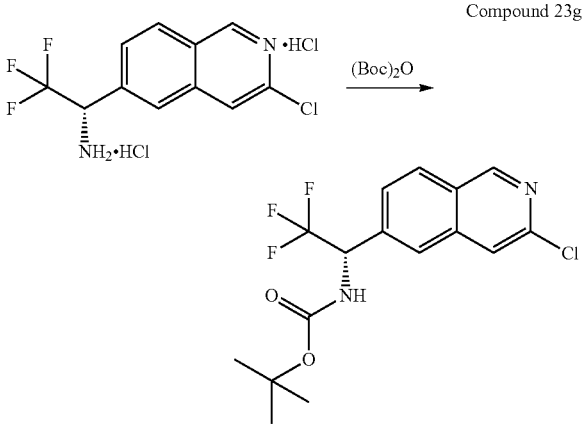

A mixture of 23f (507 mg, 1.52 mmol) and triethylamine (0.84 mL, 6.08 mmol) in dichloromethane (20 mL) was stirred at 0° C. to give a solution. Then a solution of di-tert-butyl dicarbonate (497 mg, 2.28 mmol) in dichloromethane (4 mL) was added and the reaction mixture was stirred and allowed to warm to RT over 24 h. Water (200 mL) was added and the aqueous layer extracted with dichloromethane (3×100 mL), dried over sodium sulfate, filtered and concentrated in vacuo to give a residue (816 mg). This residue was dissolved in dichloromethane (20 mL) and cooled to 0° C. then triethylamine (0.84 mL, 6.08 mmol) was added followed by a solution of di-tert-butyl dicarbonate (497 mg, 2.28 mmol) in dichloromethane (4 mL) and the reaction mixture was stirred and allowed to warm to RT over 72 h. Additional di-tert-butyl dicarbonate (162 mg, 0.74 mmol) was added and stirring continued for 30 min then water (100 mL) was added and the aqueous layer extracted with dichloromethane (2×50 mL). The combined organics were dried over sodium sulfate, filtered and concentrated in vacuo to give a crude residue. This was purified by silica gel chromatography, using gradient elution of iso-hexanes/ethyl acetate 9:1 to iso-hexanes/ethyl acetate 1:1 to give the title compound (140 mg, 25%) as an oil.

Compound 23h

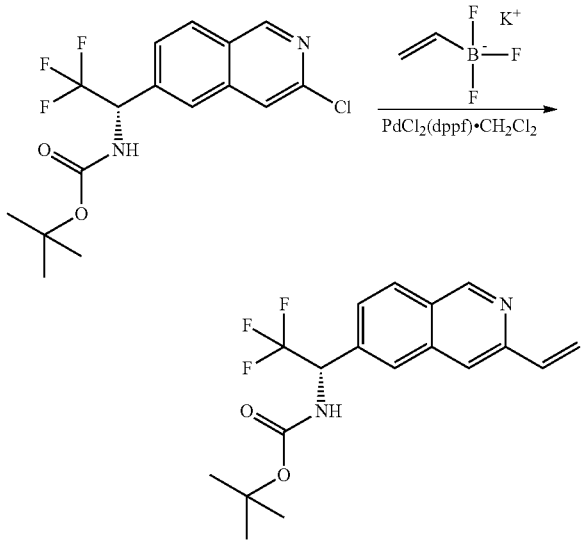

To a solution of 23 g (135 mg, 0.37 mmol) in n-propanol (6 mL) was added potassium vinyltrifluoroborate (55 mg, 0.412 mmol), [1,1'-bis(diphenylphosphino) ferrocene]dichloropalladium(II), complex with dichloromethane (5.8 mg, 0.007 mmol) and triethylamine (0.052 mL, 0.37 mmol). The suspension was evacuated and purged with nitrogen 3 times before heating to 100° C. for 2 h. After this time additional potassium vinyltrifluoroborate (100 mg, 0.748 mmol) was added and heating continued at 100° C. for 16 h. After this time, additional [1,1'-bis(diphenylphosphino)ferrocene]dichloropalladium(II), complex with dichloromethane (9 mg, 0.011 mmol) was added and the reaction mixture was heated in a microwave reactor at 150° C. for 90 min. After this time additional [1,1'-bis(diphenylphosphino)ferrocene]dichloropalladium(II), complex with dichloromethane (9 mg, 0.011 mmol) was added and the reaction mixture was heated in a microwave reactor at 150° C. for 10 min. Water (100 mL) was added to the reaction mixture and the aqueous layer was then extracted with diethyl ether (2×100 mL). The combined organics were dried over sodium sulfate, filtered and concentrated in vacuo to give the title compound (132 mg, quantitative yield).

Compound 23i

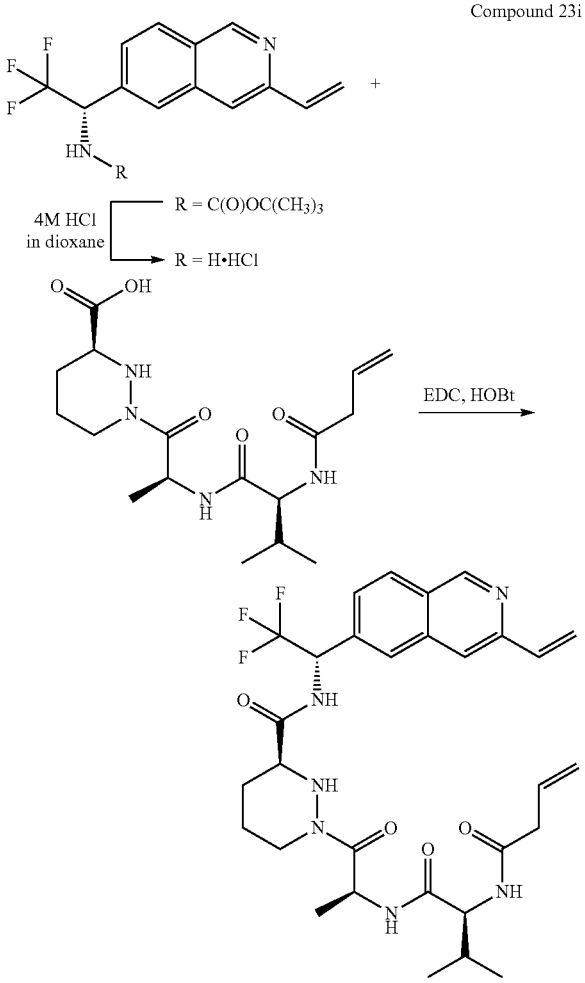

To a solution of 23 h (132 mg, 0.37 mmol) in methanol (2 mL) was added 4 M hydrochloric acid in 1,4-dioxane (0.37 mL, 0.75 mmol) and the mixture stirred at RT for 30 min. Additional 4 M hydrochloric acid in 1,4-dioxane (3.0 mL, 6.08 mmol) was added and stirring continued for 2 h then the reaction mixture was concentrated in vacuo to give a residue. The residue was then concentrated from diethyl ether (2 mL), followed by acetonitrile (10 mL) and this was repeated twice to give (S)-2,2,2-trifluoro-1-(3-vinyl-isoquinolin-6-yl)-ethylamine hydrochloric acid salt (108 mg, quantitative yield). To a suspension of (S)-2,2,2-trifluoro-1-(3-vinyl-isoquinolin-6-yl)-ethylamine hydrochloric acid salt (108 mg, 0.374 mmol) in acetonitrile (2 mL) at 0° C. under nitrogen was added (S)-1-[(S)-2-((S)-2-but-3-enoylamino-3-methyl-butyrylamino)-propionyl]-hexahydro-pyridazine-3-carboxylic acid (138 mg, 0.37 mmol), N-(3-dimethylaminopropyl)-N'-ethylcarbodiimide hydrochloride (100 mg, 0.52 mmol) and 1-hydroxybenzotriazole hydrate (63 mg, 20 wt % in water, 0.37 mmol). The resulting suspension was stirred at 0° C. for 15 min before removing from the ice-water bath and stirring at RT for 16 h. N,N-Diisopropylethylamine (0.5 mL, 2.87 mmol) was added and the solution was stirred at RT for 2.5 h where additional (S)-1-[(S)-2-((S)-2-but-3-enoylamino-3-methyl-butyrylamino)-propionyl]-hexahydro-pyridazine-3-carboxylic acid (69 mg, 0.19 mmol) was added and stirring continued. After 1 h, N-(3-dimethylaminopropyl)-N'-ethylcarbodiimide hydrochloride (134 mg, 0.70 mmol) was added and the reaction mixture was stirred at RT for 1 hour. After this time, the mixture was concentrated in vacuo and the residue diluted with ethyl acetate (60 mL). Water (50 mL) was added and the layers separated. The aqueous phase was re-extracted with ethyl acetate (2×10 mL) and the combined organics were then washed with ammonium chloride (2×50 mL), dried over sodium sulfate, filtered and concentrated in vacuo to give a crude residue. This was purified by silica gel chromatography, using gradient elution of iso-hexanes/ethyl acetate 9:1 to iso-hexanes/ethyl acetate 4:1 to iso-hexanes/ethyl acetate 1:1 and finally iso-hexanes/ethyl acetate 0:1. This gave the title compound (124 mg, 55%).

Compound 23

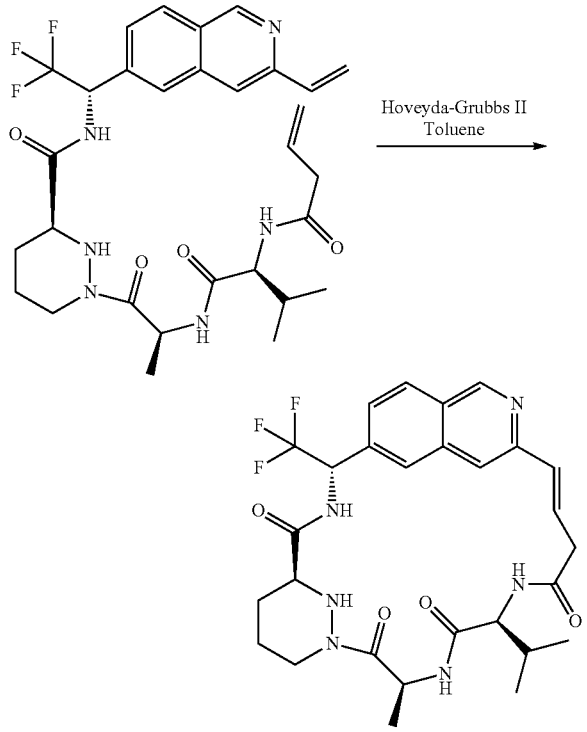

To a solution of 23i (124 mg, 0.21 mmol) in toluene (69 mL) was added Hoveyda-Grubbs $2^{nd}$ generation catalyst (13 mg, 0.02 mmol) and the reaction mixture heated at 115° C. for 1.5 h. Additional Hoveyda-Grubbs $2^{nd}$ generation catalyst (13 mg, 0.02 mmol) was added and heating continued at 120° C. for 50 min. Additional Hoveyda-Grubbs $2^{nd}$ generation catalyst (13 mg, 0.02 mmol) was added and heating continued at 120° C. for 30 min. After this time the mixture was allowed to cool to RT and concentrated in vacuo. The residue was purified by silica gel chromatography using a gradient of ethyl acetate to ethyl acetate/acetone 9:1. Impure product (28.3 mg) was collected which was further purified by preparative TLC eluting with ethyl acetate/acetone 95:5 to afford the title compound (4 mg, 3%) as a white solid. $^1$H NMR (300 MHz, $CD_3OD$) 0.99 (d, J=6.7 Hz, 3H), 1.01 (d, J=6.7 Hz, 3H), 1.29-1.39 (m, 1H), 1.69 (d, J=7.4 Hz, 3H), 1.74-2.01 (m, 5H), 2.73 (td, J=12.9, 2.9 Hz, 1H), 2.99-3.11 (m, 1H), 3.74-3.83 (m, 1H), 4.26 (d, J=10.0 Hz, 1H), 4.41 (br d, J=13.2 Hz, 1H), 5.48 (q, J=7.4 Hz, 1H), 5.84 (q, J=8.3 Hz, 1H), 6.58 (d, J=16.3 Hz, 1H), 6.62-6.71 (m, 1H), 7.47 (s, 1H), 7.76 (d, J=8.6 Hz, 1H), 7.89 (s, 1H), 8.13 (d, J=8.6 Hz, 1H), 9.22 (s, 1H). LCMS (m/z) 575.2 [M+H], Tr=1.53 min.

Example 24

Compound 24

Compound 24a

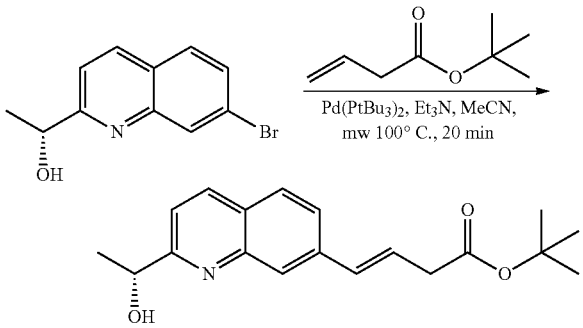

To a solution of (R)-1-(7-bromo-quinolin-2-yl)-ethanol (295 mg, 1.17 mmol) in anhydrous acetonitrile (12 mL) were added but-3-enoic acid tert-butyl ester (0.44 mL, 2.75 mmol), bis(tri-tert-butylphosphine)palladium(0) (25 mg, 0.049 mmol) and N,N-dicyclohexylmethylamine (0.39 mL, 1.83 mmol) then the mixture was heated at reflux for 2 h. The reaction mixture was concentrated in vacuo to give a crude residue. This was purified by silica gel chromatography using iso-hexanes/ethyl acetate 95:5 to yield the title compound (348 mg, 95%) as a white solid.

To 24a (363 mg, 1.16 mmol) and (S)-1-[(S)-2-((S)-2-tert-butoxycarbonylamino-3-methyl-butyrylamino)-propionyl]-hexahydro-pyridazine-3-carboxylic acid (505 mg, 1.26 mmol) in dichloromethane (20 mL) was added N-(3-dimethylaminopropyl)-N'-ethylcarbodiimide hydrochloride (311 mg, 1.62 mmol) and 4-dimethylaminopyridine (142 mg, 1.16 mmol). The reaction mixture was then stirred at RT for 16 h. To the mixture was added saturated aqueous ammonium chloride solution (100 mL) and the aqueous layer extracted with dichloromethane (2×50 mL). The aqueous phase was further washed with dichloromethane (20 mL) and the combined organics washed with brine (50 mL), dried over magnesium sulfate, filtered and concentrated in vacuo to give a crude residue. This was purified by silica gel chromatography using iso-hexanes/ethyl acetate 4:1 (120 mL) then iso-hexanes/ethyl acetate 7:3 (855 mL) then iso-hexanes/ethyl acetate 3:2 (540 mL) to yield the title compound (357 mg, 44%) as a white solid.

Compound 24

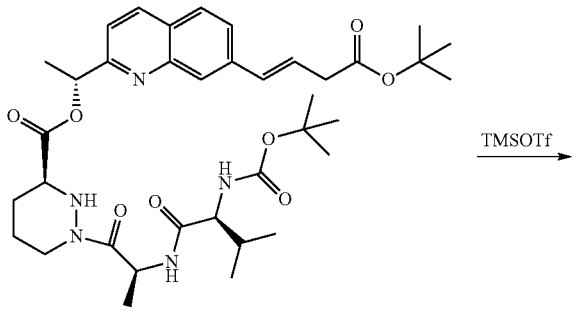

Compound 24b

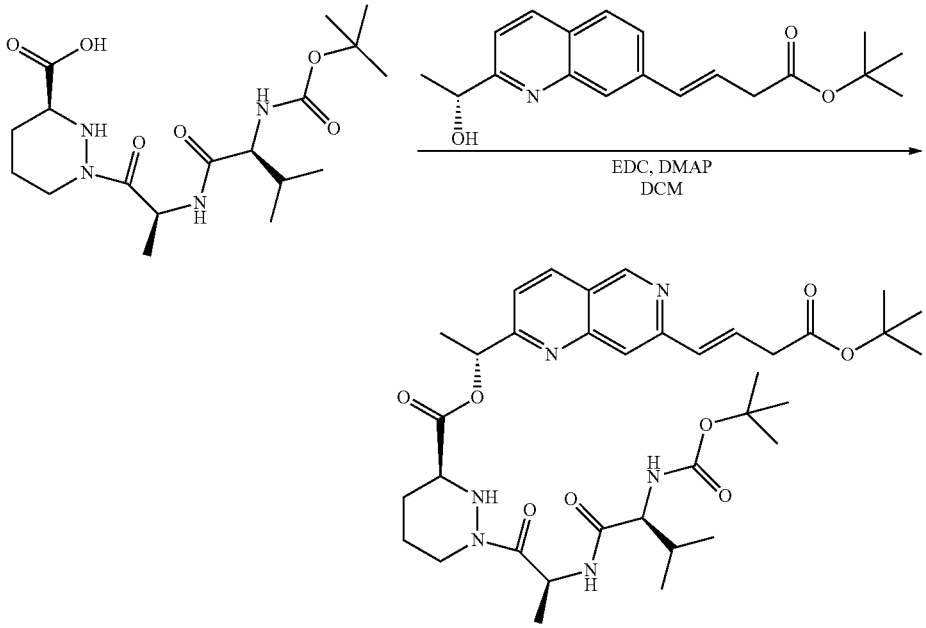

-continued

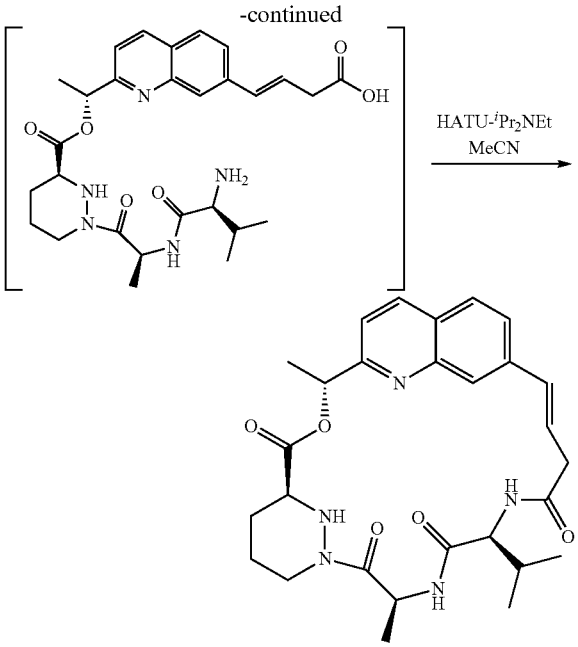

To a solution of 24b (342 mg, 0.492 mmol) in dichloromethane (2.5 mL) at 0° C. was added trimethylsilyl trifluoromethanesulfonate (0.18 mL, 0.96 mmol) and the pale yellow solution stirred at 0° C. for 2.75 h. Additional trimethylsilyl trifluoromethanesulfonate (0.073 mL, 0.45 mmol) was added and stirring continued for 1.33 h. N,N-Diisopropylethylamine (0.6 mL, 3.44 mmol) was added and the mixture stirred for 10 min then concentrated in vacuo to give intermediate (S)-1-[(S)-2-((S)-2-amino-3-methyl-butyrylamino)-propionyl]-hexahydro-pyridazine-3-carboxylic acid (R)-1-[7-((E)-3-carboxy-propenyl)-quinolin-2-yl]-ethyl ester (266 mg, 0.45 mmol). To a solution of (S)-1-[(S)-2-((S)-2-amino-3-methyl-butyrylamino)-propionyl]-hexahydro-pyridazine-3-carboxylic acid (R)-1-[7-((E)-3-carboxy-propenyl)-quinolin-2-yl]-ethyl ester (266 mg, 0.45 mmol) in acetonitrile (50 mL) at 0° C. under nitrogen was added N,N-diisopropylethylamine (0.343 mL, 1.971 mmol) and 2-(1H-7-azabenzotriazol-1-yl)-1,1,3,3-tetramethyl uronium hexafluorophosphate methanaminium (262 mg, 0.70 mmol). The mixture was stirred at 0° C. and allowed to warm to RT over 16 h. To the reaction mixture was added 2 M aqueous hydrochloric acid solution (20 mL) and the mixture concentrated in vacuo. The aqueous layer was extracted with dichloromethane/methanol 9:1 (2×100 mL). The combined organics were washed with saturated sodium hydrogen carbonate solution (2×200 mL), then brine (1×100 mL), dried over sodium sulfate, filtered and concentrated in vacuo to give a crude residue. This was purified by silica gel chromatography using gradient elution of ethyl acetate/acetone 97:3 to ethyl acetate/acetone 94:6. Collected 45 mg of impure product which was triturated with diethyl ether to give the title compound (25.4 mg, 10%) as a pale yellow solid. $^1$H NMR (300 MHz, $CD_3OD$) δ 0.99 (d, J=6.48 Hz, 3H), 1.01 (d, J=6.7 Hz, 3H), 1.64 (d, J=7.1 Hz, 3H), 1.66-1.72 (m, 1H), 1.74 (d, J=6.9 Hz, 3H), 1.85-2.08 (m, 4H), 2.75 (dd, J=2.9, 12.9 Hz, 1H), 2.97-3.07 (m, 1H), 3.35-3.40 (m, 1H), 3.79-3.88 (m, 1H), 4.23 (d, J=10.5 Hz, 1H), 4.43 (br d, J=11.2 Hz, 1H), 5.72 (q, J=7.1 Hz, 1H), 5.94 (q, J=6.9 Hz, 1H), 6.41 (d, J=16.7 Hz, 1H), 6.55 (dt, J=4.7, 16.7 Hz, 1H), 7.40 (d, J=8.5 Hz, 1H), 7.65 (s, 1H), 7.75 (dd, J=1.3, 8.7 Hz, 1H), 7.81 (d, J=8.7 Hz, 1H), 8.21 (d, J=8.5 Hz, 1H). LCMS (m/z) 522.2 [M+H], Tr=1.90 min.

Example 25

Compound 25

Compound 25a

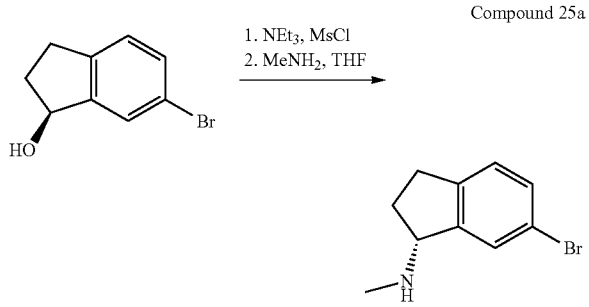

A cooled (−20° C.) solution of (S)-6-bromo-indan-1-ol (1.0462 g, 4.910 mmol, prepared as described in WO 2009/003719) in anhydrous tetrahydrofuran (20 mL) was subsequently treated with triethylamine (2.7 mL, 19.639 mmol) and methanesulfonyl chloride (760 μL, 9.820 mmol). After stirring at −30° C. for 2.5 h, a solution of methylamine (2 M in tetrahydrofuran, 25 mL, 50 mmol) was added. After stirring at RT for 22.5 h the reaction mixture was filtered. The white solid was rinsed with diethyl ether. The filtrate was evaporated to dryness to afford the title compound (1.11 g, quantitative yield) as a white solid.

Compound 25b

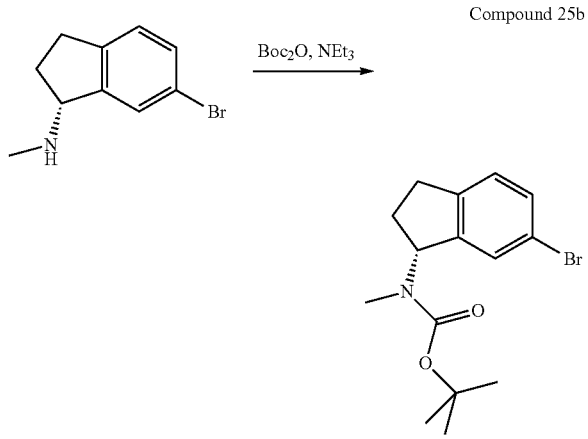

A solution of 25a (1.11 g, 4.910 mmol) was subsequently treated with di-tert-butyl dicarbonate (1.714 g, 7.856 mmol) and triethylamine (690 μL, 4.91 mmol). After stirring for 25.5 h, the volatiles were removed in vacuo and the residue was purified by silica gel chromatography using a 50 g Isolute cartridge eluted with a continuous gradient of isohexanes/ethyl acetate 1:0 to 9:1 to afford the title compound (1.4224 g, 89%) as a white solid as a mixture of rotamers.

Compound 25c

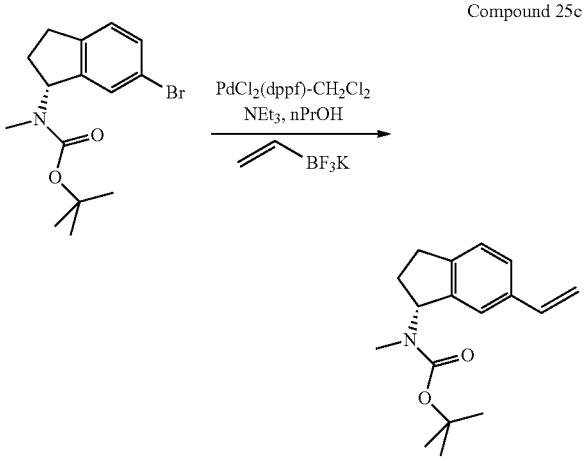

A solution of 25b (1.4224 g, 4.363 mmol), [1,1-bis (diphenylphosphino)ferrocene]dichloropalladium dichloromethane complex (71.3 mg, 0.087 mmol), potassium vinyltrifluoroborate (701.3 mg, 5.236 mmol) and triethylamine (610 μL, 4.363 mmol) in anhydrous n-propanol (40 mL) was degassed by bubbling nitrogen through for 30 min. The red suspension was then refluxed for 17.5 h. After cooling to RT, the mixture was quenched with water and the aqueous layer was extracted with diethyl ether (2×). The organics were combined, dried over sodium sulfate, filtered and the volatiles were removed in vacuo. The residue was purified by silica gel chromatography using a 50 g Isolute cartridge eluted with a continuous gradient of iso-hexanes/diethyl ether 1:0 to 4:1 to afford the title compound (977.3 mg, 82%) as a white solid as a mixture of rotamers.

Compound 25d

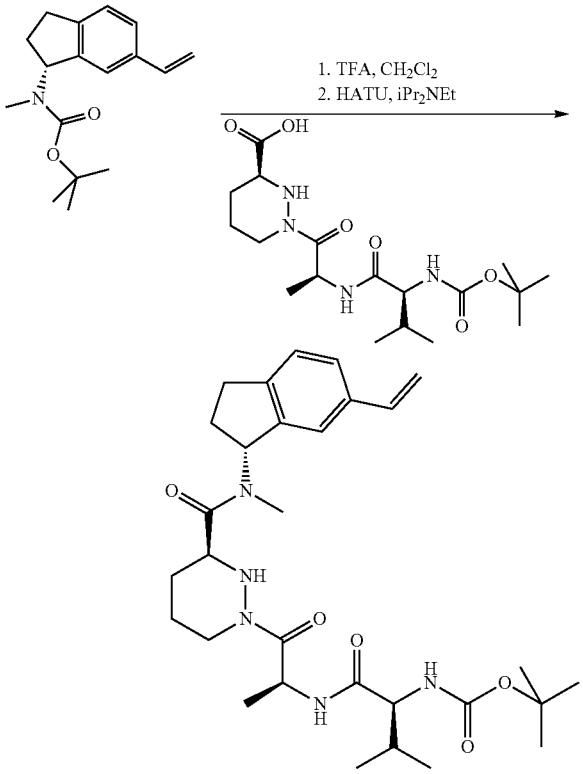

A cooled (0° C.) solution of 25c (977.3 mg, 3.575 mmol) in dichloromethane (20 mL) was treated with trifluoroacetic acid (5 mL). After stirring for 30 min at RT the volatiles were removed in vacuo and the residual trifluoroacetic acid was azeotroped off with toluene (3×) to afford the corresponding ammonium salt as a pink solid. A cooled (0° C.) solution of the crude ammonium salt, crude (S)-1-[(S)-2-((S)-2-tert-butoxycarbonylamino-3-methyl-butyrylamino)-propionyl]-hexahydro-pyridazine-3-carboxylic acid (3.932 mmol) and N,N-diisopropylethylamine (2.5 mL, 14.300 mmol) in acetonitrile (60 mL) was treated with 2-(1H-7-azabenzotriazol-1-yl)-1,1,3,3-tetramethyl uronium hexafluorophosphate methanaminium (1.903 g, 5.005 mmol). After stirring for 20 h at RT, the reaction was quenched with hydrochloric acid (1 M, 100 mL). The aqueous layer was extracted with ethyl acetate (2×). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:2 to afford the title compound in a mixture which was dissolved in ethyl acetate and washed with aqueous potassium carbonate. The organics were dried over sodium sulfate, filtered and the volatiles were removed in vacuo to afford the title compound (798.9 mg, 36%) as a white solid as a mixture of rotamers.

Compound 25e

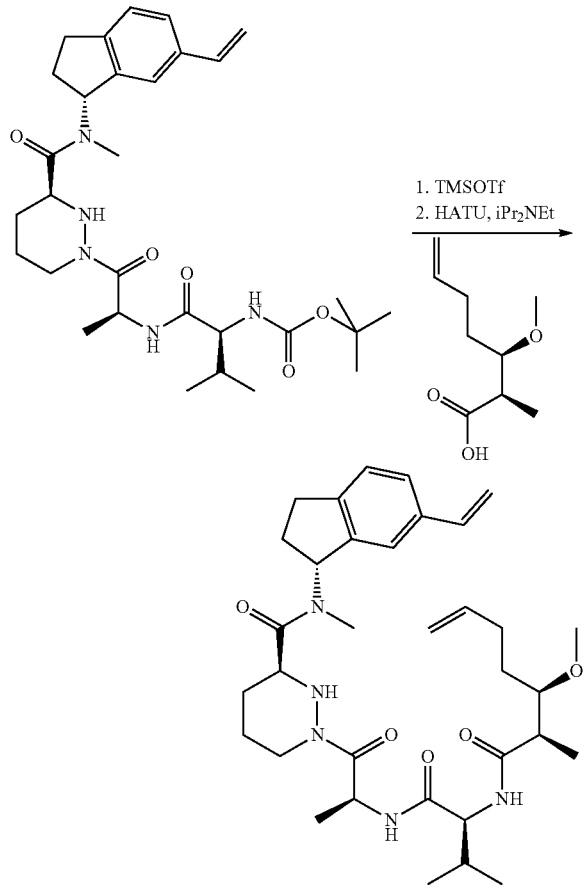

Compound 25e was prepared in the same manner as 22e using 25d and acid 28d instead of 1e and 22e, respectively in 27% yield as a complex mixture of rotamers.

Compound 25

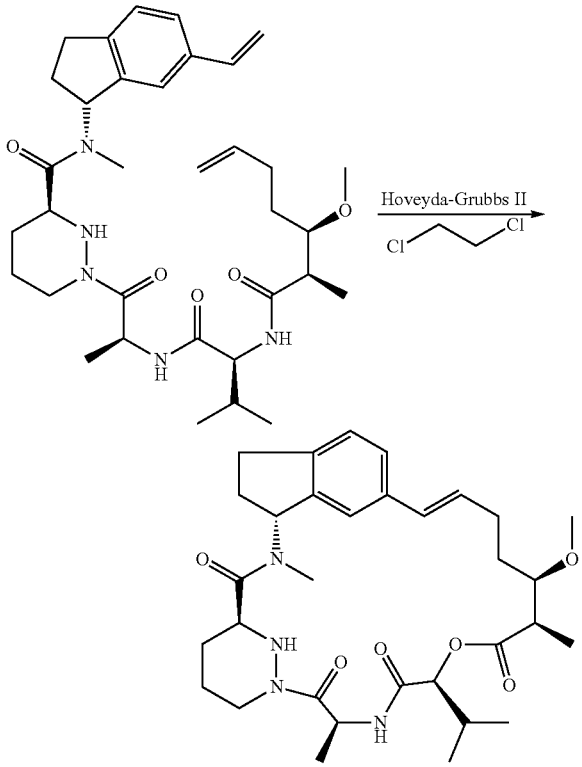

A solution of 25e (238.3 mg, 0.390 mmol) in dichloroethane (100 mL) was treated with Hoveyda-Grubbs $2^{nd}$ generation catalyst (48.9 mg, 0.078 mmol). After stirring at reflux for 1.5 h, the reaction was cooled to RT and the volatiles were removed in vacuo. The residue was purified by silica gel chromatography using a 10 g Isolute cartridge eluted by gravity with a continuous gradient of ethyl acetate/methanol 1:0 to 95:5 followed by preparative TLC eluted with ethyl acetate/methanol 97:3 (2 elutions) to provide the final compound (10.2 mg, 5%) as a white solid. $^1$H NMR (300 MHz, $CD_3CN$) δ 0.85-0.97 (m, 6H), 1.21-1.35 (m, 8H), 1.42-1.62 (m, 3H), 1.64-1.77 (m, 2H), 1.80-1.89 (m, 2H), 2.27-2.38 (m, 2H), 2.52 (dd, J=7.6, 3.1 Hz, 1H), 2.76 (s, 3H), 2.82-3.06 (m, 2H), 3.27-3.35 (m, 1H), 3.47 (s, 3H), 3.80-3.91 (m, 1H), 4.06 (dd, J=9.1, 8.2 Hz, 1H), 4.23 (d, J=11.8 Hz, 1H), 4.41 (dd, J=12.9, 3.6 Hz, 1H), 5.44 (app pentet, J=8.0 Hz, 1H), 6.10-6.30 (m, 2H), 6.43 (d, J=16.0 Hz, 1H), 6.88 (d, J=8.0 Hz, 1H), 6.96 (d, J=9.4 Hz, 1H), 7.04 (s, 1H), 7.13-7.28 (m, 2H). LCMS (m/z) 582.3 [M+H], Tr=2.57 min.

Example 26

Compound 26

Compound 26a

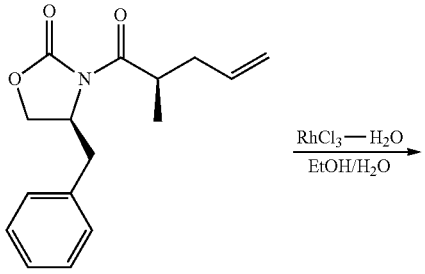

-continued

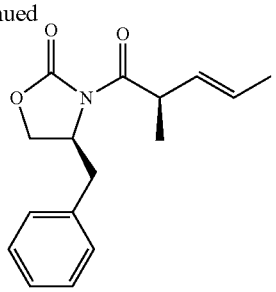

A solution of (S)-4-benzyl-3-((R)-2-methyl-pent-4-enoyl)-oxazolidin-2-one (1.65 g, 6.04 mmol, prepared as in Synlett 2002, 12, 2039-2040) in ethanol/water (22 mL, 10:1) was treated with rhodium(III) chloride hydrate (31.6 mg, 0.15 mmol). After stirring at 85° C. for 24 h, the reaction mixture was cooled to RT and the volatiles were removed in vacuo. The residue was purified by silica gel chromatography using a 50 g Isolute cartridge eluted with a continuous gradient of iso-hexanes/diethyl ether 1:0 to 4:1 to afford the title compound (892.7 mg, 54%) as a colorless oil.

Compound 26b

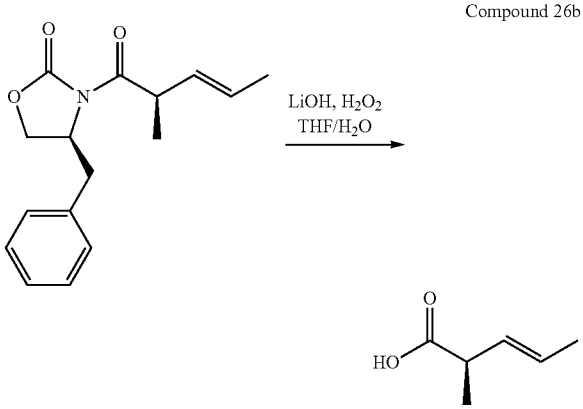

A cooled (0° C.) solution of 26a (893 mg, 3.27 mmol) in tetrahydrofuran/water (30 mL, 2:1) was subsequently treated with hydrogen peroxide (1.7 mL, 16.33 mmol, 30% in water) and lithium hydroxide hydrate (274 mg, 6.53 mmol). After stirring for 1.5 h at 0° C., the reaction was quenched with sodium metabisulfite (6.2 g, 32.66 mmol). After stirring at RT for 40 min, the mixture was acidified with hydrochloric acid (2 M) and the aqueous layer was extracted with dichloromethane (2×). The organics were combined, filtered through a phase separator and the volatiles were removed in vacuo. The residue was purified by silica gel chromatography using a 25 g Isolute cartridge eluted with a continuous gradient of iso-hexanes/ethyl acetate 1:0 to 4:1 to afford the title compound (307.1 mg, 82%) as a colorless oil.

Compound 26c

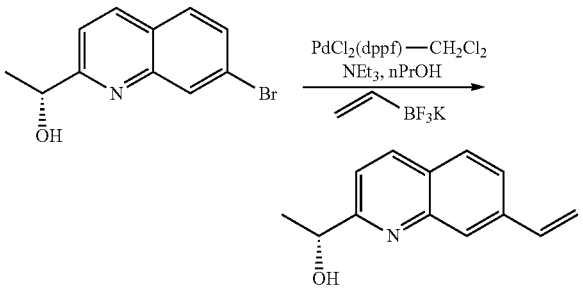

Compound 26c was prepared in the same manner as 25c using 22b instead of 25b in quantitative yield.

Compound 26d

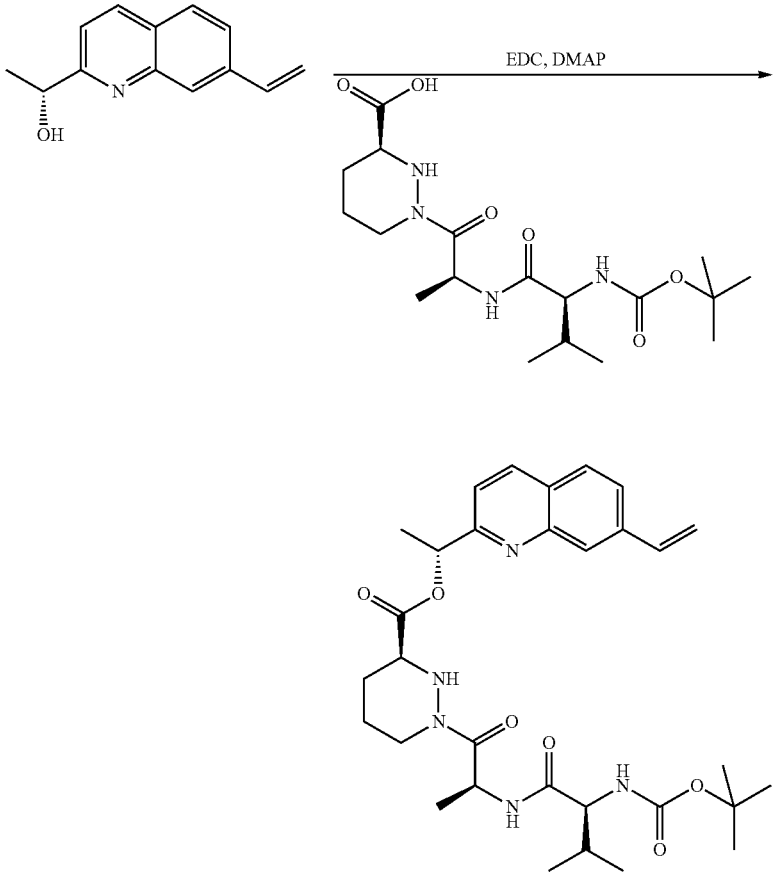

A solution of (S)-1-[(S)-2-((S)-2-tert-butoxycarbonylamino-3-methyl-butyrylamino)-propionyl]-hexahydropyridazine-3-carboxylic acid (261.2 mg, 0.653 mmol), 26c (108.4 mg, 0.544 mmol) and 4-dimethylaminopyridine (79.7 mg, 0.653 mmol) in dichloromethane (10 mL) was treated with N-(3-dimethylaminopropyl)-N'-ethylcarbodiimide hydrochloride (166.9 mg, 0.870 mmol). After stirring at RT for 17 h, the volatiles were removed in vacuo and the residue was purified by silica gel chromatography using a 50 g Isolute cartridge eluted with a continuous gradient of isohexanes/ethyl acetate 1:0 to 1:4 to 0:1 to afford the title compound (139.6 mg, 44%) as a white solid.

Compound 26e

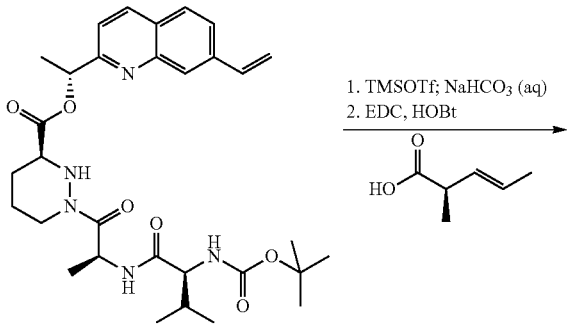

-continued

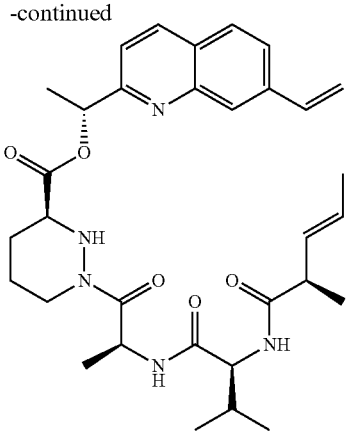

A cooled (0° C.) solution of 26d (139.6 mg, 0.240 mmol) in anhydrous dichloromethane (10 mL) was treated with trimethylsilyl methanesulfonate (90 μL, 0.480 mmol). After stirring for 1.5 h at 0° C., the reaction was quenched with saturated sodium bicarbonate. The aqueous layer was extracted with dichloromethane. The organics were combined, filtered through a phase separator and the volatiles were removed in vacuo to provide the intermediate amine. A solution of this amine, (E)-(R)-2-methyl-pent-3-enoic acid (32.9 mg, 0.288 mmol) and 1-hydroxybenzotriazole (38.9 mg, 0.288 mmol) in acetonitrile (10 mL) was treated with N-(3-dimethylaminopropyl)-N'-ethylcarbodiimide hydrochloride (64.4 mg, 0.336 mmol). After stirring at RT for 17.5 h the volatiles were removed in vacuo and the residue was purified by silica gel chromatography using a 25 g Isolute cartridge eluted with a continuous gradient of iso-hexanes/ethyl acetate 1:0 to 0:1 to afford the title compound (69.8 mg, 50%) as a colorless oil.

Compound 26

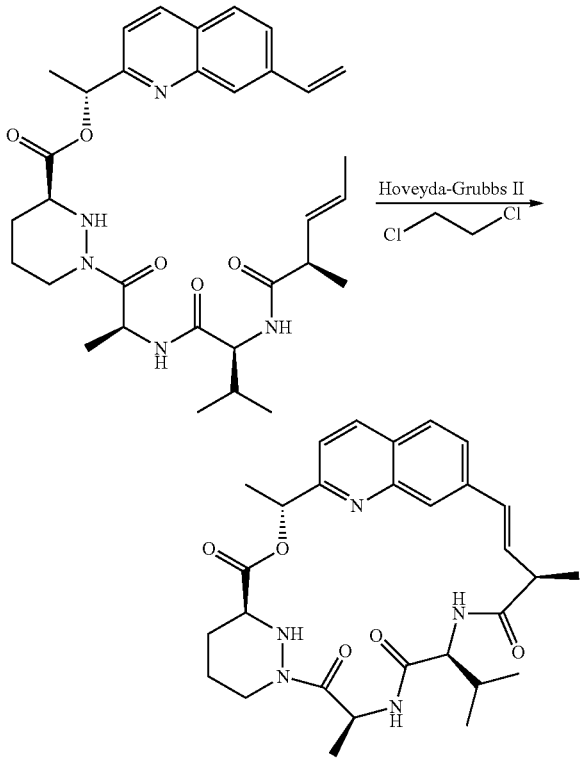

Compound 26 was prepared in the same manner as compound 25 using 26e instead of 25e in 4% yield. $^1$H NMR (300 MHz, $CD_3OD$) δ 0.94-1.00 (m, 6H), 1.47 (d, J=7.6 Hz, 3H), 1.63 (d, J=7.1 Hz, 3H), 1.67-1.80 (m, 5H), 1.85-2.07 (m, 3H), 2.76 (td, J=12.1, 3.3 Hz, 1H), 3.79-3.86 (m, 1H), 4.28 (d, J=10.5 Hz, 1H), 4.36-4.46 (m, 1H), 5.73 (q, J=7.1 Hz, 1H), 5.93 (q, J=6.9 Hz, 1H), 6.32-6.51 (m, 2H), 7.41 (d, J=8.5 Hz, 1H), 7.65 (s, 1H), 7.77-7.85 (m, 2H), 8.21 (d, J=8.5 Hz, 1H). LCMS (m/z) 536.1 [M+H], Tr=1.80 min.

Example 27

Compound 27

Compound 27a

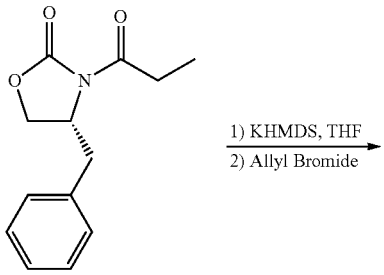

-continued

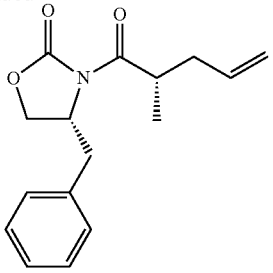

A cooled (−78° C.) solution of (R)-4-benzyl-3-propionyl-oxazolidin-2-one (3.00 g, 12.9 mmol) in anhydrous tetrahydrofuran (40 mL) was treated with potassium bis(trimethylsilyl)amide (19.3 mL, 19.3 mmol, 1 M in tetrahydrofuran). After stirring for 0.45 h at −78° C., the mixture was treated with allyl bromide (5.6 mL, 64.3 mmol). After stirring for 2 h at −40° C., the reaction was quenched with 2 M hydrochloric acid. The aqueous was extracted with ethyl acetate (2×50 The organics were combined, and the volatiles were removed in vacuo. The residue was purified by silica gel chromatography using a 50 g Biotage cartridge eluted with a continuous gradient of iso-hexanes/ethyl acetate 1:0 to 1:1 to afford the title compound (2.73 g, 78%) as a colorless oil.

Compound 27b

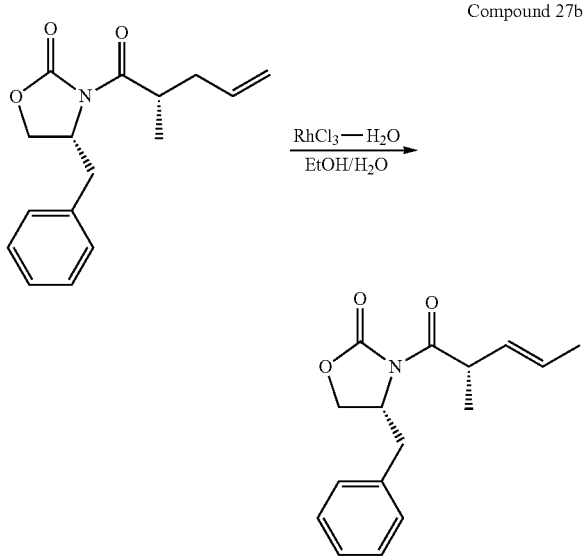

A solution of 27a (2.73 g, 9.97 mmol) in ethanol/water (22 mL, 10:1) was treated with rhodium(III) chloride hydrate (52 mg, 0.25 mmol). After stirring at 85° C. for 3 h, the reaction mixture was cooled to RT and the volatiles were removed in vacuo. The residue was purified by silica gel chromatography using a 50 g Biotage cartridge eluted with a continuous gradient of iso-hexanes/ethyl acetate 1:0 to 4:1 to afford the title compound (1.76 g, 65%) as a colorless oil.

Compound 27c

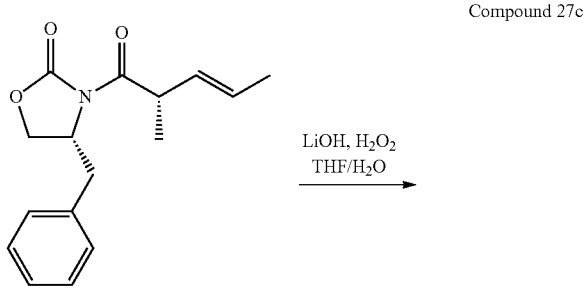

-continued

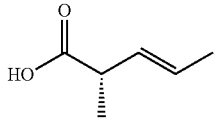

A cooled (0° C.) solution of 27b (1.76 g, 6.44 mmol) in tetrahydrofuran/water (60 mL, 2:1) was subsequently treated with hydrogen peroxide (3.3 mL, 32.2 mmol, 30% in water) and lithium hydroxide hydrate (534 mg, 12.9 mmol). After stirring for 2 h at 0° C., the reaction was quenched with sodium metabisulfite (12.2 g, 64.4 mmol). After stirring at RT for 1 h, the mixture was acidified with 2 M hydrochloric acid and the aqueous layer was extracted with dichloromethane (2×100 mL). The organics were combined, filtered and the volatiles were removed in vacuo. The residue was purified by silica gel chromatography using a 50 g Biotage cartridge eluted with a continuous gradient of iso-hexanes/ethyl acetate 1:0 to 4:1 to afford the title compound (463 mg, 63%) as a colorless oil.

Compound 27d

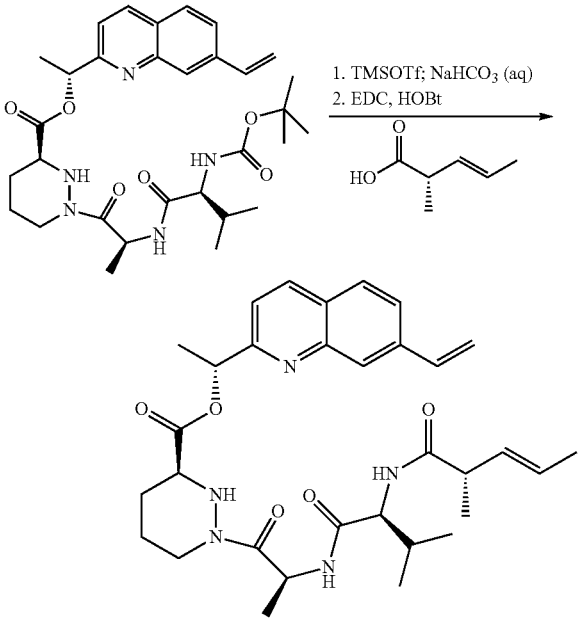

A cooled (0° C.) solution of (S)-1-[(S)-2-((S)-2-tert-butoxycarbonylamino-3-methyl-butyrylamino)-propionyl]-hexahydro-pyridazine-3-carboxylic acid (R)-1-(7-vinyl-quinolin-2-yl)-ethyl ester (380 mg, 0.65 mmol) in anhydrous dichloromethane (10 mL) was treated with trimethylsilyl methanesulfonate (237 μL, 1.31 mmol). After stirring for 1 h at 0° C., the reaction was quenched with saturated sodium bicarbonate. The aqueous layer was extracted with dichloromethane. The organics were separated and combined, volatiles were removed in vacuo to provide the intermediate amine (305 mg). A solution of this amine, 27c (90 mg, 0.76 mmol) and 1-hydroxybenzotriazole (103 mg, 0.76 mmol) in acetonitrile (20 mL) was treated with N-(3-dimethylamino-propyl)-N'-ethylcarbodiimide hydrochloride (170 mg, 0.89 mmol). After stirring at RT for 16 h the volatiles were removed in vacuo and the residue was purified by silica gel chromatography using a 25 g Biotage cartridge eluted with a continuous gradient of iso-hexanes/ethyl acetate 1:0 to 0:1 to afford the title compound (236 mg, 65%) as a colorless oil.

Compound 27

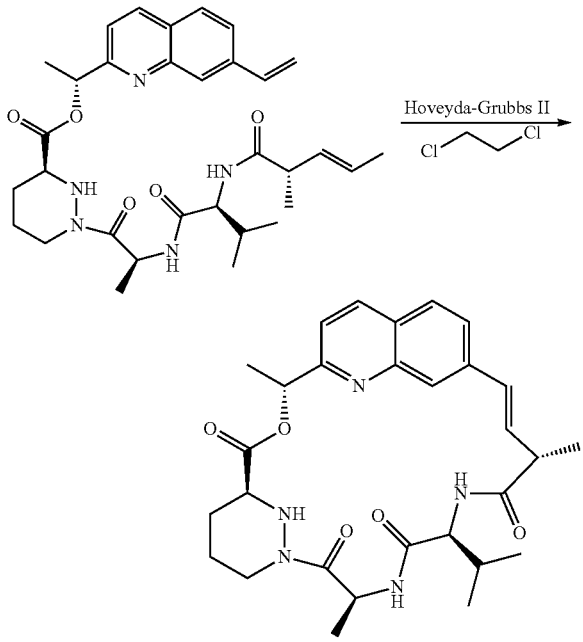

Compound 27 was prepared in the same manner as compound 25 using 27d instead of (S)-1-{(S)-2-[(S)-2-((2R,3R)-3-methoxy-2-methyl-hept-6-enoylamino)-3-methyl-butyrylamino]-propionyl}-hexahydro-pyridazine-3-carboxylic acid methyl-((R)-6-vinyl-indan-1-yl)-amide in 5% yield. $^1$H NMR (300 MHz, $CD_3OD$) δ 0.85-1.00 (m, 6H), 1.30 (d, J=6.9 Hz, 3H), 1.58 (d, J=7.1 Hz, 3H), 1.62-1.80 (m, 6H), 1.83-2.07 (m, 3H), 2.70-2.82 (m, 1H), 3.38-3.48 (m, 1H), 3.76-3.84 (m, 1H), 4.20-4.28 (m, 1H), 4.36-4.47 (m, 1H), 5.62-5.74 (m, 1H). 5.93 (q, J=6.9 Hz, 1H), 6.30-6.51 (m, 2H), 7.39 (d, J=8.5 Hz, 1H), 7.63 (s, 1H), 7.70-7.80 (m, 2H), 8.13-8.22 (m, 1H). LCMS (m/z) 536.2 [M+H], Tr=2.15 min.

Example 28

Compound 28

Compound 28a

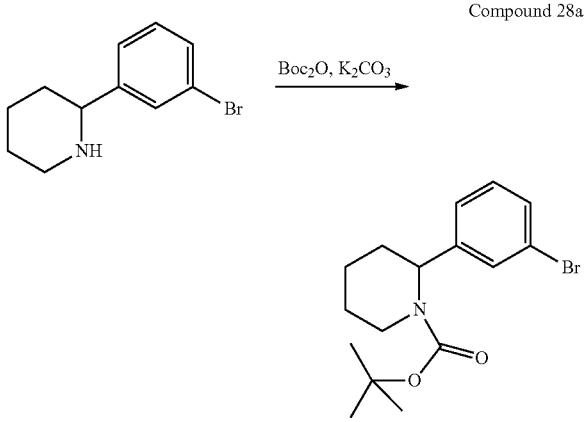

Potassium carbonate (647 mg, 4.68 mmol) and di-tert-butyl dicarbonate (716 mg, 3.28 mmol) were added to 2-(3-bromo-phenyl)-piperidine (750 mg, 3.12 mmol) in dichloromethane (10 mL). After overnight stirring at RT water (20 mL) was added to the solution. The resulting biphasic solution was separated into organic and aqueous phases. The aqueous phase was back extracted with dichloromethane (20 mL). The combined organic phases were dried over anhydrous sodium sulfate, filtered and concentrated to afford the title compound (1.03 g, 97%) as a pale yellow oil.

Compound 28b

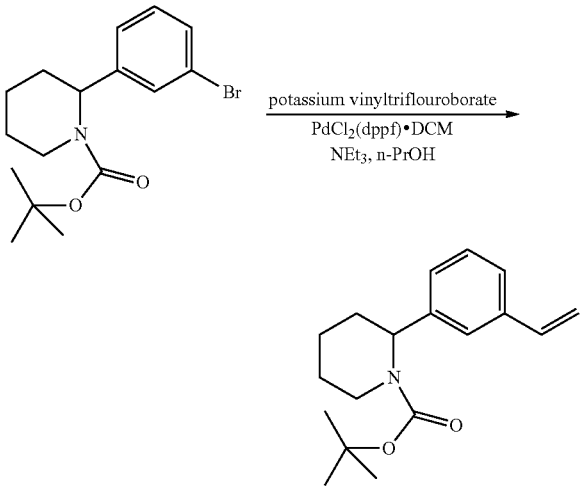

To a solution of 28a (1.03 g, 3.03 mmol) and potassium vinyltrifluoroborate (488 mg, 3.64 mmol) in n-propanol (30 mL), under an atmosphere of nitrogen was added 1,1'bis (diphenylphosphino)ferrocenedichloropalladium(II), dichloromethane adduct (49 mg, 0.06 mmol) and triethylamine (306 mg, 422 μL, 3.03 mmol). The reaction was heated to reflux and left to stir for 3 h before cooling to RT. The reaction mixture was poured onto water and the resultant solution was extracted with diethyl ether (3×30 mL). The combined organics were dried over anhydrous sodium sulfate, filtered and concentrated. The resultant residue was purified by silica gel chromatography using a stepwise gradient of iso-hexanes/ethyl acetate 1:0 to 4:1 to afford the title compound (652 mg, 75%) as a pale yellow oil.

Compound 28c

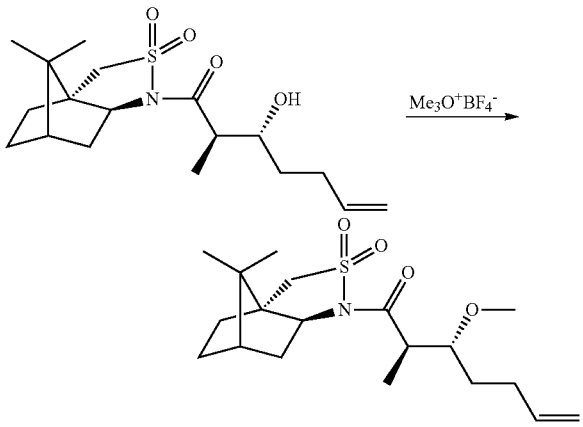

A solution of (2R,3R)-1-((1R,5S)-10,10-dimethyl-3,3-dioxo-3lambda*6*-thia-4-aza-tricyclo[5.2.1.0*1,5*]dec-4-yl)-3-hydroxy-2-methyl-hept-6-en-1-one (250 mg, 0.703 mmol) in anhydrous dichloromethane (7 mL) was prepared and trimethyloxonium tetrafluoroborate (208 mg, 1.406 mmol) was added. The reaction mixture was stirred at RT for 15 h. The reaction mixture was treated with methanol (1 mL), then 2 M hydrochloric acid (20 mL) and saturated brine (20 mL). The mixture was extracted with ethyl acetate (3×15 mL) and the extract was dried over sodium sulfate, filtered and evaporated to give a yellow gum. The gum was purified by silica gel chromatography using iso-hexanes/ethyl acetate 4:1 to give the title compound (223 mg, 86%) as a colorless gum.

Compound 28d

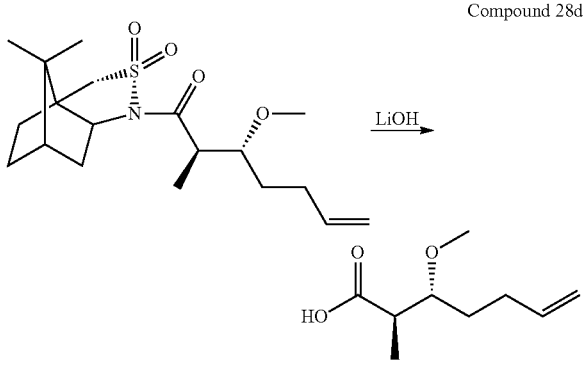

A solution of 2 M lithium hydroxide in water (5 mL, 10 mmol) was added to a stirred solution of 28c (223 mg, 0.60 mmol) in tetrahydrofuran (15 mL). The stirred mixture was heated to 60° C. for 15 h. The reaction mixture was partially evaporated before adding 2 M hydrochloric acid (20 mL). The solution was extracted with ethyl acetate (3×15 mL). The extract was dried over sodium sulfate, filtered and evaporated to give a yellow gum (209 mg). The gum was purified by silica gel chromatography using iso-hexanes/ethyl acetate 3:1 to yield the title compound (68 mg, 66%) as a yellow gum.

Compound 28e

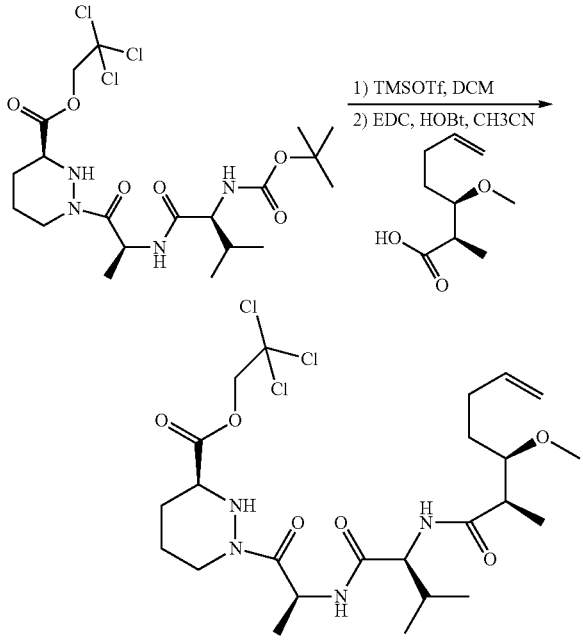

A solution of (S)-1-[(S)-2-((S)-2-tert-butoxycarbonylamino-3-methylbutyrylamino)-propionyl]-hexahydropyridazine-3-carboxylic acid 2,2,2-trichloroethyl ester (316 mg, 0.59 mmol) in anhydrous dichloromethane (10 mL) was cooled to 0° C. under a nitrogen atmosphere before adding trimethylsilyl trifluoromethanesulfonate (160 μL, 0.885 mmol). The reaction mixture was stirred at 0° C. for 2 h before adding N,N-diisopropylethylamine (413 μl, 2.36 mmol) to afford (S)-1-[(S)-2-((S)-2-amino-3-methyl-butyrylamino)-propionyl]-hexahydro-pyridazine-3-carboxylic acid 2,2,2-trichloroethyl ester. The mixture was evaporated and the residue dissolved with (2R,3R)-3-methoxy-2-methyl-hept-6-enoic acid (162 mg, 0.94 mmol.) in acetonitrile (13 mL) and N-(3-dimethylaminopropyl)-N'-ethylcarbodiimide hydrochloride (250 mg, 1.32 mmol) and 1-hydroxybenzotriazole (220 mg, 1.32 mmol) were added. The reaction was stirred at RT for 15 h then evaporated to give a yellow oil. The oil was purified by silica gel chromatography using ethyl acetate to give the title compound (425 mg, 77%) as a white solid.

Compound 28f

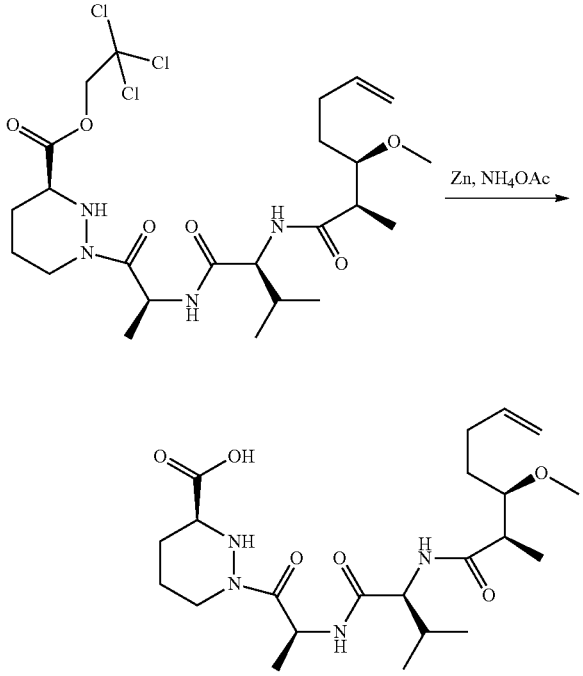

A solution of 28e (425 mg, 0.725 mmol) in tetrahydrofuran (20 mL) was prepared and zinc powder (0.48 g, 7.25 mmol) was added followed by an aqueous solution of ammonium acetate (1 M, 5 mL, 5 mmol). The reaction mixture was stirred at RT for 15 h. The reaction was filtered through hyflo-supercel washing through with ethyl acetate. The mixture was treated with hydrochloric acid (2 M, 30 mL) and the layers were separated. The aqueous layer was extracted with ethyl acetate (25 mL). The organic layers were combined, washed with brine, filtered and evaporated to give a colorless gum (299 mg) which was used directly without further purification.

Compound 28g

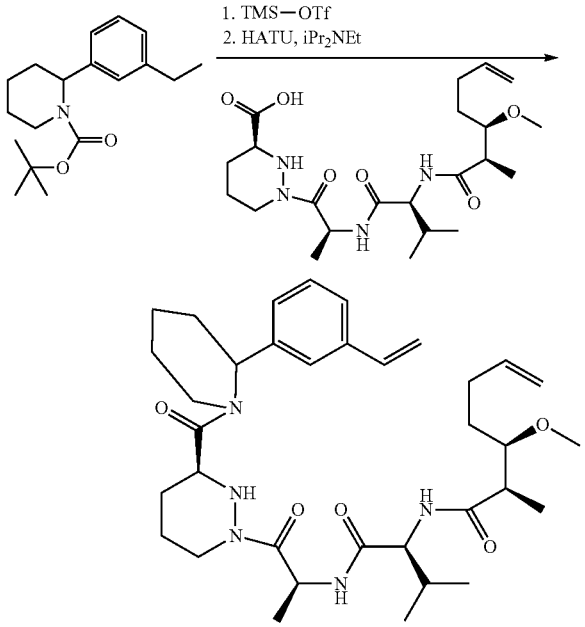

A solution of 2-(3-vinyl-phenyl)-piperidine-1-carboxylic acid tert-butyl ester (650 mg, 2.26 mmol) in dichloromethane (15 mL) was cooled to 0° C., before adding trimethylsilyl trifluoromethanesulfonate (569 μL, 3.39 mmol). The reaction mixture was stirred at 0° C. for 1 h before adding N,N-diisopropylethylamine (1.6 mL, 5.24 mmol) to afford the 2-(3-vinyl-phenyl)-piperidine as a yellow solid. The solid was redissolved, along with 28f (900 mg, 1.98 mmol) in acetonitrile (20 mL). The solution was cooled to 0° C., before adding 2-(1H-7-azabenzotriazol-1-yl)-1,1,3,3-tetramethyl uronium hexafluorophosphate methanaminium (1.05 g, 2.77 mmol) and N,N-diisopropylethylamine (1.4 mL, 7.92 mmol). The stirred reaction mixture was allowed to slowly warm to RT. After 2 h, the solvent was evaporated and the remaining residue dissolved in ethyl acetate (30 mL) and washed with water (3×30 mL). The organics were dried over anhydrous sodium sulfate, filtered and concentrated. The resultant residue was purified by silica gel chromatography using a stepwise gradient of iso-hexanes/ethyl acetate 1:0 to 0:1 to afford the title compound (1.25 g, 100%) as a yellow solid.

Compound 28

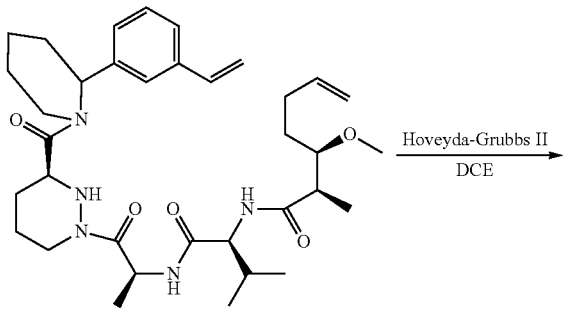

-continued

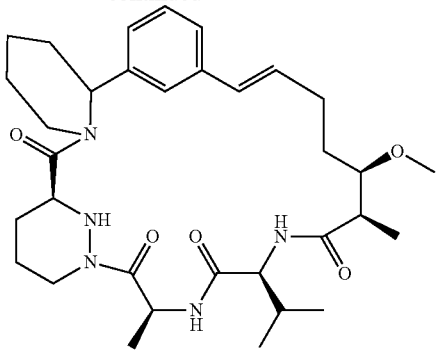

To a stirred solution of 28 g (1.05 mg, 1.68 mmol) in 1,2-dichloroethane (550 mL) was added Hoveyda-Grubbs 2$^{nd}$ generation catalyst (105 mg, 0.168 mmol). The solution was heated to 84° C. and was left to stir for 2.5 h. The solvent was evaporated and the remaining residue was purified by silica gel chromatography using a stepwise gradient of iso-hexanes/ethyl acetate/acetone 1:0:0 to 0:9:1. This material was then subjected to a second round of silica gel chromatography using the same gradient to afford a yellow solid. A final round of silica gel chromatography using neat ethyl acetate and eluting purely by gravity afforded the title compound (175 mg, 18%) as a white solid as a 6:4 mixture of diastereoisomers. $^1$H NMR (300 MHz, $CDCl_3$) δ 0.84 (d, J=6.9 Hz, 3H), 0.91-1.01 (m, 6H), 1.24-1.37 (m, 6H), 1.47-2.03 (m, 14H), 2.06 (s, 2H), 2.14-2.25 (m, 1H), 2.43-2.77 (m, 4H), 3.48 (s, 1H), 3.56 (s, 2H), 3.63-3.86 (m, 1H), 4.00 (app t, J=14.7 Hz, 1H), 4.12-4.17 (m, 1H), 4.53-4.65 (m, 1H), 5.45 (q, J=7.2 Hz, 1H), 6.27-6.50 (m, 2H), 6.99-7.10 (m, 2H), 7.14-7.22 (m, 1H), 7.32-7.38 (m, 1H). LCMS (m/z) 596.4 [M+H], Tr=2.51 min.

Examples 29 and 30

Compounds 29 and 30

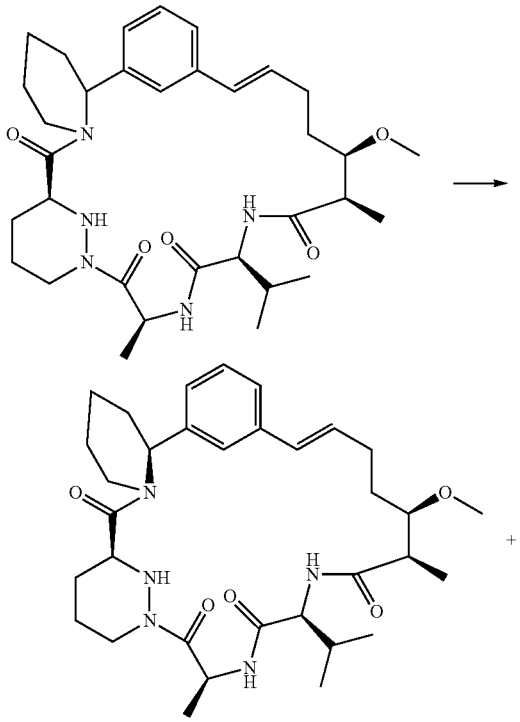

Compound 29

-continued

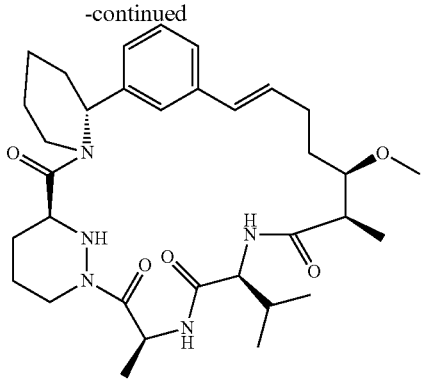

Compound 30

Compound 28 (155 mg, 0.26 mmol) was dissolved in a 1:1 mixture of acetonitrile/water to a concentration of 7.8 mg/mL. This solution was then eluted through a reverse phase HPLC system fitted with a Phenomenex Gemini 10μ 110 A, 250×21.2 mm column using an isocratic 2:3 acetonitrile/water flow at 20 mL/min. The mixture was resolved into the 2 separate diastereoisomers. On concentration each separate diastereoisomer yielded a white solid. The stereochemistry of each isomer was not determined. First isomer eluted, Compound 29 (15 mg, 10%). $^1$H NMR (300 MHz, $CDCl_3$) δ 0.89-1.05 (m, 8H), 1.20-1.44 (m, 10H), 1.51-1.79 (m, 3H), 1.83-1.99 (m, 4H), 2.03-2.27 (m, 3H), 2.33-2.67 (m, 3H), 2.76 (app t, J=12.3 Hz, 1H), 3.09 (app t, J=12.3 Hz, 1H), 3.22-3.38 (m, 1H), 3.47 (s, 3H), 3.54-3.62 (m, 1H), 4.17 (d, J=11.7 Hz, 1H), 4.59 (d, J=10.5 Hz, 1H), 5.39-5.53 (m, 1H), 6.01 (s, 1H), 6.09-6.23 (m, 1H), 6.30-6.55 (m, 2H), 6.99-7.23 (m, 4H). LCMS (m/z) 596.4 [M+H], Tr=2.53 min.

Second isomer eluted, Compound 30 (22 mg, 14%). $^1$H NMR (300 MHz, $CD_3CN$) δ 0.98-1.04 (m, 6H), 1.26-1.38 (m, 7H), 1.62-1.80 (m, 5H), 1.83-2.00 (m, 4H), 2.03-2.14 (m, 1H), 2.16-2.25 (m, 2H), 2.36-2.51 (m, 2H), 2.54-2.66 (m, 1H), 2.68-2.82 (m, 1H), 3.03-3.16 (m, 1H), 3.26-3.34 (m, 1H), 3.48 (s, 3H), 3.64-3.73 (m, 1H), 3.76-3.86 (m, 1H), 4.00 (app t, J=9.0 Hz, 1H), 4.16 (d, J=12.0 Hz, 1H), 4.55-4.66 (m, 1H), 5.41-5.53 (m, 1H), 5.97-6.06 (m, 1H), 6.10-6.22 (m, 1H), 6.35 (s, 1H), 6.38-6.49 (m, 1H), 7.00-7.11 (m, 2H), 7.14-7.23 (m, 3H). LCMS (m/z) 596.3 [M+H], Tr=2.49 min.

Example 31

Compound 31

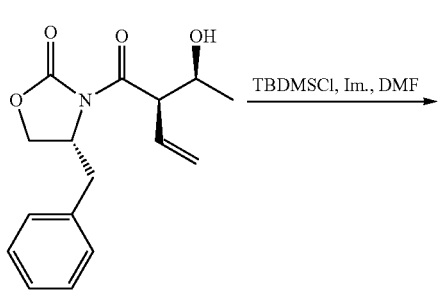

Compound 31a

-continued

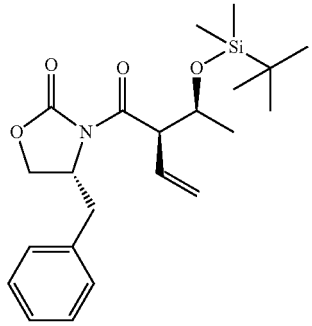

A cooled (0° C.) solution of (R)-4-benzyl-3-[(R)-2-((S)-1-hydroxy-ethyl)-but-3-enoyl]-oxazolidin-2-one (233.6 mg, 0.807 mmol, prepared as described in Org. Lett. 2007, 9, 1635-1638) and imidazole (241.7 mg, 3.551 mmol) in N,N-dimethylformamide (2 mL) was treated with tert-butyldimethylsilyl chloride (158.2 mg, 1.049 mmol). After stirring for 24 h at RT, the reaction was quenched with saturated ammonium chloride. The aqueous layer was extracted with diethyl ether (2×20 mL). The organics were combined, dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 4:1 to afford the title compound (294.6 mg, 90%) as a colorless oil.

Compound 31b

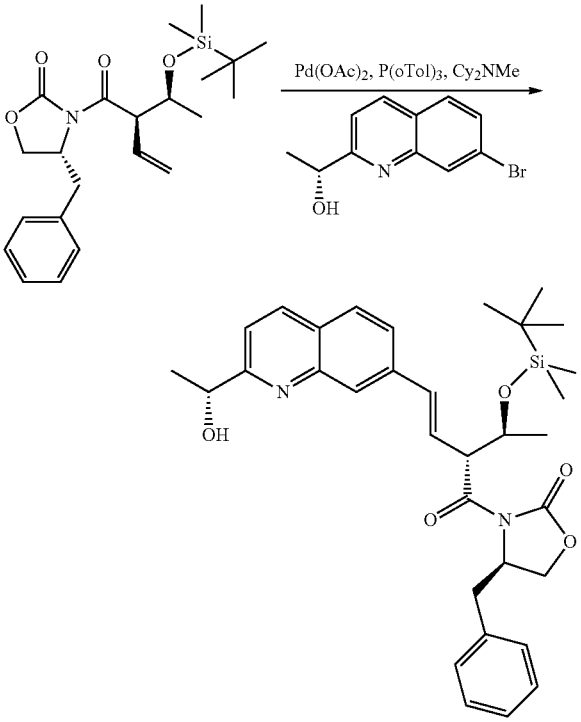

A solution of 31a (294.6 mg, 0.730 mmol), (R)-1-(7-bromo-quinolin-2-yl)-ethanol (184.0 mg, 0.730 mmol), palladium(II)acetate (32.8 mg, 0.146 mmol), tri-(o-toluoyl) phosphine (44.4 mg, 0.146 mmol) in anhydrous 1,4-dioxane (10 mL) was treated with N,N-dicylohexylmethylamine (250 μL, 1.168 mmol). After stirring at 100° C. for 5 h, the reaction was cooled to RT, diluted with dichloromethane and saturated sodium bicarbonate. The aqueous layer was extracted with dichloromethane. The organics were combined, filtered through a phase separator and the volatiles were removed in vacuo. The residue was purified by silica gel chromatography using a 25 g Isolute cartridge eluted with a continuous gradient of iso-hexanes/ethyl acetate 1:0 to 7:3 to afford the title compound (230.8 mg, 55%) as a colorless oil.

Compound 31c

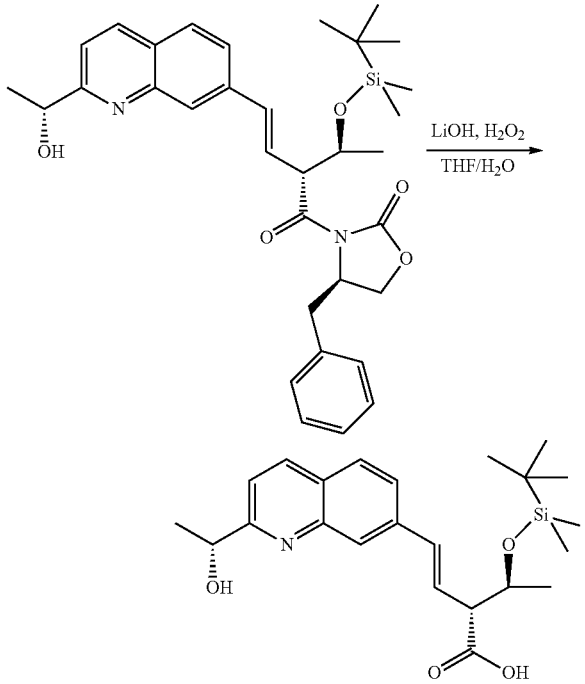

A cooled (0° C.) solution of 31b (230.8 mg, 0.401 mmol) in tetrahydrofuran/water (15 mL, 2:1) was subsequently treated with hydrogen peroxide (30% aqueous, 210 μL, 2.005 mmol) and lithium hydroxide hydrate (33.7 mg, 0.803 mmol). After stirring for 2 h at 0° C., the reaction was quenched with sodium metabisulfite (765 mg, 4.1 mmol). After stirring for 3.5 h at RT the volatiles were removed in vacuo. The mixture was then diluted with water and the pH was adjusted with potassium carbonate. The aqueous layer was washed with dichloromethane (2×20 mL) and acidified with 2 M hydrochloric acid (pH~1) then extracted with dichloromethane (3×30 mL). All the organics were combined, dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 0:1 to afford the title compound (69.8 mg, 42%) as a white solid.

Compound 31d

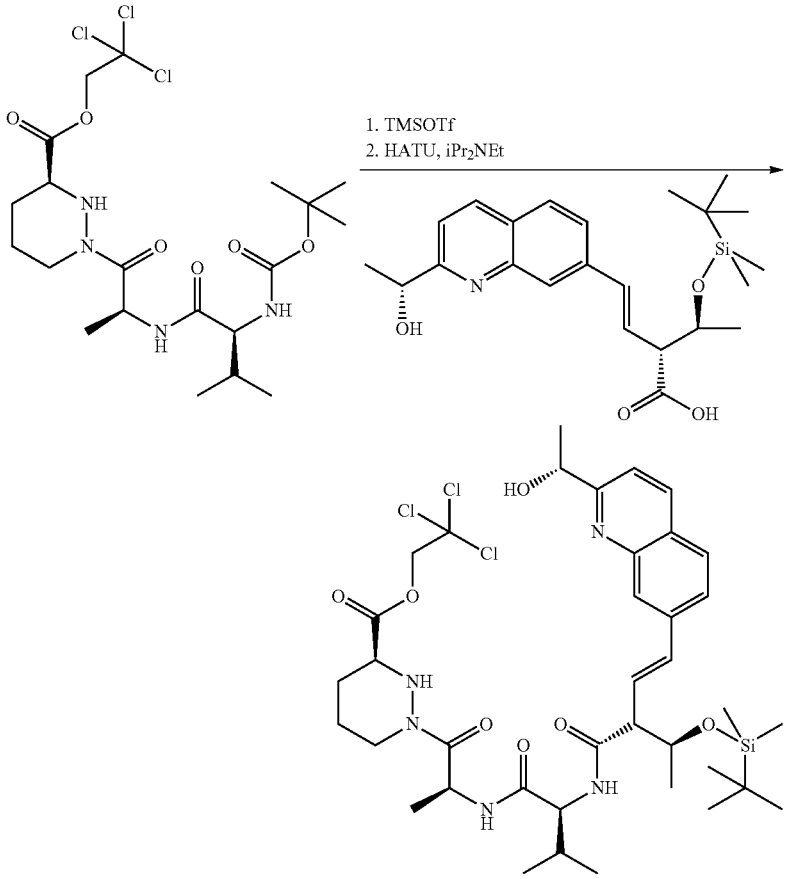

Compound 31d was prepared in the same manner as 22e using 31c instead of (E)-4-[2-((R)-1-acetoxy-ethyl)-quinolin-7-yl]-2,2-dimethyl-but-3-enoic acid in 46% yield.

Compound 31

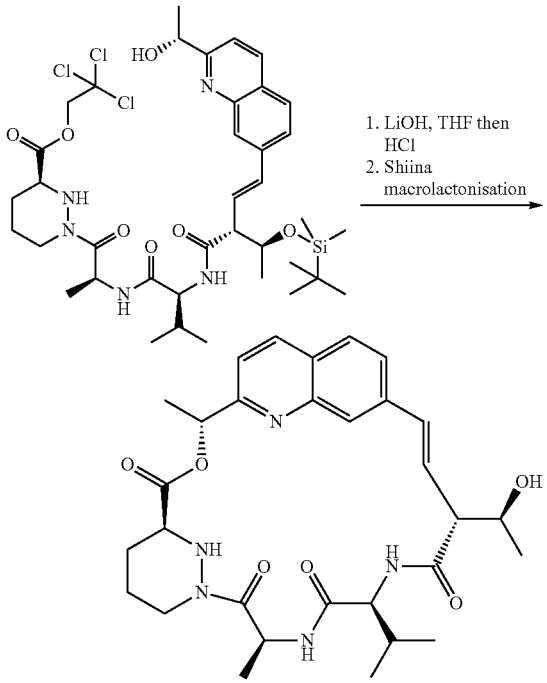

Compound 31 was prepared in the same manner as Compound 22 using 31d instead of (S)-1-[(S)-2-((S)-2-{(E)-4-[2-((R)-1-hydroxy-ethyl)-quinolin-7-yl]-2,2-dimethyl-but-3-enoylamino}-3-methyl-butyrylamino)-propionyl]-hexahydro-pyridazine-3-carboxylic acid 2,2,2-trichloro-ethyl ester in 10% yield. $^1$H NMR (300 MHz, $CDCl_3$) δ 1.00 (d, J=6.7 Hz, 3H), 1.01 (d, J=6.7 Hz, 3H), 1.22-1.44 (m, 4H), 1.64 (d, J=7.1 Hz, 3H), 1.68-1.77 (m, 4H), 1.89-2.08 (m, 3H), 2.71-2.84 (m, 1H), 3.78-3.86 (m, 1H), 4.11 (dd, J=8.2, 6.2 Hz, 1H), 4.17-4.25 (m, 2H), 4.38-4.47 (m, 1H), 5.68 (q, J=7.1 Hz, 1H), 5.94 (q, J=6.9 Hz, 1H), 6.47 (d, J=16.5 Hz, 1H), 6.69 (dd, J=16.5, 5.3 Hz, 1H), 7.40 (d, J=8.5 Hz, 1H), 7.68 (s, 1H), 7.76 (dd, J=8.7, 1.3 Hz, 1H), 7.81 (d, J=8.7 Hz, 1H), 8.21 (d, J=8.5 Hz, 1H). LCMS (m/z) 566.1 [M+H], Tr=1.65 min.

Example 32

Compound 32

Compound 32a

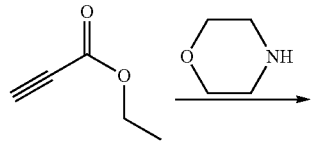

-continued

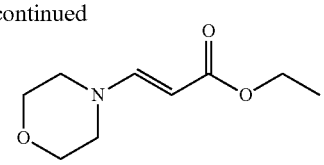

To a cooled (0° C.) solution of ethyl propionate (2 mL, 19.735 mmol) in dichloromethane (50 mL) was added dropwise morpholine (1.7 mL, 19.435 mmol). After stirring at RT for 1.5 h, the volatiles were removed in vacuo and the residue was purified by silica gel chromatography using a 50 g Isolute cartridge eluted with dichloromethane/methanol 20:1 to afford the title compound (3.5034 g, 97%) as a colorless oil.

Compound 32b

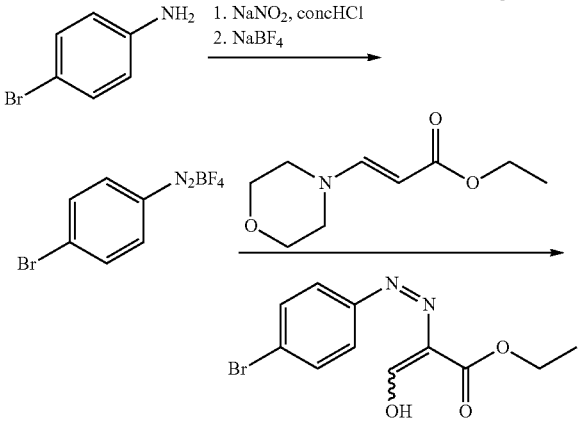

A cooled (0° C.) solution of 4-bromoaniline (2.7 g, 15.7 mmol) in water (30 mL) was subsequently treated with concentrated hydrochloric acid (3.5 mL) and sodium nitrite (1.3 g, 18.840 mmol). After 20 min at 0° C., concentrated hydrochloric acid (5.3 mL) and sodium tetrafluoroborate (6.9 g, 62.847 mmol) were added. After 40 min at 0° C., the intermediate diazonium was filtered, washed with water, methanol and diethyl ether (2.1021 g) and was used without further purification. A solution of the diazonium (7.762 mmol) in acetonitrile (50 mL) was treated with 32a (1.6614 g, 8.970 mmol). After 1 h at RT, silica gel was added. After stirring at RT for 16 h, the volatiles were removed in vacuo and the residue was purified by silica gel chromatography using a 100 g Isolute cartridge eluted with a continuous gradient of iso-hexanes/ethyl acetate 1:0 to 9:1 to afford the title compound (1.9811 g, 85%) as a highly coloured solid and as a mixture of tautomers.

Compound 32c

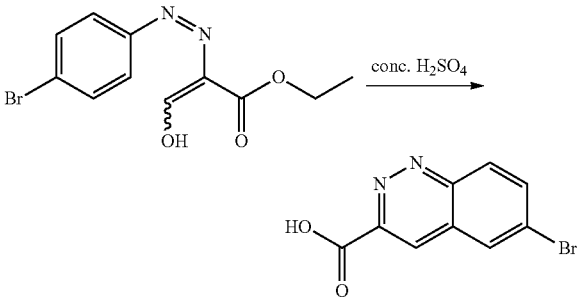

A solution of 32b (1.9811 g, 6.623 mmol) in concentrated sulphuric acid (25 mL) was heated at 100° C. for 3 h. After cooling to 0° C., the mixture was diluted with water (150 mL) and a brown solid was filtered off. The filtrate was extracted with diethyl ether (2×50 mL), dichloromethane (2×50 mL) and ethyl acetate (50 mL). The organics were combined, dried over sodium sulfate, filtered and the volatiles were removed in vacuo to provide the title compound (1.5094 g, 90%) as an orange solid that turned dark upon standing.

Compound 32d

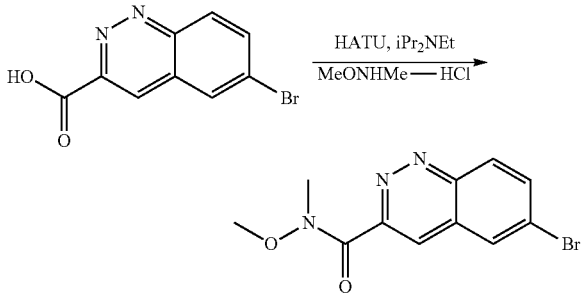

A cooled (0° C.) solution of 32c (1.5094 g, 5.964 mmol), N,O-dimethylhydroxylamine hydrochloride (755.9 mg, 7.753 mmol) and N,N-diisopropylethylamine (4.2 mL, 23.856 mmol) in acetonitrile (50 mL) was treated with 2-(1H-7-azabenzotriazol-1-yl)-1,1,3,3-tetramethyl uronium hexafluorophosphate methanaminium (3.175 g, 8.350 mmol). After stirring for 6 h at RT, the mixture was cooled to 0° C. and quenched with 1 M hydrochloric acid (60 mL). The aqueous layer was extracted with ethyl acetate (3×50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:1 to afford the title compound (1.4229 g, 81%) as a bright yellow solid.

Compound 32e

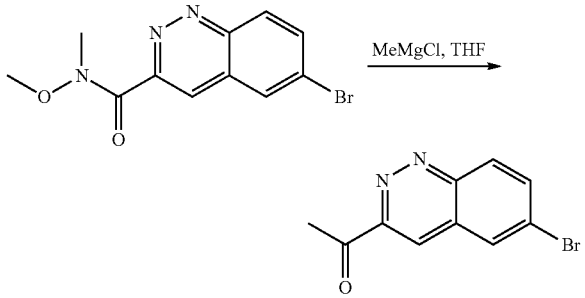

A cooled (−78° C.) solution of 32d (1.4229 g, 4.805 mmol) in tetrahydrofuran (50 mL) was treated with methylmagnesium chloride (3.2 mL, 9.610 mmol, 3 M in diethyl ether). After 1 h at −78° C. and 3 h at 0° C., the reaction was quenched with saturated ammonium chloride (30 mL). The aqueous layer was extracted with ethyl acetate (3×50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 4:1 to afford the title compound (751.5 mg, 62%) as a yellow solid.

Compound 32f

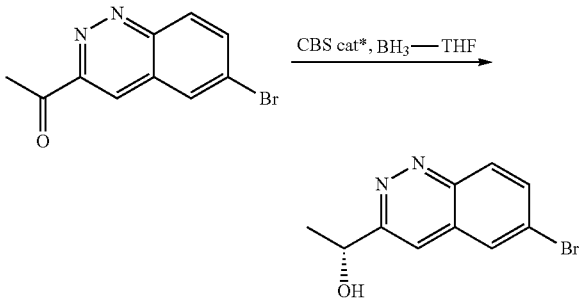

A solution of 32e (751.5 mg, 2.993 mmol) in tetrahydrofuran (30 mL) was treated with (S)-(−)-2-methyl-CBS-oxazaborolidine (3.6 mL, 3.592 mmol, 1 M in toluene). After 10 min at RT the mixture was cooled to −60° C. and treated with borane-tetrahydrofuran complex (6 mL, 5.986 mmol, 1 M in tetrahydrofuran). After 1.5 h at −55° C. to −30° C., the reaction was quenched with methanol (20 mL). After stirring at RT for 16 h, the volatiles were removed in vacuo. The residue was purified by silica gel chromatography using a 50 g Isolute cartridge eluted with a continuous gradient of iso-hexanes/ethyl acetate 1:0 to 3:2 to afford the title compound (345.0 mg, 45%) as a yellow solid.

Compound 32g

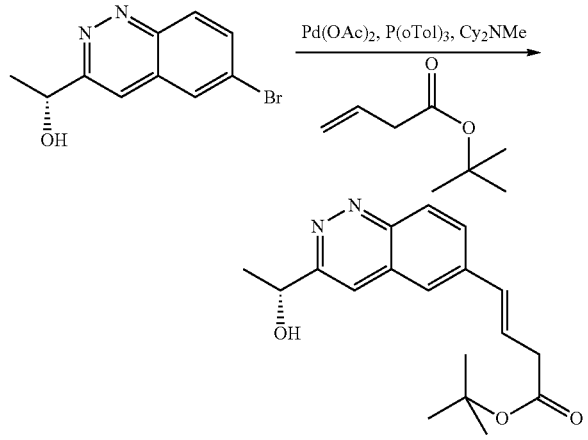

A solution of 32f (345.0 mg, 1.363 mmol), palladium II acetate (61.2 mg, 0.273 mmol), tri-(o-toluoyl)phosphine (83.1 mg, 0.273 mmol), 3-butenoic acid tert-butyl ester (560 μL, 3.407 mmol) and N,N-dicyclohexylmethylamine (470 μL, 2.181 mmol) in anhydrous 1,4-dioxane (20 mL) was heated at 100° C. for 1.7 h. After cooling to RT the volatiles were removed in vacuo. The residue was purified by silica gel chromatography using a 50 g Isolute cartridge eluted with a continuous gradient of iso-hexanes/ethyl acetate 1:0 to 2:3 to afford the title compound (244.1 mg, 57%) as a yellow solid.

Compound 32h

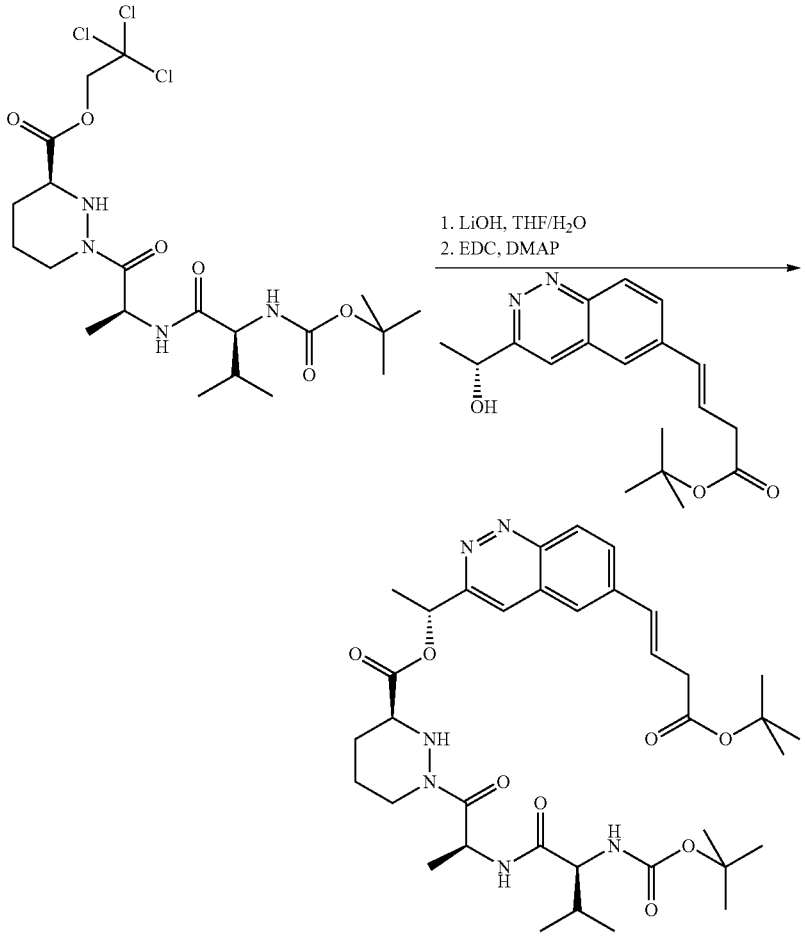

A cooled (0° C.) solution of 1e (422.0 mg, 0.793 mmol) in tetrahydrofuran/water (25 mL, 4:1) was treated with lithium hydroxide hydrate (67.0 mg, 1.587 mmol). After stirring at 0° C. for 1.5 h, the reaction was quenched with 1 M hydrochloric acid (20 mL). The aqueous layer was extracted with ethyl acetate (2×30 mL). The organics were combined, dried over sodium sulfate, filtered and the volatiles were removed in vacuo then residual trichloroethanol was azeotroped off with toluene (3×) to give the intermediate acid as a white solid which was then combined with 32 g (244.1 mg, 0.793 mmol), 4-dimethylaminopyridine (97.0 mg, 0.793 mmol), N-(3-dimethylaminopropyl)-N'-ethylcarbodiimide hydrochloride (243.3 mg, 1.269 mmol) and dichloromethane (20 mL). After stirring at RT for 16 h, the reaction was quenched with dilute hydrochloric acid. The aqueous layer was extracted with dichloromethane (30 mL). The organics were combined and filtered through a phase separator and the volatiles were removed in vacuo. The residue was purified by silica gel chromatography using a 50 g Isolute cartridge eluted with a continuous gradient of iso-hexane/sethyl acetate 1:0 to 1:2 to afford the title compound (164.4 mg, 30% over 2 steps) as a yellow glass.

Compound 32

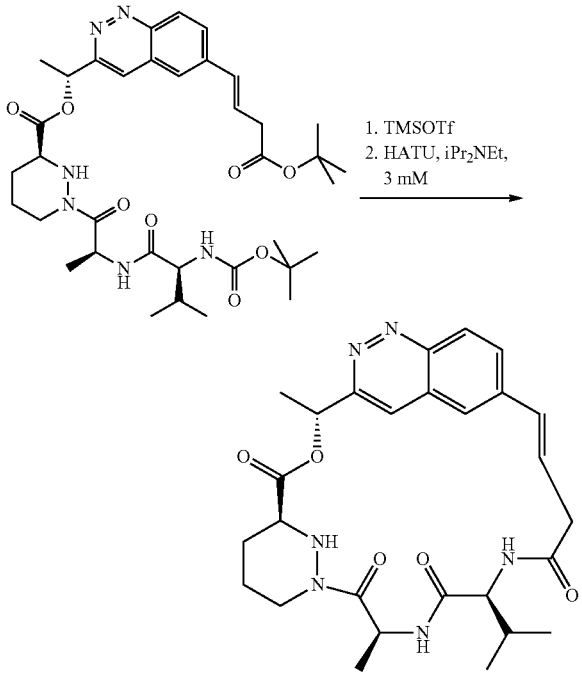

A cooled (0° C.) solution of 32 h (164.4 mg, 0.236 mmol) in anhydrous dichloromethane (20 mL) was treated with trimethylsilyl methanesulfonate (170 μL, 0.944 mmol). After stirring for 1 h at 0° C., the reaction was quenched with N,N-diisopropylethylamine (330 μL, 1.888 mmol) and the volatiles were removed in vacuo. A cooled (0° C.) solution of the crude amino acid in acetonitrile (80 mL) was subsequently treated with N,N-diisopropylethylamine (330 μL, 1.888 mmol) and 2-(1H-7-azabenzotriazol-1-yl)-1,1,3,3-tetramethyl uronium hexafluorophosphate methanaminium (125.6 mg, 0.330 mmol). After stirring at RT for 2.5 h, the volatiles were removed in vacuo. The residue was purified by silica gel chromatography using a 50 g Isolute cartridge eluted with a continuous gradient of iso-hexanes/ethyl acetate 1:0 to 0:1 to afford the final compound (170.7 mg) as a mixture. Reverse phase preparative HPLC which was eluted with a gradient of water/acetonitrile 95:5 to 0:100 provided the title compound (30.6 mg, 25%) as a white solid. $^1$H NMR (300 MHz, $CD_3OD$) δ 1.00 (d, J=6.7 Hz, 3H), 1.03 (d, J=6.7 Hz, 3H), 1.61 (d, J=7.3 Hz, 3H), 1.66-2.07 (m, 8H), 2.68-2.81 (m, 1H), 2.97-3.07 (m, 1H), 3.35-3.47 (m, 1H), 3.76-3.89 (m, 1H), 4.28 (d, J=9.4 Hz, 1H), 4.37-4.47 (m, 1H), 4.53-4.67 (m, 1H), 5.52 (q, J=7.1 Hz, 1H), 6.36-6.51 (m, 2H), 6.72 (d, J=16.0 Hz, 1H), 7.61 (s, 1H), 7.97 (dd, J=8.9, 1.6 Hz, 1H), 8.06 (s, 1H), 8.38 (d, J=8.9 Hz, 1H). LCMS (m/z) 523.1 [M+H], Tr=1.65 min.

Examples 33 and 34

Compounds 33 and 34

Compound 33a

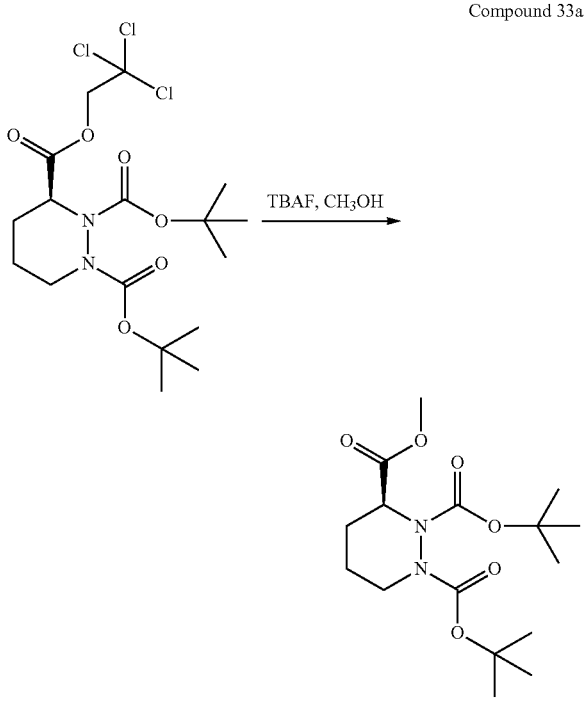

A cooled (0° C.) solution of (S)-tetrahydro-pyridazine-1,2,3-tricarboxylic acid 1,2-di-tert-butyl ester 3-(2,2,2-trichloro-ethyl)ester (5.5297 g, 11.975 mmol) in tetrahydrofuran/methanol (50 mL, 1:1) was treated with tetrabutylammonium fluoride (23.9 mL, 23.950 mmol, 1 M in tetrahydrofuran). After stirring at RT for 24 h, the volatiles were removed in vacuo. The residue was dissolved in diethyl ether and saturated sodium bicarbonate. The aqueous layer was extracted with diethyl ether (50 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 9:1 where the mixed fractions were further purified by silica gel chromatography using a 50 g Isolute cartridge eluted with a continuous gradient of iso-hexanes/ethyl acetate 1:0 to 4:1 to afford the title compound (3.9765 g, 96%) as a colorless oil and as a mixture of rotamers.

Compound 33b

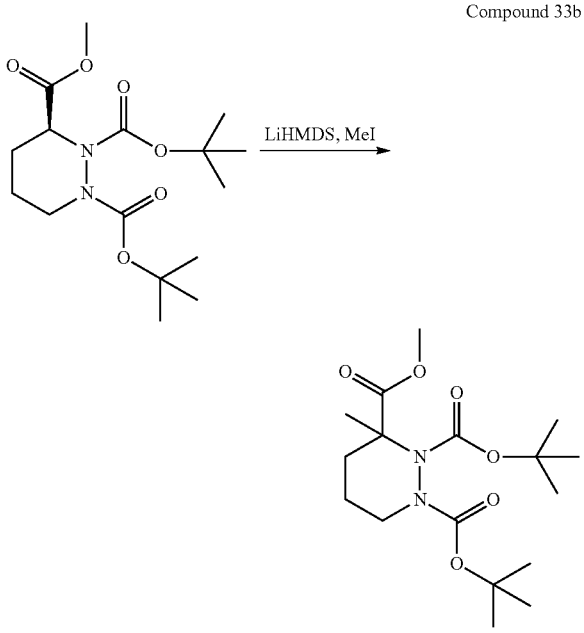

A cooled (−78° C.) solution of 33a (1.4112 g, 4.097 mmol) in anhydrous tetrahydrofuran (10 mL) was treated with lithium bis(trimethylsilyl)amide (6.2 mL, 6.146 mmol, 1 M in tetrahydrofuran). After stirring for 1.25 h at −78° C., the mixture was treated with iodomethane (640 μL, 10.242 mmol). After stirring for 1 h at −78° C., 1 h at 0° C. and 1 h at RT, the reaction was quenched with pH 7 buffer at 0° C. The aqueous was extracted with dichloromethane (2×50 mL). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (760.7 mg, 52%) as a colorless oil and as a mixture of rotamers.

Compound 33c

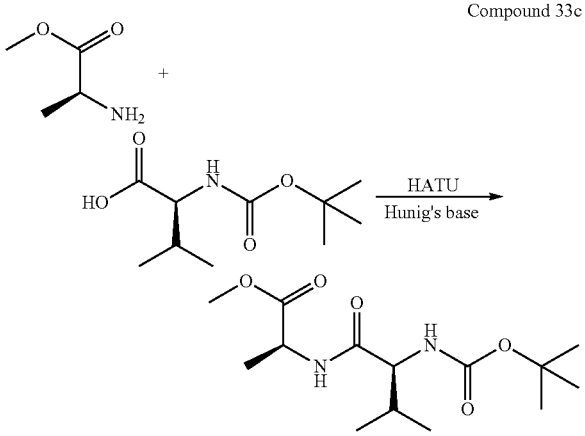

A cooled (0° C.) solution of (S)-2-tert-butoxycarbonylamino-3-methyl-butyric acid (3.020 g, 13.908 mmol), (S)-2-amino-propionic acid methyl ester hydrochloride (1.9413 g, 13.908 mmol) and N,N-diisopropylethylamine (17.1 mL, 55.632 mmol) in acetonitrile (50 mL) was treated with 2-(1H-7-azabenzotriazol-1-yl)-1,1,3,3-tetramethyl uronium hexafluorophosphate methanaminium (7.403 g, 19.471 mmol). After stirring at RT for 6 h, the reaction was quenched with hydrochloric acid (1 M, 100 mL). The aqueous layer was extracted with ethyl acetate (2×100 mL). The organics were combined, dried over sodium sulfate, filtered and the volatiles were removed in vacuo. The residue was purified by silica gel chromatography using a 100 g Isolute cartridge eluted with a continuous gradient of iso-hexanes/ethyl acetate 1:0 to 3:2 to afford the title compound (4.0996 g, 97%) as a white solid.

Compound 33d

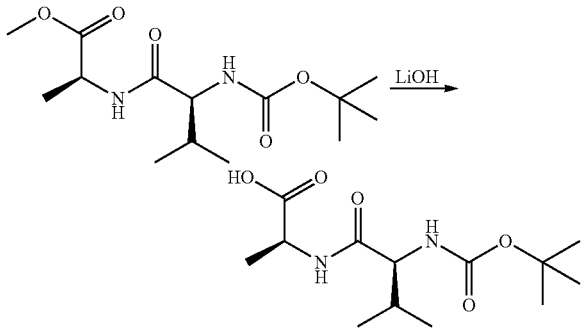

A cooled (0° C.) solution of 33c (317.0 mg, 1.048 mmol) in tetrahydrofuran/water (12 mL, 5:1) was treated with lithium hydroxide hydrate (88.0 mg, 2.096 mmol). After stirring at 0° C. for 2.5 h, the reaction was quenched with hydrochloric acid (1 M, 30 mL). The aqueous layer was extracted with dichloromethane (2×30 mL). The organics were combined, filtered through a phase separator and the volatiles were removed in vacuo to provide crude acid as a white solid.

Compound 33e

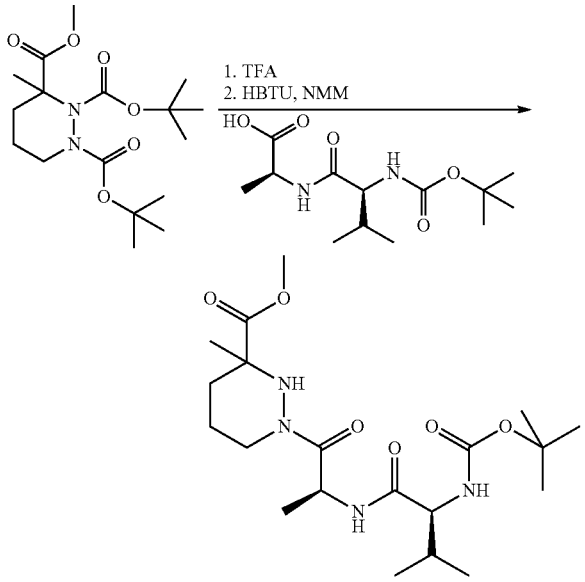

A cooled (0° C.) solution of 33b (376.0 mg, 1.049 mmol) in anhydrous dichloromethane (15 mL) was treated with trifluoroacetic acid (5 mL). After stirring at 0° C. for 30 min and RT for 2 h, trifluoroacetic acid (4 mL) was added. After 1 h, the volatiles were removed in vacuo and the residual trifluoroacetic acid azeotroped off with toluene (3×) to provide the bis-trifluoroacetic acid ammonium salt as an off-white solid. A cooled (0° C.) solution of the bis-trifluoroacetic acid ammonium salt and crude (S)-2-((S)-2-tert-butoxycarbonylamino-3-methyl-butyrylamino)-propionic acid as prepared in the previous step in anhydrous dichloromethane (15 mL) was subsequently treated with N-methylmorpholine (580 μL, 5.240 mmol) and O-(benzotriazol-1-yl)-N,N,N',N'-tetramethyluronium hexafluorophosphate (596.2 mg, 1.572 mmol). After stirring for 19 h at RT, the reaction was quenched with hydrochloric acid (1 M, 30 mL). The aqueous was extracted with dichloromethane (2×30 mL). The organics were combined, washed with saturated aqueous sodium bicarbonate and filtered through a phase separator. The volatiles were removed in vacuo and the residue was purified by silica gel chromatography using a 50 g Isolute cartridge eluted with a continuous gradient of iso-hexanes/ethyl acetate 1:0 to 1:2 to afford the title compound (373.1 mg, 83% over 2 steps) as a white foam and as a mixture of diastereoisomers.

Compound 33f

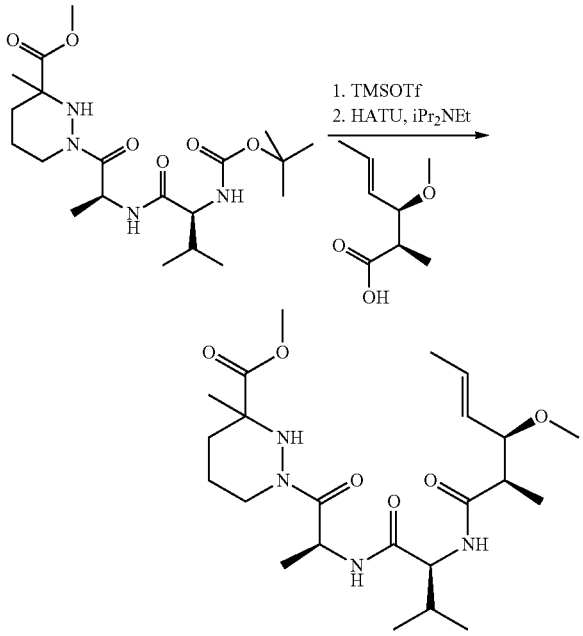

A cooled (0° C.) solution of 33e (373.1 mg, 0.871 mmol) in anhydrous dichloromethane (10 mL) was treated with trimethylsilyl methanesulfonate (310 μL, 1.741 mmol). After stirring for 1 h at 0° C., the reaction was quenched with N,N-diisopropylethylamine (610 μL, 3.484 mmol) and the volatiles were removed in vacuo. A cooled (0° C.) solution of the crude amine and (E)-(2R,3R)-3-methoxy-2-methyl-hex-4-enoic acid (137.8 mg, 0.871 mmol) in anhydrous acetonitrile (15 mL) was subsequently treated with N,N-diisopropylethylamine (610 μL, 3.484 mmol) and 2-(1H-7-azabenzotriazol-1-yl)-1,1,3,3-tetramethyl uronium hexafluorophosphate methanaminium (463.7 mg, 1.219 mmol). After stirring at RT for 18 h, the reaction was quenched with hydrochloric acid (1 M, 30 mL). The aqueous layer was extracted with ethyl acetate (2×30 mL). The organics were combined, washed with saturated sodium bicarbonate (20 mL), dried over sodium sulfate, filtered and the volatiles were removed in vacuo. The residue was purified by silica gel chromatography using a 25 g Isolute cartridge eluted with a continuous gradient of iso-hexanes/ethyl acetate 1:0 to 1:2 to 1:4 to afford the title compound (332.2 mg, 81%) as a colorless solid and as a mixture of diastereoisomers.

Compound 33g

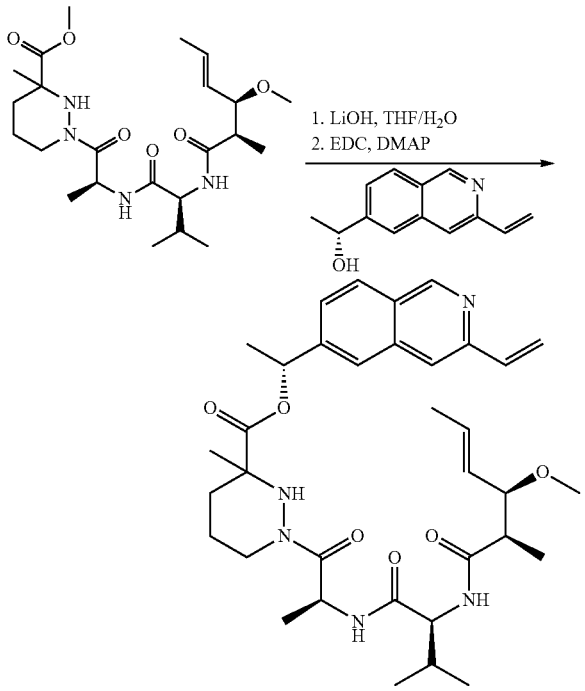

Compound 33 g was prepared in the same manner as (S)-1-[(S)-2-((S)-2-tert-butoxycarbonylamino-3-methyl-butyrylamino)-propionyl]-hexahydro-pyridazine-3-carboxylic acid (R)-1-[6-((E)-3-tert-butoxycarbonyl-propenyl)-cinnolin-3-yl]-ethyl ester using 33f and (R)-1-(3-vinyl-isoquinolin-6-yl)-ethanol instead of 1e and (E)-4-[3-((R)-1-hydroxy-ethyl)-cinnolin-6-yl]-but-3-enoic acid tert-butyl ester in 30% yield over 2 steps.

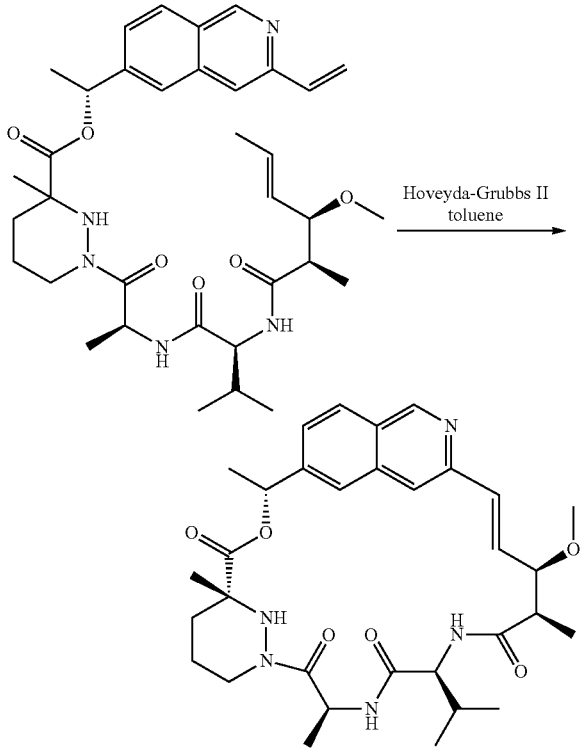

Compound 33

-continued

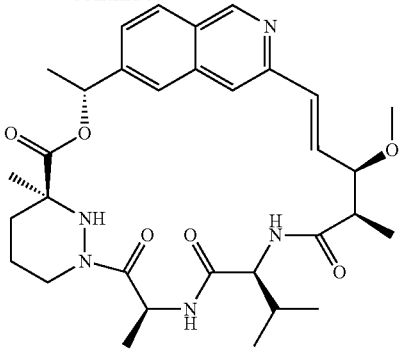

Compound 34

A solution of 33 g (136.2 mg, 0.214 mmol) in toluene (70 mL) was degassed by bubbling $N_2$ gas through for 20 min. Hoveyda-Grubbs $2^{nd}$ generation catalyst (27 mg, 0.043 mmol) was added and the mixture was refluxed for 2.5 h. More Hoveyda-Grubbs $2^{nd}$ generation catalyst (20 mg) was added and after stirring at reflux for 1 h, the mixture was cooled to RT, the volatiles were removed in vacuo and the residue was purified by silica gel chromatography using a 25 g Isolute cartridge eluted with a continuous gradient of ethyl acetate/acetone 1:0 to 10:1 to afford both diastereoisomers in separate mixtures. Both mixtures were purified by silica gel chromatography using a 10 g Isolute cartridge eluted by gravity with a continuous gradient of ethyl acetate/acetone 1:0 to 10:1 to provide the more polar diastereoisomer (19.7 mg, 15%) as a white solid. The less polar diastereomer was further purified by preparative TLC eluted with ethyl acetate (4 elutions) and subsequent preparative TLC eluted with iso-hexanes/acetone 7:3 (2 elutions) to afford the title compound (7.6 mg, 6%) as a white solid. Relative stereochemistry was not assigned. More polar diastereoisomer 33: $^1$H NMR (300 MHz, $CDCl_3$) δ 0.83-1.07 (m, 7H), 1.41 (d, J=7.1 Hz, 3H), 1.47 (d, J=6.9 Hz, 3H), 1.50 (s, 3H), 1.70 (d, J=6.7 Hz, 3H), 1.75-1.90 (m, 2H), 1.96-2.15 (m, 3H), 2.64 (dd, J=7.6, 3.1 Hz, 1H), 2.70-2.84 (m, 1H), 3.42 (s, 3H), 3.90 (dd, J=8.7, 3.1 Hz, 1H), 4.00 (app t, J=8.0 Hz, 1H), 4.10 (s, 1H), 4.58-4.69 (m, 1H), 6.00 (dd, J=9.4, 7.1 Hz, 1H), 6.22 (q, J=6.2 Hz, 1H), 6.51 (d, J=9.8 Hz, 1H), 6.93 (s, 1H), 7.13-7.23 (m, 1H), 7.34-7.43 (m, 1H), 7.90-7.97 (m, 2H), 8.47 (s, 1H). LCMS (m/z) 594.3 [M+H], Tr=1.87 min.

Less polar diastereoisomer 34: $^1$H NMR (300 MHz, $CD_3CN$) δ −0.51--0.39 (m, 5H), −0.30 (d, J=6.9 Hz, 3H), 0.06 (d, J=7.1 Hz, 3H), 0.15 (d, J=6.9 Hz, 3H), 0.19 (s, 3H), 0.25-0.34 (m, 4H), 0.38-0.45 (m, 1H), 0.81-1.02 (m, 2H), 1.14-1.42 (m, 2H), 2.69 (dd, J=8.7, 2.9 Hz, 1H), 3.00-3.10 (m, 2H), 3.45 (s, 3H), 4.32 (app pentet, J=7.1 Hz, 1H), 4.76 (q, J=6.7 Hz, 1H), 5.53 (d, J=16.3 Hz, 1H), 5.85 (dd, J=16.1, 8.9 Hz, 1H), 6.20 (dd, J=8.5, 1.6 Hz, 1H), 6.41 (d, J=8.9 Hz, 1H), 6.65-6.75 (m, 2H), 6.91 (s, 1H), 7.11 (d, J=7.3 Hz, 1H), 7.79 (s, 1H). LCMS (m/z) 594.3 [M+H], Tr=1.83 min.

Example 35

Compound 35

Compound 35a

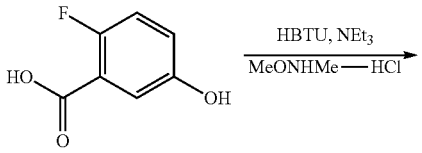

-continued

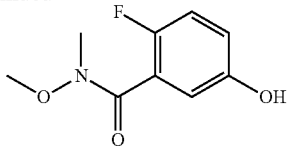

A cooled (0° C.) solution of 2-fluoro-5-hydroxy-benzoic acid (1.0051 g, 6.438 mmol), N,O-dimethylhydroxylamine hydrochloride (1.2560 g, 12.856 mmol) and triethylamine (3.6 mL, 25.752 mmol) in dichloromethane (35 mL) was treated with O-(benzotriazol-1-yl)-N,N,N',N'-tetramethyl-uronium hexafluorophosphate (3.663 g, 9.658 mmol). After stirring at RT for 20 h, the reaction was quenched at 0° C. with hydrochloric acid (2 M, 30 mL). The emulsion was filtered on Celite then the aqueous layer was extracted with dichloromethane (50 mL). The organics were combined, filtered through a phase separator and the volatiles were removed in vacuo. The residue was purified by silica gel chromatography using a 50 g Isolute cartridge eluted with a continuous gradient of toluene/diethyl ether 1:0 to 1:2 to afford the title compound (260.5 mg, 20%) as a colorless oil.

Compound 35b

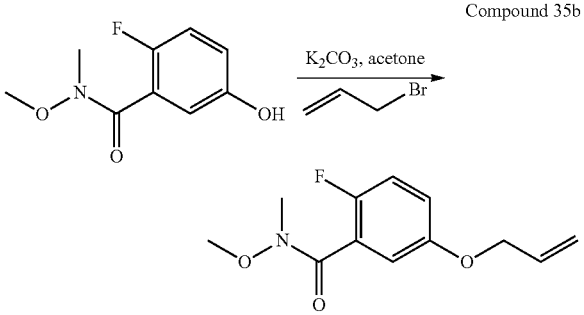

A solution of 35a (260.5 mg, 1.308 mmol) in acetone (20 mL) was subsequently treated with potassium carbonate (903.8 mg, 6.539 mmol) and allylbromide (340 μL, 3.924 mmol). After stirring at RT for 24 h, the reaction was quenched with water (20 mL). The aqueous layer was extracted with dichloromethane (2×30 mL). The organics were combined, filtered through a phase separator and the volatiles were removed in vacuo. The residue was purified by silica gel chromatography using a 25 g Isolute cartridge eluted with a continuous gradient of iso-hexanes/ethyl acetate 1:0 to 3:2 to afford the title compound (289.7 mg, 92%) as a colorless oil.

Compound 35c

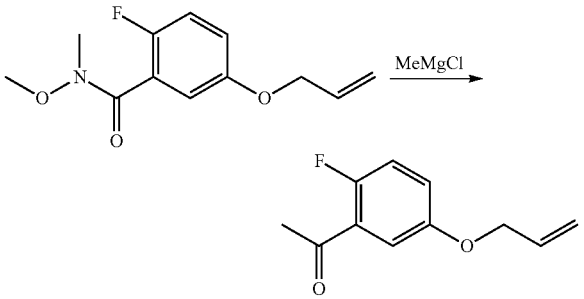

A cooled (−78° C.) solution of 35b (289.7 mg, 1.210 mmol) in tetrahydrofuran (10 mL) was treated with methylmagnesium chloride (810 μL, 2.422 mmol, 3 M in diethyl ether). After 1.25 h at −78° C., 2 h at 0° C. and 16 h at RT, methylmagnesium chloride (810 μL, 2.422 mmol, 3 M in diethyl ether) was added. After 2.5 h at −78° C. and 1.2 h at RT, the reaction was quenched with silica gel and the volatiles were removed in vacuo. The residue was purified by silica gel chromatography using a 25 g Isolute cartridge eluted with a continuous gradient of iso-hexanes/ethyl acetate 1:0 to 9:1 to afford the title compound (196.7 mg, 84%) as a colorless oil.

Compound 35d

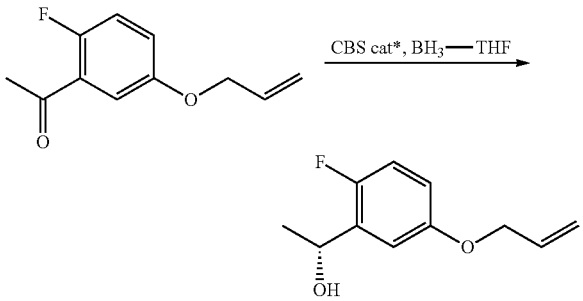

A solution of 35c (196.7 mg, 1.013 mmol) in tetrahydrofuran (15 mL) was treated with (S)-(−)-2-methyl-CBS-oxazaborolidine (1.2 mL, 1.215 mmol, 1 M in toluene). After 10 min at RT the mixture was cooled to −50° C. and treated with borane tetrahydrofuran complex (2.1 mL, 2.026 mmol, 1 M in tetrahydrofuran). After 1.5 h at −50° C. to −40° C., the reaction was quenched with methanol (6 mL). After stirring at RT for 22 h, the volatiles were removed in vacuo. The residue was purified by silica gel chromatography using a 25 g Isolute cartridge eluted with a continuous gradient of iso-hexanes/ethyl acetate 1:0 to 4:1 to afford the title compound (179.4 mg, 90%) as a white solid.

Compound 35e

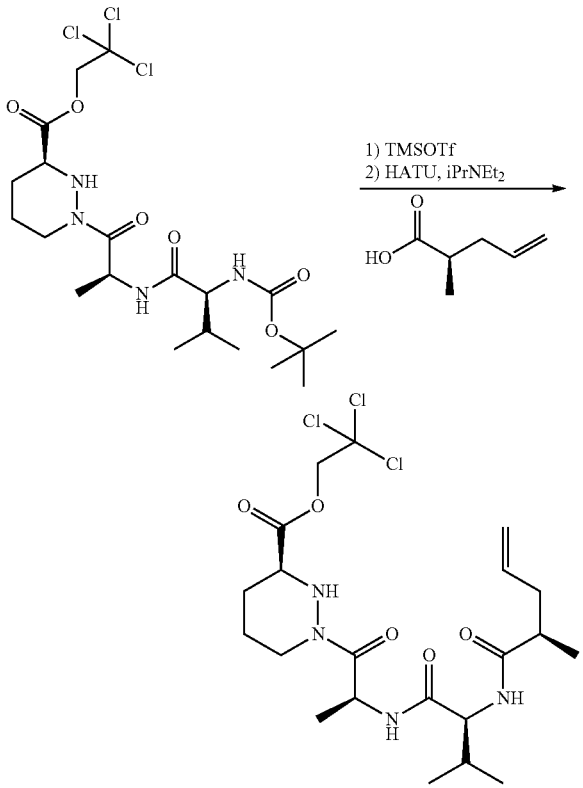

A cooled (0° C.) solution of 1e (1.9973 g, 3.755 mmol) in anhydrous dichloromethane (40 mL) was treated with trimethylsilyl trifluoromethanesulfonate (1.4 mL, 7.510 mmol). After 30 min at 0° C., the reaction mixture was treated with N,N-diisopropylethylamine (2.6 mL, 15.020 mmol) and the volatiles were removed in vacuo to afford the corresponding amine. A cooled (0° C.) solution of this amine, (E)-(2R,3R)-2-methylhex-6-enoic acid (428.6 mg, 3.755 mmol, prepared as described in Synlett 2002, 12, pp 2039-2040) and N,N-diisopropylethylamine (2.6 mL, 15.020 mmol) in acetonitrile (50 mL) was treated with 2-(1H-7-azabenzotriazol-1-yl)-1,1,3,3-tetramethyl uronium hexafluorophosphate methanaminium (1.999 g, 5.257 mmol). After stirring at RT for 20 h, the reaction was quenched with hydrochloric acid (1 M, 100 mL). The aqueous layer was extracted with ethyl acetate (2×50 mL). The organics were combined, washed with saturated sodium bicarbonate, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:4 to afford the title compound (1.6735 g, 84%) as a brown foam.

Compound 35f

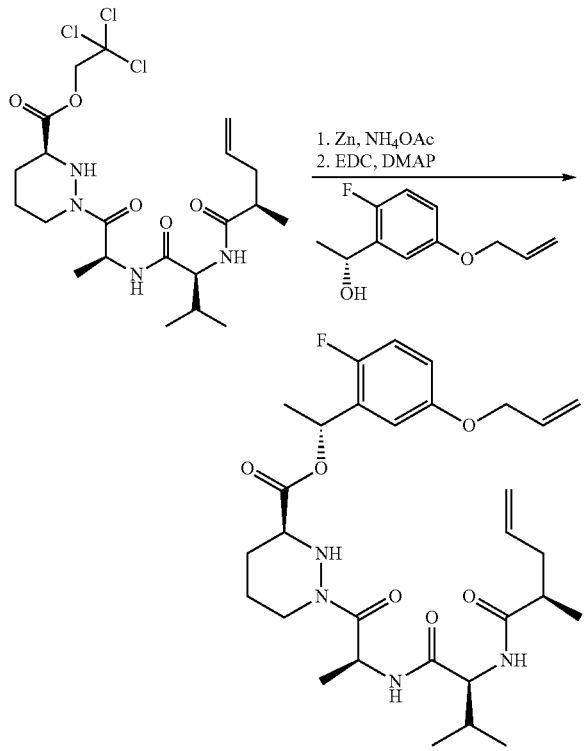

A solution of 35e (534.7 mg, 1.013 mmol) in tetrahydrofuran (20 mL) was subsequently treated with zinc powder (1.457 g, 22.286 mmol) and a solution of ammonium acetate (1.171 g, 15.195 mmol) in water (5 mL). After stirring at RT for 24 h, the mixture was filtered through Celite. The solid was rinsed with saturated potassium bisulfate and ethyl acetate. The pH of the filtrate was adjusted with 2 M hydrochloric acid then the aqueous layer was extracted with ethyl acetate (2×50 mL). The organics were combined, dried over sodium sulfate, filtered and the volatiles were removed in vacuo. Residual acetic acid was azeotroped off with toluene (3×) to provide the corresponding acid as a white solid. A solution of the crude acid, (R)-1-(5-allyloxy-2-fluoro-phenyl)-ethanol (179.4 mg, 0.914 mmol) and 4-dimethylaminopyridine (123.7 mg, 1.013 mmol) in dichloromethane (15 mL) was treated with N-(3-dimethylaminopropyl)-N'-ethylcarbodiimide hydrochloride (310.8 mg, 1.621 mmol). After stirring at RT for 20 h, the reaction was quenched at 0° C. with hydrochloric acid (2 M, 15 mL). The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:3 to afford the title compound (310.5 mg, 59% over 2 steps) as a white solid.

Compound 35

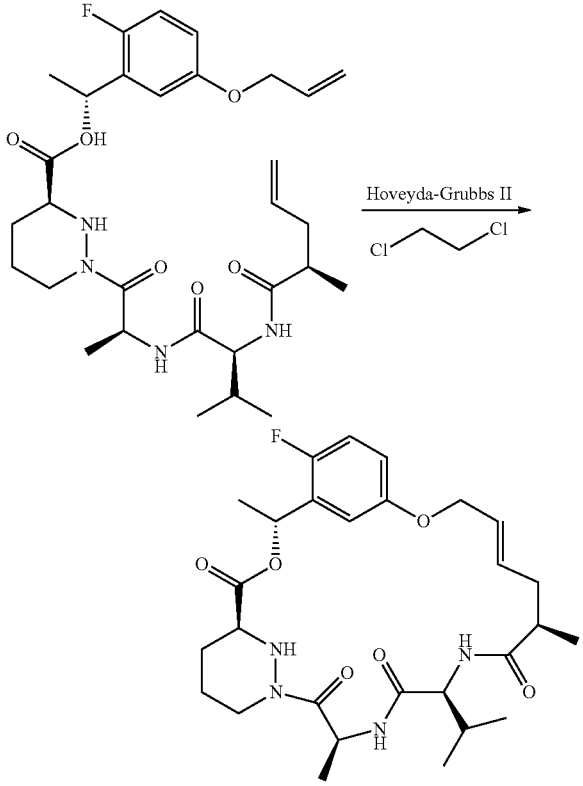

A solution of 35f (310.5 mg, 0.540 mmol) in dichloroethane (180 mL) was treated with Hoveyda-Grubbs $2^{nd}$ generation catalyst (67.7 mg, 0.108 mmol). After stirring at reflux for 2 h, the reaction was cooled to RT and the volatiles were removed in vacuo. The residue was purified by silica gel chromatography using a 50 g Isolute cartridge eluted with a continuous gradient of iso-hexanes/ethyl acetate 1:0 to 0:1 then using a 25 g Isolute cartridge eluted by gravity with a continuous gradient of iso-hexanes/ethyl acetate 1:0 to 0:1 to afford the title compound (109.9 mg) in a mixture. Purification by preparative TLC eluted with iso-hexanes/acetone 3:1 (3 elutions) followed by silica gel chromatography using a 25 g Isolute cartridge eluted with a continuous gradient of iso-hexanes/acetone 1:0 to 3:2 provided the title compound (58.7 mg, 20%) as a white solid. $^1$H NMR (300 MHz, $CD_3CN$) δ 0.85-0.97 (m, 6H), 1.17-1.22 (m, 3H), 1.28-1.39 (m, 4H), 1.44-1.63 (m, 6H), 1.70-1.82 (m, 1H), 1.83-1.92 (m, 1H), 2.30-2.45 (m, 3H), 3.62-3.73 (m, 2H), 3.89 (app t, J=8.5 Hz, 1H), 4.28 (d, J=8.0 Hz, 1H), 4.40-4.60 (m, 2H), 5.32 (app pentet, J=6.9 Hz, 1H), 5.62-5.74 (m, 1H), 5.77-5.89 (m, 1H), 6.02 (q, J=6.7 Hz, 1H), 6.40 (d, J=7.8 Hz, 1H), 6.76-6.85 (m, 2H), 7.01 (app t, J=9.4 Hz, 1H), 7.19 (br s, 1H). LCMS (m/z) 547.2 [M+H], Tr=2.39 min.

Example 36

Compound 36

Compound 36

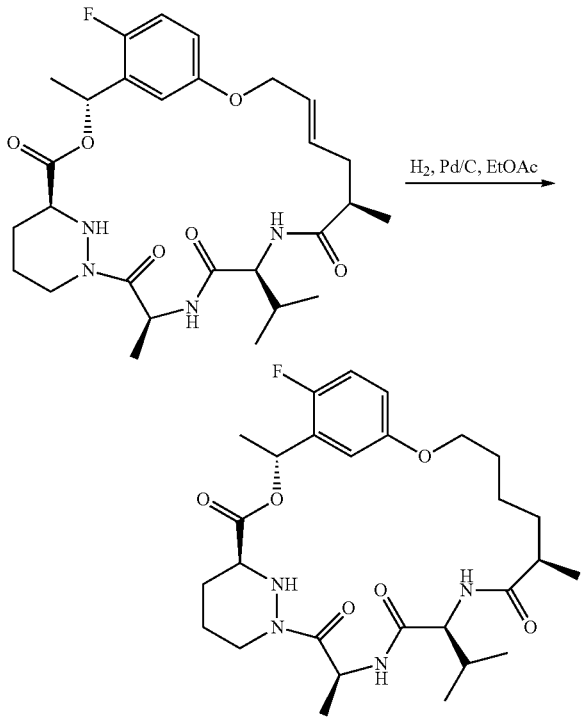

To a solution of Compound 35 (44.0 mg, 0.080 mmol) in ethyl acetate (5 mL) was added palladium on carbon (10%, 5 mg). The atmosphere was purged of oxygen. After stirring at RT under an atmosphere of hydrogen for 2.5 h, the volatiles were removed in vacuo and the residue was purified by silica gel chromatography using a 20 g Isolute cartridge eluted with a continuous gradient of iso-hexanes/acetone 1:0 to 3:2 followed by preparative TLC eluted with iso-hexanes/acetone 3:2 to afford the final compound (19.0 mg, 43%) as a white solid. $^1$H NMR (300 MHz, $CDCl_3$) δ 0.85-0.99 (m, 8H), 1.14-1.22 (m, 4H), 1.26-1.42 (m, 4H), 1.48 (d, J=6.7 Hz, 1H), 1.52-1.84 (m, 8H), 2.28-2.42 (m, 1H), 3.61-3.72 (m, 1H), 3.75-4.10 (m, 4H), 4.25 (d, J=9.4 Hz, 1H), 5.26 (app pentet, J=7.1 Hz, 1H), 6.02 (q, J=6.7 Hz, 1H), 6.34 (d, J=8.5 Hz, 1H), 6.75-6.86 (m, 2H), 6.95-7.12 (m, 2H). LCMS (m/z) 549.3 [M+H], Tr=2.54 min.

Example 37

(E)-(2R,5S,11S,14S,17R,18R)-2,14-Diisopropyl-18-methoxy-11,17-dimethyl-22-oxa-3,9,12,15,28-pentaaza-tricyclo[21.3.1.1*5,9*]octacosa-1(27),19,23,25-tetraene-4,10,13,16-tetraone: Compound 37

Compound 37a

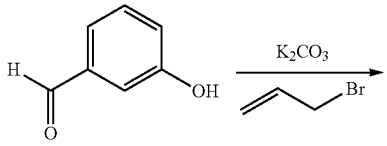

-continued

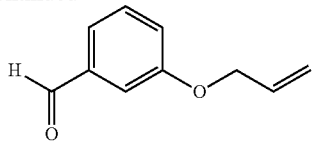

37a was prepared in the same manner as 35b using 3-hydroxybenzaldehyde instead of 2-fluoro-5-hydroxy-N-methoxy-N-methyl-benzamide in 78% yield.

Compound 37b

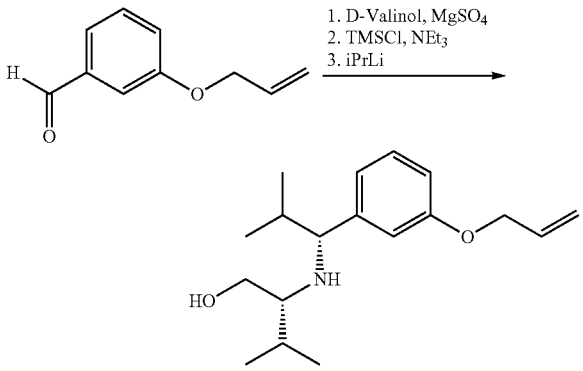

A cooled (0° C.) suspension of 37a (1.36 g, 8.434 mmol) and magnesium sulfate (5 g) in dichloromethane (40 mL) was treated with D-valinol (870.0 mg, 8.434 mmol). After stirring at 0° C. to RT for 23 h, the mixture was filtered and the volatiles were removed in vacuo. The residue was dissolved in anhydrous dichloromethane (40 mL) and was subsequently treated with triethylamine (1.3 mL, 9.277 mmol) and a solution of trimethylsilyl chloride (9.3 mL, 9.277 mmol, 1 M in dichloromethane). After stirring at RT for 24 h, the volatiles were removed in vacuo and the residue was triturated with diethyl ether/iso-hexane (100 mL, 1:1). The white solid was filtered off and the filtrate was evaporated to dryness to provide the intermediate imine. In a cooled (−40° C.) 3-neck round-bottom flask, equipped with a nitrogen line and an addition funnel was introduced anhydrous diethyl ether (25 mL) and a solution of isopropyllithium (29 mL, 20.242 mmol, 0.7 M in pentane). To this mixture, a solution of the imine in anhydrous diethyl ether (25 mL) was added dropwise over 15 min. After stirring at −40° C. for 2.5 h, the reaction was quenched with hydrochloric acid (2 M, 50 mL) and the mixture was allowed to warm to RT. The acidic aqueous layer was basified with NaOH pellets at 0° C. and then extracted with diethyl ether (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:1 to afford the title compound (470.1 mg, 19% over 3 steps) as a colorless oil.

Compound 37c

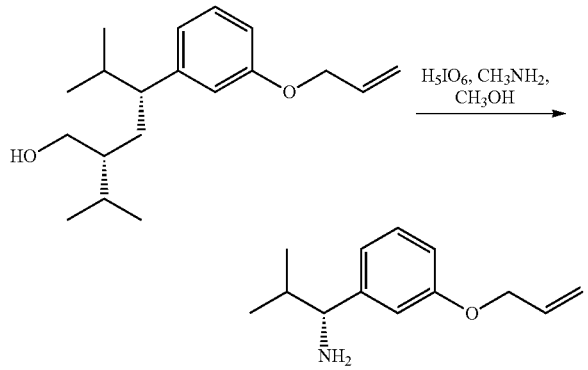

A solution of 37b (470.1 mg, 1.613 mmol) in methanol (10 mL) and aqueous methylamine (3 mL, 40 wt % in water) was treated with periodic acid (1.213 g, 5.323 mmol). After stirring for 24 h at RT more aqueous methylamine (4 mL, 40 wt % in water) and periodic acid (1.213 g, 5.323 mmol) were added. After stirring for 17 h at RT the mixture was filtered over Celite and the solid rinsed with methanol. The volatiles were removed in vacuo and the residue was partitioned between water and diethyl ether. The aqueous layer was extracted with diethyl ether, the organics were combined, dried over sodium sulfate, filtered and the volatiles were removed in vacuo. The residue was purified by silica gel chromatography using a 25 g Isolute cartridge eluted with ethyl acetate to afford the title compound (191.8 mg, 58%) as a light yellow oil.

Compound 37d

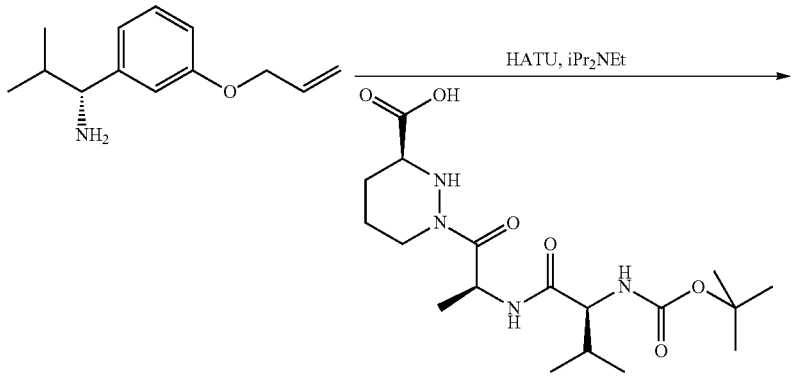

-continued

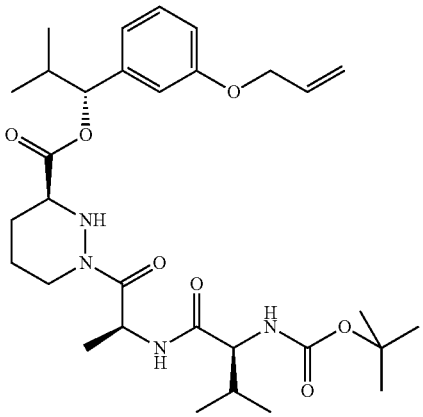

A cooled (0° C.) solution of (S)-1-[(S)-2-((S)-2-tert-butoxycarbonylamino-3-methyl-butyrylamino)-propionyl]-hexahydro-pyridazine-3-carboxylic acid (324.4 mg, 0.810 mmol), 37c (166.3 mg, 0.810 mmol) and N,N-diisopropylethylamine (560 μL, 3.240 mmol) in acetonitrile (15 mL) was treated with 2-(1H-7-azabenzotriazol-1-yl)-1,1,3,3-tetramethyl uronium hexafluorophosphate methanaminium (431.2 mg, 1.134 mmol). After stirring at RT for 20 h, the reaction was quenched with hydrochloric acid (2 M, 25 mL) at 0° C. The aqueous layer was extracted with ethyl acetate (2×). The organics were combined, dried over sodium sulfate, filtered and the volatiles were removed in vacuo. The residue was purified by silica gel chromatography using a 50 g Isolute cartridge eluted with a continuous gradient of iso-hexanes/ethyl acetate 1:0 to 0:1 to afford the title compound (230.5 mg, 48%) as a solid.

-continued

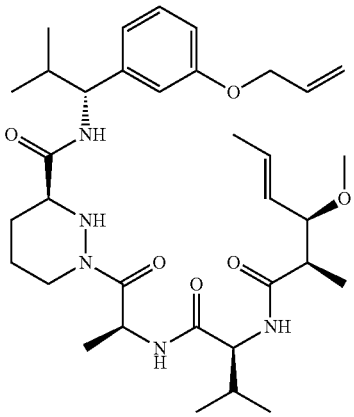

Compound 37e was prepared in the same manner as 1-{(S)-2-[(S)-2-((E)-(2R,3R)-3-methoxy-2-methyl-hex-4-enoylamino)-3-methyl-butyrylamino]-propionyl}-3-methyl-hexahydro-pyridazine-3-carboxylic acid methyl ester using 37d instead of 1-[(S)-2-((S)-2-tert-butoxycarbonylamino-3-methyl-butyrylamino)-propionyl]-3-methyl-hexahydro-pyridazine-3-carboxylic acid methyl ester in 30% yield over 2 steps.

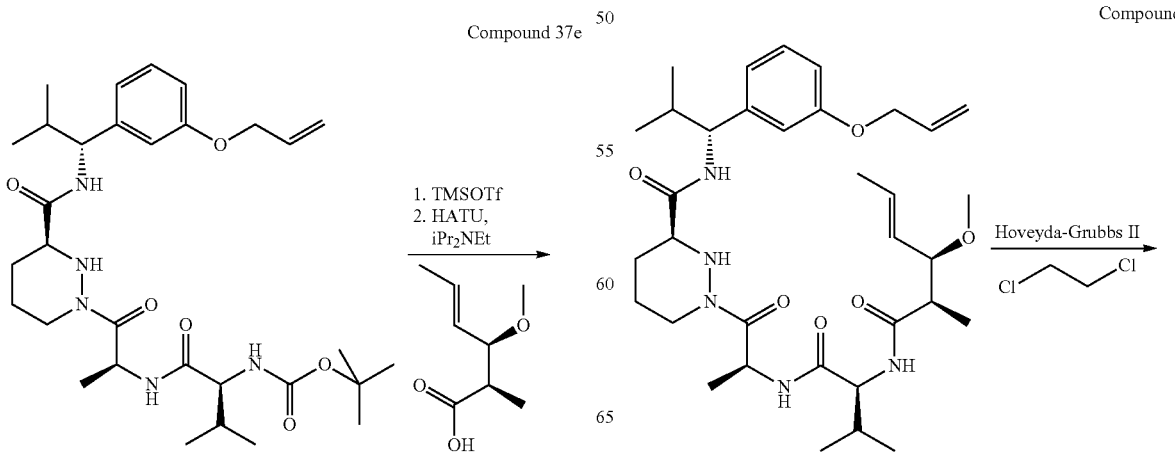

-continued

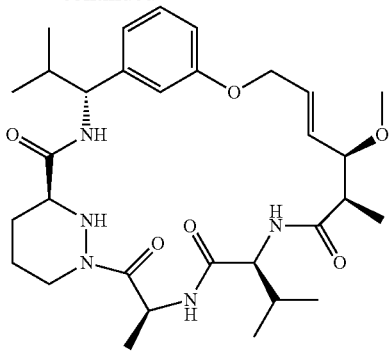

Compound 37 was prepared in the same manner as using 37e instead of (S)-1-{(S)-2-[(S)-2-((2R,3R)-3-methoxy-2-methyl-hept-6-enoylamino)-3-methyl-butyrylamino]-propionyl}-hexahydro-pyridazine-3-carboxylic acid methyl-((R)-6-vinyl-indan-1-yl)-amide in 43% yield. $^1$H NMR (300 MHz, $d_6$-DMSO) δ 0.74-0.91 (m, 12H), 1.15 (d, J=7.1 Hz, 3H), 1.28 (d, J=7.3 Hz, 3H), 1.40-1.64 (m, 3H), 1.71-1.88 (m, 3H), 1.98 (app sextet, J=6.7 Hz, 1H), 2.66-2.75 (m, 2H), 3.38-3.53 (m, 1H), 3.89 (dd, J=6.7, 2.9 Hz, 1H), 4.10 (app t, J=8.9 Hz, 1H), 4.14-4.22 (m, 1H), 4.42 (qd, J=10.0, 4.2 Hz, 1H), 4.57 (app t, J=8.2 Hz, 1H), 4.76 (d, J=11.8 Hz, 1H), 5.23 (app t, J=7.3 Hz, 1H), 5.69-5.90 (m, 2H), 6.77-6.90 (m, 3H), 7.05 (d, J=9.4 Hz, 1H), 7.16-7.24 (m, 1H), 8.01 (d, J=8.5 Hz, 1H), 8.14 (d, J=8.5 Hz, 1H). LCMS (m/z) 586.3 [M+H], Tr=2.34 min.

Example 38

Compound 38

Compound 38a

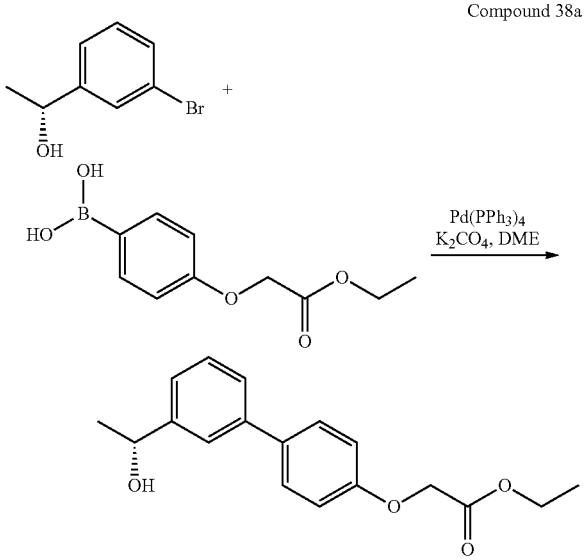

To a mixture of (R)-1-(3-bromo-phenyl)-ethanol (201 mg, 1.00 mmol), 4-(2-ethoxy-2-oxoethoxy)benzeneboronic acid (Acros Organics, 224 mg, 1.00 mmol) in 1,2-dimethoxyethane (4 mL) were added potassium carbonate (276 mg, 2.00 mmol) and water (1 mL). The mixture was stirred at RT and tetrakis(triphenylphosphine) palladium(0) (58 mg, 0.05 mmol) was added then the reaction mixture was heated at 100° C. in a microwave reactor for 30 min. The reaction mixture was then diluted with ethyl acetate and water. The layers were separated and the organics washed with water and brine, dried over magnesium sulfate, filtered and evaporated. The residue was purified by silica gel chromatography using a gradient of iso-hexanes/ethyl acetate 9:1 to 7:3 to afford the title compound (230 mg, 76%) as an oil.

Compound 38b

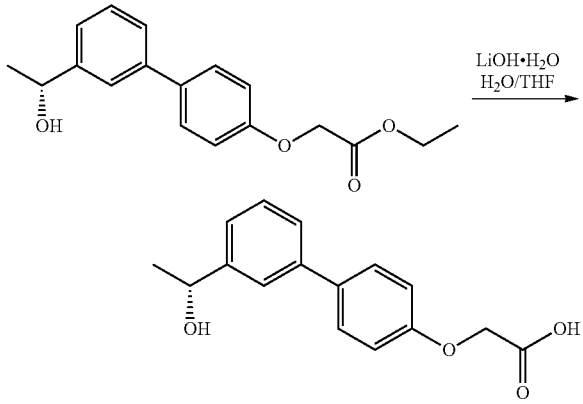

A solution of 38a (230 mg, 0.77 mmol) in tetrahydrofuran (4 mL) was stirred at 5° C. under nitrogen, a solution of lithium hydroxide monohydrate (92 mg, 1.54 mmol) was added and the reaction mixture was stirred at 5° C. for 2 h and then at RT overnight. The solution was acidified with 2 M hydrochloric acid and extracted with ethyl acetate (2×). The organic extracts were combined, washed with water and brine, dried over magnesium sulfate and evaporated to afford the title compound (175 mg, 84%) as a white solid.

Compound 38c

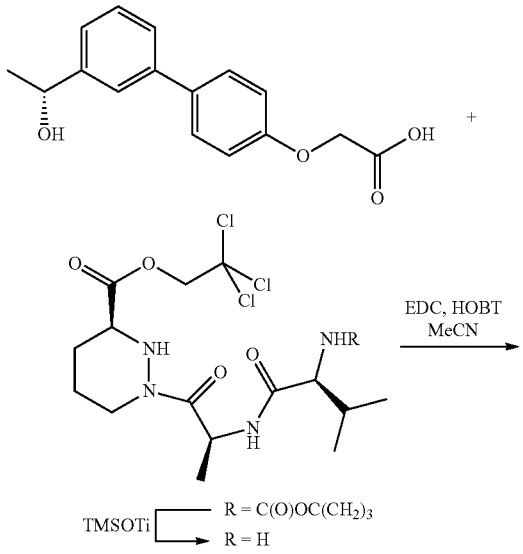

-continued

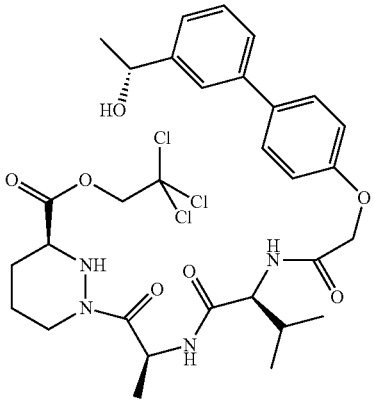

A solution of 1e (372 mg, 0.70 mmol) in dichloromethane (15 mL) was cooled in an ice-water bath under nitrogen. Trimethylsilyl trifluoromethanesulfonate (0.18 mL, 1.05 mmol) was added dropwise, and the resulting solution was stirred for 1 hour. Cold saturated aqueous sodium hydrogen carbonate solution (15 mL) was added and the mixture was stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.70 mmol) which was used without further purification. A solution of (S)-1-[(S)-2-((S)-2-amino-3-methyl-butyrylamino)-propionyl]-hexahydro-pyridazine-3-carboxylic acid 2,2,2-trichloro-ethyl ester (0.70 mmol) in acetonitrile (15 mL) was stirred at 0° C. under nitrogen. 38b (175 mg, 0.64 mmol) and 1-hydroxybenzotriazole hydrate (123 mg, 0.64 mmol, wetted with not less than 20 wt. % water) were added, followed by N-(3-dimethylaminopropyl)-N'-ethylcarbodiimide hydrochloride (173 mg, 0.90 mmol) and the reaction mixture was stirred at RT for 2 h. The solvent was evaporated. The residue was dissolved in ethyl acetate and the solution was washed with water (3×) followed by brine, dried over magnesium sulfate and evaporated. The residue was purified by silica gel chromatography using a gradient of iso-hexanes/ethyl acetate 1:2 to 0:1. The product was triturated with diethyl ether and dried to afford the title compound (367 mg, 83%) as a white solid.

Compound 38d

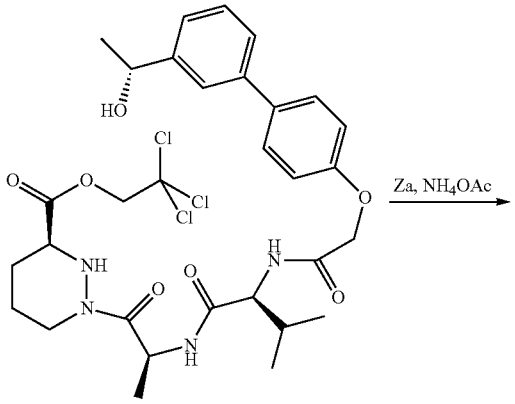

-continued

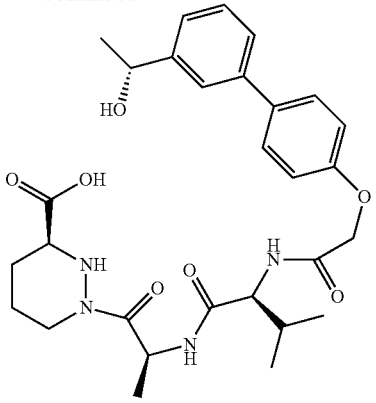

A solution of 38c (343 mg, 0.50 mmol) in tetrahydrofuran (10 mL) was stirred at RT under nitrogen. Zinc powder (715 mg, 11 mmol) was added followed by a solution of ammonium acetate (578 mg, 7.50 mmol) in water (5 mL). The reaction mixture was stirred at RT under nitrogen for 70 h. The reaction mixture was filtered through Celite and the filter pad was washed with ethyl acetate and 2 M aqueous hydrochloric acid. The filtrate was acidified to pH 2 with 2 M aqueous hydrochloric acid, solid sodium chloride was added to saturate the aqueous layer and the mixture was extracted with ethyl acetate. The ethyl acetate extracts were combined, washed with brine, dried over magnesium sulfate and evaporated. The residue was co-evaporated with toluene (3×) to afford the title compound (237 mg, 86%) as a white powder.

Compound 38

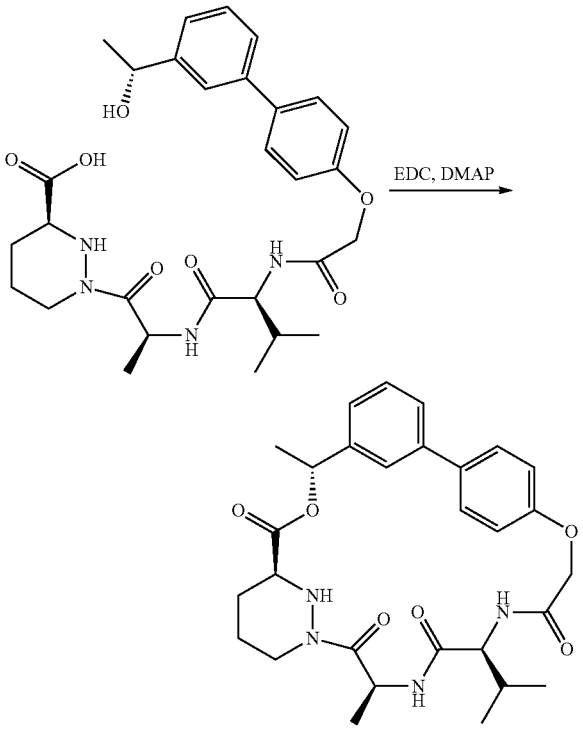

A solution of 38d (100 mg, 0.18 mmol) in dichloromethane (180 mL) was stirred at RT under nitrogen. 4-Dimethylaminopyridine (33 mg, 0.27 mmol) and N-(3-dimethylaminopropyl)-N'-ethylcarbodiimide hydrochloride (104 mg, 0.54 mmol) were added and the reaction mixture was stirred at RT for 18 h. The solvent was evaporated. The residue was purified by silica gel chromatography using a gradient of iso-hexanes/ethyl acetate 1:2 to 0:1 followed by silica gel chromatography using a gradient of ethyl acetate to ethyl acetate/acetone 4:1. The residue was co-evaporated with dichloromethane then triturated with diethyl ether to afford a solid. The solid was washed with ether and dried to afford the title compound (8 mg, 9%) as a white solid. $^1$H NMR (300 MHz, $CDCl_3$) 0.95 (d, J=6.2 Hz, 3H), 0.96 (d, J=6.5 Hz, 3H), 1.39 (d, J=7.1 Hz, 3H), 1.54-1.80 (m, 5H), 1.82-2.10 (m, 3H), 2.52-2.63 (m, 1H), 3.29-3.62 (m, 2H), 4.07 (app t, J=9.6 Hz, 1H), 4.45 (br d, J=13.6 Hz, 1H), 4.67 (ABq, $\Delta\delta_{AB}$=0.12, $J_{AB}$=16.0 Hz, 2H), 4.88-5.01 (m, 1H), 5.93-6.00 (m, 2H), 6.57 (d, J=10.3 Hz, 1H), 6.94 (d, J=8.5 Hz, 2H), 7.15-7.53 (m, 6H). LCMS (m/z) 537.2 [M+H], Tr=2.34 min.

Example 39

Compound 39

Compound 39a

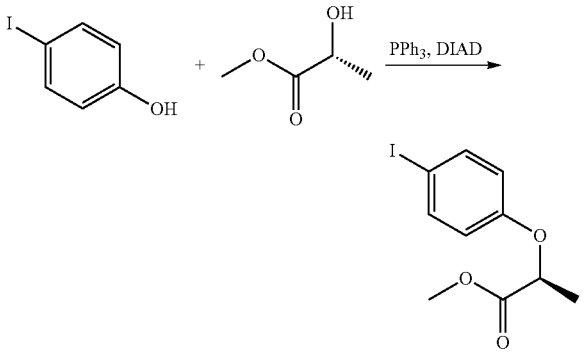

A solution of 4-iodo phenol (2.2 g, 10.0 mmol), (R)-2-hydroxy-propionic acid methyl ester (0.95 mL, 10.0 mmol) and triphenylphosphine (2.62 g, 10.0 mmol) was prepared in tetrahydrofuran (40 mL). Diisopropyl azodicarboxylate (2.0 mL. 10 mmol) was added dropwise and the reaction was stirred at −5° C. for 1 hour and then at RT for 2 h. The tetrahydrofuran was evaporated and diethyl ether/iso-hexanes (1:10, 50 mL) was added. The mixture was stirred at RT for 10 min where a precipitate formed. The filtrate was decanted off and evaporated. The residue was purified by silica gel chromatography using a gradient of iso-hexanes/ethyl acetate 20:1 to 10:1 to afford the title compound (2.02 g, 66%) as an oil.

Compound 39b

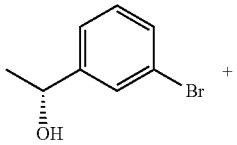

-continued

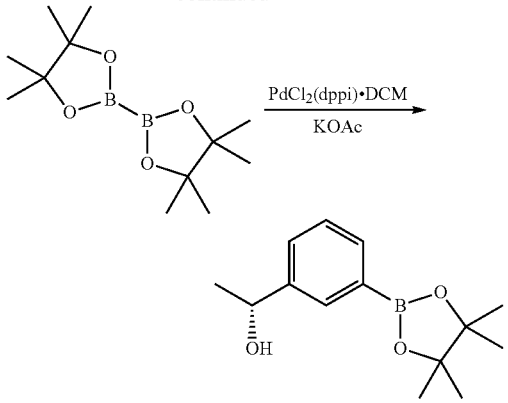

(R)-1-(3-bromophenyl)-ethanol (1.0 g, 4.97 mmol), bis(pinacolato)diboron (1.39 g, 5.47 mmol), 1,1'bis(diphenylphosphino)ferrocenedichloropalladium(II), dichloromethane adduct (203 mg, 0.249 mmol) and potassium acetate (976 mg, 9.94 mmol) were dissolved in 1,4-dioxane (10 mL) and the reaction was heated to reflux and left to stir over 3 days. The reaction was allowed to cool to RT before being filtered through a pad of Hyflo. The pad was then washed with ethyl acetate and the combined organics were then concentrated and purified by silica gel chromatography using a stepwise gradient of iso-hexanes/ethyl acetate 1:0 to 4:1 to afford the title compound (936 mg, 76%) as a pale yellow oil.

Compound 39c

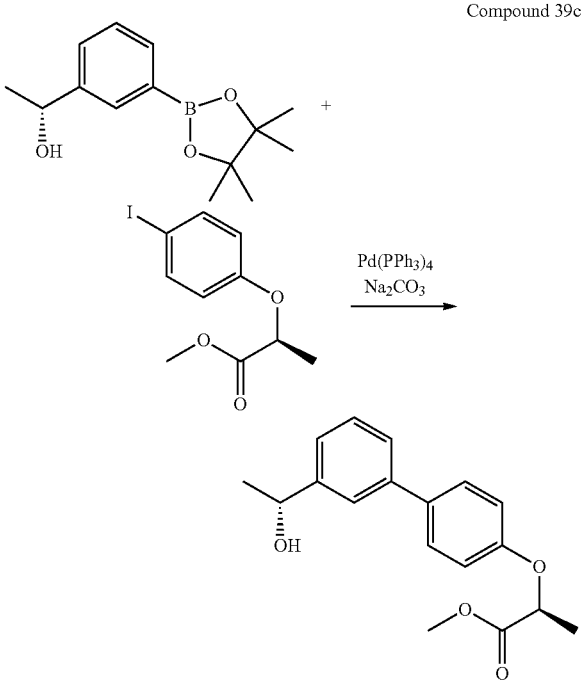

A solution of 39b (496 mg, 2.00 mmol) and 39a (612 mg, 2.00 mmol) in 1,2-dimethoxyethane (4 mL) was stirred at RT under nitrogen. A solution of 2 M aqueous sodium carbonate (4 mL) was added followed by tetrakis(triphenylphosphine) palladium(0) (116 mg, 0.1 mmol) and the reaction mixture was heated at 80° C. for 1 hour. The reaction mixture was cooled to RT, water was added and the mixture was extracted with ethyl acetate. The ethyl acetate extracts were combined, washed with brine, dried over sodium sulfate and evaporated. The residue was purified by silica gel chromatography using a gradient of iso-hexanes/ethyl acetate 17:3 to 1:1 to afford the title compound (253 mg, 42%) as a gum.

Compound 39d

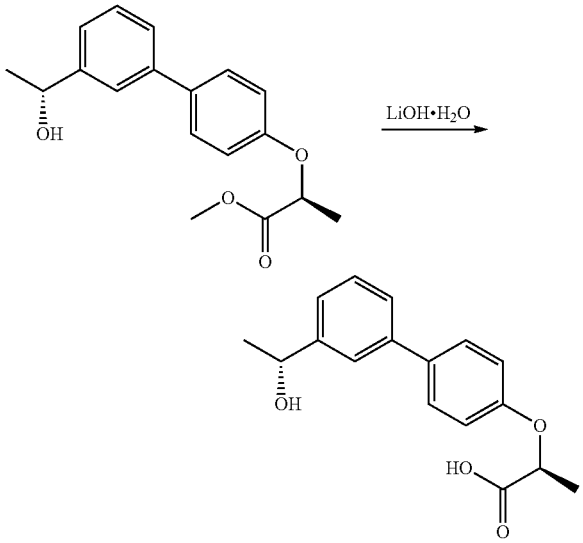

A solution of 39c (250 mg, 0.83 mmol) in tetrahydrofuran (4 mL) was stirred at 5° C. under nitrogen. A solution of lithium hydroxide monohydrate (42 mg, 1.00 mmol) in water (1 mL) was added and the reaction mixture was stirred at 5° C. for 1 hour. The reaction mixture was acidified to pH 3 with 2 M aqueous hydrochloric acid and the mixture extracted with ethyl acetate. The organic extracts were separated, washed with water and brine, dried over magnesium sulfate and evaporated to afford the title compound (224 mg, 94%) as a white foam.

Compound 39e

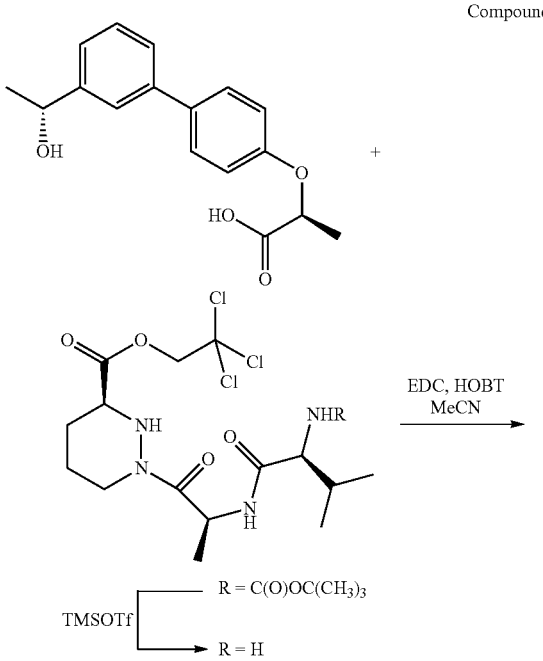

-continued

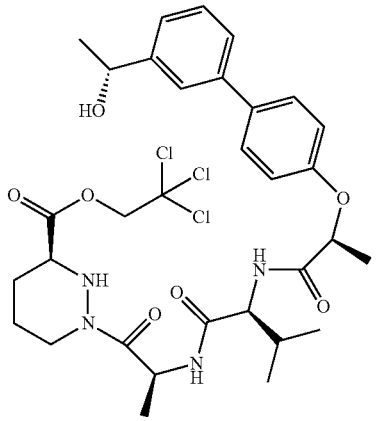

A solution of 1e (478 mg, 0.9 mmol) in dichloromethane (15 mL) was cooled in an ice-water bath under nitrogen. Trimethylsilyl trifluoromethanesulfonate (0.25 mL, 1.35 mmol) was added dropwise, and the resulting solution was stirred for 1 h. Cold saturated aqueous sodium hydrogen carbonate solution (15 mL) was added and the mixture was stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.9 mmol) which was used without further purification. A solution of (S)-1-[(S)-2-((S)-2-amino-3-methyl-butyrylamino)-propionyl]-hexahydro-pyridazine-3-carboxylic acid 2,2,2-trichloro-ethyl ester (0.9 mmol) in acetonitrile (15 mL) was stirred at 0° C. under nitrogen. 39d (224 mg, 0.78 mmol) and 1-hydroxybenzotriazole hydrate (184 mg, 0.96 mmol, wetted with not less than 20 wt. % water) were added, followed by N-(3-dimethylaminopropyl)-N'-ethylcarbodiimide hydrochloride (225 mg, 1.17 mmol) and the reaction mixture was stirred at RT for 2 h. The solvent was evaporated. The residue was dissolved in ethyl acetate and the solution was washed with water (3×) followed by brine, dried over magnesium sulfate and evaporated. The residue was purified by silica gel chromatography using a gradient of iso-hexanes/ethyl acetate 1:2 to 0:1 to afford the title compound (490 mg, 90%) as a gum.

Compound 39f

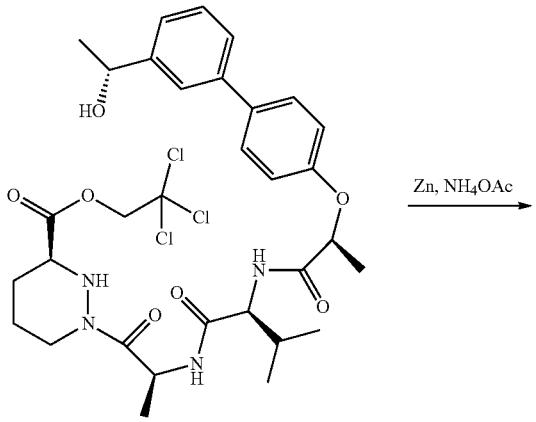

-continued

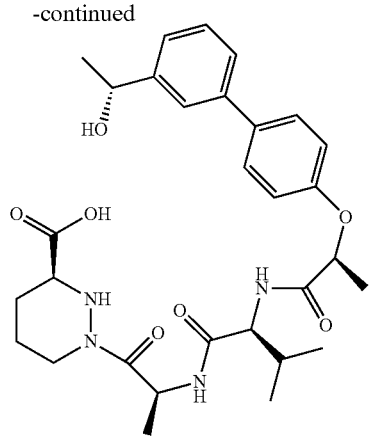

A solution of 39e (490 mg, 0.70 mmol) in tetrahydrofuran (15 mL) was stirred at RT under nitrogen. Zinc powder (1.00 g, 15.40 mmol) was added followed by a solution of ammonium acetate (810 mg, 10.50 mmol) in water (8 mL). The reaction mixture was stirred at RT under nitrogen for 24 h. The reaction mixture was filtered through Celite and the filter pad was washed with ethyl acetate and 2 M aqueous hydrochloric acid. The filtrate was acidified to pH 2-3 with 2 M aqueous hydrochloric acid. Solid sodium chloride was added to saturate the aqueous layer and the mixture was extracted with ethyl acetate. The ethyl acetate extracts were combined and washed with brine. The organic extracts were passed through a hydrophobic frit and the filtrate was evaporated. The residue was co-evaporated with ethyl acetate (3×) then toluene (3×) to afford the title compound (394 mg, 98%) as a white solid.

Compound 39

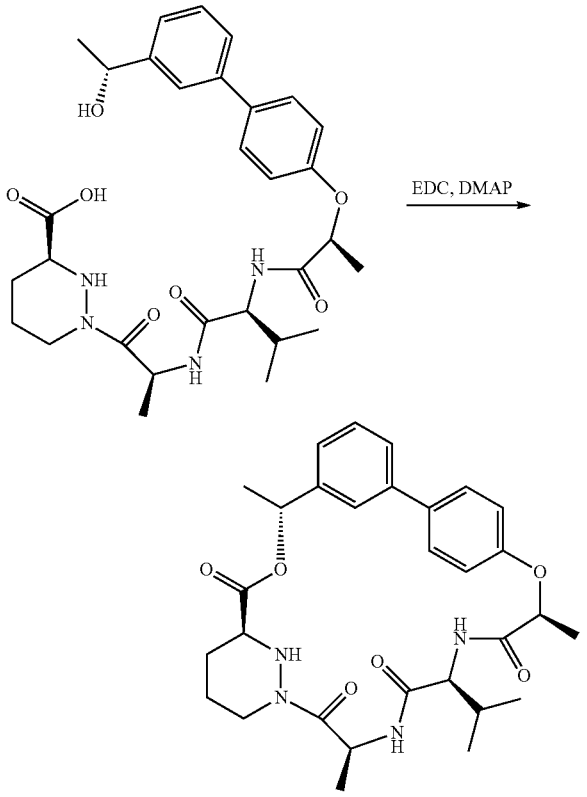

A solution of 39f (100 mg, 0.18 mmol) in dichloromethane (180 mL) was stirred at RT under nitrogen. 4-Dimethylaminopyridine (44 mg, 0.36 mmol) and N-(3-dimethylaminopropyl)-N'-ethylcarbodiimide hydrochloride (138 mg, 0.72 mmol) were added and the reaction mixture was stirred at RT for 4 h. The solvent was evaporated. Ethyl acetate was added to the residue and the mixture was washed with aqueous citric acid (pH 4) and brine. The organic layer was dried over magnesium sulfate and the solvent was evaporated. The residue was purified by silica gel chromatography using a gradient of iso-hexanes/ethyl acetate 3:7 to 0:1. The residue was triturated with diethyl ether/iso-hexanes 1:1 to afford the title compound (10 mg, 10%) as a white solid. $^1$H NMR (300 MHz, $CD_3OD$) 0.94 (d, J=6.7 Hz, 3H), 0.95 (d, J=6.9 Hz, 3H), 1.51 (d, J=7.1 Hz, 3H), 1.61 (d, J=6.5 Hz, 3H), 1.67 (d, J=6.9 Hz, 3H), 1.72-2.00 (m, 5H), 2.60-2.69 (m, 1H), 3.54-3.63 (m, 1H), 4.13 (d, J=10.5 Hz, 1H), 4.32 (br d, J=12.9 Hz, 1H), 4.57-4.66 (m, 2H), 4.78 (q, J=7.1 Hz, 1H), 5.92 (q, J=6.5 Hz, 1H), 6.91 (d, J=8.9 Hz, 2H), 7.22 (d, J=7.6 Hz, 1H), 7.34-7.61 (m, 5H). LCMS (m/z) 551.2 [M+H], Tr=2.51 min.

Example 40

Compound 40

Compound 40a

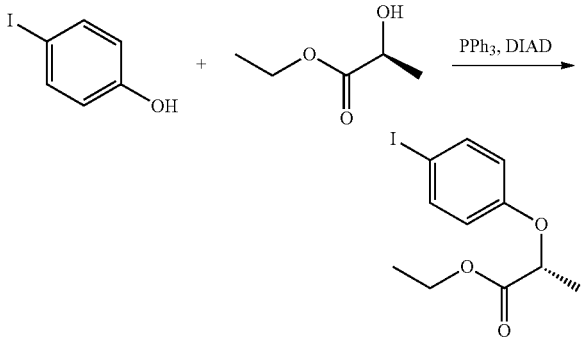

40a was prepared in the same manner as (S)-2-(4-iodophenoxy)-propionic acid methyl ester using (S)-2-hydroxypropionic acid ethyl ester instead of (R)-2-hydroxy-propionic acid methyl ester in 28% yield.

Compound 40b

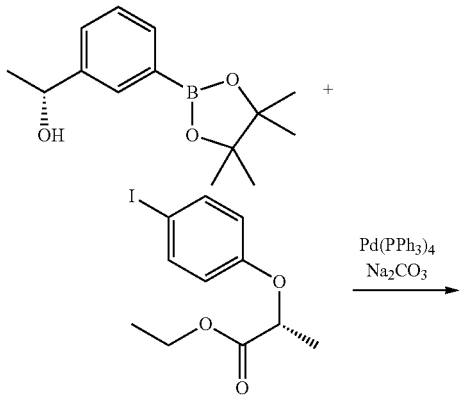

-continued

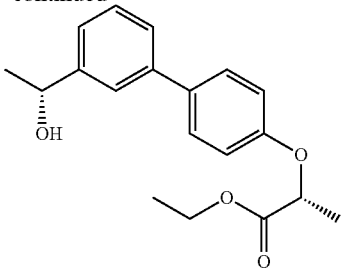

40b was prepared in the same manner as (S)-2-[3'-((R)-1-hydroxy-ethyl)-biphenyl-4-yloxy]-propionic acid methyl ester using 40a instead of (S)-2-(4-iodo-phenoxy)-propionic acid methyl ester in 54% yield.

Compound 40c

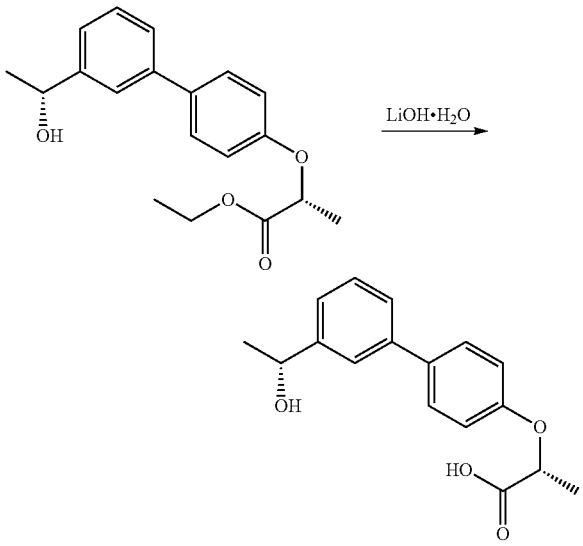

40c was prepared in the same manner as (S)-2-[3'-((R)-1-hydroxy-ethyl)-biphenyl-4-yloxy]-propionic acid using 40b instead of (S)-2-[3'-((R)-1-hydroxy-ethyl)-biphenyl-4-yloxy]-propionic acid methyl ester in 71% yield.

Compound 40d

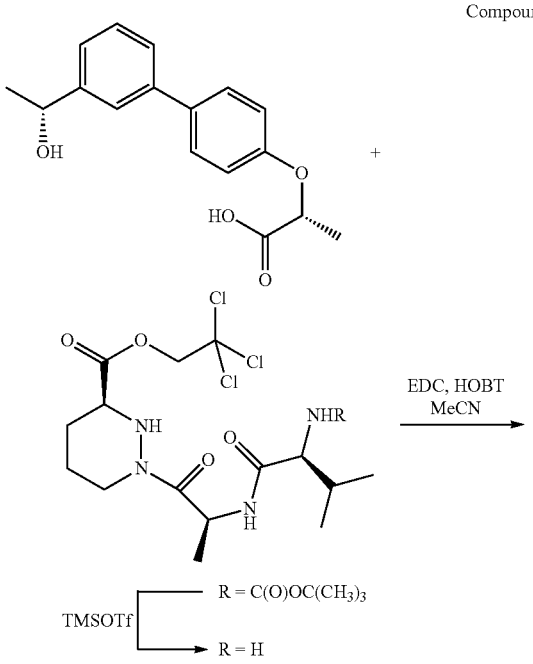

-continued

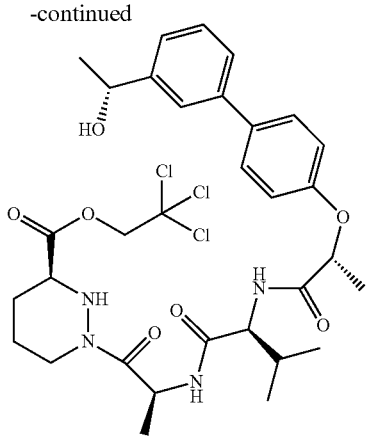

40d was prepared in the same manner as (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester using 40c instead of (S)-2-[3'-((R)-1-hydroxy-ethyl)-biphenyl-4-yloxy]-propionic acid in 71% yield.

Compound 40e

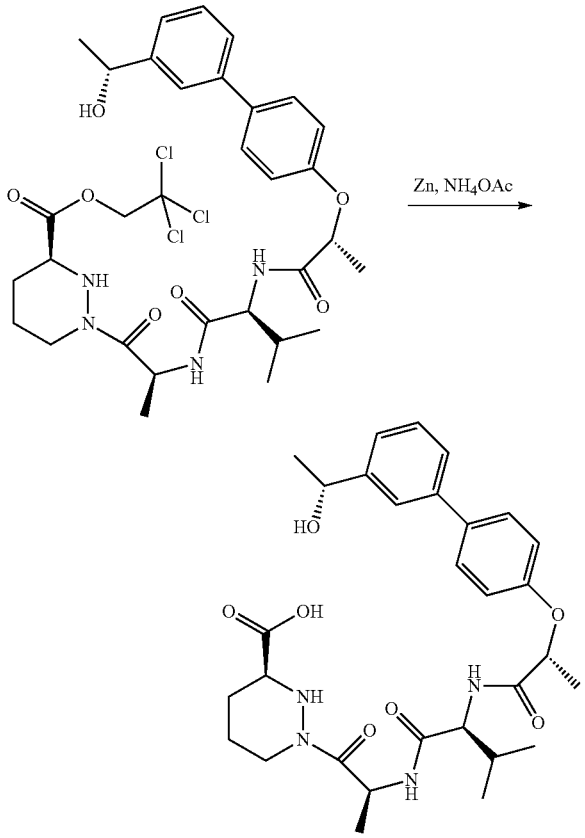

40e was prepared in the same manner as ((S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid using 40d instead of (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester in 83% yield.

Compound 40

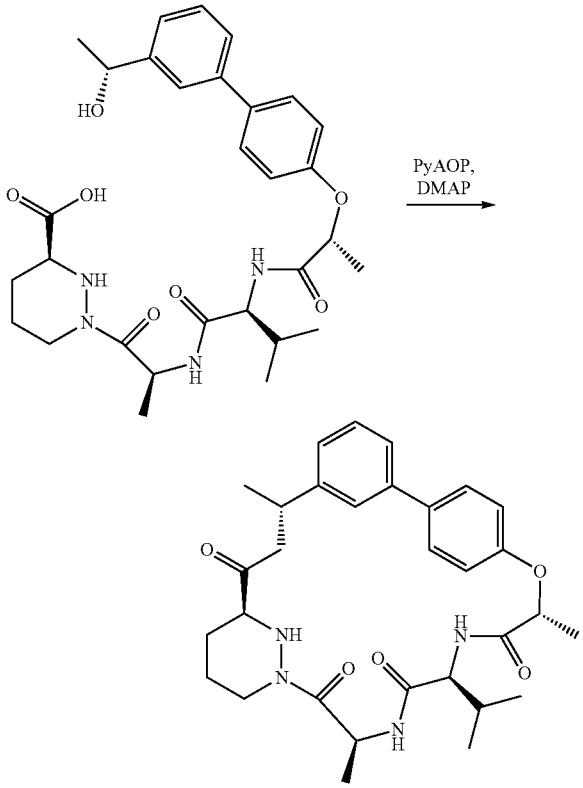

A solution of 40e (102 mg, 0.18 mmol) in dichloromethane (180 mL) was stirred at RT under nitrogen. 4-Dimethylaminopyridine (44 mg, 0.36 mmol) and (7-azabenzotriazol-1-yloxy)tripyrrolidinophosphonium hexafluorophosphate (114 mg, 0.22 mmol) were added and the reaction mixture was stirred at RT for 4 h. The solvent was evaporated. Ethyl acetate was added to the residue and the mixture was washed with aqueous citric acid (pH 4) and brine. The organic layer was separated and dried over magnesium sulfate and evaporated. The residue was purified by silica gel chromatography using a gradient of iso-hexanes/ethyl acetate 3:7 to 0:1. The residue was purified by preparative reverse phase HPLC to afford the title compound (2.8 mg, 3%) as a white solid. $^1$H NMR (300 MHz, $CD_3OD$) 1.03 (d, J=6.9 Hz, 3H), 1.05 (d, J=6.9 Hz, 3H), 1.25 (d, J=7.1 Hz, 3H), 1.56 (d, J=6.5 Hz, 3H), 1.57 (d, J=6.3 Hz, 3H), 1.64-2.10 (m, 5H), 2.75-2.83 (m, 1H), 3.60-3.66 (m, 1H), 4.08 (d, J=10.0 Hz, 1H), 4.32 (br d, J=12.9 Hz, 1H), 4.74 (q, J=6.5 Hz, 1H), 5.22 (q, J=7.3 Hz, 1H), 5.98 (q, J=6.5 Hz, 1H), 6.86 (d, J=8.5 Hz, 2H), 7.20-7.25 (m, 1H), 7.39-7.51 (m, 5H). LCMS (m/z) 551.2 [M+H], Tr=2.27 min.

Example 41

Compound 41

Compound 41a

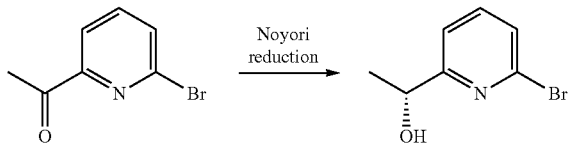

Dichloro (p-cymene) ruthenium(II) dimer (31 mg, 0.05 mmol) and (1R,2R)-(−)-N-p-tosyl-1,2-diphenylethylenediamine (44 mg, 0.12 mmol) was suspended in degassed water (20 mL) and the mixture was degassed with nitrogen for 10 min. The mixture was stirred at 70° C. under nitrogen for 90 min. The resulting yellow solution was cooled to RT. A solution of 1-(6-bromo-pyridin-2-yl)-ethanone (2.0 mg, 10 mmol) in degassed tetrahydrofuran (10 mL) and sodium formate (3.4 g, 50 mmol) was added and the reaction mixture was degassed with nitrogen for 5 min. The reaction mixture was vigorously stirred at 40° C. for 30 min. The reaction mixture was cooled to RT and was extracted with ethyl acetate. The organic extracts were combined, washed with water and brine, dried over sodium sulfate, filtered and evaporated. The residue was purified by silica gel chromatography using a gradient of iso-hexanes/ethyl acetate 3:1 to 0:1 to afford the title compound (1.78 g, 89%) as a brown oil.

Compound 41b

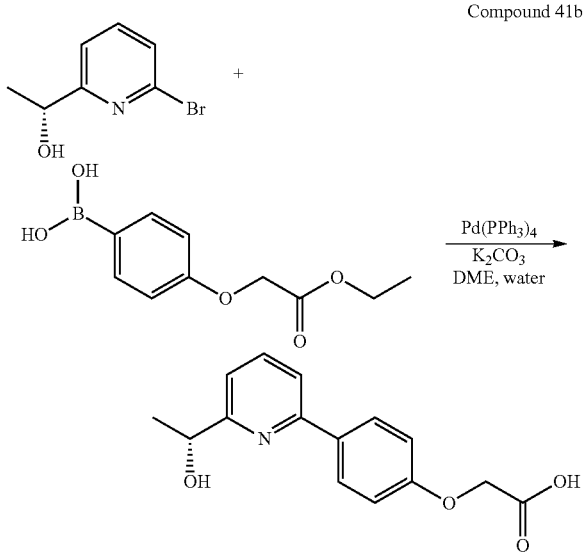

To a mixture of 41a (101 mg, 0.50 mmol), 4-(2-ethoxy-2-oxoethoxy)benzeneboronic acid (112 mg, 0.50 mmol) in 1,2-dimethoxyethane (4 mL) was added a solution of potassium carbonate (138 mg, 1.00 mmol) in water (1 mL). Tetrakis(triphenylphosphine)palladium(0) (29 mg, 0.025 mmol) was added and the reaction mixture was heated at 100° C. in a microwave reactor for 30 min. The reaction mixture was then diluted with ethyl acetate and water. 2 M Hydrochloric acid was added to adjust the pH of the reaction mixture to pH 3 and the volatiles was evaporated. Methanol was added to the residue and the mixture was filtered through a hydrophobic frit. The filtrate was evaporated and the residue was dried in vacuum to afford the title compound (143 mg, 93%) as a white solid.

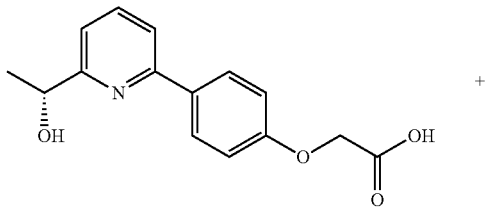

-continued

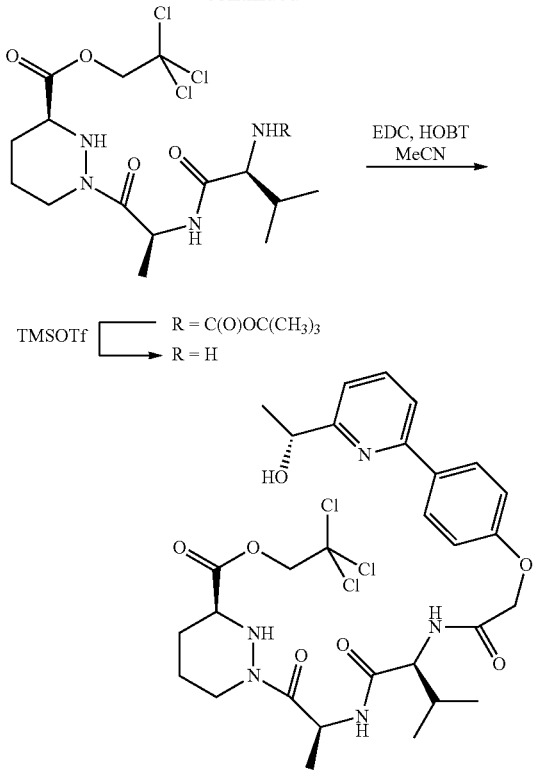

Compound 41c

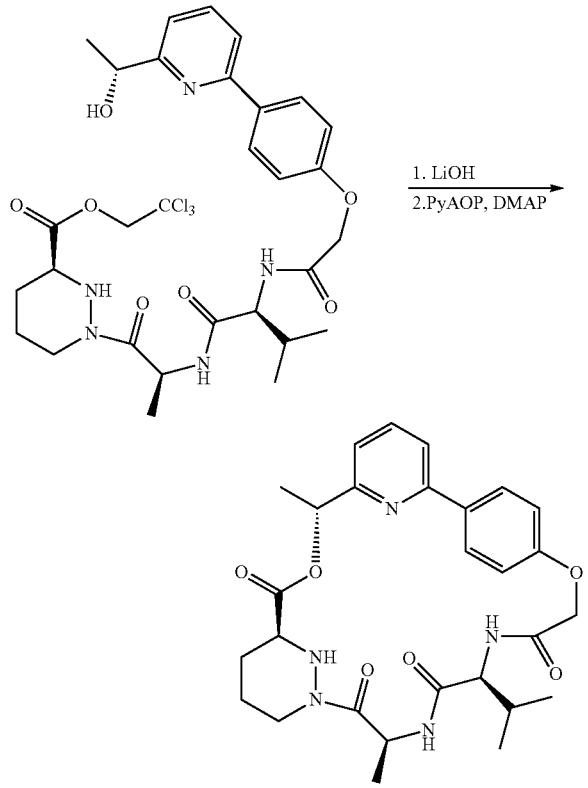

A solution of 1e (240 mg, 0.45 mmol) in dichloromethane (15 mL) was cooled in an ice-water bath under nitrogen. Trimethylsilyl trifluoromethanesulfonate (0.12 mL, 0.68 mmol) was added dropwise, and the resulting solution was stirred for 1 h. Cold saturated aqueous sodium hydrogen carbonate solution (15 mL) was added and the mixture was stirred at 0° C. for 15 min. The organic layer was separated, washed with brine, dried over magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.45 mmol) which was used without further purification. A mixture of (S)-1-[(S)-2-((S)-2-amino-3-methyl-butyrylamino)-propionyl]-hexahydro-pyridazine-3-carboxylic acid 2,2,2-trichloro-ethyl ester (0.45 mmol), 41b (143 mg, 0.45 mmol) and N,N-diisopropylethylamine (0.16 mL, 0.9 mmol) in acetonitrile (15 mL) was stirred at RT under nitrogen. 1-Hydroxybenzotriazole hydrate (108 mg, 0.56 mmol, wetted with not less than 20 wt. % water) and N-(3-dimethylaminopropyl)-N'-ethylcarbodiimide hydrochloride (130 mg, 0.675 mmol) was added and the reaction mixture was stirred at RT for 4 h. N,N-Dimethylformamide (2 mL) was added and the reaction mixture was stirred at RT for 22 h. Additional N-(3-dimethylaminopropyl)-N'-ethylcarbodiimide hydrochloride (87 mg, 0.45 mmol) was added and the reaction mixture was stirred at RT for 6 h. The solvent was evaporated. The residue was suspended in a mixture of ethyl acetate and aqueous citric acid solution (pH 3) and the mixture was extracted with ethyl acetate. The organic extracts were combined, washed with water followed by brine. The organic layer was filtered through a hydrophobic frit and the filtrate was evaporated. The residue was purified by silica gel chromatography using ethyl acetate to afford the title compound (71 mg, 23%) as a white solid.

A solution of 41c (69 mg, 0.10 mmol) in tetrahydrofuran (2 mL) was stirred at 0° C. under nitrogen, a solution of lithium hydroxide monohydrate (5 mg, 0.12 mmol) in water (0.5 mL) was added and the reaction mixture was stirred at 0° C. for 1 h. The solution was acidified to pH 3 with 2 M hydrochloric acid and the solvent was evaporated. The residue was co-evaporated with toluene (3×) to afford (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid (58 mg, 0.1 mmol) as a white solid which was used crude in the next step. A solution of (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid (56 mg, 0.1 mmol) in dichloromethane (100 mL) was stirred at RT under nitrogen. 4-Dimethylaminopyridine (49 mg, 0.4 mmol) was added and the reaction mixture was for stirred for 5 min. A solution of (7-azabenzotriazol-1-yloxy)tripyrrolidinophosphonium hexafluorophosphate (78 mg, 0.15 mmol) in dichloromethane (20 mL) was added dropwise over 5 min and the reaction mixture was stirred at RT for 2 h. The solvent was evaporated and the residue was purified by silica gel chromatography using ethyl acetate. The residue was purified by preparative reverse phase HPLC to afford the title compound (14 mg, 26%) as a white solid. $^1$H NMR (300 MHz, $CD_3OD$) 0.94 (d, J=6.7 Hz, 3H), 0.98 (d, J=6.5 Hz, 3H), 1.36 (d, J=7.1 Hz, 3H), 1.68 (d, J=6.5 Hz, 3H), 1.72-2.05 (m, 5H), 2.65-2.74 (m, 1H), 3.53-3.60 (m, 1H), 4.14 (d, J=10.7 Hz, 1H), 4.30-4.38 (m, 1H), 4.66 (ABq, $\Delta\delta_{AB}$=0.13, $J_{AB}$=15.8 Hz, 2H), 5.07 (q, J=7.1 Hz, 1H), 5.87 (q, J=6.5 Hz, 1H), 6.89 (d, J=8.9 Hz, 2H), 7.26 (br d, J=7.1 Hz, 1H), 7.71-7.78 (m, 2H), 8.06 (d, J=8.9 Hz, 2H). LCMS (m/z) 538.2 [M+H], Tr=2.07 min.

Example 42

Compound 42

Compound 42a

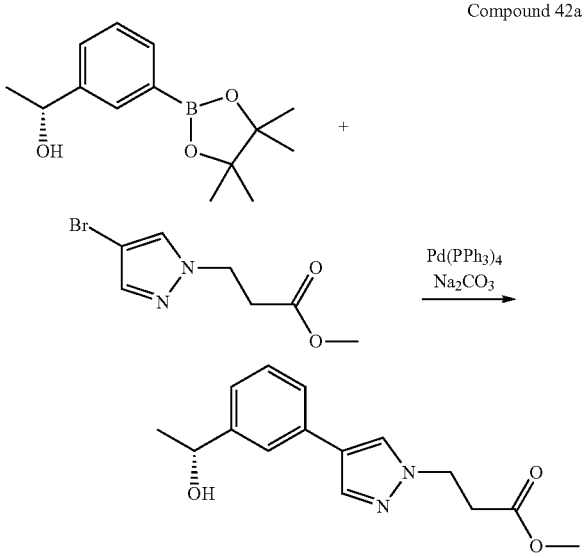

42a was prepared in the same manner as (S)-2-[3'-((R)-1-hydroxy-ethyl)-biphenyl-4-yloxy]-propionic acid methyl ester using 3-(4-bromo-pyrazol-1-yl)-propionic acid methyl ester instead of (S)-2-(4-iodo-phenoxy)-propionic acid methyl ester in 28% yield.

Compound 42b

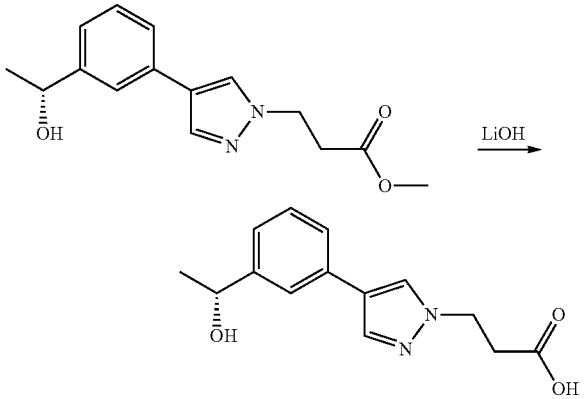

42b was prepared in the same manner as (S)-2-[3'-((R)-1-hydroxy-ethyl)-biphenyl-4-yloxy]-propionic acid using 42a instead of (S)-2-[3'-((R)-1-hydroxy-ethyl)-biphenyl-4-yloxy]-propionic acid methyl ester in 96% yield.

Compound 42c

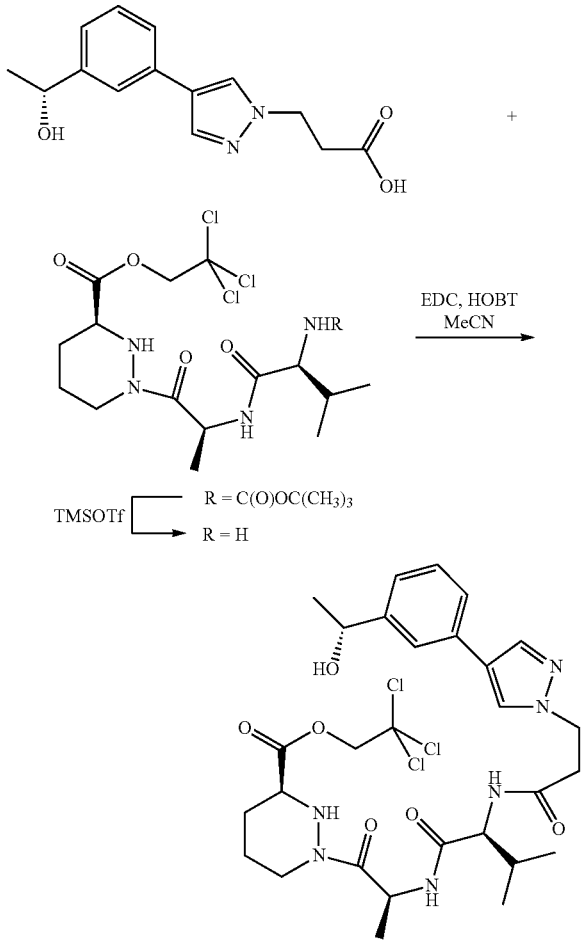

42c was prepared in the same manner as compound (S)-1-[(S)-2-((S)-2-{(S)-2-[3'-((R)-1-hydroxy-ethyl)-biphenyl-4-yloxy]-propionylamino}-3-methyl-butyrylamino)-propionyl]-hexahydro-pyridazine-3-carboxylic acid 2,2,2-trichloro-ethyl ester using 42b instead of (S)-2-[3'-((R)-1-hydroxy-ethyl)-biphenyl-4-yloxy]-propionic acid in 49% yield.

Compound 42

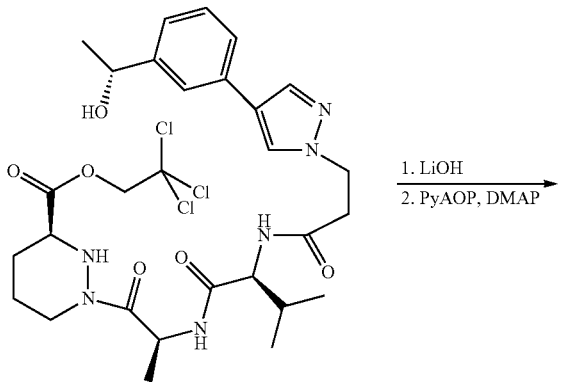

-continued

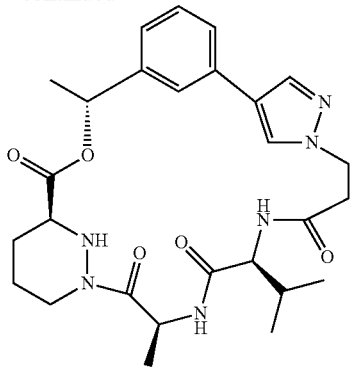

Compound 42 was prepared in the same manner as Compound 41 using 42c instead of (S)-1-{(S)-2-[(S)-2-(2-{4-[6-((R)-1-hydroxy-ethyl)-pyridin-2-yl]-phenoxy}-acetylamino)-3-methyl-butyrylamino]-propionyl}-hexahydro-pyridazine-3-carboxylic acid 2,2,2-trichloro-ethyl ester in 8% yield. $^1$H NMR (300 MHz, $CD_3OD$) 0.94 (d, J=6.7 Hz, 3H), 0.95 (d, J=6.5 Hz, 3H), 1.37 (d, J=7.1 Hz, 3H), 1.62 (d, J=6.5 Hz, 3H), 1.65-2.05 (m, 5H), 2.61-2.69 (m, 1H), 2.88-3.10 (m, 2H), 3.58-3.63 (m, 1H), 3.90-4.00 (m, 1H), 4.01 (d, J=8.5 Hz, 1H), 4.38-4.44 (m, 1H), 4.58-4.67 (m, 1H), 5.31 (q, J=7.1 Hz, 1H), 5.91 (q, J=6.5 Hz, 1H), 7.18 (d, J=7.6 Hz, 1H), 7.31 (app t, J=7.6 Hz, 1H), 7.47 (d, J=7.6 Hz, 1H), 7.58 (s, 1H), 7.77 (s, 1H), 7.95 (s, 1H). LCMS (m/z) 525.2 [M+H], Tr=4.51 min.

Example 43

Compound 43

Compound 43a

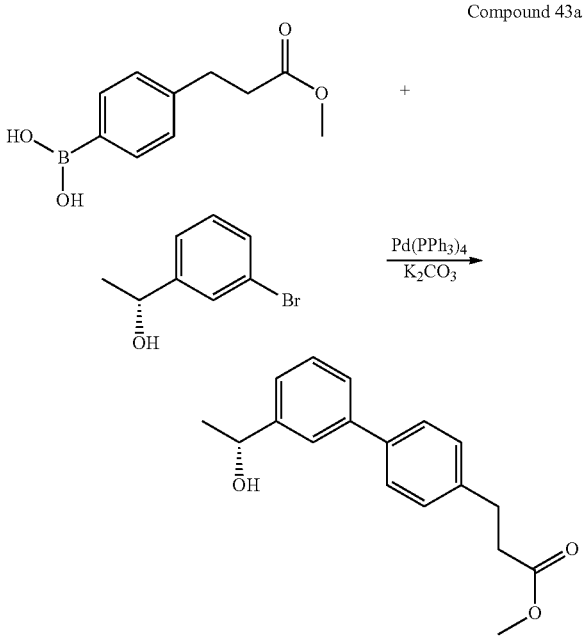

Potassium carbonate (663 mg, 4.80 mmol) and tetrakis (triphenylphosphine)palladium (0) (139 mg, 0.12 mmol) were added to a solution of (R)-1-(3-bromophenyl)-ethanol (483 mg, 2.40 mmol) and 4-(2-methoxy carbonylethyl) benzeneboronic acid (500 mg, 2.40 mmol) in 1,2-dimethoxyethane (5 mL) in a 5 mL microwave vessel. The vessel was sealed before being heated in the microwave for 20 min, using fixed hold time, on high absorption at 100° C. The reaction mixture was filtered through a pad of Hyflo and the pad was washed with ethyl acetate. The combined organics were then concentrated and the resultant brown oil was purified by silica gel chromatography using a stepwise gradient of iso-hexanes/ethyl acetate 1:0 to 3:2 to afford the title compound (416 mg, 61%) as a yellow oil.

Compound 43b

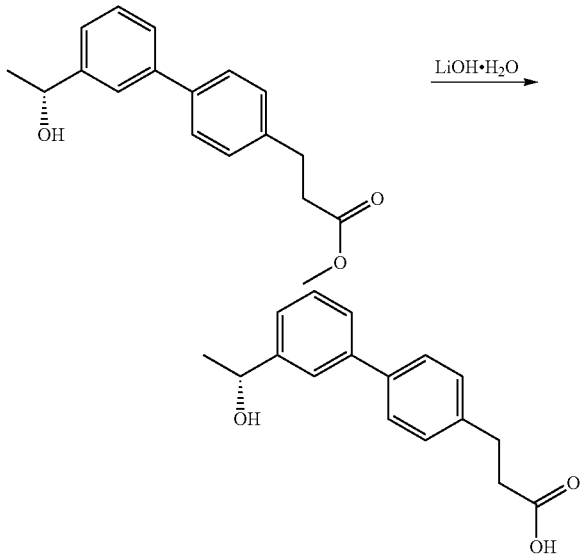

43a (416 mg, 1.46 mmol) was dissolved in a mixture of tetrahydrofuran (8 mL) and water (2 mL) and the solution was cooled using an ice bath. Lithium hydroxide monohydrate (175 mg, 2.92 mmol) was added and the solution was allowed to slowly warm to RT overnight. The solution was acidified using 2 M hydrochloric acid and then extracted with dichloromethane (2×20 mL). The combined organics were then dried over anhydrous sodium sulfate, filtered and concentrated to afford the title compound (250 mg, 89%) as a white solid.

Compound 43c

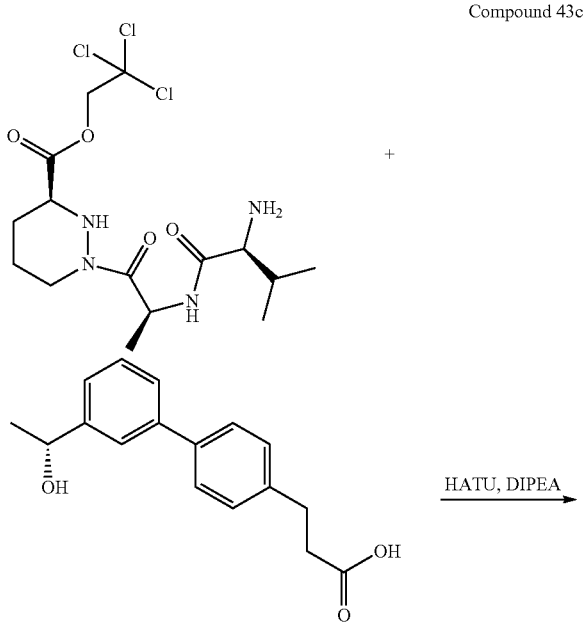

-continued

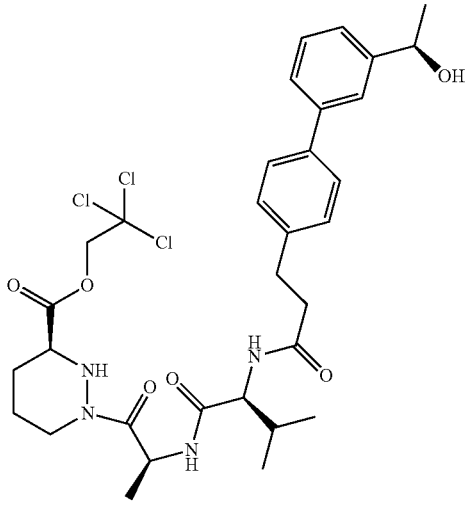

(S)-1-[(S)-2-((S)-2-Amino-3-methyl-butyrylamino)-propionyl]-hexahydro-pyridazine-3-carboxylic acid 2,2,2-trichloro-ethyl ester (669 mg, 1.55 mmol) and 43b (350 mg, 1.29 mmol) were dissolved in anhydrous acetonitrile (10 mL) and cooled using an ice bath. 2-(1H-7-Azabenzotriazol-1-yl)-1,1,3,3-tetramethyl uronium hexafluorophosphate methanaminium (688 mg, 1.81 mmol) and N,N-diisopropylethylamine (899 μL, 5.16 mmol) were then added and the reaction was allowed to slowly warm to RT and left to stir overnight. The solvent was then removed and the residue was dissolved in ethyl acetate. The solution was then washed with water (3×20 mL) and brine (20 mL), dried over anhydrous sodium sulfate, filtered and concentrated and the resultant brown oil was purified by silica gel chromatography using a stepwise gradient of iso-hexanes/ethyl acetate 1:4 to 0:1 to afford the title compound (314 mg, 36%) as a white solid.

Compound 43d

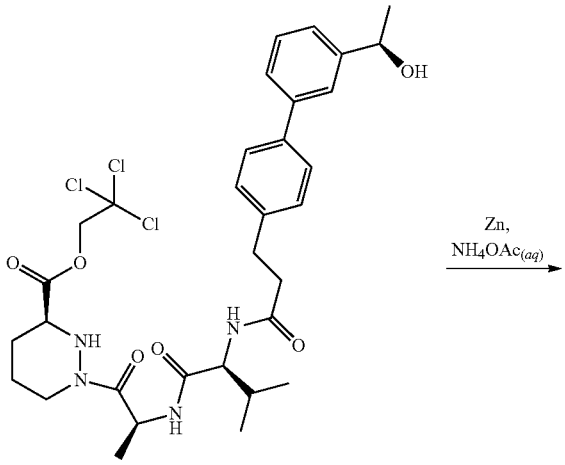

-continued

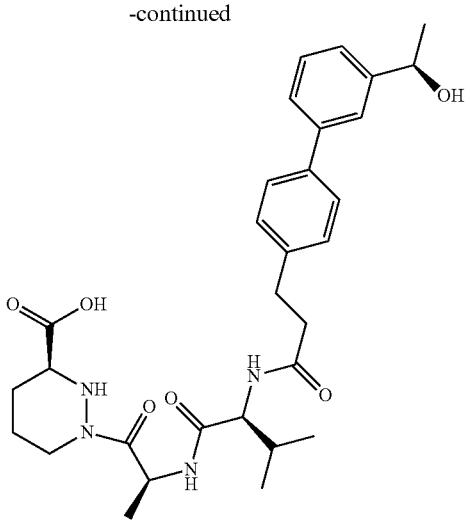

43c (314 mg, 0.459 mmol) was dissolved in tetrahydrofuran (10 mL). Zinc powder (300 mg, 4.59 mmol) was added followed by ammonium acetate (1 M in water, 3.21 mL, 3.21 mmol). The reaction was then left to stir overnight. The reaction mixture was then filtered through a pad of Hyflo. The pad was then washed with potassium hydrogen sulfate solution and ethyl acetate. The biphasic mixture was further acidified using 2 M hydrochloric acid until the solution was approximately pH 1. The phases were separated and the aqueous phase was extracted with ethyl acetate. The combined organic phases were dried over anhydrous sodium sulfate, filtered and concentrated to afford the title compound (212 mg, 84%) as a yellow solid.

Compound 43

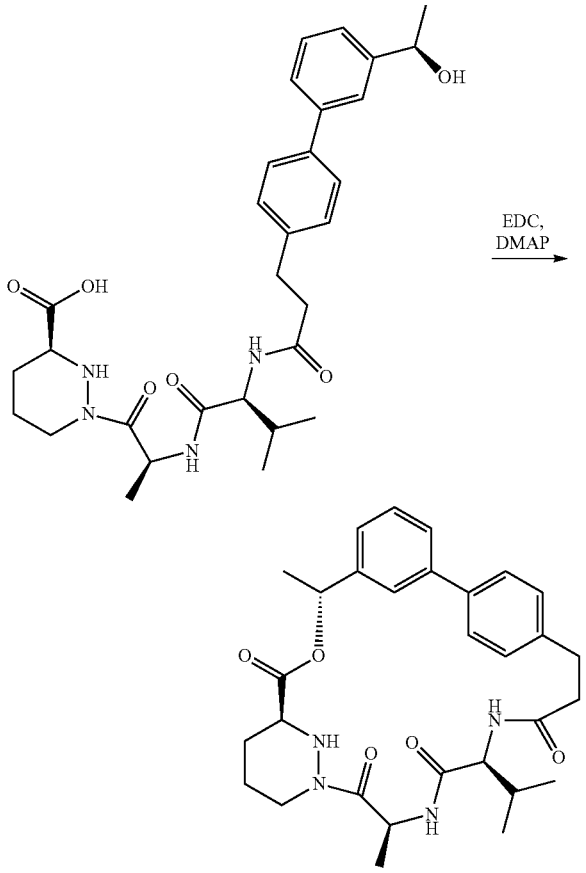

43d (100 mg, 0.181 mmol) was dissolved in dichloromethane (181 mL), under an atmosphere of nitrogen. N-(3-Dimethylaminopropyl)-N'-ethylcarbodiimide hydrochloride (142 mg, 0.724 mmol) and 4-dimethylaminopyridine (44 mg, 0.362 mmol) were added and the reaction was left to stir overnight. The solvent was removed and the residue was purified by silica gel chromatography using 100% ethyl acetate to afford the title compound (52 mg, 54%) as a white solid. $^1$H NMR (300 MHz, $CDCl_3$) δ 0.92 (d, J=6.7 Hz, 6H), 1.24-1.29 (m, 3H), 1.60-1.68 (m, 5H), 1.85-1.98 (m, 2H), 2.37-2.49 (m, 1H), 2.58-2.78 (m, 1H), 2.83-2.93 (m, 1H), 3.16-3.28 (m, 1H), 3.45 (m, 3H), 4.03-4.11 (m, 1H), 4.45-4.54 (m, 1H), 5.06-5.16 (m, 1H), 5.92-6.00 (m, 1H), 6.25 (d, J=8.5 Hz, 1H), 7.19 (s, 1H), 7.22 (s, 2H), 7.39 (app t, J=7.6 Hz, 1H), 7.48-7.56 (m, 3H), 7.62 (br s, 1H). LCMS (m/z) 535.3 [M+H], Tr=2.43 min.

Example 44

Compound 44

Compound 44a

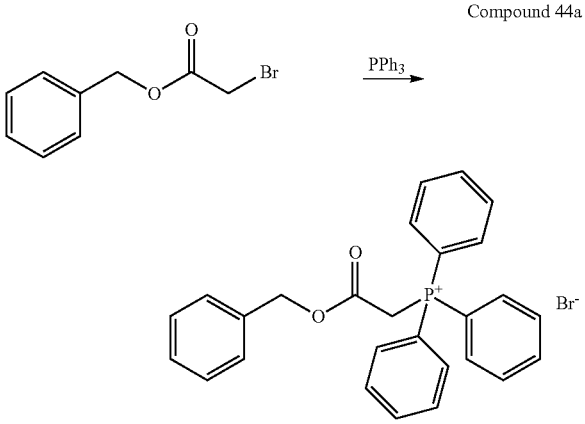

Benzyl bromoacetate (2.07 mL, 13.1 mmol) and triphenylphosphine (3.63 g, 13.8 mmol) were dissolved in toluene (60 mL) and left to stir over 3 days. A white solid was collected by filtration and washed with diethyl ether. This afforded the title compound (5.86 g, 93%) as a white solid.

Compound 44b

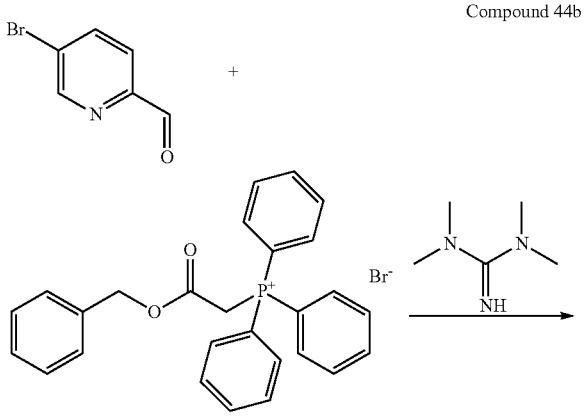

-continued

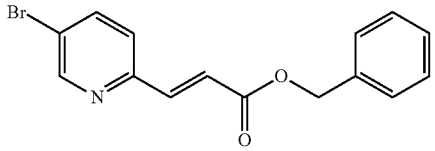

5-bromo-2-pyridine carboxaldehyde (125 mg, 0.666 mmol) and 44a (655 mg, 1.33 mmol) were dissolved in dichloromethane (5 mL). 1,1,3,3-Tetramethylguanidine (251 μL, 2 mmol) was then added and the reaction was left to stir for 3.5 h. The reaction was quenched with saturated ammonium chloride solution and the phases were separated. The organic phase was then washed with brine, dried over anhydrous sodium sulfate, filtered and concentrated. The residue was then purified by silica gel chromatography using a stepwise gradient of iso-hexanes/ethyl acetate 1:0 to 4:1 to afford the title compound (186 mg, 88%) as a yellow solid.

Compound 44c

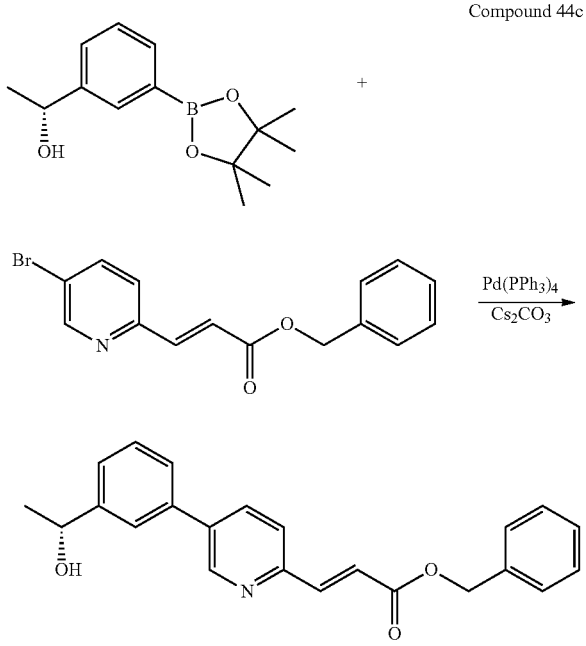

44b (186 mg, 0.585 mmol), (R)-1-[3-(4,4,5,5-tetramethyl-[1,3,2]dioxaborolan-2-yl)-phenyl]-ethanol (145 mg, 0.585 mmol), cesium carbonate (476 mg, 1.46 mmol) and tetrakis (triphenylphosphine) palladium (0) (66 mg, 0.0585 mmol) were placed in a microwave vessel. 1,2-Dimethoxyethane (2 mL) and water (0.5 mL) were added and the vessel was sealed. The reaction was heated in the microwave for 30 min, using fixed hold time, on high absorption at 150° C. The reaction mixture was poured onto water and the resultant mixture was extracted with ethyl acetate. The organics were then dried over anhydrous sodium sulfate, filtered and concentrated. The residue was then purified by silica gel chromatography using a stepwise gradient of iso-hexanes/ethyl acetate 1:0 to 1:1 to afford the title compound (150 mg, 77%) as an orange gum.

Compound 44d

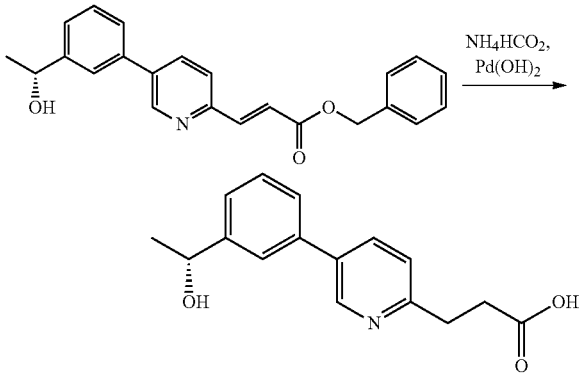

44c (150 mg, 0.417 mmol) was dissolved in ethanol (5 mL). Palladium(II) hydroxide (20% on carbon, wet, 40 mg) was then added followed by ammonium formate (132 mg, 2.09 mmol). The reaction was heated to reflux and left to stir for 30 min. The reaction was allowed to cool to RT and was then filtered through a pad of Hyflo. The pad was washed with ethanol and the combined organics were concentrated to leave the title compound (105 mg, 93%) as an orange gum.

Compound 44e

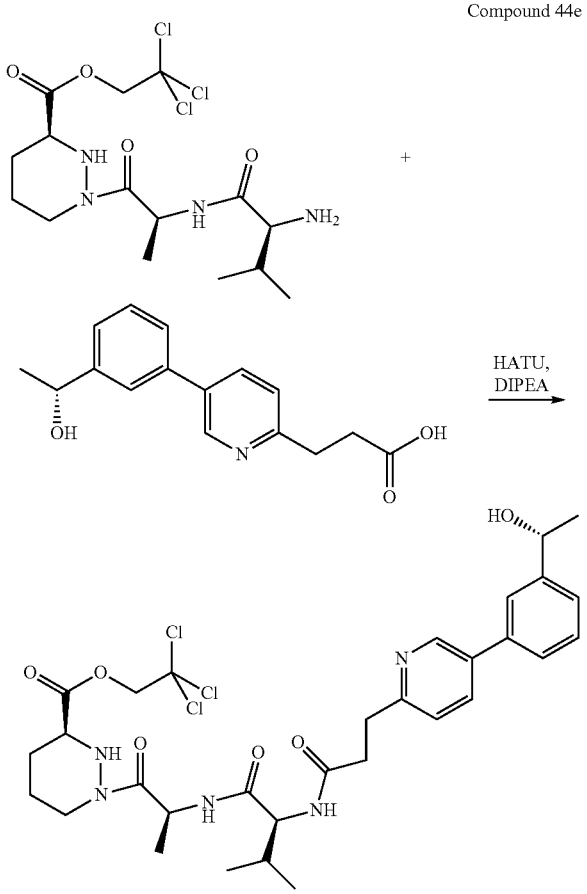

44d (105 mg, 0.387 mmol) and (S)-1-[(S)-2-((S)-2-amino-3-methyl-butyrylamino)-propionyl]-hexahydro-pyridazine-3-carboxylic acid 2,2,2-trichloro-ethyl ester (200 mg, 0.464 mmol) were dissolved in acetonitrile (5 mL) and cooled using an ice bath. 2-(1H-7-Azabenzotriazol-1-yl)-1,1,3,3-tetramethyl uronium hexafluorophosphate methanaminium (206 mg, 0.542 mmol) and N,N-diisopropylethylamine (270 μL, 1.55 mmol) were then added and the reaction was allowed to slowly warm to RT and left to stir overnight. The solvent was then removed and the residue was dissolved in ethyl acetate. The solution was then washed with water (3×20 mL) and brine (20 mL), dried over anhydrous magnesium sulfate, filtered and concentrated and the residue was purified by silica gel chromatography using a stepwise gradient of iso-hexanes/ethyl acetate/acetone 3:1:0 to 0:7:3 to afford a brown solid (110 mg). This was further purified by silica gel chromatography using a stepwise gradient of ethyl acetate/acetone 1:0 to 4:1 to afford the title compound (100 mg, 38%) as a yellow solid.

Compound 44f

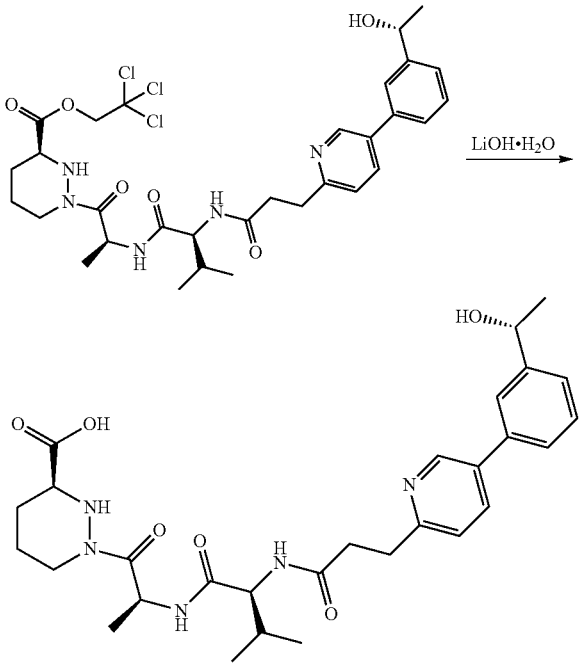

44e (100 mg, 0.146 mmol) was dissolved in a mixture of tetrahydrofuran (3 mL) and water (1 mL) and cooled using an ice bath. Lithium hydroxide monohydrate (6 mg, 0.153 mmol) was added and the reaction was stirred for 30 min. The solution was acidified to pH 1 using 2 M hydrochloric acid and evaporated to dryness. The residue was then purified by C18 chromatography using a stepwise gradient of acetonitrile/water 0:1 to 1:4 to afford the title compound (25 mg, 31%) as a white solid.

Compound 44

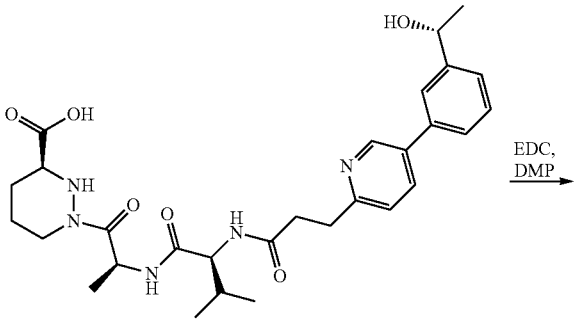

-continued

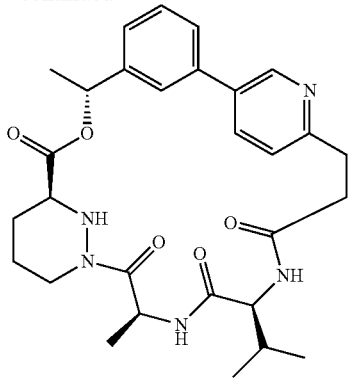

44f (25 mg, 0.045 mmol) was dissolved in dichloromethane (45 mL). N-(3-dimethylaminopropyl)-N'-ethylcarbodiimide hydrochloride (35 mg, 0.148 mmol) and 4-dimethylaminopyridine (11 mg, 0.009 mmol) were added and the reaction was left to stir for 4 h. The solvent was removed and the residue was purified by silica gel chromatography using a stepwise gradient of ethyl acetate/acetone 1:0 to 3:2 to leave a white solid (6 mg). This was then eluted through a reverse phase HPLC system fitted with a Phenomenex Gemini 10μ 110 A, 250×21.2 mm column using an isocratic 2:3 acetonitrile/water flow at 20 mL/min to afford the title compound (1.3 mg, 7%) as a white solid. $^1$H NMR (300 MHz, $CDCl_3$) δ 0.84-1.00 (m, 7H), 1.10 (d, J=6.9 Hz, 3H), 1.62-1.72 (m, 4H), 1.86-2.08 (m, 3H), 2.54-2.71 (m, 2H), 2.90-3.14 (m, 2H), 3.28-3.54 (m, 3H), 3.98 (app t, J=9.2 Hz, 1H), 4.43-4.52 (m, 1H), 5.07 (app t, J=8.0 Hz, 1H), 5.92-6.00 (m, 1H), 6.10 (d, J=8.0 Hz, 1H), 6.37 (d, J=9.1 Hz, 1H), 7.20 (d, J=8.0 Hz, 1H), 7.26-7.31 (m, 1H), 7.41-7.59 (m, 3H), 7.75 (dd, J=8.0, 2.2 Hz, 1H), 8.78 (d, J=2.4 Hz, 1H). LCMS (m/z) 536.0 [M+H], Tr=1.47 min.

Example 45

Compound 45

Compound 45a

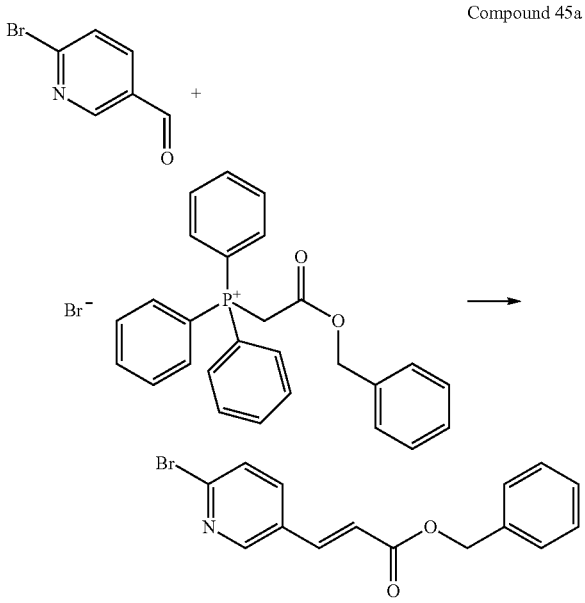

6-Bromo-3-pyridinecarboxaldehyde (500 mg, 2.69 mmol) and benzyloxycarbonylmethyl-triphenyl-phosphonium bromide (2.64 g, 5.38 mmol) were dissolved in dichloromethane (15 mL). 1,1,3,3-Tetramethylguanidine (1.01 mL, 8.03 mmol) was then added and the reaction was left to stir for 3.5 h. The reaction was quenched with saturated ammonium chloride solution and the phases were separated. The organic phase was then washed with brine, dried over anhydrous sodium sulfate, filtered and concentrated. The residue was then purified by silica gel chromatography using a stepwise gradient of iso-hexanes/ethyl acetate 1:0 to 4:1 to afford the title compound (492 mg, 57%) as a white solid.

Compound 45b

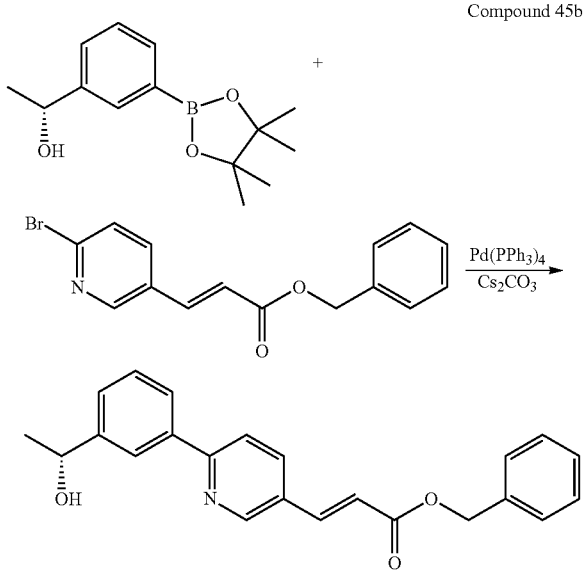

45a (382 mg, 1.54 mmol), (R)-1-[3-(4,4,5,5-tetramethyl-[1,3,2]dioxaborolan-2-yl)-phenyl]-ethanol (490 mg, 1.54 mmol), cesium carbonate (1.06 g, 3.85 mmol) and tetrakis (triphenylphosphine) palladium(0) (178 mg, 0.154 mmol) were placed in a microwave vessel. 1,2-Dimethoxyethane (4 mL) and water (1 mL) were added and the vessel was sealed. The reaction was heated in the microwave for 50 min, using fixed hold time, on high absorption at 150° C. The reaction mixture was poured onto water and the resultant mixture was extracted with ethyl acetate. The organics were then dried over anhydrous sodium sulfate, filtered and concentrated. The residue was then purified by silica gel chromatography using a stepwise gradient of iso-hexanes/ethyl acetate 1:0 to 1:1 to afford impure product. This was subjected to a second round of purification using the same conditions to afford the title compound (195 mg, 35%) as a yellow solid.

Compound 45c

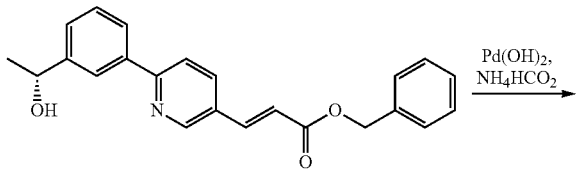

-continued

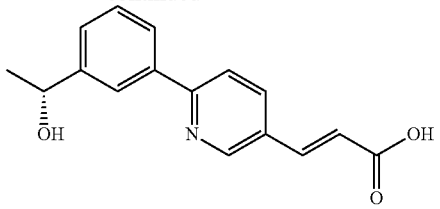

45b (195 mg, 0.543 mmol) was dissolved in ethanol (5 mL). Palladium(II) hydroxide (20% on carbon, wet, 40 mg) was then added followed by ammonium formate (172 mg, 2.72 mmol). The reaction was heated to reflux and left to stir for 30 min. The reaction was allowed to cool to RT and was then filtered through a pad of Hyflo. The pad was washed with ethanol and the combined organics were concentrated to leave the title compound (150 mg, 100%) as a pale yellow solid.

Compound 45d

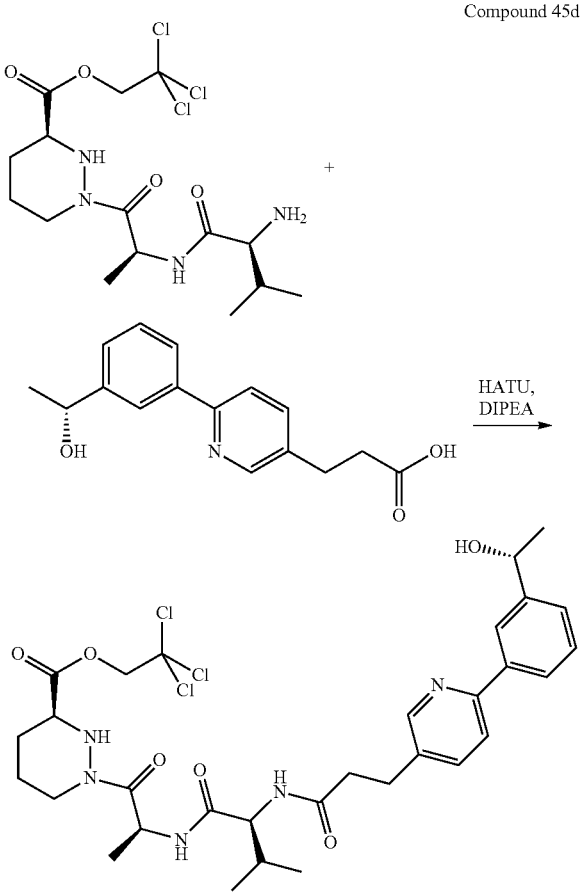

45c (150 mg, 0.553 mmol) and (S)-1-[(S)-2-((S)-2-amino-3-methyl-butyrylamino)-propionyl]-hexahydro-pyridazine-3-carboxylic acid 2,2,2-trichloro-ethyl ester (287 mg, 0.664 mmol) were dissolved in acetonitrile (5 mL) and cooled using an ice bath. 2-(1H-7-Azabenzotriazol-1-yl)-1,1,3,3-tetramethyl uronium hexafluorophosphate methanaminium (294 mg, 0.774 mmol) and N,N-diisopropylethylamine (385 μL, 2.21 mmol) were then added and the reaction was allowed to slowly warm to RT and left to stir overnight. Ethyl acetate was then poured into the reaction mixture. The resultant solution was then washed with water (3×20 mL) and brine (20 mL), dried over anhydrous sodium sulfate, filtered and concentrated and the residue was purified by silica gel chromatography using a stepwise gradient of iso-hexanes/ethyl acetate/acetone 3:1:0 to 0:7:3 to afford a solid (334 mg). This was further purified by silica gel chromatography using a stepwise gradient of ethyl acetate/acetone 1:0 to 4:1 to afford the title compound (167 mg, 44%) as a solid.

Compound 45e

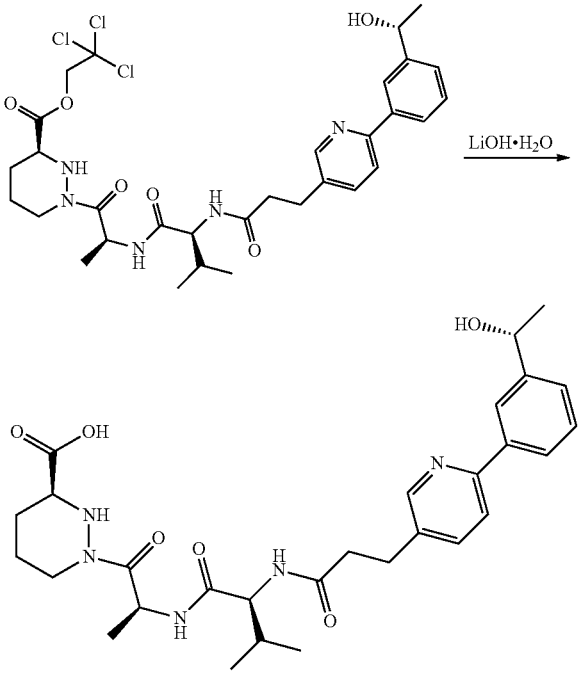

45d (160 mg, 0.234 mmol) was dissolved in a mixture of tetrahydrofuran (4 mL) and water (1 mL) and cooled using an ice bath. Lithium hydroxide monohydrate (6 mg, 0.153 mmol) was added and the reaction was stirred for 30 min. The solution was neutralised using 2 M hydrochloric acid and evaporated to dryness. The residue was then purified by C18 chromatography using a stepwise gradient of acetonitrile/water 0:1 to 1:4 to afford the title compound (21 mg, 16%) as a white solid.

Compound 45

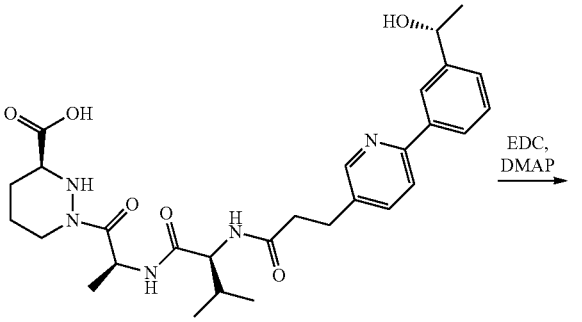

-continued

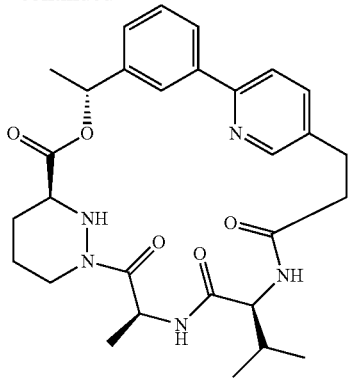

-continued

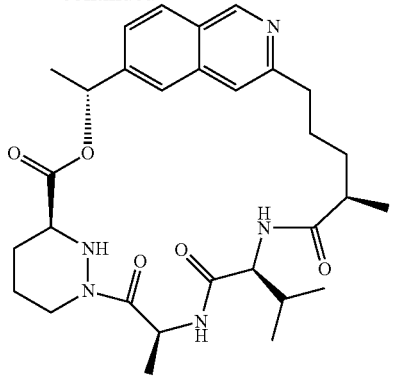

45e (21 mg, 0.0379 mmol) was dissolved in dichloromethane (38 mL). N-(3-dimethylaminopropyl)-N'-ethylcarbodiimide hydrochloride (29 mg, 0.152 mmol) and 4-dimethylaminopyridine (9 mg, 0.0758 mmol) were added and the reaction was left to stir for 4 h. The solvent was removed and the residue was purified by silica gel chromatography using 100% ethyl acetate. The resultant material was then eluted through a reverse phase HPLC system fitted with a Phenomenex Gemini 10μ 110 A, 250×21.2 mm column using an isocratic 3:7 acetonitrile/water flow at 20 mL/min to afford the title compound (1 mg, 5%). $^1$H NMR (300 MHz, $CDCl_3$) δ 0.91 (d, J=6.5 Hz, 6H), 1.48 (d, J=7.1 Hz, 3H), 1.63-1.72 (m, 7H), 1.81-1.93 (m, 2H), 2.00-2.10 (m, 1H), 2.25-2.38 (m, 1H), 2.54-2.67 (m, 1H), 3.15-3.28 (m, 1H), 3.39-3.59 (m, 2H), 4.03 (app t, J=9.6 Hz, 1H), 4.43-4.54 (m, 1H), 5.04-5.16 (m, 1H), 5.80 (d, J=9.8 Hz, 1H), 5.94 (q, J=6.7 Hz, 1H), 7.22-7.27 (m, 1H), 7.43 (app t, J=7.8 Hz, 1H), 7.55-7.57 (m, 1H), 7.69 (d, J=8.0 Hz, 1H), 7.92 (d, J=8.3 Hz, 1H), 8.19 (br s, 1H), 8.48 (d, J=2.2 Hz, 1H). LCMS (m/z) 536.2 [M+H], Tr=1.61 min.

Example 46

Compound 46

To Compound 21 (25 mg, 0.05 mmol) in ethyl acetate (5 mL) at RT was added 10% palladium on carbon (20 mg). The system was purged with hydrogen and stirred for 2 h. The reaction was filtered through Celite and concentrated in vacuo. The residue was purified by preparative TLC using ethyl acetate/acetone 5/1 to give the title compound (2.2 mg, 9%) as a white solid. $^1$H NMR (300 MHz, $CDCl_3$) 0.96 (d, J=6.7 Hz, 3H), 0.98 (d, J=6.7 Hz, 3H), 1.24 J=7.1 Hz, 3H), 1.52 (d, J=6.9 Hz, 3H), 1.67 (d, J=6.7 Hz, 3H), 1.55-2.14 (m, 10H), 2.53-2.80 (m, 2H), 2.92-3.01 (m, 2H), 3.45-3.67 (m, 1H), 4.14-4.23 (m, 1H), 4.49-4.60 (m, 1H), 5.39-5.51 (m, 1H), 5.96 (d, J=9.4 Hz, 1H), 6.06 (q, J=6.7 Hz, 1H), 6.43 (d, J=8.5 Hz, 1H), 7.39 (dd, J=8.5, 1.1 Hz, 1H), 7.56 (s, 1H), 7.75 (s, 1H), 7.93 (d, J=8.5 Hz, 1H), 9.16 (s, 1H). LCMS (m/z)=552.3 [M+H], Tr=1.25 min.

Example 47

Compound 47

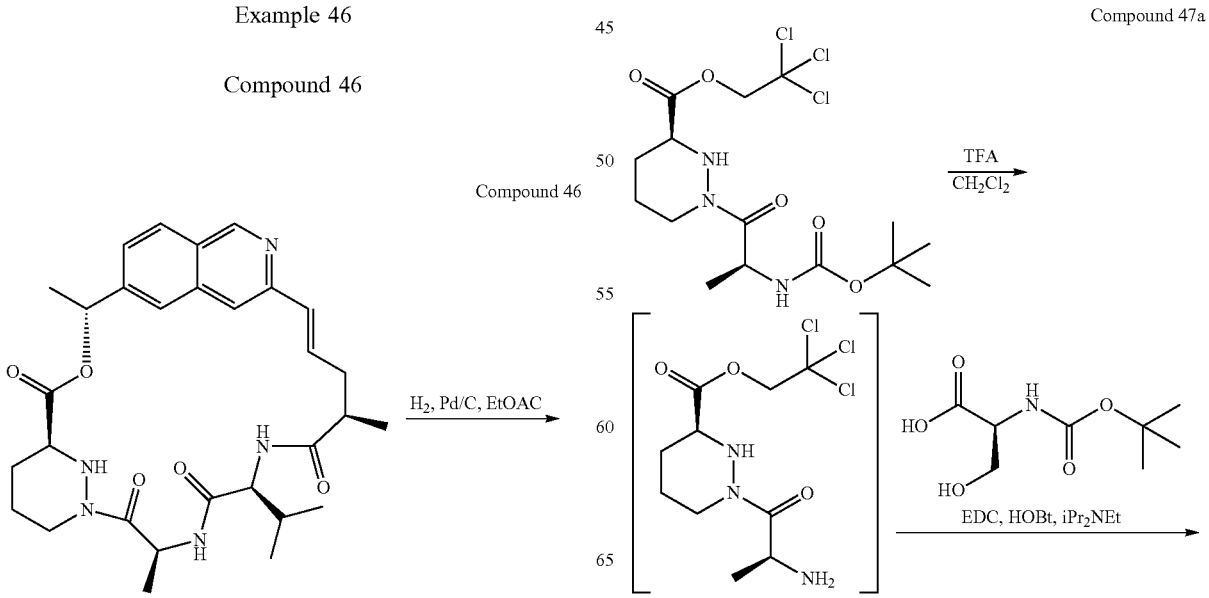

-continued

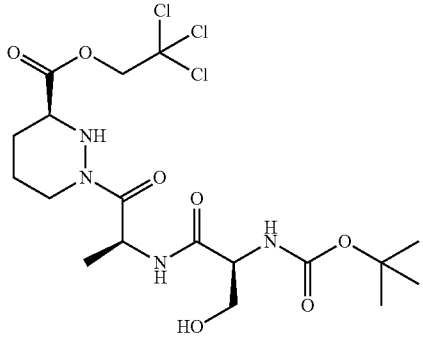

To a solution of (S)-1-((S)-2-tert-butoxycarbonylamino-propionyl)-hexahydro-pyridazine-3-carboxylic acid 2,2,2-trichloro-ethyl ester (320 mg, 0.74 mmol) in dichloromethane (8 mL) was added trifluoroacetic acid (2 mL). The reaction was stirred at RT for 105 min and was then concentrated in vacuo. The resulting crude product was dissolved in ethyl acetate (75 mL) and was washed with saturated aqueous sodium bicarbonate. The aqueous phase was extracted with ethyl acetate (2×40 mL), and the organics were dried over anhydrous sodium sulfate, filtered, and concentrated to a crude residue that was used without further purification. The residue from the previous step, 1-hydroxybenzotriazole (152 mg, 1.12 mmol) and (S)-2-tert-butoxycarbonylamino-3-hydroxy-propionic acid (154 mg, 0.75 mmol) were dissolved in dichloromethane (6 mL). N,N-Diisopropylethylamine (190 mg, 1.5 mmol) was added, and the resulting solution was cooled in an ice water bath. N-(3-Dimethylaminopropyl)-N'-ethylcarbodiimide (149 mg, 0.96 mmol) was added dropwise over 15 s. The reaction was stirred for 18 h, allowing the ice bath to slowly expire. The reaction mixture was then diluted with ethyl acetate (50 mL) and was washed with saturated aqueous sodium bicarbonate and brine. The organic phase was dried over anhydrous sodium sulfate, filtered, and concentrated to afford a crude residue that was purified by silica gel chromatography (75 to 100% ethyl acetate in iso-hexanes) to afford the title product (211 mg, 55%) as an oil.

Compound 47b

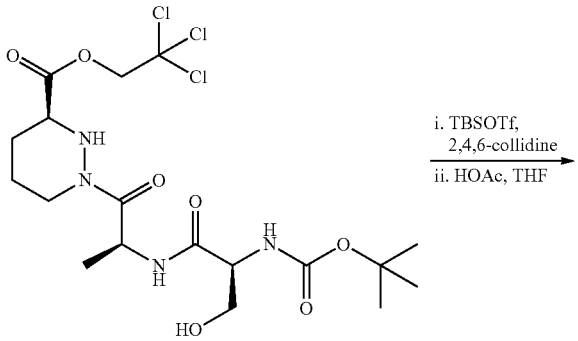

-continued

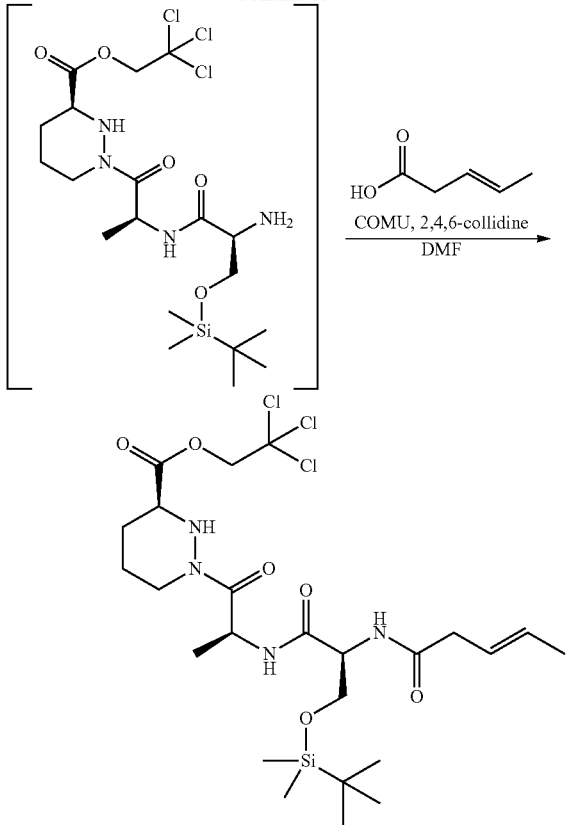

To a solution of 47a (64 mg, 0.12 mmol) in dichloromethane (1 mL) was added 2,4,6-collidine (98 mg, 1.28 mmol). tert-Butyldimethylsilyl trifluoromethanesulfonate (98 mg, 0.37 mmol) was added dropwise over 20 sec. The reaction mixture was stirred for 15 h and was quenched with saturated aqueous sodium bicarbonate (1 mL). The mixture was further diluted with ethyl acetate, water, and 0.1 N aqueous hydrochloric acid to afford an acidic aqueous layer. The phases were separated, and the organics were dried over sodium sulfate, filtered, and concentrated in vacuo to afford a crude residue that was used without further purification. The crude product was dissolved in tetrahydrofuran (3 mL). Acetic acid (115 mg, 1.9 mmol) was added in one portion and the resulting solution was stirred for 3.25 h. The reaction was then diluted with ethyl acetate (25 mL) and washed with saturated aqueous sodium bicarbonate (25 mL). The phases were separated, and the aqueous phase was extracted with ethyl acetate (25 mL). The combined organic phases were washed with brine (25 mL) and dried over anhydrous sodium sulfate. The mixture was filtered, and the filtrate was concentrated in vacuo to afford crude amine which was used without further purification. The crude amine was dissolved in N,N-dimethylformamide (1.5 mL). 2,4,6-Collidine (31 mg, 0.26 mmol) and trans-3-pentenoic acid (15.3 mg, 0.152 mmol) were added, and the resulting solution was cooled in an ice water bath. (1-Cyano-2-ethoxy-2-oxoethylidenaminooxy)dimethylamino-morpholino-carbenium hexafluorophosphate (72.4 mg, 0.169 mmol) was added in one portion, and the reaction was stirred for 30 min. The reaction was then removed from the cold bath and warmed to ambient temperature. After 15 h, the reaction was diluted with ethyl acetate (35 mL), saturated aqueous sodium bicarbonate (20 mL), and brine (5 mL). The phases were separated, and the organic layer was washed with 0.1 N aqueous hydrochloric acid (25 mL) and then brine (5 mL). The acidic aqueous layer was extracted with ethyl acetate (25 mL), and the combined organic phases were then dried over anhydrous sodium sulfate, filtered, and concentrated. The resulting crude residue was purified by silica gel chromatography (50 to 80% ethyl acetate in iso-hexanes) to afford the title compound (46.9 mg, 62% over 3 steps) as a white foam.

Compound 47c

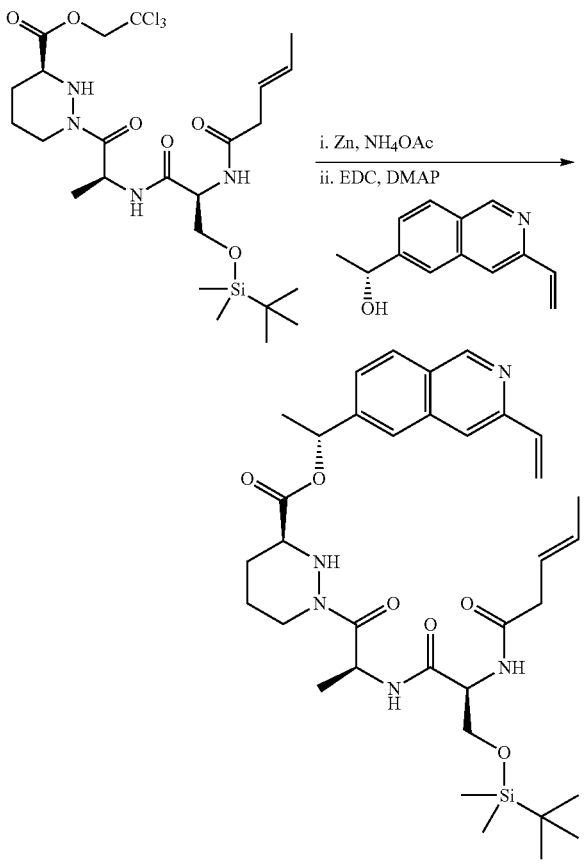

To a solution of 47b (46.9 mg, 0.0761 mmol) in tetrahydrofuran (1.5 mL) was added water (0.30 mL), ammonium acetate (96 mg, 1.2 mmol), and zinc powder (109 mg, 1.7 mmol). The reaction mixture was stirred vigorously at RT for 17.5 h, at which time the temperature was increased to 35° C. After 25.5 h, additional zinc powder (60 mg, 0.92 mmol) was added and the reaction temperature was increased to 45° C. After 39.5 h, the reaction mixture was filtered through a pad of Celite washing with water and ethyl acetate. The aqueous phase was acidified with 2 M aqueous hydrochloric acid (15 mL), and the phases were separated. The aqueous phase was extracted with ethyl acetate (2×20 mL), and the combined organic phases were dried over sodium sulfate, filtered, and concentrated to afford a white solid (34.9 mg, 95%) that was used without further purification. The crude acid (0.072 mmol) was dissolved with (R)-1-(3-vinyl-isoquinolin-6-yl)-ethanol (17.4 mg, 0.087 mmol) in dichloromethane (1.0 mL). 4-Dimethylaminopyridine (13.3 mg, 0.109 mmol) was added followed by N-(3-dimethylaminopropyl)-N'-ethylcarbodiimide hydrochloride (17 mg, 0.085 mmol). The reaction was stirred for 16.5 h, at which time it was loaded directly onto a silica gel column. Elution with 60 to 100% ethyl acetate in iso-hexanes provided the title compound (20 mg, 43%) as an amorphous residue.

Compound 47d

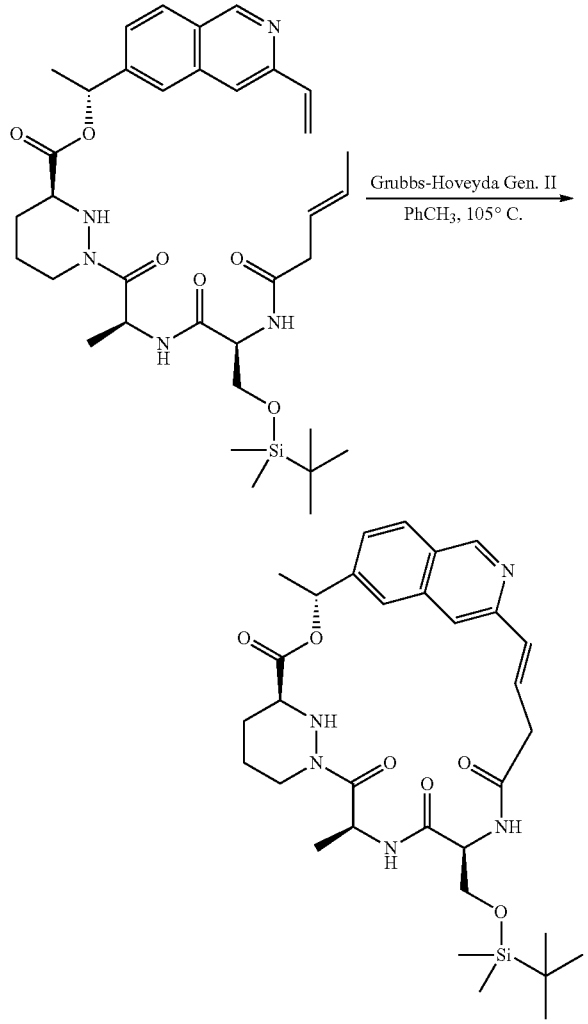

A solution of 47c (19.6 mg, 0.0294 mmol) in toluene (9.4 mL) was sparged with argon for 10 min with stirring. Hoveyda-Grubbs $2^{nd}$ generation-catalyst (2.8 mg, 0.0045 mmol) was then added as a solution in degassed toluene (0.45 mL), and the resulting solution was heated to 105° C. After 25 min, an additional portion of Hoveyda-Grubbs $2^{nd}$ generation catalyst (1.4 mg, 0.0022 mmol) was added. After 10 additional min, the reaction was cooled to ambient temperature and was concentrated in vacuo to ~4.5 mL. The solution was loaded directly onto a silica gel column which was eluted with 80 to 100% ethyl acetate in iso-hexanes to afford the title compound (6.9 mg, 38%) as an amorphous solid.

Compound 47

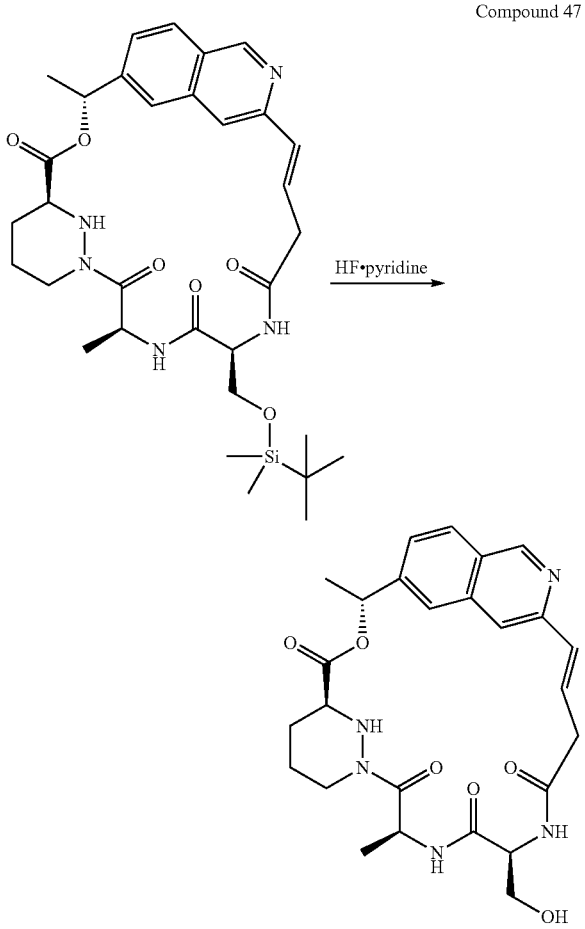

In a polypropylene vial, 47d (4.7 mg, 0.0075 mmol) was dissolved in tetrahydrofuran (0.90 mL) under argon and the resulting solution was cooled in an ice water bath. HF•pyridine (0.10 mL) was added dropwise. After 10 min, the reaction was quenched by addition to a stirred mixture of ethyl acetate (15 mL) and saturated aqueous sodium bicarbonate (15 mL). The phases were separated, and the aqueous phase was extracted with ethyl acetate (3×30 mL). The combined organic phases were dried over sodium sulfate, filtered and concentrated to afford a crude residue. In a polypropylene vial under argon, the aforementioned residue was dissolved in tetrahydrofuran (0.90 mL) and the resulting solution was cooled in an ice water bath. HF•pyridine (0.10 mL) was added dropwise, and the reaction mixture was removed from the cold bath. After 45 min, the reaction was worked up as described above to afford a crude residue. Purification by reverse-phase HPLC (5 to 100% acetonitrile in water, +0.1% trifluoroacetic acid) provided the title compound (1.6 mg, 34%) as an amorphous white solid. $^1$H NMR (400 MHz, $CD_3OD$) 9.54 (s, 1H), 8.38 (d, J=8.7 Hz, 1H), 8.29 (s, 1H), 8.17 (s, 1H), 7.87 (d, J=8.5 Hz, 1H), 6.90-6.75 (m, 2H), 6.18 (q, J=6.9 Hz, 1H), 5.84-5.74 (m, 1H), 4.71-4.64 (m, 1H), 4.50-4.42 (m, 1H), 3.88-3.81 (m, 2H), 3.78 (dd, J=11.3, 6.4 Hz, 1H), 3.52 (dd, J=12.9, 6.2 Hz, 1H), 3.52 (dd, J=12.9, 6.2 Hz, 1H), 2.81-2.70 (m, 1H), 2.11-2.04 (m, 1H), 1.99-1.91 (m, 1H), 1.85-1.69 (m, 2H), 1.73 (d, J=6.7 Hz, 3H), 1.60 (d, J=7.1 Hz, 3H). LCMS (m/z) 510.2 [M+H], Tr=2.19 min.

Example 48

Compound 48

Compound 48a

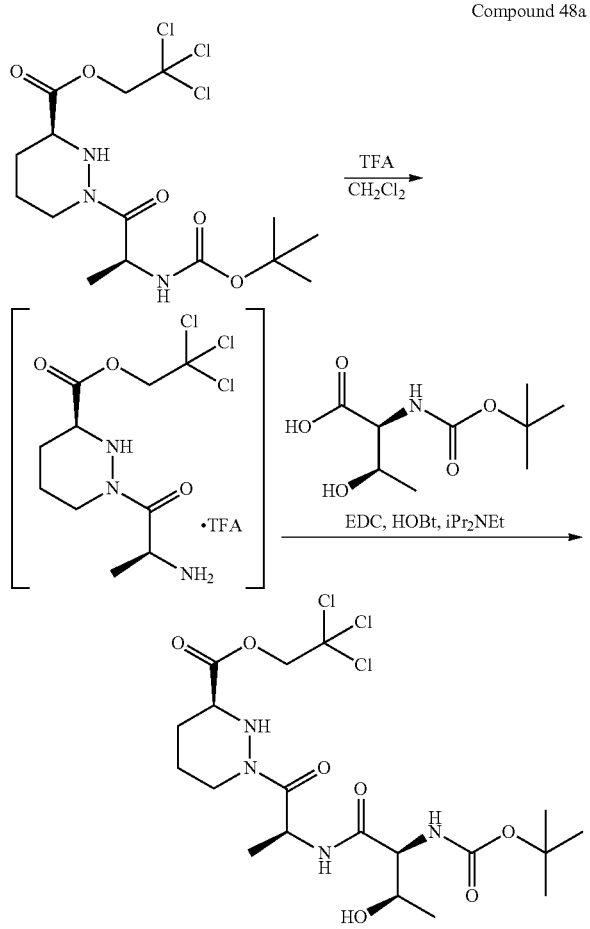

To a solution of (S)-1-((S)-2-tert-butoxycarbonylamino-propionyl)-hexahydro-pyridazine-3-carboxylic acid 2,2,2-trichloro-ethyl ester (320 mg, 0.74 mmol) in dichloromethane (8.8 mL) was added trifluoroacetic acid (2.2 mL). The reaction was stirred at RT for 45 min and was concentrated in vacuo. The resulting crude product was twice dissolved in and concentrated from anhydrous toluene (10 mL). The resulting crude residue was used without further purification. The crude residue (ca. 0.74 mmol), 1-hydroxybenzotriazole (153.8 mg, 1.1 mmol), and (2S,3R)-2-tert-butoxycarbonylamino-3-hydroxy-butyric acid (161.2 mg, 0.735 mmol) were dissolved in dichloromethane (4 mL). N,N-Diisopropylethylamine (192 mg, 1.5 mmol) was added, and the resulting solution was cooled in an ice water bath. N-(3-Dimethylaminopropyl)-N'-ethylcarbodiimide (132 mg, 0.85 mmol) was added dropwise over 15 s. The reaction was removed from the cold bath and was stirred for 21.5 h. The reaction mixture was then diluted with ethyl acetate (50 mL) and washed with half-saturated aqueous sodium bicarbonate (30 mL). The organic phase was washed with brine, dried over anhydrous sodium sulfate, filtered, and concentrated to afford a crude residue that was purified by silica gel chromatography eluting with 65 to 90% ethyl acetate in iso-hexanes. Impure fractions were repurified by silica gel chromatography and collated with the first product to provide the title compound (230 mg, 58%).

Compound 48b

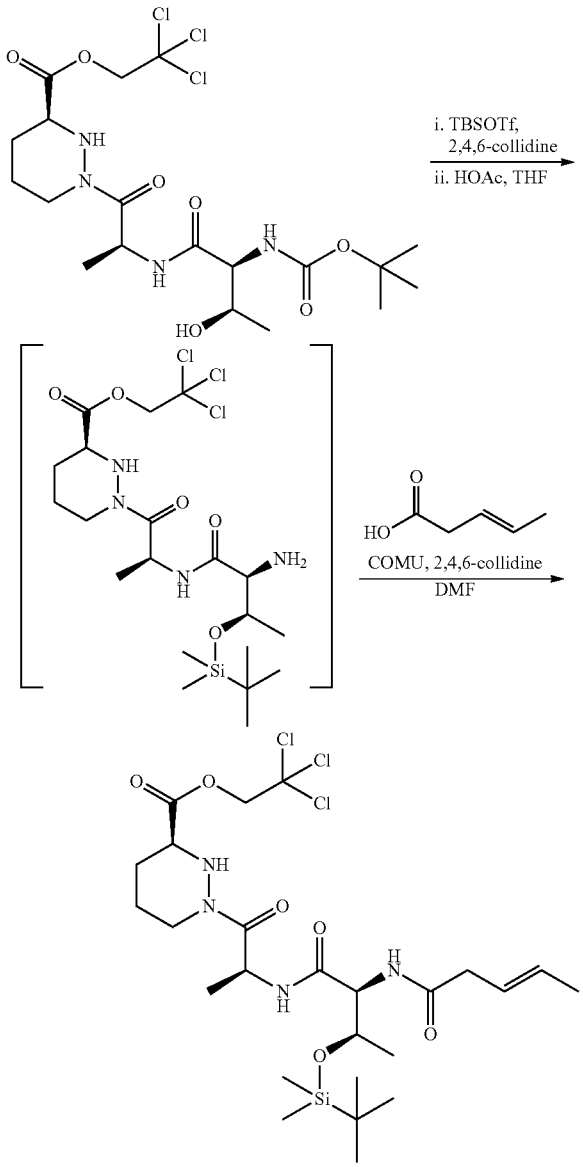

To a solution of 48a (62.3 mg, 0.12 mmol) in dichloromethane (1 mL) was added 2,4,6-collidine (146 mg, 1.21 mmol). tert-Butyldimethylsilyl trifluoromethanesulfonate (94 mg, 0.36 mmol) was added dropwise over 20 s. The reaction mixture was stirred for 15 h and was quenched with saturated aqueous sodium bicarbonate (1 mL). The mixture was further diluted with ethyl acetate (2 mL) and brine (1 mL). The phases were separated, and the aqueous phase was extracted with ethyl acetate (4×1.5 mL). The combined organic phases were dried over sodium sulfate, filtered, and concentrated in vacuo to afford a crude residue that was used without further purification. The crude product was dissolved in tetrahydrofuran (3 mL). Acetic acid (104 mg, 1.6 mmol) was added in one portion and the resulting solution was stirred for 3.5 h. The reaction was then diluted with ethyl acetate (30 mL), saturated aqueous sodium bicarbonate (20 mL) and brine (10 mL). The phases were separated, and the aqueous phase was extracted with ethyl acetate (20 mL). The combined organic phases were dried over anhydrous sodium sulfate. The mixture was filtered, and the filtrate was concentrated in vacuo to afford crude intermediate amine which was used without further purification. The crude amine was dissolved in N,N-dimethylformamide (1.5 mL). 2,4,6-Collidine (28 mg, 0.23 mmol) and trans-3-pentenoic acid (14.3 mg, 0.143 mmol) were added, and the resulting solution was cooled in an ice water bath. (1-Cyano-2-ethoxy-2-oxoethylidenaminooxy)dimethylamino-morpholino-carbenium hexafluorophosphate (69 mg, 0.16 mmol) was added in one portion, and the reaction was stirred for 30 min. The reaction was then removed from the cold bath and warmed to ambient temperature. After 15 h, the reaction was diluted with ethyl acetate (25 mL), 0.1 N aqueous hydrochloric acid (30 mL), and brine (5 mL). The phases were separated, and the acidic aqueous layer was extracted with ethyl acetate (25 mL). The combined organic phases were washed with saturated aqueous sodium bicarbonate (25 mL), with brine (5 mL), dried over anhydrous sodium sulfate, filtered, and concentrated. The resulting crude residue was purified by silica gel chromatography (50 to 75% ethyl acetate in iso-hexanes) to afford the title compound (74 mg, quantitative yield over 3 steps) as a white foam.

Compound 48c

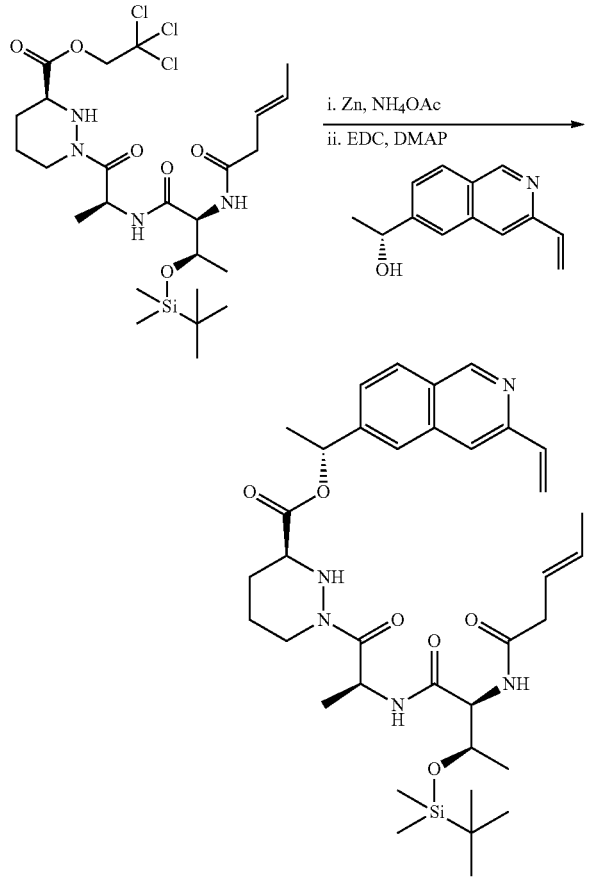

To a solution of 48b (74 mg, 0.117 mmol) in tetrahydrofuran (2.3 mL) was added water (0.47 mL), ammonium acetate (138 mg, 1.8 mmol), and zinc powder (164 mg, 2.5 mmol). The reaction mixture was stirred vigorously at RT for 17.5 h, at which time the temperature was increased to 35° C. After 25.5 h, additional zinc powder (85 mg, 1.3 mmol) was added and the reaction temperature was increased to 45° C. After 39.5 total hours, the reaction mixture was filtered through a pad of Celite, washing with water and ethyl acetate. The aqueous phase was acidified with 2 N aqueous hydrochloric acid (15 mL), and the phases were separated. The aqueous phase was extracted with ethyl acetate (2×20 mL), and the combined organic phases were dried over anhydrous sodium sulfate, filtered, and concentrated to afford an amorphous white solid (50 mg, 86%) that was used without further purification. The crude product (0.10 mmol) was dissolved along with (R)-1-(3-vinyl-isoquinolin-6-yl)-ethanol (23.9 mg, 0.12 mmol) in dichloromethane (1.0 mL). 4-Dimethylaminopyridine (15 mg, 0.12 mmol) was added followed by N-(3-dimethylaminopropyl)-N'-ethylcarbodiimide hydrochloride (17 mg, 0.019 mmol). The reaction was stirred for 16 h, at which time it was loaded directly onto a silica gel column. Elution with 50 to 85, and then to 100% ethyl acetate in iso-hexanes provided the title compound (40 mg, 58%) as a solid.

Compound 48d

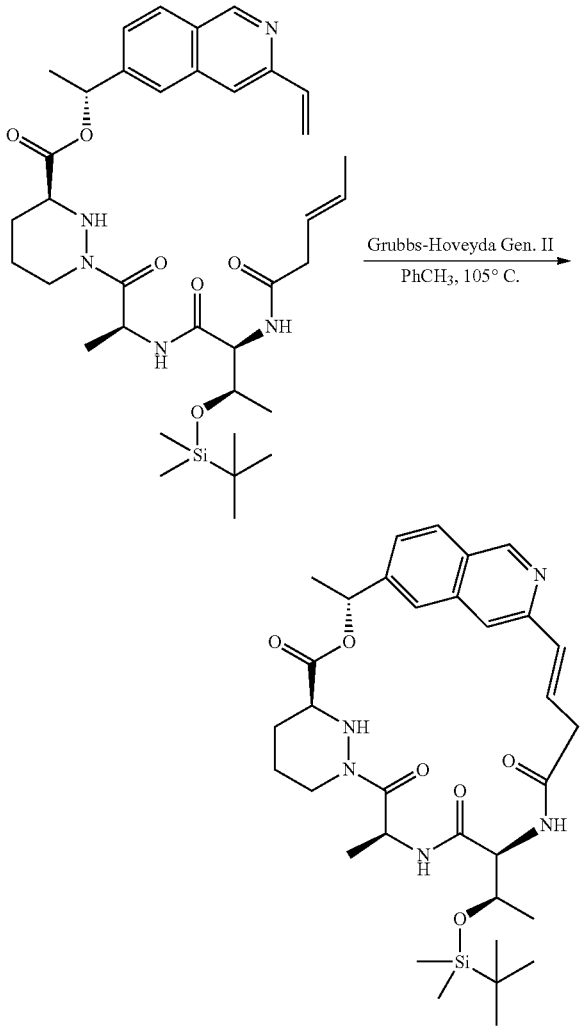

A solution of 48c (26 mg, 0.037 mmol) in toluene (12 mL) was sparged with argon for several min with stirring. Hoveyda-Grubbs 2$^{nd}$ generation catalyst (3.4 mg, 0.0054 mmol) was then added as a solution in degassed toluene (0.40 mL), and the resulting solution was heated to 105° C. After 20 min, an additional portion of Hoveyda-Grubbs 2$^{nd}$ generation catalyst (1.7 mg, 0.0027 mmol) was added as a solution in toluene (0.20 mL). After 40 additional min, the reaction was cooled to RT and was concentrated in vacuo to ~3 mL. The solution was loaded directly onto a silica gel column, which was eluted with 70 to 100% ethyl acetate in iso-hexanes to afford the title compound (10 mg, 42%) as an amorphous solid.

Compound 48

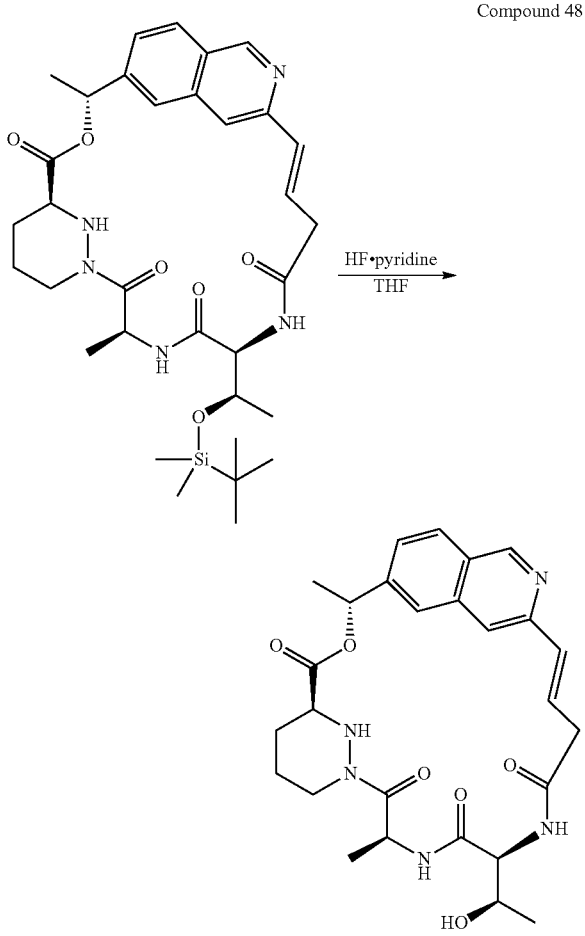

In a polypropylene vial under argon atmosphere, 48d (10 mg, 0.016 mmol) was dissolved in tetrahydrofuran (900 μL). HF•pyridine (~70% as HF, 100 μL) was added dropwise via syringe, and the resulting solution was stirred for 130 min. An additional aliquot of HF•pyridine (100 μL) was then added via syringe, and the resulting solution was stirred for an additional 80 min. The reaction mixture was quenched by its careful addition to a stirred mixture of ethyl acetate (50 mL) and saturated aqueous sodium bicarbonate (50 mL). The phases were separated, and the aqueous phase was extracted with ethyl acetate (2×30 mL). The combined organic phases were dried over anhydrous sodium sulfate, filtered, and concentrated to afford a crude residue that was purified by reverse phase HPLC (C18, 15 to 100% acetonitrile/water, 0.1% trifluoroacetic acid). Impure fractions from this run were re-purified in the same manner to afford the title compound as the trifluoroacetic acid salt (5.0 mg, 49%) as an amorphous white solid following lyophilization. $^{1}$H NMR (400 MHz, $CD_3OD$) δ 9.55 (s, 1H), 8.38 (d, J=8.6 Hz, 1H), 8.22 (s, 1H), 8.15 (s, 1H), 7.87 (dd, J=8.7, 1.4 Hz, 1H), 6.86-6.75 (m, 2H), 6.15 (q, J=6.6 Hz, 1H), 5.80-5.70 (m, 1H), 4.47 (d, J=5.6 Hz, 1H), 4.45 4.38 (m, 1H), 4.09-4.01 (m, 1H), 3.83-3.78 (m, 1H), 3.55 (dd, J=13.5, 5.6 Hz, 1H), 3.11 (dd, J=13.2, 4.7 Hz, 1H), 2.78-2.67 (m, 1H), 2.09-1.99 (m, 1H), 1.96-1.89 (m, 1H), 1.82-1.64 (m, 5H), 1.60-1.54 (m, 3H), 1.25 (d, J=6.3 Hz, 3H). LCMS (m/z) 524.6 [M+H], Tr=2.15 min.

Example 49

Compound 49

Compound 49a

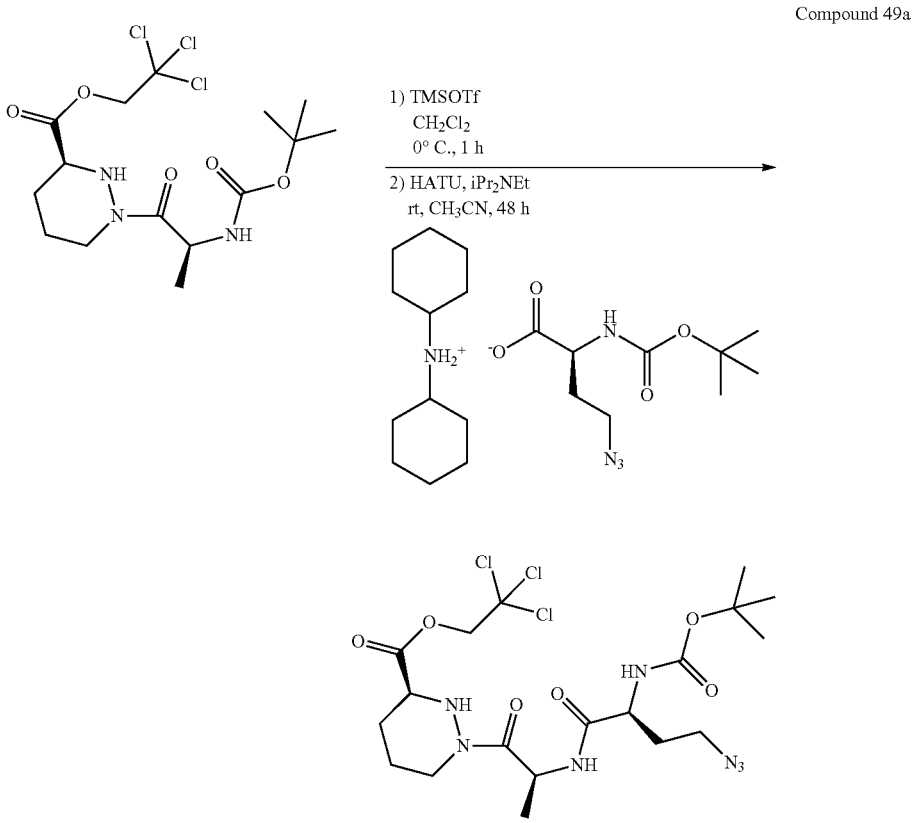

A solution of (S)-1-((S)-2-tert-butoxycarbonylamino-propionyl)-hexahydro-pyridazine-3-carboxylic acid 2,2,2-trichloro-ethyl ester (865 mg, 2 mmol) in dichloromethane (20 mL) was cooled in an ice water bath. Trimethylsilyl trifluoromethanesulfonate (667 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., (S)-4-azido-2-(tert-butoxycarbonylamino)butanoic acid dicyclohexylamine salt (936 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (100 mL) and the solution was washed with 20% water solution of citric acid (2×100 mL), water (100 mL) and brine (100 mL), dried over magnesium sulfate, filtered and evaporated. The residue was purified by silica gel chromatography (gradient from 0-40% ethyl acetate+methanol (4/1) in iso-hexanes) to afford the title compound (783 mg, 70%) as a white solid after evaporation. $R_f$=0.40, iso-hexanes/ethyl acetate/methanol (6/4/1).

Compound 49b

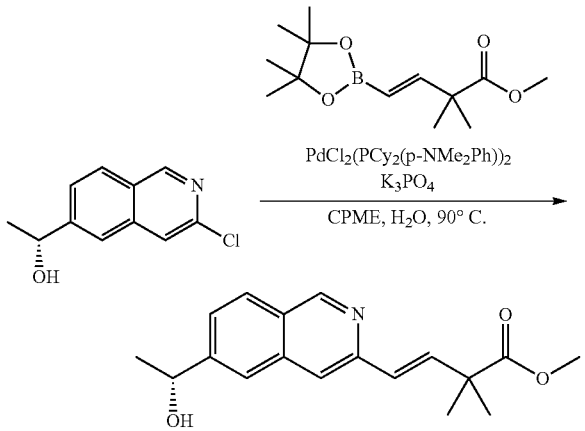

Under argon, (R)-1-(3-chloro-isoquinolin-6-yl)-ethanol (880 mg, 4.23 mmol), (E)-2,2-dimethyl-4-(4,4,5,5-tetramethyl-[1,3,2]dioxaborolan-2-yl)-but-3-enoic acid methyl ester (1.24 g, 4.88 mmol), $PdCl_2(PCy_2(p\text{-}NMe_2Ph))_2$(bis[(dicyclohexyl)(4-dimethylaminophenyl)phosphine]palladium(II)chloride) 173 mg, 0.21 mmol) and potassium phosphate tribasic (2.64 g, 12.4 mmol) were dissolved in cyclopentyl methyl ether (11.9 mL) and water (5.1 mL). The resulting biphasic mixture was vigorously stirred at 90° C.

for 3.5 h, at which time the reaction was cooled to ambient temperature and was diluted with ethyl acetate (50 mL) and water (40 mL). The phases were separated, and the aqueous phase was extracted with ethyl acetate (2×50 mL). The combined organic phases were dried over anhydrous magnesium sulfate, filtered, and concentrated to afford a crude residue that was purified by silica gel chromatography (25 to 60% ethyl acetate in iso-hexanes) to afford the title compound (1.07 g, 85%) as a yellow oil.

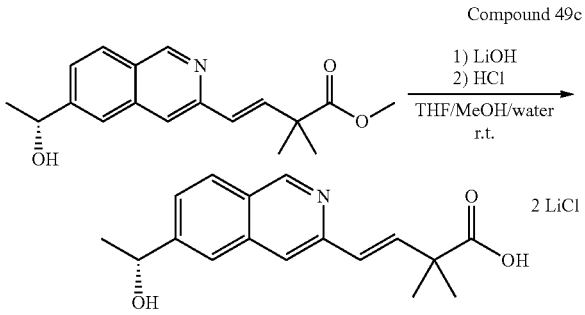

To a solution of 49b (600 mg, 2 mmol) in tetrahydrofuran (8 mL) was added methanol (4 mL), water (4 mL) and lithium hydroxide (96 mg, 4 mmol). The resulting mixture was stirred at RT for 10 h and quenched with 1 M hydrochloric acid (4.2 mL, 4.2 mmol). The resulting solution was concentrated to a crude residue which was co-distilled twice with tetrahydrofuran (20 mL), twice with anhydrous acetonitrile (20 mL) and twice with anhydrous toluene (20 mL). The resulting white solid was dried under high vacuum overnight and it was used without further purification (735 mg, quantitative yield).

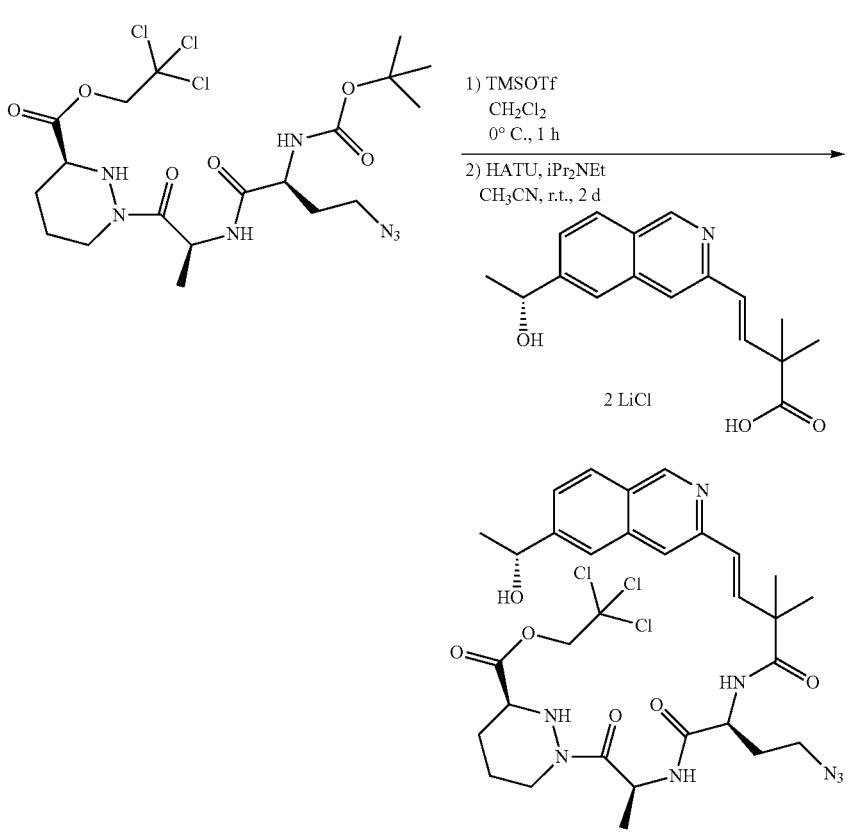

A solution of 49a (169 mg, 0.302 mmol) in dichloromethane (10 mL) was cooled in an ice water bath. Trimethylsilyl trifluoromethanesulfonate (101 mg, 0.455 mmol) was added dropwise at 0° C. under argon, and the resulting solution was stirred at RT for 30 min. The reaction mixture was evaporated to dryness and the resulting crude residue was dissolved in anhydrous acetonitrile (20 mL) under argon. Reaction mixture was stirred at 0° C., (E)-4-[6-((R)-1-hydroxy-ethyl)-isoquinolin-3-yl]-2,2-dimethyl-but-3-enoic acid (123 mg, 0.333 mmol) and N,N-diisopropylethylamine (151 mg, 1.220 mmol) were added followed by 2-(1H-7-azabenzotriazol-1-yl)-1,1,3,3-tetramethyl uronium hexafluorophosphate methanaminium (161 mg, 0.423 mmol). The reaction mixture was stirred at RT for 2 days. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol mixture (4/1) in iso-hexanes) to afford the title compound (198 mg, 90%) as a white solid after evaporation. $R_f$=0.18, iso-hexanes/ethyl acetate/methanol (6/4/1).

Compound 49

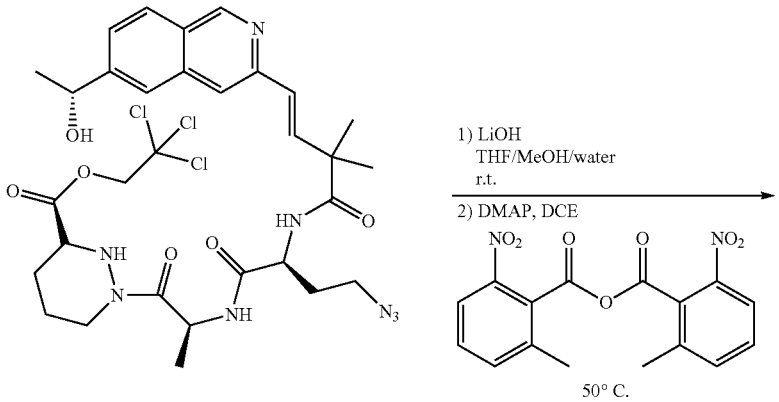

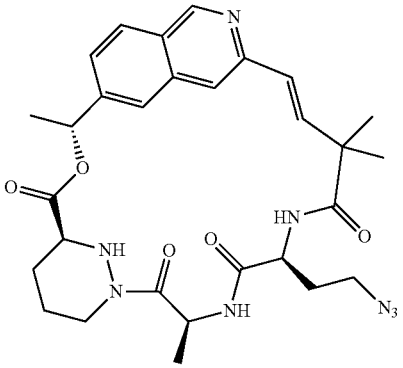

To a solution of 49d (170 mg, 0.23 mmol) in tetrahydrofuran (2 mL) was added methanol (1 mL), water (1 mL) and lithium hydroxide hydrate (7 mg, 0.28 mmol). The mixture was stirred for 2 h at ambient temperature and was quenched with aqueous 1 M hydrochloric acid (0.30 mL, 0.30 mmol). The resulting solution was concentrated to a crude residue which was co-evaporated twice with tetrahydrofuran (5 mL), twice with anhydrous acetonitrile (5 mL) and twice with anhydrous toluene (5 mL). The resulting white solid was dried under high vacuum overnight and used without further purification (151 mg, quantitative yield). Into oven-dried, argon purged flask were placed 2-methyl-6-nitrobenzoic anhydride (317 mg, 0.92 mmol), 4-dimethylaminopyridine (337 mg, 2.76 mmol) and anhydrous 1,2-dichloroethane (300 mL). The resulting solution was heated at 50° C., and the crude seco-acid was added dropwise by syringe as a solution in dry N,N-dimethylformamide (5 mL) over 12 h. An additional portion of dry N,N-dimethylformamide (2×1 ml) was used to complete the quantitative transfer. After stirring for additional 2 h at 50° C., the reaction mixture was transferred to a separatory funnel and washed with water (200 mL, 10 mL of brine was added to support the separation). The aqueous phase was extracted with dichloromethane (100 mL). Combined organic extracts were washed with brine (100 mL) and dried over magnesium sulfate, filtered and concentrated under reduced pressure. The resulting residue was dissolved in ethyl acetate (250 mL) and was washed with water (300 mL, 10 mL of brine was added to support the separation). The aqueous phase was extracted with ethyl acetate (150 mL). Combined organic extracts were washed with water (200 mL, 10 mL of brine was added to support the separation). Resulting aqueous phase was extracted with ethyl acetate (150 mL). Combined organic extracts were washed with brine (150 mL) and dried over magnesium sulfate, filtered and concentrated under reduced pressure. The residue was purified by silica gel chromatography (gradient from 0-40% ethyl acetate and methanol mixture (4/1) in iso-hexanes) to afford the title compound (76 mg, 57%) as a white solid after evaporation. $R_f$=0.51, 10% methanol in dichloromethane. $^1$H NMR (400 MHz, $CD_3OD$) δ 9.03 (s, 1H), 7.95 (d, J=8.5 Hz, 1H), 7.81 (s, 1H), 7.49 (s, 1H), 7.46 (dd, J=8.5, 1.6 Hz, 1H), 6.49 (d, J=16.1 Hz, 1H), 6.40 (d, J=16.1 Hz, 1H), 5.95 (q, J=6.6 Hz, 1H), 5.51 (q, J=7.2 Hz, 1H), 4.67 (dd, J=8.6, 6.3 Hz, 1H), 4.29 (m, 1H), 3.68 (dd, J=11.2, 2.7 Hz, 1H), 3.28 (td, J=6.8, 3.7 Hz, 2H), 2.67-2.56 (m, 1H), 1.88 (m, 2H), 1.85-1.60 (m, 4H), 1.57 (d, J=6.7 Hz, 3H), 1.54 (d, J=7.3 Hz, 3H), 1.42 (s, 3H), 1.27 (s, 3H). LCMS (m/z) 557.3 ([M+H], Tr=3.15 min.

Example 50

Compound 50

Compound 50

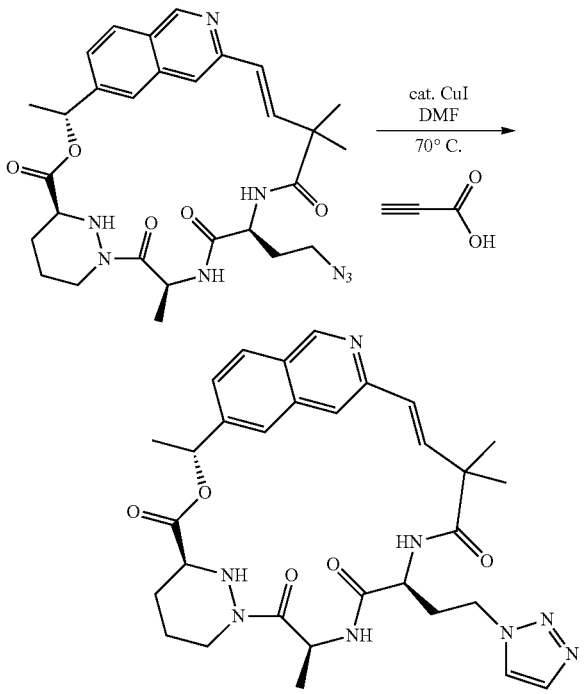

Into an oven-dried, argon purged flask, Compound 49 (20 mg, 0.034 mmol), copper(I) iodide (1 mg, 0.005 mmol) and propiolic acid (5 mg, 0.070 mmol) were added. The flask was sealed with septa and repurged with argon three times. Anhydrous N,N-dimethylformamide (5 mL) was added and the reaction mixture was repurged with argon three times. This reaction mixture was heated at 70° C. for 2 days. After evaporation of the solvent under reduced pressure, the crude residue was dissolved in ethyl acetate (10 mL) and filtered through Celite and the filter pad was washed with ethyl acetate (10 mL). After concentration under reduced pressure, the residue was purified by silica gel chromatography (gradient from 0-40% ethyl acetate and methanol mixture (4/1) in iso-hexanes) to afford the title compound (7 mg, 34%) as a white solid. $R_f$=0.36, 5% methanol in dichloromethane. $^1$H NMR (400 MHz, $CD_3OD$): δ 9.05 (s, 1H), 8.11 (br s, 1H), 8.00 (br s, 1H), 7.95 (d, J=8.8 Hz, 1H), 7.82 (s, 1H), 7.66 (s, 1H), 7.48 (d, J=10.0 Hz, 1H), 6.50 (d, J=16.2 Hz, 1H), 6.42 (d, J=16.2 Hz, 1H), 5.97 (m, 1H), 5.56 (m, 1H), 4.60 (m, 1H), 4.29 (m, 1H), 3.66 (m, 1H), 3.21 (m, 2H), 2.69-2.47 (m, 1H), 1.89 (m, 2H), 1.87-1.55 (m, 4H), 1.53 (d, J=6.7 Hz, 3H), 1.50 (d, J=7.1 Hz, 3H), 1.40 (s, 3H), 1.28 (s, 3H). LCMS (m/z) 603.1 [M+H], Tr=2.62 min.

Example 51

Compound 51

Compound 51a

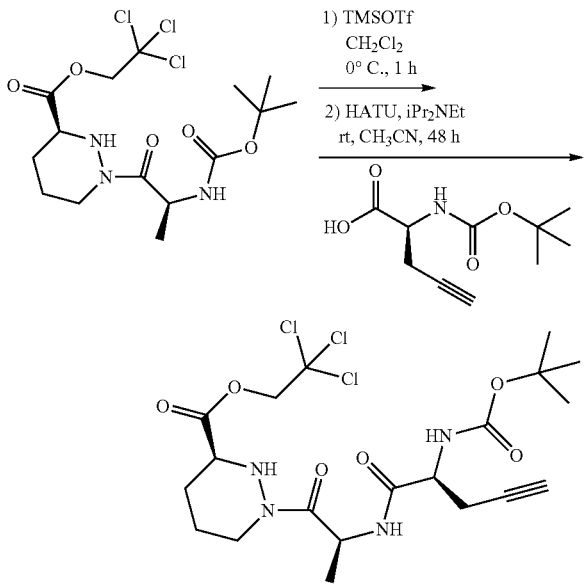

A solution of (S)-1-((S)-2-tert-butoxycarbonylamino-propionyl)-hexahydro-pyridazine-3-carboxylic acid 2,2,2-trichloro-ethyl ester (865 mg, 2 mmol) in dichloromethane (20 mL) was cooled in an ice water bath. Trimethylsilyl trifluoromethanesulfonate (667 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. Reaction mixture was stirred at 0° C., (S)-2-(tert-butoxycarbonylamino)pent-4-ynoic acid (469 mg, 2.2 mmol, source: Matrix Scientific, Catalog Number 041479) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). Reaction mixture was stirred at RT for 48 h. The solvent was evaporated, the residue was dissolved in ethyl acetate (100 mL) and the solution was washed with 20% water solution of citric acid (2×100 mL), water (100 mL) and brine (100 mL), dried over magnesium sulfate, filtered and evaporated. The residue was purified by silica gel chromatography (gradient from 0-40% ethyl acetate and methanol (4/1) in iso-hexanes) to afford the title compound (738 mg, 70%) as a white solid after evaporation. $R_f$=0.30, iso-hexanes/ethyl acetate/methanol (6/4/1).

Compound 51b

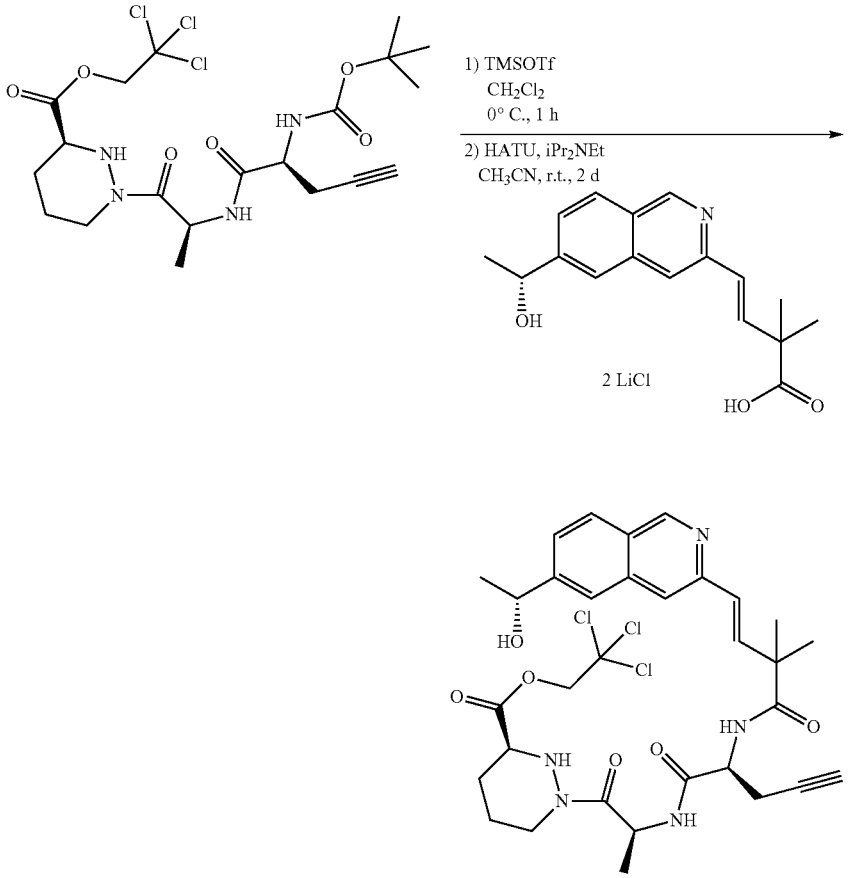

A solution of 51a (145 mg, 0.275 mmol) in dichloromethane (10 mL) was cooled in an ice water bath. Trimethylsilyl trifluoromethanesulfonate (92 mg, 0.414 mmol) was added dropwise at 0° C. under argon, and the resulting solution was stirred at RT for 30 min. The reaction mixture was evaporated to dryness and the resulting crude residue was dissolved in anhydrous acetonitrile (20 mL) under argon. The reaction mixture was stirred at 0° C., (E)-4-[6-((R)-1-hydroxy-ethyl)-isoquinolin-3-yl]-2,2-dimethyl-but-3-enoic acid (112 mg, 0.303 mmol) and N,N-diisopropylethylamine (137 mg, 1.101 mmol) were added followed by 2-(1H-7-azabenzotriazol-1-yl)-1,1,3,3-tetramethyl uronium hexafluorophosphate methanaminium (147 mg, 0.385 mmol). The reaction mixture was stirred at RT for 2 days. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (163 mg, 85%) as a white solid after evaporation. $R_f$=0.29, iso-hexanes/ethyl acetate/methanol (6/4/1).

Compound 51

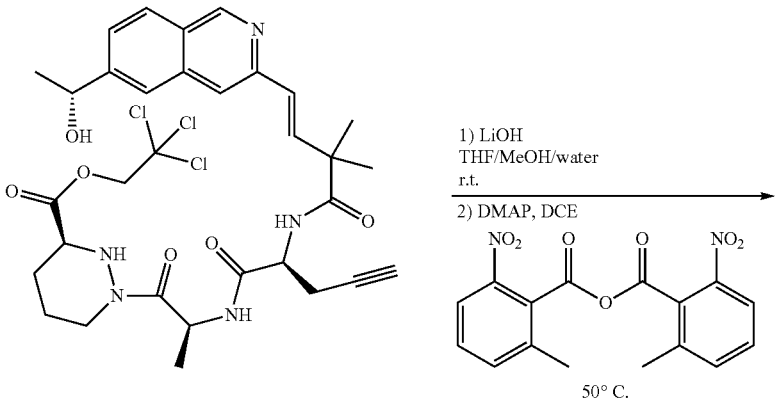

-continued

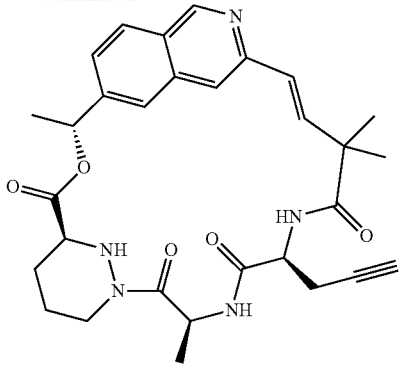

To a solution of 51b (125 mg, 0.18 mmol) in tetrahydrofuran (2 mL) was added methanol (1 mL), water (1 mL) and lithium hydroxide hydrate (5.2 mg, 0.22 mmol). The mixture was stirred for 2 h at ambient temperature and was quenched with aqueous 1 M hydrochloric acid (0.25 mL, 0.25 mmol). The resulting solution was concentrated to a crude residue which was co-evaporated twice with tetrahydrofuran (5 mL), twice with anhydrous acetonitrile (5 mL) and twice with anhydrous toluene (5 mL). The resulting white solid was dried under high vacuum overnight and it was used without further purification (113 mg, quantitative yield). Into an oven-dried, argon purged flask were placed 2-methyl-6-nitrobenzoic anhydride (248 mg, 0.72 mmol), 4-dimethylaminopyridine (264 mg, 2.16 mmol) and anhydrous 1,2-dichloroethane (200 mL). The resulting solution was heated at 50° C., and the crude seco-acid was added dropwise via syringe as a solution in anhydrous N,N-dimethylformamide (5 mL) over 12 h. An additional portion of anhydrous N,N-dimethylformamide (2×1 ml) was used to complete the quantitative transfer. After stirring for additional 2 h at 50° C., the reaction mixture was transferred to a separatory funnel and washed with water (200 mL, 10 mL of brine was added to support the separation). The aqueous phase was extracted with dichloromethane (100 mL). Combined organic extracts were washed with brine (100 mL) and dried over magnesium sulfate, filtered and concentrated under reduced pressure. The resulting residue was dissolved in ethyl acetate (250 mL) and was washed with water (300 mL, 10 mL of brine was added to support the separation). The aqueous phase was extracted with ethyl acetate (150 mL). Combined organic extracts were washed with water (200 mL, 10 mL of brine was added to support the separation). Resulting aqueous phase was extracted with ethyl acetate (150 mL). Combined organic extracts were washed with brine (150 mL) and dried over magnesium sulfate, filtered and concentrated under reduced pressure. The residue was purified by silica gel chromatography (gradient from 0-40% ethyl acetate+methanol (4/1) in iso-hexanes) to afford the title compound (56 mg, 57%) as a white solid after evaporation. $R_f$=0.53, 10% methanol in dichloromethane. $^1$H NMR (400 MHz, $CD_3OD$) δ 9.03 (s, 1H), 7.94 (d, J=8.5 Hz, 1H), 7.79 (s, 1H), 7.54 (s, 1H), 7.45 (d, J=8.5 Hz, 1H), 6.52 (d, J=16.1 Hz, 1H), 6.40 (d, J=16.1 Hz, 1H), 5.95 (q, J=6.6 Hz, 1H), 5.52 (q, J=7.2 Hz, 1H), 4.70 (dd, J=7.7, 6.7 Hz, 1H), 4.30 (m, 1H), 4.00 (q, J=7.2 Hz, 1H), 3.72-3.64 (m, 1H), 2.63 (m, 2.55-2.40 (m, 2H), 1.91 (s, 1H), 1.88 (m, 1H), 1.80 (m, 1H), 1.64 (m, 1H), 1.57 (d, J=6.7 Hz, 3H), 1.53 (d, J=7.2 Hz, 3H), 1.42 (s, 3H), 1.27 (s, 3H). LCMS (m/z) 546.2 [M+H], Tr=3.04 min.

Example 52

Compound 52

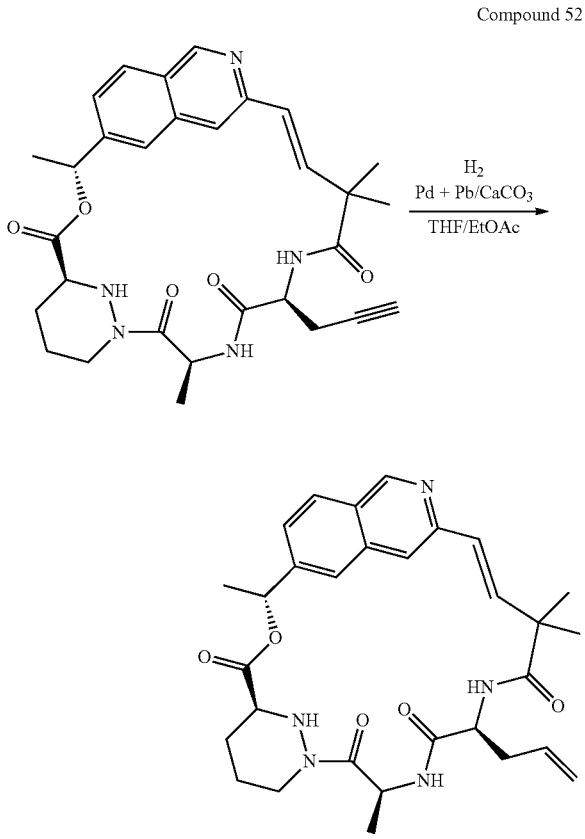

A solution of Compound 51 (10 mg, 0.018 mmol) in a mixture of ethyl acetate (4 mL) and tetrahydrofuran (4 mL) containing 5% palladium on calcium carbonate poisoned with lead-Lindlar catalyst (10 mg) was hydrogenated at RT and pressure of hydrogen for 3 h. The reaction mixture was filtered through Celite and the filter pad was washed with tetrahydrofuran (10 mL). The filtrate was evaporated to afford the title compound (10 mg, quantitative yield) as a white solid. $R_f$=0.19, iso-hexanes/ethyl acetate/methanol (6/4/1). $^1$H NMR (400 MHz, $CD_3OD$): δ 9.04 (s, 1H), 7.95 (d, J=8.4 Hz, 1H), 7.82 (s, 1H), 7.54 (s, 1H), 7.46 (d, J=8.3 Hz, 1H), 6.50 (d, J=16.1 Hz, 1H), 6.39 (d, J=16.1 Hz, 1H), 5.95 (q, J=6.4 Hz, 1H), 5.76-5.62 (m, 1H), 5.57 (q, J=7.0 Hz, 1H), 5.02 (d, J=17.0 Hz, 1H), 4.96 (d, J=10.1 Hz, 1H), 4.61-4.54 (m, 1H), 4.29 (m, 1H), 3.68n (m, 1H), 2.61 (m, 1H), 2.42-2.34 (m, 1H), 2.30-2.20 (m, 1H), 1.90 (m, 1H), 1.81 (m, 1H), 1.68-1.60 (m, 2H), 1.57 (d, J=6.6 Hz, 3H), 1.53 (d, J=7.2 Hz, 3H), 1.39 (s, 3H), 1.26 (s, 3H). LCMS (m/z) 548.3 [M+H], Tr=2.85 min.

Example 53

Compound 53

Compound 53a

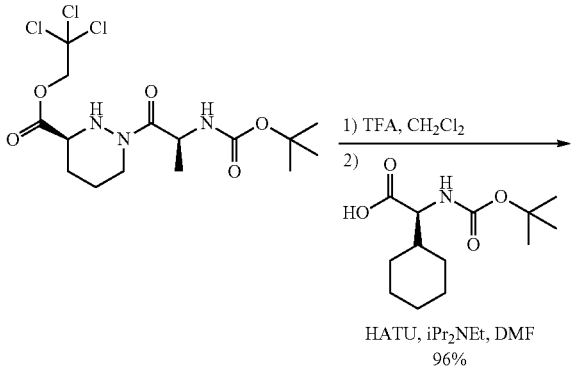

-continued

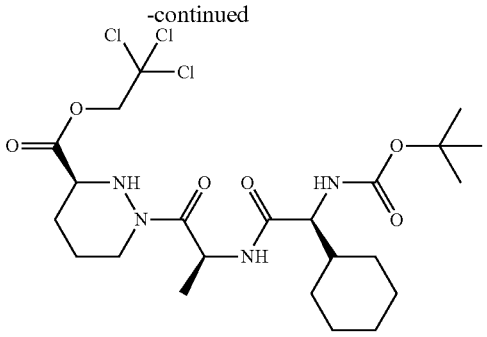

To a solution of (S)-1-((S)-2-tert-butoxycarbonylamino-propionyl)-hexahydro-pyridazine-3-carboxylic acid 2,2,2-trichloro-ethyl ester (300 mg, 0.69 mmol) in dichloromethane (1.84 mL) was slowly added trifluoroacetic acid (460 μL, 6.00 mmol) at 0° C. under an argon atmosphere. After 3 h, the reaction mixture was concentrated under reduced pressure. The crude residue was dissolved in N,N-dimethylformamide (3.45 mL) and (S)-tert-Butoxycarbonylamino-cyclohexyl-acetic acid (195 mg, 0.760 mmol), 2-(1H-7-azabenzotriazol-1-yl)-1,1,3,3-tetramethyl uronium hexafluorophosphate methanaminium (289 mg, 0.760 mmol), and N,N-diisopropylethylamine (180 μL, 1.04 mmol) were sequentially added at 23° C. under an argon atmosphere. After 18 h, the reaction mixture was diluted with ethyl acetate (300 mL), and the resulting mixture was washed with brine (4×100 mL), was dried over anhydrous sodium and was concentrated under reduced pressure. The crude residue was purified by silica gel chromatography (12 g Combiflash HP Gold Column, 0-100% ethyl acetate/iso-hexanes gradient) to afford the title compound (380 mg, 96%) as a colorless oil.

Compound 53b

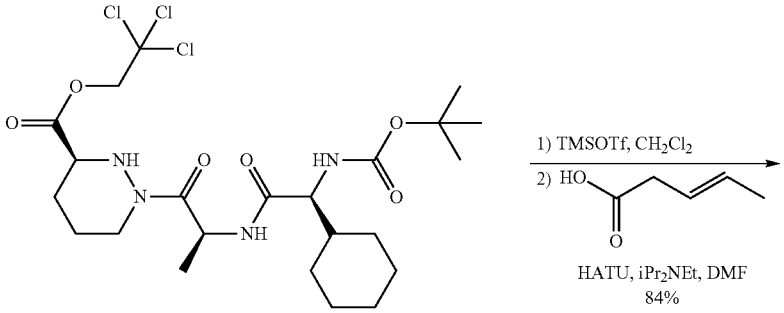

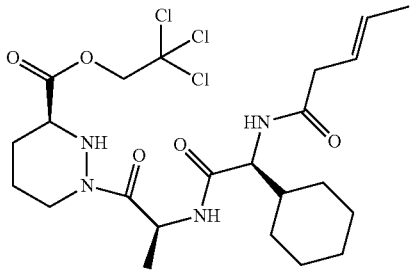

To a solution of 53a (220 mg, 0.385 mmol) in dichloromethane (1.92 mL) was added trimethylsilyl trifluoromethanesulfonate (128 mg, 0.587 mmol) at 0° C. under an argon atmosphere. After 1.5 h, the reaction mixture was concentrated under reduced pressure. The resulting residue was diluted with acetonitrile (1.92 mL) and 2-(1H-7-azabenzotriazol-1-yl)-1,1,3,3-tetramethyl uronium hexafluorophosphate methanaminium (146 mg, 0.385 mmol), N,N-diisopropylethylamine (267 μL, 1.54 mmol), and (E)-pent-3-enoic acid (39.4 μL, 0.385 mmol) were sequentially added at 23° C. under an argon atmosphere. After 20 h, the reaction mixture was diluted with dichloromethane (40 mL) and the resulting mixture was washed with saturated aqueous sodium bicarbonate solution (40 mL) and with brine (2×40 mL). The organic layer was separated, was dried over anhydrous sodium sulfate, and was concentrated under reduced pressure. The crude residue was purified by silica gel flash column chromatography (12 g Combiflash HP Gold Column, 0-100% ethyl acetate/iso-hexanes gradient) to afford the title compound (180 mg, 84%) as a colorless oil. $R_f$=0.75 (ethyl acetate) $I_2$/silica stain.

Compound 53c

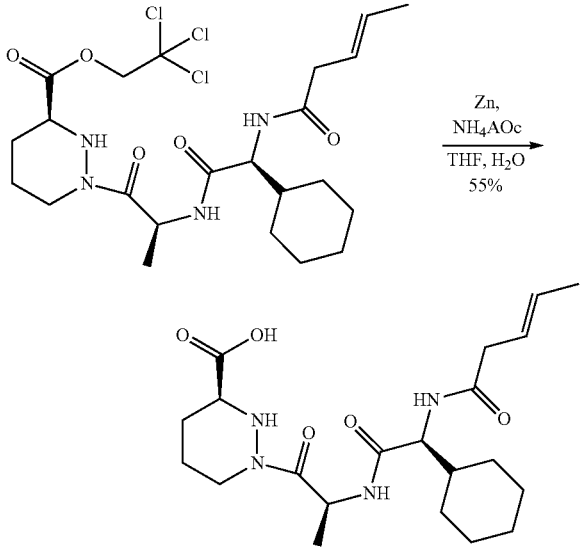

To a solution of 53b (180 mg, 0.320 mmol) in tetrahydrofuran (5.3 mL) was added zinc powder (418 mg, 6.40 mmol) followed by a solution of ammonium acetate (370 mg, 4.80 mmol) in water (3.5 mL) at 23° C. under an argon atmosphere. After 15 h, the reaction mixture was warmed to 45° C. After 2 h, the reaction mixture was allowed to cool to RT and was filtered through a pad of Celite washing with water (10 mL) and ethyl acetate (10 mL). The filtrate layers were split and the aqueous layer was diluted with brine (80 mL) and was acidified to pH 1 with 12 N aqueous hydrogen chloride solution. The aqueous layer was extracted with ethyl acetate (3×100 mL), and the combined organic extracts were dried over anhydrous sodium sulfate, and were concentrated under reduced pressure. Residual acetic acid was removed azeotropically via addition of toluene (5 mL) followed by concentration under reduced pressure (3×) to afford the title compound (74.5 mg, 55%) as a white solid.

Compound 53d

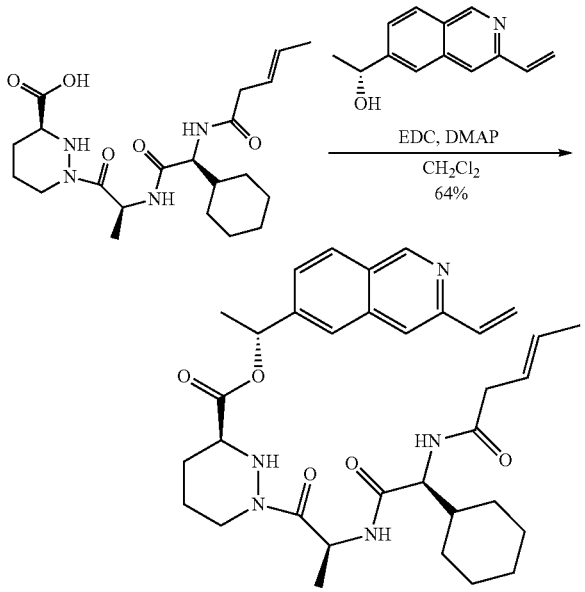

To a solution of 53c (74.5 mg, 0.176 mmol) and (R)-1-(3-vinyl-isoquinolin-6-yl)-ethanol (42.1 mg, 0.212 mmol) in dichloromethane (3.5 mL) were added N-(3-dimethylaminopropyl)-N'-ethylcarbodiimide hydrochloride (47.2 mg, 0.246 mmol) and 4-dimethylaminopyridine (11 mg, 88 μmol) at 23° C. under an argon atmosphere. After 18 h, the reaction mixture was purified directly by silica gel chromatography (12 g Combiflash HP Gold Column, 0-100% ethyl acetate/iso-hexanes gradient) to afford the title compound (67.6 mg, 64%) as a white solid.

Compound 53

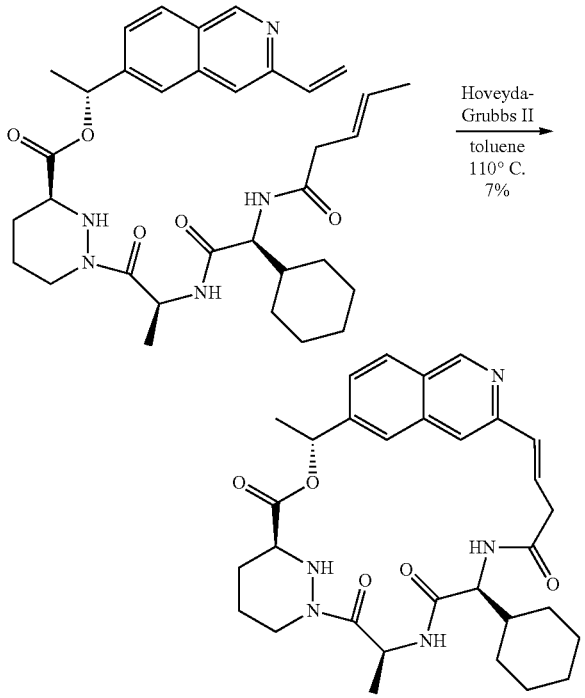

To a solution of 53d (25 mg, 41 μmol) in toluene (8.2 mL) was added the Hoveyda-Grubbs 2nd Generation catalyst (2.5 mg, 4.1 μmol) at 23° C. under an argon atmosphere, and the resulting mixture was heated to 110° C. After 2 h, the reaction mixture was quenched with ethyl vinyl ether (300 μL) and the resulting mixture was allowed to cool to 23° C. The reaction mixture was concentrated under reduced pressure and the crude residue was purified by silica gel chromatography (12 g Combiflash HP Gold Column, 0-100% ethyl acetate/iso-hexanes gradient). The fractions containing the desired product were combined and were repurified by preparatory HPLC to afford the title compound (1.7 mg, 7%) as a white powder as a trifluoroacetic acid salt. $R_f$=0.40 (ethyl acetate) UV. $^1$H NMR (400 MHz, $CD_3OD$) δ 9.13 (s, 1H), 8.53 (br s, 1H), 8.07 (d, J=7.6 Hz, 1H), 8.05 (d, J=8.5 Hz, 1H), 7.83 (s, 1H), 7.55 (d, J=8.3 Hz, 1H), 7.44 (s, 1H), 6.62 (d, J=16.3 Hz, 1H), 6.55-6.45 (m, 1H), 6.04 (q, J=6.5 Hz, 1H), 5.50 (q, J=6.9 Hz, 1H), 4.40 (d, J=14.1 Hz, 1H), 4.33 (d, J=9.7 Hz, 1H), 3.78 (d, J=11.0 Hz, 1H), 3.36 (app dd, J=14.7, 6.7 Hz, 1H), 2.99 (dd, J=14.5, 4.9 Hz, 1H), 2.90-2.66 (m, 4H), 2.02-1.83 (m, 4H), 1.82-1.70 (m, 3H), 1.68 (d, J=6.7 Hz, 3H), 1.65 (d, J=7.3 Hz, 3H), 1.33-1.16 (m, 4H), 1.16-0.94 (m, 2H). HPLC Tr=$t_R$ (min), 3.091 (Synergi 4u hydro-RP, 50×4.60 mm 4 micron column, 7 min, 2 ml/min, 5-100% acetonitrile/water, 0.05% trifluoroacetic acid modifier gradient). LCMS (m/z) 562.3 [M+H], Tr=2.17 min.

Example 54

Compound 54

To a solution of (S)-1-((S)-2-tert-butoxycarbonylamino-propionyl)-hexahydro-pyridazine-3-carboxylic acid 2,2,2-trichloro-ethyl ester (300 mg, 0.69 mmol) in dichloromethane (1.84 mL) was slowly added trifluoroacetic acid (460 μL, 6.00 mmol) at 0° C. under an argon atmosphere. After 2 h, the reaction mixture was concentrated under reduced pressure. The crude residue was dissolved in N,N-dimethylformamide (3.45 mL) and (S)-2-tert-Butoxycarbonylamino-3-phenyl-propionic acid (201 mg, 0.760 mmol), 2-(1H-7-azabenzotriazol-1-yl)-1,1,3,3-tetramethyl uronium hexafluorophosphate methanaminium (289 mg, 0.760 mmol), and N,N-diisopropylethylamine (180 μL, 1.04 mmol) were sequentially added at 23° C. under an argon atmosphere. After 22 h, the reaction mixture was diluted with ethyl acetate (300 mL), and the resulting mixture was washed with brine (3×200 mL), was dried over anhydrous sodium sulfate, and was concentrated under reduced pressure. The crude residue was purified by silica gel chromatography (24 g Combiflash HP Gold Column, 0-100% ethyl acetate/iso-hexanes gradient) to afford the title compound (319 mg, 96%) as a colorless oil. $R_f$=0.75 (ethyl acetate) $I_2$/silica stain.

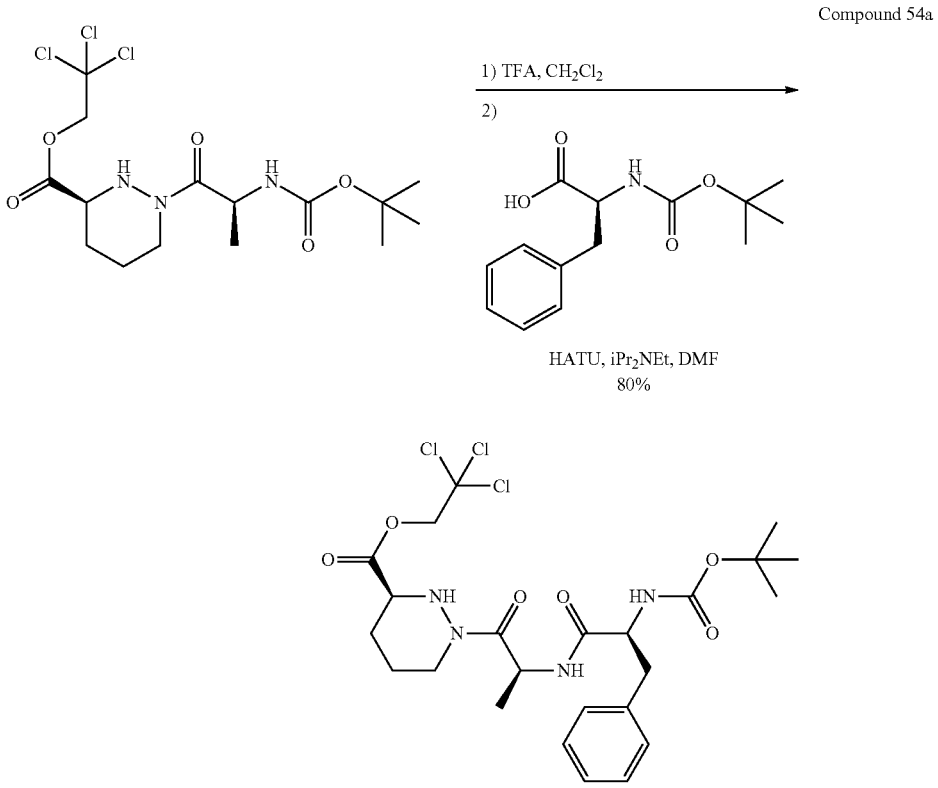

Compound 54b

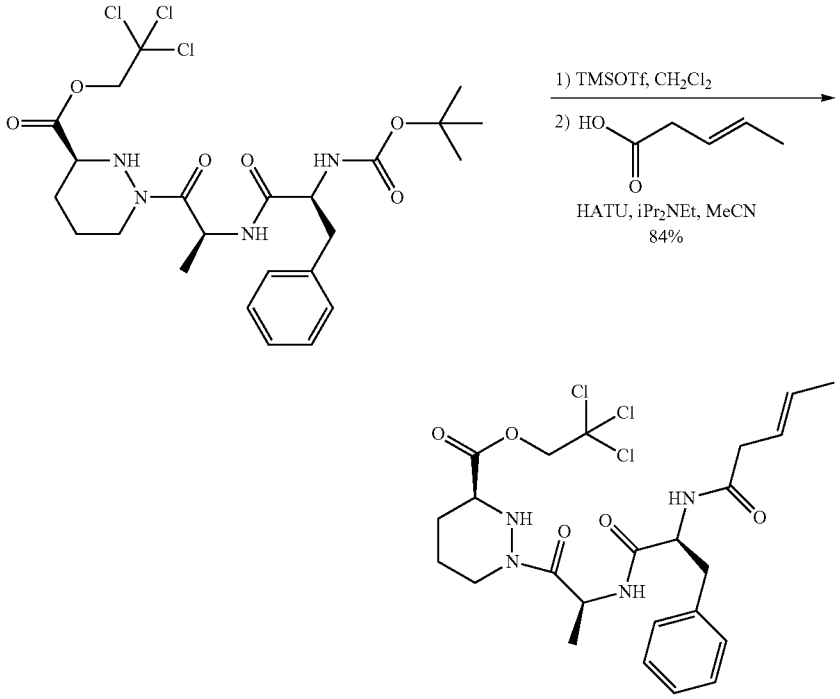

To a solution of 54a (414 mg, 0.716 mmol) in dichloromethane (3.58 mL) was added trimethylsilyl trifluoromethanesulfonate (238.7 mg, 1.07 mmol) at 0° C. under an argon atmosphere. After 1 h, the reaction mixture was concentrated under reduced pressure. The resulting residue was diluted with acetonitrile (3.58 mL) and 2-(1H-7-azabenzotriazol-1-yl)-1,1,3,3-tetramethyl uronium hexafluorophosphate methanaminium (272 mg, 0.716 mmol), N,N-diisopropylethylamine (498 μL, 2.86 mmol), and (E)-pent-3-enoic acid (73.3 μL, 0.716 mmol) were sequentially added at 23° C. under an argon atmosphere. After 17 h, the reaction mixture was diluted with dichloromethane (50 mL) and the resulting mixture was washed with saturated aqueous sodium bicarbonate solution (50 mL). The organic layer was separated, was dried over anhydrous sodium sulfate, and was concentrated under reduced pressure. The crude residue was purified by silica gel chromatography to afford the title compound (386 mg, 96%) as white solid.

Compound 54c

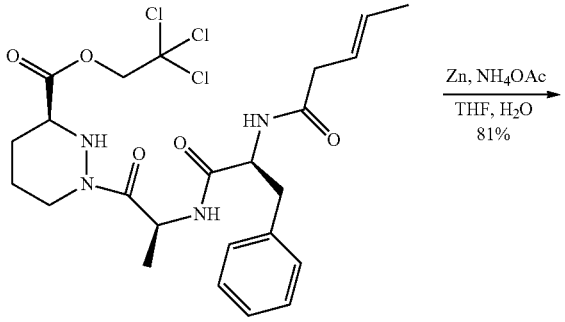

-continued

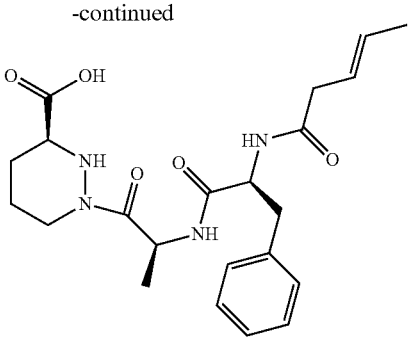

To a solution of 54b (443 mg, 0.789 mmol) in tetrahydrofuran (13.2 mL) was added zinc powder (1.03 g, 15.8 mmol) followed by a solution of ammonium acetate (912 mg, 11.8 mmol) in water (8.77 mL) at 23° C. under an argon atmosphere. After 17 h, the reaction mixture was warmed to 45° C. After 2 h, the reaction mixture was allowed to cool to RT and was filtered through a pad of Celite washing with water (10 mL) and ethyl acetate (10 mL). The filtrate layers were split and the aqueous layer was diluted with brine (20 mL) and was acidified to pH 2 with 12 N aqueous hydrogen chloride solution. The aqueous layer was extracted with dichloromethane (3×100 mL), and the combined organic extracts were dried over anhydrous sodium sulfate, and were concentrated under reduced pressure. Residual acetic acid was removed azeotropically via addition of toluene (5 mL) followed by concentration under reduced pressure (3×) to afford the title compound (276.2 mg, 81%) as a white solid.

Compound 54d

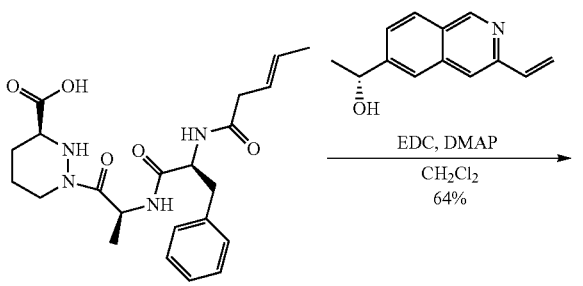

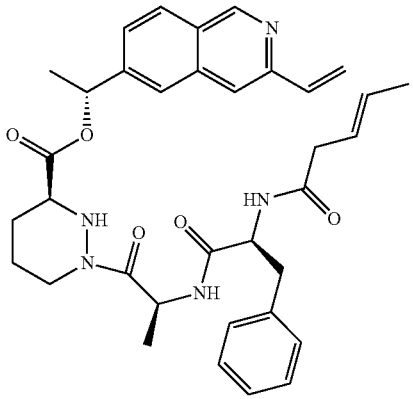

To a solution of 54c (275 mg, 0.640 mmol) and (R)-1-(3-vinyl-isoquinolin-6-yl)-ethanol (153 mg, 0.770 mmol) in dichloromethane (3.2 mL) were added N-(3-dimethylamino-propyl)-N'-ethylcarbodiimide hydrochloride (172 mg, 0.90 mmol) and 4-dimethylaminopyridine (39 mg, 32 μmol) at 23° C. under an argon atmosphere. After 23 h, the reaction mixture was purified directly by silica gel chromatography (24 g Combiflash HP Gold Column, 0-100% ethyl acetate/iso-hexanes gradient) to afford the title compound (203 mg, 52%) as a white solid.

Compound 54

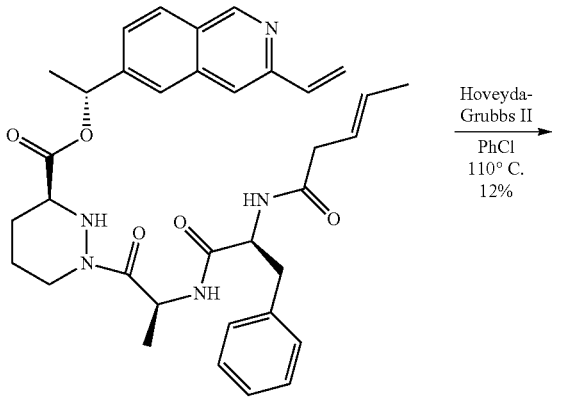

-continued

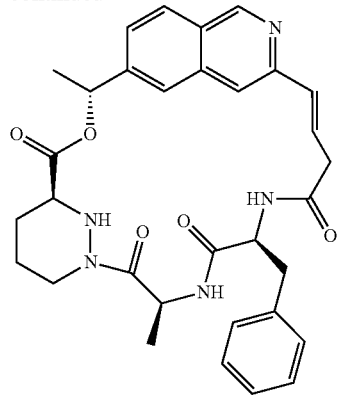

To a solution of 54d (170 mg, 278 μmol) in chlorobenzene (56 mL) was added the Hoveyda-Grubbs 2$^{nd}$ Generation catalyst (8.7 mg, 14.0 μmol) at 23° C. under an argon atmosphere, and the resulting mixture was heated to 110° C. After 3 h, the reaction mixture was quenched with ethyl vinyl ether (300 μL) and the resulting mixture was allowed to cool to 23° C. The reaction mixture was concentrated under reduced pressure and the crude residue was purified by silica gel chromatography (12 g Combiflash HP Gold Column, 0-100% ethyl acetate/iso-hexanes gradient) to afford the title compound (18.9 mg, 12%) as a tan solid. $R_f$=0.25 (ethyl acetate) UV. $^1$H NMR (400 MHz, $CD_3OD$) δ 9.12 (s, 1H), 8.05 (d, J=8.7 Hz, 1H), 7.84 (s, 1H), 7.56 (d, J=8.5 Hz, 1H), 7.53 (s, 1H), 7.32-7.12 (m, 5H), 6.66 (d, J=16.5 Hz, 1H), 6.48 (dt, J=12.8, 5.6 Hz, 1H), 6.05 (q, J=6.4 Hz, 1H), 5.53 (q, J=6.7 Hz, 1H), 4.73 (d, J=12.2 Hz, 1H), 4.43 (d, J=11.9 Hz, 1H), 3.80 (app t, J=10.2 Hz, 1H), 3.30-3.22 (m, 1H), 3.09 (dd, J=14.5, 4.9 Hz, 1H), 2.96-2.69 (m, 3H), 2.04-1.87 (m, 2H), 1.82-1.56 (m, 2H), 1.68 (d, J=6.5 Hz, 3H), 1.64 (d, J=6.9 Hz, 3H). HPLC Tr=3.060 min. LCMS (m/z) 570.5 [M+H], Tr=2.14 min.

Example 55

Compound 55

Compound 55a

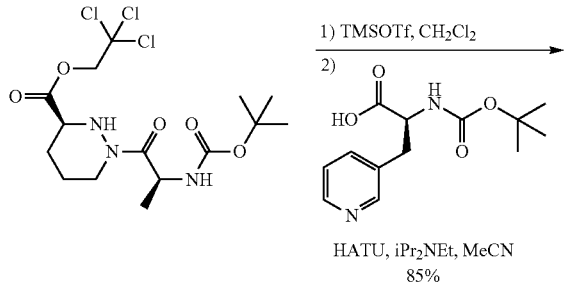

-continued

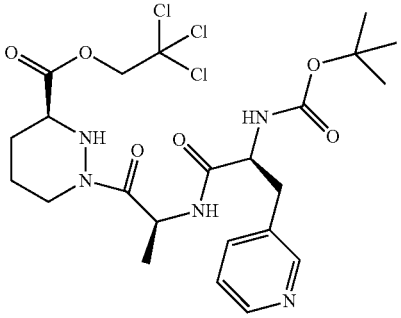

To a solution of (S)-1-((S)-2-tert-butoxycarbonylamino-propionyl)-hexahydro-pyridazine-3-carboxylic acid 2,2,2-trichloro-ethyl ester (500 mg, 0.1.16 mmol) in dichloromethane (5.8 mL) was added trimethylsilyl trifluoromethanesulfonate (386 mg, 1.74 mmol) at 0° C. under an argon atmosphere. After 1 h, the reaction mixture was concentrated under reduced pressure. The resulting residue was diluted with acetonitrile (5.8 mL) and 2-(1H-7-azabenzotriazol-1-yl)-1,1,3,3-tetramethyl uronium hexafluorophosphate methanaminium (485 mg, 1.28 mmol), N,N-diisopropylethylamine (302 μL, 1.74 mmol), N-tert-butoxycarbonyl-3-(3-pyridyl)-L-alanine (337 mg, 1.27 mmol) were sequentially added at 23° C. under an argon atmosphere. After 20 h, the reaction mixture was concentrated under reduced pressure, and the crude residue was purified by silica gel chromatography (40 g Combiflash HP Gold Column, 0-100% ethyl acetate/iso-hexanes gradient) to afford the title compound (570 mg, 85%) as light yellow oil.

Compound 55b

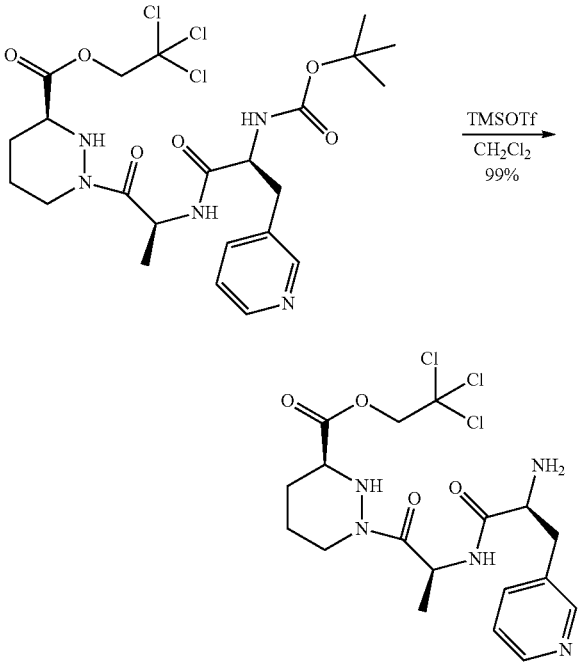

To a solution of 55a (570 mg, 0.984 mmol) in dichloromethane (5.8 mL) was added trimethylsilyl trifluoromethanesulfonate (386 mg, 1.74 mmol) at 0° C. under an argon atmosphere. After 1 h, the reaction mixture was concentrated under reduced pressure to afford the title compound (478 mg) as light yellow oil which was used without further purification.

Compound 55c

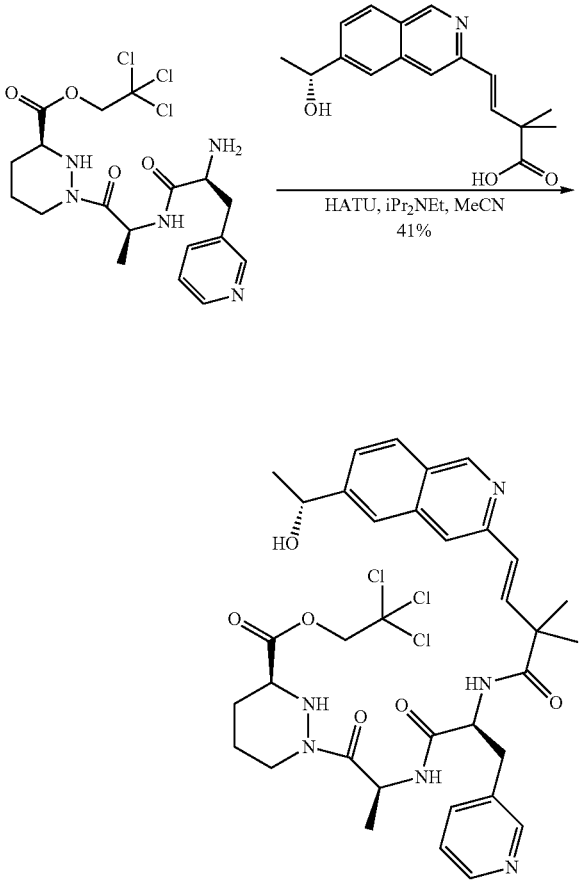

To a solution of 55b (120 mg, 0.250 mmol) in acetonitrile (1.25 mL) were sequentially added (E)-4-[6-((R)-1-hydroxy-ethyl)-isoquinolin-3-yl]-2,2-dimethyl-but-3-enoic acid (75 mg, 0.25 mmol), 2-(1H-7-azabenzotriazol-1-yl)-1,1,3,3-tetramethyl uronium hexafluorophosphate methanaminium (95 mg, 0.25 mmol), and N,N-diisopropylethylamine (173 μL, 1.00 mmol) at 23° C. under an argon atmosphere. N,N-Dimethylformamide (100 μL) was then added to promote solubility of the reagents. After 23 h, the reaction mixture was diluted with saturated aqueous sodium bicarbonate solution (25 mL) and brine (25 mL) and the resulting mixture was extracted with dichloromethane (2×25 mL). The combined organic extracts were dried over anhydrous sodium sulfate and were concentrated under reduced pressure. The crude residue was purified by silica gel chromatography to afford the title compound (76 mg, 41%) as a colorless solid.

Compound 55d

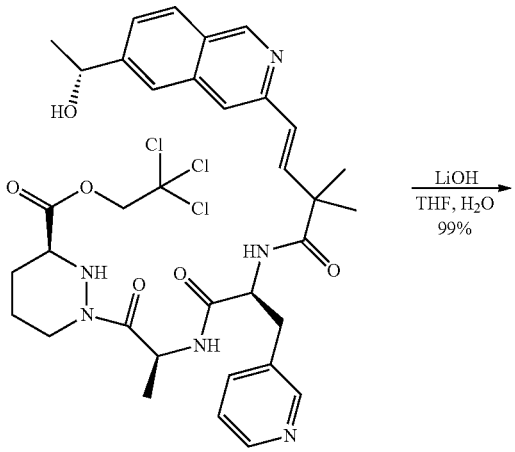

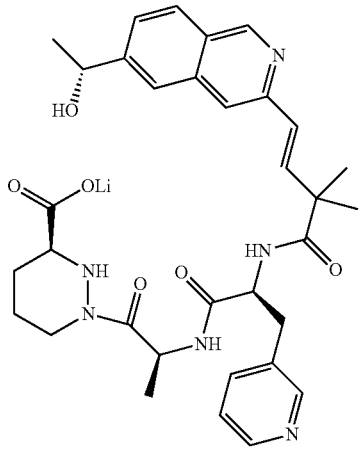

To a solution of 55c (76 mg, 0.10 mmol) in tetrahydrofuran (0.3 mL) and water (0.2 mL) was added lithium hydroxide hydrate (2.4 mg, 0.10 mmol) at 23° C. under an argon atmosphere. After 2 h, the reaction mixture was concentrated under reduced pressure to afford the title compound (61 mg, 99%) as a white solid lithium carboxylate salt.

Compound 55

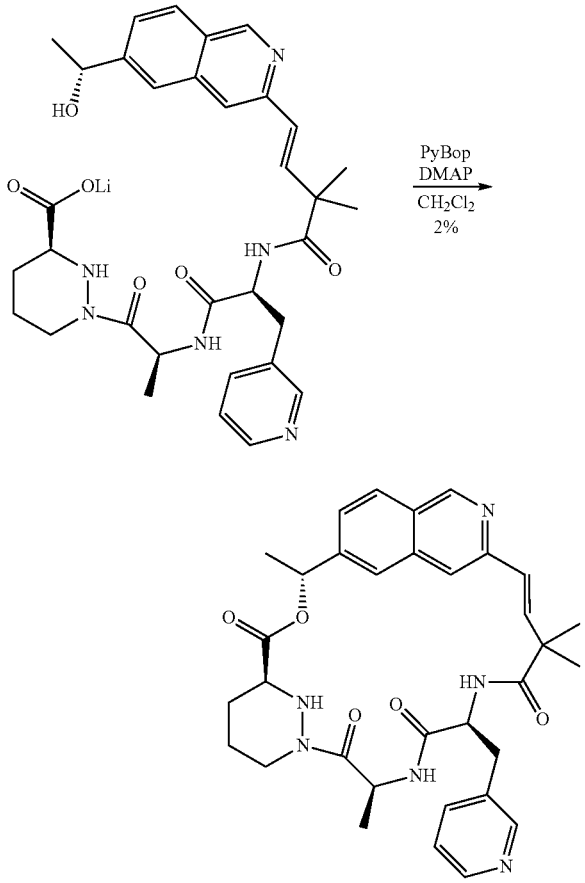

To a solution of 55d (61 mg, 0.10 mmol) in dichloromethane (50 mL) were added benzotriazol-1-yl-oxytripyrrolidinophosphonium hexafluorophosphate (208 mg, 400 μmol) and 4-dimethylaminopyridine (366 mg, 3.00 mmol) at 23° C. under an argon atmosphere. After 17 h, the reaction mixture was concentrated under reduced pressure and the crude residue was purified by silica gel chromatography (4 g Combiflash HP Gold Column, 0-20% methanol/dichloromethane gradient) to afford the title compound (1.2 mg, 2%) as a colorless solid. $R_f$=0.40 (10% methanol in dichloromethane) UV. $^1$H NMR (400 MHz, $CD_3OD$) δ 9.03 (s, 1H), 8.31 (d, J=1.6 Hz, 1H), 8.27 (dd, J=4.9, 1.5 Hz, 1H), 7.95 (d, J=8.5 Hz, 1H), 7.82 (s, 1H), 7.64 (d, J=8.0 Hz, 1H), 7.53 (s, 1H), 7.46 (dd, J=8.5, 1.5 Hz, 1H), 7.24 (dd, J=7.9, 4.9 Hz, 1H), 6.49 (d, J=16.1 Hz, 1H), 6.37 (d, J=16.1 Hz, 1H), 5.95 (q, J=6.5 Hz, 1H), 5.57 (q, J=7.3 Hz, 1H), 4.65 (d, J=12.0 Hz, 1H), 4.32 (br d, J=12.1 Hz, 1H), 3.83 (d, J=11.8 Hz, 1H), 3.73-3.65 (m, 1H), 3.00 (dd, J=14.2, 5.0 Hz, 1H), 2.83 (dd, J=13.9, 9.7 Hz, 1H), 2.64 (br t, J=11.2 Hz, 1H), 1.95-1.73 (m, 2H), 1.69-1.59 (m, 1H), 1.57 (d, J=6.7 Hz, 3H), 1.54 (d, J=7.2 3H), 1.33 (s, 3H), 1.16 (s, 3H). HPLC Tr=4.491 min Example 56

Compound 56

Compound 56a

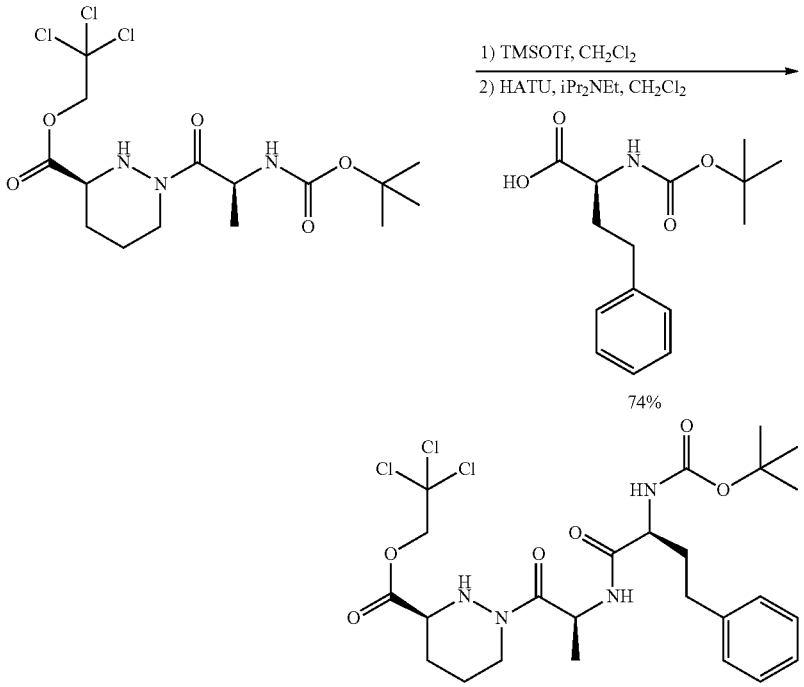

To a solution of (S)-1-((S)-2-tert-butoxycarbonylamino-propionyl)-hexahydro-pyridazine-3-carboxylic acid 2,2,2-trichloro-ethyl ester (791 mg, 1.82 mmol) in dichloromethane (10.0 mL) was slowly added trimethylsilyl trifluoromethanesulfonate (483 μL, 2.73 mmol) at 0° C. under an argon atmosphere. After 45 min, the reaction mixture was concentrated under reduced pressure. The resulting residue was diluted with dichloromethane (10.0 mL) and 2-(1H-7-azabenzotriazol-1-yl)-1,1,3,3-tetramethyl uronium hexafluorophosphate methanaminium (761 mg, 2.00 mmol), N,N-diisopropylethylamine (1.26 mL, 7.28 mmol), and (S)-2-(tert-butoxycarbonylamino)-4-phenylbutanoic acid (Fluka, 560 mg, 2.00 mmol) were sequentially added at 23° C. under an argon atmosphere. After 18 h, the reaction mixture was concentrated under reduced pressure. The residue was pre-absorbed on silica and purified by silica gel chromatography (40 g Isco Rf Gold Column, 0-100% ethyl acetate/iso-hexanes gradient) to afford the title compound (799 mg, 74%) as a colorless oil.

Compound 56b

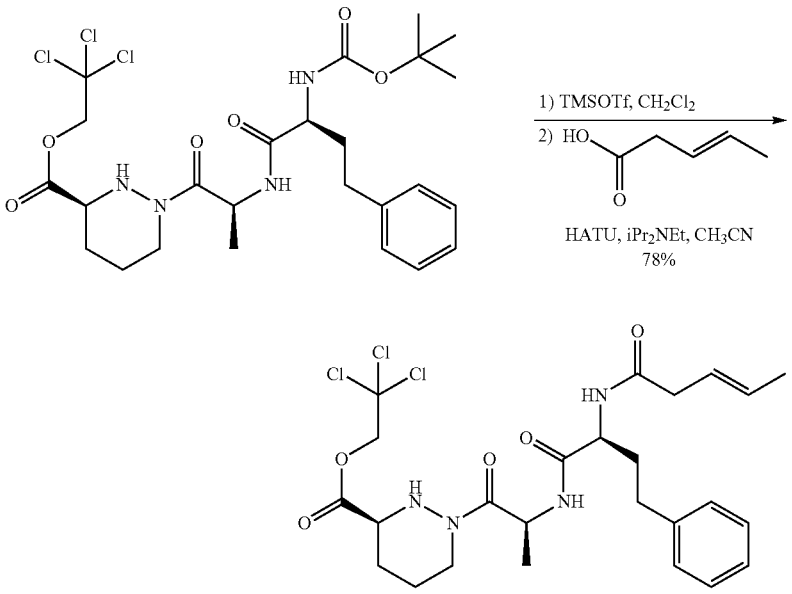

To a solution of 56a (799 mg, 1.34 mmol) in dichloromethane (10.0 mL) was added trimethylsilyl trifluoromethanesulfonate (356 μL, 2.01 mmol) at 0° C. under an argon atmosphere. After 30 min, the reaction mixture was concentrated under reduced pressure. The resulting residue was diluted with acetonitrile (6.0 mL) and 2-(1H-7-azabenzotriazol-1-yl)-1,1,3,3-tetramethyl uronium hexafluorophosphate methanaminium (560 mg, 1.47 mmol), N,N-diisopropylethylamine (932 μL, 5.36 mmol), and (E)-pent-3-enoic acid (150 μL, 1.47 mmol) were sequentially added at 23° C. under an argon atmosphere. After 19 h, the reaction mixture was concentrated under reduced pressure. The residue was pre-absorbed on silica and purified by silica gel chromatography to afford the title compound (598 mg, 78%) as a colorless oil.

Compound 56c

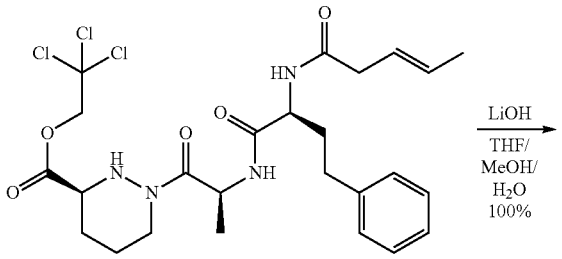

-continued

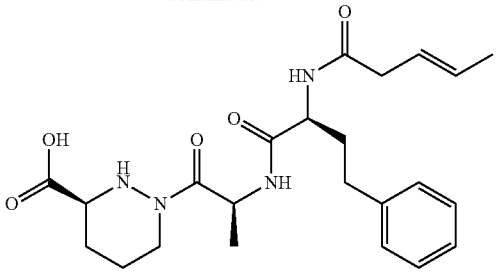

To a solution of 56b (167 mg, 0.29 mmol) in tetrahydrofuran (3 mL), methanol (1 mL) and water (1 mL) was added lithium hydroxide hydrate (7.6 mg, 0.32 mmol) at 23° C. After 15 min, the reaction mixture was concentrated to dryness under reduced pressure. The residue was dissolved in water (25 mL) and washed with ethyl acetate. The organic layer was extracted with saturated aqueous sodium bicarbonate solution (25 mL). The combined aqueous layers were acidified with 1 M aqueous hydrochloric acid solution to pH~2 and extracted with ethyl acetate (3×25 mL), and the combined organic extracts were dried over anhydrous magnesium sulfate, and were concentrated under reduced pressure to afford the title compound (129 mg, 100%) as a white solid.

Compound 56d

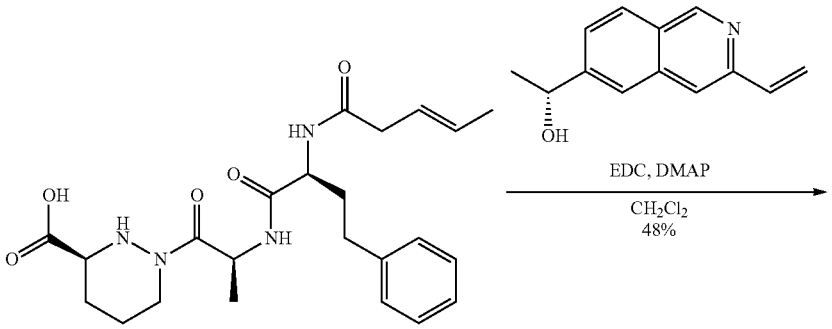

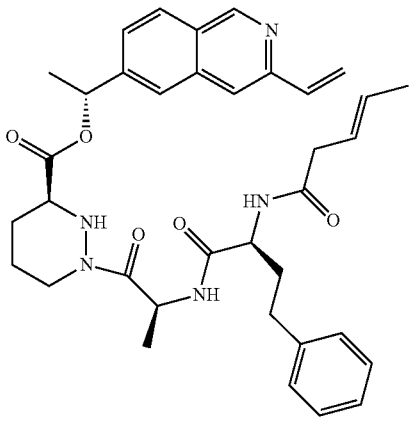

To a solution of 56c (129 mg, 0.29 mmol) and (R)-1-(3-vinyl-isoquinolin-6-yl)-ethanol (64 mg, 0.31 mmol) in dichloromethane (3.0 mL) was added N-(3-dimethylamino-propyl)-N'-ethylcarbodiimide hydrochloride (89 mg, 0.46 mmol) and 4-dimethylaminopyridine (18 mg, 0.14 mmol) at 23° C. under an argon atmosphere. After 16 h, the reaction mixture was purified directly by silica gel chromatography to afford the title compound (87 mg, 48%) as a white solid.

Compound 56

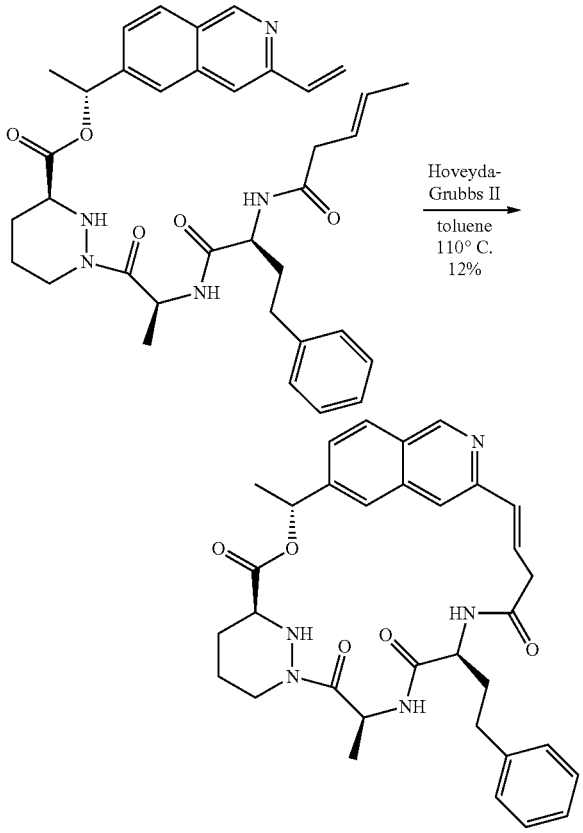

To a solution of 56d (84 mg, 0.13 mmol) in chlorobenezene (27 mL) was added the Hoveyda-Grubbs 2$^{nd}$ Generation catalyst (8 mg, 13 μmol) at 23° C. under an argon atmosphere, and the resulting mixture was heated to 110° C. After 2 h, the Hoveyda-Grubbs 2$^{nd}$ Generation catalyst (7.3 mg, 11 μmol) was added under argon at 110° C. The Hoveyda-Grubbs 2$^{nd}$ Generation Catalyst (5 mg, 8 μmol) was then added in the interval of 30 min for three times at which point the reaction was complete. The reaction mixture was quenched with ethyl vinyl ether (1.0 μL) and the resulting mixture was allowed to cool to 23° C. The reaction mixture was concentrated under reduced pressure and the crude residue was purified by silica gel chromatography (24 g Isco Rf Gold Column, 0-100% ethyl acetate/iso-hexanes gradient for 10 min and then 100% ethyl acetate for 25 min) to afford the title compound (9.1 mg, 12%) as a pale brown solid. $R_f$=0.20 (ethyl acetate). $^1$H NMR (400 MHz, $CD_3OD$) δ 9.00 (s, 1H), 7.93 (d, J=8.5 Hz, 1H), 7.71 (s, 1H), 7.45 (dd, J=8.5, 1.5 Hz, 1H), 7.36 (s, 1H), 7.20-7.08 (m, 4H), 7.08-7.00 (m, 1H), 6.55 (d, J=15.9 Hz, 1H), 6.40 (ddd, J=15.9, 7.0, 5.1 Hz, 1H), 5.95 (q, J=6.5 Hz, 1H), 5.40 (q, J=7.2 Hz, 1H), 4.60 (d, J=12.1 Hz, 1H), 4.53 (dd, J=8.2, 6.9 Hz, 1H), 4.30 (d, J=12.5 Hz, 1H), 3.70-3.63 (m, 1H), 3.31-3.23 (m, 1H), 2.93 (ddd, J=14.0, 5.1, 1.6 Hz, 1H), 2.69-2.52 (m, 3H), 2.01-1.73 (m, 4H), 1.71-1.54 (m, 2H), 1.59 (d, J=6.7 Hz, 3H), 1.46 (d, J=7.3 Hz, 3H). HPLC Tr=5.108 min. LCMS (m/z) 584.3 [M+H], Tr=2.12 min.

Example 57

Compound 57

Compound 57a

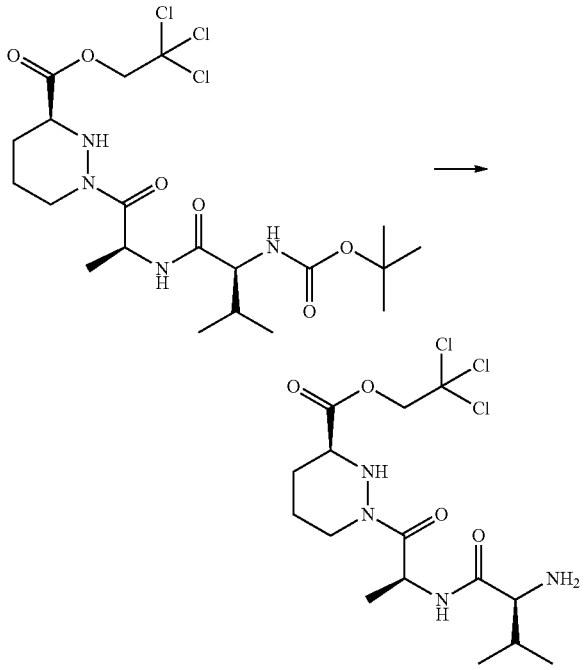

A solution of (S)-1-[(S)-2-((S)-2-tert-butoxycarbonylamino-3-methylbutyrylamino)-propionyl]-hexahydro-pyridazine-3-carboxylic acid 2,2,2-trichloroethyl ester (1.61 g, 3.03 mmol) in dichloromethane (31 mL) was cooled in an ice water bath under argon. Trimethylsilyl trifluoromethanesulfonate (1.23 g, 5.5 mmol) was added dropwise, and the resulting solution was stirred for 2 h. The reaction was quenched with N,N-diisopropylethylamine (1.2 g, 9.2 mmol) and methanol (8.5 mL). The mixture was concentrated in vacuo and was redissolved and concentrated from toluene (2×25 mL). The resulting crude residue containing (S)-1-[(S)-2-((S)-2-amino-3-methyl-butyrylamino)-propionyl]-hexahydro-pyridazine-3-carboxylic acid 2,2,2-trichloro-ethyl ester (1.05 g) was used without further purification.

Compound 57b

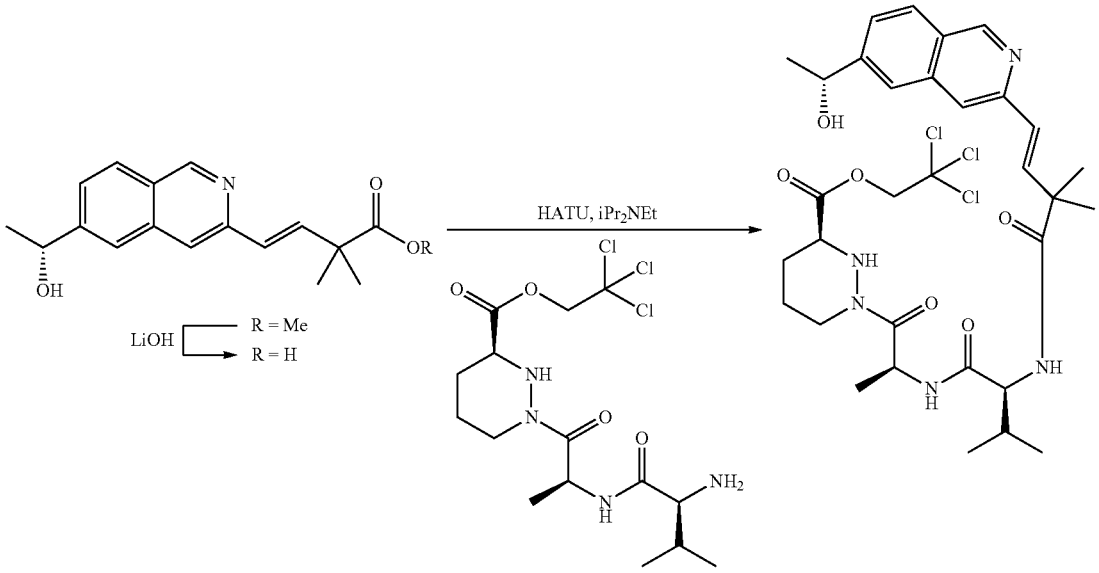

To a solution of (E)-4-[6-((R)-1-hydroxy-ethyl)-isoquinolin-3-yl]-2,2-dimethyl-but-3-enoic acid methyl ester (1.05 g, 3.51 mmol) in tetrahydrofuran (8 mL) was added methanol (4 mL), water (4 mL), and lithium hydroxide hydrate (297 mg, 7.08 mmol). The resulting mixture was stirred for 6 h and was quenched with 1 M aqueous hydrochloric acid (7.2 mL, 7.2 mmol). The resulting solution was concentrated to a crude residue that was redissolved and concentrated from anhydrous methanol (50 mL) followed by toluene (50 mL). The resulting yellow solid (1.3 g, 100%) (E)-4-[6-((R)-1-hydroxy-ethyl)-isoquinolin-3-yl]-2,2-dimethyl-but-3-enoic acid was used without further purification. A portion of crude (E)-4-[6-((R)-1-hydroxy-ethyl)-isoquinolin-3-yl]-2,2-dimethyl-but-3-enoic acid (1.05 g, 2.84 mmol) was dissolved in N,N-dimethylformamide (12 mL) under argon. N,N-diisopropylethylamine (1.85 g, 14.3 mmol) was added followed by 2-(1H-7-azabenzotriazol-1-yl)-1,1,3,3-tetramethyl uronium hexafluorophosphate methanaminium (1.42 g, 3.73 mmol). The resulting mixture was stirred for 3 min, at which time crude 57a was added as a solution in N,N-dimethylformamide (8.5 mL), washing with additional N,N-dimethylformamide (2×5 mL). The reaction was stirred for 40 min and was then diluted with ethyl acetate (200 mL) and water (300 mL). The phases were separated, and the aqueous phase was extracted with ethyl acetate (200 mL). The combined organic phases were washed with water (150 mL), and the second aqueous layer was extracted with ethyl acetate (100 mL). The combined organics were dried over anhydrous sodium sulfate, filtered, and concentrated. The crude residue was purified by silica gel chromatography (35 to 60% acetone in iso-hexanes, continuous gradient) to afford the title compound (1.51 g, 71% over 2 steps) as a colorless oil. $R_F$ 0.5 (50% acetone in iso-hexanes).

Compound 57

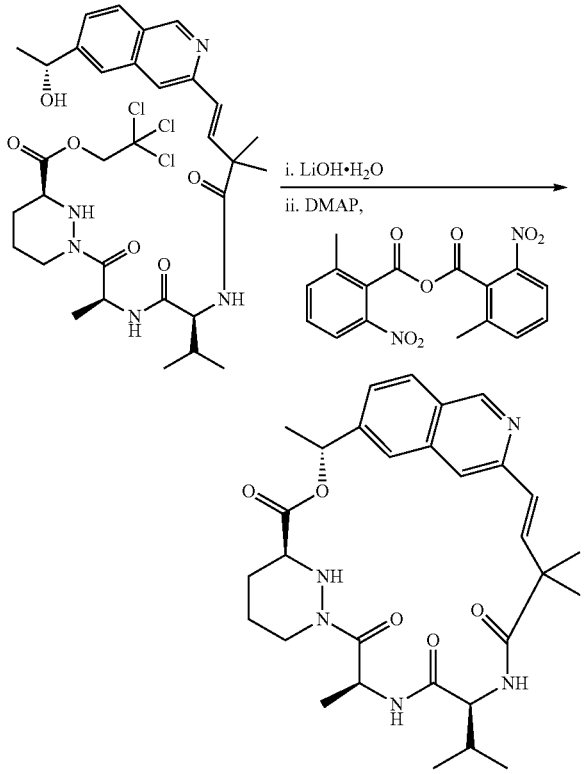

To a solution of 57b (1.50 g, 2.15 mmol) in tetrahydrofuran (20 mL) was added methanol (10 mL), water (10 mL), and lithium hydroxide hydrate (365 mg, 8.7 mmol). The mixture was stirred for 75 min at ambient temperature and was then quenched with aqueous 1 M hydrochloric acid (8.8 mL, 8.8 mmol). The resulting solution was concentrated in vacuo, and the crude product was twice dissolved and concentrated from methanol (40 mL) and suspended and concentrated from acetonitrile (6×30 mL) to afford 1.71 g of a colorless solid that was used without further purification. Under argon, 2-methyl-6-nitrobenzoic anhydride (1.85 g, 5.37 mmol) and 4-dimethylaminopyridine (1.97 g, 16.1 mmol) were dissolved in 1,2-dichloroethane (700 The resulting solution was heated to 50° C., and the crude seco-acid was added dropwise via syringe as a solution in N,N-dimethylformamide (22 mL) over 6 h. An additional wash with N,N-dimethylformamide (1.5 mL) was then added in the same manner over 15 min. After stirring an additional 1.25 h, the reaction mixture was concentrated to a final volume of 200 mL in vacuo. The solution was washed with water (250 mL), and the aqueous phase was extracted with dichloromethane (150 mL). The organic phase was dried over anhydrous magnesium sulfate, filtered, and concentrated. The resulting residue was dissolved in ethyl acetate (200 mL) and was washed with water (150 mL). The aqueous phase was extracted with ethyl acetate (150 mL). The combined organics were washed with water (100 mL), and the second aqueous phase was extracted with ethyl acetate (100 mL). The combined organics were dried over anhydrous magnesium sulfate, filtered and concentrated. The crude residue was purified by silica gel chromatography (35 to 65% acetone in iso-hexanes continuous gradient) to afford 445 mg of the pure title compound as an amorphous white solid along with 389 mg of impure product. The impure fractions were purified by recrystallization from acetone:iso-hexanes to afford an additional 173.5 mg of pure title compound (total: 618.5 mg, 52%). $R_F$ 0.5 (50% acetone in iso-hexanes). $^1$H NMR (400 MHz, $CD_3OD$) δ 9.13 (s, 1H), 8.04 (d, J=8.5 Hz, 1H), 7.89 (s, 1H), 7.55 (dd, J=8.5, 1.6 Hz, 1H), 7.53 (s, 1H), 6.73-6.34 (m, 2H), 6.03 (q, J=6.6 Hz, 1H), 5.63 (q, J=7.2 Hz, 1H), 4.67 (d, J=12.2 Hz, 1H), 4.47-4.21 (m, 2H), 3.81-3.73 (m, 1H), 2.76-2.64 (m, 1H), 2.08-1.81 (m, 3H), 1.80-1.58 (m, 8H), 1.51 (s, 3H), 1.35 (s, 3H), 0.98 (d, J=6.7 Hz, 3H), 0.93 (d, J=6.7 Hz, 3H). LCMS (m/z) 550.2 [M+H], Tr=2.74 min.

Example 58

Compound 58

Compound 58a

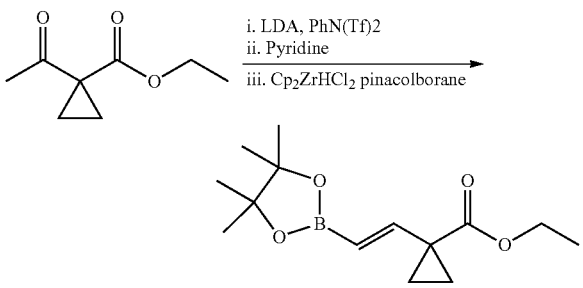

A solution of N,N-diisopropylamine (2.51 g, 24.8 mmol) in tetrahydrofuran (150 mL) under argon was cooled in an ice water bath. A solution of n-butyllithium in hexanes (2.5 M, 9.7 mL, 24 mmol) was added dropwise over 2 min, and the resulting solution was stirred for 15 additional minutes. The solution was then cooled to −78° C. via $CO_{2(s)}$:acetone bath, and ethyl 1-acetylcyclopropanecarboxylate (3.47 g, 22.2 mmol) was added dropwise over 2 min. The solution was stirred for an additional 20 min, and N-Phenyl-bis (trifluoromethanesulfonimide) (8.4 g, 23.5 mmol) was added as a solution in tetrahydrofuran (24 mL) via canula over 5 min, washing with additional portions of tetrahydrofuran (2×5 mL). The resulting solution was removed from the cold bath. After an additional 30 min, the reaction mixture was concentrated in vacuo and was diluted with diethyl ether (200 mL). The organic phase was washed with 1 M aqueous sodium hydroxide (1×100 mL, 1×30 mL), dried over anhydrous magnesium sulfate, filtered, and concentrated to afford 6.6 g of a crude oil that was used without further purification. A solution of the crude material from the previous step in anhydrous pyridine (11 mL) was heated to 90° C. After 16.5 h, the reaction mixture was diluted with diethyl ether (200 mL) and 3 M hydrochloric acid (100 mL) and the phases were separated. The organic phase was washed with 3 M hydrochloric acid (50 mL) and 1 M sodium hydroxide (50 mL), dried over magnesium sulfate, filtered, and concentrated to afford 2.2 g of a crude liquid that was used without further purification. To an argon-flushed vessel containing zirconocene dichloride (410 mg, 1.6 mmol) was added a solution of the crude product from the previous step (2.2 g, ca. 16 mmol) and pinacolborane (3.1 g, 24 mmol) in dichloromethane (8 mL). After 116 h, the stirred reaction mixture was diluted with ethyl acetate (50 mL) and was quenched by dropwise addition of water. The mixture was further diluted with water (50 mL), and the phases were separated. The aqueous phase was extracted with ethyl acetate (2×50 mL). The combined organic phases were dried over magnesium sulfate, filtered, and concentrated to a crude residue that was purified by silica gel chromatography (5 to 20% ethyl acetate in iso-hexanes, continuous gradient) to afford the title compound (1.26 g, 21% over 3 steps) as an oil that crystallized on standing at −15° C.

Compound 58b

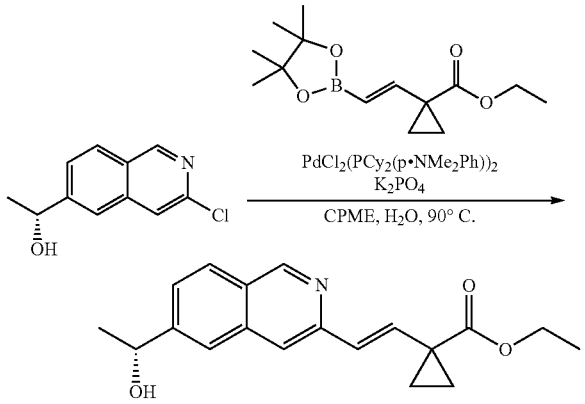

To a round-bottomed flask was added (R)-1-(3-chloroisoquinolin-6-yl)ethanol (204 mg, 0.982 mmol), 58a (314 mg, 1.18 mmol), $PdCl_2(PCy_2(p\text{-}NMe_2Ph))_2$ (bis[(dicyclohexyl)(4-dimethylaminophenyl)phosphine]palladium(II) chloride) (40 mg, 0.049 mmol) and potassium phosphate tribasic (680 mg, 3.2 mmol). The vessel was sealed with a septum cap and was flushed with argon. Cyclopentyl methyl ether (2.8 mL) and water (1.2 mL) were added, and the resulting biphasic mixture was vigorously stirred in an oil bath pre-heated to 90° C. After 6.75 h, the reaction was cooled to ambient temperature and was diluted with ethyl acetate (50 mL) and water (40 mL). The phases were separated, and the aqueous phase was extracted with ethyl acetate (50 mL). The combined organic phases were dried over magnesium sulfate, filtered, and concentrated to afford a crude residue that was purified by silica gel chromatography (35 to 60% ethyl acetate in iso-hexanes) to afford the title compound (266 mg, 85%).

Compound 58c

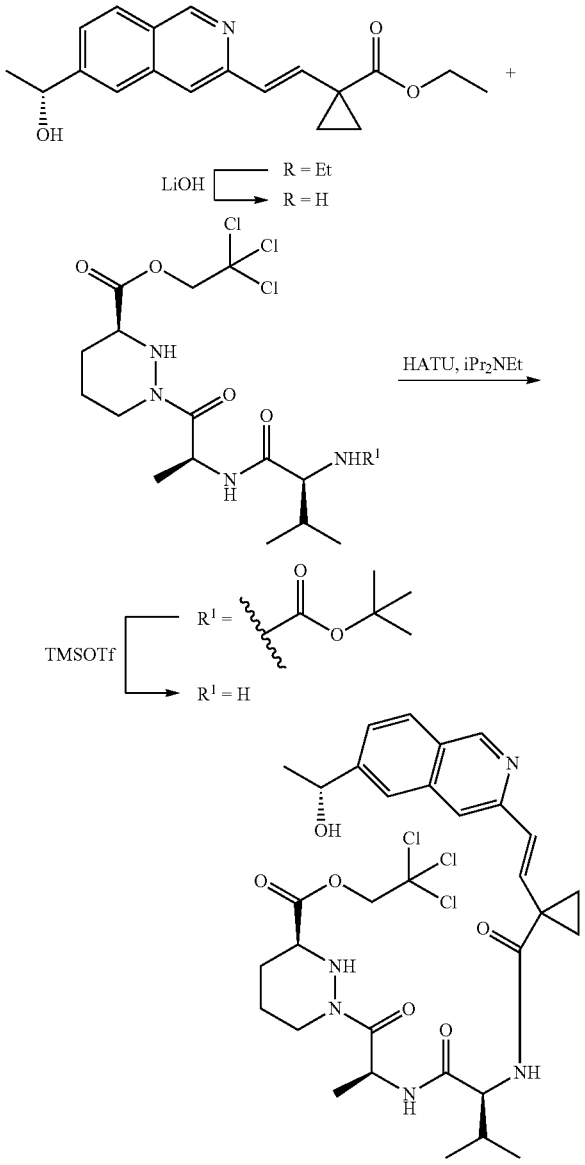

To a solution of 58b (266 mg, 0.854 mmol) in tetrahydrofuran (2 mL) was added methanol (1 mL), water (1 mL), and lithium hydroxide hydrate (70.8 mg, 1.69 mmol). The resulting mixture was stirred for 3 h and was then quenched with 1 M aqueous hydrochloric acid (1.8 mL, 1.8 mmol). Volatiles were removed in vacuo, and the resulting solid was suspended in toluene. Volatiles were removed in vacuo, and the resulting yellow solid 1-{(E)-2-[6-((R)-1-hydroxy-ethyl)-isoquinolin-3-yl]vinyl}-cyclopropanecarboxylic acid was used without further purification. A solution of (S)-1-[(S)-2-((S)-2-tert-butoxycarbonylamino-3-methylbutyry-lamino)-propionyl]-hexahydropyridazine-3-carboxylic acid 2,2,2-trichloroethyl ester (486 mg, 0.914 mmol) in dichloromethane (9.4 mL) was cooled in an ice water bath under argon. Trimethylsilyl trifluoromethanesulfonate (370 mg, 1.7 mmol) was added dropwise, and the resulting solution was stirred for 4 h. The reaction was quenched with N,N-diisopropylethylamine (360 mg, 2.7 mmol) and methanol (2.5 mL). The mixture was concentrated in vacuo and the resulting residue was redissolved and concentrated from toluene (2×15 mL). The resulting crude amine was used without further purification. To a solution of crude 1-{(E)-2-[6-((R)-1-hydroxy-ethyl)-isoquinolin-3-yl]-vinyl}-cyclopropanecarboxylic acid (ca. 0.854 mmol) in N,N-dimethylformamide (3.5 mL) under argon was added N,N-diisopropylethylamine (560 mg, 4.3 mmol) and 2-(1H-7-azabenzotriazol-1-yl)-1,1,3,3-tetramethyl uronium hexafluorophosphate methanaminium (427 mg, 1.12 mmol). The resulting mixture was stirred for 2 min, at which time crude (S)-1-[(S)-2-((S)-2-amino-3-methyl-butyrylamino)-propionyl]-hexahydro-pyridazine-3-carboxylic acid 2,2,2-trichloro-ethyl ester from the previous step was added as a solution in N,N-dimethylformamide (2.5 mL), washing with two additional portions of N,N-dimethylformamide (1.5 mL each). The reaction was stirred for 45 min and was diluted with ethyl acetate (100 mL) and water (150 mL). The phases were separated, and the aqueous phase was extracted with ethyl acetate (100 mL). The combined organic phases were washed with water (75 mL), and the second aqueous layer was extracted with ethyl acetate (75 mL). The combined organics were dried over anhydrous magnesium sulfate, filtered, and concentrated. The crude residue was purified by silica gel chromatography (35 to 60% acetone in iso-hexanes, continuous gradient) to afford title compound (467 mg, 78% over 2 steps) as a colorless oil.

Compound 58

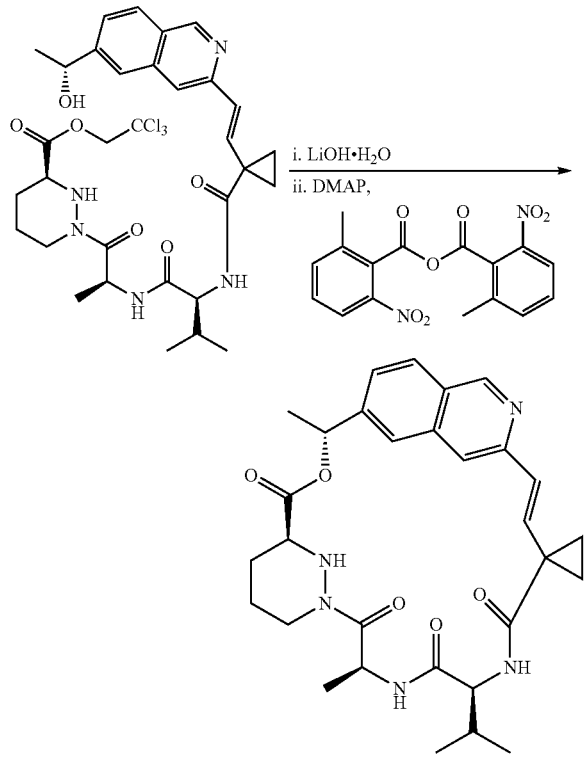

To a solution of 58c (467 mg, 0.67 mmol) in tetrahydrofuran (6 mL) was added methanol (3 mL), water (3 mL), and lithium hydroxide hydrate (113 mg, 2.69 mmol). The mixture was stirred for 1.75 h at ambient temperature and was quenched with aqueous 1 M hydrochloric acid (2.8 mL, 2.8 mmol). The resulting solution was concentrated in vacuo, and the crude product was suspended and concentrated from acetonitrile (5×20 mL) to afford 530 mg of a pale yellow solid that was used without further purification. Under argon, 2-methyl-6-nitrobenzoic anhydride (283 mg, 0.82 mmol) and 4-dimethylaminopyridine (307 mg, 2.51 mmol) were dissolved in 1,2-dichloroethane (100 mL). The resulting solution was heated to 50° C., and a portion of the crude seco-acid (260 mg, ca. 0.33 mmol) was added dropwise via syringe as a solution in N,N-dimethylformamide (3.5 mL) and 1,2-dichloroethane (10 mL) over 6 h. An additional wash of N,N-dimethylformamide (1 mL) was then added in the same manner. After stirring an additional 1.25 h, the reaction mixture was concentrated to ~35 mL in vacuo. The solution was diluted with ethyl acetate (100 mL) and washed with water (100 mL). The aqueous phase was extracted with ethyl acetate (75 mL), and the combined organic phases were washed with water (50 mL). The second aqueous phase was extracted with ethyl acetate (50 mL), and the combined organics were dried over magnesium sulfate, filtered and concentrated. The crude residue was purified by silica gel chromatography (35 to 60 and then to 100% acetone in iso-hexanes) to afford 101 mg of impure product containing the title compound. This material was purified by silica gel chromatography (0 to 5% methanol in ethyl acetate) followed by reverse-phase HPLC (5 to 100% acetonitrile/water+0.1% trifluoroacetic acid) to afford the title compound as its trifluoroacetic acid salt (37 mg, 17% over 2 steps). $^1$H NMR (400 MHz, $CD_3OD$) δ 9.55 (s, 1H), 8.37 (d, J=8.6 Hz, 1H), 8.06 (s, 1H), 7.89 (s, 1H), 7.85 (d, J=8.6 Hz, 1H), 6.69 (d, J=16.4 Hz, 1H), 6.54 (d, J=16.4 Hz, 1H), 6.11 (q, J=6.7 Hz, 1H), 5.75-5.67 (m, 1H), 4.46-4.36 (m, 1H), 4.36-4.28 (m, 1H), 3.90-3.78 (m, 1H), 2.80-2.68 (m, 1H), 2.05-1.86 (m, 3H), 1.80-1.68 (m, 1.66-1.57 (m, 5H), 1.40-1.30 (m, 1H), 1.30-1.21 (m, 1H), 1.03-0.93 (m, 4H), 0.90 (d, J=6.7 Hz, 3H). LCMS (m/z) 548.4 [M+H], Tr=2.79 min.

Example 59

Compound 59

Compound 59a

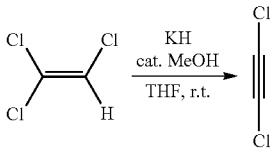

Into an oven dried, argon purged flask were placed oil-free potassium hydride (from 1740 mg of ca. 30% dispersion in mineral oil, ca. 13 mmol), anhydrous tetrahydrofuran (10 mL) and hexane (1 mL). The flask was repurged with argon and trichloroethylene (900 μL, 1.32 g, 10 mmol) was added followed by dry methanol (10 μL, 7.9 mg, 0.25 mmol). This mixture was stirred at RT for two h. After this time, hexane (10 mL) was added and the resulting solution was immediately used in the subsequent step.

Compound 59b

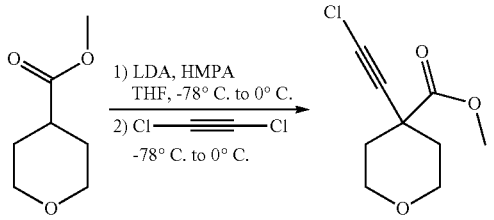

Into an oven dried, argon purged flask tetrahydrofuran (50 mL) was added and the solution was cooled with an ice bath. A 1.8 M solution of lithium diisopropylamide (7.2 mL, 13 mmol) in tetrahydrofuran/heptane/ethylbenzene was added. The resulting solution was cooled to −78° C., and treated dropwise with methyl tetrahydro-2H-pyran-4-carboxylate (1.20 mL. 1.30 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloro-ethyne (ca. 10 mmol). The reaction mixture was stirred at −78° C. for 30 min and then allowed to warm to RT. After 4 h at RT, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-15% ethyl acetate in iso-hexanes) to afford the title compound (1.22 g, 67%) as a colorless oil. $R_f$=0.48, 30% ethyl acetate in iso-hexanes, phosphomolybdic acid in ethanol.

Compound 59c

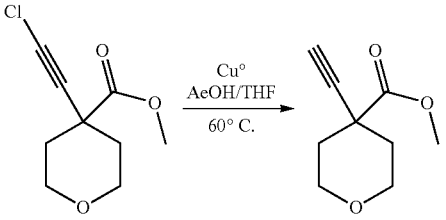

59b (1.01 g, 5 mmol) and copper powder (1.6 g, 25 mmol) were suspended in tetrahydrofuran (100 mL). Acetic acid (15 mL) was added and the reaction mixture was heated to 60° C. for 3 h. After this time, the reaction mixture was poured onto water (copper powder was filtered off with the use of the filtration paper) and extracted with diethyl ether (3×50 mL). The combined organic extracts were washed with saturated solution of ammonium chloride (3×50 mL), with saturated solution of sodium bicarbonate (2×50 mL) and with water (50 mL). This water phase was extracted with diethyl ether (50 mL). Combined organic extracts were washed with brine (50 mL) and dried over magnesium sulfate, filtered through a 2 cm layer of silica gel (silica gel layer was washed with 50 mL of ethyl acetate), and concentrated under reduced pressure. After drying under high vacuum for one day, the title compound was isolated (0.84 g, quantitative yield) as a colorless oil. $R_f$=0.37, 30% ethyl acetate in iso-hexanes, phosphomolybdic acid in ethanol.

Compound 59d

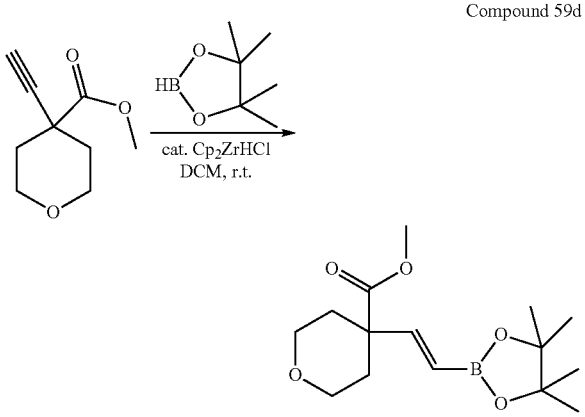

Into an oven dried, argon purged flask were placed 59c (0.84 g, 5 mmol) and dichloromethane (2 mL). This mixture was cooled to 0° C. Pinacolborane (0.96 g, 7.5 mmol) was then added dropwise via syringe. After the mixture was stirred for 1 min., it was transferred by a syringe into another oven dried, argon purged flask, immersed in an ice bath and protected from light, containing zirconocene dichloride (0.13 g, 0.5 mmol). An additional portion of dichloromethane (2 mL) was used to complete the quantitative transfer. After this the mixture was warmed to ambient temperature, it was stirred in the dark for 72 h to achieve full The reaction mixture was diluted with ethyl acetate (50 mL) and carefully quenched with water (1 ml). Water (50 mL) was added and the organic and aqueous phases were separated. The aqueous phase was extracted with ethyl acetate (3×40 mL). The combined organic phases were dried over magnesium sulfate, filtered and evaporated to afford the crude residue which was dissolved in iso-hexanes (50 mL) and extracted with 5-10% aqueous methanol (3×50 mL) and with brine (50 mL). The hexane phase was dried over magnesium sulfate. The title compound was isolated as the white crystalline compound after evaporation (1.42 g, 93%). $R_f$=0.38, 30% ethyl acetate in iso-hexanes, iodine vapor.

Compound 59e

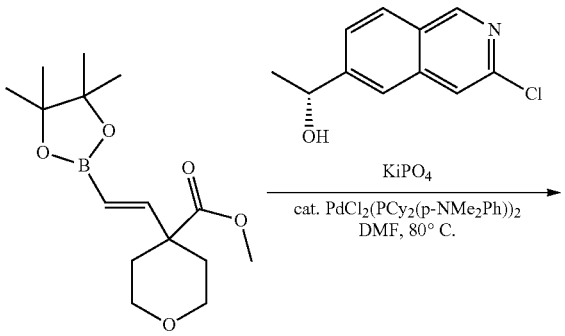

-continued

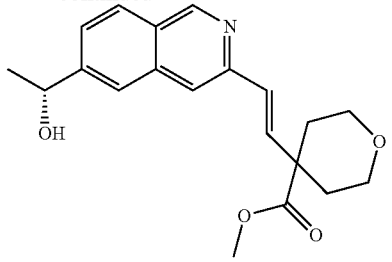

Into an oven dried, argon purged flask were placed (R)-1-(3-chloro-isoquinolin-6-yl)-ethanol (0.83 g, 4 mmol), 59d (1.40 g, 4.7 mmol), $PdCl_2(PCy_2(p\text{-}NMe_2Ph))_2$ (bis[(dicyclohexyl)(4-dimethylaminophenyl)phosphine]palladium(II) chloride) (173 mg, 0.21 mmol) and potassium phosphate tribasic (2.64 g, 12.4 mmol). The flask was sealed with a septum cap and was re-purged with argon. N,N-Dimethylformamide (10 mL) was added and, and the resulting reaction mixture was vigorously stirred in an oil bath pre-heated to 80° C. After 2 h, the reaction was cooled to ambient temperature and was diluted with ethyl acetate (100 mL) and water (100 mL). The phases were separated, and the aqueous phase was extracted with ethyl acetate (2×50 mL). The combined organic phases were dried over magnesium sulfate, filtered, and concentrated to afford a crude residue that was purified by silica gel chromatography (gradient from 0-40% ethyl acetate and methanol (4/1) in iso-hexanes) to afford the title compound (1.06 g, 78%) as a colorless oil after evaporation. $R_f$=0.48, iso-hexanes/ethyl acetate/methanol (6/4/1).

Compound 59f

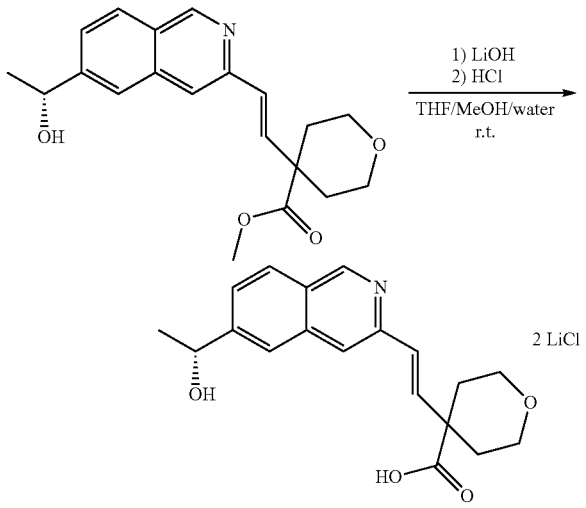

To a solution of 59e (1.02 g, 3 mmol) in tetrahydrofuran (8 mL) was added methanol (4 mL), water (4 mL) and lithium hydroxide hydrate (0.15 g, 6.3 mmol). The resulting mixture was stirred at RT for 10 h and quenched with 1 M hydrochloric acid (6.5 mL, 6.5 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and used without further purification (1.24 g, quantitative yield).

Compound 59g

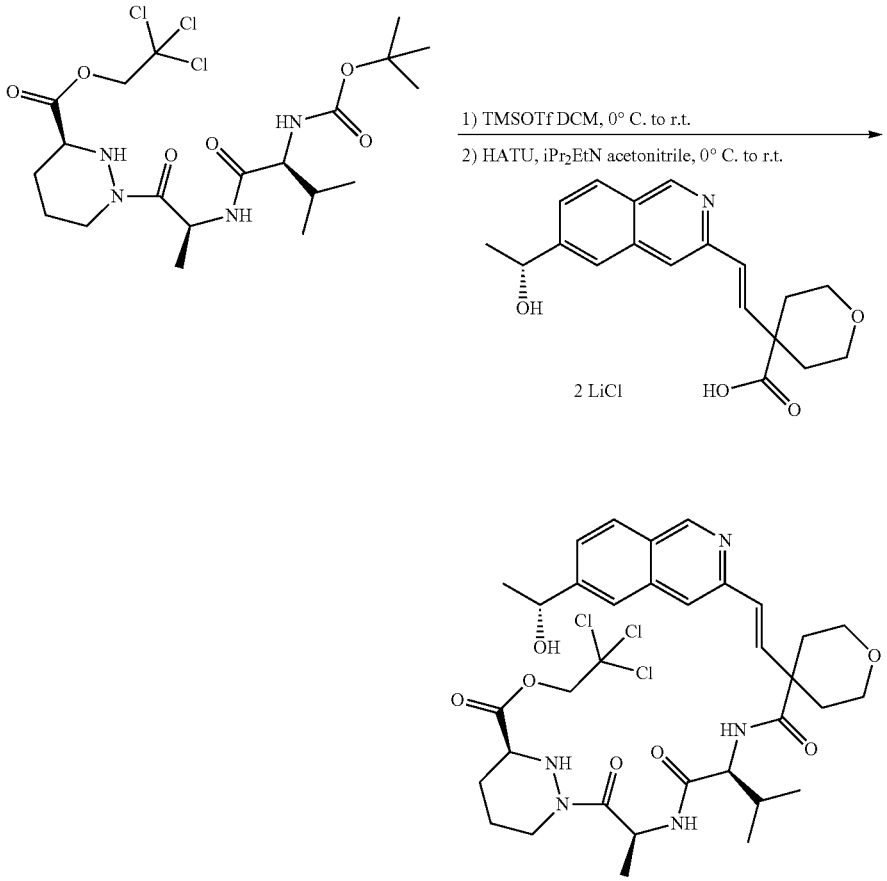

A solution of 1e (0.53 g, 1 mmol) in dichloromethane (10 mL) was cooled in an ice water bath. Trimethylsilyl trifluoromethanesulfonate (0.69 g, 1.80 mmol) was added dropwise at 0° C. under argon, and the resulting solution was stirred at RT for 30 min. The reaction mixture was evaporated to dryness and the resulting crude residue was dissolved in anhydrous acetonitrile (12 mL) under argon. The reaction mixture was stirred at 0° C., 59f (371 mg, 0.9 mmol) and N,N-diisopropylethylamine (517 mg, 4 mmol) were added followed by 2-(1H-7-azabenzotriazol-1-yl)-1,1,3,3-tetramethyl uronium hexafluorophosphate methanaminium (570 mg, 1.5 mmol). The reaction mixture was stirred at RT for 48 h. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (560 mg, 84%) as a white solid after evaporation. $R_f$=0.13, iso-hexanes/ethyl acetate/methanol (6/4/1).

Compound 59

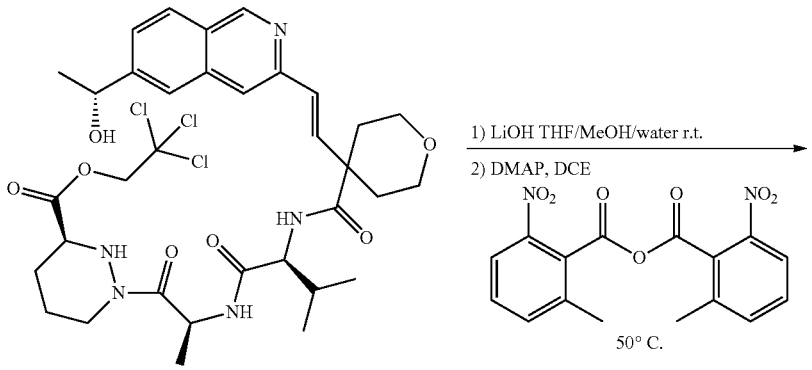

-continued

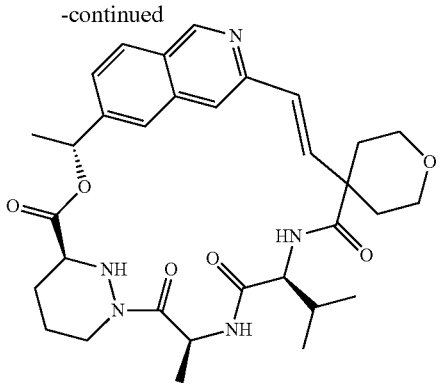

To a solution of 59 g (371 mg, 0.5 mmol) in tetrahydrofuran (8 mL) was added methanol (4 mL), water (4 mL) and lithium hydroxide hydrate (36 mg, 1.5 mmol). The mixture was stirred for 2 h at ambient temperature and was quenched with aqueous 1 M hydrochloric acid (1.6 mL, 1.6 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification (365 mg, quantitative yield). Into oven dried, argon purged flask were placed 2-methyl-6-nitrobenzoic anhydride (258 mg, 0.75 mmol), 4-dimethylaminopyridine (275 mg, 2.25 mmol) and anhydrous 1,2-dichloroethane (150 mL). The resulting solution was heated at 50° C., and the crude seco-acid was added dropwise via syringe as a solution in dry N,N-dimethylformamide (10 mL) over 12 h. An additional portion of dry N,N-dimethylformamide (2×5 mL) was used to complete the quantitative transfer. After stirring for additional 2 h at 50° C., the reaction mixture was transferred to a separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with water (100 mL, 5 mL of brine was added to support the separation). The aqueous phase was extracted with ethyl acetate (50 mL). Combined organic extracts were washed with water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-40% ethyl acetate and methanol (4/1) in iso-hexanes) to afford the title compound (72 mg, 24%) as a white solid after evaporation. $R_f$=0.42, 10% methanol in dichloromethane. $^1$H NMR (400 MHz, $CD_3OD$): δ 9.04 (s, 1H), 7.95 (d, J=8.5 Hz, 1H), 7.76 (s, 1H), 7.47 (dd, J=8.5, 1.5 Hz, 1H), 7.31 (s, 1H), 6.43 (m, 2H), 5.93 (q, J=6.6 Hz, 1H), 5.44-5.36 (m, 1H), 4.33-4.23 (m, 2H), 3.84 (dt, J=11.6, 4.1 Hz, 1H), 3.76-3.69 (m, 1H), 3.68-3.61 (m, 2H), 3.48 (m, 1H), 2.65-2.56 (m, 1H), 2.16-2.07 (m, 2H), 2.03-1.93 (m, 1H), 1.91-1.82 (m, 2H), 1.79e (m, 1H), 1.67-1.62 (m, 3H), 1.59 (d, J=6.6 Hz, 3H), 1.51 (d, J=7.2 Hz, 3H), 0.90 (d, J=6.7 Hz, 3H), 0.85 (d, J=6.7 Hz, 3H). LCMS (m/z) 592.3 [M+H], Tr=3.12 min.

Example 60

Compound 60

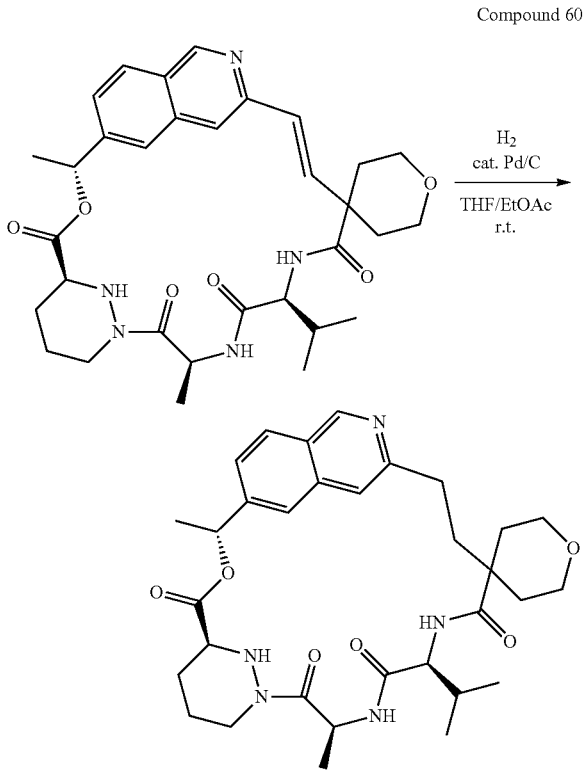

A solution of Compound 59 (10 mg, 0.017 mmol) in a mixture of ethyl acetate (4 mL) and tetrahydrofuran (4 mL)

containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (10 mg, quantitative yield) as a white solid. $R_f$=0.47, 10% methanol in dichloromethane. $^1$H NMR (400 MHz, $CD_3OD$): δ 9.02 (s, 1H), 7.94 (d, J=8.5 Hz, 1H), 7.81 (s, 1H), 7.44 (d, J=8.5 Hz, 1H), 7.20 (s, 1H), 6.02 (q, J=6.5 Hz, 1H), 5.78-5.71 (m, 1H), 5.24 (m, 1H), 4.33-4.23 (m, 2H), 3.83-3.61 (m, 6H), 3.52 (m, 1H), 2.71-2.66 (m, 1H), 2.43-2.36 (m, 2H), 2.14-2.05 (m, 2H), 2.08-1.91 (m, 1H), 1.90-1.82 (m, 2H), 1.76 (m, 1H), 1.67-1.62 (m, 2H), 1.57 (d, J=6.6 Hz, 3H), 1.54 (d, J=7.2 Hz, 3H), 0.96 (d, J=6.7 Hz, 3H), 0.88 (d, J=6.7 Hz, 3H). LCMS (m/z) 594.3 [M+H], Tr=2.72 min.

Example 61

Compound 61

Compound 61a

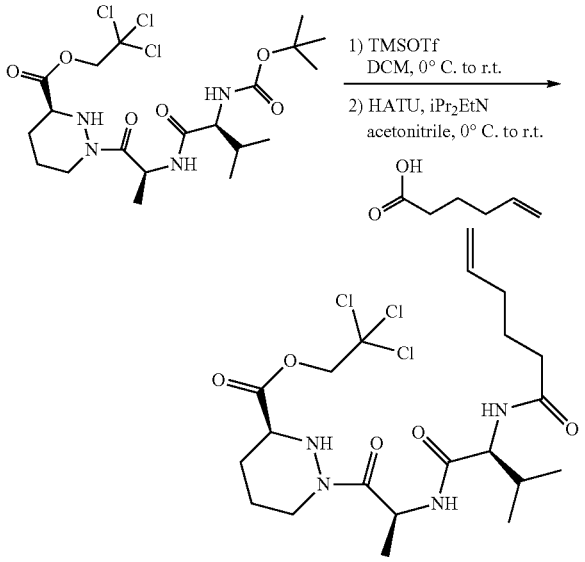

A solution of 1e (1064 mg, 2 mmol) in dichloromethane (30 mL) was cooled in an ice water bath. Trimethylsilyl trifluoromethanesulfonate (666 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., hex-5-enoic acid (251 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (200 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (864 mg, 82%) as a white solid after evaporation. $R_f$=0.35, iso-hexanes/ethyl acetate/methanol (6/4/1).

Compound 61b

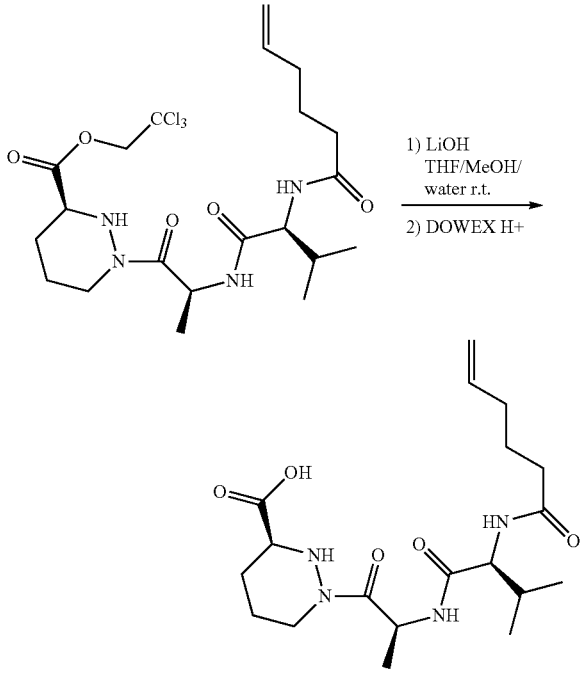

To a solution of 61a (830 mg, 1.57 mmol) in tetrahydrofuran (40 mL) were added water (10 mL) and lithium hydroxide hydrate (57 mg, 2.38 mmol). The mixture was stirred for 2 h at ambient temperature and then filtered through a 5 cm layer of DOWEX D50×8 resin in $H^+$ cycle (resin firstly washed with water). Resin was washed with additional water (50 mL). Filtrates were collected, concentrated under reduced pressure and co-evaporated twice with toluene (10 mL). After drying under high vacuum for one day, the title compound was isolated (590 mg, 95%) as a white solid. $R_f$=0.4, 30% methanol in dichloromethane.

Compound 61c

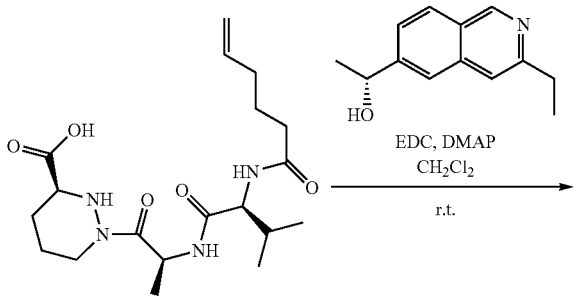

-continued

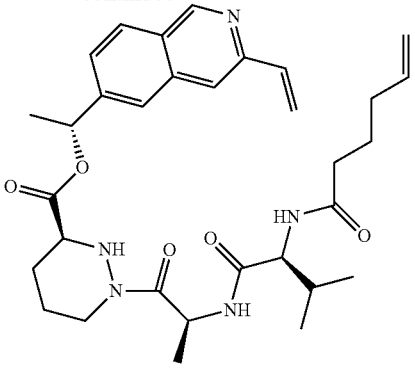

Into an oven dried, argon purged flask were added 61b (238 mg, 0.60 mmol) and (R)-1-(3-vinyl-isoquinolin-6-yl)-ethanol (120 mg, 0.6 mmol). The flask was sealed and the reaction mixture was repurged twice with argon. Anhydrous dichloromethane (10 mL) was added and the reaction mixture was repurged twice with argon. N-(3-dimethylamino-propyl)-N'-ethylcarbodiimide hydrochloride (148 mg, 0.77 mmol) was added followed by 4-dimethylaminopyridine (67 mg, 0.55 mmol). Reaction mixture was quickly repurged twice with argon and was stirred at RT for 12 h. The reaction mixture was diluted with dichloromethane (100 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (307 mg, 89%) as a white solid after evaporation. $R_f$=0.29, iso-hexanes/ethyl acetate/methanol (6/4/1).

Compound 61

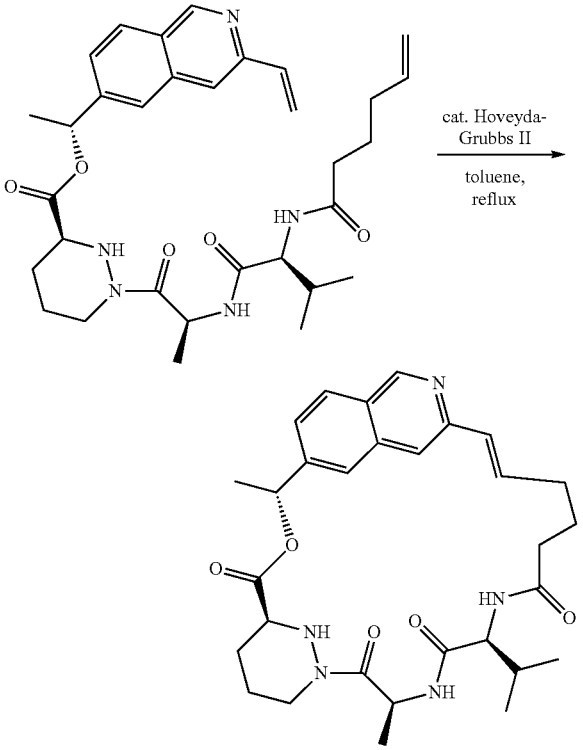

A solution of 61c (209 mg, 0.362 mmol) in toluene (150 mL) was stirred at RT under argon. Hoveyda-Grubbs 2$^{nd}$ generation catalyst (23 mg, 0.036 mmol) was added and the reaction mixture was heated at reflux under argon for 30 min. Reaction mixture was cooled to RT and ethyl acetate (50 mL) was added. This solution was washed twice with aqueous solution of tris(hydroxymethyl)phosphine (372 mg, 3 mmol in 100 mL of water), with water (2×50 mL) and with brine (50 mL). The organic phase was dried over magnesium sulfate, filtered and evaporated. The residue was purified by silica gel chromatography (gradient from 0-40% ethyl acetate and methanol (4/1) in iso-hexanes) to afford the title compound (125 mg, 63%) as a white solid after evaporation. $R_f$=0.25, iso-hexanes/ethyl acetate/methanol (6/4/1). $^1$H NMR (400 MHz, $CD_3OD$): δ 9.00 (s, 1H), 7.91 (d, J=8.4 Hz, 1H), 7.77 (s, 1H), 7.41 (d, J=8.4 Hz, 1H), 7.23 (s, 1H), 6.64 (m, 1H), 6.29 (d, J=15.4 Hz, 1H), 5.97 (q, J=5.9 Hz, 1H), 5.53 (q, J=7.0 Hz, 1H), 4.37-4.18 (m, 2H), 3.65 (d, J=9.8 Hz, 1H), 2.65 (t, J=12.3 Hz, 1H), 2.36-2.18 (m, 4H), 1.98 (m, 1H), 1.94-1.73 (m, 3H), 1.71-1.57 (m, 3H), 1.55 (d, J=5.6 Hz, 6H), 0.83 (d, J=6.6 Hz, 3H), 0.78 (d, J=6.6 Hz, 3H). LCMS (m/z) 550.2 [M+H], Tr=2.55 min.

Example 62

Compound 62

Compound 62

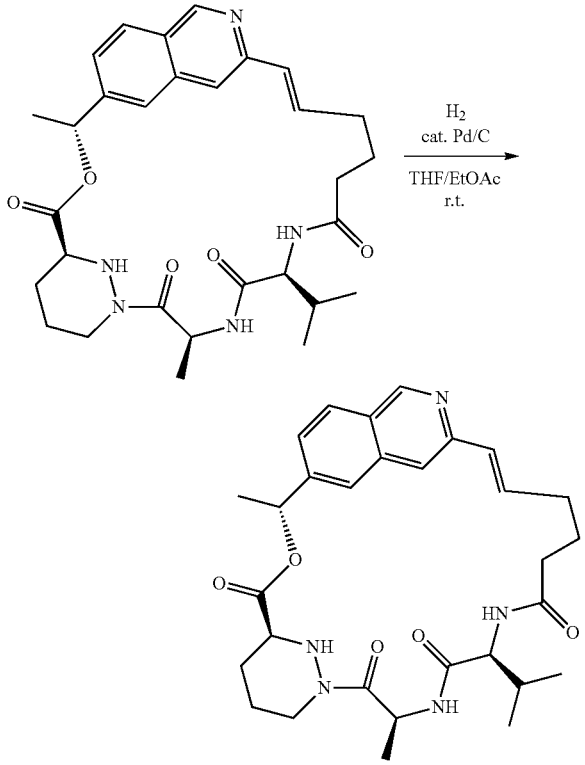

A solution of Compound 61 (10 mg, 0.018 mmol) in a mixture of ethyl acetate (4 mL) and tetrahydrofuran (4 mL) containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (9 mg, 89%) as a white solid. $R_f$=0.16, iso-hexanes/ethyl acetate/methanol (6/4/1). $^1$H NMR (400 MHz, $CD_3OD$) δ 9.02 (s, 1H), 7.93 (d, J=8.7 Hz, 1H), 7.62 (s, 1H), 7.47 (s, 1H), 7.44 (d, J=8.7 Hz, 1H), 6.02-5.93 (m, 1H), 5.39 (m, 1H), 4.03 (m, 1H), 3.69 (m, 1H), 2.84 (m, 2H), 2.27 (s, 1H), 2.10 (m, 1H), 1.97 (m, 1H), 1.85 (m, 2H), 1.76 (m, 2H), 1.62 (m, 4H), 1.54 (d, J=5.1 Hz, 3H), 1.39 (d, J=6.6 Hz, 3H), 1.19 (m, 4H), 0.78 (d, J=5.0 Hz, 3H), 0.73 (d, J=5.8 Hz, 3H). LCMS (m/z) 552.3 [M+H], Tr=2.10 min.

Example 63

Compound 63

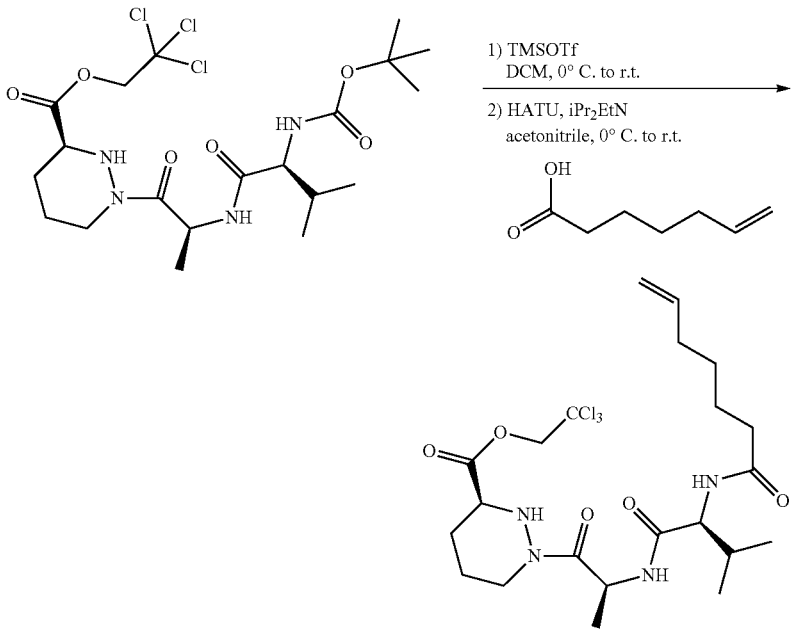

Compound 63a

A solution of 1e (1064 mg, 2 mmol) in dichloromethane (30 mL) was cooled in an ice water bath. Trimethylsilyl trifluoromethanesulfonate (666 mg, 3 mmol) was added dropwise at 0° C. under argon, and the resulting solution was stirred at RT for 30 min. The reaction mixture was evaporated to dryness and the resulting crude residue was dissolved in anhydrous acetonitrile (25 mL) under argon. The reaction mixture was stirred at 0° C., hept-6-enoic acid (281 mg, 2.2 mmol) and N,N-diisopropylethylamine (1034 mg, 8 mmol) were added followed by 2-(1H-7-azabenzotriazol-1-yl)-1,1,3,3-tetramethyl uronium hexafluorophosphate methanaminium (1065 mg, 2.8 mmol). The reaction mixture was stirred at RT for 48 h. The solvent was evaporated, the residue was dissolved in ethyl acetate (200 mL) and the solution was washed twice with 20% water solution of citric acid (2×150 mL), water (150 mL) and brine (150 mL), dried over magnesium sulfate, filtered and evaporated. The residue was purified by silica gel chromatography (gradient from 0-40% ethyl acetate+methanol (4/1) in iso-hexanes) to afford the title compound (817 mg, 75%) as a white solid after evaporation. $R_f$=0.37, iso-hexanes/ethyl acetate/methanol (6/4/1).

Compound 63b

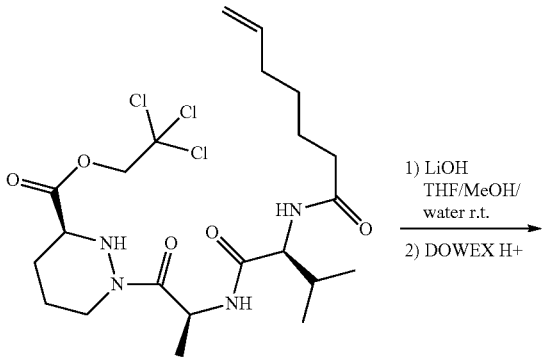

-continued

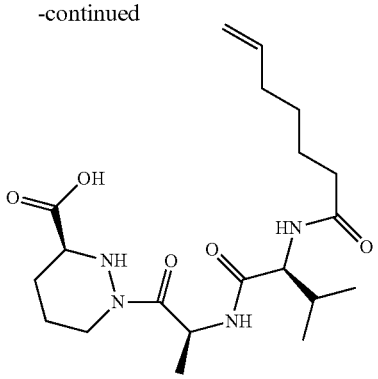

To a solution of 63a (790 mg, 1.46 mmol) in tetrahydrofuran (40 mL) was added water (10 mL) and lithium hydroxide hydrate (52 mg, 2.19 mmol). The mixture was stirred for 2 h at ambient temperature and then filtered through a 5 cm layer of DOWEX D50×8 resin in $H^+$ cycle (resin firstly washed with water). Resin was washed with additional water (50 mL). The filtrates were collected, concentrated under reduced pressure and co-evaporated twice with toluene (10 mL). After drying under high vacuum for one day, the title compound was isolated (583 mg, 97%) as a white solid. $R_f$=0.4, 30% methanol in dichloromethane.

Compound 63c

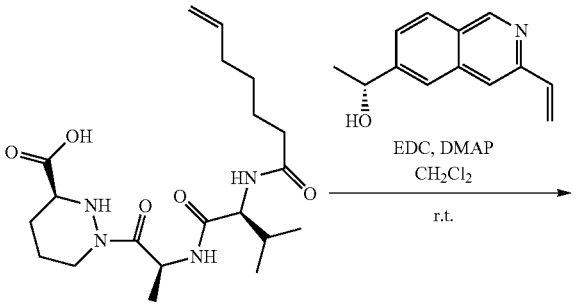

-continued

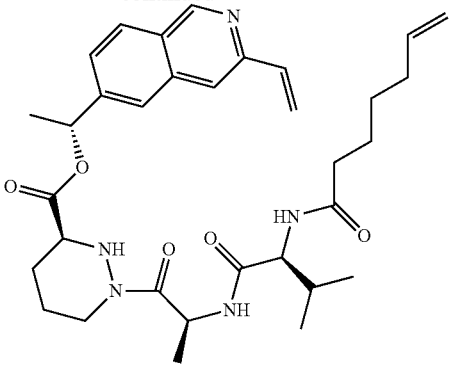

Into an oven dried, argon purged flask were added 63b (276 mg, 0.67 mmol) and (R)-1-(3-vinyl-isoquinolin-6-yl)-ethanol (134 mg, 0.67 mmol). The flask was sealed and the reaction mixture was repurged twice with argon. Anhydrous dichloromethane (10 mL) was added and the reaction mixture was repurged twice with argon. N-(3-Dimethylamino-propyl)-N'-ethylcarbodiimide hydrochloride (168 mg, 0.87 mmol) was added followed by 4-dimethylaminopyridine (75 mg, 0.62 mmol). The reaction mixture was quickly repurged twice with argon and was stirred at RT for 12 h. The reaction mixture was diluted with dichloromethane (100 mL) and the solution was washed with 20% water solution of citric acid (2×150 mL), water (150 mL) and brine (150 mL), dried over magnesium sulfate, filtered and evaporated. The residue was purified by silica gel chromatography (gradient from 0-40% ethyl acetate and methanol (4/1) in iso-hexanes) to afford the title compound (316 mg, 79%) as a white solid after evaporation. $R_f$=0.30, iso-hexanes/ethyl acetate/methanol (6/4/1).

Compound 63

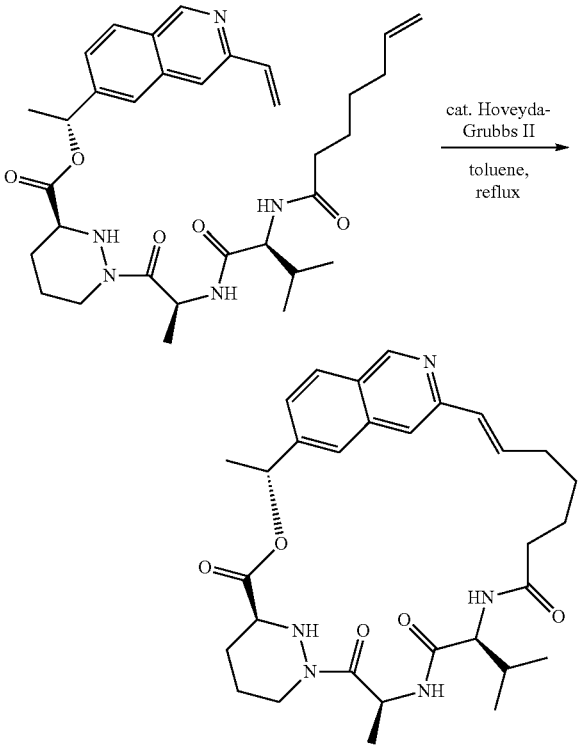

A solution of 63c (255 mg, 0.431 mmol) in toluene (200 mL) was stirred at RT under argon. Hoveyda-Grubbs 2$^{nd}$ generation catalyst (27 mg, 0.043 mmol) was added and the reaction mixture was heated at reflux under argon for 30 min. Reaction mixture was cooled to RT and ethyl acetate (50 mL) was added. This solution was washed twice with aqueous solution of tris(hydroxymethyl)phosphine (372 mg, 3 mmol in 100 mL of water), twice with water (50 mL) and with brine (50 mL). The organic phase was dried over magnesium sulfate, filtered and evaporated. The residue was purified by silica gel chromatography (gradient from 0-40% ethyl acetate and methanol (4/1) in iso-hexanes) to afford the title compound (76 mg, 31%) as a white solid after evaporation. $R_f$=0.20, iso-hexanes/ethyl acetate/methanol (6/4/1). $^1$H NMR (400 MHz, $CD_3OD$): δ 9.01 (s, 1H), 7.93 (d, J=8.5 Hz, 1H), 7.69 (s, 1H), 7.57 (s, 1H), 7.43 (d, J=8.5 Hz, 1H), 6.55 (m, 1H), 5.95 (m, 1H), 5.43 (m, 1H), 5.23 (m, 3H), 4.32 (m, 1H), 4.20 (m, 1H), 3.67 (m, 1H), 2.69 (m, 1H), 2.30 (m, 2H), 2.13 (m, 2H), 1.96 (m, 3H), 1.83 (m, 1H), 1.64 (m, 3H), 1.56 (d, J=6.7 Hz, 3H), 1.44 (d, J=7.4 Hz, 3H), 0.92-0.72 (m, 6H). LCMS (m/z) 564.4 [M+H], Tr=2.60 min.

Example 64

Compound 64

Compound 64

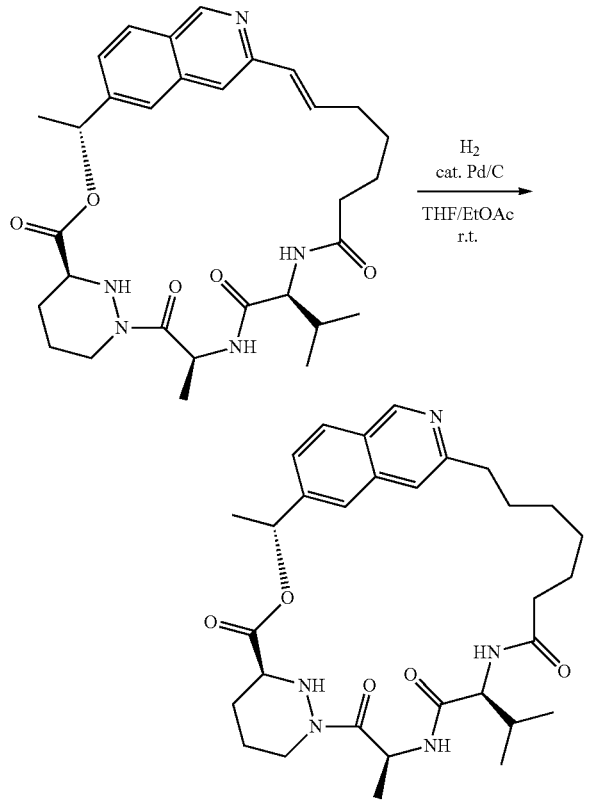

A solution of Compound 63 (15 mg, 0.027 mmol) in a mixture of ethyl acetate (4 mL) and tetrahydrofuran (4 mL) containing 10% palladium on carbon (10 mg) was hydrogenated at RT and at atmospheric pressure of hydrogen for 3 h. The reaction mixture was filtered through Celite and the filter pad was washed with tetrahydrofuran (10 mL). The filtrate was evaporated to afford the title compound (13 mg, 87%) as a white solid. $R_f$=0.11, iso-hexanes/ethyl acetate/ methanol (6/4/1). $^1$H NMR (400 MHz, $CD_3OD$) δ 9.02 (s, 1H), 7.95 (d, J=8.7 Hz, 1H), 7.68 (s, 1H), 7.50 (s, 1H), 7.45 (d, J=8.7 Hz, 1H), 5.93 (q, J=6.3 Hz, 1H), 5.20 (m, 1H), 4.21 (m, 1H), 4.07 (d, J=8.0 Hz, 1H), 3.66 (m, 1H), 2.83 (m, 4H), 2.25 (m, 1H), 2.07 (m, 1H), 1.94 (m, 2H), 1.80e (m, 1H), 1.63 (m, 3H), 1.55 (d, J=6.6 Hz, 3H), 1.51-1.42 (m, 2H), 1.37 (d, J=7.0 Hz, 3H), 1.25 (m, 4H), 0.83 (d, J=6.7 Hz, 6H). LCMS (m/z) 566.3 [M+H], Tr=2.27 min.

Example 65

Compound 65

Compound 65a

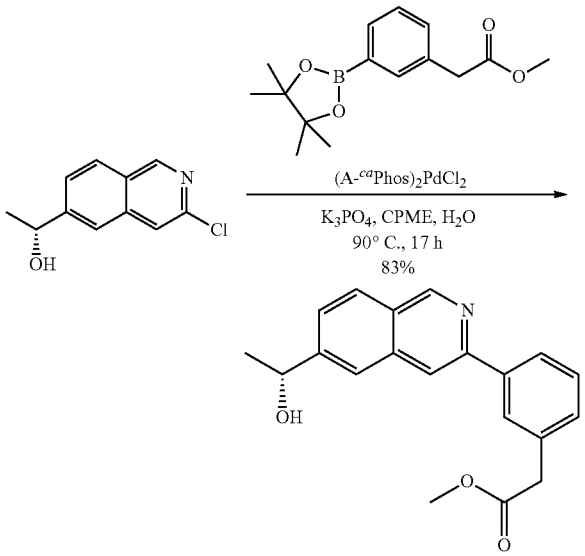

To a solution of (R)-1-(3-chloro-isoquinolin-6-yl)-ethanol (250 mg, 1.21 mmol), and potassium phosphate tribasic (770 mg, 3.63 mmol) in cyclopentyl methy ether (4.5 mL) and water (1.5 mL) preheated to 90° C. under an argon atmosphere were added 3-(2-methoxy-2-oxoethyl)phenylboronic acid, pinacol ester (Combi-Blocks, 387 mg, 1.33 mmol) and (A-$^{ca}$Phos)$_2$PdCl$_2$(49 mg, 60 μmol). After 17 h, the reaction was allowed to cool to 23° C., and was partitioned between dichloromethane (50 mL) and saturated aqueous sodium bicarbonate solution (50 mL). The phases were split and the aqueous layer was extracted with dichloromethane (50 mL). The combined organic layers were dried over anhydrous sodium sulfate, and were concentrated under reduced pressure. The crude residue was purified by silica gel chromatography (24 g Combiflash HP Gold Column, 0-100% ethyl acetate/iso-hexanes gradient) to afford the title compound (321 mg, 83%) as a faint yellow oil.

Compound 65b

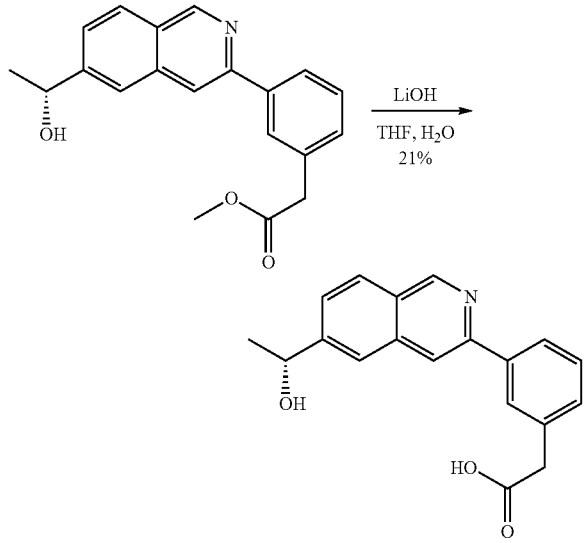

To a solution of 65a (320 mg, 1.00 mmol) in tetrahydrofuran (3 mL) and water (2 mL) was added lithium hydroxide (26 mg, 1.1 mmol) at 23° C. under an argon atmosphere. After 3 h, the reaction mixture was concentrated under reduced pressure and the crude residue was purified by silica gel chromatography (24 g Combiflash HP Gold Column, 0-20% methanol/dichloromethane gradient) to afford the title compound (64.2 mg, 21%) as a colorless oil. $R_f$=0.5 (20% methanol in dichloromethane) $I_2$/silica stain.

Compound 65c

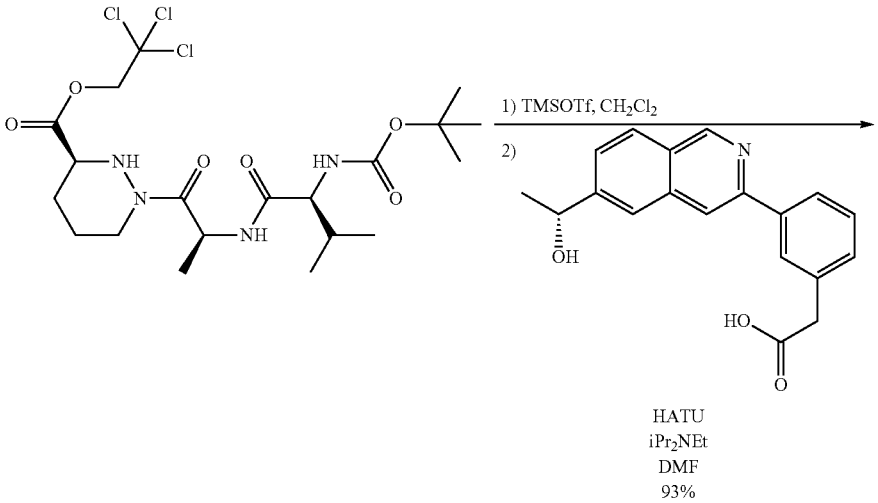

-continued

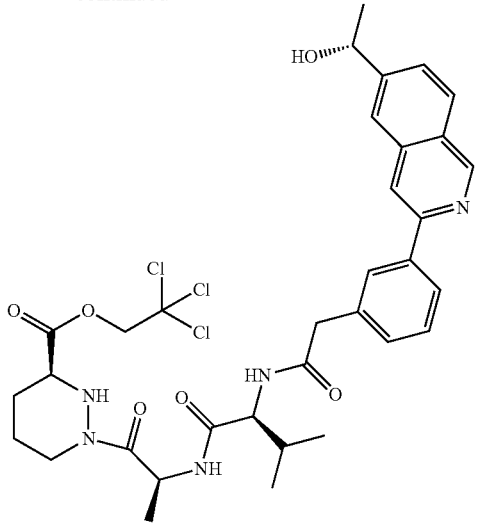

To a solution of 1e (104 mg, 0.21 mmol) in dichloromethane (1.05 mL) was added trimethylsilyl trifluoromethanesulfonate (70 mg, 1.07 mmol) at 0° C. under an argon atmosphere. After 1 h, the reaction mixture was concentrated under reduced pressure. The resulting residue was diluted with acetonitrile (1.05 mL) and 2-(1H-7-azabenzotriazol-1-yl)-1,1,3,3-tetramethyl uronium hexafluorophosphate methanaminium (79.8 mg, 0.210 mmol), N,N-diisopropylethylamine (140 μL, 0.840 mmol), and 65b (64 mg, 0.21 mmol) were sequentially added at 23° C. under an argon atmosphere. After 18 h, the reaction mixture was concentrated under reduced pressure, and the crude residue was purified by silica gel chromatography to afford the title compound (140 mg, 93%) as a faint yellow oil.

Compound 65d

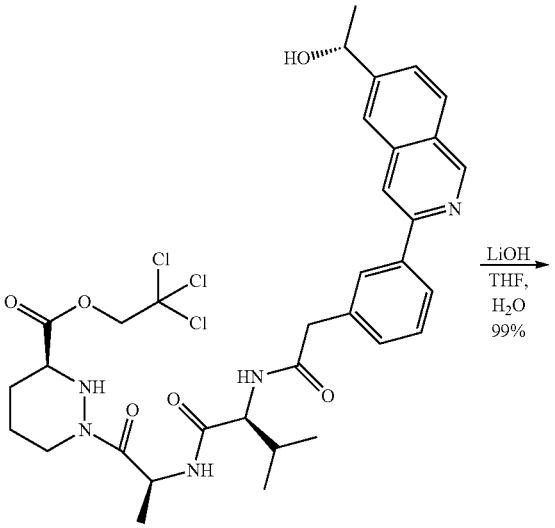

-continued

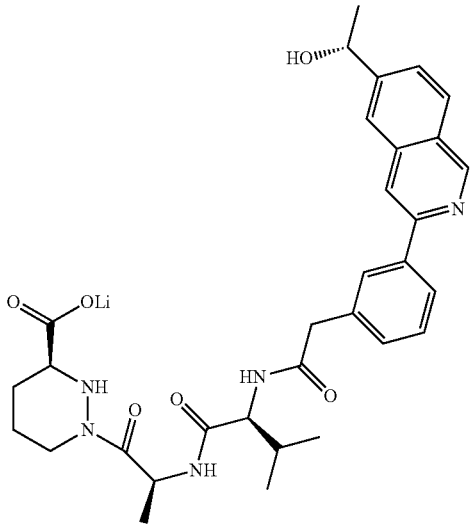

To a solution of 65c (140 mg, 0.195 mmol) in tetrahydrofuran (0.9 mL) and water (0.3 mL) was added lithium hydroxide hydrate (4.6 mg, 0.195 mmol) at 23° C. under an argon atmosphere. After 3 h, the reaction mixture was concentrated under reduced pressure to afford the title compound (131 mg, 99%) as a white solid lithium carboxylate salt.

Compound 65

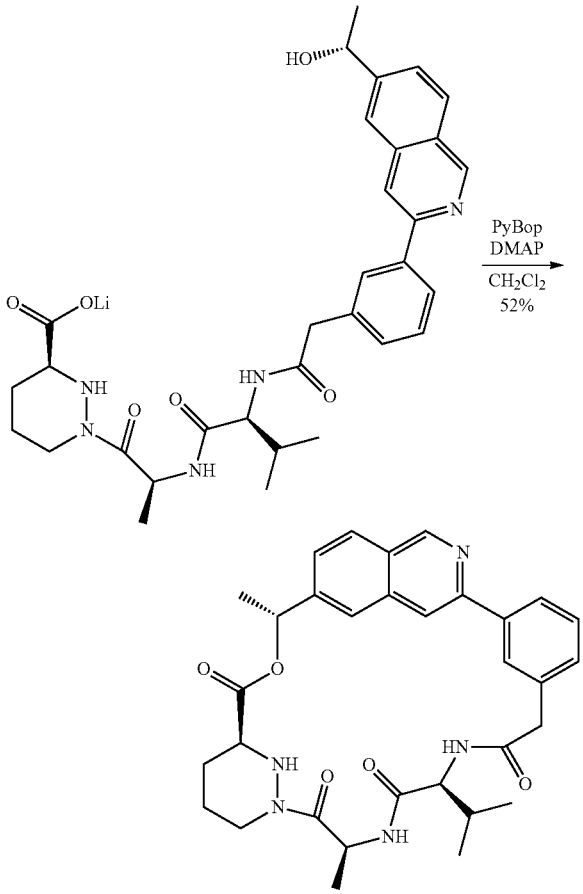

To a solution of benzotriazol-1-yl-oxytripyrrolidinophosphonium hexafluorophosphate (35.3 mg, 68 μmol) and 4-dimethylaminopyridine (62.3 mg, 510 μmol) in dichloromethane (5.7 mL) was added 65d (10 mg, 17 μmol) at 23° C. under an argon atmosphere. After 16 h, the reaction mixture was concentrated under reduced pressure and the crude residue was purified by preparative HPLC (Gemini 5u C18 110 Å column, 5-100% acetonitrile/water, 0.1% trifluoroacetic acid modifier) to afford the title compound (6.0 mg, 52%) as a white solid trifluoroacetic acid salt. $^1$H NMR (400 MHz, $CD_3OD$) δ 9.70 (s, 1H), 8.58 (s, 1H), 8.48 (d, J=8.6 Hz, 1H), 8.32 (s, 1H), 7.97-7.87 (m, 2H), 7.79 (d, J=7.9 Hz, 1H), 7.62 (app t, J=7.7 Hz, 1H), 7.53 (d, J=7.8 Hz, 1H), 6.21 (q, J=6.6 Hz, 1H), 5.84-5.71 (m, 1H), 4.45-4.29 (m, 2H), 3.96 (d, J=15.5 Hz, 1H), 3.75 (dd, J=11.1, 2.7 Hz, 1H), 3.64 (d, J=15.5 Hz, 1H), 2.74 (td, J=12.8, 3.1 Hz, 1H), 2.13-1.96 (m, 2H), 1.91 (br d, J=13.0 Hz, 1H), 1.81-1.65 (m, 2H), 1.67 (d, J=6.6 Hz, 3H), 1.62 (d, J=7.1 Hz, 3H), 1.01 (d, J=6.8 Hz, 3H), 0.94 (d, J=6.8 Hz, 3H). HPLC Tr=3.040 min. LCMS (m/z) 572.3 [M+H], Tr=2.07 min.

Example 66

Compound 66

Compound 66a

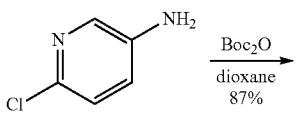

-continued

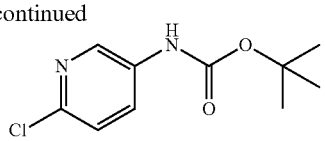

To a solution of 6-chloropyridin-3-amine (5.00 g, 38.8 mmol) in dioxane (194 mL) was added di-tert-butyl dicarbonate (10.2 g, 46.7 mmol) at 23° C. under an argon atmosphere, and the resulting mixture was heated to 100° C. After 17 h, the reaction mixture was allowed to cool to 23° C., and was diluted with water (500 mL). The resulting mixture was extracted with ethyl acetate (2×500 mL), and the combined organic extracts were dried over anhydrous sodium sulfate and were concentrated under reduced pressure. The crude residue was purified by silica gel chromatography (120 g Combiflash HP Gold Column, 0-100% ethyl acetate/iso-hexanes gradient) to afford the title compound (7.69 g, 87%) as a colorless oil.

Compound 66b

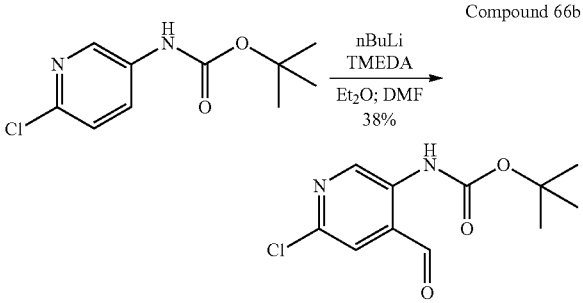

To a solution of 66a (2.00 g, 8.80 mmol) and tetramethylethylenediamine (2.70 mL, 18.0 mmol) in diethyl ether (44 mL) was added n-butyllithium (2.5 M in hexanes, 7.2 mL, 18.0 mmol) at −78° C. under an argon atmosphere. After 10 min, the resulting mixture was allowed to warm to −15° C. over a 50 min period. The reaction mixture was cooled to −78° C., and N,N-dimethylformamide (1.9 g, 26 mmol) was added via syringe. After 30 min, the reaction mixture was quenched with saturated aqueous ammonium chloride solution (20 mL) and was allowed to warm to 23° C. The resulting mixture was extracted with ethyl acetate (2×20 mL), and the combined organic layers were dried over anhydrous sodium sulfate and were concentrated under reduced pressure. The crude residue was purified by silica gel chromatography (120 g Combiflash HP Gold Column, 0-100% ethyl acetate/iso-hexanes gradient) to afford the title compound (849 mg, 38%) as colorless oil.

Compound 66c

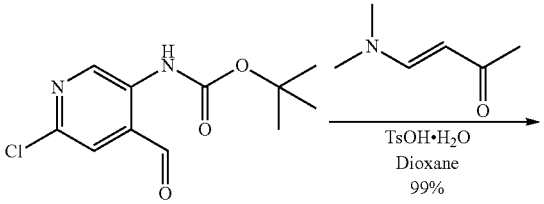

-continued

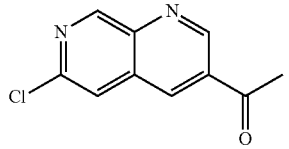

To a solution of 66b (258 mg, 1.00 mmol) and (E)-4-(dimethylamino)but-3-en-2-one (452 mg, 4.00 mmol) in 1,4-dioxane (10 mL) was added p-toluenesulfonic acid monohydrate (761 mg, 4 mmol) at 23° C. under an argon atmosphere and the resulting mixture was heated to 80° C. After 2 h, the reaction mixture was allowed to cool to 23° C. and was partitioned between saturated aqueous sodium bicarbonate solution (200 mL) and ethyl acetate (200 mL). The layers were split and the aqueous layer was extracted with ethyl acetate (200 mL). The combined organic layers were dried over anhydrous sodium sulfate and were concentrated under reduced pressure. The crude residue was purified by silica gel chromatography to afford the title compound (107 mg, 51%) as an off-white solid.

Compound 66d

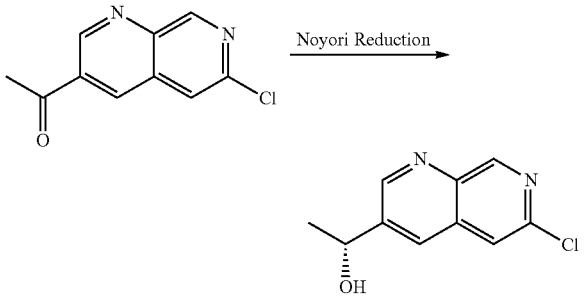

Dichloro (p-cymene) ruthenium(II) dimer (5 mg, 8 μmol) and (1R,2R)-(−)-N-p-tosyl-1,2-diphenylethylenediamine (7 mg, 19 μmol) were suspended in degassed water (6 mL) and the mixture was degassed with argon for 15 min. The mixture was stirred at 70° C. under argon for 90 min. The resulting yellow solution was cooled to RT. 66c (329 mg, 1.56 mmol), sodium formate (543 mg, 7.98 mmol) and degassed tetrahydrofuran (1 mL) were added and the reaction mixture was degassed for 10 min. The reaction mixture was vigorously stirred at 40° C. for 2.5 h. The reaction mixture was cooled to RT and was extracted with ethyl acetate (20 mL). The organic layer was separated, washed with water (20 mL), brine (20 mL), dried over anhydrous magnesium sulfate, and concentrated under reduced pressure. The residue was purified by silica gel chromatography to afford the title compound (180 mg, 54%) as a solid.

Compound 66e

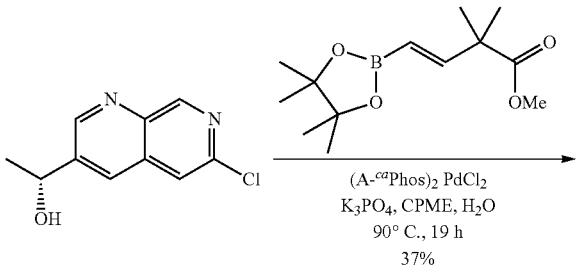

-continued

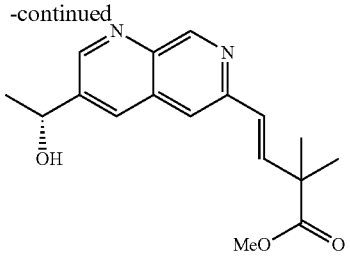

To a suspension of potassium phosphate tribasic (550 mg, 2.59 mmol) in cyclopentyl methyl ether (4.5 mL) and water (3 mL) was added 66d (180 mg, 0.89 mmol) and heated to 90° C. At this temperature, (A-$^{ca}$Phos)$_2$PdCl$_2$(35 mg, 43 μmol) was added and stirred for 2 min. A solution of (E)-2,2-dimethyl-4-(4,4,5,5-tetramethyl-[1,3,2]dioxaborolan-2-yl)-but-3-enoic acid methyl ester (286 mg, 1.12 mmol) in cyclopentyl methyl ether (4.5 mL) was added dropwise and stirred for 19 h at 90° C. The reaction mixture was cooled to RT, diluted with ethyl acetate (40 mL) and water (20 mL). The layers were separated and the aqueous layer was extracted with ethyl acetate (2×20 mL). The combined organic layers were dried over anhydrous magnesium sulfate, concentrated and the resulting crude residue was purified via silica gel chromatography (24 g $SiO_2$ Isco Rf Gold Column, 0-100% ethyl acetate/iso-hexanes gradient) to afford the title compound (95 mg, 37%) as a pale brown solid.

Compound 66f

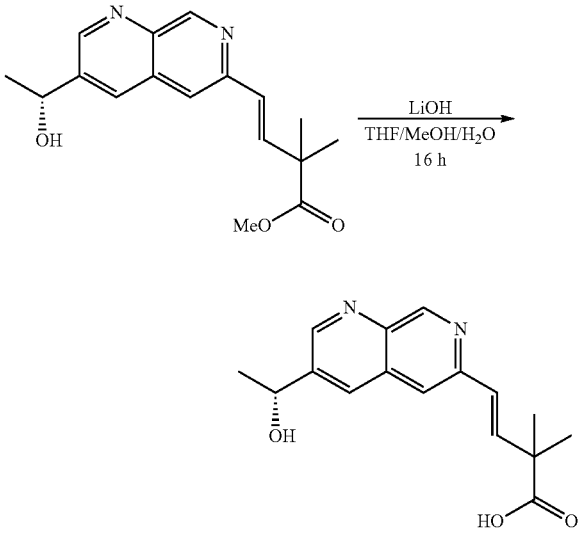

To a solution of 66e (95 mg, 0.32 mmol) in tetrahydrofuran (1.8 mL), methanol (0.6 mL) and water (0.6 mL) was added lithium hydroxide hydrate (15 mg, 0.63 mmol) at 23° C. After 16 h, the resulting mixture was concentrated under reduced pressure and residual solvents were removed azeotropically by addition of toluene (5 mL) followed by concentration under reduced pressure (2×) to afford the title compound. This was used in the subsequent amide coupling without further purification.

Compound 66g

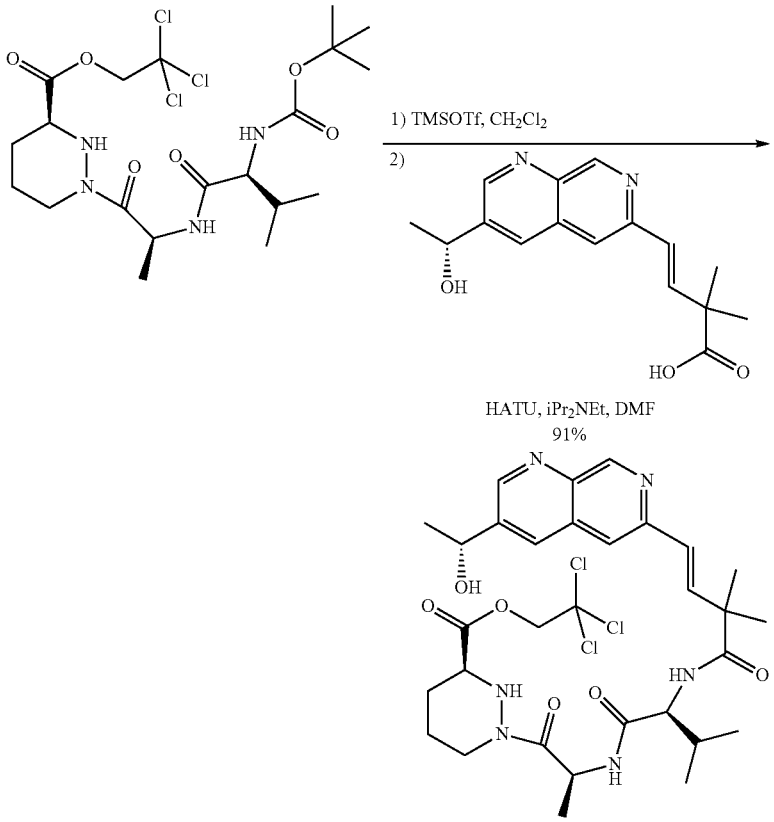

To a solution of 1e (212 mg, 0.40 mmol) in dichloromethane (3 mL) was slowly added trimethylsilyl trifluoromethanesulfonate (106 μL, 0.60 mmol) at 0° C. under an argon atmosphere. After 1 h, the resulting mixture was concentrated under reduced pressure and was used in the subsequent amide coupling without further purification. To a solution of 66f (90.5 mg, 0.32 mmol) in acetonitrile (3 mL), 2-(1H-7-azabenzotriazol-1-yl)-1,1,3,3-tetramethyl uronium hexafluorophosphate methanaminium (180 mg, 0.47 mmol), N,N-diisopropylethylamine (330 μL, 1.90 mmol) and (S)-1-[(S)-2-((S)-2-amino-3-methyl-butyrylamino)-propionyl]-hexahydro-pyridazine-3-carboxylic acid 2,2,2-trichloroethyl ester (232 mg, 0.4 mmol) in acetonitrile (2 mL) were added sequentially at 23° C. After 16 h, the resulting mixture was concentrated under reduced pressure and the residue was purified directly by silica gel chromatography to afford the title compound (201 mg, 91%) as a solid.

Compound 66h

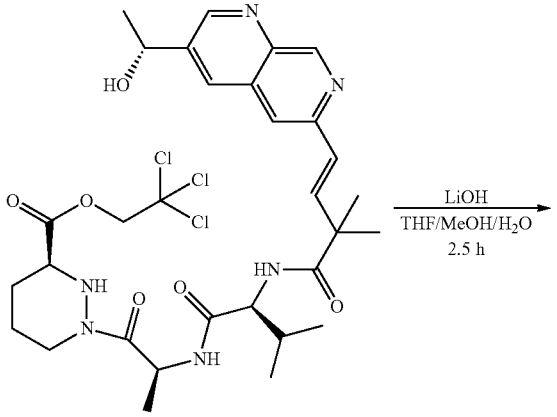

-continued

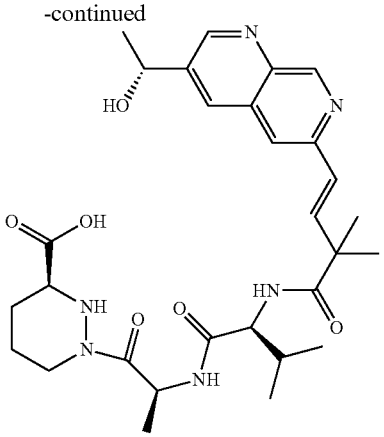

To a solution of 66 g (201 mg, 0.29 mmol) in tetrahydrofuran (2 mL), methanol (0.4 mL) and water (0.4 mL) was added lithium hydroxide hydrate (14 mg, 0.57 mmol) at 23° C. After 40 min, lithium hydroxide hydrate (14 mg, 0.57 mmol) was added at 23° C. After 1 h, the resulting mixture was concentrated under reduced pressure and residual solvents were removed azeotropically by addition of toluene (2 mL) followed by concentration under reduced pressure (3×) to afford the title compound. This was used in the subsequent macrolactonization without further purification.

Compound 66

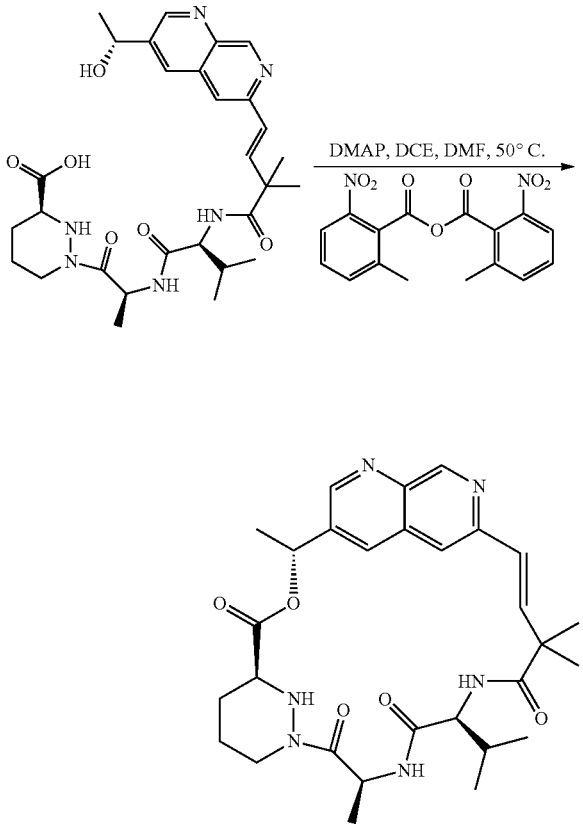

To 2-methyl-6-nitrobenzoic anhydride (43 mg, 0.12 mmol) and 4-dimethylaminopyridine (48 mh, 0.39 mmol) was added 1,2-dichloroethane (20 mL) under nitrogen atmosphere and heated to 50° C. At this temperature, 66 h (28 mg, 0.049 mmol) in N,N-dimethylformamide (1 mL) was added dropwise via syringe pump over 6 h. An additional wash of N,N-dimethylformamide (0.5 mL) was then added in the same manner over 15 min. After stirring an additional 1.25 h, reaction mixture was cooled to RT. It was diluted with ethyl acetate (20 mL) and washed with water (2×10 mL). The organic layer was dried over anhydrous magnesium sulfate and filtered. The solvent was removed under reduced pressure and the residue was purified by preparative HPLC (Gemini 5u C18 110 Å column, 5-100% acetonitrile/water, 0.1% trifluoroacetic acid modifier) to afford the title compound as a white powder trifluoroacetic acid salt. It was washed with saturated solution of sodium bicarbonate to remove acid impurities formed from 2-methyl-6-nitrobenzoic anhydride to afford the title compound (1.5 mg, 5%) as a white solid. $^1$H NMR (400 MHz, $CD_3OD$) δ 9.19 (s, 1H), 8.86 (d, J=2.1 Hz, 1H), 8.67 (d, J=7.5 Hz, 1H), 8.21 (s, 1H), 7.59 (s, 1H), 6.89 (d, J=9.5 Hz, 1H), 6.58 (d, J=16.1 Hz, 1H), 6.46 (d, J=16.1 Hz, 1H), 6.04 (q, J=6.4 Hz, 1H), 5.52-5.41 (m, 1H), 4.26 (d, J=14.4 Hz, 1H), 4.18 (app t, J=9.1 Hz, 1H), 3.65 (dd, J=11.4, 2.8 Hz, 1H), 2.58 (td, J=12.9, 3.2 Hz, 1H), 1.91-1.75 (m, 3H), 1.68-1.53 (m, 2H), 1.63 (d, J=6.7 Hz, 3H), 1.51 (d, J=7.3 Hz, 3H), 1.43 (s, 3H), 1.26 (s, 3H), 0.87 (d, J=6.7 Hz, 3H), 0.82 (d, J=6.7 Hz, 3H). LCMS (m/z) 551.2 [M+H], Tr=2.19 min.

Example 67

Compound 67

Compound 67a

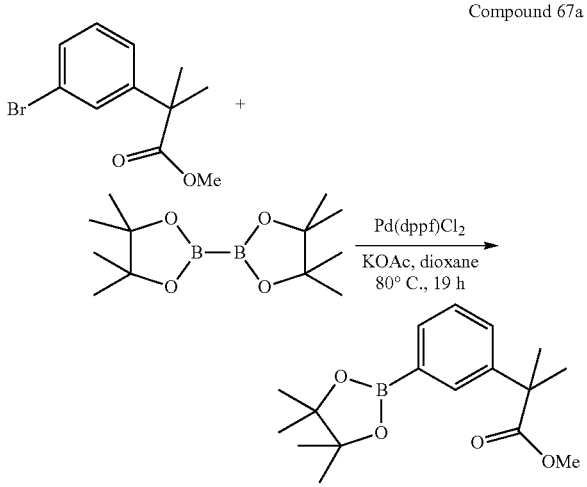

Methyl 2-(3-bromophenyl)-2-methylpropanoate (Pharmabridge, Doylestown, Pa., USA (190 mg, 0.74 mmol), 4,4,4',4',5,5,5',5'-octamethyl-2,2'-bi(1,3,2-dioxaborolane) (206 mg, 0.81 mmol), [1,1'-bis(diphenylphosphino)ferrocene]dichloropalladium(II), complex with dichloromethane (27 mg, 0.04 mmol) and potassium acetate (217 mg, 2.22 mmol) were placed in a screw cap vial and flushed with a vacuum and argon cycle three times. Anhydrous 1,4-dioxane (4 mL) was added under argon and the resulting mixture was heated to 80° C. for 19 h. The reaction mixture was cooled to RT and was diluted with ethyl acetate (20 mL). Celite (~1 g) was added and filtered through a pad of celite. Solvents were removed under reduced pressure to afford the title compound which was used directly in the subsequent reaction.

Compound 67b

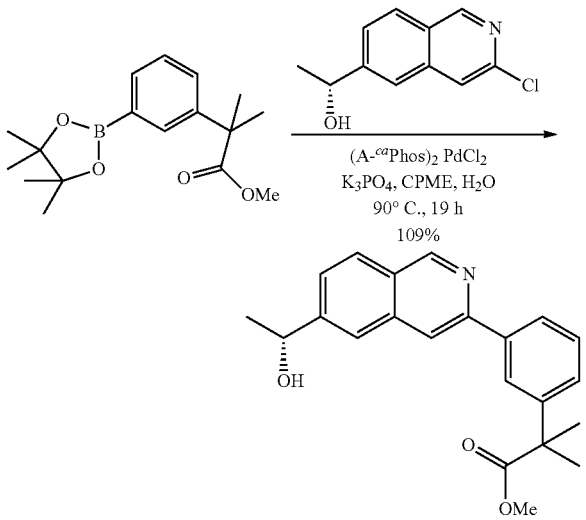

To a suspension of potassium phosphate tribasic (445 mg, 2.10 mmol) in cyclopentyl methyl ether (2.5 mL) and water (1.5 mL) was added (R)-1-(3-chloro-isoquinolin-6-yl)-ethanol (180 mg, 0.89 mmol) and the reaction mixture was heated to 90° C. At this temperature, (A-$^{ca}$Phos)$_2$PdCl$_2$(28 mg, 35 μmol) was added and the reaction mixture was stirred for 2 min. A solution of 67a (225 mg, 0.74 mmol) in cyclopentyl methyl ether (2.5 mL) was added dropwise and stirred for 19 h at 90° C. The reaction mixture was cooled to RT, diluted with ethyl acetate (30 mL) and water (15 mL). The layers were separated and the aqueous layer was extracted with ethyl acetate (2×15 mL). The combined organic layers were dried over anhydrous magnesium sulfate, concentrated and the resulting crude residue was purified by silica gel column chromatography to afford the title compound (267 mg, quantitative) as a pale brown solid.

Compound 67c

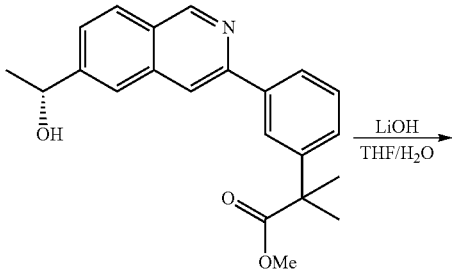

-continued

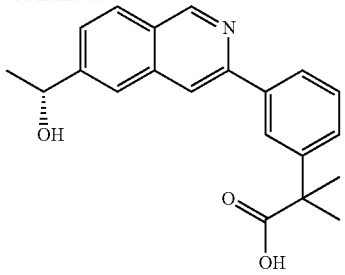

To a solution of 67b (244 mg, 0.7 mmol) in tetrahydrofuran (10 mL), and water (2.5 mL) was added lithium hydroxide hydrate (18.5 mg, 0.77 mmol) at 23° C. After 48 h, lithium hydroxide hydrate (17 mg, 0.70 mmol) was added to the reaction mixture. After 24 h, the reaction mixture was concentrated under reduced pressure and residual solvents were removed azeotropically by addition of toluene (5 mL) followed by concentration under reduced pressure (2×) to afford the title compound. This was used in the subsequent amide coupling without further purification.

Compound 67d

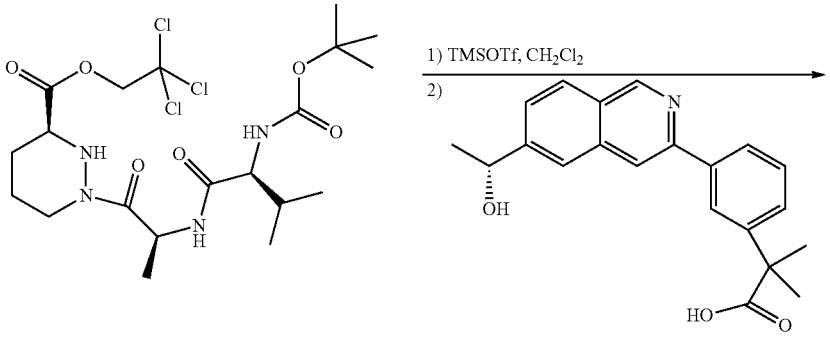

HATU, iPr2NEt, DMF
44%

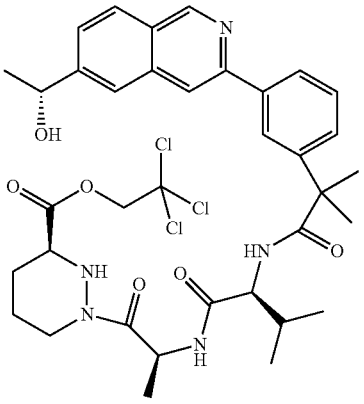

To a solution of 1e (397 mg, 0.75 mmol) in dichloromethane (5 mL) was slowly added trimethylsilyl trifluoromethanesulfonate (199 μL, 1.12 mmol) at 0° C. under an argon atmosphere. After 1 h, the resulting mixture was concentrated under reduced pressure to give (S)-1-[(S)-2-((S)-2-amino-3-methyl-butyrylamino)-propionyl]-hexahydro-pyridazine-3-carboxylic acid 2,2,2-trichloro-ethyl ester as a triflate salt. This was used in the subsequent amide coupling without further purification. To a solution of 67c (234 mg, 0.7 mmol) in acetonitrile (7 mL), 2-(1H-7-azabenzotriazol-1-yl)-1,1,3,3-tetramethyl uronium hexafluorophosphate methanaminium (532 mg, 1.4 mmol), N,N-diisopropylethylamine (730 μL, 4.2 mmol) and (S)-1-[(S)-2-((S)-2-amino-3-methyl-butyrylamino)-propionyl]-hexahydro-pyridazine-3-carboxylic acid 2,2,2-trichloro-ethyl ester (435 mg, 0.75 mmol) in acetonitrile (3 mL) were added sequentially at 23° C. After 16 h, the resulting mixture was concentrated under reduced pressure and the residue was purified directly by silica gel chromatography (40 g $SiO_2$ Isco Rf Gold Column, 0-100% ethyl acetate/iso-hexanes gradient) to afford the title compound (230 mg, 44%) as a solid.

Compound 67e

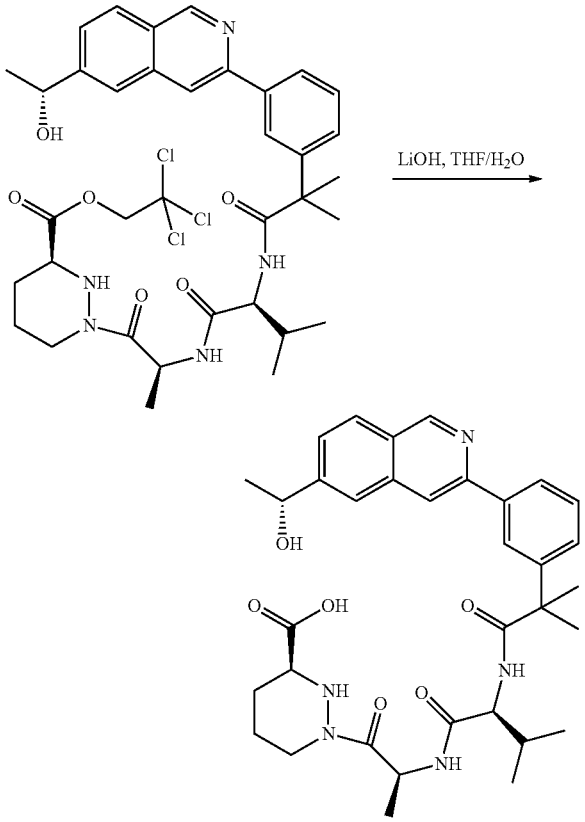

To a solution of 67d (94 mg, 0.13 mmol) in tetrahydrofuran (3 mL), and water (1 mL) was added lithium hydroxide hydrate (3.1 mg, 0.13 mmol) at 23° C. After 48 h, lithium hydroxide hydrate (17 mg, 0.70 mmol) was added to the reaction mixture. After 1 h, the reaction mixture was concentrated under reduced pressure and residual solvents were removed azeotropically by addition of toluene (5 mL) followed by concentration under reduced pressure (2×) to afford the title compound. This was used in the subsequent macrolactonization without further purification.

Compound 67

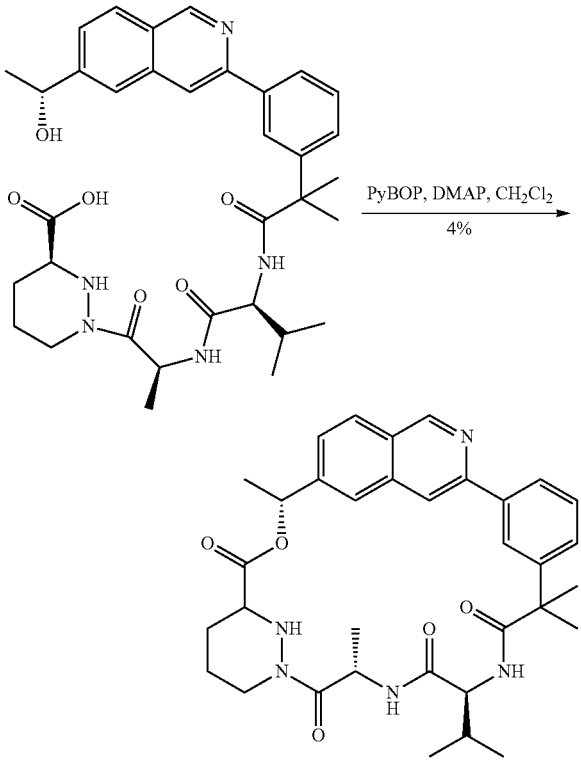

To a suspension of 67e (78 mg, 0.13 mmol) in dichloromethane (42 mL) was added benzotriazol-1-yl-oxytripyrrolidinophosphonium hexafluorophosphate (520 mg, 0.50 mmol) and 4-dimethylaminopyridine (462 mg, 4.0 mmol) at 23° C. After 24 h, the solvent was removed under reduced pressure and the residue was purified by preparative HPLC (Gemini 5u C18 110 Å column, 5-100% acetonitrile/water, 0.1% trifluoroacetic acid modifier) to afford the title compound (3.2 mg, 4%) as a white powder and as a trifluoroacetic acid salt. $^1$H NMR (400 MHz, $CD_3OD$) δ 9.65 (s, 1H), 8.69 (s, 1H), 8.49 (d, J=8.7 Hz, 1H), 8.44 (d, J=8.6 Hz, 1H), 8.34 (s, 1H), 7.90 (dd, J=8.7, 1.5 Hz, 1H), 7.83 (d, J=7.7 Hz, 1H), 7.78 (d, J=7.9 Hz, 1H), 7.74 (s, 1H), 7.69 (app t, J=7.8 Hz, 1H), 6.82 (d, J=8.6 Hz, 1H), 6.21 (q, J=6.5 Hz, 1H), 5.92-5.84 1H), 4.41-4.30 (m, 2H), 3.75 (dd, J=14.4, 6.0 Hz, 1H), 2.71 (td, J=13.0, 3.0 Hz, 1H), 2.06-1.99 (m, 1H), 1.96 (dd, J=14.2, 7.1 Hz, 1H), 1.93-1.86 (m, 1H), 1.75 (s, 3H), 1.73-1.59 (m, 2H), 1.68 (d, J=6.6 Hz, 3H), 1.63 (d, J=7.1 Hz, 3H), 1.47 (s, 3H), 0.96 (d, J=6.8 Hz, 3H), 0.84 (d, J=6.7 Hz, 3H). HPLC Tr=5.319 min. LCMS (m/z) 600.5 [M+H], Tr=2.71 min.

Examples 68 and 69

Compounds 68 and 69

Compound 68a

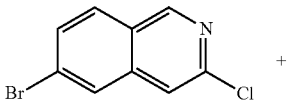

-continued

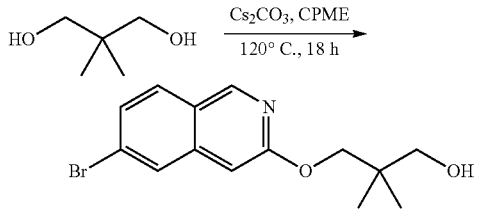

To a solution of 6-bromo-3-chloroisoquinoline (Frontier Scientific, 1.594 g, 6.57 mmol) and 2,2-dimethylpropane-1,3-diol (684 mg, 6.57 mmol) in cyclopentyl methyl ether (20 mL) was added cesium carbonate (2.354 g, 7.23 mmol) at 23° C. The reaction mixture was heated to 120° C. for 18 h. The reaction mixture was cooled to RT, diluted with ethyl acetate (50 mL) and washed with water (30 mL), brine (30 mL) and the resulting organic layer was dried over anhydrous magnesium sulfate and concentrated under reduced pressure. The residue was purified by silica gel chromatography (80 g Isco Rf Gold Column, 0-100% ethyl acetate/iso-hexanes gradient) to afford the title compound (461 mg, 23%) as a white solid.

Compound 68b

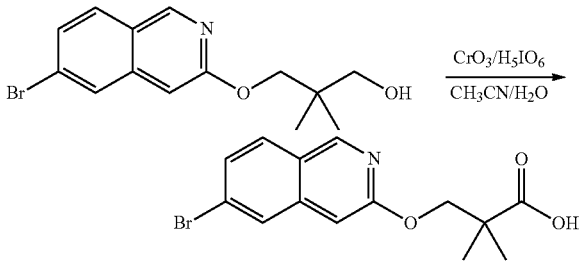

To a solution of 68a (461 mg, 1.49 mmol) in acetonitrile (10 mL) and water (2.5 mL) was added periodic acid (1.698 g, 7.45 mmol) at 23° C. The reaction mixture was cooled to 0° C. and chromium trioxide (30 mg, 0.298 mmol) was added in one portion. After 2.5 hour, the reaction mixture was diluted with ethyl acetate (30 mL) and water (30 mL) and the layers were separated. The aqueous layer was extracted with ethyl acetate (30 mL) and combined organic layers were washed with brine, dried over anhydrous magnesium sulfate and concentrated under reduced pressure to afford the title compound which was used without purification (481 mg).

Compound 68c

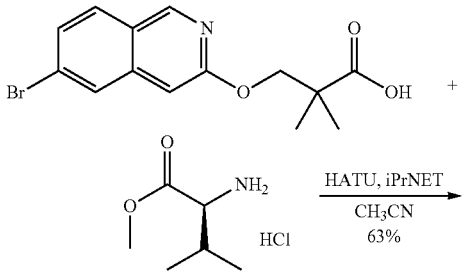

-continued

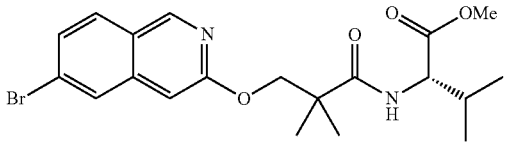

To a solution of 68b (481 mg, 1.49 mmol) in acetonitrile (10 mL), 2-(1H-7-azabenzotriazol-1-yl)-1,1,3,3-tetramethyl uronium hexafluorophosphate methanaminium (1.133 g, 2.98 mmol), N,N-diisopropylethylamine (1.55 mL, 8.94 mmol) and (S)-methyl 2-amino-3-methylbutanoate hydrochloride (749 mg, 4.47 mmol) were added sequentially at 23° C. After 16 h, the resulting mixture was concentrated under reduced pressure and the residue was purified directly by silica gel chromatography (24 g Isco Rf Gold Column, 0-100% ethyl acetate/iso-hexanes gradient) to afford the title compound (412 mg, 63% over 2 steps) as a brown oil.

Compound 68d

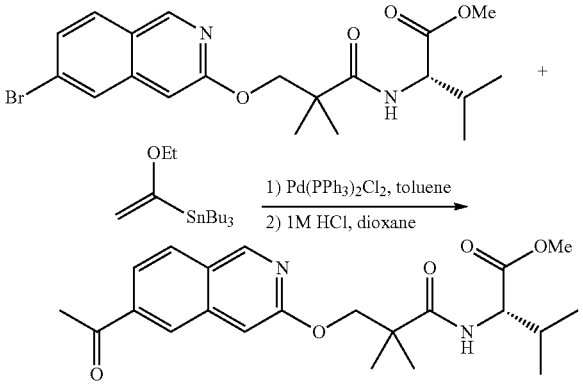

To a suspension of 68c (412 mg, 0.95 mmol) and bis (triphenylphosphine) palladium (II) dichloride in toluene (5 mL) was added tributyl(1-ethoxyvinyl)tin (962 μL, 2.85 mmol) under argon at 23° C. The reaction mixture was heated to 50° C. After 18 h, water (1 mL) was added at 50° C. After 2 h, the reaction mixture was cooled to RT, diluted with ethyl acetate (15 mL) and 1 M solution of potassium fluoride (5 mL) was added. The resulting mixture was vigorously stirred at 23° C. After 2 h, the mixture was filtered through a short pad of Celite and washed with ethyl acetate (10 mL). The filtrate was washed with water (15 mL), brine (15 mL), dried over anhydrous magnesium sulfate and concentrated. This residue was dissolved in 1,4-dioxane (8 mL) and 1 M aqueous hydrochloric acid (1 mL) was added at 23° C. After 5 min, the reaction mixture was quenched with a saturated solution of sodium bicarbonate (2 mL) and concentrated to dryness. The residue was taken up in ethyl acetate (20 mL) and water (20 mL) and layers were separated. The aqueous layer was extracted with ethyl acetate (2×10 mL) and the combined organic layers were washed with brine (20 mL), dried over anhydrous magnesium sulfate and concentrated. The residue was purified by silica gel chromatography to afford the title compound (236 mg, 62%) as a brown gum.

Compound 68e

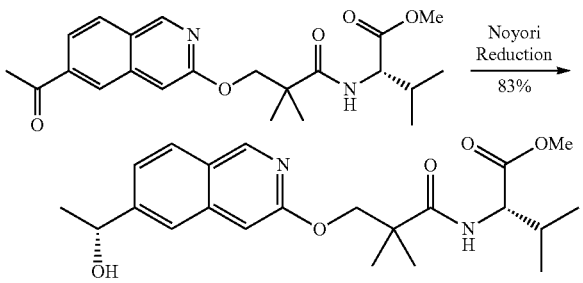

Dichloro (p-cymene) ruthenium(II) dimer (2 mg, 3 μmol) and (1R,2R)-(−)-N-p-tosyl-1,2-diphenylethylenediamine (2.6 mg, 7 μmol) were suspended in degassed water (2.5 mL) and the mixture was degassed with argon for 15 min. The mixture was stirred at 70° C. under nitrogen for 90 min. The resulting yellow solution was cooled to RT. 68d (236 mg, 0.59 mmol), sodium formate (200 mg, 2.95 mmol) and degassed tetrahydrofuran (1.25 mL) were added and the reaction mixture was degassed for 10 min. The reaction mixture was vigorously stirred at 40° C. for 3.5 h. The reaction mixture was cooled to RT and was extracted with ethyl acetate (15 mL). The organic layer was separated, washed with water (20 mL), brine (20 mL), dried over anhydrous magnesium sulfate, and concentrated under reduced pressure. The residue was purified by silica gel chromatography to afford the title compound (196 mg, 83%) as a pale brown solid.

Compound 68f

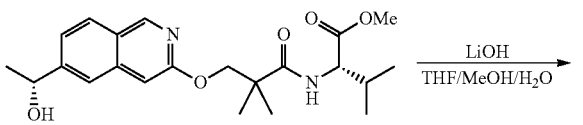

-continued

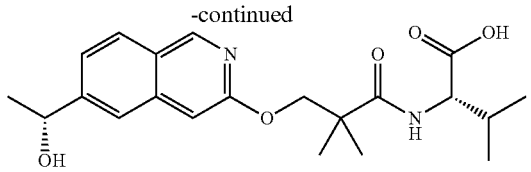

To a solution of 68e (196 mg, 0.487 mmol) in tetrahydrofuran (3 mL), methanol (1 mL) and water (1 mL) was added lithium hydroxide hydrate (23 mg, 0.97 mmol) at 23° C. After 16 h, the reaction mixture was concentrated under reduced pressure. The residue was taken up in ethyl acetate (10 mL) and water (10 mL) and acidified with 1 M aqueous hydrochloric acid solution to pH~2. The resulting layers were separated. The aqueous layer was extracted with ethyl acetate (2×10 mL) and the combined organic layers were washed with brine, dried over anhydrous magnesium sulfate and concentrated under reduced pressure to afford the title compound which was used without purification.

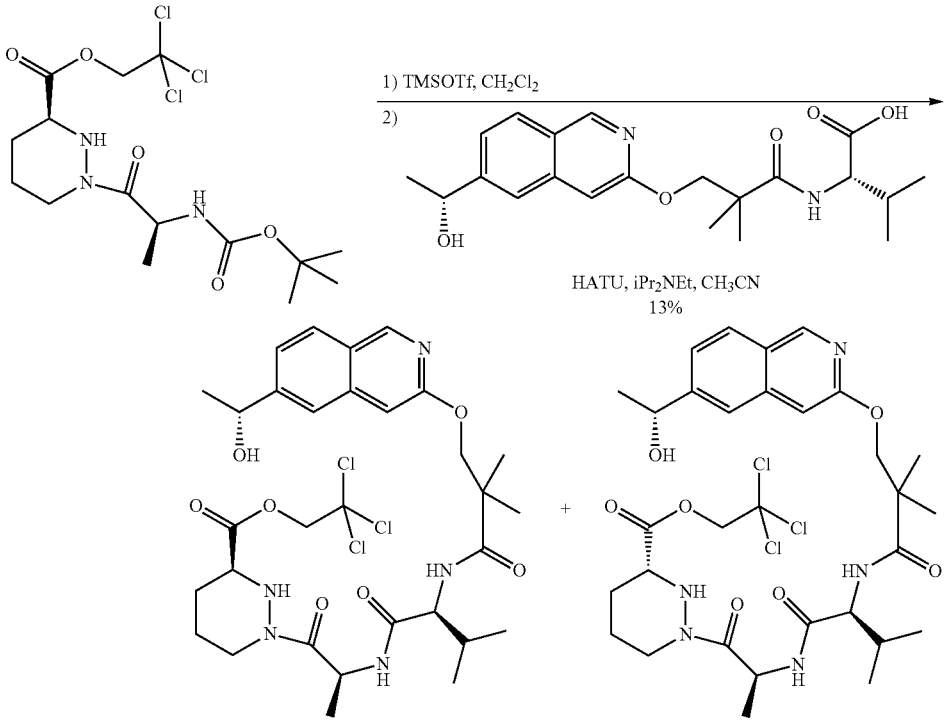

Compound 68g Compound 68h

To a solution of (S)-1-((S)-2-tert-butoxycarbonylamino-propionyl)-hexahydro-pyridazine-3-carboxylic acid 2,2,2-trichloro-ethyl ester (270 mg, 0.62 mmol) in dichloromethane (5 mL) was slowly added trimethylsilyl trifluoromethanesulfonate (165 μL, 0.93 mmol) at 0° C. under an argon atmosphere. After 1 hour, the reaction mixture was concentrated under reduced pressure to afford the triflate salt of (S/R)-1-((S)-2-amino-propionyl)-hexahydro-pyridazine-3-carboxylic acid 2,2,2-trichloro-ethyl ester as yellow oil which was used it without purification. To a solution of 68f (189 mg, 0.49 mmol) in acetonitrile (7 mL), 2-(1H-7-azabenzotriazol-1-yl)-1,1,3,3-tetramethyl uronium hexafluorophosphate methanaminium (278 mg, 0.73 mmol), N,N-diisopropylethylamine (730 μL, 4.2 mmol) and (S/R)-1-((S)-2-amino-propionyl)-hexahydro-pyridazine-3-carboxylic acid 2,2,2-trichloro-ethyl ester (435 mg, 0.62 mmol) in acetonitrile (3 mL) were added sequentially at 23° C. After 16 h, the resulting mixture was concentrated under reduced pressure and the residue was purified directly by silica gel chromatography (40 g $SiO_2$ Isco Rf Gold Column, 0-100% ethyl acetate/iso-hexanes gradient) to afford an inseparable diastereomeric mixture of the title compounds (43 mg, 13%) as a colorless residue.

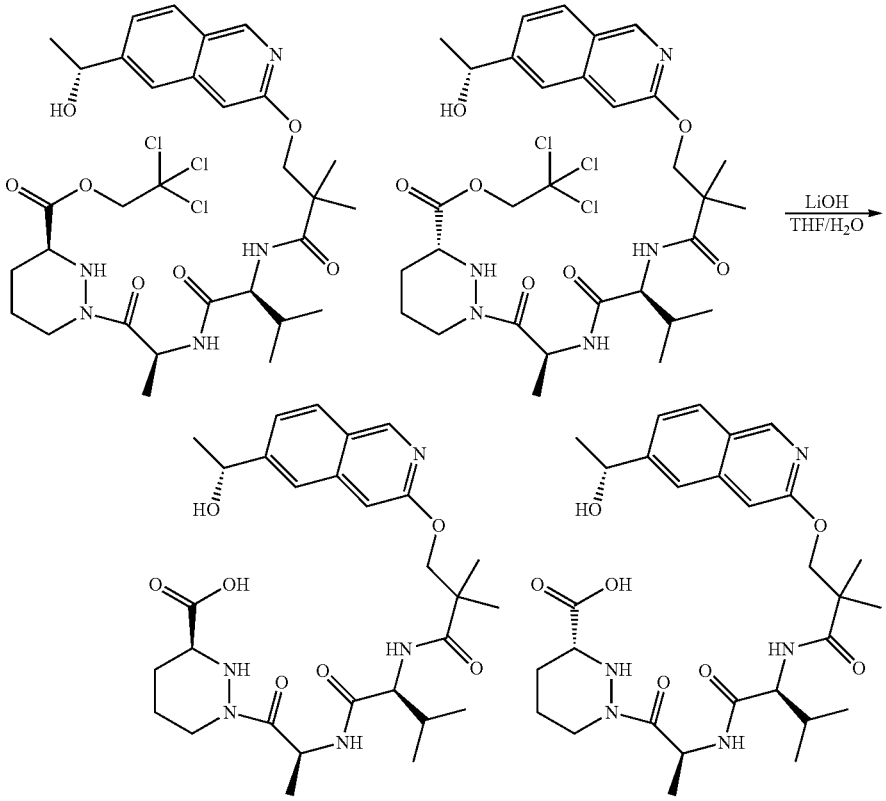

Compound 68i Compound 68j

To a solution of a mixture of 68 g and 68 h (43 mg, 61 μmol) in tetrahydrofuran (4 mL) and water (2 mL) was added lithium hydroxide hydrate (3.2 mg, 0.13 mmol) at 23° C. After 1 h, the reaction mixture was concentrated under reduced pressure and residual solvents were removed azeotropically by addition of toluene (5 mL) followed by concentration under reduced pressure (2×) to afford the title compounds as a mixture. This was used in the subsequent macrolactonization without further purification. LCMS (m/z) 572.2 [M+H], Tr=2.21 min.

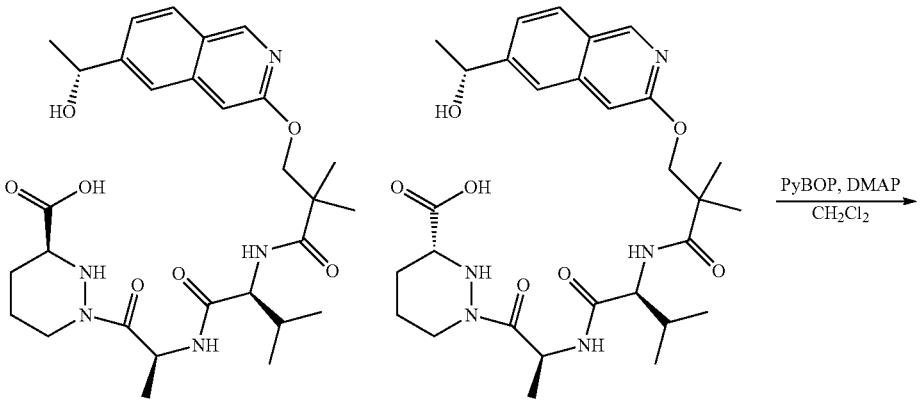

-continued

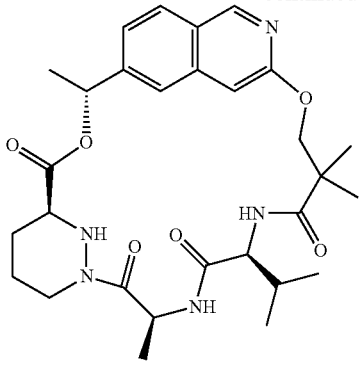

Compound 68

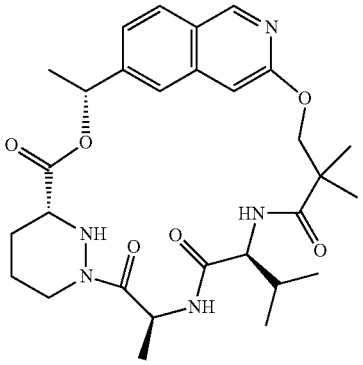

Compound 69

To a suspension of 68i and 68j (34.8 mg, 61 μmol) in dichloromethane (20 mL) was added benzotriazol-1-yl-oxytripyrrolidinophosphonium hexafluorophosphate (127 mg, 0.24 mmol) and 4-dimethylaminopyridine (224 mg, 1.83 mmol) at 23° C. After 24 h, the solvent was removed under reduced pressure and the residue was purified by preparative HPLC (Gemini 5u C18 110 Å column, 5-100% acetonitrile/water, 0.1% trifluoroacetic acid modifier) to afford both compounds (12 mg, 35%) as a ratio mixture of diastereomers. The diastereomers were separated using Chiral preparative HPLC to afford first eluting (Tr=3.73 min) Compound 68 (2.17 mg, 6%) and the second eluting (Tr=5.713 min) Compound 69 (1.85 mg, 5%). Compound 68: $^1$H NMR (400 MHz, $CD_3OD$) δ 8.89 (s, 1H), 7.94 (d, J=8.6 Hz, 1H), 7.86 (s, 7.37 (dd, J=8.6, 1.5 Hz, 1H), 7.28 (d, J=9.2 Hz, 1H), 6.93 (s, 1H), 6.09 (q, J=6.5 Hz, 1H), 5.54 (q, J=7.2 Hz, 1H), 4.36-4.26 (m, 3H), 4.21 (d, J=9.7 Hz, 1H), 3.69 (dd, J=11.2, 2.6 Hz, 1H), 2.77 (td, J=12.9, 3.0 Hz, 1H), 2.00-1.84 (m, 2H), 1.83-1.77 (m, 1H), 1.76-1.62 (m, 2H), 1.67 (d, J=6.7 Hz, 3H), 1.47 (d, J=7.3 Hz, 3H), 1.38 (s, 3H), 1.27 (s, 3H), 0.99 (d, J=6.7 Hz, 3H), 0.95 (d, J=6.7 Hz, 3H). HPLC Tr=5.866 min. LCMS (m/z) 554.2 [M+H], Tr=2.44 min.

Compound 69: $^1$H NMR (400 MHz, $CD_3OD$) δ 8.78 (s, 1H), 7.83 (d, J=8.6 Hz, 1H), 7.74 (s, 1H), 7.24 (dd, J=8.6, 1.6 Hz, 1H), 7.03 (s, 1H), 5.93 (q, J=6.7 Hz, 1H), 5.35 (q, J=6.8 Hz, 1H), 4.31 (d, J=9.8 Hz, 1H), 4.18 (d, J=13.3 Hz, 1H), 4.02-3.97 (m, 2H), (d, J=10.0 Hz, 1H), 3.65 (dd, J=10.8, 2.8 Hz, 1H), 2.71 (td, J=12.7, 2.8 Hz, 1H), 1.98-1.89 (m, 1H), 1.87-1.77 (m, 2H), 1.73-1.64 (m, 1H), 1.57 (d, J=6.7 Hz, 3H), 1.49 (d, J=7.0 Hz, 3H), 1.40 (s, 3H), 1.13 (s, 3H), 0.89 (d, J=6.7 Hz, 3H), 0.85 (d, J=6.5 Hz, 3H) HPLC Tr=5.951 min. LCMS (m/z) 555.2 [M+H], Tr=2.49 min.

Example 70

Compound 70

Compound 70a

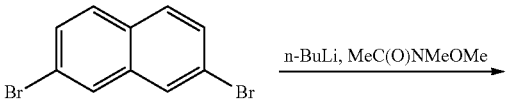

-continued

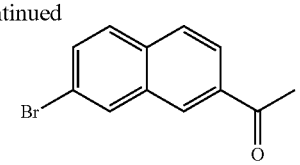

To 2,7-dibromonaphthalene (1 g, 3.50 mmol) in anhydrous tetrahydrofuran (18 mL), at −78° C. and under an atmosphere of nitrogen, was added a solution of n-butyllithium (2.5 M in hexanes, 1.5 mL, 3.67 mmol) dropwise. The reaction was stirred at −78° C. for 20 min after which N-methoxy-N-methylacetamide (409 μL, 3.85 mmol) was added. After 15 min, the reaction was warmed to RT and stirred for 30 min. The reaction was quenched with 2 M hydrochloric acid and extracted twice with dichloromethane. The combined organic layers were dried through a hydrophobic frit and concentrated in vacuo. The product was purified by silica flash chromatography (iso-hexanes/ethyl acetate, 7/1) to afford the title compound (650 mg, 75%) as a colorless solid.

Compound 70b

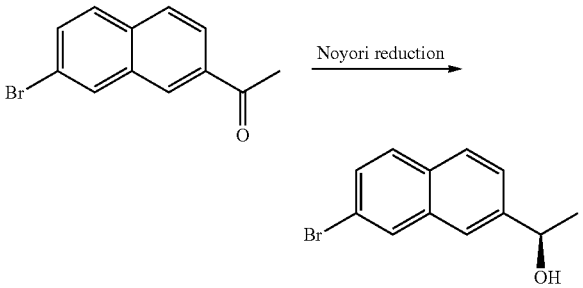

To dichloro (p-cymene) ruthenium (II) dimer (8 mg, 0.013 mmol) in water (5 mL) at RT was added (1R,2R)-(−)-N-p-tosyl-1,2-diphenylethylenediamine (11.5 mg, 0.031 mmol). The system was degassed for 15 min and then heated to 70° C. for 1.5 h. The reaction was cooled and was added a solution of 70a (650 mg, 2.61 mmol) in degassed anhydrous tetrahydrofuran (2 mL) followed by sodium formate (874 mg, 13.1 mmol). The reaction was heated at 40° C. for 3 h, cooled to RT and extracted twice with dichloromethane. The combined organic layers were dried through a hydrophobic frit and concentrated in vacuo. The product was purified by silica gel chromatography (iso-hexanes/ethyl acetate, 4/1) to afford the title compound (450 mg, 69%) as a colorless solid.

Compound 70c

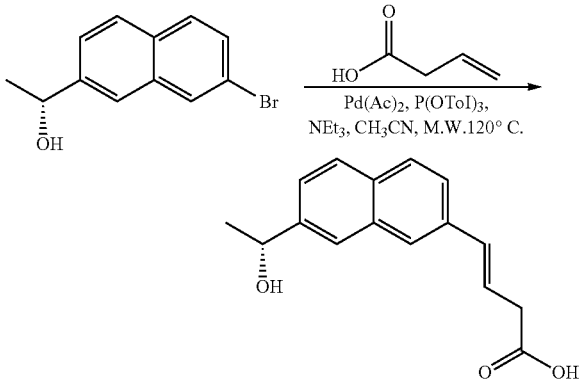

70b (42 mg, 0.17 mmol) was dissolved in acetonitrile (2 ml) in a microwave vial, to the mixture was added 3-butenoic acid (35 mg, 0.41 mmol), palladium (II) acetate (4 mg, 0.017 mmol), tri-(o-tolyl)phosphine (10 mg, 0.034 mmol) and triethylamine (0.12 ml). The vial was heated at 120° in the microwave reactor for 15 mins. The reaction mixture was then filtered, the solvent was evaporated and purified with combi-flash column chromatography (Eluent methanol/dichloromethane 1:3) to afford the title compound (35 mg, 81%) as a yellow solid.

Compound 70d

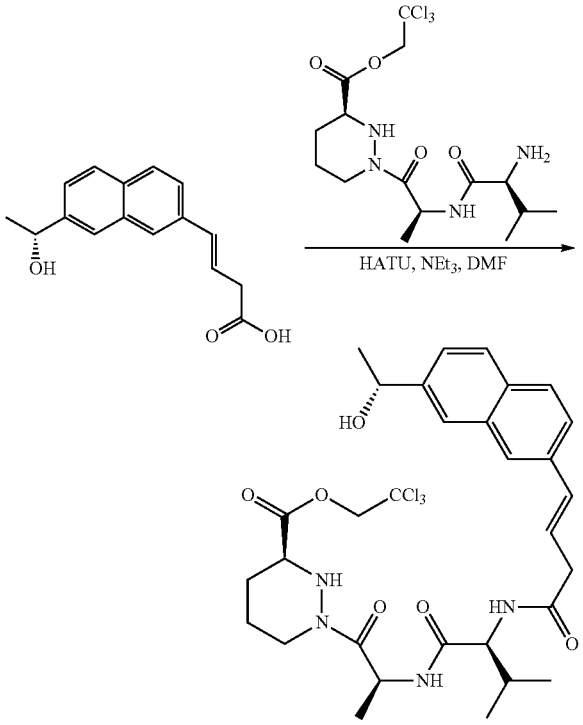

70c (40 mg, 0.08 mmol) was dissolved in N,N-dimethylformamide (2 mL), to the solution was added 2-(1H-7-azabenzotriazol-1-yl)-1,1,3,3-tetramethyl uronium hexafluorophosphate methanaminium (36 mg, 0.1 mmol), the reaction mixture was stirred at RT for 10 min. Then (S)-1-[(S)-2-((S)-2-amino-3-methylbutyrylamino)-propionyl]-hexahydro-pyridazine-3-carboxylic acid 2,2,2-trichloro-ethyl ester (0.18 mmol) in N,N-dimethylformamide (1 ml) was added to above reaction mixture followed by triethylamine (32 mg, 0.32 mmol). The reaction mixture was stirred at RT for 1 h, and then it was diluted with ethyl acetate (20 mL) and washed with brine. The aqueous layer was back extracted with ethyl acetate and the combined organic solvent was evaporated and purified with combi-flash column chromatography (Eluent methanol/dichloromethane 1:10) to afford the title compound (68 mg, 65%) as a yellow solid.

Compound 70e

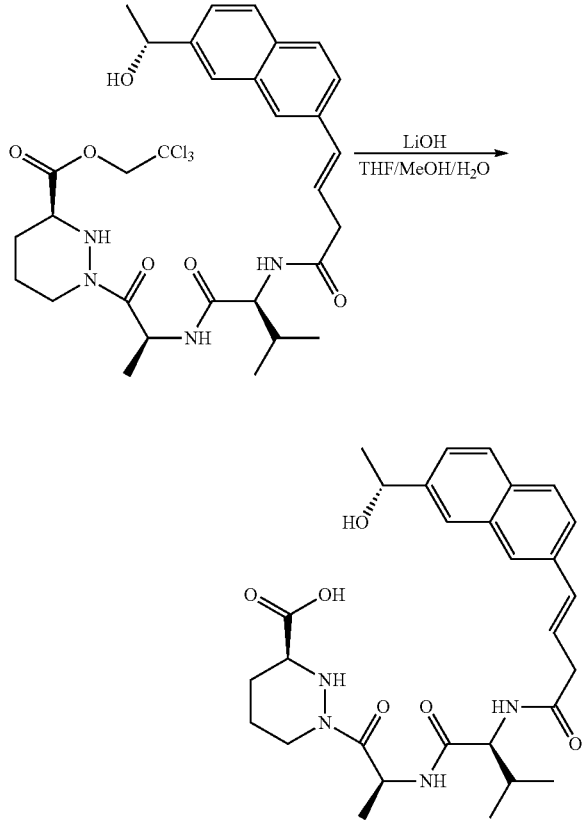

70d (55 mg, 0.08 mmol) was dissolved in the mixture of tetrahydrofuran (2 mL), methanol (1 mL) and water (1 mL). To the solution was added lithium hydroxide hydrate (4 mg, 0.16 mmol). The reaction mixture was stirred at RT for 1 h. Dichloromethane (10 mL) and water (10 mL) were added to the reaction mixture. 1 N Hydrochloric acid was added to the aqueous layer until pH reached 2, the acidic aqueous layer was extracted with dichloromethane (2×10 mL). The organic solvent was then evaporated to afford the title compound (37 mg, 84%) as a white solid.

Compound 70

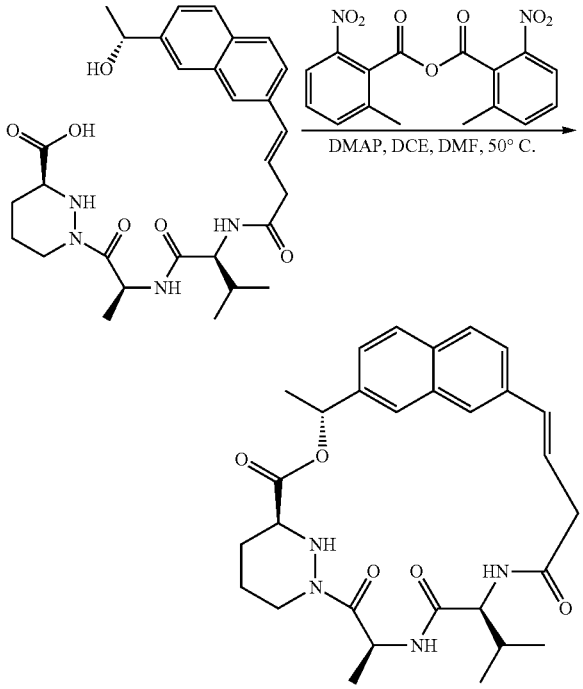

2-Methyl-6-nitrobenzoic anhydride (19 mg, 0.056 mmol) and 4-dimethylaminopyridine (23 mg, 0.185 mmol) were dissolved in 1,2-dichloroethane (18 mL) and the solution was heated at 50° C. To the above solution was added 70e (20 mg, 0.037 mmol) in N,N-dimethylformamide (1 mL) via syringe pump in 10 h. The reaction mixture was stirred at 50° C. for 2 h after the completion of addition. The solvent was then evaporated and the residue was purified by reverse phase preparative HPLC (0-100% acetonitrile/water) to afford the title compound (4 mg, 22%) as a white solid. $^1$H NMR (400 MHz, $CD_3OD$) δ 7.79-7.72 (m, 3H), 7.52 (dd, J=1.6, 8.8 Hz, 1H), 7.41 (s, 1H), 7.33 (dd, J=8.4, 1.6 Hz, 1H), 6.48 (d, J=16.4 Hz, 1H), 6.31-6.24 (m, 1H), 6.02 (q, J=7.6 Hz, 1H), 4.64 (d, J=12.4 Hz, 1H), 4.40 (d, J=12.8 Hz, 1H), 4.30 (d, J=10.4 Hz, 1H), 3.78-3.72 (m, 1H), 3.36-3.32 (m, 2H), 2.99-2.93 (m, 1H), 2.77-2.71 (m, 1H), 1.99-1.69 (m, 5H), 1.66 (d, J=6.8 Hz, 3H), 1.58 (d, J=7.2 Hz, 3H), 0.99 (d, J=6.8 Hz, 6H). LCMS (m/z) 521.1 [M−H], Tr=3.18 min.

Example 71

Compound 71

Compound 71

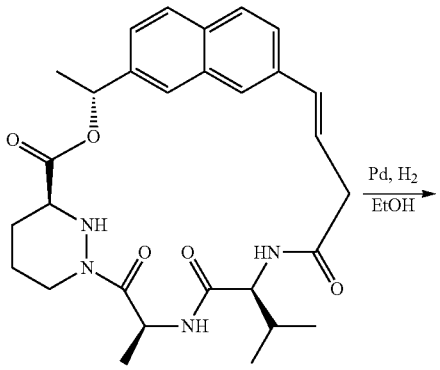

-continued

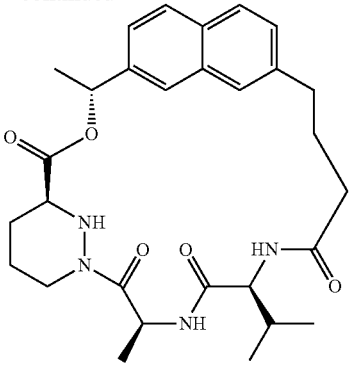

Compound 70 (5 mg, 0.01 mmol) was dissolved in ethanol (5 mL) under argon, to the solution was added Pd (10% on activated carbon, 3 mg). The reaction flask was then purged and then charged with $H_2$ using a balloon. The reaction was filtered through Celite after 2 h, the filtrate was evaporated under reduced pressure and purified by reverse phase preparative HPLC (0-100% acetonitrile/water) to afford the title compound (3.2 mg, 64%) as a white powder. $^1$H-NMR (400 MHz, $CD_3OD$) δ 8.47 (d, J=6.0 Hz, 1H), 7.97 (d, J=8.8 Hz, 1H), 7.69-7.62 (m, 3H), 7.31 (s, 1H), 7.24-7.19 (m, 2H), 5.97 (dd, J=12.8, 6.0 Hz, 1H), 5.62 (pent, J=7.2 Hz, 1H), 4.76-4.16 (m, 1H), 4.10 (app t, J=12.8 Hz, 1H), 4.05-3.69 (m, 1H), 2.85 (br s, 1H), 2.73-2.41 (m, 2H), 2.40-2.37 (m, 1H), 2.10-1.93 (m, 1H), 1.92-1.70 (m, 6H), 1.53 (d, J=6.8 Hz, 3H), 1.49 (d, J=7.6 Hz, 3H), 0.99 (d, J=6.8 Hz, 6H). LCMS (m/z) 523.140 [M+H], Tr=3.16 min.

Example 72

Compound 72

Compound 72

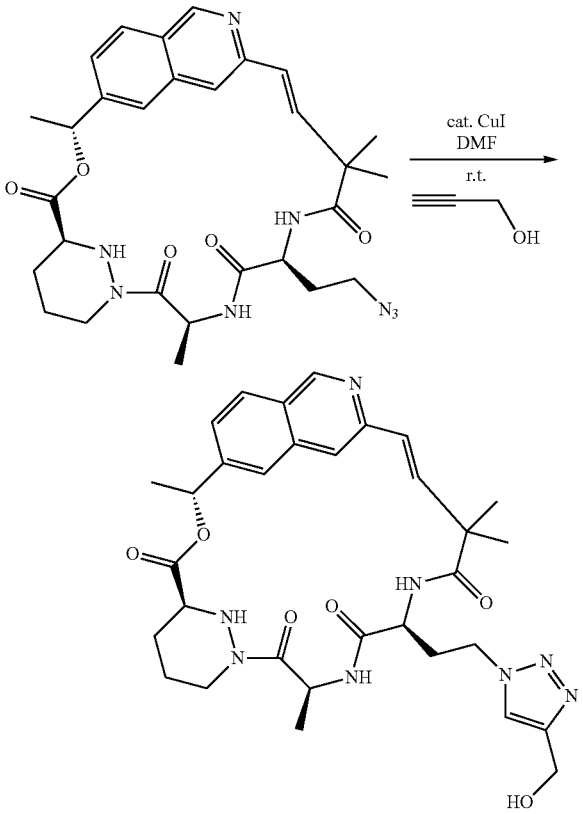

Into an oven dried, argon purged flask Compound 49 (10 mg, 0.017 mmol), copper(I) iodide (1 mg, 0.005 mmol) and prop-2-yn-1-ol (4 mg, 0.07 mmol) were added. The flask was sealed and repurged with argon three times. Anhydrous N,N-dimethylformamide (5 mL) was added and the reaction mixture was repurged with argon three times. This reaction mixture was stirred at RT for 12 h. After evaporation of the solvent under reduced pressure, the crude residue was dissolved in ethyl acetate (10 mL) and filtered through filter aid and the filter pad was washed with ethyl acetate (10 mL). After concentration under reduced pressure, the residue was purified by silica gel chromatography (gradient from 0-40% ethyl acetate and methanol (4/1) in iso-hexanes) to afford the title compound (10 mg, 93%) as a white solid after evaporation. $R_f$=0.33, 10% methanol in dichloromethane. $^1$H NMR (400 MHz, $CD_3OD$) δ 9.05 1H), 7.95 (d, J=8.6 Hz, 1H), 7.94 (s, 1H), 7.82 (s, 1H), 7.50 (s, 1H), 7.46 (d, J=8.6 Hz, 1H), 6.49 (d, J=16.0 Hz, 1H), 6.40 (d, J=16.0 Hz, 1H), 5.95 (m, 1H), 5.50 (m, 1H), 4.59-4.53 (m, 3H), 4.36 (m, 2H), 4.30 (m, 1H), 3.68 (m, 1H), 2.80 (m, 1H), 2.60 (m, 1H), 2.23 (m, 1H), 2.14 (m, 1H), 1.90-1.58 (m, 4H), 1.57 (d, J=6.6 Hz, 3H), 1.55 (d, J=7.6 Hz, 3H), 1.41 (s, 3H), 1.27 (s, 3H). LCMS (m/z) 633.4 [M+H], Tr=2.66 min.

Example 73

Compound 73

Compound 73a

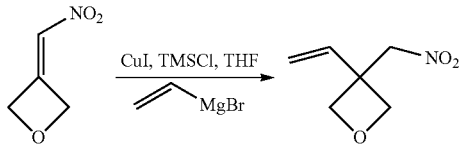

To 3-Nitromethylene-oxetane (Angew. Chem. Int. Ed. 2006, 45 (46), 7736, 2.5 g, 21.7 mmol) in anhydrous tetrahydrofuran (40 mL) at RT and under an atmosphere of nitrogen was added copper(I) iodide (413 mg, 2.17 mmol) and chlorotrimethylsilane (3.0 mL, 23.9 mmol). The resulting yellow solution was stirred for 5 min and cooled to between −15° C. and −11° C. with a methanol ice bath. Vinyl magnesium bromide (43.5 mL, 43.5 mmol, 1.0 M in tetrahydrofuran) was slowly added over 3 h via a syringe pump. Following the addition the reaction was quenched with a saturated aqueous solution of ammonium chloride, filtered and extracted with diethyl ether (3×). The combined organics were dried through a hydrophobic frit and concentrated in vacuo. The residue was purified by silica gel chromatography using diethyl ether to give the title compound as a yellow oil (2.0 g, 64%).

Compound 73b

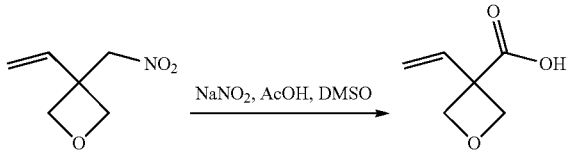

To 73a (600 mg, 4.2 mmol) in anhydrous dimethylsulfoxide (13 mL) was added acetic acid (2.4 mL, 42 mmol) and sodium nitrite (869 mg, 12.6 mmol) and the mixture heated to 35° C. for 16 h. The reaction was cooled to RT and diluted with water. The pH was adjusted to pH 3-4 with 10% aqueous hydrochloric acid and the product extracted with diethyl ether (3×) and diethyl ether/ethyl acetate (1:1). The combined organics were dried through a hydrophobic frit and concentrated in vacuo. The residue was purified by silica gel chromatography using iso-hexanes/ethyl acetate (2/1 then 1/1) to afford impure acid. This was dissolved in diethyl ether and extracted with a saturated solution of sodium carbonate. The aqueous was acidified to pH 2 with concentrated hydrochloric acid and extracted with ethyl acetate (3×). The organics were dried through a hydrophobic frit and concentrated in vacuo to give the title compound as a yellow oil (228 mg, 43%).

Compound 73c

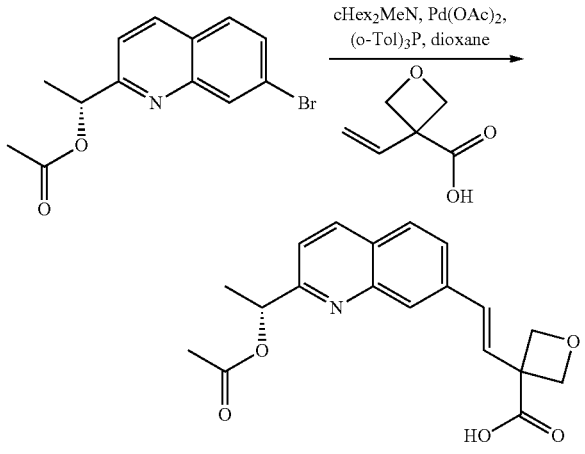

To 73b (150 mg, 1.18 mmol) in anhydrous dioxane (1 mL), was added acetic acid (R)-1-(7-bromo-quinolin-2-yl)-ethyl ester (347 mg, 1.18 mmol) followed by dicyclohexylmethylamine (0.76 mL, 3.54 mmol), palladium(II) acetate (53 mg, 0.24 mmol) and Tri(o-tolyl) phosphine (72 mg, 0.24 mmol). The mixture was heated at 100° C. for 1 hour. An additional amount of palladium(II) acetate (26 mg, 0.12 mmol) and Tri(o-tolyl) phosphine (36 mg, 0.12 mmol) was added and heating continued at 100° C. for a further 45 min. The reaction was cooled to RT and 2M HCl added until pH 3-4 was reached. The product was extracted with ethyl acetate (3×) and ethyl acetate/10% methanol (2×). The combined organics were dried through a hydrophobic frit and concentrated in vacuo to yield the title compound as a brown oil.

Compound 73d

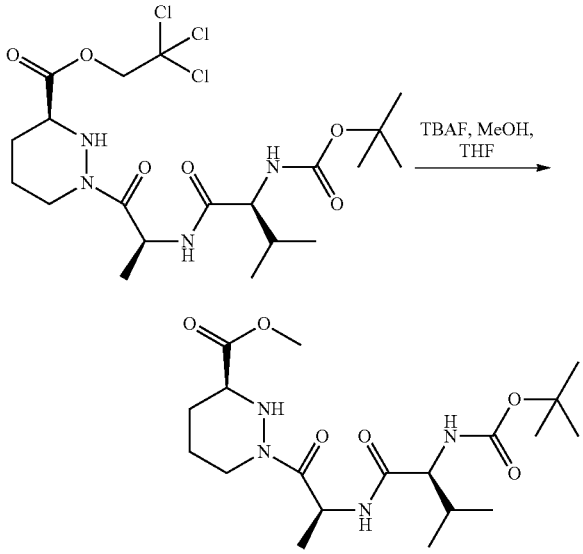

A solution of 1e (3.01 g, 5.66 mmol) in tetrahydrofuran: methanol (1:1, 60 mL) was stirred at 0° C. Tetra-n-butylammonium fluoride (1 M in tetrahydrofuran, 11.3 mL, 11.3 mmol) was added and the reaction mixture was stirred at RT for 22 h. The solvent was evaporated and the residue was purified by silica gel chromatography using iso-hexane to iso-hexane/ethyl acetate 1:1 afford the title compound (2.14 g, 91%) as a white foam.

To 73d (365 mg, 0.88 mmol) in anhydrous dichloromethane (15 mL) at 0° C. and under an atmosphere of nitrogen, was added trimethylsilyl trifluoromethanesulfonate (239 μL, 1.32 mmol). The reaction mixture was stirred at 0° C. for 1 hour before adding N,N-diisopropylethylamine (613 μL, 3.52 mmol) and then concentrated in vacuo, and co-evaporated with toluene to afford (S)-1-[(S)-2-((S)-2-amino-3-methyl-butyrylamino)-propionyl]-hexahydro-pyridazine-3-carboxylic acid 2,2,2-trichloro-ethyl ester as a white solid. To 73c (300 mg, 0.88 mmol) in anhydrous acetonitrile (9 mL) at 0° C. and under an atmosphere of nitrogen was added N,N-diisopropylethylamine (766 μL, 4.4 mmol) and 2-(1H-7-azabenzotriazol-1-yl)-1,1,3,3-tetramethyl uronium hexafluorophosphate methanaminium (401 mg, 1.06 mmol). The solution was stirred at 0° C. for 3 min before adding a solution of (S)-1-[(S)-2-((S)-2-amino-3-methyl-butyrylamino)-propionyl]-hexahydro-pyridazine-3-carboxylic acid 2,2,2-trichloro-ethyl ester in anhydrous acetonitrile (2 mL). The reaction was warmed to RT and stirred for 2 h. The reaction was quenched with 1M HCl and extracted with ethyl acetate (3×). The combined organic layers were dried through a hydrophobic frit and concentrated in vacuo. The residue was purified by silica gel chromatography using ethyl acetate to give the title compound as a viscous yellow oil (160 mg, 22%, 2 steps).

Compound 73e

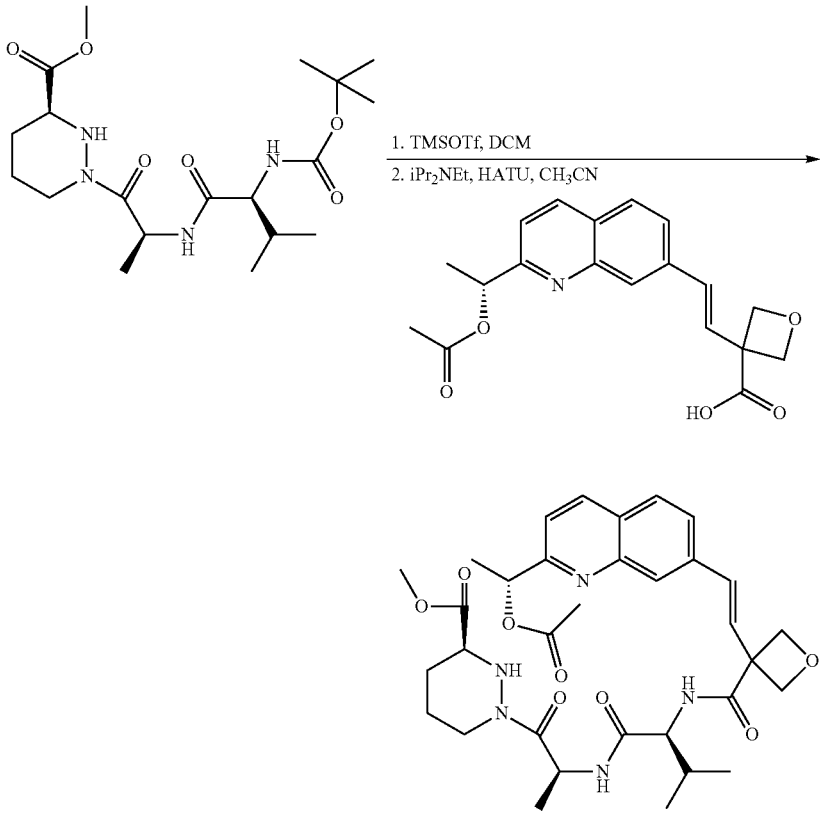

Compound 73

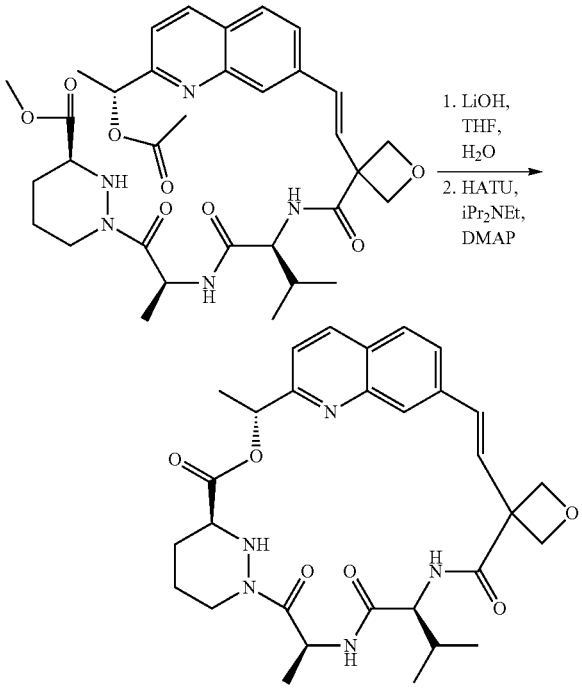

To 73e (160 mg, 0.25 mmol) in tetrahydrofuran (10 mL) and water (2 mL) was added lithium hydroxide monohydrate (53 mg, 1.25 mmol) at 0° C. The reaction was stirred at 0° C. for 2 h and quenched by adding 2M aqueous hydrochloric acid (0.63 mL). The reaction was concentrated in vacuo, followed by co-evaporation from toluene/methanol (3×) and then toluene (3×) and dried on a high vacuum for 15 min. The resulting residue was dissolved in anhydrous tetrahydrofuran (83 mL) and at RT was added N,N-diisopropylethylamine (223 μL, 1.25 mmol), 2-(1H-7-azabenzotriazol-1-yl)-1,1,3,3-tetramethyl uronium hexafluorophosphate methanaminium (114 mg, 1.3 mmol) and 4-dimethylaminopyridine (3 mg, 0.03 mmol). The reaction was stirred for 24 h, diluted with ethyl acetate and washed with 1M HCl (1×) and brine (1×). The organic layer was dried through a hydrophobic frit and concentrated in vacuo. The residue was purified by silica gel chromatography using ethyl acetate/methanol 1:0 then 20/1 to give a viscous yellow oil (52 mg). This was further purified by preparative thin layer chromatography (ethyl acetate) to afford the title compound as a white solid which was triturated with diethyl ether, filtered and vacuum dried. (22 mg, 16%, 2 steps). $^1$H NMR (300 MHz, $CDCl_3$) 0.96 (d, J=6.5 Hz, 3H), 1.00 (d, J=6.5 Hz, 3H), 1.50 (d, J=7.1 Hz, 3H), 1.69 (d, J=6.9 Hz, 3H), 1.81-2.16 (m, 4H), 2.63-2.74 (m, 1H), 3.26-3.38 (m 1H), 3.70-3.83 (m, 1H), 3.98 (d, J=12.3 Hz, 1H), 4.28 (t, J=9.8 Hz, 1H), 4.33-4.43 (m, 1H), 4.57 (d, J=5.8 Hz, 1H), 4.86 (q, J=6.7 Hz, 2H), 5.13 (d, J=5.8 Hz, 1H), 5.73 (t, J=6.9 Hz, 1H), 5.96 (q, J=6.7 Hz, 1H), 6.24 (d, J=16.3 Hz, 1H), 6.61-6.73 (m, 1H), 7.00 (d, J=16.3 Hz, 1H), 7.09-7.20 (m, 1H), 7.40 J=8.5 Hz, 1H), 7.58 (s, 1H), 7.81-7.93 (m, 2H), 8.22 (d, J=8.7 Hz, 1H). LCMS (m/z)=564.2 [M+H], Tr=1.96 min.

Example 74

Compound 74

Compound 74

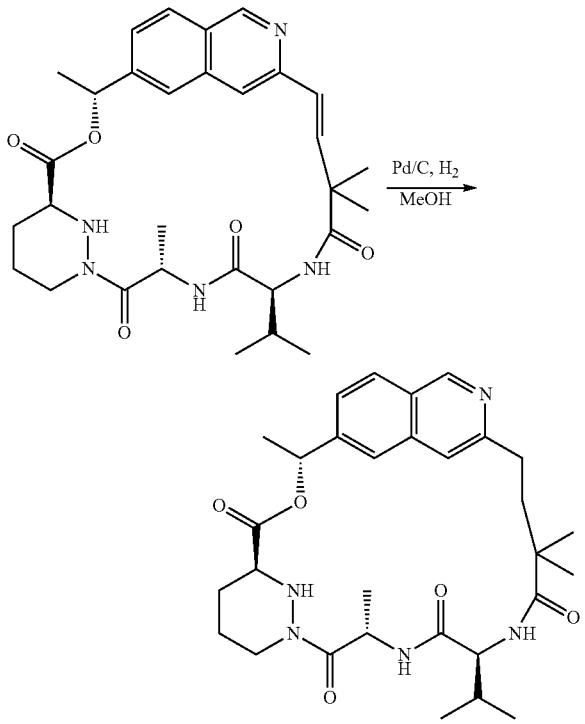

Compound 57 (20 mg, 0.036 mmol) was dissolved in methanol (5 mL) and catalytic amount of 10% Pd on carbon was added. The reaction mixture was stirred under atmosphere hydrogen for 2 h. The catalyst was removed by filtration and the eluent was concentrated under reduced pressure. Purification by reverse phase preparative HPLC gave the title compound (8.4 mg, 42% yield) as a white powder. $^1$H NMR (300 MHz, $CD_3OD$): δ 9.61 (s, 1H), 8.42 (d, J=9.0 Hz, 1H), 7.99 (s, 1H), 7.89 (d, J=9.0 Hz, 1H), 7.83 (br s, 1H), 7.29 (d, J=8.7 Hz, 1H), 6.27-6.21 (m, 1H), 5.92-5.82 (m, 1H), 3.96-3.5 (m, 4H), 3.28-3.19 (m, 1H), 3.08-2.98 (m, 1H), 2.30-2.20 (m, 1H), 2.10-1.90 (m, 4H), 1.78-1.72 (m, 5H), 1.56-1.51 (m, 6H), 1.21 (s, 3H), 0.89 (d, J=7.2 Hz, 6H). LCMS (m/z): 552.3 [M+H], Tr=1.74 min.

Example 75

Compound 75

Compound 75a

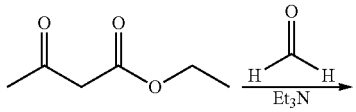

-continued

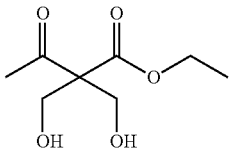

A solution of ethyl acetoacetate (20 g, 19.4 mL, 0.154 mol) in a mixture of dioxane (120 mL) and aqueous formaldehyde (37% solution in water, 57.7 mL, 0.77 mol) was stirred at RT. Triethylamine (1.0 M in tetrahydrofuran, 7.7 mL, 7.7 mmol) was added and the reaction mixture was heated at 60° C. for 20 h and then heated at 100° C. for 4 h. The reaction mixture was cooled to RT and was poured into water (1500 mL). The aqueous solution was washed with toluene. The aqueous layer was concentrated to ~50% of the initial volume and extracted with ethyl acetate. The organic extracts were combined and evaporated. The residue was purified by silica gel chromatography using a gradient of iso-hexane to iso-hexane/ethyl acetate 1:1 followed by silica gel chromatography using a gradient of iso-hexane to iso-hexane/ethyl acetate 3:2 to afford the title compound (2.33 g, 8%) as a yellow oil.

Compound 75b

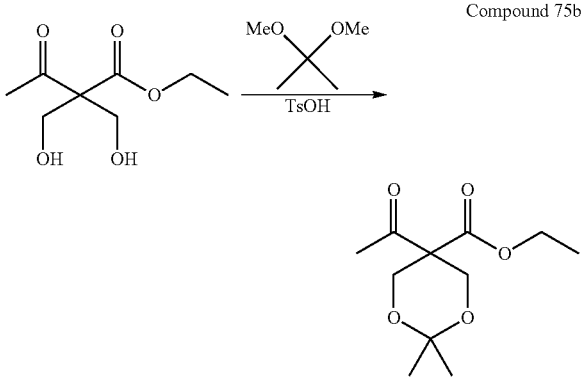

A solution of 75a (2.10 g, 11 mmol), 2,2-dimethoxypropane (13.5 mL, 110 mmol) and 4-toluenesulfonic acid hydrate (209 mg, 1.1 mmol) in acetone (8 mL) was stirred at RT for 18 h. Saturated sodium hydrogen carbonate solution was added and the mixture was extracted with ethyl acetate. The organic extracts were combined, washed with water and brine. The organic layer was filtered through a hydrophobic frit and the filtrate was evaporated. The residue was purified by silica gel chromatography using a gradient of iso-hexane/ethyl acetate 1:5 to 3:7 to afford the title compound (1.88 g, 74%) as a colorless oil.

Compound 75c

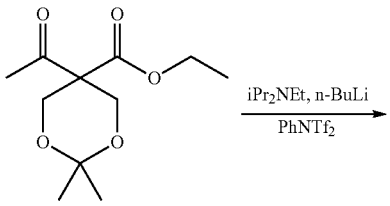

-continued

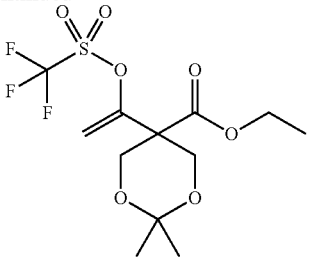

A solution of N,N-diisopropylethylamine (0.55 mL, 3.9 mmol) in tetrahydrofuran (20 mL) was stirred at −78° C. under nitrogen. n-Butyl lithium (1.6 M in hexane, 2.25 mL, 3.6 mmol) was added dropwise and the reaction mixture was warmed to 0° C. The reaction mixture was stirred at 0° C. for 5 min and then cooled to −78° C. A solution of 75b (690 mg, 3.0 mmol) in tetrahydrofuran (3 mL) was added dropwise and the reaction mixture was stirred at −78° C. for 15 min. A solution of N-phenyl-(bistrifluoromethanesulfonamide) (1.18 g, 3.3 mmol) in tetrahydrofuran (10 mL) was added dropwise over 5 min and the reaction mixture was stirred at −78° C. for 15 min. The cooling bath was removed and the reaction mixture was warmed to RT and then stirred at RT for 90 min. The solvent was evaporated and diethyl ether (30 mL) was added. The solution was cooled to 5° C. and was washed with cold 1 M sodium hydroxide solution (3×30 mL). The organic layer was separated, washed with brine, dried over anhydrous sodium sulfate, filtered and the solvent evaporated to afford the title compound (960 mg, 88%) as a yellow oil which was used directly in the next step.

Compound 75d

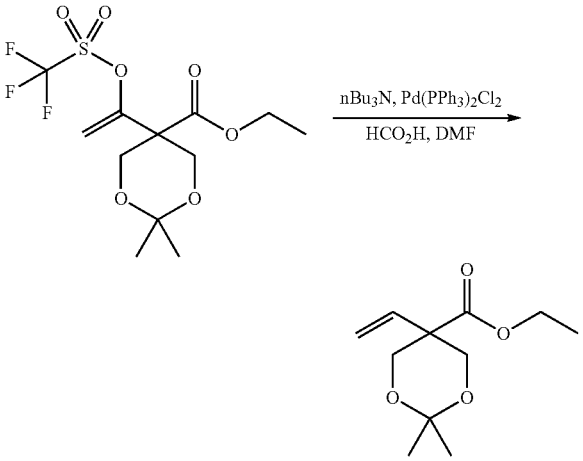

A solution of 75c (470 mg, 1.3 mmol) and tri-n-butylamine (721 mg, 0.93 mL, 3.9 mmol) in N,N-dimethylformamide (3 mL) was stirred at RT under nitrogen. Bis(triphenylphosphine)palladium(II) dichloride (45 mg, 0.065 mmol) and formic acid (120 mg, 0.1 mL, 2.6 mmol) was added and the reaction mixture was heated at 60° C. for 90 min. The reaction mixture was cooled to RT and ethyl acetate and water was added. The organic extract was separated, washed with water (5×), and brine. The organic solution was filtered through a hydrophobic frit and the filtrate was evaporated. The residue was purified by silica gel chromatography using iso-hexane/ethyl acetate 1:9 to afford the title compound (1.88 g, 74%) as a colorless oil.

Compound 75e

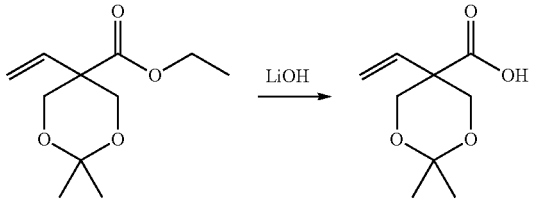

A solution of 75d (150 mg, 0.7 mmol) in tetrahydrofuran (3 mL) was stirred at 5° C. under nitrogen. A solution of lithium hydroxide monohydrate (59 mg, 1.4 mmol) in water (1 mL) was added and the reaction mixture was stirred at 5° C. for 30 min and then at RT for 5 h. Methanol (0.5 mL) was added to give a clear solution and the reaction mixture was stirred at RT for 22 h. The solvent was evaporated. Water (2 mL) was added to the residue and the solution was acidified to pH 2 with 2 M hydrochloric acid. Brine was added and the mixture was extracted with ethyl acetate. The organic extracts were combined, washed with brine. The organic extract was separated, washed with water (×5), and brine. The organic solution was filtered through a hydrophobic frit and the filtrate was evaporated to afford the title compound (117 mg, 90%) as a colorless oil.

Compound 75f

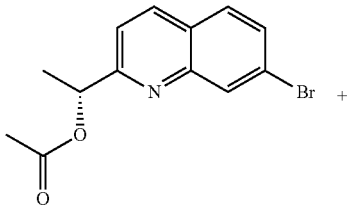

-continued

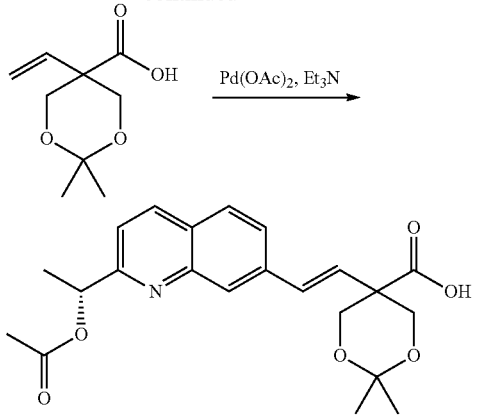

A mixture of 75e (96 mg, 0.5 mmol) and acetic acid (R)-1-(7-bromo-quinolin-2-yl)-ethyl ester (147 mg, 0.5 mmol) in acetonitrile (4 mL) was stirred at RT. Tri(o-tolyl) phosphine (46 mg, 0.15 mmol), palladium(II) acetate (17 mg, 0.075 mmol) and triethylamine (101 mg, 0.14 mL, 1.0 mmol) was added and the reaction mixture was heated in a microwave reactor at 100° C. for 20 min. The solvent was evaporated. Water and ethyl acetate was added and the mixture was acidified to pH 3-4 with 2 M hydrochloric acid. The mixture was extracted with ethyl acetate and the organic extracts were combined and washed with brine. The organic solution was filtered through a hydrophobic frit and the filtrate was evaporated. The residue was purified by silica gel chromatography using iso-hexane/ethyl acetate 1:1 to ethyl acetate to ethyl acetate/methanol 5:1. The residue was co-evaporated with ethyl acetate and then dichloromethane and dried to afford the title compound (134 mg, 67%) as a yellow gum.

Compound 75g

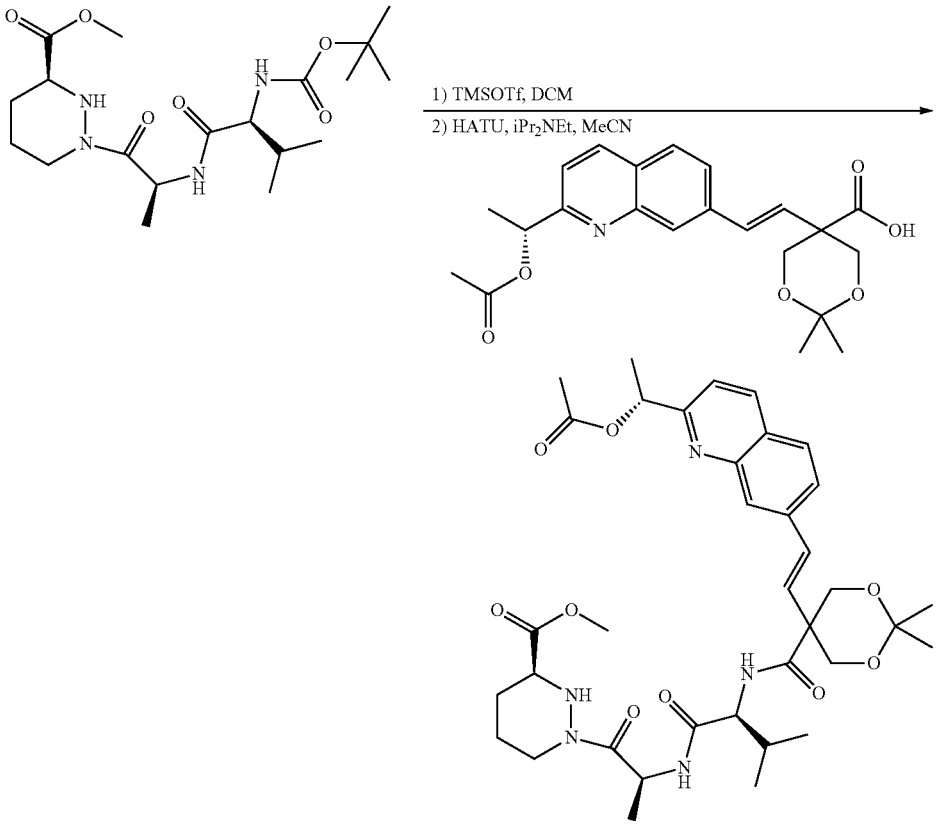

A solution of (S)-1-[(S)-2-((S)-2-tert-butoxycarbonylamino-3-methyl-butyrylamino)-propionyl]-hexahydro-pyridazine-3-carboxylic acid methyl ester (150 mg, 0.36 mmol) in dichloromethane (5 mL) was stirred at 0° C. under nitrogen. Trimethylsilyl trifluoromethanesulfonate (160 mg, 0.13 mL, 0.72 mmol) was added and the reaction mixture was stirred at 0° C. for 1 hour. N,N-Diisopropylethylamine (186 mg, 0.25 mL, 1.44 mmol) was added and the solvent was evaporated to afford (S)-1-[(S)-2-((S)-2-amino-3-methyl-butyrylamino)-propionyl]-hexahydro-pyridazine-3-carboxylic acid methyl ester (0.36 mmol) as a white solid which was used without further purification. A solution of 75f (134 mg, 0.33 mmol) in acetonitrile was stirred at 0° C. under nitrogen. A solution of (S)-1-[(S)-2-((S)-2-amino-3-methyl-butyrylamino)-propionyl]-hexahydro-pyridazine-3-carboxylic acid methyl ester (0.36 mmol) and N,N-diisopropylethylamine (129 mg, 0.17 mL, 1.0 mmol) in acetonitrile (5 mL) was added followed by 2-(1H-7-azabenzotriazol-1-yl)-1,1,3,3-tetramethyl uronium hexafluorophosphate methanaminium (175 mg, 0.46 mmol) and the reaction mixture was stirred at 0° C. for 10 min and then at RT for 1 hour. The solvent was evaporated and the residue was apportioned between ethyl acetate and water. The organic extracts were combined and washed with brine. The organic solution was filtered through a hydrophobic frit and the filtrate was evaporated. The residue was purified by silica gel chromatography using iso-hexane/ethyl acetate 1:5 to ethyl acetate to afford the title compound (165 mg, 72%) as a yellow solid.

Compound 75h

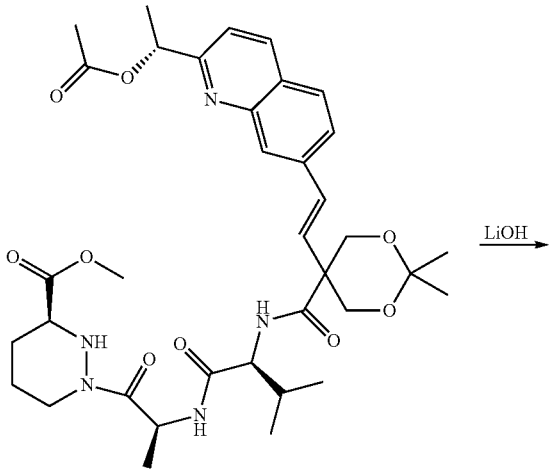

-continued

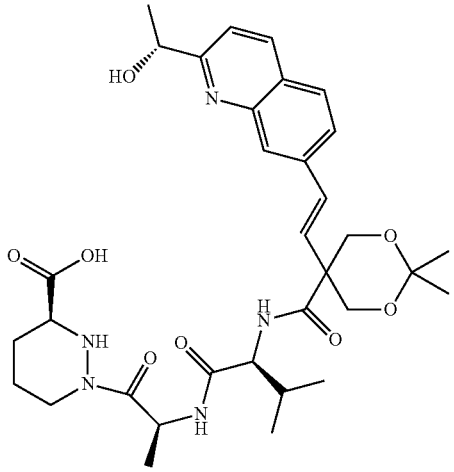

A solution of 75 g (35 mg, 0.05 mmol) in tetrahydrofuran (0.5 mL) was stirred at 5° C. under nitrogen. A solution of lithium hydroxide monohydrate (8.4 mg, 0.2 mmol) in water (0.5 mL) was added followed by methanol (0.5 mL) and the reaction mixture was stirred at 5° C. for 1 hour. 1 M hydrochloric acid (0.2 mL) was added and the solvent was evaporated. The residue was co-evaporated with methanol/toluene (1:1, 2×) followed by toluene (2×). The residue was triturated with diethyl ether (3×) and dried to afford the title compound (0.05 mmol) as a pale yellow solid which was used crude in the next reaction.

Compound 75

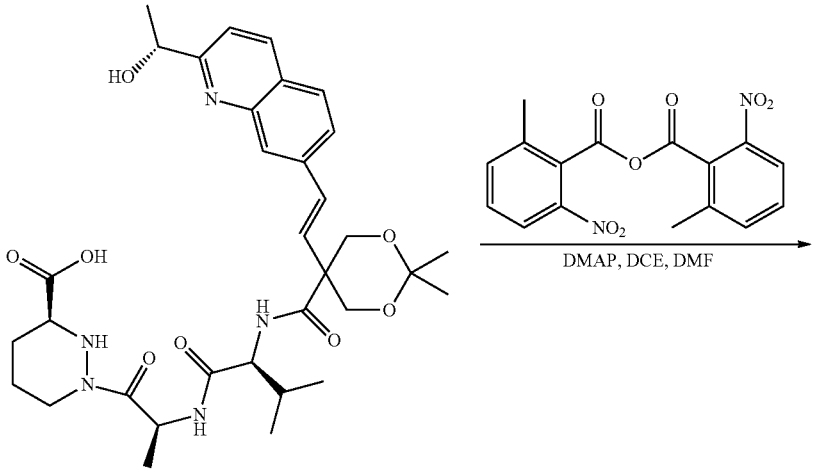

-continued

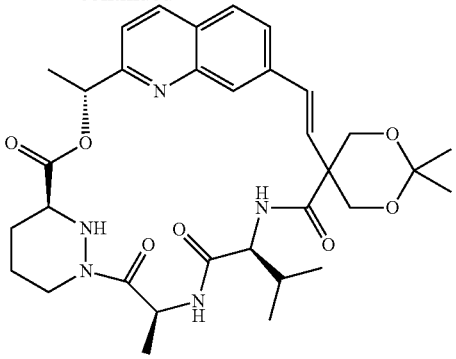

A solution of 2-methyl-6-nitrobenzoic anhydride (86 mg, 0.25 mmol) and 4-dimethylaminopyridine (46 mg, 0.38 mmol) in 1,2-dichloroethane (16 mL) was stirred at RT under nitrogen. A molecular sieves (400 mg) was added and the suspension was heated at 50° C. A solution of crude 75 h (0.05 mmol) in N,N-dimethylformamide (2 mL) was added dropwise over 4 h and the reaction mixture was stirred at 50° C. for an additional 1 hour. The reaction mixture was cooled to RT and the mixture was filtered through celite. The filter pad was washed with ethyl acetate and the filtrate was evaporated. The residue was diluted with ethyl acetate and the solution was washed with brine (3×). The organic layer was separated and evaporated. The organic solution was filtered through a hydrophobic frit and the filtrate was evaporated. The residue was purified by preparative HPLC to afford the title compound (4.2 mg, 13%) as a white solid. $^1$H NMR (300 MHz, $CD_3OD$) 1.00 (d, J=6.7 Hz, 3H), 1.01 (d, J=6.6 Hz, 3H), 1.37 (s, 3H), 1.47 (s, 3H), 1.63 (d, J=7.1 Hz, 3H), 1.64-1.70 (m, 2H), 1.73 (d, J=6.9 Hz, 3H), 1.85-2.10 (m, 3H), 2.70-2.80 (m, 1H), 3.78-3.87 (m, 1H), 3.87 (d, J=11.1 Hz, 1H), 4.03-4.07 (m, 1H), 4.26-4.46 (m, 5H), 5.72 (q, J=7.1 Hz, 1H), 5.93 (q, J=6.8 Hz, 1H), 6.38 (s, 2H), 7.42 (d, J=8.5 Hz, 1H), 7.61 (br s, 1H), 7.78-7.86 (m, 2H), 8.22 (d, J=8.5 Hz, 1H). LCMS (m/z) 622.2 [M+H], Tr=2.24 min.

Example 76

Compound 76

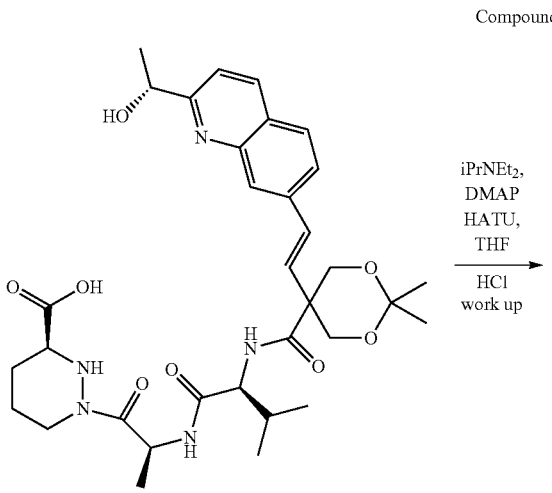

-continued

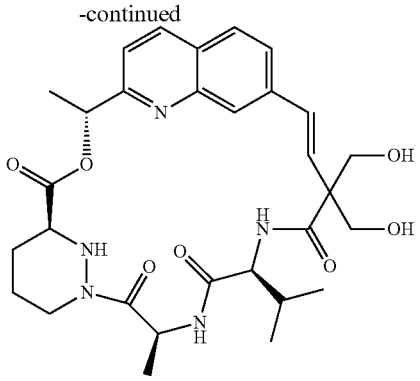

A suspension of crude 75 h (200 mg, 0.25 mmol) in tetrahydrofuran (100 mL) was stirred at RT under nitrogen. N,N-diisopropylethylamine (161 mg, 0.22 mL, 1.25 mmol) and 4-dimethylaminopyridine (15 mg, 0.125 mmol) was added and the suspension was stirred for 5 min. 2-(1H-7-Azabenzotriazol-1-yl)-1,1,3,3-tetramethyl uronium hexafluorophosphate methanaminium (133 mg, 0.35 mmol) was added and the reaction mixture was stirred at RT for 2 h. Additional 2-(1H-7-azabenzotriazol-1-yl)-1,1,3,3-tetramethyl uronium hexafluorophosphate methanaminium (57 mg, 0.15 mmol) was added and the reaction mixture was stirred at RT for 1 hour. The solvent was evaporated and the residue was diluted with ethyl acetate and 2 M hydrochloric acid. The organic solution was separated and washed with water, saturated sodium hydrogen carbonate solution, and brine. The organic solution was filtered through a hydrophobic frit and the filtrate was evaporated. The residue was purified by silica gel chromatography using iso-hexane/ethyl acetate 7:3 to ethyl acetate to ethyl acetate/methanol 9:1. The residue was purified by preparative HPLC to afford the title compound (20 mg, 14%) as a white solid. $^1$H NMR (500 MHz, $CD_3OD$) 1.00 (d, J=6.5 Hz, 3H), 1.01 (d, J=6.5 Hz, 3H), 1.68 (d, J=7.1 Hz, 3H), 1.73 (d, J=6.7 Hz, 3H), 1.74-2.05 (m, 5H), 2.72-2.80 (m, 1H), 3.70 (d, J=11.1 Hz, 1H), 3.81-4.07 (m, 4H), 4.35-4.47 (m, 3H), 5.77 (q, J=7.1 Hz, 1H), 5.92 (q, J=6.8 Hz, 1H), 6.43 (s, 2H), 7.40 (d, J=8.5 Hz, 1H), 7.63 (s, 1H), 7.82 (s, 2H), 8.21 (d, J=8.5 Hz, 1H). LCMS (m/z) 582.2 [M+H], Tr=1.66 min.

Example 77

Compound 77

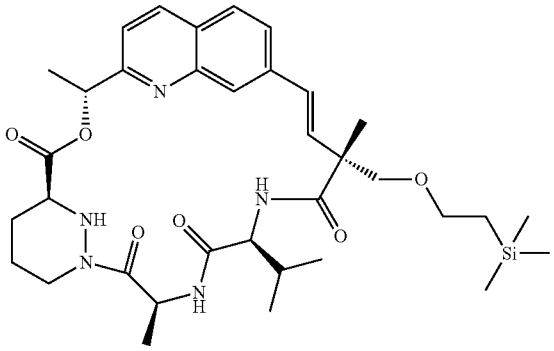

Compound 77a. (R)-4-Isopropyl-3-((E)-2-methyl-but-2-enoyl)-oxazolidin-2-one

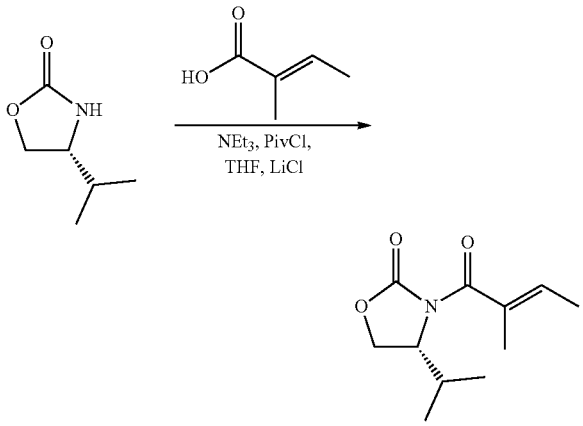

A cooled (−20° C.) solution of tiglic acid (2.005 g, 20.031 mmol) in anhydrous tetrahydrofuran (50 mL) was sequentially treated with triethylamine (6.1 mL, 44.068 mmol) and dropwise pivaloyl chloride (2.7 mL, 22.034 mmol). After stirring at −20° C. for 30 min, lithium chloride (1.019 g, 24.037 mmol) and (R)-(+)-4-isopropyl-2-oxazolidinone (2.587 g, 20.031 mmol) were added. The reaction mixture was allowed to slowly warm to room temperature, stirred for 3 days and was then quenched with saturated ammonium chloride. The aqueous layer was extracted with ethyl acetate (2×). The organics were combined, dried over anhydrous sodium sulfate, filtered and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (3.307 g, 78%) as a colourless solid. $^1$H NMR (300 MHz, $CDCl_3$): δ 0.92 (d, J=6.9 Hz, 3H), 0.94 (d, J=7.1 Hz, 3H), 1.83 (d, J=6.9 Hz, 3H), 1.93 (s, 3H), 2.38 (d of heptet, J=6.9, 4.2 Hz, 1H), 4.19 (dd, J=8.9, 4.6 Hz, 1H), 4.33 (app t, J=8.9 Hz, 1H), 4.49-4.58 (m, 1H), 6.23 (q, J=7.1 Hz, 1H).

Compound 77b. (R)-4-Isopropyl-3-[(R)-2-methyl-2-(2-trimethylsilanyl-ethoxymethyl)-but-3-enoyl]-oxazolidin-2-one

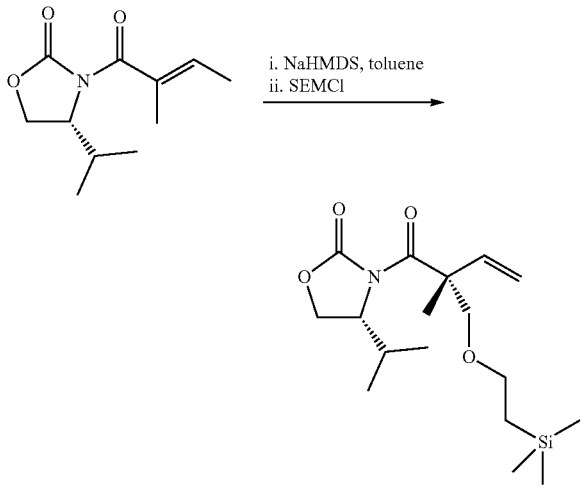

Residual moisture in (R)-4-isopropyl-3-((E)-2-methyl-but-2-enoyl)-oxazolidin-2-one (458.9 mg, 2.172 mmol) was removed by azeotroping with anhydrous toluene. A cooled (−78° C.) solution of dried (R)-4-isopropyl-3-((E)-2-methyl-but-2-enoyl)-oxazolidin-2-one in anhydrous toluene (10 mL) was treated dropwise with a solution of sodium bis (trimethylsily)amide in toluene (0.6 M, 5.4 mL, 3.258 mmol). After stirring the yellow solution at −78° C. for 35 min, 2-(trimethylsilyl)ethoxymethyl chloride (1.1 mL, 6.516 mmol) was added. After stirring at 0° C. for 3.5 h, the reaction was quenched with saturated ammonium chloride. The aqueous layer was extracted with dichloromethane (2×). The organics were combined, filtered through a phase separator and the volatiles were removed in vacuo. The residue was purified by silica gel chromatography using a 50 g Isolute cartridge eluted with a continuous gradient of iso-hexanes/ethyl acetate 1:0 to 9:1 to afford the title compound (543.3 mg, 73%) as a colourless oil and as a 5:1 mixture of diastereoisomers. $^1$H NMR (300 MHz, $CDCl_3$) δ 0.01 (s, 9H), 0.77-0.99 (m, 8H), 1.49 (s, 3H), 2.36 (d of heptet, J=6.9, 3.8 Hz, 1H), 3.42-3.60 (m, 3H), 4.15-4.31 (m, 3H), 4.49-4.57 (m, 1H), 5.00 (d, J=17.6 Hz, 1H), 5.10 (d, J=10.7, 1H), 6.19 (dd, J=17.8, 10.7 Hz, 1H). LCMS (m/z) 364.1 [M+Na], Tr=3.32 min.

Compound 77c. (R)-2-Methyl-2-(2-trimethylsilanyl-ethoxymethyl)-but-3-enoic acid

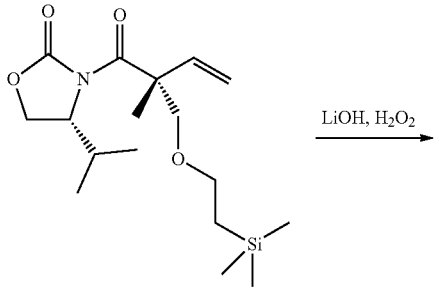

-continued

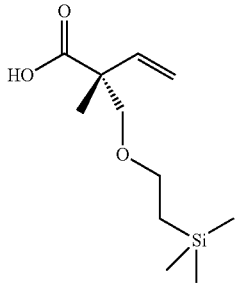

A cooled (0° C.) solution of (R)-4-isopropyl-3-[(R)-2-methyl-2-(2-trimethylsilanyl-ethoxymethyl)-but-3-enoyl]-oxazolidin-2-one (543.3 mg, 1.591 mmol) in tetrahydrofuran/water (15 mL, 2:1) was subsequently treated with hydrogen peroxide (30%, 820 μL, 7.955 mmol) and lithium hydroxide monohydrate (133.5 mg, 3.181 mmol). After stirring at 0° C. for 2 h, the reaction was quenched with solid sodium metabisulfite (3 g, 16 mmol). After stirring at room temperature for 30 min, the mixture was acidified with hydrochloric acid (1 M) to pH 2, the aqueous layer was extracted with dichloromethane (2×). The organics were combined, filtered through a phase separator and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (322.3 mg, 88%) as a colourless oil. $^1$H NMR (300 MHz, $CDCl_3$) δ 0.03 (s, 9H), 0.98 (app t, J=8.5 Hz, 2H), 1.34 (s, 3H), 3.46 (d, J=8.9 Hz, 1H), 3.57-3.67 (m, 3H), 5.19-5.29 (m, 2H), 6.00 (dd, J=17.4, 10.7 Hz, 1H), 10.80 (br s, 1H).

Compound 77d. (E)-(R)-4-[2-((R)-1-Acetoxy-ethyl)-quinolin-7-yl]-2-methyl-2-(2-trimethylsilanyl-ethoxymethyl)-but-3-enoic acid

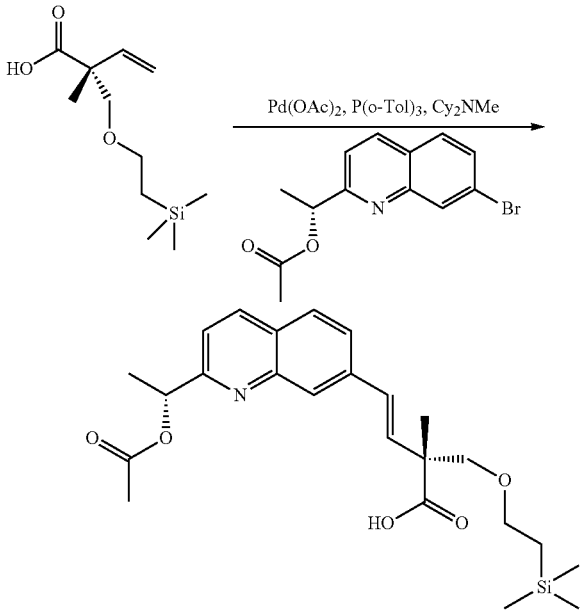

A solution of (R)-2-methyl-2-(2-trimethylsilanyl-ethoxymethyl)-but-3-enoic acid (214.1 0.728 mmol), acetic acid (R)-1-(7-bromo-quinolin-2-yl)-ethyl ester (167.7 mg, 0.728 mmol), palladium(II)acetate (33.0 mg, 0.146 mmol), tri(o-tolyl)phosphine (44.4 mg, 0.146 mmol) and N,N-dicyclohexylmethylamine (390 μL, 1.820 mmol) in anhydrous 1,4-dioxane (10 mL) was heated at reflux for 3 h, after which palladium(II)acetate (33.0 mg, 0.146 mmol) and tri(o-tolyl) phosphine (44.4 mg, 0.146 mmol) were added. After 1.5 h, the heating was stopped and the reaction was allowed to stand at room temperature overnight. The mixture was then treated with palladium(II)acetate (33.0 mg, 0.146 mmol) and tri(o-tolyl)phosphine (44.4 mg, 0.146 mmol). After stirring at reflux for 3 h, the mixture was cooled to room temperature, quenched with hydrochloric acid (1 M, 10 mL). The aqueous layer was extracted with ethyl acetate (2×). The organics were combined, dried over anhydrous sodium sulfate, filtered and the volatiles were removed in vacuo. The residue was purified by silica gel chromatography using a 25 g Isolute cartridge eluted with a continuous gradient of iso-hexanes/ethyl acetate 1:0 to 1:1 to afford the title compound (275.5 mg, 85%) as a yellow oil. $^1$H NMR (300 MHz, $CDCl_3$) δ 0.04 (s, 9H), 1.02 (dd, J=9.1, 7.3 Hz, 2H), 1.50 (s, 3H), 1.69 (d, J=6.7 Hz, 3H), 2.18 (s, 3H), 3.59-3.76 (m, 4H), 6.07 (q, J=6.7 Hz, 1H), 6.67 (ABq, $\Delta\delta_{AB}$=0.15, $J_{AB}$=16.3 Hz, 2H), 7.44 (d, J=8.2 1H), 7.62 (dd, J=8.5, 1.3 Hz, 1H), 7.75 (d, J=8.5 Hz, 1H), 8.05 (s, 1H), 8.12 (d, J=8.5 Hz, 1H). LCMS (m/z) 444.1 [M+H], Tr=3.29 min.

Compound 77e. (S)-1-[(S)-2-((S)-2-tert-Butoxycarbonylamino-3-methyl-butyrylamino)-propionyl]-hexahydro-pyridazine-3-carboxylic acid methyl ester

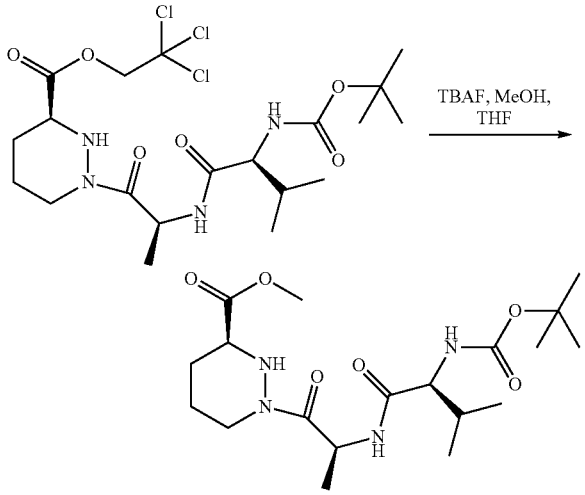

A solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (3.01 g, 5.66 mmol) in tetrahydrofuran/methanol (1:1, 60 mL) was stirred at 0° C. Tetra-n-butylammonium fluoride (1 M in tetrahydrofuran, 11.3 mL, 11.3 mmol) was added and the reaction mixture was stirred at room temperature for 22 h. The solvent was removed in vacuo and the residue was purified by silica gel chromatography using a continuous gradient of iso-hexanes/ethyl acetate 1:0 to 1:1 afford the title compound (2.14 g, 91%) as a white foam. $^1$H NMR (300 MHz, $CDCl_3$) δ □0.91 (d, J=6.9 Hz, 3H), 0.95 (d, J=6.9 Hz, 3H), 1.32 (d, J=6.9 Hz, 3H), 1.46 (s, 9H), 1.61-2.17 (m, 6H), 2.80-2.88 (m, 1H), 3.47-3.58 (m, 1H), 3.73-3.78 (s, 3H), 3.94-4.02 (m, 1H), 4.33-4.38 (m, 1H), 5.13 (d, J=8.3 Hz, 1H), 5.27-5.37 (m, 1H), 6.75 (d, J=7.6 Hz, 1H). LCMS (m/z) 415.1 [M+H], Tr=3.17 min.

Compound 77f. (S)-1-((S)-2-{(S)-2-[(E)-(R)-4-[7-((R)-1-Acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester

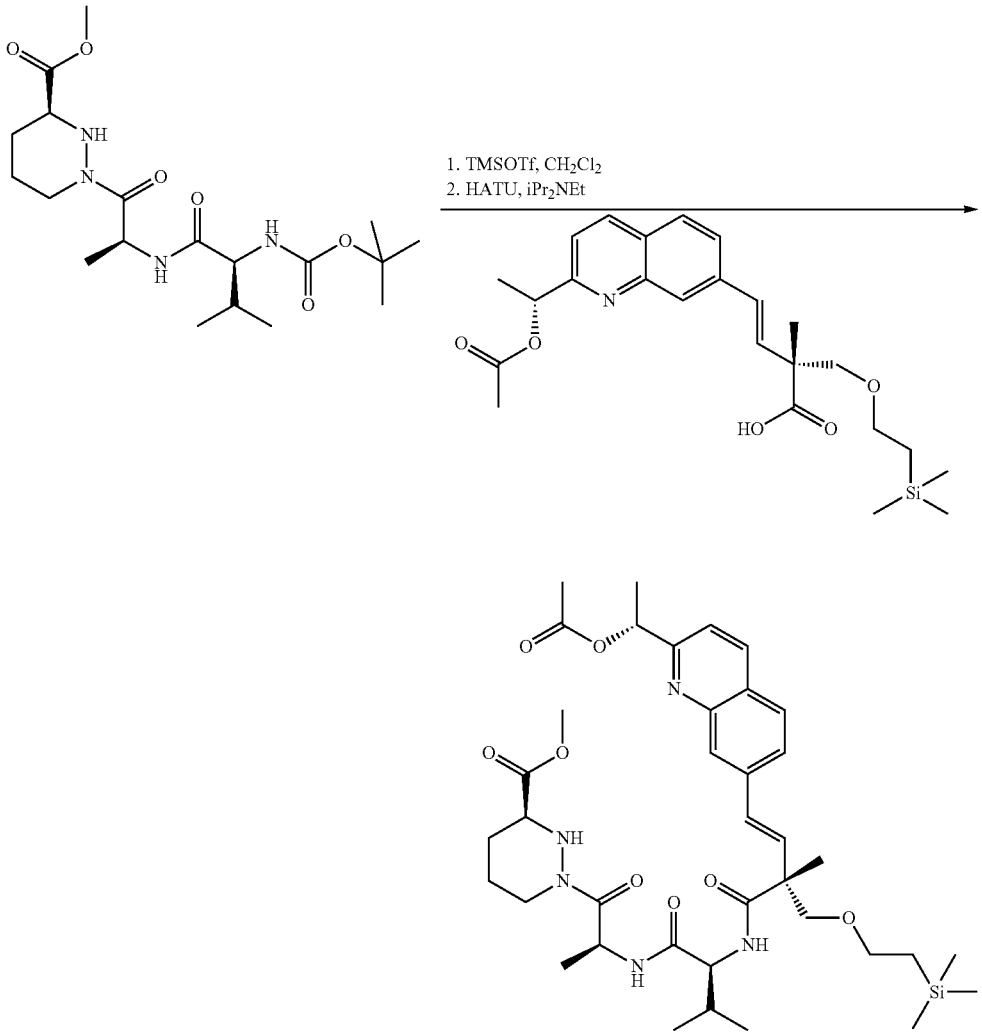

A cooled (0° C.) solution of (S)-1-[(S)-2-((S)-2-tert-butoxycarbonylamino-3-methyl-butyrylamino)-propionyl]-hexahydro-pyridazine-3-carboxylic acid methyl ester (257.4 mg, 0.621 mmol) in dichloromethane (15 mL) was treated with trimethylsilyl-trifluoromethanesulfonate (230 μL, 1.242 mmol). After stirring at 0° C. for 50 min, the reaction mixture was treated with N,N-diisopropylethylamine (430 μL, 2.484 mmol) and the volatiles were removed in vacuo. To the white solid was added a solution of (E)-(R)-4-[2-((R)-1-acetoxy-ethyl)-quinolin-7-yl]-2-methyl-2-(2-trimethylsilanyl-ethoxymethyl)-but-3-enoic acid (275.5 mg, 0.621 mmol) in acetonitrile (15 mL) and the solution was cooled to 0° C. then treated with N,N-diisopropylethylamine (430 μL, 2.484 mmol) and 2-(1H-7-azabenzotriazol-1-yl)-1,1,3,3-tetramethyl uronium hexafluorophosphate methanaminium (283.4 mg, 0.745 mmol). After stirring at room temperature for 20 h, the reaction was quenched with hydrochloric acid (1 M, 20 mL). The aqueous layer was extracted with ethyl acetate (2×). The organics were combined, dried over anhydrous sodium sulfate, filtered and the volatiles were removed in vacuo. The residue was purified by silica gel chromatography using a 25 g Isolute cartridge eluted with a continuous gradient of iso-hexanes/ethyl acetate 1:0 to 1:3 to 0:1 to afford a yellow gum that was dissolved in ethyl acetate and washed with saturated sodium bicarbonate. The organics were then dried over anhydrous sodium sulfate, filtered and the volatiles were removed in vacuo to provide the title compound (319.4 mg, 69%) as a yellow glass. $^1$H NMR (300 MHz, $CDCl_3$) δ 0.04 (s, 9H), 0.83-1.01 (m, 8H), 1.21-1.34 (m, 4H), 1.43 (s, 3H), 1.56-1.76 (m, 5H), 1.82-1.95 (m, 1H), 1.99-2.11 (m, 1H), 2.18 (s, 3H), 2.23-2.41 (m, 2H), 2.73-2.88 (m, 1H), 3.48-3.57 (m, 1H), 3.59-3.66 (m, 2H), 3.69-3.81 (m, 4H), 4.07-4.17 (m, 1H), 4.33-4.43 (m, 2H), 5.31 (app pentet, J=7.1 Hz, 1H), 6.06 (q, J=6.7 Hz, 1H), 6.73 (ABq, $\Delta\delta_{AB}$=0.06, $J_{AB}$=16.3 Hz, 2H), 6.86 (d, J=7.6 Hz, 1H), 7.42 (d, J=8.5 Hz, 1H), 7.55 (d, J=8.5 Hz, 1H), 7.62 (dd, J=8.5, 1.3 Hz, 1H), 7.74 (d, J=8.7 Hz, 1H), 8.02 (s, 1H), 8.11 (d, J=8.7 Hz, 1H). LCMS (m/z) 740.4 [M+H], Tr=3.41 min.

Compound 77

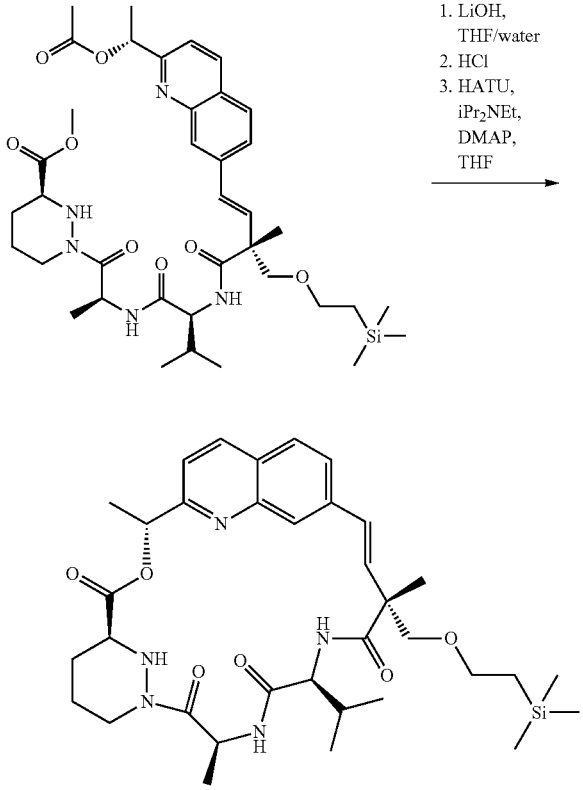

A cooled (0° C.) solution of (S)-1-((S)-2-{(S)-2-[(E)-(R)-4-[7-((R)-1-acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester (319.4 mg, 0.432 mmol) in tetrahydrofuran/water (30 mL, 5:1) was treated with lithium hydroxide monohydrate (130.2 mg, 3.105 mmol). After stirring at 0° C. for 4.75 h, the reaction mixture was quenched with hydrochloric acid (2 M, 2.1 mL). The volatiles were removed in vacuo. Residual acetic acid and methanol were azeotroped off with methanol/toluene (3×) then toluene (3×). To the white solid was added N,N-dimethylaminopyridine (8.0 mg, 0.062 mmol), 4 Å molecular sieves and dry tetrahydrofuran (210 mL). The reaction mixture was subsequently treated with N,N-diisopropylethylamine (540 μL, 3.105 mmol) and 2-(1H-7-azabenzotriazol-1-yl)-1,1,3,3-tetramethyl uronium hexafluorophosphate methanaminium (283.3 mg, 0.745 mmol). After stirring at room temperature for 4 h, the volatiles were removed in vacuo. The residue was partitioned between ethyl acetate and hydrochloric acid (1 M). The organic layer was washed with saturated sodium bicarbonate, dried over anhydrous sodium sulfate, filtered and the volatiles were removed in vacuo. The residue was purified by silica gel chromatography using a 25 g Isolute cartridge eluted with a continuous gradient of iso-hexanes/acetone 1:0 to 7:3 to afford the title compound (152.6 mg, 37%) as a white solid. A 20 mg sample was purified by preparative reverse phase HPLC eluted with a gradient of acetonitrile/water 1:1 to 1:0 to afford the title compound (5.5 mg, 27%) as a white solid. $^1$H NMR (300 MHz, $CD_3OD$) δ 0.04 (s, 9H), 0.90-1.01 (m, 8H), 1.55 (s, 3H), 1.61 (d, J=7.3 Hz, 3H), 1.65-1.78 (m, 5H), 1.86-2.07 (m, 3H), 2.67-2.81 (m, 1H), 3.47 (d, J=8.7 Hz, 1H), 3.54-3.68 (m, 2H), 3.74-3.84 (m, 2H), 4.28 (d, J=10.5 Hz, 1H), 4.35-4.47 (m, 1H), 5.72 (q, J=7.1 Hz, 1H), 5.92 (q, J=6.9 Hz, 1H), 6.38 (ABq, $\Delta\delta_{AB}$=0.02, $J_{AB}$=16.7 Hz, 2H), 7.41 (d, J=8.5 Hz, 1H), 7.64 (s, 1H), 7.73 (dd, J=8.7, 1.6 Hz, 1H), 7.80 (d, J=8.5 Hz, 1H), 8.21 (d, J=8.5 Hz, 1H). LCMS (m/z) 667.1 [M+H], Tr=3.40 min.

Example 78

Compound 78

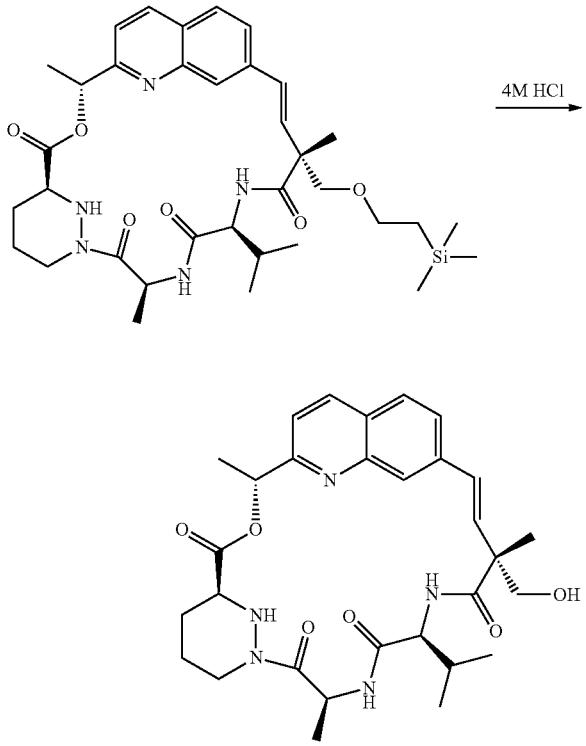

A solution of compound 77 (126.2 mg, 0.189 mmol) in hydrochloric acid (4 M in 1,4-dioxane, 10 mL) was stirred at room temperature for 23 h. The reaction mixture was then slowly added to solid sodium bicarbonate. The residue was partitioned between ethyl acetate and water. The aqueous layer was extracted with ethyl acetate (2×). The organics were combined, dried over anhydrous sodium sulfate, filtered and the volatiles were removed in vacuo. The residue was purified by silica gel chromatography using a 25 g Isolute cartridge eluted with a continuous gradient of iso-hexanes/acetone 1:0 to 2:3 to afford the title compound (53.6 mg, 50%) as a white solid. $^1$H NMR (300 MHz, $CD_3OD$) δ 0.90-1.02 (m, 6H), 1.22-1.37 (m, 2H), 1.52 (s, 3H), 1.61-1.78 (m, 8H), 1.86-2.06 (m, 3H), 2.68-2.81 (m, 1H), 3.65 (d, J=10.9 Hz, 1H), 3.76-3.93 (m, 2H), 4.29 (d, J=10.5 Hz, 1H), 4.35-4.47 (m, 1H), 5.75 (q, J=7.1 Hz, 1H), 5.92 (q, J=6.9 Hz, 1H), 6.38 (ABq, $\Delta\delta_{AB}$=0.05, $J_{AB}$=16.7 Hz, 2H), 7.41 (d, J=8.5 Hz, 1H), 7.66 (s, 1H), 7.75-7.84 (m, 2H), 8.21 (d, J=7.6 Hz, 1H). LCMS (m/z) 566.2 [M+H], Tr=1.83 min.

Example 79

Compound 79

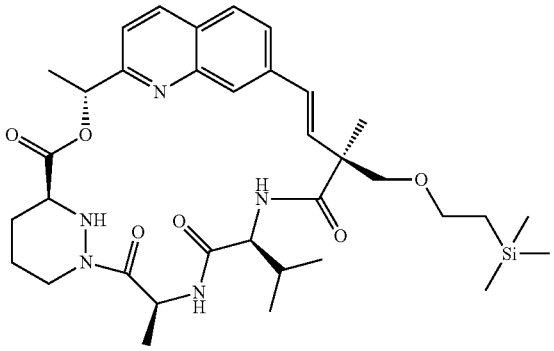

Compound 79a. (E)-(S)-4-[2-((R)-1-Acetoxy-ethylyquinolin-7-yl]-2-methyl-2-(2-trimethylsilanyl-ethoxymethyl)-but-3-enoic acid

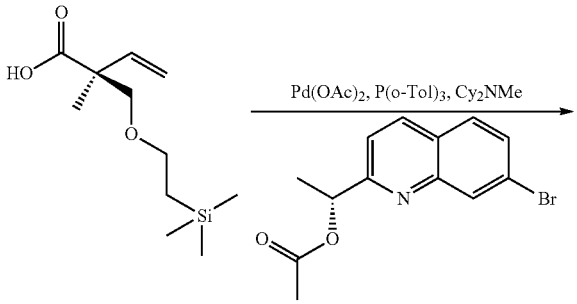

-continued

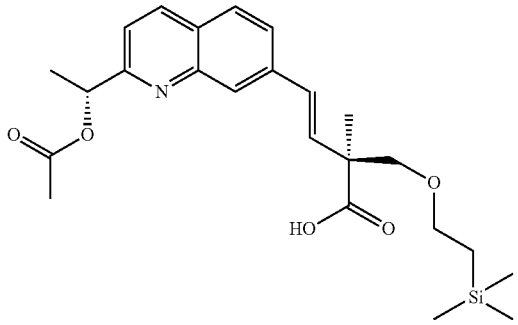

Compound 79a (the enantiomer of the previously described 77c) was prepared in the same manner as compound 77d using (S)-2-methyl-2-(2-trimethylsilanyl-ethoxymethyl)-but-3-enoic acid instead of (R)-2-methyl-2-(2-trimethylsilanyl-ethoxymethyl)-but-3-enoic acid in 86% yield. $^1$H NMR (300 MHz, $CDCl_3$) δ 0.04 (s, 9H), 1.03 (dd, J=9.6, 7.1 Hz, 2H), 1.49 (s, 3H), 1.69 (d, J=6.9 Hz, 3H), 2.18 (s, 3H), 3.59-3.77 (m, 4H), 6.07 (q, J=6.7 Hz, 1H), 6.66 (ABq, $\Delta\delta_{AB}$=0.16, $J_{AB}$=16.3 Hz, 2H), 7.44 (d, J=8.5 Hz, 1H), 7.61 (dd, J=8.5, 1.6 Hz, 1H), 7.75 (d, J=8.7 Hz, 1H), 8.05 (s, 1H), 8.12 (d, J=8.5 Hz, 1H). LCMS (m/z) 444.1 [M+H], Tr=3.27 min.

Compound 79b. (S)-1-((S)-2-{(S)-2-[(E)-(S)-4-[7-((R)-1-Acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester

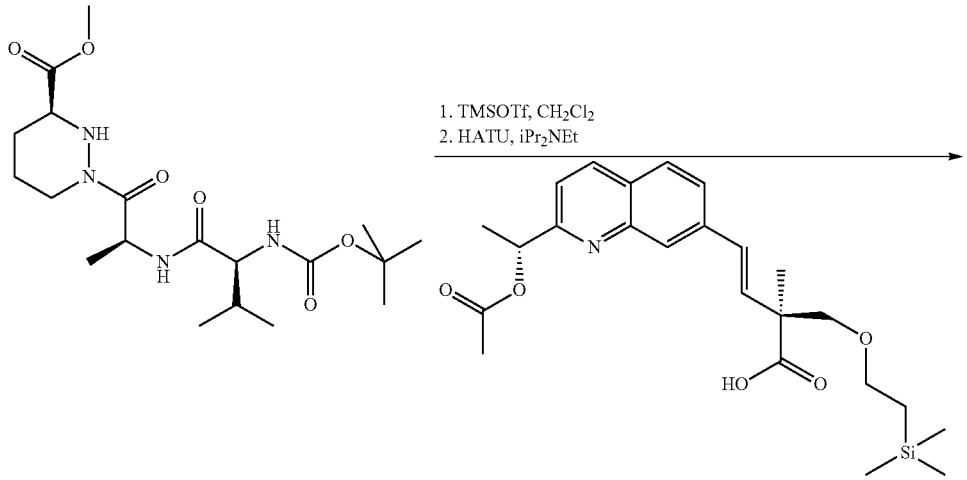

-continued

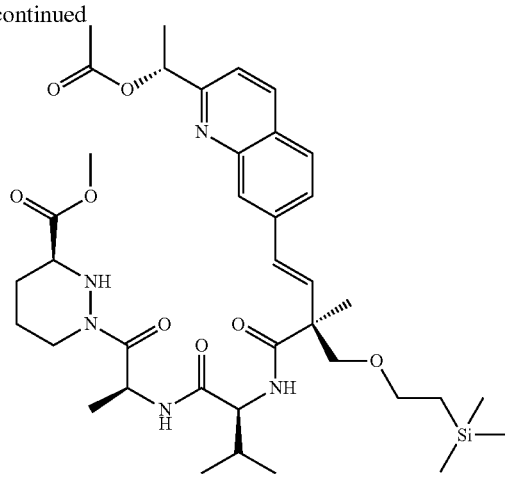

Compound 79b was prepared in the same manner as compound 77f using (E)-(S)-4-[2-((R)-1-acetoxy-ethyl)-quinolin-7-yl]-2-methyl-2-(2-trimethylsilanyl-ethoxymethyl)-but-3-enoic acid instead of (E)-(R)-4-[2-((R)-1-acetoxy-ethyl)-quinolin-7-yl]-2-methyl-2-(2-trimethylsilanyl-ethoxymethyl)-but-3-enoic acid in 60% yield. $^1$H NMR (300 MHz, $CDCl_3$) δ 0.04 (s, 9H), 0.83-1.10 (m, 8H), 1.28 (d, J=6.7 Hz, 3H), 1.45 (s, 3H), 1.64-1.72 (m, 5H), 1.81-1.94 (m, 1H), 1.99-2.09 (m, 1H), 2.18 (s, 3H), 2.19-2.31 (m, 1H), 2.69-2.79 (m, 1H), 3.45-3.55 (m, 1H), 3.59-3.69 (m, 4H), 3.71-3.80 (m, 4H), 4.29-4.42 (m, 2H), 5.28 (app pentet, J=6.9 Hz, 1H), 6.06 (q, J=6.7 Hz, 1H), 6.68-6.87 (m, 3H), 7.32 (d, J=8.2 Hz, 1H), 7.42 (d, J=8.5 Hz, 1H), 7.66-7.77 (m, 2H), 8.05 (s, 1H), 8.11 (d, J=8.5 Hz, 1H). LCMS (m/z) 740.4 [M+H], Tr=3.46 min.

Compound 79

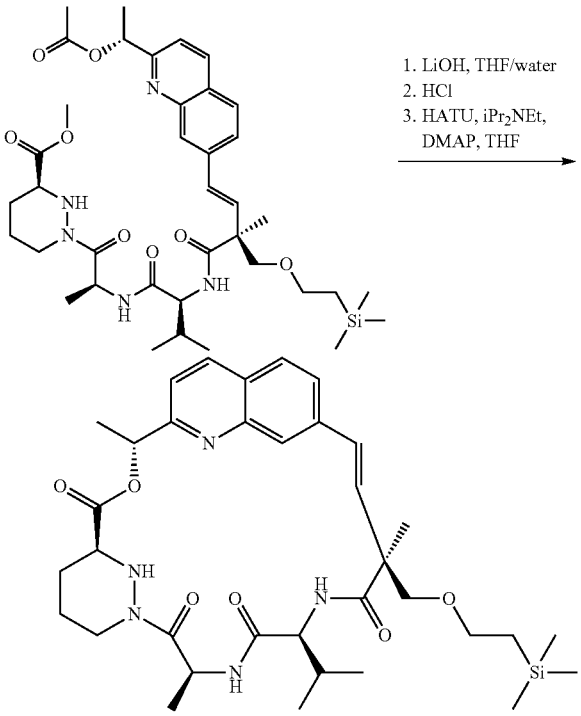

Compound 79 was prepared in the same manner as compound 77 using (S)-1-((S)-2-{(S)-2-[(E)-(S)-4-[7-((R)-1-acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester instead of (S)-1-((S)-2-{(S)-2-[(E)-(R)-4-[7-((R)-1-acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester in 71% yield. $^1$H NMR (300 MHz, $CD_3OD$) δ 0.00 (s, 9H), 0.93-1.04 (m, 8H), 1.29 (s, 3H), 1.63-1.76 (m, 7H), 1.87-2.04 (m, 3H), 2.69-2.82 (m, 1H), 3.61-3.72 (m, 4H), 3.77-3.89 (m, 1H), 4.32-4.47 (m, 3H), 5.75 (q, J=7.1 Hz, 1H), 5.92 (q, J=6.9 Hz, 1H), 6.38 (ABq, $\Delta\delta_{AB}$=0.18, $J_{AB}$=16.5 Hz, 2H), 7.40 (d, J=8.5 Hz, 1H), 7.61 (s, 1H), 7.76-7.87 (m, 2H), 8.21 (d, J=8.5 Hz, 1H). LCMS (m/z) 667.3 [M+H], Tr=3.28 min.

Example 80

Compound 80

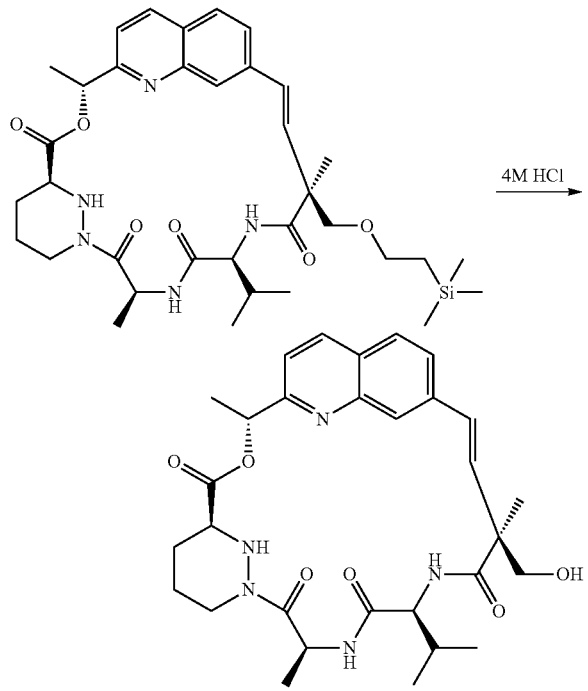

Compound 80 was prepared in the same manner as compound 78 using compound 79 instead of compound 77 in 13% yield. $^1$H NMR (300 MHz, $CD_3OD$) δ 1.01 (d, J=6.7 Hz, 6H), 1.24 (s, 3H), 1.62-1.76 (m, 8H), 1.84-2.06 (m, 3H), 2.70-2.82 (m, 1H), 3.72-3.89 (m, 3H), 4.33-4.48 (m, 3H), 5.78 (q, J=7.1 Hz, 1H), 5.93 (q, J=6.9 Hz, 1H), 6.38 (ABq, $\Delta\delta_{AB}$=0.12, $J_{AB}$=16.5 Hz, 2H), 7.40 (d, J=8.5 Hz, 1H), 7.62 (s, 1H), 7.82 (s, 2H), 8.21 (d, J=8.5 Hz, 1H). LCMS (m/z) 566.2 [M+H], Tr=1.99 min.

Example 81

Compound 81

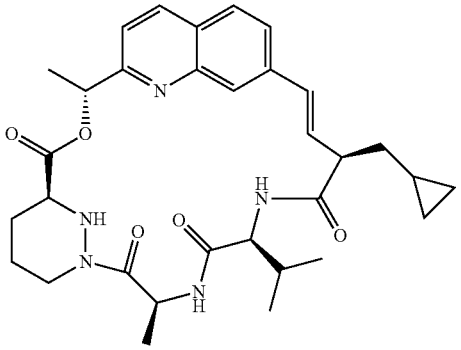

Compound 81a. (S)-4-Benzyl-3-(3-cyclopropyl-propionyl)-oxazolidin-2-one

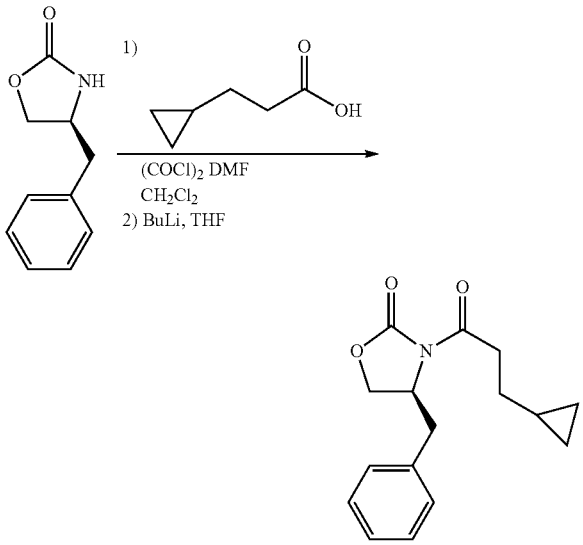

A solution of 3-cyclopropylpropionic acid (5.0 g, 44.0 mmol) in anhydrous dichloromethane (75 mL) was prepared and oxalyl chloride (11.5 mL, 131.5 mmol) was added followed by N,N-dimethylformamide (5 μL). The reaction was stirred at room temperature and gas evolution was observed. After 1.5 h the solution was evaporated to yield the acid chloride as a colourless gum.

In a separate flask a solution of (S)-4-benzyl-2-oxazolidinone (7.75 g, 43.8 mmol) in anhydrous tetrahydrofuran (75 mL) was cooled to −78° C. under a nitrogen atmosphere. A solution of n-butyllithium (2.5 M in hexanes, 17.5 mL, 43.8 mmol) was added dropwise. The reaction was stirred at −78° C. for 15 minutes. A solution of the acid chloride in anhydrous tetrahydrofuran (40 mL) was then added. The reaction mixture was stirred at −78° C. for 20 minutes then allowed to warm to room temperature over 1 h. A saturated aqueous solution of ammonium chloride (80 mL) was added. The layers were separated and the aqueous layer was extracted with ethyl acetate (50 mL). The organic layers were combined, dried over anhydrous sodium sulfate, filtered and evaporated to give a brown oil. The residue was purified by silica gel chromatography using iso-hexanes/ethyl acetate 4:1 to yield the title compound (8.88 g, 74%) as a colourless oil. $^1$H NMR (300 MHz, $CDCl_3$) δ 0.08-0.15 (m, 2H), 0.42-0.52 (m, 2H), 0.73-0.89 (m, 1H), 1.55-1.67 (m, 2H), 2.73-2.85 (m, 1H), 2.97-3.18 (m, 2H), 3.27-3.37 (m, 1H), 4.14-4.26 (m, 2H), 4.65-4.75 (m, 1H), 7.19-7.40 (m, 5H). LCMS (m/z) 274.1 [M+H], Tr=2.82 min.

Compound 81b. (S)-4-Benzyl-3-((S)-2-cyclopropyl-methyl-pent-4-enoyl)-oxazolidin-2-one

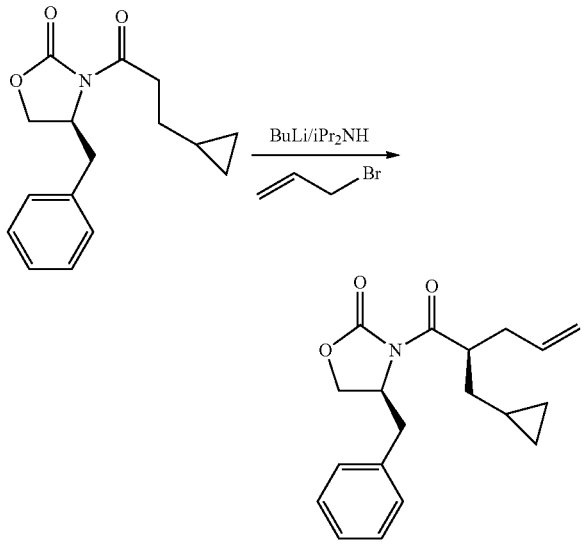

A solution of N,N-diisopropylamine (5.46 mL, 39 mmol) in anhydrous tetrahydrofuran (90 mL) was cooled to −10° C. before adding a solution of n-butyllithium (2.5 M in hexanes, 15 mL, 37.5 mmol) dropwise over 10 minutes maintaining the temperature below 0° C. The reaction mixture was stirred at 0° C. for 10 minutes before cooling to −78° C. A solution of (S)-4-benzyl-3-(3-cyclopropyl-propionyl)-oxazolidin-2-one (8.88 g, 32.5 mmol) in tetrahydrofuran (35 mL) was added dropwise over 10 minutes keeping the temperature below −70° C. The reaction mixture was stirred at −78° C. for 1 h then warmed to −15° C. for 2 h. The reaction mixture was diluted with saturated aqueous ammonium chloride solution (100 mL) and extracted with ethyl acetate (2×60 mL). The extract was dried over anhydrous sodium sulfate, filtered and evaporated to give a yellow gum. The gum was purified by silica gel chromatography using iso-hexanes/ethyl acetate 4:1 to yield the title compound (5.3 g, 52%) as a colourless oil. $^1$H NMR (300 MHz, $CDCl_3$) δ 0.01-0.15 (m, 2H), 0.35-0.50 (m, 2H), 0.65-0.82 (m, 1H), 1.50-1.60 (m, 2H), 2.32-2.45 (m, 1H), 2.47-2.60

(m, 1H), 2.66-2.77 (m, 1H), 3.27-3.37 (m, 1H), 4.05-4.25 (m, 3H), 4.65-4.76 (m, 1H), 5.03-5.16 (m, 2H), 5.78-5.93 (m, 1H), 7.20-7.36 (m, 5H). LCMS (m/z) 314.1 [M+H], Tr=2.83 min.

Compound 81c. (S)-4-Benzyl-3-((E)-(R)-2-cyclopropylmethyl-pent-3-enoyl)-oxazolidin-2-one

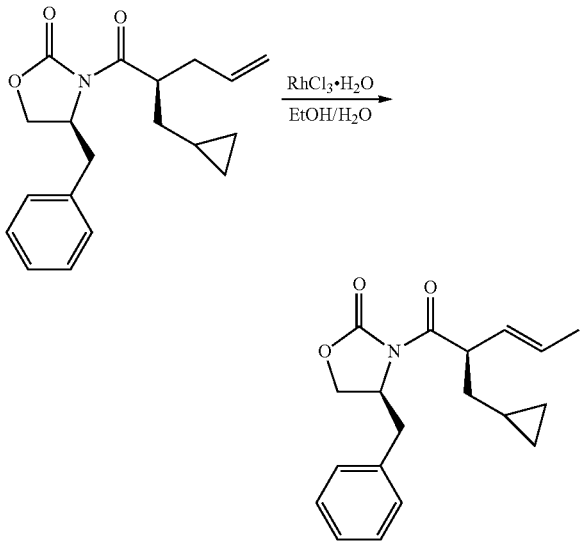

A solution of (S)-4-benzyl-3-(2-cyclopropylmethyl-pent-4-enoyl)-oxazolidin-2-one (4.3 g, 13.8 mmol) in ethanol (35 mL) and water (4.3 mL) was prepared and rhodium(III) chloride hydrate (70 mg, 0.35 mmol) was added. The reaction mixture was heated to 80° C. for 16 h. A further quantity of rhodium(III) chloride hydrate (35 mg, 0.18 mmol) was added and the reaction was heated to 80° C. for a further 4 h. The reaction mixture was evaporated and the residue was purified by silica gel chromatography using iso-hexanes/ethyl acetate 7:3 to yield the title compound (3.5 g, 81%) as a colourless oil. $^1$H NMR (300 MHz, $CDCl_3$) δ 0.01-0.15 (m, 2H), 0.35-0.50 (m, 2H), 0.65-0.82 (m, 1H), 1.57-1.65 (m, 2H), 1.74 (d, J=6.2 Hz, 3H), 2.74-2.85 (m, 2H), 4.07-4.25 (m, 2H), 4.50-4.60 (m, 1H), 4.64-4.75 (m, 1H), 5.49-5.65 (m, 1H), 5.66-5.82 (m, 1H), 7.15-7.46 (m, 5H).

Compound 81d. (E)-(R)-2-Cyclopropylmethyl-pent-3-enoic acid

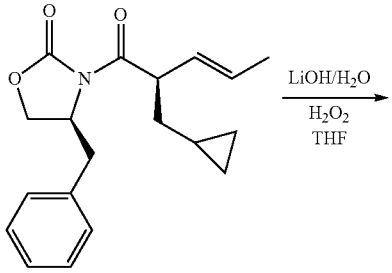

-continued

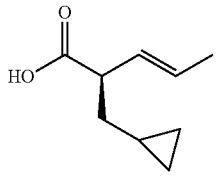

A solution of (S)-4-benzyl-3-((E)-(R)-2-cyclopropylmethyl-pent-3-enoyl)-oxazolidin-2-one (3.50 g, 10.92 mmol) in tetrahydrofuran (75 mL) was cooled to 0° C. before addition of a 30% aqueous solution of hydrogen peroxide (5.8 mL, 56 mmol) and a solution of lithium hydroxide monohydrate (950 mg, 22.6 mmol) in water (37 mL). The reaction was stirred at 0° C. for 2.5 h. The reaction mixture was treated with an aqueous solution of sodium metabisulphite and stirred for 10 minutes before acidifying to pH 1 with hydrochloric acid (2 M). The mixture was extracted with ethyl acetate (3×50 mL). The extract was dried over anhydrous sodium sulfate, filtered and evaporated to give a colourless oil. The oil was purified by silica gel chromatography using iso-hexanes/ethyl acetate 7:3 to yield the title compound (1.32 g, 78%) as a colourless oil and as a mixture of 2.5:1 E/Z isomers. $^1$H NMR (300 MHz, $CDCl_3$) δ 0.02-0.15 (m, 1.96H), 0.39-0.52 (m, 1.96H), 0.65-0.81 (m, 0.98H), 1.47-1.63 (m, 1.96H), 1.71 (d, J=6.7 Hz, 2.94H), 3.06-3.17 (m, 0.98H), 3.45-3.56 (m, 0.28H), 5.40-5.56 (m, 0.98H), 5.57-5.72 (m, 0.98H), 10.5-12.0 (bs, LCMS (m/z) 153.1 [M−H], Tr=1.91 min.

Compound 81e. (S)-1-[(S)-2-((S)-2-tert-Butoxycarbonylamino-3-methyl-butyrylamino)-propionyl]-hexahydro-pyridazine-3-carboxylic acid (R)-1-(7-vinyl-quinolin-2-yl)-ethyl ester

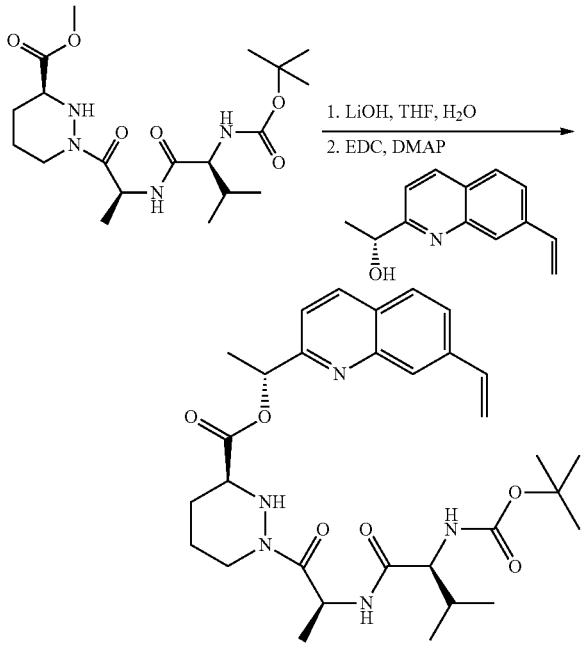

(S)-1-[(S)-2-((S)-2-tert-Butoxycarbonylamino-3-methyl-butyrylamino)-propionyl]-hexahydro-pyridazine-3-carboxylic acid methyl ester (562 mg, 1.36 mmol) was suspended in tetrahydrofuran (14 mL) then lithium hydroxide monohydrate (63 mg, 1.49 mmol) and water (3 mL) were added. The mixture was rapidly stirred for 30 minutes and then hydrochloric acid (2 M, 0.68 mL) was added. The mixture was evaporated and the residue was then suspended in anhydrous dichloromethane (13.5 mL) with 4 Å molecular sieves (powdered, 2 g). To the stirred mixture, under nitrogen, was added (R)-1-(7-vinyl-quinolin-2-yl)-ethanol (271 mg, 1.36 mmol) in anhydrous dichloromethane (13.5 mL), followed by N-(3-dimethylaminopropyl)-N'-ethylcarbodiimide hydrochloride (366 mg, 1.90 mmol) and 4-dimethylaminopyridine (166 mg, 1.36 mmol) and the resulting mixture was stirred for 16 h. A further portion of N-(3-dimethylaminopropyl)-N'-ethylcarbodiimide hydrochloride (131 mg, 0.68 mmol) and 4-dimethylaminopyridine (83 mg, 0.68 mmol) were then added and the reaction mixture stirred for a further 5 h. The mixture was filtered through Celite and the filtrate washed with saturated aqueous ammonium chloride solution, followed by water and then brine. The organics were dried over anhydrous sodium sulfate, filtered and the filtrate evaporated. The residue was purified by silica gel chromatography using a gradient of iso-hexanes/ethyl acetate 1:3 to 1:1 to afford the title compound (366 mg, 46%) as a white foam. $^1$H NMR (300 MHz, $CDCl_3$) δ 0.86-1.00 (m, 6H), 1.33 (d, J=6.7 Hz, 3H), 1.46 (s, 9H), 1.52-1.61 (m, 1H), 1.74 (d, J=6.7 Hz, 3H), 1.84-2.27 (m, 4H), 2.74-2.88 (m, 1H), 3.58-3.69 (m, 1H), 3.74-3.87 (m, 1H), 3.91-4.02 (m, 1H), 4.41-4.51 (m, 1H), 5.06-5.16 (m, 1H), 5.29 (app pentet, J=6.9 Hz, 1H), 5.44 (d, J=10.9 Hz, 1H), 5.97 (d, J=17.6 Hz, 1H), 6.13 (q, J=6.7 Hz, 1H), 6.73 (d, J=7.1 Hz, 1H), 6.94 (dd, J=17.8, 10.7 Hz, 1H), 7.41 (d, J=8.5 Hz, 1H), 7.69 (dd, J=8.5, 1.3 Hz, 1H), 7.79 (d, J=8.7 Hz, 1H), 8.03 (s, 1H), 8.18 (d, J=8.5 Hz, 1H). LCMS (m/z) 582.2 [M+H], Tr=2.58 min.

Compound 81f. (S)-1-{(S)-2-[(S)-2-((E)-(R)-2-Cyclopropylmethyl-pent-3-enoylamino)-3-methyl-butyrylamino]-propionyl}-hexahydro-pyridazine-3-carboxylic acid (R)-1-(7-vinyl-quinolin-2-yl)-ethyl ester

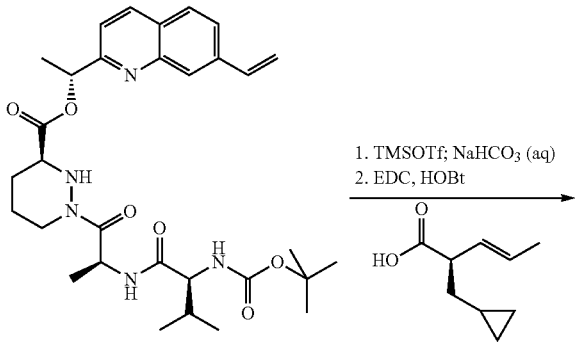

-continued

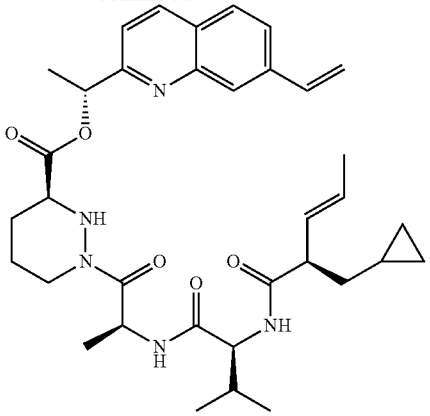

A cooled (0° C.) solution of (S)-1-[(S)-2-((S)-2-tert-butoxycarbonylamino-3-methyl-butyrylamino)-propionyl]-hexahydro-pyridazine-3-carboxylic acid (R)-1-(7-vinyl-quinolin-2-yl)-ethyl ester (340 mg, 0.585 mmol) in anhydrous dichloromethane (20 mL) under nitrogen was treated with trimethylsilyl-trifluoromethanesulfonate (212 μL, 1.17 mmol). After stirring for 1.5 h at 0° C., the reaction was quenched with saturated sodium bicarbonate solution and stirred for 20 minutes. The organic layer was separated and washed with saturated sodium bicarbonate solution. The organics were dried over anhydrous sodium sulfate, filtered and evaporated. To the residue in anhydrous acetonitrile (15 mL) was added 4 Å molecular sieves (1 g) followed by a solution of (E)-(R)-2-cyclopropylmethyl-pent-3-enoic acid (108 mg, 0.702 mmol) in anhydrous acetonitrile (5 mL). N-(3-dimethylaminopropyl)-N'-ethylcarbodiimide hydrochloride (157 mg, 0.819 mmol) and 1-hydroxybenzotriazole (119 mg, 0.702 mmol) were then added and the resulting mixture stirred for 69 h. The reaction mixture was filtered through Celite with dichloromethane and the filtrate was washed with saturated aqueous ammonium chloride solution, water then brine. The organics were dried over anhydrous sodium sulfate, filtered and evaporated. The residue was purified by silica gel chromatography using a gradient of iso-hexanes/ethyl acetate 1:1 to 0:1 to afford the title compound (142 mg, 39%) as a white solid. $^1$H NMR (300 MHz, $CDCl_3$) δ 0.03-0.12 (m, 2H), 0.37-0.45 (m, 2H), 0.63-0.71 (m, 1H), 0.87-0.94 6H), 1.30 (d, J=6.9 Hz, 3H), 1.45-1.66 (m, 2H), 1.71-1.74 (m, 6H), 1.92-1.95 (m, 1H), 2.02-2.09 (m, 1H), 2.12-2.20 (m, 1H), 2.75-2.87 (m, 1H), 2.93 (q, J=7.3 Hz, 1H), 3.58-3.68 (m, 1H), 3.81-3.91 (m, 1H), 4.27 (dd, J=8.5, 6.1 Hz, 1H), 4.45 (br d J=12.5 Hz, 1H), 5.28 (app pentet, J=6.9 Hz, 1H), 5.44 (br d J=10.9 Hz, 1H), 5.48-5.65 (m, 2H), 5.98 (d, J=17.6 Hz, 1H), 6.13 (q, J=6.7 Hz, 1H), 6.19-6.24 (m, 1H), 6.65 (br d, J=7.6 Hz, 1H), 6.93 (dd, J=17.5, 10.8 Hz, 1H), 7.41 (d, J=8.5 Hz, 1H), 7.69 (dd, J=8.5, 1.3 Hz, 1H), 7.79 (d, J=8.5 Hz, 1H), 8.04 (s, 1H), 8.18 (d, J=8.5 Hz, 1H). LCMS (m/z) 618.3 [M+H], Tr=3.07 min.

Compound 81

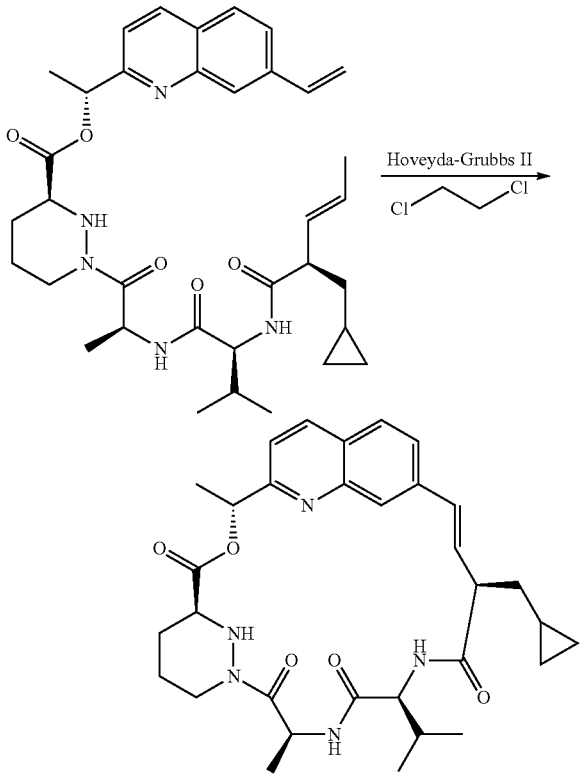

To a stirred solution of (S)-1-{(S)-2-[(S)-2-((E)-(R)-2-cyclopropylmethyl-pent-3-enoylamino)-3-methyl-butyrylamino]-propionyl}-hexahydro-pyridazine-3-carboxylic acid (R)-1-(7-vinyl-quinolin-2-yl)-ethyl ester (128 mg, 0.207 mmol) in 1,2-dichloroethane (85 mL) under nitrogen at 80° C. was added Hoveyda-Grubbs catalyst 2$^{nd}$ generation (26 mg, 0.041 mmol) and the reaction mixture heated at reflux for 45 minutes. A further portion of Hoveyda-Grubbs catalyst 2$^{nd}$ generation (26 mg, 0.041 mmol) was added and the mixture heated at reflux for 2.5 h, where a further portion of Hoveyda-Grubbs catalyst 2$^{nd}$ generation (26 mg, 0.041 mmol) was added and the mixture heated at reflux for 7 h before allowing to cool to room temperature. A solution of potassium isocyanoacetate (76 mg, 0.621 mmol) was added in methanol (1 mL) and the mixture was stirred for 2.5 h. Silica was added and the organics evaporated. The solid residue was dry loaded onto a silica cartridge and purified by silica gel chromatography using a gradient of iso-hexanes/ethyl acetate 1:0 to 0:1. Fractions containing the desired material were collected, combined and re-purified using reverse phase preparative HPLC using a gradient of acetonitrile/water 2:3 to 3:7 then 1:4 to 3:7 to give the title compound (1.5 mg, 1.3%) as a white solid. $^1$H NMR (300 MHz, $CD_3OD$) δ 0.19-0.25 (m, 2H), 0.53-0.61 (m, 2H), 0.86-0.94 (m, 1H), 0.98 (d, J=6.7 Hz, 3H), 0.98 (d, J=6.6 Hz, 3H), 0.99-1.08 (m, 1H), 1.47-1.50 (m, 1H), 1.53-1.60 (m, 1H), 1.64 (d, J=7.1 Hz, 3H), 1.69-1.75 (m, 2H), 1.74 (d, J=6.7 Hz, 3H), 1.86-1.92 (m, 1H), 2.69-2.81 (m, 1H), 3.37-3.43 (m, 1H), 3.71-3.77 (m, 1H), 3.79-3.86 (m, 1H), 4.31 (d, J=10.3 Hz, 1H), 4.45 (br d, J=11.6 Hz, 1H), 5.74 (q, J=7.1 Hz, 1H), 5.93 (q, J=6.7 Hz, 1H), 6.38 (d, J=16.7 Hz, 1H), 6.49 (dd, J=16.5, 3.8 Hz, 1H), 7.41 (d, J=8.5 Hz, 1H), 7.65 (s, 1H), 7.77 (dd, J=8.7, 1.3 Hz, 1H), 7.82 (d, J=8.7 Hz, 1H), 8.21 (d, J=8.5 Hz, 1H). LCMS (m/z) 576.2 [M+H], Tr=2.49 min.

Example 82

Compound 82

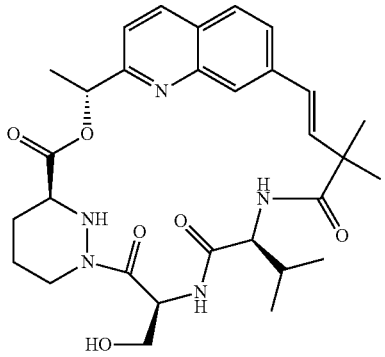

Compound 82a. (S)-1-[(S)-2-tert-Butoxycarbonylamino-3-(tert-butyl-diphenyl-silanyloxy)-propionyl]-hexahydro-pyridazine-3-carboxylic acid 2,2,2-trichloro-ethyl ester

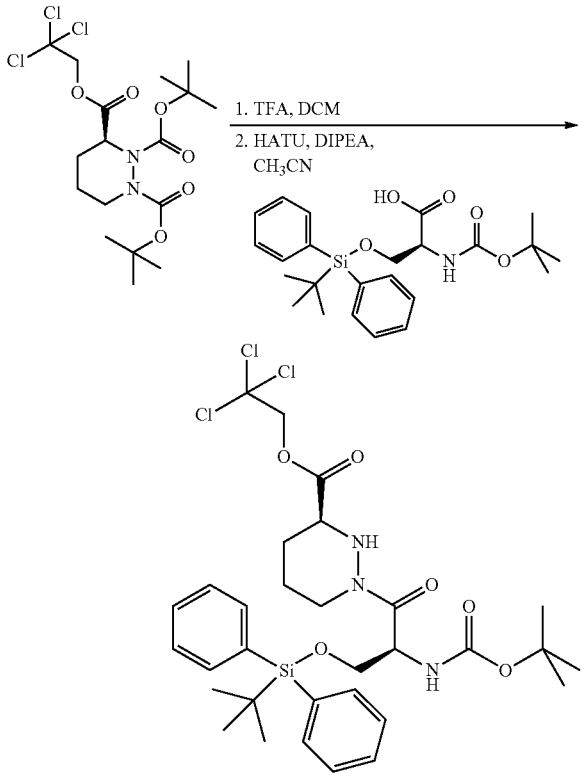

To (S)-tetrahydro-pyridazine-1,2,3-tricarboxylic acid 1,2-di-tert-butyl ester 3-(2,2,2-trichloro-ethyl)ester (5.0 g, 10.8 mmol) in anhydrous dichloromethane (33 mL) at 0° C. and under an atmosphere of nitrogen was added trifluoroacetic acid (33 mL, 432 mmol). The solution was warmed to room temperature and stirred for 16 h. The reaction was concentrated in vacuo and the residue co-evaporated from toluene (3×). The resulting brown viscous oil was dissolved in anhydrous acetonitrile (5 mL) and added to a solution of (S)-2-tert-butoxycarbonylamino-3-(tert-butyl-diphenyl-silanyloxy)-propionic acid (2.39 g, 5.4 mmol, prepared as in PCT Int. Appl. 2006, WO 2006004880 A2), N,N-diisopropylethylamine (3.76 mL, 21.6 mmol) and 2-(1H-7-azabenzotriazol-1-yl)-1,1,3,3-tetramethyl uronium hexafluorophosphate methanaminium (2.05 g, 5.4 mmol) in anhydrous acetonitrile (25 mL) that had been previously stirred at 0° C. for 20 minutes. The reaction was warmed to room temperature and stirred for 16 h before being concentrated in vacuo. The residue was purified by silica gel chromatography using iso-hexanes/ethyl acetate 4:1 to give the title compound (1.8 g, 49%) as a clear viscous oil. $^1$H NMR (300 MHz, $CDCl_3$) δ 1.08 (s, 9H), 1.46 (s, 9H), 1.53-1.67 (m, 1H), 1.80-2.01 (m, 2H), 2.82-2.96 (m, 1H), 3.19-3.32 (m, 1H), 3.62 (d, J=10.9 Hz, 1H), 3.80-3.97 (m, 3H), 4.23-4.34 (m, 1H), 4.61 (d, J=12.0 Hz, 1H), 4.90 (d, J=12.0 Hz, 1H), 5.18-5.27 (m, 1H), 5.51-5.63 (m, 1H), 7.35-7.49 (m, 6H), 7.58-7.70 (m, 4H). LCMS (m/z) 686.2 [M+H], Tr=4.32 min.

Compound 82b. (S)-1-[(S)-2-((S)-2-tert-Butoxycarbonylamino-3-methyl-butyrylamino)-3-(tert-butyl-diphenyl-silanyloxy)-propionyl]-hexahydro-pyridazine-3-carboxylic acid 2,2,2-trichloro-ethyl ester

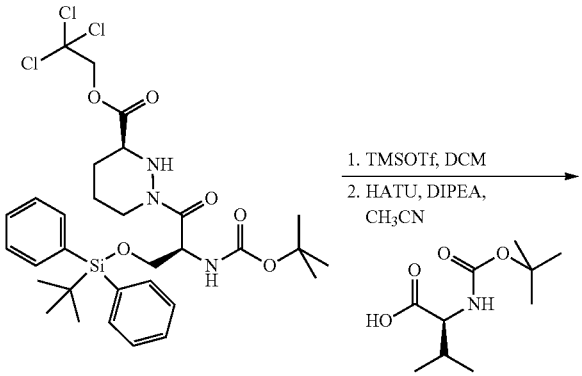

-continued

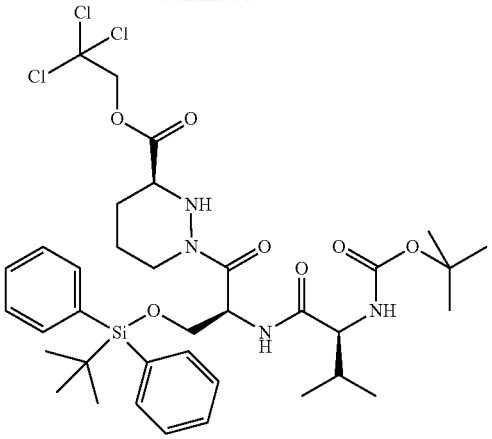

To (S)-1-[(S)-2-tert-butoxycarbonylamino-3-(tert-butyl-diphenyl-silanyloxy)-propionyl]-hexahydro-pyridazine-3-carboxylic acid 2,2,2-trichloro-ethyl ester (1.0 g, 1.46 mmol) in anhydrous dichloromethane (25 mL) at 0° C. and under an atmosphere of nitrogen was added trimethylsilyl trifluoromethanesulfonate (400 μL, 2.19 mmol). The reaction mixture was stirred at 0° C. for 2 h before adding N,N-diisopropylethylamine (1.0 mL, 5.84 mmol) and concentrating in vacuo. The residue was dissolved in anhydrous acetonitrile (15 mL) at room temperature and under an atmosphere of nitrogen was added N,N-diisopropylethylamine (763 μL, 4.38 mmol), N-(tert-butoxycarbonyl)-L-valine, (317 mg, 1.46 mmol) and 2-(1H-7-azabenzotriazol-1-yl)-1,1,3,3-tetramethyl uronium hexafluorophosphate methanaminium (777 mg, 2.04 mmol). Following 2 h at room temperature the reaction was quenched with water and extracted with ethyl acetate (2×). The combined organic layers were dried through a hydrophobic frit and concentrated in vacuo. The residue was purified by silica gel chromatography using iso-hexanes/ethyl acetate 2:1 to give the title compound (500 mg, 44%) as a white foam. $^1$H NMR (300 MHz, $CDCl_3$) δ 0.88-1.00 (m, 6H), 1.07 (s, 9H), 1.48 (s, 9H), 1.50-1.70 (m, 2H), 1.78-1.89 (m, 1H), 1.92-2.02 (m, 1H), 2.10-2.25 (m, 1H), 2.81-3.02 (m, 1H), 3.15-3.30 (m, 1H), 3.60 (d, J=10.7 Hz, 1H), 3.95 (br d, J=3.6 Hz, 2H), 3.98-4.06 (m, 1H), 4.19-4.30 (m, 1H), 4.59 (d, J=12.0 Hz, 1H), 4.90 (d, J=12.0 Hz, 1H), 5.10-5.20 (m, 1H), 5.36-5.47 (m, 1H), 6.77-6.88 (m, 1H), 7.36-7.50 (m, 6H), 7.56-7.70 (m, 4H). LCMS (m/z)=785.3 [M+H], Tr=4.25 min.

Compound 82c. (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-(tert-butyl-diphenyl-silanyloxy)-propionyl]-hexahydro-pyridazine-3-carboxylic acid 2,2,2-trichloro-ethyl ester

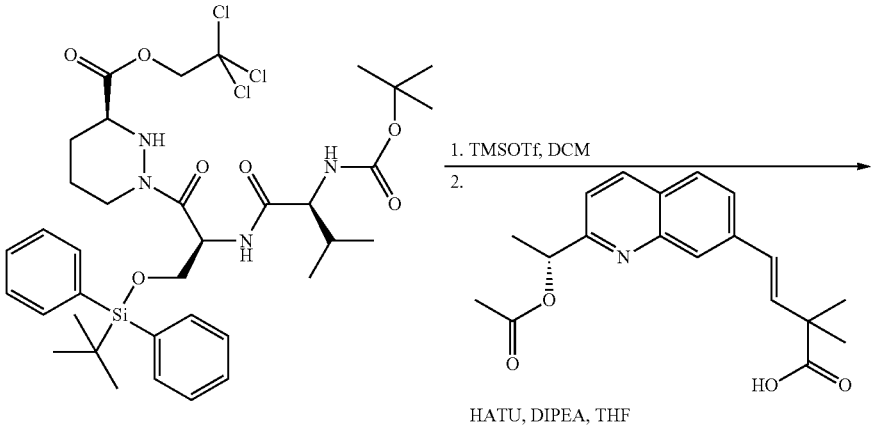

-continued

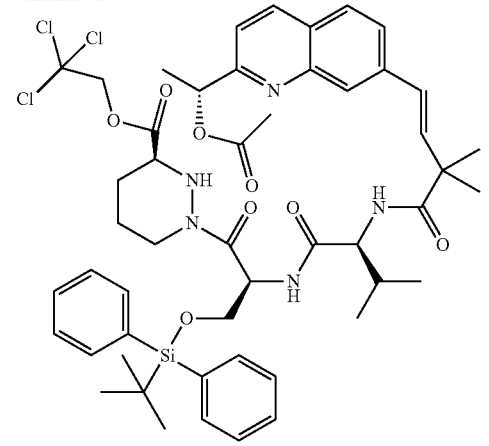

To a solution of (S)-1-[(S)-2-((S)-2-tert-butoxycarbonylamino-3-methyl-butyrylamino)-3-(tert-butyl-diphenyl-silanyloxy)-propionyl]-hexahydro-pyridazine-3-carboxylic acid 2,2,2-trichloro-ethyl ester (450 mg, 0.57 mmol) in anhydrous dichloromethane (10 mL) at 0° C. and under an atmosphere of nitrogen, was added trimethylsilyl trifluoromethanesulfonate (156 μL, 0.86 mmol). The reaction mixture was stirred at 0° C. for 2 h before adding N,N-diisopropylethylamine (410 μL, 2.30 mmol) and then concentrated in vacuo to afford (S)-1-[(S)-2-((S)-2-amino-3-methyl-butyrylamino)-3-(tert-butyl-diphenyl-silanyloxy)-propionyl]-hexahydro-pyridazine-3-carboxylic acid 2,2,2-trichloro-ethyl ester as a white solid.

To (E)-4-[2-((R)-1-acetoxy-ethyl)-quinolin-7-yl]-2,2-dimethyl-but-3-enoic acid (196 mg, 0.57 mmol) in anhydrous acetonitrile (5 mL) at 0° C. and under an atmosphere of nitrogen was added N,N-diisopropylethylamine (307 μL, 1.72 mmol) and 2-(1H-7-azabenzotriazol-1-yl)-1,1,3,3-tetramethyl uronium hexafluorophosphate methanaminium (306 mg, 0.80 mmol). The solution was stirred at 0° C. for 3 minutes before adding a solution of (S)-1-[(S)-2-((S)-2-amino-3-methyl-butyrylamino)-3-(tert-butyl-diphenyl-silanyloxy)-propionyl]-hexahydro-pyridazine-3-carboxylic acid 2,2,2-trichloro-ethyl ester in anhydrous acetonitrile (2 mL). The reaction was warmed to room temperature, stirred for 16 h and concentrated in vacuo. The residue was purified by silica gel chromatography using iso-hexanes/ethyl acetate 2:1 to give the title compound (350 mg, 62%, 2 steps) as a viscous oil. $^1$H NMR (300 MHz, $CDCl_3$) δ 0.85-0.99 (m, 6H), 1.05 (s, 9H), 1.32-1.43 (m, 1H), 1.49 (s, 3H), 1.50 (s, 3H), 1.53-1.57 (m, 1H), 1.69 (d, J=6.7 Hz, 3H), 1.75-2.00 (m, 3H), 2.08-2.15 (m, 1H), 2.18 (s, 3H), 2.86-2.96 (m, 1H), 3.11-3.22 (m, 1H), 3.56 (d, J=10.9 Hz, 1H), 3.90-3.95 (m, 2H), 4.34 (dd, J=8.3, 5.1 Hz, 1H), 4.58 (d, J=12.0 Hz, 1H), 4.89 (d, J=12.0 Hz, 1H), 5.33-5.41 (m, 1H), 6.06 (q, J=6.7 Hz, 1H), 6.45 (d, J=8.3 Hz, 1H), 6.63 (d, J=16.1 Hz, 1H), 6.72 (d, J=8.0 Hz, 1H), 6.77 (d, J=16.1 Hz, 1H), 7.34-7.49 (m, 7H), 7.54-7.69 (m, 5H), 7.73 (d, J=8.5 Hz, 1H), 8.03 (s, 1H), 8.11 (d, J=8.5 Hz, 1H). LCMS (m/z)=994.5 [M+H], Tr=4.30 min.

Compound 82d

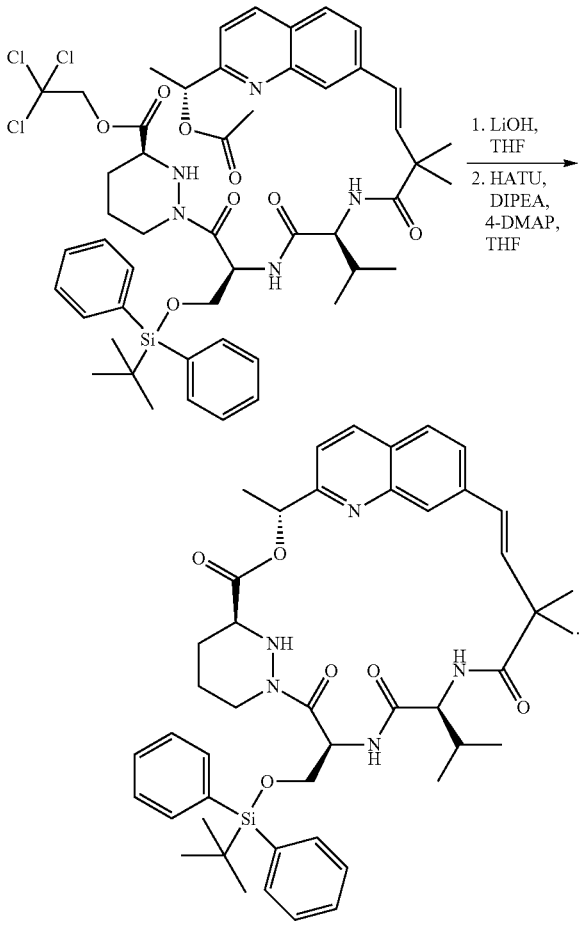

To (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-(tert-butyl-diphenyl-silanyloxy)-propionyl]-hexahydro-pyridazine-3-carboxylic acid 2,2,2-trichloro-ethyl ester (350 mg, 0.35 mmol) in tetrahydrofuran (14 mL) and water (3 mL) was added lithium hydroxide monohydrate (74 mg, 1.76 mmol) at 0° C. The reaction was stirred at 0° C. for 4 h and quenched by acidifying to pH 6 with 2 M aqueous hydrochloric acid. The mixture was concentrated in vacuo, followed by co-evaporation from acetonitrile (2×) and then toluene (2×) and dried on a high vacuum for 16 h. The resulting residue was dissolved in anhydrous tetrahydrofuran (117 mL) and at room temperature was added N,N-diisopropylethylamine (314 μL, 1.76 mmol), 2-(1H-7-azabenzotriazol-1-yl)-1,1,3,3-tetramethyl uronium hexafluorophosphate methanaminium (187 mg, 0.49 mmol) and 4-dimethylaminopyridine (4 mg, 0.1 mmol). The reaction was stirred for 7 h, diluted with ethyl acetate and washed with hydrochloric acid (1 M, 1×) and brine (1×). The organic layer was dried through a hydrophobic frit and concentrated in vacuo. The residue was purified by silica gel chromatography using iso-hexanes/ethyl acetate 1:1 to afford the title compound (137 mg, 48%) as a viscous oil. $^1$H NMR (300 MHz, $CDCl_3$) δ 0.89-1.03 (m, 6H), 1.10 (s, 9H), 1.40 (s, 3H), 1.47 (s, 3H), 1.59-1.64 (m, 1H), 1.68 (d, J=6.7 Hz, 3H), 1.80-2.03 (m, 4H), 2.54-2.67 (m, 1H), 3.46-3.55 (m, 2H), 4.19-4.28 (m, 1H), 4.43-4.54 (m, 1H), 5.87 (q, J=6.7 Hz, 1H), 5.92-6.01 (m, 2H), 6.20 (d, J=9.1 Hz, 1H), 6.28 (d, J=16.1 Hz, 1H), 6.29 (d, J=7.6 Hz, 1H), 6.39 (d, J=16.1 Hz, 1H), 7.21 (d, J=8.3 Hz, 1H), 7.35-7.48 (m, 6H), 7.54-7.61 (m, 2H), 7.70 (d, J=8.5 Hz, 1H), 7.73-7.83 (m, 5H), 8.05 (d, J=8.3 Hz, 1H). LCMS (m/z)=804.4 [M+H], Tr=4.13 min.

Compound 82

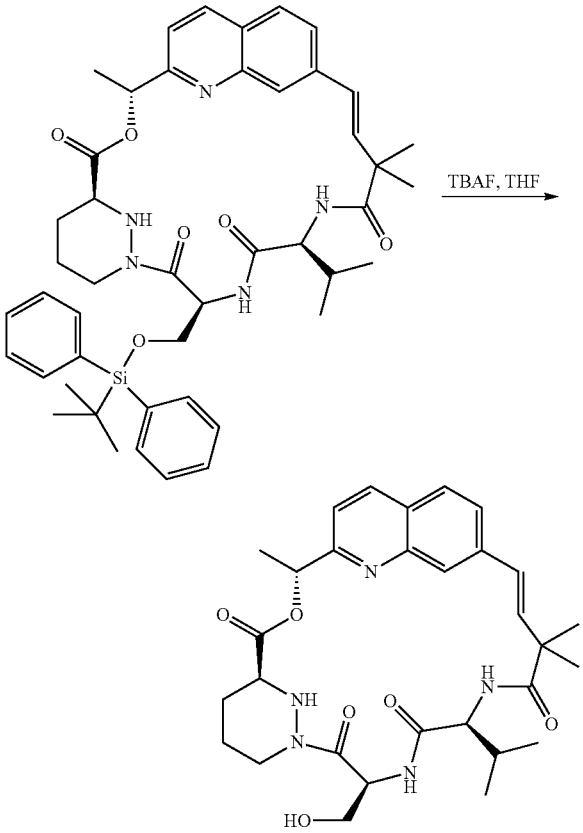

To compound 82d (130 mg, 0.16 mmol) in anhydrous tetrahydrofuran (810 μL) at 0° C. and under an atmosphere of nitrogen was added tetrabutylammonium fluoride (1.0 M solution in THF, 810 μL, 0.81 mmol). The reaction was stirred at 0° C. for 1 h before being quenched with a saturated aqueous solution of ammonium chloride. The reaction was extracted with dichloromethane (2×), the organics dried through a hydrophobic frit and concentrated in vacuo. The product was purified by silica gel chromatography using iso-hexanes/acetone 1:1 to afford the title compound (50 mg, 55%) as a white solid. $^1$H NMR (300 MHz, $CD_3CN$) δ□□ 0.94-0.95 (m, 6H), 1.32 (s, 3H), 1.47 (s, 3H), 1.48-1.50 (m, 2H), 1.55-1.64 (m, 2H), 1.67 (d, J=6.7 Hz, 3H), 1.81-2.01 (m, 2H), 2.59-2.77 (m, 1H), 3.69-3.86 (m, 2H), 3.91 (d, J=12.3 Hz, 1H), 4.01-4.11 (m, 1H), 4.15-4.29 (m, 1H), 4.30-4.39 (m, 1H), 5.58-5.67 (m, 1H), 5.96 (q, J=6.7 Hz, 1H), 6.34 (d, J=8.9 Hz, 1H), 6.43 (s, 2H), 7.10 (d, J=8.0 Hz, 1H), 7.40 (d, J=8.5 Hz, 1H), 7.67 (dd, J=8.5, 1.6 Hz, 1H), 7.85 (d, J=8.5 Hz, 1H), 7.97 (s, 1H), 8.24 (d, J=8.5 Hz, 1H). LCMS (m/z)=566.3 [M+H], Tr=2.10 min.

Example 83

Compound 83

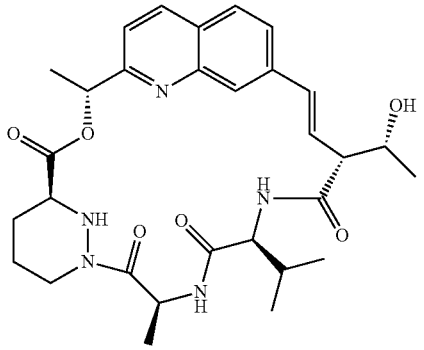

Compound 83a. (R)-3-{(R)-2-[(R)-1-(tert-Butyl-dimethyl-silanyloxy)-ethyl]-but-3-enoyl}-4-isopropyl-5,5-dimethyl-oxazolidin-2-one

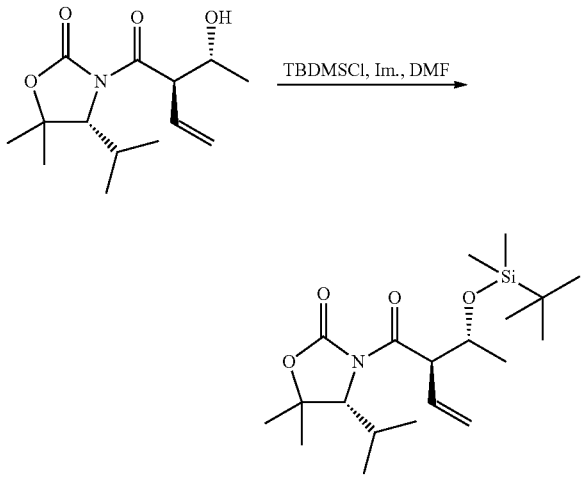

A cooled (0° C.) solution of (R)-3-[(R)-2-((R)-1-hydroxy-ethyl)-but-3-enoyl]-4-isopropyl-5,5-dimethyl-oxazolidin-2-one (654 mg, 2.43 mmol, prepared as described in Tetrahedron 2009, 65, 7837-7851) and imidazole (727 mg, 10.68 mmol) in N,N-dimethylformamide (5 mL) was treated with tert-butyldimethylsilyl chloride (474 mg, 3.16 mmol). After stirring for 5 h at room temperature, the reaction was quenched with saturated ammonium chloride. The aqueous layer was extracted with diethyl ether (2×20 mL). The organics were combined and the volatiles were removed in vacuo. The residue was purified by silica gel chromatography using a 25 g Biotage cartridge eluted with a continuous gradient of iso-hexanes/ethyl acetate 1:0 to 4:1 to afford the title compound (800 mg, 86%) as a colourless oil. $^1$H NMR (300 MHz, $CDCl_3$) δ 0.03 (s, 3H), 0.09 (s, 3H), 0.84 (s, 9H), 0.92 (d, J=6.7 Hz, 3H), 1.01 (d, J=7.1 Hz, 3H), 1.16 (d, J=6.2 Hz, 3H), 1.40 (s, 3H), 1.50 (s, 3H), 2.05-2.20 (m, 1H), 4.17 (d, J=3.3 Hz, 1H), 4.25-4.40 (m, 1H), 4.67 (t, J=9.1 Hz, 1H), 5.25 (dd, J=10.3, 1.6 Hz, 1H), 5.46 (dd, J=17.2, 1.3 Hz, 1H), 5.65-5.79 (m, 1H).

Compound 83b. (R)-2-[(R)-1-(tert-Butyl-dimethyl-silanyloxy)-ethyl]-but-3-enoic acid

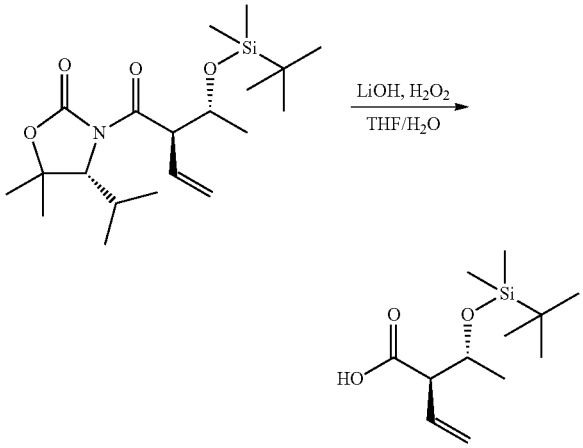

A cooled (0° C.) solution of (R)-3-{(R)-2-[(R)-1-(tert-butyl-dimethyl-silanyloxy)-ethyl]-but-3-enoyl}-4-isopropyl-5,5-dimethyl-oxazolidin-2-one (400 mg, 1.04 mmol) in tetrahydrofuran/water (15 mL, 2:1) was subsequently treated with hydrogen peroxide (30% aqueous, 537 μL, 5.21 mmol) and lithium hydroxide monohydrate (87 mg, 2.09 mmol). The mixture was allowed to warm up to room temperature overnight. The reaction was quenched with sodium metabisulfite until KI/starch paper negative. After stirring for 2 h at room temperature the volatiles were removed in vacuo. The mixture was then diluted with water and the pH was adjusted with potassium carbonate. The aqueous layer was washed with dichloromethane (2×20 mL) and acidified with hydrochloric acid (pH~1) then extracted with ethyl acetate (3×30 mL). All ethyl acetate layers were combined and the volatiles were removed in vacuo to afford the title compound (200 mg, 79%) as a clear oil. $^1$H NMR (300 MHz, $CDCl_3$) δ 0.09 (s, 3H), 0.11 (s, 3H), 0.89 (s, 9H), 1.22 (d, J=6.0 Hz, 3H), 3.07 (t, J=8.7 Hz, 4.11 (pentet, J=6.5 Hz, 1H), 5.20-5.35 (m, 2H), 5.70-5.90 (m, 1H).

Compound 83c. (E)-(R)-4-[2-((R)-1-Acetoxy-ethyl)-quinolin-7-yl]-2-[(R)-1-(tert-butyl-dimethyl-silanyloxy)-ethyl]-but-3-enoic acid

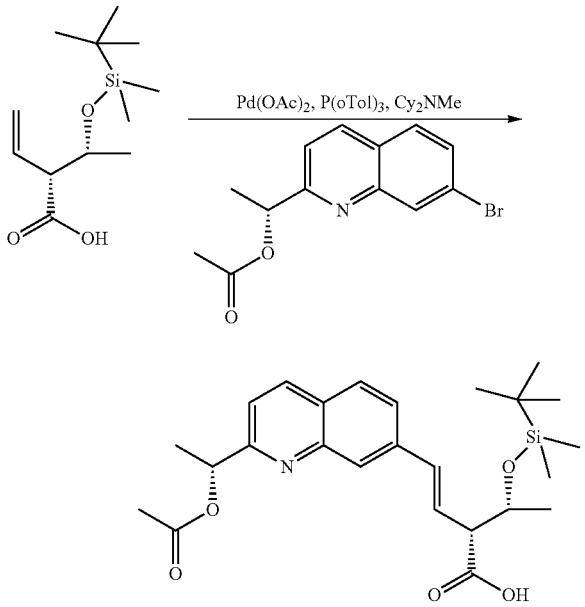

A solution of (R)-2-[(R)-1-(tert-butyl-dimethyl-silanyloxy)-ethyl]-but-3-enoic acid (200 mg, 0.82 mmol), acetic acid (R)-1-(7-bromo-quinolin-2-yl)-ethyl ester (241 mg, 0.82 mmol), palladium(II) acetate (37 mg, 0.16 mmol), tri-(o-tolyl)phosphine (50 mg, 0.16 mmol) in anhydrous 1,4-dioxane (10 mL) was treated with N,N-dicylohexylmethylamine (280 μL, 1.31 mmol). After stirring at 100° C. for 6 h, the reaction was cooled to room temperature, filtered off and the volatiles were removed in vacuo. The residue was partitioned between ethyl acetate and hydrochloric acid (1 M). The organics were combined and the volatiles were removed in vacuo. The residue was purified by silica gel chromatography using a 25 g Biotage cartridge eluted with a continuous gradient of dichloromethane/methanol 1:0 to 9:1 to afford the title compound (115 mg, 31%) as a colourless oil. $^1$H NMR (300 MHz, $CDCl_3$) δ 0.10 (s, 3H), 0.11 (s, 3H), 0.89 (s, 9H), 1.25 (d, J=6.0 Hz, 3H), 1.68 (d, J=6.4 Hz, 3H), 2.17 (s, 3H), 3.22-3.37 (m, 1H), 3.65-3.80 (m, 1H), 4.26 (pentet, J=6.7 Hz, 1H), 6.08 (q, J=6.7 Hz, 1H), 6.40 (dd, J=15.8, 9.1 Hz, 1H), 6.76 (d, J=15.8 Hz, 1H), 7.42 (d, J=8.7 Hz, 1H), 7.40-7.55 (m, 1H), 7.55-7.75 (m, 1H), 8.03 (s, 1H), 8.11 (d, J=8.5 Hz, 1H). LCMS (m/z) 458.2 [M+H], Tr=3.45 min.

Compound 83d. (S)-1-[(S)-2-((S)-2-{(E)-(R)-4-[2-((R)-1-Acetoxy-ethyl)-quinolin-7-yl]-2-[(R)-1-(tert-butyl-dimethyl-silanyloxy)-ethyl]-but-3-enoy-lamino}-3-methyl-butyrylamino)-propionyl]-hexahydro-pyridazine-3-carboxylic acid methyl ester

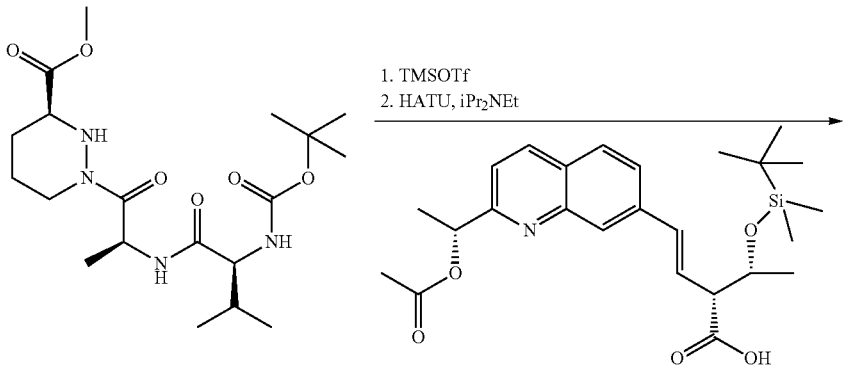

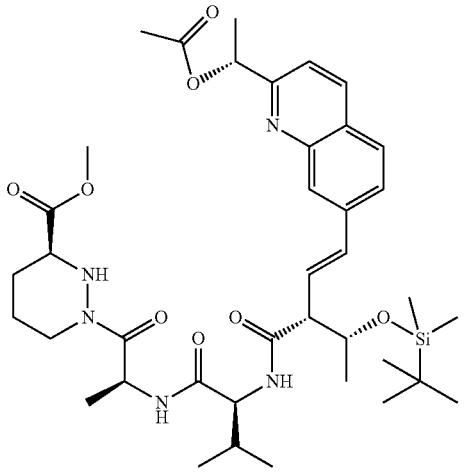

Compound 83d was prepared in the same manner as compound 77f using (E)-(R)-4-[2-((R)-1-acetoxy-ethyl)-quinolin-7-yl]-2-[(R)-1-(tert-butyl-dimethyl-silanyloxy)-ethyl]-but-3-enoic acid instead of (E)-(R)-4-[2-((R)-1-acetoxy-ethyl)-quinolin-7-yl]-2-methyl-2-(2-trimethylsilanyl-ethoxymethyl)-but-3-enoic acid in 64% yield. $^1$H NMR (300 MHz, $CDCl_3$) δ 0.09 (s, 3H), 0.14 (s, 3H), 0.81-1.03 (m, 13H), 1.30-1.40 (m, 3H), 1.55-1.75 (m, 7H), 1.75-1.95 (m, 2H), 2.05 (s, 3H), 2.10-2.22 (m, 4H), 3.20-3.60 (m, 2H), 3.75 (s, 3H), 4.08-4.42 (m, 3H), 5.32 (q, J=6.7 Hz, 1H), 6.05 (q, J=6.7 Hz, 1H), 6.42-6.55 (m, 1H), 6.62-6.82 (m, 2H), 7.41 (d, J=8.5 Hz, 1H), 7.55-7.65 (m, 1H), 7.70-7.80 (m, 1H), 7.96 (s, 1H), 8.11 (d, J=8.5 Hz, 1H). LCMS (m/z) 754.4 [M+H], Tr=3.47 min.

Compound 83e

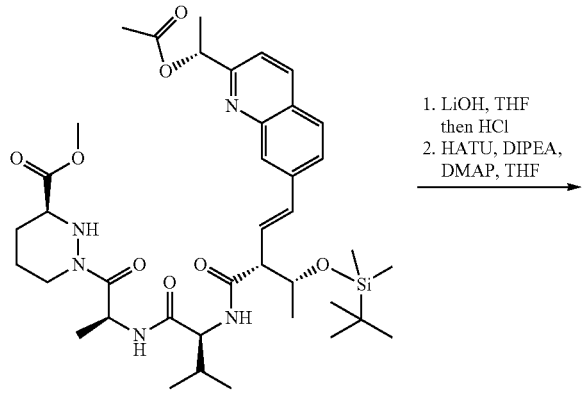

-continued

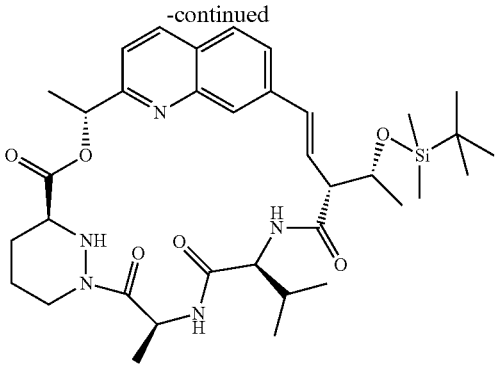

Compound 83e was prepared in the same manner as compound 77 using (S)-1-[(S)-2-((S)-2-{(E)-(R)-4-[2-((R)-1-acetoxy-ethyl)-quinolin-7-yl]-2-[(R)-1-(tert-butyl-dimethyl-silanyloxy)-ethyl]-but-3-enoylamino}-3-methyl-butyrylamino)-propionyl]-hexahydro-pyridazine-3-carboxylic acid methyl ester instead of (S)-1-((S)-2-{(S)-2-[(E)-(R)-4-[7-((R)-1-acetoxy-ethyl)-quinolin-7-yl]-2-methyl-2-(2-trimethylsilanyl-ethoxymethyl)-but-3-enoylamino]-3-methyl-butyrylamino}-propionyl)-hexahydro-pyridazine-3-carboxylic acid methyl ester in 40% yield. $^1$H NMR (300 MHz, $CDCl_3$) δ 0.09 (s, 3H), 0.14 (s, 3H), 0.85-1.05 (m, 15H), 1.28 (d, J=7.1 Hz, 3H), 1.50 (d, J=7.1 Hz, 3H), 1.75 (d, J=7.1 Hz, 3H), 1.85-2.08 (m, 4H), 3.00-3.10 (m, 1H), 3.60-3.80 (m, 2H), 4.25-4.60 (m, 2H), 5.56 (q, J=7.1 Hz, 1H), 5.94 (q, J=6.9 Hz, 1H), 6.20-6.35 (m, 2H), 6.52 (d, J=16.3 Hz, 1H), 6.69 (d, J=7.6 Hz, 1H), 7.23 (d, J=8.5 Hz, 1H), 7.42-7.65 (m, 2H), 7.70 (s, 1H), 8.02 (d, J=8.5 Hz, 1H). LCMS (m/z) 680.4 [M+H], Tr=3.56 min.

Compound 83

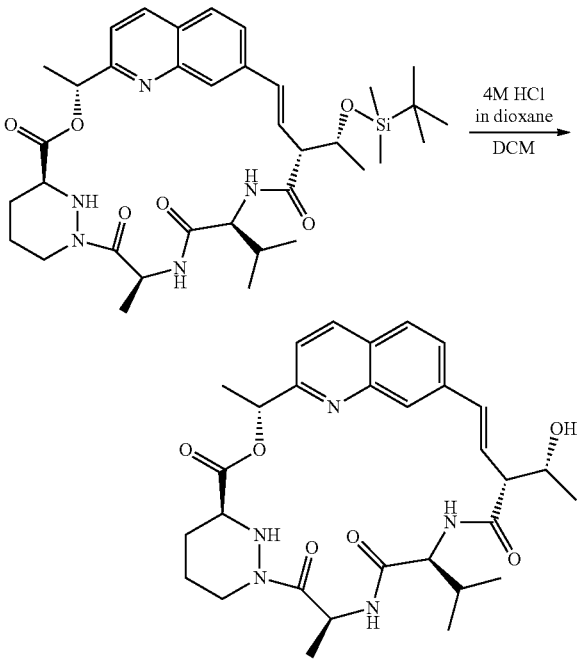

A cooled (0° C.) solution of compound 83e (44 mg, 0.065 mmol), in dichloromethane (10 mL) was treated with hydrochloric acid (4 M in 1,4-dioxane, 5 mL). After stirring at 0° C. for 2 h, the volatiles were removed in vacuo. The residue was partitioned between dichloromethane and saturated sodium bicarbonate. The organics were combined and the volatiles were removed in vacuo. The residue was purified by silica gel chromatography using a 10 g Biotage cartridge eluted with a continuous gradient of iso-hexanes/acetone 1:0 to 4:1 to afford the title compound (18 mg, 49%) as a white solid. $^1$H NMR (300 MHz, $CD_3OD$) δ 0.85-1.05 (m, 6H), 1.34 (d, J=7.1 Hz, 3H), 1.61 (d, J=7.1 Hz, 3H), 1.74 (d, J=7.1 Hz, 3H), 1.85-2.08 (m, 4H), 2.68-2.82 (m, 1H), 3.72-3.83 (m, 1H), 4.10-4.28 (m, 3H), 4.38-4.47 (m, 1H), 5.62 (q, J=7.1 Hz, 1H), 5.91 (q, J=6.9 Hz, 1H), 6.35-6.57 (m, 2H), 7.40 (d, J=8.5 Hz, 1H), 7.65-7.85 (m, 3H), 8.19-8.25 (m, 2H), 8.46 (d, J=6.9 Hz, 1H). LCMS (m/z) 566.2 [M+H], Tr=1.80 min.

Example 84

Compound 84

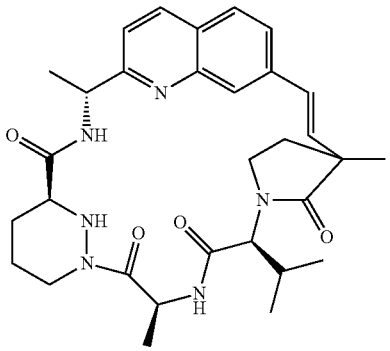

Compound 84a. ((S)-2-{(S)-3-[(R)-1-(7-Bromo-quinolin-2-yl)-ethylcarbamoyl]-tetrahydro-pyridazin-1-yl}-1-methyl-2-oxo-ethyl)-carbamic acid tert-butyl ester

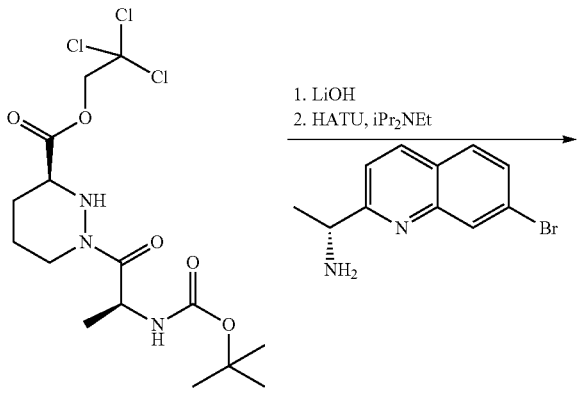

-continued

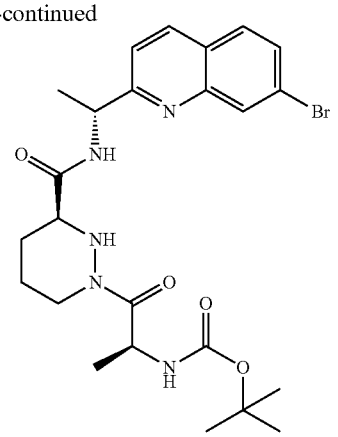

A cooled (0° C.) solution of (S)-1-((S)-2-tert-butoxycarbonylamino-propionyl)-hexahydro-pyridazine-3-carboxylic acid 2,2,2-trichloro-ethyl ester (3.007 g, 6.948 mmol) in tetrahydrofuran/water (60 mL, 5:1) was treated with lithium hydroxide monohydrate (874.4 mg, 20.844 mmol). After stirring at 0° C. for 40 minutes the reaction was quenched with hydrochloric acid (1 M, 50 mL). The aqueous layer was extracted with ethyl acetate (2×). The organics were combined, dried over anhydrous sodium sulfate, filtered and the volatiles were removed in vacuo. Residual trichlorethanol was azeotroped off with toluene (3×) to provide (S)-1-((S)-2-tert-butoxycarbonylamino-propionyl)-hexahydro-pyridazine-3-carboxylic acid as a white solid which was then combined with (R)-1-(7-bromo-quinolin-2-yl)-ethylamine hydrochloride (1.998 g, 6.948 mmol) and suspended in anhydrous acetonitrile (60 mL) and tetrahydrofuran (10 mL). The suspension was cooled to 0° C. and subsequently treated with N,N-diisopropylethylamine (6 mL, 34.740 mmol) and 1-[bis(dimethylamino)methylene]-1H-1,2,3-triazolo[4,5-b]pyridinium 3-oxide hexafluorophosphate (3.699 g, 9.727 mmol). After slowly warming to room temperature and stirring for 16 h, the reaction was quenched at 0° C. with hydrochloric acid (1 M, 70 mL). The aqueous layer was extracted with ethyl acetate (2×). The organics were combined, washed with a saturated solution of sodium bicarbonate, dried over anhydrous sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:4 to afford the title compound (3.702 g, 99%) as a white foam. $^1$H NMR (300 MHz, $CDCl_3$) δ 1.38 (d, J=6.9 Hz, 3H), 1.43 (s, 9H), 1.47-1.55 (m, 2H), 1.58 (d, J=6.9 Hz, 3H), 1.60-1.78 (m, 2H), 2.22-2.31 (m, 1H), 2.65-2.78 (m, 1H), 3.39-3.52 (m, 1H), 4.55 (d, J=13.4 Hz, 1H), 5.18-5.34 (m, 2H), 5.36-5.45 (m, 1H), 7.37 (d, J=8.5 Hz, 1H), 7.65 (dd, J=8.5, 1.6 Hz, 1H), 7.70 (d, J=8.5 Hz, 1H), 8.04 (d, J=6.5 Hz, 1H), 8.14 (d, J=8.5 Hz, 1H), 8.36 (s, 1H). LCMS (m/z) 536.1, 537.1 [M+H], Tr=2.58 min.

Compound 84b.
3-Methyl-3-vinyl-dihydro-furan-2-one

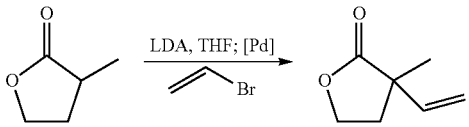

A cooled (−78° C.) solution of N,N-diisopropylamine (4.7 mL, 33.815 mmol, dried over calcium hydride) in anhydrous tetrahydrofuran (20 mL) was treated with a solution of n-butyllithium in hexanes (12.7 mL, 31.702 mmol, 2.5 M). After stirring at −78° C. for 25 minutes, the mixture was treated with 3-methyl-dihydro-furan-2-one (2 mL, 21.135 mmol). After stirring at 0° C. for 1 h, the reaction was subsequently treated with a solution of di-μ-bromobis(tri-tert-butylphosphino)dipalladium(I) (164.2 mg, 0.211 mmol) in anhydrous tetrahydrofuran (5 mL) and a solution of vinyl bromide in tetrahydrofuran (31.7 mL, 81.702 mmol, 1 M). The reaction was slowly warmed to room temperature. After stirring for 16 h, the reaction was quenched with hydrochloric acid (2 M) and water. The aqueous layer was extracted with diethyl ether (2×). The organics were combined, dried over anhydrous sodium sulfate, filtered and the volatiles were removed in vacuo. The residue was purified by silica gel chromatography using a 100 g Isolute cartridge eluted with a continuous gradient of iso-hexanes/diethyl ether 1:0 to 3:2 to afford the title compound (1.272 g, 48%) as an orange oil. $^1$H NMR (300 MHz, $CDCl_3$) δ 1.38 (s, 3H), 2.11-2.22 (m, 1H), 2.31-2.41 (m, 1H), 4.20-4.36 (m, 2H), 5.16-5.26 (m, 2H), 5.84-5.96 (m, 1H).

Compound 84c. (S)-2-[2-(2-Hydroxy-ethyl)-2-methyl-but-3-enoylamino]-3-methyl-butyric acid

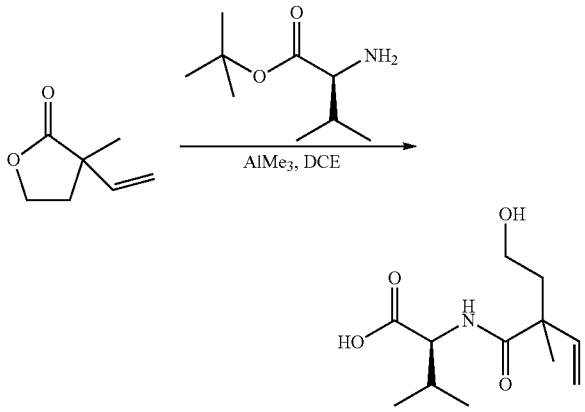

L-valine tert-butyl ester hydrochloride (3.2 g, 15.259 mmol) was partitioned between dichloromethane and a saturated solution of sodium bicarbonate. The aqueous layer was extracted with dichloromethane. The organics were combined, filtered through a phase separator and the volatiles were removed in vacuo to provide L-valine tert-butyl ester as a colourless oil which was dissolved in anhydrous dichloroethane (40 mL). This solution was treated with a solution of trimethylaluminum (15.2 mL, 30.516 mmol, 2 M in toluene). After stirring at room temperature for 1.5 h, the mixture was treated with a solution of 3-methyl-3-vinyl-dihydro-furan-2-one (641.7 mg, 5.086 mmol) in dichloroethane (10 mL). After stirring at 85° C. for 15 h, the reaction was cooled to 0° C., slowly quenched with hydrochloric acid (2 M). The aqueous layer was extracted with ethyl acetate (3×), the organics were combined, dried over anhydrous sodium sulfate, filtered and the volatiles were removed in vacuo to provide the title compound (1.053 g, 85%) as a white solid and as a 1:1 mixture of diastereoisomers.

Compound 84d. (S)-1-((S)-2-{(S)-2-[2-(2-Hydroxy-ethyl)-2-methyl-but-3-enoylamino]-3-methyl-butyrylamino}-propionyl)-hexahydro-pyridazine-3-carboxylic acid [(R)-1-(7-bromo-quinolin-2-yl)-ethyl]-amide

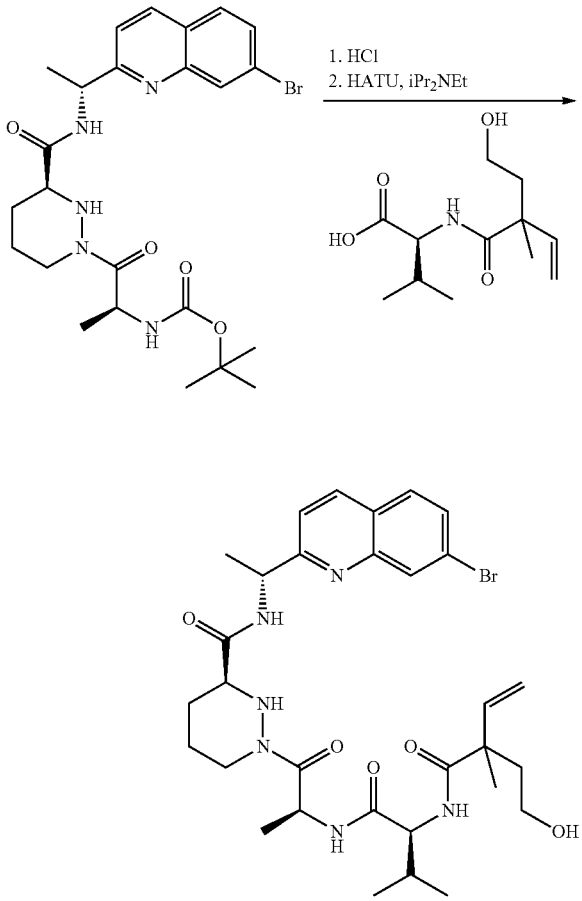

A cooled (0° C.) solution of ((S)-2-{(S)-3-[(R)-1-(7-bromo-quinolin-2-yl)-ethylcarbamoyl]-tetrahydro-pyridazin-1-yl}-1-methyl-2-oxo-ethyl)-carbamic acid tert-butyl ester (432.0 mg, 0.808 mmol) in dichloromethane (30 mL) was treated with a solution of hydrochloric acid (2.4 mL, 9.699 mmol, 4 M in 1,4-dioxane). After stirring for 2 h at room temperature the volatiles were removed in vacuo. Residual water was azeotroped off with toluene to provide a white solid that was combined with (S)-2-[2-(2-hydroxy-ethyl)-2-methyl-but-3-enoylamino]-3-methyl-butyric acid (196.6 mg, 0.808 mmol) and anhydrous acetonitrile (30 mL). This mixture was cooled to 0° C. and subsequently treated with N,N-diisopropylethylamine (0.71 mL, 4.04 mmol) and 1-[bis(dimethylamino)methylene]-1H-1,2,3-triazolo[4,5-b]pyridinium 3-oxide hexafluorophosphate (430.1 mg, 1.131 mmol). The reaction was slowly warmed to room temperature. After stirring at room temperature for 20 h, the volatiles were removed in vacuo and the residue was purified by silica gel chromatography using a 50 g Isolute cartridge eluted with a continuous gradient of iso-hexanes/acetone 1:0 to 1:1 to afford the title compound (186.4 mg, 35%) as a yellow foam and as a 1:1 mixture of diastereoisomers. LCMS (m/z) 659.2, 661.1 [M+H], Tr=2.21 min.

Compound 84e. (S)-1-{(S)-2-[(S)-3-Methyl-2-(3-methyl-2-oxo-3-vinyl-pyrrolidin-1-yl)-butyrylamino]-propionyl}-hexahydro-pyridazine-3-carboxylic acid [(R)-1-(7-bromo-quinolin-2-yl)-ethyl]-amide

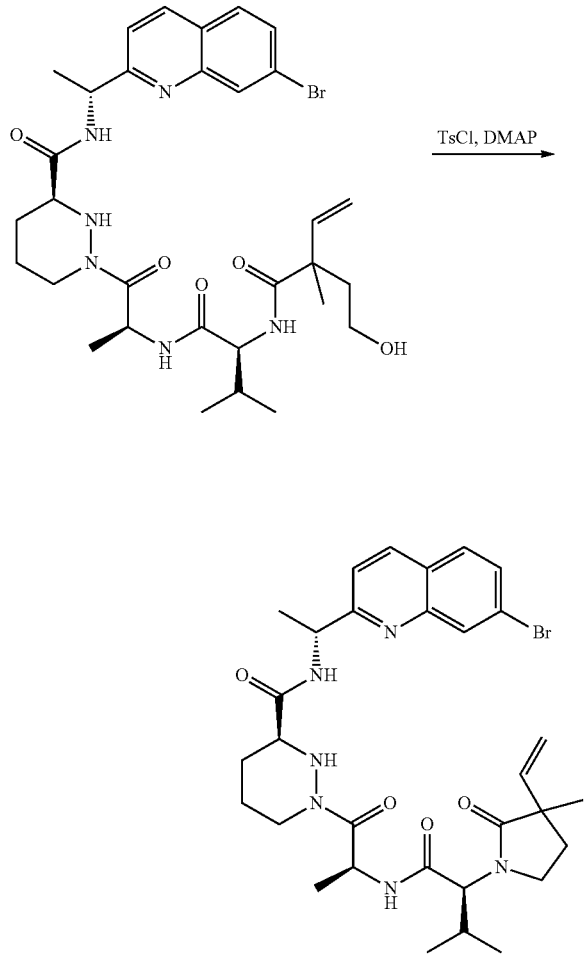

A solution of (S)-1-((S)-2-{(S)-2-[2-(2-hydroxy-ethyl)-2-methyl-but-3-enoylamino]-3-methyl-butyrylamino}-propionyl)-hexahydro-pyridazine-3-carboxylic acid [(R)-1-(7-bromo-quinolin-2-yl)-ethyl]-amide (186.4 mg, 0.282 mmol) and 4-dimethylaminopyridine (206.7 mg, 1.692 mmol) in dichloromethane (20 mL) was treated with para-toluenesulfonyl chloride (161.6 mg, 0.848 mmol). After stirring at room temperature for 2.5 h, more 4-dimethylaminopyridine (206.7 mg, 1.692 mmol) and para-toluenesulfonyl chloride (161.6 mg, 0.848 mmol) were added. After stirring at room temperature for 1.5 h, the volatiles were removed in vacuo. The residue was purified by silica gel chromatography using a 20 g Isolute cartridge eluted with a continuous gradient of iso-hexanes/acetone 1:0 to 3:2 to afford the title compound (77.0 mg, 42%) as a colourless gum and as a 1:1 mixture of diastereoisomers. LCMS (m/z) 643.1 [M+H], Tr=1.90 min and LCMS (m/z) 643.1 [M+H], Tr=1.99 min.

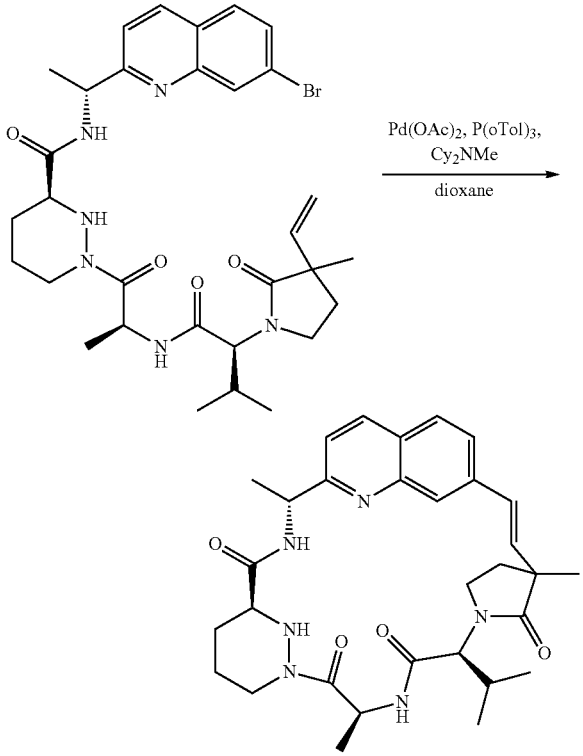

A warm (80° C.) solution of (S)-1-{(S)-2-[(S)-3-methyl-2-(3-methyl-2-oxo-3-vinyl-pyrrolidin-1-yl)-butyrylamino]-propionyl}-hexahydro-pyridazine-3-carboxylic acid [(R)-1-(7-bromo-quinolin-2-yl)-ethyl]-amide (77.0 mg, 0.12 mmol) and N,N-dicyclohexylmethylamine (0.08 mL, 0.360 mmol) in anhydrous 1,4-dioxane (60 mL) was treated with palladium(II)acetate (27 mg, 0.12 mmol) and tri(o-tolyl)phosphine (37 mg, 0.12 mmol). After stirring at 100° C. for 40 minutes the reaction was cooled to room temperature, filtered over Celite and the volatiles were removed in vacuo. The residue was purified by silica gel chromatography using a 20 g Isolute cartridge eluted with a continuous gradient of dichloromethane/methanol 1:0 to 9:1 followed by reverse phase preparative HPLC eluted with a gradient of water/acetonitrile 95:5 to 0:1 to afford the title compound (2.9 mg, 4%) as a white solid. $^1$H NMR (300 MHz, $CD_3OD$) δ 0.90 (d, J=6.7 Hz, 3H), 1.07 (d, J=6.5 Hz, 3H), 1.51 (s, 3H), 1.57-1.77 (m, 8H), 1.86-2.08 (m, 2H), 2.14-2.34 (m, 4H), 2.65-2.79 (m, 1H), 3.59-3.67 (m, 1H), 4.08-4.21 (m, 2H), 4.35-4.52 (m, 2H), 5.07 (q, J=6.9 Hz, 1H), 5.70 (q, J=7.3 Hz, 1H), 6.39, 6.52 (ABq, $J_{AB}$=16.3 Hz, 2H), 7.47 (d, J=8.5 Hz, 1H), 7.67 (s, 1H), 7.78 (dd, J=8.5, 1.6 Hz, 1H), 7.85 (d, J=8.5 Hz, 1H), 8.25 (d, J=8.5 Hz, 1H). LCMS (m/z) 561.2 [M+H], Tr=1.26 min.

Examples 85 and 86

Compounds 85 and 86

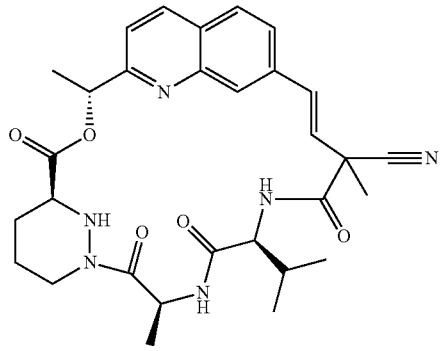

Compound 85a: 2-Cyano-2-methyl-but-3-enoic acid tert-butyl ester

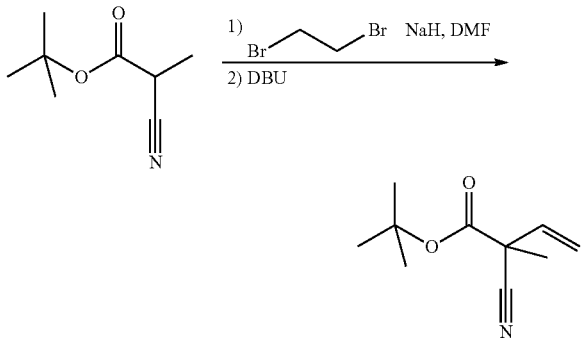

To a stirred slurry of sodium hydride (60% in mineral oil, 880 mg, 22 mmol) in dry N,N-dimethylformamide (100 mL) at 0° C., under nitrogen, was added dropwise cyano-methyl-acetic acid tert-butyl ester (prepared as in J. Am. Chem. Soc. 2011, 133, 8165, 3.10 g, 20 mmol). Any residual cyano-methyl-acetic acid tert-butyl ester was transferred by washing its original vessel with a little N,N-dimethylformamide and transferring to the reaction mixture. The reaction mixture was allowed to warm to ambient temperature for 40 minutes and then cooled to 0° C. 1,2-Dibromoethane (3.95 g, 1.81 mL, 21 mmol) was added dropwise via syringe pump over 30 minutes. The reaction mixture was stirred at 0° C. for a further 3 h and then allowed to warm to ambient temperature for 1 h. The mixture was poured into water and extracted with ethyl acetate (3×) and the combined organic extracts were washed with water (3×), dried over anhydrous magnesium sulfate, filtered and evaporated. To the residue was added 1,8-diazabicyclo[5.4.0]undec-7-ene (3.14 g, 3.07 mL, 20.6 mmol) and the mixture stirred and heated to 80° C. for 30 minutes and then allowed to cool. Saturated ammonium chloride solution was added and the mixture extracted with diethyl ether (2×). The organic extracts were washed with 0.5 M Hydrochloric acid, saturated sodium bicarbonate solution, saturated brine, dried over anhydrous magnesium sulfate, filtered and evaporated. The residue was purified by silica gel chromatography using iso-hexanes/ethyl acetate 19:1 to afford the title compound (3.15 g, 87%) as a pale yellow oil. $^1$H NMR (300 MHz, $CDCl_3$) δ 1.52 (s, 9H), 1.68 (s, 3H), 5.37 (d, J=10.0 Hz, 1H), 5.63 (d, J=17.0 Hz, 1H), 5.89 (dd, J=17.0, 10.0 Hz, 1H).

Compound 85b: 2-Cyano-2-methyl-but-3-enoic acid

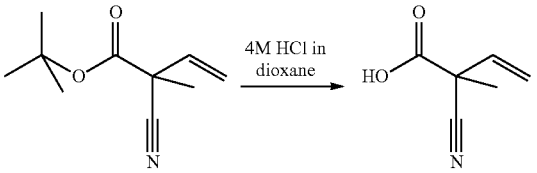

2-Cyano-2-methyl-but-3-enoic acid tert-butyl ester (362 mg, 2 mmol) was suspended in 4 M hydrochloric acid in dioxane (10 mL) and the reaction mixture stirred for 38 h and then evaporated. The residue was used directly in the next reaction.

Compound 85c: (S)-1-{(S)-2-[(S)-2-(2-Cyano-2-methyl-but-3-enoylamino)-3-methyl-butyrylamino]-propionyl}-hexahydro-pyridazine-3-carboxylic acid 2,2,2-trichloro-ethyl ester

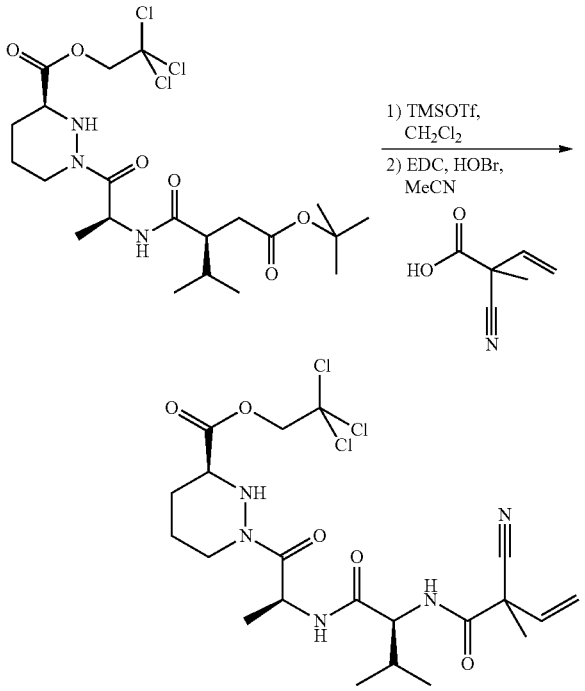

A stirred solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (692 mg, 1.3 mmol) in dry dichlormethane (39 mL) was cooled to 0° C. under nitrogen and then trimethylsilyl trifluoromethanesulfonate (578 mg, 471 μL, 2.6 mmol) was added. The reaction was stirred for 1 h and then quenched with saturated sodium bicarbonate solution. The organic layer was separated and washed with further saturated sodium bicarbonate solution (2×), dried over anhydrous sodium sulfate, filtered and evaporated. To the residue was added 4 Å molecular sieves (powdered, 1.3 g) and a solution of the crude 2-cyano-2-methyl-but-3-enoic acid (2 mmol) in dry acetonitrile (39 mL) followed by 1-hydroxybenzotriazole (containing 20% $H_2O$) (307 mg, 1.82 mmol) and N-(3-dimethylaminopropyl)-N'-ethylcarbodiimide hydrochloride (349 mg, 1.82 mmol). The mixture was stirred for 3.5 h, filtered through Celite, washing with extra dichloromethane and the filtrate washed with saturated ammonium chloride solution, water then saturated brine, dried over anhydrous sodium sulfate, filtered and evaporated. The residue was purified by silica gel chromatography using a gradient of iso-hexanes/ethyl acetate 1:1 to 1:3 to afford the title compound (356 mg, 51%) as a white solid as a mixture of diastereoisomers. $^1$H NMR (300 MHz, $CDCl_3$) δ 0.90-0.97 (m, 3H), 0.99 (d, J=6.9 Hz, 3H), 1.33 (app t, J=7.1 Hz, 3H), 1.54-1.61 (m, 1H), 1.70-1.79 (m, 1H), 1.71 (s, 1.5H), 1.72 (s, 1.5H), 1.89-2.00 (m, 1H), 2.09-2.25 (m, 2H), 2.91-3.02 (m, 1H), 3.65-3.76 (m, 1H), 3.84 (d, J=11.2 Hz, 1H), 4.22-4.36 2H), 4.72 (d, J=12.1 Hz, 1H), 4.97 (dd, J=12.1 Hz, 2.5 Hz, 1H), 5.31-5.38 (m, 1H), 5.44 (t, J=9.8 Hz, 1H), 5.70 (dd, J=17.2, 10.3 Hz, 1H), 5.87-6.02 (m, 1H), 6.53-6.60 (m, 1H), 6.73-6.87 (m, 1H). LCMS (m/z) 538.0, 540.0, 542.0 [M+H], Tr=2.68 min.

Compound 85d: (S)-1-[(S)-2-((S)-2-{(E)-2-Cyano-4-[2-((R)-1-hydroxy-ethyl)-quinolin-7-yl]-2-methyl-but-3-enoylamino}-3-methyl-butyrylamino)-propionyl]-hexahydro-pyridazine-3-carboxylic acid 2,2,2-trichloro-ethyl ester

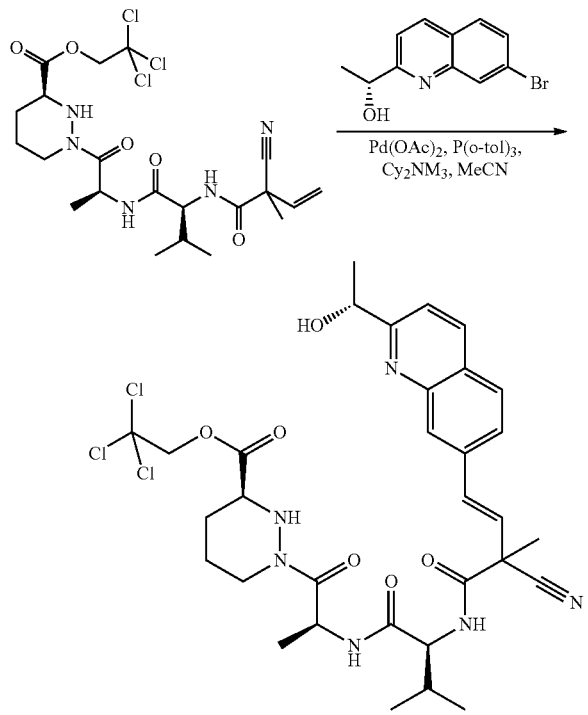

(S)-1-{(S)-2-[(S)-2-(2-Cyano-2-methyl-but-3-enoylamino)-3-methyl-butyrylamino]-propionyl}-hexahydro-pyridazine-3-carboxylic acid 2,2,2-trichloro-ethyl ester (283 mg, 0.527 mmol), (R)-1-(7-bromo-quinolin-2-yl)-ethanol (146 mg, 0.580 mmol), palladium(II) acetate (24 mg, 0.105 mmol) and tri(o-tolyl)phosphine (32 mg, 0.105 mmol) were suspended in anhydrous acetonitrile and N,N-dicyclohexylmethylamine (113 mg, 124 μL, 0.580 mmol) added. The vessel was sealed and heated in a microwave reactor at 120° C. for 40 minutes. The mixture was evaporated and the residue dissolved in ethyl acetate and washed with saturated ammonium chloride solution (2×), water then saturated brine. The organic layer was dried over anhydrous sodium sulfate, filtered and evaporated. The residue was purified by silica gel chromatography using a gradient of iso-hexanes/ethyl acetate 1:1 to 0:1 to give the title compound (68 mg, 39%) as a yellow solid as a mixture of diastereoisomers. $^1$H NMR (300 MHz, $CD_3OD$) δ 0.92-0.98 (m, 3H) 1.01 (d, J=6.9 Hz, 3H), 1.27 (app t, J=7.1 Hz, 3H), 1.59 (d, J=5.5 Hz, 3H), 1.68-1.81 (m, 2H), 1.86 (s, 3H), 1.88-1.99 (m, 1H), 2.10-2.25 (m, 2H), 2.86-3.05 (m, 1H), 3.60-3.75 (m, 1H), 3.85 (t, J=8.7 Hz, 1H), 4.22-4.38 (m, 2H), 4.69 (dd, J=12.0, 8.6 Hz, 1H), 4.95 (dd, J=12.0, 7.2 Hz, 1H), 4.98-5.09 (m, 2H), 5.26-5.42 (m, 1H), 6.48 (dd, J=16.1, 13.8 Hz, 1H), 6.62-6.68 (m, 1H), 6.96 (dd, J=15.5, 8.2 Hz, 1H), 7.16 (dd, J=16.1, 4.9 Hz, 1H), 7.35 (dd, J=8.5, 2.0 Hz, 1H), 7.64 (d, J=8.5 Hz, 1H), 7.81 (dd, J=8.5, 2.7 Hz, 1H), 8.09 (d, J=5.4 Hz, 1H), 8.13 (d, J=8.5 Hz, 1H). LCMS (m/z) 709.1, 711.1, 713.2 [M+H], Tr=2.38 min.

methyl-butyrylamino)-propionyl]-hexahydro-pyridazine-3-carboxylic acid 2,2,2-trichloro-ethyl ester (92 mg, 0.130 mmol) and lithium hydroxide monohydrate (11 mg, 0.260 mmol) were dissolved in tetrahydrofuran (2 mL) and water (2 mL) and the reaction mixture stirred for 1 h. Further tetrahydrofuran (6 mL) added and reaction mixture stirred for 15 minutes. Further lithium hydroxide monohydrate (5 mg, 0.12 mmol) was added and the reaction mixture stirred for a further 30 minutes. 2 M Hydrochloric acid (0.190 mL) was added and the mixture evaporated and triturated several times with ether. The residue was dissolved in N,N-dimethylformamide (5 mL) and added via syringe pump over 3.5 h to a stirred slurry of 2-methyl-6-nitrobenzoic anhydride (224 mg, 0.650 mmol), 4-dimethylaminopyridine (119 mg, 0.975 mmol) and powdered 4 Å molecular sieves (ca 2.3 g) in 1,2-dichloroethane (43 mL) at 50° C. under nitrogen. The original flask containing the seco-acid was washed with N,N-dimethylformamide (1 mL) and this washing added over 30 minutes to the reaction mixture via syringe pump. The reaction mixture was stirred at 50° C. for a further h and then allowed to cool. The mixture was filtered through Celite and evaporated to near dryness. The residue was purified by reverse phase preparative HPLC using a gradient of acetonitrile/water 2:8 to 3:7 to give the title compounds.

Less polar, second eluting diastereoisomer (6.3 mg, 9%) 86 as a white solid $^1$H NMR (300 MHz, $CD_3OD$) δ 0.98 (d, J=6.7 Hz, 3H), 1.02 (d, J=6.7 Hz, 3H), 1.63 (d, J=7.1 Hz, 3H), 1.66-1.77 (m, 1H), 1.73 (d, J=7.0 Hz, 3H), 1.75 (s, 3H), 1.88-1.95 (m, 1H), 1.96-2.11 (m, 2H), 2.70-2.80 (m, 1H),

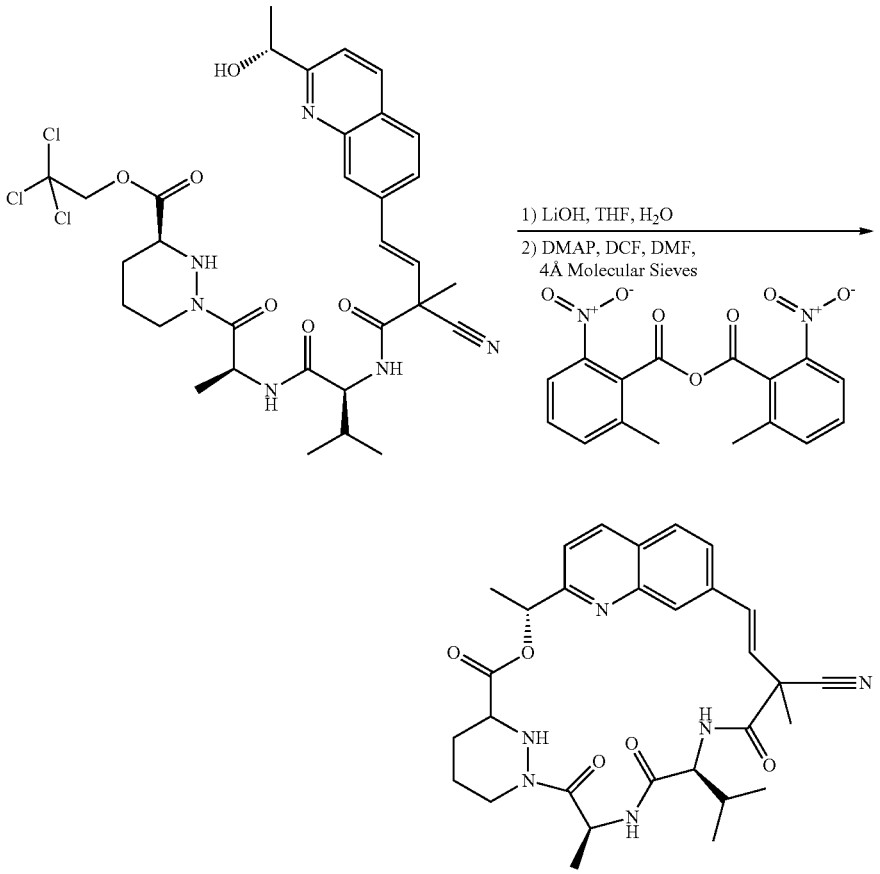

(S)-1-[(S)-2-((S)-2-{(E)-2-Cyano-4-[2-((R)-1-hydroxy-ethyl)-quinolin-7-yl]-2-methyl-but-3-enoylamino}-3-

3.78-3.84 (m, 1H), 4.27 (d, J=10.5 Hz, 1H), 4.40 (br d, J=7.4 Hz, 1H), 5.74 (q, J=7.1 Hz, 1H), 5.93 (q, J=6.9 Hz, 1H), 6.57

(s, 2H), 7.45 (d, J=8.5 Hz, 1H), 7.74 (s, 1H), 7.79 (dd, J=8.7, 1.6 Hz, 1H), 7.88 (d, J=8.5 Hz, 1H), 8.25 (d, J=8.5 Hz, 1H). LCMS (m/z) 561.2 [M+H], Tr=2.35 min.

More polar, first eluting diastereoisomer (1.0 mg, 1%) 85 as a white solid. $^1$H NMR (300 MHz, $CDCl_3$) δ 0.96 (d, J=6.7 Hz, 3H), 1.00 (d, J=6.7 Hz, 3H), 1.53 (d, J=7.3 Hz, 3H), 1.67-1.78 (m, 2H), 1.76 (d, J=6.9 Hz, 3H), 1.93 (s, 3H), 1.96-2.11 (m, 2H), 2.61-2.73 (m, 1H), 3.70 (app t, J=10.6 Hz, 1H), 4.22 (app t, J=9.1 Hz, 1H), 4.53 (br d, J=14.0 Hz, 1H), 5.85 (app t, J=7.8 Hz, 1H), 5.96 (q, J=6.9 Hz, 1H), 6.21-6.38 (m, 4H), 6.73 (d, J=17.1 Hz, 1H), 7.58-7.63 (m, 1H), 7.72-7.79 (m, 1H), 7.83 (s, 1H), 8.07-8.14 (m, 2H). LCMS (m/z) 561.2 [M+H], Tr=2.19 min.

Examples 87 and 88

Compounds 87 and 88

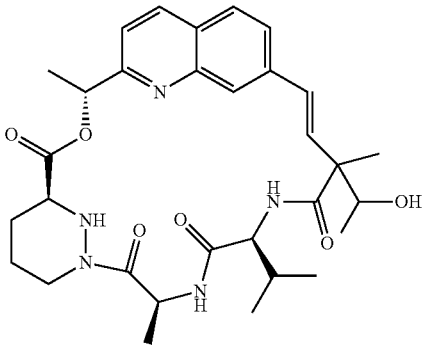

Compound 87a. (S)-3-[2-(1-Hydroxy-ethyl)-2-methyl-but-3-enoyl]-4-isopropyl-oxazolidin-2-one

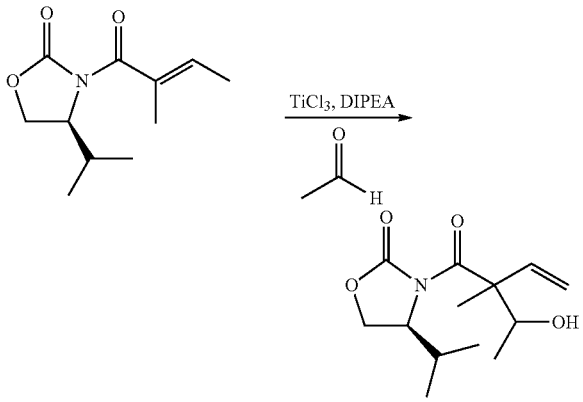

A cooled (−78° C.) solution of (S)-4-isopropyl-3-((E)-2-methyl-but-2-enoyl)-oxazolidin-2-one (the enantiomer of the previously described compound 77a) (2.316 g, 10.962 mmol) in anhydrous dichloromethane (50 mL) was treated with a solution of titanium(IV) chloride (1 M, 12 mL, 11.510 mmol) in dichloromethane. After stirring the orange solution for 5 minutes, the mixture was treated with N,N-diisopropylethylamine (4.8 mL, 27.405 mmol). After stirring at −78° C. for 2 h, the purple solution was treated with acetaldehyde (4.3 mL, 76.374 mmol). After stirring at −78° C. for 1.5 h and at room temperature for 50 minutes, the reaction was quenched with a saturated solution of ammonium chloride (60 mL). The aqueous layer was extracted with dichloromethane. The organics were combined, filtered through a phase separator and the volatiles were removed in vacuo. The residue was purified by silica gel chromatography using a 100 g Isolute cartridge eluted with a continuous gradient of iso-hexanes/diethyl ether 1:0 to 1:1 to afford the title compound (1.742 g, 62%) as a 1:1.13:1.85:2.60 mixture of diastereoisomers and as a yellow oil.

Compound 87b. (S)-3-{2-[1-(tert-Butyl-dimethyl-silanyloxy)-ethyl]-2-methyl-but-3-enoyl}-4-isopropyl-oxazolidin-2-one

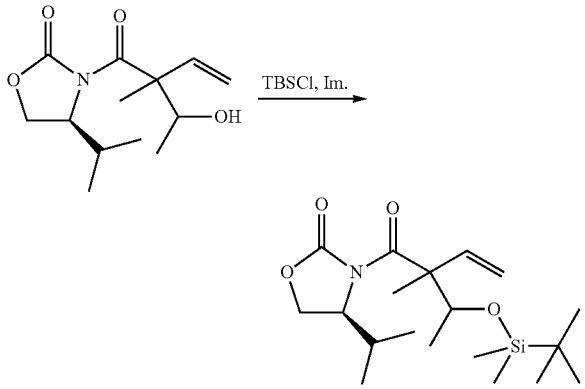

A solution of (S)-3-[2-(1-hydroxy-ethyl)-2-methyl-but-3-enoyl]-4-isopropyl-oxazolidin-2-one (1.742 g, 6.809 mmol) and tert-butyldimethylsilyl chloride (1.231 g, 8.17 mmol) in anhydrous N,N-dimethylformamide (10 mL) was treated with imidazole (927 mg, 13.618 mmol). After stirring at room temperature for 6 h, tert-butyldimethylsilyl chloride (1.1 g, 7.3 mmol) and imidazole (950 mg, 13.954 mmol) were added. After stirring at room temperature for 12 days, the reaction was quenched with a saturated solution of ammonium chloride. The aqueous layer was extracted with diethyl ether (2×). The organics were combined, dried over anhydrous sodium sulfate, filtered and the volatiles were removed in vacuo. The residue was purified by silica gel chromatography using a 100 g Isolute cartridge eluted with a continuous gradient of iso-hexanes/diethyl ether 1:0 to 1:1 to afford the title compound (1.729 g, 69%) as an undetermined mixture of diastereoisomers and as a yellow oil. LCMS (m/z) 370.1 [M+H], Tr=3.96 min and 370.1 [M+H], Tr=4.22 min.

Compound 87c. 2-[1-(tert-Butyl-dimethyl-silanyloxy)-ethyl]-2-methyl-but-3-enoic acid

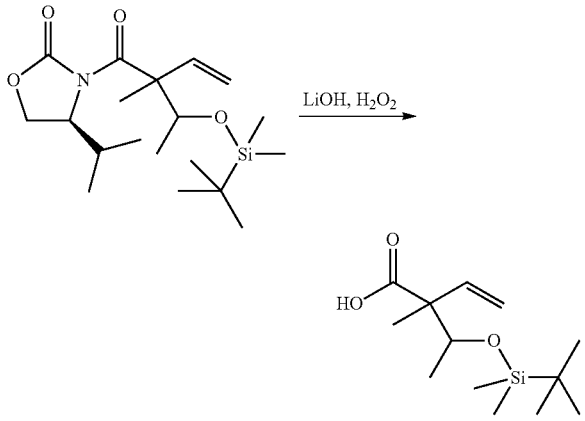

A cooled (0° C.) solution of (S)-3-{2-[1-(tert-butyl-dimethyl-silanyloxy)-ethyl]-2-methyl-but-3-enoyl}-4-isopropyl-oxazolidin-2-one (1.729 g, 4.677 mmol) in tetrahydrofuran/water (60 mL, 2:1) was subsequently treated with hydrogen peroxide (30% aqueous, 2.4 mL, 23.385 mmol) and lithium hydroxide monohydrate (392.4 mg, 9.355 mmol). After stirring for 2 days at room temperature, hydrogen peroxide (30% aqueous, 2.4 mL, 23.385 mmol) and lithium hydroxide monohydrate (400 mg, 9.535 mmol) were added at 0° C. After stirring at room temperature for 4 days, the reaction was quenched with solid sodium metabisulfite (18 g). After stirring for 1 h at room temperature, the pH was adjusted with hydrochloric acid (1 M) to pH 2 at 0° C. The aqueous layer was extracted with ethyl acetate (2×). The organics were combined, dried over anhydrous sodium sulfate, filtered and the volatiles were removed in vacuo. The residue was purified by silica gel chromatography using a 100 g Isolute cartridge eluted with a continuous gradient of iso-hexanes/diethyl ether 1:0 to 7:3 to afford the title compound (488.0 mg, 40%) as a yellow solid and as a single pair of enantiomers along with unreacted (S)-3-{2-[1-(tert-butyl-dimethyl-silanyloxy)-ethyl]-2-methyl-but-3-enoyl}-4-isopropyl-oxazolidin-2-one (431.5 mg, 25%, LCMS (m/z) 370.1 [M+H], Tr=3.93 min) as the other single pair of enantiomers as a colourless oil. $^1$H NMR (300 MHz, $CDCl_3$) δ 0.12 (s, 6H), 0.92 (s, 9H), 1.18 (d, J=6.0 Hz, 3H), 1.34 (s, 3H), 3.99 (q, J=6.2 Hz, 1H), 5.18 (d, J=17.8 Hz, 1H), 5.28 (d, J=10.5 Hz, 1H), 6.22 (dd, J=17.6, 11.2 Hz, 1H).

Compound 87d. (E)-4-[2-((R)-1-Acetoxy-ethyl)-quinolin-7-yl]-2-[1-(tert-butyl-dimethyl-silanyloxy)-ethyl]-2-methyl-but-3-enoic acid

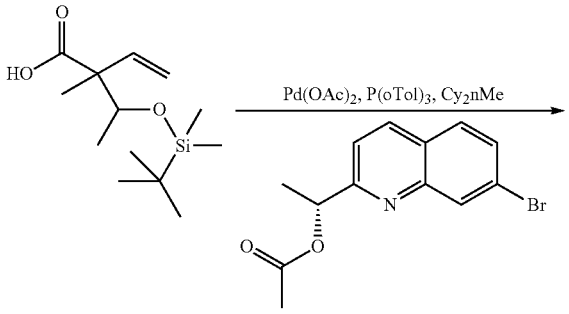

-continued

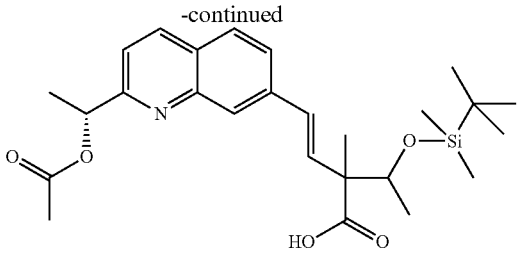

A solution of acetic acid (R)-1-(7-bromo-quinolin-2-yl)-ethyl ester (555.4 mg, 1.888 mmol), 2-[1-(tert-butyl-dimethyl-silanyloxy)-ethyl]-2-methyl-but-3-enoic acid (488.0 mg, 1.888 mmol), palladium(II)acetate (85 mg, 0.378 mmol), tri(o-tolyl)phosphine (115 mg, 0.378 mmol) and N,N-dicyclohexylmethylamine (1.0 mL, 4.720 mmol) in anhydrous 1,4-dioxane (15 mL) was heated at reflux for 2 h. After cooling to warm temperature the reaction was quenched with hydrochloric acid (1 M, 30 mL). The aqueous layer was extracted with ethyl acetate (2×). The combined organics were dried over anhydrous sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:1 to afford the title compound (252.7 mg, 28%) as a yellow solid along with a 1:3 mixture of 2-[1-(tert-butyl-dimethyl-silanyloxy)-ethyl]-2-methyl-but-3-enoic acid and acetic acid (R)-1-(7-bromo-quinolin-2-yl)-ethyl ester (474.6 mg) which was dissolved in anhydrous 1,4-dioxane (10 mL), treated with palladium(II)acetate (85 mg, 0.378 mmol), tri(o-tolyl)phosphine (115 mg, 0.378 mmol) and N,N-dicyclohexylmethylamine (1.0 mL, 4.720 mmol) and heated at reflux for 5 h. After cooling to room temperature the mixture was quenched with hydrochloric acid (1 M, 20 mL). The aqueous layer was extracted with ethyl acetate (2×). The combined organics were dried over anhydrous sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:1 to afford the title compound (149.6 mg, 17%) as a yellow solid. $^1$H NMR (300 MHz, $CDCl_3$) δ 0.12 (s, 3H), 0.15 (s, 3H), 0.93 (s, 9H), 1.25 (d, J=6.0 Hz, 3H), 1.69 (d, J=6.7 Hz, 3H), 2.18 (s, 3H), 2.51 (s, 3H), 4.14 (q, J=6.2 Hz, 1H), 6.08 (q, J=6.7 Hz, 1H), 6.74 (ABq, $\Delta\delta_{AB}$=0.12, $J_{AB}$=16.7 Hz, 2H), 7.44 (d, J=8.5 Hz, 1H), 7.64-7.70 (m, 1H), 7.76 (d, J=8.7 Hz, 1H), 8.03 (s, 1H), 8.12 (d, J=8.5 Hz, 1H). LCMS (m/z) 472.2 [M+H], Tr=3.61 min.

Compound 87e. (S)-1-[(S)-2-((S)-2-{(E)-4-[2-((R)-1-Acetoxy-ethyl)-quinolin-7-yl]-2-[1-(tert-butyl-dimethyl-silanyloxy)-ethyl]-2-methyl-but-3-enoylamino}-3-methyl-butyrylamino)-propionyl] hexahydro-pyridazine-3-carboxylic acid 2,2,2-trichloro-ethyl ester

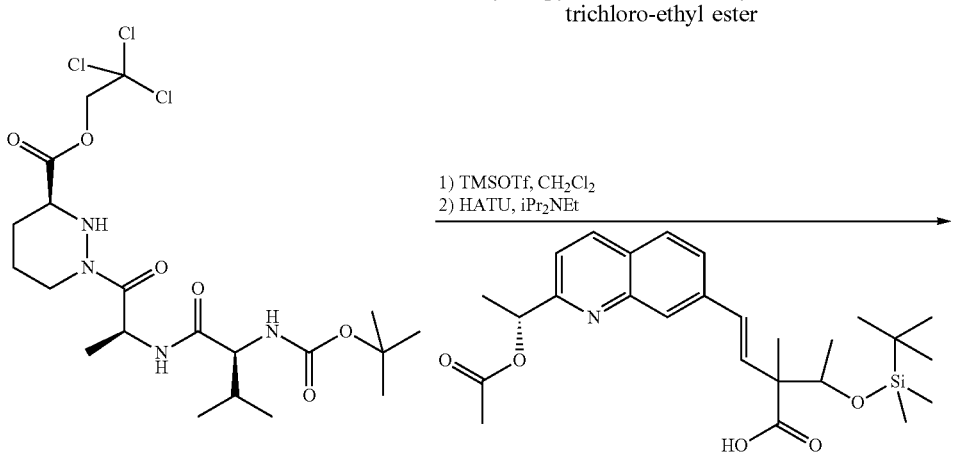

-continued

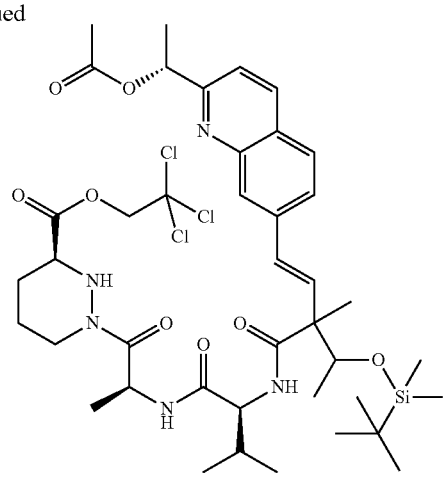

A solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (285.0 mg, 0.536 mmol) in dichloromethane (15 mL) at 0° C. was treated with trimethylsilyl-trifluoromethanesulfonate (200 μL, 1.072 mmol). After stirring at 0° C. for 45 min, the reaction was quenched with a saturated solution of sodium bicarbonate. The aqueous layer was extracted with dichloromethane. The combined organics were filtered through a phase separator and the volatiles were removed in vacuo to provide (S)-1-[(S)-2-((S)-2-amino-3-methyl-butyrylamino)-propionyl]-hexahydro-pyridazine-3-carboxylic acid 2,2,2-trichloro-ethyl ester as a white solid. To the white solid was added a solution of (E)-4-[2-((R)-1-acetoxy-ethyl)-quinolin-7-yl]-2-[1-(tert-butyl-dimethyl-silanyloxy)-ethyl]-2-methyl-but-3-enoic acid (252.7 mg, 0.536 mmol) in anhydrous acetonitrile (10 mL) and the solution was cooled to 0° C. then treated with N,N-diisopropylethylamine (380 μL, 2.144 mmol) and 2-(1H-7-azabenzotriazol-1-yl)-1,1,3,3-tetramethyl uronium hexafluorophosphate methanaminium (244.6 mg, 0.643 mmol). After stirring at room temperature for 20 h, the reaction was quenched with hydrochloric acid (1 M, 40 mL). The aqueous layer was extracted with ethyl acetate (2×). The organics were combined, washed with a saturated solution of sodium bicarbonate, dried over anhydrous sodium sulfate, filtered and the volatiles were removed in vacuo. The residue was purified by silica gel chromatography using a 50 g Isolute cartridge eluted with a continuous gradient of iso-hexanes/ethyl acetate 1:0 to 1:4 to provide the title compound (377.2 mg, 80%) as a 1:1 mixture of diastereosiomers and as a white foam. LCMS (m/z) 886.3/884.5 [M+H], Tr=4.14 min.

Compound 87f

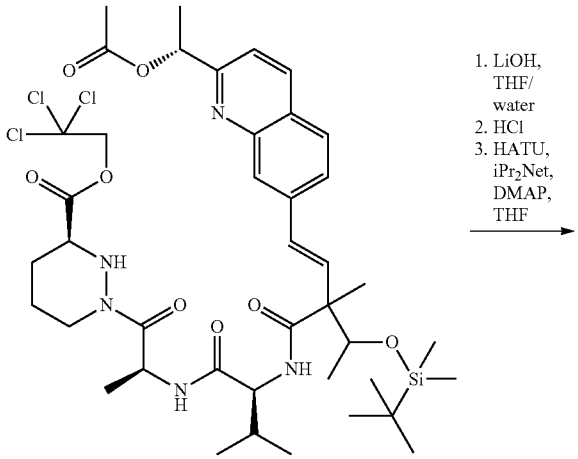

-continued

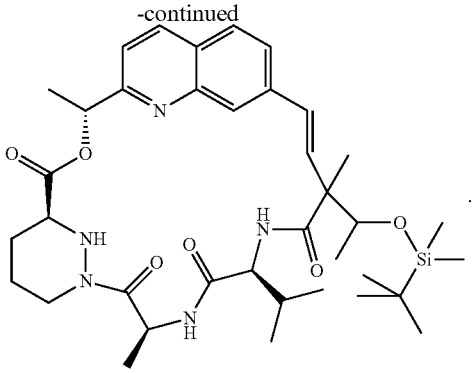

A cooled (0° C.) solution of (S)-1-[(S)-2-((S)-2-{(E)-4-[2-((R)-1-acetoxy-ethyl)-quinolin-7-yl]-2-[1-(tert-butyl-dimethyl-silanyloxy)-ethyl]-2-methyl-but-3-enoylamino}-3-methyl-butyrylamino)-propionyl]-hexahydro-pyridazine-3-carboxylic acid 2,2,2-trichloro-ethyl ester (377.2 mg, 0.426 mmol) in tetrahydrofuran/water (25 mL, 4:1) was treated with lithium hydroxide monohydrate (89 mg, 2.130 mmol). After stirring at 0° C. for 2 h, the reaction mixture was quenched with hydrochloric acid (2 M, 1.1 mL). The volatiles were removed in vacuo. Residual acetic acid and trichloroethanol were azeotroped off with tetrahydrofuran/toluene (6×) then triturated with diethyl ether and dried in vacuo. To the white solid was added dry tetrahydrofuran (150 mL), 4 Å molecular sieves. This solution was cooled to 0° C. and subsequently treated with N,N-diisopropylethylamine (370 μL, 2.130 mmol), N,N-dimethylaminopyridine (5.2 mg, 0.043 mmol) and 2-(1H-7-azabenzotriazol-1-yl)-1,1,3,3-tetramethyl uronium hexafluorophosphate methanaminium (194.4 mg, 0.511 mmol). After stirring at room temperature for 4 h, the volatiles were removed in vacuo. The residue was partitioned between ethyl acetate and hydrochloric acid (1 M). The organic layer was washed with a saturated solution of sodium bicarbonate, dried over anhydrous sodium sulfate, filtered and the volatiles were removed in vacuo. The residue was purified by silica gel chromatography using a 25 g Isolute cartridge eluted with a continuous gradient of iso-hexanes/acetone 1:0 to 3:2 to afford the title compound (134.8 mg, 45%, LCMS (m/z) 694.4 [M+H], Tr=3.75 min) as a white solid and as a mixture of diastereoisomers along with compound 87 (46.1 mg, 19%, LCMS (m/z) 580.3 [M+H], Tr=2.02 min) as a white solid and as a mixture of diastereoisomers.

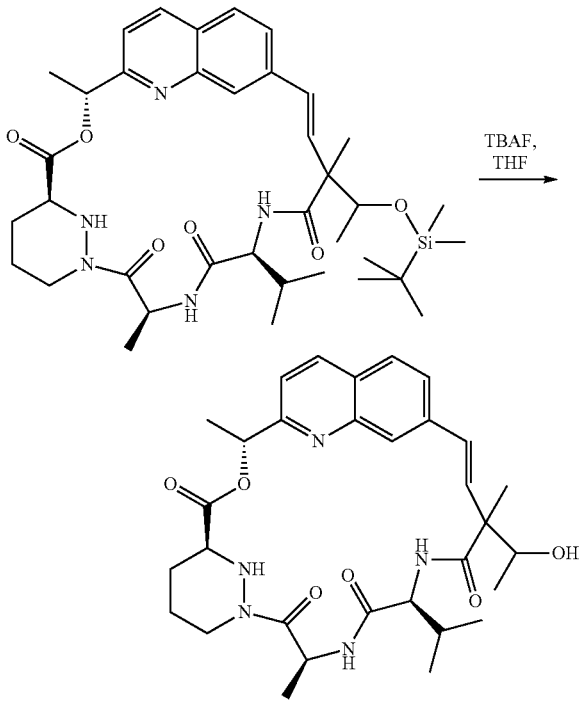

A cooled (0° C.) solution of compound 87f (121 mg, 0.174 mmol) in anhydrous tetrahydrofuran (10 mL) was treated with a solution of n-tetrabutylammonium fluoride (1 M in tetrahydrofuran, 0.87 mL, 0.871 mmol). After stirring for 4 h at 0° C., the yellow solution was treated with n-tetrabutylammonium fluoride (1 M in tetrahydrofuran, 0.87 mL, 0.871 mmol). After standing at 4° C. for 20 h the reaction was quenched with a saturated solution of sodium bicarbonate (20 mL). The aqueous layer was extracted with ethyl acetate (2×). The combined organics were dried over anhydrous sodium sulfate, filtered and the volatiles were removed in vacuo. The crude product was combined with unclean compound 87 obtained from the previous step and purified by silica gel chromatography using a 10 g Isolute cartridge eluted with a continuous gradient of iso-hexanes/acetone 1:0 to 1:1 then by reverse phase preparative HPLC eluted with a gradient of acetonitrile/water 5:95 to 1:0 to afford two different diastereoisomers.

Example 87, Compound 87 First eluting Diastereoisomer 1: (3.5 mg, 3.5%) as a white solid. $^1$H NMR (300 MHz, $CD_3OD$) δ 1.00-1.07 (m, 6H), 1.58-1.65 (m, 6H), 1.70-1.76 (m, 6H), 1.87-1.97 (m, 4H), 1.98-2.07 (m, 2H), 2.71-2.84 (m, 1H), 3.76-3.87 (m, 1H), 4.23 (d, J=10.0 Hz, 1H), 4.38-4.47 (m, 1H), 5.69 (q, J=7.4 Hz, 1H), 5.95 (q, J=6.7 Hz, 1H), 6.45 (ABq, $\Delta\delta_{AB}$=0.05, $J_{AB}$=16.5 Hz, 2H), 7.42 (d, J=8.5 Hz, 1H), 7.68 (s, 1H), 7.74 (dd, J=8.5, 1.6 Hz, 1H), 7.83 (d, J=8.7 Hz, 1H), 8.22 (d, J=8.5 Hz, 1H). LCMS (m/z) 580.3 [M+H], Tr=1.94 min.

Example 88, Compound 88 Second eluting Diastereoisomer 2: (7.6 mg, 7.5%) as a white solid. $^1$H NMR (300 MHz, $CD_3OD$) δ 1.01-1.11 (m, 6H), 1.62 (d, J=7.1 Hz, 3H), 1.65-1.77 (m, 9H), 1.83-1.96 (m, 4H), 1.98-2.09 (m, 2H), 2.72-2.86 (m, 1H), 3.76-3.87 (m, 1H), 4.34 (d, J=10.3 Hz, 1H), 4.38-4.47 (m, 1H), 5.77 (q, J=7.1 Hz, 1H), 5.95 (q, J=6.9 Hz, 1H), 6.41 (ABq, $\Delta\delta_{AB}$=0.15, $J_{AB}$=16.5 Hz, 2H), 7.43 (d, J=8.2 Hz, 1H), 7.65 (s, 1H), 7.74-7.87 (m, 2H), 8.22 (d, J=8.7 Hz, 1H). LCMS (m/z) 580.3 [M+H], Tr=2.02 min.

Examples 89 and 90

Compounds 89 and 90

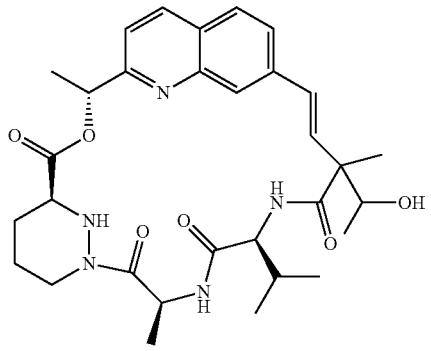

Compound 89a. 2-[1-(tert-Butyl-dimethyl-silanyloxy)-ethyl]-2-methyl-but-3-enoic acid

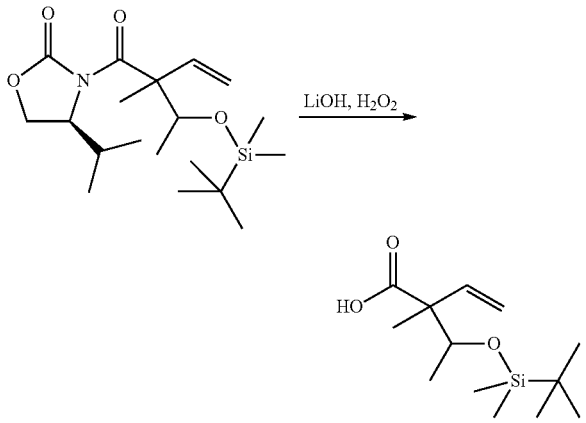

A cooled (0° C.) solution of recovered (S)-3-{2-[1-(tert-butyl-dimethyl-silanyloxy)-ethyl]-2-methyl-but-3-enoyl}-4-isopropyl-oxazolidin-2-one (431.5 mg, 1.167 mmol) in tetrahydrofuran/water (15 mL, 2:1) was subsequently treated with hydrogen peroxide (30% aqueous, 600 μL, 5.835 mmol) and lithium hydroxide monohydrate (98 mg, 2.335 mmol). After stirring for 2 days at room temperature, hydrogen peroxide (30% aqueous, 600 μL, 5.835 mmol) and lithium hydroxide monohydrate (175 mg, 4.171 mmol) were added at 0° C. After stirring at room temperature for 17 days, the reaction was quenched with solid sodium metabisulfite (4.4 g). After stirring for 1 h at room temperature, the pH was adjusted with hydrochloric acid (1 M) to pH 2 at 0° C. The aqueous layer was extracted with ethyl acetate (2×). The organics were combined, dried over anhydrous sodium sulfate, filtered and the volatiles were removed in vacuo. The residue was purified by silica gel chromatography using a 50 g Isolute cartridge eluted with a continuous gradient of iso-hexanes/diethyl ether 1:0 to 7:3 to afford the title compound (115.8 mg, 38%) as a white solid and as a single diastereoisomer. $^1$H NMR (300 MHz, $CDCl_3$) δ 0.14 (s, 3H), 0.16 (s, 3H), 0.92 (s, 9H), 1.20-1.26 (m, 6H), 3.97 (q, J=6.5 Hz, 1H), 5.16-5.26 (m, 2H), 5.88 (dd, J=17.4, 10.7 Hz, 1H), 10.33 (br s, 1H).

Compound 89b. (E)-4-[2-((R)-1-Acetoxy-ethyl)-quinolin-7-yl]-2-[1-(tert-butyl-dimethyl-silanyloxy)-ethyl]-2-methyl-but-3-enoic acid

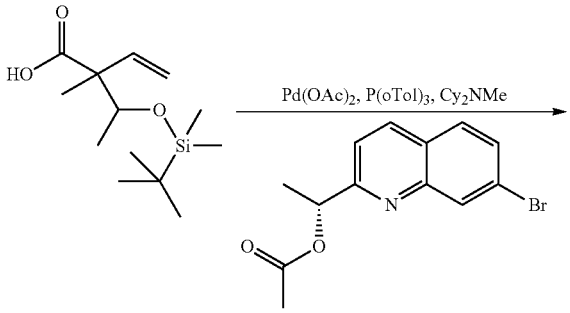

-continued

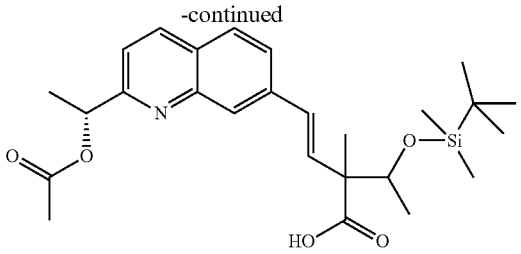

Compound 89b was prepared in the same manner as compound 87d. $^1$H NMR (300 MHz, $CDCl_3$) δ 0.10 (s, 3H), 0.16 (s, 3H), 0.89 (s, 9H), 1.29 (d, J=6.7 Hz, 3H), 1.40 (s, 3H), 1.69 (d, J=6.9 Hz, 3H), 2.18 (s, 3H), 4.07-4.19 (m, 1H), 6.06 (q, J=6.5 Hz, 1H), 6.44 (d, J=16.5 Hz, 1H), 6.70 (d, J=16.5 Hz, 1H), 7.44 (d, J=8.5 Hz, 1H), 7.57 (d, J=8.2 Hz, 1H), 7.75 (d, J=8.7 Hz, 1H), 8.02 (s, 1H), 8.12 (d, J=8.7 Hz, 1H). LCMS (m/z) 472.2 [M+H], Tr=3.71 min.

Compound 89c. (S)-1-[(S)-2-((S)-2-{(E)-4-[2-((R)-1-Acetoxy-ethyl)-quinolin-7-yl]-2-[1-(tert-butyl-dimethyl-silanyloxy)-ethyl]-2-methyl-but-3-enoylamino}-3-methyl-butyrylamino)-propionyl]-hexahydro-pyridazine-3-carboxylic acid 2,2,2-trichloro-ethyl ester

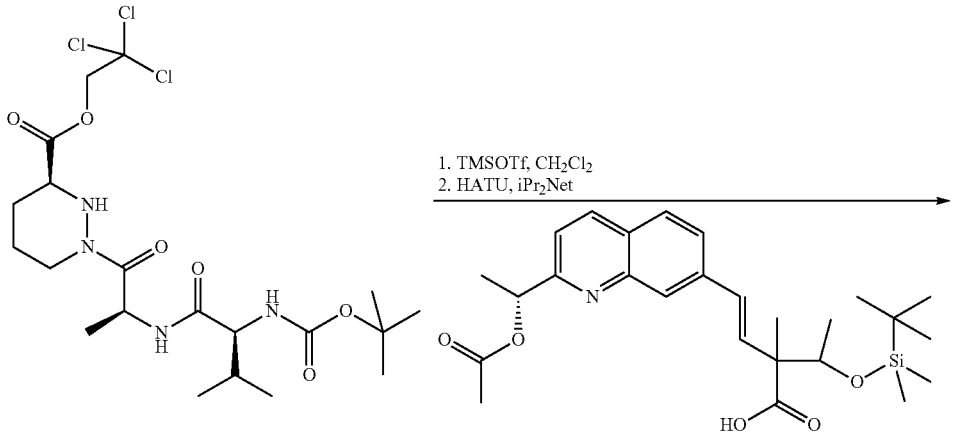

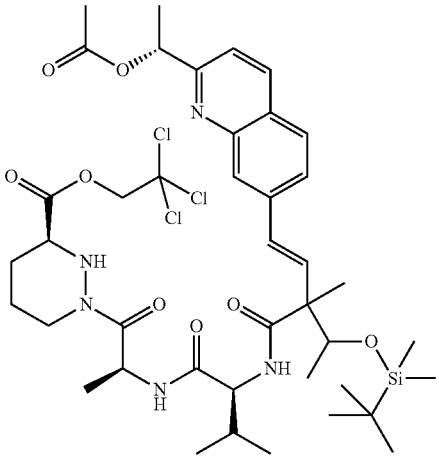

Compound 89c, as a mixture of diastereoisomers, was prepared in the same manner as compound 87e in 63% yield. LCMS (m/z) 886.3/884.4 [M+H], Tr=4.08 min.

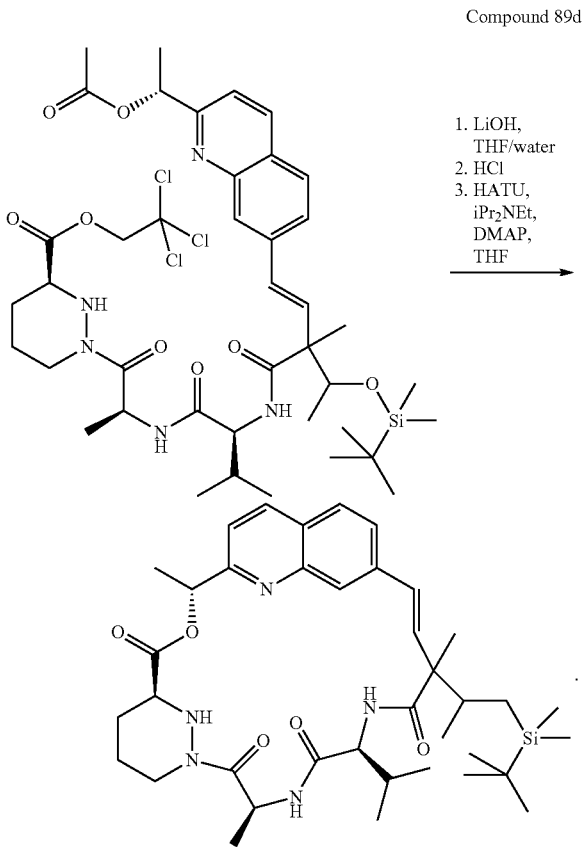

Compound 89d, as a mixture of diastereoisomers, was prepared in the same manner as compound 87f in 42% yield. LCMS (m/z) 694.5 [M+H], Tr=5.61 min.

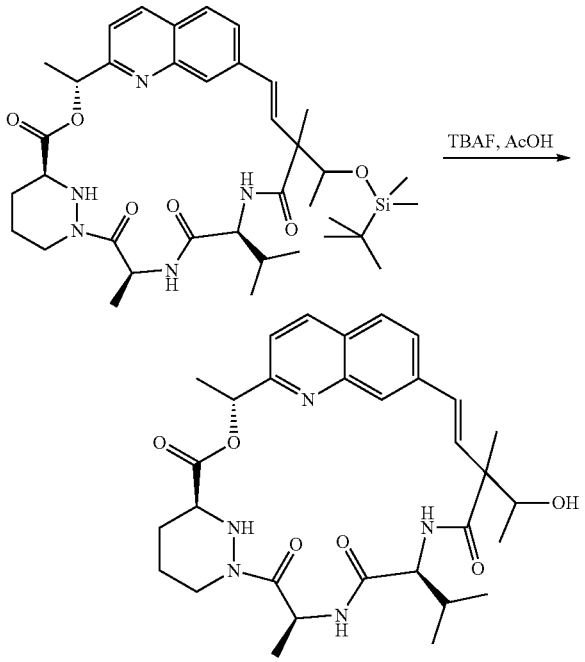

A cooled (0° C.) solution of compound 89d (83.0 mg, 0.120 mmol) in anhydrous tetrahydrofuran (2 mL) was treated with a solution of n-tetrabutylammonium fluoride (1 M in tetrahydrofuran, 0.6 mL, 0.600 mmol) and acetic acid (35 μL, 0.600 mmol). After stirring for 24 h at 0° C., the yellow solution was treated with n-tetrabutylammonium fluoride (1 M in tetrahydrofuran, 0.6 mL, 0.600 mmol) and acetic acid (35 μL, 0.600 mmol). After standing at 4° C. for 7 days the reaction was quenched with a saturated solution of sodium bicarbonate. The aqueous layer was extracted with ethyl acetate (2×). The combined organics were dried over anhydrous sodium sulfate, filtered and the volatiles were removed in vacuo. The residue was purified by silica gel chromatography using a 25 g Isolute cartridge eluted with a continuous gradient of iso-hexanes/acetone 1:0 to 3:2 to provide compound 89d (21.7 mg, 26%) as a single diastereoisomer along with compound 89 (54.7 mg, 79%) as a white solid which was then purified by preparative reverse phase HPLC eluted with a gradient of acetonitrile/water 5:95 to 1:0 to afford compound 89 (13.6 mg, 19%) as a white solid and as a single diastereoisomer. $^1$H NMR (300 MHz, $CD_3OD$) δ 1.02 (d, J=6.7 Hz, 3H), 1.04 (d, J=6.7 Hz, 3H), 1.24 (s, 3H), 1.32 (d, J=6.3 Hz, 3H), 1.62-1.75 (m, 8H), 1.86-2.04 (m, 3H), 2.68-2.81 (m, 1H), 3.77-3.88 (m, 1H), 3.98 (q, J=6.5 Hz, 1H), 4.36-4.47 (m, 2H), 5.79 (q, J=7.1 Hz, 1H), 5.92 (q, J=6.7 Hz, 1H), 6.28 (d, J=16.5 Hz, 1H), 6.58 (d, J=16.5 Hz, 1H), 7.39 (d, J=8.5 Hz, 1H), 7.60 (s, 1H), 7.78-7.86 (m, 2H), 8.20 (d, J=8.5 Hz, 1H). LCMS (m/z) 580.2 [M+H], Tr=2.10 min.

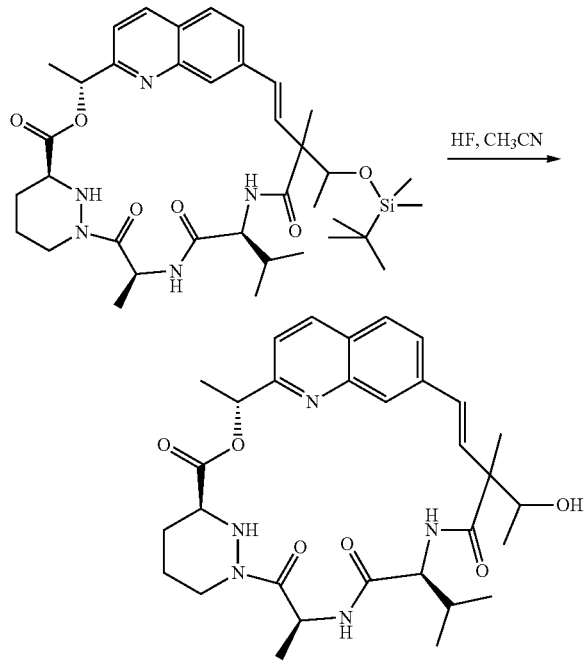

A solution of compound 89d recovered from the previous step (21.7 mg, 0.031 mmol) in acetonitrile/tetrahydrofuran (5 mL, 9:1) was treated with hydrofluoric acid (48 wt % in water, 120 μL, 3.127 mmol). After stirring at room temperature for 6 h, the mixture was slowly poured over a saturated solution of sodium bicarbonate. The aqueous layer was extracted with ethyl acetate (2×). The organics were combined, dried over anhydrous sodium sulfate, filtered and the volatiles were removed in vacuo. The residue was purified by reverse phase preparative HPLC to afford compound 90 (5.6 mg, 31%) as a white solid. $^1$H NMR (300 MHz, $CD_3OD$) δ 0.97 (d, J=6.5 Hz, 6H), 1.23 (d, J=6.7 Hz, 3H), 1.48 (s, 3H), 1.63-1.76 (m, 8H), 1.87-2.05 (m, 3H), 2.67-2.79 (m, 1H), 3.77-3.87 (m, 1H), 4.19-4.31 (m, 2H), 4.40 (d, J=12.5 Hz, 1H), 5.71 (q, J=7.3 Hz, 1H), 5.91 (q, J=6.9 Hz, 1H), 6.37 (s, 2H), 7.41 (d, J=8.5 Hz, 1H), 7.66 (s, 1H), 7.76-7.85 (m, 2H), 8.22 (d, J=8.7 Hz, 1H). LCMS (m/z) 580.3 [M+H], Tr=2.03 min.

Example 91

Compound 91

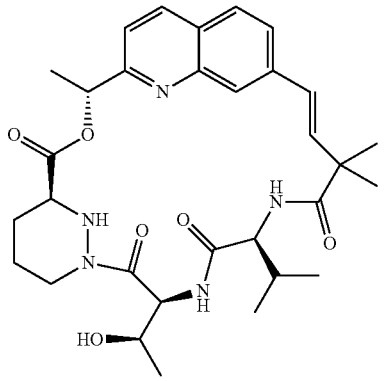

Compound 91a: (2S,3R)-2-tert-Butoxycarbonylamino-3-hydroxy-butyric acid methyl ester

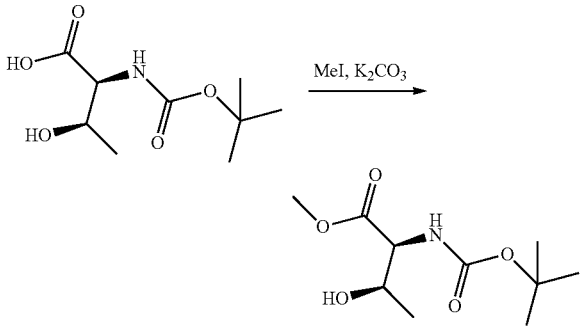

(2S,3R)-2-tert-Butoxycarbonylamino-3-hydroxy-butyric acid (2 g, 9.12 mmol) was dissolved in N,N-dimethylformamide (15 mL), under an atmosphere of nitrogen. Potassium carbonate (2.02 g, 14.6 mmol) was added and the reaction was cooled using an ice bath. Iodomethane (679 μL, 10.9 mmol) was added and the reaction was stirred for 2 h, and allowed to slowly warm to room temperature. The reaction mixture was diluted with water and extracted with diethyl ether. The organic phase was washed with brine, dried over anhydrous sodium sulfate, filtered and concentrated to afford the title compound (1.85 g, 87%) as a colourless oil. $^1$H NMR (300 MHz, $CDCl_3$) δ 1.26 (d, J=6.6 Hz, 3H), 1.47 (s, 9H), 2.24-2.45 (m, 1H), 3.78 (s, 3H), 4.15-4.37 (m, 2H), 5.21-5.45 (m, 1H). LCMS (m/z) 234.0 [M+H], Tr=1.57 min.

Compound 91b: (2S,3R)-2-tert-Butoxycarbonylamino-3-(tert-butyl-diphenyl-silanyloxy)-butyric acid methyl ester

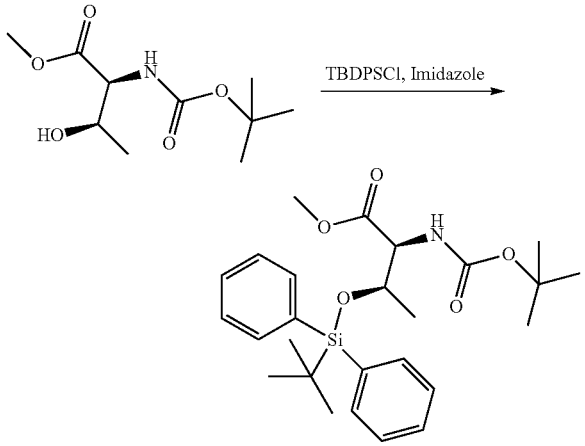

(2S,3R)-2-tert-Butoxycarbonylamino-3-hydroxy-butyric acid methyl ester (1.85 g, 7.93 mmol) was dissolved in N,N-dimethylformamide (10 mL), under an atmosphere of nitrogen. tert-Butyl(chloro)diphenylsilane (2.89 mL, 11.1 mmol) was added followed by imidazole (1.08 g, 15.9 mmol) and the reaction was left to stir for 72 h. The reaction mixture was diluted with water and then extracted with ethyl acetate. The combined organics were dried over anhydrous sodium sulfate, filtered and concentrated. The residue was purified by silica gel chromatography using a stepwise gradient iso-hexanes/ethyl acetate from 1:0 to 4:1 to afford the title compound (3.56 g, 95%) as a pale Greene oil. $^1$H NMR (300 MHz, $CDCl_3$) δ 0.89 (d, J=6.6 Hz, 3H), 1.04 (s, 9H), 1.10 (s, 9H), 3.64 (s, 3H), 4.18-4.26 (m, 1H), 4.39-4.50 (m, 1H), 5.34 (d, J=9.9 Hz, 1H), 7.36-7.50 (m, 6H), 7.60-7.69 (m, 2H), 7.71-7.77 (m, 2H). LCMS (m/z) 472.2 [M+H], Tr=4.13 min.

Compound 91c: (2S,3R)-2-tert-Butoxycarbonylamino-3-(tert-butyl-diphenyl-silanyloxy)-butyric acid

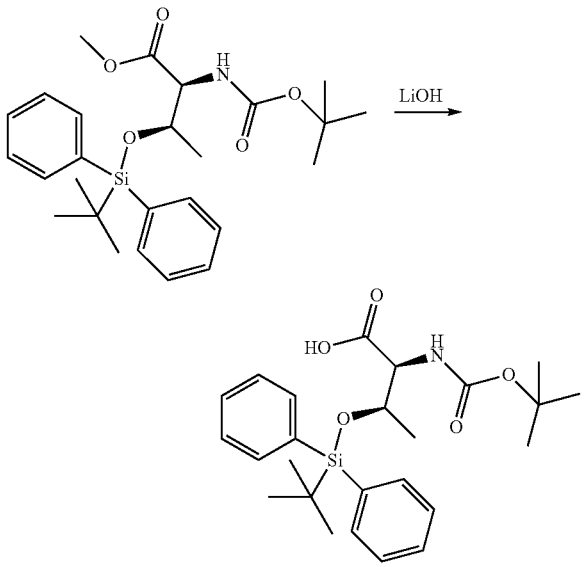

(2S,3R)-2-tert-Butoxycarbonylamino-3-(tert-butyl-diphenyl-silanyloxy)-butyric acid methyl ester (3.56 g, 7.55 mmol) was taken up in a mixture of tetrahydrofuran (10 mL) and water (3 mL) and cooled using an ice bath. Lithium hydroxide monohydrate (1.27 g, 30.2 mmol) was then added and the reaction was left to stir overnight. The solution was acidified using hydrochloric acid (2 M) until the solution was pH 2. The solution was then extracted with ethyl acetate. The organics were dried over anhydrous sodium sulfate, filtered and concentrated to afford the title compound (3.41 g, 98%) as a yellow oil. $^1$H NMR (300 MHz, $CDCl_3$) δ 1.02-1.11 (m, 21H), 4.26-4.35 (m, 1H), 4.41-4.51 (m, 1H), 5.34 (d, J=9.0 Hz, 1H), 7.35-7.49 (m, 6H), 7.63-7.77 (m, 4H). LCMS (m/z) 458.1 [M+H], Tr=3.68 min.

Compound 91d: (S)-1-[(2S,3R)-2-tert-Butoxycarbonylamino-3-(tert-butyl-diphenyl-silanyloxy)-butyryl]-hexahydro-pyridazine-3-carboxylic acid 2,2,2-trichloro-ethyl ester

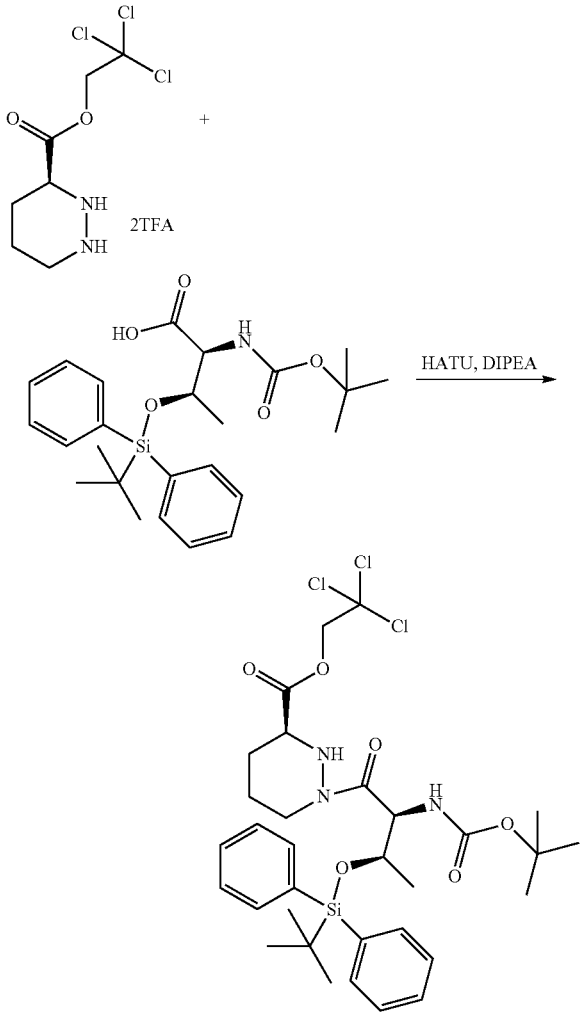

(S)-Hexahydro-pyridazine-3-carboxylic acid 2,2,2-trichloro-ethyl ester bis trifluoroacetic acid salt (4.1 g, 8.33 mmol) and (2S,3R)-2-tert-butoxycarbonylamino-3-(tert-butyl-diphenyl-silanyloxy)-butyric acid (3.4 g, 7.45 mmol) were dissolved in anhydrous acetonitrile (25 mL), under an atmosphere of nitrogen and cooled using an ice bath. 2-(1H-7-azabenzotriazol-1-yl)-1,1,3,3-tetramethyl uronium hexafluorophosphate methanaminium (3.95 g, 10.4 mmol) and N,N-diisopropylethylamine (5.2 mL, 29.8 mmol) were then added and the reaction was allowed to slowly warm to room temperature and left to stir for 2 h. The solvent was removed and the residue was dissolved in ethyl acetate and washed with water. The organics were dried over anhydrous sodium sulfate, filtered and concentrated. The residue was purified by silica gel chromatography using a stepwise gradient iso-hexanes/ethyl acetate from 1:0 to 1:1 to afford the title compound (1.95 g, 38%) as a white solid. $^1$H NMR (300 MHz, $CDCl_3$) δ 1.07 (s, 9H), 1.14 (d, J=6.3 Hz, 3H), 1.43-1.51 (m, 10H), 1.73-2.01 (m, 3H), 2.68-2.84 (m, 1H), 3.45 (d, J=11.4 Hz, 1H), 4.02-4.09 (m, 1H), 4.19-4.31 (m, 1H), 4.67 (d, J=11.4 Hz, 1H), 4.83-4.92 (m, 2H), 5.56 (d, J=9.6 Hz, 1H), 7.34-7.47 (m, 6H), 7.58-7.65 (m, 2H), 7.66-7.74 (m, 2H). LCMS (m/z) 702.2 [M+H], Tr=4.36 min.

Compound 91e: (S)-1-[(2S,3R)-2-((S)-2-tert-Butoxycarbonylamino-3-methyl-butyrylamino)-3-(tert-butyl-diphenyl-silanyloxy)-butyryl]-hexahydro-pyridazine-3-carboxylic acid 2,2,2-trichloro-ethyl ester

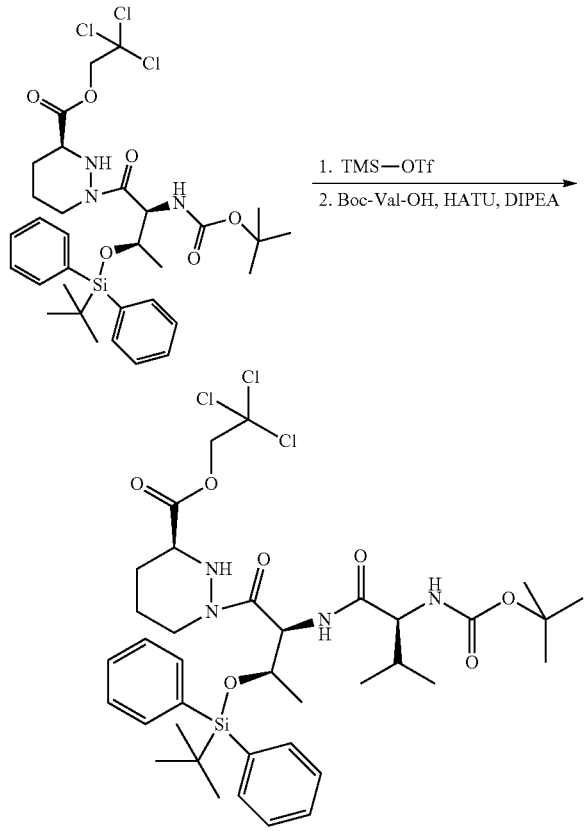

(S)-1-[(2S,3R)-2-tert-Butoxycarbonylamino-3-(tert-butyl-diphenyl-silanyloxy)-butyryl]-hexahydro-pyridazine-3-carboxylic acid 2,2,2-trichloro-ethyl ester (1.95 g, 2.79 mmol) was dissolved in dichloromethane (10 mL), under an atmosphere of nitrogen and cooled using an ice bath before adding trimethylsilyl trifluoromethanesulfonate (379 μL, 4.19 mmol). The reaction mixture was stirred for 1 h before adding N,N-diisopropylethylamine (1.95 mL, 11.2 mmol) and removing all volatiles. The residue was redissolved, along with (S)-2-tert-butoxycarbonylamino-3-methyl-butyric acid (728 mg, 3.35 mmol) in anhydrous acetonitrile (10 mL). The solution was cooled using an ice bath, before adding 2-(1H-7-azabenzotriazol-1-yl)-1,1,3,3-tetramethyl uronium hexafluorophosphate methanaminium (1.49 g, 3.91 mmol) and N,N-diisopropylethylamine (1.95 mL, 11.2 mmol). The reaction mixture was allowed to slowly warm to room temperature and left to stir overnight. The solvent was evaporated and the remaining residue was purified by silica gel chromatography using a stepwise gradient of isohexanes/ethyl acetate 1:0 to 1:1 to afford the title compound (1.02 g, 46%) as a white solid. $^1$H NMR (300 MHz, $CDCl_3$) δ 1.03 (d, J=6.9 Hz, 6H), 1.12 (d, J=6.3 Hz, 3H), 1.49 (s, 9H), 1.21-1.25 (m, 1H), 1.74-1.94 (m, 2H), 2.12-2.24 (m, 1H), 2.66-2.86 (m, 2H), 3.48 (d, J=11.1 Hz, 1H), 4.06-4.29 (m, 4H), 4.76 (ABq, Δδ=0.24, $J_{AB}$=11.8 Hz, 2H), 5.16 (d, J=9.3 Hz, 1H), 5.25 (d, J=9.0 Hz, 1H), 6.72 (d, J=8.7 Hz, 1H), 7.34-7.47 (m, 6H), 7.57-7.65 (m, 2H), 7.66-7.74 (m, 2H). LCMS (m/z) 801.2 [M+H], Tr=4.31 min.

Compound 91f: (S)-1-[(2S,3R)-2-((S)-2-{(E)-4-[2-((R)-1-Acetoxy-ethyl)-quinolin-7-yl]-2,2-dimethyl-but-3-enoylamino}-3-methyl-butyrylamino)-3-(tert-butyl-diphenyl-silanyloxy)-butyryl]-hexahydro-pyridazine-3-carboxylic acid 2,2,2-trichloro-ethyl ester

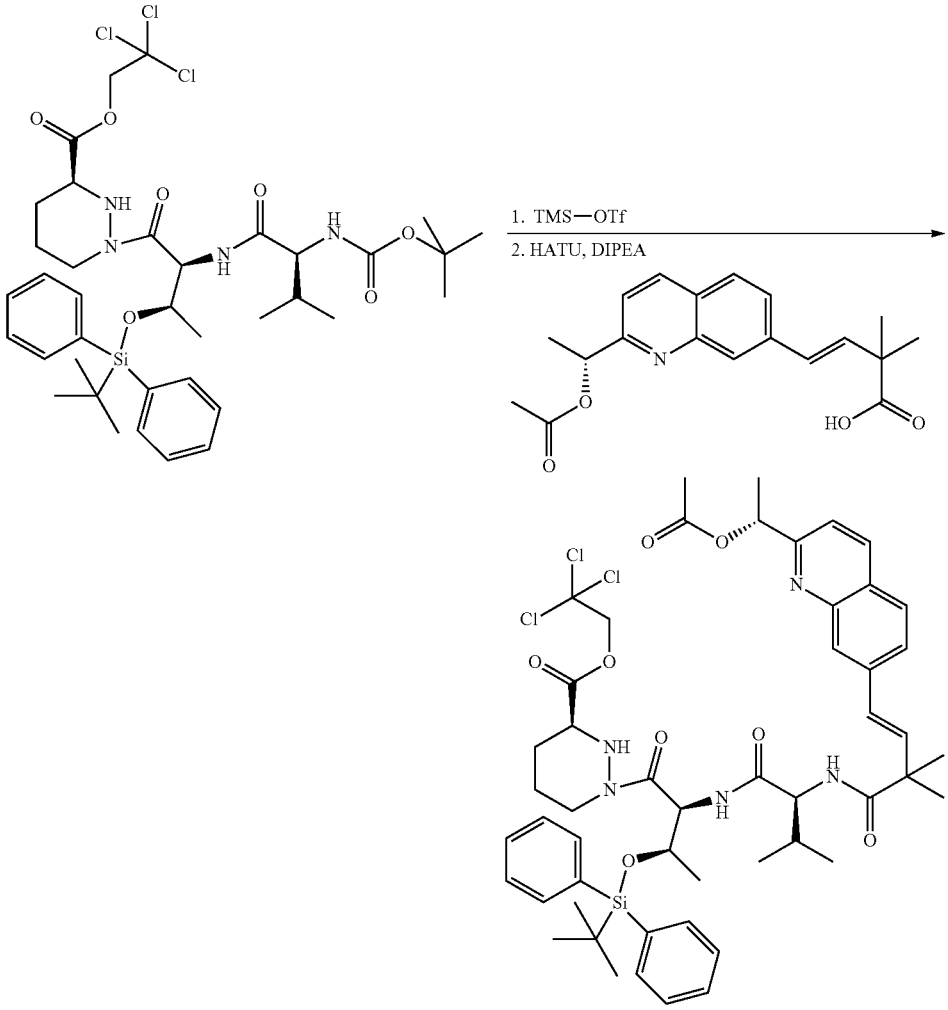

(S)-1-[(2S,3R)-2-((S)-2-tert-Butoxycarbonylamino-3-methyl-butyrylamino)-3-(tert-butyl-diphenyl-silanyloxy)-butyryl]-hexahydro-pyridazine-3-carboxylic acid 2,2,2-trichloro-ethyl ester (1.02 g, 1.27 mmol) was dissolved in dichloromethane (10 mL), under an atmosphere of nitrogen and cooled using an ice bath before adding trimethylsilyl trifluoromethanesulfonate (173 μL, 1.91 mmol). The reaction mixture was stirred for 1 h before adding N,N-diisopropylethylamine (885 μL, 5.08 mmol) and removing all volatiles. The residue was redissolved, along with (E)-4-[2-((R)-1-acetoxy-ethyl)-quinolin-7-yl]-2,2-dimethyl-but-3-enoic acid (498 mg, 1.52 mmol) in anhydrous acetonitrile (10 mL). The solution was cooled using an ice bath, before adding 2-(1H-7-azabenzotriazol-1-yl)-1,1,3,3-tetramethyl uronium hexafluorophosphate methanaminium (677 mg, 1.78 mmol) and N,N-diisopropylethylamine (885 μL, 5.08 mmol). The reaction mixture was allowed to slowly warm to room temperature and left to stir overnight. The solvent was evaporated and the remaining residue was purified by silica gel chromatography using a stepwise gradient of iso-hexanes/ethyl acetate 1:0 to 1:1 to afford the title compound (671 mg, 53%) as a white solid. $^1$H NMR (300 MHz, $CDCl_3$) δ 1.00-1.05 (m, 6H), 1.07 (s, 9H), 1.10 (d, J=6.0 Hz, 3H), 1.15-1.20 (m, 1H), 1.51 (s, 6H), 1.61 (s, 3H), 1.69 (d, J=6.7 Hz, 3H), 1.74-1.93 (m, 2H), 2.18 (s, 3H), 2.64-2.81 (m, 2H), 3.45 (d, J=11.2 Hz, 1H), 4.02-4.10 (m, 1H), 4.48 (dd, J=8.0, 5.6 Hz, 1H), 4.74 (ABq, Δδ=0.23, $J_{AB}$=11.8 Hz, 2H), 5.12 (d, J=9.4 Hz, 1H), 6.06 (q, J=6.7 Hz, 1H), 6.54 (d, J=8.0 Hz, 1H), 6.59-6.82 (m, 3H), 7.35-7.50 (m, 7H), 7.58-7.66 (m, 3H), 7.67-7.77 (m, 3H), 8.04 (s, 1H), 8.11 (d, J=8.4 Hz, 1H). LCMS (m/z) 1010.5 [M+H], Tr=3.80 min.

Compound 91g: (S)-1-[(2S,3R)-3-(tert-Butyl-diphenyl-silanyloxy)-2-((S)-2-{(E)-4-[2-((R)-1-hydroxy-ethyl)-quinolin-7-yl]-2,2-dimethyl-but-3-enoylamino}-3-methyl-butyrylamino)-butyryl]-hexahydro-pyridazine-3-carboxylic acid (S)-1-[(2S,3R)-2-((S)-2-{(E)-4-[2-((R)-1-Acetoxy-ethyl)-quinolin-7-yl]-2,2-dimethyl-but-3-enoylamino}-3-methyl-butyrylamino)-3-(tert-butyl-diphenyl-silanyloxy)-butyryl]-hexahydro-pyridazine-3-carboxylic acid 2,2,2-trichloro-ethyl ester (444 mg, 0.440 mmol) was taken up in a mixture of tetrahydrofuran (10 mL) and water (3 mL) and cooled using an ice bath. Lithium hydroxide monohydrate (148 mg, 3.52 mmol) was then added and the reaction was allowed to slowly warm to room temperature and left to stir for eighty minutes. The solution was then neutralised with hydrochloric acid (2 M) and concentrated until all volatiles had been removed to afford the title compound (368 mg, 100%) as a yellow solid. $^1$H NMR (300 MHz, $CD_3OD$) δ 0.83 (d, J=6.5 Hz, 3H), 0.87-93 (m, 7H), 0.96 (s, 9H), 1.16-1.61 (m, 13H), 1.63-1.81 (m, 2H), 2.10-2.23 (m, 2H), 2.26-2.33 (m, 1H), 2.64-2.76 (m, 1H), 3.98-4.21 (m, 3H), 4.86 (d, J=11.8 Hz, 1H), 5.08 (d, J=9.6 Hz, 1H), 6.81 (ABq, Δδ=0.17, $J_{AB}$=16.2 Hz, 2H), 7.13-7.19 (m, 1H), 7.22-7.29 (m, 1H), 7.32-7.47 (m, 6H), 7.52-7.63 (m, 4H), 7.72-8.12 (m, 3H). LCMS (m/z) 836.6 [M+H], Tr=3.03 min.

Compound 91h

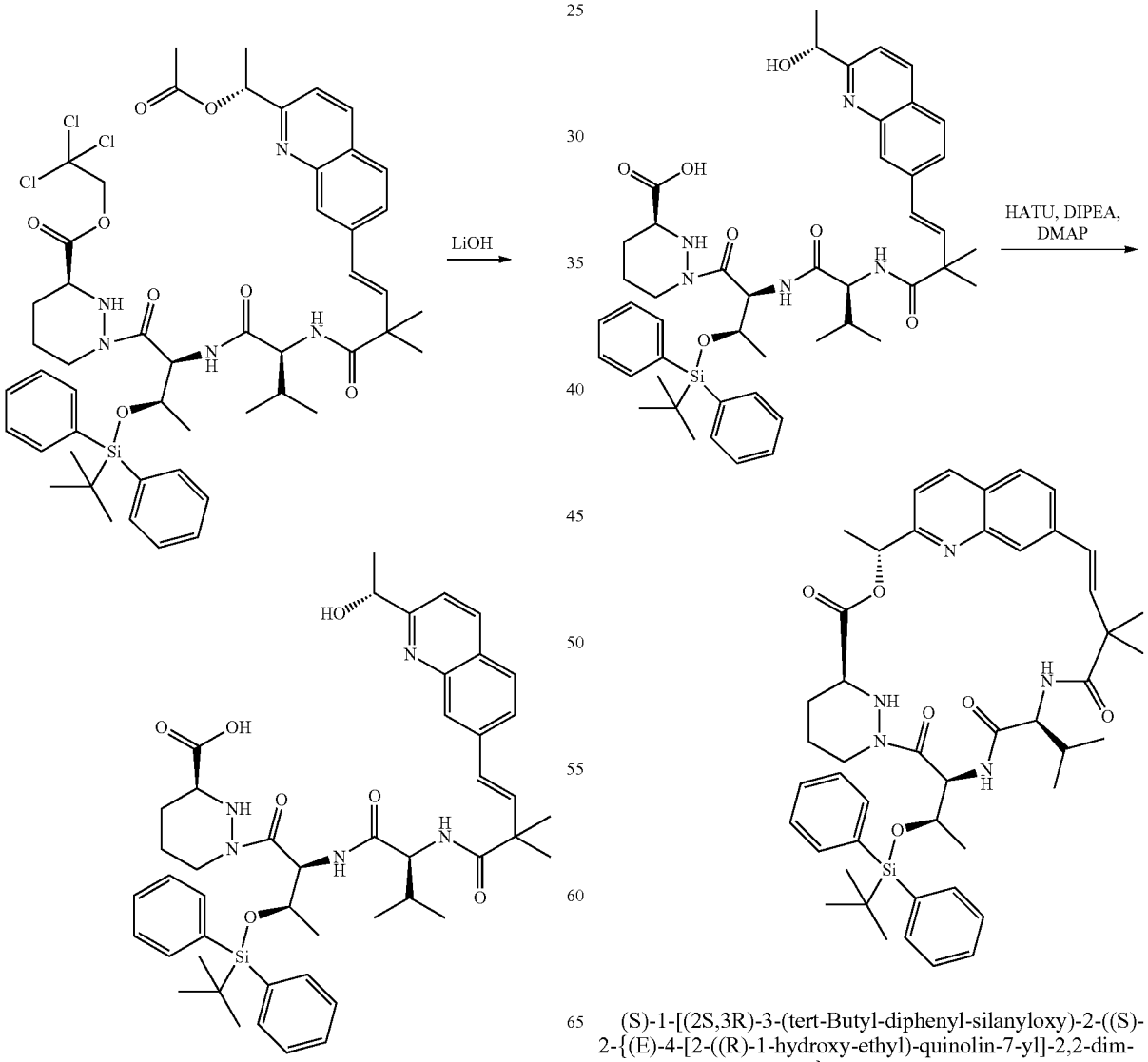

(S)-1-[(2S,3R)-3-(tert-Butyl-diphenyl-silanyloxy)-2-((S)-2-{(E)-4-[2-((R)-1-hydroxy-ethyl)-quinolin-7-yl]-2,2-dimethyl-but-3-enoylamino}-3-methyl-butyrylamino)-butyryl]- hexahydro-pyridazine-3-carboxylic acid (368 mg, 0.440 mmol) was dissolved in anhydrous tetrahydrofuran (150 mL). N,N-dimethylaminopyridine (5 mg, 0.044 mmol), N,N-diisopropylethylamine (383 μL, 2.2 mmol) and 2-(1H-7-azabenzotriazol-1-yl)-1,1,3,3-tetramethyl uronium hexafluorophosphate methanaminium (201 mg, 0.528 mmol) were then added and the reaction was placed under an atmosphere of nitrogen. The reaction was left to stir overnight. All volatiles were removed and the residue was dissolved in ethyl acetate and washed with hydrochloric acid (1 M). The organics were dried over anhydrous sodium sulfate, filtered and concentrated. The residue was purified by silica gel chromatography using a stepwise gradient of iso-hexanes/ethyl acetate 4:1 to 3:2 afforded the title compound (175 mg, 49%) as a white solid. $^1$H NMR (300 MHz, $CD_3CN$) δ 0.94-1.06 (m, 6H), 1.09 (s, 9H), 1.15 (s, 9H), 1.55 (d, J=6.7 Hz, 3H), 1.67-1.79 (m, 2H), 1.92-2.00 (m, 6H), 2.49-2.61 (m, 1H), 2.73-2.86 (m, 1H), 3.44 (q, J=6.9 Hz, 1H), 3.61 (d, J=12.5 Hz, 1H), 4.14-4.24 (m, 1H), 4.29-4.39 (m, 1H), 4.43-4.52 (m, 1H), 5.62 (dd, J=8.5, 2.2 Hz, 1H), 5.82 (q, J=7.1 Hz, 1H), 6.29-6.52 (m, 3H), 7.04 (d, J=8.7 Hz, 1H), 7.34 (d, J=8.5 Hz, 1H), 7.38-7.54 (m, 6H), 7.61 (dd, J=8.4, 1.6 Hz, 1H), 7.71-7.84 (m, 4H), 8.17 (d, J=8.7 Hz, 1H). LCMS (m/z) 818.5 [M+H], Tr=4.30 min.

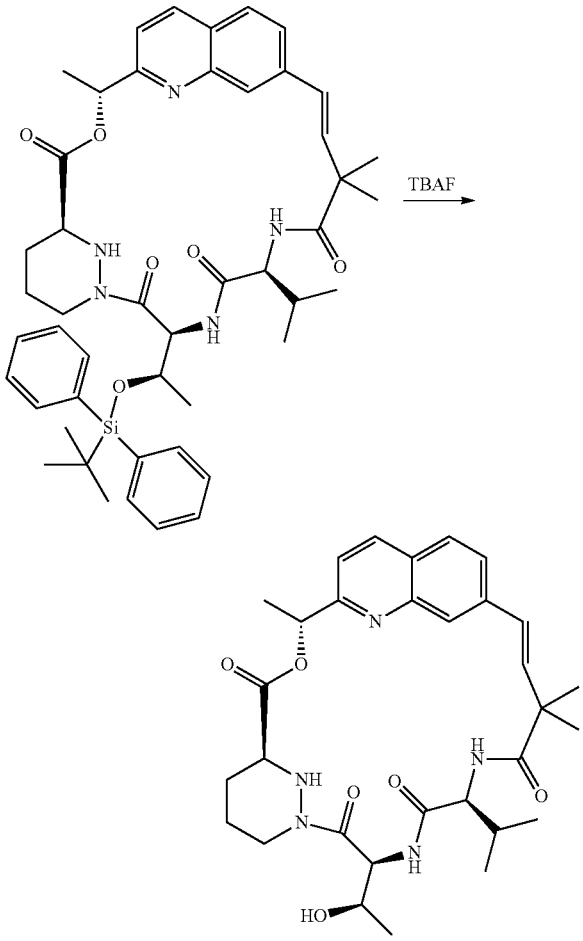

Compound 91 h was dissolved in tetrahydrofuran (1.07 mL) and cooled using an ice under an atmosphere of nitrogen. N-Tetrabutylammonium fluoride (1.07 mL, 0.903 mmol) was added and the reaction was left to stir for 2.5 h. The reaction was then quenched with saturated ammonium chloride solution and extracted with dichloromethane. The organics were dried over anhydrous sodium sulfate, filtered and concentrated. The residue was purified by silica gel chromatography using a stepwise gradient of iso-hexanes/ethyl acetate 1:1 to 0:1. The isolated material still contained tetrabutylammonium salts so the residue was dissolved in dichloromethane, washed with saturated ammonium chloride solution, dried over anhydrous sodium sulfate, filtered and concentrated. The residue was purified by silica gel chromatography using 1:1 iso-hexanes/ethyl acetate to afford the title compound (17 mg, 14%) as a white solid. $^1$H NMR (300 MHz, $CDCl_3$) δ 0.78-1.02 (m, 10H), 1.23 (s, 6H), 1.35-1.42 (m, 3H), 1.69-1.74 (m, 1H), 1.89-2.12 (m, 3H), 2.53-2.78 (m, 1H), 3.63-3.98 (m, 3H), 4.16 (m, 2H), 4.51-4.68 (m, 1H), 5.79-6.12 (m, 2H), 6.17-6.66 (m, 4H), 7.38-7.48 (m, 1H), 7.53-7.65 (m, 1H), 7.68-7.80 (m, 1H), 7.88 (s, 1H), 8.00-8.17 (m, 1H). LCMS (m/z) 580.2 [M+H], Tr=2.25 min.

Example 92

Compound 92

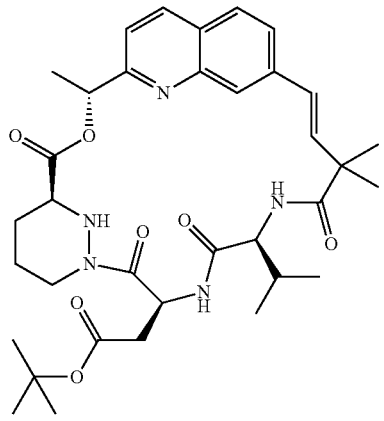

Compound 92a. (S)-1-[(S)-3-tert-Butoxycarbonyl-2-(9H-fluoren-9-ylmethoxy carbonylamino)-propionyl]-hexahydro-pyridazine-3-carboxylic acid 2,2,2-trichloro-ethyl ester

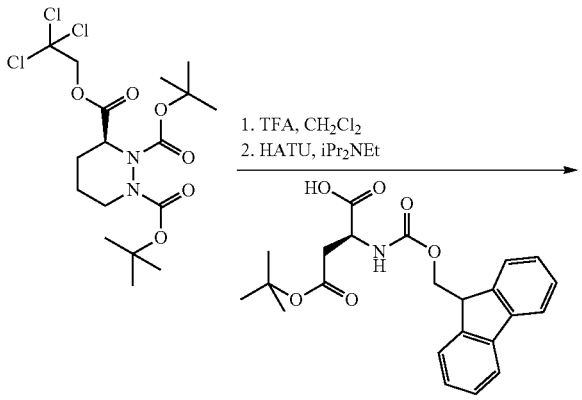

-continued

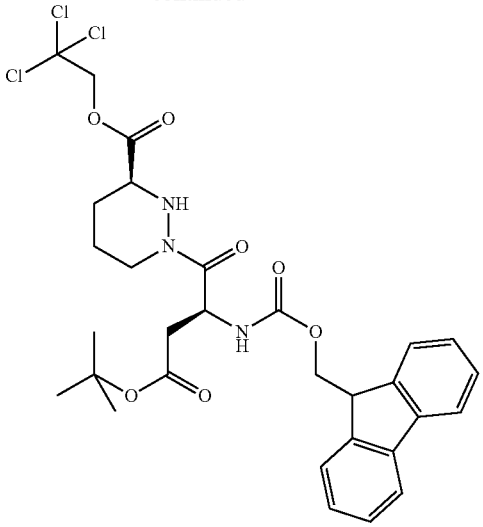

To (S)-tetrahydro-pyridazine-1,2,3-tricarboxylic acid 1,2-di-tert-butyl ester 3-(2,2,2-trichloro-ethyl)ester (2.0 g, 4.3 mmol) in anhydrous dichloromethane (13 mL) at 0° C. and under an atmosphere of nitrogen was added trifluoroacetic acid (13 mL, 173 mmol). The solution was warmed to room temperature and stirred for 16 h. The reaction was concentrated in vacuo and the residue co-evaporated from toluene (3×). The resulting brown, viscous oil was dissolved in anhydrous acetonitrile (5 mL) and added to a solution of Fmoc-L-aspartic acid 4-tert-butyl ester (1.78 g, 4.3 mmol), N,N-diisopropylethylamine (3.0 mL, 17.3 mmol) and 2-(1H-7-azabenzotriazol-1-yl)-1,1,3,3-tetramethyl uronium hexafluorophosphate methanaminium (1.60 g, 4.3 mmol) in anhydrous acetonitrile (25 mL) that had been previously stirred at 0° C. for 20 minutes. The reaction was warmed to room temperature and stirred for 16 h before being concentrated in vacuo. The residue was purified by silica gel chromatography using iso-hexanes/ethyl acetate 2:1 to give the title compound (2.5 g, 88%) as a clear, viscous oil. $^1$H NMR (300 MHz, $CDCl_3$) δ 1.46 (s, 9H), 1.69-1.83 (m, 2H), 1.87-2.00 (m, 1H), 2.15-2.27 (m, 1H), 2.79-2.67 (m, 2H), 2.90-3.02 (m, 1H), 3.81-3.93 (m, 2H), 4.21-4.29 (m, 1H), 4.32-4.44 3H), 4.71 (d, J=12.0 Hz, 1H), 4.96 (d, J=12.0 Hz, 1H), 5.31-5.43 (m, 1H), 5.85 (d, J=8.5 Hz, 1H), 7.33 (app t, J=7.4 Hz, 2H), 7.41 (app t, J=7.4 Hz, 2H), 7.59-7.66 (m, 2H), 7.78 (d, J=7.6 Hz, 2H). LCMS (m/z)=654.2 [M+H], Tr=3.63 min.

Compound 92b. (S)-1-{(S)-3-tert-Butoxycarbonyl-2-[(S)-2-(9H-fluoren-9-ylmethoxycarbonylamino)-3-methyl-butyrylamino]-propionyl}-hexahydro-pyridazine-3-carboxylic acid 2,2,2-trichloro-ethyl ester

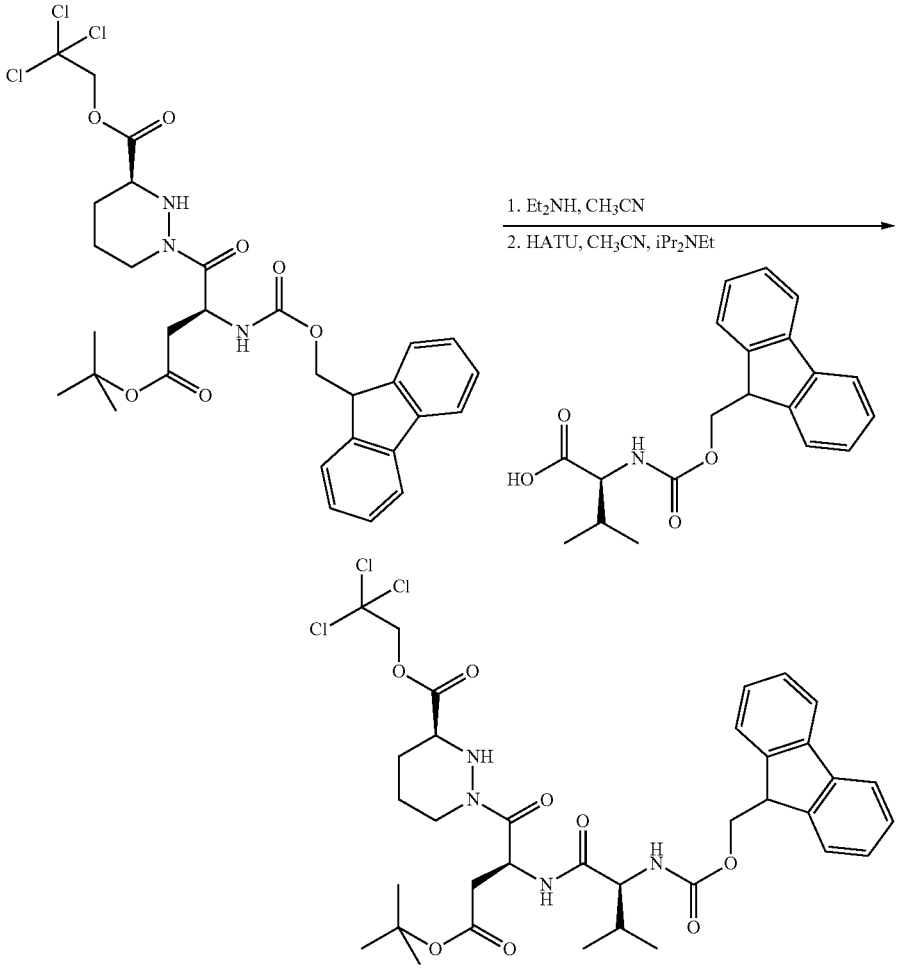

To (S)-1-[(S)-3-tert-butoxycarbonyl-2-(9H-fluoren-9-ylmethoxycarbonylamino)-propionyl]-hexahydro-pyridazine-3-carboxylic acid 2,2,2-trichloro-ethyl ester (2.5 g, 3.8 mmol) in anhydrous acetonitrile (40 mL) at room temperature and under an atmosphere of nitrogen was added diethylamine (7.7 mL, 76.6 mmol). The reaction mixture was stirred at room temperature for 45 minutes before concentrating in vacuo. The residue was dissolved in anhydrous acetonitrile (40 mL) at room temperature and under an atmosphere of nitrogen was added N,N-diisopropylethylamine (2.0 mL, 3.8 mmol), Fmoc-L-valine (1.3 g, 3.8 mmol) and 2-(1H-7-azabenzotriazol-1-yl)-1,1,3,3-tetramethyl uronium hexafluorophosphate methanaminium (2.0 g, 5.4 mmol). Following 16 h at room temperature the reaction was concentrated in vacuo. The residue was purified by silica gel chromatography using iso-hexanes/ethyl acetate 3:1 then 1:1 to give the title compound (2.0 g, 70%) as a white foam. $^1$H NMR (300 MHz, $CDCl_3$) δ 0.85-1.05 (m, 6H), 1.43 (s, 9H), 1.67-1.82 (m, 2H), 1.84-1.99 (m, 1H), 2.09-2.29 (m, 2H), 2.65-2.81 (m, 2H), 2.83-3.03 (m, 1H), 3.79-3.93 (m, 2H), 4.04-4.13 (m, 1H), 4.25 (t, J=6.9 Hz, 1H), 4.29-4.54 (m, 3H), 4.71 (d, J=12.0 Hz, 1H), 4.98 (d, J=12.0 Hz, 1H), 5.40-5.52 (m, 1H), 6.87 (d, J=8.0 Hz, 1H), 7.34 (app t, J=7.4 Hz, 2H), 7.42 (app t, J=7.4 Hz, 2H), 7.56-7.67 (m, 2H), 7.78 (app t, J=7.4 Hz, 2H). LCMS (m/z)=753.3 [M+H], Tr=3.63 min.

Compound 92c. (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-tert-butoxy-carbonyl-propionyl]-hexahydro-pyridazine-3-carboxylic acid 2,2,2-trichloro-ethyl ester To (S)-1-{(S)-3-tert-butoxycarbonyl-2-[(S)-2-(9H-fluoren-9-ylmethoxycarbonylamino)-3-methyl-butyrylamino]-propionyl}-hexahydro-pyridazine-3-carboxylic acid 2,2,2-trichloro-ethyl ester (1.5 g, 1.99 mmol) in anhydrous acetonitrile (30 mL) at room temperature and under an atmosphere of nitrogen, was added diethylamine (4.1 mL, 39.9 mmol). The reaction mixture was stirred at room temperature for 45 minutes before concentrated in vacuo. This residue was dissolved in anhydrous dichloromethane (21 mL) and at room temperature and under an atmosphere of nitrogen was added (E)-4-[2-((R)-1-acetoxy-ethyl)-quinolin-7-yl]-2,2-dimethyl-but-3-enoic acid (434 mg, 1.33 mmol), N,N-diisopropylethylamine (2.8 mL, 16.0 mmol) and 2-(1H-7-azabenzotriazol-1-yl)-1,1,3,3-tetramethyl uronium hexafluorophosphate methanaminium (759 mg, 1.99 mmol). The solution was stirred at room temperature for 2 h, quenched with a saturated aqueous solution of sodium bicarbonate and extracted with dichloromethane. The organic layer was dried through a hydrophobic frit and concentrated in vacuo. The residue was purified by silica gel chromatography using iso-hexanes/ethyl acetate 1:1, 1:2 then 0:1 to give the title compound (550 mg, 33%) as a viscous oil. $^1$H NMR (300 MHz, $CDCl_3$) δ□ 0.90 (d, J=6.9 Hz, 3H), 0.95 (d, J=6.9 Hz, 3H), 1.42 (s, 9H), 1.48 (s, 3H), 1.61 (s, 3H), 1.69 (d, J=6.7 Hz, 3H), 1.69-1.79 (m, 2H), 1.83-1.97 (m, 1H), 2.18 (s, 3H), 2.10-2.25 (m, 2H), 2.68-2.76 (m, 2H), 2.83-2.97 (m, 1H), 3.77-3.94 (m, 2H), 4.27-4.41 (m, 2H), 4.69 (d, J=11.8 Hz, 1H), 4.95 (d, J=11.8 Hz, 1H), 5.36-5.46 (m, 1H), 6.06 (q, J=6.7 Hz, 1H), 6.37 (d, J=8.5 Hz, 1H), 6.64, 6.78 (ABq, J=16.3 Hz, 2H), 6.78-6.88

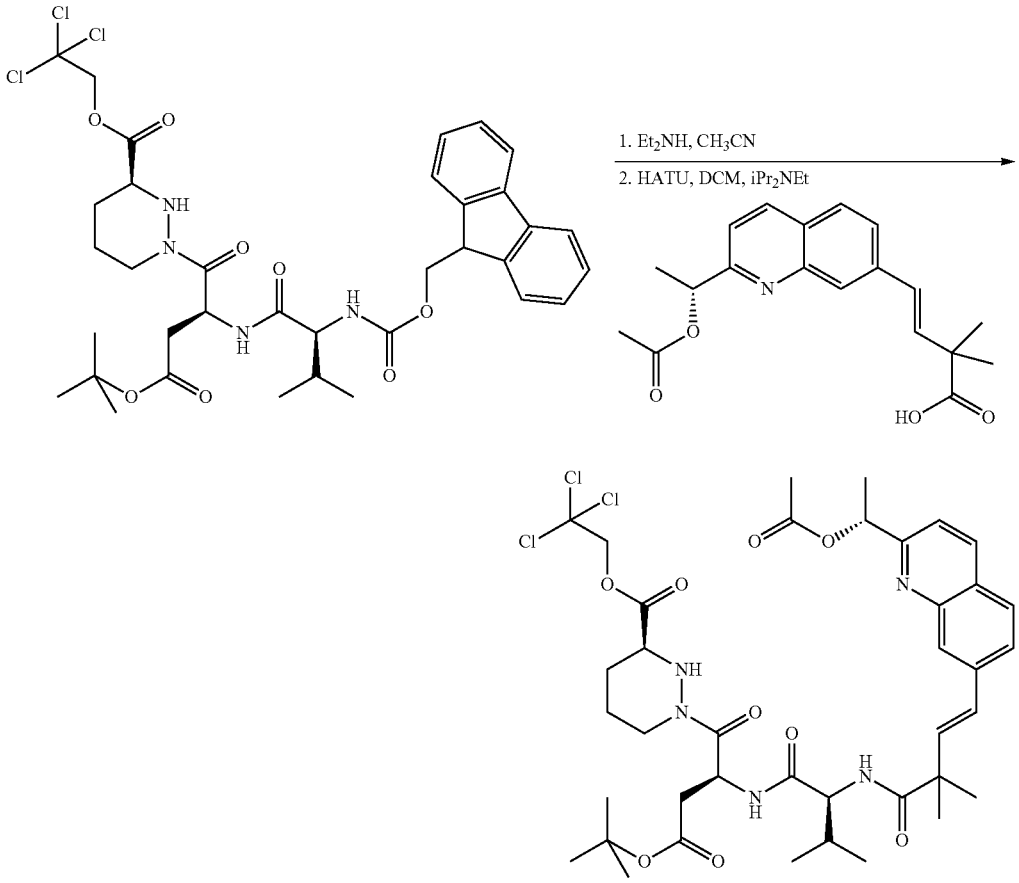

(m, 1H), 7.44 (d, J=8.5 Hz, 1H), 7.67 (dd, J=8.5, 1.6 Hz, 1H), 7.76 (d, J=8.5 Hz, 1H), 8.05 (s, 1H), 8.12 (d, J=8.5 Hz, 1H). LCMS (m/z)=840.4 [M+H], Tr=3.40 min.

Compound 92

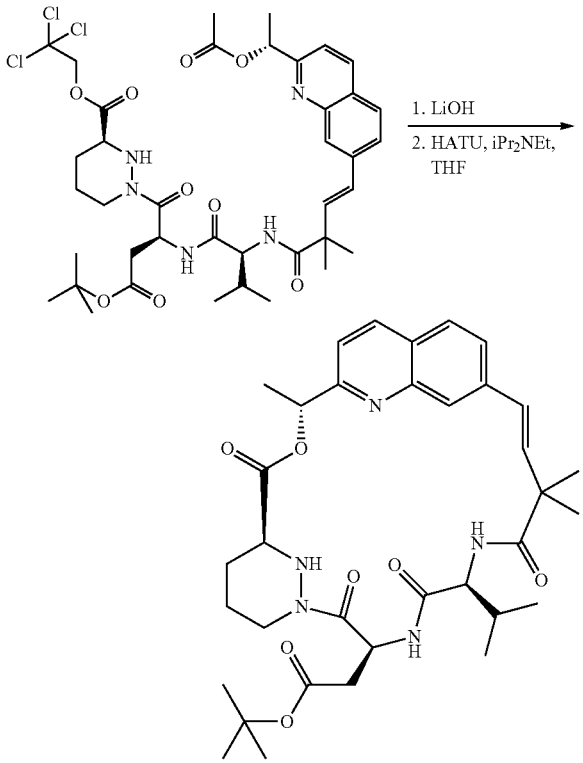

To (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-tert-butoxycarbonyl-propionyl]-hexa-hydro-pyridazine-3-carboxylic acid 2,2,2-trichloro-ethyl ester (500 mg, 0.59 mmol) in tetrahydrofuran (23 mL) and water (5 mL) was added lithium hydroxide monohydrate (125 mg, 2.97 mmol) at 0° C. The reaction was stirred at 0° C. for 3 h and quenched by acidifying to pH 6 with hydrochloric acid (2 M). The reaction was concentrated in vacuo, followed by co-evaporation from toluene (3×) and then acetonitrile (3×) and dried on a high vacuum for 16 h. The resulting residue was dissolved in anhydrous tetrahydrofuran (200 mL) and at room temperature was added N,N-diisopropylethylamine (523 μL, 2.95 mmol), 2-(1H-7-azabenzotriazol-1-yl)-1,1,3,3-tetramethyl uronium hexafluorophosphate methanaminium (337 mg, 0.89 mmol) and 4-dimethylaminopyridine (7 mg, 0.06 mmol). The reaction was stirred for 16 h. A further amount of 2-(1H-7-azabenzotriazol-1-yl)-1,1,3,3-tetramethyl uronium hexafluorophosphate methanaminium (300 mg, 0.79 mmol) was added and the reaction heated to 40° C. for 6 h. The reaction was cooled and concentrated in vacuo. The ensuing residue was diluted with ethyl acetate and washed with water. The organic layer was dried through a hydrophobic frit and concentrated in vacuo. The residue was purified by silica gel chromatography using iso-hexanes/ethyl acetate 1:1 then 0:1 to afford the title compound as an oil. This was further purified by silica gel chromatography using iso-hexanes/ethyl acetate 1:1 then 0:1 to afford the title compound as a white solid (120 mg, 31%, 2 steps). An analytical sample was further purified by reverse phase preparative HPLC. $^1$H NMR (300 MHz, $CD_3CN$) δ 0.94-0.87 (m, 6H), 1.31 (s, 3H), 1.46 (s, 3H), 1.47 (s, 9H), 1.58-1.65 (m, 1H), 1.67 (d, J=6.9 Hz, 3H), 1.80-2.01 (m, 4H), 2.63-2.75 (m, 1H), 2.78 (dd, J=15.4, 5.9 Hz, 1H), 2.91 (dd, J=15.4, 7.8 Hz, 1H), 3.74-3.87 (m, 1H), 3.96 (d, J=12.3 Hz, 1H), 4.21 (t, J=9.4 Hz, 1H), 4.30-4.40 (m, 1H), 5.82-5.93 (m, 3H), 6.36 (d, J=9.4 Hz, 1H), 7.11 (d, J=7.8 Hz, 1H), 7.37 (d, J=8.5 Hz, 1H), 7.68 (dd, J=8.5, 1.3 Hz, 1H), 7.84 (d, J=8.5 Hz, 1H), 7.97 (s, 1H), 8.21 (d, J=8.5 Hz, 1H). LCMS (m/z)=650.3 [M+H], Tr=2.88 min.

Example 93

Compound 93

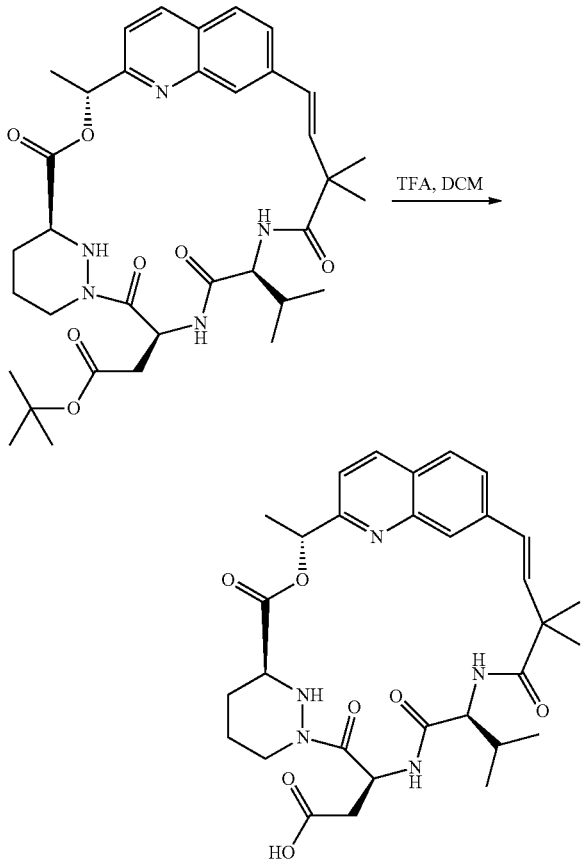

To compound 92 (70 mg, 0.11 mmol) in anhydrous dichloromethane (0.5 mL), at room temperature and under an atmosphere of nitrogen, was added trifluoroacetic acid (150 μL). The reaction was stirred for 2 h and a further amount of trifluoroacetic acid (300 μL) was added. Following a further 2 h of stirring the reaction was concentrated in vacuo. The residue was purified by silica gel chromatography using ethyl acetate/methanol 4:1 to afford the title compound (40 mg, 61%) as a white solid. $^1$H NMR (300 MHz, $CD_3OD$) δ 0.89-1.01 (m, 6H), 1.37 (s, 3H), 1.52 (s, 3H), 1.63-1.79 (m, 2H), 1.72 (d, J=6.7 Hz, 3H), 1.84-2.04 (m, 3H), 2.67-2.77 (m, 1H), 2.88-3.01 (m, 2H), 3.91-4.01 (m, 1H), 4.16-4.28 (m, 1H), 4.42 (d, J=12.9 Hz, 1H), 5.84-6.00 (m, 2H), 6.47, 6.51 (ABq, J=16.7 Hz, 2H), 7.39 (d, J=8.5 Hz, 1H), 7.74 (d, J=8.5 Hz, 1H), 7.81 (d, J=8.5 Hz, 1H), 7.85-7.93 (m, 1H), 8.20 (d, J=8.5 Hz, 1H). LCMS (m/z)=594.2 [M+H], Tr=2.06 min.

Example 94
Compound 94
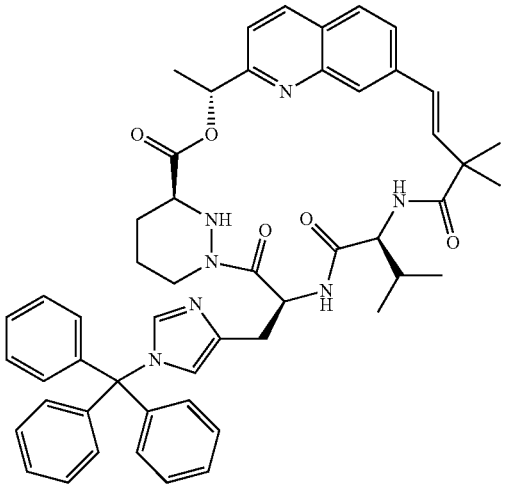
Compound 94a. (S)-1-[(S)-2-(9H-Fluoren-9-yl-methoxycarbonylamino)-3-(1-trityl-1H-imidazol-4-yl)-propionyl]-hexahydro-pyridazine-3-carboxylic acid 2,2,2-trichloro-ethyl ester
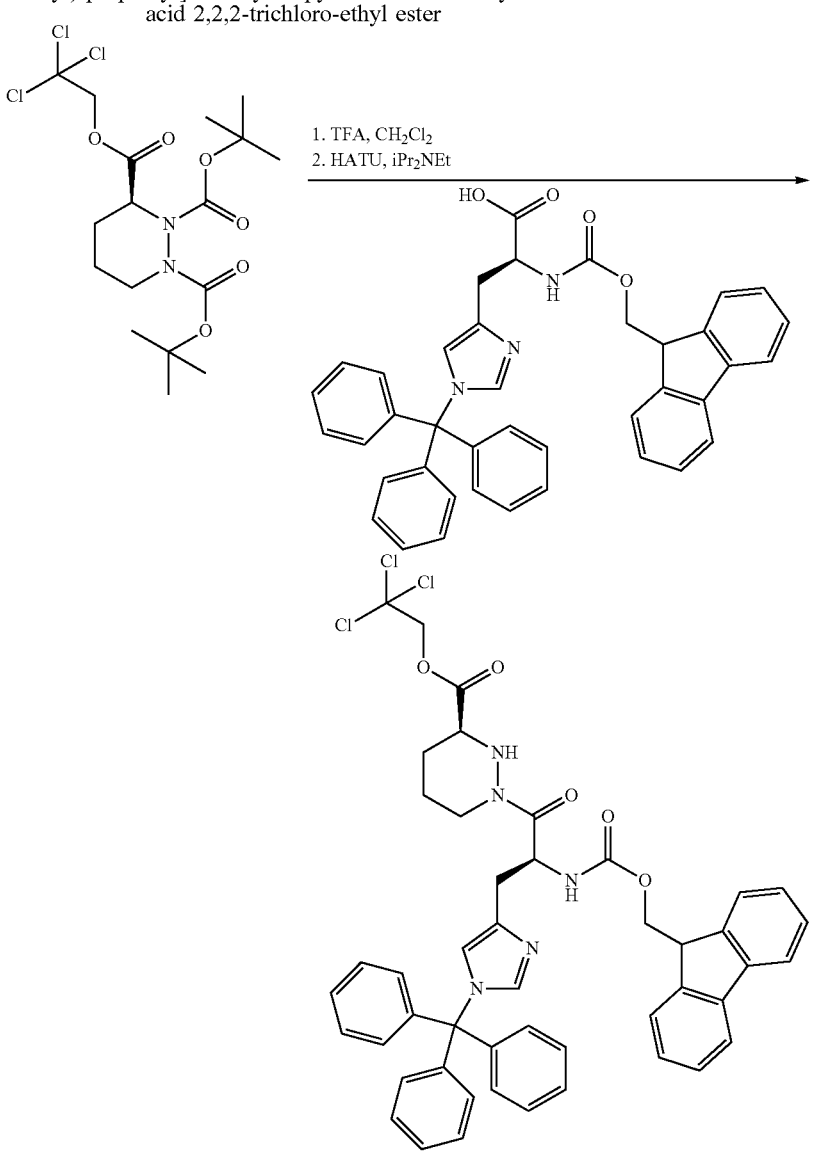

To (S)-tetrahydro-pyridazine-1,2,3-tricarboxylic acid 1,2-di-tert-butyl ester 3-(2,2,2-trichloro-ethyl)ester (2.5 g, 5.41 mmol) in anhydrous dichloromethane (16 mL) at 0° C. and under an atmosphere of nitrogen was added trifluoroacetic acid (16 mL, 217 mmol). The solution was warmed to room temperature and stirred for 16 h. The reaction was concentrated in vacuo and the residue co-evaporated from toluene (3×). The resulting brown viscous oil was dissolved in anhydrous acetonitrile (5 mL) and added to a solution of $N_{\alpha}$-Fmoc-$N_{(im)}$-trityl-L-histidine (3.4 g, 5.4 mmol), N,N-diisopropylethylamine (3.8 mL, 21.6 mmol) and 2-(1H-7-azabenzotriazol-1-yl)-1,1,3,3-tetramethyl uronium hexafluorophosphate methanaminium (2.1 g, 5.4 mmol) in anhydrous acetonitrile (25 mL) that had been previously stirred at 0° C. for 20 minutes. The reaction was warmed to room temperature and stirred for 72 h before being concentrated in vacuo. The residue was purified by silica gel chromatography using ethyl acetate to give the title compound (4.0 g, 86%) as a white foam. $^1$H NMR (300 MHz, $CDCl_3$) δ 1.52-1.91 (m, 4H), 2.03-2.18 (m, 1H), 2.93-3.19 (m, 3H), 3.77-3.91 (m, 1H), 3.99 (d, J=9.8 Hz, 1H), 4.21-4.37 (m, 3H), 4.63 (d, J=12.0 Hz, 1H), 4.94 (d, J=12.0 Hz, 1H), 5.35-5.48 (m, 1H), 6.04-6.17 (m, 1H), 6.63 (s, 1H), 7.04-7.47 (m, 20H), 7.52-7.63 (2H), 7.72-7.81 (m, 2H). LCMS (m/z)=862.3 [M+H], Tr=2.97 min.

Compound 94b. (S)-1-[(S)-2-[(S)-2-(9H-Fluoren-9-ylmethoxycarbonylamino)-3-methyl-butyrylamino]-3-(1-trityl-1H-imidazol-4-yl)-propionyl]-hexahydro-pyridazine-3-carboxylic acid 2,2,2-trichloro-ethyl ester

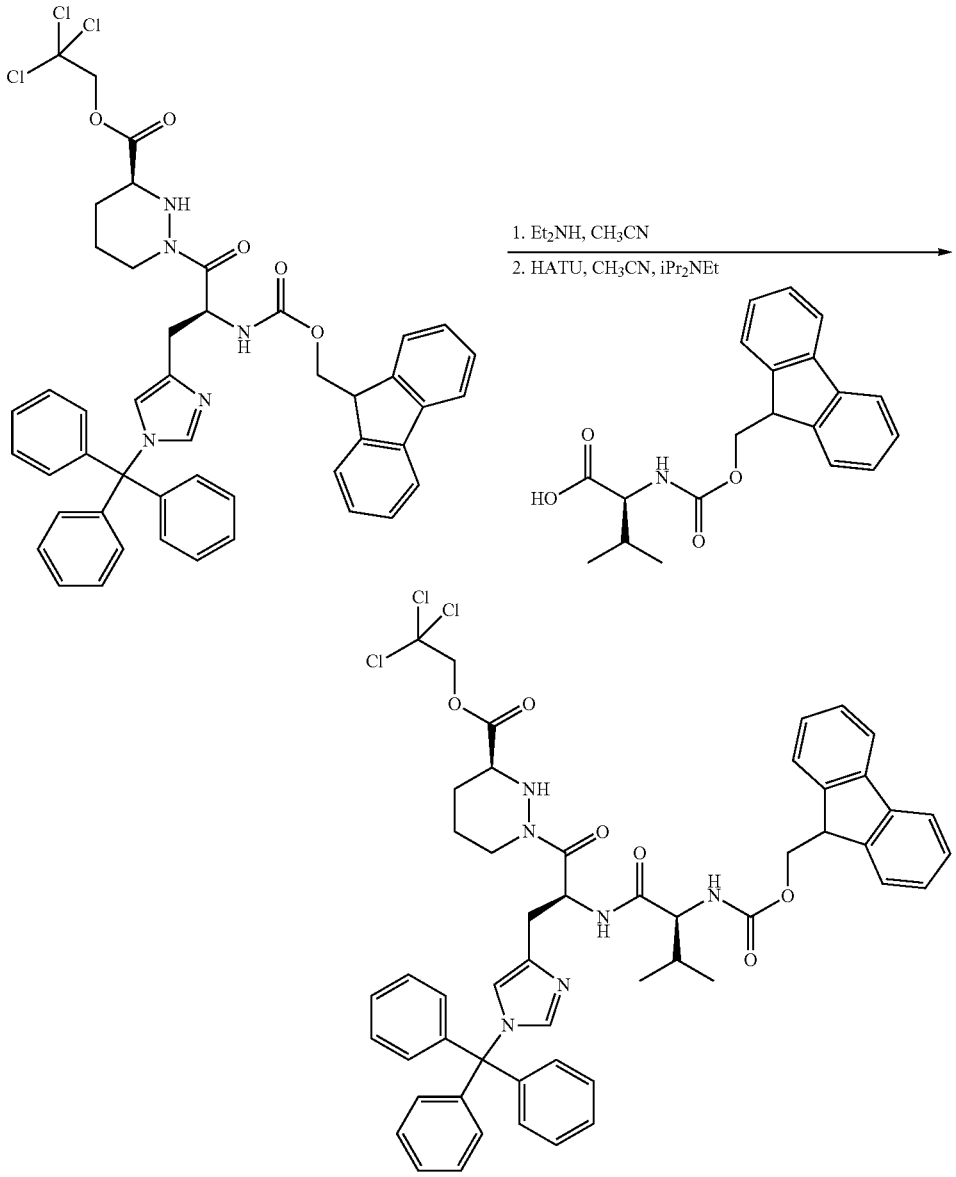

To (S)-1-[(S)-2-(9H-fluoren-9-ylmethoxycarbonylamino)-3-(1-trityl-1H-imidazol-4-yl)-propionyl]-hexahydro-pyridazine-3-carboxylic acid 2,2,2-trichloro-ethyl ester (4.0 g, 4.64 mmol) in anhydrous acetonitrile (50 mL) at room temperature and under an atmosphere of nitrogen was added diethylamine (9.4 mL, 92.8 mmol). The reaction mixture was stirred at room temperature for 45 minutes before concentrating in vacuo. The residue was dissolved in anhydrous acetonitrile (50 mL) at room temperature and under an atmosphere of nitrogen was added N,N-diisopropylethylamine (2.4 mL, 13.9 mmol), Fmoc-L-valine (1.6 g, 4.64 mmol) and 2-(1H-7-azabenzotriazol-1-yl)-1,1,3,3-tetramethyl uronium hexafluorophosphate methanaminium (2.5 g, 6.5 mmol). Following 16 h at room temperature the reaction was concentrated in vacuo. The residue was purified by silica gel chromatography using iso-hexanes/ethyl acetate 1:1 then 0:1 to give the title compound (2.5 g, 56%) as a viscous oil. $^1$H NMR (300 MHz, $CDCl_3$) δ 0.88 (d, J=6.5 Hz, 3H), 0.95 (d, J=6.5 Hz, 3H), 1.51-1.91 (m, 4H), 2.07-2.28 (m, 2H), 2.87-3.09 (m, 3H), 3.77-3.99 (m, 2H), 4.01-4.05 (m, 1H), 4.18-4.52 (m, 4H), 4.65 (d, J=12.0 Hz, 1H), 4.95 (d, J=12.0 Hz, 1H), 5.44-5.53 (m, 1H), 5.58 (d, J=8.7 Hz, 1H), 6.56 (s, 1H), 7.03-7.45 (m, 20H), 7.54-7.65 (m, 2H), 7.73-7.81 (m, 2H). LCMS (m/z)=961.5 [M+H], Tr=3.02 min.

Compound 94c. (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-(1-trityl-1H-imidazol-4-yl)-propionyl]-hexahydro-pyridazine-3-carboxylic acid 2,2,2-trichloro-ethyl ester

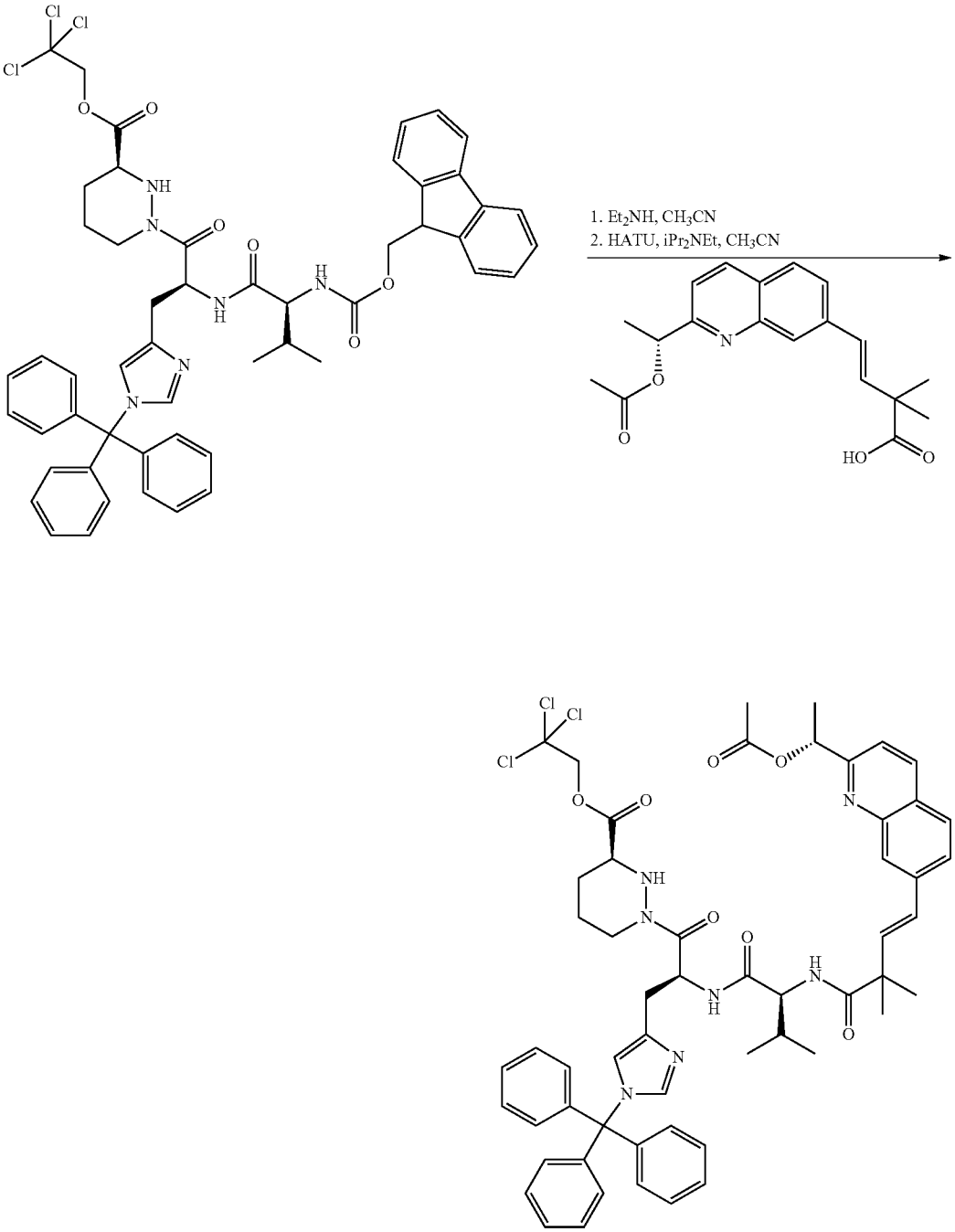

To (S)-1-[(S)-2-[(S)-2-(9H-fluoren-9-ylmethoxycarbonylamino)-3-methyl-butyrylamino]-3-(1-trityl-1H-imidazol-4-yl)-propionyl]-hexahydro-pyridazine-3-carboxylic acid 2,2,2-trichloro-ethyl ester (2.5 g, 2.60 mmol) in anhydrous acetonitrile (40 mL) at room temperature and under an atmosphere of nitrogen, was added diethylamine (5.4 mL, 52.0 mmol). The reaction mixture was stirred at room temperature for 1 h before concentrated in vacuo. This residue was dissolved in anhydrous acetonitrile (28 mL) and at room temperature and under an atmosphere of nitrogen was added (E)-4-[2-((R)-1-acetoxy-ethyl)-quinolin-7-yl]-2,2-dimethyl-but-3-enoic acid (567 mg, 1.73 mmol), N,N-diisopropylethylamine (3.7 mL, 20.8 mmol) and 2-(1H-7-azabenzotriazol-1-yl)-1,1,3,3-tetramethyl uronium hexafluorophosphate methanaminium (989 mg, 2.60 mmol). The solution was stirred at room temperature for 16 h and concentrated in vacuo. The residue was purified by silica gel chromatography using iso-hexanes/ethyl acetate 1:1 then 0:1 to give the title compound (1.5 g, 55%, 2 steps) as a brown oil. LCMS (m/z)=1050.4 [M+H], Tr=2.86 min.

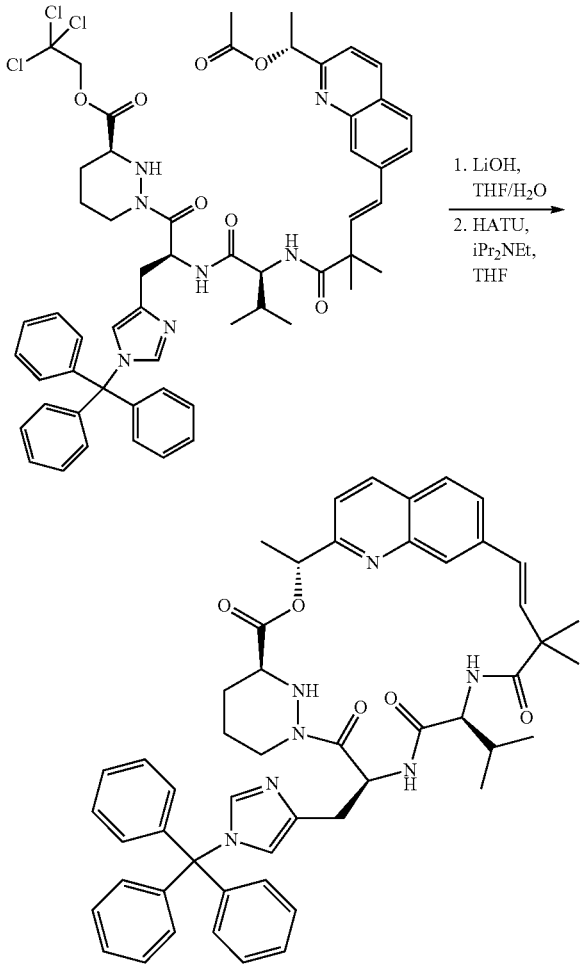

To (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-(1-trityl-1H-imidazol-4-yl)-propionyl]-hexahydro-pyridazine-3-carboxylic acid 2,2,2-trichloro-ethyl ester (1.5 g, 1.43 mmol) in tetrahydrofuran (55 mL) and water (12 mL) was added lithium hydroxide monohydrate (300 mg, 7.15 mmol) at 0° C. The reaction was stirred at 0° C. for 3 h and quenched by acidifying to pH 6 with hydrochloric acid (2 M). The reaction was concentrated in vacuo, followed by co-evaporation from toluene (3×) then acetonitrile (3×) and dried on a high vacuum for 16 h. The resulting residue was dissolved in anhydrous tetrahydrofuran (477 mL) and at room temperature was added N,N-diisopropylethylamine (1.3 mL, 7.15 mmol), 2-(1H-7-azabenzotriazol-1-yl)-1,1,3,3-tetramethyl uronium hexafluorophosphate methanaminium (816 mg, 2.15 mmol) and 4-dimethylaminopyridine (17 mg, 0.14 mmol). The reaction was stirred for 16 h, diluted with ethyl acetate and washed with water. The organic layer was dried through a hydrophobic frit and concentrated in vacuo. To yield the crude title compound as a yellow oil (600 mg, 49%, 2 steps). An analytical sample was obtained by reverse phase preparative HPLC. $^1$H NMR (300 MHz, $CD_3CN$) δ 0.82-0.97 (m, 6H), 1.30 (s, 3H), 1.45 (s, 3H), 1.48-1.57 (m, 1H), 1.59 (d, J=6.7 Hz, 3H), 1.63-2.04 (m, 5H), 2.67 (td, J=12.7, 2.7 Hz, 1H), 3.02-3.21 (m, 2H), 3.68-3.81 (m, 1H), 3.92 (d, J=11.8 Hz, 1H), 4.11-4.20 (m, 1H), 4.26-4.39 (m, 1H), 5.74-5.85 (m, 1H), 5.90 (q, J=6.7 Hz, 1H), 6.19 (d, J=16.3 Hz, 1H), 6.30-6.40 (m, 1H), 6.44 (d, J=16.3 Hz, 1H), 6.90 (s, 1H), 6.97-7.12 (m, 6H), 7.15-7.32 (m, 8H), 7.34-7.43 (m, 2H), 7.60 (s, 1H), 7.71 (d, J=8.7 Hz, 1H), 7.82 (d, J=8.5 Hz, 1H), 7.85-8.01 (m, 1H), 8.21 (d, J=8.5 Hz, 1H). LCMS (m/z)=858.5 [M+H], Tr=2.44 min.

Example 95

Compound 95

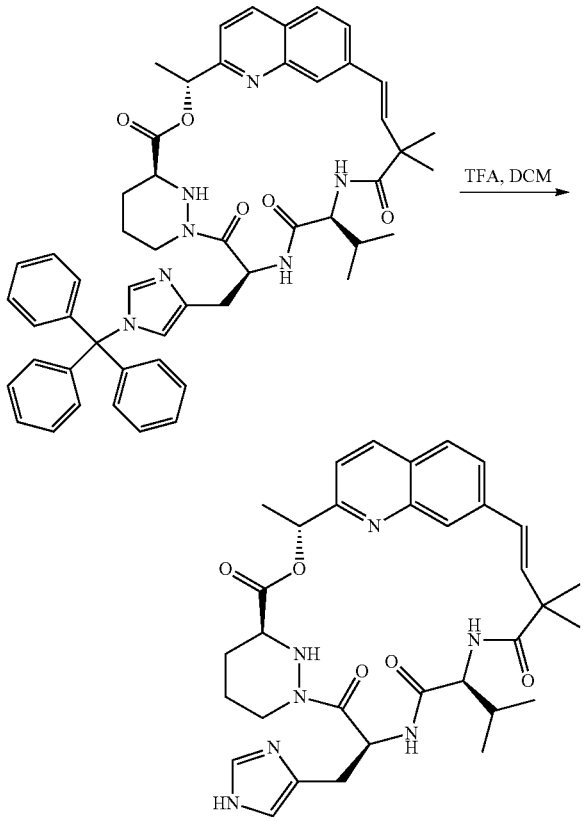

To compound 94 (400 mg, 0.47 mmol) in anhydrous dichloromethane (5 mL), at room temperature and under an atmosphere of nitrogen, was added trifluoroacetic acid (500 μL). The reaction was stirred for 1 h and concentrated in vacuo. The residue was purified by reverse phase preparative HPLC to afford the title compound (12 mg, 4%) as a white solid. $^1$H NMR (300 MHz, $CD_3OD$) δ 0.93 (d, J=6.7 Hz, 3H), 0.97 (d, J=6.7 Hz, 3H), 1.33 (s, 3H), 1.50 (s, 1.53-1.73 (m, 2H), 1.79 (d, J=6.7 Hz, 3H), 1.82-2.01 (m, 3H), 2.62-2.75 (m, 1H), 3.07-3.30 (m, 3H), 4.27 (t, J=9.4 Hz, 1H), 4.32-4.44 (m, 1H), 5.99 (q, J=6.7 Hz, 1H), 6.11-6.20 (m, 1H), 6.26, 6.31 (ABq, J=16.5 Hz, 2H), 7.12 (d, J=9.4 Hz, 1H), 7.31 (s, 1H), 7.49 (d, J=8.5 Hz, 1H), 7.59 (s, 1H), 7.67 (d, J=8.5 Hz, 1H), 7.86 (d, J=8.5 Hz, 1H), 8.15 (s, 1H), 8.29 (d, J=8.5 Hz, 1H). LCMS (m/z)=616.3 [M+H], Tr=1.55 min.

Example 96

Compound 96

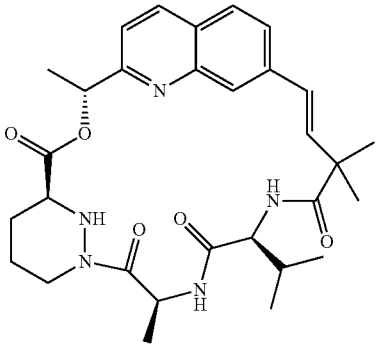

Compound 96a. N-(5-Bromo-2-formyl-phenyl)-2-(tert-butyl-dimethyl-silanyloxy)-propionamide

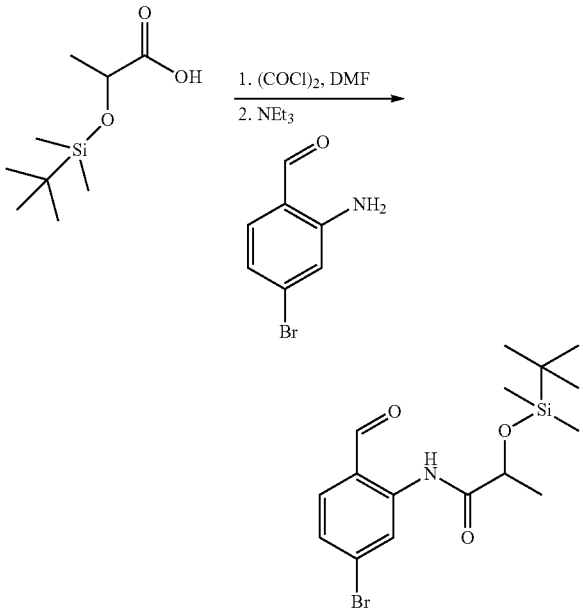

A solution of 2-(tert-butyl-dimethyl-silanyloxy)-propionic acid (3.11 g, 15.2 mmol) in anhydrous dichloromethane (40 mL) was prepared and oxalyl chloride (2.0 mL, 22.8 mmol) was added followed by N,N-dimethylformamide (5 μL). The reaction mixture was stirred for 2 h at room temperature and then evaporated to give a colourless oil. The oil was dissolved in anhydrous dichloromethane (40 mL) and oxalyl chloride (1.0 mL, 11.4 mmol) and N,N-dimethylformamide (5 μL) were added. After stirring at room temperature for 30 minutes, more oxalyl chloride (0.25 mL, 2.8 mmol) was added. After stirring for 30 minutes the reaction mixture was evaporated to dryness. The residue was dissolved in anhydrous dichloromethane (40 mL) and added to a stirred solution of 2-amino-4-bromobenzaldehyde (2.54 g, 12.7 mmol) and triethylamine (2.12 mL, 15.2 mmol) in dichloromethane (60 mL), cooled over an ice-bath. The reaction mixture was allowed to warm to room temperature and was stirred for 15 h. The resulting solution was washed with saturated aqueous sodium bicarbonate solution (100 mL). The aqueous layer was extracted with dichloromethane (80 mL). The organic layers were combined and washed with brine (120 mL) then dried over anhydrous sodium sulfate, filtered and evaporated to give a yellow oil. The oil was purified by silica gel chromatography using iso-hexanes/ethyl acetate 9:1 to yield the title compound (3.64 g, 83%) as an off-white solid. $^1$H NMR (300 MHz, $CDCl_3$) δ 0.20 (s, 6H), 0.99 (s, 9H), 1.49 (d, J=6.7 Hz, 3H), 4.39 (q, J=6.7 1H), 7.40 (d, J=8.3 Hz, 1H), 7.54 (d, J=8.3 Hz, 1H), 9.10 (s, 1H), 9.91 (s, 1H), 11.82-11.98 (br s, 1H). LCMS (m/z) 386.0, 388.0 [M+H], Tr=4.01 min.

Compound 96b. 7-Bromo-2-[1-(tert-butyl-dimethyl-silanyloxy)-ethyl]-quinazoline

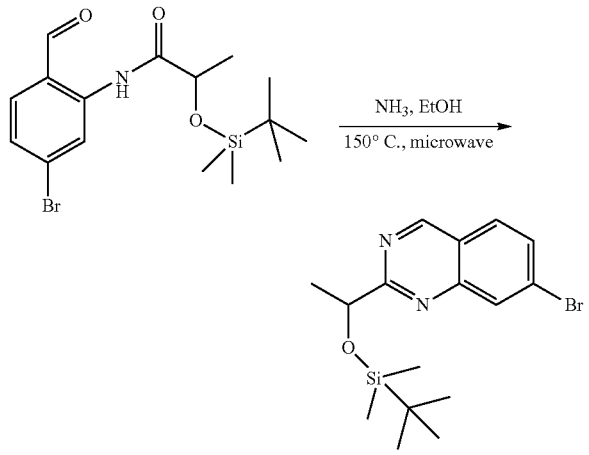

A solution of ammonia in ethanol (2 M, 14 mL, 28 mmol) was added to N-(5-bromo-2-formyl-phenyl)-2-(tert-butyl-dimethyl-silanyloxy)-propionamide (0.5 g, 1.36 mmol). The mixture was heated in a microwave reactor at 150° C. for 2 h. A second solution of ammonia in ethanol (2 M, 14 mL, 28 mmol) was added to N-(5-bromo-2-formyl-phenyl)-2-(tert-butyl-dimethyl-silanyloxy)-propionamide (1.0 g, 2.72 mmol). The mixture was heated in a microwave reactor at 150° C. for 2 h. The two resultant solutions were combined and evaporated and the residue purified by silica gel chromatography using iso-hexanes/dichloromethane 1:1 to 1:3 to 0:1 to yield the title compound (1.34 g, 94%) as a yellow gum. $^1$H NMR (300 MHz, $CDCl_3$) δ 0.08 (s, 6H), 0.91 (s, 9H), 1.64 (d, J=6.7 Hz, 3H), 5.22 (q, J=6.5 Hz, 1H), 7.71-7.83 (m, 2H), 8.26 (s, 1H), 9.40 (s, 1H). LCMS (m/z) 367.0, 369.0 [M+H], Tr=4.00 min.

Compound 96c. (E)-4-{2-[1-(tert-Butyl-dimethyl-silanyloxy)-ethyl]-quinazolin-7-yl}-2,2-dimethyl-but-3-enoic acid methyl ester

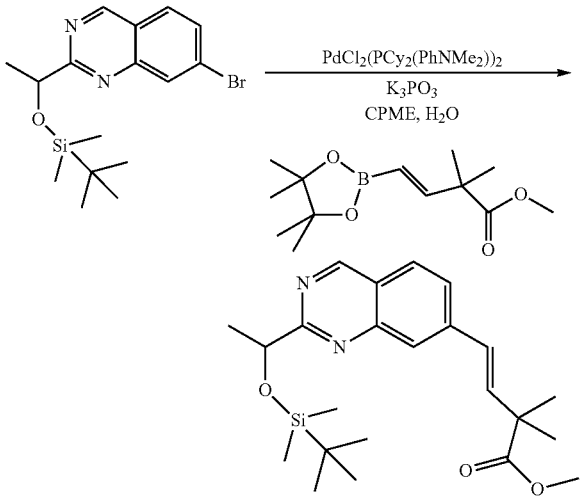

A solution of 7-bromo-2-[1-(tert-butyl-dimethyl-silanyloxy)-ethyl]-quinazoline (1.0 g, 2.72 mmol) and (E)-2,2-dimethyl-4-(4,4,5,5-tetramethyl-[1,3,2]dioxaborolan-2-yl)-but-3-enoic acid methyl ester (65% pure, 1.08 g, 2.75 mmol) in cyclopentyl methyl ether (20 mL) and water (10 mL) was prepared and potassium phosphate tribasic (1.73 g, 8.16 mmol) and bis[(dicyclohexyl)(4-dimethylaminophenyl) phosphine]palladium(II) chloride (110 mg, 0.14 mmol) were added. The stirred mixture was heated to 80° C. for 4.5 h then cooled to room temperature and diluted with water (30 mL). The mixture was extracted with ethyl acetate (3×30 mL). The organics were dried over anhydrous sodium sulfate, filtered and evaporated to give a red gum. The gum was purified by silica gel chromatography using iso-hexanes/ethyl acetate 9:1 to yield the title compound (1.07 g, 95%) as a yellow gum. $^1$H NMR (300 MHz, $CDCl_3$) δ 0.07 (s, 6H), 0.90 (s, 9H), 1.48 (s, 6H), 1.64 (d, J=6.5 Hz, 3H), 3.75 (s, 3H), 5.21 (q, J=6.5 Hz, 1H), 6.64-6.80 (m, 2H), 7.72 (d, J=8.5 Hz, 1H), 7.86 (d, J=8.5 Hz, 1H), 7.96 (s, 1H), 9.35 (s, 1H). LCMS (m/z) 415.2 [M+H], Tr=3.97 min.

Compound 96d. (E)-4-{2-[1-(tert-Butyl-dimethyl-silanyloxy)-ethyl]-quinazolin-7-yl}-2,2-dimethyl-but-3-enoic acid

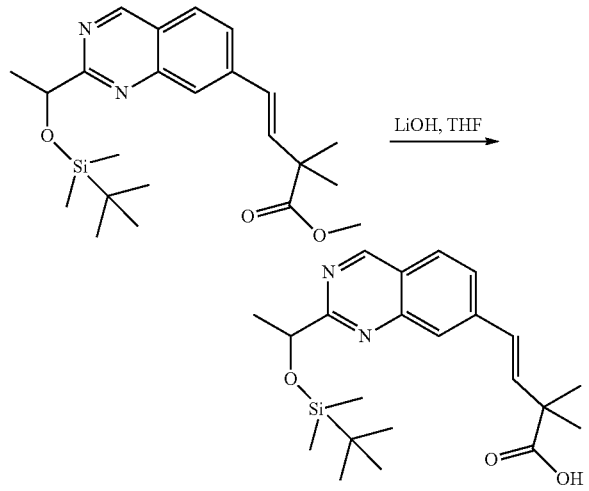

A solution of (E)-4-{2-[1-(tert-butyl-dimethyl-silanyloxy)-ethyl]-quinazolin-7-yl}-2,2-dimethyl-but-3-enoic acid methyl ester (1.07 g, 2.58 mmol) in tetrahydrofuran (50 mL) was cooled to 0° C. before adding an aqueous solution of lithium hydroxide (1 M, 8 mL, 8 mmol). The reaction mixture was allowed to warm to room temperature and was stirred for 20 h. The reaction mixture was diluted with water (50 mL) then washed with diethyl ether (60 mL) before acidifying to pH 2 with a saturated solution of potassium bisulfate. The resulting mixture was extracted with diethyl ether (3×30 mL). The extract was dried over anhydrous sodium sulfate, filtered and evaporated to yield the title product (0.605 g, 59%) as a yellow gum. $^1$H NMR (300 MHz, $CDCl_3$) δ 0.06 (s, 3H), 0.08 (s, 3H), 0.90 (s, 9H), 1.53 (s, 6H), 1.64 (d, J=6.5 Hz, 3H), 5.22 (q, J=6.5 Hz, 1H), 6.64-6.81 (m, 2H), 7.73, 7.87 (ABq, J=8.5 Hz, 2H), 7.99 (s, 1H), 9.40 (s, 1H). LCMS (m/z) 401.2 [M+H], Tr=3.43 min.

Compound 96e. (S)-1-{(S)-2-[(S)-2-((E)-4-{2-[1-(tert-Butyl-dimethyl-silanyloxy)-ethyl]-quinazolin-7-yl}-2,2-dimethyl-but-3-enoylamino)-3-methyl-butyrylamino]-propionyl}-hexahydro-pyridazine-3-carboxylic acid 2,2,2-trichloro-ethyl ester

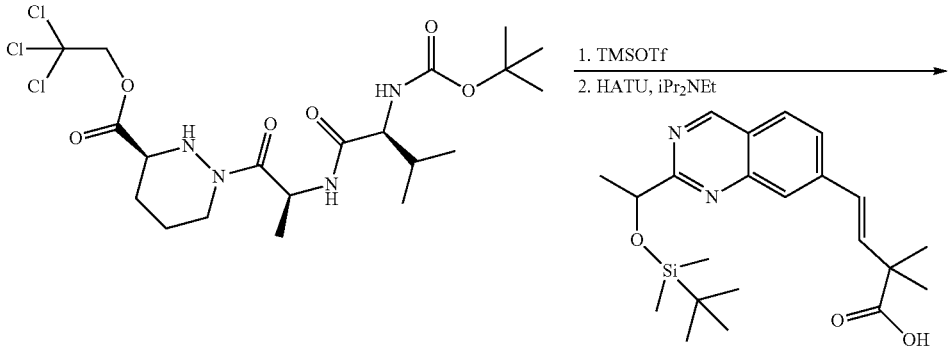

-continued

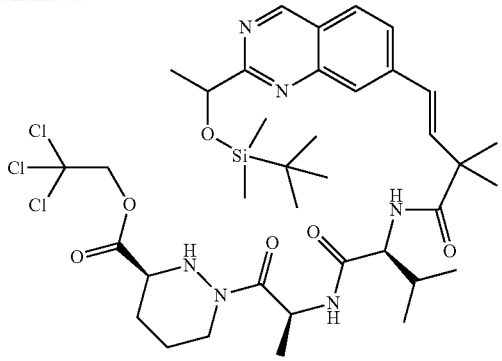

A solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (645 mg, 1.49 mmol) in anhydrous dichloromethane (20 mL) was cooled to 0° C. under a nitrogen atmosphere before adding trimethylsilyl trifluoromethanesulfonate (345 μL, 3.0 mmol). The reaction mixture was stirred at 0° C. for 1 h, then N,N-diisopropylethylamine (1.03 mL, 5.97 mmol) was added, before evaporating to dryness to give the crude amine. A solution of (E)-4-{2-[1-(tert-butyl-dimethyl-silanyloxy)-ethyl]-quinazolin-7-yl}-2,2-dimethyl-but-3-enoic acid (505 mg, 1.26 mmol) in acetonitrile (40 mL) was prepared and N,N-diisopropylethylamine (1.03 mL, 5.97 mmol) and 2-(1H-7-azabenzotriazol-1-yl)-1,1,3,3-tetramethyl uronium hexafluoro phosphate methanaminium (718 mg, 1.89 mmol) were added. The reaction mixture was stirred at room temperature for 5 minutes before the addition of a solution of the crude amine in acetonitrile (20 mL). The reaction mixture was stirred for 2 h. The solution was evaporated and the residue purified by silica gel chromatography using a gradient from iso-hexanes/acetone 4:1 to 3:2 to yield unpure title compound (1.406 g) as a yellow solid and as a 1:1 mixture of diastereosiomers. LCMS (m/z) 813.4, 815.3, 817.4 [M+H], Tr=3.98 min.

Compound 96f. (S)-1-[(S)-2-((S)-2-{(E)-4-[2-(1-Hydroxy-ethyl)-quinazolin-7-yl]-2,2-dimethyl-but-3-enoylamino}-3-methyl-butyrylamino)-propionyl]-hexahydro-pyridazine-3-carboxylic acid -continued

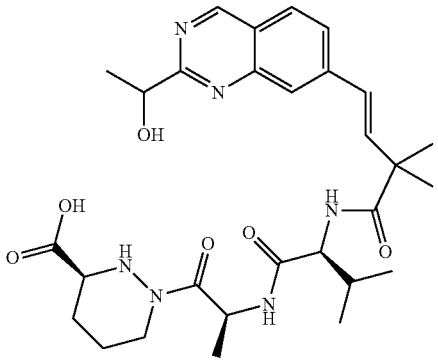

A solution of crude (S)-1-{(S)-2-[(S)-2-((E)-4-{2-[1-(tert-butyl-dimethyl-silanyloxy)-ethyl]-quinazolin-7-yl}-2,2-dimethyl-but-3-enoylamino)-3-methyl-butyrylamino]-propionyl}-hexahydro-pyridazine-3-carboxylic acid 2,2,2-trichloroethyl ester (675 mg, 0.6 mmol) in tetrahydrofuran (20 mL) was prepared and a solution of n-tetrabutylammonium fluoride in tetrahydrofuran (1 M, 5 mL, 5 mmol) was added. The reaction was stirred at room temperature for 3 h and then more solution of tetrabutylammonium fluoride in tetrahydrofuran (1 M, 2 mL, 2 mmol) was added. The reaction was stirred at room temperature for 2 h then evaporated to give a yellow oil. This was purified by silica chromatography using a gradient of dichloromethane/methanol 1:0 to 19:1 to 4:1 to yield the title compound (76 mg, 22%) as a yellow gum and as a 1:1 mixture of diastereoisomers. LCMS (m/z) 569.2 [M+H], Tr=1.80 min.

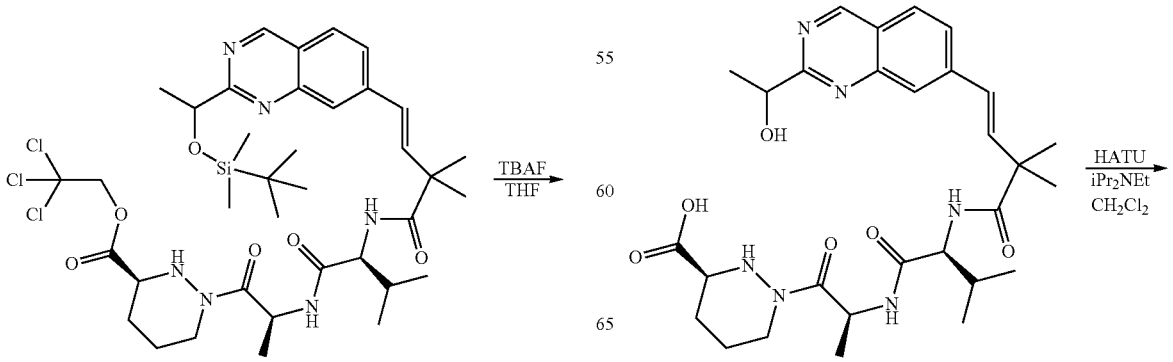

-continued

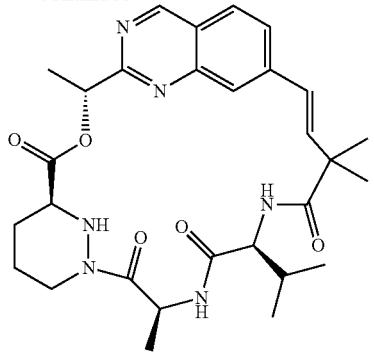

A solution of (S)-1-[(S)-2-((S)-2-{(E)-4-[2-(1-hydroxyethyl)-quinazolin-7-yl]-2,2-dimethyl-but-3-enoylamino}-3-methyl-butyrylamino)-propionyl]-hexahydro-pyridazine-3-carboxylic acid (37 mg, 0.065 mmol) in anhydrous dichloromethane (20 mL) was cooled to 0° C. before adding N,N-diisopropylethylamine (35 μL, 0.195 mmol) and 2-(1H-7-azabenzotriazol-1-yl)-1,1,3,3-tetramethyl uronium hexafluorophosphate methanaminium (55 mg, 0.145 mmol). The reaction was allowed to warm to room temperature and was stirred for 16 h. The reaction mixture was evaporated to dryness and purified by reverse phase preparative HPLC using a C18 column and a gradient of water/acetonitrile 4:1 to 0:1 over 27 minutes to yield the title product (3.8 mg, 11%) as a white solid. $^1$H NMR (300 MHz, $CD_3OD$) δ 0.96 (d, J=6.5 Hz, 3H), 0.98 (d, J=6.5 Hz, 3H), 1.37 (s, 3H)), 1.52 (s, 3H), 1.62 (d, J=7.1 Hz, 3H), 1.65-1.76 (m, 2H), 1.79 (d, J=6.9 Hz, 3H), 1.84-2.07 (m, 2H), 2.67-2.88 (m, 1H), 3.77-3.89 (m, 1H), 4.32 (d, J=10.5 Hz, 1H), 4.40 (d, J=11.8 Hz, 1H), 4.49 (d, J=12.3 Hz, 1H), 5.80 (q, J=7.1 Hz, 1H), 5.89 (q, J=6.9 Hz, 1H), 6.30 (d, J=16.5 Hz, 1H), 6.60 (d, J=16.5 Hz, 1H), 7.56 (s, 1H), 7.91 (d, J=8.5 Hz, 1H), 8.00 (d, J=8.5 Hz, 1H), 9.39 (s, 1H). LCMS (m/z) 551.2 [M+H], Tr=2.16 min.

Example 97

Compound 97

-continued

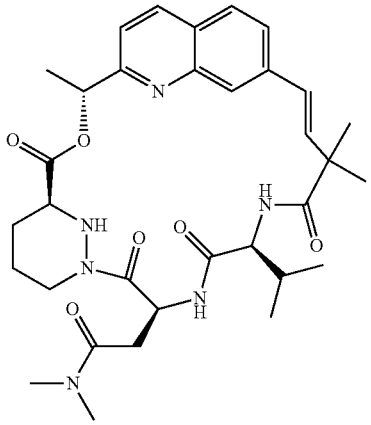

To compound 93 (5 mg, 0.008 mmol) in anhydrous tetrahydrofuran (100 μL), at 0° C. and under an atmosphere of nitrogen, was added N,N-diisopropylethylamine (7.5 μL, 0.04 mmol), 2-(1H-7-azabenzotriazol-1-yl)-1,1,3,3-tetramethyl uronium hexafluorophosphate methanaminium (4.8 mg, 0.013 mmol) and stirred for 2 minutes. Dimethylamine hydrochloride salt (1 mg, 0.013 mmol) was added and the reaction was stirred at room temperature for 2 h. The reaction mixture was placed directly on silica gel and purified using ethyl acetate/methanol 4:1 to afford the title compound (2.5 mg, 50%) as a white solid. $^1$H NMR (300 MHz, $CD_3OD$) δ 0.93 (d, J=6.7 Hz, 3H), 0.95 (d, J=6.7 Hz, 3H), 1.36 (s, 3H), 1.50 (s, 3H), 1.73 (d, J=6.7 Hz, 3H), 1.82-2.01 (m, 3H), 2.67-2.82 (m, 3H), 2.83 (s, 3H), 2.96 (d, J=8.0 Hz, 1H), 3.00 (s, 3H), 3.08 (d, J=7.1 Hz, 1H), 3.80-3.87 (m, 1H), 4.27 (d, J=9.6 Hz, 1H), 4.39-4.48 (m, 1H), 5.88 (q, J=6.7 HZ, 1H), 6.13 (t, J=7.6 Hz, 1H), 6.49, 6.52 (ABq, J=16.5 Hz, 2H), 7.39 (d, J=8.5 Hz, 1H), 7.71 (dd, J=8.5, 1.3 Hz, 1H), 7.81 (d, J=8.5 Hz, 1H), 7.94 (s, 1H), 8.20 (d, J=8.5 Hz, 1H). LCMS (m/z)=621.3 [M+H], Tr=1.92 min.

Example 98

Compound 98

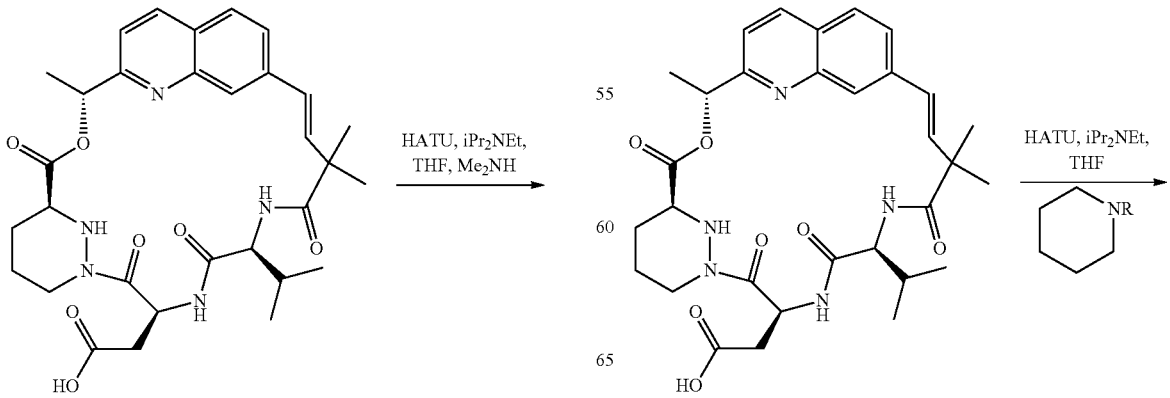

-continued

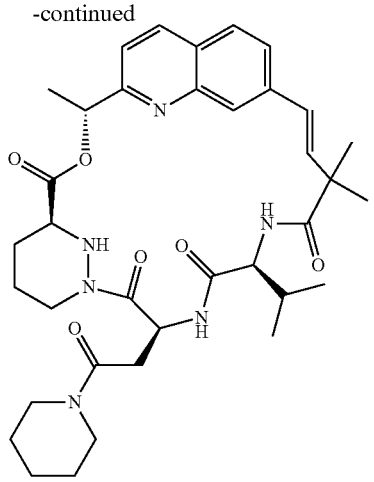

To compound 93 (9 mg, 0.015 mmol) in anhydrous tetrahydrofuran (200 μL) at 0° C. and under an atmosphere of nitrogen, was added N,N-diisopropylethylamine (14 μL, 0.08 mmol), 2-(1H-7-azabenzotriazol-1-yl)-1,1,3,3-tetramethyl uronium hexafluorophosphate methanaminium (9.0 mg, 0.02 mmol) and stirred for 2 minutes. Piperidine (2 μL, 0.02 mmol) was added and the reaction was stirred at room temperature for 1.5 h. The reaction mixture was placed directly on silica gel and purified using ethyl acetate/methanol 10:1 to afford the title compound (2.5 mg, 25%) as a white solid. $^1$H NMR (300 MHz, $CD_3OD$) δ 0.93 (d, J=6.5 Hz, 3H), 0.95 (d, J=6.5 Hz, 3H), 1.37 (s, 3H), 1.51 (s, 3H), 1.52-1.65 (m, 7H), 1.66-1.74 (m, 2H), 1.75 (d, J=6.7 Hz, 3H), 1.83-2.01 (m, 3H), 2.71-2.79 (m, 1H), 2.84-2.96 (m, 1H), 3.10-3.21 (m, 1H), 3.46-3.59 1H), 3.67-3.88 (m, 3H), 4.20-4.31 (m, 1H), 4.38-4.50 (m, 1H), 5.90 (q, J=6.7 Hz, 1H), 6.07 (t, J=6.5 Hz, 1H), 6.49, 6.52 (ABq, J=16.3 Hz, 2H), 7.40 (d, J=8.5 Hz, 1H), 7.72 (dd, J=8.5, 1.3 Hz, 1H), 7.82 (d, J=8.5 Hz, 1H), 7.95 (s, 1H), 8.21 (d, J=8.5 Hz, 1H). LCMS (m/z)=661.2 [M+H], Tr=2.14 min.

Example 99

Compound 99

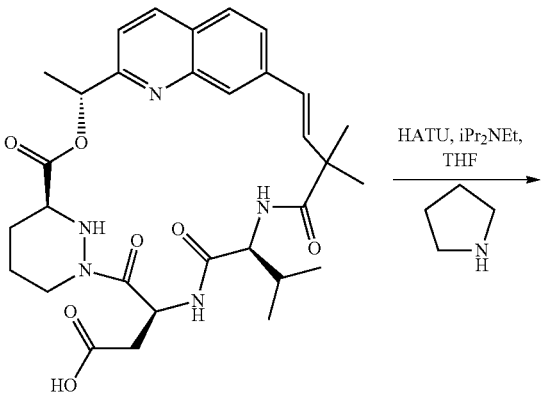

-continued

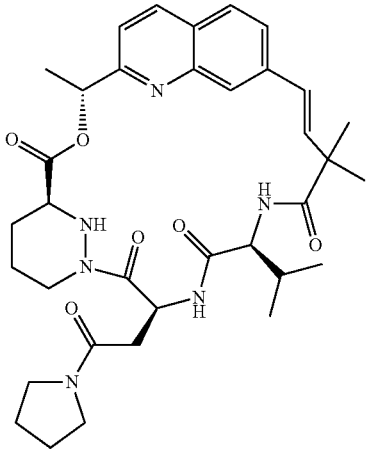

To compound 93 (5 mg, 0.008 mmol) in anhydrous tetrahydrofuran (100 μL), at room temperature and under an atmosphere of nitrogen, was added N,N-diisopropylethylamine (7.5 μL, 0.04 mmol), 2-(1H-7-azabenzotriazol-1-yl)-1,1,3,3-tetramethyl uronium hexafluorophosphate methanaminium (4.8 mg, 0.013 mmol) and pyrrolidine (1 μL, 0.013 mmol). The reaction was stirred at room temperature for 2 h. The reaction mixture was placed directly on silica gel and purified using ethyl acetate/methanol 10:1 to afford the title compound (3.8 mg, 74%) as a white solid. $^1$H NMR (300 MHz, $CD_3OD$) δ 0.93 (d, J=6.9 Hz, 3H), 0.96 (d, J=6.9 Hz, 3H), 1.36 (s, 3H), 1.50 (s, 3H), 1.72 (d, J=6.9 Hz, 3H), 1.72-2.02 (m, 9H), 2.70-2.80 (m, 1H), 2.89-2.98 (m, 2H), 3.45-3.54 (m, 1H), 3.66-3.78 (m, 1H), 3.83-3.96 (m, 2H), 4.28 (t, J=9.6 Hz, 1H), 4.41-4.50 (m, 1H), 5.92 (q, J=6.9 Hz, 1H), 6.15 (t, J=7.4 Hz, 1H), 6.47 (s, 2H), 7.22-7.33 (m, 1H), 7.39 (d, J=8.5 Hz, 1H), 7.73 (dd, J=8.5, 1.3 Hz, 1H), 7.82 (d, J=8.5 Hz, 1H), 7.84-7.88 (m, 1H), 8.20 (d, J=8.5 Hz, 1H). LCMS (m/z)=647.4 [M+H], Tr=2.09 min.

Examples 100 and 101

Compounds 100 and 101

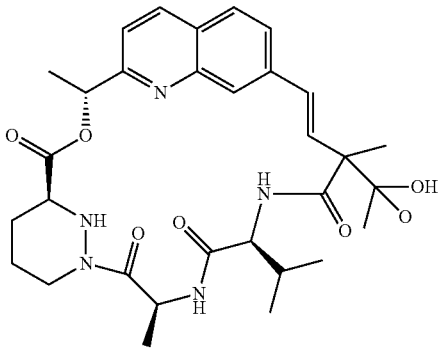

Compound 100a. 2-(1-Hydroxy-1-methyl-ethyl)-2-methyl-but-3-enoic acid

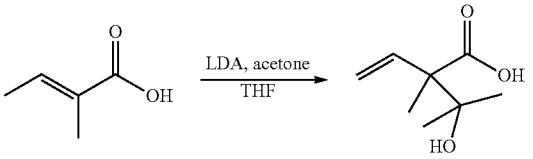

A cooled (−78° C.) solution of N,N-diisopropylamine (12.5 g, 123 mmol) in anhydrous tetrahydrofuran (100 mL) was treated with n-butyllithium (2.5 M solution in hexanes, 49 mL, 123 mmol). Temperature was raised to 0° C. for 30 minutes, then re-cooled down to −78° C. Tiglic acid (5.00 g, 49.4 mmol) in anhydrous tetrahydrofuran (100 mL) was added dropwise. Temperature was raised to room temperature for 1 h then re-cooled down to −78° C. Acetone (2.86 g, 49.4 mmol) in anhydrous tetrahydrofuran (100 mL) was added dropwise. After stirring for 3 h, the reaction was quenched with a saturated solution of ammonium chloride and allowed to warm up to room temperature. The pH was adjusted to pH 2 by addition of concentrated hydrochloric acid and diethyl ether (400 mL) was added. The organic layer was separated, and the volatiles removed in vacuo. The residue was partitioned between diethyl ether (200 mL) and a saturated solution of sodium bicarbonate (300 mL). The aqueous layer was acidified to pH 1 with concentrated hydrochloric acid, then re-extracted with diethyl ether (2×100 mL). The organics were combined and the volatiles were removed in vacuo. The residue was purified by silica gel chromatography using a 100 g Biotage cartridge eluted with a continuous gradient of iso-hexanes/acetone 1:0 to 3:2 to afford the title compound (5.129 g, 66%) as a colourless oil. $^1$H NMR (300 MHz, $CDCl_3$) δ 1.27 (s, 3H), 1.31 (s, 3H), 1.38 (s, 3H), 5.28 (d, J=17.6 Hz, 1H), 5.34 (d, J=10.9 Hz, 1H), 6.25 (dd, J=17.6, 10.9 Hz, 1H).

Compound 100b. 2-[1-(tert-Butyl-dimethyl-silanyloxy)-1-methyl-ethyl]-2-methyl-but-3-enoic acid

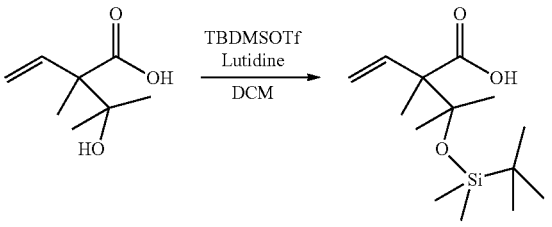

A cooled (0° C.) solution of 2-(1-hydroxy-1-methyl-ethyl)-2-methyl-but-3-enoic acid (2.0 g, 12.6 mmol) and 2,6-lutidine (13.5 g, 126.4 mmol) in dichloromethane (150 mL) was treated with tert-butyldimethylchlorosilane (16.7 g, 63.2 mmol). After stirring for 1 h, the volatiles were removed in vacuo, the residue was taken in methanol (100 mL) and water (50 mL) and treated with potassium carbonate (20 g). After stirring for 16 h, the volatiles were removed in vacuo, the residue was diluted with water (50 mL), acidified to pH 2 with potassium hydrogen sulfate, and extracted with dichloromethane (3×25 mL). All the organics were combined and the volatiles were removed in vacuo to afford the title compound (3.288 g, 95%) as a clear oil. $^1$H NMR (300 MHz, $CDCl_3$) δ 0.24 (s, 3H), 0.25 (s, 3H), 0.94 (s, 9H), 1.34 (s, 3H), 1.37 (s, 3H), 1.38 (s, 3H), 5.29 (m, 2H), 6.17 (dd, J=17.6, 10.9 Hz, 1H), 10.99 (br s, 1H).

Compound 100c. (E)-4-[2-((R)-1-Acetoxy-ethyl)-quinolin-7-yl]-2-[1-(tert-butyl-dimethyl-silanyloxy)-1-methyl-ethyl]-2-methyl-but-3-enoic acid

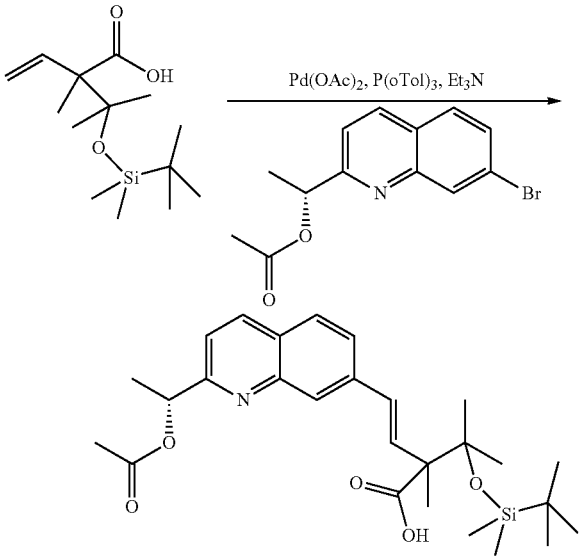

A solution of 2-[1-(tert-butyl-dimethyl-silanyloxy)-1-methyl-ethyl]-2-methyl-but-3-enoic acid (258 mg, 0.95 mmol), acetic acid (R)-1-(7-bromo-quinolin-2-yl)-ethyl ester (279 mg, 0.95 mmol), palladium(II) acetate (43 mg, 0.19 mmol), tris-(o-tolyl)phosphine (87 mg, 0.29 mmol) in anhydrous acetonitrile (3 mL) was treated with triethylamine (265 μL, 1.90 mmol). After stirring at 100° C. under microwave for 20 min, the reaction was cooled to room temperature and the volatiles were removed in vacuo. The residue was partitioned between dichloromethane and a saturated potassium hydrogen sulfate solution. The organics were combined and the volatiles were removed in vacuo. The residue was purified by silica gel chromatography using a 25 g Biotage cartridge eluted with a continuous gradient of iso-hexanes/ethyl acetate 1:0 to 0:1 to afford the title compound (300 mg, 65%) as a colourless oil. $^1$H NMR (300 MHz, $CDCl_3$) δ 0.20 (s, 3H), 0.22 (s, 3H), 0.94 (s, 9H), 1.44 (s, 3H), 1.45 (s, 3H), 1.50 (s, 3H), 1.68 (d, J=6.7 Hz, 3H), 2.17 (s, 3H), 6.06 (q, J=6.7 Hz, 1H), 6.76 (m, 2H), 7.43 (d, J=8.5 Hz, 1H), 7.62 (d, J=8.5 Hz, 1H), 7.74 (d, J=8.7 Hz, 1H), 8.03 (s, 1H), 8.11 (d, J=8.5 Hz, 1H). LCMS (m/z) 486.3 [M+H], Tr=3.64 min.

Compound 100d and 100e. (S)-1-[(S)-2-((S)-2-{(E)-4-[2-((R)-1-Acetoxy-ethyl)-quinolin-7-yl]-2-[1-(tert-butyl-dimethyl-silanyloxy)-1-methyl-ethyl]-2-methyl-but-3-enoylamino}-3-methyl-butyrylamino)-propionyl]-hexahydro-pyridazine-3-carboxylic acid 2,2,2-trichloro-ethyl ester and (E)-4-[2-((R)-1-acetoxy-ethyl)-quinolin-7-yl]-2-[1-(tert-butyl-dimethyl-silanyloxy)-1-methyl-ethyl]-2-methyl-but-3-enoic acid [1,2,3]triazolo[4,5-b]pyridin-1-yl ester

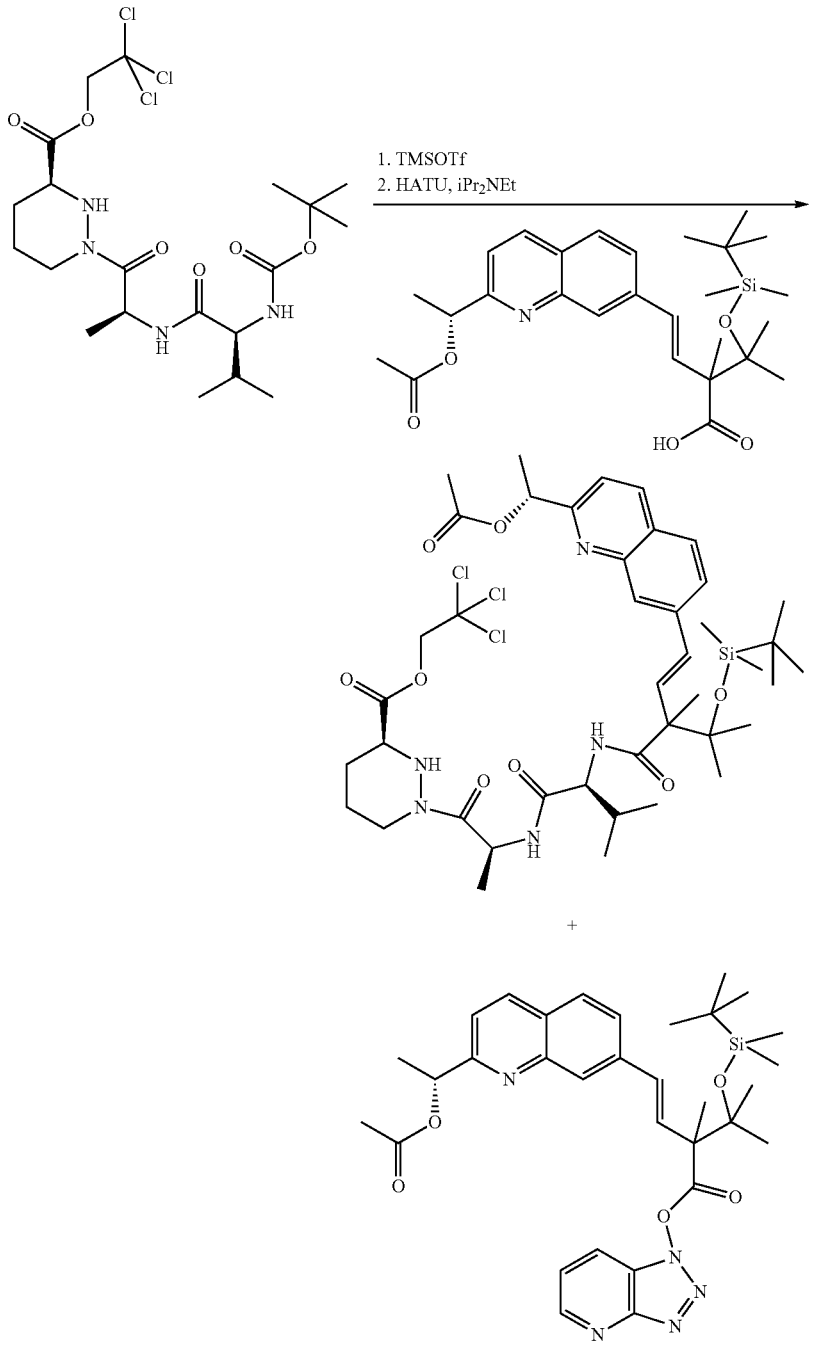

Compound 100d and 100e were prepared in the same manner as compound 82c using (E)-4-[2-((R)-1-acetoxy-ethyl)-quinolin-7-yl]-2-[1-(tert-butyl-dimethyl-silanyloxy)-1-methyl-ethyl]-2-methyl-but-3-enoic acid instead of (E)-4-[2-((R)-1-acetoxy-ethyl)-quinolin-7-yl]-2,2-dimethyl-but-3-enoic acid in 21% yield for 100d LCMS (m/z) 898.5, 900.5, 902.5 [M+H], Tr=4.14 min and 54% yield for 100e. LCMS (m/z) 604.3 [M+H], Tr=4.13 min.

Compound 100f. (S)-1-[(S)-2-((S)-2-{(E)-4-[2-((R)-1-Acetoxy-ethyl)-quinolin-7-yl]-2-[1-(tert-butyl-dimethyl-silanyloxy)-1-methyl-ethyl]-2-methyl-but-3-enoylamino}-3-methyl-butyrylamino)-propionyl]-hexahydro-pyridazine-3-carboxylic acid 2,2,2-trichloro-ethyl ester

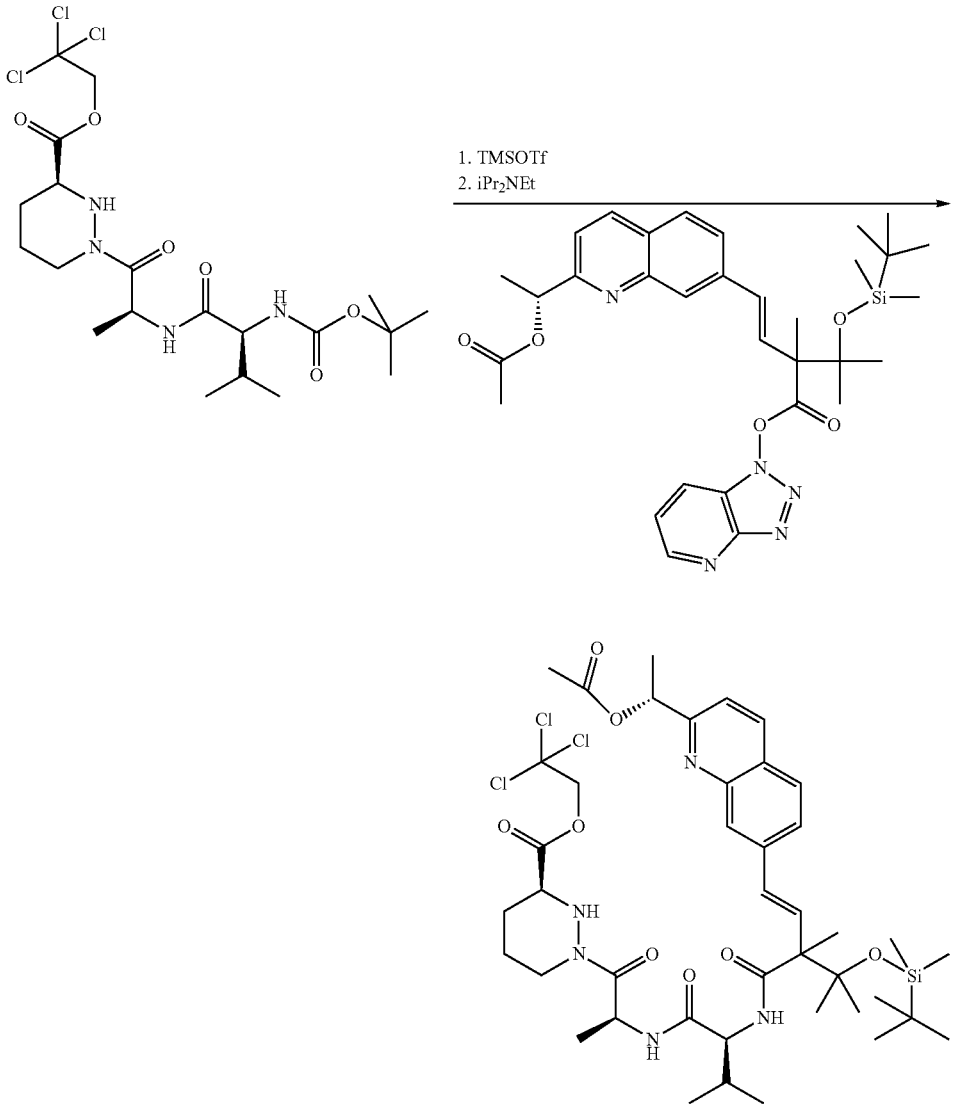

A cooled (0° C.) solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (176.5 mg, 0.332 mmol) in dichloromethane (10 mL) was treated with trimethylsilyl-trifluoromethanesulfonate (120 μL, 0.664 mmol). After stirring at 0° C. for 70 min, the reaction was quenched with a saturated solution of sodium bicarbonate. The aqueous layer was extracted with dichloromethane. The combined organics were filtered through a phase separator and the volatiles were removed in vacuo to provide (S)-1-[(S)-2-((S)-2-amino-3-methyl-butyrylamino)-propionyl]-hexahydro-pyridazine-3-carboxylic acid 2,2,2-trichloro-ethyl ester as a white solid. To the white solid was added a solution of (E)-4-[2-((R)-1-acetoxy-ethyl)-quinolin-7-yl]-2-[1-(tert-butyl-dimethyl-silanyloxy)-1-methyl-ethyl]-2-methyl-but-3-enoic acid [1,2,3]triazolo[4,5-b]pyridin-1-yl ester (200.0 mg, 0.332 mmol) in anhydrous acetonitrile (10 mL) and N,N-diisopropylethylamine (120 μL, 0.664 mmol). After stirring at room temperature for 19 h, the reaction was quenched at 0° C. with hydrochloric acid (1 M, 30 mL). The aqueous layer was extracted with ethyl acetate. The combined organics were washed with a saturated solution of sodium bicarbonate, dried over anhydrous sodium sulfate, filtered and the volatiles were removed in vacuo. The crude residue was combined with (S)-1-[(S)-2-((S)-2-{(E)-4-[2-((R)-1-acetoxy-ethyl)-quinolin-7-yl]-2-[1-(tert-butyl-dimethyl-silanyloxy)-1-methyl-ethyl]-2-methyl-but-3-enoylamino}-3-methyl-butyrylamino)-propionyl]-hexahydro-pyridazine-3-carboxylic acid 2,2,2-trichloro-ethyl ester obtained in the previous step and purified by silica gel chromatography using a 50 g Isolute cartridge eluted with a continuous gradient of iso-hexanes/ethyl acetate 1:0 to 1:3 to afford the title compound (305.0 mg, 55%, over 3 steps) as a white solid and as a 1:1 mixture of diastereoisomers. LCMS (m/z) 898.5/900.5 [M+H], Tr=4.16 min.

Compound 100g and Compound 100

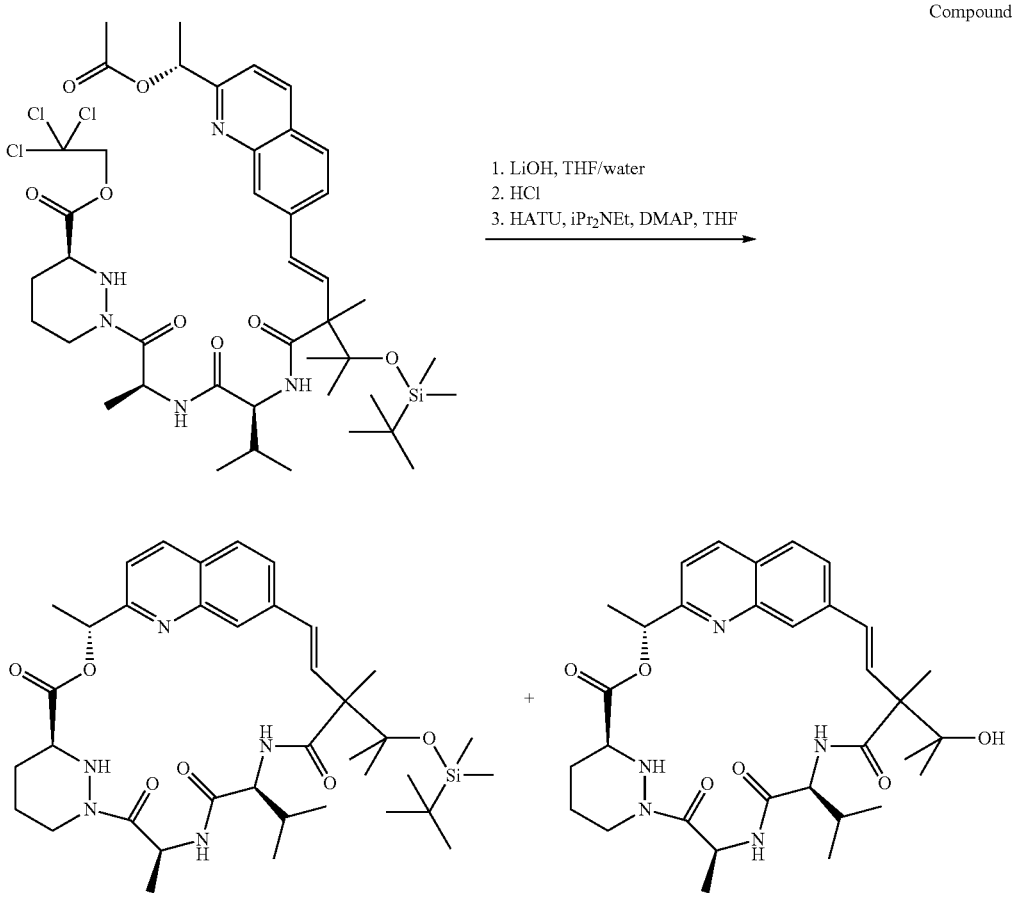

A cooled (0° C.) solution of (S)-1-[(S)-2-((S)-2-{(E)-4-[2-((R)-1-acetoxy-ethyl)-quinolin-7-yl]-2-[1-(tert-butyl-dimethyl-silanyloxy)-1-methyl-ethyl]-2-methyl-but-3-enoylamino}-3-methyl-butyrylamino)-propionyl]-hexahydro-pyridazine-3-carboxylic acid 2,2,2-trichloro-ethyl ester (305.0 mg, 0.339 mmol) in tetrahydrofuran/water (25 mL, 4:1) was treated with lithium hydroxide monohydrate (72 mg, 1.695 mmol). After stirring at 0° C. for 2 h, the reaction mixture was quenched with hydrochloric acid (2 M, 1.0 mL). The volatiles were removed in vacuo. Residual acetic acid and trichloroethanol were azeotroped off with tetrahydrofuran/toluene (3×) then the residue was triturated with diethyl ether and dried in vacuo. To the white solid was added dry tetrahydrofuran (120 mL), 4 Å molecular sieves. This solution was cooled to 0° C. and subsequently treated with N,N-diisopropylethylamine (300 μL, 1.695 mmol), N,N-dimethylaminopyridine (4.0 mg, 0.034 mmol) and 2-(1H-7-azabenzotriazol-1-yl)-1,1,3,3-tetramethyl uronium hexafluorophosphate methanaminium (154.7 mg, 0.407 mmol). After stirring at 0° C. for 1.5 h and at room temperature for 18 h, the volatiles were removed in vacuo. The residue was partitioned between ethyl acetate and hydrochloric acid (1 M, 30 mL). The aqueous layer was extracted with ethyl acetate. The combined organic layers were washed with a saturated solution of sodium bicarbonate, dried over anhydrous sodium sulfate, filtered and the volatiles were removed in vacuo. The residue was purified by silica gel chromatography using a 25 g Isolute cartridge eluted with a continuous gradient of iso-hexanes/acetone 1:0 to 1:1 to afford compound 100 g (59.3 mg, 25%, LCMS (m/z) 708.5 [M+H], Tr=3.49 min and 708.5 [M+H], Tr=3.98 min) as a white solid and as a mixture of diastereoisomers along with compound 100 which was further purified by preparative reverse phase HPLC to afford compound 100 (10.3 mg, 5.1%) as a white solid and as a single diastereoisomer. $^1$H NMR (300 MHz, $CD_3OD$) δ 0.93-1.05 (m, 6H), 1.33 (s, 3H), 1.37 (s, 3H), 1.53 (s, 3H), 1.65 (d, J=7.4 Hz, 3H), 1.69-1.80 (m, 4H), 1.85-2.07 (m, 4H), 2.68-2.81 (m, 1H), 3.76-3.86 (m, 1H), 4.31 (d, J=10.3 Hz, 1H), 4.35-4.45 (m, 1H), 5.74 (q, J=7.3 Hz, 1H), 5.93 (q, J=6.7 Hz, 1H), 6.43, 6.59 (ABq, $J_{AB}$=16.5 Hz, 2H), 7.41 (d, J=8.5 Hz, 1H), 7.70 (s, 1H), 7.76-7.86 (m, 2H), 8.22 (d, J=9.1 Hz, 1H). LCMS (m/z) 594.3 [M+H], Tr=2.21 min.

Compound 101

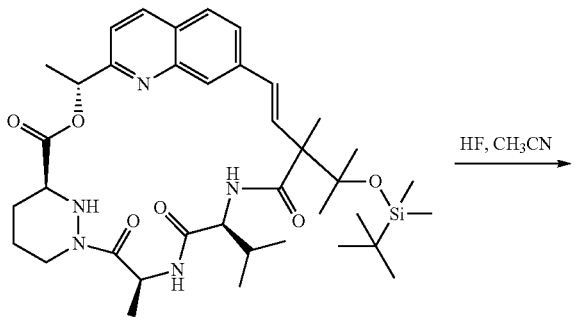

-continued

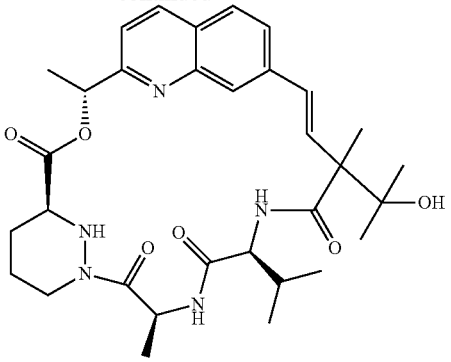

A solution of compound 100 g (49.1 mg, 0.070 mmol) in acetonitrile/tetrahydrofuran (10 mL, 9:1) was treated with hydrofluoric acid (48 wt % in water, 260 μL, 7.062 mmol). After stirring at room temperature for 2 h, the mixture was slowly poured over a saturated solution of sodium bicarbonate. The aqueous layer was extracted with ethyl acetate (2×). The organics were combined, dried over anhydrous sodium sulfate, filtered and the volatiles were removed in vacuo. The residue was purified by reverse phase preparative HPLC to afford compound 101 (2.6 mg, 12%) as a white solid. $^1$H NMR (300 MHz, $CD_3OD$) δ 0.94-1.02 (m, 6H), 1.33 (s, 3H), 1.37 (s, 3H), 1.60-1.76 (m, 7H), 1.87-1.96 (m, 4H), 1.97-2.07 (m, 2H), 2.68-2.80 (m, 1H), 3.74-3.86 (m, 1H), 4.28-4.50 (m, 2H), 5.73 (q, J=7.1 Hz, 1H), 5.93 (q, J=6.9 Hz, 1H), 6.42, 6.58 (ABq, J=16.5 Hz, 2H), 7.41 (d, J=8.5 Hz, 1H), 7.70 (s, 1H), 7.76-7.86 (m, 2H), 8.22 (d, J=8.5 Hz, 1H). LCMS (m/z) 594.3 [M+H], Tr=2.20 min.

Examples 102 and 103

Compounds 102 and 103

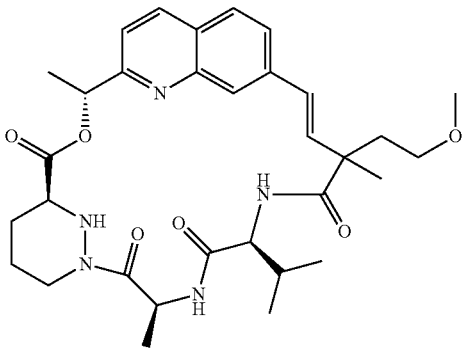

Compound 102a.
3-Methyl-3-vinyl-dihydro-furan-2-one

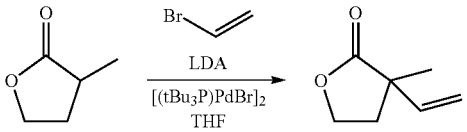

A solution of N,N-diisopropylamine (1.68 mL, 0.012 mol) in anhydrous tetrahydrofuran (20 mL) was cooled to −30° C. under a nitrogen atmosphere. A 2.5 M solution of n-butyllithium (4.4 mL, 0.011 mol) in hexanes was added and the reaction was allowed to warm to −10° C. The solution was stirred for 10 minutes before adding 3-methyl-dihydro-furan-2-one (1.0 g, 0.01 mol) in tetrahydrofuran (10 mL). The reaction mixture was stirred at −5° C. for 15 minutes before adding di-μ-bromobis(tri-tert-butylphosphino) dipalladium (I) (93 mg, 0.12 mmol) and vinyl bromide (1 M in tetrahydrofuran, 13 mL, 0.13 mmol). The reaction was allowed to warm to room temperature and was stirred for 2 h. The reaction mixture was then cooled to −10° C. before adding saturated aqueous ammonium chloride solution (20 mL) then hydrochloric acid (2 M) to pH 1. The layers were separated and the aqueous layer was extracted with diethyl ether (20 mL). The organic layers were combined, dried over anhydrous sodium sulfate, filtered and evaporated to give an orange gum. The gum was purified by silica gel chromatography eluting with iso-hexanes/diethyl ether 1:1 to yield the title product (0.533 g, 42%) as a yellow oil. $^1$H NMR (300 MHz, $CDCl_3$) δ 1.38 (s, 3H), 2.11-2.22 (m, 1H), 2.31-2.41 (m, 1H), 4.20-4.36 (m, 2H), 5.16-5.26 (m, 2H), 5.84-5.96 (m, 1H).

Compound 102b. 7-Bromo-2-[(R)-1-(tert-butyl-dimethyl-silanyloxy)-ethyl]-quinoline

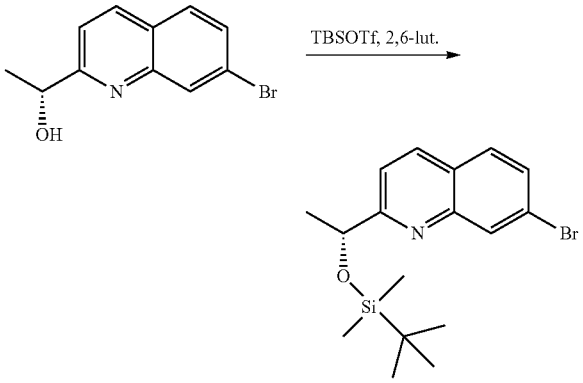

A solution of (R)-1-(7-bromo-quinolin-2-yl)-ethanol (2.52 g, 10 mmol) in dichloromethane (55 mL) was cooled to 0° C. before adding trimethylsilyl trifluoromethanesulfonate (2.7 mL, 12 mmol) and 2,6-lutidine (1.75 mL, 15 mmol). The reaction mixture was stirred for 2 h then treated with a saturated solution of potassium phosphate monobasic in water. The aqueous layer was extracted with dichloromethane. The extracts were combined, dried over anhydrous magnesium sulfate and the volatiles were evaporated. A second batch was made in the same way from (R)-1-(7-bromo-quinolin-2-yl)-ethanol (375 mg, 1.49 mmol) using the same proportions of reagents. After the same work up the crudes were combined, and purified by silica gel chromatography using a stepwise gradient of iso-hexanes/ethyl acetate 99:1 to 24:1 to yield the title product (3.96 g, 94%) as a solid. $^1$H NMR (300 MHz, $CDCl_3$) δ 0.02 (s, 3H), 0.12 (s, 3H), 0.94 (s, 9H), 1.54 (d, J=6.5 Hz, 3H), 5.12 (q, J=6.5 Hz, 1H), 7.61 (dd, J=8.7, 1.8 Hz, 1H), 7.69 (d, J=8.5 Hz, 1H), 7.75 (d, J=8.5 Hz, 1H), 8.15 (d, J=8.5 Hz, 1H), 8.24 (s, 1H).

Compound 102c. 3-((E)-2-{2-[(R)-1-(tert-Butyl-dimethyl-silanyloxy)-ethyl]-quinolin-7-yl}-vinyl)-3-methyl-dihydro-furan-2-one

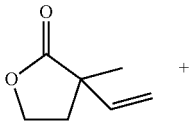

-continued

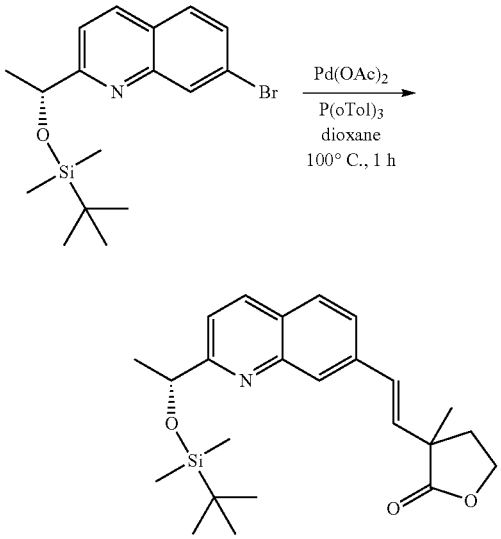

A solution of 7-bromo-2-[(R)-1-(tert-butyl-dimethyl-silanyloxy)-ethyl]-quinoline (1.26 g, 3.43 mmol) and 3-methyl-3-vinyl-dihydro-furan-2-one in 1,4-dioxane (52 mL) was prepared and tri(o-tolyl)phosphine (420 mg, 1.37 mmol), palladium(II) acetate (307 mg, 1.37 mmol) and N,N-dicyclohexylmethylamine (1.18 mL, 5.5 mmol) were added. The stirred reaction mixture was heated to reflux under a nitrogen atmosphere for 3.5 h. It was briefly cooled before adding more palladium(II) acetate (77 mg, 0.34 mmol) and tri(o-tolyl)phosphine (105 mg, 0.34 mmol). It was reheated to reflux and stirred for 1 h before cooling to room temperature. The reaction mixture was evaporated to dryness then purified by silica gel chromatography eluting with iso-hexanes/ethyl acetate 4:1 to yield the title product as a yellow semi-solid. The material was dissolved in dichloromethane (50 mL) and filtered to remove an insoluble solid. The solution was evaporated to give the title product (1.25 g, 88%) as a yellow gum. $^1$H NMR (300 MHz, $CDCl_3$) δ 0.02 (s, 3H), 0.14 (s, 3H), 0.94 (s, 9H), 1.49 (s, 3H), 1.52 (d, J=6.5 Hz, 3H), 2.31-2.43 (m, 1H), 2.56-2.67 (m, 1H), 4.32-4.43 (m, 2H), 5.12 (q, J=6.5 Hz, 1H), 6.65 (d, J=16.3 Hz, 1H), 6.82 (d, J=16.3 Hz, 1H), 7.69 (d, J=8.5 Hz, 1H), 7.77 (d, J=8.5 Hz, 1H), 7.89 (d, J=8.5 Hz, 1H), 7.97 (s, 1H), 8.30 (d, J=8.5 Hz, 1H). LCMS (m/z) 412.2 [M+H], Tr=3.47 min.

Compound 102d. (E)-4-[2-((R)-1-Hydroxy-ethyl)-quinolin-7-yl]-2-(2-methoxy-ethyl)-2-methyl-but-3-enoic acid methyl ester

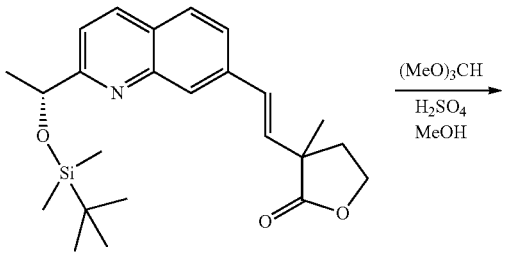

-continued

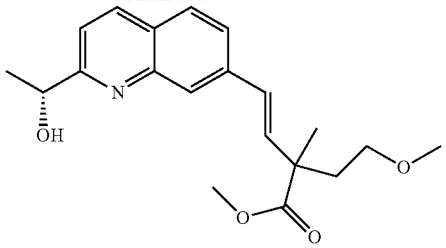

A stirred solution of 3-((E)-2-{2-[(R)-1-(tert-butyl-dimethyl-silanyloxy)-ethyl]-quinolin-7-yl}-vinyl)-3-methyl-dihydro-furan-2-one (1.25 g, 3.03 mmol) in methanol (12 mL) was prepared and trimethyl orthoformate (1.33 mL, 12.1 mmol) was added, followed by concentrated sulfuric acid (20 μL). It was heated at reflux for 18 h. After brief cooling more trimethyl orthoformate (1.33 12.1 mmol) and concentrated sulfuric acid (20 μL) was added and heated at reflux for 4.5 h. The reaction mixture was cooled to room temperature then neutralised by addition of a few drops of saturated aqueous sodium bicarbonate solution. The solution was evaporated to give a thick slurry which was then partitioned between water (25 mL) and dichloromethane (25 mL). The aqueous phase was extracted with dichloromethane (2×15 mL). The organic phases were combined, dried over anhydrous sodium sulfate, filtered and evaporated to give a brown gum. The gum was purified by silica gel chromatography eluting with dichloromethane/methanol 98:2 to yield the title product (815 mg, 78%) as yellow oil. $^1$H NMR (300 MHz, $CDCl_3$) δ 1.50 (s, 3H), 1.59 (d, J=6.5 Hz, 3H), 1.99-2.11 (m, 1H), 2.16-2.28 (m, 1H), 3.33 (s, 3H), 3.48 (t, J=6.7 Hz, 2H), 3.75 (s, 3H), 4.98-5.09 (m, 2H), 6.66 (s, 2H), 7.31 (d, J=8.5 Hz, 1H), 7.65 (d, J=8.5 Hz, 1H), 7.77 (d, J=8.5 Hz, 1H), 8.00 (s, 1H), 8.11 (d, J=8.5 Hz, 1H). LCMS (m/z) 344.2 [M+H], Tr=1.55 min.

Compound 102e. (E)-4-[2-((R)-1-Hydroxy-ethyl)-quinolin-7-yl]-2-(2-methoxy-ethyl)-2-methyl-but-3-enoic acid

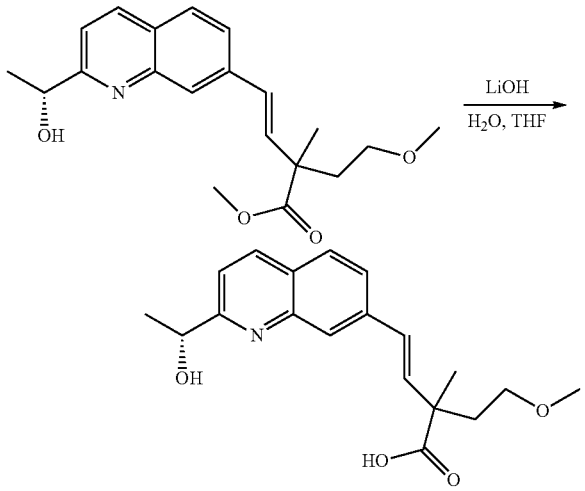

A solution of (E)-4-[2-((R)-1-hydroxy-ethyl)-quinolin-7-yl]-2-(2-methoxy-ethyl)-2-methyl-but-3-enoic acid methyl ester (815 mg, 2.37 mmol) in tetrahydrofuran (25 mL) was prepared and a solution of lithium hydroxide monohydrate (395 mg, 9.49 mmol) in water (10 mL) was added. The reaction mixture was stirred at room temperature for 18 h. It was then acidified to pH 1 with hydrochloric acid (2 M) before evaporating to give the crude title product (2.43 g) as a yellow solid and as a mixture of diastereoisomers. LCMS (m/z) 330.2 [M+H], Tr=1.21 min.

Compound 102f. (S)-1-((S)-2-{(S)-2-[(E)-4-[2-((R)-1-Hydroxy-ethyl)-quinolin-7-yl]-2-(2-methoxy-ethyl)-2-methyl-but-3-enoylamino]-3-methyl-butyrylamino}-propionyl)-hexahydro-pyridazine-3-carboxylic acid 2,2,2-trichloro-ethyl ester

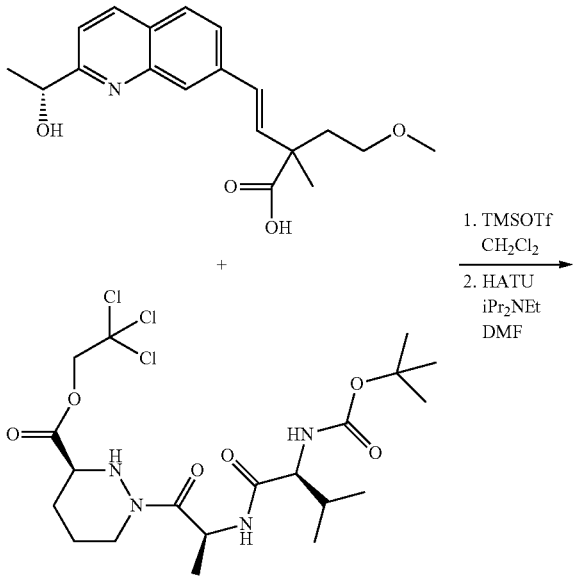

-continued

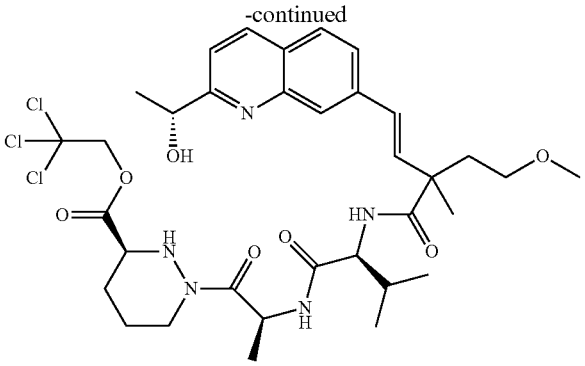

A solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (1.24 g, 2.38 mmol) in anhydrous dichloromethane (40 mL) was cooled to 0° C. before adding trimethylsilyl trifluoromethanesulfonate (660 μL, 3.62 mmol). The reaction mixture was stirred at 0° C. for 1.5 h before addition of N,N-diisopropylethylamine (1.65 mL, 9.47 mmol). The reaction mixture was then evaporated to dryness and the residue was dissolved in N,N-dimethylformamide (20 mL) and added to a stirred solution of crude (E)-4-[2-((R)-1-hydroxy-ethyl)-quinolin-7-yl]-2-(2-methoxy-ethyl)-2-methyl-but-3-enoic acid (2.43 g) and N,N-diisopropylethylamine (1.65 mL, 9.47 mmol) in N,N-dimethylformamide (50 mL). The reaction was treated with 2-(1H-7-azabenzotriazol-1-yl)-1,1,3,3-tetramethyluronium hexafluorophosphate methanaminium (1.37 g, 3.78 mmol) and stirred at room temperature for 3 h. It was evaporated then purified by silica gel chromatography eluting with iso-hexanes/dichloromethane/methanol 1:1:0 to 0:1:0 to 0:98:2 to 0:24:1 to yield the title product (1.17 g, 66%) as a pale yellow solid and as a mixture of diastereoisomers. LCMS (m/z) 742.3, 744.2, 746.2 [M+H], Tr=2.15 min.

Compound 102 and 103

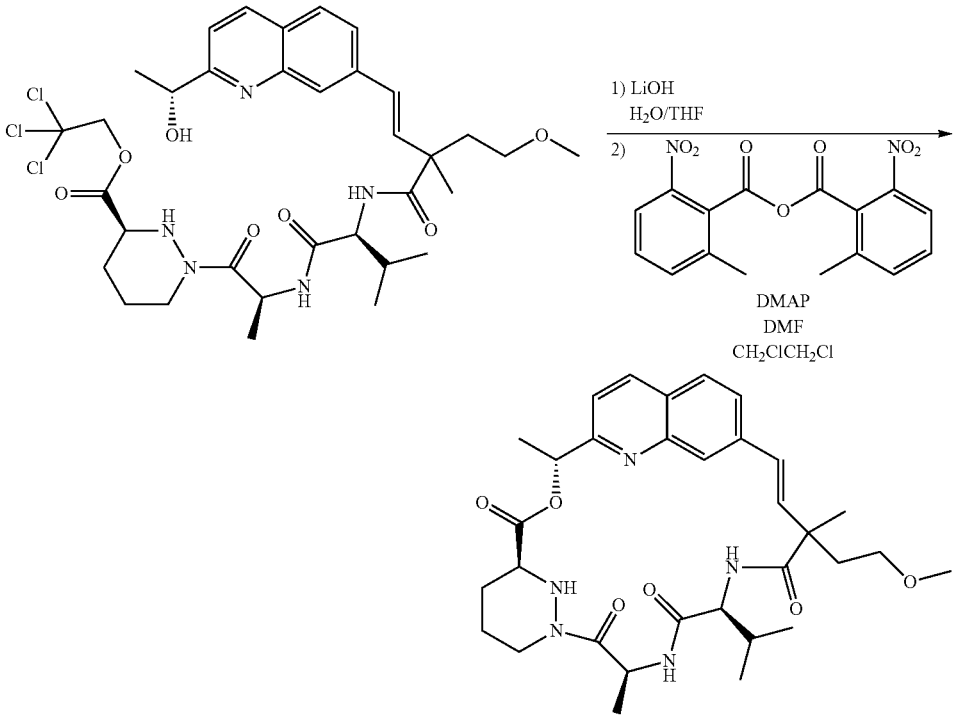

A solution of (S)-1-((S)-2-{(S)-2-[(E)-4-[2-((R)-1-hydroxy-ethyl)-quinolin-7-yl]-2-(2-methoxy-ethyl)-2-methyl-but-3-enoylamino]-3-methyl-butyrylamino}-propionyl)-hexahydro-pyridazine-3-carboxylic acid 2,2,2-trichloro-ethyl ester (200 mg, 0.242 mmol) in tetrahydrofuran (10 mL) was prepared and a solution of lithium hydroxide monohydrate (30.5 mg, 0.726 mmol) in water (2 mL) was added. The solution was stirred at room temperature for 2.5 h. The reaction was diluted with water (20 mL) and washed with diethyl ether (15 mL). The ether was back extracted with water (15 mL). The aqueous phases were combined and acidified to pH 1 with hydrochloric acid (2 M). The solution was evaporated to give a yellow gum which was triturated with diethyl ether then dried in vacuo for 24 h to yield a yellow solid.

The solid was dissolved in anhydrous N,N-dimethylformamide (3 mL) and the resulting solution was added, using a syringe pump, to a stirred solution of 2-nitro-6-methyl-benzoic anhydride (418 mg, 1.21 mmol) and 4-(dimethyl-amino)pyridine (206 mg, 1.7 mmol) in 1,2-dichloroethane (82 mL) at 50° C., over 3 h. After the end of the addition the reaction was stirred for 30 minutes at 50° C. then cooled to room temperature. The reaction mixture was washed with iced brine (50 mL), a 5% aqueous solution of citric acid (50 mL), a saturated aqueous solution of sodium bicarbonate (50 mL) and brine (50 mL). The solution was dried over anhydrous sodium sulfate, filtered and evaporated to give a white gum (290 mg). The gum was purified by silica gel chromatography eluting with dichloromethane/methanol 1:0 to 24:1 to give a colourless gum (76 mg). The gum was further purified by HPLC using an Agilent Eclipse XDB/C18 7 micron, 250×21.2 mm column and eluting with a gradient of water/acetonitrile 4:1 to 0:1 over 30 minutes at 20 mL/min to give the two separate diastereoisomers.

Compound 102 First eluting Diastereomer 1 (10.9 mg, 8%) as a white solid $^1$H NMR (300 MHz, $CD_3OD$) δ 0.97 (d, J=6.7 Hz, 3H), 0.98 (d, J=6.7 Hz, 3H), 1.51 (s, 3H), 1.60-1.76 (m, 1H), 1.64 (d, J=7.1 Hz, 3H), 1.73 (d, J=6.7 Hz, 3H), 1.85-2.05 (m, 4H), 2.09-2.21 (m, 1H), 2.66-2.81 (m, 1H), 3.30 (s, 3H), 3.46-3.62 (m, 2H), 3.75-3.87 (m, 1H), 4.28 (d, J=10.3 Hz, 1H), 4.35-4.47 (m, 2H), 5.74 (q, J=7.1 Hz, 1H), 5.92 (q, J=6.9 Hz, 1H), 6.28 (d, J=16.5 Hz, 1H), 6.46 (d, J=16.5 Hz, 1H), 7.41 (d, J=8.5 Hz, 1H), 7.65 (s, 1H), 7.74-7.85 (m, 2H), 8.21 (d, J=8.5 Hz, 1H). LCMS (m/z) 594.3 [M+H], Tr=2.21 min.

Example 103 Second eluting Diastereomer 2 (24.2 mg, 17%) as a white solid. $^1$H NMR (300 MHz, $CD_3OD$) δ 0.99 (d, J=6.7 Hz, 6H), 1.36 (s, 3H), 1.68-1.75 (m, 1H), 1.64 (d, J=7.1 Hz, 3H), 1.73 (d, J=6.7 Hz, 3H), 1.84-2.04 (m, 4H), 2.05-2.28 (m, 2H), 2.66-2.81 (m, 1H), 3.30 (s, 3H), 3.46-3.63 (m, 2H), 3.76-3.89 (m, 1H), 4.31 (d, J=10.3 Hz, 1H), 4.36-4.46 (m, 2H), 5.77 (q, J=7.1 Hz, 1H), 5.92 (q, J=6.7 Hz, 1H), 6.26 (d, J=16.5 Hz, 1H), 6.54 (d, J=16.5 Hz, 1H), 7.41 (d, J=8.5 Hz, 1H), 7.63 (s, 1H), 7.79-7.82 (m, 2H), 8.21 (d, J=8.5 Hz, 1H). LCMS (m/z) 594.3 [M+H], Tr=2.27 min.

Examples 104 and 105

Compounds 104 and 105

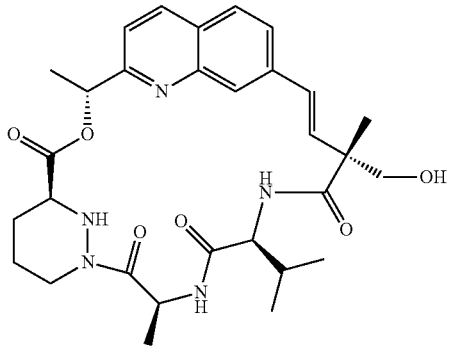

Compound 104a. (R)-3-((R)-2-Hydroxymethyl-2-methyl-but-3-enoyl)-4-isopropyl-oxazolidin-2-one

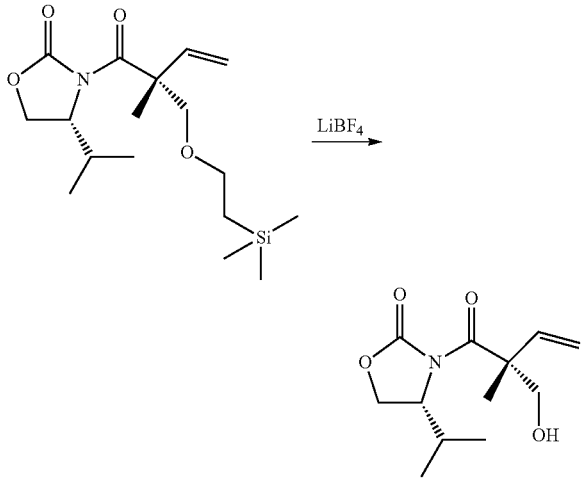

To a stirred solution of (R)-4-isopropyl-3-[(R)-2-methyl-2-(2-trimethylsilanyl-ethoxymethyl)-but-3-enoyl]-oxazolidin-2-one (2.93 g, 8.58 mmol) in a mixture of acetonitrile (86 mL) and water (1.72 mL) was added lithium tetrafluoroborate (1 M in acetonitrile, 42.9 mL, 42.9 mmol). The mixture was heated at reflux under nitrogen for 5 h and allowed to cool to ambient temperature. More lithium tetrafluoroborate (1 M in acetonitrile, 8.6 mL, 8.6 mmol) was added and the mixture heated at reflux for a further 75 minutes and allowed to cool to ambient temperature. The mixture was diluted with water/diethyl ether (2:3, 100 mL) and the organic layer was separated and washed with water. The combined aqueous washes were back-extracted with diethyl ether and the combined organic extracts dried over anhydrous sodium sulfate, filtered and evaporated to give the title compound (1.89 g, 91%) as a yellow oil. $^1$H NMR (300 MHz, $CDCl_3$) δ 0.89 (d, J=6.9 Hz, 3H), 0.95 (d, J=6.9 Hz, 3H), 1.35 (s, 3H), 2.36-2.47 (m, 1H), 2.56-2.70 (br s, 1H), 3.47-3.54 (m, 1H), 3.91 (d, J=11.6 Hz, 1H), 4.22-4.31 (m, 2H), 4.47-4.53 (m, 1H), 4.97 (d, J=17.8 Hz, 1H), 5.17 (d, J=10.7 Hz, 1H), 6.09 (dd, J=17.8, 10.7 Hz, 1H). LCMS (m/z) 242.2 [M+H], Tr=1.82 min.

Compound 104b. (R)-3-[(R)-2-(tert-Butyl-dimethyl-silanyloxymethyl)-2-methyl-but-3-enoyl]-4-isopropyl-oxazolidin-2-one

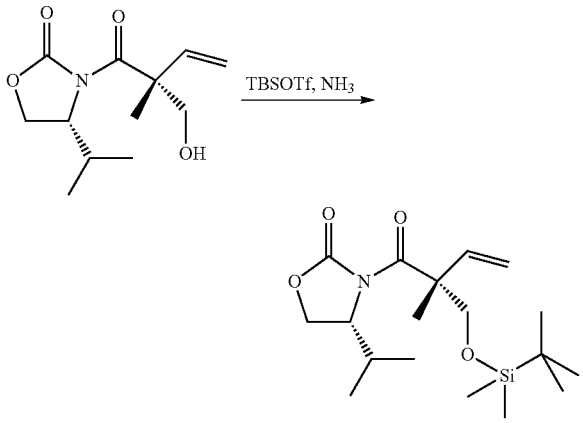

To a stirred solution of (R)-3-((R)-2-hydroxymethyl-2-methyl-but-3-enoyl)-4-isopropyl-oxazolidin-2-one (660 mg, 2.74 mmol) and tert-butyldimethylsilyl chloride (533 mg, 3.56 mmol) in N,N-dimethylformamide (10 mL) at 0° C. under nitrogen was added in one portion imidazole (821 mg, 12.1 mmol). The reaction was stirred at 0° C. for 15 minutes and then allowed to warm to ambient temperature and stirred for 5 h. The mixture was concentrated and then partitioned between saturated ammonium chloride solution and ether. The organic layer was separated and washed with water (3×), dried over anhydrous sodium sulfate, filtered and evaporated. The residue was purified on silica gel chromatography eluting with iso-hexanes/ethyl acetate 1:0 to 19:1 to afford the title compound (316 mg, 32%) as a colourless oil. $^1$H NMR (300 MHz, $CDCl_3$) δ 0.05 (s, 3H), 0.06 (s, 3H), 0.86-0.94 (m, 6H), 0.89 (s, 9H), 1.45 (s, 3H), 2.27-2.40 (m, 1H), 3.71 (d, J=9.6 Hz, 1H), 4.10-4.30 (m, 2H), 4.43 (d, J=9.6 Hz, 1H), 4.49-4.55 (m, 1H), 4.99 (d, J=17.8 Hz, 1H), 5.10 (d, J=9.6 Hz, 1H), 6.17 (dd, J=17.8, 10.9 Hz, 1H). LCMS (m/z) 356.2 [M+H], Tr=4.02 min Compound 104c. (R)-3-{(E)-(R)-2-(tert-Butyl-dimethyl-silanyloxymethyl)-4-[7-((R)-1-hydroxy-ethyl)-naphthalen-2-yl]-2-methyl-but-3-enoyl}-4-isopropyl-oxazolidin-2-one

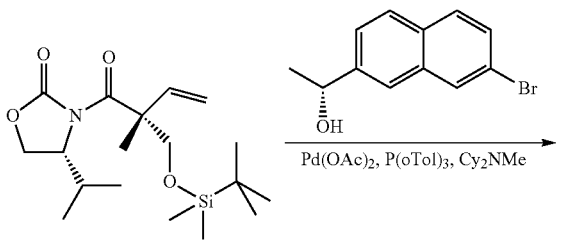

-continued

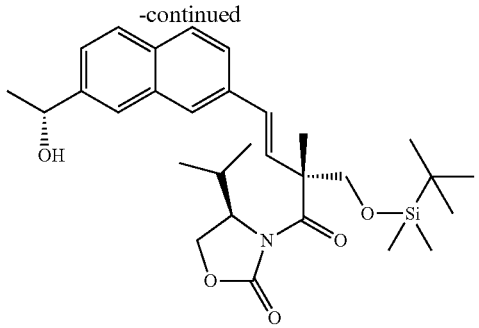

A solution of (R)-1-(7-bromo-naphthalen-2-yl)-ethanol (121.5 mg, 0.484 mmol), (R)-3-[(R)-2-(tert-butyl-dimethyl-silanyloxymethyl)-2-methyl-but-3-enoyl]-4-isopropyl-oxazolidin-2-one (172.0 mg, 0.484 mmol), palladium(II)acetate (22 mg, 0.097 mmol), tri(o-tolyl)phosphine (29.5 mg, 0.097 mmol) and N,N-dicylohexylmethylamine (0.26 mL, 1.210 mmol) in anhydrous 1,4-dioxane (10 mL) was heated at reflux for 1.5 h. The mixture was treated with palladium (II) acetate (22 mg, 0.097 mmol) and tri(o-tolyl)phosphine (29.5 mg, 0.097 mmol). After stirring at reflux for 24 h and cooling to warm temperature the reaction was quenched with hydrochloric acid (1 M, 20 mL). The aqueous layer was extracted with ethyl acetate. The combined organics were washed with a saturated solution of sodium bicarbonate dried over anhydrous sodium sulfate, filtered and the volatiles were removed in vacuo. The residue was purified by silica gel chromatography using a 25 g Isolute cartridge eluted with a continuous gradient of iso-hexanes/ethyl acetate 1:0 to 4:1 to afford the title compound (116.7 mg, 46%) as a yellow solid. $^1$H NMR (300 MHz, $CDCl_3$) δ 0.07 (s, 6H), 0.91 (s, 9H), 1.15-1.30 (m, 6H), 1.55-1.65 (m, 6H), 2.29-2.46 (m, 1H), 3.83 (d, J=9.6 Hz, 1H), 4.10-4.33 (m, 2H), 4.50-4.60 (m, 2H), 5.00-5.15 (m, 1H), 6.47 (d, J=16.5 Hz, 1H), 6.70 (d, J=16.5 Hz, 1H), 7.11-7.22 (m, 2H), 7.40-7.50 (m, 2H), 7.72-7.82 (m, 2H). LCMS (m/z) 526.3 [M+H], Tr=4.03 min.

Compound 104d. (E)-(R)-2-(tert-Butyl-dimethyl-silanyloxymethyl)-4-[7-((R)-1-hydroxy-ethyl)-naphthalen-2-yl]-2-methyl-but-3-enoic acid

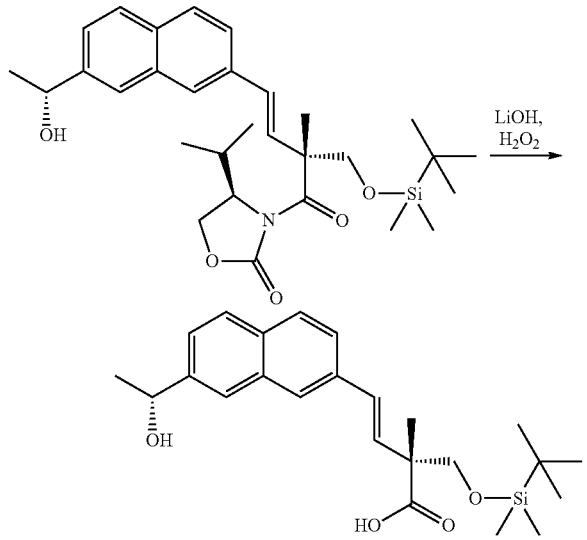

A cooled (0° C.) solution of (R)-3-{(E)-(R)-2-(tert-butyl-dimethyl-silanyloxymethyl)-4-[7-((R)-1-hydroxy-ethyl)-naphthalen-2-yl]-2-methyl-but-3-enoyl}-4-isopropyl-oxazolidin-2-one (116.7 mg, 0.222 mmol) in tetrahydrofuran/water (12 mL, 5:1) was subsequently treated with hydrogen peroxide (30% aqueous, 120 μL, 1.110 mmol) and lithium hydroxide monohydrate (18.6 mg, 0.444 mmol). After stirring at 0° C. for 3.5 h, the reaction mixture was treated with hydrogen peroxide (30% aqueous, 120 μL, 1.110 mmol) and lithium hydroxide monohydrate (18.6 mg, 0.444 mmol). After stirring at 0° C. for 2.5 h the reaction was quenched with solid sodium metabisulfite (850 mg). After stirring at room temperature for 45 mins the mixture was acidified with hydrochloric acid (1 M, 20 mL). The aqueous layer was extracted with dichloromethane (2×). The combined organics were filtered through a phase separator and the volatiles were removed in vacuo. The residue was purified by silica gel chromatography using a 25 g Isolute cartridge eluted with a continuous gradient of iso-hexanes/ethyl acetate 1:0 to 3:2 to afford the title compound (77.1 mg, 84%) as a yellow solid. $^1$H NMR (300 MHz, $CDCl_3$) δ 0.15 (s, 6H), 0.94 (s, 9H), 1.47 (s, 3H), 1.60 (d, J=6.5 Hz, 3H), 3.79, 3.92 (ABq, $J_{AB}$=9.6 Hz, 2H), 5.08 (q, J=6.5 Hz, 1H), 6.43 (d, J=16.5 Hz, 1H), 6.72 (d, J=16.5 Hz, 1H), 7.06-7.22 (m, 2H), 7.40-7.60 (m, 2H), 7.70-7.84 (m, 2H). LCMS (m/z) 415.2 [M+H], Tr=3.40 min.

Compound 104e. (S)-1-[(S)-2-((S)-2-{(E)-(R)-2-(tert-Butyl-dimethyl-silanyloxymethyl)-4-[2-((R)-1-hydroxy-ethyl)-naphthalen-7-yl]-2-methyl-but-3-enoylamino}-3-methyl-butyrylamino)-propionyl]-hexahydro-pyridazine-3-carboxylic acid 2,2,2-trichloro-ethyl ester A cooled (0° C.) solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (98.9 mg, 0.186 mmol) in dichloromethane (10 mL) was treated with trimethylsilyl-trifluoromethanesulfonate (70 μL, 0.372 mmol). After stirring at 0° C. for 60 min, the reaction was quenched with a saturated solution of sodium bicarbonate. The aqueous layer was extracted with dichloromethane. The combined organics were filtered through a phase separator and the volatiles were removed in vacuo to provide (S)-1-[(S)-2-((S)-2-amino-3-methyl-butyrylamino)-propionyl]-hexahydro-pyridazine-3-carboxylic acid 2,2,2-trichloro-ethyl ester as a white solid. To the white solid was added a solution of (E)-(R)-2-(tert-butyl-dimethyl-silanyloxymethyl)-4-[7-((R)-1-hydroxy-ethyl)-naphthalen-2-yl]-2-methyl-but-3-enoic acid (77.1 mg, 0.186 mmol) in anhydrous acetonitrile (10 mL) and the solution was cooled to 0° C. then treated with N,N-diisopropylethylamine (130 μL, 0.744 mmol) and 2-(1H-7-azabenzotriazol-1-yl)-1,1,3,3-tetramethyl uronium hexafluorophosphate methanaminium (85 mg, 0.223 mmol). After stirring at room temperature for 20 h, the reaction was quenched with hydrochloric acid (1 M, 20 mL). The aqueous layer was extracted with ethyl acetate (2×). The organics were combined, washed with a saturated solution of sodium bicarbonate, dried over anhydrous sodium sulfate, filtered and the volatiles were removed in vacuo. The residue was purified by silica gel chromatography using a 25 g Isolute cartridge

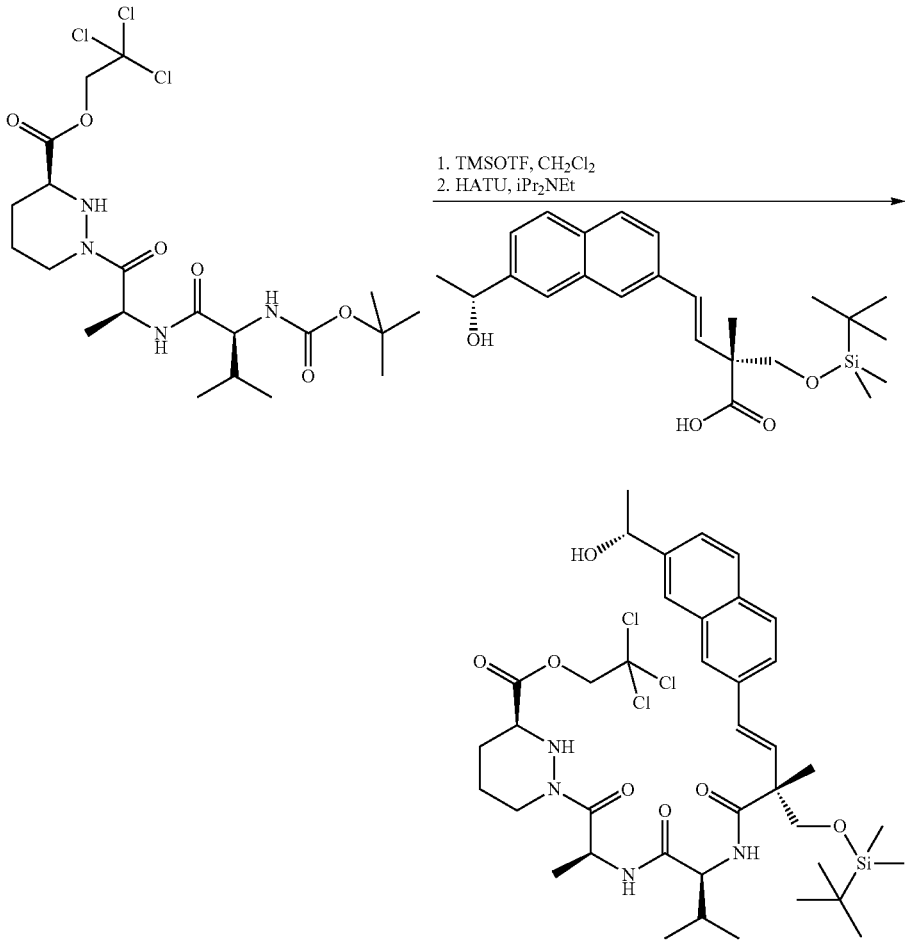

eluted with a continuous gradient of iso-hexanes/ethyl acetate 1:0 to 1:4 to provide the title compound (48.0 mg, 31%) as a yellow gum. $^1$H NMR (300 MHz, $CDCl_3$) δ 0.11-0.16 (m, 6H), 0.95 (s, 9H), 1.20-1.35 (m, 9H), 1.43 (s, 3H), 1.60 (d, J=6.4 Hz, 3H), 1.66-1.79 (m, 2H), 1.88-1.97 (m, 1H), 2.13-2.29 (m, 2H), 3.63-3.73 (m, 1H), 3.78-3.85 (m, 2H), 3.92 (d, J=10.0 Hz, 1H), 4.30-4.44 (m, 2H), 4.72 (d, J=12.0 Hz, 1H), 4.95 (d, J=12.0 Hz, 1H), 5.02-5.13 (m, 1H), 5.25-5.36 (m, 1H), 6.56 (d, J=16.5 Hz, 1H), 6.69-6.78 (m, 2H), 7.34 (d, J=8.5 Hz, 1H), 7.48 (dd, J=8.5, 1.3 Hz, 1H), 7.59 (dd, J=8.7, 1.6 Hz, 1H), 7.69-7.83 (m, 4H). LCMS (m/z) 829.4/827.4 [M+H], Tr=3.88 min.

Compound 104 and 105

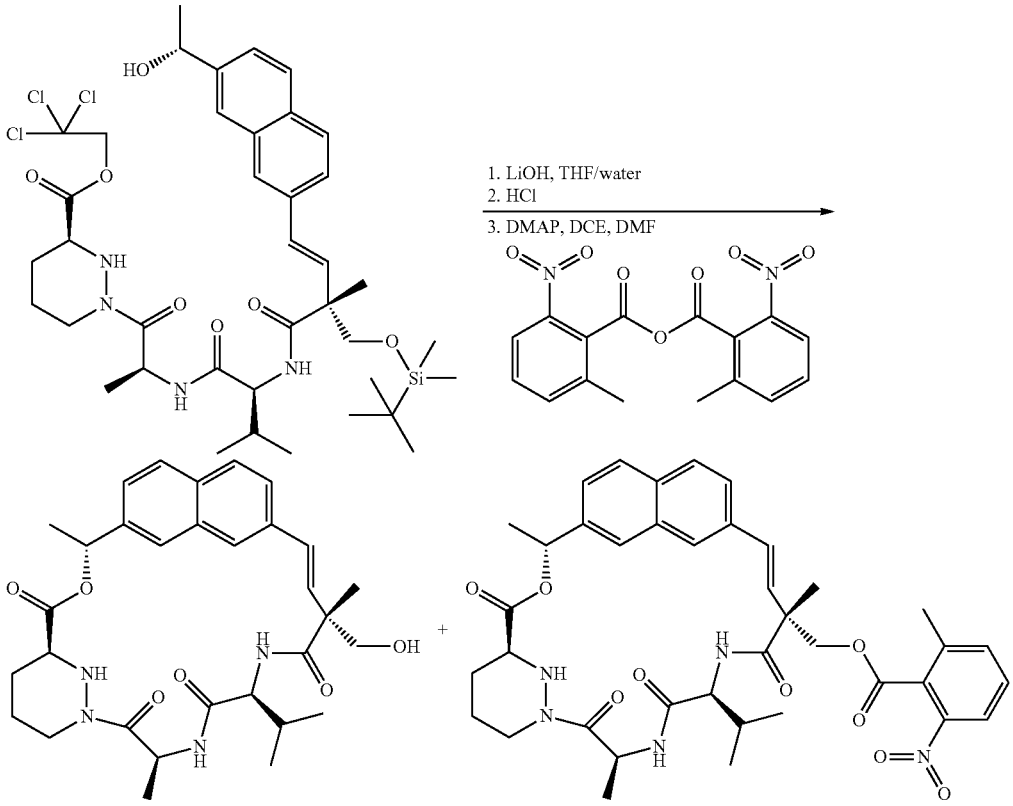

A cooled (0° C.) solution of (S)-1-[(S)-2-((S)-2-{(E)-(R)-2-(tert-Butyl-dimethyl-silanyloxymethyl)-4-[2-((R)-1-hydroxy-ethyl)-naphthalen-7-yl]-2-methyl-but-3-enoylamino}-3-methyl-butyrylamino)-propionyl]-hexahydro-pyridazine-3-carboxylic acid 2,2,2-trichloro-ethyl ester (48.0 mg, 0.058 mmol) in tetrahydrofuran/water (6 mL, 5:1) was treated with lithium hydroxide monohydrate (31.2 mg, 0.743 mmol). After stirring at 0° C. for 1.6 h, the reaction was quenched with hydrochloric acid (2 M, 380 μL, 0.743 mmol). The volatiles were removed in vacuo and the residual acetic acid and trichloroethanol were azeotroped off with toluene/tetrahydrofuran (6×). The solid was then triturated with diethyl ether to provide (S)-1-[(S)-2-((S)-2-{(E)-(R)-4-[7-((R)-1-hydroxy-ethyl)-naphthalen-2-yl]-2-hydroxymethyl-2-methyl-but-3-enoylamino}-3-methyl-butyrylamino)-propionyl]-hexahydro-pyridazine-3-carboxylic acid as a white solid. LCMS (m/z) 583.3 [M+H], Tr=1.97 min. In a 3-neck 100 mL round bottom flask was introduced 4 Å molecular sieves, 2-methyl-6-nitrobenzoic anhydride (50 mg, 0.145 mmol), N,N-dimethylaminopyridine (53.1 mg, 0.435 mmol) and 1,2-dichloroethane (20 mL). The mixture was maintained at 50° C. while a solution of (S)-1-[(S)-2-((S)-2-{(E)-(R)-4-[7-((R)-1-hydroxy-ethyl)-naphthalen-2-yl]-2-hydroxymethyl-2-methyl-but-3-enoylamino}-3-methyl-butyrylamino)-propionyl]-hexahydro-pyridazine-3-carboxylic acid in N,N-dimethylformamide (1.5 mL) was added via syringe pump over 2 h. The flask was rinsed with N,N-dimethylformamide (1.5 mL) which was then added at the same rate to the reaction mixture. After stirring at 50° C. for 2 h, 2-methyl-6-nitrobenzoic anhydride (50 mg, 0.145 mmol) and N,N-dimethylaminopyridine (53.1 mg, 0.435 mmol) were added. After stirring at 50° C. for 1 h, the heating was stopped and the reaction was allowed to stand at room temperature overnight. The volatiles were removed in vacuo and the residual N,N-dimethylformamide was azeotroped off with toluene. The residue was partitioned between ethyl acetate and hydrochloric acid (1 M). The organics were then washed with a saturated solution of sodium bicarbonate, dried over anhydrous sodium sulfate, filtered and the volatiles were removed in vacuo. The residue was first purified by silica gel chromatography using a 10 g Isolute cartridge eluted with ethyl acetate then by reverse phase preparative HPLC to provide compound 104 (2.9 mg, 8.8%) as a white solid and compound 105 (3.7 mg) as a white solid.

Example 104, Compound 104. $^1$H NMR (300 MHz, $CD_3OD$) δ 0.96 (d, J=6.7 Hz, 3H), 1.01 (d, J=6.7 Hz, 3H), 1.50 (s, 3H), 1.61-1.81 (m, 7H), 1.86-2.03 (m, 3H), 2.67-2.79 (m, 1H), 3.69 (d, J=10.9 Hz, 1H), 3.74-3.85 (m, 2H), 4.32-4.44 (m, 2H), 4.63 (d, J=12.5 Hz, 1H), 5.64 (q, J=7.1 Hz, 1H), 6.02 (q, J=6.5 Hz, 1H), 6.25, 6.46 (ABq, $J_{AB}$=16.5

Hz, 2H), 7.36 (dd, J=8.5, 1.8 Hz, 1H), 7.49 (s, 1H), 7.60 (d, J=8.7 Hz, 1H), 7.75-7.85 (m, 3H). LCMS (m/z) 565.3 [M+H], Tr=2.31 min.

Compound 105. $^1$H NMR (300 MHz, $CD_3OD$) δ 0.84 (d, J=6.9 Hz, 3H), 0.96 (d, J=6.9 Hz, 3H), 1.33 (d, J=7.1 Hz, 3H), 1.52 (s, 3H), 1.64-1.78 (m, 5H), 2.08-2.19 (m, 1H), 2.29 (s, 3H), 2.37 (app sextet, J=6.7 Hz, 1H), 2.81-2.94 (m, 1H), 3.52-3.62 (m, 1H), 4.21-4.31 (m, 1H), 4.36-4.44 (m, 2H), 4.62-4.77 (m, 2H), 5.20 (d, J=10.9 Hz, 1H), 6.35 (q, J=6.5 Hz, 1H), 6.77 (d, J=16.5 Hz, 1H), 7.04 (d, J=16.5 Hz, 1H), 7.52-7.62 (m, 2H), 7.66 (d, J=7.3 Hz, 1H), 7.76 (dd, J=8.7, 1.3 Hz, 1H), 7.83-7.95 (m, 4H), 8.03 (d, J=8.0 Hz, 1H). LCMS (m/z) 728.4 [M+H], Tr=3.08 min.

Example 106

Compound 106

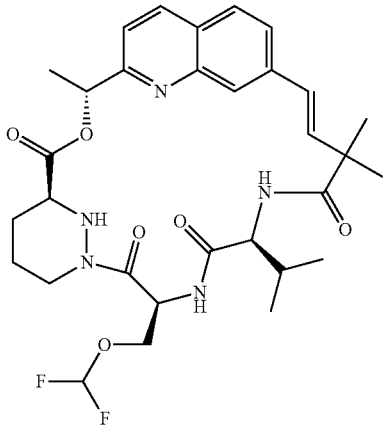

Compound 106a.
(S)-2-Dibenzylamino-3-hydroxy-propionic acid benzyl ester

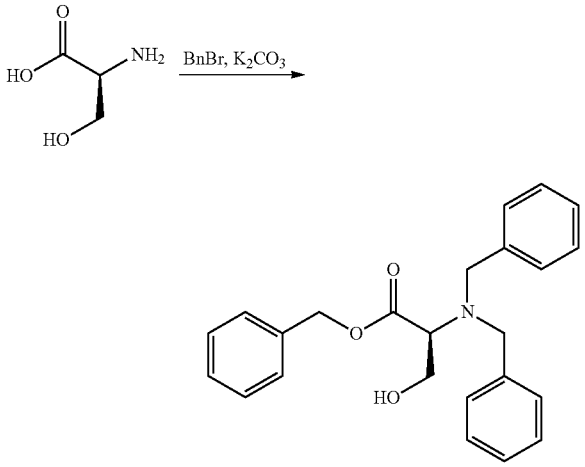

A solution of L-serine (2.1 g, 20 mmol) in acetonitrile/water (52 mL, 25:1) was added to solid potassium carbonate (13.8 g, 100 mmol) and the mixture was treated with benzyl bromide (8.92 mL, 75 mmol). After stirring for 20 h at 55° C. the mixture was cooled to room temperature, filtered, diluted with ethyl acetate and the organics were washed with water, dried over anhydrous sodium sulfate, filtered and the volatiles were removed in vacuo. The residue was purified by silica gel chromatography eluting with a stepwise gradient of iso-hexanes/ethyl acetate 1:0 to 4:1 to afford the title compound (3.9 g, 52%) as a pale yellow oil. $^1$H NMR (300 MHz, $CDCl_3$) δ 2.52 (dd, J=7.3, 4.5 Hz, 1H), 3.61 (d, J=7.6 Hz, 1H), 3.67 (d, J=13.6 Hz, 2H), 3.75-3.85 (m, 2H), 3.92 (d, J=13.6 Hz, 2H), 5.23, 5.32 (ABq, $J_{AB}$=12.0 Hz, 2H), 7.22-7.37 (m, 10H), 7.38-7.48 (m, 5H). LCMS (m/z) 376.2 [M+H], Tr=3.25 min.

Compound 106b.
(S)-2-Dibenzylamino-3-difluoromethoxy-propionic acid benzyl ester

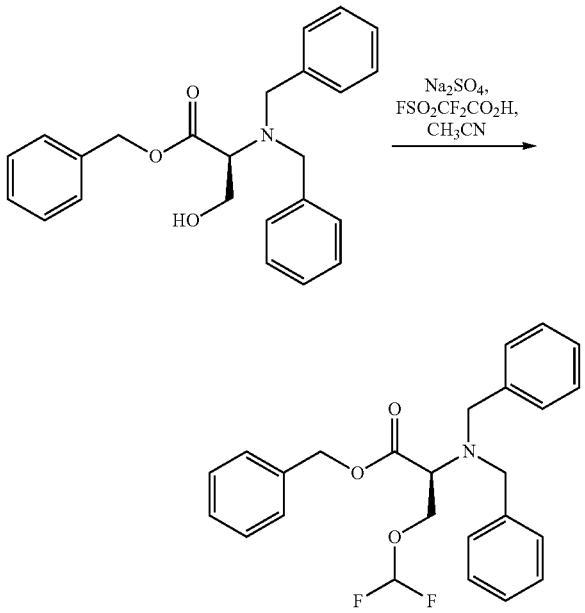

A solution of (S)-2-dibenzylamino-3-hydroxy-propionic acid benzyl ester (4.9 g, 13.1 mmol) in acetonitrile (50 mL) was treated with anhydrous sodium sulfate (466 mg, 3.28 mmol) and warmed to 40° C. Difluoro(fluorosulfonyl)acetic acid (1.62 mL, 19.7 mmol) was then added over 90 minutes using a syringe pump. After the end of addition, the volatiles were removed in vacuo and the residue was purified by silica gel chromatography using a gradient of iso-hexanes/ethyl acetate 1:0 to 95:5 to provide (760 mg, 14%) as a pale yellow oil. $^1$H NMR (300 MHz, $CDCl_3$) δ 3.64 (d, J=13.8 Hz, 2H), 3.73 (app t, J=6.5 Hz, 1H), 3.87 (d, J=13.8 Hz, 2H), 4.09 (dd, J=10.3, 6.2 Hz, 1H), 4.22 (dd, J=10.3, 6.9 Hz, 1H), 5.21, 5.32 (ABq, $J_{AB}$=12.3 Hz, 2H), 6.16 (t, J=74.7 Hz, 1H), 7.21-7.37 (m, 10H), 7.38-7.47 (m, 5H). LCMS (m/z) 426.1 [M+H], Tr=3.76 min.

Compound 106c. (S)-2-tert-Butoxycarbonylamino-3-difluoromethoxy-propionic acid

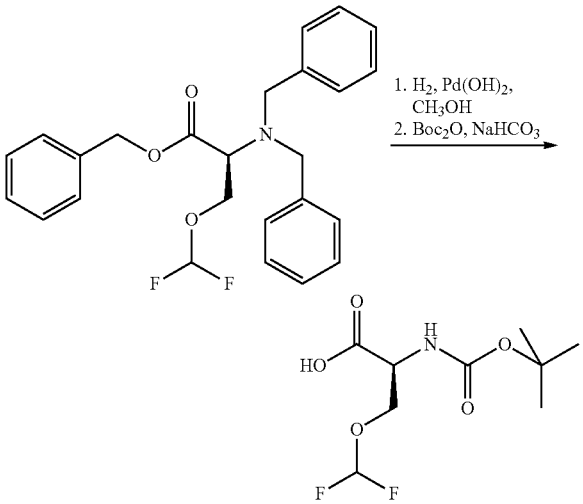

A solution of (S)-2-dibenzylamino-3-difluoromethoxy-propionic acid benzyl ester (760 1.79 mmol) in methanol (10 mL) was treated with palladium hydroxide on carbon (20 wt % loading, wet support, 30 mg) and the atmosphere was purged of oxygen, flushed with nitrogen and the reaction was stirred under an atmosphere of hydrogen for 16 h. The mixture was filtered over Celite and fresh palladium hydroxide on carbon (20 wt % loading, wet support, 30 mg) was added. The atmosphere was purged of oxygen, flushed with nitrogen and the reaction was stirred under an atmosphere of hydrogen for 40 h. The mixture was filtered over Celite and the volatiles were removed in vacuo to provide a 1:1 mixture of (S)-2-amino-3-difluoromethoxy-propionic acid and (S)-2-benzylamino-3-difluoromethoxy-propionic acid (208 mg) as a grey solid which was then dissolved in methanol/water (10 mL, 4:1) and the mixture was subsequently treated with sodium bicarbonate (225 mg, 2.68 mmol) and di-tert-butyl-dicarbonate (351 mg, 1.61 mmol). After stirring at room temperature for 16 h, the volatiles were removed in vacuo and the residue was partitioned between ethyl acetate and hydrochloric acid (1 M). The aqueous layer was extracted with ethyl acetate. The organics were combined, dried over anhydrous sodium sulfate, filtered and the volatiles were removed in vacuo to provide the title compound (170 mg, 50%) as a yellow oil and as a complex mixture of rotamers. LCMS (m/z) 254.0 [M−H], Tr=2.59 min.

Compound 106d. (S)-1-((S)-2-tert-Butoxycarbonylamino-3-difluoromethoxy-propionyl)-hexahydro-pyridazine-3-carboxylic acid 2,2,2-trichloro-ethyl ester

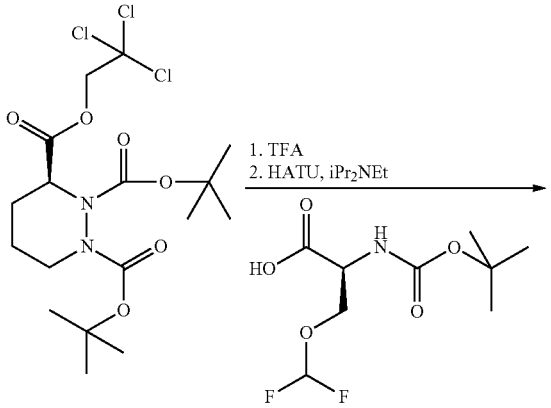

-continued

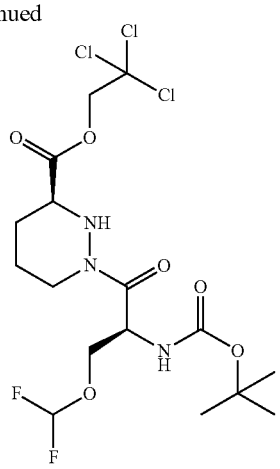

A cooled (0° C.) solution of (S)-tetrahydro-pyridazine-1,2,3-tricarboxylic acid 1,2-di-tert-butyl ester 3-(2,2,2-trichloro-ethyl)ester (923 mg, 2.0 mmol) in dichloromethane (3 mL) was treated with trifluoroacetic acid (3 mL). After stirring at room temperature for 1.5 h, the volatiles were removed in vacuo and residual trifluoroacetic acid was azeotroped off with toluene. The residue was combined with (S)-2-tert-butoxycarbonylamino-3-difluoromethoxy-propionic acid (260 mg, 1.02 mmol) and dissolved in anhydrous acetonitrile (10 mL). The cooled (0° C.) mixture was subsequently treated with 1-[bis(dimethylamino)methylene]-1H-1,2,3-triazolo[4,5-b]pyridinium 3-oxide hexafluorophosphate (543 mg, 1.43 mmol) and N,N-diisopropylethylamine (0.71 mL, 4.08 mmol). After stirring at room temperature for 3 days, the volatiles were removed in vacuo and the residue was partitioned between ethyl acetate and water. The organics were separated, dried over anhydrous sodium sulfate, filtered and the volatiles were removed in vacuo. The residue was purified by silica gel chromatography eluting with a stepwise gradient of isohexanes/ethyl acetate 1:0 to 7:3 to provide the title compound (143 mg, 28%) as a pale Greene gum and as a complex mixture of rotamers. LCMS (m/z) 498.0, 500.0 [M+H], Tr=2.91 min.

Compound 106e. (S)-1-[(S)-2-((S)-2-tert-Butoxycarbonylamino-3-methyl-butyrylamino)-3-difluoromethoxy-propionyl]-hexahydro-pyridazine-3-carboxylic acid 2,2,2-trichloro-ethyl ester

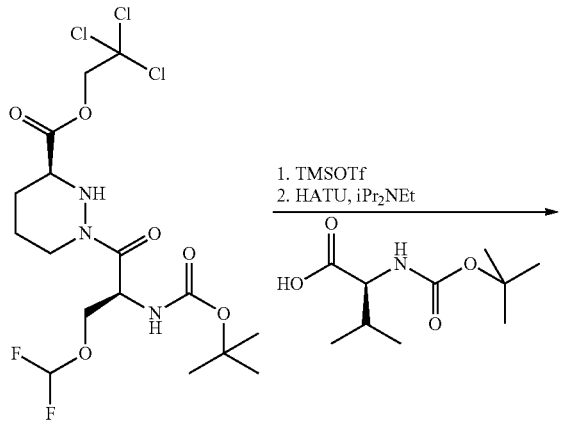

-continued

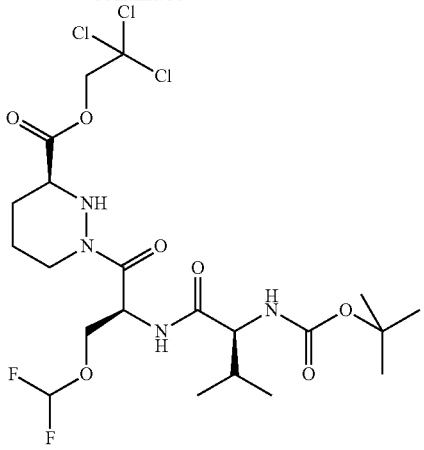

A cooled (0° C.) solution of (S)-1-((S)-2-tert-butoxycarbonylamino-3-difluoromethoxy-propionyl)-hexahydro-pyridazine-3-carboxylic acid 2,2,2-trichloro-ethyl ester (143 mg, 0.287 mmol) in dichloromethane (5 mL) was treated with trimethylsilyl trifluoromethanesulfonate (72 μL, 0.431 mmol). After stirring at 0° C. for 30 minutes the reaction mixture was treated with N,N-diisopropylethylamine (0.2 mL, 1.15 mmol) and the volatiles were removed in vacuo to provide a brown solid which was then dissolved in anhydrous acetonitrile (5 mL) and this mixture was subsequently treated with N-(tert-butoxycarbonyl)-L-valine (75 mg, 0.344 mmol), 1-[bis(dimethylamino)methylene]-1H-1,2,3-triazolo[4,5-b]pyridinium 3-oxide hexafluorophosphate (153 mg, 0.402 mmol) and N,N-diisopropylethylamine. After stirring at room temperature for 16 h, the volatiles were removed in vacuo and the residue was partitioned between ethyl acetate and water. The organics were dried over anhydrous sodium sulfate, filtered and the volatiles were removed in vacuo. The residue was purified by silica gel chromatography eluting with a stepwise gradient of iso-hexanes/ethyl acetate 1:0 to 1:1 to provide the title compound (105 mg, 61%) as a pale yellow gum and as a complex mixture of rotamers. LCMS (m/z) 597.0, 599.0 [M+H], Tr=3.18 min.

Compound 106f. (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-difluoromethoxy-propionyl]-hexahydro-pyridazine-3-carboxylic acid 2,2,2-trichloro-ethyl ester

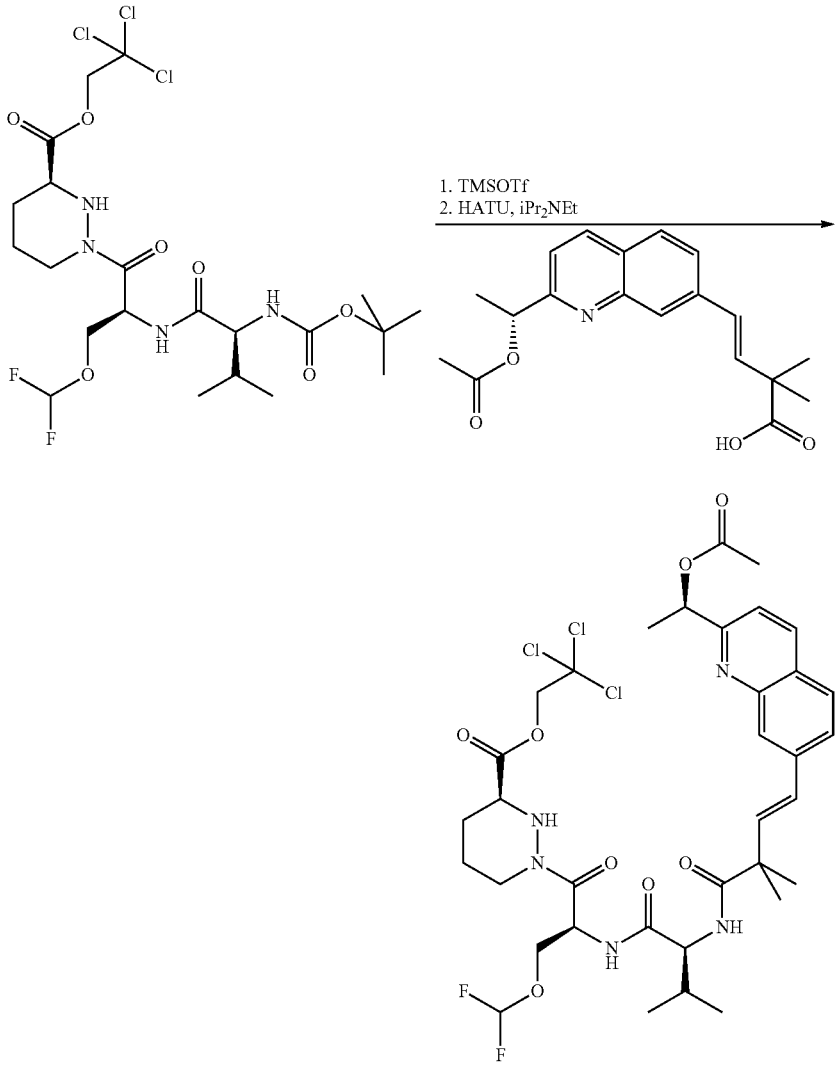

Compound 106f was prepared in the same manner as compound 82c using (S)-1-[(S)-2-((S)-2-tert-butoxycarbonylamino-3-methyl-butyrylamino)-3-difluoromethoxy-propionyl]-hexahydro-pyridazine-3-carboxylic acid 2,2,2-trichloro-ethyl ester instead of (S)-1-[(S)-2-((S)-2-tert-butoxycarbonylamino-3-methyl-butyrylamino)-3-(tert-butyl-diphenyl-silanyloxy)-propionyl]-hexahydro-pyridazine-3-carboxylic acid 2,2,2-trichloro-ethyl ester in 41% yield. $^1$H NMR (300 MHz, $CDCl_3$) δ 0.81-0.98 (m, 6H), 1.17 (s, 3H), 1.22 (s, 3H), 1.34-1.60 (m, 4H), 1.68 (d, J=6.7 Hz, 3H), 1.71-1.81 (m, 1H), 2.17 (s, 3H), 2.90-3.05 (m, 1H), 3.66-3.81 (m, 1H), 3.92 (d, J=10.7 Hz, 1H), 4.05-4.20 (m, 1H), 4.21-4.39 (m, 3H), 4.69 (d, J=12.0 Hz, 1H), 4.95 (d, J=12.0 Hz, 1H), 5.46-5.54 (m, 1H), 6.06 (q, J=6.7 Hz, 1H), 6.21 (t, J=73.8 Hz, 1H), 6.34 (d, J=8.2 Hz, 1H), 6.63, 6.79 (ABq, $J_{AB}$=16.0 Hz, 2H), 6.95 (d, J=7.6 Hz, 1H), 7.43 (d, J=8.5 Hz, 1H), 7.66 (dd, J=8.5, 1.3 Hz, 1H), 7.76 (d, J=8.5 Hz, 1H), 8.05 (s, 1H), 8.12 (d, J=8.5 Hz, 1H). LCMS (m/z) 806.4, 808.4 [M+H], Tr=3.19 min.

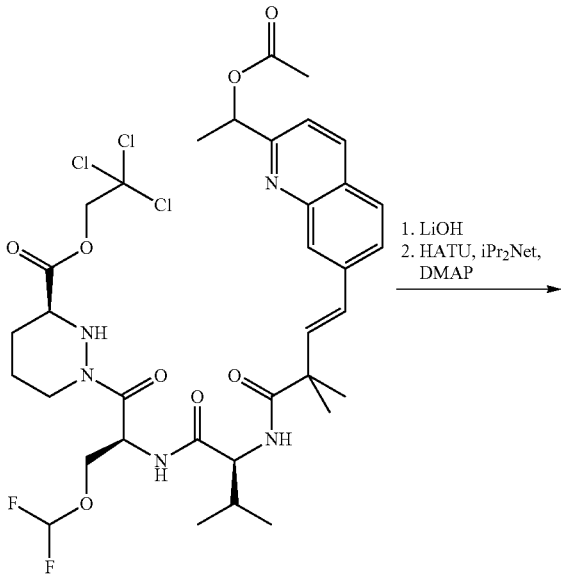

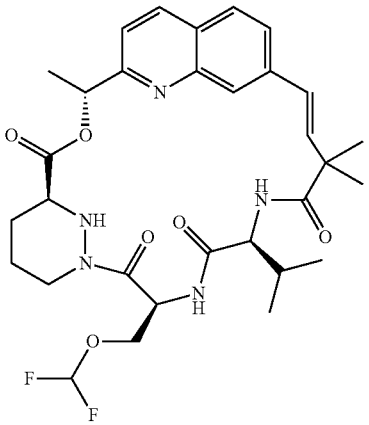

Compound 106 was prepared in the same manner as compound 82d using (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-difluoromethoxy-propionyl]-hexahydro-pyridazine-3-carboxylic acid 2,2,2-trichloro-ethyl ester instead of (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-(tert-butyl-diphenyl-silanyloxy)-propionyl]-hexahydro-pyridazine-3-carboxylic acid 2,2,2-trichloro-ethyl ester in 9% yield. $^1$H NMR (300 MHz, $CDCl_3$) δ 0.77-0.91 (m, 1H), 0.96 (d, J=6.7 Hz, 3H), 1.02 (d, J=6.7 Hz, 3H), 1.17-1.36 (m, 1H), 1.41 (s, 3H), 1.49 (s, 3H), 1.65-1.79 (m, 4H), 1.88-2.13 (m, 3H), 2.60-2.74 1H), 3.56-3.82 (m, 2H), 4.20-4.35 (m, 2H), 4.48-4.60 (m, 2H), 5.94 (q, J=6.7 Hz, 1H), 5.99-6.08 (m, 1H), 6.16 (d, J=9.1 Hz, 1H), 6.33, 6.43 (ABq, $J_{AB}$=16.5 Hz, 2H), 6.47 (t, J=73.8 Hz, 1H), 6.52-6.60 (m, 1H), 7.58 (d, J=8.5 Hz, 1H), 7.73 (d, J=8.5 Hz, 1H), 7.77 (s, 1H), 8.08 (d, J=8.5 Hz, 1H). LCMS (m/z) 616.3 [M+H], Tr=2.63 min.

Example 107

Compound 107

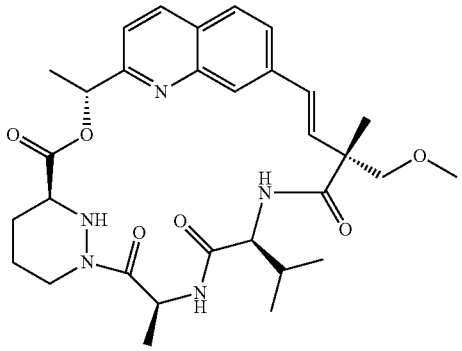

Compound 107a. (R)-4-Isopropyl-3-((R)-2-methoxymethyl-2-methyl-but-3-enoyl)-oxazolidin-2-one

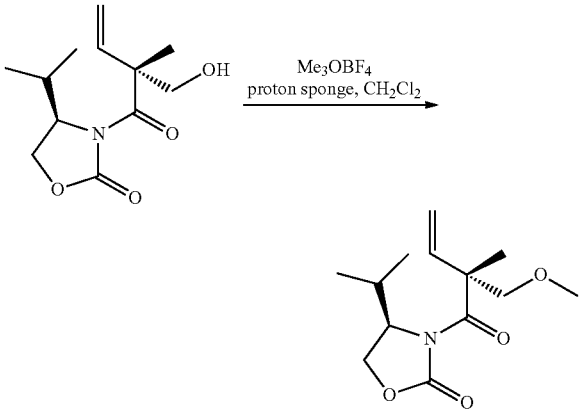

To a stirred solution of (R)-3-((R)-2-hydroxymethyl-2-methyl-but-3-enoyl)-4-isopropyl-oxazolidin-2-one (724 mg, 3.00 mmol) and N,N,N',N'-tetramethyl-1,8-naphthalenediamine (2.57 g, 11.0 mmol) in dichloromethane (15 mL) at 0° C. under nitrogen was added trimethyloxonium tetrafluoroborate (1.33 g, 9.00 mmol). The reaction was stirred at 0° C. for 15 minutes and then 4.5 h at ambient temperature. Saturated ammonium chloride solution was added and the mixture diluted with dichloromethane. The aqueous layer was separated and extracted with dichloromethane and the combined organic extracts washed with ammonium chloride solution, dried over anhydrous sodium sulfate filtered and evaporated. The residue was suspended in diethyl ether and filtered, the solids were washed with diethyl ether and the filtrate evaporated. The residue was purified by silica gel chromatography using a gradient of iso-hexanes/ethyl acetate 1:0 to 4:1 followed by purification on an SCX cartridge eluting with methanol to give the title compound (263 mg, 34%) as a colourless oil. $^1$H NMR (300 MHz, $CDCl_3$) δ 0.91 (app t, J=7.0 Hz, 6H), 1.50 (s, 3H), 2.32-2.43 (m, 1H), 3.35 (s, 3H), 3.46 (d, J=8.7 Hz, 1H), 4.19 (app dd, J=9.1, 3.6 Hz, 1H), 4.27 (app t, J=8.6 Hz, 1H), 4.50-4.57 (m, 1H), 5.00 (d, J=17.9 Hz, 1H), 5.12 (d, J=10.7 Hz, 1H), 6.19 (dd, J=17.9, 10.7 Hz, 1H). LCMS (m/z) 256.2 [M+H], Tr=2.53 min.

Compound 107b: Acetic acid (R)-1-{7-[(E)-(R)-4-((R)-4-isopropyl-2-oxo-oxazolidin-3-yl)-3-methoxymethyl-3-methyl-4-oxo-but-1-enyl]-quinolin-2-yl}-ethyl ester

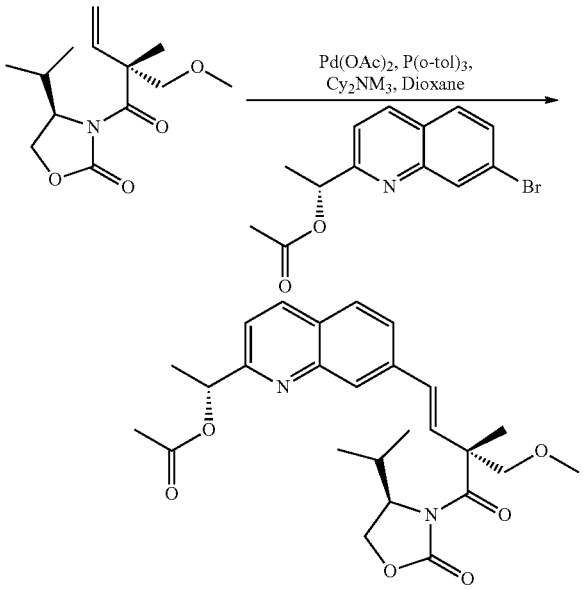

To a mixture of (R)-4-isopropyl-3-((R)-2-methoxymethyl-2-methyl-but-3-enoyl)-oxazolidin-2-one (226 mg, 0.769 mmol), acetic acid (R)-1-(7-bromo-quinolin-2-yl)-ethyl ester (196 mg, 0.666 mmol), palladium(II) acetate (35 mg, 0.154 mmol) and tri(o-tolyl)phosphine (47 mg, 0.154 mmol) were suspended in anhydrous 1,4-dioxane (15 mL) and N,N-dicyclohexylmethylamine (222 mg, 244 μL, 1.14 mmol) was added. The mixture was stirred at reflux for 90 minutes under nitrogen and more palladium(II) acetate (35 mg, 0.154 mmol) and tri(o-tolyl)phosphine (47 mg, 0.154 mmol) were added and the mixture heated for 2 h. More palladium(II) acetate (18 mg, 0.077 mmol) and tri(o-tolyl) phosphine (24 mg, 0.077 mmol) were added and heated continued for 45 minutes. The reaction was allowed to cool and diluted with ethyl acetate and washed with saturated ammonium chloride solution (2×), saturated brine, dried over anhydrous sodium sulfate, filtered and evaporated. The residue was purified by silica gel chromatography using a gradient of iso-hexanes/ethyl acetate 4:1 to 7:3 to give the title compound (227 mg, 73%) as a yellow foam. $^1$H NMR (300 MHz, $CDCl_3$) δ 0.90 (d, J=7.1 Hz, 3H), 0.94 (d, J=7.1 Hz, 3H), 1.64 (s, 3H), 1.68 (d, J=6.7 Hz, 3H), 2.18 (s, 3H), 2.36-2.48 (m, 1H), 3.40 (s, 3H), 3.59 (d, J=8.9 Hz, 1H), 4.19 (dd, J=9.1, 3.1 Hz, 2H), 4.23-4.32 (m, 2H), 4.55-4.61 (m, 1H), 6.05 (q, J=6.7 Hz, 1H), 6.49 (d, J=16.3 Hz, 1H), 6.79 (d, J=16.3 Hz, 1H), 7.42 (d, J=8.5 Hz, 1H), 7.65 (dd, J=8.5, 1.5 Hz, 1H), 7.73 (d, J=8.5 Hz, 1H), 7.94 (s, 1H), 8.11 (d, J=8.5 Hz, 1H). LCMS (m/z) 469.2 [M+H], Tr=2.91 min.

Compound 107c. (E)-(R)-4-[2-((R)-1-Hydroxy-ethyl)-quinolin-7-yl]-2-methoxymethyl-2-methyl-but-3-enoic acid

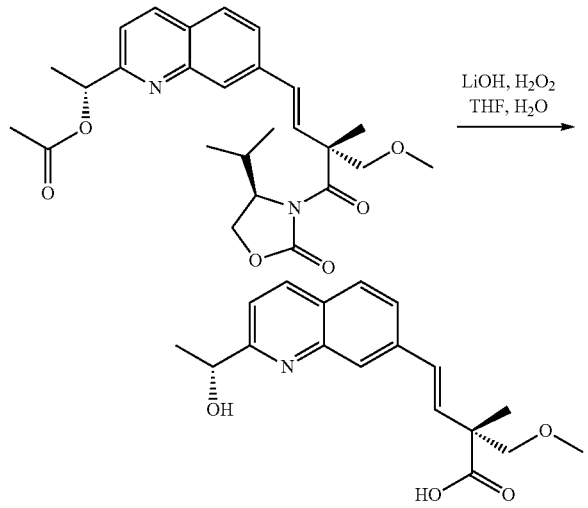

A stirred solution of acetic acid (R)-1-{7-[(E)-(R)-4-((R)-4-isopropyl-2-oxo-oxazolidin-3-yl)-3-methoxymethyl-3-methyl-4-oxo-but-1-enyl]-quinolin-2-yl}-ethyl ester (183 mg, 0.391 mmol) in tetrahydrofuran (4 mL) and water (2 mL) was cooled to 0° C. and hydrogen peroxide (30% in water, 222 mg, 201 μL, 1.96 mmol.) and lithium hydroxide.monohydrate (49 mg, 1.17 mmol) were added. After a minute the reaction mixture was allowed to warm to ambient temperature and stirred for 4 h after which it was cooled to 0° C. Sodium metabisulfite was added until the solution was saturated and the reaction mixture stirred for 15 minutes and then acidified to pH 1 with hydrochloric acid (2 M) and extracted with dichloromethane (3×). The aqueous layer was saturated with sodium chloride and extracted with 1:9 methanol:dichloromethane and the combined organics dried over anhydrous sodium sulfate, filtered and evaporated. The residue was purified by SCX cartridge eluting with methanol and then methanolic ammonia and the basic fraction collected and evaporated to give the title compound (101 mg, 82%) as a yellow film. $^1$H NMR (300 MHz, $CDCl_3$) δ 1.53 (s, 3H), 1.60 (d, J=6.5 Hz, 3H), 3.51 (s, 3H), 3.62 (d, J=8.9 Hz, 1H), 3.75 (d, J=9.1 Hz, 1H), 5.06 (q, J=6.5 Hz, 1H), 6.64, 6.78 (ABq, J=16.5 Hz, 2H), 7.34 (d, J=8.3 Hz, 1H), 7.64 (dd, J=8.5, 1.5 Hz, 1H), 7.78 (d, J=8.5 Hz, 1H), 8.06 (s, 1H), 8.13 (d, J=8.5 Hz, 1H). LCMS (m/z) 316.2 [M+H], Tr=1.28 min.

Compound 107d. (S)-1-[(S)-2-((S)-2-{(E)-(R)-4-[2-((R)-1-Hydroxy-ethyl)-quinolin-7-yl]-2-methoxymethyl-2-methyl-but-3-enoylamino}-3-methyl-butyrylamino)-propionyl]-hexahydro-pyridazine-3-carboxylic acid 2,2,2-trichloro-ethyl ester

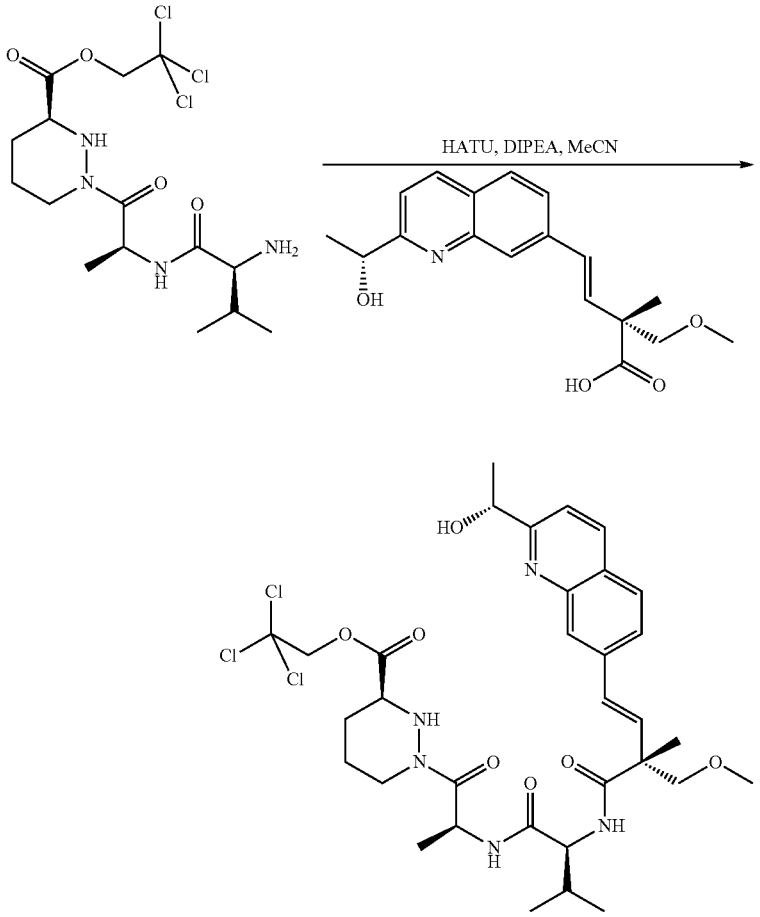

To freshly prepared (S)-1-[(S)-2-((S)-2-amino-3-methyl-butyrylamino)-propionyl]-hexahydro-pyridazine-3-carboxylic acid 2,2,2-trichloro-ethyl ester (139 mg, 0.321 mmol) in dichloromethane (25 mL) was added (E)-(R)-4-[2-((R)-1-hydroxy-ethyl)-quinolin-7-yl]-2-methoxymethyl-2-methyl-but-3-enoic acid (101 mg, 0.321 mmol) and the mixture was evaporated. The residue was dissolved in anhydrous acetonitrile (6.4 mL) and the mixture cooled to 0° C. with stirring under nitrogen. 1-[Bis(dimethylamino)methylene]-1H-1,2,3-triazolo[4,5-b]pyridinium 3-oxide hexafluorophosphate (146 mg, 0.38 mmol) and N,N-diisopropylethylamine (168 μL, 0.963 mmol) were added and the reaction mixture stirred for 5 minutes and then allowed to warm to ambient temperature. The mixture was stirred for 19 h and evaporated and the residue dissolved in dichloromethane and washed sequentially with saturated sodium bicarbonate solution, water, saturated ammonium chloride solution, brine then was dried over anhydrous sodium sulfate, filtered and evaporated. The residue was purified on silica eluting with ethyl acetate to afford the title compound (123 mg, 53%) as a yellow gum. $^1$H NMR (300 MHz, $CDCl_3$) δ 0.91 (d, J=6.7 Hz, 3H), 0.97 (d, J=6.7 Hz, 3H), 1.33 (d, J=6.7 Hz, 3H), 1.45 (s, 3H), 1.59 (d, J=6.5 Hz, 3H), 1.67-1.78 (m, 2H), 1.90-2.00 (m, 1H), 2.15-2.33 (m, 2H), 2.82-2.91 (m, 1H), 3.47-3.54 (m, 1H), 3.51 (s, 3H), 3.60 (d, J=9.2 Hz, 1H), 3.68-3.76 (m, 1H), 3.73 (d, J=11.4 Hz, 1H), 3.85 (d, J=9.2 Hz, 1H), 4.33-4.45 (m, 2H), 4.72 (d, J=12.0 Hz, 1H), 4.96 (d, J=12.0 Hz, 1H), 4.99-5.08 (m, 2H), 5.27-5.37 (m, 1H), 6.70 (ABq, J=16.5 Hz, 1H), 6.80 (d, J=16.5 Hz, 1H), 6.80 (d, J=8.0 Hz, 1H), 7.31 (d, J=8.3 Hz, 1H), 7.66 (dd, J=8.6, 1.2 Hz, 1H), 7.77 (d, J=8.3 Hz, 1H), 8.01 (s, 1H), 8.12 (d, J=8.7 Hz, 1H). LCMS (m/z) 728.3, 730.3 [M+H], Tr=2.25 min.

Compound 107

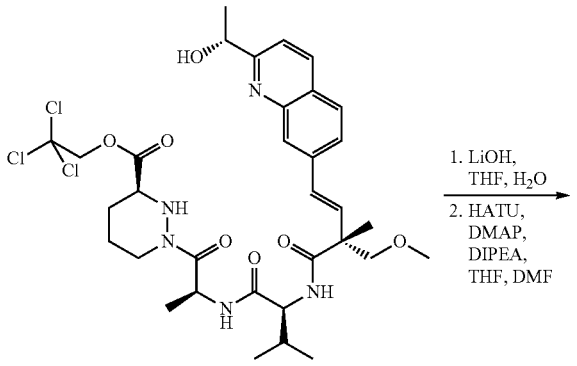

-continued

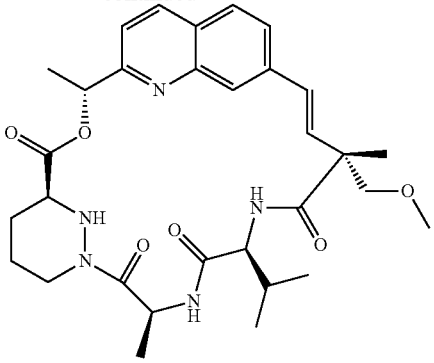

To a stirred solution of (S)-1-[(S)-2-((S)-2-{(E)-(R)-4-[2-((R)-1-hydroxy-ethyl)-quinolin-7-yl]-2-methoxymethyl-2-methyl-but-3-enoylamino}-3-methyl-butyrylamino)-propionyl]-hexahydro-pyridazine-3-carboxylic acid 2,2,2-trichloro-ethyl ester (23 mg, 0.032 mmol) in tetrahydrofuran (3 mL) was added lithium hydroxide monohydrate (2 mg, 0.047 mmol) and water (0.75 mL) and the reaction mixture stirred for 30 minutes. Hydrochloric acid (2 M, 0.032 mL) was added the mixture stirred for 5 minutes then evaporated and residual trichloroethanol was azeotroped off with toluene. The residue was dissolved in tert-butanol and acetonitrile and evaporated (2×) then azeotroped with acetonitrile/toluene (2×). The residue was dissolved in tetrahydrofuran (10.5 mL) and cooled to 0° C. with stirring. 1-[Bis(dimethylamino)methylene]-1H-1,2,3-triazolo[4,5-b]pyridinium 3-oxide hexafluorophosphate (14 mg, 0.038 mmol), 4-dimethylaminopyridine (0.4 mg, 0.003 mmol) and N,N-diisopropylethylamine (10 μL, 0.063 mmol) were added and the reaction stirred for 10 minutes. N,N-Dimethylformamide (1 mL) was added and the reaction was allowed to warm to ambient temperature over 5 h. the mixture was evaporated and then purified by reverse phase preparative HPLC using a gradient of acetonitrile/water 4:1 to 1:4 to afford the title compound (6.3 mg, 35%) as a white solid. $^1$H NMR (300 MHz, $CD_3OD$) δ 0.97 (d, J=6.7 Hz, 3H), 0.98 (d, J=6.7 Hz, 3H), 1.54 (s, 3H), 1.66 (d, J=7.1 Hz, 3H), 1.67-1.72 (m, 2H), 1.73 (d, J=6.7; H, 3H), 1.87-2.04 (m, 3H), 2.69-2.80 (m, 1H), 3.39 (s, 3H), 3.46 (d, J=8.9 Hz, 1H), 3.75 (d, J=8.9 Hz, 1H), 3.78-3.86 (m, 1H), 4.27 (d, J=10.5 Hz, 1H), 4.36-4.47 (m, 1H), 5.74 (q, J=7.1 Hz, 1H), 5.92 (q, J=6.7 Hz, 1H), 6.37, 6.40 (ABq, $J_{AB}$=16.6 Hz, 2H), 7.41 (d, J=8.5 Hz, 1H), 7.66 (dd, J=8.7, 1.5 Hz, 1H), 7.76 (s, 1H), 7.82 (d, J=8.7 Hz, 1H), 8.22 (d, J=8.5 Hz, 1H). LCMS (m/z) 580.3 [M+H], Tr=2.22 min.

Examples 108 and 109

Compounds 108 and 109

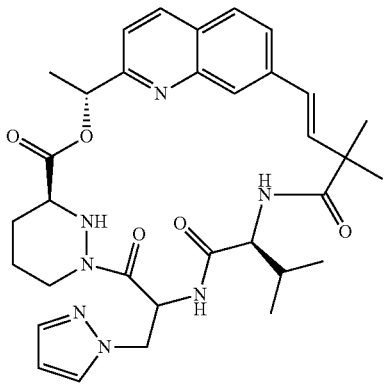

Compound 108a: (S)-1-((S)-2-tert-Butoxycarbonylamino-3-pyrazol-1-yl-propionyl)-hexahydro-pyridazine-3-carboxylic acid 2,2,2-trichloro-ethyl ester

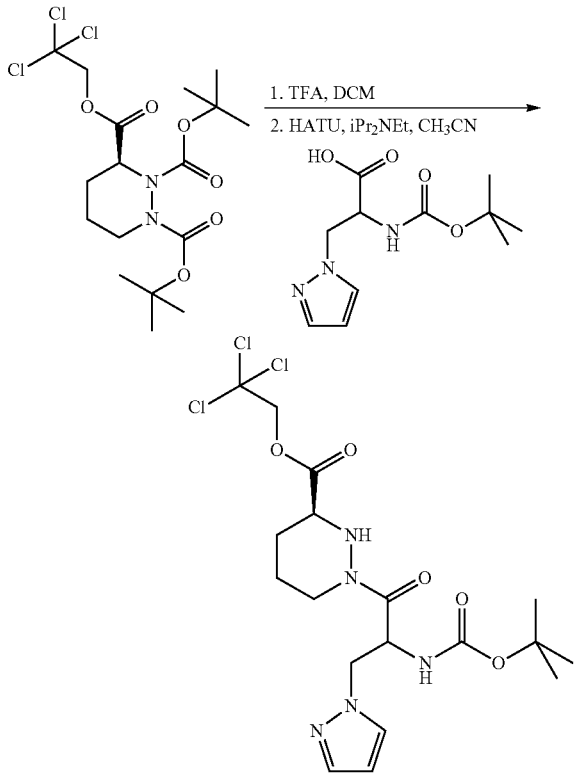

To (S)-tetrahydro-pyridazine-1,2,3-tricarboxylic acid 1,2-di-tert-butyl ester 3-(2,2,2-trichloro-ethyl)ester (909 mg, 1.97 mmol) in anhydrous dichloromethane (6 mL) at room temperature and under an atmosphere of nitrogen was added trifluoroacetic acid (6 mL, 173 mmol). The solution was warmed to room temperature and stirred for 16 h. The reaction was concentrated in vacuo and the residue co-evaporated from toluene (3×). The resulting brown viscous oil was dissolved in anhydrous acetonitrile (2 mL) and added to a solution of L-N-Boc-3-pyrazol-1-yl-alanine (500 mg, 1.97 mmol), N,N-diisopropylethylamine (1.4 mL, 7.87 mmol) and 2-(1H-7-azabenzotriazol-1-yl)-1,1,3,3-tetramethyl uronium hexafluorophosphate methanaminium (747 mg, 1.97 mmol) in anhydrous acetonitrile (10 mL) that had been previously stirred at 0° C. for 20 minutes. The reaction was warmed to room temperature and stirred for 16 h. The reaction was cooled to 0° C. diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:1 then 2:1 to give the title compound (999 mg, 95%) as a white foam, as a 2:1 mixture of diastereoisomers. LCMS (m/z) 500.1 [M+H], Tr=2.71 min.

Compound 108b: (S)-1-[(S)-2-((S)-2-tert-Butoxy-carbonylamino-3-methyl-butyrylamino)-3-pyrazol-1-yl-propionyl]-hexahydro-pyridazine-3-carboxylic acid 2,2,2-trichloro-ethyl ester

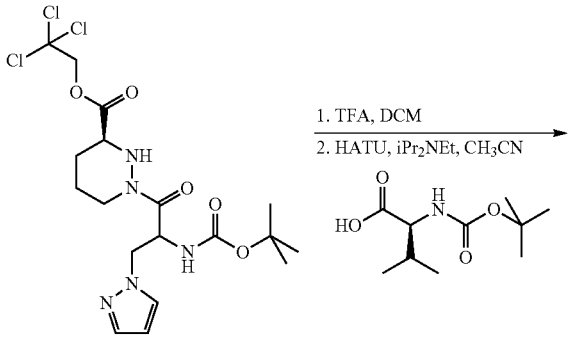

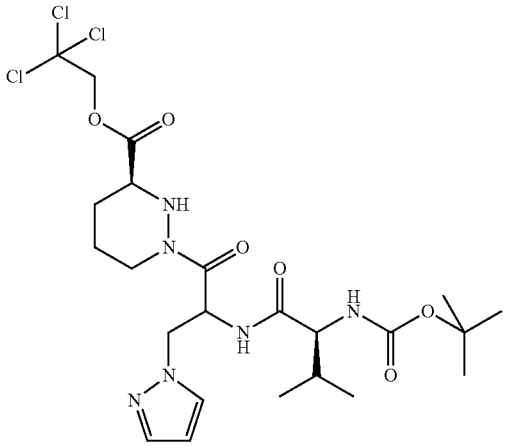

To (S)-1-((S)-2-tert-butoxycarbonylamino-3-pyrazol-1-yl-propionyl)-hexahydro-pyridazine-3-carboxylic acid 2,2,2-trichloro-ethyl ester (730 mg, 1.47 mmol) in anhydrous dichloromethane (3 mL) at 0° C. and under an atmosphere of nitrogen was added trifluoroacetic acid (1.1 mL, 14.7 mmol). The reaction mixture was warmed to room temperature and stirred for 3 h before concentrating in vacuo. The residue was dissolved in anhydrous acetonitrile (7 mL) at room temperature and under an atmosphere of nitrogen was added N,N-diisopropylethylamine (1.3 mL, 7.3 mmol), N-(tert-Butoxycarbonyl)-L-valine (319 mg, 1.5 mmol) and 2-(1H-7-azabenzotriazol-1-yl)-1,1,3,3-tetramethyl uronium hexafluorophosphate methanaminium (782 mg, 2.1 mmol). Following 16 h at room temperature the reaction was cooled to 0° C., diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:2 then 1:3 to give the title compound (460 mg, 52%) as a viscous clear oil, as a 2:1 mixture of diastereoisomers. LCMS (m/z) 599.1 [M+H], Tr=2.83 min.

Compound 108c: (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-pyrazol-1-yl-propionyl]-hexahydro-pyridazine-3-carboxylic acid 2,2,2-trichloro-ethyl ester

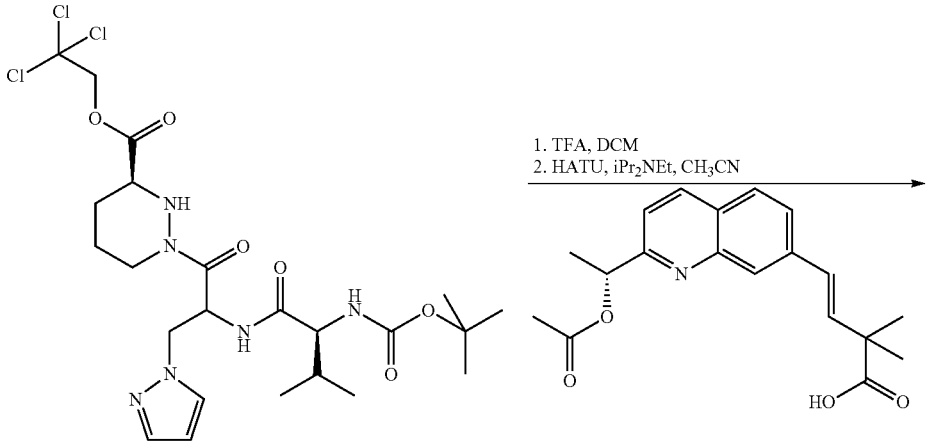

-continued

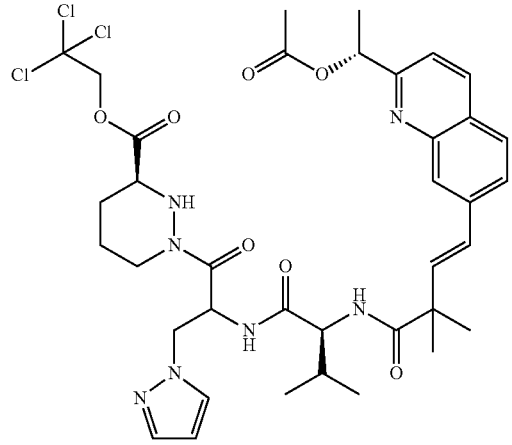

To (S)-1-[(S)-2-((S)-2-tert-butoxycarbonylamino-3-methyl-butyrylamino)-3-pyrazol-1-yl-propionyl]-hexahydro-pyridazine-3-carboxylic acid 2,2,2-trichloro-ethyl ester (450 mg, 0.75 mmol) in anhydrous dichloromethane (1 mL) at 0° C. and under an atmosphere of nitrogen was added trifluoroacetic acid (0.58 mL, 7.6 mmol). The reaction mixture was warmed to room temperature and stirred for 3 h before concentrating in vacuo and co-evaporating from toluene. This residue was dissolved in anhydrous acetonitrile (7.5 mL) and at 0° C. and under an atmosphere of nitrogen was added (E)-4-[2-((R)-1-acetoxy-ethyl)-quinolin-7-yl]-2,2-dimethyl-but-3-enoic acid (246 mg, 0.75 mmol), N,N-diisopropylethylamine (0.66 mL, 3.76 mmol) and 2-(1H-7-azabenzotriazol-1-yl)-1,1,3,3-tetramethyl uronium hexafluorophosphate methanaminium (401 mg, 1.05 mmol). The solution was warmed to room temperature and stirred for 2 h. The reaction was cooled to 0° C., diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:1 then 0:1 to give the title compound (433 mg, 72%) as a viscous clear oil, as a 2:1 mixture of diastereoisomers. LCMS (m/z)=806.3 [M+H], Tr=2.91 min.

Compound 108 and 109

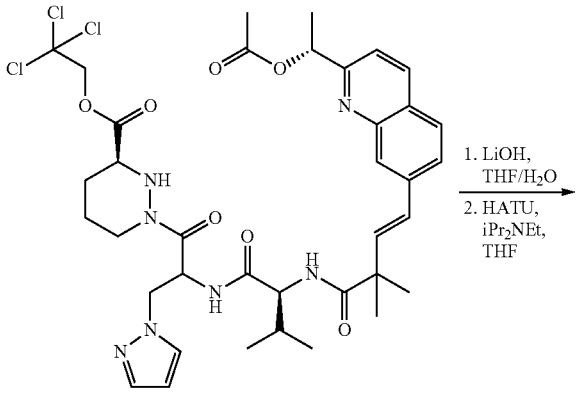

-continued

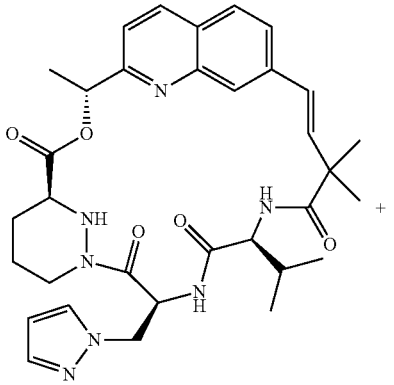

Diastereoisomer 1

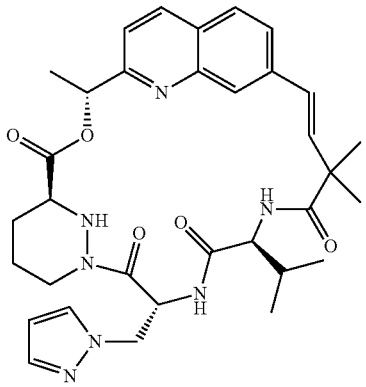

Diastereoisomer 2

To (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-pyrazol-1-yl-propionyl]-hexahydro-pyridazine-3-carboxylic acid 2,2,2-trichloro-ethyl ester (200 mg, 0.25 mmol) in tetrahydrofuran (10 mL) and water (2 mL) was added lithium hydroxide monohydrate (52 mg, 1.24 mmol) at 0° C. The reaction was stirred at 0° C. for 30 minutes and then warmed to room temperature and stirred for 3 h, before being acidified to pH 2 with 2 M hydrochloric acid. The reaction was concentrated in vacuo, followed by co-evaporation from toluene (3×) and then acetonitrile (3×).

The resulting residue was triturated with diethyl ether to yield an off white powder. This powder was dissolved in anhydrous tetrahydrofuran (200 mL) and cooled to 0° C., under an atmosphere of nitrogen. N,N-diisopropylethylamine (216 μL, 1.24 mmol), 2-(1H-7-azabenzotriazol-1-yl)-1,1,3,3-tetramethyl uronium hexafluorophosphate methanaminium (132 mg, 0.35 mmol) and 4-dimethylaminopyridine (3 mg, 0.03 mmol) were then added and the reaction warmed to room temperature and stirred for 16 h. The reaction was concentrated in vacuo. The ensuing residue was diluted with ethyl acetate and washed with 1M hydrochloric acid (1×), a saturated aqueous solution of sodium bicarbonate (2×) and brine (1×). The organic layer was then dried through a hydrophobic frit and concentrated in vacuo to yield a yellow viscous oil (189 mg). The residue was purified by preparative HPLC using and Agilent Eclipse XDB/C18 7 micron, 250×21.2 mm column to afford two diastereoisomers as white solids.

Example 108, Compound 108. First eluting Diastereoisomer 1: (20.0 mg, 13%): $^1$H NMR (300 MHz, $CD_3OD$) δ 0.92 (d, J=6.9 Hz, 3H), 0.95 (d, J=6.9 Hz, 3H), 1.34 (s, 3H), 1.49 (s, 3H), 1.59-1.73 (m, 3H), 1.75 (d, J=6.7 Hz, 3H), 1.81-1.94 (m, 3H), 2.63-2.77 (m, 1H), 3.55-3.62 (m, 1H), 4.28 (t, J=9.4 Hz, 1H), 4.32-4.41 (m, 1H), 4.59-4.78 (m, 2H), 5.93 (q, J=6.7 Hz, 1H), 6.27-6.37 (m, 4H), 7.10 (d, J=9.6 Hz, 1H), 7.41 (d, J=8.5 Hz, 1H), 7.51 (d, J=1.6 Hz, 1H), 7.65 (dd, J=8.5, 1.6 Hz, 1H), 7.71 (s, 1H), 7.81 (d, J=8.5 Hz, 1H), 8.21 (d, J=8.5 Hz, 1H), 8.40 (d, J=2.2 Hz, 1H). LCMS (m/z) 616.3 [M+H], Tr=2.17 min.

Example 109, Compound 109. Second eluting Diastereoisomer 2: (4.0 mg, 3%): $^1$H NMR (300 MHz, $CD_3OD$) δ 0.75 (d, J=6.0 Hz, 3H), 0.97 (d, J=6.5 Hz, 3H), 1.35 (s, 3H), 1.43-1.51 (m, 1H), 1.53 (s, 3H), 1.69 (d, J=6.7 Hz, 3H), 1.74-2.13 (m, 5H), 2.37-2.50 (m, 1H), 2.65-2.86 (m, 1H), 3.97-4.14 (m, 1H), 4.26-4.53 (m, 4H), 5.81-5.91 (m, 1H), 6.04 (s, 1H), 6.07-6.21 (m, 1H), 6.58, 6.71 (ABq, J=16.1 Hz, 2H), 7.06-7.20 (m, 1H), 7.27-7.50 (m, 3H), 7.62 (d, J=7.8 Hz, 1H), 7.87 (d, J=7.8 Hz, 1H), 8.02 (s, 1H), 8.28 (d, J=8.9 Hz, 1H). LCMS (m/z) 616.3 [M+H], Tr=2.54 min.

Example 110

Compound 110

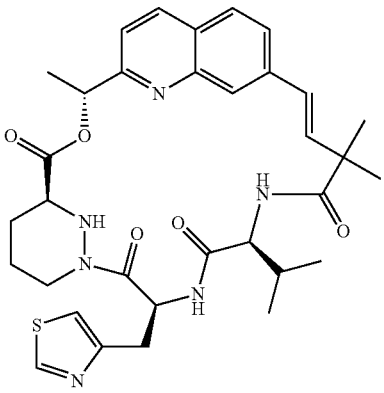

Compound 110a: (S)-1-((S)-2-tert-Butoxycarbonylamino-3-thiazol-4-yl-propionyl)-hexahydro-pyridazine-3-carboxylic acid 2,2,2-trichloro-ethyl ester

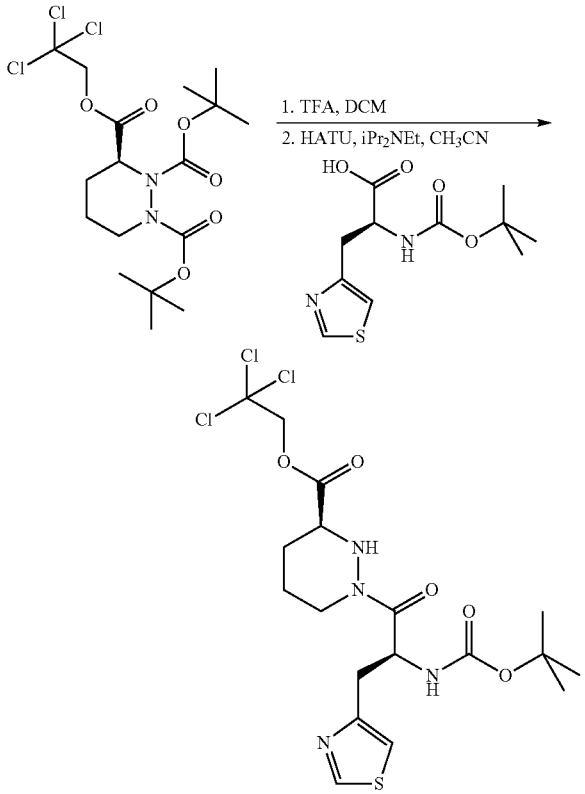

Compound 110a was prepared in like manner to compound 106d, replacing L-N—(S)-2-tert-butoxycarbonylamino-3-difluoromethoxy-propionic acid with (S)-2-tert-butoxycarbonylamino-3-thiazol-4-yl-propionic acid (500 mg, 1.84 mmol) to afford the title compound as an off white solid (750 mg, 79%). $^1$H NMR (300 MHz, $CDCl_3$) δ 1.43 (s, 9H), 1.61-1.79 (m, 3H), 1.85-1.97 (m, 1H), 2.01-2.20 (m, 1H), 2.84-2.97 (m, 1H), 3.21-3.28 (m, 2H), 3.56-3.68 (m, 1H), 3.88 (d, J=10.9 Hz, 1H), 4.32 (d, J=12.9 Hz, 1H), 4.76, 4.93 (ABq, J=12.1 Hz, 2H), 5.38-5.60 (m, 1H), 7.12 (d, J=1.8 Hz, 1H), 8.74 (d, J=1.8 Hz, 1H). LCMS (m/z) 516.9 [M+H], Tr=2.68 min.

Compound 110b: (S)-1-[(S)-2-((S)-2-tert-Butoxycarbonylamino-3-methyl-butyrylamino)-3-thiazol-4-yl-propionyl]-hexahydro-pyridazine-3-carboxylic acid 2,2,2-trichloro-ethyl ester

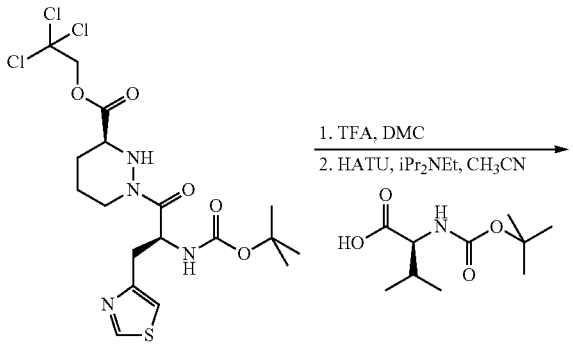

-continued

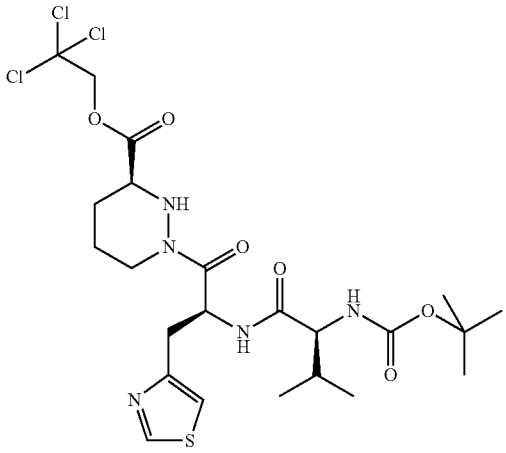

Compound 110b was prepared in the same manner as compound 106e, replacing (S)-1-((S)-2-tert-butoxycarbonylamino-3-difluoromethoxy-propionyl)-hexahydro-pyridazine-3-carboxylic acid 2,2,2-trichloro-ethyl ester with (S)-1-((S)-2-tert-butoxycarbonylamino-3-thiazol-4-yl-propionyl)-hexahydro-pyridazine-3-carboxylic acid 2,2,2-trichloro-ethyl ester to afford the title compound as a light brown foam (730 mg, 81%). $^1$H NMR (300 MHz, $CDCl_3$) δ 0.91 (d, J=6.7 Hz, 3H), 0.95 (d, J=6.7 Hz, 3H), 1.47 (s, 9H), 1.66-1.96 (m, 4H), 2.09-2.28 (m, 2H), 2.84-3.00 (m, 1H), 3.22-3.42 (m, 2H), 3.80-4.00 (m, 2H), 4.21-4.33 (m, 1H), 4.72, 4.97 (ABq, J=11.9 Hz, 2H), 5.06-5.15 (m, 1H), 5.57-5.65 (m, 1H), 6.87 (d, J=7.1 Hz, 1H), 7.17 (s, 1H), 8.72 (d, J=1.8 Hz, 1H). LCMS (m/z) 616.2 [M+H], Tr=2.78 min.

Compound 110c: (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-thiazol-4-yl-propionyl]-hexahydro-pyridazine-3-carboxylic acid 2,2,2-trichloro-ethyl ester

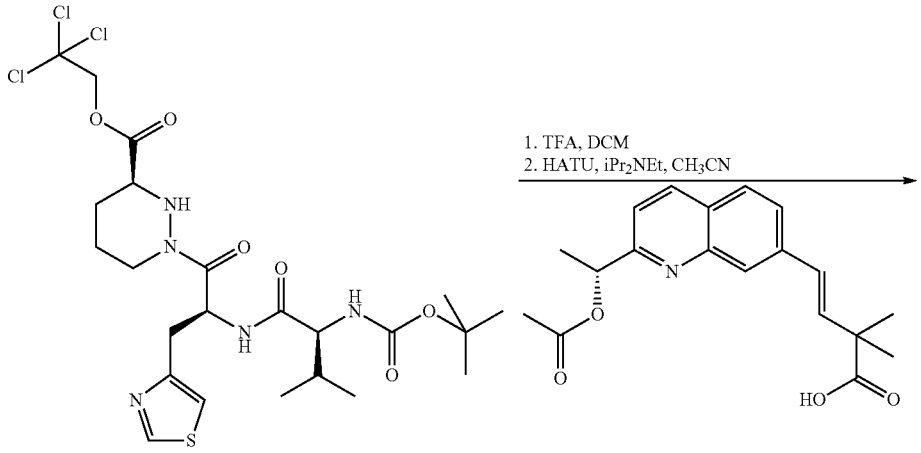

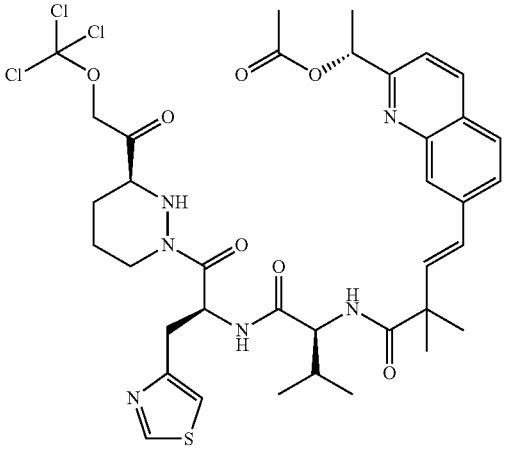

Compound 110c was prepared in the same manner as compound 82c, replacing (S)-1-[(S)-2-((S)-2-tert-butoxycarbonylamino-3-methyl-butyrylamino)-3-(tert-butyl-diphenyl-silanyloxy)-propionyl]-hexahydro-pyridazine-3-carboxylic acid 2,2,2-trichloro-ethyl ester with (S)-1-[(S)-2-((S)-2-tert-butoxycarbonylamino-3-methyl-butyrylamino)-3-thiazol-4-yl-propionyl]-hexahydro-pyridazine-3-carboxylic acid 2,2,2-trichloro-ethyl ester (730 mg, 1.19 mmol), to afford the title compound as a viscous clear oil (500 mg, 51%). $^1$H NMR (300 MHz, $CDCl_3$) δ 0.88 (d, J=6.7 Hz, 3H), 0.93 (d, J=6.7 Hz, 3H), 1.48 (s, 3H), 1.69 (d, J=6.7 Hz, 3H), 1.71-1.97 (m, 5H), 2.06 (s, 3H), 2.07-2.15 (m, 1H), 2.17 (s, 3H), 2.86-3.00 (m, 1H), 3.18-3.37 (m, 2H), 3.75-3.89 (m, 1H), 3.93 (d, J=10.7 Hz, 1H), 4.27 (dd, J=6.3, 2.2 Hz, 1H), 4.70, 4.95 (ABq, J=11.9 Hz, 2H), 5.59 (q, J=5.6 Hz, 1H), 6.06 (q, J=6.7 Hz, 1H), 6.35 (d, J=8.5 Hz, 1H), 6.63, 6.77 (ABq, J=16.2 Hz, 2H), 6.89 (d, J=7.6 Hz, 1H), 7.11 (d, J=2.0 Hz, 1H), 7.43 (d, J=8.3 Hz, 1H), 7.65 (dd, J=8.5, 1.6 Hz, 1H), 7.76 (d, J=8.5 Hz, 1H), 8.05 (s, 1H), 8.13 (d, J=8.5 Hz, 1H), 8.69 (s, 1H). LCMS (m/z) 825.3 [M+H], Tr=2.97 min.

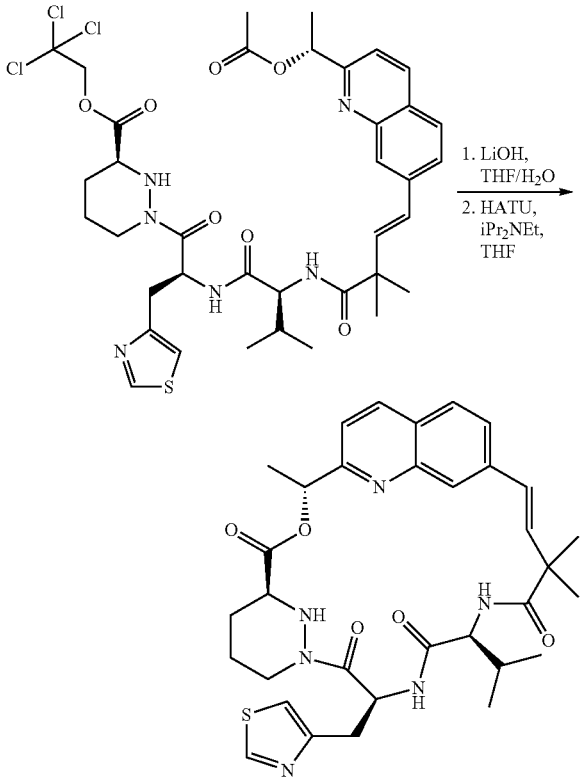

Compound 110 was prepared in the same manner as compound 82d, replacing (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-(tert-butyl-diphenyl-silanyloxy)-propionyl]-hexahydro-pyridazine-3-carboxylic acid 2,2,2-trichloro-ethyl ester with (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-thiazol-4-yl-propionyl]-hexahydro-pyridazine-3-carboxylic acid 2,2,2-trichloro-ethyl ester (500 mg, 0.61 mmol), to afford the title compound as a white solid (35 mg, 9%). $^1$H NMR (300 MHz, $CD_3OD$) δ 0.94 (d, J=6.5 Hz, 3H), 0.97 (d, J=6.5 Hz, 3H), 1.34 (s, 3H), 1.48 (s, 3H), 1.55-1.73 (m, 3H), 1.75 (d, J=6.7 Hz, 3H), 1.81-2.03 (m, 3H), 2.66-2.80 (m, 1H), 3.36-3.61 (m, 3H), 4.31 (t, J=9.6 Hz, 1H), 4.40 (d, J=13.4 Hz, 1H), 4.53 (d, J=12.3 Hz, 1H), 5.91 (q, J=6.7 Hz, 1H), 6.18 (dd, J=8.3, 6.0 Hz, 1H), 6.23, 6.33 (ABq, J=16.4 Hz, 2H), 7.17 (d, J=9.6 Hz, 1H), 7.39 (d, J=8.5 Hz, 1H), 7.58 (s, 1H), 7.66 (dd, J=8.5, 1.6 Hz, 1H), 7.79 (d, J=8.5 Hz, 1H), 8.03 (d, J=1.6 Hz, 1H), 8.19 (d, J=8.5 Hz, 1H), 8.90 (d, J=2.0 Hz, 1H). LCMS (m/z) 633.2 [M+H], Tr=2.23 min.

Example 111

Compound 111

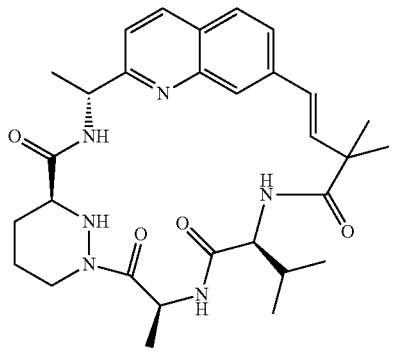

Compound 111a (R)-2-Methyl-propane-2-sulfinic acid [1-(7-bromo-quinolin-2-yl)-eth-(E)-ylidene]-amide

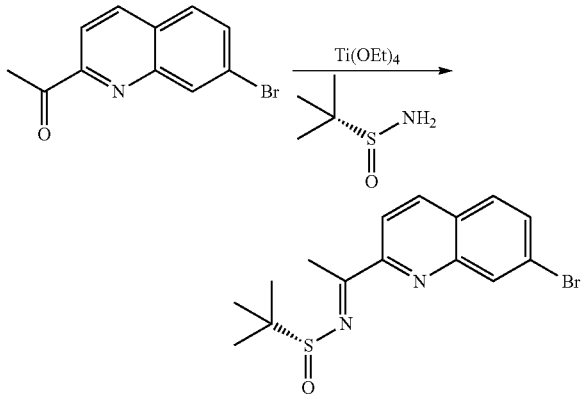

To a solution of 1-(7-bromo-quinolin-2-yl)-ethanone (1.42 g, 5.68 mmol) in THF (28 mL) was added titanium (IV) ethoxide (2.6 g, 2.35 mL, 11.4 mmol, tech. grade) followed by (R)-(+)-2-methyl-propanesulfinamide (825 mg, 6.82 mmol). The reaction mixture was stirred at 60° C. under nitrogen for 6 hours and allowed to cool. Brine was added followed by ethyl acetate and the suspension filtered through celite and the filter pad was washed with ethyl acetate. The ethyl acetate layer was separated, dried over sodium sulphate, filtered and evaporated. The residue was purified by silica gel chromatography using a gradient of iso-hexane/ethyl acetate 9:1 to 3:1 to give the title compound (448 mg, 22%) as an orange solid. $^1$H NMR (300 MHz, $CDCl_3$) δ 1.38 (s, 9H), 2.99 (s, 3H), 7.71 (m, 2H), 8.16 (d, J=8.6 Hz, 1H), 8.24 (d, J=8.6 Hz, 1H), 8.37 (s, 1H). LCMS (m/z) 352.9/354.9 [M+H], Tr 3.14 minutes.

Compound 111b (R)-2-Methyl-propane-2-sulfinic acid [(R)-1-(7-bromo-quinolin-2-yl)-ethyl]-amide

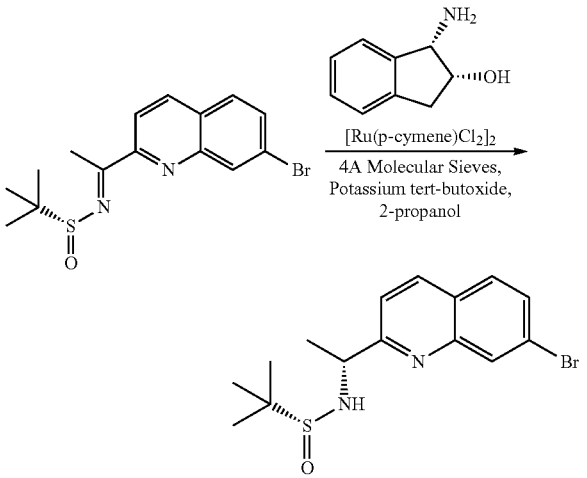

A mixture of (1S,2R)-(−)-cis-1-amino-2-indanol (19 mg, 0.13 mmol), [Ru (p-cymen) $Cl_2]_2$ (39 mg, 0.064 mmol) and powdered 4 Å Molecular Sieves (0.7 g) was suspended in anhydrous 2-propanol (3 mL) and stirred under nitrogen. The suspension was heated at 90° C. for 30 minutes. The reaction mixture was cooled to 40° C. and a solution of (R)-2-methyl-propane-2-sulfinic acid [1-(7-bromo-quinolin-2-yl)-eth-(E)-ylidene]-amide (448 mg, 1.27 mmol) in 2-propanol (9 mL) was added followed by a solution of potassium tert-butoxide (36 mg, 0.32 mmol) in 2-propanol (3 mL). The reaction mixture was stirred for 2 hours at 40° C. and then allowed to cool. The mixture was poured directly onto a silica gel cartridge and eluted with ethyl acetate. After concentration the residue was further purified by silica gel chromatography using a gradient of iso-hexane/ethyl acetate 1:1 to 0:1 to give the title compound (287 mg, 64%) as a brown gum. $^1$H NMR (300 MHz, $CDCl_3$) δ 1.33 (s, 9H), 1.60 (d, J=6.7 Hz, 3H), 4.80 (m, 1H), 5.42 (br d, J=4.2 Hz, 1H), 7.42 (d, J=8.5 Hz, 1H), 7.62 (dd, J=8.5, 1.2 Hz, 1H), 7.68 (d, J=8.7 Hz, 1H), 8.12 (d, J=8.7 Hz, 1H), 8.25 (s, 1H). LCMS (m/z) 354.9/356.8 [M+H], Tr 2.49 min Compound 111c. (E)-2,2-Dimethyl-4-{2-[(R)-1-((R)-2-methyl-propane-2-sulfinylamino)-ethyl]-quinolin-7-yl}-but-3-enoic acid methyl ester

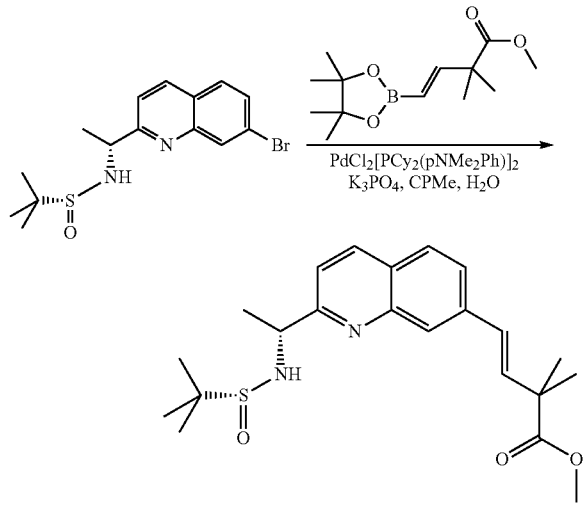

Compound 111c was prepared in the same manner as compound 49b using 2-methyl-propane-2-sulfinic acid [(R)-1-(7-bromo-quinolin-2-yl)-ethyl]-amide 111b instead of (R)-1-(3-chloro-isoquinolin-6-yl)-ethanol in 93% yield. $^1$H NMR (300 MHz, $CDCl_3$) δ 1.33 (s, 9H), 1.48 (s, 6H), 1.59 (d, J=6.7 Hz, 3H), 3.74 (s, 3H), 4.74-4.85 (m, 1H), 5.48 (d, J=4.0 Hz, 1H), 6.63 (s, 2H), 7.35 (d, J=8.5 Hz, 1H), 7.62 (dd, J=8.5, 1.8 Hz, 1H), 7.73 (d, J=8.5 Hz, 1H), 7.93 (s, 1H), 8.08 (d, J=8.5 Hz, 1H). LCMS (m/z) 403.2 [M+H], Tr=2.56 min.

Compound 111d. (E)-4-{2-[(R)-1-({(S)-1-[(S)-2-((S)-2-tert-Butoxycarbonylamino-3-methyl-butyrylamino)-propionyl]-hexahydro-pyridazine-3-carbonyl}-amino)-ethyl]-quinolin-7-yl}-2,2-dimethyl-but-3-enoic acid methyl ester

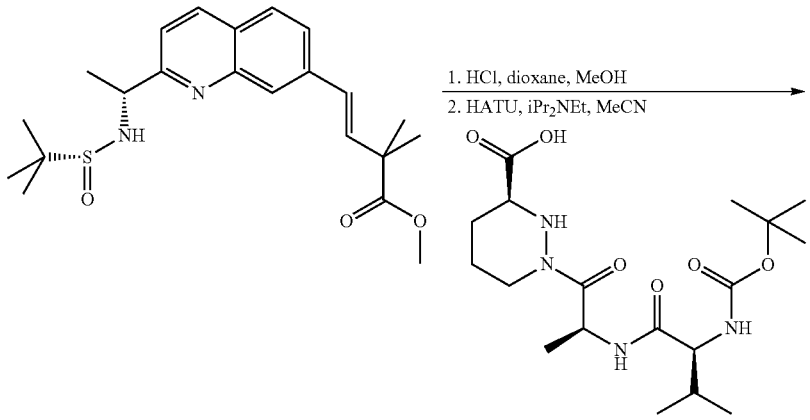

-continued

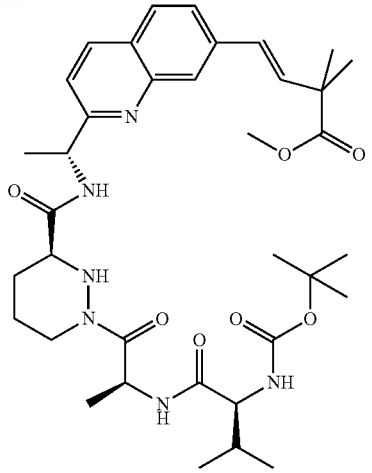

A solution of (E)-2,2-dimethyl-4-{2-[(R)-1-((R)-2-methyl-propane-2-sulfinylamino)-ethyl]-quinolin-7-yl}-but-3-enoic acid methyl ester (700 mg, 1.74 mmol) in methanol (20 mL) was treated with hydrochloric acid in 1,4-dioxane (4 M, 10 mL). After stirring at room temperature for 2 h, the volatiles were removed in vacuo. The residual solvent was azeotroped off with toluene (3×15 mL) to give crude (E)-4-[2-((R)-1-amino-ethyl)-quinolin-7-yl]-2,2-dimethyl-but-3-enoic acid methyl ester hydrochloride.

A cooled (0° C.) solution of (S)-1-[(S)-2-((S)-2-tert-butoxycarbonylamino-3-methyl-butyrylamino)-propionyl]-hexahydro-pyridazine-3-carboxylic acid (696 mg, 1.74 mmol) and crude (E)-4-[2-((R)-1-amino-ethyl)-quinolin-7-yl]-2,2-dimethyl-but-3-enoic acid methyl ester hydrochloride in acetonitrile (20 mL) was subsequently treated with N,N-diisopropylethylamine (1.52 mL, 8.71 mmol) and 2-(1H-7-azabenzotriazol-1-yl)-1,1,3,3-tetramethyl uronium hexafluorophosphate methanaminium (861 mg, 2.26 mmol). After stirring at room temperature for 2 h, the volatiles were removed in vacuo. The residue was dissolved in ethyl acetate, and subsequently washed with saturated ammonium chloride solution and sodium hydrogen carbonate solution. The organics were combined and the volatiles were removed in vacuo. The residue was purified by silica gel chromatography using a 100 g Biotage cartridge eluted with a continuous gradient of iso-hexanes/acetone 1:0 to 1:1 to afford the title compound (868 mg, 73%) as a white solid. $^1$H NMR (300 MHz, $CD_3OD$) δ 0.82-0.97 (m, 6H), 1.36 (d, J=6.9 Hz, 3H), 1.45 (s, 9H), 1.48 (s, 6H), 1.61 (d, J=6.9 Hz, 3H), 1.66-1.76 (m, 2H), 1.83-2.12 (m, 3H), 2.78-2.92 (m, 1H), 3.52-3.61 (m, 1H), 3.74 (s, 3H), 3.82-3.95 (m, 1H), 4.25-4.35 (m, 1H), 5.23 (q, J=6.9 Hz, 1H), 5.36 (q, J=6.9 Hz, 1H), 6.36-6.51 (m, 2H), 7.51 (d, J=8.5 Hz, 1H), 7.73 (d, J=8.5 Hz, 1H), 7.85 (d, J=8.5 Hz, 1H), 7.99 (s, 1H), 8.25 (d, J=8.5 Hz, 1H). LCMS (m/z) 681.4 [M+H], Tr=2.62 min.

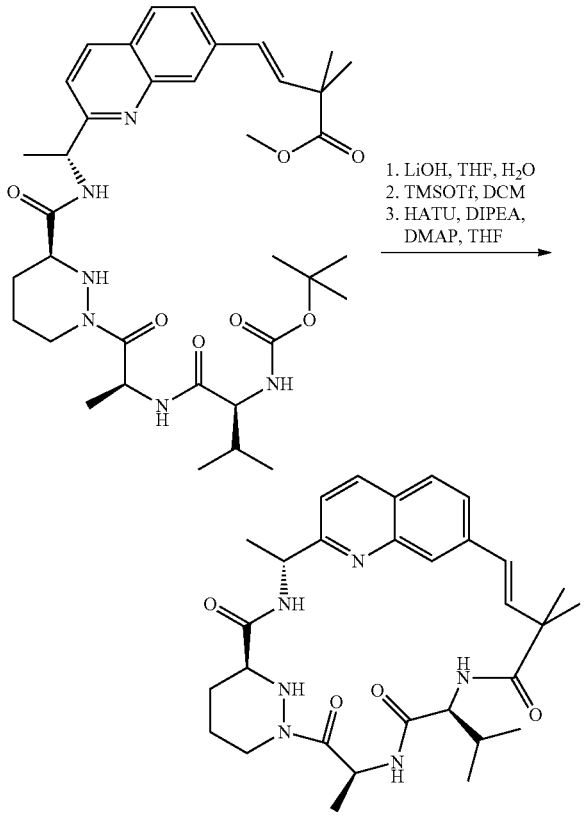

A solution of (E)-4-{2-[(R)-1-({(S)-1-[(S)-2-((S)-2-tert-butoxycarbonylamino-3-methyl-butyrylamino)-propionyl]-hexahydro-pyridazine-3-carbonyl}-amino)-ethyl]-quinolin-7-yl}-2,2-dimethyl-but-3-enoic acid methyl ester (868 mg, 1.28 mmol) in 1,4-dioxane (100 mL) was treated with a solution of lithium hydroxide monohydrate (306 mg, 12.8 mmol) in water (20 mL) After stirring at 65° C. for 1 h, the volatiles were removed in vacuo. The residue was partitioned between water and diethyl ether. The aqueous layer was acidified to pH 2 by addition of concentrated hydrochloric acid then extracted with ethyl acetate (3×). The organics were combined and the volatiles were removed in vacuo. The residue was dissolved in dichloromethane (20 mL) and treated with trimethylsilyl trifluoromethanesulfonate (503 mg, 2.26 mmol) at 0° C. for 1 h. N,N-diisopropylethylamine (0.5 mL) was added and the volatiles were removed in vacuo. The residue was dissolved in tetrahydrofuran (850 mL), treated with catalytic 4-dimethylaminopyridine (30 mg) and 2-(1H-7-azabenzotriazol-1-yl)-1,1,3,3-tetramethyl uronium hexafluorophosphate methanaminium (515 mg, 1.36 mmol). After stirring at room temperature for 3 h, the volatiles were removed in vacuo. The residue was partitioned between ethyl acetate and saturated sodium bicarbonate, the organic layer was dried over anhydrous sodium sulfate, filtered and the volatiles were removed in vacuo. The residue was purified by silica gel chromatography using a 100 g Biotage cartridge eluted with a continuous gradient of iso-hexanes/acetone 1:0 to 1:3 to afford the title compound (420 mg, 60%) as a white solid. $^1$H NMR (300 MHz, $CD_3OD$) δ 0.96 (d, J=6.9 Hz, 3H), 1.05 (d, J=6.9 Hz, 3H), 1.37 (s, 3H), 1.51 (s, 3H), 1.59 (d, J=6.7 Hz, 3H), 1.64 (d, J=7.4 Hz, 3H), 1.85-2.00 (m, 2H), 2.20-2.35 (m, 1H), 2.60-2.75 (m, 1H), 3.55-3.65 (m, 1H), 4.35-4.48 (m, 2H), 4.95-5.15 (m, 2H), 5.78 (q, J=7.2 Hz, 1H), 6.25-6.60 (m, 2H), 7.12 (d, J=9.4 Hz, 1H), 7.44 (d, J=8.5 Hz, 1H), 7.67 (d, J=8.5 Hz, 1H), 7.75 (s, 1H), 7.85 (d, J=8.5 Hz, 1H), 8.25 (d, J=8.5 Hz, 1H). LCMS (m/z) 549.2 [M+H], Tr=2.21 min.

Examples 112 and 113

Compounds 112 and 113

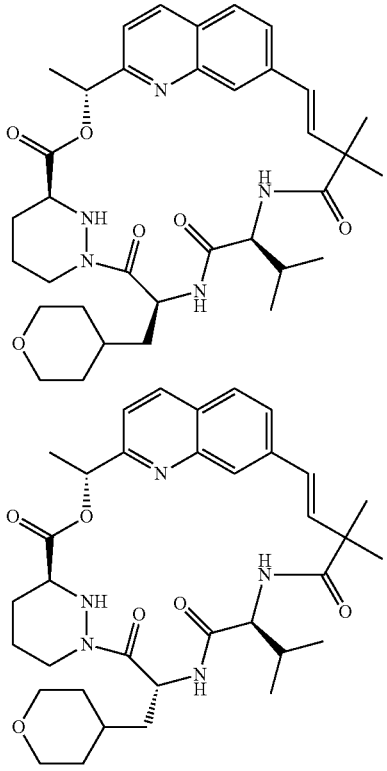

Compound 112a: (S)-1-[2-tert-Butoxycarbonylamino-3-(tetrahydro-pyran-4-yl)-propionyl]-hexahydro-pyridazine-3-carboxylic acid 2,2,2-trichloro-ethyl ester

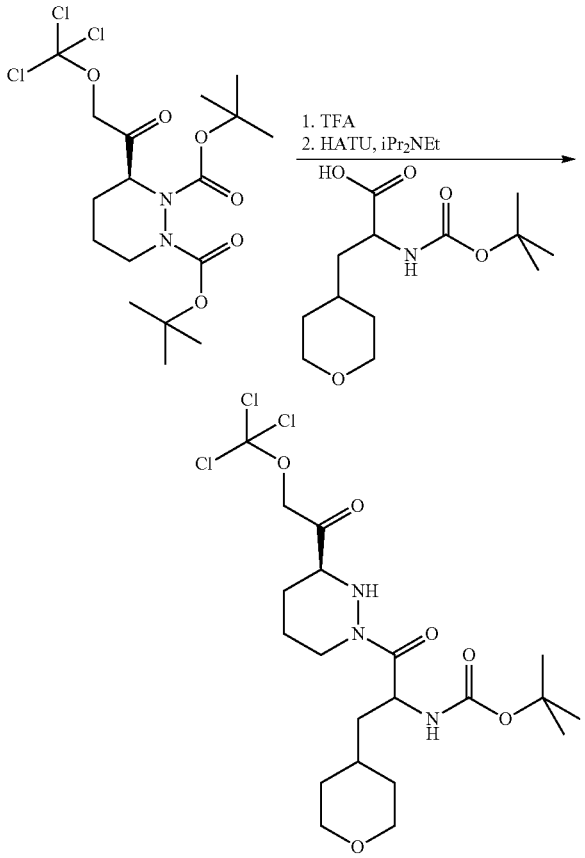

Compound 112a was prepared in the same manner as compound 106d, replacing L-N—(S)-2-tert-butoxycarbonylamino-3-difluoromethoxy-propionic acid with 2-Boc-3-(tetrahydropyran-4-yl)-DL-alanine (500 mg, 1.83 mmol) to afford the title compound as a clear viscous oil (940 mg, 100%) and as a 1:1 mixture of diastereoisomers. LCMS (m/z) 516.3 [M+H], Tr=2.75 min.

Compound 112b: (S)-1-[2-((S)-2-tert-Butoxycarbonylamino-3-methyl-butyrylamino)-3-(tetrahydro-pyran-4-yl)-propionyl]-hexahydro-pyridazine-3-carboxylic acid 2,2,2-trichloro-ethyl ester

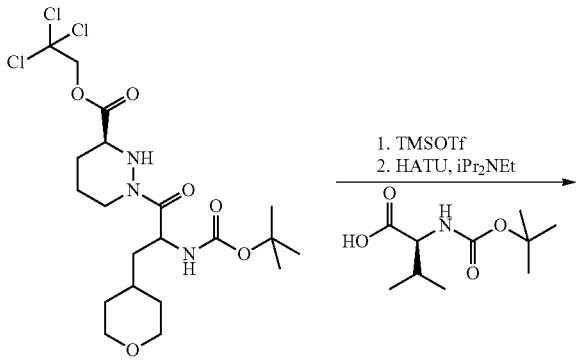

-continued

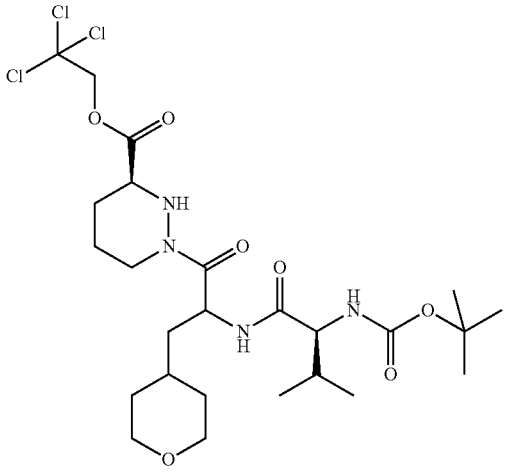

Compound 112b was prepared in the same manner as compound 106e, replacing (S)-1-((S)-2-tert-butoxycarbonylamino-3-difluoromethoxy-propionyl)-hexahydro-pyridazine-3-carboxylic acid 2,2,2-trichloro-ethyl ester with (S)-1-[2-tert-butoxycarbonylamino-3-(tetrahydro-pyran-4-yl)-propionyl]-hexahydro-pyridazine-3-carboxylic acid 2,2,2-trichloro-ethyl ester (940 mg, 1.83 mmol) to afford the title compound as a viscous clear oil (1.0 g, 90%) and as a 1:1 mixture of diastereoisomers. LCMS (m/z) 615.7 [M+H], Tr=2.78 min.

Compound 112c: (S)-1-[2-((S)-2-{(E)-4-[2-((R)-1-Acetoxy-ethyl)-quinolin-7-yl]-2,2-dimethyl-but-3-enoylamino}-3-methyl-butyrylamino)-3-(tetrahydro-pyran-4-yl)-propionyl]-hexahydro-pyridazine-3-carboxylic acid 2,2,2-trichloro-ethyl ester

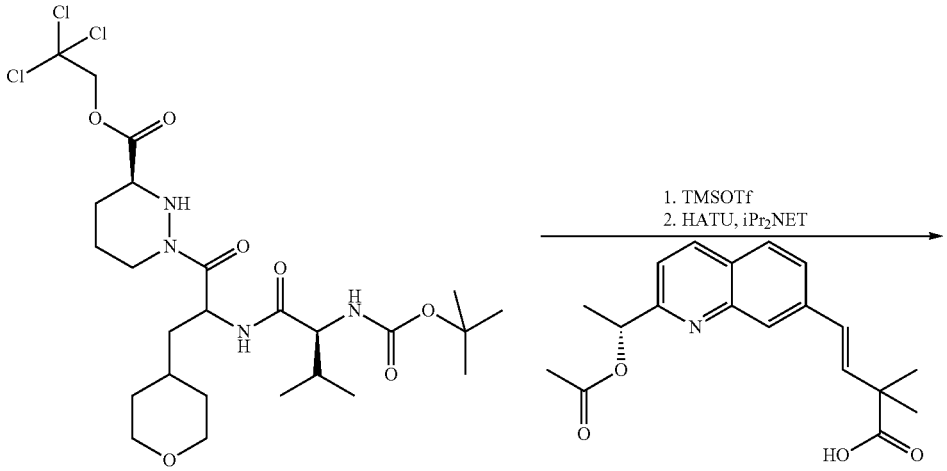

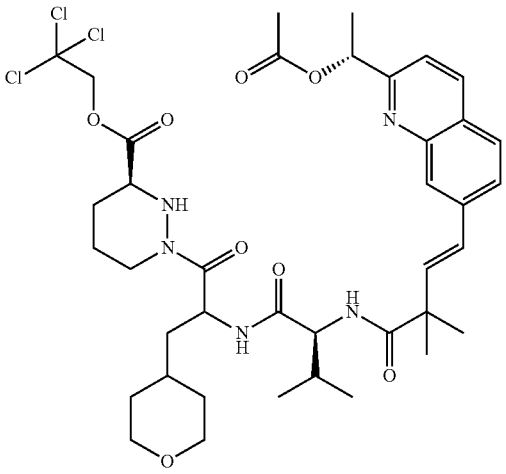

Compound 112c was prepared in the same manner as compound 82c, replacing (S)-1-[(S)-2-((S)-2-tert-butoxy-carbonylamino-3-methyl-butyrylamino)-3-(tert-butyl-di-phenyl-silanyloxy)-propionyl]-hexahydro-pyridazine-3-carboxylic acid 2,2,2-trichloro-ethyl ester with (S)-1-[2-((S)-2-tert-butoxycarbonylamino-3-methyl-butyrylamino)-3-(tetrahydro-pyran-4-yl)-propionyl]-hexahydro-pyridazine-3-carboxylic acid 2,2,2-trichloro-ethyl ester (1.0 g, 1.63 mmol), to afford the title compound as an off white foam (620 mg, 46%) and as a 1:1 mixture of diastereoisomers. LCMS (m/z) 824.3 [M+H], Tr=3.04 min.

Compounds 112 and 113

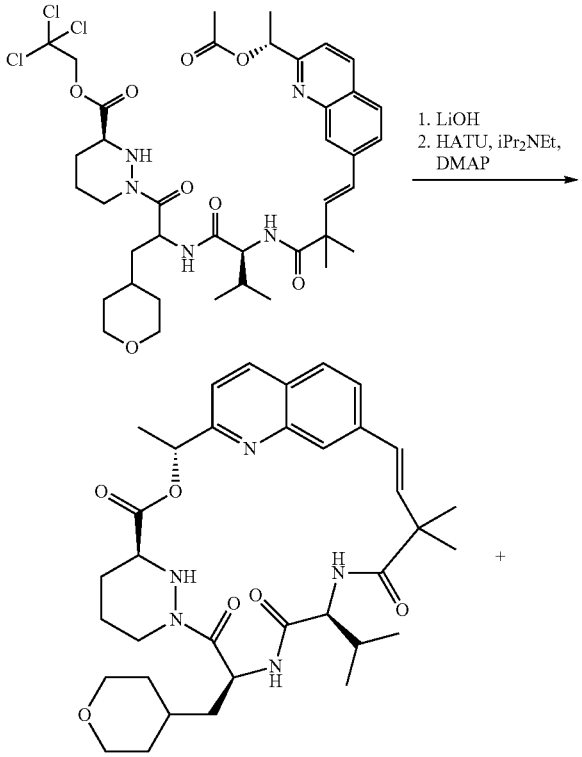

Diastereoisomer 1

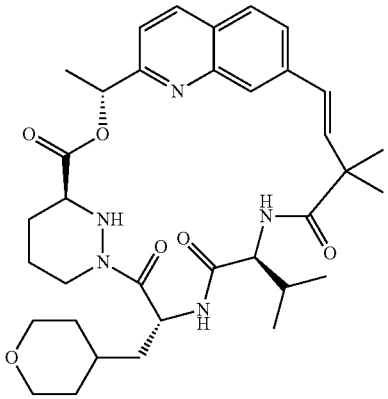

Diastereoisomer 2

Compounds 112 and 113 was prepared in the same manner as compound 108 and 109, replacing (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-pyrazol-1-yl-propionyl]-hexahydro-pyridazine-3-carboxylic acid 2,2,2-trichloro-ethyl ester with (S)-1-[2-((S)-2-{(E)-4-[2-((R)-1-acetoxy-ethyl)-quinolin-7-yl]-2,2-dimethyl-but-3-enoylamino}-3-methyl-butyrylamino)-3-(tetrahydro-pyran-4-yl)-propionyl]-hexahydro-pyridazine-3-carboxylic acid 2,2,2-trichloro-ethyl ester (600 mg, 0.73 mmol), to afford two diastereoisomers as white solids after isolation via reverse phase HPLC using and Agilent Eclipse XDB/C18 7 micron, 250×21.2 mm column and eluting with acetonitrile/water.

Example 112, Compound 112 First eluting Diastereoisomer 1 (20.0 mg, 4%); $^1$H NMR (300 MHz, $CD_3OD$) δ 0.96 (d, J=6.0 Hz, 3H), 0.98 (d, J=6.0 Hz, 3H), 1.37 (s, 3H), 1.25-1.49 (m, 4H), 1.52 (s, 3H), 1.71 (d, J=6.7 Hz, 3H), 1.73-2.10 (m, 9H), 2.19-2.31 (m, 1H), 2.68-2.82 (m, 1H), 3.14-3.44 (m, 2H), 3.62-3.71 (m, 1H), 3.74-3.90 (m, 2H), 4.31 (t, J=9.6 Hz, 1H), 4.43 (d, J=13.2, 1H), 5.92 (q, J=6.7 Hz, 1H), 6.01-6.16 (m, 1H), 6.40, 6.46 (ABq, J=16.4 Hz, 2H), 7.27 (d, J=8.7 Hz, 1H), 7.38 (d, J=8.5 Hz, 1H), 7.69 (d, J=8.5 Hz, 1H), 7.75-7.84 (m, 2H), 8.19 (d, J=8.5 Hz, 1H). LCMS (m/z) 634.3 [M+H], Tr=2.50 min.

Example 113, Compound 113 Second Eluting Diastereoisomer 2 (20.0 mg, 4%); $^1$H NMR (300 MHz, $CD_3OD$) δ 0.82 (d, J=6.5 Hz, 3H), 0.99 (d, J=6.5 Hz, 3H), 1.05-1.25 (m, 2H), 1.38 (s, 3H), 1.53 (s, 3H), 1.44-1.61 (m, 5H), 1.70 (d, J=6.7 Hz, 3H), 1.74-2.19 (m, 6H), 2.41-2.54 (m, 1H), 2.71-2.84 (m, 1H), 2.92-3.06 (m, 1H), 3.13-3.25 (m, 2H), 3.47-3.58 (m, 1H), 3.69-3.84 (m, 1H), 3.99-4.14 (m, 1H), 4.34-4.42 (m, 1H), 4.42-4.53 (m, 1H), 5.72-5.81 (m, 1H), 6.07-6.19 (m, 1H), 6.65, 6.83 (ABq, J=15.9 Hz, 2H), 7.42 (d, J=8.5 Hz, 1H), 7.60 (d, J=8.5 Hz, 1H), 7.87 (d, J=8.5 Hz, 1H), 8.17 (s, 1H), 8.26 (d, J=8.5 Hz, 1H). LCMS (m/z) 634.3 [M+H], Tr=2.55 min.

Example 114

Compound 114

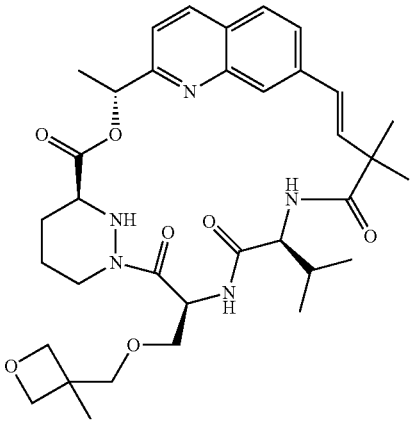

Compound 114a: (S)-2-tert-Butoxycarbonylamino-3-(3-methyl-oxetan-3-ylmethoxy)-propionic acid

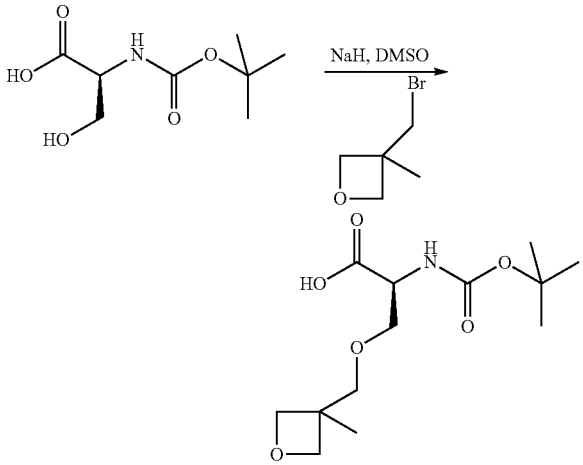

To N-(tert-Butoxycarbonyl)-L-serine (1.2 g, 6.06 mmol) in anhydrous dimethyl sulfoxide (20 mL) at room temperature and under an atmosphere of nitrogen was added sodium hydride (60% in mineral oil, 363 mg, 9.1 mmol) in three portions. The reaction was stirred for 1 h after which was added 3-bromomethyl-3-methyl oxetane (obtained from Fluorochem Ltd., UK), 1 g, 6.06 mmol) and a further amount of sodium hydride (60% in mineral oil, 363 mg, 9.1 mmol). The reaction was stirred for 16 h and quenched by careful addition of water. The solution was washed with diethyl ether (1×) and acidified to pH 2 with 2 M hydrochloric acid. The solution was extracted with ethyl acetate (2×) and the combined organics washed with brine. The organic layer was dried through a hydrophobic frit and concentrated in vacuo to yield the title compound (1.1 g, 63%) as a clear oil. $^1$H NMR (300 MHz, $CDCl_3$) δ 1.30 (s, 3H), 1.48 (s, 9H), 3.50, 3.53 (ABq, J=9.4 Hz, 2H), 3.77 (dd, J=9.4, 3.8 Hz, 1H), 3.98 (dd, J=9.4, 2.9 Hz, 1H), 4.37 (d, J=5.8 Hz, 2H), 4.47-4.55 (m, 1H), 4.57 (d, J=5.8 Hz, 2H), 5.47 (d, J=8.3 Hz, 1H). LCMS (m/z) 289.3 [M+H], Tr=1.67 min.

Compound 114b: (S)-1-[(S)-2-tert-Butoxycarbonylamino-3-(3-methyl-oxetan-3-ylmethoxy)-propionyl]-hexahydro-pyridazine-3-carboxylic acid 2,2,2-trichloro-ethyl ester

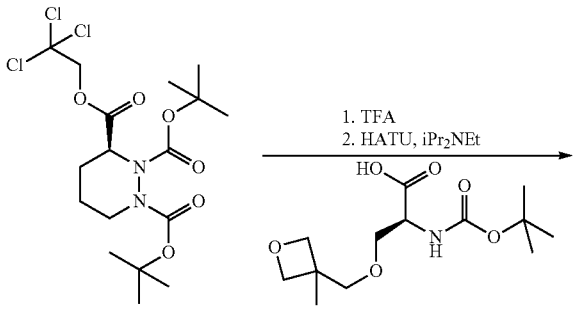

-continued

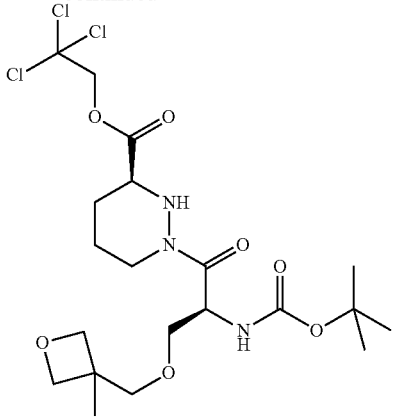

To (S)-tetrahydro-pyridazine-1,2,3-tricarboxylic acid 1,2-di-tert-butyl ester 3-(2,2,2-trichloro-ethyl)ester (1.76 g, 3.81 mmol) in anhydrous dichloromethane (12 mL) at room temperature and under an atmosphere of nitrogen was added trifluoroacetic acid (12 mL, 152 mmol). The solution was warmed to room temperature and stirred for 16 h. The reaction was concentrated in vacuo and the residue co-evaporated from toluene (3×). The resulting residue was dissolved in anhydrous acetonitrile (5 mL) and added to a solution of (S)-2-tert-butoxycarbonylamino-3-(3-methyl-oxetan-3-ylmethoxy)-propionic acid (1.1 mg, 3.81 mmol), N,N-diisopropylethylamine (2.7 mL, 15.2 mmol) and 2-(1H-7-azabenzotriazol-1-yl)-1,1,3,3-tetramethyl uronium hexafluorophosphate methanaminium (1.40 g, 3.81 mmol) in anhydrous acetonitrile (20 mL) that had been previously stirred at 0° C. for 20 minutes. The reaction was warmed to room temperature and stirred for 16 h. The reaction was cooled to 0° C. diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:1 to give the title compound (1.2 g, 59%) as a clear viscous oil. $^1$H NMR (300 MHz, $CDCl_3$) δ 1.27 (s, 3H), 1.46 (s, 9H), 1.63-2.18 (m, 5H), 3.13-3.27 (m, 1H), 3.45-3.60 (m, 3H), 3.73-3.87 (m, 2H), 4.05-4.17 (m, 1H), 4.38 (d, J=5.6 Hz, 2H), 4.57 (dd, J=7.8, 5.6 Hz, 2H), 4.79 (d, J=11.8 Hz, 1H), 4.91 (d, J=11.8 Hz, 1H), 5.33-5.60 (m, 2H). LCMS (m/z) 532.3 [M+H], Tr=2.75 min.

Compound 114c: (S)-1-[(S)-2-[(S)-2-(9H-Fluoren-9-ylmethoxycarbonylamino)-3-methyl-butyrylamino]-3-(3-methyl-oxetan-3-ylmethoxy)-propionyl]-hexahydro-pyridazine-3-carboxylic acid 2,2,2-trichloro-ethyl ester

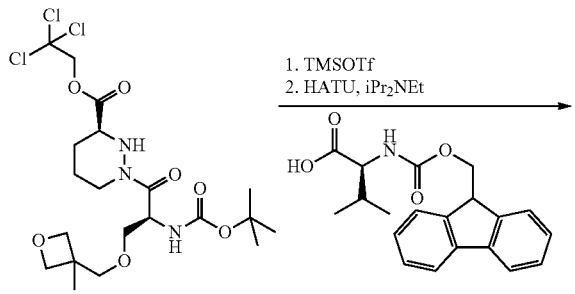

-continued

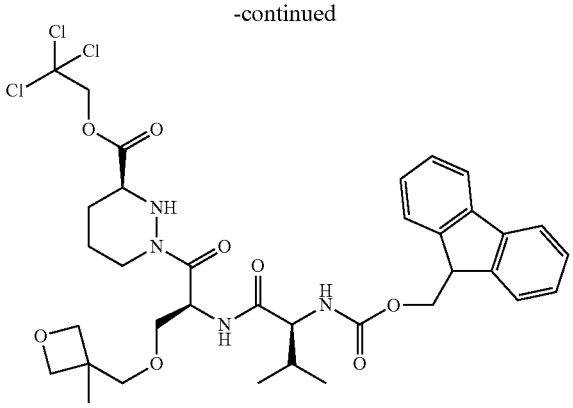

To (S)-1-[(S)-2-tert-butoxycarbonylamino-3-(3-methyl-oxetan-3-ylmethoxy)-propionyl]-hexahydro-pyridazine-3-carboxylic acid 2,2,2-trichloro-ethyl ester (1.2 g, 2.26 mmol) in anhydrous dichloromethane (10 mL) at 0° C. and under an atmosphere of nitrogen was added trifluoroacetic acid (1.7 mL, 22.6 mmol). The reaction mixture was stirred for 3 h before concentrating in vacuo and co-evaporating from toluene (1×). The residue was dissolved in anhydrous acetonitrile (24 mL) at room temperature and under an atmosphere of nitrogen was added N,N-diisopropylethylamine (2.0 mL, 11.3 mmol), N-(9-fluorenylmethoxycarbonyl)-L-valine (767 mg, 2.26 mmol) and 2-(1H-7-azabenzotriazol-1-yl)-1,1,3,3-tetramethyl uronium hexafluorophosphate methanaminium (1.2 g, 3.2 mmol). Following 2 h at room temperature the reaction was cooled to 0° C., diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:1 then 1:2 to give the title compound (1.4 g, 82%) as a viscous clear oil. $^1$H NMR (300 MHz, $CDCl_3$) δ 0.89-1.07 (m, 6H), 1.23 (s, 3H), 1.54-1.95 (m, 5H), 2.10-2.23 (m, 1H), 3.29-3.48 (m, 3H), 3.52-3.62 (m, 1H), 3.72-4.00 (m, 3H), 4.20-4.30 (m, 2H), 4.31-4.44 (m, 4H), 4.48 (d, J=5.6 Hz, 1H), 4.54 (d, J=5.6 Hz, 1H), 4.69 (d, J=12.3 Hz, 1H), 4.94 (d, J=12.3 Hz, 1H), 5.44-5.54 (m, 1H), 5.71-5.82 (m, 1H), 6.76 (d, J=7.6 Hz, 1H), 7.30-7.37 (m, 2H), 7.38-7.46 (m, 2H), 7.57-7.67 (m, 2H), 7.75-7.82 (m, 2H). LCMS (m/z) 753.2 [M+H], Tr=3.34 min.

Compound 114d: (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-(3-methyl-oxetan-3-ylmethoxy)-propionyl]-hexahydro-pyridazine-3-carboxylic acid 2,2,2-trichloroethyl ester

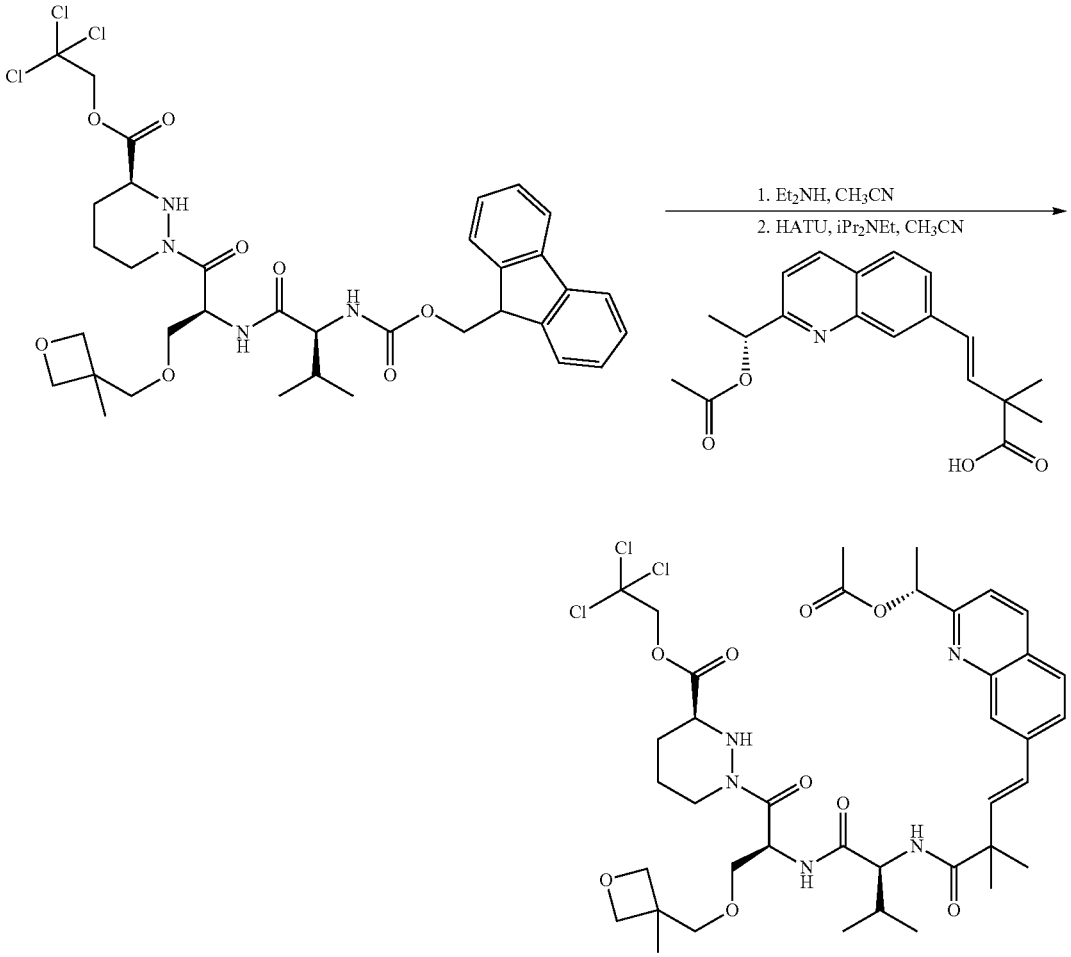

To (S)-1-[(S)-2-[(S)-2-(9H-fluoren-9-ylmethoxycarbonylamino)-3-methyl-butyrylamino]-3-(3-methyl-oxetan-3-ylmethoxy)-propionyl]-hexahydro-pyridazine-3-carboxylic acid 2,2,2-trichloro-ethyl ester (1.1 g, 1.46 mmol) in anhydrous acetonitrile (20 mL) at room temperature and under an atmosphere of nitrogen was added diethylamine (3.0 mL, 29.2 mmol). The reaction mixture was stirred for 2 h before concentrating in vacuo and co-evaporating from dichloromethane. This residue was dissolved in anhydrous acetonitrile (10 mL) and at 0° C. and under an atmosphere of nitrogen was added (E)-4-[2-((R)-1-acetoxy-ethyl)-quinolin-7-yl]-2,2-dimethyl-but-3-enoic acid (478 mg, 1.46 mmol), N,N-diisopropylethylamine (1.3 mL, 7.30 mmol) and 2-(1H-7-azabenzotriazol-1-yl)-1,1,3,3-tetramethyl uronium hexafluorophosphate methanaminium (778 mg, 2.05 mmol). The solution was warmed to room temperature and stirred for 16 h. The reaction was diluted with ethyl acetate and quenched with 1 M hydrochloric acid. The organic layer was separated and washed with a saturated aqueous solution of sodium bicarbonate (2×) and brine (1×). The organic layer was then dried through a hydrophobic frit and concentrated in vacuo. The residue was purified by silica gel chromatography using iso-hexanes/ethyl acetate 1:1 then 0:1 to give the title compound (650 mg, 53%) as a viscous clear oil. $^1$H NMR (300 MHz, $CDCl_3$) δ 0.89 (d, J=6.5 Hz, 3H), 0.95 (d, J=6.5 Hz, 3H), 1.22 (s, 3H), 1.49 (s, 3H), 1.63 (s, 3H), 1.69 (d, J=6.7 Hz, 3H), 1.63-1.95 (m, 4H), 2.08-2.14 (m, 1H), 2.18 (s, 3H), 3.26-3.45 (m, 3H), 3.48-3.60 (m, 1H), 3.71-3.87 (m, 2H), 3.89-4.03 (m, 1H), 4.23 (d, J=9.2 Hz, 1H), 4.27-4.41 (m, 3H), 4.47 (d, J=5.6 Hz, 1H), 4.51 (d, J=5.6 Hz, 1H), 4.67 (d, J=11.8 Hz, 1H), 4.92 (d, J=11.8 Hz, 1H), 5.69-5.80 (m, 1H), 6.06 (q, J=6.5 Hz, 1H), 6.39 (d, J=8.3 Hz, 1H), 6.67 (d, J=7.8 Hz, 1H), 6.64, 6.78 (ABq, J=16.3 Hz, 2H), 7.44 (d, J=8.5 Hz, 1H), 7.63-7.71 (m, 1H), 7.77 (d, J=8.5 Hz, 1H), 8.05 (s, 1H), 8.13 (d, J=8.5 Hz, 1H). LCMS (m/z) 842.4 [M+H], Tr=3.02 min.

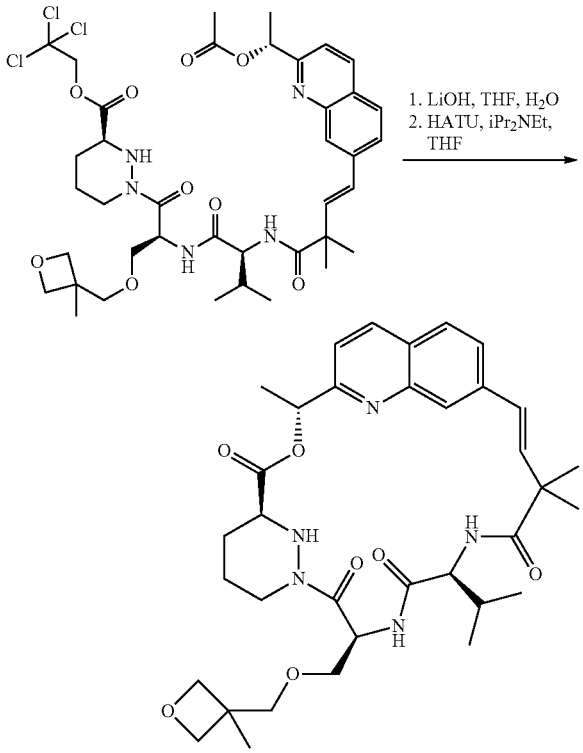

To (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-(3-methyl-oxetan-3-ylmethoxy)-propionyl]-hexahydro-pyridazine-3-carboxylic acid 2,2,2-trichloroethyl ester (600 mg, 0.71 mmol) in tetrahydrofuran (30 mL) and water (6 mL) was added lithium hydroxide monohydrate (150 mg, 3.56 mmol) at 0° C. The reaction was stirred at 0° C. for 2 h and then warmed to room temperature and stirred for 1 h, before being neutralised to pH 7 with 2 M hydrochloric acid. The reaction was concentrated in vacuo, followed by co-evaporation from toluene (3×) and then acetonitrile (3×). The resulting residue was triturated with diethyl ether to yield an off white powder. This powder was dissolved in anhydrous tetrahydrofuran (238 mL) and cooled to 0° C., under an atmosphere of nitrogen. N,N-diisopropylethylamine (621 μL, 3.56 mmol), 2-(1H-7-azabenzotriazol-1-yl)-1,1,3,3-tetramethyl uronium hexafluorophosphate methanaminium (379 mg, 1.00 mmol) and 4-dimethylaminopyridine (9 mg, 0.07 mmol). The reaction was warmed to room temperature and stirred for 16 h. To the reaction was added a further amount of 2-(1H-7-azabenzotriazol-1-yl)-1,1,3,3-tetramethyl uronium hexafluorophosphate methanaminium (271 mg, 0.71 mmol) and the solution heated to 40° C. for 5 h. The reaction was concentrated in vacuo and the ensuing residue was diluted with ethyl acetate and washed with cold 0.5 M hydrochloric acid (1×), a saturated aqueous solution of sodium bicarbonate (2×) and brine (1×). The organic layer was then dried through a hydrophobic frit and concentrated in vacuo. The residue was purified by preparative HPLC to afford the title compound (30 mg, 6%) as a white solid. $^1$H NMR (300 MHz, $CD_3OD$) δ 0.91-1.01 (m, 6H), 1.28 (s, 3H), 1.35 (s, 3H), 1.50 (s, 3H), 1.71 (d, J=6.7 Hz, 3H), 1.59-1.80 (m, 3H), 1.84-2.09 (m, 3H), 2.69-2.83 (m, 1H), 3.68, 3.84 (ABq, J=9.1 Hz, 2H), 3.88-3.98 (m, 2H), 4.04 (dd, J=9.6, 5.1 Hz, 1H), 4.15 (d, J=5.8 Hz, 1H), 4.23 (d, J=5.8 Hz, 1H), 4.30-4.38 (m, 1H), 4.38-4.46 (m, 1H), 4.52 (d, J=12.3 Hz, 1H), 4.58, 4.59 (ABq, J=3.9 Hz, 2H), 5.91 (q, J=6.7 Hz, 1H), 6.12-6.20 (m, 1H), 6.35, 6.47 (ABq, J=16.5 Hz, 2H), 7.26 (d, J=9.6 Hz, 1H), 7.38 (d, J=8.5 Hz, 1H), 7.73 (dd, J=8.5, 1.0 Hz, 1H), 7.80 (d, J=8.5 Hz, 1H), 7.86 (s, 1H), 8.18 (d, J=8.5 Hz, 1H). LCMS (m/z) 650.3 [M+H], Tr=2.46 min.

Example 115

Compound 115

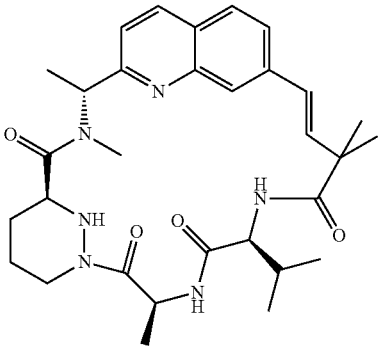

Compound 115a. 2-Methyl-propane-2-sulfinic acid (R)-[(R)-1-(7-bromo-quinolin-2-yl)-ethyl]-methyl-amide

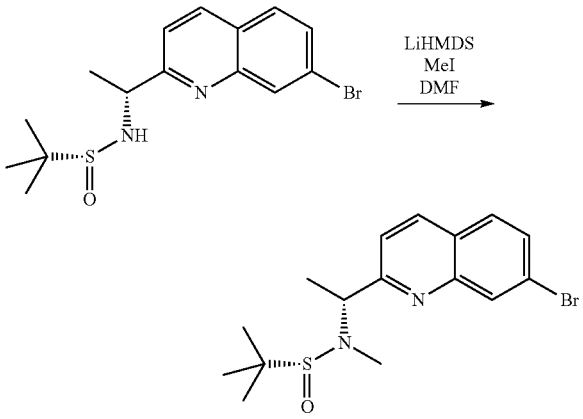

A cooled (−20° C.) solution of 2-methyl-propane-2-sulfinic acid [(R)-1-(7-bromo-quinolin-2-yl)-ethyl]-amide (100 mg, 0.28 mmol) in N,N-dimethylformamide (5 mL) was treated with lithium bis(trimethylsilyl)amide (0.28 mL, 0.28 mmol, 1 M in hexane). After stirring at this temperature for 1 h, iodomethane (0.035 mL, 0.56 mmol) was added and the temperature raised to room temperature. After stirring at room temperature for 1 h, the reaction was quenched by addition of water (10 mL). The mixture was extracted with diethyl ether (3×20 mL). The organics were combined and the volatiles were removed in vacuo. The residue was purified by silica gel chromatography using a 10 g Biotage cartridge eluted with a continuous gradient of iso-hexanes/ethyl acetate 1:0 to 1:1 to afford the title compound (149 mg, 62%) as a white solid. $^1$H NMR (300 MHz, $CDCl_3$) δ 1.25 (s, 9H), 1.74 (d, J=6.9 Hz, 3H), 2.53 (s, 3H), 4.81 (q, J=6.9 Hz, 1H), 7.55-7.70 (m, 3H), 8.11 (d, J=8.5 Hz, 1H), 8.27 (s, 1H). LCMS (m/z) 369.0, 371.0 [M+H], Tr=2.91 min.

Compound 115b. (E)-2,2-Dimethyl-4-(2-{(R)-1-[methyl-((R)-2-methyl-propane-2-sulfinyl)-amino]-ethyl}-quinolin-7-yl)-but-3-enoic acid methyl ester

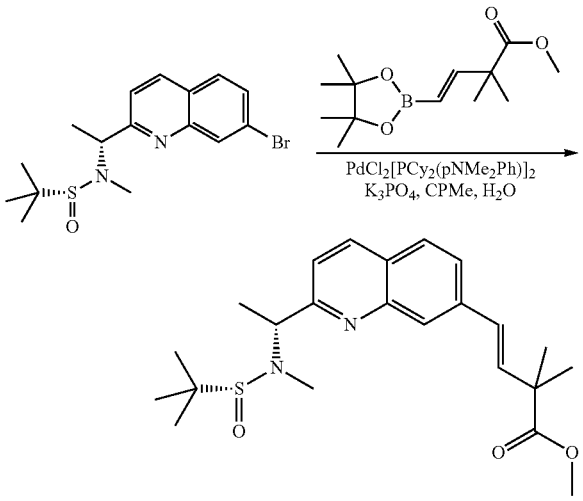

Compound 115b was prepared in the same manner as compound 49b using 2-methyl-propane-2-sulfinic acid (R)-[(R)-1-(7-bromo-quinolin-2-yl)-ethyl]-methyl-amide instead of (R)-1-(3-chloro-isoquinolin-6-yl)-ethanol in 46% yield. $^1$H NMR (300 MHz, $CDCl_3$) δ 1.26 (s, 9H), 1.47 (s, 6H), 1.76 (d, J=6.9 Hz, 3H), 2.55 (s, 3H), 3.74 (s, 3H), 4.80 (q, J=6.9 Hz, 1H), 6.63 (s, 2H), 7.52-7.65 (m, 2H), 7.74 (d, J=8.5 Hz, 1H), 8.01 (s, 1H), 8.10 (d, J=8.5 Hz, 1H). LCMS (m/z) 417.1 [M+H], Tr=2.70 min.

Compound 115c. (E)-4-{2-[(R)-1-({(S)-1-[(S)-2-((S)-2-tert-butoxycarbonylamino-3-methyl-butyrylamino)-propionyl]-hexahydro-pyridazine-3-carbonyl}-methyl-amino)-ethyl]-quinolin-7-yl}-2,2-dimethyl-but-3-enoic acid methyl ester

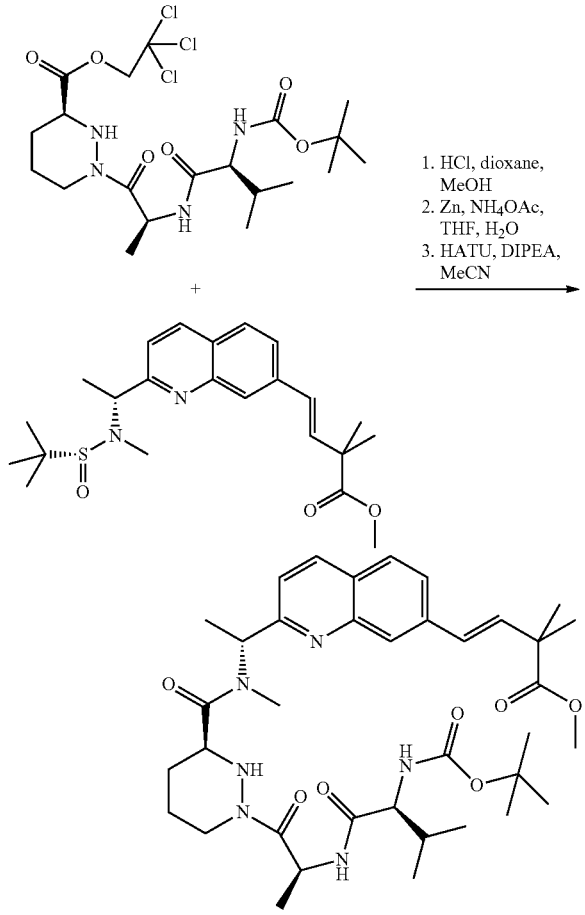

A solution of (E)-2,2-dimethyl-4-(2-{(R)-1-[methyl-((R)-2-methyl-propane-2-sulfinyl)-amino]-ethyl}-quinolin-7-yl)-but-3-enoic acid methyl ester (77 mg, 0.19 mmol) in methanol (10 mL) was treated with hydrochloric acid in 1,4-dioxane (4 M, 5 mL). After stirring at room temperature for 2 h, the volatiles were removed in vacuo. The residual solvent was removed by azeotroping with toluene (3×10 mL) to give crude (E)-2,2-dimethyl-4-[2-((R)-1-methyl-amino-ethyl)-quinolin-7-yl]-but-3-enoic acid methyl ester hydrochloride.

Zinc dust (273 mg, 4.18 mmol) was added to a solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (98 mg, 0.19 mmol) in tetrahydrofuran (15 mL). This suspension was treated with a solution of ammonium acetate (220 mg, 2.85 mmol) in water (5 mL). After stirring at room temperature for 3 h, zinc residues were filtered off and the volatiles were removed in vacuo. The residue was partitioned between ethyl acetate and saturated potassium hydrogen sulfate solution and the volatiles were removed in vacuo. The residual acetic acid was removed by azeotroping with toluene (3×10 mL) to give crude (S)-1-[(S)-2-((S)-2-tert-butoxycarbonylamino-3-methyl-butyrylamino)-propionyl]-hexahydro-pyridazine-3-carboxylic acid which was combined with crude (E)-2,2-dimethyl-4-[2-((R)-1-methylamino-ethyl)-quinolin-7-yl]-but-3-enoic acid methyl ester in anhydrous acetonitrile (10 mL) and N,N-diisopropylethylamine (0.165 mL, 0.95 mmol). This solution was then treated with 2-(1H-7-azabenzotriazol-1-yl)-1,1,3,3-tetramethyl uronium hexafluorophosphate methanaminium (94 mg, 0.25 mmol). After stirring at room temperature for 16 h, the volatiles were removed in vacuo. The residue was dissolved in ethyl acetate, and subsequently washed with saturated ammonium chloride solution and sodium bicarbonate solution. The organics were combined and the volatiles were removed in vacuo. The residue was purified by silica gel chromatography using a 10 g Biotage cartridge eluted with a continuous gradient of iso-hexanes/acetone 1:0 to 1:1 to afford the title compound (90 mg, 68%) as a white solid. $^1$H NMR (300 MHz, $CD_3OD$) δ 0.82-1.00 (m, 6H), 1.28-1.40 (m, 3H), 1.50-1.55 (m, 15H), 1.69 (d, J=6.9 Hz, 3H), 1.73-2.12 (m, 5H), 2.76-2.92 (m, 5H), 3.74 (s, 3H), 3.84-4.00 (m, 1H), 4.25-4.45 (m, 1H), 5.22-5.40 (m, 1H), 6.25 (q, J=6.9 Hz, 1H), 6.57-6.74 (m, 2H), 7.35-7.48 (m, 1H), 7.69-7.77 (m, 1H), 7.80-7.88 (m, 1H), 7.90-8.00 (m, 2H), 8.18-8.30 (m, 1H). LCMS (m/z) 695.4 [M+H], Tr=3.00 min.

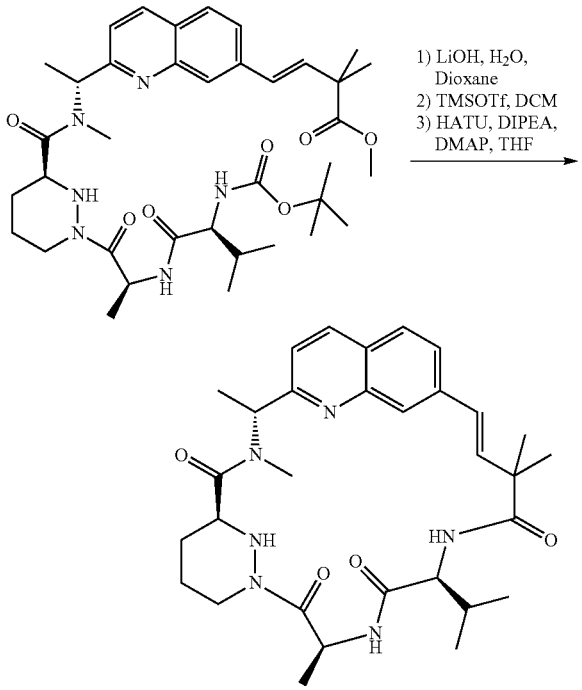

A solution of (E)-4-{2-[(R)-1-({(S)-1-[(S)-2-((S)-2-tert-butoxycarbonylamino-3-methyl-butyrylamino)-propionyl]-hexahydro-pyridazine-3-carbonyl}-methyl-amino)-ethyl]-quinolin-7-yl}-2,2-dimethyl-but-3-enoic acid methyl ester (90 mg, 0.13 mmol) in 1,4-dioxane (10 mL) was treated with a solution of lithium hydroxide monohydrate (31 mg, 1.30 mmol) in water (5 mL). After stirring at 65° C. for 1 h, the volatiles were removed in vacuo. The residue was partitioned between water and diethyl ether. The aqueous layer was acidified to pH 2 by addition of concentrated hydrochloric acid then extracted with ethyl acetate (3×). The organics were combined and the volatiles were removed in vacuo. The residue was dissolved in dichloromethane (10 mL) and treated with trimethylsilyl trifluoromethanesulfonate (58 mg, 0.26 mmol) at 0° C. for 1 h. N,N-diisopropylethylamine (0.079 mL, 0.45 mmol) was added and the volatiles were removed in vacuo. The residue was dissolved in tetrahydrofuran (150 mL), treated with catalytic 4-dimethylaminopyridine (5 mg) and 2-(1H-7-azabenzotriazol-1-yl)-1,1,3,3-tetramethyl uronium hexafluorophosphate methanaminium (59 mg, 0.16 mmol). After stirring at room temperature for 3 h, the volatiles were removed in vacuo. The residue was partitioned between ethyl acetate and saturated sodium bicarbonate, the organic layer was dried over anhydrous sodium sulfate, filtered and the volatiles were removed in vacuo. The residue was purified by preparative reverse phase HPLC to afford the title compound (7 mg, 10%) as a white solid. $^1$H NMR (300 MHz, $CD_3OD$) δ 0.96 (d, J=6.7 Hz, 3H), 1.00 (d, J=6.7 Hz, 3H), 1.36 (s, 3H), 1.50 (s, 3H), 1.57 (d, J=7.1 Hz, 3H), 1.72 (d, J=7.4 Hz, 3H), 1.85-2.00 (m, 5H), 2.65-2.80 (m, 1H), 3.37 (s, 3H), 4.10-4.25 (m, 1H), 4.27-4.50 (m, 3H), 5.87 (q, J=6.9 Hz, 1H), 6.30-6.48 (m, 2H), 7.43 (d, J=8.7 Hz, 1H), 7.62-7.82 (m, 3H), 8.17 (d, J=8.7 Hz, 1H). LCMS (m/z) 563.3 [M+H], Tr=2.25 min.

Example 116

Compound 116

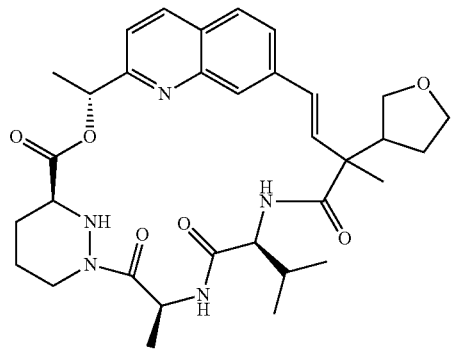

Compound 116a. (Tetrahydro-furan-3-yl)-acetic acid ethyl ester

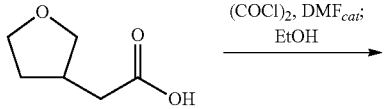

-continued

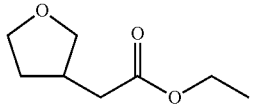

A solution of (tetrahydrofuran-3-yl)acetic acid (1.03 g, 7.91 mmol) in dichloromethane (20 mL) was prepared and oxalyl chloride (1340 μL, 15.4 mmol) was added followed by N,N-dimethylformamide (5 μL). The reaction was stirred at room temperature for 2 h then evaporated to dryness. The residue was dissolved in dichloromethane (10 mL) and anhydrous ethanol (5 mL) was added. The reaction mixture was stirred at room temperature for 15 minutes and then evaporated to give the title product (1.23 g, 98%) as a brown oil. $^1$H NMR (300 MHz, $CDCl_3$) δ 1.26 (t, J=7.1 Hz, 3H), 1.50-1.64 (m, 1H), 2.05-2.18 (m, 1H), 2.40 (d, J=7.8 Hz, 2H), 2.54-2.71 (m, 1H), 3.37-3.45 (m, 1H), 3.71-3.98 (m, 3H), 4.14 (q, J=7.1 Hz, 2H).

Compound 116b.
2-(Tetrahydro-furan-3-yl)-propionic acid ethyl ester

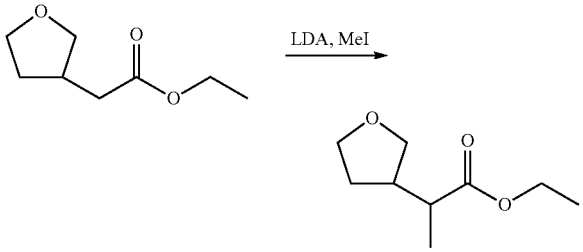

A stirred solution of N,N-diisopropylamine (2.38 mL, 17.0 mmol) in anhydrous tetrahydrofuran (40 mL) was cooled to −20° C. before adding n-butyllithium (6.3 mL, 15.8 mmol, 2.5 M in hexanes). The reaction was allowed to warm to −10° C. for 10 minutes then cooled to −78° C. A solution of (tetrahydro-furan-3-yl)-acetic acid ethyl ester (1.23 g, 7.77 mmol) in tetrahydrofuran (10 mL) was added dropwise. The reaction was stirred for 2.5 h at −78° C. and then methyl iodide (3.92 mL, 63.2 mmol) was added. The reaction was stirred for 15 h gradually warming to room temperature. The reaction was quenched with a saturated aqueous ammonium chloride solution (60 mL) and then extracted with ethyl acetate (3×30 mL). The organic phases were combined, dried over anhydrous sodium sulfate, filtered and evaporated. The residue was purified by silica gel chromatography using iso-hexanes/ethyl acetate 4:1 to yield the title product (0.87 g, 65%) as a yellow oil. $^1$H NMR (300 MHz, $CDCl_3$) δ 1.13-1.30 (m, 6H), 1.51-1.69 (m, 1H), 1.96-2.11 (m, 1H), 2.29-2.51 (m, 2H), 3.39-3.48 (m, 1H), 3.67-3.80 (m, 1H), 3.81-3.95 (m, 2H), 4.08-4.20 (m, 2H).

Compound 116c. 2-Methyl-2-(tetrahydro-furan-3-yl)-but-3-enoic acid ethyl ester

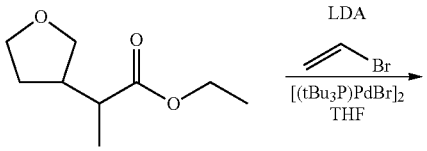

-continued

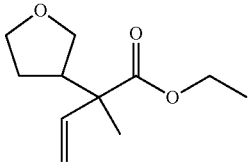

A solution of N,N-diisopropylamine (1.28 mL, 9.1 mmol) in anhydrous tetrahydrofuran (15 mL) was cooled to −30° C. before adding n-butyllithium (3.22 mL, 8.08 mmol, 2.5 M in hexanes). The reaction mixture was stirred at −30° C. for 15 minutes before adding a solution of 2-(tetrahydro-furan-3-yl)-propionic acid ethyl ester (0.87 g, 5.05 mmol) in tetrahydrofuran (6 mL) dropwise over 3 minutes. The reaction mixture was stirred for a further 15 minutes at −30° C. before adding dibromobis(tributylphosphine)palladium(II) (40 mg, 50 μmol) and then a solution of vinylbromide (9.0 mL, 9.0 mmol, 1 M in tetrahydrofuran). The reaction mixture was stirred at −30° C. for 30 minutes then warmed to room temperature for 18 h. The reaction mixture was treated with hydrochloric acid (2 M, 20 mL). The mixture was extracted with diethyl ether (3×20 mL). The organics extract was dried over anhydrous sodium sulfate, filtered and evaporated. The residue was purified by silica gel chromatography using iso-hexanes/diethyl ether 3:2 to yield the title product (237 mg, 24%) as a yellow oil. $^1$H NMR (300 MHz, $CDCl_3$) δ 1.14-1.30 (m, 6H), 1.61-1.75 (m, 1H), 1.84-1.99 (m, 1H), 2.68-2.82 (m, 1H), 3.52-3.95 (m, 4H), 4.10-4.21 (m, 2H), 5.09-5.23 (m, 2H), 5.95-6.07 (m, 1H). LCMS (m/z) 199.2 [M+H], Tr=2.17 min.

Compound 116d. (E)-4-[2-((R)-1-Hydroxy-ethyl)-quinolin-7-yl]-2-methyl-2-(tetrahydro-furan-3-yl)-but-3-enoic acid ethyl ester

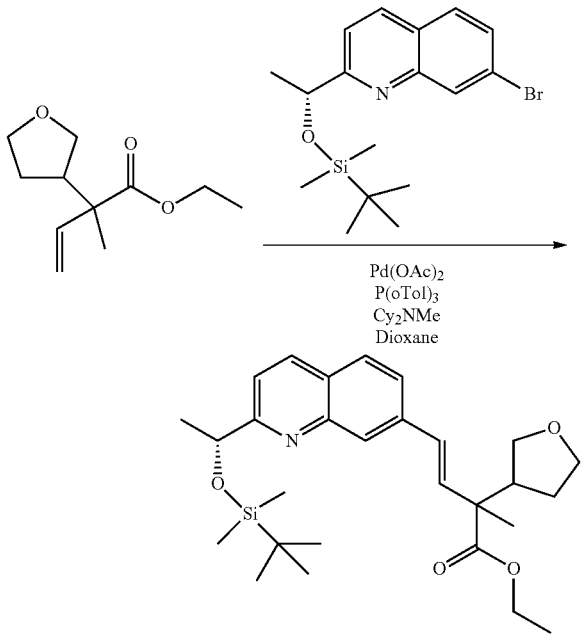

A solution of 2-methyl-2-(tetrahydro-furan-3-yl)but-3-enoic acid ethyl ester (187 mg, 0.94 mmol) in 1,4-dioxane (4.5 mL) and acetonitrile (0.5 mL) was prepared and 7-bromo-2-[(R)-1-(tert-butyl-dimethyl-silanyloxy)-ethyl]-quinoline 102b (344 mg, 0.94 mmol) was added followed by N,N-dicyclohexylmethylamine (403 μL, 1.88 mmol), palladium(II)acetate (85 mg, 0.38 mmol) and tri(o-tolyl)phosphine (116 mg, 0.38 mmol). The reaction mixture was heated to 140° C. in a sealed tube in a microwave for 4 h then evaporated to dryness. The residue was purified by silica gel chromatography using iso-hexanes/ethyl acetate 4:1 to yield the title product (312 mg, 68%) as a yellow gum and as a complex mixture of diastereoisomers. LCMS (m/z) 484.2 [M+H], Tr=4.11 min.

Compound 116e. (E)-4-[2-((R)-1-Hydroxy-ethyl)-quinolin-7-yl]-2-methyl-2-(tetrahydro-furan-3-yl)-but-3-enoic acid

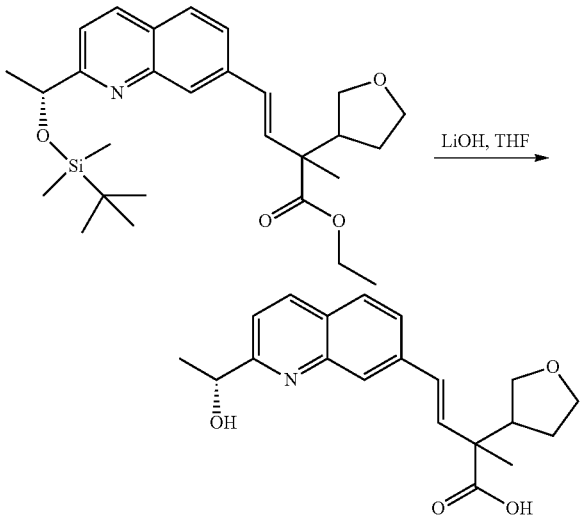

A solution of (E)-4-[2-((R)-1-hydroxy-ethyl)-quinolin-7-yl]-2-methyl-2-(tetrahydro-furan-3-yl)-but-3-enoic acid ethyl ester (312 mg, 0.645 mmol) in tetrahydrofuran (10 mL) was prepared and a solution of lithium hydroxide monohydrate (108 mg, 2.58 mmol) in water (2 mL) was added. The reaction mixture was stirred at room temperature for 16 h. More lithium hydroxide monohydrate (108 mg, 2.58 mmol) was added and the reaction mixture was heated at reflux for 20 h. The reaction mixture was treated with methanol (2 mL) and heated at reflux for 3 h. The reaction mixture was cooled with an ice bath before acidifying with hydrochloric acid (2 M) to pH 1. The resulting solution was warmed to room temperature, stirred for 1 h and evaporated to dryness. The residue was dissolved in a minimum of methanol and loaded on to a 25 g SCX Isolute cartridge. The cartridge was flushed with methanol, with a solution of ammonia in methanol (7 M, 4×10 mL). The solution was evaporated and left to dry under vacuum for 16 h to yield the title product (174 mg, 79%) as a yellow gum and as a complex mixture of diastereoisomers. LCMS (m/z) 342.1 [M+H], Tr=2.06 min.

Compound 116f. (S)-1-((S)-2-{(S)-2-[(E)-4-[2-((R)-1-Hydroxy-ethyl)-quinolin-7-yl]-2-methyl-2-(tetrahydro-furan-3-yl)-but-3-enoylamino]-3-methyl-butyrylamino}-propionyl)-hexahydro-pyridazine-3-carboxylic acid 2,2,2-trichloroethyl ester

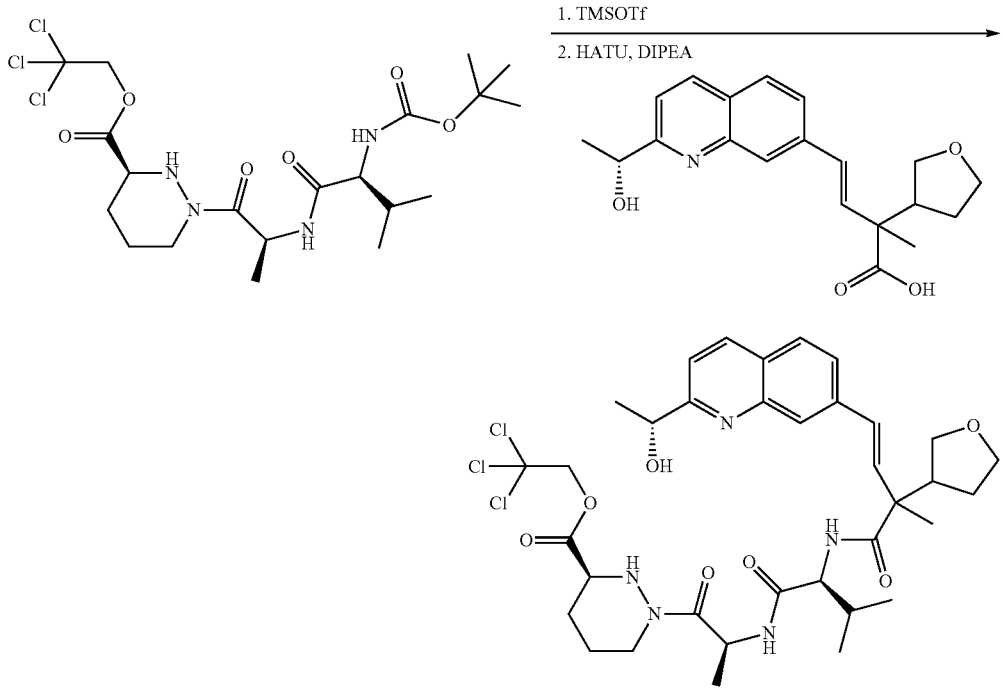

A solution of (S)-1-[(S)-2-((S)-2-tert-butoxycarbonylamino-3-methyl-butyrylamino)-propionyl]-hexahydro-pyridazine-3-carboxylic acid 2,2,2-trichloro-ethyl ester (343 mg, 0.645 mmol) in dichloromethane (12 mL) was prepared and trimethylsilyl trifluoromethanesulfonate (180 μL, 0.98 mmol) was added. The reaction was stirred for 4 h at room temperature before adding a saturated aqueous solution of sodium bicarbonate (20 mL). The layers were separated and the aqueous layer was extracted with dichloromethane (2×15 mL). The organic phases were combined and filtered through a phase separating cartridge, evaporated and left to dry under vacuum to yield a colourless gum. The gum was dissolved in anhydrous N,N-dimethylformamide (5 mL) and added to a solution of (E)-4-[2-((R)-1-hydroxy-ethyl)-quinolin-7-yl]-2-methyl-2-(tetrahydro-furan-3-yl)-but-3-enoic acid (174 mg, 0.51 mmol) in N,N-dimethylformamide (10 mL). The stirred mixture was treated with N,N-diisopropylethylamine (450 μL, 2.58 mmol) and (dimethylamino)-N,N-dimethyl(3H-[1,2,3]triazolo[4,5-b]pyridin-3-yloxy) methaniminium hexafluorophosphate (513 mg, 1.35 mmol). The reaction was stirred at room temperature for 20 h then heated to 40° C. for 4 h. The reaction mixture was cooled, evaporated and purified by silica gel chromatography using a gradient of dichloromethane/methanol 1:0 to 49:1 to 24:1 to yield the title product (160 mg, 33%) as a yellow gum and as a complex mixture of diastereoisomers. LCMS (m/z) 754.2, 756.1, 758.2 [M+H], Tr=1.23 min.

washed with diethyl ether (15 mL). The organic was extracted with water (10 mL). The aqueous phases were combined, acidified with hydrochloric acid (2 M) to pH 1 then evaporated to dryness. The residual trichloroethanol was azeotroped off with a mixture of acetonitrile and toluene. The resultant gum was triturated with diethyl ether and dried under vacuum to give a white solid (230 mg). The solid was dissolved in anhydrous N,N-dimethylformamide (2 mL) and the resulting solution was added over 4 h via syringe pump to a solution of 2-methyl-6-nitro-benzoic anhydride (362 mg, 1.05 mmol) and 4-(dimethylamino)pyridine (180 mg, 1.47 mmol) in 1,2-dichloroethane (70 mL) at 50° C. It was stirred for a further 20 minutes at 50° C., then cooled over an ice-bath. The organic was washed with an aqueous citric acid solution (5%, 50 mL), a saturated aqueous solution of sodium bicarbonate (50 mL), brine (25 mL) and filtered through a phase separating cartridge and evaporated to give a brown oil. The residue was purified by reverse phase preparative HPLC, using a C18 column and a gradient of acetonitrile/water+0.1% formic acid 3:7 to 2:3 over 26 minutes. The fractions containing the title product were combined, evaporated then dissolved in dichloromethane (2.5 mL), washed with a saturated aqueous sodium bicarbonate solution (1 mL) and filtered through a phase separating cartridge. The volatiles were evaporated to yield the title product (1.5 mg, 1.2%) as a white solid and as a single

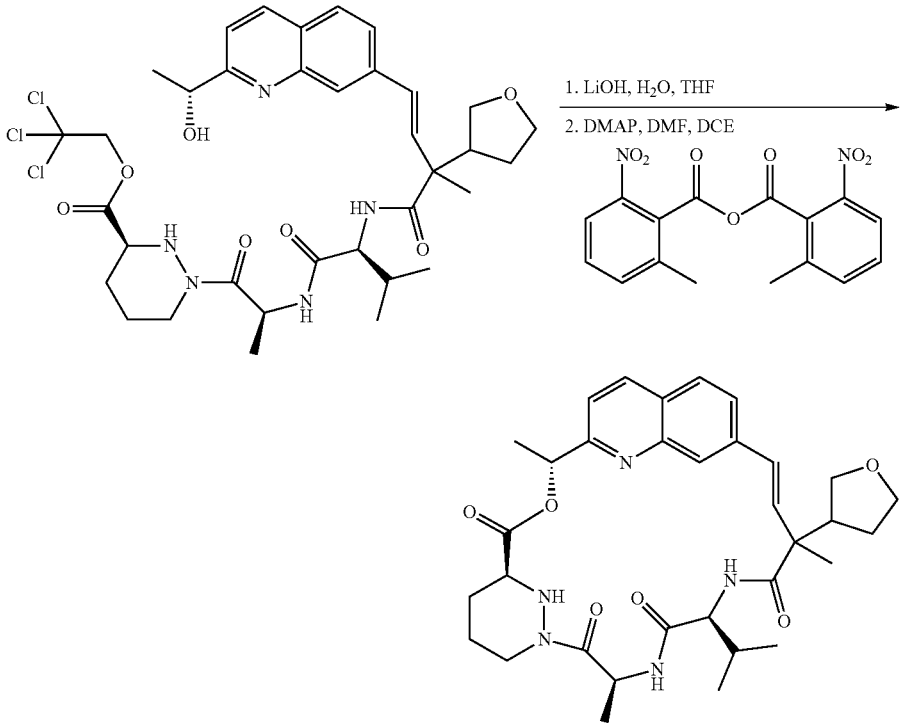

A solution of (S)-1-((S)-2-{(S)-2-[(E)-4-[2-((R)-1-hydroxy-ethyl)-quinolin-7-yl]-2-methyl-2-(tetrahydro-furan-3-yl)-but-3-enoylamino]-3-methyl-butyrylamino}-propionyl)-hexahydro-pyridazine-3-carboxylic acid 2,2,2-trichloroethyl ester (160 mg, 0.21 mmol) in tetrahydrofuran (10 mL) was prepared and a solution of lithium hydroxide monohydrate (27 mg, 0.63 mmol) in water (2 mL) was added. The reaction mixture was stirred at room temperature for 1.5 h and diluted with water (20 mL). The aqueous was unassigned diastereoisomer. $^1$H NMR (300 MHz, $CD_3OD$) δ 0.94 (d, J=6.5 Hz, 3H), 0.97 (d, J=6.5 Hz, 3H), 1.34 (s, 3H), 1.64 (d, J=7.1 Hz, 3H), 1.73 (d, J=6.9 Hz, 3H), 1.85-2.08 (m, 4H), 2.15-2.30 (m, 1H), 2.67-2.80 (m, 1H), 2.92-3.02 (m, 1H), 3.16-3.38 (m, 2H), 3.65-3.87 (m, 4H), 3.95-4.05 (m, 1H), 4.28-4.43 (m, 2H), 5.72-5.82 (m, 1H), 5.87-5.96 (m, 1H), 6.33, 6.59 (ABq, J=16.7 Hz, 1H), 7.42 (d, J=8.5 Hz, 1H), 7.65 (s, 1H), 7.82 (s, 2H), 8.22 (d, J=8.5 Hz, 1H). LCMS (m/z) 606.2 [M+H], Tr=2.17 min.

Examples 117 and 118

Compounds 117 and 118

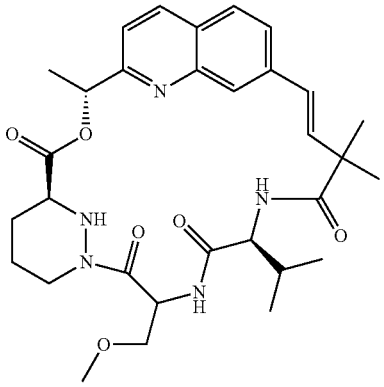

Compound 117a: (S)-1-((S)-2-tert-Butoxycarbonylamino-3-methoxy-propionyl)-hexahydro-pyridazine-3-carboxylic acid 2,2,2-trichloro-ethyl ester

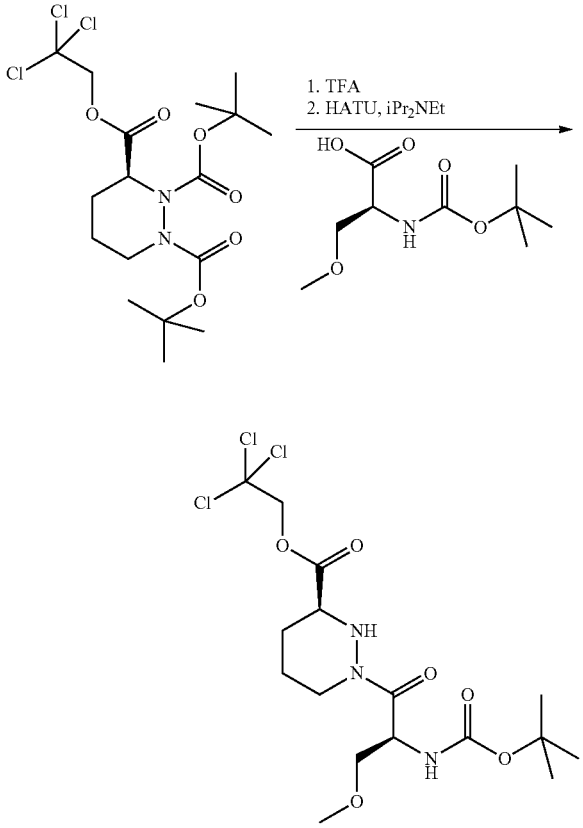

Compound 117a was prepared in the same manner as (S)-1-((S)-2-tert-butoxycarbonylamino-3-pyrazol-1-yl-propionyl)-hexahydro-pyridazine-3-carboxylic acid 2,2,2-trichloro-ethyl ester 108a using N-α-Boc-O-methyl serine (1 g, 4.56 mmol) instead of L-N-Boc-3-pyrazol-1-yl-alanine to afford the title compound as a clear viscous oil (1.5 g, 71%) and as a 1:1 mixture of two diastereoisomers. LCMS (m/z) 462.7 [M+H], Tr=2.71 min.

Compound 117b: (S)-1-[(S)-2-((S)-2-tert-Butoxycarbonylamino-3-methyl-butyrylamino)-3-methoxy-propionyl]-hexahydro-pyridazine-3-carboxylic acid 2,2,2-trichloro-ethyl ester

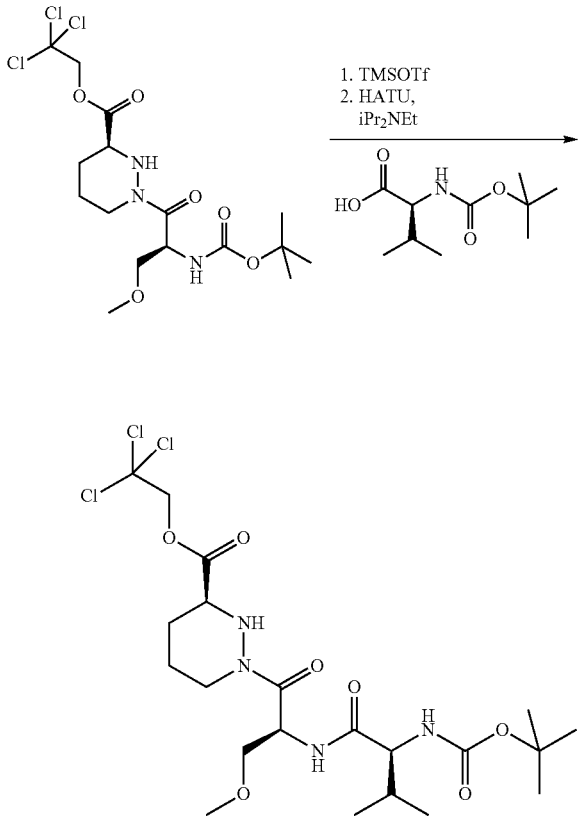

Compound 117b was prepared in the same manner as (S)-1-[(S)-2-((S)-2-tert-butoxycarbonylamino-3-methyl-butyrylamino)-3-pyrazol-1-yl-propionyl]-hexahydro-pyridazine-3-carboxylic acid 2,2,2-trichloro-ethyl ester using (S)-1-((S)-2-tert-butoxycarbonylamino-3-methoxy-propionyl)-hexahydro-pyridazine-3-carboxylic acid 2,2,2-trichloro-ethyl ester (750 mg, 1.62 mmol) instead of (S)-1-((S)-2-tert-butoxycarbonylamino-3-pyrazol-1-yl-propionyl)-hexahydro-pyridazine-3-carboxylic acid 2,2,2-trichloro-ethyl ester to afford the title compound as a viscous oil (700 mg, 77%) and as a 1:1 mixture of two diastereoisomers. LCMS (m/z) 563.3 [M+H], Tr=2.81 min.

Compound 117c: (S)-1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-3-methoxy-propionyl]-hexahydro-pyridazine-3-carboxylic acid 2,2,2-trichloro-ethyl ester

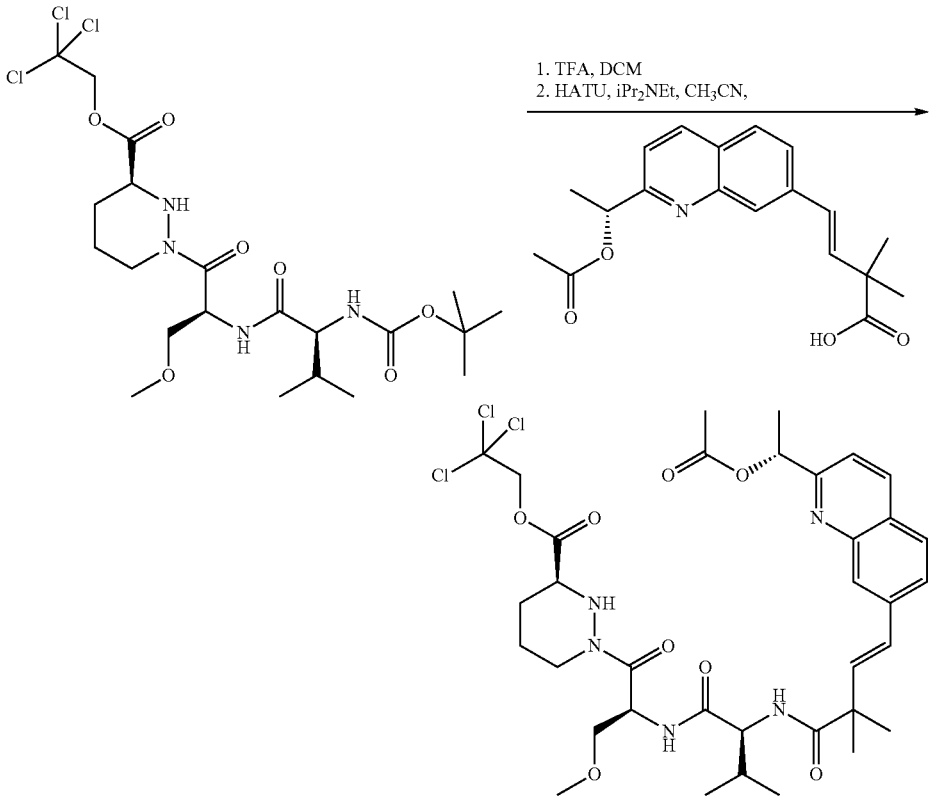

Compound 117c was prepared in the same manner as (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-pyrazol-1-yl-propionyl]-hexahydro-pyridazine-3-carboxylic acid 2,2,2-trichloro-ethyl ester using (S)-1-[(S)-2-((S)-2-tert-butoxycarbonylamino-3-methyl-butyrylamino)-3-methoxy-propionyl]-hexahydro-pyridazine-3-carboxylic acid 2,2,2-trichloro-ethyl ester (700 mg, 1.25 mmol) instead of (S)-1-[(S)-2-((S)-2-tert-butoxycarbonylamino-3-methyl-butyrylamino)-3-pyrazol-1-yl-propionyl]-hexahydro-pyridazine-3-carboxylic acid 2,2,2-trichloro-ethyl ester to afford the title compound as an off white foam (460 mg, 48%) and as a 1:1 mixture of two diastereoisomers. LCMS (m/z) 770.2 [M+H], Tr=3.06 min.

-continued

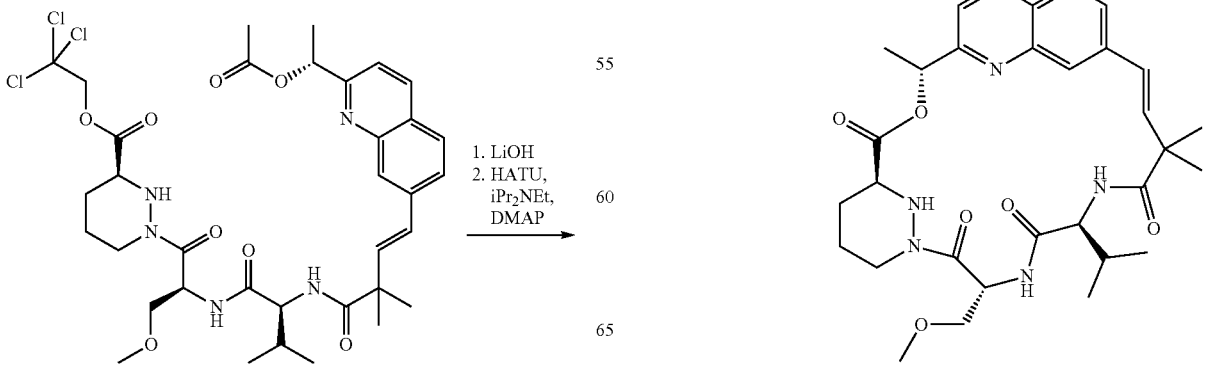

Compound 117 was prepared in the same manner as compound 108, using (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-methoxy-propionyl]-hexahydro-pyridazine-3-carboxylic acid 2,2,2-trichloroethyl ester (450 mg, 0.58 mmol) instead of (S)-1-[(S)-2-((S)-2-{(E)-4-[2-((R)-1-acetoxy-ethyl)-quinolin-7-yl]-2,2-dimethyl-but-3-enoylamino}-3-methyl-butyrylamino)-3-pyrazol-1-yl-propionyl]-hexahydro-pyridazine-3-carboxylic acid 2,2,2-trichloro-ethyl ester to afford two diastereoisomers as white solids after isolation following HPLC using an Agilent Eclipse XDB/C18 7 micron, 250× 21.2 mm column and elution with acetonitrile/water.

Example 117, Compound 117 First eluting Diastereoisomer 1 (26 mg, 8%); $^1$H NMR (300 MHz, $CD_3OD$) δ 0.96 (d, J=6.5 Hz, 3H), 0.97 (d, J=6.5 Hz, 3H), 1.36 (s, 3H), 1.36-1.43 (m, 2H), 1.51 (s, 3H), 1.63-1.70 (m, 1H), 1.71 (d, J=6.7 Hz, 3H), 1.83-2.05 (m, 3H), 2.68-2.81 (m, 1H), 3.57 (s, 3H), 3.81-3.98 (m, 3H), 4.31 (d, J=10.0 Hz, 1H), 4.35-4.46 (m, 1H), 5.91 (q, J=6.7 Hz, 1H), 5.95-6.02 (m, 1H), 6.38, 6.48 (ABq, J=16.6 Hz, 2H), 7.26 (d, J=8.7 Hz, 1H), 7.39 (d, J=8.5 Hz, 1H), 7.70-7.92 (m, 3H), 8.19 (d, J=8.5 Hz, 1H). LCMS (m/z) 580.2 [M+H], Tr=2.40 min.

Example 118, Compound 118 Second eluting Diastereoisomer 2 (20 mg, 6%); $^1$H NMR (300 MHz, $CD_3OD$) δ 0.84 (d, J=6.5 Hz, 3H), 0.96 (d, J=6.0 Hz, 3H), 1.37 (s, 3H), 1.54 (s, 3H), 1.69 (d, J=6.3 Hz, 3H), 1.74-2.13 (m, 5H), 2.37-2.52 (m, 1H), 2.72-2.89 (m, 1H), 3.20 (s, 3H), 3.41-3.61 (m, 3H), 4.03 (d, J=11.6 Hz, 1H), 4.33-4.45 (m, 1H), 4.50 (d, J=12.7 Hz, 1H), 5.81 (s, 1H), 6.05-6.23 (m, 1H), 6.61, 6.78 (ABq, J=16.3 Hz, 2H), 7.15 (d, J=7.6 Hz, 1H), 7.42 (d, J=8.7 Hz, 1H), 7.62 (d, J=8.0 Hz, 1H), 7.86 (d, J=8.0 Hz, 1H), 8.11 (s, 1H), 8.26 (d, J=8.3 Hz, 1H). LCMS (m/z) 580.2 [M+H], Tr=2.60 min.

Example 119

Compound 119

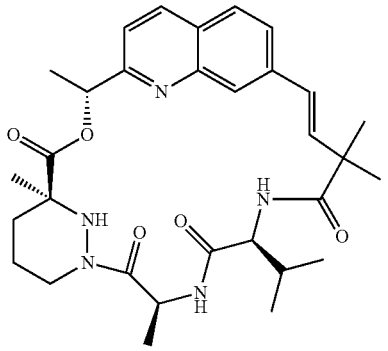

Compound 119a. 1-[(S)-2-((S)-2-{(E)-4-[2-((R)-1-Acetoxy-ethyl)-quinolin-7-yl]-2,2-dimethyl-but-3-enoylamino}-3-methyl-butyrylamino)-propionyl]-3-methyl-hexahydro-pyridazine-3-carboxylic acid methyl ester

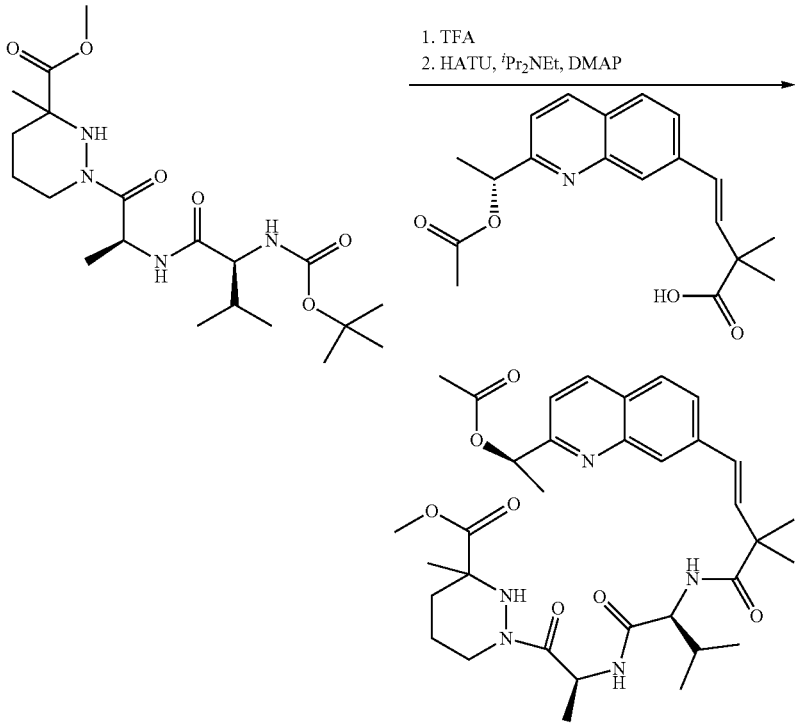

To a solution of 1-[(S)-2-((S)-2-tert-butoxycarbonylamino-3-methyl-butyrylamino)-propionyl]-3-methyl-hexahydro-pyridazine-3-carboxylic acid methyl ester (630 mg, 1.47 mmol) in dichloromethane (10 mL) at 0° C. was added trifluoroacetic acid (1.2 mL). The reaction mixture was allowed to warm to room temperature and stirred for 3 h. A further aliquot of trifluoroacetic acid (0.5 mL) was added and the reaction stirred for a further 1 h. The volatiles were removed in vacuo and the residual trifluoroacetic acid azeotroped off with toluene (3×). To a solution of the crude amine in acetonitrile (10 mL) was added a solution of (E)-4-[2-((R)-1-acetoxy-ethyl)-quinolin-7-yl]-2,2-dimethyl-but-3-enoic acid (480 mg, 1.47 mmol) in acetonitrile (5 mL) at 0° C. The solution was treated with N,N-diisopropylethylamine (1.6 mL, 9.20 mmol) and (dimethylamino)-N,N-dimethyl(3H-[1,2,3]triazolo[4,5-b]pyridin-3-yloxy)methaniminium hexafluorophosphate (782 mg, 2.06 mmol). The reaction mixture was allowed to warm to room temperature, stirred for 16 h and then concentrated in vacuo. The residue was re-dissolved in dichloromethane and washed with hydrochloric acid (1 M). After separation of the layers, the aqueous phase was re-extracted with dichloromethane and then the combined organic layers were washed with saturated aqueous sodium hydrogen carbonate solution. The organic phase was passed through a hydrophobic frit and the solvent evaporated in vacuo. The product was purified by silica gel chromatography eluting with a gradient of iso-hexanes/ethyl acetate 95:5 to 3:2 to afford the title compound (795 mg, 85% over 2 steps) as a yellow foam and as a 1:1 mixture of diastereoisomers. LCMS (m/z) 638 [M+H], Tr=2.58 min.

Compound 119b. 1-[(S)-2-((S)-2-{(E)-4-[2-((R)-1-Hydroxy-ethyl)-quinolin-7-yl]-2,2-dimethyl-but-3-enoylamino}-3-methyl-butyrylamino)-propionyl]-3-methyl-hexahydro-pyridazine-3-carboxylic acid

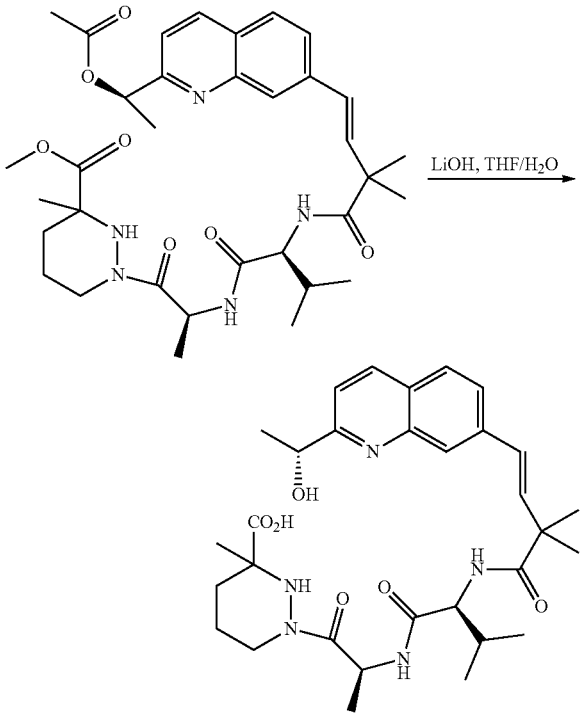

To a solution of 1-[(S)-2-((S)-2-{(E)-4-[2-((R)-1-acetoxy-ethyl)-quinolin-7-yl]-2,2-dimethyl-but-3-enoylamino}-3-methyl-butyrylamino)-propionyl]-3-methyl-hexahydro-pyridazine-3-carboxylic acid methyl ester (790 mg, 1.24 mmol) in tetrahydrofuran/water (60 mL, 5:1) at 0° C. was added lithium hydroxide monohydrate (380 mg, 9.04 mmol). After stirring at 0° C. for 5 h, the reaction was quenched with hydrochloric acid (1 M, 12 mL). The volatiles were removed in vacuo and residual acetic acid and methanol were azeotroped off with toluene (3×). The residue was partitioned between ethyl acetate and water. After separation of the layers, the aqueous phase was extracted with ethyl acetate (4×) and dichloromethane (5×). The combined organic layers were dried over anhydrous magnesium sulfate, filtered and concentrated in vacuo to afford the title compound (668 mg, 93%) as a pale yellow solid and as a 1:1 mixture of diastereoisomers. LCMS (m/z) 582 [M+H], Tr=1.54 min.

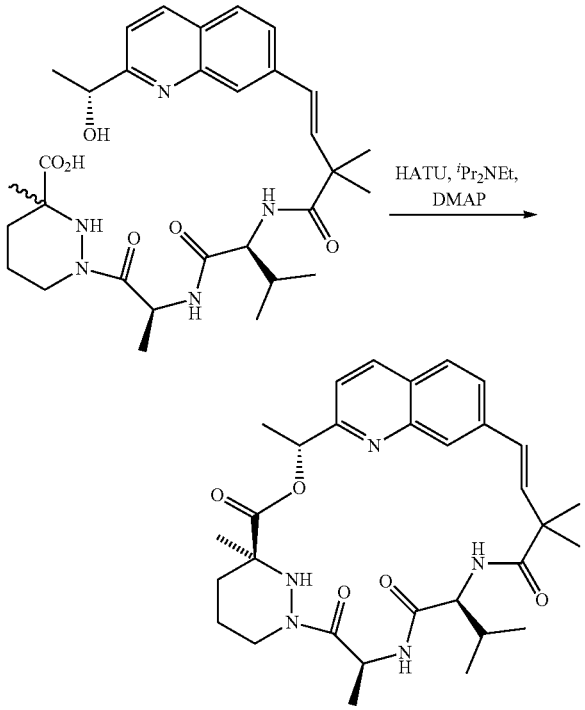

To a solution of 1-[(S)-2-((S)-2-{(E)-4-[2-((R)-1-hydroxy-ethyl)-quinolin-7-yl]-2,2-dimethyl-but-3-enoylamino}-3-methyl-butyrylamino)-propionyl]-3-methyl-hexahydro-pyridazine-3-carboxylic acid (500 mg, 0.86 mmol) in tetrahydrofuran (250 mL) at 0° C. was added 4-dimethylaminopyridine (16 mg, 0.13 mmol), 4 Å molecular sieves (2 g), N,N-diisopropylethylamine (1.04 mL, 5.98 mmol) and (dimethylamino)-N,N-dimethyl(3H-[1,2,3]triazolo[4,5-b]pyridin-3-yloxy)methaniminium hexafluorophosphate (540 mg, 1.42 mmol). The reaction mixture was stirred at room temperature for 36 h and then at 45° C. for a further 16 h. The reaction was concentrated in vacuo and then purified by silica gel chromatography eluting with iso-hexanes/ethyl acetate 2:3 to 0:1. The more polar diastereoisomer was isolated (110 mg, 23%) as a colourless solid. $^1$H NMR (300 MHz, $CD_3OD$) δ 0.93 (d, J=6.7 Hz, 3H), 0.96 (d, J=6.7 Hz, 3H), 1.35 (s, 3H), 1.50 (s, 3H), 1.54 (d, J=7.1 Hz, 3H), 1.65 (s, 3H), 1.70-1.73 (m, 2H), 1.76 (d, J=6.7 Hz, 3H), 1.81-2.03 (m, 3H), 2.69 (m, 1H), 4.25 (m, 1H), 4.41 (br d, J=13.6 Hz, 1H), 5.77 (q, J=7.1 Hz, 1H), 5.90 (q, J=6.7 Hz, 1H), 6.38, 6.50 (ABq, J=16.4 Hz, 2H), 7.41 (d, J=8.26 Hz, 1H), 7.71-7.85 (m, 3H), 8.22 (d, J=8.3 Hz, 1H). LCMS (m/z) 564 [M+H], Tr=2.25 min.

Example 120

Compound 120

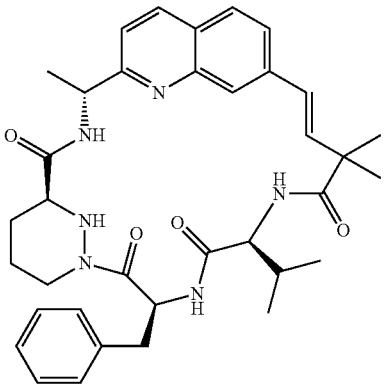

Compound 120a. (S)-1-((S)-2-tert-Butoxycarbonylamino-3-phenyl-propionyl)-hexahydro-pyridazine-3-carboxylic acid 2,2,2-trichloro-ethyl ester

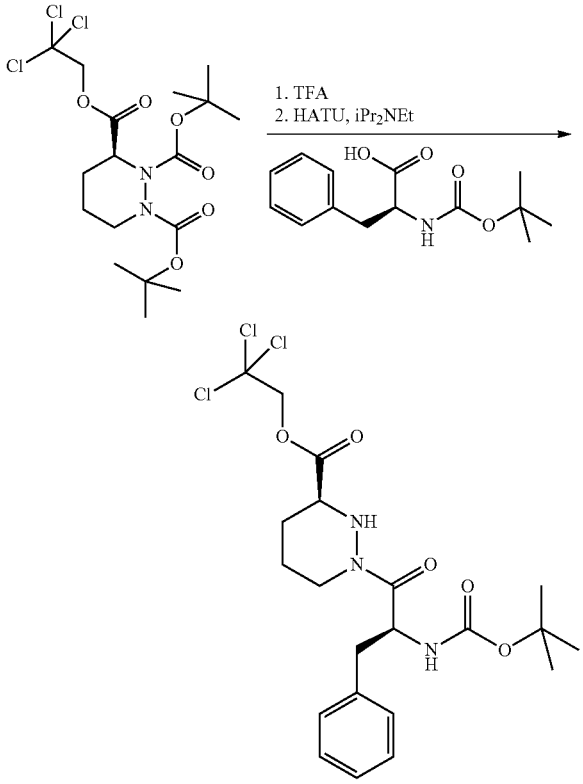

To a solution of (S)-tetrahydro-pyridazine-1,2,3-tricarboxylic acid 1,2-di-tert-butyl ester 3-(2,2,2-trichloro-ethyl) ester (1.0 g, 2.2 mmol) in anhydrous dichloromethane (7 mL) at room temperature and under an atmosphere of nitrogen was added trifluoroacetic acid (6.7 mL, 86.6 mmol). The solution was warmed to room temperature and stirred for 16 h. The reaction was concentrated in vacuo and the residue co-evaporated from toluene (3×). The resulting brown viscous oil was dissolved in anhydrous acetonitrile (2 mL) and added to a solution of Boc-Phe-Ala-OH (574 mg, 2.2 mmol), N,N-diisopropylethylamine (1.5 mL, 8.7 mmol) and 2-(1H-7-azabenzotriazol-1-yl)-1,1,3,3-tetramethyl uronium hexafluorophosphate methanaminium (821 mg, 2.5 mmol) in anhydrous acetonitrile (10 mL) that had been previously stirred at 0° C. for 20 minutes. The reaction was warmed to room temperature and stirred for 16 h. The reaction was cooled to 0° C. diluted with ethyl acetate and quenched with hydrochloric acid (1 M). The organic layer was separated and washed with a saturated aqueous solution of sodium bicarbonate and brine. The organic layer was then dried through a hydrophobic frit and concentrated in vacuo. The residue was purified by silica gel chromatography using iso-hexanes/ethyl acetate 1:1 to give the title compound (1.0 g, 91%) as a white foam. $^1$H NMR (300 MHz, $CDCl_3$) δ 1.43 (s, 9H), 1.45-1.51 (m, 1H), 1.72-1.95 (m, 2H), 2.14-2.33 (m, 1H), 2.61-2.76 (m, 1H), 2.84-3.10 (m, 3.58 (d, J=11.6 Hz, 1H), 4.34-4.48 (m, 1H), 4.76, 4.76 (ABq, J=12.4 Hz, 2H), 5.18-5.31 (m, 1H), 5.46-5.61 (m, 2H), 7.17-7.36 (m, 5H). LCMS (m/z) 508.0 [M+H], Tr=3.18 min.

Compound 120b. (S)-1-[(S)-2-((S)-2-tert-Butoxycarbonylamino-3-methyl-butyrylamino)-3-phenyl-propionyl]-hexahydro-pyridazine-3-carboxylic acid 2,2,2-trichloro-ethyl ester

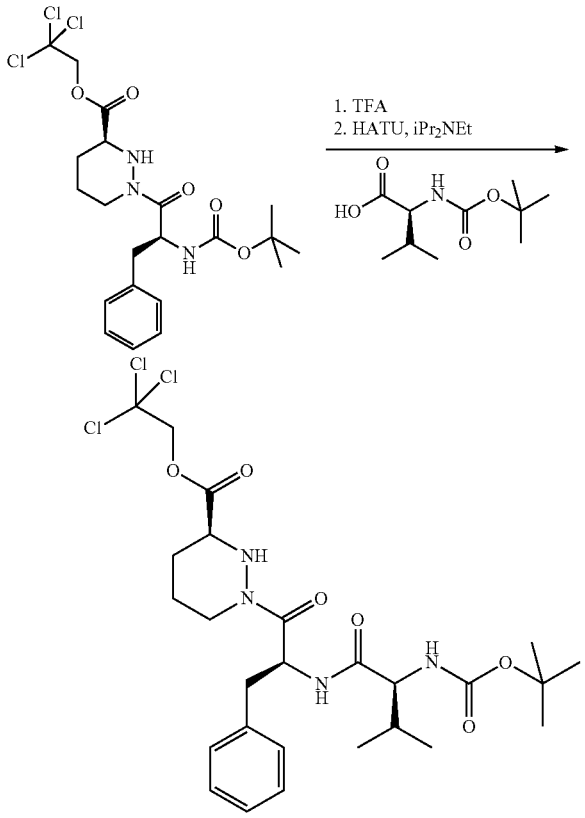

To a solution of (S)-1-((S)-2-tert-butoxycarbonylamino-3-phenyl-propionyl)-hexahydro-pyridazine-3-carboxylic acid 2,2,2-trichloro-ethyl ester (1.0 g, 2.0 mmol) in anhydrous dichloromethane (7 mL) at 0° C. and under an atmosphere of nitrogen was added trifluoroacetic acid (1.5 mL, 19.7 mmol). The reaction mixture was warmed to room temperature and stirred for 2 h before concentrating in vacuo. The residue was dissolved in anhydrous acetonitrile (11 mL), cooled to 0° C. and under an atmosphere of nitrogen was added N,N-diisopropylethylamine (1.8 mL, 9.8 mmol), N-Boc-Val-OH (428 mg, 2.0 mmol) and 2-(1H-7-azabenzotriazol-1-yl)-1,1,3,3-tetramethyl uronium hexafluorophosphate methanaminium (1.1 g, 2.8 mmol). After 16 h at room temperature the reaction was diluted with ethyl acetate and quenched with hydrochloric acid (1 M). The organic layer was separated and washed with a saturated aqueous solution of sodium bicarbonate and brine. The organic layer was then dried through a hydrophobic frit and concentrated in vacuo. The residue was purified by silica gel chromatography using iso-hexanes/ethyl acetate 1:1 to give the title compound (1.0 g, 84%) as a viscous oil. $^1$H NMR (300 MHz, $CDCl_3$) δ 0.89 (d, J=6.7 Hz, 3H), 0.95 (d, J=6.9 Hz, 3H), 1.47 (s, 9H), 1.47-1.56 (m, 1.72-1.94 (m, 2H), 2.08-2.20 (m, 1H), 2.23-2.36 (m, 1H), 2.67-2.84 (m, 1H), 2.91 (dd, J=12.9, 9.4 Hz, 1H), 3.05 (dd, J=12.9, 5.4 Hz, 1H), 3.53 (d, J=10.9 Hz, 1H), 3.90-4.03 (m, 1H), 4.23-4.36 (m, 1H), 4.70, 4.84 (ABq, J=12.0 Hz, 2H), 5.00-5.14 (m, 1H), 5.73-5.86 (m, 1H), 6.55 (d, J=8.3 Hz, 1H), 7.16-7.34 (m, 5H). LCMS (m/z) 607.1 [M+H], Tr=3.24 min.

Compound 120c. (S)-1-[(S)-2-((S)-2-{(E)-4-[2-((R)-1-tert-Butoxycarbonylamino-ethyl)-quinolin-7-yl]-2,2-dimethyl-but-3-enoylamino}-3-methyl-butyrylamino)-3-phenyl-propionyl]-hexahydro-pyridazine-3-carboxylic acid 2,2,2-trichlo-ethyl ester

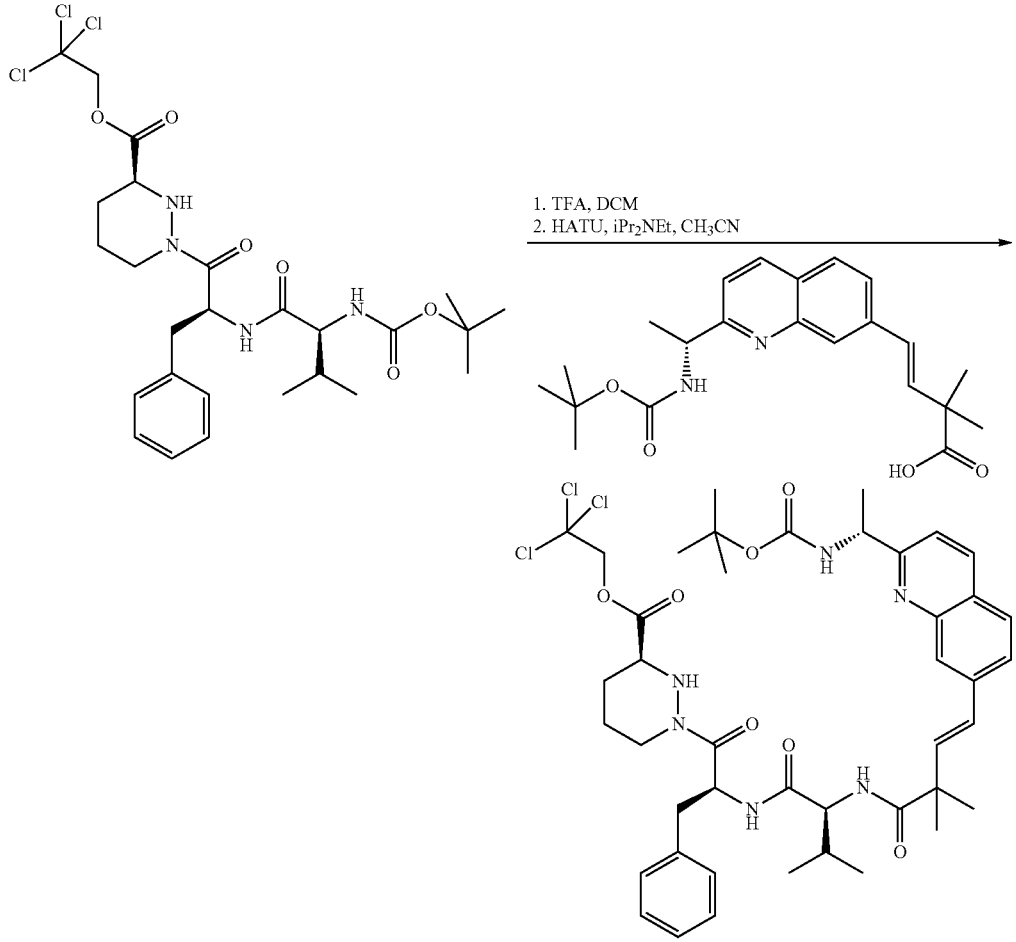

To a solution of (S)-1-[(S)-2-((S)-2-tert-butoxycarbonylamino-3-methyl-butyrylamino)-3-phenyl-propionyl]-hexahydro-pyridazine-3-carboxylic acid 2,2,2-trichloro-ethyl ester (395 mg, 0.65 mmol) in anhydrous dichloromethane (2 mL) at 0° C. and under an atmosphere of nitrogen was added trifluoroacetic acid (0.5 mL, 6.5 mmol). The reaction mixture was warmed to room temperature and stirred for 3 h before concentrating in vacuo and co-evaporating from toluene (3×). This residue was dissolved in anhydrous acetonitrile (7 mL) and at 0° C. and under an atmosphere of nitrogen was added (E)-4-[2-((R)-1-tert-butoxycarbonylamino-ethyl)-quinolin-7-yl]-2,2-dimethyl-but-3-enoic acid (250 mg, 0.65 mmol), N,N-diisopropylethylamine (0.57 mL, 3.25 mmol) and 2-(1H-7-azabenzotriazol-1-yl)-1,1,3,3-tetramethyl uronium hexafluorophosphate methanaminium (346 mg, 0.91 mmol). The solution was warmed to room temperature and stirred overnight. The reaction was cooled to 0° C., diluted with ethyl acetate and quenched with hydrochloric acid (1 M). The organic layer was separated and washed with a saturated aqueous solution of sodium bicarbonate (2×) and brine. The organic layer was then dried through a hydrophobic frit and concentrated in vacuo. The residue was purified by silica gel chromatography using iso-hexanes/ethyl acetate 1:2 to give the title compound (324 mg, 57%) as a viscous clear oil. $^1$H NMR (300 MHz, $CDCl_3$) δ 0.87 (d, J=6.7 Hz, 3H), 0.93 (d, J=6.9 Hz, 3H), 1.41-1.53 (m, 17H), 1.56 (d, J=6.7 Hz, 3H), 1.73-1.94 (m, 2H), 2.10-2.19 (m, 1H), 2.30-2.43 (m, 1H), 2.70-2.85 (m, 1H), 2.85-3.05 (m, 2H), 3.48-3.58 (m, 1H), 4.20-4.34 (m, 2H), 4.83 (ABq, J=12.1 Hz, 2H), 4.94-5.08 (m, 1H), 5.69-5.81 (m, 1H), 6.17-627 (m, 1H), 6.31 (d, J=8.5 Hz, 1H), 6.44 (d, J=8.0 Hz, 1H), 6.63, 6.79 (ABq, J=16.3 Hz, 2H), 7.13-7.36 (m, 6H), 7.65 (d, J=8.3 Hz, 1H), 7.76 (d, J=8.3 Hz, 1H), 8.04 (s, 1H), 8.08 (d, J=8.3 Hz, 1H). LCMS (m/z) 873.4 [M+H], Tr=3.41 min.

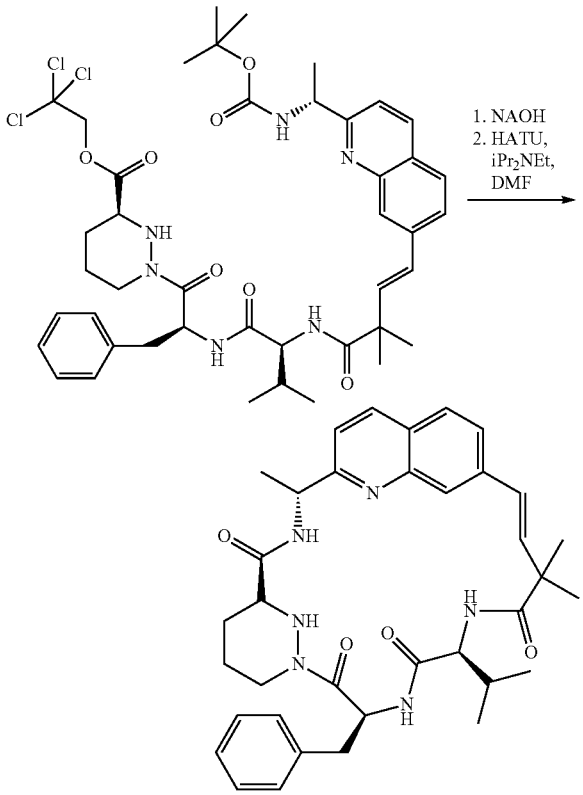

To a solution of (S)-1-[(S)-2-((S)-2-{(E)-4-[2-((R)-1-tert-butoxycarbonylamino-ethyl)-quinolin-7-yl]-2,2-dimethyl-but-3-enoylamino}-3-methyl-butyrylamino)-3-phenyl-propionyl]-hexahydro-pyridazine-3-carboxylic acid 2,2,2-trichlo-ethyl ester (320 mg, 0.37 mmol) in anhydrous tetrahydrofuran (5 mL) at 0° C. was added a 0.4 M aqueous solution of sodium hydroxide (1.1 mL, 0.44 mmol). The reaction was stirred at 0° C. for 1 h before being acidified to pH 5 with hydrochloric acid (2 M) and concentrated in vacuo. The resulting residue was partitioned between dichloromethane and water and the organic layer separated, dried through a hydrophobic frit and concentrated in vacuo. The residue was dissolved in anhydrous 1,4-dioxane (2 mL) and at room temperature was added a 4 M solution of hydrochloric acid in 1,4-dioxane (0.46 mL, 1.8 mmol). The reaction was stirred for 1.5 h, concentrated in vacuo and the resulting solid triturated with diethyl ether to afford a light yellow solid. The solid was dissolved in anhydrous N,N-dimethylformamide (2 mL) and N,N-diisopropylethylamine (0.33 mL, 1.8 mmol) and this solution was added to a pre-stirred solution of 2-(1H-7-azabenzotriazol-1-yl)-1,1,3,3-tetramethyl uronium hexafluorophosphate methanaminium (209 mg, 0.6 mmol) in anhydrous dichloromethane (122 mL) at 0° C. and under an atmosphere of nitrogen. Following the addition the reaction was stirred at room temperature for 30 minutes before being concentrated in vacuo. The ensuing residue was dissolved in ethyl acetate and washed with hydrochloric acid (0.5 M), saturated sodium bicarbonate, brine and 5% aqueous lithium chloride. The organic layer was dried through a hydrophobic frit and concentrated in vacuo. The residue was purified by silica gel chromatography using iso-hexanes/acetone 1:1 to give the crude title compound (130 mg) as a brown solid. This was further purified by silica gel chromatography using iso-hexanes/ethyl acetate 1:3 then 0:1 to give the title compound (40 mg, 17%) as a white solid. $^1$H NMR (300 MHz, $CD_3OD$) δ 0.90 (d, J=6.7 Hz, 3H), 0.98 (d, J=6.7 Hz, 3H), 1.31 (s, 3H), 1.33-1.43 (m, 1H), 1.48 (s, 3H), 1.51-1.61 (m, 1H), 1.65 (d, J=6.5 Hz, 3H), 1.82-1.98 (m, 2H), 2.18-2.28 (m, 2H), 2.55-2.78 (m, 2H), 3.03 (dd, J=13.2, 9.1 Hz, 1H), 3.19 (dd, J=13.2, 6.5 Hz, 1H), 4.27 (t, J=8.9 Hz, 1H), 4.42-4.52 (m, 1H), 5.08 (d, J=12.0 Hz, 1H), 5.17 (t, J=6.5 Hz, 1H), 5.92 (d, J=16.1 Hz, 1H), 6.12 (q, J=6.5 Hz, 1H), 6.68 (d, J=16.1 Hz, 1H), 6.85 (d, J=9.4 Hz, 1H), 7.07-7.21 (m, 3H), 7.45 (d, J=8.5 Hz, 1H), 7.50 (dd, J=8.5, 1.3 Hz, 1H), 7.56-7.65 (m, 2H), 7.79 (s, 1H), 7.84 (d, J=8.5 Hz, 1H), 8.27 (d, J=8.5 Hz, 1H). LCMS (m/z) 625.3 [M+H], Tr=2.71 min.

Example 121

Compound 121

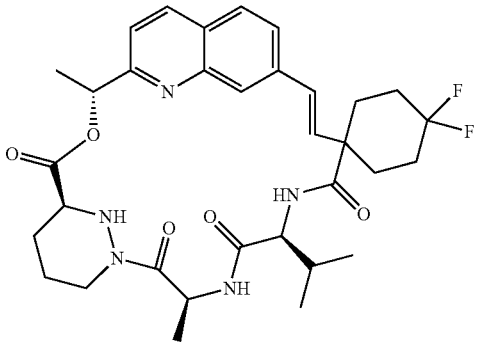

Compound 121a

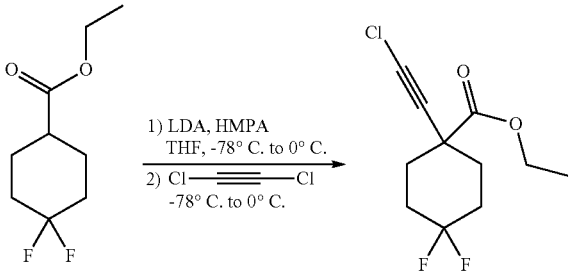

Into an oven dried, argon purged flask tetrahydrofuran (50 mL) was added and the solution was cooled with the ice bath. A 1.8 M solution of lithium diisopropylamide (7.2 mL, 13 mmol) in tetrahydrofuran/heptane/ethylbenzene was added through the septa. The resulting solution of lithium diisopropylamide was cooled to −78° C., and treated dropwise with ethyl 4,4-difluorocyclohexanecarboxylate (CAS: 178312-47-5, Oakwood Products, Inc.) (1.73 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloroethyne (ca. 10 mmol). The reaction mixture was stirred at −78° C. for 30 min. and then allowed to warm to the room temperature. After 4 hours at room temperature, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-20% ethyl acetate in iso-hexanes) to afford the title compound (1068 mg, 47%) as a colorless oil. $^1$H NMR (400 MHz, $CDCl_3$) δ 4.21 (q, J=7.1 Hz, 2H), 2.08-2.00 (m, 8H), 1.28 (t, J=7.1 Hz, 3H). Tr=2.71 min.

Compound 121b

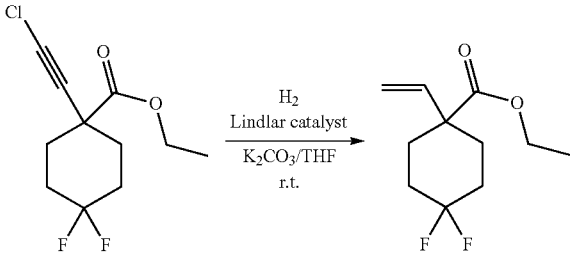

A solution of compound Intermediate 121a (900 mg, 3.6 mmol) in tetrahydrofuran (100 mL) containing Lindlar catalyst (300 mg, Sigma-Aldrich) and potassium carbonate (2480 mg, 18 mmol) was hydrogenated at room temperature and at atmospheric pressure of hydrogen for 12 hours. The reaction mixture was filtered through Celite and the filter pad was washed with tetrahydrofuran (50 mL). The filtrate was evaporated to afford the title compound (780 mg, 99%) as a colourless oil. $^1$H NMR (400 MHz, $CDCl_3$) δ 5.79 (dd, J=17.5, 10.7 Hz, 1H), 5.17 (approx. d, J=17 Hz, 1H), 5.14 (approx. d, J=10 Hz, 1H), 4.15 (q, J=7.0 Hz, 2H), 2.30-2.17 (m, 2H), 2.04-1.90 (m, 2H), 1.91-1.67 (m, 4H), 1.24 (t, J=7.1 Hz, 3H). Tr=2.66 min.

Compound 121c

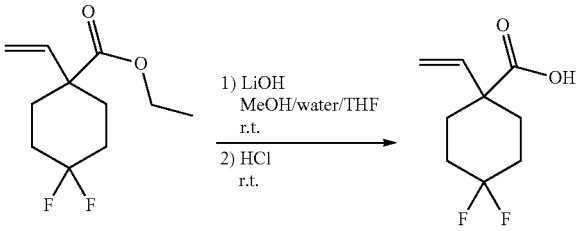

A solution of 121b (654 mg, 3 mmol) in tetrahydrofuran/water/methanol (25 mL, 4:1:1) was treated with lithium hydroxide (144 mg, 6 mmol). After stirring at room temperature overnight, the reaction was quenched with 1 M hydrochloric acid (20 mL), concentrated down under reduced pressure, dissolved in water (50 mL) and extracted with ethyl acetate (2×100 mL). The organics were combined, washed with brine, dried over sodium sulfate and filtered. The filtrate was evaporated to afford the title compound (560 mg, 98%) as a white solid. $^1$H NMR (400 MHz, $CDCl_3$) δ 5.83 (dd, J=17.4, 10.7 Hz, 1H), 5.27 (approx. d, J=17 Hz, 1H), 5.23 (approx. d, J=10 Hz, 1H), 2.28-2.19 (m, 2H), 2.07-1.72 (m, 6H). LCMS (m/z) 188.9 [M−H], Tr=2.18 min.

Compound 121d

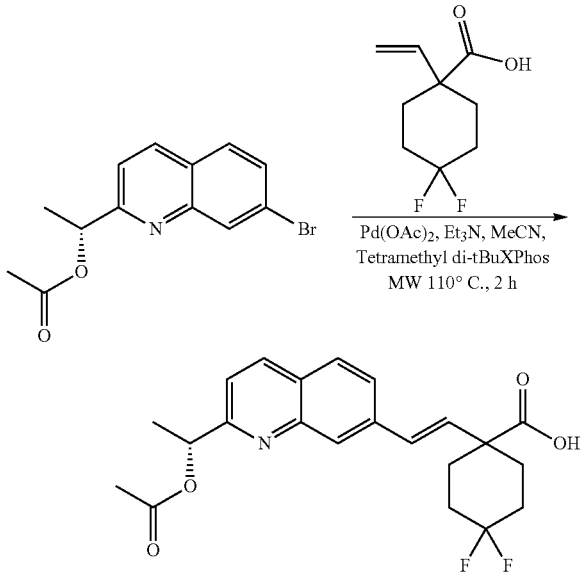

To a solution of acetic acid (R)-1-(7-bromo-quinolin-2-yl)-ethyl ester (294 mg, 1 mmol) in anhydrous acetonitrile (20 mL) was added palladium(II) acetate (22 mg, 0.1 mmol), 121c (190 mg, 1 mmol), 2-di-tert-butylphosphino-3,4,5,6-tetramethyl-2',4',6'-triisopropyl-1,1'-biphenyl (48 mg, 0.1 mmol) and triethylamine (0.64 mL, 3 mmol) then the mixture was heated in the microwave at 110° C. for 2 hours. The reaction mixture was filtered through Celite and the filter pad was washed with tetrahydrofuran (30 mL). The filtrate was evaporated then water (200 mL) was added and the organics extracted with ethyl acetate (2×50 mL). The combined organics were dried over sodium sulfate, filtered and concentrated under reduced pressure to give a crude residue. This was subjected to silica gel chromatography (gradient from 0-50% ethyl acetate in iso-hexanes) to afford the title compound (264 mg, 66%) as a white solid. $^1$H NMR (400 MHz, $CDCl_3$) δ 8.15 (d, J=8.5 Hz, 1H), 8.07 (s, 1H), 7.74 (d, J=8.5 Hz, 1H), 7.62 (d, J=8.5 Hz, 1H), 7.45 (d, J=8.5 Hz, 1H), 6.78 (d, J=16.3 Hz, 1H), 6.42 (d, J=16.3 Hz, 1H), 6.08 (q, J=6.6 Hz, 1H), 2.48-2.38 (m, 2H), 2.13 (s, 3H), 2.10-1.83 (m, 6H), 1.64 (d, J=6.7 Hz, 3H). LCMS (m/z) 404.1 [M+H], Tr=3.69 min (Gemini 5u C18 110 Å, 50×4.60 mm 5 micron column, 6 min, 2 ml/min, 5-100% acetonitrile/water, 0.1% acetic acid modifier gradient).

Compound 121e

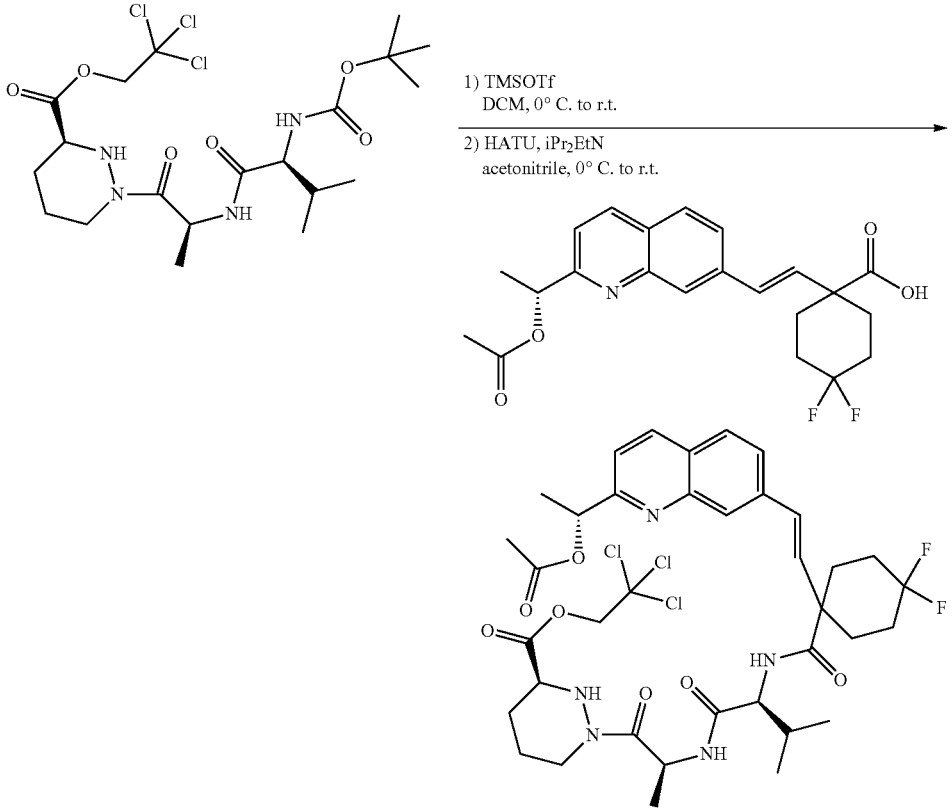

A solution of 1e (0.37 g, 0.7 mmol) in dichloromethane (10 mL) was cooled in an ice water bath. Trimethylsilyl trifluoromethanesulfonate (0.31 g, 1.4 mmol) was added dropwise at 0° C. under argon, and the resulting solution was stirred at room temperature for 30 minutes. The reaction mixture was evaporated to dryness and the resulting crude residue (LCMS (m/z) 431.2/433.3 [M+H], Tr=2.06 min) was dissolved in anhydrous acetonitrile (12 mL) under argon. The reaction mixture was stirred at 0° C., 121d (201 mg, 0.5 mmol) and N,N-diisopropylethylamine (387 mg, 3 mmol) were added followed by 2-(1H-7-azabenzotriazol-1-yl)-1,1,3,3-tetramethyl uronium hexafluorophosphate methanaminium (285 mg, 0.75 mmol). The reaction mixture was stirred at room temperature for 12 hours. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-30% ethyl acetate and methanol (4/1) in iso-hexanes) to afford the title compound (245 mg, 60%) as a white solid after evaporation. $^1$H NMR (400 MHz, $CD_3OD$) δ 8.77-8.68 (m, 1H), 8.42 (dd, J=8.4, 1.3 Hz, 1H), 8.30 (d, J=8.5 Hz, 1H), 8.04-7.94 (m, 2H), 7.87 (d, J=8.6 Hz, 1H), 7.78 (d, J=8.6 Hz, 1H), 7.57-7.47 (m, 2H), 7.43 (d, J=8.4 Hz, 1H), 6.86 (d, J=16.4 Hz, 1H), 6.58 (d, J=16.4 Hz, 1H), 5.97 (q, J=6.8 Hz, 1H), 5.42-5.21 (m, 2H), 4.97 (d, J=12.1 Hz, 1H), 4.76 (d, J=12.1 Hz, 1H), 3.83-3.72 (m, 2H), 2.45-2.33 (m, 2H), 2.15 (s, 3H), 2.10-1.73 (m, 10H), 1.66-1.64 (d, J=6.6 Hz, 3H), 1.26 (d, J=7.0 Hz, 3H), 0.99-0.89 (m, 6H). LCMS (m/z) 816.2/818.2 [M+H], Tr=4.34 min.

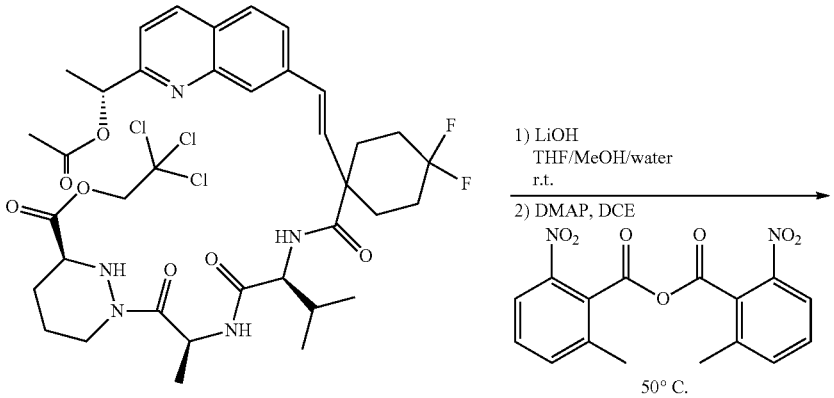

-continued

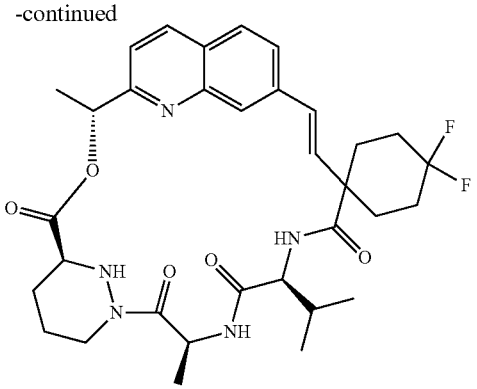

To a solution of 121e (200 mg, 0.24 mmol) in tetrahydrofuran (10 mL) was added methanol (4 mL), water (4 mL) and lithium hydroxide (12 mg, 0.52 mmol). The mixture was stirred for 2 hours at ambient temperature and was quenched with aqueous 1 M hydrochloric acid (0.6 mL, 0.6 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification. Into oven dried, argon purged flask were placed 2-methyl-6-nitrobenzoic anhydride (344 mg, 1 mmol), 4-dimethylaminopyridine (366 mg, 3 mmol) and anhydrous 1,2-dichloroethane (200 mL). The resulting solution was heated at 50 50° C., and the crude seco-acid was added dropwise via syringe as a solution in dry N,N-dimethylformamide (10 mL) over 12 hours. An additional portion of dry N,N-dimethylformamide (2×5 mL) was used to complete the quantitative transfer. After stirring for additional 2 hours at 50° C., the reaction mixture was transferred to a separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with 10% citric acid (100 mL), saturated $NaHCO_3$ (100 mL), water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-40% ethyl acetate and methanol (4/1) in iso-hexanes) to afford the title compound (139 mg, 93%) as a white solid after evaporation. $^1$H NMR (400 MHz, $CD_3OD$): δ 8.55 (d, J=7.2 Hz, 1H), 8.09 (d, J=8.5 Hz, 1H), 7.70-7.66 (m, 2H), 7.52-7.48 (m, 2H), 7.30 (d, J=8.5 Hz, 1H), 6.33 (d, J=16.5 Hz, 1H), 6.22 (d, J=16.5 Hz, 1H), 5.80 (q, J=6.8 Hz, 1H), 5.67-5.55 (m, 1H), 4.32-4.16 (m, 2H), 3.73-3.64 (m, 1H), 2.63 (td, J=12.6, 3.3 Hz, 1H), 2.33-2.17 (m, 2H), 2.09-1.71 (m, 6H), 1.82-1.73 (m, 2H), 1.62 (d, J=6.8 Hz, 3H), 1.61-1.54 (m, 1.51 (d, J=7.2 Hz, 3H), 0.89-0.84 (m, 6H). LCMS (m/z) 626.3 [M+H], Tr=3.71 min.

Example 122

Compound 122

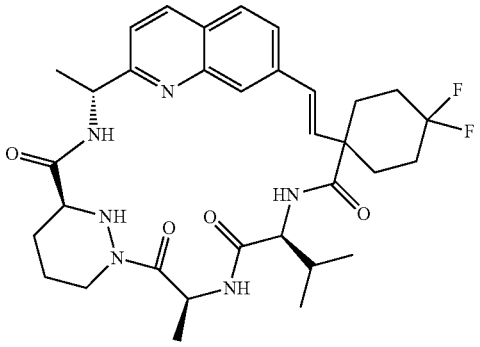

Compound 122a

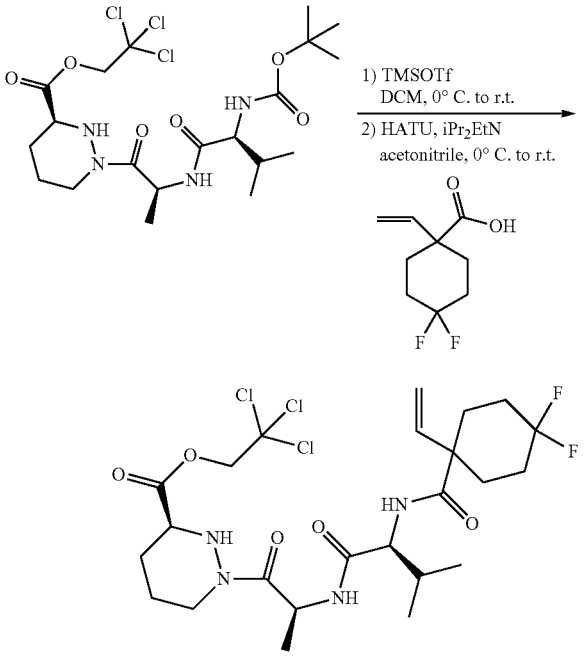

A solution of 1e (745 mg, 1.4 mmol) in dichloromethane (20 mL) was cooled in an ice water bath. Trimethylsilyl trifluoromethanesulfonate (666 mg, 3 mmol) was added dropwise at 0 0° C. under argon, and the resulting solution was stirred at room temperature for 30 minutes. The reaction mixture was evaporated to dryness and the resulting crude residue (LCMS (m/z) 431.2/433.3 [M+H], Tr=2.06 min) was dissolved in anhydrous acetonitrile (30 mL) under The reaction mixture was stirred at 0° C., 121c (190 mg, 1 mmol) and N,N-diisopropylethylamine (387 mg, 3 mmol) were added followed by 2-(1H-7-azabenzotriazol-1-yl)-1,1,3,3-tetramethyl uronium hexafluorophosphate methanaminium (570 mg, 1.5 mmol). The reaction mixture was stirred at room temperature for 12 hours. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-50% ethyl acetate and methanol (4/1) in iso-hexanes) to afford the title compound (512 mg, 85%) as a white solid after evaporation. $^1$H NMR (400 MHz, $CD_3OD$) δ 6.02 (dd, J=17.6, 10.8 Hz, 1H), 5.53-5.36 (m, 3H), 5.12 (d, J=12.1 Hz, 1H), 4.90 (d, J=12.1 Hz, 1H), 4.31 (d, J=7.5 Hz, 1H), 3.96-3.84 (m, 1H), 2.92-2.90 (s, 4H), 2.37-2.26 (m, 2H), 2.24-2.12 (m, 2H), 2.08-1.86 (m, 7H), 1.86-1.72 (m, 1H), 1.39 (d, J=7.0 Hz, 3H), 1.06 (d, J=6.8 Hz, 3H), 1.00 (d, J=6.7 Hz, 3H). LCMS (m/z) 603.2/605.2 [M+H], Tr=3.84 min (Gemini 5u C18 110 Å, 50×4.60 mm 5 micron column, 6 min, 2 ml/min, 5-100% acetonitrile/water, 0.1% acetic acid modifier gradient).

Compound 122b: (R)-2-Methyl-propane-2-sulfinic acid [1-(7-bromo-quinolin-2-yl)-eth-(E)-ylidene]-amide

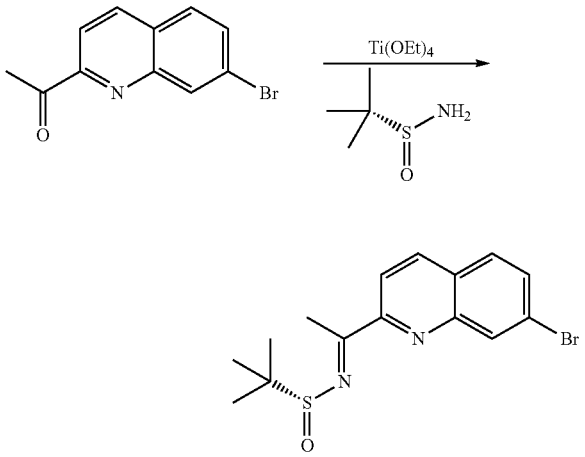

To a solution of 1-(7-bromo-quinolin-2-yl)-ethanone (1.42 g, 5.68 mmol) in THF (28 mL) was added titanium (IV) ethoxide (2.6 g, 2.35 mL, 11.4 mmol, tech. grade) followed by (R)-(+)-2-methyl-propanesulfinimide (825 mg, 6.82 mmol). The reaction mixture was stirred at 60° C. under nitrogen for 6 hours and allowed to cool. Brine was added followed by ethyl acetate and the suspension filtered through celite and the filter pad was washed with ethyl acetate. The ethyl acetate layer was separated, dried over sodium sulphate, filtered and evaporated. The residue was purified by silica gel chromatography using a gradient of iso-hexane/ethyl acetate 9:1 to 3:1 to give the title compound (448 mg, 22%) 122b as an orange solid. $^1$H NMR (300 MHz, $CDCl_3$) δ 1.38 (s, 9H), 2.99 (s, 3H), 7.71 (m, 2H), 8.16 (d, J=8.6 Hz, 1H), 8.24 (d, J=8.6 Hz, 1H), 8.37 (s, 1H). LCMS (m/z) 352.9/354.9 [M+H], Tr 3.14 minutes.

Compound 122c: (R)-2-Methyl-propane-2-sulfinic acid [(R)-1-(7-bromo-quinolin-2-yl)-ethyl]-amide

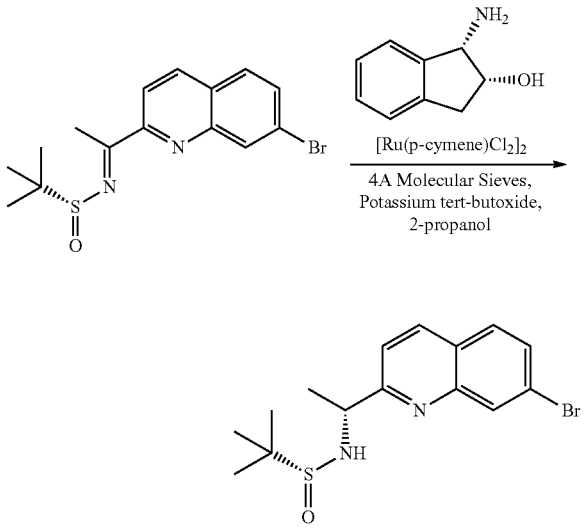

A mixture of (1S,2R)-(−)-cis-1-amino-2-indanol (19 mg, 0.13 mmol), [Ru (p-cymen) $Cl_2]_2$ (39 mg, 0.064 mmol) and powdered 4 Å Molecular Sieves (0.7 g) was suspended in anhydrous 2-propanol (3 mL) and stirred under nitrogen. The suspension was heated at 90° C. for 30 minutes. The reaction mixture was cooled to 40° C. and a solution of (R)-2-methyl-propane-2-sulfinic acid [1-(7-bromo-quinolin-2-yl)-eth-(E)-ylidene]-amide (448 mg, 1.27 mmol) in 2-propanol (9 mL) was added followed by a solution of potassium tert-butoxide (36 mg, 0.32 mmol) in 2-propanol (3 mL). The reaction mixture was stirred for 2 hours at 40° C. and then allowed to cool. The mixture was poured directly onto a silica gel cartridge and eluted with ethyl acetate. After concentration the residue was further purified by silica gel chromatography using a gradient of iso-hexane/ethyl acetate 1:1 to 0:1 to give 122c (287 mg, 64%) as a brown gum. $^1$H NMR (300 MHz, $CDCl_3$) δ 1.33 (s, 9H), 1.60 (d, J=6.7 Hz, 3H), 4.80 (m, 1H), 5.42 (br d, J=4.2 Hz, 1H), 7.42 (d, J=8.5 Hz, 1H), 7.62 (dd, J=8.5, 1.2 Hz, 1H), 7.68 (d, J=8.7 Hz, 1H), 8.12 (d, J=8.7 Hz, 1H), 8.25 (s, 1H). LCMS (m/z) 354.9/356.8 [M+H], Tr 2.49 min Compound 122d

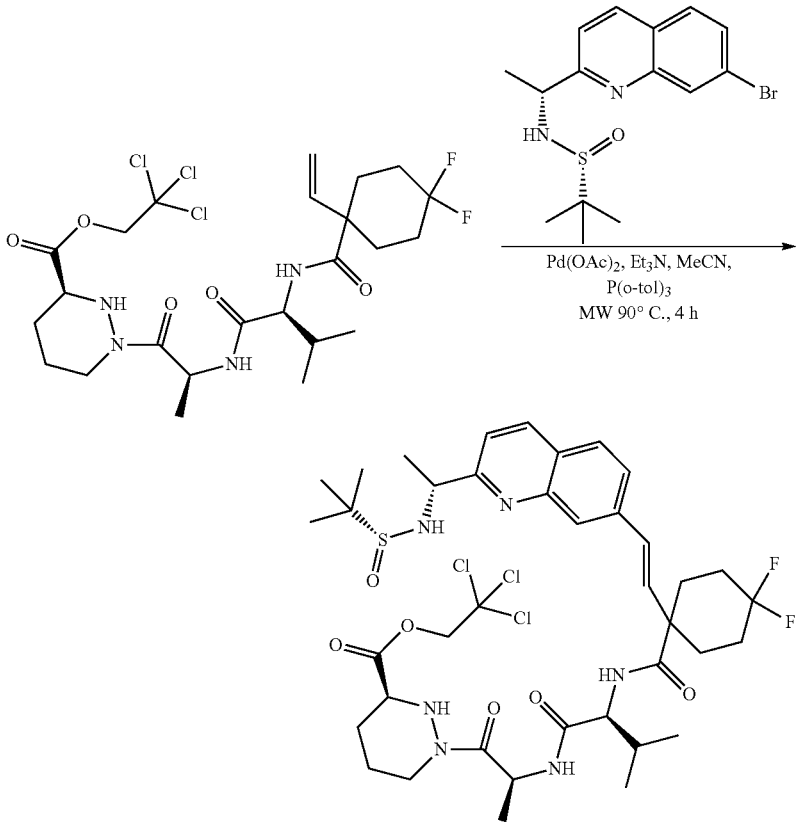

To a solution of (R)—N—((R)-1-(7-bromoquinolin-2-yl) ethyl)-2-methylpropane-2-sulfinamide 122c (36 mg, 0.1 mmol) in anhydrous acetonitrile (5 mL) was added palladium(II) acetate (4 mg, 0.02 mmol), 122a (60 mg, 0.1 mmol), tri(o-tolyl)phosphine (6 mg, 0.02 mmol) and triethylamine (20 mg, 0.2 mmol) then the mixture was heated in the microwave at 90° C. for 4 hours. The reaction mixture was filtered through Celite and the filter pad was washed with tetrahydrofuran (10 mL). The filtrate was evaporated then water (20 mL) was added and the organics extracted with ethyl acetate (2×20 mL). The combined organics were dried over sodium sulfate, filtered and concentrated under reduced pressure to give a crude residue. This was subjected to silica gel chromatography (gradient from 0-50% ethyl acetate in iso-hexanes) to afford the 122d (32 mg, 37%) as a white solid. $^1$H NMR (400 MHz, $CD_3OD$) δ□8.31 (d, J=8.3 Hz, 1H), 7.99 (s, 1H), 7.90 (d, J=8.4 Hz, 1H), 7.80 (d, J=8.8 Hz, 1H), 7.65 (d, J=8.6 Hz, 1H), 6.89 (d, J=16.2 Hz, 1H), 6.60 (d, J=16.5 Hz, 1H), 5.42-5.35 (m, 1H), 5.01 (d, J=12.0 Hz, 1H), 4.80 (d, J=12.0 1H), 4.78-4.73 (m, 1H), 4.63-4.59 (m, 1H), 4.28 (d, J=7.9 Hz, 1H), 3.83-3.78 (m, 1H), 2.45-2.36 (m, 2H), 2.16-1.98 (m, 8H), 1.96-1.83 (m, 2H), 1.64 (d, J=6.8 Hz, 3H), 1.35 (d, J=14.4 Hz, 3H), 1.32 (s, 9H), 1.29 (d, J=6.8 Hz, 3H), 1.00 (d, J=6.7 Hz, 3H), 0.94 (d, J=6.7 Hz, 3H). LCMS (m/z) 877.2/879.2 [M+H], Tr=4.32 min.

Compound 122

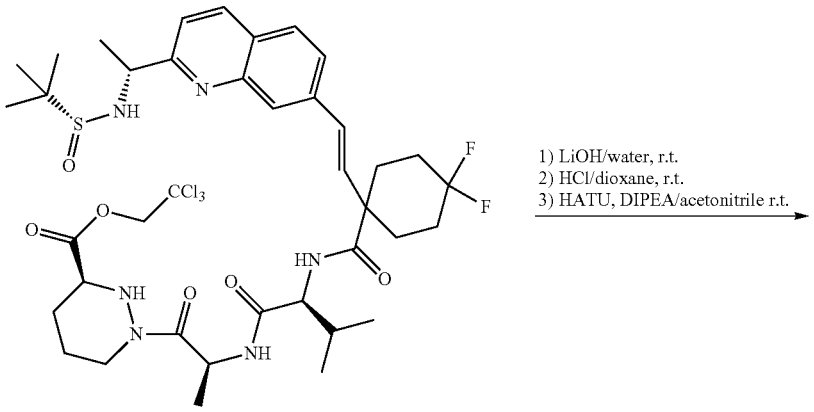

-continued

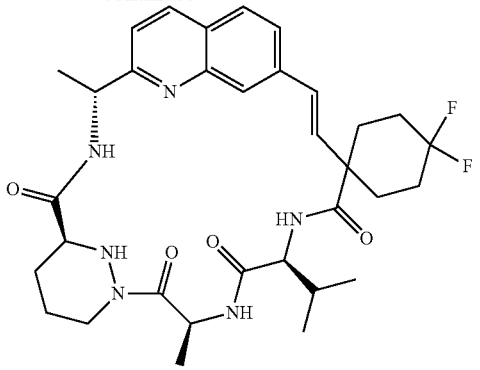

To 122b (31 mg, 0.035 mmol) in tetrahydrofuran (10 mL) was added a solution of lithium hydroxide (1.4 mg, 0.060 mmol) in water (5 mL). After stirring at room temperature for 2 hour, 1M hydrochloric acid was added (0.10 mL of 1M solution in water, 0.10 mmol) and the reaction mixture was concentrated under reduced pressure. The residue was treated with 1M hydrogen chloride in 1,4-dioxane (5 mL, 5 mmol) at room temperature under argon for 4 hours. Reaction mixture was concentrated under reduced pressure and dried under high vacuum for one day. This residue was dissolved in N,N-dimethylformamide (2 mL) and the obtained solution was added into an argon purged flask containing 2-(1H-7-azabenzotriazol-1-yl)-1,1,3,3-tetramethyl uronium hexafluorophosphate methanaminium (21 mg, 0.056 mmol), N,N-diisopropylethylamine (21 mg, 0.159 mmol) and acetonitrile (50 mL). The reaction mixture was re-purged with argon and stirred at room temperature for 12 hours. The obtained reaction mixture was concentrated under reduced pressure, dissolved in ethyl acetate (20 mL), washed with water (20 ml) and brine (20 mL), dried over magnesium sulfate, filtered and concentrated under reduced pressure. The residue was purified by silica gel chromatography (gradient from 0-50% ethyl acetate+methanol (4/1) in iso-hexanes) to afford the title compound (9 mg, 41%) as a white solid after evaporation. $^1$H NMR (400 MHz, $CD_3OD$) δ 8.34 (d, J=8.5 Hz, 1H), 7.94 (d, J=8.5 Hz, 1H), 7.83-7.76 (m, 2H), 6.61 (d, J=16.5 Hz, 1H), 6.40 (d, J=16.4 Hz, 1H), 5.84 (q, J=7.1 Hz, 1H), 5.46-5.42 (m, 1H), 5.19-5.13 (m, 1H), 4.63-4.44 (m, 2H), 3.74-3.68 (m, 1H), 2.81-3.72 (m, 1H), 2.53-2.40 (m, 2H), 2.39-1.92 (m, 12H), 1.77 (d, J=7.2 Hz, 3H), 1.68 (d, J=6.6 Hz, 3H), 1.18 (d, J=6.7 Hz, 3H), 1.08 (d, J=6.6 Hz, 3H). LCMS (m/z) 625.4 [M+H], Tr=3.53 min.

Examples 123 and 124

Compounds 123 and 124

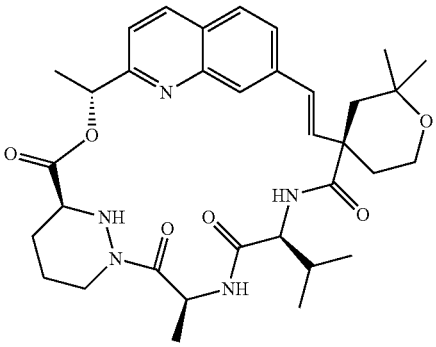

-continued

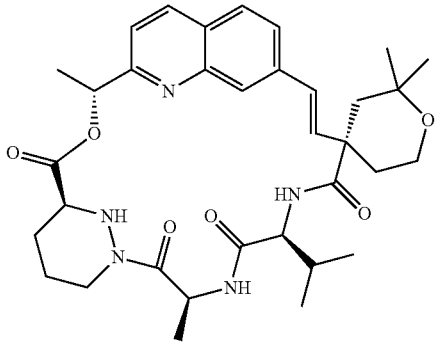

Compound 124a

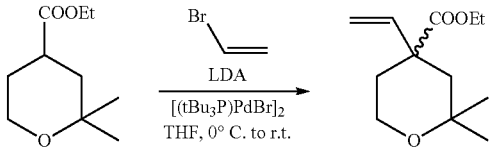

Into an oven dried, argon purged flask dry tetrahydrofuran (50 mL) was added and the solution was cooled with the ice bath. A 1.8 M solution of lithium diisopropylamide (7.2 mL, 13 mmol) in tetrahydrofuran/heptane/ethylbenzene was added through the septa. The resulting solution of lithium diisopropylamide was cooled to 0° C., and treated dropwise with ethyl 2,2-dimethyltetrahydro-2H-pyran-4-carboxylate (CAS: 371227-37-1, InterBioScreen Ltd.) (1.86 g, 10 mmol). The resulting solution was warmed to r.t. stirred for 20 min., cooled to 0° C., and treated with bromo(tri-tert-butylphosphine)palladium(I) dimmer (78 mg, 0.1 mmol) in dry tetrahydrofuran (5 mL), followed by slow addition of the 1M solution of bromoethene (15 mL 1M, 15 mmol) in tetrahydrofuran. The reaction mixture was stirred at 0° C. for 30 min. and then allowed to warm to the room temperature. After 4 hours at room temperature, the reaction mixture was quenched by the addition of 1M aqueous acetic acid (10 mL 1 M, 10 mmol). This mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with saturated solution of sodium bicarbonate (50 mL), brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-20% ethyl acetate in iso-hexanes) to afford the title compound (695 mg, 33%) as a colorless oil. $^1$H NMR (400 MHz, $CDCl_3$) δ 5.78 (dd, J=17.6, 10.1 Hz, 1H), 5.10 (s, 1H), 5.06 (d, J=5.4 Hz, 1H), 4.24-4.03 (m, 2H), 3.83-3.60 (m, 2H), 2.23-2.09 (m, 2H), 1.61-1.47 (m, 2H), 1.32-1.22 (m, 3H), 1.19 (s, 3H), 1.09 (s, 3H). LCMS (m/z) 213.0 [M+H], Tr=3.31 min.

Compound 123b

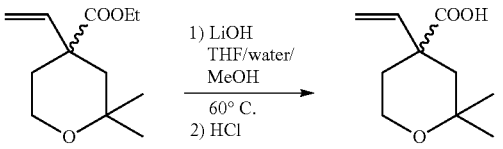

A solution of 123a (680 mg, 3.2 mmol) in tetrahydrofuran/water/methanol (25 mL, 4:1:1) was treated with lithium hydroxide (154 mg, 6.4 mmol). After stirring at 60° C. for 6 hours, the reaction was quenched with 1 M hydrochloric acid (20 mL), concentrated down under reduced pressure, dissolved in water (50 mL) and extracted with ethyl acetate (2×100 mL). The organics were combined, washed with brine, dried over sodium sulphate and filtered. The filtrate was evaporated to afford the title compound (496 mg, 85%) as a white solid. $^1$H NMR (400 MHz, $CDCl_3$) δ 5.83 (dd, J=17.5, 10.6 Hz, 1H), 5.18 (d, J=6.4 Hz, 1H), 5.15 (s, 1H), 3.90-3.64 (m, 2H), 2.29-1.98 (m, 2H), 1.66-1.59 (m, 1H), 1.56 (d, J=13.8 Hz, 1H), 1.20 (s, 3H), 1.16 (s, 3H). LCMS (m/z) 182.9 [M−H], Tr=2.14 min.

Compound 123c

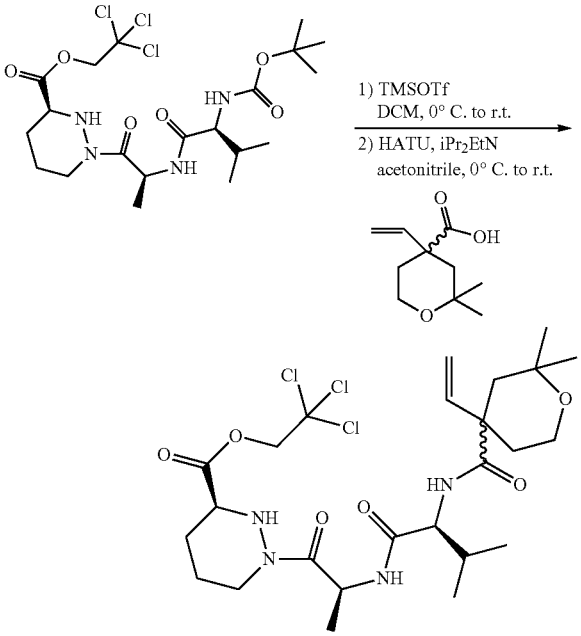

A solution of 1e (1471 mg, 2.77 mmol) in dichloromethane (30 mL) was cooled in an ice water bath. Trimethylsilyl trifluoromethanesulfonate (837 mg, 3.77 mmol) was added dropwise at 0° C. under argon, and the resulting solution was stirred at room temperature for 30 minutes. The reaction mixture was evaporated to dryness and the resulting crude residue (LCMS (m/z) 431.2/433.3 [M+H], Tr=2.05 min) was dissolved in anhydrous acetonitrile (30 mL) under The reaction mixture was stirred at 0° C., 123b (464 mg, 2.51 mmol) and N,N-diisopropylethylamine (1297 mg, 10 mmol) were added followed by 2-(1H-7-azabenzotriazol-1-yl)-1,1,3,3-tetramethyl uronium hexafluorophosphate methanaminium (1336 mg, 3.51 mmol). The reaction mixture was stirred at room temperature for 12 hours. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-50% ethyl acetate and methanol (4/1) in iso-hexanes) to afford the title compound (1193 mg, 80%) as a white solid after evaporation. $^1$H NMR (400 MHz, $CDCl_3$) δ 6.56 (d, J=7.6 Hz, 1H), 6.36-6.29 (m, 1H), 5.90 (dt, J=17.6, 10.1 Hz, 1H), 5.32-5.18 (m, 3H), 4.92 (d, J=11.9 1H), 4.68 (d, J=11.9, 1H), 4.22 (td, J=8.6, 6.1 Hz, 1H), 3.90-3.56 (m, 4H), 2.28-1.87 (m, 4H), 1.77-1.44 (m, 4H), 1.26 (dd, J=6.8, 3.8 Hz, 3H), 1.19 (s, 3H), 1.14 (d, J=17.1 Hz, 3H), 0.92-0.84 (m, 6H). LCMS (m/z) 597.1/599.0 [M+H], Tr=3.61 min.

Compound 123d

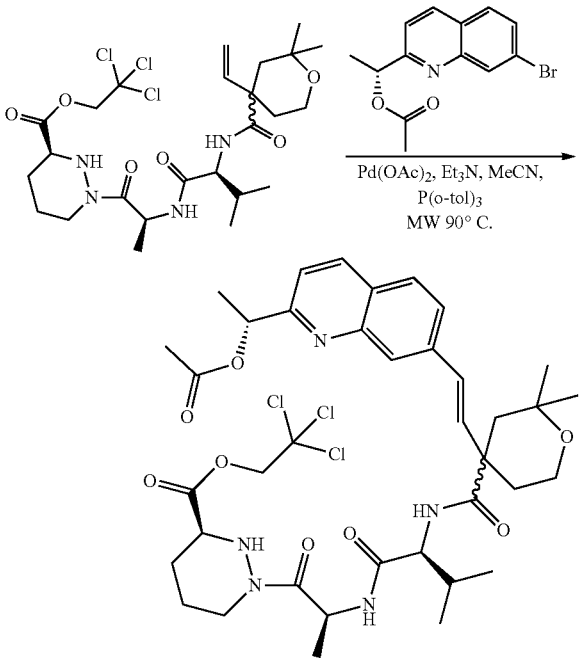

To a solution of acetic acid (R)-1-(7-bromo-quinolin-2-yl)-ethyl ester (294 mg, 1 mmol) in anhydrous acetonitrile (25 mL) was added palladium(II) acetate (45 mg, 0.2 mmol), 123c (598 mg, 1 mmol), tri(o-tolyl)phosphine (61 mg, 0.2 mmol) and triethylamine (202 mg, 2 mmol) then the mixture was heated in the microwave at 90° C. for 6 hours. The reaction mixture was filtered through Celite and the filter pad was washed with tetrahydrofuran (50 mL). The filtrate was evaporated then water (50 mL) was added and the organics extracted with ethyl acetate (2×50 mL). The combined organics were washed with brine, dried over sodium sulfate, filtered and concentrated under reduced pressure to give a crude residue. This was subjected to silica gel chromatography (gradient from 0-50% ethyl acetate in iso-hexanes) to afford the title compound (246 mg, 30%) as a white solid. $^1$H NMR (400 MHz, $CD_3OD$) δ 8.33 (d, J=8.5 Hz, 1H), 7.98 (s, 1H), 7.90 (d, J=8.5 Hz, 1H), 7.83-7.74 (m, 1H), 7.56 (d, J=8.5 Hz, 1H), 6.86-6.76 (m, 1H), 6.67-6.57 (m, 1H), 5.99 (q, J=6.7 Hz, 1H), 5.43-5.24 (m, 1H), 4.31-4.19 (m, 1H), 4.11 (m, 3.98-3.76 (m, 3H), 3.66-3.57 (m, 1H), 3.29-3.16 (m, 2H), 2.41-2.21 (m, 3H), 2.18 (s, 3H), 2.15-1.95 (m, 3H), 1.93-1.73 (m, 5H), 1.67 (d, J=6.8 Hz, 3H), 1.28-1.18 (m, 6H), 1.06-0.77 (m, 6H). LCMS (m/z) 810.2/812.2 [M+H], Tr=4.05 min.

was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with 10% citric acid (100 mL), saturated $NaHCO_3$ (100 mL), water (100 mL, 5 mL of brine was added to support the separation). Resulting aqueous phase was extracted with ethyl acetate (50 mL). Combined organic extracts were washed with brine (50 mL)

Compounds 123 and 124

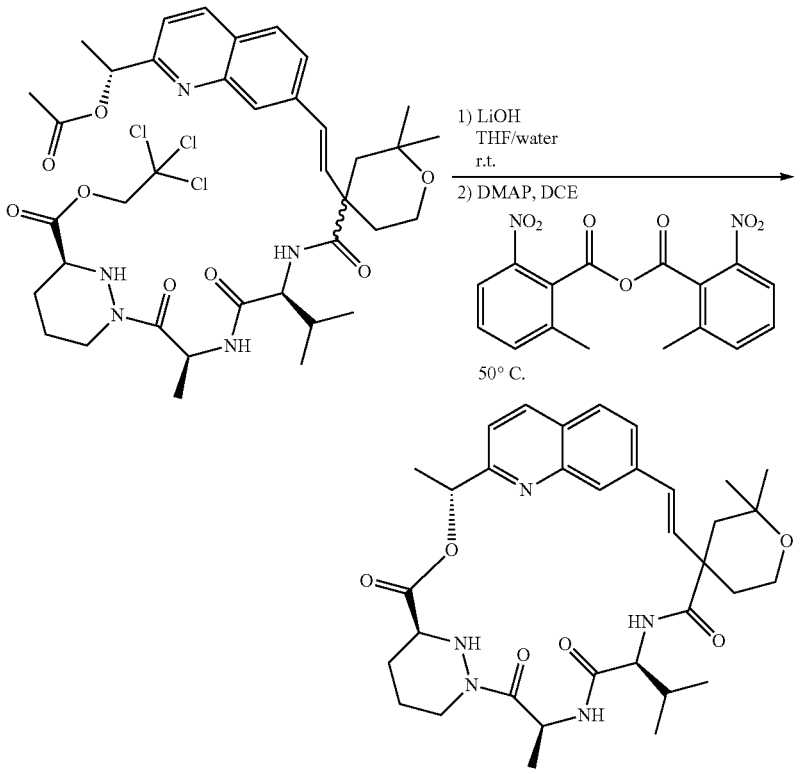

To 123d (170 mg, 0.21 mmol) in tetrahydrofuran (20 mL) was added a solution of lithium hydroxide (15 mg, 0.63 mmol) in water (10 mL). After stirring at room temperature for 2 hour, 1M hydrochloric acid was added (0.63 mL of 1M solution in water, 0.63 mmol) and the reaction mixture was concentrated under reduced pressure to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification. The resulting white solid was dried under high vacuum overnight and it was used without further purification. Into oven dried, argon purged flask were placed 2-methyl-6-nitrobenzoic anhydride (289 mg, 0.84 mmol), 4-dimethylaminopyridine (308 mg, 2.52 mmol) and anhydrous 1,2-dichloroethane (200 mL). The resulting solution was heated at 50° C., and the crude seco-acid was added dropwise via syringe as a solution in dry N,N-dimethylformamide (10 mL) over 12 hours. An additional portion of dry N,N-dimethylformamide (2×5 mL) was used to complete the quantitative transfer. After stirring for additional 2 hours at 50° C., the reaction mixture was transferred to a separatory funnel and washed with water (100 mL, 5 mL of brine was added to support the separation). The aqueous phase and dried over magnesium sulfate, filtered and concentrated under reduced pressure. The residue was purified by silica gel chromatography (gradient from 0-50% ethyl acetate and methanol (4/1) in iso-hexanes) to afford firstly Compound 123 (53 mg, 41%) and then Compound 124 (42 mg, 32%) both as a white solid after evaporation.

Compound 123 $^1$H NMR (500 MHz, $CD_3OD$): δ 8.43 (d, J=8.5 Hz, 1H), 7.93 (d, J=8.6 Hz, 1H), 7.87 (dd, J=8.6, 1.6 Hz, 1H), 7.71 (s, 1H), 7.59 (d, J=8.5 Hz, 1H), 6.49 (d, J=16.4 Hz, 1H), 6.36 (d, J=16.5 Hz, 1H), 6.00 (q, J=6.8 Hz, 1H), 5.67 (q, J=7.1 Hz, 1H), 4.42-4.35 (m, 1H), 4.34 (d, J=10.0 Hz, 1H), 3.96 (td, J=12.0, 2.2 Hz, 1H), 3.85-3.78 (m, 1H), 3.75-3.69 (m, 1H), 2.72 (td, J=12.6, 3.4 Hz, 1H), 2.42 (dd, J=14.3, 2.1 Hz, 1H), 2.28-2.20 (dq, J=13.5, 2.1 Hz, 1H), 2.06-1.98 (m, 2H), 1.99-1.85 (m, 2H), 1.79 (d, J=6.9 Hz, 3H), 1.73-1.66 (m, 2H), 1.60 (d, J=7.1 Hz, 3H), 1.59-1.54 (m, 1H), 1.29 (d, J=11.7 Hz, 6H), 0.98 (dd, J=8.7, 6.7 Hz, 6H). LCMS (m/z) 620.5 [M+H], Tr=3.19 min (Gemini 5u C18 110 Å, 50×4.60 mm 5 micron column, 6 min, 2 ml/min, 5-100% acetonitrile/water, 0.1% acetic acid modifier gradient).

Compound 124 $^1$H NMR (500 MHz, $CD_3OD$): δ 8.37 (d, J=8.5 Hz, 1H), 7.89 (d, J=8.5 Hz, 1H), 7.83 (dd, J=8.8, 1.7 Hz, 1H), 7.65 (s, 1H), 7.54 (d, J=8.5 Hz, 1H), 6.44-6.36 (m, 2H), 5.99 (q, J=6.8 Hz, 1H), 5.63 (q, J=7.1 Hz, 1H), 4.45-4.37 (m, 1H), 4.37-4.30 (m, 1H), 3.88-3.82 (m, 2H), 3.79-3.74 (m, 1H), 2.76 (td, J=12.8, 3.5 Hz, 1H), 2.40 (dd, J=13.8, 1.8 Hz, 1H), 2.27-2.18 (m, 1H), 2.12-2.05 (m, 1H), 2.05-1.93 (m, 2H), 1.92-1.87 (m, 2H), 1.80 (d, J=6.9 Hz, 3H), 1.76-1.61 (m, 3H), 1.59-1.51 (m, 2H), 1.27 (s, 3H), 1.21 (s, 3H), 1.02 (dd, J=6.6, 2.3 Hz, 6H). LCMS (m/z) 620.5 [M+H], Tr=3.22 min (Gemini 5u C18 110 Å, 50×4.60 mm 5 micron column, 6 min, 2 ml/min, 5-100% acetonitrile/water, 0.1% acetic acid modifier gradient).

Example 125

Compound 125

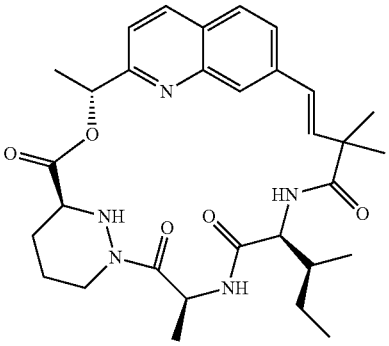

Compound 125a

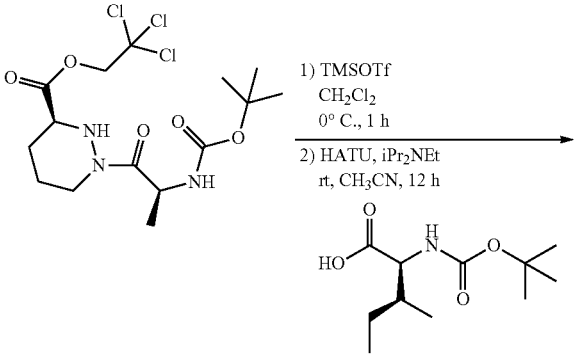

-continued

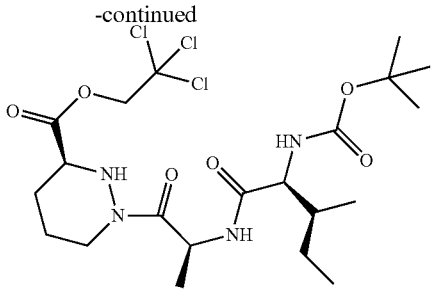

A solution of 1d (981 mg, 2.27 mmol) in dichloromethane (20 mL) was cooled in an ice water bath. Trimethylsilyl trifluoromethanesulfonate (756 mg, 3.4 mmol) was added dropwise at 0° C. under argon, and the resulting solution was stirred at room temperature for 60 minutes. The reaction mixture was evaporated to dryness and the resulting crude residue (LCMS (m/z) 332.2/334.3 [M+H]; Tr=2.01 min) was dissolved in anhydrous acetonitrile (25 mL) under argon. The reaction mixture was stirred at 0° C., N-(tert-Butoxycarbonyl)-L-isoleucine (580 mg, 2.5 mmol) and N,N-diisopropylethylamine (1173 mg, 9.1 mmol) were added followed by 2-(1H-7-azabenzotriazol-1-yl)-1,1,3,3-tetramethyl uronium hexafluorophosphate methanaminium (1300 mg, 3.4 mmol). The reaction mixture was stirred at room temperature for 12 hours. The solvent was evaporated, the residue was dissolved in ethyl acetate (100 mL) and the solution was washed with 20% water solution of citric acid (2×100 mL), water (100 mL) and brine (100 mL), dried over magnesium sulfate, filtered and evaporated. The residue was purified by silica gel chromatography (gradient from 0-40% ethyl acetate+methanol (4/1) in iso-hexanes) to afford the title compound (1109 mg, 89%) as a white solid after evaporation. $^1$H NMR (400 MHz, $CD_3OD$) δ 5.55-5.28 (m, 1H), 5.05 (d, J=12.2 Hz, 1H), 4.85 (d, J=12.1 Hz, 1H), 4.14 (q, J=7.1 Hz, 1H), 4.01-3.93 (m, 1H), 3.89-3.81 (m, 1H), 2.17-2.07 (m, 1H), 2.00-1.81 (m, 3H), 1.80-1.69 (m, 1H), 1.60-1.50 (m, 2H), 1.48 (s, 9H), 1.33 (d, J=7.0 Hz, 3H), 1.25-1.11 (m, 1H), 1.01-0.86 (m, 6H). LCMS (m/z) 545.3/547.3 [M+H]; Tr=4.13 min.; (Gemini 5u C18 110 Å, 50×4.60 mm 5 micron column, 6 min, 2 ml/min, 5-100% acetonitrile/water, 0.1% acetic acid modifier gradient).

Compound 125b

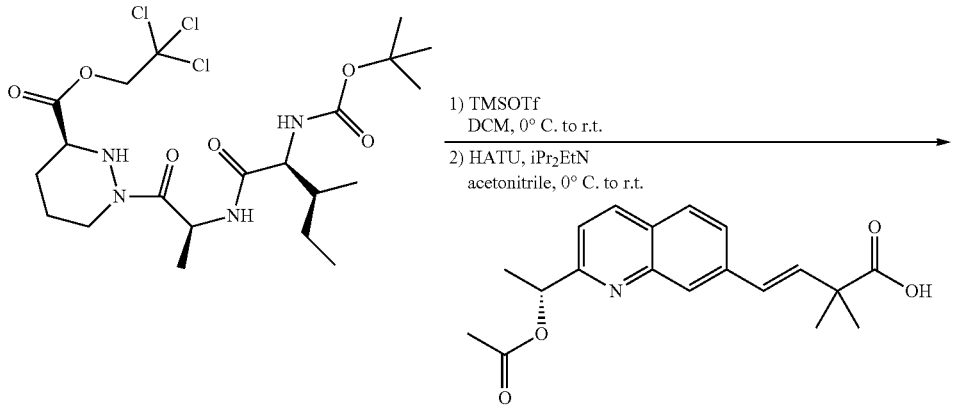

-continued

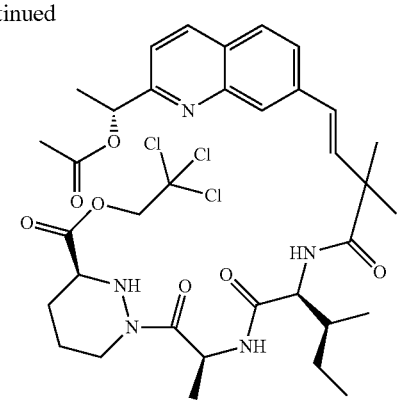

A solution of 125a (273 mg, 0.5 mmol) in dichloromethane (5 mL) was cooled in an ice water bath. Trimethylsilyl trifluoromethanesulfonate (167 mg, 0.75 mmol) was added dropwise at 0° C. under argon, and the resulting solution was stirred at room temperature for 30 minutes. The reaction mixture was evaporated to dryness and the resulting crude residue (LCMS (m/z) 431.2/433.3 [M+H], Tr=2.06 min) was dissolved in anhydrous acetonitrile (10 mL) under argon. The reaction mixture was stirred at 0° C., the O-Acetyl-quinoline carboxylic acid 22d (164 mg, 0.5 mmol) and N,N-diisopropylethylamine (260 mg, 2 mmol) were added followed by 2-(1H-7-azabenzotriazol-1-yl)-1,1,3,3-tetramethyl uronium hexafluorophosphate methanaminium (266 mg, 0.7 mmol). The reaction mixture was stirred at room temperature for 12 hours. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (283 mg, 75%) as a white solid after evaporation. $^1$H NMR (400 MHz, $CD_3OD$) δ 8.33 (d, J=8.5 Hz, 1H), 7.99 (s, 1H), 7.90 (d, J=8.6 Hz, 1H), 7.82 (dd, J=8.6, 1.6 Hz, 1H), 7.56 (d, J=8.5 Hz, 1H), 7.16 (d, J=8.6 Hz, 1H), 6.84 (d, J=16.3 Hz, 1H), 6.74 (d, J=16.3 Hz, 1H), 6.00 (q, J=6.7 Hz, 1H), 5.54-5.30 (m, 1H), 5.02 (d, J=12.1 Hz, 1H), 4.80 (d, J=12.1 Hz, 1H), 4.48-4.16 (m, 1H), 3.81 (dd, J=7.6, 4.3 Hz, 1H), 2.18 (s, 3H), 2.13-2.02 (m, 1H), 1.96-1.80 (m, 3H), 1.77-1.68 (m, 1H), 1.67 (d, J=6.7 Hz, 3H), 1.59-1.51 (m, 1H), 1.49 (d, J=1.8 Hz, 6H), 1.31 (d, J=7.0 Hz, 3H), 1.27-1.11 (m, 1H), 0.98 (d, J=6.8 Hz, 3H), 0.90 (t, J=7.4 Hz, 3H). LCMS (m/z) 754.3/756.3 [M+H], Tr=4.28 min.

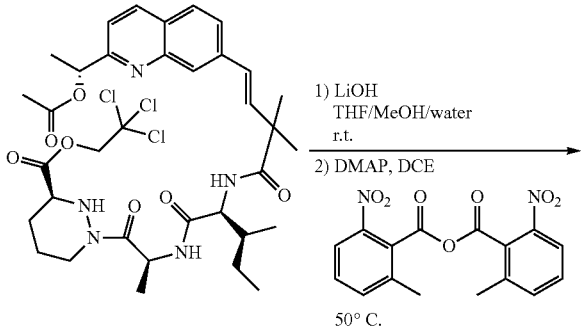

-continued

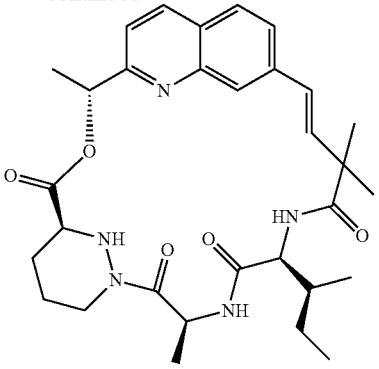

To a solution of 125b (248 mg, 0.33 mmol) in tetrahydrofuran (10 mL) was added methanol (4 mL), water (4 mL) and lithium hydroxide (24 mg, 1 mmol). The mixture was stirred for 2 hours at ambient temperature and was quenched with aqueous 1 M hydrochloric acid (1 mL, 1 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification. Into oven dried, argon purged flask were placed 2-methyl-6-nitrobenzoic anhydride (452 mg, 1.3 mmol), 4-dimethylaminopyridine (481 mg, 4 mmol) and anhydrous 1,2-dichloroethane (200 mL). The resulting solution was heated at 50° C., and the crude seco-acid was added dropwise via syringe as a solution in dry N,N-dimethylformamide (10 mL) over 12 hours. An additional portion of dry N,N-dimethylformamide (2×5 mL) was used to complete the quantitative transfer. After stirring for additional 2 hours at 50° C., the reaction mixture was transferred to a separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with 10% citric acid (100 mL), saturated $NaHCO_3$ (100 mL), water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-50% ethyl acetate and methanol (4/1) in iso-hexanes) to afford the title compound (167 mg, 90%) as a white solid after evaporation. $^1$H NMR (400 MHz, $CD_3OD$): δ 8.09 (d, J=8.4 Hz, 1H), 7.75-7.63 (m, 2H), 7.52 (s, 1H), 7.29 (d, J=8.5 Hz, 1H), 6.37 (d, J=16.5 Hz, 1H), 6.15 (d, J=16.5 Hz, 1H), 5.80 (q, J=6.8 Hz, 1H), 5.63 (q, J=7.2 Hz, 1H), 4.33-4.24 (m, 2H), 3.70 (dd, J=11.1, 2.8 Hz, 1H), 2.63 (td, J=12.6, 3.0 Hz, 1H), 1.93-1.85 (m, 1H), 1.83-1.65 (m, 2H), 1.62 (d, J=6.9 Hz, 3H), 1.52 (d, J=7.2 Hz, 3H), 1.50-1.41 (m, 2H), 1.38 (s, 3H), 1.24 (s, 3H), 1.19-1.02 (m, 2H), 0.84-0.77 (m, 6H). LCMS (m/z) 564.3 [M+H], Tr=3.51 min.

Example 126

Compound 126

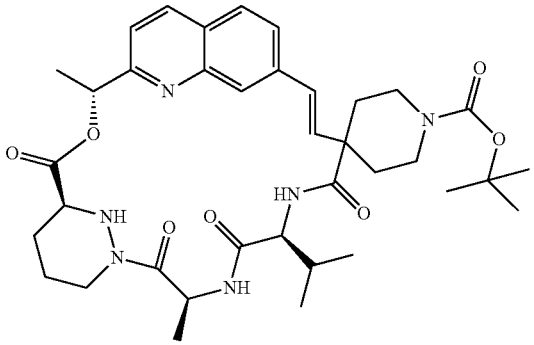

Compound 126a

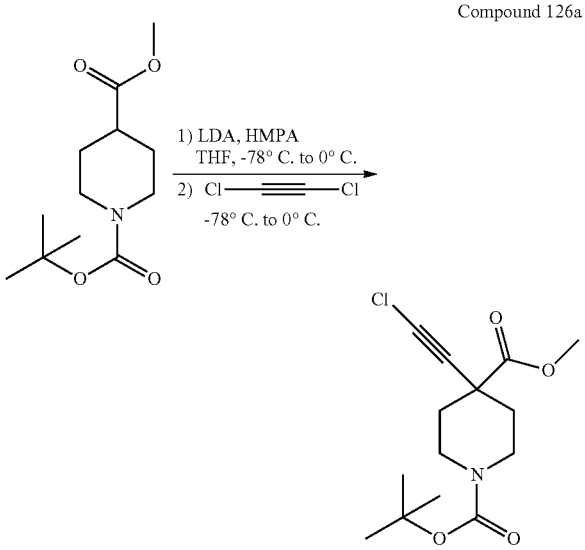

Into an oven dried, argon purged flask tetrahydrofuran (50 mL) was added and the solution was cooled with the ice bath. A 1.8 M solution of lithium diisopropylamide (13.9 mL, 25 mmol) in tetrahydrofuran/heptane/ethylbenzene was added through the septa. The resulting solution of lithium diisopropylamide was cooled to −78° C., and treated dropwise with 1-tert-butyl 4-methyl piperidine-1,4-dicarboxylate (CAS: 124443-68-1, Oakwood Products, Inc.) (2.19 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloroethyne (ca. 10 mmol). The reaction mixture was stirred at −78° C. for 30 min. and then allowed to warm to the room temperature. After 4 hours at room temperature, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-15% ethyl acetate in iso-hexanes) to afford the title compound (818 mg, 34%) as a white solid after evaporation. $^1$H NMR (400 MHz, $CDCl_3$) δ 3.97-3.83 (m, 2H), 3.75 (s, 3H), 3.23-3.01 (m, 2H), 1.92-1.75 (m, 4H), 1.43 (s, 9H). LCMS (m/z) 202.0 [M-Boc+H], Tr=4.29 min.

Compound 126b

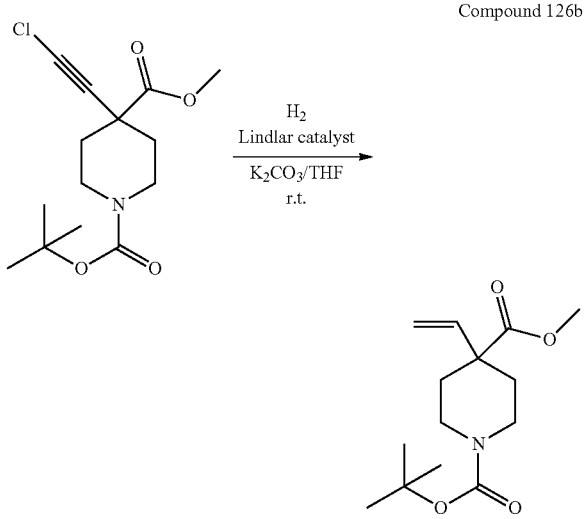

A solution of compound 126a (787 mg, 2.61 mmol) in tetrahydrofuran (50 mL) containing Lindlar catalyst (100 mg, Sigma-Aldrich) and potassium carbonate (1920 mg, 13.9 mmol) was hydrogenated at room temperature and at atmospheric pressure of hydrogen for 12 hours. The reaction mixture was filtered through Celite and the filter pad was washed with tetrahydrofuran (30 mL). The filtrate was evaporated to afford the title compound (702 mg, quantitative yield) as a white solid after evaporation. $^1$H NMR (400 MHz, $CDCl_3$) δ 5.75 (dd, J=17.6, 10.7 Hz, 1H), 5.20-5.01 (m, 2H), 3.67 (s, 3H), 3.10-2.93 (m, 2H), 2.16-2.04 (m, 2H), 1.63-1.48 (m, 2H), 1.41 (s, 9H), 1.32-1.14 (m, 2H). LCMS (m/z) 170.1 [M-Boc+H], Tr=3.93 min.

Compound 126c

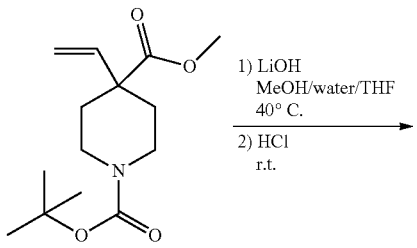

-continued

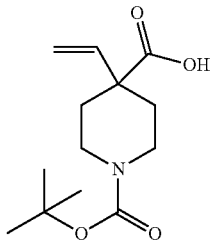

A solution of 126b (539 mg, 2 mmol) in tetrahydrofuran/water/methanol (100 mL, 4:1:1) was treated with lithium hydroxide (96 mg, 4 mmol) at 40° C. for 5 hours. The reaction was quenched with 1 M hydrochloric acid (4.2 mL, 4.2 mmol), concentrated down under reduced pressure, dissolved in water (50 mL) and extracted with ethyl acetate (2×100 mL). The organics were combined, washed with brine, dried over sodium sulphate and filtered. The filtrate was evaporated to afford the title compound (502 mg, 98%) as a white solid. $^1$H NMR (400 MHz, $CDCl_3$) δ□5.82 (dd, J=17.5, 10.7 Hz, 1H), 5.27-5.16 (m, 2H), 3.81-3.62 (m, 2H), 3.20-3.03 2H), 2.17-2.06 (m, 2H), 1.70-1.53 (m, 2H), 1.43 (s, 9H). LCMS (m/z) 254.0 [M−H], Tr=3.35

Intermediate 126d

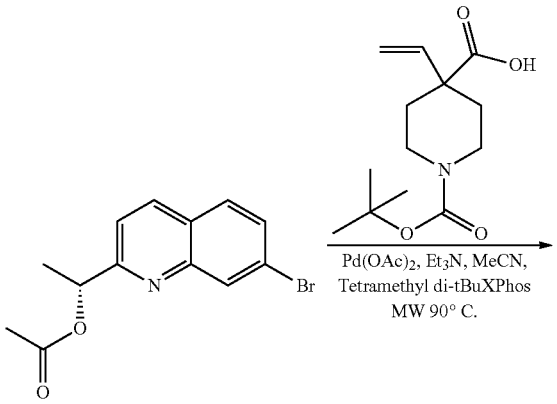

-continued

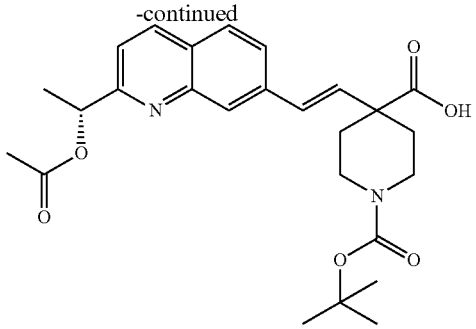

To a solution of acetic acid (R)-1-(7-bromo-quinolin-2-yl)-ethyl ester (540 mg, 1.84 mmol) in anhydrous acetonitrile (60 mL) was added palladium(II) acetate (45 mg, 0.2 mmol), 126c (459 mg, 1.8 mmol), 2-di-tert-butylphosphino-3,4,5,6-tetramethyl-2',4',6'-triisopropyl-1,1'-biphenyl (90 mg, 0.2 mmol) and triethylamine (0.80 mL, 6 mmol) then the mixture was heated in the microwave at 90° C. for 2 hours. The reaction mixture was filtered through Celite and the filter pad was washed with tetrahydrofuran (30 mL). The filtrate was evaporated then water (200 mL) was added and the organics extracted with ethyl acetate (2×50 mL). The combined organics were dried over sodium sulfate, filtered and concentrated under reduced pressure to give a crude residue. This was subjected to silica gel chromatography (gradient from 0-30% ethyl acetate in iso-hexanes) to afford the title compound (732 mg, 87%) as a white solid. $^1$H NMR (400 MHz, $CDCl_3$) δ 8.28-8.04 (m, 2H), 7.75 (d, J=8.4 Hz, 1H), 7.61 (d, J=8.9 Hz, 1H), 7.45 (d, J=8.5 Hz, 1H), 6.73 (d, J=16.3 Hz, 1H), 6.42 (d, J=16.3 Hz, 1H), 6.13-5.96 (m, 1H), 3.94-3.75 (m, 1H), 3.25-3.08 (m, 1H), 2.38-2.25 (m, 2H), 2.13 (s, 3H), 1.81-1.71 (m, 2H), 1.67 (d, J=6.7 Hz, 3H), 1.45 (s, 9H), 1.36-1.20 (m, 2H). LCMS (m/z) 469.1 [M+H], Tr=3.78.

Compound 126e

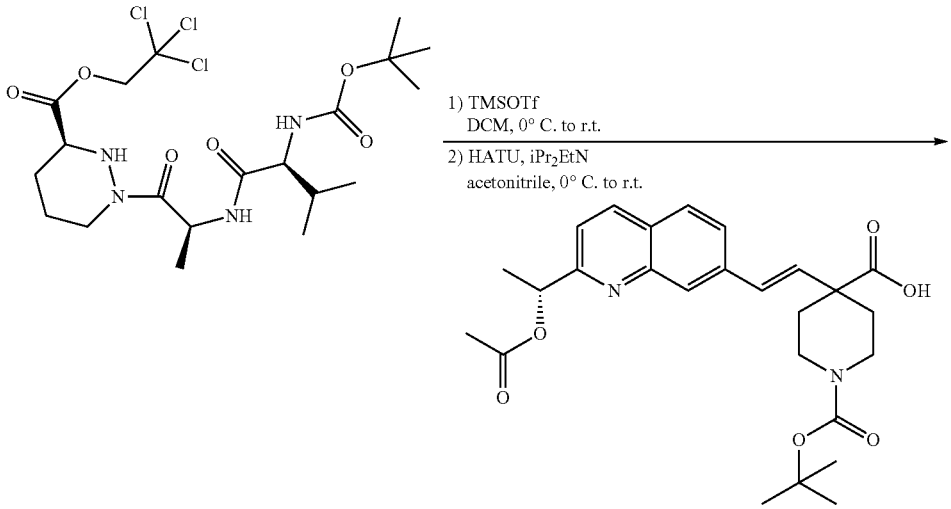

-continued

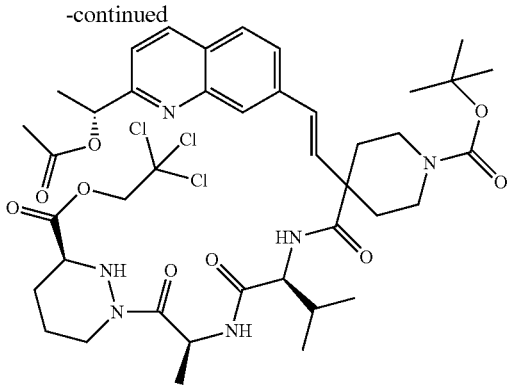

A solution of 1e (0.32 g, 0.6 mmol) in dichloromethane (10 mL) was cooled in an ice water bath. Trimethylsilyl trifluoromethanesulfonate (0.20 g, 0.90 mmol) was added dropwise at 0° C. under argon, and the resulting solution was stirred at room temperature for 30 minutes. The reaction mixture was evaporated to dryness and the resulting crude residue (LCMS (m/z) 431.2/433.3 [M+H], Tr=2.04 min) was dissolved in anhydrous acetonitrile (12 mL) under argon. The reaction mixture was stirred at 0° C., 126d (195 mg, 0.40 mmol) and N,N-diisopropylethylamine (0.28 mL, 1.6 mmol) were added followed by 2-(1H-7-azabenzotriazol-1-yl)-1,1,3,3-tetramethyl uronium hexafluorophosphate methanaminium (228 mg, 0.6 mmol). The reaction mixture was stirred at room temperature for 12 hours. The solvent was evaporated, the residue was dissolved in ethyl acetate (50 mL) and the solution was washed with 20% water solution of citric acid (2×50 mL), water (50 mL) and brine (50 mL), dried over magnesium sulfate, filtered and evaporated. The residue was purified by silica gel chromatography (gradient from 0-40% ethyl acetate and methanol (4/1) in iso-hexanes) to afford the title compound (295 mg, 84%) as a white solid after evaporation. $^1$H NMR (400 MHz, $CD_3OD$) δ 8.33 (d, J=8.5 Hz, 1H), 7.99 (s, 1H), 7.90 (d, J=8.6 Hz, 1H), 7.81 (dd, J=8.6, 1.5 Hz, 1H), 7.57 (d, J=8.5 Hz, 1H), 7.44 (d, J=8.4 Hz, 1H), 6.86 (d, J=16.4 Hz, 1H), 6.60 (d, J=16.4 Hz, 1H), 6.00 (q, J=6.7 Hz, 1H), 5.44-5.26 (m, 1H), 5.01 (d, J=12.1 Hz, 1H), 4.80 (d, J=12.1 Hz, 1H), 4.61 (bs, 1H), 4.33-4.19 (m, 1H), 3.81 (dd, J=7.4, 4.3 Hz, 1H), 3.71-3.59 (m, 2H) 3.53-3.38 (m, 2H), 2.34-2.22 (m, 2H), 2.18 (s, 3H), 2.15-2.00 (m, 2H), 1.97-1.81 (m, 3H), 1.75-1.68 (m, 3H), 1.67 (d, J=6.7 Hz, 3H), 1.50 (s, 9H), 1.29 (d, J=7.0 Hz, 3H), 1.00 (d, J=6.8 Hz, 3H), 0.94 (d, J=6.7 Hz, 3H). LCMS (m/z) 881.1/883.1 [M+H], Tr=4.37 min.

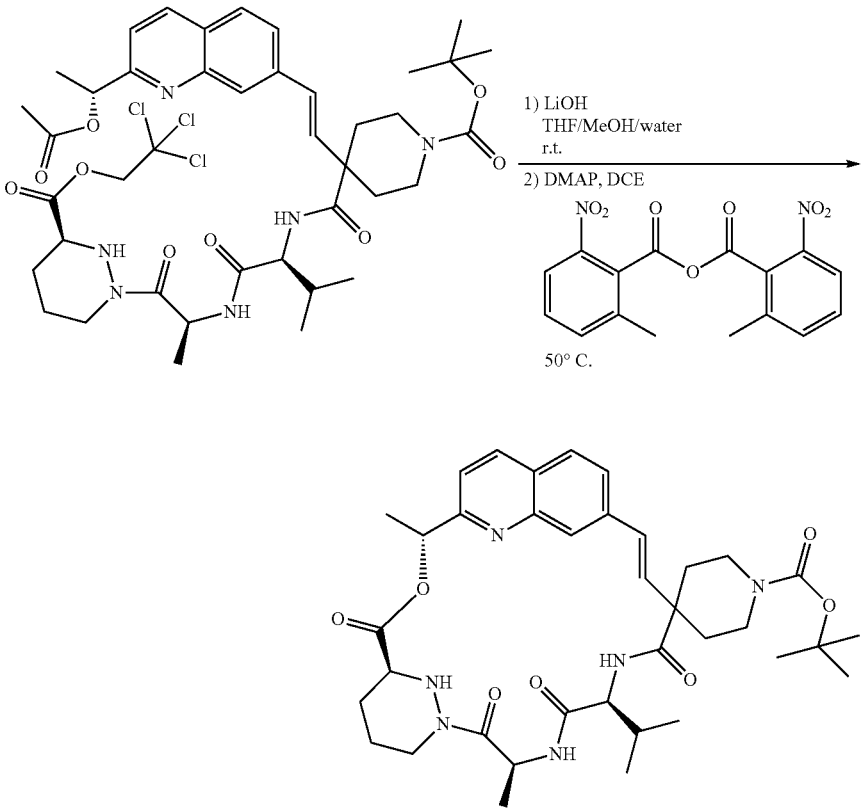

To a solution of 126e (227 mg, 0.26 mmol) in tetrahydrofuran (10 mL) was added water (4 mL) and lithium hydroxide (19 mg, 0.77 mmol). The mixture was stirred for 2 hours at ambient temperature and was quenched with aqueous 1 M hydrochloric acid (0.25 mL, 0.25 mmol). The resulting solution was concentrated to a crude residue which was co-evaporated twice with tetrahydrofuran (20 mL), twice with anhydrous acetonitrile (20 mL) and twice with anhydrous toluene (20 mL). The resulting white solid was dried under high vacuum overnight and it was used without further purification. Into oven dried, argon purged flask were placed 2-methyl-6-nitrobenzoic anhydride (344 mg, 1 mmol), 4-dimethylaminopyridine (366 mg, 3 mmol) and anhydrous 1,2-dichloroethane (200 mL). The resulting solution was heated at 50° C., and the crude seco-acid was added dropwise via syringe as a solution in dry N,N-dimethylformamide (10 mL) over 12 hours. An additional portion of dry N,N-dimethylformamide (2×5 mL) was used to complete the quantitative transfer. After stirring for additional 2 hours at 50° C., the reaction mixture was transferred to a separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with 10% citric acid (100 mL), saturated $NaHCO_3$ (100 mL), water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-40% ethyl acetate and methanol (4/1) in iso-hexanes) to afford the title compound (145 mg, 81%) as a white solid after evaporation. $^1$H NMR (400 MHz, $CD_3OD$): δ 8.23 (d, J=8.5 Hz, 1H), 8.04-7.93 (m, 1H), 7.82 (s, 2H), 7.68-7.60 (m, 1H), 7.43 (d, J=8.6 Hz, 1H), 6.47 (d, J=16.4 Hz, 6.35 (d, J=16.6 Hz, 1H), 5.98-5.85 (m, 1H), 5.81-5.64 (m, 1H), 4.45-4.27 (m, 1H), 3.94-3.78 (m, 1H), 2.34-2.20 (m, 2H), 2.10-1.99 (m, 2H), 1.97-1.87 (m, 2H), 1.75 (d, J=6.9 Hz, 3H), 1.68 (d, J=7.2 Hz, 3H), 1.51 (s, 9H), 1.41-1.29 (m, 4H), 1.07-0.93 (m, 6H). LCMS (m/z) 691.3 [M+H], Tr=2.72 min.

Example 127

Compound 127

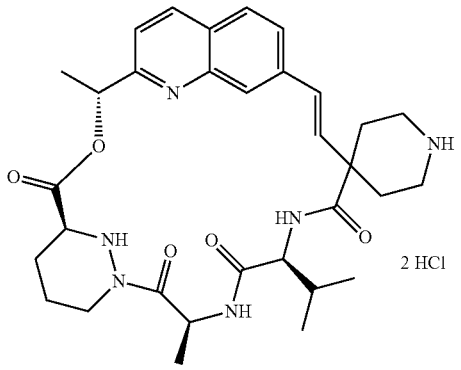

-continued

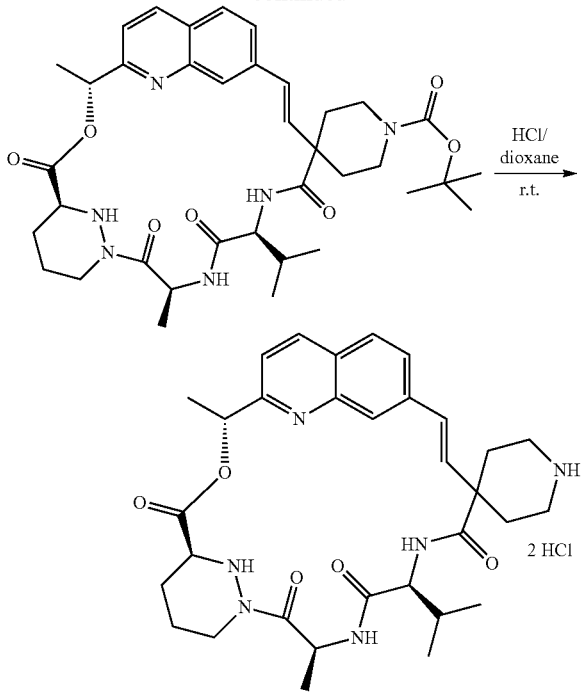

Compound 126 (140 mg, 0.2 mmol) was dissolved in dry 1,4-dioxane (5 mL). This mixture was purged twice with argon and treated with 4M hydrogen chloride in 1,4-dioxane (5 mL, 20 mmol) at room temperature under argon for 6 hours. Reaction mixture was concentrated under reduced pressure, co-evaporated twice with tetrahydrofuran (20 mL), twice with anhydrous acetonitrile (20 mL) and twice with anhydrous toluene (20 mL). The resulting white solid was dried under high vacuum overnight to afford the bis-hydrogen chloride salt of the title compound (118 mg, quantitative yield) as a white solid after evaporation. $^1$H NMR (400 MHz, $CD_3OD$): δ 8.87 (d, J=8.4 Hz, 1H), 8.19 (d, J=8.6 Hz, 1H), 8.11 (d, J=8.6 Hz, 1H), 7.93 (d, J=8.4 Hz, 1H), 7.84 (s, 1H), 7.64 (d, J=9.4 Hz, 1H), 6.71 (d, J=16.4 Hz, 1H), 6.63 (d, J=16.4 Hz, 1H), 6.15 (q, J=6.7 Hz, 1H), 5.59 (q, J=7.0 Hz, 1H), 4.42-4.35 (m, 1H), 4.34-4.25 (m, 1H), 3.90-3.79 (m, 1H), 3.60-3.47 (m, 1H), 3.19-3.01 (m, 1H), 2.74-2.45 (m, 3H), 2.39-2.20 (m, 1H), 2.10-1.92 (m, 4H), 1.89 (d, J=6.9 Hz, 3H), 1.76-1.66 (m, 2H), 1.59 (d, J=7.1 Hz, 3H), 1.38-1.28 (m, 2H), 0.99 (d, J=6.7 Hz, 3H), 0.97 (d, J=6.6 Hz, 3H). LCMS (m/z) 591.3 [M+H], Tr=1.81 min.

Example 128

Compound 128

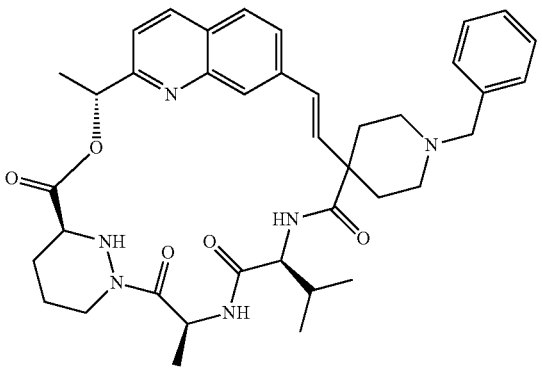

-continued

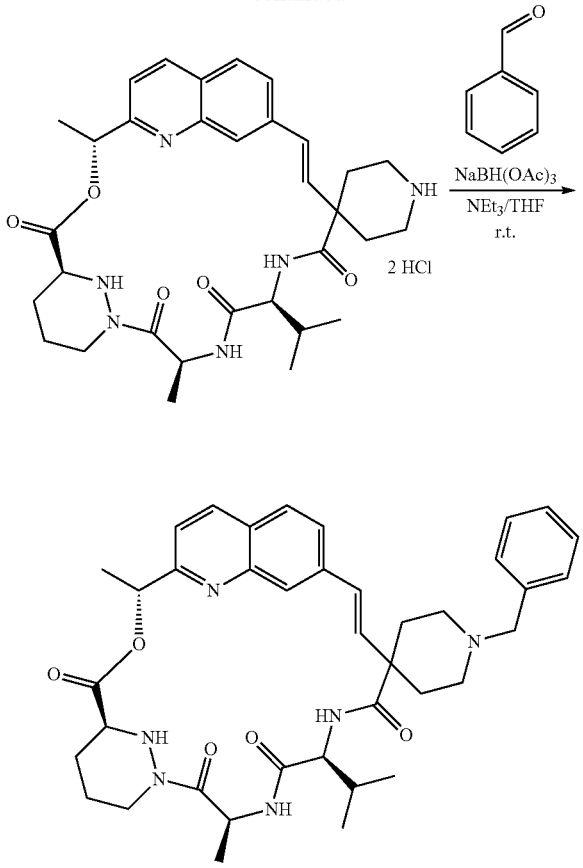

Compound 127 (9 mg, 0.014 mmol) was dissolved in dry THF (5 mL). This mixture was purged twice with argon and benzaldehyde (1.6 mg, 0.015 mmol), triethyl amine (4.1 mg, 0.04 mmol) and sodium triacetoxyborohydride (4 mg, 0.019 mmol) were added. Reaction mixture was stirred at room temperature for 2 days, concentrated under reduced pressure, the resulting residue was dissolved in ethyl acetate (10 mL) and was washed saturated $NaHCO_3$ (10 mL), water (10 mL, 5 mL of brine was added to support the separation). Resulting aqueous phase was extracted with ethyl acetate (10 mL). Combined organic extracts were washed with brine (10 mL) and dried over magnesium sulfate, filtered and concentrated under reduced pressure. The residue was purified by preparatory HPLC (Gemini 5u C18 110 Å column, 5-100% acetonitrile/water, 0.1% trifluoroacetic acid modifier) to afford the bis-trifluoroacetic acid salt of the title compound (2 mg, 16%) as a white powder after evaporation. $^1$H NMR (400 MHz, $CD_3OD$): δ 8.24 (d, J=8.1 Hz, 1H), 7.85 (d, J=8.1 Hz, 1H), 7.80 (s, 1H), 7.66 (s, 1H), 7.57 (s, 1H), 7.56-7.53 (m, 5H), 6.39-6.37 (m, 2H), 5.93 (q, J=6.5 Hz, 1H), 5.76 (q, J=7.1 Hz, 1H), 5.40-5.35 (m, 1H), 4.42-4.30 (m, 2H), 3.90-3.81 (m, 1H), 3.72-3.61 (m, 3H), 3.19-3.01 (m, 1H), 2.80-2.50 (m, 3H), 2.10-1.92 (m, 4H), 1.74 (d, J=6.9 Hz, 3H), 1.73-1.68 (m, 2H), 1.67 (d, J=7.0 Hz, 3H), 1.38-1.28 (m, 2H), 0.99 (d, J=6.7 Hz, 3H), 0.95 (d, J=6.6 Hz, 3H). LCMS (m/z) 681.3 [M+H], Tr=2.21 min.

Example 129

Compound 129

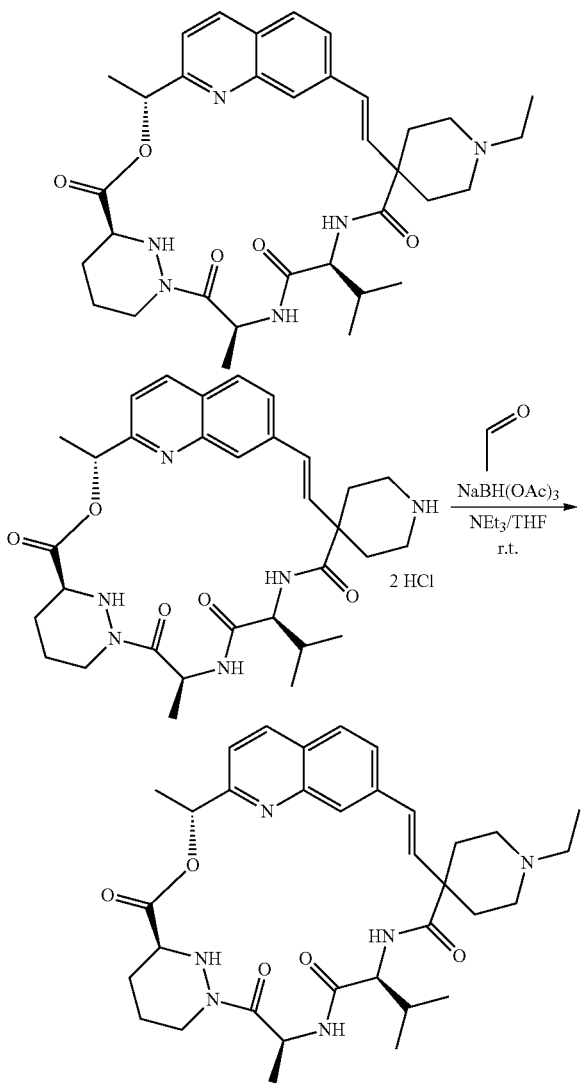

Compound 127 (9 mg, 0.014 mmol) was dissolved in dry tetrahydrofuran (5 mL). This mixture was purged twice with argon and acetaldehyde (1.2 mg, 0.027 mmol), triethyl amine (4.1 mg, 0.04 mmol) and sodium triacetoxyborohydride (6 mg, 0.027 mmol) were added. The reaction mixture was stirred at room temperature for one day, concentrated under reduced pressure, the resulting residue was dissolved in ethyl acetate (10 mL) and was washed saturated $NaHCO_3$ (10 mL), water (10 mL, 5 mL of brine was added to support the separation). The resulting aqueous phase was extracted with ethyl acetate (10 mL). Combined organic extracts were washed with brine (10 mL) and dried over magnesium sulfate, filtered and concentrated under reduced pressure. The residue was purified by preparatory HPLC (Gemini 5u C18 110 Å column, 5-100% acetonitrile/water, 0.1% trifluoroacetic acid modifier) to afford the bis-trifluoroacetic acid salt of the title compound (8 mg, 68%) as a white powder after evaporation. $^1$H NMR (400 MHz, $CD_3OD$): δ 8.24 (d, J=8.4 Hz, 1H), 7.86 (d, J=8.5 Hz, 1H), 7.83 (s, 1H), 7.66 (dd, J=8.4, 1.7 Hz, 1H), 7.47 (d, J=8.4 Hz, 1H), 6.72 (d, J=16.3 Hz, 1H), 6.31 (d, J=16.3 Hz, 1H), 6.23 (q, J=6.6 Hz, 1H), 5.65 (q, J=7.2 Hz, 1H), 4.43 (d, J=9.1 Hz, 1H), 3.87-3.77 (m, 1H), 3.71-3.60 (m, 1H), 3.24-3.12 (m, 2H), 2.90-2.75 (m, 2H), 2.66-2.57 (m, 1H), 2.51-2.35 (m, 2H), 1.97-1.81 (m, 1H), 1.77 (d, J=6.6 Hz, 3H), 1.62 (d, J=7.2 Hz, 3H), 1.43-1.31 (m, 8H), 1.29-1.22 (m, 3H), 1.10 (d, J=6.7 Hz, 3H), 0.99 (d, J=6.6 Hz, 3H). LCMS (m/z) 619.4 [M+H], Tr=1.88 min.

Example 130

Compound 130

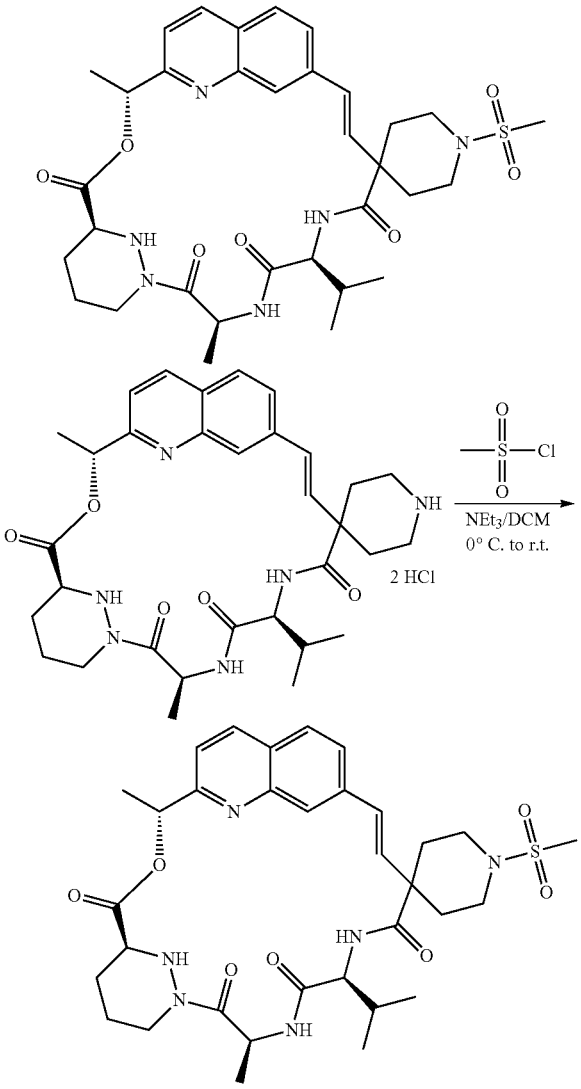

Compound 127 (15 mg, 0.023 mmol) was suspended in dry dichloromethane (10 mL). This mixture was purged twice with argon and cooled to 0° C. Triethyl amine (9 mg, 0.092 mmol) was at 0° C. After stirring for 10 minutes at 0° C., methanesulfonyl chloride (3 mg, 0.025 mmol) was added as a solution in dry dichloromethane (5 mL) via syringe. The reaction mixture was stirred at room temperature for 10 minutes then washed with saturated $NaHCO_3$ (10 mL), water (10 mL, 5 mL of brine was added to support the separation). Resulting aqueous phase was extracted with dichloromethane (10 mL). Combined organic extracts were washed with brine (10 mL) and dried over magnesium sulfate, filtered and concentrated under reduced pressure. The residue was purified by silica gel chromatography (gradient from 0-10% methanol in dichloromethane) to afford the title compound (10 mg, 65%) as a white solid after evaporation. $^1$H NMR (400 MHz, $CD_3OD$): δ 8.10 (d, J=8.5 Hz, 1H), 7.75-7.65 (m, 2H), 7.52 (s, 1H), 7.30 (d, J=8.5 Hz, 1H), 6.37 (d, J=16.5 Hz, 1H), 6.24 (d, J=16.5 Hz, 1H), 5.80 (q, J=6.8 Hz, 1H), 5.61 (q, J=7.2 Hz, 1H), 4.36-4.24 (m, 1H), 4.21 (d, J=10.6 Hz, 1H), 4.00 (q, J=7.1 Hz, 1H), 3.76-3.66 (m, 1H), 3.63-3.52 (m, 1H), 3.51-3.41 (m, 1H), 3.05-2.92 (m, 1H), 2.86-2.76 (m, 1H), 2.74 (s, 3H), 2.68-2.55 (m, 1H), 2.37-2.18 (m, 2H), 2.07-1.85 (m, 5H), 1.84-1.77 (m, 1H), 1.69-1.64 (m, 1H), 1.62 (d, J=6.9 Hz, 3H), 1.56-1.50 (m, 3H), 0.87 (d, J=6.7 Hz, 6H). LCMS (m/z) 669.3 [M+H], Tr=3.08 min.

Example 131

Compound 131

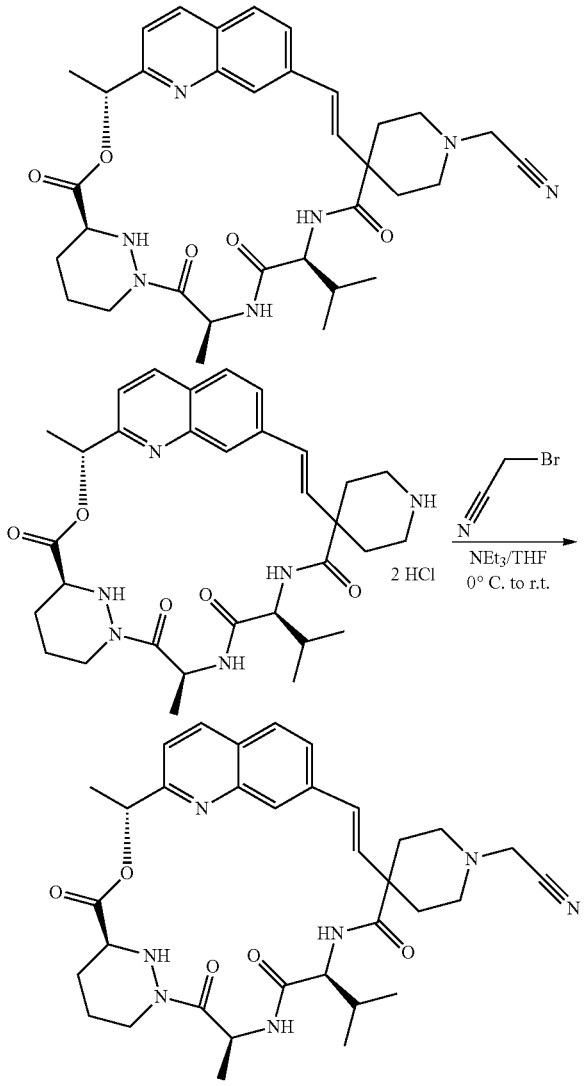

Compound 127 (15 mg, 0.023 mmol) was dissolved in dry tetrahydrofuran (10 mL). This mixture was purged twice with argon and cooled to 0° C. Triethyl amine (9 mg, 0.092 mmol) was at 0° C. After stirring for 10 minutes at 0° C., 2-bromoacetonitrile (3 mg, 0.025 mmol) was added as a solution in dry tetrahydrofuran (2 mL) via syringe. The reaction mixture was stirred at room temperature for 12 hours, concentrated under reduced pressure, the resulting residue was dissolved in ethyl acetate (10 mL) and was washed saturated $NaHCO_3$ (10 mL), water (10 mL, 5 mL of brine was added to support the separation). The resulting aqueous phase was extracted with ethyl acetate (10 mL). Combined organic extracts were washed with brine (10 mL) and dried over magnesium sulfate, filtered and concentrated under reduced pressure. The residue was purified by silica gel chromatography (gradient from 0-15% methanol in dichloromethane) to afford the title compound (9 mg, 62%) as a white solid after evaporation. $^1$H NMR (400 MHz, $CD_3OD$) δ 8.23 (d, J=8.5 Hz, 1H), 7.85-7.78 (m, 2H), 7.64 (s, 1H), 7.43 (d, J=8.5 Hz, 1H), 6.44 (d, J=16.5 Hz, 1H), 6.34 (d, J=16.5 Hz, 1H), 5.94 (q, J=6.8 Hz, 1H), 5.74 (q, J=7.3 Hz, 1H), 4.66-4.57 (m, 1H), 4.47-4.39 (m, 1H), 4.38-4.29 (m, 2H), 3.88-3.79 (m, 1H), 3.70 (s, 2H), 2.94-2.87 (m, 1H), 2.85-2.69 (m, 2H), 2.66-2.47 (m, 2H), 2.47-2.31 (m, 2H), 2.14-1.99 (m, 4H), 1.97-1.88 (m, 1H), 1.75 (d, J=6.9 Hz, 3H), 1.67 (d, J=7.2 Hz, 3H), 1.05-0.97 (m, 6H). LCMS (m/z) 630.3 [M+H], Tr=2.94 min.

Example 132

Compound 132

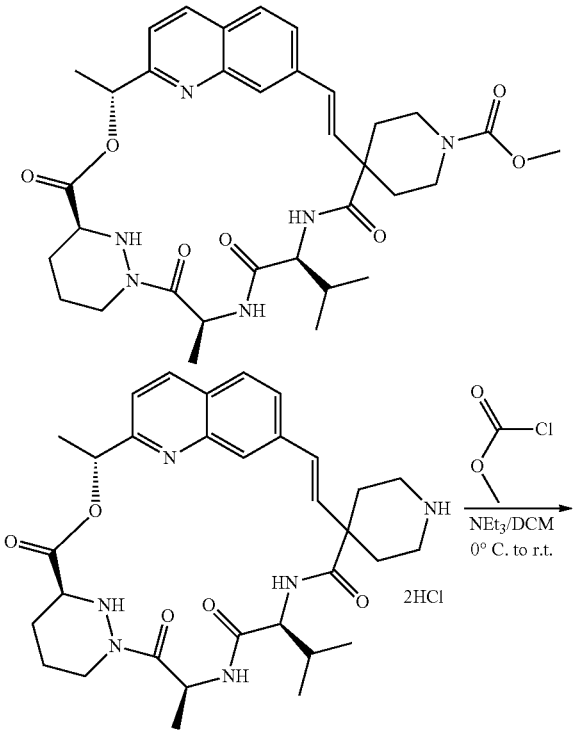

-continued

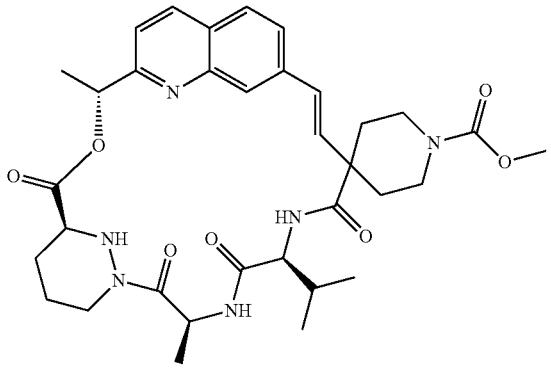

Compound 127 (15 mg, 0.023 mmol) was suspended in dry dichloromethane (10 mL). This mixture was purged twice with argon and cooled to 0° C. Triethyl amine (9 mg, 0.092 mmol) was at 0° C. After stirring for 10 minutes at 0° C., methyl chloroformate (3.3 mg, 0.025 mmol) was added as a solution in dry dichloromethane (5 mL) via syringe. The reaction mixture was stirred at room temperature for 10 minutes then washed with saturated $NaHCO_3$ (10 mL), water (10 mL, 5 mL of brine was added to support the separation). Resulting aqueous phase was extracted with dichloromethane (10 mL). Combined organic extracts were washed with brine (10 mL) and dried over magnesium sulfate, filtered and concentrated under reduced pressure. The residue was purified by silica gel chromatography (gradient from 0-10% methanol in dichloromethane) to afford the title compound (9 mg, 60%) as a white solid after evaporation. $^1$H NMR (400 MHz, $CD_3OD$) δ 8.23 (d, J=8.4 Hz, 1H), 7.87-7.81 (m, 2H), 7.65 (s, 1H), 7.46-7.40 (m, 1H), 6.47 (d, J=16.5 Hz, 1H), 6.35 (d, J=16.5 Hz, 1H), 5.93 (q, J=6.8 Hz, 1H), 5.74 (q, J=7.2 Hz, 1H), 4.64-4.59 (m, 1H), 4.46-4.40 (m, 1H), 4.37-4.28 (m, 2H), 4.09-4.01 (m, 1H), 3.98-3.89 (m, 2H), 3.87-3.80 (m, 1H), 3.73 (s, 3H), 3.21-3.01 (m, 2H), 2.82-2.71 (m, 1H), 2.38-2.20 (m, 2H), 2.09-1.88 (m, 6H), 1.75 (d, J=6.9 Hz, 3H), 1.67 (d, J=7.2 Hz, 3H), 1.01 (d, J=4.0 Hz, 3H), 0.99 (d, J=3.9 Hz, 3H). LCMS (m/z) 649.3 [M+H], Tr=3.18 min.

Example 133

Compound 133

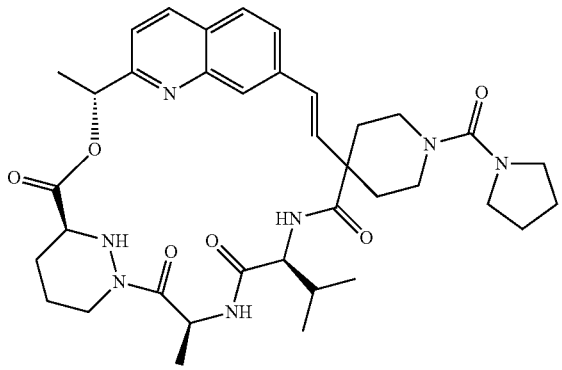

-continued

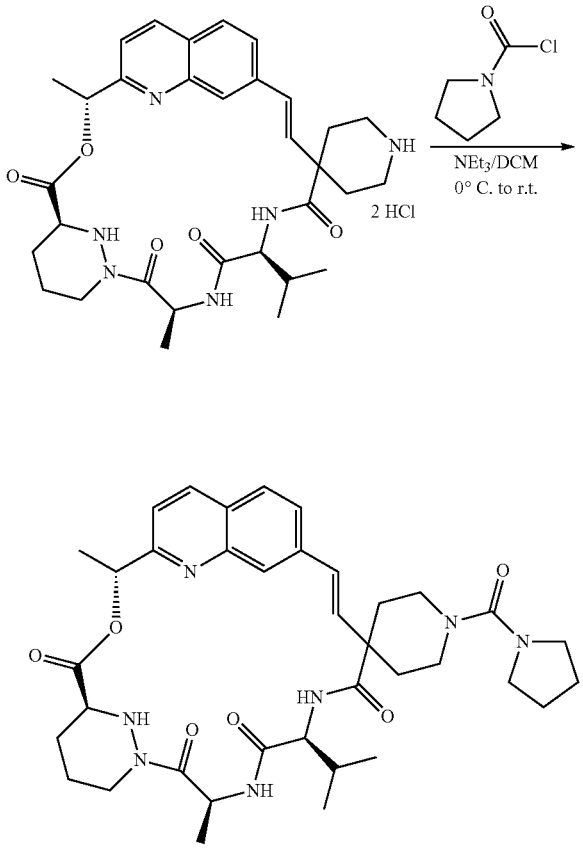

Compound 127 (15 mg, 0.023 mmol) was suspended in dry dichloromethane (10 mL). This mixture was purged twice with argon and cooled to 0° C. Triethyl amine (9 mg, 0.092 mmol) was at 0° C. After stirring for 10 minutes at 0° C., pyrrolidine-1-carbonyl chloride (4.6 mg, 0.035 mmol) was added as a solution in dry dichloromethane (5 mL) via syringe. The reaction mixture was stirred at room temperature for 12 hours then washed with saturated $NaHCO_3$ (10 mL), water (10 mL, 5 mL of brine was added to support the separation). Resulting aqueous phase was extracted with dichloromethane (10 mL). Combined organic extracts were washed with brine (10 mL) and dried over magnesium sulfate, filtered and concentrated under reduced pressure. The residue was purified by silica gel chromatography (gradient from 0-10% methanol in dichloromethane) to afford the title compound (10 mg, 63%) as a white solid after evaporation. $^1$H NMR (400 MHz, $CD_3OD$) δ 8.67 (d, J=7.0 Hz, 1H), 8.23 (d, J=8.2 Hz, 1H), 7.85-7.79 (m, 2H), 7.65 (s, 1H), 7.48-7.34 (m, 1H), 6.49 (d, J=16.6 Hz, 1H), 6.35 (d, J=16.4 Hz, 1H), 5.99-5.87 (m, 1H), 5.81-5.69 (m, 1H), 4.48-4.27 (m, 1H), 3.87-3.58 (m, 1H), 3.45-3.39 (m, 4H), 3.22-3.12 (m, 1H), 3.08-2.97 (m, 1H), 2.82-2.70 (m, 1H), 2.37-2.17 (m, 3H), 2.08-1.97 (m, 6H), 1.97-1.84 (m, 4H), 1.75 (d, J=7.0 Hz, 3H), 1.66-1.44 (m, 2H), 1.68 (d, J=7.1 Hz, 3H), 1.01 (d, J=6.6 Hz, 6H). LCMS (m/z) 688.4 [M+H], Tr=3.16 min.

Example 134

Compound 134

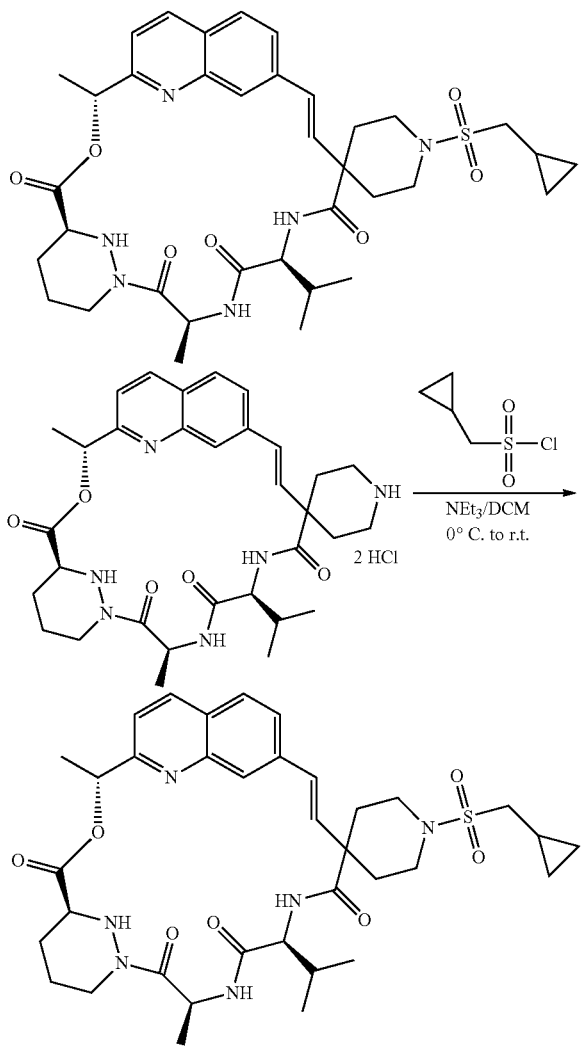

Compound 127 (15 mg, 0.023 mmol) was suspended in dry dichloromethane (10 mL). This mixture was purged twice with argon and cooled to 0° C. Triethyl amine (9 mg, 0.092 mmol) was at 0° C. After stirring for 10 minutes at 0° C., cyclopropylmethanesulfonyl chloride (4 mg, 0.025 mmol) was added as a solution in dry dichloromethane (5 mL) via syringe. The reaction mixture was stirred at room temperature for 10 minutes then washed with saturated $NaHCO_3$ (10 mL), water (10 mL, 5 mL of brine was added to support the separation). Resulting aqueous phase was extracted with dichloromethane (10 mL). Combined organic extracts were washed with brine (10 mL) and dried over magnesium sulfate, filtered and concentrated under reduced pressure. The residue was purified by silica gel chromatography (gradient from 0-10% methanol in dichloromethane) to afford the title compound (9 mg, 55%) as a white solid after evaporation. $^1$H NMR (400 MHz, $CD_3OD$): δ 8.23 (d, J=8.5 Hz, 1H), 7.87-7.77 (m, 2H), 7.66 (s, 1H), 7.43 (d, J=8.5 Hz, 1H), 6.48 (d, J=16.8 Hz, 1H), 6.36 (d, J=16.4 Hz, 1H), 5.94 (q, J=7.2 Hz, 1H), 5.75 (q, J=7.3 Hz, 1H), 4.48-4.39 (m, 1H), 4.37-4.27 (m, 1H), 3.88-3.76 (m, 2H), 3.71-3.62 (m, 1H), 3.28-3.15 (m, 4H), 3.07-2.96 (m, 1H), 2.82-2.66 (m, 1H), 2.49-2.25 (m, 2H), 2.14-1.85 (m, 3H), 1.75 (d, J=7.0 Hz, 3H), 1.68 (d, J=7.2 Hz, 3H), 1.20-1.07 (m, 1H), 1.00 (d, J=6.2 Hz, 6H), 0.80-0.64 (m, 4H), 0.53-0.35 (m, 4H). LCMS (m/z) 709.4 [M+H], Tr=3.43 min.

Example 135

Compound 135

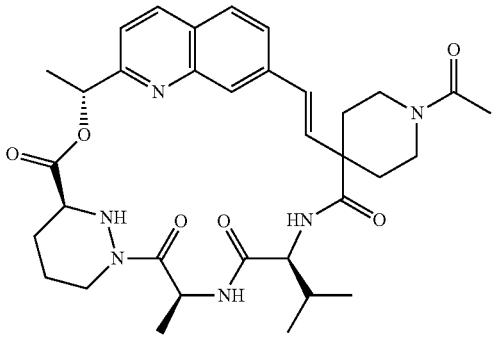

Compound 135a

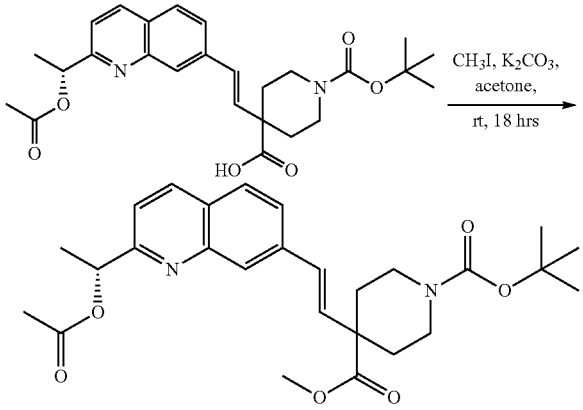

To 126d (1.3 g, 2.77 mmol) in acetone (30 mL, 0.1 M) was added potassium carbonate (595.2 mg, 5.55 mmol) and methyl iodide (0.35 mL, 4.16 mmol). After 18 hours, the reaction was filtered and concentrated in vacuo. Purification by column chromatography (25-50% EtOAc/hexane) afforded 135a (541.4 mg, 41%) as a yellow oil. $_1$H NMR (400 MHz, $CDCl_3$) δ 8.10 (d, J=8.5 Hz, 1H), 8.02 (s, 1H), 7.74 (d, J=8.5 Hz, 1H), 7.56 (d, J=8.5 Hz, 1H), 7.42 (d, J=8.4 Hz, 1H), 6.63 (d, J=16.3 Hz, 1H), 6.37 (d, J=16.3 Hz, 1H), 6.04 (q, J=6.6 Hz, 1H), 3.80 (m, 2H), 3.75 (s, 3H), 3.13 (m, 2H), 2.28 (m, 2H), 2.04 (s, 6H), 1.76 (m, 2H), 1.67 (d, J=6.7 Hz, 3H), 1.46 (s, 9H). LCMS (m/z) $^1$H NMR (400 MHz, $CDCl_3$) δ 8.10 (d, J=8.5 Hz, 1H), 8.02 (s, 1H), 7.74 (d, J=8.5 Hz, 1H), 7.56 (d, J=8.5 Hz, 1H), 7.42 (d, J=8.4 Hz, 1H), 6.63 (d, J=16.3 Hz, 1H), 6.37 (d, J=16.3 Hz, 1H), 6.04 (q, J=6.6 Hz, 1H), 3.80 (m, 2H), 3.75 (s, 3H), 3.13 (t, J=11.2 Hz, 2H), 2.28 (d, J=14.0 Hz, 2H), 2.16 (s, 3H), 1.76 (t, J=10.0 Hz, 2H), 1.67 (d, J=6.7 Hz, 3H), 1.47 (d, J=12.0 Hz, 9H). LCMS (m/z) 483.51 [M+H].

Compound 135b

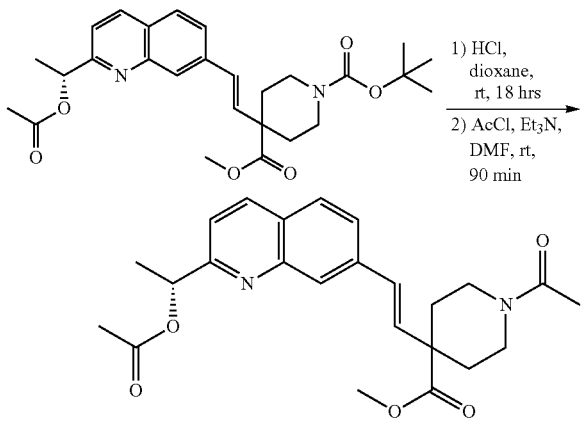

To 135a (541.5 mg, 1.12 mmol) was added an HCl solution (11.2 mL, 4 M in dioxane, 0.1 M). After stirring for 18 hours, the reaction was concentrated in vacuo to afford the free amine as a yellow solid (502.0 mg).

To the free amine (99.5 mg, 0.220 mmol) in DMF (2.2 mL, 0.1 M) was added triethyl amine (0.10 mL, 0.725 mmol) followed by acetyl chloride (0.02 mL, 0.264 mmol). After 90 minutes, water (3 mL) and sat. $NaHCO_{3(aq)}$ (2 mL) were added. The reaction was then extracted with EtOAc (2×20 mL), washed with brine (20 mL), dried over MgSO4, and concentrated in vacuo to afford 135b (73.7 mg, 79%) as a yellow residue. $_1$H NMR (400 MHz, $CDCl_3$) δ 8.12 (d, J=7.4 Hz, 1H), 8.02 (s, 1H), 7.75 (d, J=8.5 Hz, 1H), 7.57 (d, J=8.2 Hz, 1H), 7.43 (d, J=8.4 Hz, 1H), 6.64 (d, J=16.3 Hz, 1H), 6.38 (d, J=16.2 Hz, 1H), 6.06 (m, 1H), 4.18 (m, 1H), 3.77 (s, 3H), 3.68 (m, 1H), 3.33 (m, 1H), 3.12 (m, 1H), 2.34 (m, 2H), 2.16 (s, 3H), 2.11 (s, 3H), 1.78 (m, 2H), 1.68 (d, J=6.7 Hz, 3H). LCMS (m/z) 425.35 [M+H].

Compound 135c

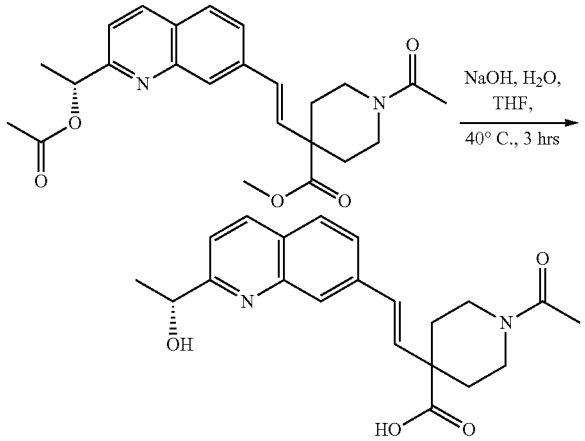

To 135b (117.3 mg, 0.353 mmol) in THF (1.5 mL, 0.25 M) and water (1.5 mL, 0.25 M) was added lithium hydroxide monohydrate (236.7 mg, 1.06 mmol) and the mixture was warmed to 40° C. After 5 hours, the reaction was cooled to rt, acidified with 1 M $HCl_{(aq)}$ to ~pH 4 and concentrated in vacuo to afford 135c (166.5 mg, 99%) as an orange solid. LCMS (m/z) 369.10 [M+H].

Compound 135d

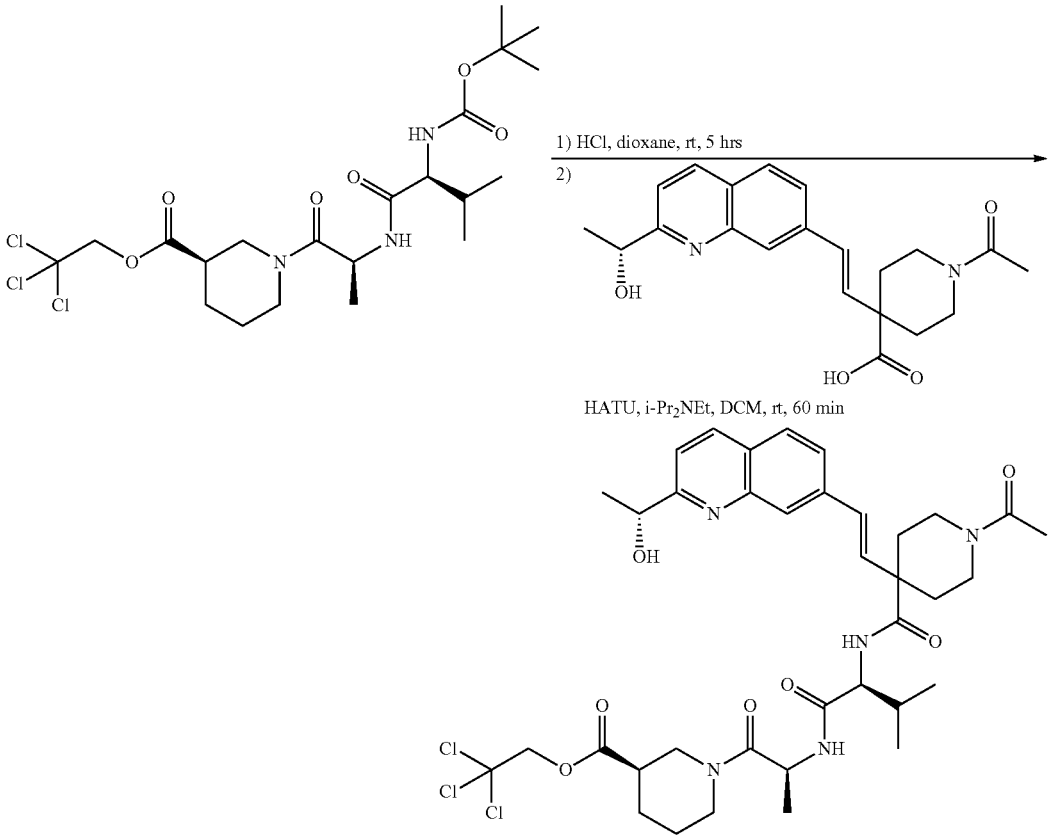

To 1e (166.5 mg, 0.366 mmol) in DCM (0.73 mL, 0.5 M) was added an HCl solution (0.37 mL, 4 M in dioxane, 1 M). After stirring for 30 minutes, the reaction was concentrated in vacuo to afford the free dipeptide as an amorphous, pale yellow solid.

To 135c (90.0 mg, 0.244 mmol) in DCM (5 mL, 0.05 M) was added i-$Pr_2NEt$ (0.51 mL, 2.93 mmol) and dipeptide in DCM (5 mL), followed by HATU (110.3 mg, 0.366 mmol). After 60 minutes, sat. $NaHCO_{3(aq)}$ (10 mL) was added and the phases were separated. The aqueous was extracted with DCM (2×15 mL); and the combined organics were dried over $MgSO_4$ and concentrated in vacuo. Purification by column chromatography (20-100% EtOAc/hexane) afforded 135d (19.7 mg, 10%) as a yellow foam. $^1$H NMR (400 MHz, $CDCl_3$) δ 8.11 (t, J=7.0 Hz, 1H), 7.99 (s, 1H), 7.75 (dd, J=8.5, 4.5 Hz, 1H), 7.59 (t, J=7.8 Hz, 1H), 7.34 (dd, J=8.4, 3.9 Hz, 1H), 6.75 (m, 2H), 6.43 (m, 1H), 5.04 (m, 1H), 4.93 (m, 1H), 4.68 (t, J=11.7 Hz, 2H), 4.28 (m, 2H), 3.62 (m, 4H), 3.10 (m, 1H), 2.90 (m, 2H), 2.34 (m, 2H), 2.17 (m, 2H), 1.93 (m, 3H), 1.73 (m, 3H), 1.57 (dd, J=6.5, 4.3 Hz, 3H), 1.29 (m, 3H), 0.88 (m, 6H). LCMS (m/z) 781.17 [M+H].

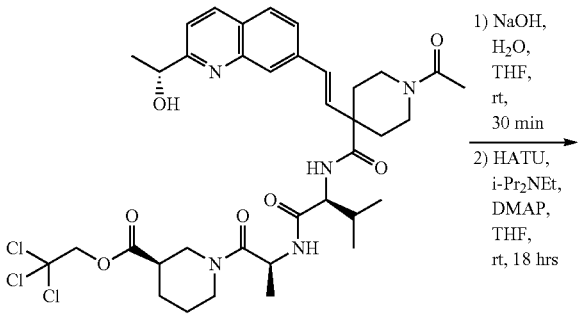

-continued

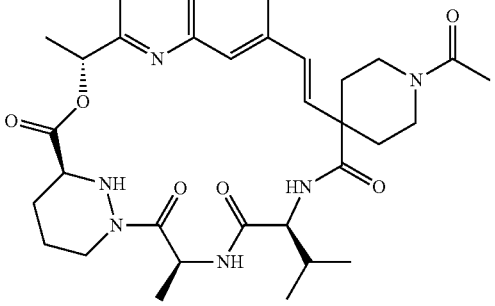

To 135d (19.7 mg, 0.026 mmol) in THF (1 mL, 0.025 M) was added 0.1 M $NaOH_{(aq)}$ (0.51 mL, 0.051 mmol). After, 60 minutes, the reaction was acidified with to ~pH 4 with 1 M $HCl_{(aq)}$, concentrated in vacuo, and triturated with $Et_2O$.

The crude material was dissolved in DCE (1 mL, 0.05 M) and added dropwise via a syringe pump to a mixture of DMAP (31.3 mg, 0.230 mmol) and 2-methyl-6-nitrobenzoic anhydride (54.1 mg, 0.153 mmol) in DCE (13 mL, 0.005 M) at 45° C. The react was cooled to room temperature as the addition went over 30 min. After 18 hours, the reaction was diluted with MeCN and purified by prep HPLC (Gemini, 30-70% MeCN/$H_2O$) to afford Compound 135 (3.2 mg, 20%) as a white solid. $^1$H NMR (400 MHz, $CDCl_3$) δ 8.01 (d, J=7.9 Hz, 1H), 7.71 (s, 1H), 7.63 (d, J=8.2 Hz, 1H), 7.51 (d, J=8.5 Hz, 1H), 7.45 (t, J=6.3 Hz, 1H), 6.33 (dd, J=22.5, 12.3 Hz, 2H), 6.14 (d, J=16.3 Hz, 1H), 5.86 (m, 1H), 5.74 (m, 1H), 4.45 (d, J=14.1 Hz, 2H), 3.69 (m, 2H), 3.60 (m, 1H), 2.58 (m, 1H), 2.28 (m, 1H), 1.97 (s, 1H), 1.93 (s, 3H), 1.82 (m, 1H), 1.66 (d, J=6.8 Hz, 3H), 1.60 (m, 2H), 1.53 (d, J=7.0 Hz, 6H), 1.45 (d, J=6.8 Hz, 3H), 0.91 (d, J=6.3 Hz, 3H), 0.87 (d, J=6.5 Hz, 3H). LCMS (m/z) 781.17 [M+H]. LCMS (m/z) 633.28 [M+H]. Tr=5.29 min.

Example 136

Compound 136

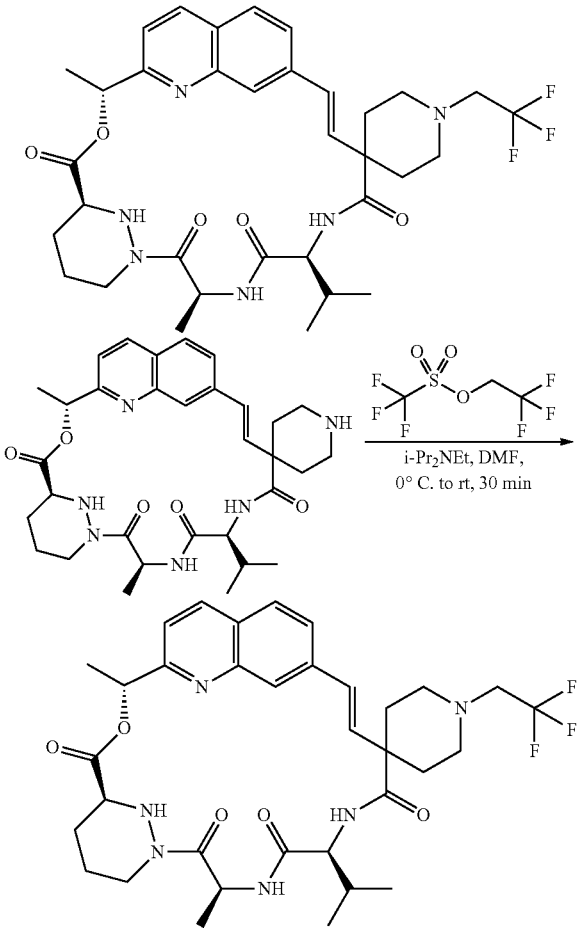

To 127 (16.5 mg, 0.025 mmol) in DMF (0.50 mL, 0.05 M) at 0° C. was added i-$Pr_2NEt$ (0.30 mL, 1.63 mmol), followed by 2,2,2-trifluoroethyl trifluoromethanesulfonate (231.3 mg, 0.025 mmol) in DMF (0.25 mL, 0.1 M) and the mixture was warmed to rt. After 30 min, the crude reaction was diluted with MeCN (2 mL) and purified by prep HPLC (Gemini, 50-65% MeCN/$H_2O$) to afford Compound 136 (3.1 mg, 16%) as a white solid. $^1$H NMR (400 MHz, $CDCl_3$) δ 8.06 (d, J=8.5 Hz, 1H), 7.69 (d, J=8.7 Hz, 2H), 7.58 (d, J=8.5 Hz, 1H), 6.37 (d, J=16.3 Hz, 2H), 6.22 (d, J=16.5 Hz, 1H), 6.16 (d, J=10.2 Hz, 1H), 5.95 (m, 1H), 5.80 (m, 1H), 4.53 (d, J=12.9 Hz, 1H), 4.22 (t, J=9.7 Hz, 1H), 3.71 (m, 4H), 3.37 (m, 2H), 3.10 (m, 1H), 3.01 (m, 3H), 2.88 (m, 1H), 2.69 (m, 2H), 2.55 (m, 1H), 2.34 (d, J=13.8 Hz, 1H), 2.04 (d, J=29.6 Hz, 4H), 1.72 (d, J=6.8 Hz, 6H), 1.60 (d, J=7.1 Hz, 3H), 1.52 (d, J=7.1 Hz, 3H), 1.44 (d, J=6.5 Hz, 6H), 1.00 (d, J=6.5 Hz, 3H), 0.96 (d, J=6.7 Hz, 3H). $^{19}$F NMR (376 MHz, $CDCl_3$) δ −69.44 (s). LCMS (m/z) 673.26 [M+H]. Tr=5.13 min.

Example 137

Compound 137

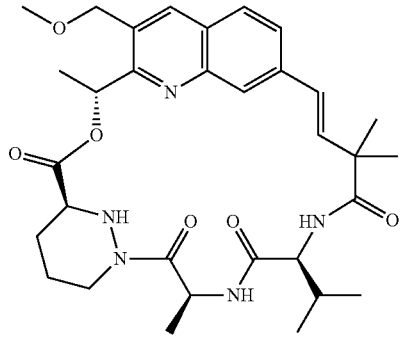

Compound 137a

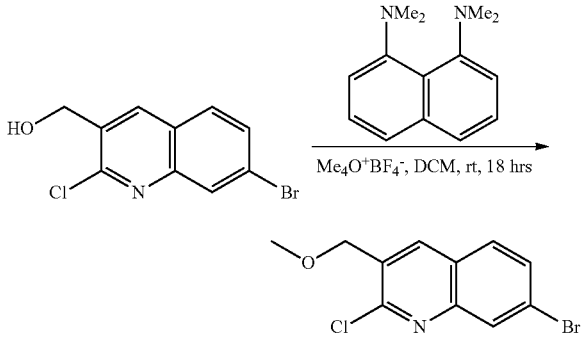

To (7-bromo-2-chloroquinolin-3-yl)methanol (obtained from BioBlocks, Inc.), (2.5 g, 9.17 mmol) in DCM (45 mL, 0.2 mmol) was added $N^1$,$N^1$,$N^8$,$N^8$-tetramethylnaphthalene-1,8-diamine (9.44 g, 45.9 mmol) and trimethyloxonium tetrafluoroborate (5.14 g, 45.9 mmol). After 18 hours, 1 M $HCl_{(aq)}$ (37 mL, 36.7 mmol) was added and the layers were separated. The aqueous was extracted with DCM (75 mL), and the combined organics were washed with brine (200 mL), dried over $MgSO_4$, and concentrated in vacuo. Purification by column chromatography (20-100% EtOAc/hexane) afforded 137a (1.08 g, 50%) as a pale yellow oil. $^1$H NMR (400 MHz, $CDCl_3$) δ 8.23 (s, 1H), 8.21 (s, 1H), 7.71 (d, J=8.7 Hz, 1H), 7.65 (dd, J=8.7, 1.8 Hz, 1H), 4.64 (d, J=1.1 Hz, 2H), 3.58 (s, 3H). LCMS (m/z) 288.01 [M+H].

Compound 137b

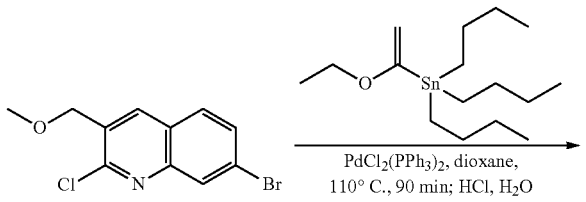

-continued

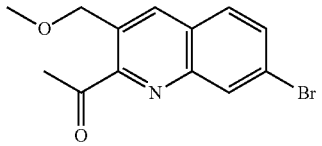

To 137a (1.29 g, 4.19 mmol) and bis(triphenylphosphine) palladium(II) dichloride (588.2 mg, 0.838 mmol) in dioxane (8.5 mL, 0.5 M) was added tributyl(1-ethoxyvinyl)tin (1.4 mL, 4.19 mmol) and the mixture was heated to 100° C. After 2 hours, the reaction was cooled to rt and 1 M $HCl_{(aq)}$ (8.38 mL) was added. After 18 hours, the reaction was extracted with EtOAc (100 mL), washed with sat. $NaHCO_{3(aq)}$ (100 mL), dried over $MgSO_4$, and concentrated in vacuo. Purification by column chromatography (0-50% EtOAc/hexane) afforded 137b (429.6 mg, 33%) as a pale yellow oil. $^1$H NMR (400 MHz, $CDCl_3$) δ 8.45 (s, 1H), 8.41 (s, 1H), 7.73 (m, 2H), 4.92 (s, 2H), 3.56 (s, 3H), 2.84 (s, 3H). LCMS (m/z) 295.82 [M+H].

Compound 137c

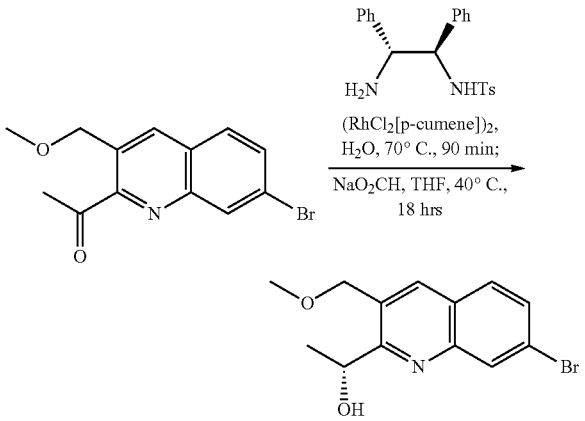

A mixture of dichloro(p-cymene)ruthenium(II) dimer (5.0 mg, 0.007 mmol) and (1R,2R)-(−)-N-p-tosyl-1,2-diphenylethylenediamine (0.6 mg, 0.001 mmol) in water (3 mL) was sparged with argon. After 10 minutes, the mixture was heated to 70° C. After 90 minutes, the mixture was cooled to rt. Then 137b (429.6 mg, 1.46 mmol) in THF (3 mL, 0.5 M) and sodium formate (484.8 mg, 7.30 mmol) were added, and the mixture was heated to 40° C. After 18 hours, the reaction was cooled to rt, extracted with EtOAc (60 mL), washed with water (40 mL) and brine (40 mL), dried over $MgSO_4$, and concentrated in vacuo. Purification by column chromatography (15-75% EtOAc/hexane) afforded 137c (152.7 mg, 35%) as a pale yellow residue. $^1$H NMR (400 MHz, $CDCl_3$) δ 8.25 (s, 1H), 8.15 (s, 1H), 7.68 (d, J=8.6 Hz, 1H), 7.61 (dd, J=8.7, 1.8 Hz, 1H), 5.11 (dd, J=12.7, 6.3 Hz, 1H), 4.59 (d, J=2.8 Hz, 2H), 3.48 (s, 3H), 1.48 (d, J=6.4 Hz, 3H). LCMS (m/z). 297.91 [M+H].

Compound 137d

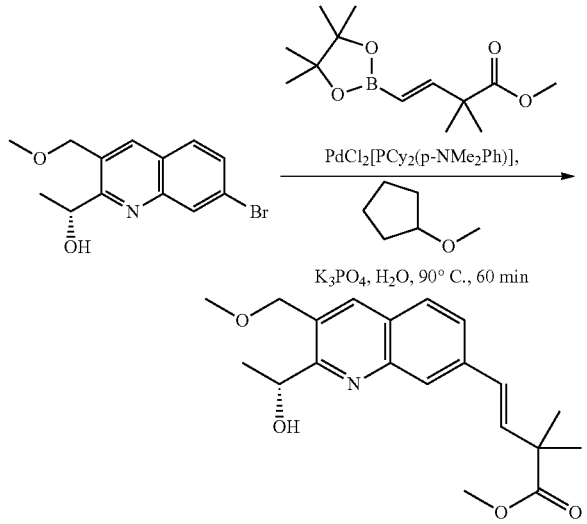

To 137c (152.3 mg, 0.516 mmol) and the indicated borinate ester (166.4, 0.619 mmol) in cyclopentyl methyl ether (1.7 ml, 0.3 M) was added bis[(dicyclohexyl)(4-dimethylaminophenyl)phosphine]palladium(II) chloride (22.5 mg, 0.025 mmol) and 3M aq. $K_3PO_4$ (0.51 mL, 1.55 mmol) and heated to 90° C. After 60 minutes, the reaction was cooled to diluted with water (10 mL) and extracted with EtOAc (2×10 mL). The combined organics were dried over $MgSO_4$ and concentrated in vacuo to afford 137d (325.5 mg, 99%) as a brown oil. $^1$H NMR (400 MHz, $CDCl_3$) δ 8.13 (s, 1H), 8.00 (s, 1H), 7.76 (d, J=8.5 Hz, 1H), 7.64 (d, J=8.5 1H), 6.63 (m, 2H), 5.15 (s, 1H), 4.62 (s, 2H), 3.73 (s, 3H), 3.49 (s, 3H), 1.51 (d, J=6.0 Hz, 3H), 1.47 (s, 6H). LCMS (m/z) 344.06 [M+H].

Compound 137e

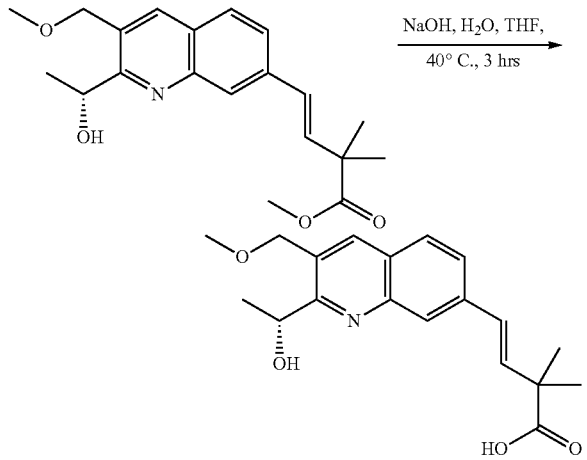

To 137d (325.5 mg, 0.516 mmol) in THF (9.5 mL, 0.1 M) was added 0.1 M $NaOH_{(aq)}$ (9.5 mL, 1.03 mmol) and warmed to 40° C. After 4 hours, the reaction was cooled to rt, acidified with 1 M $HCl_{(aq)}$ (3.6 mL) to ~pH 4 and concentrated in vacuo to afford 137e (169.8 mg, 99%) as a yellow solid. LCMS (m/z) 330.07 [M+H].

Compound 137f

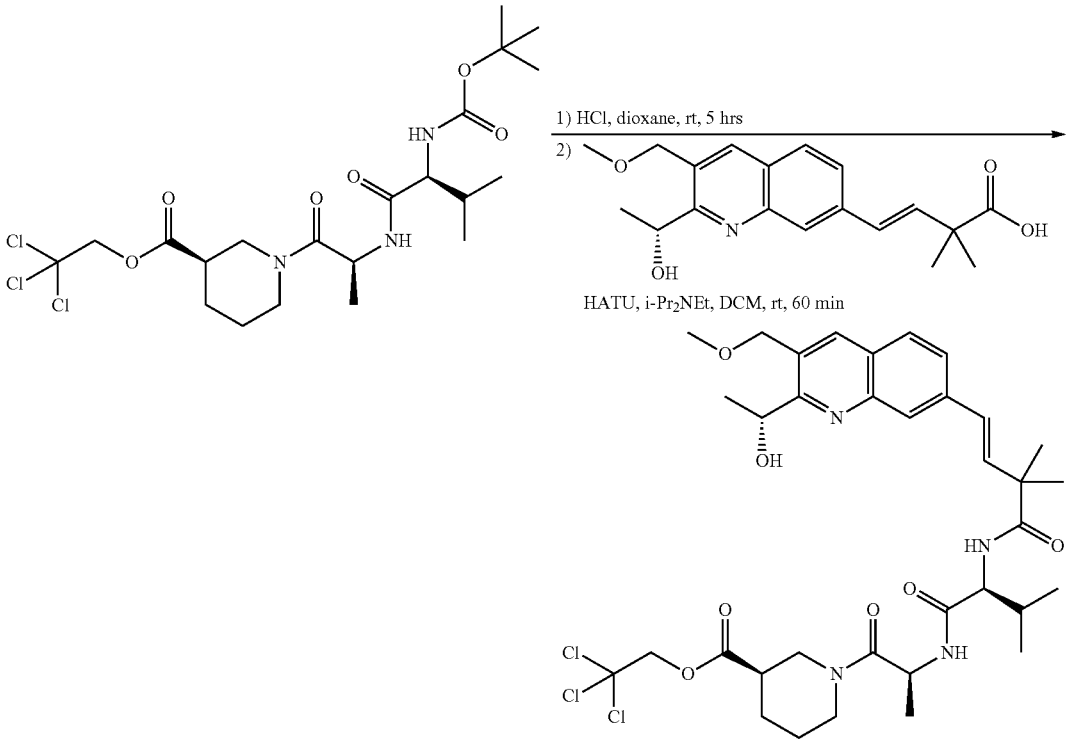

To 1d (411.0 mg, 0.773 mmol) in DCM (0.6 mL, 0.5 M) was added an HCl solution (0.78 mL, 4 M in dioxane, 1 M). After stirring for 18 hours, the reaction was concentrated in vacuo to afford the free dipeptide as an amorphous, pale yellow solid.

To 137e (169.8 mg, 0.516 mmol) in DCM (16 mL, 0.3 M) was added i-$Pr_2NEt$ (0.5 mL, 3.09 mmol) followed by HATU (296.2 mg, 0.773 mmol). After 15 minutes, the free dipeptide and $Pr_2NEt$ (0.5 mL, 3.09 mmol) in DCM (5 mL) was added to the activated ester mixture. After 60 minutes, sat. $NaHCO_{3(aq)}$ (15 mL) was added and the phases were separated. The aqueous was extracted with DCM (2×20 mL); and the combined organics were dried over $MgSO_4$ and concentrated in vacuo. Purification by column chromatography (50-100% EtOAc/hexane) afforded 137f (473.6 mg, 95%) as a yellow foam. $^1$H NMR (400 MHz, $CDCl_3$) δ 8.12 (s, 1H), 8.00 (s, 1H), 7.76 (d, J=8.5 Hz, 1H), 7.64 (d, J=8.3 Hz, 1H), 6.75 (d, J=16.2 Hz, 1H), 6.60 (d, J=16.2 Hz, 1H), 6.34 (d, J=8.6 Hz, 1H), 5.27 (p, J=6.9 Hz, 1H), 5.12 (m, 1H), 4.90 (d, J=11.9 Hz, 1H), 4.66 (d, J=11.9 Hz, 1H), 4.60 (d, J=2.3 Hz, 2H), 4.25 (m, 1H), 3.81 (d, J=11.0 Hz, 1H), 3.70 (m, 3H), 3.47 (s, 3H), 3.17 (m, 2H), 2.12 (m, 2H), 1.89 (s, 1H), 1.69 (t, J=9.5 Hz, 2H), 1.49 (d, J=6.2 Hz, 4H), 1.46 (s, 10H), 1.44 (s, 4H), 1.41 (d, J=6.6 Hz, 7H), 1.27 (d, J=6.9 Hz, 3H), 0.91 (d, J=6.7 Hz, 3H), 0.85 (d, J=6.8 Hz, 3H). LCMS (m/z) 744.23 [M+H].

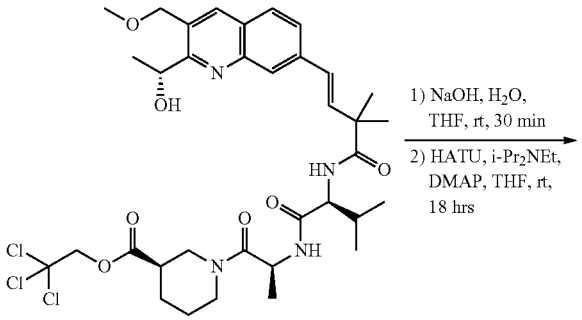

-continued

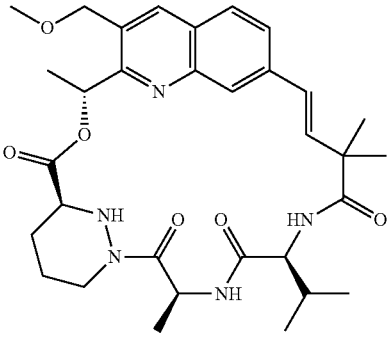

To 137f (365.0 mg, 0.492 mmol) in THF (10 mL, 0.05 M) was added 0.1 M $NaOH_{(aq)}$ (10 mL, 1.00 mmol). After, 30 minutes, the reaction was acidified with to ~pH 4 with 1 M $HCl_{(aq)}$ (0.9 mL), concentrated in vacuo, and triturated with THF/hexane.

The crude material was dissolved in THF (545 mL, 0.0003 M) and added i-$Pr_2NEt$ (0.30 mL, 1.63 mmol), DMAP (5.3 mg, 0.032 mmol), and HATU (95.1 mg, 0.245 mmol). After 18 hours, the reaction was concentrated in vacuo, diluted with water (30 mL), extracted with EtOAc (2×30 mL), dried over $MgSO_4$, and concentrated in vacuo. Purification by prep HPLC (Gemini, 40-65% MeCN/$H_2O$) afforded Compound 137 (33.0 mg, 11%) as a white solid. $^1$H NMR (400 MHz, $CDCl_3$) δ 8.17 (s, 2H), 7.78 (d, J=9.0 Hz, 1H), 7.65 (d, J=8.7 Hz, 1H), 6.47 (d, J=6.1 Hz, 2H), 6.09 (t, J=8.4 Hz, 2H), 5.99 (m, 2H), 5.66 (m, 1H), 4.83 (d, J=12.3 Hz, 1H), 4.59 (d, J=12.3 Hz, 1H), 4.48 (d, J=13.8 Hz, 1H), 4.15 (t, J=8.7 Hz, 1H), 3.75 (m, 1H), 2.54 (t, J=11.3 Hz, 1H), 1.94 (m, 3H), 1.84 (s, 3H), 1.63 (d, J=6.9 Hz, 6H), 1.55 (d, J=20.0 Hz, 3H), 1.46 (s, 3H), 1.39 (s, 3H), 0.95 (d, J=6.7 Hz, 3H), 0.90 (d, J=6.6 Hz, 3H). LCMS (m/z) 594.52 [M+H]. Tr=5.28 min.

Example 138

Compound 138

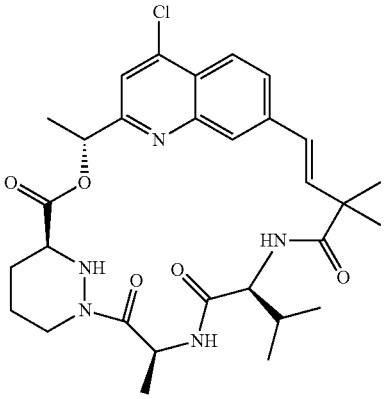

Compound 138a

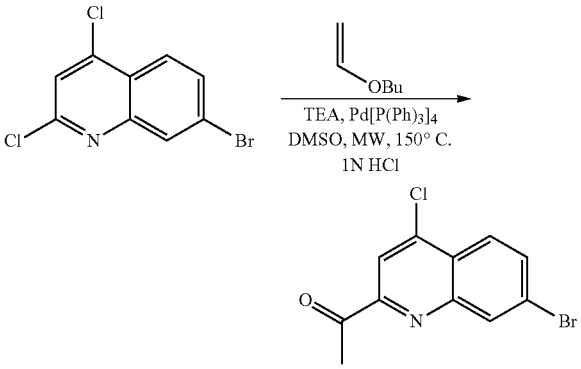

A mixture of 7-Bromo-2,4-dichloroquinoline (obtained from Aces Pharma, Inc.), (1.2 g, 4.1 mmol), triethylamine (2.07 g, 20.5 mmol), 1-(vinyloxy)butane (7 mL) and Tetrakis (triphenylphosphine)palladium(0) (0.3 g, 0.26 mmol) in anhydrous DMSO (10 mL) in a microwave tube was heated to 150° C. for 5 hours and diluted with EtOAc (100 mL). The crude was washed with water and dried over $Na_2SO_4$. After concentration, the crude was dissolved in acetonitrile (20 mL) and 1 N HCl (20 mL). After extraction with EtOAc (2×50 mL), dried over $Na_2SO_4$ and concentration, the residue was purified by silica gel chromatography using a gradient of iso-hexanes/ethyl acetate 1:0 to 1:1 to afford the title compound 138a (420 mg, 34%). $^1$H NMR (400 MHz, Chloroform-d) δ 8.16 (s, 1H), 7.96 (d, J=8.8 Hz, 1H), 7.83 (d, J=8.9 Hz, 1H), 2.95 (s, 3H), 2.89 (s, 3H).

LCMS (m/z) 286.0[M+H]. Tr=2.86 min.

Compound 138b

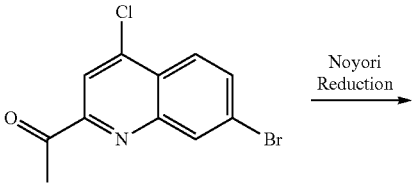

-continued

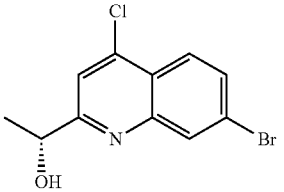

Dichloro (p-cymene) ruthenium(II) dimer (5.1 mg, 0.0084 mmol) and (1R,2R)-(−)-N-p-tosyl-1,2-diphenylethylenediamine (7.5 mg, 0.001 mmol) were suspended in degassed water (7.5 mL) and the mixture was degassed with nitrogen for 15 minutes. The mixture was stirred at 70° C. under nitrogen for 90 minutes. The resulting turbid orange mixture was allowed to cool to room temperature. Solid 138a (0.5 g, 1.67 mmol) followed by degassed tetrahydrofuran (7.5 mL) and sodium formate (0.57 g, 8.35 mmol) were added and the reaction mixture was degassed with nitrogen for 5 minutes. The reaction mixture was vigorously stirred at 40° C. for 3 hours and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ethyl acetate 2:1 to afford the title compound 138b (0.36 g, 72%) as a purple solid. $^1$H NMR (400 MHz, Chloroform-d) δ 7.93 (d, J=9.0 Hz, 1H), 7.76 (dd, J=8.9, 1.2 Hz, 1H), 7.46 (s, 1H), 5.17-4.76 (m, 1H), 2.91 (d, J=1.2 Hz, 3H), 1.57 (dd, J=6.7, 1.2 Hz, 3H). LCMS (m/z) 288.1 [M+H]. Tr=2.06 min.

Compound 138c

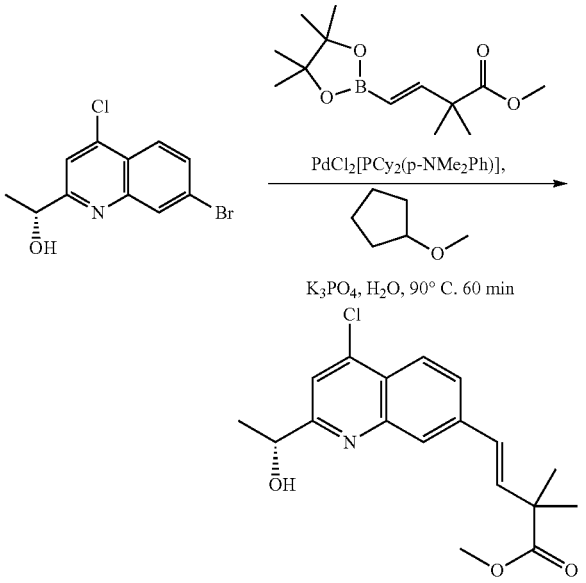

To 138b (152.3 mg, 0.5 mmol) and borinate ester (166.4, 0.619 mmol) in cyclopentyl methyl ether (1.7 ml, 0.3 M) was added bis[(dicyclohexyl)(4-dimethylaminophenyl) phosphine]palladium(II) chloride (22.5 mg, 0.025 mmol) and 3 M $K_3PO_{4(aq)}$ (0.51 mL, 1.55 mmol) and heated to 90° C. After 60 minutes, the reaction was cooled to rt, diluted with water (10 mL) and extracted with EtOAc (2×10 mL). The combined organics were dried over $MgSO_4$ and concentrated in vacuo to afford Intermediate 138c (325.5 mg, 99%) as a brown oil. $^1$H NMR (400 MHz, $CDCl_3$) δ 8.14 (s, 1H), 8.00 (s, 1H), 7.72 (d, J=8.5 Hz, 1H), 7.64 (d, J=8.5 Hz, 1H), 6.60 (m, 2H), 5.14 (s, 1H), 4.62 (s, 2H), 3.71 (s, 3H), 3.49 (s, 3H), 1.50 (d, J=6.0 Hz, 3H), 1.47 (s, 6H). LCMS (m/z) 334.06 [M+H].

To Intermediate 138c (325.5 mg, 0.5 mmol) in THF (9.5 mL, 0.1 M) was added 0.1 M aq. NaOH (9.5 mL, 1.03 mmol) and warmed to 40° C. After 4 hours, the reaction was cooled to rt, acidified with 1M aq. HCl (3.6 mL) to ~pH 4 and concentrated in vacuo to afford 138d (169.8 mg, 99%) as a yellow solid. LCMS (m/z) 320.2 [M+H].

Compound 138e

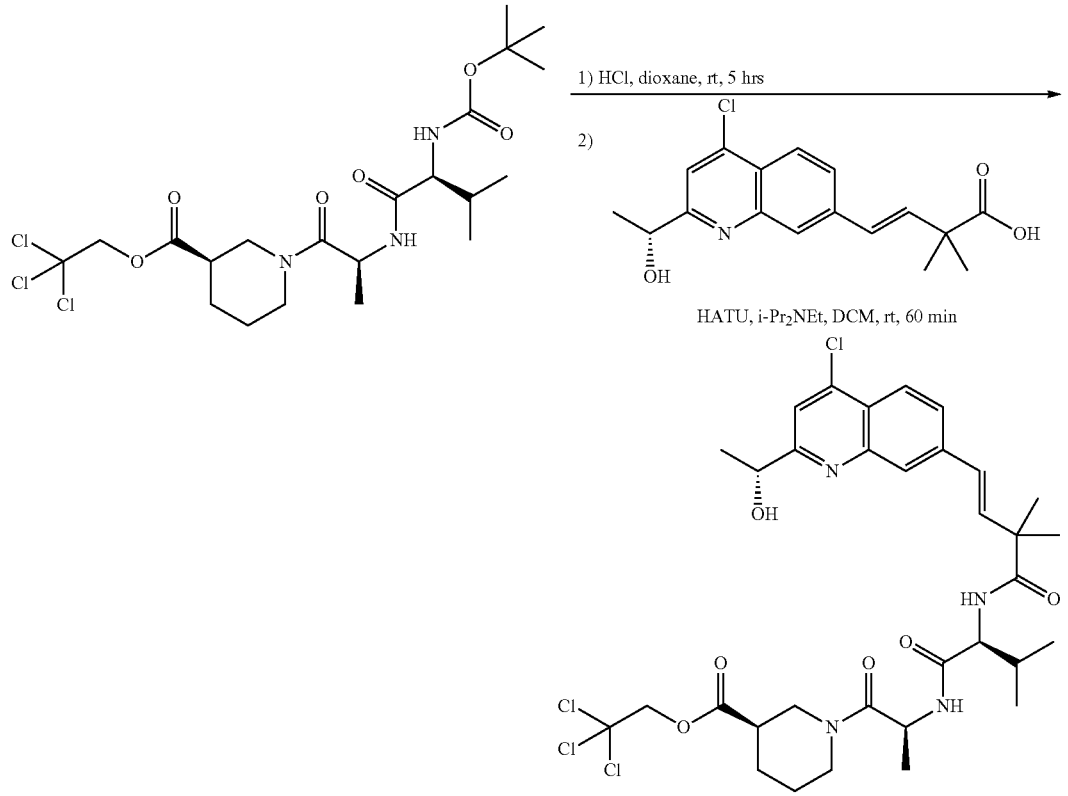

Compound 138d

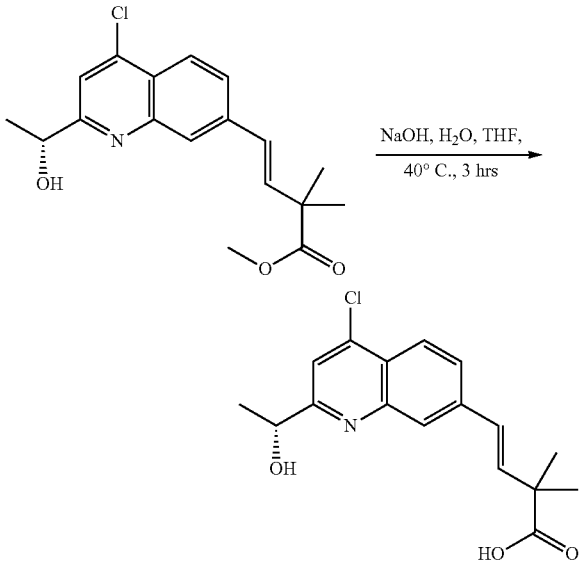

To 1d (411.0 mg, 0.773 mmol) in DCM (0.6 mL, 0.5 M) was added an HCl solution (0.78 mL, 4 M in dioxane, 1 M). After stirring for 18 hours, the reaction was concentrated in vacuo to afford the free dipeptide as an amorphous, pale yellow solid.

To 138d (170 mg, 0.516 mmol) in DCM (17 mL, 0.3 M) was added i-$Pr_2$NEt (0.5 mL, 3.09 mmol) followed by HATU (296.2 mg, 0.773 mmol). After 15 minutes, the free dipeptide and i$Pr_2$NEt (0.5 mL, 3.09 mmol) in DCM (5 mL) was added to the activated ester mixture. After 60 minutes, sat. $NaHCO_{3(aq)}$ (15 mL) was added and the phases were separated. The aqueous was extracted with DCM (2×20 mL); and the combined organics were dried over $MgSO_4$ and concentrated in vacuo. Purification by column chromatography (50-100% EtOAc/hexane) afforded 138e (473.6 mg, 95%) as a yellow foam. $^1$H NMR (400 MHz, $CDCl_3$) δ 8.12 (s, 1H), 8.02 (s, 1H), 7.74 (d, J=8.5 Hz, 1H), 7.62 (d, J=8.3 Hz, 1H), 6.75 (d, J=16.2 Hz, 1H), 6.65 (d, J=16.2 Hz, 1H), 6.34 (d, J=8.6 Hz, 1H), 5.27 (p, J=6.9 Hz, 1H), 5.12 (m, 1H), 4.95 (d, J=11.9 Hz, 1H), 4.66 (d, J=11.9 Hz, 1H), 4.62 (d, J=2.3 Hz, 2H), 4.25 (m, 1H), 3.81 (d, J=11.0 Hz, 1H), 3.70 (m, 3H), 3.47 (s, 3H), 3.21 (m, 2H), 2.12 (m, 2H), 1.89 (s, 1H), 1.69 (t, J=9.5 Hz, 2H), 1.49 (d, J=6.2 Hz, 4H), 1.46 (s, 10H), 1.34 (s, 4H), 1.41 (d, J=6.6 Hz, 7H), 1.26 (d, J=6.9 Hz, 3H), 0.92 (d, J=6.7 Hz, 3H), 0.87 (d, J=6.8 Hz, 3H). LCMS (m/z) 733.1 [M+H].

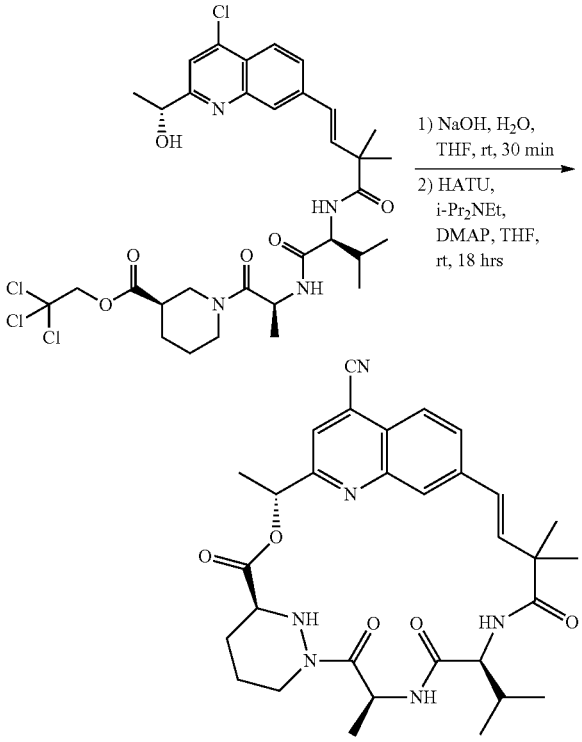

To 138e (365.0 mg, 0.492 mmol) in THF (10 mL, 0.05 M) was added 0.1 M aq. NaOH (10 mL, 1.00 mmol). After, 30 minutes, the reaction was acidified to ~pH 4 with 1 M $HCl_{(aq)}$ (0.9 mL), concentrated in vacuo, and triturated with THF/hexane.

The crude material was dissolved in THF (545 mL, 0.0003 M) and added i-$Pr_2NEt$ (0.30 mL, 1.63 mmol), DMAP (5.3 mg, 0.032 mmol), and HATU (95.1 mg, 0.245 mmol). After 18 hours, the reaction was concentrated in vacuo, diluted with water (30 mL), extracted with EtOAc (2×30 mL), dried over $MgSO_4$, and concentrated in vacuo. Purification by prep HPLC (Gemini, 40-65% MeCN/$H_2O$) afforded Compound 138 (30 mg, 10%) as a white solid. $^1H$ NMR (400 MHz, $CD_3OD$) δ 8.11 (d, J=6 Hz, 1H), 7.89 (m, 1H), 7.63 (s, 1H), 7.56 (s, 1H), 6.52 (d, J=12 Hz, 1H), 6.22 (d, J=12 Hz, 1H), 5.84 (m, 1H), 5.69 (m, 1H), 4.42 (cm, 2H), 4.26 (d, J=6 Hz, 1H), 3.77 (bm, 1H), 2.73 (m, 1H), 1.90 (m, 3H), 1.65 (m, 6H), 1.44 (s, 3H), 1.33 (s, 3H), 0.94 (m, 6H). LCMS (m/z) 584.5 [M+H]. Tr=2.28 min.

Example 139

Compound 139

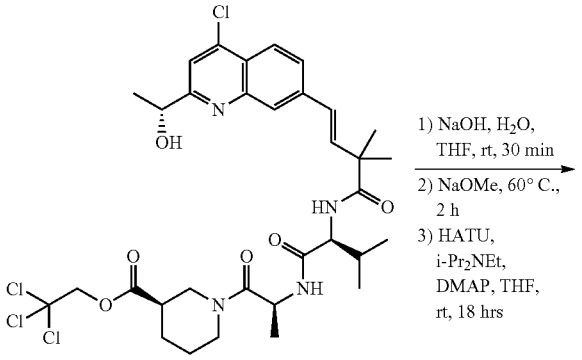

-continued

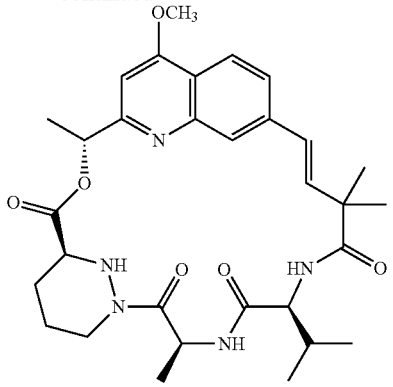

138e, 50 mg in 5 mL in THF/water is first hydrolyzed to remove the TCE ester. The resulting crude product was taken up in MeOH/NaOMe solution heated at 60° C. for 1 h. The reaction mixture was adjusted to pH 7 with 1N aq. HCl and the crude mixture concentrated to a residue which was taken up in DMF and cyclized using HATU. The resulting cyclization product was purified via reverse phase preparative HPLC. The resulting product, 6 mg, was obtained after removal of solvent via rotavap and hi-vacuum. $^1H$ NMR (400 MHz, $CD_3CN$) δ 8.03 (s, 1H), 7.60 (m, 1H), 7.46 (m, 1H), 6.68 (s, 2H), 6.43 (d, J=12 Hz, 1H), 6.29 (d, J=12 Hz, 1H), 5.85 (m, 1H), 5.66 (m, 1H), 4.37 (m, 2H), 4.06 (s, 3H), 3.73 (m, 1H), 3.49 (m, 1H), 1.51 (m, 3H), 1.70-1.45 (cm, 9H). LCMS (m/z) 580.1 [M+H]. Tr=2.15 min.

Examples 140 and 141

Compounds 140 and Compound 141

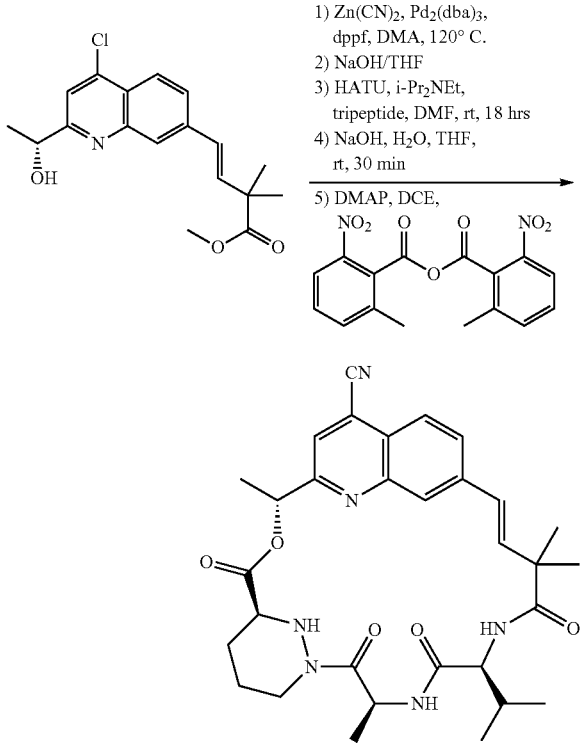

Compound 138c, 150 mg (0.5 mmol, 1 equiv) in 5 mL in DMA is heated with 1.2 equiv $Zn(CN)_2$ at 120° C. in the presence of Pd catalyst for 1 h. The unpurified product (150 mg) was then hydrolyzed, and coupled with tripeptide 1e using conditions reported for Example 7. Following TCE hydrolysis via NaOH treatment and neutralization, the intermediate seco-acid was lactonized using standard Shiina conditions. The reaction mixture was adjusted to pH 7 with 1N aq. HCl and the crude mixture concentrated to a residue which was taken up in DMF and purified via reverse phase preparative HPLC. The resulting product compound 140, 2 mg, was obtained in 0.7% overall yield after removal of solvent via rotavap and hi-vacuum. $^1$H NMR (400 MHz, $CD_3CN$) δ 8.07 (d, J=6 Hz, 1H), 8.02 (m, 1H), 7.76 (m, 1H), 7.64 (m, J=6.5 Hz, 1H), 6.73 (m, 1H), 6.48 (m, 1H), 5.99 (m, 2H), 5.15 (s, 1H), 3.83 (bm, 2H), 2.76 (m, 1H), 1.91-1.65 (cm, 8H), 0.81 (m, 6H). LCMS (m/z) 575.3 [M+H]. Tr=2.01 min.

Upon HPLC purification, 0.5 mg of a second product isomer, 141, was isolated via HPLC purification.

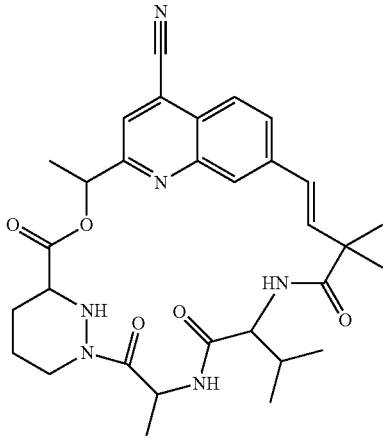

$^1$H NMR (400 MHz, $CD_3CN$): δ 8.05 (d, J=6.4 Hz, 1H), 7.98 (m, 1H), 7.86 (m, 1H), 7.60 (m, J=6.5 Hz, 1H), 6.65 (m, 1H), 6.40 (m, 1H), 5.89 (m, 2H), 5.05 (s, 1H), 3.80 (bm, 2H), 2.71 (m, 1H), 1.81-1.60 (cm, 8H), 0.88 (m, 6H). LCMS (m/z) 575.3 [M+H]. Tr=2.05 min.

Example 142

Compound 142

Compound 142a

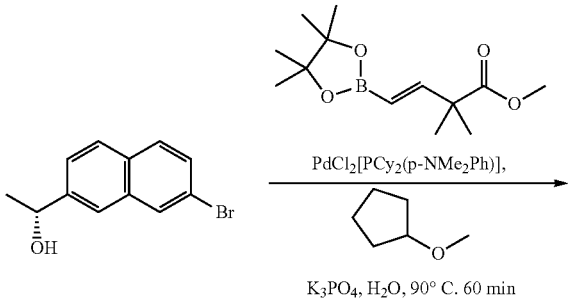

-continued

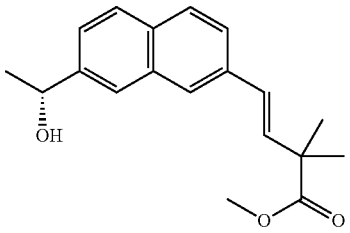

To (R)-1-(7-bromonaphthalen-2-yl)ethanol 70b, (1.5 g, 5.16 mmol) and the indicated borinate ester 17c (1.66 g, 6.6 mmol) in cyclopentyl methyl ether (17 ml, 0.3 M) was added bis[(dicyclohexyl)(4-dimethylaminophenyl)phosphine]palladium(II) chloride (225 mg, 0.25 mmol) and 3 M $K_3PO_4$ (5.1 mL, 15.5 mmol) and heated to 90° C. After 60 minutes, the reaction was cooled to rt, diluted with water (10 mL) and extracted with EtOAc (2×10 mL). The combined organics were dried over $MgSO_4$ and concentrated in vacuo to afford 142a (1.80 g, ca. quant. yield) as a brown oil. $^1$H NMR (400 MHz, $CDCl_3$) δ 8.12 (s, 1H), 8.01 (s, 1H), 7.75 (d, 1H), 7.63 (d, J=8.5 Hz, 1H), 6.62 (m, 2H), 5.14 (s, 1H), 4.61 (s, 2H), 3.72 (s, 3H), 3.48 (s, 3H), 1.50 (d, 3H), 1.46 (s, 6H). LCMS (m/z) 299.1 [M+H].

Compound 142b

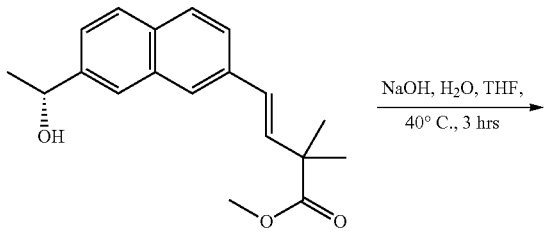

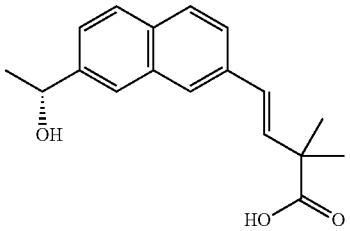

To 142a (326 mg, 0.516 mmol) in THF (9.5 mL, 0.1 M) was added 0.1 M NaOH (9.5 mL, 1.03 mmol) and warmed to 40° C. After 4 hours, the reaction was cooled to rt, acidified with 1 M aq. HCl (3.6 mL) to ~pH 4 and concentrated in vacuo to afford 142b (307 mg, 99%) as a yellow solid. LCMS (m/z) 285.2 [M+H].

Compound 142c

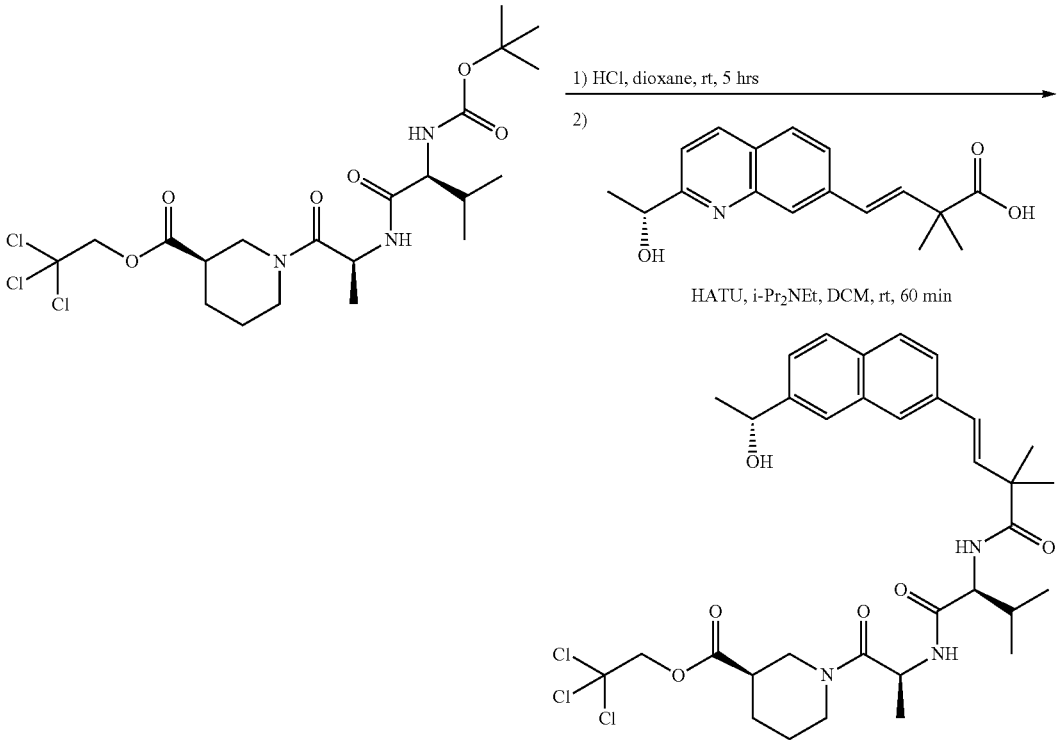

To 1d (411.0 mg, 0.773 mmol) in DCM (0.6 mL, 0.5 M) was added an HCl solution (0.78 mL, 4 M in dioxane, 1 M). After stirring for 18 hours, the reaction was concentrated in vacuo to afford the free dipeptide as an amorphous, pale yellow solid.

To 142b (169.8 mg, 0.516 mmol) in DCM (16 mL, 0.3 M) was added i-$Pr_2NEt$ (0.5 mL, 3.09 mmol) followed by HATU (296.2 mg, 0.773 mmol). After 15 minutes, the free dipeptide and i$Pr_2NEt$ (0.5 mL, 3.09 mmol) in DCM (5 mL) was added to the activated ester mixture. After 60 minutes, sat. aq. $NaHCO_3$ (15 mL) was added and the phases were separated. The aqueous was extracted with DCM (2×20 mL); and the combined organics were dried over $MgSO_4$ and concentrated in vacuo. Purification by column chromatography (50-100% EtOAc/hexane) afforded 142c (580 mg, 94%) as a yellow foam. $^1$H NMR (400 MHz, $CDCl_3$) δ 8.12 (s, 1H), 8.02 (s, 1H), 7.75 (d, J=8.5 Hz, 1H), 7.63 (d, J=8.3 Hz, 1H), 6.75 (d, J=16.2 Hz, 1H), 6.62 (d, J=16.2 Hz, 1H), 6.35 (d, J=8.6 Hz, 1H), 5.28 (p, J=6.9 Hz, 1H), 5.12 (m, 1H), 4.92 (d, J=11.9 Hz, 1H), 4.64 (d, J=11.9 Hz, 1H), 4.68 (d, J=2.3 Hz, 2H), 4.24 (m, 1H), 3.80 (d, J=11.0 Hz, 1H), 3.72 (m, 3H), 3.45 (s, 3H), 3.15 (m, 2H), 2.12 (m, 2H), 1.88 (s, 1H), 1.68 (t, J=9.5 Hz, 2H), 1.45 (d, J=6.2 Hz, 4H), 1.44 (s, 10H), 1.42 (s, 4H), 1.39 (d, J=6.6 Hz, 7H), 1.26 (d, J=6.9 Hz, 3H), 0.90 (d, J=6.7 Hz, 3H), 0.84 (d, J=6.8 Hz, 3H). LCMS (m/z) 696.23 [M+H].

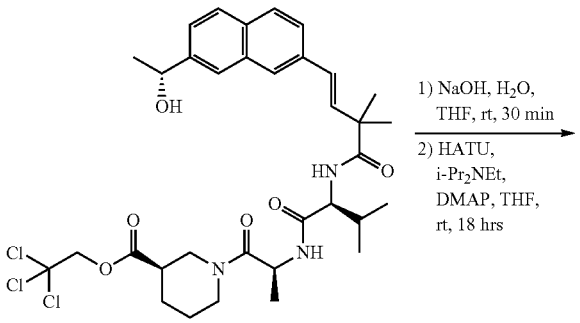

-continued

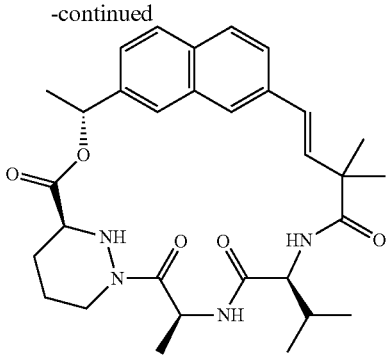

To Intermediate 142c (365.0 mg, 0.492 mmol) in THF (10 mL, 0.05 M) was added 0.1 M $NaOH_{(aq)}$ (10 mL, 1.00 mmol). After, 30 minutes, the reaction was acidified to ~pH 4 with 1 M $HCl_{(aq)}$ (0.9 mL), concentrated in vacuo, and triturated with THF/hexane.

The crude material was dissolved in THF (545 mL, 0.0003 M) and added i-$Pr_2NEt$ (0.30 mL, 1.63 mmol), DMAP (5.3 mg, 0.032 mmol), and HATU (95.1 mg, 0.245 mmol). After 18 hours, the reaction was concentrated in vacuo, diluted with water (30 mL), extracted with EtOAc (2×30 mL), dried over $MgSO_4$, and concentrated in vacuo. Purification by prep HPLC (Gemini, 40-65% MeCN/$H_2O$) afforded Compound 142 (28.0 mg, 11%) as a white solid. $^1$H NMR (400 MHz, $CD_3OD$) δ 7.82 (s, 2H), 7.75 (t, 1H), 7.54 (d, 1H), 7.45 (s, 1H), 6.37 (d, J=12 Hz, 1H), 6.24 (d, J=12 Hz, 1H), 5.99 (m, 1H), 5.62 (m, 1H), 4.62 (d, J=9 Hz, 1H), 4.39 (m, 2H), 3.75 (m, 1H), 2.69 (m, 1H), 1.90 (m, 3H), 1.63 (m, 6H), 1.46 (s, 3H), 1.31 (s, 3H), 0.98 (d, J=6 Hz, 3H), 0.92 (d, J=6 Hz, 3H). LCMS (m/z) 549.52 [M+H]. Tr=2.28 min.

Example 143

Compound 143

Compound 143a
(R)-1-(3-Chloro-isoquinolin-6-yl)ethylamine hydrochloride 143a

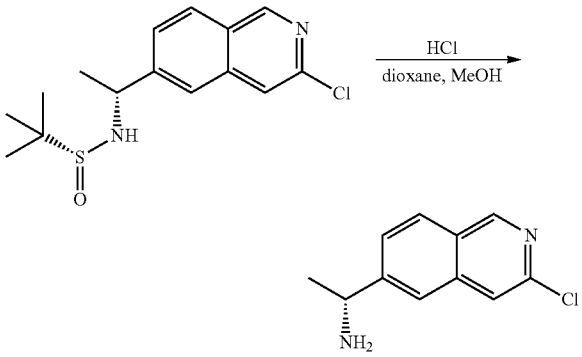

A solution of (R,R)-2-methyl-propane-2-sulfinic acid [1-(3-chloro-isoquinolin-6-yl)-ethyl]-amide (932 mg, 3 mmol) in methanol (9 mL) was stirred at room temperature under nitrogen. 4M HCl in dioxane (3 mL, 12 mmol) was added and the reaction mixture was stirred at room temperature for 30 minutes. The solvent was evaporated and the residue was triturated with ether. The orange solid was collected, washed with ether and dried to afford the title compound (777 mg). $^1$H NMR (300 MHz, d6-DMSO) δ 1.61 (d, J=6.7 Hz, 3H), 4.58-4.67 (m, 1H), 7.90 (dd, J=8.5, 1.4 Hz, 1H), 8.04 (br, 1H), 8.05 (br, 1H), 8.26 (d, J=8.5, 1H), 8.65-8.8 (br, 3H), 9.25 (s, 1H). LCMS (m/z) 207/209 [M+H], Tr 0.72 minutes.

[(R)-1-(3-Chloro-isoquinolin-6-yl)ethyl]-carbamic acid tert-butyl ester 143b

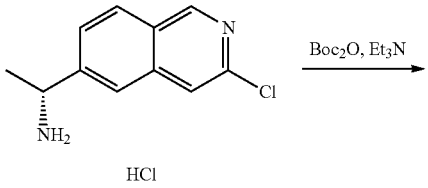

-continued

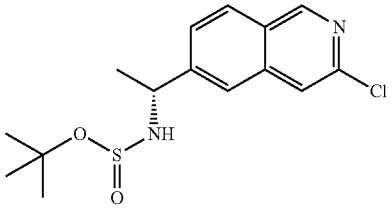

A mixture of (R)-1-(3-chloro-isoquinolin-6-yl)-ethylamine hydrochloride 143a (730 mg, 3 mmol) and triethylamine (909 mg, 1.25 mL, 9 mmol) in dichloromethane (25 mL0 was stirred at room temperature to give a solution. A solution of di-tert-butyl dicarbonate (981 mg, 4.5 mmol) in dichloromethane (5 mL) was added and the reaction mixture was stirred at room temperature for 20 hours. The solution was washed with water and brine, dried, filtered and evaporated. The residue was purified by silica gel chromatography eluting with 10-30% ethyl acetate in isohexanes to afford the title compound (714 mg, 79% over 2 steps) as a white solid. $^1$H NMR (300 MHz, $CDCl_3$) δ 1.44 (s, 9H), 1.53 (d, J=6.5 Hz, 3H), 4.9-5.0 (br, 2H), 7.57 (dd, J=8.5, 1.4 Hz, 1H), 7.67 (br, 1H), 7.71 (br, 1H), 7.96 (d, J=8.5, 1H), 9.05 (s, 1H). LCMS (m/z) 307/309 [M+H], Tr 2.67 minutes.

Compound 143c

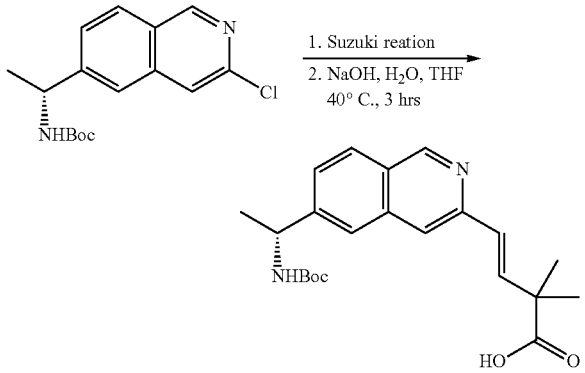

143b (200 mg, 0.51 mmol) was submitted to Suzuki reaction using the method described in Example 49. The unpurified product was dissolved in THF (9.5 mL, 0.1 M) and to this solution was added 0.1 M NaOH (9.5 mL, 1.03 mmol), followed by warming to 40° C. After 3 hours, the reaction was cooled to rt, acidified with 1 M HCl (3.6 mL) to ~pH 4 and concentrated in vacuo to afford 143c (191 mg, 99%) as a yellow solid. LCMS (m/z) 385.07 [M+H].

Compound 143d

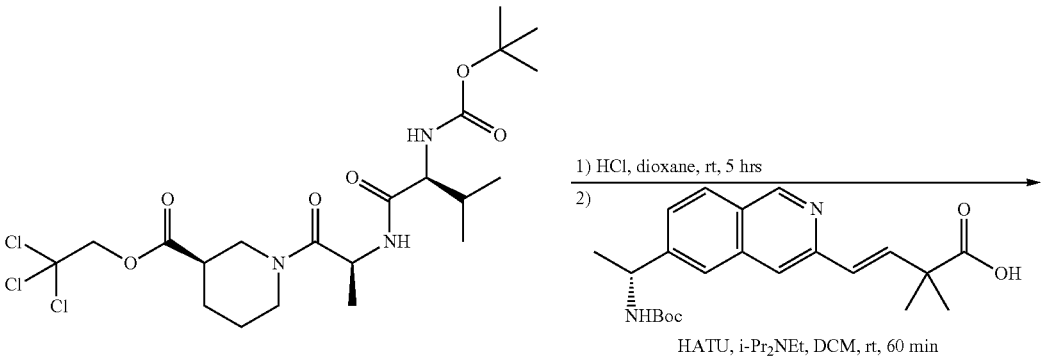

-continued

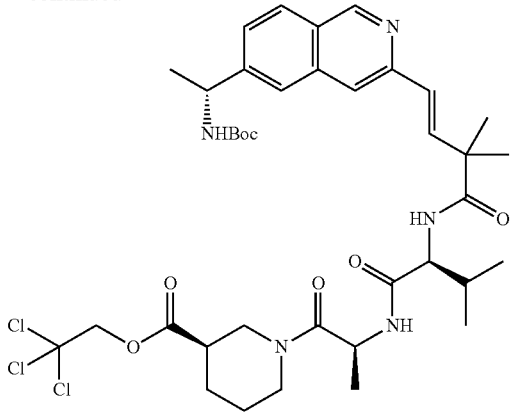

To 1e (411.0 mg, 0.773 mmol) in DCM (0.6 mL, 0.5 M) was added an HCl solution (0.78 mL, 4 M in dioxane, 1 M). After stirring for 18 hours, the reaction was concentrated in vacuo to afford the free dipeptide as an amorphous, pale yellow solid.

To 143c (170 mg, 0.516 mmol) in DMF (12 mL, 0.3 M) was added i-$Pr_2NEt$ (0.9 mL, 3.09 mmol) followed by HATU (296.2 mg, 0.773 mmol). After 15 minutes, the free dipeptide and i$Pr_2NEt$ (0.9 mL, 5.09 mmol) in DCM (5 mL) was added to the activated ester mixture. After 60 minutes, sat. aq. $NaHCO_3$ (15 mL) was added and the phases were separated. The aqueous was extracted with DCM (2×20 mL); and the combined organics were dried over sodium sulfate and concentrated in vacuo. Purification by column chromatography (50-100% EtOAc/hexane) afforded 143d (780 mg) as a yellow foam. $^1$H NMR (400 MHz, $CDCl_3$) δ 8.14 (s, 1H), 8.00 (s, 1H), 7.66 (d, J=8 Hz, 1H), 7.53 (d, J=8 Hz, 1H), 6.75 (d, J=16.2 Hz, 1H), 6.60 (d, J=16.2 Hz, 1H), 6.34 (d, J=8.6 Hz, 1H), 5.27 (m, 1H), 5.12 (m, 1H), 4.85 (m, 1H), 4.56 (d, J=11.9 Hz, 1H), 4.60 (d, J=2.3 Hz, 2H), 4.25 (m, 1H), 3.81 (d, J=11.0 Hz, 1H), 3.70 (m, 3H), 3.47 (s, 3H), 3.17 (m, 2H), 2.12 (m, 2H), 1.89 (s, 1H), 1.69 (t, J=9.5 Hz, 2H), 1.49 (d, J=6.2 Hz, 4H), 1.46 (s, 10H), 1.44 (s, 4H), 1.41 (d, J=6.6 Hz, 7H), 1.27 (d, J=6.9 Hz, 3H), 0.91 (d, J=6.7 Hz, 3H), 0.85 (m, 3H). LCMS (m/z) 796.3 [M+H].

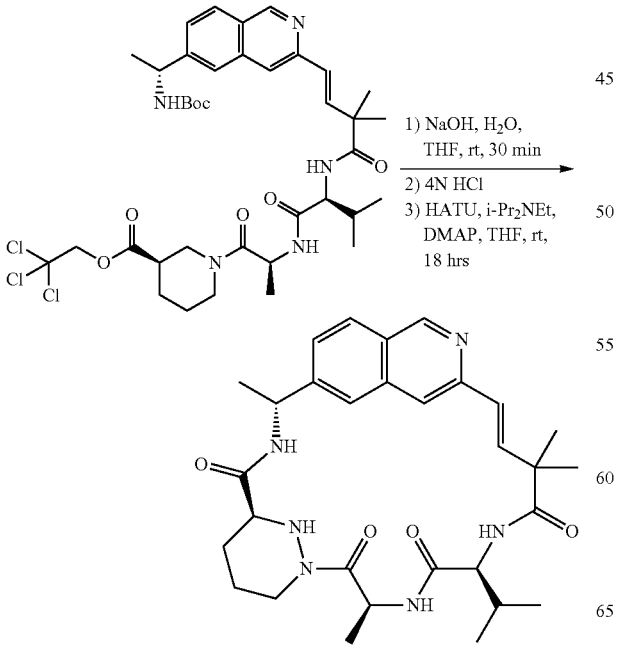

To 143c (350 mg, 0.49 mmol) in THF (10 mL, 0.05 M) was added 0.1 M NaOH (10 mL, 1.00 mmol). After, 30 minutes, the reaction was acidified to ~pH 4 with 1 M aq. HCl (0.9 mL), concentrated in vacuo, and triturated with THF/hexane. N-Boc removal was than carried out using the standard procedure to render the material as a solid upon solvent removal. The resulting crude material (ca. 100 mg) was dissolved in THF (445 mL, 0.001 M) and added i-$Pr_2NEt$ (0.30 mL, 1.63 mmol), DMAP (5.3 mg, 0.032 mmol), and HATU (95.1 mg, 0.245 mmol). After 18 hours, the reaction was concentrated in vacuo, diluted with water (30 mL), extracted with EtOAc (2×30 mL), dried over $MgSO_4$, and concentrated in vacuo. Purification by prep HPLC (Gemini, 40-65% MeCN/$H_2O$) afforded Compound 143 (4 mg) as a white solid. $^1$H NMR (400 MHz, $CDCl_3$) δ 8.17 (s, 2H), 7.78 (d, J=9.0 Hz, 1H), 7.65 (d, J=8.7 Hz, 1H), 6.47 (d, J=6.1 Hz, 2H), 6.09 (t, J=8.4 Hz, 2H), 5.99 (m, 2H), 5.66 (m, 1H), 4.83 (d, J=12.3 Hz, 1H), 4.59 (d, J=12.3 Hz, 1H), 4.48 (d, J=13.8 Hz, 1H), 4.15 (t, J=8.7 Hz, 1H), 3.75 (m, 1H), 2.54 (t, J=11.3 Hz, 1H), 1.94 (m, 3H), 1.84 (s, 3H), 1.63 (d, J=6.9 Hz, 6H), 1.55 (d, J=20.0 Hz, 3H), 1.46 (s, 3H), 1.39 (s, 3H), 0.95 (d, J=6.7 Hz, 3H), 0.90 (d, J=6.6 Hz, 3H). LCMS (m/z) 550.52 [M+H]. Tr=1.75 min.

Example 144

Compound 144

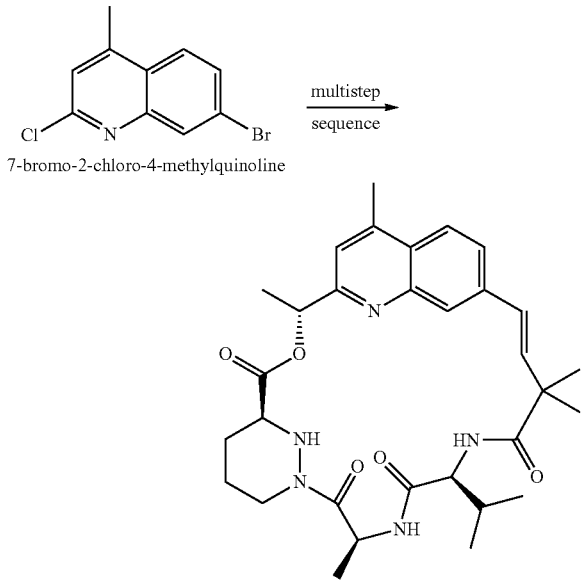

Following the synthetic scheme of Example 148, 2 g 7-bromo-2-chloro-4-methyl quinoline (obtained from Bio-Blocks, Inc.) was advanced until final HATU mediated cyclization rendered 25 mg of the final compound 144. The crude product was purified by prep-HPLC to obtain 144 (20 mg, 0.3%) as a white solid. $^1$H NMR (400 MHz, Methanol-$d_4$) δ 7.88 (d, J=6.8 Hz, 1H), 7.68 (d, J=6.8 Hz, 1H), 7.53 (s, 1H), 7.16 (s1H), 6.38 (d, J=12.2 Hz, 1H), 6.15 (d, J=12.2 Hz), 5.76 (m, 1H), 5.64 (m, 1H), 4.32 (m, 1H), 4.17 (d, J=9.0 Hz), 3.71 (m, 1H), 3.22 (s, 3H), 2.06 (m, 1H), 1.92-1.71 (m, 8H), 1.57 (s, 3H), 1.44 (s, 3H), 0.93 (m, 6H). LCMS (m/z) 564.2 [M+H]. Tr=2.10 min.

Example 145

Compound 145

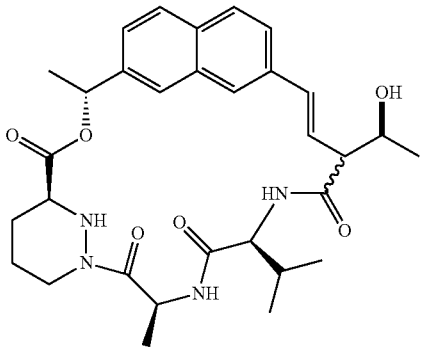

145 was prepared utilizing the synthetic sequence reported to compound 31, instead starting from 2 g (R)-1-(7-bromonaphthalen-2-yl)ethanol 70b. After a multistep sequence following that reported for Example 31, final TBS removal on the penultimate macrocycle using aq. HF/pyridine followed by HPLC furnished 2 mg (0.05% yield) final compound 145. $^1$H NMR (400 MHz, $CD_3CN$) δ 7.93 (s, 1H), 7.81 (cm, 3H), 7.69-7.60 (cm, 2H), 6.90 (m, 1H), 6.52 (d, J=12.2 Hz, 1H), 6.05 (m, 2H), 5.55-5.40 (cm, 2H), 4.98 (q, J=6.6 Hz, 1H), 4.42-4.15 (m, 1H), 2.78 (m, 2H), 2.06 (m, 1H), 1.92-1.71 (m, 3H), 1.55-1.51 (m, 3H), 1.46 (m, 6H), 1.25 (m, 3H), 0.93-0.85 (cm, J=6.5 Hz, 6H). LCMS (m/z) 565.2 [M+H]. Tr=2.25 min.

Example 146

Compound 146

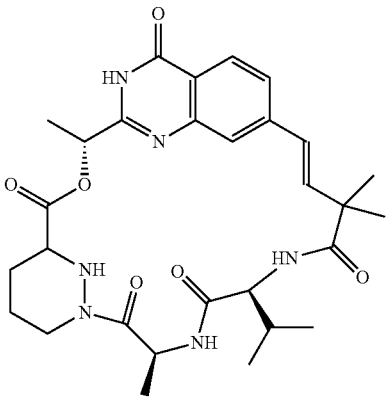

-continued

Compound 146a

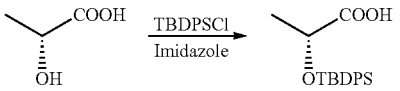

A mixture of D-lactic acid (1.004 g, 11.15 mmol) and imidazole (1.895 g, 27.84 mmol) in $CH_2Cl_2$ (15 mL) and DMF (5 mL) was stirred at rt as tert-butyldiphenylsilyl chloride (3.15 mL, 12.31 mmol) was added. After the resulting mixture was stirred at rt for 3 days, the reaction mixture was concentrated to remove $CH_2Cl_2$ and diluted with ethyl acetate before washing with 5% aq. LiCl solution (×2). After the aqueous fractions were extracted with ethyl acetate (×1), the organic fractions were combined, dried ($Na_2SO_4$) and concentrated. The residue was purified by CombiFlash (120 g column) using hexanes-ethyl acetate as eluents to obtain 2.28 g (62%) of the product. $^1$H NMR (400 MHz, Chloroform-d) δ 7.71-7.58 (m, 4H), 7.53-7.34 (m, 6H), 4.33 (q, J=6.8 Hz, 1H), 1.31 (d, J=6.9 Hz, 3H), 1.12 (s, 9H).

LCMS (m/z) 327.0 [M−H], Tr 2.59 min.

Compound 146b

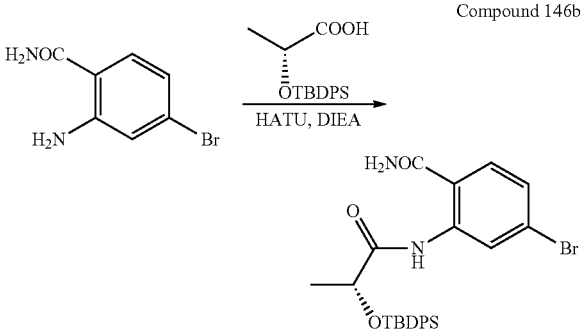

A mixture the reactant (1.027 g, 4.776 mmol), the acid 146a (1.572 g, 4.786 mmol), and HATU (2.726 g, 7.169 mmol) in DMF (10 mL) was stirred at rt as DIEA (3.25 mL, 19.233 mmol) was added. After 2 h, the reaction mixture was diluted with ethyl acetate and washed with 5% aq. LiCl solution (×2). After the aqueous fractions were extracted with ethyl acetate (×1), the organic fractions were combined, dried ($Na_2SO_4$), and concentrated. The residue was purified by CombiFlash using hexanes-ethyl acetate as eluents to obtain 1.298 g (52%) of the product. $^1$H NMR (400 MHz, Chloroform-d) δ 11.74 (s, 1H), 8.88 (d, J=1.9 Hz, 1H), 7.77-7.71 (m, 2H), 7.69-7.61 (m, 2H), 7.52-7.30 (m, 7H), 7.27-7.23 (m, 1H), 5.82 (s, 2H), 4.31 (q, J=6.7 Hz, 1H), 1.24 (d, J=6.7 Hz, 3H), 1.15 (s, 9H).

Compound 146c

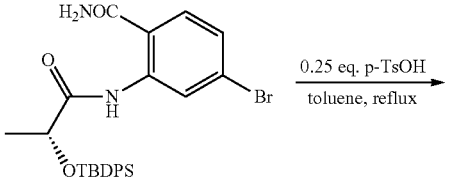

-continued

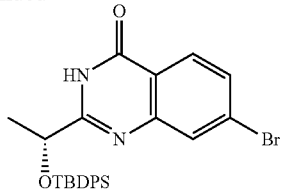

A mixture of the reactant 146b (1.186 g, 2.257 mmol) and p-TsOH monohydrate (22 mg, 0.116 mmol) in toluene (20 mL) was refluxed for 15 h. After additional p-TsOH monohydrate (64 mg, 0.336 mmol) was added, the mixture was further refluxed for 4 h before concentration. The residue was purified by CombiFlash using hexanes-ethyl acetate as eluents to obtain 591 mg (52%) of 146c. $^1$H NMR (400 MHz, Chloroform-d) δ 9.57 (s, 1H), 8.11 (d, J=8.5 Hz, 1H), 7.89 (d, J=1.7 Hz, 1H), 7.70-7.64 (m, 2H), 7.59 (m, 3H), 7.49-7.29 (m, 6H), 4.97 (q, J=6.6 Hz, 1H), 1.47 (d, J=6.6 Hz, 3H), 1.16 (s, 9H).

LCMS (m/z) 506.9 [M+H], Tr 2.69 min.

Compound 146d

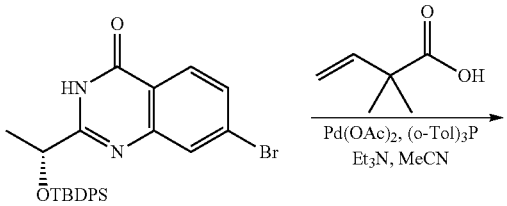

-continued

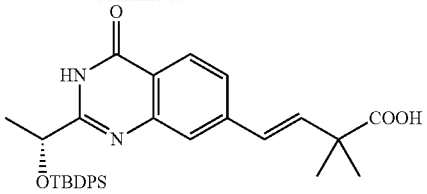

A mixture of the reactant 146c (200 mg, 0.394 mmol), $Pd(OAc)_2$ (9.2 mg, 0.041 mmol), $(o\text{-}Tol)_3P$ (12.5 mg, 0.041 mmol), the acid (50.6 mg, 0.443 mmol), and $NEt_3$ (0.25 mL, 1.794 mmol) in acetonitrile (4 mL) was heated for 20 min at 100° C. at MW reactor. After the mixture was concentrated and the residue was treated with water (20 mL) and saturated $NH_4Cl$ solution (20 mL), the product was extracted with ethyl acetate (×2) and the combined extracts were dried ($Na_2SO_4$) and concentrated. The residue was purified by CombiFlash using hexanes-ethyl acetate as eluents to obtain 182 mg (85%) of the product 146d. $^1$H NMR (400 MHz, Chloroform-d) δ 10.14 (s, 1H), 8.19 (d, J=8.3 Hz, 1H), 7.70 (ddd, J=6.8, 1.9, 1.0 Hz, 2H), 7.61-7.52 (m, 3H), 7.52-7.23 (m, 8H), 6.71-6.61 (m, 1H), 6.54 (d, J=16.2 Hz, 1H), 4.85 (q, J=6.5 Hz, 1H), 1.45 (s, 6H), 1.42 (d, J=6.6 Hz, 3H), 1.16-1.10 (m, 9H).

LCMS (m/z) 541.0 [M+H], Tr 2.69 min.

Compound 146e

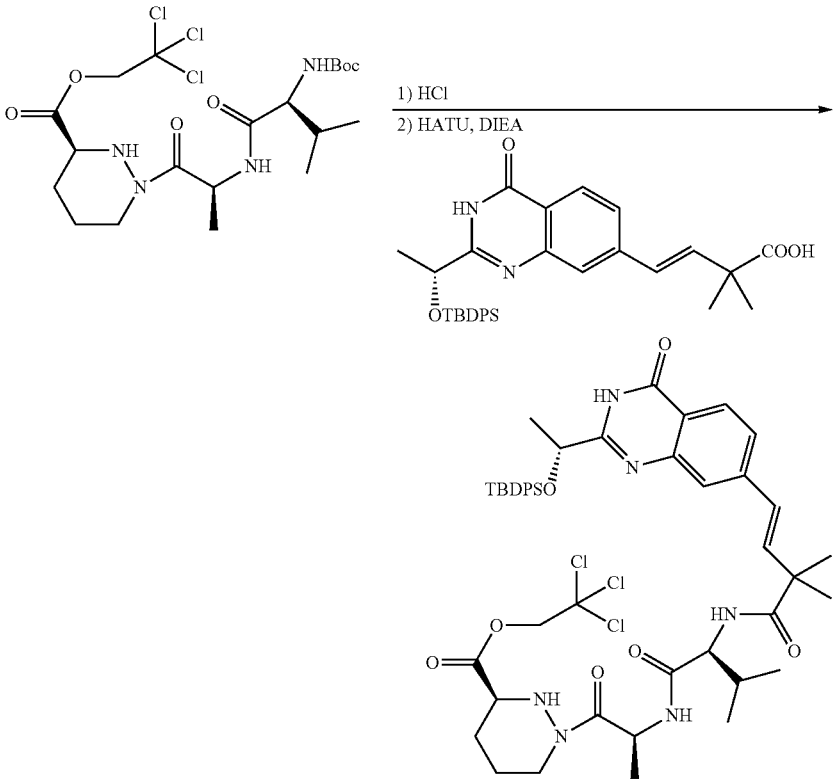

To a solution of the tripeptide (183 mg, 0.344 mmol) in $CH_2Cl_2$ (2 mL) was added 4 N HCl in dioxane (2 mL) and the mixture was stirred at rt for 1 h. The mixture was concentrated and the residue was co-evaporated with toluene (×3). After the residue was dried in vac and HATU (154 mg, 0.405 mmol) was added to the residue, a solution of the reactant (182 mg, 0.337 mmol) in $CH_2Cl_2$ (2 mL) and DMF (2 mL) was added. The resulting mixture was stirred at 0° C. as DIEA (0.22 mL, 1.263 mmol) was added. After 1 h, the reaction mixture was diluted with 5% aq. LiCl solution and the product was extracted with ethyl acetate (×2). The extracts were washed with 5% aq. LiCl solution (×1), combined, dried ($Na_2SO_4$), and concentrated. The residue was purified by CombiFlash using hexanes-ethyl acetate as eluents to obtain 271 mg (84%) of the product 146e. $^1$H NMR (400 MHz, Chloroform-d) δ 8.21 (d, J=8.2 Hz, 1H), 7.68 (dd, J=7.8, 1.7 Hz, 2H), 7.62-7.56 (m, 2H), 7.53 (d, J=10.3 Hz, 2H), 7.47 (t, J=6.9 Hz, 1H), 7.44-7.35 (m, 4H), 7.32 (dd, J=8.0, 6.6 Hz, 2H), 6.69-6.54 (m, 3H), 6.30 (d, J=8.3 Hz, 1H), 5.33-5.23 (m, 1H), 4.93 (d, J=11.9 Hz, 1H), 4.85 (br, 1H), 4.68 (dd, J=11.9 Hz, 1H), 4.32 (br d, J=13.9 Hz, 1H), 4.29-4.23 (m, 1H), 3.80 (d, J=11.1 Hz, 1H), 3.67 (m, 1H), 2.89 (br, 1H), 2.17 (br, 1H), 2.09 (m, 1H), 1.91 (br, 1H), 1.71 (m, 2H), 1.42 (m, 7H), 1.33-1.20 (m, 3H), 1.15 (d, J=1.4 Hz, 9H), 0.92 (dd, J=6.9, 1.9 Hz, 3H), 0.87 (d, J=6.5 Hz, 3H).

LCMS (m/z) 954.2 [M+H], Tr 2.88 min.

Compound 146f

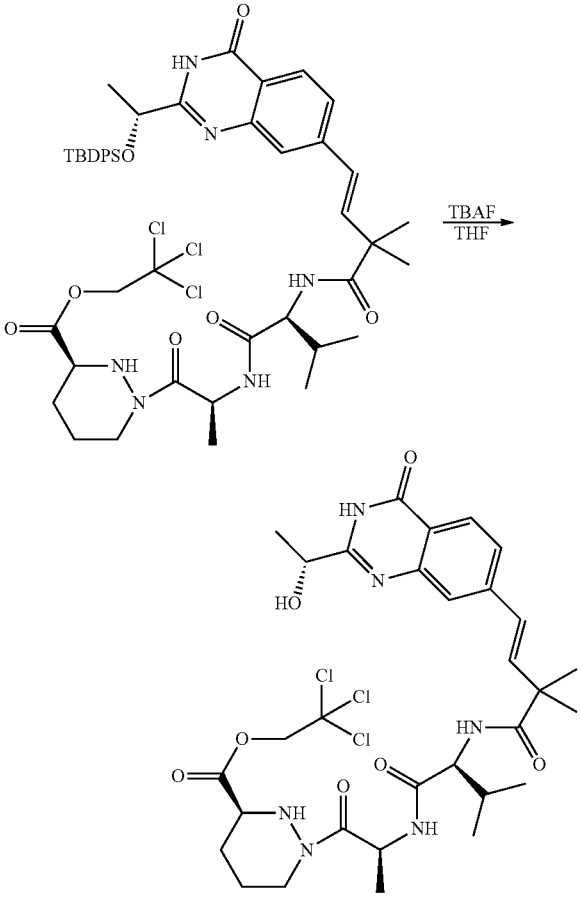

A solution of the reactant 146e (271 mg, 0.284 mmol) and TBAF (95 mg, 0.363 mmol) in THF (3 mL) was stirred at rt for 1 h. The reaction mixture was diluted with $CH_2Cl_2$ and washed with water (×2). After the aqueous fractions were extracted with $CH_2Cl_2$ (×1), the organic fractions were combined, dried ($Na_2SO_4$) and concentrated. The residue was purified by CombiFlash using ethyl acetate −20% MeOH/ethyl acetate as eluents to obtain 43 mg (21%) of the product 146f. $^1$H NMR (400 MHz, Chloroform-d) δ 7.75 (d, J=8.3 Hz, 1H), 7.50-7.18 (m, 4H), 7.09 (s, 1H), 6.56 (s, 2H), 5.44-5.25 (m, 1H), 4.98 (d, J=11.9 Hz, 1H), 4.88-4.75 (m, 1H), 4.68 (d, J=12.0 Hz, 1H), 4.34 (m, 1H), 4.23 (t, J=8.6 Hz, 1H), 3.71 (m, 1H), 2.92 (br, 1H), 2.18 (m, 2H), 1.92 (m, 1H), 1.73 (m, 3H), 1.65 (d, J=6.6 Hz, 3H), 1.51 (br, 3H), 1.45-1.30 (m, 7H), 0.98 (d, J=6.6 Hz, 3H), 0.97 (d, J=6.6 Hz, 3H).

LCMS (m/z) 715.1 [M+H], Tr 2.15 min.

Compound 146g

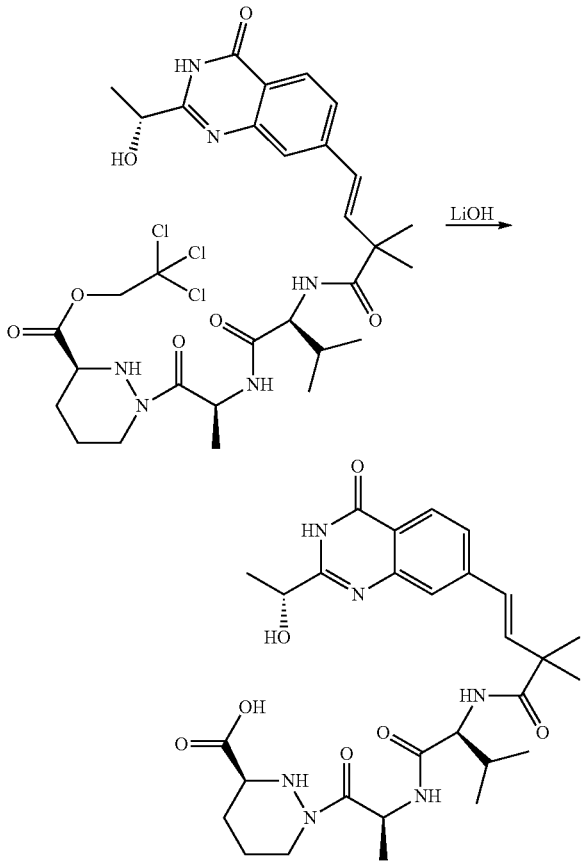

A suspension of the reactant 146f (43 mg, 0.060 mmol) and LiOH (6.0 mg, 0.143 mmol) in THF (2 mL) and water (2 mL) was stirred at rt for 1 h. After the reaction mixture was concentrated to a small volume, the remaining residue was co-evaporated with toluene (×4) and DMF (×1). The residue was mixed with dioxane and freeze-dried to get a crude acid.

LCMS (m/z) 585.1 [M+H], Tr 1.75 min.

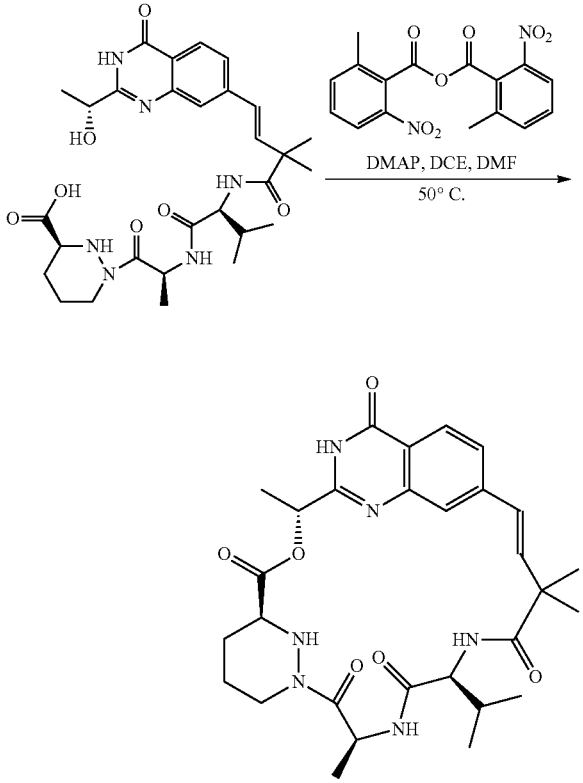

A solution of 2-Methyl-6-nitrobenzoic anhydride (126 mg, 0.365 mmol) and DMAP (72 mg, 0.589 mmol) in DCE (50 mL) was stirred at 50° C. bath as a solution of the crude reactant 146 g in DMF (2.5 mL) was added over 6 h. After 40 min since the addition, the solution was concentrated and the residual DMF mixture was diluted with 5% LiCl solution before extractions with ethyl acetate (×2). After the extracts were washed with 5% LiCl solution (×1), combined, dried ($Na_2SO_4$), and concentrated, the residue was purified by CombiFlash using ethyl acetate −20% MeOH/ethyl acetate as eluents. The collected product was further purified by preparative HPLC (×2). The collected fractions were combined, concentrated to remove most of MeCN, diluted with water, neutralized with some $NaHCO_3$ solution, and extracted with ethyl acetate (×2). The organic extracts were washed with water (×1), combined, dried ($Na_2SO_4$), and concentrated to get the pure product. The product was dissolved in dioxane and freeze-dried to get 8.4 mg (25%). $^1$H NMR (400 MHz, Methanol-$d_4$) δ 8.65 (d, J=6.9 Hz, 1H), 8.14-7.97 (m, 1H), 7.65 (dd, J=8.4, 1.6 Hz, 1H), 7.29 (d, J=1.6 Hz, 1H), 7.20 (d, J=9.6 Hz, 1H), 6.49 (d, J=16.4 Hz, 1H), 6.22 (d, J=16.5 Hz, 1H), 5.61 (p, J=7.1 Hz, 1H), 5.42 (q, J=6.8 Hz, 1H), 4.36 (d, J=13.2 Hz, 1H), 4.27 (t, J=9.9 Hz, 1H), 3.79-3.66 (m, 1H), 2.82-2.65 (m, 1H), 1.99-1.79 (m, 2H), 1.67 (d, J=7.2 Hz, 3H), 1.72-1.62 (m, 1H), 1.56 (d, J=7.1 Hz, 3H), 1.48 (s, 1.32 (s, 3H), 1.40-1.15 (m, 3H), 0.94 (d, J=6.7 Hz, 3H), 0.92 (d, J=8.0 Hz, 3H).

LCMS (m/z) 567.2 [M+H], Tr 3.70 min.

Example 147

Compound 147

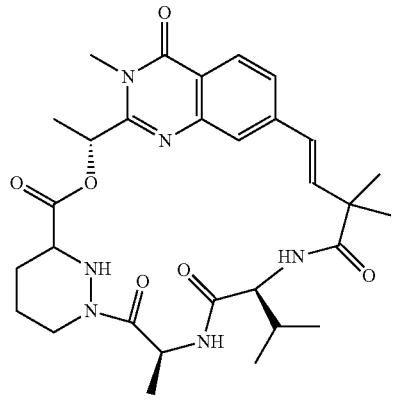

Compound 147a

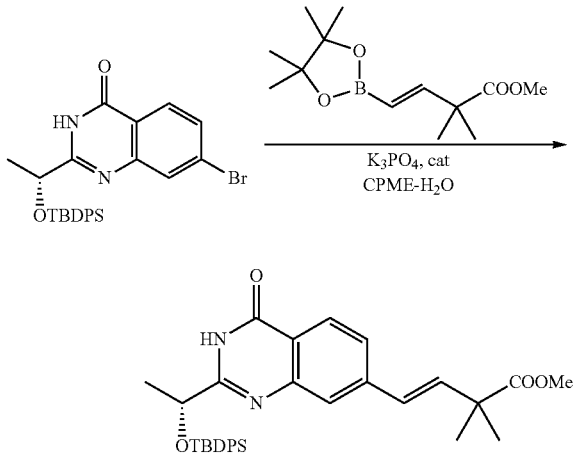

A suspension of the bromide 146c (435 mg, 0.857 mmol), the boronate ester 17c (246 mg, 0.968 mmol), $PdCl_2$-$[(cyHex)_2(Me_2NPh)_2P]_2$ (38 mg, 0.047 mmol), and $K_3PO_4$ (556 mg, 2.619 mmol), in cyclopentyl methyl ether (4 mL) and water (2 mL) was degassed and stirred at 90° C. for 3.5 h. The mixture was diluted with EA and washed with water (×2). After the aqueous fractions were extracted with ethyl acetate (×1), the organic fractions were combined, dried ($Na_2SO_4$), and concentrated. The residue was purified by CombiFlash using hexanes-ethyl acetate as eluents to obtain 369 mg (78%) of the product 147a. $^1$H NMR (400 MHz, Chloroform-d) δ 9.65 (s, 1H), 8.20 (d, J=8.3 Hz, 1H), 7.69 (dd, J=8.0, 1.5 Hz, 2H), 7.58 (dd, J=6.7, 1.5 Hz, 2H), 7.53 (s, 1H), 7.47 (td, J=7.1, 1.6 Hz, 2H), 7.43-7.35 (m, 3H), 7.35-7.24 (m, 2H), 6.62 (d, J=16.2 Hz, 1H), 6.49 (d, J=16.1 Hz, 1H), 4.83 (q, J=6.6 Hz, 1H), 3.70 (s, 3H), 1.43 (s, 6H), 1.41 (d, J=6.6 Hz, 3H), 1.14 (s, 9H).

LCMS (m/z) 555.1 [M+H], Tr 2.72 min.

Compound 147b

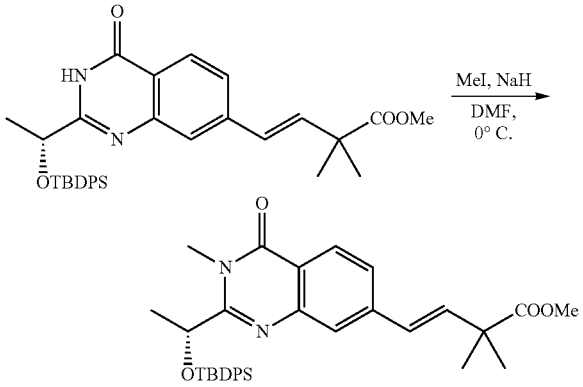

A solution of the 147a (369 mg, 0.665 mmol) in DMF (4 mL) was stirred at 0° C. as NaH (60% in mineral oil, 42 mg, 1.05 mmol) was added. After stirring at 0° C. for 1 h, MeI (0.1 mL, 1.606 mmol) was added to the resulting suspension and the mixture was stirred at 0° C. for 1 h. The mixture was diluted with EA and washed with 5% LiCl solution (×2). After the aqueous fractions were extracted with ethyl acetate (×1), the organic fractions were combined, dried ($Na_2SO_4$), and concentrated. The residue was purified by CombiFlash using hexanes-ethyl acetate as eluents to obtain 358 mg (95%) of the N-alkylated product 147b. $^1$H NMR (400 MHz, Chloroform-d) δ 8.13 (d, J=8.2 Hz, 1H), 7.70-7.62 (m, 2H), 7.60-7.52 (m, 2H), 7.48 (d, J=1.6 Hz, 1H), 7.47-7.39 (m, 2H), 7.37 (tt, J=7.7, 1.2 Hz, 2H), 7.32-7.23 (m, 1H), 7.23-7.14 (m, 2H), 6.60 (d, J=16.2 Hz, 1H), 6.49 (d, J=16.3 Hz, 1H), 5.05 (q, J=6.7 Hz, 1H), 3.72 (s, 3H), 3.63 (s, 3H), 1.59 (d, J=6.7 Hz, 3H), 1.44 (s, 6H), 1.08 (s, 9H).

LCMS (m/z) 569.1 [M+H], Tr 3.02 min.

Compound 147c

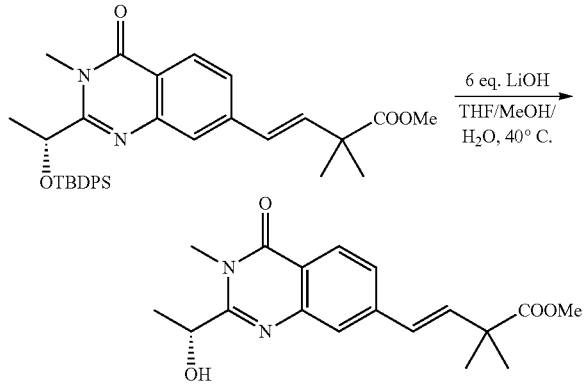

A mixture of the 147b (358 mg, 0.629 mmol) and LiOH (53 mg, 1.263 mmol) in THF (5 mL), MeOH (5 mL), and water (5 mL) was stirred at 0° C. for 1 h, at rt for 4 h, and then at 40° C. for 1.5 h. After additional LiOH (106 mg, 2.526 mmol) was added and stirred at 40° C. overnight, the reaction mixture was neutralized with 1 N HCl (3.8 mL) and concentrated. The residue was co-evaporated with toluene (×3 and dried in vacuum to get a crude 147c.

LCMS (m/z) 317.1 [M+H], Tr 1.91 min.

Compound 147d

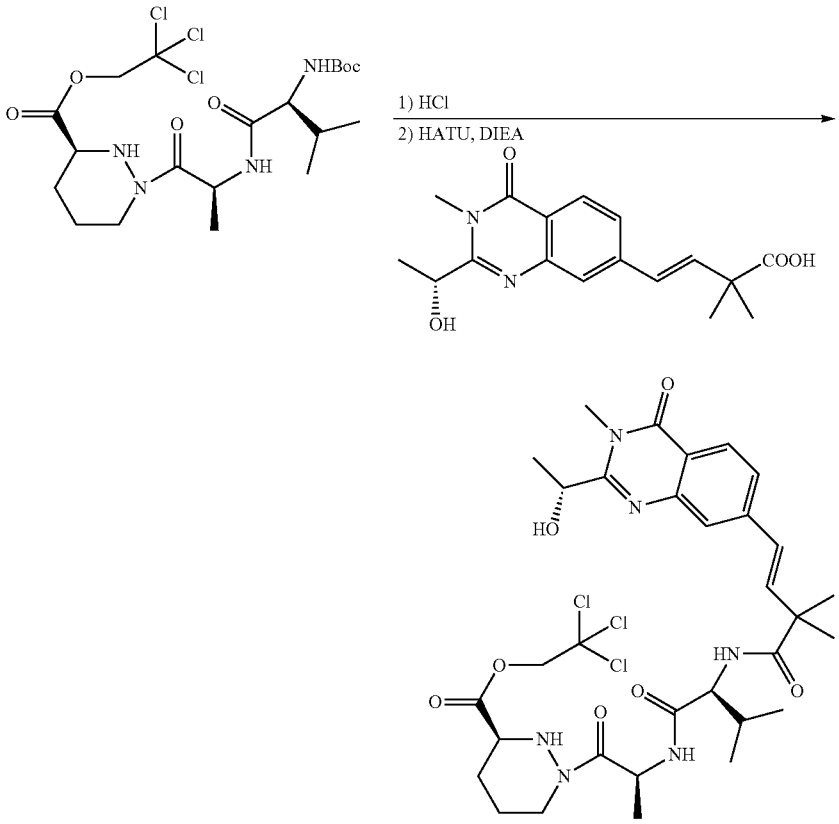

To a solution of 1e (350 mg, 0.658 mmol) in $CH_2Cl_2$ (3.25 mL) was added 4 N HCl in dioxane (3.25 mL) and the mixture was stirred at rt for 1.5 h. The mixture was concentrated and the residue was co-evaporated with toluene (×3). After the residue was dried in vacuum and HATU (379 mg, 0.997 mmol) was added to the residue, a solution of the crude acid 147c in $CH_2Cl_2$ (4 mL) and DMF (4 mL) was added. The resulting mixture was stirred at 0° C. as DIEA (0.7 mL, 4.02 mmol) was added. After 1 h, the reaction mixture was diluted with 5% aq. LiCl solution and the product was extracted with ethyl acetate (×2). The extracts were washed with 5% aq. LiCl solution (×1), combined, dried ($Na_2SO_4$), and concentrated. The residue was purified by CombiFlash using hexanes-ethyl acetate −20% MeOH/ethyl acetate as eluents to obtain 380 mg (83%) of the product. $^1$H NMR (400 MHz, Chloroform-d) δ 8.21 (d, J=8.3 Hz, 1H), 7.68 (s, 1H), 7.55 (d, J=8.4 Hz, 1H), 6.65 (ABqt, J=16.4 Hz, 2H), 6.64-6.58 (m, 1H), 6.33 (d, J=8.4 Hz, 1H), 5.30 (m, 1H), 4.93 (d, J=11.7 Hz, 1H), 4.92 (m, 1H), 4.68 (d, J=11.7 Hz, 1H), 4.34 (br, 1H), 4.31-4.23 (m, 1H), 3.83 (d, J=11.2 Hz, 1H), 3.69 (m, 1H), 3.59 (s, 3H), 2.90 (br, 1H), 2.18 (m, 1H), 2.14-2.06 (m, 1H), 1.92 (s, 1H), 1.71 (m, 1H), 1.56 (d, J=6.0 Hz, 3H), 1.46 (s, 6H), 1.36-1.28 (d, J=6.8 Hz, 3H), 0.93 (d, J=6.9 Hz, 3H), 0.88 (d, J=6.9 Hz, 3H).

LCMS (m/z) 729.2 [M+H], Tr 2.34 min.

Compound 147e

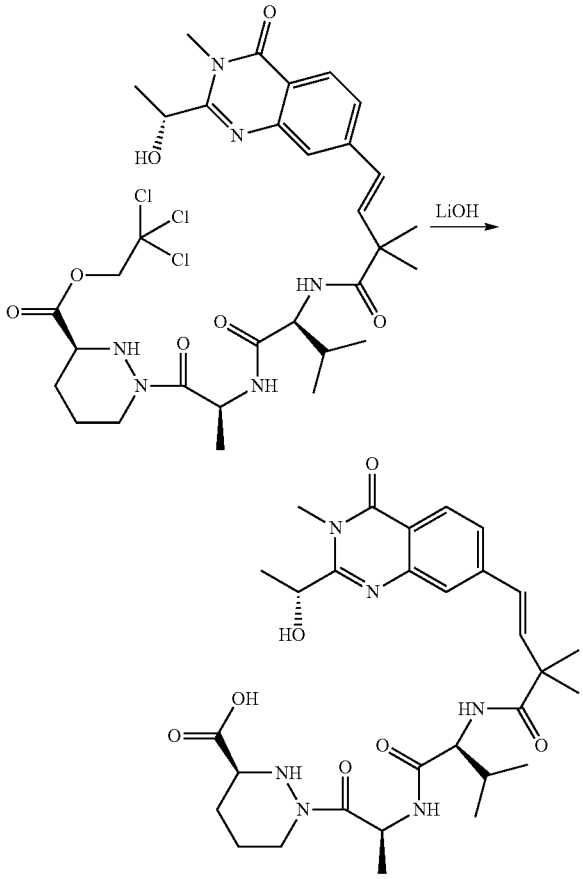

A suspension of the reactant 148d (380 mg, 0.521 mmol) and LiOH hydrate (30 mg, 0.715 mmol) in THF (5 mL) and water (5 mL) was stirred at rt for 2 h. After the reaction mixture was acidified with 1 N HCl (0.73 mL) and concentrated to a small volume, the remained residue was co-evaporated with toluene (×3) and DMF (×1). The resulting crude 148e was used for the next reaction.

LCMS (m/z) 599.4 [M+H], Tr 0.36 min.

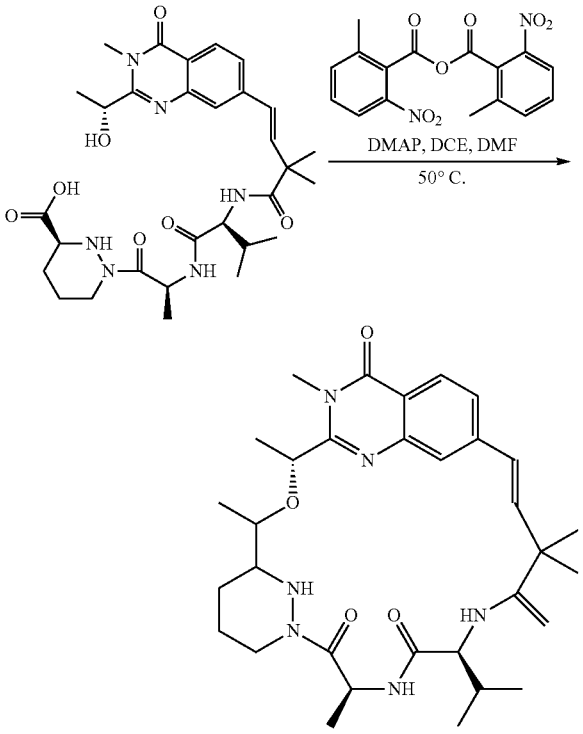

A solution of 2-Methyl-6-nitrobenzoic anhydride (1079 mg, 3.134 mmol) and DMAP (579 mg, 4.739 mmol) in DCE (200 mL) was stirred at 50° C. bath as a solution of the crude 147e in DMF (8 mL) was added over 2.5 h. After 30 min since the addition, the solution was concentrated and the residual DMF mixture was diluted with 5% LiCl solution before extractions with ethyl acetate (×2). After the extracts were washed with 5% LiCl solution (×1), combined, dried ($Na_2SO_4$), and concentrated, the residue was purified by CombiFlash (×2) using ethyl acetate −20% MeOH/ethyl acetate as eluents to obtain 66 mg (5%) of the product 147. $^1$H NMR (400 MHz, Methanol-$d_4$) δ 8.67-8.55 (d, J=6.8 Hz, 1H), 8.08 (d, J=8.5 Hz, 1H), 7.67 (dd, J=8.6, 1.8 Hz, 1H), 7.23 (d, J=1.6 Hz, 1H), 7.20 (d, J=9.6 Hz, 1H), 6.51 (d, J=16.5 Hz, 1H), 6.18 (d, J=16.4 Hz, 1H), 5.80 (q, J=6.7 Hz, 1H), 5.53-5.40 (m, 1H), 4.35 (d, J=13.0 1H), 4.27 (t, J=9.9 Hz, 1H), 3.68 (s, 3H), 3.68 (m, 1H), 2.78-2.65 (m, 1H), 1.99-1.89 (m, 1.86 (m, 1H), 1.71 (d, J=6.7 Hz, 3H), 1.66 (m, 2H), 1.53 (d, J=7.2 Hz, 3H), 1.47 (s, 3H), 1.32 (s, 3H), 0.94 (d, J=6.6 Hz, 3H), 0.92 (d, J=6.6 Hz, 3H). LCMS (m/z) 581.6 [M+H], Tr 0.96 min.

Example 148

Compound 148

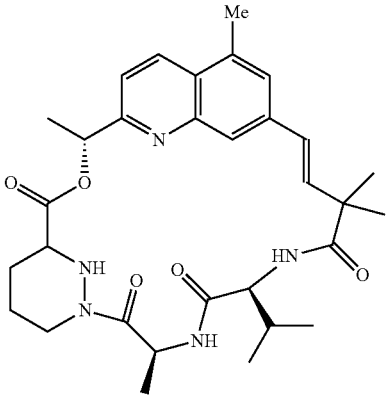

Intermediate 148a

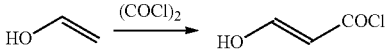

A flask containing $(COCl)_2$ (13 mL, 153.6 mmol) was stirred at 0° C. as ethyl vinyl ether (9.6 mL, 100.2 mmol) was added over 20 min. After 20 min at 0° C. and 15 h at rt, the solution was evaporated on rotorvap and the resulting dark mixture was refluxed at 120° C. for 30 min and then distilled at 15 mmHg at 65-68° C. to get 7.828 g (58%) of 148a. $^1$H NMR (400 MHz, Chloroform-d) δ 7.78 (d, J=12.1 Hz, 1H), 5.51 (d, J=12.1 Hz, 1H), 4.05 (q, J=7.1 Hz, 2H), 1.39 (t, J=7.1 Hz, 3H).

Compound 148b

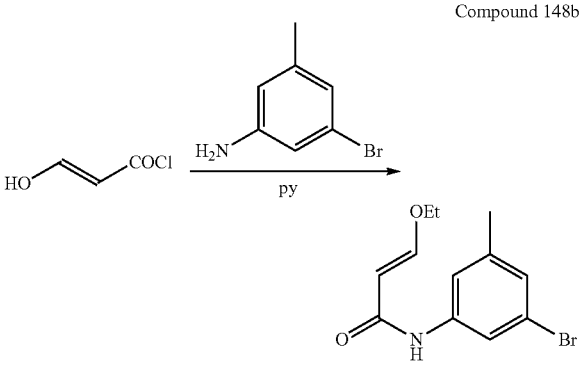

A solution of the aniline (3.008 g, 16.17 mmol) and pyridine (2.4 mL, 29.67 mmol) in $CH_2Cl_2$ (50 mL) was stirred at 0° C. as a solution of the acyl chloride 148a (3.264 g, 24.26 mmol) in $CH_2Cl_2$ (10 mL) was added over 3 min. After 1 h at rt, the reaction mixture was washed with 1 N HCl (×1) and water (×1). After the aqueous fractions were extracted with $CH_2Cl_2$ (×1), the organic fractions were combined, dried ($MgSO_4$), and concentrated. The residue was purified by CombiFlash using $CH_2Cl_2$ as eluents to obtain 3.392 g (74%) of the product 148b. $^1$H NMR (400 MHz, Chloroform-d) δ 7.69 (d, J=12.6 Hz, 0.15H), 7.63 (d, J=12.0 Hz, 0.85H), 7.58 (s, 0.15H), 7.53 (s, 0.85H), 7.29 (s, 1H), 7.15 (s, 0.15H), 7.05 (s, 0.85H), 6.86 (s, 1H), 5.28 (d, J=12.0 Hz, 0.85H), 5.26 (d, J=12.6 Hz, 0.15H), 3.97 (q, J=7.0 Hz, 0.3H), 3.95 (q, J=7.0 Hz, 1.7H), 2.33 (s, 0.5H), 2.32-2.27 (m, 2.5H), 1.64 (s, 1H), 1.37 (t, J=7.0 Hz, 0.5H), 1.36 (t, J=7.0 Hz, 2.5H). LCMS (m/z) 284.0 [M+H], Tr 1.40 min.

Compound 148c

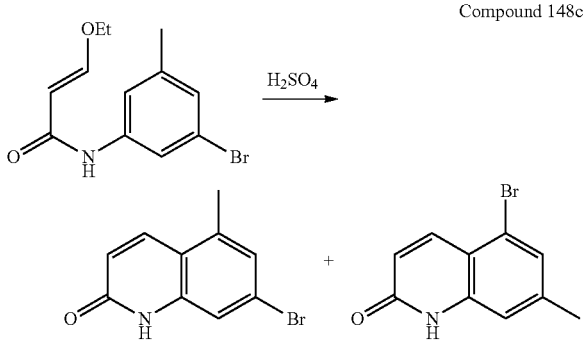

148c 148d

A flask containing $H_2SO_4$ (35 mL) was stirred at rt as the 148b (3.392 g, 11.94 mmol) was added. After stirring at rt for 2.5 h, the mixture was poured to ice (150~180 g) and the resulting mixture was stirred at rt for 1 h. The mixture was filtered and the solids were washed with water and ether. Solids collected were dried in vacuum to get 2.645 g (93% of product as a mixture of 53:47 (148c vs. 148d) ratio. $^1$H NMR (400 MHz, Chloroform-d) δ~12.2 (br, 1H), 8.25 (d, J=9.8 Hz, 0.53H), 8.05 (d, J=9.5 Hz, 0.47H), 7.49 (s, 0.47H), 7.39 (s, 0.53H), 7.28 (s, 0.47H), 7.22 (s, 0.53H), 6.81 (d, J=9.8 Hz, 1H), 2.57 (s, 1.41H), 2.47 (s, 1.59H). LCMS (m/z) 238.0 [M+H], Tr 1.04 & 1.06 min.

Compound 148e

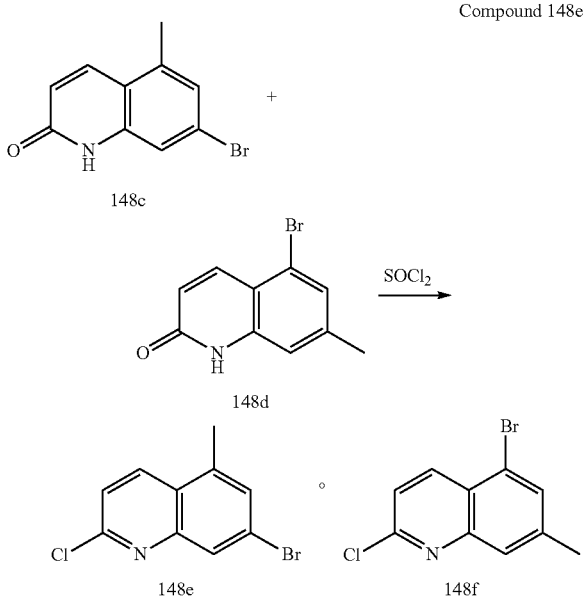

148c 148d 148e 148f

To a suspension of the mixture of the reactant 148c (2.645 g, 11.11 mmol) in DMF (0.95 mL, 12.17 mmol) and $CH_2Cl_2$ (100 mL) was added $SOCl_2$ (2.5 mL, 34.27 mmol). After the mixture was refluxed for 1.5 h, additional $SOCl_2$ (7.5 mL, 102.82 mmol) was added and the resulting mixture was further refluxed for 1 h. The solution was cooled to rt and quenched with ice and water and the separated organic fraction was washed with water (×1). The aqueous fractions were extracted with $CH_2Cl_2$ (×1), and the organic fractions were combined, dried ($MgSO_4$), and concentrated. The residue was purified by CombiFlash (×2) using hexanes-ethyl acetate as eluents to obtain 1.079 g (38%) of 148e and 1.358 g (48%) of 148f.

Compound 148e: $^1$H NMR (400 MHz, Chloroform-d) δ 8.22 (d, J=8.8 Hz, 1H), 8.06 (d, J=1.9 Hz, 1H), 7.51 (d, J=1.9

Hz, 1H), 7.42 (d, J=8.8 Hz, 1H), 2.79-2.54 (s, 3H). LCMS (m/z) 256.0 [M+H], Tr 1.59 min.

Compound 148f: $^1$H NMR (400 MHz, Chloroform-d) δ 8.41 (d, J=8.8 Hz, 1H), 7.76 (d, J=1.5 Hz, 1H), 7.68 (d, J=1.5 Hz, 1H), 7.40 (d, J=8.8 Hz, 1H), 2.54 (s, 3H). LCMS (m/z) 256.0 [M+H], Tr 1.63 min.

Compound 148g

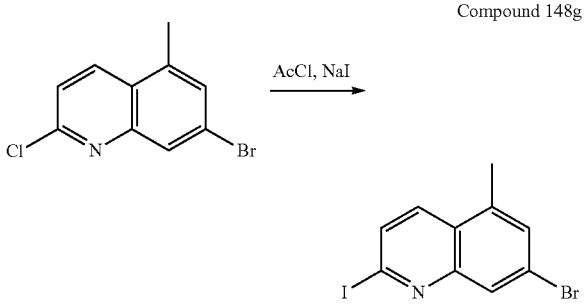

To a suspension of the reactant 148e (500 mg, 1.949 mmol) and NaI (2.925 g, 19.51 mmol) in MeCN (15.7 mL) was added AcCl (0.42 mL, 5.907 mmol) and the resulting mixture was stirred at 80° C. for 4 h. After the reaction mixture was concentrated, the residue was dissolved in $CH_2Cl_2$ (100 mL) before washing with 10% (w/w) $K_2CO_3$ (×1) saturated $Na_2S_2O_3$ (×1), and water (×1). After the aqueous fractions were extracted with $CH_2Cl_2$ (×1), the organic fractions were combined, dried ($Na_2SO_4$), and concentrated to get 661 mg (98%) of the crude iodide 148 g. LCMS (m/z) 347.9 [M+H], Tr 1.71 min.

Compound 148h

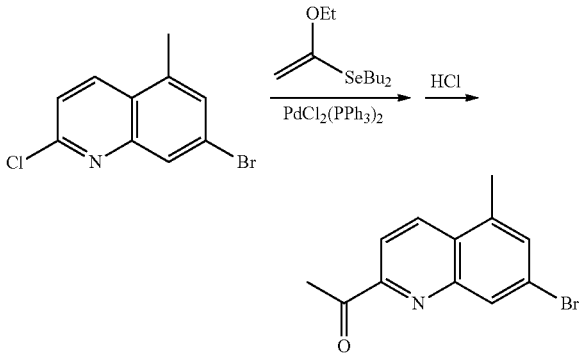

A mixture of the reactant 148 g (661 mg, 1.900 mmol), $PdCl_2(PPh_3)_2$ (138 mg, 0.197 mmol), and 1-ethoxyethenyltributylstanane (0.79 mL, 2.338 mmol) in dioxane (3.9 mL) was stirred at 100° C. for 13 h. After addition of 2 N HCl (4 mL) and stirring at rt for 1 h, the mixture was diluted with ethyl acetate (30 mL) and filtered through celite. After the organic fraction in the filtrate was washed with water (×1) and the aqueous fractions were extracted with ethyl acetate (×1), the combined organic fractions were dried ($Na_2SO_4$) and concentrated. The residue was purified by CombiFlash (×2) using hexanes-ethyl acetate as eluents to obtain 404 mg (81%) 148 h, which contained some impurities. $^1$H NMR (400 MHz, Chloroform-d) (58.36 (d, J=8.4 Hz, 1H), 8.22 (sz, 1H), 8.11 (d, J=8.4 Hz, 1H), 7.55 (s, 1H), 2.83 (s, 3H), 2.67 (s, 3H).

LCMS (m/z) 264.0 [M+H], Tr 1.64 min.

Compound 148i

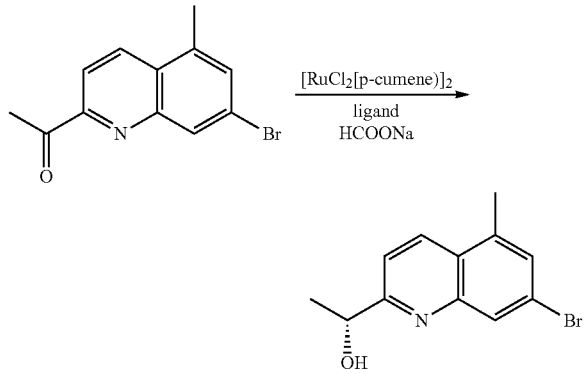

Dichloro(p-cumene)ruthenium(II) dimer (4.7 mg, 0.008 mmol) and (1R,2R)-(−)-N-p-tosyl-1,2-diphenylethylenediamine (6.8 mg, 0.019 mmol) was suspended in degassed water (3.1 mL) and the mixture was degassed with nitrogen for 15 minutes. The mixture was stirred at 70° C. under nitrogen for 1.5 h. The resulting yellow solution was cooled to room temperature. 1-(7-bromo-5-methyl-quinolin-2-yl)-ethanone (4.4 mg, 1.530 mmol), sodium formate (522 mg, 7.675 mmol) and degassed tetrahydrofuran (3.1 mL) were added and the reaction mixture was degassed with nitrogen for 5 minutes. The reaction mixture was vigorously stirred at 40° C. for 4 h. The reaction mixture was cooled to rt and diluted with ethyl acetate before washing with water (×2). After the aqueous fractions were extracted with ethyl acetate (×1), the organic fractions were combined, dried ($Na_2SO_4$) and concentrated. The residue was purified by CombiFlash (×2) using hexanes-ethyl acetate as eluents to obtain 275 mg (68%) of the product 148i. $^1$H NMR (400 MHz, Chloroform-d) δ 8.25 (d, J=8.7 Hz, 1H), 8.09 (s, 1H), 7.45 (s, 1H), 7.38 (d, J=8.8 Hz, 1H), 5.03 (q, J=6.6 Hz, 1H), 4.89 (s, 1H), 2.64 (s, 3H), 1.56 (d, J=6.6 Hz, 3H).

LCMS (m/z) 266.2 [M+H], Tr 0.81 min.

Compound 148j

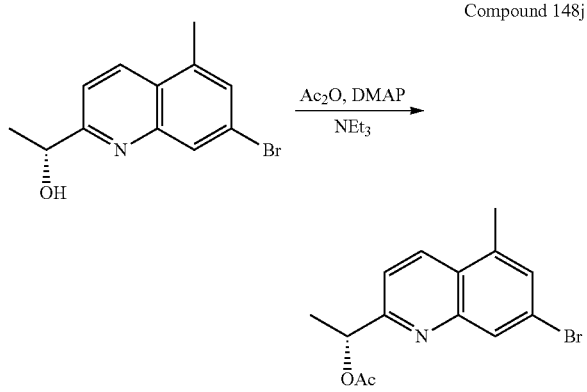

A solution of the reactant (275 mg, 1.033 mmol), DMAP (6.8 mg, 0.056 mmol), and $NEt_3$ (0.45 mL, 3.229 mmol) in $CH_2Cl_2$ (3.5 mL) was stirred at 0° C. as $Ac_2O$ (0.2 mL, 2.116 mmol) was added. The resulting solution was stirred at 0° C. for 2 h and diluted with ethyl acetate before washing with water (×2). After the aqueous fractions were extracted with ethyl acetate (×1), the organic fractions were combined, dried ($Na_2SO_4$) and concentrated. The residue was purified by CombiFlash (×2) using hexanes-ethyl acetate as eluents to obtain 308 mg (97%) of the product 148j. $^1$H NMR (400 MHz, Chloroform-d) δ 8.27 (d, J=8.7 Hz, 1H), 8.13 (s, 1H), 7.48 (d, J=8.7 Hz, 1H), 7.45 (s, 1H), 6.03 (q, J=6.7 Hz, 1H), 2.64 (s, 3H), 2.16 (s, 3H), 1.66 J=6.7 Hz, 3H).

LCMS (m/z) 308.0 [M+H], Tr 1.34 min.

Compound 148k

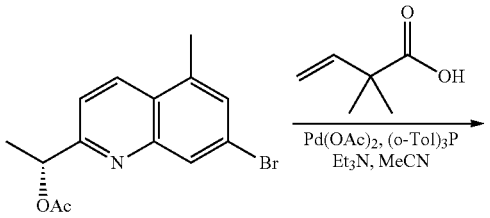

To a mixture of the reactant (308 mg, 0.999 mmol), $Pd(OAc)_2$ (22.5 mg, 0.100 mmol), and $(o\text{-Tol})_3P$ (30.5 mg, 0.100 mmol), and the acid (128.5 mg, 1.126 mmol) in MeCN (10.5 mL) was added $NEt_3$ (0.63 mL, 4.52 mmol). The resulting mixture was stirred at 100° C. for 20 min in a □W reactor. After the mixture was concentrated, the residue was dissolved in aqueous $NH_4Cl$ and the product was extracted with ethyl acetate (×3). The extracts were combined, dried ($Na_2SO_4$), and concentrated. The residue was purified by CombiFlash (×2) using hexanes-ethyl acetate as eluents to obtain 337 mg (99%) of compound 148k with ~90% purity. $^1$H NMR (400 MHz, Chloroform-d) δ 8.28 (d, J=8.6 Hz, 1H), 7.95 (s, 1H), 7.47 (s, 1H), 7.44 (d, J=8.6 Hz, 1H), 6.66 (d, J=16.0 Hz, 1H), 6.63 (s, J=16.0 Hz, 1H), 6.09 (q, J=6.6 Hz, 1H), 2.65 (s, 3H), 2.15 (s, 3H), 1.68 (d, J=6.7 Hz, 3H), 1.49 (s, 6H).

LCMS (m/z) 342.1 [M+H], Tr 1.04 min.

Compound 148l

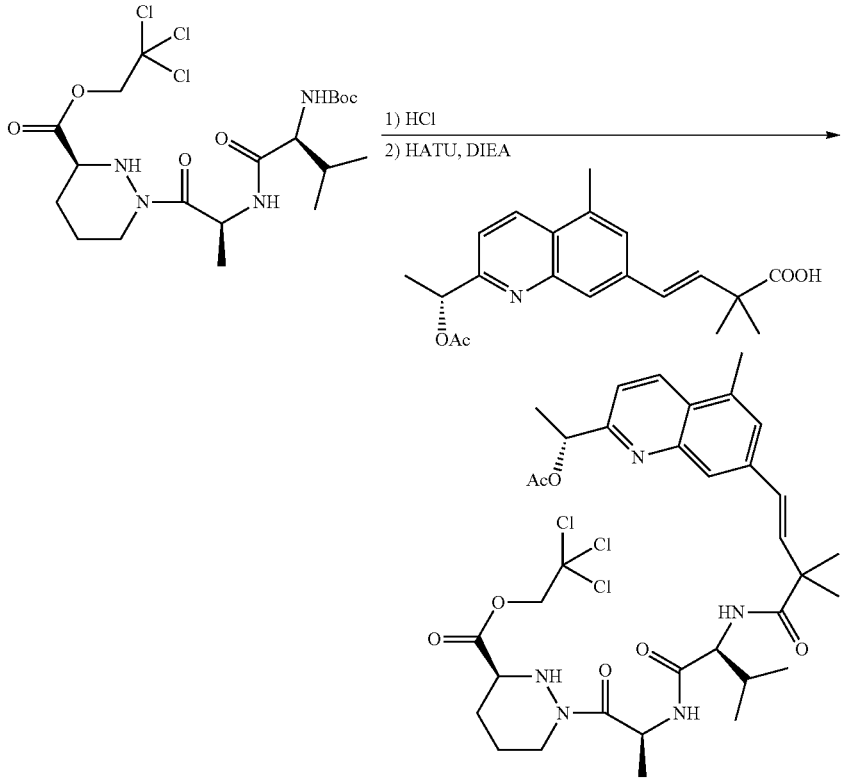

-continued

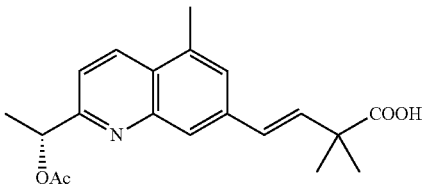

To a solution of the tripeptide (525 mg, 0.987 mmol) in $CH_2Cl_2$ (2.5 mL) was added 4 N HCl in dioxane (2.5 mL) and the mixture was stirred at rt for 1 h. The mixture was concentrated and the residue was co-evaporated with toluene (×2). After the residue was dried in vacuum and HATU (379 mg, 0.997 mmol) was added to the residue, a solution of the acid 148k (337 mg, 0.987 mmol) in $CH_2Cl_2$ (5 mL) and DMF (5 mL) was added. The resulting mixture was stirred at 0° C. as DIEA (0.7 mL, 4.02 mmol) was added. After 1 h, the reaction mixture was diluted with 5% aq. LiCl solution and the product was extracted with ethyl acetate (×2). The extracts were washed with 5% aq. LiCl solution (×1), combined, dried ($Na_2SO_4$), and concentrated. The residue was purified by CombiFlash using hexanes-ethyl acetate as eluents to obtain 664 mg (89%) of the product. $^1$H NMR (400 MHz, Chloroform-d) δ 8.30 (d, J=8.7 Hz, 1H), 7.86 (s, 1H), 7.46 (s, 1H), 7.45 (d, J=8.7 Hz, 1H), 6.78 (d, J=7.6 Hz, 1H), 6.69 (d, J=16.2 Hz, 1H), 6.61 (d, J=16.2 Hz, 1H), 6.40 (d, J=8.4 Hz, 1H), 6.04 (q, J=6.7 Hz, 1H), 5.27 (p, J=7.0 Hz, 1H), 4.90 (d, J=11.9 Hz, 1H), 4.66 (d, J=12.0 Hz, 1H), 4.28 (dd, J=8.4, 6.0 Hz, 1H), 3.90 (d, J=11.0 Hz, 1H), 3.65 (td, J=10.5, 3.7 Hz, 1H), 2.89 (s, 1H), 2.79 (d, J=1.1 Hz, 2H), 2.65 (s, 3H), 2.15 (s, 3H), 2.09 (m, J=6.7 Hz, 1H), 1.89 (td, J=9.5, 8.5, 4.4 Hz, 1H), 1.67 (d, J=6.7 Hz, 3H), 1.45 (s, 6H), 1.35-1.25 (m, 4H), 0.92 (d, J=6.8 Hz, 3H), 0.86 (d, J=6.7 Hz, 3H).

LCMS (m/z) 754.1 [M+H], Tr 2.54 min.

The residue was purified by CombiFlash (×3) using hexanes-ethyl acetate −20% MeOH/ethyl acetate as eluents to obtain 23.8 mg (61%) compound 148. $^1$H NMR (400 MHz, Methanol-$d_4$) δ 8.61 (d, J=7.0 Hz, 1H), 8.32 (dd, J=8.6, 0.9 Hz, 1H), 7.58 (s, 1H), 7.46 (s, 1H), 7.39 (d, J=8.6 Hz, 1H), 7.25 (d, J=9.6 Hz, 1H), 6.44 (d, J=16.5 Hz, 1H), 6.19 (d, J=16.5 Hz, 1H), 5.89 (q, J=6.8 Hz, 1H), 5.76-5.62 (m, 1H), 4.42-4.33 (d, J=10.8 Hz, 1H), 4.28 (t, J=10.0 Hz, 1H), 3.81-3.72 (m, 1H), 2.71 (td, J=12.6, 3.3 Hz, 1H), 2.63 (s, 3H), 1.95 (m, 3H), 1.85 (m, 3.7 Hz, 1H), 1.70 (d, J=6.9 Hz, 3H), 1.68-1.59 (m, 1H), 1.55 (d, J=7.2 Hz, 3H), 1.47 (s, 3H), 1.33 (s, 3H), 0.94 (t, J=6.4 Hz, 3H), 0.92 (t, J=6.4 Hz, 3H).

LCMS (m/z) 564.3 [M+H], Tr 2.21 min.

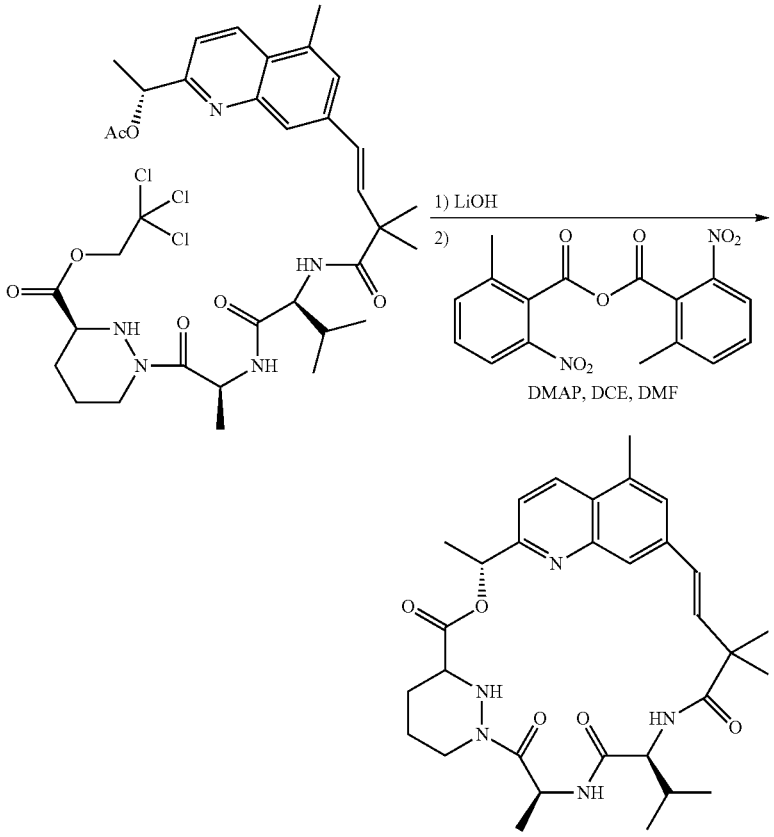

A mixture of the reactant 148l (116 mg, 0.154 mmol) and LiOH (15 mg, 0.626 mmol) in THF (4 mL) and water (2 mL) was stirred at rt for 2 h. After additional LiOH (15 mg, 0.626 mmol) was added, the mixture was stirred for 1 h at rt, neutralized with 1 N HCl (1.25 mL), concentrated, and co-evaporated with toluene (×3). The residue was dissolved in DMF (20 mL) and took 1 mL for purification of the hydroxyl-acid by HPLC to get 4.5 mg (quantitative) of the hydroxyl-acid.

The 9 mL of the DMF solution (0.691 mmol) was concentrated and dried in vacuum. The residue and DIEA (0.1 mL, 0.574 mmol) in THF (70 mL) was sonicated and then stirred at rt as HATU (58 mg, 0.153 mmol) was added. The resulting mixture was stirred at rt for 3 h, concentrated, and the residue was treated with water before extraction with ethyl acetate (×2). The organic extracts were washed with water (×1), combined, dried ($Na_2SO_4$), and concentrated.

Example 149

Compound 149

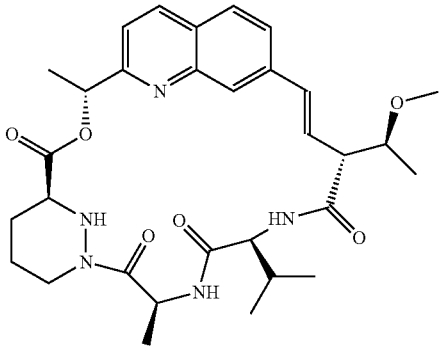

-continued

Compound 149

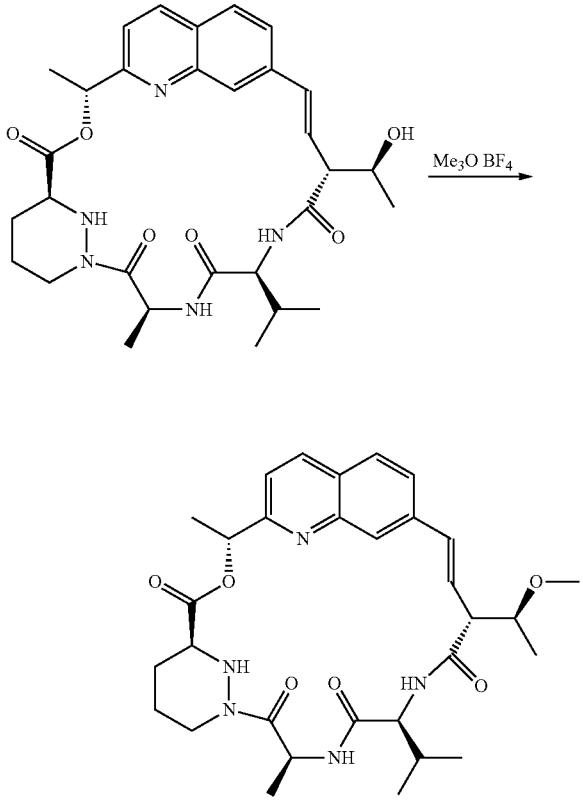

A mixture of 31 (9.7 mg, 0.017 mmol) and proton sponge (20.2 mg 0.094 mmol) in $CH_2Cl_2$ (1 mL) was stirred at 0° C. as $Me_3OBF_4$ (12.7 mg, 0.086 mmol) was added. After 1 h, at 0° C., additional proton sponge (31.2 mg, 0.146 mmol) and $Me_3OBF_4$ (13.5 mg, 0.091 mmol) were added and the resulting mixture was stirred at −18° C. for 63.5 h. After additional proton sponge (24.5 mg, 0.114 mmol) and $Me_3OBF_4$ (16.5 mg, 0.112 mmol) were added at 0° C., and the resulting mixture was stirred at 0° C. for 1 h, the mixture was treated with aqueous $NaHCO_3$ solution, and the product was extracted with $CH_2Cl_2$ (×2). The extracts were combined, dried ($Na_2SO_4$), and concentrated. The residue was purified by CombiFlash using ethyl acetate −20% MeOH/ethyl acetate as eluents to obtain 5.2 mg (52%) of the product 149. $^1$H NMR (400 MHz, Methanol-$d_4$) δ 8.49 (d, J=6.6 Hz, 1H), 8.00 (d, J=8.5 Hz, 1H), 7.37 (m, 3H), 7.25 (d, J=8.5 Hz, 1H), 6.57 (dd, J=16.6, 4.6 Hz, 1H), 6.30 (dd, J=16.7, 1.9 Hz, 1H), 6.01 (q, J=6.7 Hz, 1H), 5.61 (m, 1H), 4.49-4.34 (d, J=12.0 Hz, 1H), 4.25 (d, J=10.8 Hz, 1H), 3.78-3.69 (m, 1H), 3.64 (m, 1H), 3.48 (s, 3H), 3.47-3.38 (m, 1H), 2.84 (td, J=12.6, 3.5 Hz, 1H), 2.04 (m, 1.90 (d, J=8.6 Hz, 1H), 1.74 (d, J=6.8 Hz, 3H), 1.71 (m, 2H), 1.42 (d, J=7.2 Hz, 3H), 1.28 (s, 1H), 1.23 (d, J=5.9 Hz, 3H), 1.00 (d, J=6.6 Hz, 3H), 0.97 (d, J=6.6 Hz, 3H).

LCMS (m/z) 580.3 [M+H], Tr 4.05 min.

Examples 150 and 151

Compounds 150 and 151

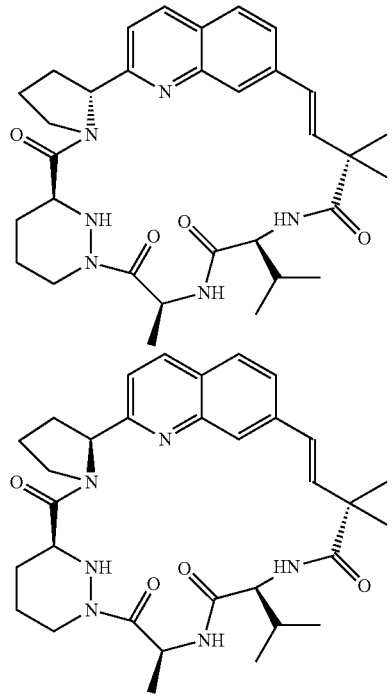

Compound 150a

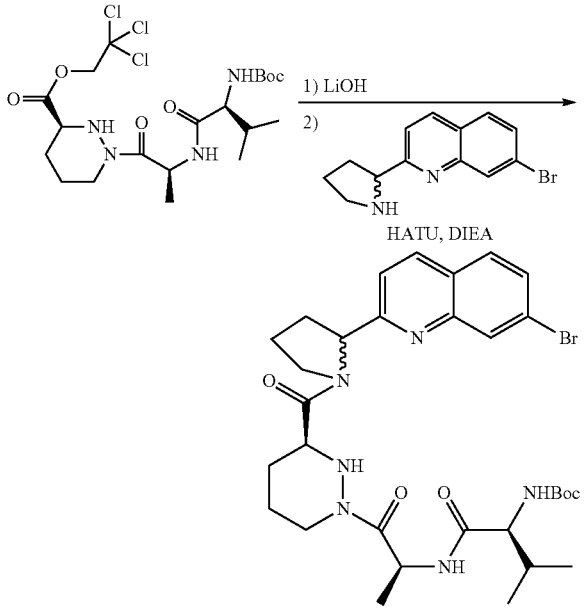

A mixture of 1e (225 mg, 0.423 mmol) and LiOH (38 mg, 0.906 mmol) in THF (2 mL), MeOH (2 mL), and water (2 mL) was stirred at rt for 30 min and concentrated to remove THF and MeOH. The resulting aqueous solution was diluted with water, washed with ether (×1), and acidified with 1 N HCl (0.95 mL). After the aqueous solution was saturated with NaCl, the product acid was extracted with ethyl acetate (×2), and the extracts were combined, dried ($Na_2SO_4$), concentrated, and dried in vacuum to get 169 mg (quant.) of the acid. LCMS (m/z) 401.1 [M+H]

A solution of the crude acid (169 mg, 0.422 mmol), 2-(7-bromoquinolin-2-yl)pyrrolidine hydrochloride (obtained from ASIBA, Inc., 134 mg, 0.427 mmol), and HATU (241 mg, 0.634 mmol) in DMF (3 mL) was stirred at 0° C. as DIEA (0.35 mL, 2.009 mmol) was added. After 1.5 h at 0° C., the reaction mixture was diluted with 5% LiCl solution and the product was extracted with ethyl acetate (×2). The extracts were washed with 5% LiCl solution (×1), combined, dried ($Na_2SO_4$), and concentrated. The residue was purified by CombiFlash using hexanes-ethyl acetate −20% MeOH/ethyl acetate as eluents to obtain 200 mg (72%) of the product 150a as diastereomer mixture. LCMS (m/z) 659.2 [M+H], Tr 1.25 min.

Compound 150b

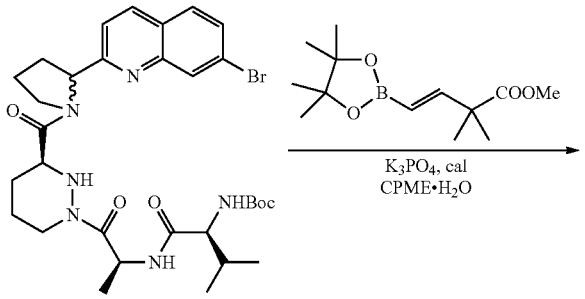

-continued

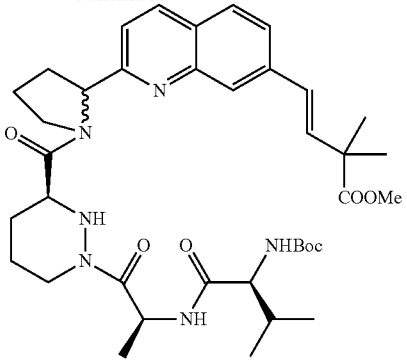

A mixture of the 150a (195 mg, 0.296 mmol), vinyl boronate 17c (97.1 mg, 0.361 mmol), $PdCl_2(PCy_2(p\text{-}NMe_2Ph))_2$ (25 mg, 0.031 mmol), and $K_3PO_4$ (215 mg, 1.013 mmol) in cyclopentyl methyl ether (5 mL) and $H_2O$ (2.5 mL) was degassed and stirred at 90° C. for 3.5 h before additional 17c (104 mg, 0.409 mmol), $PdCl_2(PCy_2(p\text{-}NMe_2Ph))_2$ (25.7 mg, 0.032 mmol), and $K_3PO_4$ (201 mg, 0.949 mmol) were added. After degassing, the mixture was stirred at 90° C. for 0.5 h, cooled to rt, and dissolved in ethyl acetate and water before filtration through celite. After two phases were separated, the aqueous fraction was extracted with ethyl acetate (×1), and the organic fractions were washed with water (×1), combined, dried ($Na_2SO_4$), and concentrated. The residue was purified by CombiFlash using hexanes-ethyl acetate −20% MeOH/ethyl acetate as eluents to obtain 193 mg (92%) 150b. LCMS (m/z) 707.2 [M+H], Tr 1.23 min.

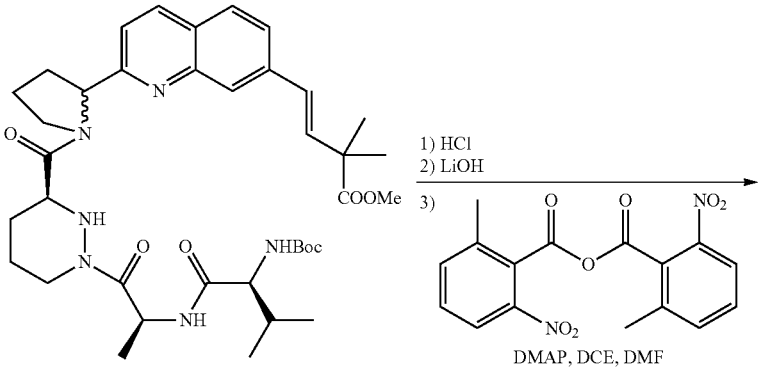

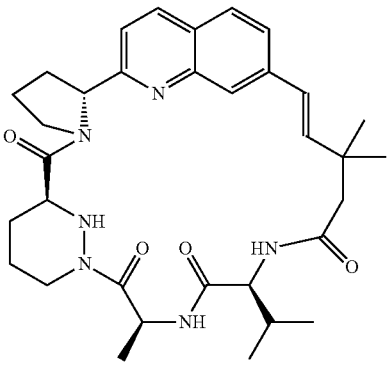

150

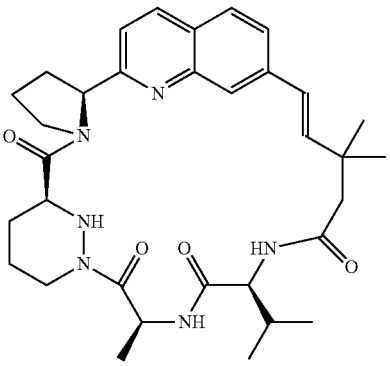

151

To a flask containing the reactant 150b (193 mg, 0.273 mmol) were added $CH_2Cl_2$ (3 mL) and 4 N HCl in dioxane (3 mL) and the mixture was stirred at rt for 1.5 h. The mixture was concentrated and dried in vacuum. The residue was dissolved in THF (2 mL), MeOH (2 mL), and water (2 mL) and LiOH (57.4 mg, 1.368 mmol) was added. After 5.5 h at rt, additional LiOH (11.4 mg, 0.271 mmol) was added and the resulting mixture was stirred at rt for 17 h more. The mixture was concentrated to ~⅓ volume, neutralized with 1 N HCl (1.65 mL), and concentrated. After co-evaporation with toluene (×3) and DMF (×1), the residue was dissolved in DMF (3 mL) and used in the next reaction.

A solution of HATU (317 mg, 0.834 mmol) in DMF (135 mL) and $CH_2Cl_2$ (135 mL) was stirred at rt as DIEA (0.4 mL, 2.30 mmol) was added. The resulting solution was stirred at rt as the previous DMF solution of the amino acid was added over 4 h. After addition, the mixture was stirred at rt for 15 min and additional HATU (100 mg, 0.263 mmol) was added to the mixture. After 30 min, the mixture was concentrated and residue was diluted with ethyl acetate before washing with 5% LiCl solution (×3). After the aqueous fractions were extracted with ethyl acetate (×1), the organic fractions were combined, dried ($Na_2SO_4$), and concentrated. The residue was purified by preparative HPLC. Two fractions collected were separately concentrated to remove MeCN, neutralized with some $NaHCO_3$ solution, and extracted with ethyl acetate (×2). The extracts were dried ($Na_2SO_4$), and concentrated to obtain 28.3 mg (18%) of 150 and 59.6 mg (38%) of 151 after HPLC purification using an Phenomenex Gemini 7 micron C18 250×21.2 mm column and using acetonitrile/water as eluent.

Compound 150, first eluting diastereomer: $^1$H NMR (400 MHz, Methanol-$d_4$) δ 8.73-8.64 (m, 1H), 8.12 (d, J=8.4 Hz, 1H), 7.75 (d, J=8.6 Hz, 1H), 7.68 (dd, J=8.6, 1.7 Hz, 1H), 7.58 (d, J=1.7 Hz, 1H), 7.36 (d, J=8.4 Hz, 1H), 7.22 (d, J=9.6 Hz, 1H), 6.42 (d, J=16.4 Hz, 1H), 6.27 (d, J=16.4 Hz, 1H), 5.72 (q, J=7.2 Hz, 1H), 5.30 (dd, J=8.0, 3.4 Hz, 1H), 4.37 (d, J=14.0 Hz, 1H), 4.30 (t, J=9.8 Hz, 1H), 4.21-4.13 (m, 1H), 3.99-3.80 (m, 2H), 2.69 (td, J=12.6, 3.4 Hz, 1H), 2.46 (dq, J=12.1, 8.0 Hz, 1H), 2.21-2.02 (m, 2H), 1.99-1.90 (m, 1H), 1.90-1.80 (m, 2H), 1.80-1.65 (m, 2H), 1.60 (d, J=7.2 Hz, 3H), 1.48 (s, 3H), 1.33 (s, 3H), 1.28 (s, 1H), 0.97 (d, J=6.7 Hz, 3H), 0.93 (d, J=6.6 Hz, 3H). LCMS (m/z) 575.3 [M+H], Tr 0.96 min.

Compound 151, second eluting diastereomer: $^1$H NMR (400 MHz, Methanol-$d_4$) δ 8.22 (d, J=8.5 Hz, 1H), 8.00-7.90 (m, 1H), 7.81 (d, J=8.5 Hz, 1H), 7.67 (dd, J=8.5, 1.7 Hz, 1H), 7.45 (d, J=8.5 Hz, 1H), 7.06 (d, J=9.4 Hz, 1H), 6.72 (d, J=16.3 Hz, 1H), 6.37 (d, J=16.3 Hz, 1H), 5.45-5.34 (m, 1H), 5.19 (q, J=7.0 Hz, 1H), 4.29-4.18 (d, J=13.6 Hz, 1H), 3.90 (d, J=10.5 Hz, 1H), 3.81 (ddd, J=12.1, 9.1, 2.8 Hz, 1H), 3.63-3.46 (m, 1H), 3.27 (dd, J=11.2, 3.2 Hz, 1H), 2.72-2.51 (m, 2H), 2.38 (dd, J=12.8, 6.4 Hz, 1H), 2.05-1.89 (m, 3H), 1.79 (dt, J=13.3, 3.3 Hz, 1H), 1.72-1.55 (m, 2H), 1.52 (s, 3H), 1.44 (s, 3H), 1.43-1.34 (m, 1H), 1.28 (s, 1H), 0.91 (d, J=6.7 Hz, 3H), 0.82 (d, J=6.6 Hz, 3H), −0.45 (d, J=7.1 Hz, 3H). LCMS (m/z) 575.3 [M+H], Tr 1.04 min.

Example 152

Compound 152

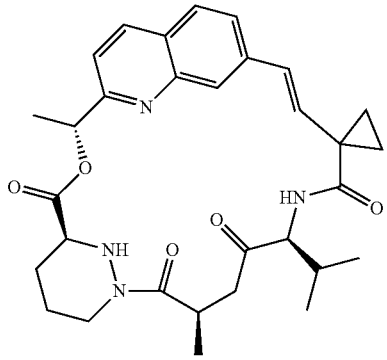

Compound 152a

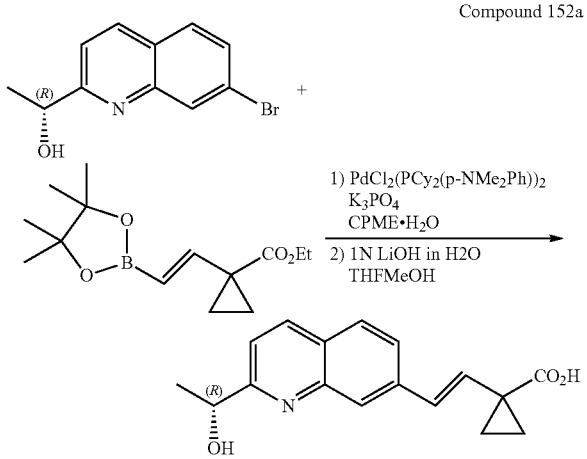

A mixture of the reactant (R)-1-(7-bromoquinolin-2-yl) ethanol (200 mg, 0.793 mmol), (E)-ethyl1-(2-(4,4,5,5-tetramethyl-1,3,2-dioxaborolan-2-yl)vinyl)cyclopropanecarboxylate 58a (226 mg, 0.912 mmol), $PdCl_2(PCy_2(p\text{-}NMe_2Ph))_2$ (32 mg, 0.04 mmol), and $K_3PO_4$ (509 mg, 2.4 mmol) in cyclopentyl methyl ether (5 mL) and $H_2O$ (2.5 mL) was degassed and stirred at 90° C. for 2 h. After cooling to rt, it was extracted with EtOAc (×1) and dried ($Na_2SO_4$) then concentrated. The residue was purified by flash chromatography on silica gel with EtOAc/Hexane to obtain 240 mg (99%) of the product, methyl 1-(2-(2-(1-hydroxyethyl) quinolin-7-yl)vinyl)cyclopropanecarboxylate.

$^1$H NMR (400 MHz, Chloroform-d) δ 8.06 (d, J=8.5 Hz, 1H), 7.91 (d, J=1.9 Hz, 1H), 7.72 (d, J=8.5 Hz, 1H), 7.62 (dd, J=8.5, 1.7 Hz, 1H), 7.32-7.19 (m, 1H), 7.10 (d, J=16.2 Hz, 1H), 6.40 (d, J=16.2 Hz, 1H), 5.15-4.88 (m, 2H), 4.18 (q, J=7.1 Hz, 2H), 1.60 (q, J=4.0 Hz, 2H), 1.55 (d, J=6.5 Hz, 3H), 1.27 (t, J=7.1 Hz, 3H), 1.25-1.22 (m, 2H), 1.21 (s, 3H).

LCMS $[M+H]^+$=312.1; Tr=1.93 min.

Compound 152b

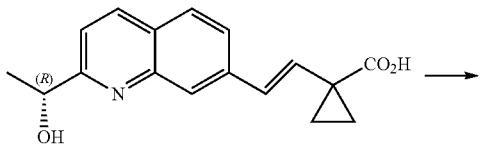

-continued

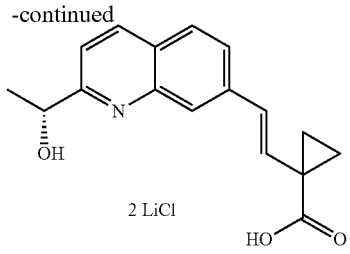

The 152a (240 mg, 0.791 mmol) was dissolved in a mixture of tetrahydrofuran (4 mL)/Methanol (2 mL) at RT. Lithium hydroxide monohydrate (67 mg, 1.6 mmol) in water (2 mL) was added and the solution was stirred at room temperature for 2 h. The solution was acidified using 2 M hydrochloric acid and then concentrated to dryness as crude acid for the next step.

concentrated. The residue was purified by CombiFlash using 0-20% MeOH/EA as eluents to obtain 330 mg (69%) of 152c. $^1$H NMR (400 MHz, Methanol-$d_4$) δ 8.25 (d, J=8.5 Hz, 1H), 7.93-7.88 (m, 1H), 7.83 (d, J=8.5 Hz, 1H), 7.75 (dd, J=8.6, 1.6 Hz, 1H), 7.63 (d, J=8.5 Hz, 1H), 7.33 (d, J=8.6 Hz, 1H), 6.91-6.73 (m, 2H), 5.36 (q, J=6.9, 6.5 Hz, 1H), 5.06-4.91 (m, 2H), 4.74 (d, J=12.1 Hz, 1H), 4.37-4.24 (m, 1H), 3.76 (dd, J=7.7, 4.2 Hz, 1H), 2.78 (s, 3H), 2.05 (tt, J=14.5, 7.4 Hz, 2H), 1.83 (qd, J=10.0, 4.1 Hz, 2H), 1.65 J=10.4, 9.9, 5.8 Hz, 1H), 1.52 (d, J=6.6 Hz, 3H), 1.45-1.33 (m, 2H), 1.28 (d, J=7.0 Hz, 3H), 1.21 (t, J=7.1 Hz, 1H), 1.17-1.06 (m, 2H), 0.97 (d, J=6.7 Hz, 3H), 0.91 (d, J=6.7 Hz, 3H).

LCMS $[M+H]^+$=696.21, 698.20; Tr=2.18 min.

Compound 152c

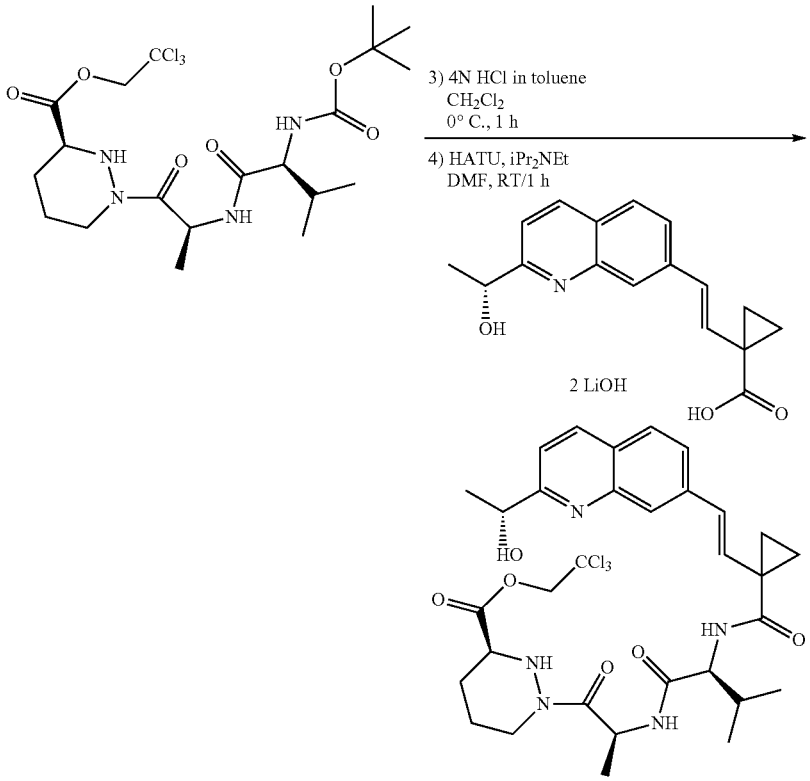

To a solution of the tripeptide (365 mg, 0.683 mmol) in $CH_2Cl_2$ (4 mL) was added 4 N HCl in dioxane (2 mL) and the mixture was stirred at rt for 1 h. The mixture was concentrated and the residue was co-evaporated with toluene (×2). After the residue amine was dried in vac, it was dissolved in DMF with DIPEA (0.6 mL, 3.4 mmol) and HATU (395 mg, 1.04 mmol). The solution of the acid 152b (0.791 mmol) in DMF (5 mL) was added. The resulting mixture was stirred at RT. After 1 h, the reaction mixture was diluted with 5% aq. LiCl solution and the product was extracted with EA (×2). The extracts were washed with 5% aq. LiCl solution (×1), combined, dried ($Na_2SO_4$), and

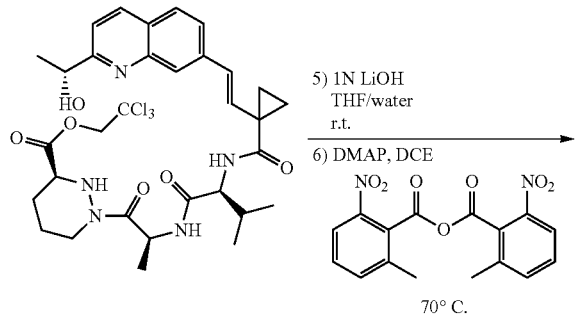

-continued

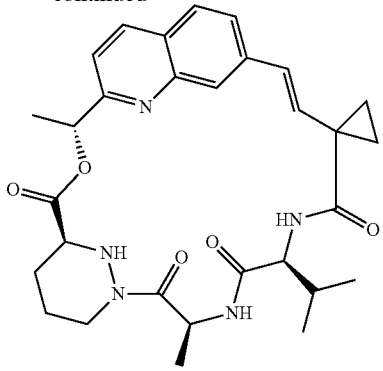

A mixture of the reactant (330 mg, 0.473 mmol) and LiOH (79 mg, 1.894 mmol) in THF (4 mL) and water (2 mL) was stirred at rt for 2 h. It was neutralized with 1 N HCl and concentrated, and co-evaporated with toluene (×3). The residue was dissolved in DMF (6 mL) as solution A which was used in the next step. LCMS $[M+H]^+$=566.16; Tr=1.69 min.

A solution of 2-Methyl-6-nitrobenzoic anhydride (415 mg, 1.18 mmol) and DMAP (433 mg, 3.55 mmol) in DCE (450 mL) was stirred at 50° C. as the solution A (6 mL) was added over 6 h via syringe pump. After 24 h at 50° C., the solution was concentrated and the residual DMF mixture was diluted with 5% LiCl solution before extractions with EA (×2). After the extracts were washed with 5% LiCl solution (×1), combined, dried ($Na_2SO_4$), and concentrated, the residue was purified by CombiFlash (×2) using EA −20% MeOH/EA as eluents then HPLC to obtain 62 mg (24%) of Compound 152. $^1$H NMR (400 MHz, Methanol-$d_4$) δ 8.22-8.06 (m, 1H), 7.80-7.66 (m, 2H), 7.56 (s, 1H), 7.35 (d, J=8.5 Hz, 1H), 6.36 (d, J=16.4 Hz, 1H), 6.04 (d, J=16.4 Hz, 1H), 5.89 (p, J=6.6 Hz, 1H), 5.79 (qd, J=7.1, 4.3 Hz, 1H), 4.39 (d, J=13.4 Hz, 1H), 4.30-4.17 (m, 1H), 3.90-3.74 (m, 1H), 2.73 (td, J=12.6, 3.3 Hz, 1H), 2.12-1.80 (m, 2H), 1.70 (d, J=6.9 Hz, 2H), 1.66 (d, J=11.7 Hz, 1H), 1.61 (d, J=7.2 Hz, 2H), 1.44-1.10 (m, 4H), 0.94 (d, J=6.7 Hz, 2H), 0.92-0.87 (m, 3H). LCMS $[M+H]^+$=548.21; Tr=2.17 min.

Example 153

Compound 153

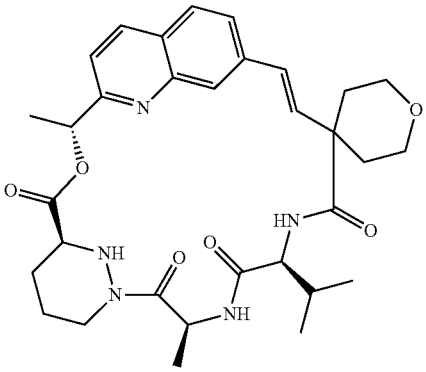

-continued

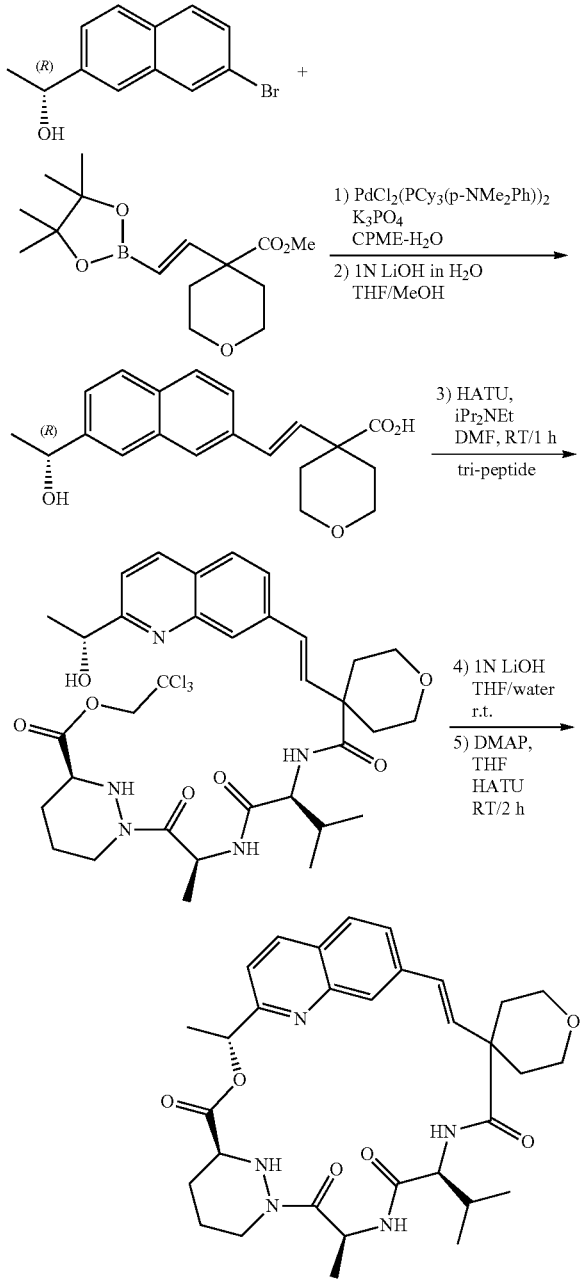

Compound 153 was prepared in the same manner as in Example 152 using (E)-methyl 4-(2-(4,4,5,5-tetramethyl-1,3,2-dioxaborolan-2-yl)vinyl)tetrahydro-2H-pyran-4-carboxylate (345 mg) instead of (E)-ethyl 1-(2-(4,4,5,5-tetramethyl-1,3,2-dioxaborolan-2-yl)vinyl) cyclopropanecarboxylate. The last step of macrocyclization using HATU/DIPEA/DMAP/THF provided 153 (107 mg) in 66% yield. $^1$H NMR (400 MHz, Methanol-$d_4$) δ 8.17 (dd, J=8.5, 0.8 Hz, 1H), 7.74 (d, J=1.8 Hz, 2H), 7.56 (d, J=1.5 Hz, 1H), 7.38 (d, J=8.5 Hz, 1H), 6.54-6.18 (m, 2H), 5.88 (q, J=6.8 Hz, 1H), 5.63 (d, J=7.2 Hz, 1H), 4.37 (dd, J=11.5, 4.3 Hz, 2H), 4.03-3.41 (m, 6H), 2.71 (td, J=12.6, 3.4 Hz, 1H), 2.19 (t, J=14.3 Hz, 2.09-1.91 (m, 3H), 1.84 (d, J=9.0 Hz, 1H), 1.79-1.55 (m, 6H), 1.47 (d, J=7.2 Hz, 3H), 0.94 (t, J=6.6 Hz, 6H). LCMS $[M+H]^+$=592.24; Tr=2.13 min.

Example 154

Compound 154

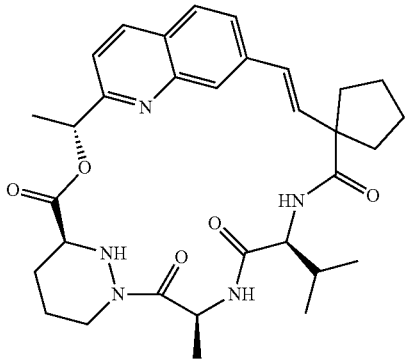

Compound 154a

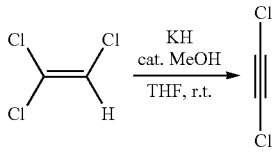

Into an oven dried, argon purged flask were placed oil-free potassium hydride (from 1740 mg of a ca. 30% dispersion in mineral oil, ca. 13 mmol), dry tetrahydrofuran (10 mL) and hexane (1 mL). The flask was repurged with argon and trichloroethylene (900 uL, 1.32 g, 10 mmol) were added through the septa followed by dry methanol (10 μL, 7.9 mg, 0.25 mmol). This mixture was stirred at room temperature for two hours (connected to the argon line through the needle—to continually remove forming hydrogen). After this time, hexane (10 mL) was added and the resulting solution was immediately used in subsequent steps.

Compound 154b

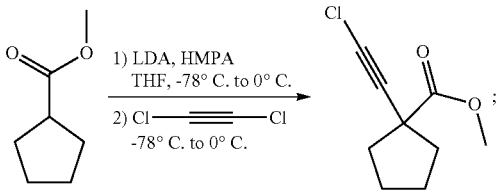

Into an oven dried, argon purged flask tetrahydrofuran (50 mL) was added and the solution was cooled with the ice bath. A 1.8 M solution of lithium diisopropylamide (7.2 mL, 13 mmol) in tetrahydrofuran/heptane/ethylbenzene was added through the septa. The resulting solution of lithium diisopropylamide was cooled to −78° C., and treated dropwise with methyl cyclopentanecarboxylate (CAS: 4630-80-2, Ark Pharm, Inc.) (1.15 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloroethyne (ca. 10 mmol, see 154a). The reaction mixture was stirred at −78° C. for 30 min. and then allowed to warm to the room temperature. After 4 hours at room temperature, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-15% ethyl acetate in isohexanes) to afford the title compound (634 mg, 37%) as a colorless oil. $^1$H NMR (400 MHz, $CDCl_3$) δ 3.73 (s, 3H), 2.25-2.08 (m, 2H), 2.06-1.93 (m, 2H), 1.86-1.66 (m, 4H). LCMS (m/z) no MS signal, Tr=3.34 min (Gemini 5u C18 110 Å, 50×4.60 mm 5 micron column, 3.5 min, 2 ml/min, 5-100% acetonitrile/water, 0.1% acetic acid modifier gradient).

Compound 154c

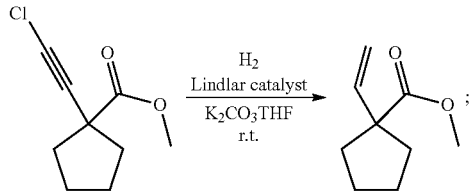

A solution of compound 154b (520 mg, 2.78 mmol) in tetrahydrofuran (50 mL) containing Lindlar catalyst (100 mg, Sigma-Aldrich) and potassium carbonate (1920 mg, 13.9 mmol) was hydrogenated at room temperature and at atmospheric pressure of hydrogen for 12 hours. The reaction mixture was filtered through Celite and the filter pad was washed with tetrahydrofuran (30 mL). The filtrate was evaporated to afford the title compound (410 mg, 96%) as a colourless oil. $^1$H NMR (400 MHz, $CDCl_3$) δ 6.08-5.85 (m, 1H), 5.07 (s, 1H), 5.04 (d, J=6.2 Hz, 1H), 3.66 (s, 3H), 2.21-2.06 (m, 2H), 1.79-1.68 (m, 2H), 1.67-1.57 (m, 4H). LCMS (m/z) no MS signal, Tr=3.30 min (Gemini 5u C18 110 Å, 50×4.60 mm 5 micron column, 3.5 min, 2 ml/min, 5-100% acetonitrile/water, 0.1% acetic acid modifier gradient).

Compound 154d

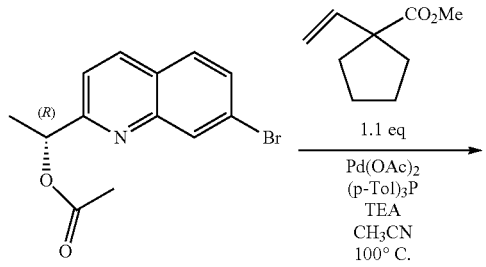

-continued

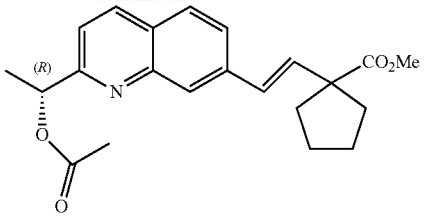

To reactant (R)-1-(7-bromoquinolin-2-yl)ethyl acetate (538 mg, 1.83 mmol) in anhydrous acetonitrile (10 mL), was added methyl 1-vinylcyclopentanecarboxylate (310 mg, 2.01 mmol) followed by triethylamine (0.51 mL, 3.66 mmol), palladium(II) acetate (41 mg, 0.183 mmol) and Tri(o-tolyl) phosphine (111 mg, 0.366 mmol). The mixture was heated at 100° C. for 1.5 hour. The reaction was cooled to room temperature and added EtOAc. It washed with sat'd $NH_4Cl$ twice, sat'd $NaHCO_3$ solution once and brine once. The organic layer was dried through ($Na_2SO_4$), and concentrated; the residue was purified by CombiFlash using EtOAC/Hexane as eluents. Yield: 124 mg 154d, 18%. $^1H$ NMR (400 MHz, Chloroform-d) δ 8.08 (d, J=8.5 Hz, 1H), 8.00 (s, 1H), 7.71 (d, J=8.5 Hz, 1H), 7.57 (dd, J=8.6, 1.7 Hz, 1H), 7.38 (d, J=8.5 Hz, 1H), 6.58 (d, J=1.3 Hz, 1H), 6.03 (q, J=6.7 Hz, 1H), 4.10 (q, J=7.1 Hz, 2H), 3.71 (s, 2H), 2.40-2.22 (m, 2H), 2.14 (s, 3H), 1.87 (dd, J=13.2, 6.6 Hz, 2H), 1.80-1.56 (m, 4H), 1.24 (t, J=7.1 Hz, 3H), 0.92-0.78 (m, 2H). LCMS $[M+H]^+$=367.98; Tr=2.44 min.

Compound 154 was prepared from 154d (124 mg) in the same manner as reported for example 153. The last step of macrocyclization was using HATU/DIPEA/DMAP/THF condition to give 15 mg pure compound in 36% yield. $^1H$ NMR (400 MHz, Methanol-$d_4$) δ 8.63 (d, J=6.9 Hz, 1H), 8.16 (dd, J=8.5, 0.8 Hz, 1H), 7.75 (d, J=1.1 Hz, 2H), 7.55 (s, 1H), 7.38 (dd, J=17.5, 9.1 Hz, 2H), 6.50 (d, J=16.4 Hz, 1H), 6.20 (d, J=16.4 Hz, 1H), 5.88 (q, J=6.8 Hz, 1H), 5.69 (p, J=7.1 Hz, 1H), 4.36 (d, J=12.4 Hz, 1H), 4.28 (t, J=10.1 Hz, 1H), 3.80-3.71 (m, 1H), 2.71 (td, J=12.6, 3.4 Hz, 1H), 2.49 (dt, J=12.3, 5.8 Hz, 1H), 2.19 (dd, J=12.8, 6.8 Hz, 1H), 2.03-1.90 (m, 4H), 1.85 (ddt, J=13.9, 9.1, 4.9 Hz, 2H), 1.79-1.61 (m, 8H), 1.57 (d, J=7.2 Hz, 4H), 0.93 (dd, J=9.6, 6.6 Hz, 6H). LCMS $[M+H]^+$=576.25; Tr=2.34 min.

Example 155

Compound 155

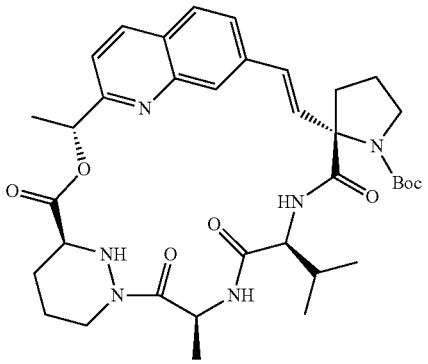

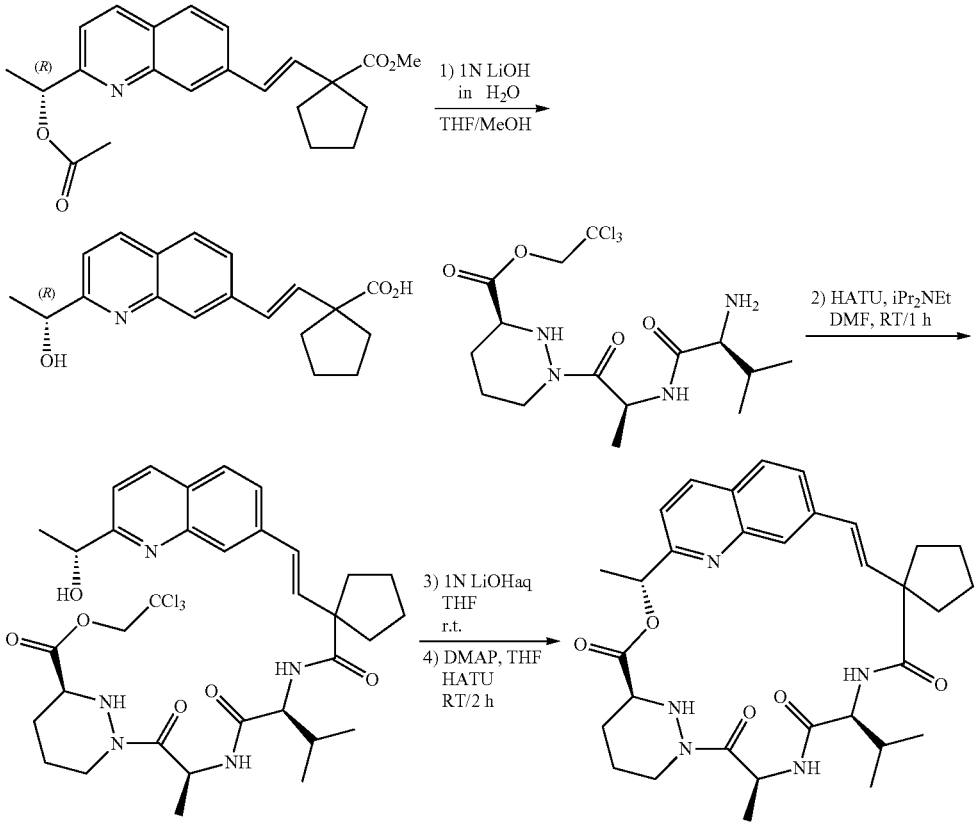

-continued

Compound 155a

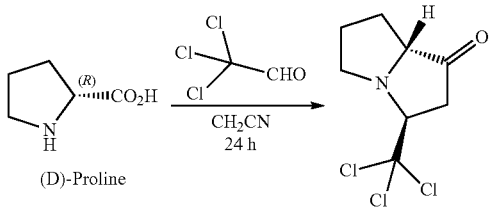

(D)-Proline

To reactant (D)-Proline (4.6 g, 40 mmol) suspended in anhydrous acetonitrile (100 mL), was added 2,2,2-trichloroacetaldehyde (11.78 g, 80 mmol) slowly. The mixture was stirred at RT for 20 hour and was clear solution. After concentrated in vacuum, the residue was purified by CombiFlash on a 80 g silica gel column using EtOAC/Hexane as eluents to give (3S,7aR)-3-(trichloromethyl)tetrahydropyrrolo[1,2-c]oxazol-1(3H)-one 155a: 3.63 g, 37%. $^1$H NMR (400 MHz, Chloroform-d) δ 5.14 (s, 1H), 4.10 (dd, J=8.9, 4.7 Hz, 1H), 3.40 (ddd, J=10.9, 7.8, 6.0 Hz, 1H), 3.11 (dt, J=11.4, 6.0 Hz, 1H), 2.21 (dtd, J=13.0, 8.5, 6.8 Hz, 1H), 2.09 (ddt, J=12.7, 7.0, 5.2 Hz, 1H), 1.91 (ddq, J=12.4, 6.7, 5.7 Hz, 1H), 1.81-1.64 (m, 1H).

Compound 155b

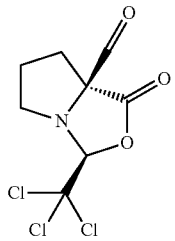

To reactant 155a (4.8 g, 19.8 mmol) suspended in anhydrous THF (100 mL) at −78° C., was added 2.0 M LDA in Hexane (14.9 mL, 29.7 mmol) over 20 min period. The mixture was stirred at −78° C. for 45 min, then let it warm up to 0° C. over 3 hour. Reaction was monitored by TLC. After completion, the reaction was quenched by adding aq. 10% citric acid slowly. It was extracted with EtOAc twice, washed with brine. The organic layer was dried through ($Na_2SO_4$), and concentrated; the residue was purified by CombiFlash using EtOAC/Hexane as eluents to give (3S,7aS)-1-oxo-3-(trichloromethyl)hexahydropyrrolo-[1,2-c] oxazole-7a-carbaldehyde 155b 1.99 g, 37%.

$^1$H NMR (400 MHz, Chloroform-d) δ 9.58 (s, 1H), 5.17 (s, 1H), 3.51 (ddd, J=11.3, 7.8, 6.2 Hz, 1H), 3.37-3.18 (m, 1H), 2.45-2.32 (m, 2H), 2.27 (dt, J=13.3, 6.6 Hz, 1H), 2.01-1.89 (m, 1H), 1.84 (dtd, J=14.5, 7.5, 6.1 Hz, 1H).

Compound 155c

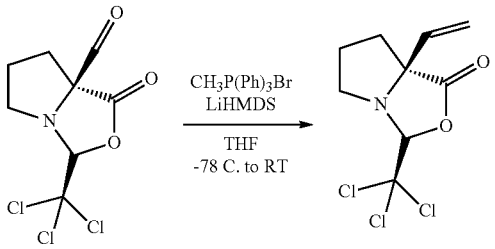

The solution of $CH_3P(Ph)_3Br$ (268 mg, 0.736 mmol) in anhydrous THF (5 mL) was cooled to −78° C. under $N_2$. LiHMDS (1 M in THF, 0.69 mL) was added dropwise via syringe. The mixture was stirred at 0° C. for 1 h then cooled down to −78° C. again. To it, was added the reactant carbaldehyde 155b (125 mg, 0.46 mmol) in anhydrous THF (5 mL) at −78° C. dropwise. The mixture was stirred at −78° C. to RT over 2 h period, then RT for 2 h. Reaction was monitored by TLC. After completion, the reaction was quenched by adding sat'd $NH_4Cl$. It was extracted with EtOAc twice, washed with brine. The organic layer was dried through ($Na_2SO_4$), and concentrated; the residue was purified by CombiFlash on silica gel column using EtOAC/Hexane as eluents to give (3S,7aS)-3-(trichloromethyl)-7a-vinyltetrahydropyrrolo[1,2-c]oxazol-1(3H)-one 30 mg, 24%.

$^1$H NMR (400 MHz, Chloroform-d) δ 5.99 (ddd, J=16.9, 10.3, 1.1 Hz, 1H), 5.49 (dt, J=17.0, 1.2 Hz, 1H), 5.20 (dd, J=10.3, 1.2 Hz, 1H), 3.45 (dt, J=11.1, 6.4 Hz, 1H), 3.18 (dt, J=11.1, 6.5 Hz, 1H), 2.16 (dt, J=12.4, 7.4 Hz, 1H), 2.01 (dt, J=12.6, 6.3 Hz, 1H), 1.91 (dtd, J=12.7, 6.3, 1.1 Hz, 1H), 1.87-1.76 (m, 1H).

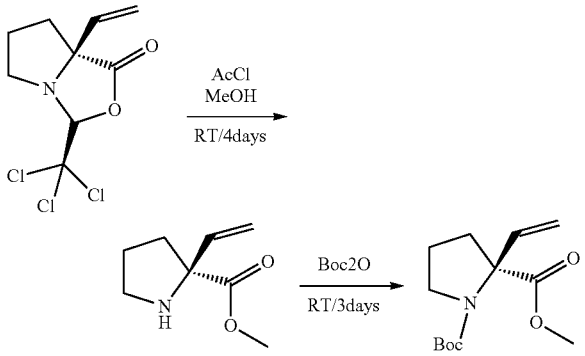

To a round bottom flask containing 1 mL of MeOH at 0° C. under $N_2$ was added AcCl (0.08 mL, 1.11 mmol) and stirred for 5 min. The reactant (3S,7aS)-3-(trichloromethyl)-7a-vinyltetrahydropyrrolo[1,2-c]oxazol-1(3H)-one (30 mg, 0.111 mmol) in 1 mL of MeOH was added dropwise via syringe. The mixture was stirred at 0° C. for 10 min then RT over 4 days period.

Reaction was monitored by TLC. After completion, the reaction was concentrated and co-evaporated with MeOH twice to give crude mixture of (S)-methyl 2-vinylpyrrolidine-2-carboxylate.

To the crude mixture of (S)-methyl 2-vinylpyrrolidine-2-carboxylate in DCM was added DIPEA/$Boc_2O$/DMAP (cat.) for standard Boc protection. After purified by CombiFlash on silica gel column using EtOAC/Hexane as eluents to give (S)-1-tert-butyl 2-methyl 2-vinylpyrrolidine-1,2-dicarboxylate 155d 14 mg, 50%.

$^1$H NMR (400 MHz, Chloroform-d) δ 6.37-6.20 (m, 1H), 5.14 (dd, J=10.2, 6.5 Hz, 1H), 5.07-4.91 (m, 1H), 3.70 (s, 1H), 3.66-3.43 (m, 2H), 2.17 (qd, J=12.2, 7.1 Hz, 1H), 1.98 (q, J=9.7, 8.7 Hz, 1H), 1.91-1.72 (m, 2H), 1.44-1.28 (m, 9H).

Compound 155e

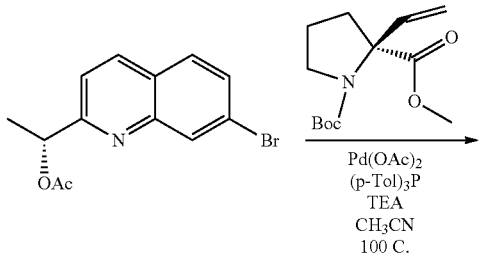

-continued

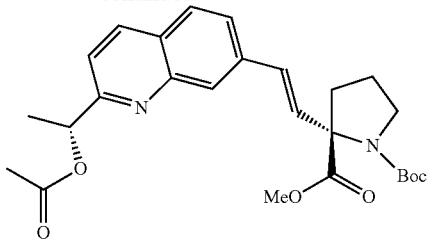

The Heck reaction to form compound (S)-1-tert-butyl 2-methyl 2-((E)-2-(2-((R)-1-acetoxyethyl)quinolin-7-yl)vinyl)pyrrolidine-1,2-dicarboxylate was done in the same manner as in Example 154 using 155d (20 mg) as reacting partner to give 155e (17 mg) in 51% yield $^1$H NMR (400 MHz, Chloroform-d) δ 8.12-8.05 (m, 1H), 8.02 (s, 1H), 7.95 (s, OH), 7.77-7.57 (m, 2H), 7.44-7.35 (m, 2H), 6.91 (dd, J=15.5, 10.5 Hz, 1H), 6.49 (d, J=15.8 Hz, 1H), 6.11-5.95 (m, 2H), 3.76 (d, J=1.5 Hz, 5H), 3.64 (td, J=10.0, 7.1 Hz, 2H), 2.94 (q, J=7.3 Hz, 1H), 2.47 (s, 1H), 2.36-2.21 (m, 2H), 2.18-2.04 (m, 7H), 1.97-1.79 (m, 3H), 1.66 (qd, J=8.6, 7.0, 3.5 Hz, 6H), 1.47 (s, 3H), 1.31 (d, J=1.8 Hz, 9H), 1.22 (dd, J=9.2, 5.1 Hz, 4H). LCMS [M+H]$^+$=469.28; Tr=1.12 min.

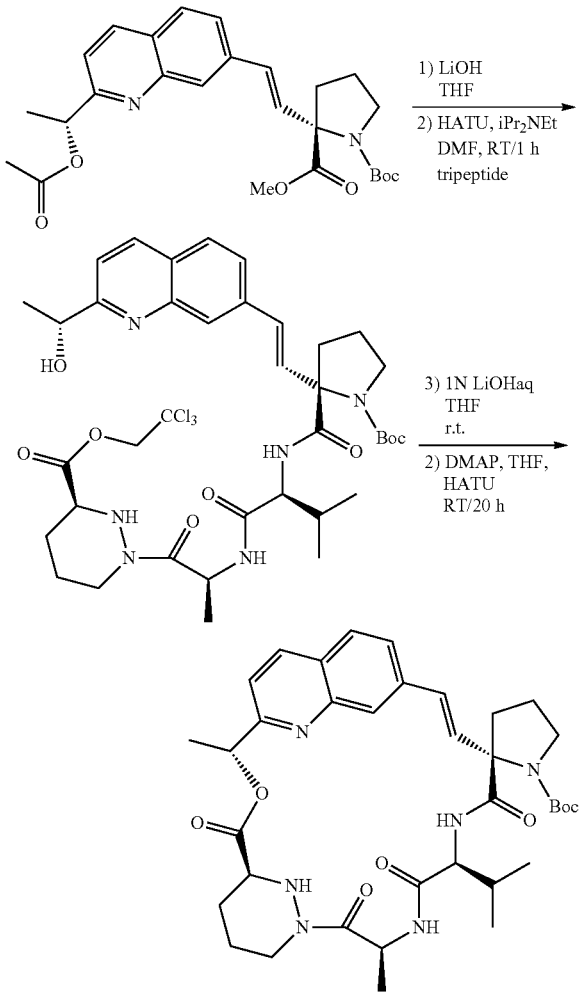

Compound 155 (2 mg) was completed in the same manner as in Example 154, starting from 155e (20 mg). The last step of macrocyclization used HATU/DIPEA/DMAP/THF condition.

$^1$H NMR (400 MHz, Methanol-$d_4$) δ 8.91 (d, J=7.0 Hz, 1H), 8.21 (d, J=8.4 Hz, 1H), 7.91-7.77 (m, 2H), 7.36 (dd, J=35.9, 9.3 Hz, 2H), 6.68-6.40 (m, 2H), 5.89 (q, J=6.9 Hz, 2H), 4.44-4.20 (m, 2H), 3.80 (d, J=9.6 Hz, 1H), 3.67-3.48 (m, 3H), 3.36 (q, J=7.2 Hz, 1H), 2.68 (d, J=12.5 Hz, 1H), 2.42 (q, J=7.4, 6.7 Hz, 1H), 2.08-1.74 (m, 3H), 1.76-1.48 (m, 10H), 1.49-1.14 (m, 14H). LCMS [M+H]$^+$=677.54; Tr=1.14 min.

Example 156

Compound 156

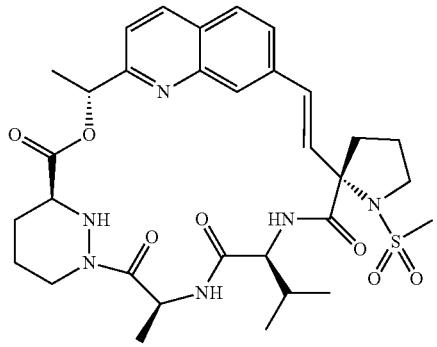

Compound 156a

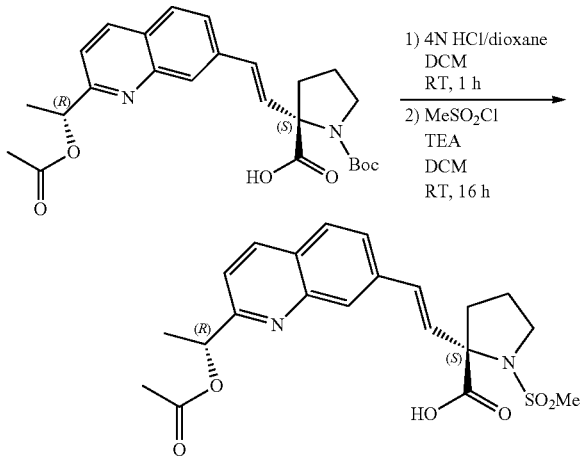

The Boc-protected reactant 155e (59 mg, 0.13 mmol) was treated with 4N HCl in Dioxane in DCM for 1 h to remove Boc group in standard condition. After concentrated to dryness, the residue was added DCM (2 mL), $Et_3N$ (0.067 mL, 0.78 mmol) and $MeSO_2Cl$ (0.020 mL, 0.26 mmol). The mixture was stirred at RT for 16 hour. After concentrated in vacuum, the residue was purified by HPLC to give (S)-2-((E)-2-(2-((R)-1-acetoxyethyl)quinolin-7-yl)vinyl)-1-(methylsulfonyl)pyrrolidine-2-carboxylic acid 156a, 36 mg, 64%.

LCMS [M+H]$^+$=433.53; Tr=0.95 min.

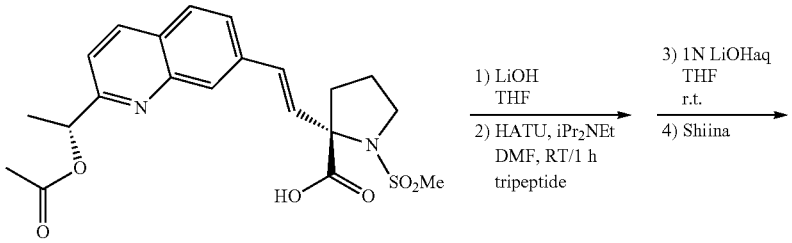

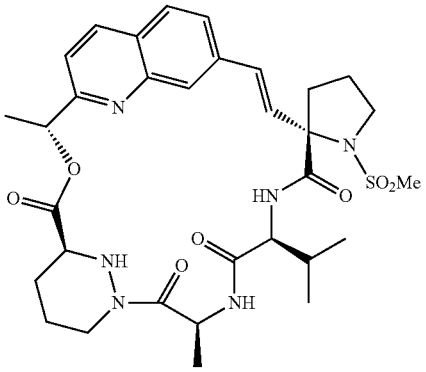

From 156a (59 mg), compound 156 (4 mg) was prepared in the same manner as in Example 155. The last step of macrocyclization used Shiina conditions.

$^1$H NMR (400 MHz, Methanol-$d_4$) δ 8.20 (d, J=8.4 Hz, 1H), 7.82 (d, J=1.6 Hz, 2H), 7.72 (s, 1H), 7.40 (dd, J=9.1, 5.5 Hz, 2H), 6.58 (s, 2H), 5.95-5.77 (m, 2H), 4.41-4.24 (m, 2H), 3.84-3.75 (m, 1H), 3.65-3.54 (m, 2H), 3.06 (s, 3H), 2.70 (td, J=12.6, 3.3 Hz, 1H), 2.46 (ddp, J=19.4, 12.9, 6.9, 6.3 Hz, 2H), 2.29-2.02 (m, 2H), 2.01-1.82 (m, 4H), 1.73-1.56 (m, 9H), 0.95-0.83 (m, 7H). LCMS $[M+H]^+$=655.21; Tr=2.05 min.

Examples 157 and 158

Compounds 157 and 158

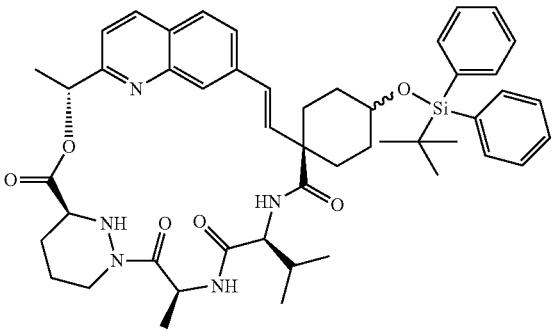

-continued

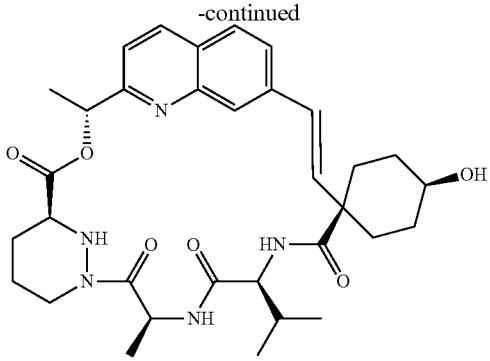

Compound 157a

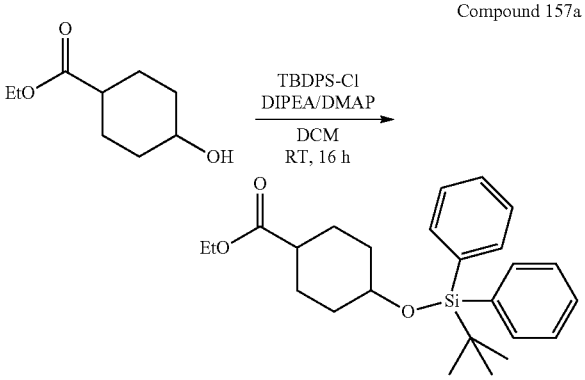

The reactant ethyl 4-hydroxycyclohexanecarboxylate (5.4 g, 30.73 mmol) in DCM (100 mL) was treated with DIPEA (16.06 mL, 92.2 mmol), DMAP (4.13 g, 30.80 mmol) and TBDPS-Cl (11.8 mL, 46.1 mmol) at RT for 16 h. After concentrated in vacuum, the residue was purified by CombiFlash on silica gel column using EtOAC/Hexane as eluents to give ethyl 4-(tert-butyldiphenylsilyloxy)cyclohexanecarboxylate 157a, 12.6 g, 99% yield.

$^1$H NMR (400 MHz, Chloroform-d) δ 7.77-7.58 (m, 4H), 7.47-7.29 (m, 6H), 4.09 (dq, J=34.5, 7.1 Hz, 2H), 2.32-1.96 (m, 2H), 1.92-1.57 (m, 2H), 1.42-1.28 (m, 2H), 1.27-1.17 (m, 3H), 1.05 (s, 9H). LCMS $[M+H]^+$=411.44; Tr=1.79 min.

Compound 157b

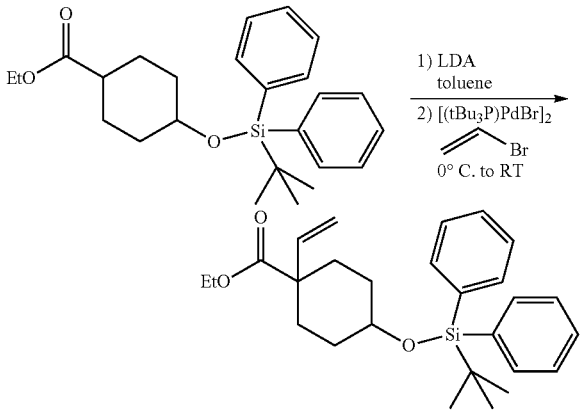

To the solution of LDA (2.0 M in Hexane, 2.44 mL, 4.876 mmol) in anhydrous toluene (10 mL) at 0° C. under $N_2$, was added the solution of the reactant 157a (1.82 g, 4.43 mmol) in toluene (10 mL) slowly. It was stirred at 0° C. for 10 min, and RT for 30 min. It was added $[(tBu3P)PdBr]_2$ (34.4 mg, 0.044 mmol) in 5 mL of toluene followed by bromoethene (1M in 5.76 mL, 5.76 mmol) at RT and stirred for 24 h. After completion of the reaction, it was diluted with EtOAc, quenched with 1M AcOH (aq.) (10 mL) to make the solution as pH about 7-7.5. It was extracted with EtOAc, washed with sat'd $NaHCO_3$ solution once and brine once. The organic layer was dried through ($Na_2SO_4$), and concentrated; the residue was purified by CombiFlash on silica gel column using EtOAC/Hexane as eluents. Yield: 1.15 g, 63%. (it was a mixture of SM and vinylcyclohexanecarboxylate cis/trans vinyl over oxygen)(SM:Product=2:1, cis:trans=4:1).

Compound 157c

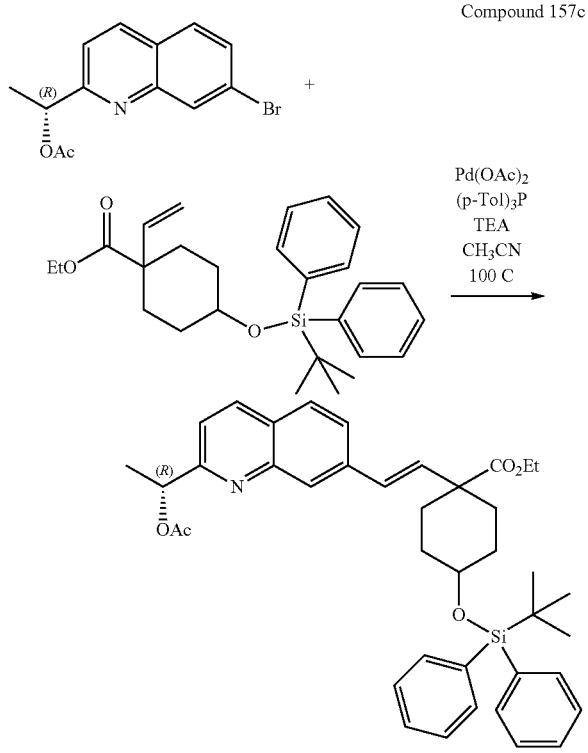

The Heck reaction to form compound (R,E)-ethyl 1-(2-(2-(1-acetoxyethyl)quinolin-7-yl)vinyl)-4-(tert-butyldiphenylsilyloxy)cyclohexanecarboxylate was done in the same manner as in Example 154 using the mixture of 157b (1.15 g) to generate intermediate product 157c (356 mg) in 63% yield LCMS $[M+H]^+$=650.64; Tr=1.62 min.

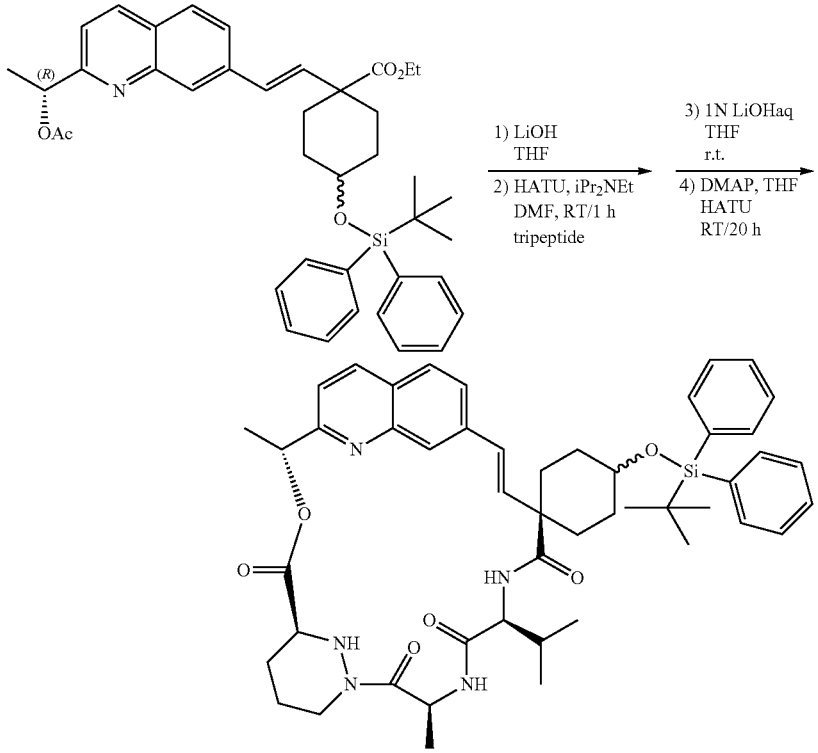

From 157c (356 mg), compound 157 was prepared in the same manner as in Example 154. The last step of macrocyclization was performed using HATU conditions to generate 157 (53 mg) in 54% yield.

$^1$H NMR (400 MHz, Methanol-$d_4$) δ 8.64 (d, J=7.0 Hz, 1H), 8.15 (d, J=8.5 Hz, 1H), 7.72 (d, J=8.6 Hz, 1H), 7.66 (ddd, J=8.0, 4.6, 1.7 Hz, 5H), 7.54 (s, 1H), 7.39 (dddd, J=13.4, 10.7, 8.0, 5.3 Hz, 6H), 6.31-6.14 (m, 2H), 5.87 (d, J=6.8 Hz, 1H), 5.74-5.63 (m, 1H), 4.45-4.17 (m, 2H), 3.74 (d, J=16.0 Hz, 2H), 2.79 (s, 3H), 2.71 (s, 1H), 2.21 (d, J=14.0 Hz, 2H), 2.15-1.92 (m, 3H), 1.90-1.40 (m, 4H), 1.68 (d, J=6.8 Hz, 3H), 1.60 (d, J=7.2 Hz, 3H), 1.35-1.23 (m, 4H), 1.02 (s, 9H), 1.02-0.95 (m, 2H). LCMS $[M+H]^+$=844.41; Tr=2.86 min.

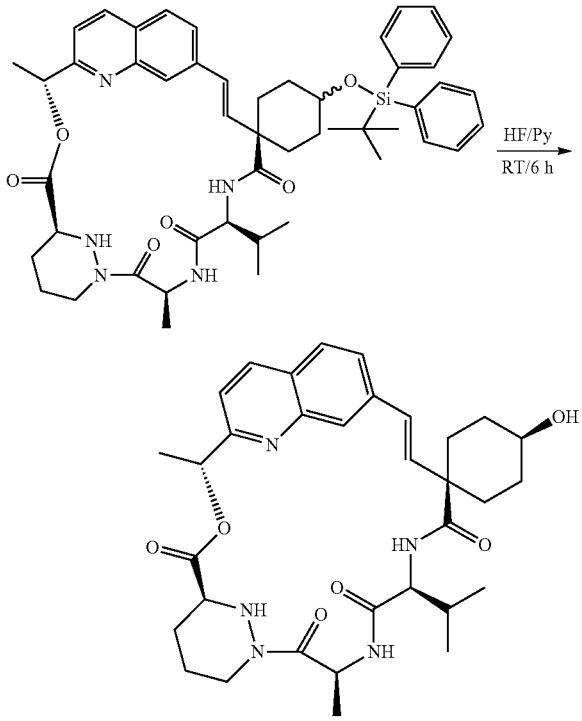

In a plastic reaction vessel, the starting material 157 (49 mg, 0.058 mmol) dissolved in THF (5 mL) was treated with HF-Pyridine solution (1 mL). It was stirred at RT for 3 h. The reaction was not very clean and both the starting material and product started to decompose at this condition. 5 mg of 158 was isolated after work up and HPLC. (cis:trans=3.4:1 by NMR)

$^1$H NMR (400 MHz, Methanol-$d_4$) δ 8.64 (d, J=7.0 Hz, 1H), 8.16 (dd, J=8.5, 2.9 Hz, 1H), 7.80-7.67 (m, 2H), 7.56 (d, J=11.9 Hz, 1H), 7.44 (d, J=9.6 Hz, 1H), 7.37 (dd, J=8.5, 4.5 Hz, 1H), 6.37-6.17 (m, 2H), 5.88 (q, J=6.8 Hz, 1H), 5.67 (ddt, J=13.9, 10.8, 7.2 Hz, 1H), 4.43-4.24 (m, 2H), 3.79-3.70 (m, 1H), 3.59 (tt, J=10.4, 4.4 Hz, 1H), 2.72 (td, J=12.6, 3.8 Hz, 1H), 2.41-2.24 (m, 2H), 2.06-1.80 (m, 5H), 1.79-1.59 (m, 5H), 1.56 (d, J=7.3 Hz, 3H), 1.42 (tdd, J=24.9, 18.0, 11.3 Hz, 2H), 1.27 (s, 1H), 0.97 (dd, J=6.7, 4.6 Hz, 6H), 0.93 (dd, J=6.8, 4.1 Hz, 1H). LCMS $[M+H]^+$=606.26; Tr=1.97 min.

Example 159

Compound 159

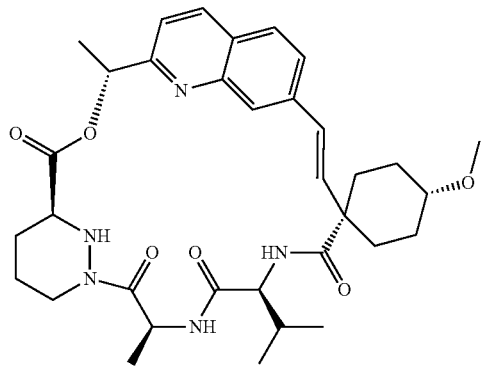

Compound 159a

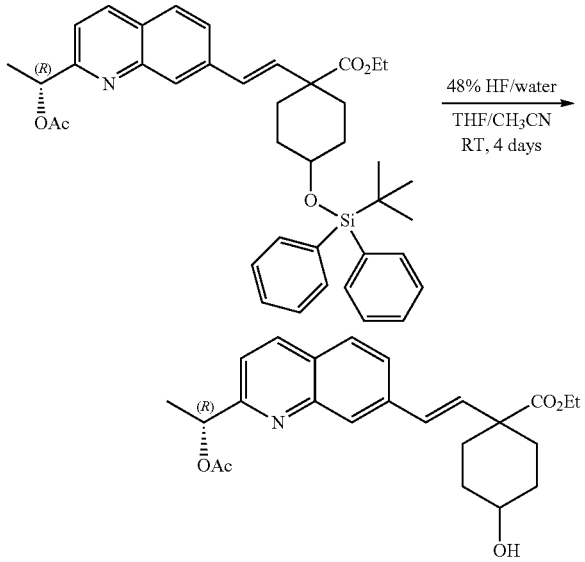

The reactant 157c (1096 mg, 1.7 mmol) in THF/$CH_3CN$ (100/10 mL) was treated with 48% HF in water (7 mL) at RT for 4 days. After quenched with sat'd $NaHCO_3$ solution until pH>7, it was extracted with EtOAc and washed with brine once. The organic layer was dried through ($Na_2SO_4$), and concentrated; the residue was purified by CombiFlash on silica gel column using EtOAC/Hexane as eluents. It gave 214 mg 159a, 31%. (cis:trans=4:1 by NMR).

$^1$H NMR (400 MHz, Chloroform-d) δ 8.07 (d, J=8.4 Hz, 1H), 8.01-7.94 (m, 1H), 7.70 (dd, J=8.5, 4.0 Hz, 1H), 7.55 (ddd, J=10.3, 8.5, 1.7 Hz, 1H), 7.38 (d, J=8.4 Hz, 1H), 6.62 (dd, J=22.0, 16.3 Hz, 1H), 6.36 (dd, J=16.3, 5.2 Hz, 1H), 6.02 (qd, J=6.7, 2.5 Hz, 1H), 4.16 (dq, J=16.5, 7.1 Hz, 2H), 3.65 (tt, J=9.5, 4.1 Hz, 1H), 2.61-2.27 (m, 2H), 2.13 (d, J=1.1 Hz, 3H), 1.98-1.89 (m, 2H), 1.64 (dd, J=6.6, 2.0 Hz, 3H), 1.57-1.34 (m, 4H), 1.25 (dt, J=12.1, 7.1 Hz, 3H). LCMS $[M+H]^+$=412.05; Tr=2.17 min.

Compound 159b

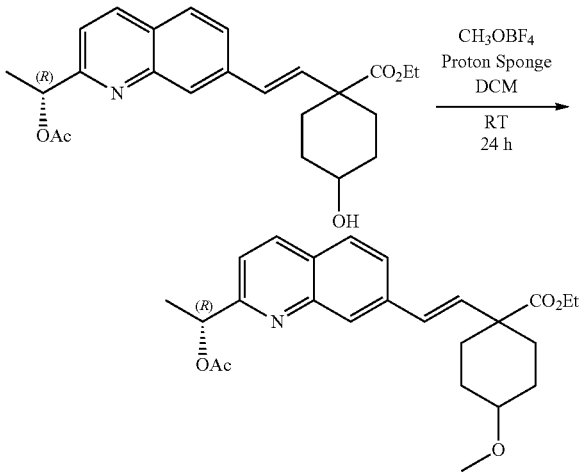

The reactant 159a (214 mg, 0.52 mmol) in DCM (25 mL) was added with $CH_3OBF_4$ (1.21 g, 7.80 mmol) and Proton Sponge (1.67 g, 7.80 mmol) and stirred at RT for 24 h. After quenched with water, it was extracted with DCM twice. The organic layer was dried through ($Na_2SO_4$), and concentrated; the residue was purified by CombiFlash on silica gel column using EtOAC/Hexane as eluents. The fractions containing desired product with proton sponge contamination was concentrated. This mixture was diluted with EtOAc, washed with 0.5N HCl (aq.) solution twice and brine once. After dried ($Na_2SO_4$), and concentrated, it gave 12 mg 159b product, 5% yield. Most of the by-product was bis-methylated.

LCMS $[M+H]^+$=426.05; Tr=2.45 min.

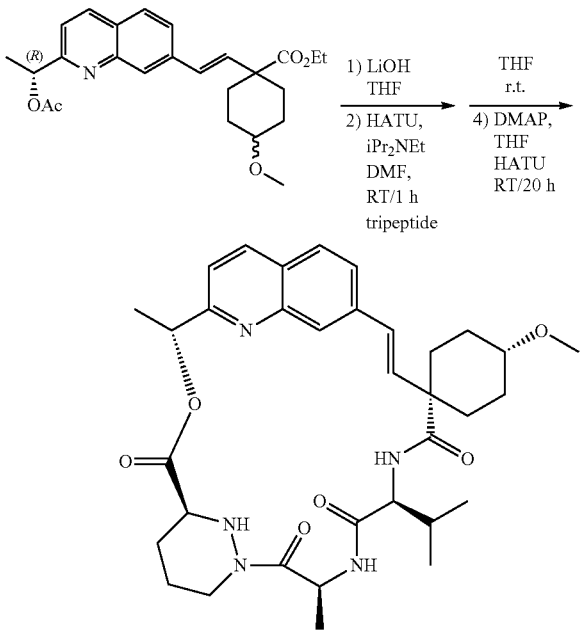

From compound 159b (12 mg), compound 159 was prepared in the same manner as in Example 154. The last step of macrocyclization used HATU coupling conditions to effect ring closure, which gave 2 mg of compound 159.

$^1$H NMR (400 MHz, $CDCl_3$) δ 8.08 (d, J=8.4 Hz, 1H), 7.74 (s, 1H), 7.68 (d, J=8.5 Hz, 1H), 7.58 (d, J=8.6 Hz, 1H), 6.47 (d, J=7.8 Hz, 1H), 6.37 (d, J=16.4 Hz, 1H), 6.28-6.12 (m, 2H), 5.94 (t, J=6.9 Hz, 1H), 5.77-5.67 (m, 1H), 4.51 (d, J=13.1 Hz, 1H), 4.17 (t, J=9.6 Hz, 1H), 3.74 (m, 1H), 3.34 (s, 3H), 3.26-3.15 (m, 1H), 2.63 (d, J=12.8 Hz, 1H), 2.42 (d, J=13.9 Hz, 1H), 2.14 (d, J=15.3 Hz, 1H), 2.03 (m, 1H), 1.99-1.76 (m, 8H), 1.73 (d, J=6.9 Hz, 3H), 1.68 (s, 1H), 1.57 (d, J=7.1 Hz, 3H), 1.39 (t, J=10.9 Hz, 1H), 0.96 (dd, J=6.7, 5.2 Hz, 3H), 0.90-0.80 (m, 2H). LCMS $[M+H]^+$=620.35; Tr=1.13 min.

Examples 160 and 161

Compounds 160 and 161

160

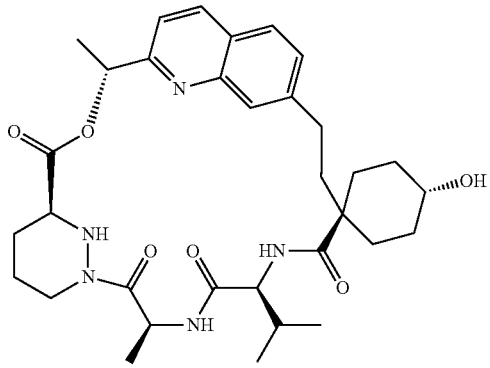

161

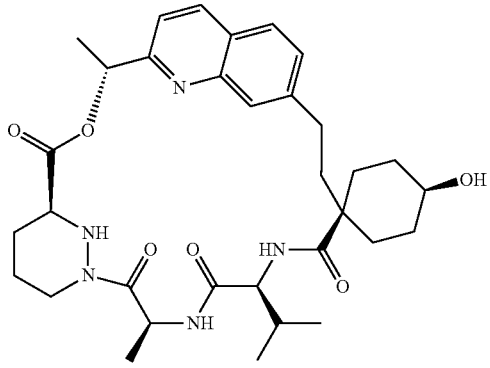

Compound 160a

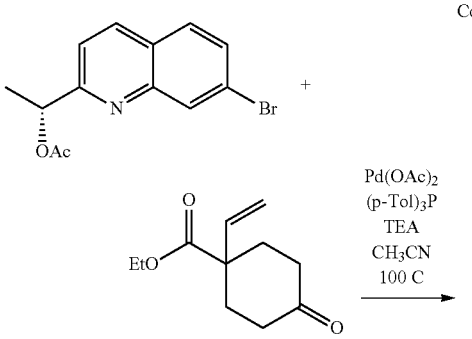

-continued

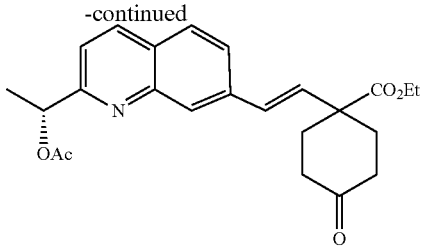

The Heck reaction to form compound (R,E)-ethyl 1-(2-(2-(1-acetoxyethyl)quinolin-7-yl)vinyl)-4-oxocyclohexanecarboxylate 160a (3.22 g) was done in the same manner as in Example 154 using ethyl 4-oxo-1-vinylcyclohexanecarboxylate (Obtained from Small Inc.) (2.88 g), in 80% yield.

$^1$H NMR (400 MHz, Chloroform-d) δ 8.09 (d, J=8.5 Hz, 1H), 8.02 (d, J=1.6 Hz, 1H), 7.73 (d, J=8.5 Hz, 1H), 7.56 (dd, J=8.5, 1.7 Hz, 1H), 7.41 (d, J=8.5 Hz, 1H), 6.74-6.36 (m, 2H), 6.02 (q, J=6.7 Hz, 1H), 4.24 (q, J=7.1 Hz, 2H), 2.59 (dt, J=12.3, 5.5 Hz, 2H), 2.50-2.39 (m, 4H), 2.13 (s, 3H), 2.07 (d, J=6.8 Hz, 2H), 1.65 (d, J=6.7 Hz, 3H), 1.29 (t, J=7.1 Hz, 3H). LCMS $[M+H]^+$=410.27; Tr=1,11 min.

Compounds 160b and 160c

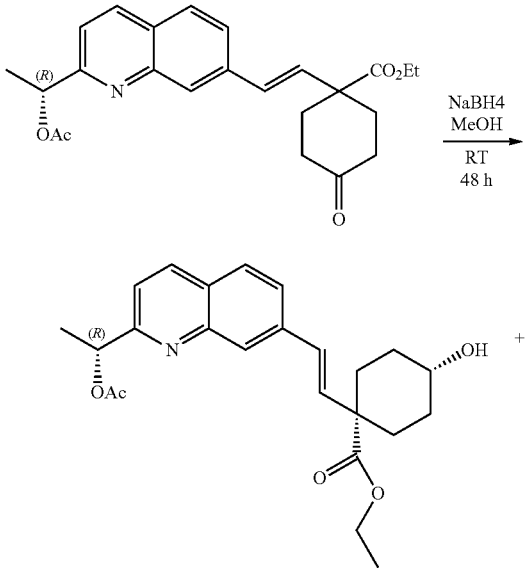

cis-isomer

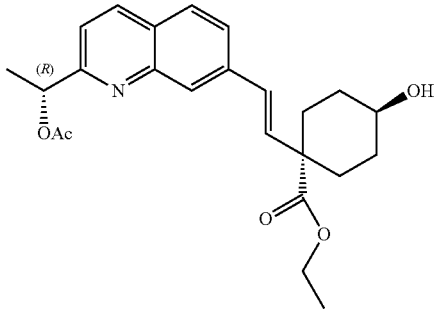

trans-isomer

-continued

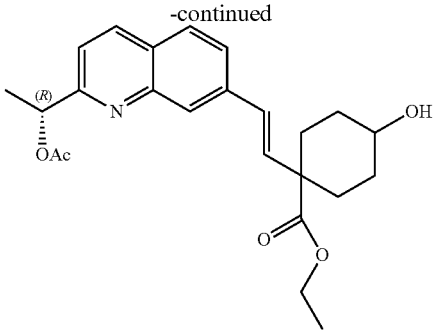

By-Product

The reactant ketone 160a (3.2 g, 7.81 mmol) in MeOH (40 mL) in a flask equipped with a dropping funnel was added a MeOH (40 mL) solution of $NaBH_4$ (355 mg, 9.38 mmol) dropwise at 0° C. It was stirred at 0° C. for 10 min, and RT for 24 h. After quenched with sat'd $NH_4Cl$ solution, it was extracted with EtOAc and washed with brine once. The organic layer was dried through ($Na_2SO_4$), and concentrated. The cis and trans isomers were separated by CombiFlash on silica gel column using EtOAC/Hexane as eluents. On TLC with EA/HEX=1/1, Rf of trans=0.4, Rf of cis=0.3, Rf of by-product=0.3. Yield: trans-isomer 160c was 200 mg, cis-isomer 160b was 420 mg, by-product was 750 mg. Total yield of (cis+trans) was 620 mg, 19%.

160c:

$^1$H NMR (400 MHz, Chloroform-d) δ 8.09 (d, J=8.5 Hz, 1H), 8.01 (d, J=1.7 Hz, 1H), 7.71 (d, J=8.5 Hz, 1H), 7.57 (dd, J=8.5, 1.7 Hz, 1H), 7.39 (d, J=8.5 Hz, 1H), 6.51 (dd, J=110.7, 16.3 Hz, 2H), 6.03 (q, J=6.7 Hz, 1H), 4.15 (q, J=7.1 Hz, 2H), 3.84 (dt, J=7.4, 3.8 Hz, 1H), 2.14 (s, 3H), 2.07 (dd, J=8.5, 4.1 Hz, 2H), 2.00 (ddd, J=13.6, 8.6, 4.1 Hz, 2H), 1.79 (ddt, J=12.4, 7.9, 3.8 Hz, 2H), 1.65 (d, J=6.7 Hz, 3H), 1.63-1.54 (m, 2H), 1.24 (t, J=7.1 Hz, 3H).

LCMS $[M+H]^+$=412.39; Tr=3.16 min

160b:

$^1$H NMR (400 MHz, Chloroform-d) δ 8.08 (d, J=8.4 Hz, 1H), 7.98 (s, 1H), 7.70 (d, J=8.5 Hz, 1H), 7.54 (dd, J=8.5, 1.7 Hz, 1H), 7.39 (d, J=8.5 Hz, 1H), 6.67-6.25 (m, 2H), 6.02 (q, J=6.7 Hz, 1H), 4.19 (q, J=7.1 Hz, 2H), 3.66 (tt, J=9.4, 4.2 Hz, 1H), 2.50-2.38 (m, 2H), 2.14 (s, 3H), 2.00-1.89 (m, 2H), 1.65 (d, J=6.7 Hz, 3H), 1.59-1.36 (m, 4H), 1.27 (t, J=7.1 Hz, 3H). LCMS $[M+H]^+$=412.39; Tr=3.14 min

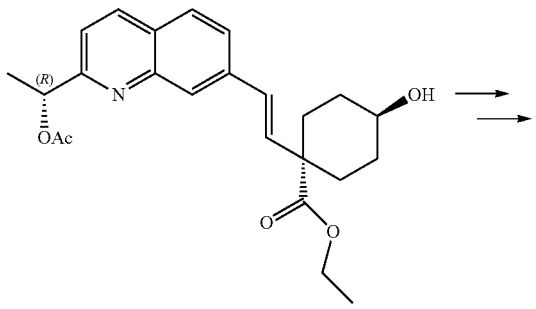

-continued

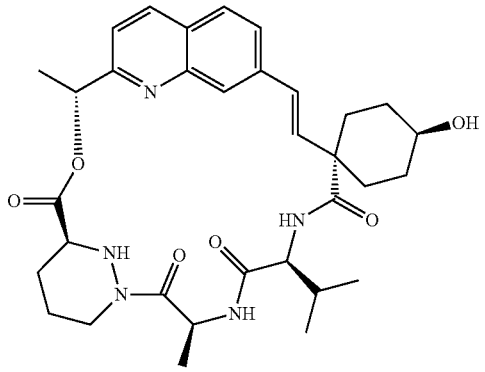

The compound 160 (23 mg) was prepared in the same manner as in Compound 161 starting from trans isomer 160c (1R,4R)-ethyl 1-((E)-2-(2-((R)-1-acetoxyethyl)quinolin-7-yl)vinyl)-4-hydroxycyclohexanecarboxylate (192 mg). $^1$H NMR (400 MHz, Methanol-$d_4$) δ 8.57 (d, J=7.1 Hz, 1H), 8.17 (d, J=8.4 Hz, 1H), 7.85-7.71 (m, 2H), 7.59 (s, 1H), 7.36 (dd, J=13.8, 8.9 Hz, 2H), 6.57-6.18 (m, 2H), 5.88 (q, J=6.8 Hz, 1H), 5.65 (t, J=7.1 Hz, 1H), 4.43-4.18 (m, 2H), 3.80 (dd, J=29.3, 7.5 Hz, 2H), 2.70 (s, 1H), 2.18 (t, J=11.6 Hz, 1H), 2.06-1.91 (m, 4H), 1.92-1.73 (m, 1H), 1.70 (d, J=6.9 Hz, 4H), 1.64 (d, J=10.2 Hz, 1H), 1.27 (s, 1H), 0.93 (dd, J=6.6, 2.8 Hz, 6H). LCMS $[M+H]^+$=606.27; Tr=1.96 min.

Compound 160d

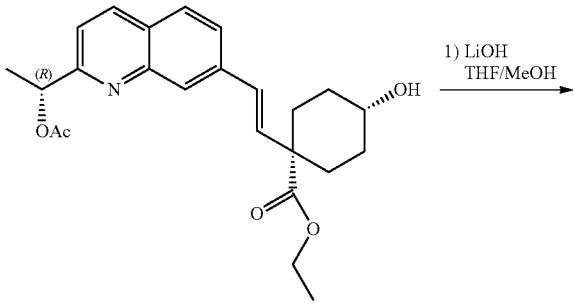

-continued

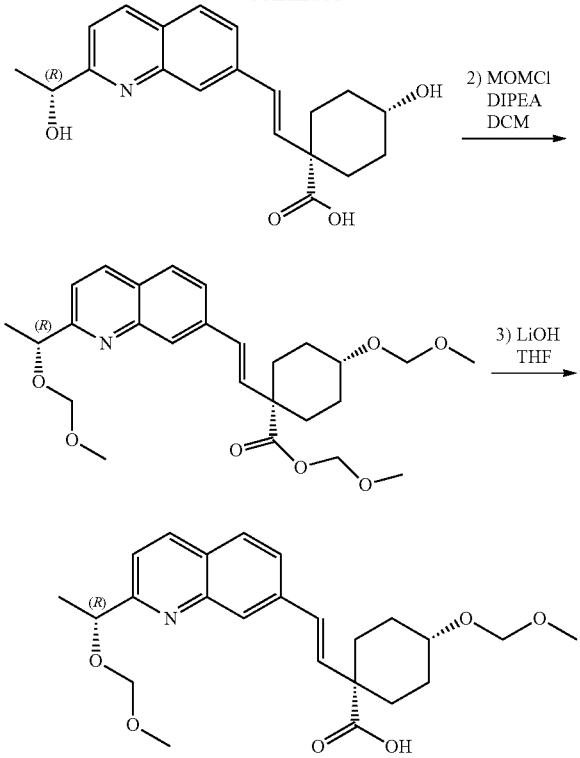

The hydrolysis of 160b (350 mg) with 1N LiOH in THF/MeOH to form (1s,4S)-4-hydroxy-1-((E)-2-(2-((R)-1-hydroxyethyl)quinolin-7-yl)vinyl)cyclohexanecarboxylic acid was done in 3 days in the standard procedure in quantitative yield. LCMS $[M+H]^+$=342.17; Tr=1.50 min.

The reactant cyclohexanecarboxylic (237 mg, 0.695 mmol) in DCM (10 mL) was added DIPEA (1.94 mL, 11.2 mmol) and MOMCl (0.634 mL, 8.34 mmol) It was stirred at RT for 24 h. After quenched with MeOH (5 mL), it was concentrated; the residue was purified by CombiFlash on silica gel column using EtOAC/Hexane as eluents to give 241 mg MOM protected product, 73% yield. LCMS $[M+H]^+$=474.12; Tr=2.30 min.

The hydrolysis of MOM protected intermediate (122 mg, 0.258 mmol) with 1N LiOH in THF to form (1s,4S)-4-(methoxymethoxy)-1-((E)-2-(2-((R)-1-(methoxymethoxy) ethyl)quinolin-7-yl)vinyl)cyclohexanecarboxylic acid was done in 3 h at 60° C. in the standard procedure in quantitative yield. LCMS $[M+H]^+$=430.12; Tr=2.01 min.

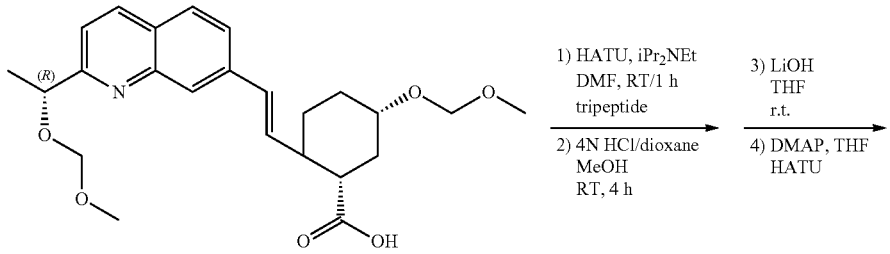

-continued

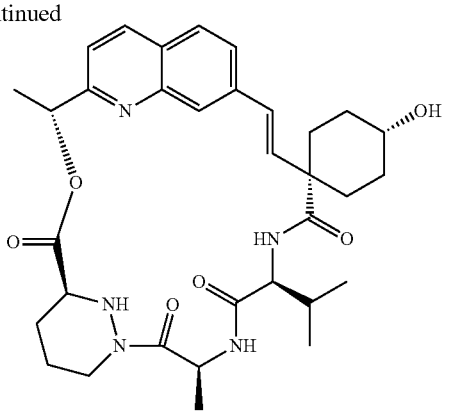

From carboxylate 160d (0.258 mmol), compound 161 was prepared in the same manner as in Example 154. After HATU coupling with tripeptide, it was treated with 4N HCl in dioxane and MeOH to remove MOM protecting group followed by LiOH hydrolysis and standard macrocyclization. It gave 23 mg of compound 161.

$^1$H NMR (400 MHz, Methanol-$d_4$) δ 8.07 (d, J=8.5 Hz, 1H), 7.58 (d, J=8.5 Hz, 1H), 7.39 (d, J=1.6 Hz, 1H), 7.33-7.19 (m, 2H), 5.83 (q, J=6.8 Hz, 1H), 5.52 (q, J=7.3 Hz, 1H), 4.36 (d, J=12.2 Hz, 1H), 4.27 (d, J=10.6 Hz, 2H), 3.70-3.37 (m, 3H), 2.71 (dtd, J=25.2, 13.0, 4.1 Hz, 2H), 2.46-2.17 (m, 3H), 2.02-1.92 (m, 1H), 1.90-1.67 (m, 6H), 1.66-1.46 (m, 4H), 1.45-1.21 (m, 3H), 1.17 (dd, J=9.4, 2.9 Hz, 3H), 1.14-1.00 (m, 2H), 0.88 (dd, J=6.6, 3.2 Hz, 6H). LCMS $[M+H]^+$=606.34; Tr=1.95 min.

From carboxylate 160d, compound 161 was prepared in the same manner as in Example 154. After HATU coupling with tripeptide, it was treated with 4N HCl in dioxane and MeOH to remove MOM protecting group followed by LiOH hydrolysis and standard macrocyclization.

LCMS $[M+H]^+$=606.34

$^1$H NMR (400 MHz, Methanol-$d_4$) δ 8.07 (d, J=8.5 Hz, 1H), 7.58 (d, J=8.5 Hz, 1H), 7.39 (d, J=1.6 Hz, 1H), 7.33-7.19 (m, 2H), 5.83 (q, J=6.8 Hz, 1H), 5.52 (q, J=7.3 Hz, 1H), 4.36 (d, J=12.2 Hz, 1H), 4.27 (d, J=10.6 Hz, 2H), 3.70-3.37 (m, 3H), 2.71 (dtd, J=25.2, 13.0, 4.1 Hz, 2H), 2.46-2.17 (m, 3H), 2.02-1.92 (m, 1H), 1.90-1.67 (m, 6H), 1.66-1.46 (m, 4H), 1.45-1.21 (m, 3H), 1.17 (dd, J=9.4, 2.9 Hz, 3H), 1.14-1.00 (m, 2H), 0.88 (dd, J=6.6, 3.2 Hz, 6H).

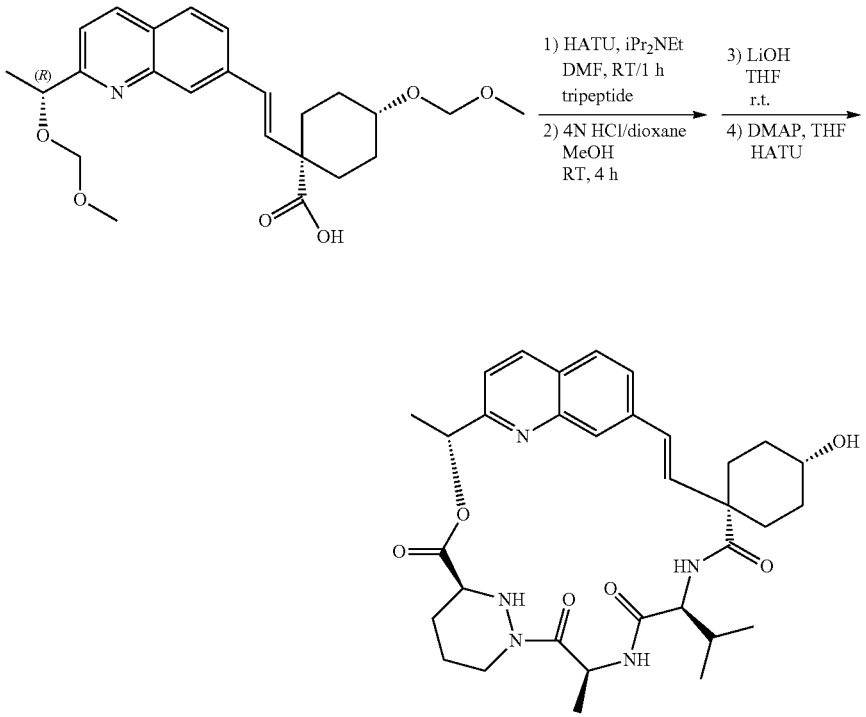

Example 162

Compound 162

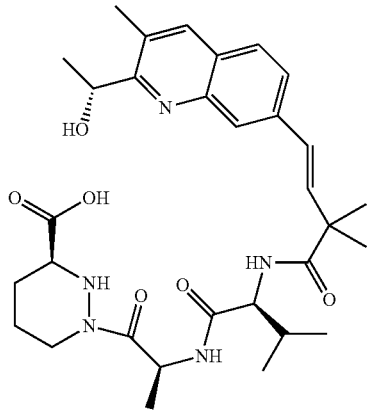

Example 163

Compound 163

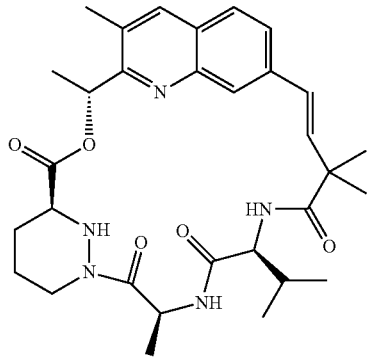

Compound 163a

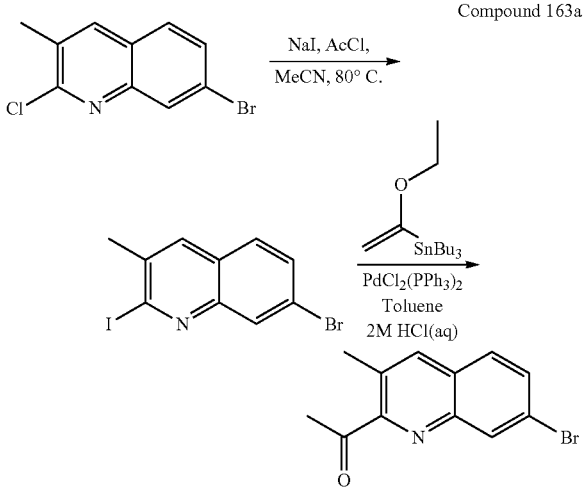

To a solution of 7-Bromo-2-chloro-3-methylquinoline (obtained from BioBlocks, Inc.), (2.0 g, 7.8 mmol) in anhydrous acetonitrile (50 mL) were added sodium iodide (11.7 g, 78 mmol) and acetyl chloride (0.92 g, 11.7 mmol). The mixture was heated to 80° C. for 4 h. The reaction mixture was cooled to room temperature, diluted with dichloromethane (200 mL), washed with 20% potassium carbonate aqueous solution, 20% sodium thiosulfate aqueous solution and dried over $Na_2SO_4$. After concentration, the crude residue was purified by silica gel chromatography using iso-hexanes/ethyl acetate 1:0 to 1:1 to yield the intermediate iodide (2.3 g, 84%) as a solid. LCMS (m/z) 348.1/350.1 [M+H]. Tr=2.53 min Then, a mixture of this iodide (2.2 g, 6.3 mmol) and tributyl(1-ethoxyvinyl)tin (2.73 g, 2.55 mL, 7.56 mmol) in 1,4-dioxane (20 mL) was degassed for 20 minutes. Bis (triphenylphosphine)palladium(II) dichloride (440 mg, 0.63 mmol) was added and the reaction mixture stirred under nitrogen and heated at 80° C. for 3 hours before allowing to cool. The volatiles were evaporated and the residue suspended in 1,4-dioxane (15 mL), 2 M aqueous hydrochloric acid (15 mL) was added and the reaction mixture stirred for 45 minutes and then evaporated to remove the volatiles. The residue was diluted with water and extracted with ethyl acetate (2×) and the combined organic extracts were washed with brine, dried over magnesium sulfate, filtered and evaporated. The product was purified by chromatography using silica gel doped with 10% w/w potassium carbonate eluting using a gradient of iso-hexanes/ethyl acetate 1:0 to 9:1 to afford the title compound 3 (1.5 g, 90%) as a yellow solid. $^1$H NMR (400 MHz, Chloroform-d) δ 8.31 (d, J=2.3 Hz, 1H), 8.11-7.85 (m, 1H), 7.82-7.55 (m, 2H), 2.80 (s, 3H), 2.66 (d, J=1.0 Hz, 3H). LCMS (m/z) 264.0/266.0 [M+H]. Tr=2.58 min.

Compound 163b

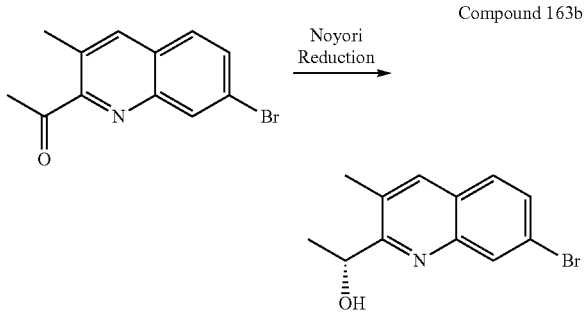

Dichloro (p-cymene) ruthenium(II) dimer (12 mg, 0.019 mmol) and (1R,2R)-(−)-N-p-tosyl-1,2-diphenylethylenediamine (17 mg, 0.045 mmol) were suspended in degassed water (7.5 mL) and the mixture was degassed with nitrogen for 15 minutes. The mixture was stirred at 70° C. under nitrogen for 90 minutes. The resulting turbid orange mixture was allowed to cool to room temperature. 163a (1.0 g, 3.78 mmol) followed by degassed tetrahydrofuran (7.5 mL) and sodium formate (1.29 g, 18.9 mmol) were added and the reaction mixture was degassed with nitrogen for 5 minutes. The reaction mixture was vigorously stirred at 40° C. for 3 hours and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ ethyl acetate 2:1 to afford the title compound 163b (0.91 g, 91%) as a purple solid. $^1$H NMR (400 MHz, Chloroform-d) δ 8.36-8.07 (m, 1H), 8.03-7.78 (m, 1H), 7.78-7.47 (m, 2H), 5.35-4.91 (m, 2H), 2.44 (d, J=1.0 Hz, 3H), 1.46 (d, J=6.4 Hz, 3H). LCMS (m/z) 266.0/268.0 [M+H]. Tr=1.77 min.

Compound 163c

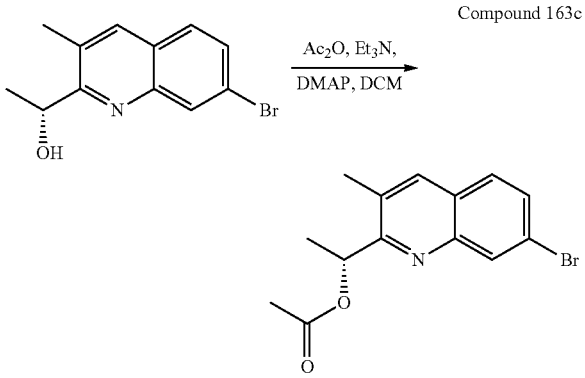

To a solution of 163b (0.9 g, 3.4 mmol) in anhydrous dichloromethane (20 mL) were added triethylamine (1.0 g, 10.2 mmol) and acetyl anhydride (0.69 g, 6.8 mmol). The mixture was stirred at room temperature for 1 h. After concentration, the crude was diluted with EtOAc (50 mL), washed with water (2×) and dried over $Na_2SO_4$. After concentration, the crude residue was purified by silica gel chromatography using iso-hexanes/ethyl acetate 1:0 to 1:1 to give the title compound 163c (1.0 g, 96%) as solid. LCMS (m/z) 308.1/310.1 [M+H]. Tr=2.44 min.

Compound 163d

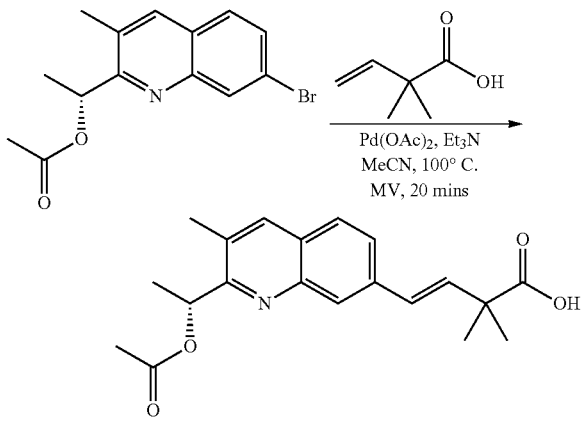

To a mixture of 163c (400 mg, 1.30 mmol), triethylamine (394 mg 3.9 mmol) and 2,2-dimethylbut-3-enoic acid (223 mg 1.95 mmol) in anhydrous acetonitrile (7 mL) in a microwave tube was added palladium acetate (29 mg, 0.13 mmol) and tri-o-tolyphosphine (79 mg, 0.26 mmol). The reaction mixture was heated to 100° C. for 20 minutes and diluted with EtOAc (30 mL). The crude was washed with water and dried over $Na_2SO_4$. After concentration, the residue was purified by silica gel chromatography using a gradient of iso-hexanes/ethyl acetate 1:0 to 0:1 to afford the title compound 163d as a yellow oil (300 mg, 67%). $^1$H NMR (400 MHz, Chloroform-d) δ 10.06-9.39 (br, 1H), 8.05 (dd, J=9.1, 2.3 Hz, 1H), 7.93-7.75 (m, 1H), 7.74-7.41 (m, 2H), 6.62 (m, 2H), 6.14 (dt, J=12.6, 6.6 Hz, 1H), 2.51 (m, 3H), 2.09 (d, J=1.6 Hz, 3H), 1.65 (m, 3H), 1.47 (m, 6H). LCMS (m/z) 342.1 [M+H]. Tr=2.31 min.

Compound 163e

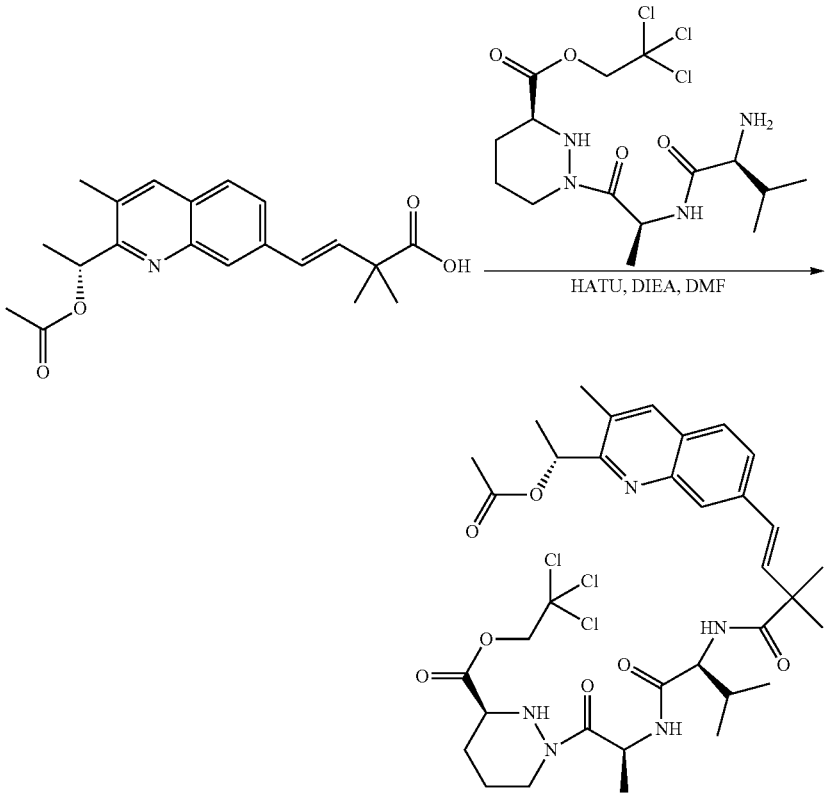

To 163d (300 mg, 0.88 mmol) in anhydrous N,N-dimethylformamide (2 mL) at room temperature and under an atmosphere of nitrogen was added N,N-diisopropylethylamine (568 mg, 4.39 mmol) and 2-(1H-7-azabenzotriazol-1-yl)-1,1,3,3-tetramethyl uronium hexafluorophosphate methanaminium (368 mg, 0.97 mmol). The solution was stirred at room temperature for 3 minutes before adding a solution of (S)-1-[(S)-2-((S)-2-amino-3-methyl-butyrylamino)-propionyl]-hexahydro-pyridazine-3-carboxylic acid 2,2,2-trichloro-ethyl ester in anhydrous N,N-dimethylformamide (2 mL). The reaction was stirred for 1 hour. The reaction was quenched with water and extracted with ethyl acetate (2×). The combined organic layers were dried over sodium sulfate, filtered and concentrated in vacuo. The residue was purified by silica gel chromatography using iso-hexanes/ethyl acetate 1:0 to 0:1 to give the title compound 163e (470 mg, 70%) as a white solid. $^1$H NMR (400 MHz, Methanol-$d_4$) δ 8.01 (s, 1H), 7.96 (s, 1H), 7.81-7.69 (m, 2H), 6.78 (d, J=16.3 Hz, 1H), 6.66 (d, J=16.3 Hz, 1H), 6.11 (q, J=6.7 Hz, 1H), 5.33 (q, J=7.0 Hz, 1H), 4.96 (d, J=12.1 Hz, 1H), 4.75 (d, J=12.1 Hz, 1H), 4.24 (d, J=7.2 Hz, 1H), 3.76 (dd, J=7.8, 4.2 Hz, 1H), 2.10 (s, 3H), 2.05 (m, 1H), 1.99 (s, 3H), 1.84 (d, J=11.9 Hz, 2H), 1.62 (d, J=6.7 Hz, 6H), 1.44 (d, J=2.6 Hz, 5H), 1.36-1.13 (m, 4H), 0.92 (dd, J=26.3, 6.8 Hz, 6H). LCMS (m/z)=755.1 [M+H]. Tr=2.48 min.

Compound 162

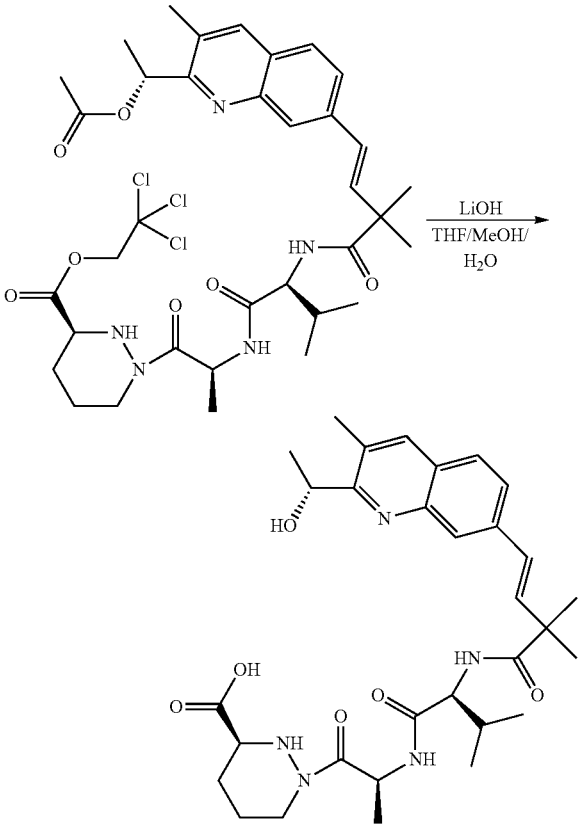

To a solution of 163e (0.47 g, 0.62 mmol) in THF (7 mL) and methanol (3.5 mL) was added a solution of lithium hydroxide (0.06 g, 2.5 mmol) in water (3.5 mL). The reaction mixture was stirred at room temperature for 1 hour. 1 N HCl (2.5 mL) was added to the reaction mixture. After concentration, the crude was purified by prep-HPLC to obtain the tile compound 163f (0.324 g, 90%)) as a white solid. $^1$H NMR (400 MHz, Methanol-$d_4$) δ 8.82 (s, 1H), 8.31 (s, 1H), 8.27-7.93 (m, 3H), 7.11 (d, J=8.5 Hz, 1H), 7.05-6.76 (m, 2H), 5.47 (q, J=6.6 Hz, 1H), 5.42-5.17 (m, 1H), 4.25 (t, J=7.9 Hz, 1H), 4.06 (s, 1H), 3.66-3.38 (m, 1H), 3.13-2.87 (m, 1H), 2.63 (d, J=0.9 Hz, 3H), 2.05 (dt, J=14.8, 7.8 Hz, 2H), 1.87 (d, J=37.6 Hz, 1H), 1.61 (d, J=6.6 Hz, 3H), 1.46 (d, J=8.7 Hz, 6H), 1.27 (d, J=7.0 Hz, 3H), 0.92 (dd, J=23.9, 6.7 Hz, 6H). LCMS (m/z) 582.3 [M+H]. Tr=1.75.

Example 163

Compound 163

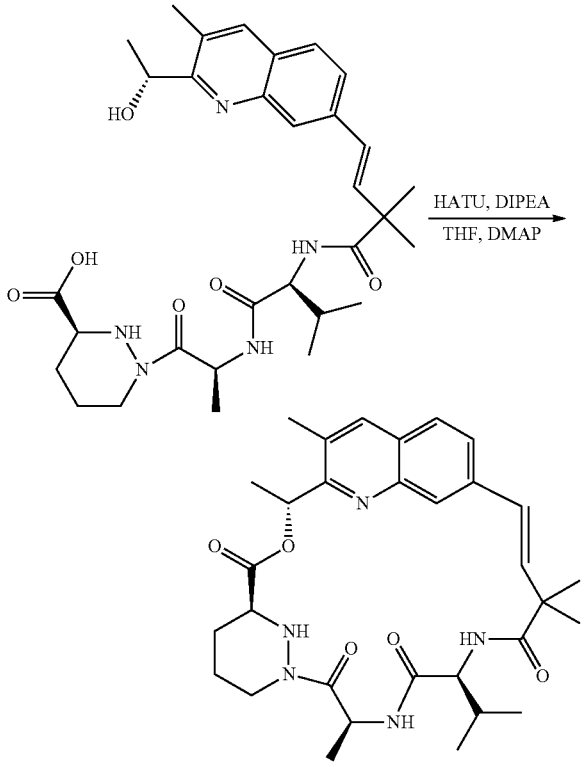

To a solution of 162 (0.02 g, 0.034 mmol) in THF (10 mL) were added N,N-diisopropylethylamine (0.022 g, 0.17 mmol), DMAP (catalytic amount) and 2-(1H-7-azabenzotriazol-1-yl)-1,1,3,3-tetramethyl uronium hexafluorophosphate methanaminium (0.026 g, 0.069 mmol). The reaction mixture was stirred at room temperature for 2 hour. After concentration, the crude was purified by prep-HPLC to obtain the tile compound 163 (0.016 g, 80%) as a white solid. $^1$H NMR (400 MHz, Methanol-$d_4$) δ 7.95 (s, 1H), 7.70 (d, J=1.1 Hz, 2H), 7.56 (s, 1H), 7.17 (d, J=9.7 Hz, 1H), 6.45 (d, J=16.5 Hz, 1H), 6.22 (d, J=16.4 Hz, 1H), 5.97 (q, J=6.7 Hz, 1H), 5.54 (q, J=7.2 Hz, 1H), 4.46-4.11 (m, 2H), 3.76 (s, 1H), 3.64 (s, 1H), 2.65 (t, J=13.2 Hz, 1H), 2.52 (d, J=1.0 Hz, 3H), 2.04-1.76 (m, 2H), 1.65 (dd, J=8.1, 6.9 Hz, 6H), 1.46 (s, 3H), 1.38 (s, 1H), 1.32 (s, 3H), 0.92 (t, J=6.5 Hz, 6H). LCMS (m/z) 564.3 [M+H]. Tr=2.19 min.

Example 164

Compound 164

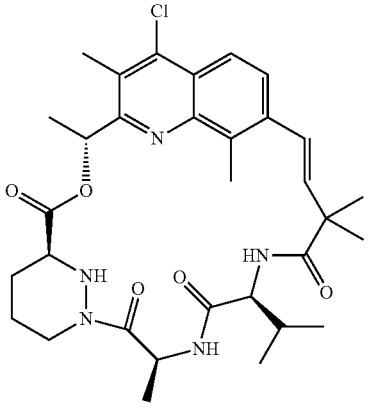

Compound 164a

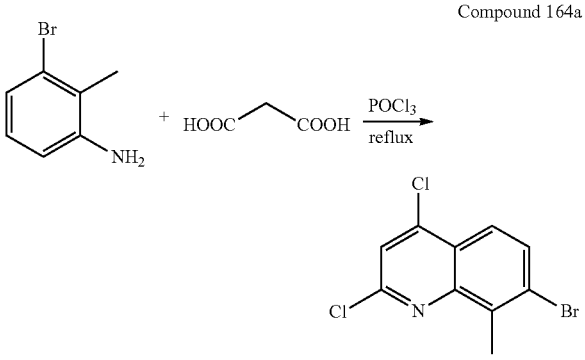

To a mixture of starting bromo-aniline (5.0 g, 27 mmol) and malonic acid (4.2 g, 41 mmol) was added $POCl_3$ (25 mL). The reaction mixture was heated to reflux for 2 hours. Then the reaction mixture was poured to ice water (100 mL) and extracted with EtOAc (2×100 mL). After concentration, the residue was purified by silica gel chromatography using a gradient of iso-hexanes/ethyl acetate 1:0 to 5:1 to afford the 164a (2.0 g, 26%) as a white solid. $^1$H NMR (400 MHz, Chloroform-d) δ 7.89 (d, J=9.0 Hz, 1H), 7.76 (d, J=8.9 Hz, 1H), 7.49 (d, J=1.0 Hz, 1H), 2.85 (s, 3H). LCMS (m/z) 290.2/292.2 [M+H].

Compound 164b

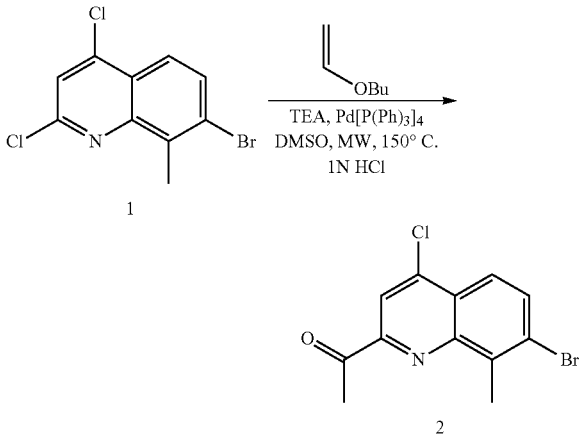

A mixture of 164a (1.2 g, 4.1 mmol), triethylamine (2.07 g, 20.5 mmol), 1-(vinyloxy)butane (7 mL) and Tetrakis (triphenylphosphine)palladium(0) (0.3 g, 0.26 mmol) in anhydrous DMSO (10 mL) in a microwave tube was heated to 150° C. for 5 hours and diluted with EtOAc (100 mL). The crude was washed with water and dried over $Na_2SO_4$. After concentration, the crude was dissolved in acetonitrile (20 mL) and 1 N HCl (20 mL). After extraction with EtOAc (2×50 mL), dried over $Na_2SO_4$ and concentration, the residue was purified by silica gel chromatography using a gradient of iso-hexanes/ethyl acetate 1:0 to 1:1 to afford 164b (420 mg, 34%). $^1$H NMR (400 MHz, Chloroform-d) δ 8.16 (s, 1H), 7.96 (d, J=8.8 Hz, 1H), 7.83 (d, J=8.9 Hz, 1H), 2.95 (s, 3H), 2.89 (s, 3H).

LCMS (m/z) 298.1/300.1 [M+H]. Tr=2.96 min.

Compound 164c

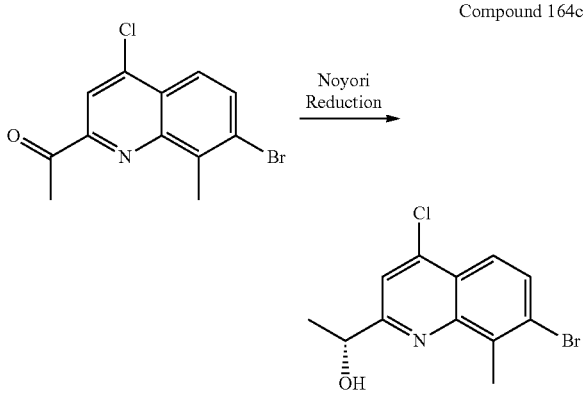

Dichloro (p-cymene) ruthenium(II) dimer (5.1 mg, 0.0084 mmol) and (1R,2R)-(−)-N-p-tosyl-1,2-diphenylethylenediamine (7.5 mg, 0.001 mmol) were suspended in degassed water (7.5 mL) and the mixture was degassed with nitrogen for 15 minutes. The mixture was stirred at 70° C. under nitrogen for 90 minutes. The resulting turbid orange mixture was allowed to cool to room temperature. 164b (0.5 g, 1.67 mmol) followed by degassed tetrahydrofuran (7.5 mL) and sodium formate (0.57 g, 8.35 mmol) were added and the reaction mixture was degassed with nitrogen for 5 minutes. The reaction mixture was vigorously stirred at 40° C. for 3 hours and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ethyl acetate 2:1 to afford the title compound 164c (0.36 g, 72%) as a purple solid. $^1$H NMR (400 MHz, Chloroform-d) δ 7.93 (d, J=9.0 Hz, 1H), 7.76 (dd, J=8.9, 1.2 Hz, 1H), 7.46 (s, 1H), 5.17-4.76 (m, 1H), 2.91 (d, J=1.2 Hz, 3H), 1.57 (dd, J=6.7, 1.2 Hz, 3H). LCMS (m/z) 300.1/302.1 [M+H]. Tr=2.11 min.

Compound 164d

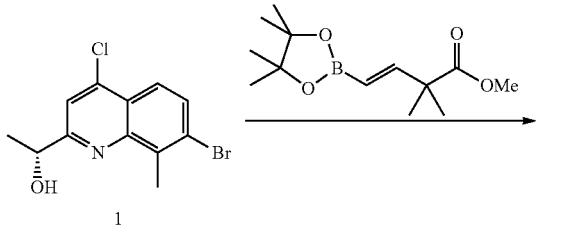

-continued

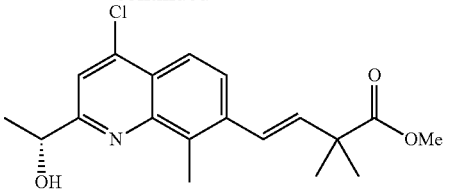

2

A round bottom flask was charged with 164c (150 mg, 0.5 mmol), (E)-2,2-dimethyl-4-(4,4,5,5-tetramethyl-[1,3,2]dioxaborolan-2-yl)-but-3-enoic acid methyl ester (140 mg, 0.55 mmol), bis[(dicyclohexyl)(4-dimethylaminophenyl) phosphine]palladium(II) chloride (20 mg, 0.025 mmol) and potassium phosphate tribasic (318 mg, 1.5 mmol). The system was flushed with nitrogen and cyclopentyl methyl ether (2 mL) and water (1 mL) were added. The reaction was heated for 1 hour at 90° C. and then cooled to room temperature. Ethyl acetate was added and the solution was washed with water. The organic layer was dried over magnesium sulfate, filtered and concentrated in vacuo. The residue was purified by silica gel chromatography using iso-hexanes/ethyl acetate 1:2 to give 164d (130 mg, 75%). LCMS (m/z) 348.2 [M+H]. Tr=2.61 min.

A solution of 164d (0.26 g, 0.748 mmol) in tetrahydrofuran (2 mL) and methanol (2 ml) was prepared and a 2M aqueous solution of sodium hydroxide (1 mL) was added. The reaction mixture was stirred at room temperature for 1 hour. The reaction was acidified with 2 M hydrochloric acid (1 mL). After extraction with EtOAc (2×30 mL), the organic layers were combined, dried over sodium sulfate and concentrated. To the crude acid in anhydrous N,N-dimethylformamide (5 mL) at room temperature and under an atmosphere of nitrogen was added N,N-diisopropylethylamine (568 mg, 4.39 mmol) and 2-(1H-7-azabenzotriazol-1-yl)-1,1,3,3-tetramethyl uronium hexafluorophosphate methanaminium (368 mg, 0.97 mmol). The solution was stirred at room temperature for 3 minutes before adding a solution of (S)-1-[(S)-2-((S)-2-amino-3-methyl-butyrylamino)-propionyl]-hexahydro-pyridazine-3-carboxylic acid 2,2,2-trichloro-ethyl ester resulting from N-Boc removal of tripeptide 1e (0.355 g, 0.823 mmol) in anhydrous N,N-dimethylformamide (2 mL). The reaction was stirred for 1 hour. The reaction was quenched with water and extracted with ethyl acetate (2×). The combined organic layers were dried over sodium sulfate, filtered and concentrated in vacuo. The residue was purified by silica gel chromatography using iso-hexanes/ethyl acetate 1:0 to 0:1 to give 164e (500 mg, 90%) as a white solid. LCMS (m/z) 746.2 [M+H]. Tr=2.68 min.

Compound 164e

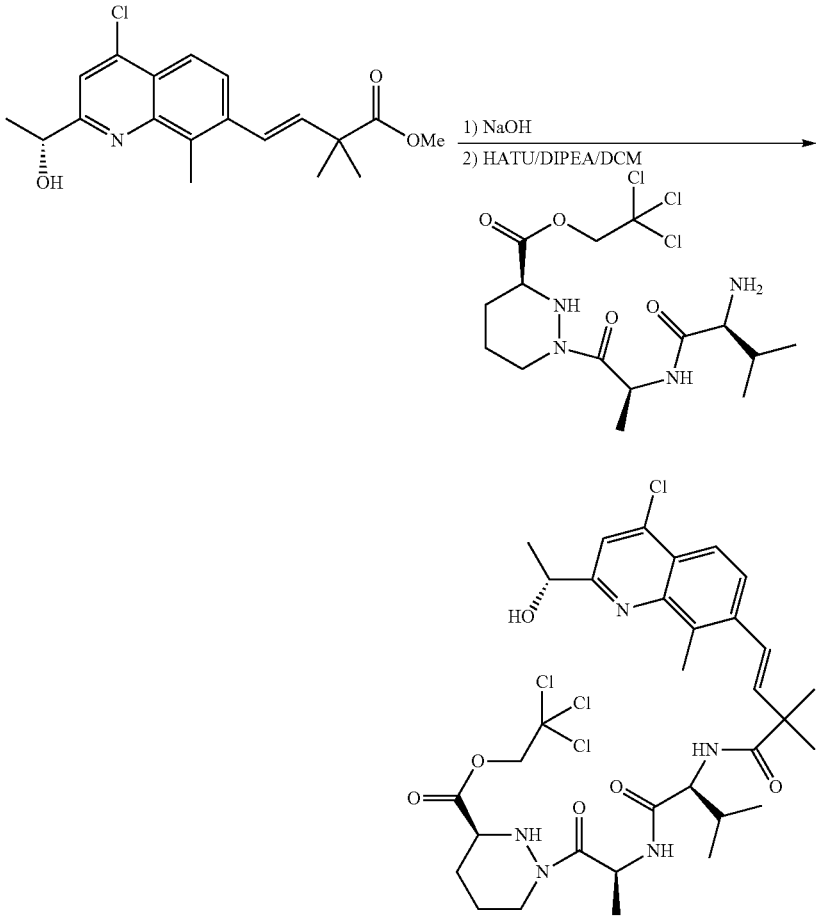

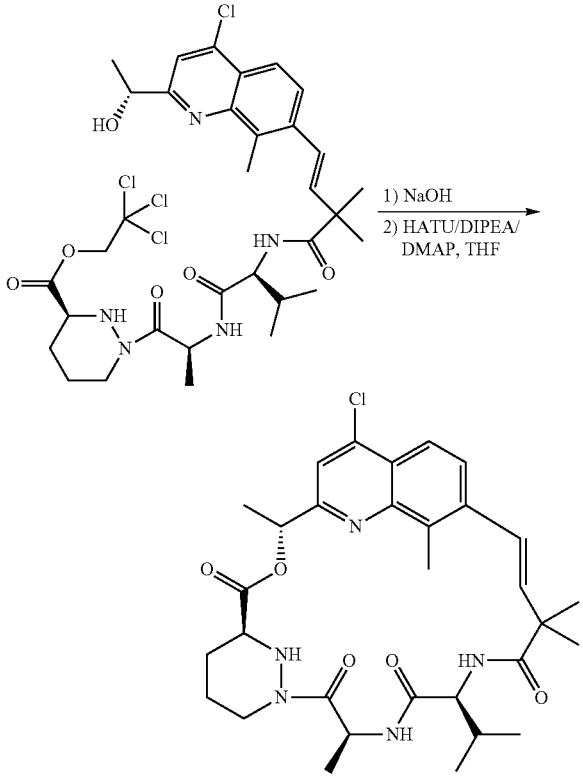

To 164e (0.462 g, 0.62 mmol) in THF (7 mL) and methanol (3.5 mL) was added a solution of sodium hydroxide (0.10 g, 2.5 mmol) in water (3.5 mL). The reaction mixture was stirred at room temperature for 1 hour. 1 N HCl (2.5 mL) was added to the reaction mixture. After concentration, the crude acid in THF (200 mL) were added N,N-diisopropylethylamine (0.431 g, 3.34 mmol), DMAP (catalytic amount) and 2-(1H-7-azabenzotriazol-1-yl)-1,1,3,3-tetramethyl uronium hexafluorophosphate methanaminium (0.305 g, 0.802 mmol). The reaction mixture was stirred at room temperature for overnight. After concentration, the crude was purified by prep-HPLC to obtain 164 (1 mg 0.3%) as a white solid. $^1$H NMR (400 MHz, Methanol-$d_4$) δ 7.99 (d, J=8.8 Hz, 1H), 7.77 (d, J=8.9 Hz, 1H), 7.69 (s, 1H), 6.50 (dd, J=16.1, 1.0 Hz, 1H), 6.22 (d, J=16.2 Hz, 1H), 5.26 (dd, J=7.0, 2.2 Hz, 1H), 4.98 (q, J=6.6 Hz, 1H), 4.42-4.15 (m, 1H), 3.67 (ddd, J=11.4, 7.1, 5.0 Hz, 2H), 2.78 (s, 3H), 2.20 (dd, J=6.5, 3.0 Hz, 2H), 2.06 (q, J=6.7 Hz, 1H), 1.92-1.71 (m, 3H), 1.55 (dd, J=6.7, 1.0 Hz, 3H), 1.46 (d, J=8.2 Hz, 6H), 1.35 (s, 3H), 0.93 (t, J=6.5 Hz, 6H). LCMS (m/z) 598.2 [M+H]. Tr=2.31 min.

Example 165

Compound 165

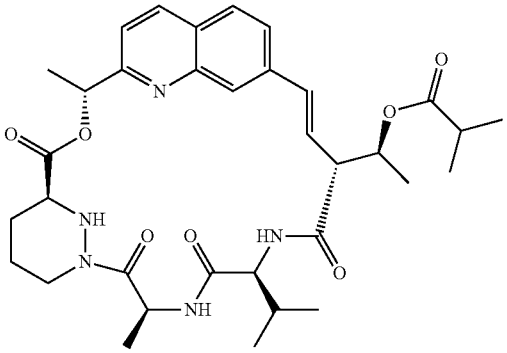

-continued

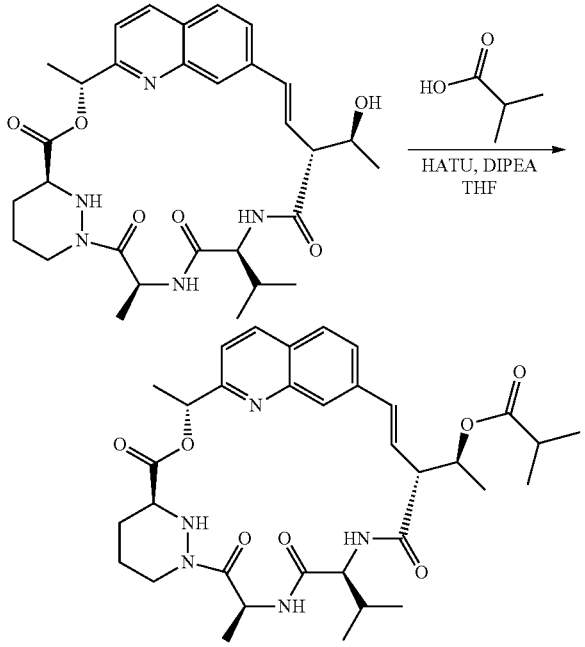

Beginning with 31 (0.015 g, 0.0265 mmol), isobutyric acid (0.005 g, 0.053 mmol), N,N-diisopropylethylamine (0.014 g, 0.106 mmol) and DMAP (catalytic amount) in THF (1 mL) was added 2-(1H-7-azabenzotriazol-1-yl)-1,1,3,3-tetramethyl uronium hexafluorophosphate methanaminium (0.03 g, 0.08 mmol). The reaction mixture was stirred at room temperature for overnight. After concentration, the crude was purified by prep-HPLC to obtain the 165 (12 mg 79%) as a white solid. $^1$H NMR (400 MHz, Methanol-$d_4$) δ 8.18 (d, J=8.5 Hz, 1H), 7.88-7.71 (m, 1H), 7.67 (d, J=2.0 Hz, 1H), 7.58 (d, J=8.7 Hz, 1H), 7.38 (d, J=8.5 Hz, 1H), 6.51 (d, J=16.4 Hz, 1H), 6.37 (dd, J=16.3, 6.1 Hz, 1H), 5.88 (t, J=6.8 Hz, 1H), 5.72-5.48 (m, 1H), 5.27 (dd, J=9.4, 6.2 Hz, 1H), 4.49-4.28 (m, 1H), 4.15 (d, J=10.6 Hz, 1H), 3.78 (s, 1H), 3.56-3.37 (m, 1H), 2.72 (s, 1H), 2.68-2.48 (m, 1H), 2.13-1.79 (m, 3H), 1.81-1.61 (m, 6H), 1.63-1.51 (m, 3H), 1.30 (d, J=6.2 Hz, 3H), 1.16 (dd, J=8.2, 7.0 Hz, 6H), 0.96 (t, J=7.0 Hz, 6H). LCMS (m/z) 636.3 [M+H]. Tr=2.31 min.

Example 166

Compound 166

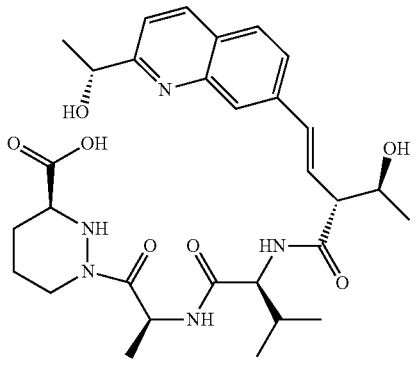

-continued

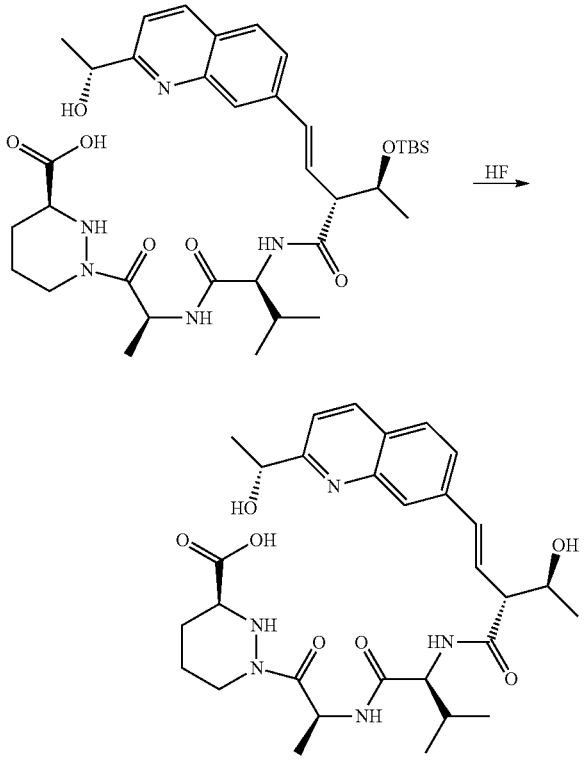

Proceeding from an intermediate from the synthesis of Compound 31 (0.01 g, 0.014 mmol) in acetonitrile (0.5 mL) and THF (0.05 mL) was added hydrofluoric acid (48 wt. % in water, 0.2 mL). The reaction mixture was stirred at room temperature for 2 hours. After concentration, the crude was purified by prep-HPLC to obtain the tile compound 2 (0.007 g, 73%) as a white solid. $^1$H NMR (400 MHz, Methanol-$d_4$) δ 8.84 (d, J=8.6 Hz, 1H), 8.35-8.07 (m, 3H), 8.07-7.86 (m, 3H), 7.01-6.62 (m, 2H), 5.52-5.02 (m, 1H), 4.37-4.18 (m, 1H), 4.20-4.11 (m, 1H), 3.99 (m, 1H), 3.62-3.39 (m, 1H), 2.98 (m, 1H), 2.28-1.99 (m, 1H), 1.98 (m, 1H), 1.63 (d, J=6.8 Hz, 6H), 1.23 (dd, J=8.8, 6.6 Hz, 6H), 0.97 (t, J=6.9 Hz, 6H). LCMS (m/z) 584.3 [M+H]. Tr=1.67 min.

Example 167

Compound 167

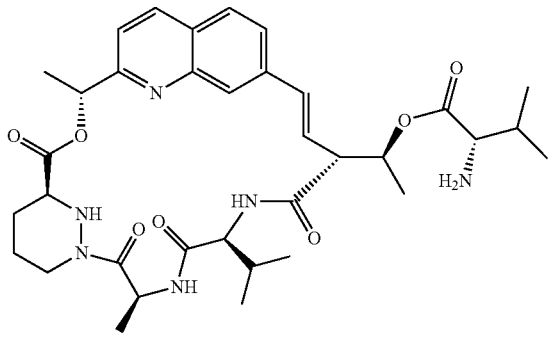

-continued

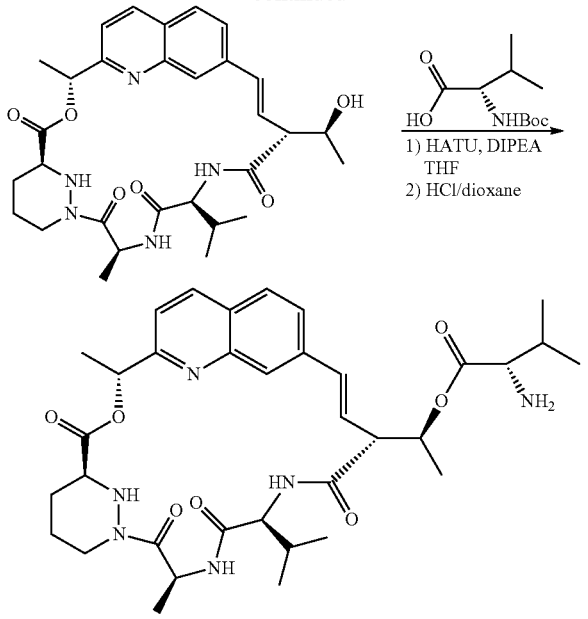

Proceeding from 31, (0.015 g, 0.0265 mmol), Boc-L-valine (0.012 g, 0.053 mmol), N,N-diisopropylethylamine (0.014 g, 0.106 mmol) and DMAP (catalytic amount) in THF (1 mL) was added 2-(1H-7-azabenzotriazol-1-yl)-1,1,3,3-tetramethyl uronium hexafluorophosphate methanaminium (0.03 g, 0.08 mmol). The reaction mixture was stirred at room temperature for overnight. After concentration, the crude was treated with 4 N HCl in dioxane (1 mL) with stirring for 1 hour to remove the protection group. After concentration, the crude was purified by prep-HPLC to obtain 167 (13 mg 73%) as a white solid. $^1$H NMR (400 MHz, Methanol-$d_4$) δ 8.17 (d, J=8.5 Hz, 1H), 7.75 (d, J=8.5 Hz, 1H), 7.65 (d, J=1.6 Hz, 1H), 7.62-7.54 (m, 1H), 7.39 (d, J=8.5 Hz, 1H), 6.53 (d, J=16.4 Hz, 1H), 6.40 (dd, J=16.3, 6.1 Hz, 1H), 5.89 (t, J=6.8 Hz, 1H), 5.54 (d, J=7.2 Hz, 1H), 5.31 (dd, J=9.6, 6.1 Hz, 1H), 4.51-4.29 (m, 1H), 4.17 (d, J=10.5 1H), 3.86-3.63 (m, 4H), 3.60-3.42 (m, 2H), 2.72 (dd, J=13.4, 9.4 Hz, 1H), 2.17-1.77 (m, 4H), 1.80-1.58 (m, 4H), 1.53 (d, J=7.2 Hz, 3H), 1.34 (d, J=6.1 Hz, 3H), 1.32-1.19 (m, 1H), 1.09-0.89 (m, 9H), 0.85 (d, J=6.9 Hz, 3H). LCMS (m/z) 665.3 [M+H]. Tr=2.31 min.

Example 168

Compound 168

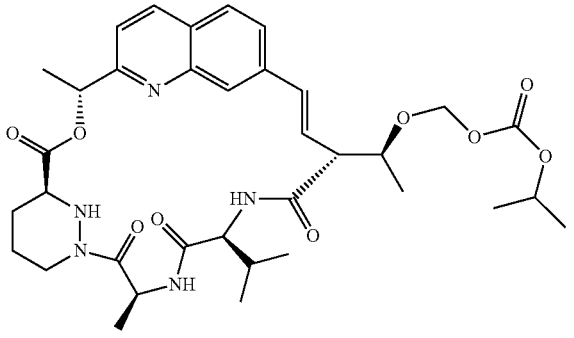

-continued

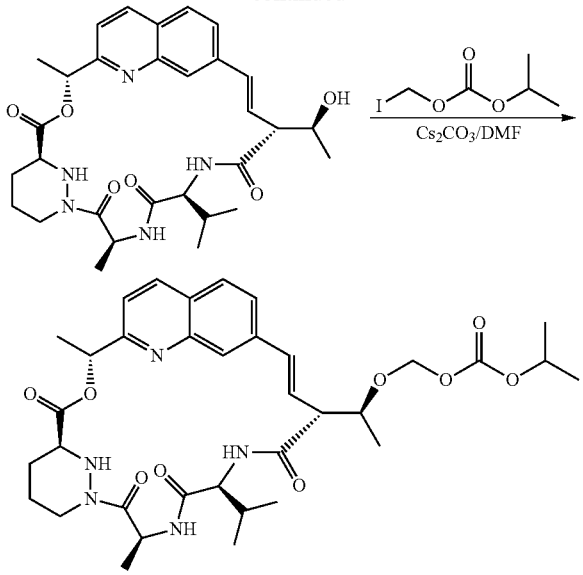

To 31 (0.025 g, 0.045 mmol) and iodomethyl isopropyl carbonate (0.022 g, 0.090 mmol) in DMF (2 mL) was added $Cs_2CO_3$ (0.028 g, 0.090 mmol). The reaction mixture was stirred at room temperature for overnight. After filtration, the crude was purified by prep-HPLC to obtain 168 (0.005 g, 17%). $^1$H NMR (400 MHz, Methanol-$d_4$) δ 8.46 (dd, J=20.7, 8.2 Hz, 2H), 8.18 (d, J=8.5 Hz, 1H), 7.85-7.61 (m, 2H), 7.59 (s, 1H), 7.40 (d, J=8.5 Hz, 1H), 6.62 (dd, J=16.6, 5.3 Hz, 1H), 6.42 (d, J=16.3 Hz, 1H), 5.93 (q, J=6.9 Hz, 1H), 5.72-5.54 (m, 1H), 4.45 (m, 1H), 4.38 (m, 1H), 4.25-3.90 (m, 3H), 3.86-3.69 (m, 1H), 2.75 (m, 1H), 2.14-1.82 (m, 2H), 1.72 (d, J=6.9 Hz, 3H), 1.58 (m, 4H), 1.25 (d, J=6.0 Hz, 3H), 1.11 (dd, J=27.8, 6.2 Hz, 6H), 0.97 (d, J=6.6 Hz, 6H). LCMS (m/z) 682.3 [M+H]. Tr=2.29 min.

Examples 169 and 170

Compounds 169 and 170

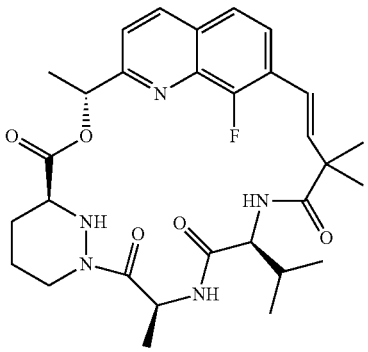

Compound 170a

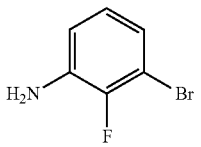

-continued

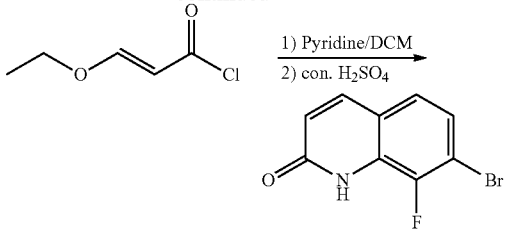

To a solution of 3-bromo-2-fluoroaniline, obtained from Apollo Scientific, (2.0 g, 10.53 mmol) and pyridine (1.5 g, 19.3 mmol) in anhydrous dichloromethane (30 mL) were added 2 (2.1 g, 15.8 mmol) dropwise. The mixture was stirred at room temperature for 1 h. After concentration, the crude was diluted with EtOAc (200 mL), washed with water (2×) and dried over $Na_2SO_4$. After concentration, the crude residue was purified by silica gel chromatography using iso-hexanes/ethyl acetate 1:0 to 1:1 to give 2.8 g amide intermediate which was dissolved in con. $H_2SO_4$ (10 ml) and stirred for 3 hours. The reaction mixture was poured to ice water (100 mL) and stirred for 1 hour. After filtration, the solid was collected and dried overnight to afford the tile compound 170a (1.5 g, 59%) as a solid. LCMS (m/z) 242.2/244.2 [M+H]. Tr=2.10 min.

Compound 170b

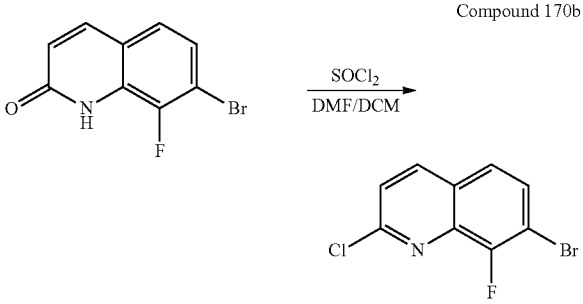

To a solution of 170a (1.5 g, 6.2 mmol) and DMF (0.5 g, 6.8 mmol) in anhydrous dichloromethane (50 mL) were added thionyl chloride (2.27 g, 19.1 mmol) dropwise. The mixture was stirred at 50° C. for 3 hours. After concentration, the crude was diluted with EtOAc (200 mL), washed with water (2×) and dried over $Na_2SO_4$. After concentration, the crude residue was purified by silica gel chromatography using iso-hexanes/ethyl acetate 1:0 to 1:1 to give the tile compound 170b (0.9 g, 56%) as a solid. LCMS (m/z) 260.1/262.1 [M+H]. Tr=2.20 min.

Compound 170c

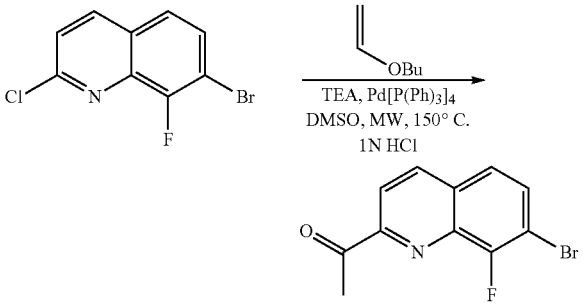

A mixture of quinoline (0.9 g, 3.46 mmol), triethylamine (1.75 g, 17.28 mmol), 1-(vinyloxy)butane (6 mL) and Tetrakis(triphenylphosphine)palladium(0) (0.3 g, 0.26 mmol) in anhydrous DMSO (10 mL) in a microwave tube was heated to 150° C. for 5 hours and diluted with EtOAc (100 mL). The crude was washed with water and dried over $Na_2SO_4$. After concentration, the crude was dissolved in acetonitrile (20 mL) and 1 N HCl (20 mL). After extraction with EtOAc (2×50 mL), dried over $Na_2SO_4$ and concentration, the residue was purified by silica gel chromatography using a gradient of iso-hexanes/ethyl acetate 1:0 to 1:1 to afford 170c (0.20 g, 22%). LCMS (m/z) 268.1/270.1 [M+H]. Tr=2.08 min.

Compound 170d

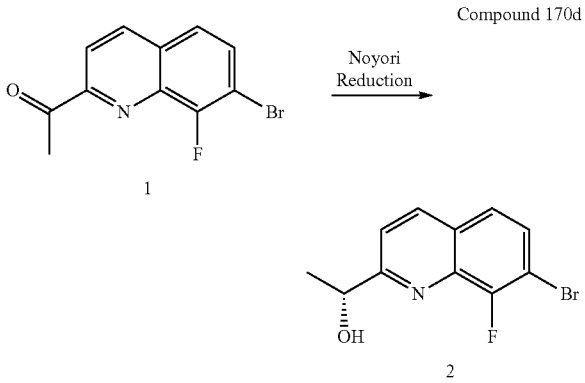

Dichloro (p-cymene) ruthenium(II) dimer (2.2 mg, 0.0038 mmol) and (1R,2R)-(−)-N-p-tosyl-1,2-diphenylethylenediamine (3.2 mg, 0.00045 mmol) were suspended in degassed water (7.5 mL) and the mixture was degassed with nitrogen for 15 minutes. The mixture was stirred at 70° C. under nitrogen for 90 minutes. The resulting turbid orange mixture was allowed to cool to room temperature. Solid 170c (0.2 g, 0.746 mmol) followed by degassed tetrahydrofuran (7.5 mL) and sodium formate (0.25 g, 3.7 mmol) were added and the reaction mixture was degassed with nitrogen for 5 minutes. The reaction mixture was vigorously stirred at 40° C. for 3 hours and allowed to cool. It was then diluted with ethyl acetate and the mixture washed with water (2×). The aqueous washes were back-extracted with ethyl acetate and the combined organics washed with brine, dried over magnesium sulfate, filtered and evaporated. The residue was purified by silica gel chromatography eluting with iso-hexanes/ethyl acetate 2:1 to afford the 170d (0.18 g, 90%) as a purple solid. LCMS (m/z) 270.1/272.1 [M+H]. Tr=1.81 min.

Compound 170e

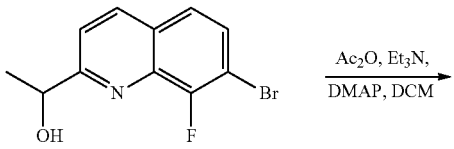

-continued

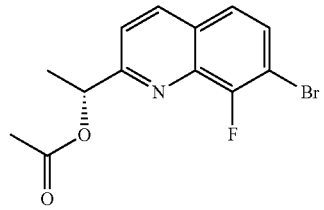

To a solution of 170d (0.18 g, 0.67 mmol) in anhydrous dichloromethane (5 mL) were added triethylamine (0.226 g, 2.24 mmol) and acetyl anhydride (0.15 g, 1.49 mmol). The mixture was stirred at room temperature for 1 h. After concentration, the crude was diluted with EtOAc (50 mL), washed with water (2×) and dried over $Na_2SO_4$. After concentration, the crude residue was purified by silica gel chromatography using iso-hexanes/ethyl acetate 1:0 to 1:1 to give the 170e (0.18 g, 86%) as a solid. LCMS (m/z) 312.1/314.1 [M+H]. Tr=2.35 min.

Compound 170f

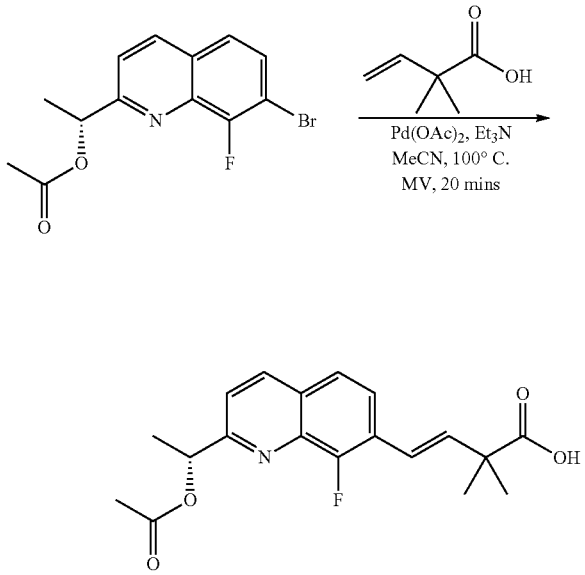

To a mixture of 170e (180 mg, 0.577 mmol), triethylamine (175 mg, 1.73 mmol) and 2,2-dimethylbut-3-enoic acid (99 mg, 0.865 mmol) in anhydrous acetonitrile (2 mL) in a microwave tube was added palladium acetate (13 mg, 0.058 mmol) and tri-o-tolyphosphine (35 mg, 0.12 mmol). The reaction mixture was heated to 100° C. for 20 minutes and diluted with EtOAc (30 mL). The crude was washed with water and dried over $Na_2SO_4$. After concentration, the residue was purified by silica gel chromatography using a gradient of iso-hexanes/ethyl acetate 1:0 to 0:1 to afford 170f (150 mg, 75%). LCMS (m/z) 346.1 [M+H]. Tr=2.20.

Compound 170g

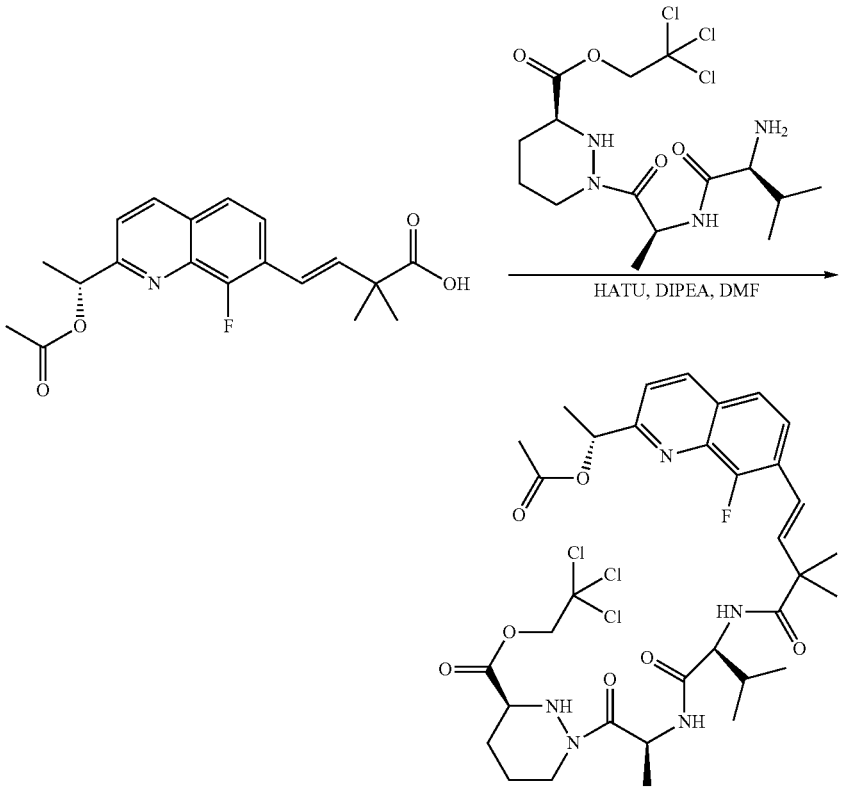

To 170f (100 mg, 0.29 mmol) in anhydrous N,N-dimethylformamide (5 mL) at room temperature and under an atmosphere of nitrogen was added N,N-diisopropylethylamine (112 mg, 0.87 mmol) and 2-(1H-7-azabenzotriazol-1-yl)-1,1,3,3-tetramethyl uronium hexafluorophosphate methanaminium (165 mg, 0.44 mmol). The solution was stirred at room temperature for 3 minutes before adding a solution of (S)-1-[(S)-2-((S)-2-amino-3-methyl-butyrylamino)-propionyl]-hexahydro-pyridazine-3-carboxylic acid 2,2,2-trichloro-ethyl ester (125 mg, 0.29 mmol) in anhydrous N,N-dimethylformamide (2 mL). The reaction was stirred for 1 hour. The reaction was quenched with water and extracted with ethyl acetate (2×). The combined organic layers were dried over sodium sulfate, filtered and concentrated in vacuo. The residue was purified by silica gel chromatography using iso-hexanes/ethyl acetate 1:0 to 0:1 to give the 170 g (152 mg, 69%) as a white solid. LCMS (m/z)=759.2 [M+H]. Tr=2.54 min.

Compound 169

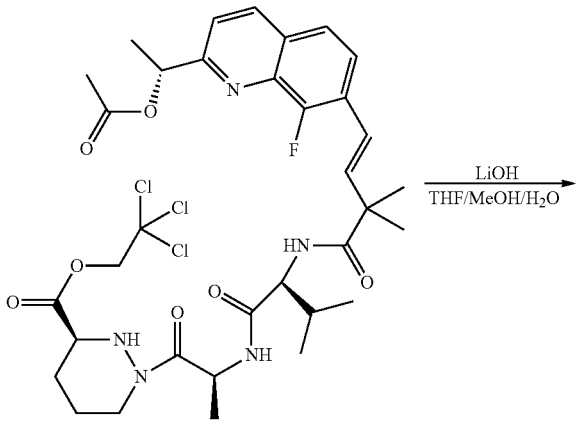

-continued

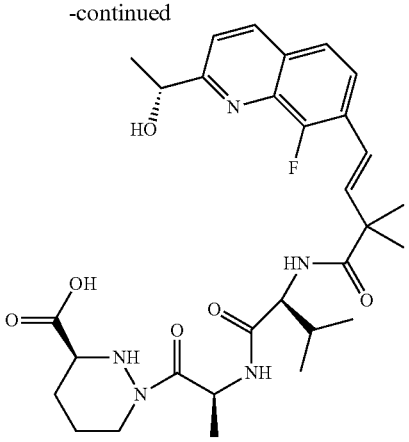

To a solution of 170 g (0.152 g, 0.20 mmol) in THF (2 mL) and methanol (2 mL) was added a solution of lithium hydroxide (0.02 g, 0.83 mmol) in water (2 mL). The reaction mixture was stirred at room temperature for 1 hour. 1 N HCl (0.9 mL) was added to the reaction mixture. After concentration, the crude was purified by prep-HPLC to obtain 169 (0.110 g, 91%) as a white solid. $^{1}$H NMR (400 MHz, Methanol-$d_4$) δ 8.41 (dd, J=8.6, 1.6 Hz, 1H), 7.80 (dd, J=8.7, 6.6 Hz, 1H), 7.75 (d, J=8.6 Hz, 1H), 7.68 (d, J=8.7 Hz, 1H), 7.04 (d, J=8.6 Hz, 1H), 6.92 (d, J=16.4 Hz, 1H), 6.72 (d, J=16.4 Hz, 1H), 5.22 (q, J=7.0 Hz, 1H), 5.06 (q, J=6.6 Hz, 1H), 4.31-4.08 (m, 1H), 3.96 (s, 1H), 3.41 (dd, J=9.8, 3.6 Hz, 1H), 2.88 (s, 1H), 2.19-1.87 (m, 2H), 1.72 (dd, J=10.4, 5.9 Hz, 1H), 1.63-1.51 (m, 2H), 1.47 (d, J=6.6 Hz, 3H), 1.38 (d, J=4.5 Hz, 6H), 1.19 (d, J=7.0 Hz, 3H), 0.87 (d, J=6.7 Hz, 3H), 0.82 (d, J=6.7 Hz, 3H). $^{19}$F NMR (376 MHz, Methanol-$d_4$) δ −135.18 (d, J=6.6 Hz). LCMS (m/z) 586.3 [M+H]. Tr=1.97 min.

Compound 170

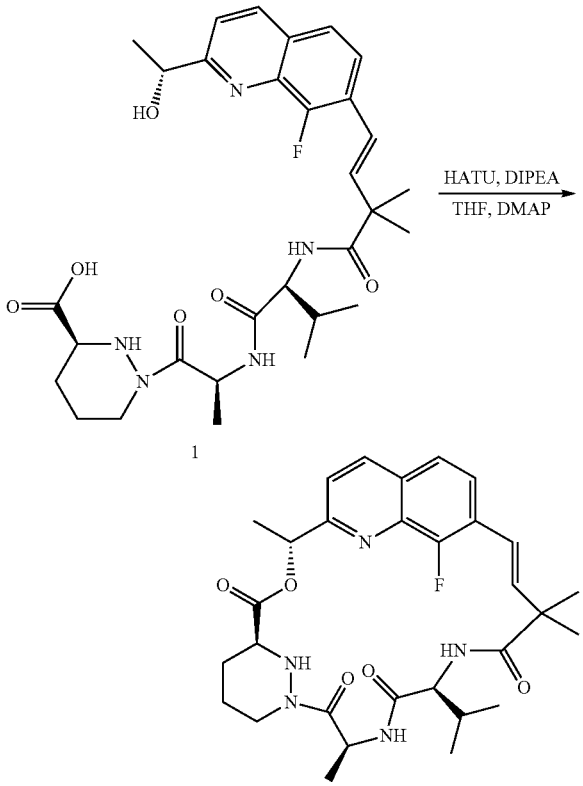

To a solution of 169 (0.05 g, 0.085 mmol) in THF (85 mL) were added N,N-diisopropylethylamine (0.055 g, 0.128 mmol), DMAP (catalytic amount) and 2-(1H-7-azabenzotriazol-1-yl)-1,1,3,3-tetramethyl uronium hexafluorophosphate methanaminium (0.048 g, 0.128 mmol). The reaction mixture was stirred at room temperature for 2 hour. After concentration, the crude was purified by prep-HPLC to obtain 170 (0.004 g, 8%) as a white solid. $^1$H NMR (400 MHz, Methanol-$d_4$) δ 8.34-8.11 (m, 1H), 7.72 (dd, J=8.7, 6.5 Hz, 1H), 7.68-7.52 (m, 1H), 7.45 (d, J=8.5 Hz, 1H), 7.17 (d, J=9.6 Hz, 1H), 6.77-6.31 (m, 2H), 5.84 (q, J=6.8 Hz, 1H), 5.75-5.63 (m, 1H), 4.49-4.10 (m, 2H), 3.76 (m, 1H), 2.67 (dt, J=13.5, 6.5 Hz, 1H), 1.98-1.76 (m, 3H), 1.71 (d, J=6.8 Hz, 3H), 1.63 (m, 1H), 1.60-1.45 (m, 7H), 1.43-1.21 (m, 3H), 1.13-0.79 (m, 6H). LCMS (m/z) 568.3 [M+H]. Tr=2.13 min.

Example 171

Compound 171

Compound 171

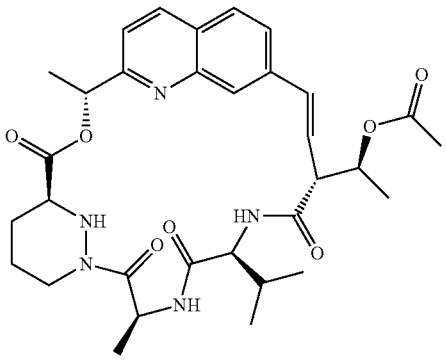

-continued

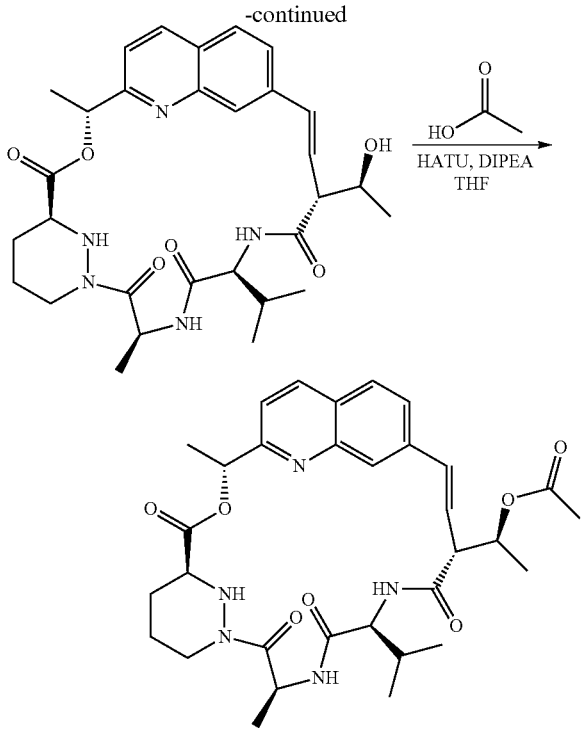

Starting from 31, (0.06 g, 0.106 mmol), acetic acid (0.064 g, 1.06 mmol), N,N-diisopropylethylamine (0.205 g, 1.59 mmol) and DMAP (catalytic amount) in THF (1 mL) was added 2-(1H-7-azabenzotriazol-1-yl)-1,1,3,3-tetramethyl uronium hexafluorophosphate methanaminium (0.201 g, 0.53 mmol). The reaction mixture was stirred at room temperature for overnight. After concentration, the crude was purified by prep-HPLC to obtain 171 (50 mg 81%) as a white solid. $^1$H NMR (400 MHz, Methanol-$d_4$) δ 8.18 (d, J=8.5 Hz, 1H), 7.78 (d, J=9.0 Hz, 1H), 7.72-7.60 (m, 2H), 7.39 (d, J=8.5 Hz, 1H), 6.62-6.45 (m, 1H), 6.43 (m, 1H), 5.91 (m, 1H), 5.60 (q, J=7.3 Hz, 1H), 5.27 (dd, J=9.6, 6.1 Hz, 1H), 4.42 (dd, J=18.8, 12.5 Hz, 1H), 4.18 (d, J=10.5 Hz, 1H), 3.77 (d, J=9.3 Hz, 1H), 3.55-3.37 (m, 1H), 2.74 (t, J=11.2 Hz, 1H), 2.08 (s, 3H), 2.05-1.80 (m, 3H), 1.71-1.62 (m, 5H), 1.58 (d, J=7.2 Hz, 3H), 1.32 (d, J=6.1 Hz, 3H), 1.12-0.84 (m, 6H). LCMS (m/z) 608.3 [M+H]. Tr=2.18 min.

Example 172

Compound 172

Compund 172

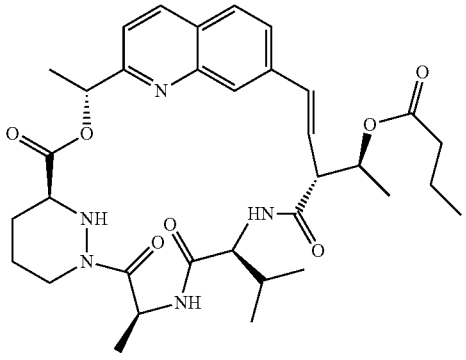

-continued

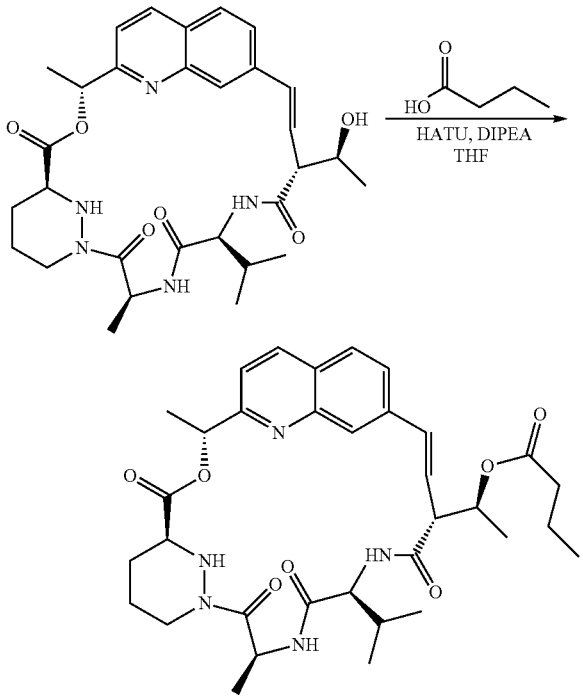

Starting from a 31, (0.015 g, 0.0265 mmol), n-butyric acid (0.023 g, 0.265 mmol), N,N-diisopropylethylamine (0.051 g, 0.398 mmol) and DMAP (catalytic amount) in THF (1 mL) was added 2-(1H-7-azabenzotriazol-1-yl)-1,1,3,3-tetramethyl uronium hexafluorophosphate methanaminium (0.05 g, 0.133 mmol). The reaction mixture was stirred at room temperature for overnight. After concentration, the crude was purified by prep-HPLC to obtain 172 (12 mg 79%) as a white solid. $^1$H NMR (400 MHz, Methanol-$d_4$) δ 8.18 (d, J=8.4 Hz, 1H), 7.74 (d, J=8.5 Hz, 1H), 7.71-7.54 (m, 2H), 7.40 (d, J=8.5 Hz, 1H), 6.64-6.43 (m, 1H), 6.39 (dd, J=16.4, 5.8 Hz, 1H), 5.91 (d, J=6.9 Hz, 1H), 5.57 (q, J=7.1 Hz, 1H), 5.30 (dd, J=9.6, 6.1 Hz, 1H), 4.39 (dd, J=13.8, 3.5 Hz, 1H), 4.20 (d, J=10.5 Hz, 1H), 3.85-3.66 (m, 1H), 3.48 (ddd, J=9.5, 5.8, 1.3 Hz, 1H), 2.74 (td, J=12.7, 3.4 Hz, 1H), 2.35 (td, J=7.3, 3.3 Hz, 2H), 2.11-1.80 (m, 3H), 1.73 (d, J=6.9 Hz, 3H), 1.71-1.60 (m, 4H), 1.52 (d, J=7.2 Hz, 3H), 1.33 (d, J=6.1 Hz, 3H), 1.07-0.83 (m, 9H). LCMS (m/z) 636.3 [M+H]. Tr=2.31 min.

Examples 173 and 174

Compounds 173 and 174

Compound 173a

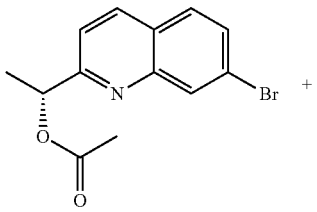

-continued

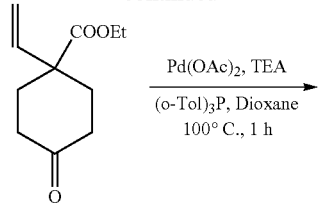

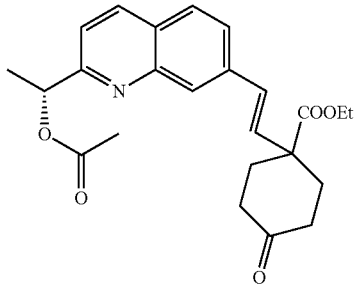

To a mixture of starting (R)-1-(7-bromoquinolin-2-yl) ethyl acetate (200 mg, 0.683 mmol), triethylamine (137 mg 1.36 mmol) and commercially supplied vinyl cyclohexanone carboxylate (obtained from Small Molecules, Inc.), (134 mg 0.683 mmol) in anhydrous dioxane (7 mL) in a microwave tube were added palladium acetate (29 mg, 0.13 mmol) and tri-o-tolyphosphine (79 mg, 0.26 mmol). The reaction mixture was heated to 100° C. for 20 minutes and diluted with EtOAc (30 mL). The crude was washed with water and dried over $Na_2SO_4$. After concentration, the residue was purified by silica gel chromatography using a gradient of isohexanes/ethyl acetate 1:0 to 0:1 to afford 173a (200 mg, 71%). LCMS (m/z) 410.2 [M+H]. Tr=2.81 min.

Compounds 173b and 174a

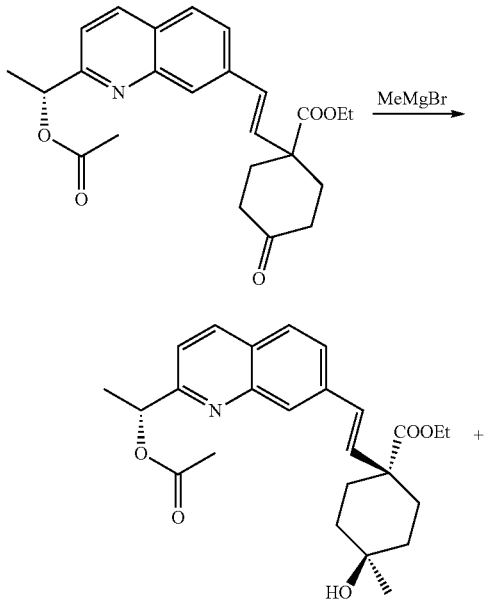

-continued

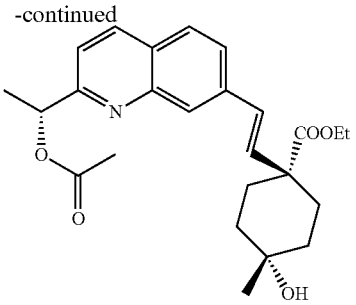

A solution of 173a (0.3 g, 0.73 mmol) in anhydrous THF (5 mL) was cooled to −78° C. Methyl magnesium bromide (3.0 M solution in ether, 0.37 mL) was added to the reaction mixture drop wise. The mixture was stirred at −78° C. for 1 h. The reaction mixture was diluted with EtOAc (30 mL) and quenched with sat. $NH_4Cl$ (2 mL). After layers separation, the organic layer was dried over $Na_2SO_4$ and concentrated. the crude residue was purified by silica gel chromatography using iso-hexanes/ethyl acetate 1:0 to 1:1 to give 173b (0.1 g, 32%) and 174a (0.1 g, 32%). LCMS (m/z) 426.1 [M+H]. Tr=2.31 min and Tr=2.44 min.

A solution of 173b (0.05 g, 0.118 mmol) in tetrahydrofuran (1 mL) and methanol (1 ml) was prepared and a 1 M aqueous solution of potassium hydroxide (1 mL) was added. The reaction mixture was stirred at room temperature for 1 hour. The reaction was acidified with 1 M hydrochloric acid (1 mL). After extraction with EtOAc (2×30 mL), the organic layers were combined, dried over sodium sulfate and concentrated. To the crude acid in anhydrous N,N-dimethylformamide (2 mL) at room temperature and under an atmosphere of nitrogen was added N,N-diisopropylethylamine (46 mg, 0.354 mmol) and 2-(1H-7-azabenzotriazol-1-yl)-1,1,3,3-tetramethyl uronium hexafluorophosphate methanaminium (90 mg, 0.236 mmol). The solution was stirred at room temperature for 3 minutes before adding a solution of (S)-1-[(S)-2-((S)-2-amino-3-methyl-butyrylamino)-propionyl]-hexahydro-pyridazine-3-carboxylic acid 2,2,2-trichloro-ethyl ester (66 mg, 0.153 mmol) in anhydrous N,N-dimethylformamide (2 mL). The reaction was stirred for 1 hour. The reaction was quenched with water and extracted with ethyl acetate (2×). The combined organic layers were dried over sodium sulfate, filtered and concentrated in vacuo. The residue was purified by silica gel chromatography using iso-hexanes/ethyl acetate 1:0 to 0:1 to give 173c (70 mg, 77%) as a white solid. LCMS (m/z) 769.2 [M+H]. Tr=2.65 min.

Compound 173c

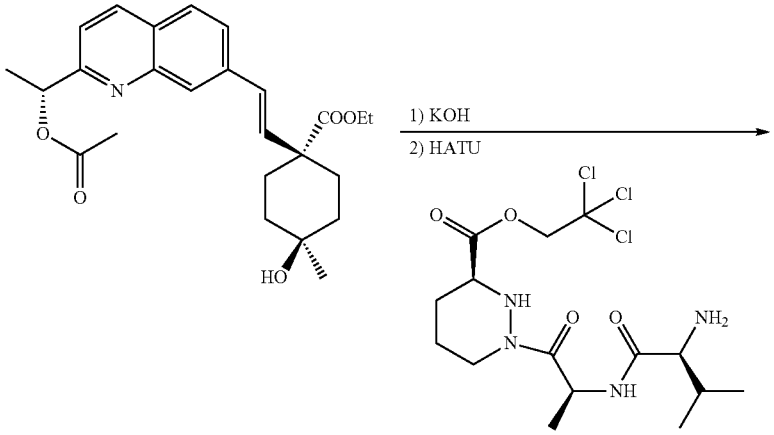

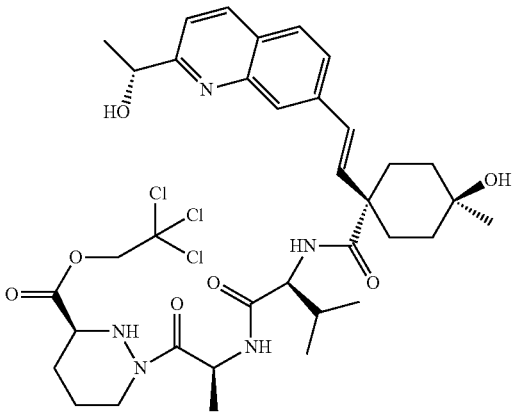

Compound 173

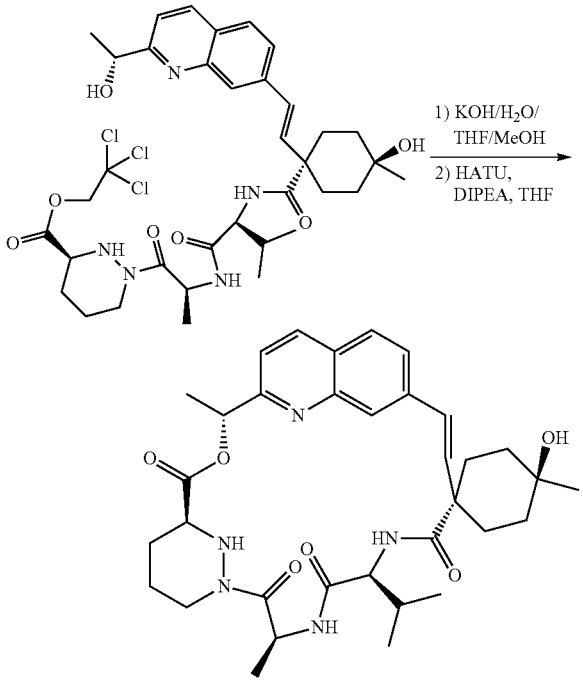

To a solution of 173c (0.040 g, 0.052 mmol) in THF (1 mL) and methanol (1 mL) was added a solution of 1N KOH in water (0.21 mL). The reaction mixture was stirred at room temperature for 1 hour. 1 N HCl (0.21 mL) was added to the reaction mixture. After concentration, the crude was under high vacuum over night. To the crude acid from above in THF (30 mL) were added N,N-diisopropylethylamine (0.013 g, 0.104 mmol), DMAP (catalytic amount) and 2-(1H-7-azabenzotriazol-1-yl)-1,1,3,3-tetramethyl uronium hexafluorophosphate methanaminium (0.030 g, 0.078 mmol). The reaction mixture was stirred at room temperature for 3 hour. After concentration, the crude was purified by prep-HPLC to obtain 173 (0.01 g, 25%) as a white solid. $^1$H NMR (400 MHz, Methanol-$d_4$) δ 8.57 (d, J=7.1 Hz, 1H), 8.30 (d, J=8.4 Hz, 1H), 8.02-7.72 (m, 2H), 7.62 (s, 1H), 7.47 (d, J=8.5 Hz, 1H), 7.32 (d, J=9.3 Hz, 1H), 6.52 (d, J=16.5 Hz, 1H), 6.35 (d, J=16.4 Hz, 1H), 5.93 (q, J=6.8 Hz, 1H), 5.63 (dd, J=7.9, 5.7 Hz, 1H), 4.51-4.27 (m, 1H), 3.77 (d, J=9.0 Hz, 1H), 2.69 (t, J=11.5 Hz, 1H), 2.24 (s, 2H), 1.92 (dt, J=26.0, 10.1 Hz, 4H), 1.72 (d, J=6.9 Hz, 3H), 1.70-1.60 (m, 6H), 1.59 (d, J=7.1 Hz, 3H), 1.27 (s, 3H), 0.95 (dd, J=6.7, 3.3 Hz, 6H). LCMS (m/z) 620.3 [M+H]. Tr=2.10 min.

Compound 174b

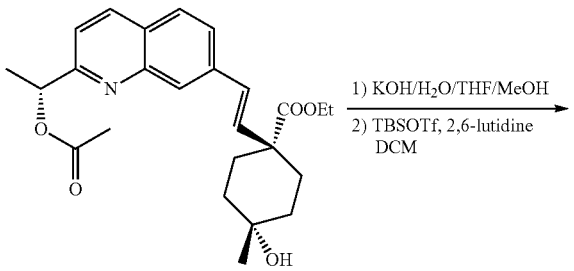

-continued

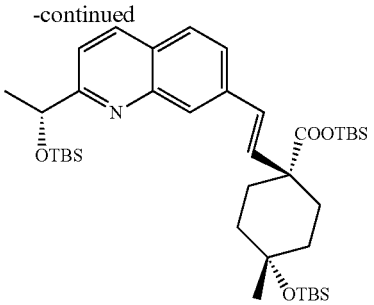

To a solution of 174a (0.10 g, 0.235 mmol) in THF (2 mL) and methanol (1 mL) was added a solution of 1N KOH in water (1.2 mL). The reaction mixture was stirred at room temperature for 1 hour. 1 N HCl (1.2 mL) was added to the reaction mixture. After concentration, the crude was under high vacuum over night. The crude above and 2,6-lutidine (0.15 g, 1.41 mmol) were dissolved in DCM (5 mL). The reaction mixture was cooled to 0° C., TBSOTf (0.248 g, 0.94 mmol) was added drop wise to the reaction mixture. After stirred at room temperature for 1 hour and concentrated, the crude was purified by silica gel chromatography using iso-hexanes/ethyl acetate 1:0 to 1:1 to give 174b (0.07 g, 43%). LCMS (m/z) 698.4 [M+H]. Tr=3.79 min.

Compound 174c

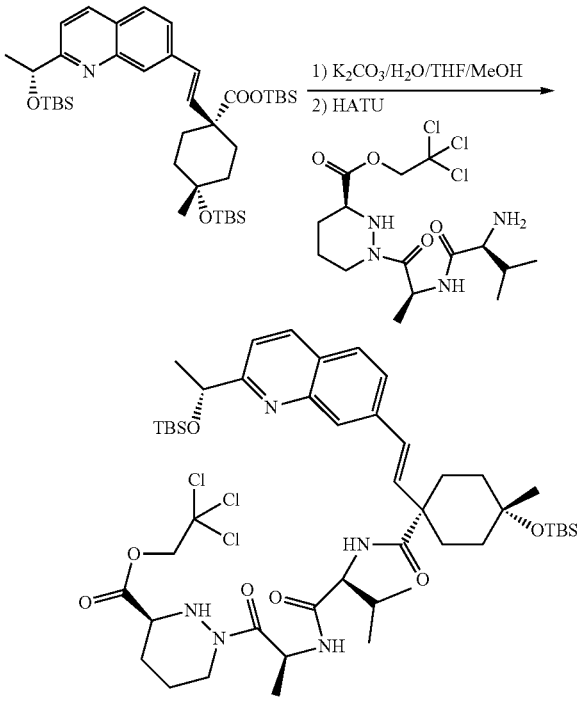

A solution of 174b (0.07 g, 0.10 mmol) in tetrahydrofuran (1 mL) and methanol (1 ml) was prepared and a 1 M aqueous solution of potassium carbonate (0.4 mL) was added. The reaction mixture was stirred at room temperature for 1 hour. 1N aq. HCl in water (0.8 mL) was added to the reaction solution. After concentration and co-evaporated with toluene (3×) to give the crude acid. To the crude acid in anhydrous N,N-dimethylformamide (2 mL) at room temperature and under an atmosphere of nitrogen was added N,N-diisopropylethylamine (39 mg, 0.30 mmol) and 2-(1H-7-azabenzotriazol-1-yl)-1,1,3,3-tetramethyl uronium hexafluorophosphate methanaminium (76 mg, 0.20 mmol). The solution was stirred at room temperature for 3 minutes before adding a solution of (S)-1-[(S)-2-((S)-2-amino-3-methyl-butyrylamino)-propionyl]-hexahydro-pyridazine-3-carboxylic acid 2,2,2-trichloro-ethyl ester (66 mg, 0.153 mmol) in anhydrous N,N-dimethylformamide (2 mL). The reaction was stirred for 1 hour. The reaction was quenched with water and extracted with ethyl acetate (2×). The combined organic layers were dried over sodium sulfate, filtered and concentrated in vacuo. The residue was purified by silica gel chromatography using iso-hexanes/ethyl acetate 1:0 to 0:1 to give 174c (70 mg, 70%) as a white solid. LCMS (m/z) 997.2 [M+H]. Tr=3.24 min.

Compound 174

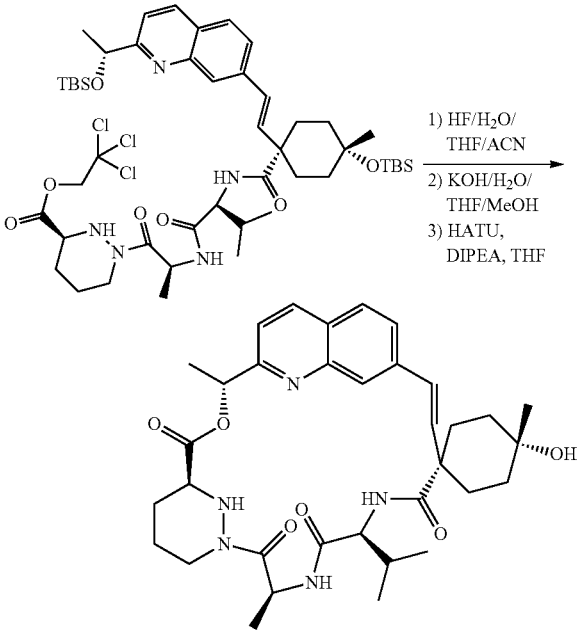

To a solution of 174c (0.07 g, 0.07 mmol) in acetonitrile (2 mL) and THF (2 mL) was added hydrofluoric acid (48 wt. % in water, 1.3 mL). The reaction mixture was stirred at room temperature for 2 hours and cooled to 0° C. Sat $NaHCO_3$ water solution was added drop wise to neutralize the reaction mixture. After extracted with EtOAc (2×), dried over $Na_2SO_4$ and concentration, the crude was dissolved in THF (2 mL) and MeOH (2 ml). 1 N KOH in water (0.21 mmol) was added to the reaction mixture. After stirred at room temperature for 1 hour, the reaction mixture was acidified by adding 1 N HCl in water (0.21 mL). After concentration and co-evaporated with toluene (3×), the crude acid from above in THF (70 mL) were added N,N-diisopropylethylamine (0.045 g, 0.35 mmol), DMAP (catalytic amount) and 2-(1H-7-azabenzotriazol-1-yl)-1,1,3,3-tetramethyl uronium hexafluorophosphate methanaminium (0.053 g, 0.14 mmol). The reaction mixture was stirred at room temperature for 3 hour. After concentration, the crude was purified by prep-HPLC to obtain 174 (0.014 g, 20%) as a white solid. $^1$H NMR (400 MHz, Methanol-$d_4$) δ 8.30 (d, J=8.5 Hz, 1H), 7.95 (d, J=1.7 Hz, 1H), 7.87 (d, J=8.5 Hz, 1H), 7.84-7.72 (m, 1H), 7.66 (d, J=8.5 Hz, 1H), 6.85 (d, J=16.4 Hz, 1H), 6.55 (d, J=16.4 Hz, 1H), 5.48-5.20 (m, 1H), 5.16-4.92 (m, 2H), 4.77 (d, J=12.1 Hz, 1H), 4.26 (d, J=7.2 Hz, 1H), 3.77 (dd, J=7.6, 4.2 Hz, 1H), 2.44-2.23 (m, 2H), 2.21-1.94 (m, 2H), 1.97-1.74 (m, 4H), 1.80-1.57 (m, 4H), 1.55 (d, J=6.6 Hz, 3H), 1.25 (d, J=6.9 Hz, 3H), 1.20 (s, 3H), 1.03-0.75 (m, 9H). LCMS (m/z) 620.3 [M+H]. Tr=2.02 min.

Example 175

Compound 175

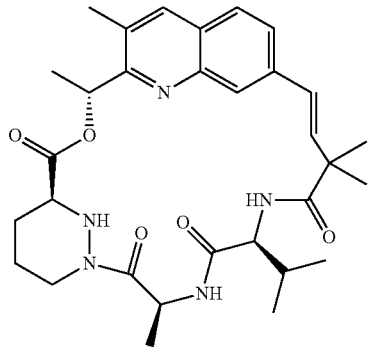

Compound 175a

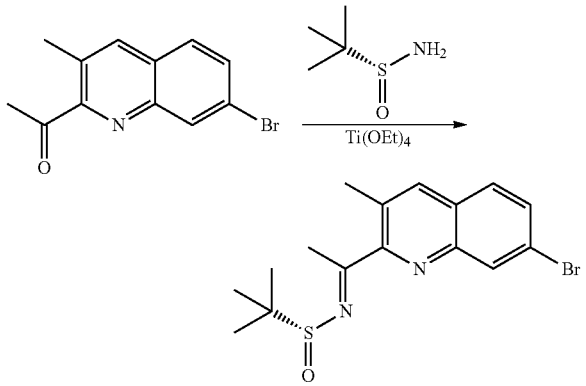

To a solution of 1-(7-bromo-3-methylquinolin-2-yl)ethanone (4.8 g, 18.1 mmol) in anhydrous THF (200 mL) were added titanium ethoxide (8.4 g, 36.7 mmol) and (R)-2-methylpropane-2-sulfinamide (2.7 g, 22.02 mmol). The mixture was stirred at 60° C. for overnight. After cooled back to room temperature, brine (100 mL) was added to the reaction mixture. Solid was filtrated away. The filtrate was extracted with EtOAc (2×100 mL). The combined organic layers were dried over $Na_2SO_4$. After concentration, the crude residue was purified by silica gel chromatography using iso-hexanes/ethyl acetate 1:0 to 1:1 to give 175a (2.8 g, 43%) as a solid. LCMS (m/z) 367.1/369.1 [M+H]. Tr=2.47 min.

Compound 175b

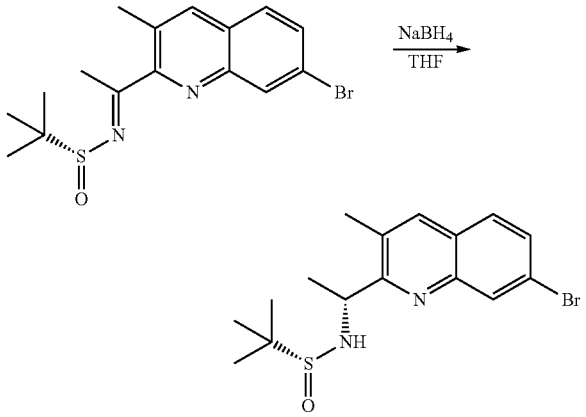

A solution of 175a (0.4 g, 1.09 mmol) in anhydrous THF (10 mL) was cooled to 0° C. $NaBH_4$ (0.062 g, 1.63 mmol) was added to the reaction mixture portion wise. After stirred at room temperature for 1 hour, the reaction mixture was quenched by adding water (1 mL). Then diluted with EA (50 mL), washed with brine and dried over $Na_2SO_4$. After concentration, the crude residue was purified by silica gel chromatography using iso-hexanes/ethyl acetate 1:0 to 1:1 to give 175b (0.15 g, 38%) as a solid. LCMS (m/z) 369.1/371.1 [M+H]. Tr=2.41 min.

Compound 175c

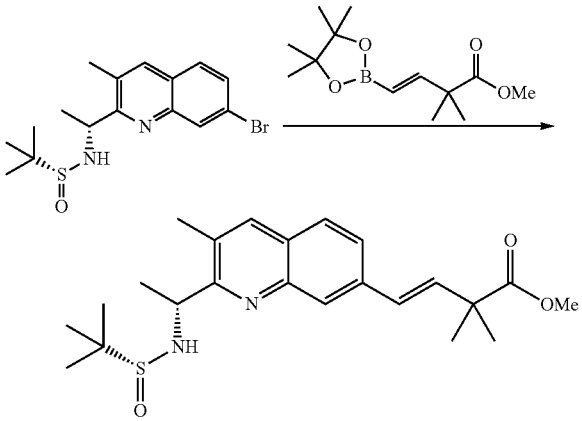

A round bottom flask was charged with 175b (150 mg, 0.41 mmol), (E)-2,2-dimethyl-4-(4,4,5,5-tetramethyl-[1,3,2]dioxaborolan-2-yl)-but-3-enoic acid methyl ester (114 mg, 0.45 bis[(dicyclohexyl)(4-dimethylaminophenyl)phosphine]palladium(II) chloride (16.7 mg, 0.021 mmol) and potassium phosphate tribasic (261 mg, 1.23 mmol). The system was flushed with nitrogen and cyclopentyl methyl ether (2 mL) and water (1 mL) were added. The reaction was heated for 1 hour at 90° C. and then cooled to room temperature. Ethyl acetate was added and the solution was washed with water. The organic layer was dried over magnesium sulfate, filtered and concentrated in vacuo. The residue was purified by silica gel chromatography using iso-hexanes/ethyl acetate 1:2 to give 175c (140 mg, 82%). LCMS (m/z) 417.2 [M+H]. Tr=2.37 min.

A solution of 175c (0.14 g, 0.336 mmol) was dissolved in 4N HCl/dioxane (1 mL). The reaction mixture was stirred at room temperature for 1 hour. After concentration, the obtained amine, 2 (0.20 g, 0.504 mmol), N,N-diisopropylethylamine (0.194 g, 1.5 mmol) and 2-(1H-7-azabenzotriazol-1-yl)-1,1,3,3-tetramethyl uronium hexafluorophosphate methanaminium (0.255 g, 0.672 mmol) was dissolved in DCM (10 ml). The reaction mixture was stirred at room temperature for 1 hour, diluted with EA (50 mL), washed with brine and dried over $Na_2SO_4$. After concentration, the crude residue was purified by silica gel chromatography using iso-hexanes/ethyl acetate 1:0 to 1:1 to give 175d (0.20 g, 86%) as a solid. LCMS (m/z) 695.4 [M+H]. Tr=2.48 min.

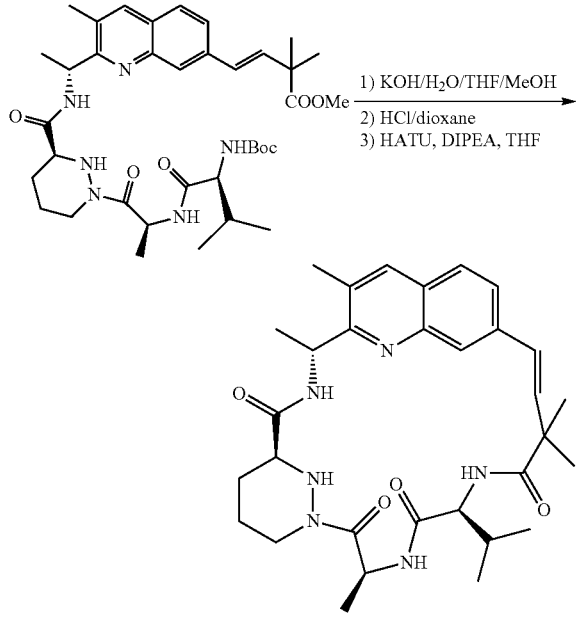

Compound 175d

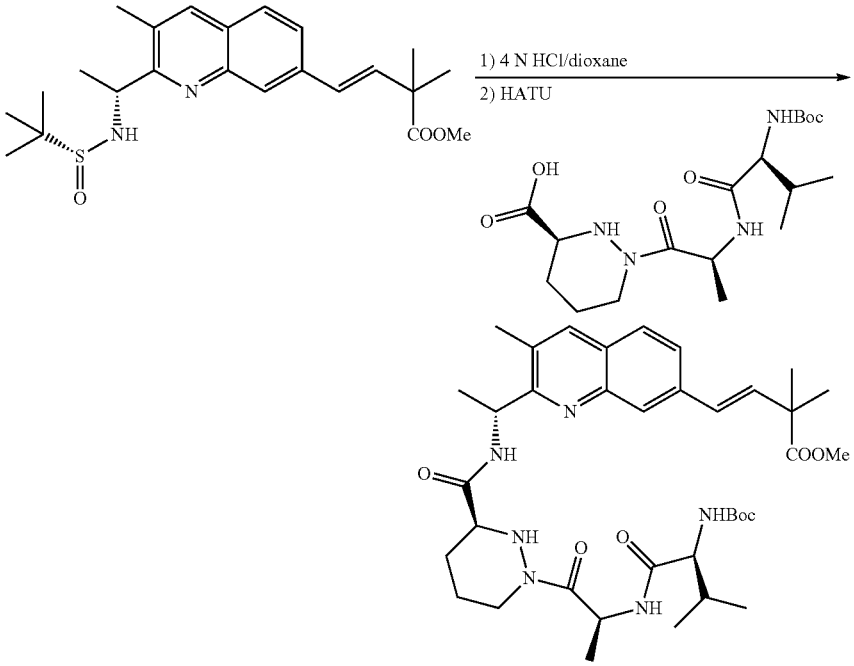

To a solution of 175d (0.20 g, 0.288 mmol) in THF (2 mL) and MeOH (2 ml) was added 1 N KOH in water (1.15 mL). The reaction mixture was stirred at room temperature for 1 hour and was acidified by adding 1 N HCl in water (1.15 mL). After concentration, the crude was dissolved in 4 N HCl/dioxane (2 ml) and stirred for 1 hour. After concentration and co-evaporated with toluene (3×), the crude above was dissolved in THF (150 mL). N,N-diisopropylethylamine (0.11 g, 0.86 mmol), DMAP (catalytic amount) and 2-(1H-7-azabenzotriazol-1-yl)-1,1,3,3-tetramethyl uronium hexafluorophosphate methanaminium (0.216 g, 0.57 mmol). The reaction mixture was stirred at room temperature for 3 hour. After concentration, the crude was purified by prep-HPLC to obtain the title compound 175 (0.07 g, 20%) as a white solid. $^1$H NMR (400 MHz, Methanol-$d_4$) δ 8.22 (s, 1H), 7.83 (d, J=8.9 Hz, 1H), 7.71 (d, J=6.6 Hz, 2H), 7.04 (d, J=9.4 Hz, 1H), 6.61-6.24 (m, 2H), 5.64 (dd, J=7.4, 2.5 Hz, 1H), 5.26 (q, J=6.7 Hz, 1H), 4.49-4.21 (m, 2H), 3.56 (dd, J=11.6, 2.9 Hz, 1H), 2.77-2.45 (m, 4H), 2.35-2.06 (m, 1H), 1.96-1.76 (m, 2H), 1.57 (m, 8H), 1.48 (s, 3H), 1.32 (s, 3H), 0.95 (dd, J=35.2, 6.7 Hz, 6H). LCMS (m/z) 563.3 [M+H]. Tr=2.22 min.

Biological Examples

Inhibition of Peptidyl-Prolyl Isomerase (PPIase) Activity

The PPIase assay was based on the procedure reported by Janowski et al. (Anal. Biochem. 1997, 252, 299). Assay buffer (1980 L of a solution containing 35 mM HEPES pH 7.8, 50M DTT, and 0.01% NP40) was pre-equilibrated to 10° C. in a quartz cuvette equipped with an overhead stirrer. To this solution was added 10 L of compound in DMSO (final concentration: 0.5% DMSO), followed by 5 L of a 2M stock solution of cyclophilin A (final concentration: 5 nM). The reaction was initiated with the addition of 5 L of 40 mM of the tetrapeptide Succ-AAPF-pNA (100M final concentration) dissolved in a solution of 0.5M LiCl in trifluoroethanol. Upon the initiation of the reaction, the absorbance of the peptide substrate was monitored at 330 nm for five minutes using a Beckman Coulter DU800 spectrophotometer. Progress curves were fit with a single-exponential decay model to calculate rates. The $IC_{50}$ values were calculated with a four-parameter logistic fit using Graph Pad Prism software.

Cyclophilin A TR-FRET Competitive Binding Assay

Inhibitor potency was measured using a competitive binding assay with a time-resolved fluorescence resonance energy transfer (TR-FRET) readout. To a reaction buffer consisting of 35 mM HEPES pH 7.8, 100 mM NaCl, 0.01% NP-40 (Pierce), 1 mM DTT, and 1% DMSO were added the following: 5 nM of cyclophilin A modified at the N-terminus with an 8×histidine affinity tag (CypA); 150 nM of cyclosporin A modified with a linker attached to a Cy5 fluorophore (CsA-Cy5); 1 nM Eu-labeled anti-(6×His) antibody (Perkin-Elmer); and test compound at one of various concentrations. The total volume of the assay solution was 100 L. After a two-hour incubation, the TR-FRET was measured using a Perkin Elmer Envision plate reader (excitation at 340 nm, emission measured at 590 nm and 665 nm). The signal was calculated as the ratio of the emission at 665 nm to that at 590 nm. An $IC_{50}$ value was calculated using a four-parameter logistic fit.

When tested, certain compounds of this invention were found to inhibit cyclophilin binding as listed in Table 1 below. The $IC_{50}$'s are presented as ranges wherein A is ≤100 nM, B is 101 to 1000 nM and C is 1001 to 10,000 nM.

Antiviral Activity

The antiviral activity of a compound can be measured using standard screening protocols: for example, cell-based Flavivirus immunodetection assay and cell-based Flavivirus cytopathic effect assay as described in U.S. Patent Publication Number US/20130022573, which is hereby incorporated by reference in its entirety.

One aspect of the invention relates to methods of inhibiting viral infections, comprising the step of treating a sample or subject suspected of needing such inhibition with a composition of the invention. The antiviral activity of a compound of the invention can be measured using standard screening protocols that are known.

The anti-HCV activity of the compounds of this invention was tested in a human hepatoma Huh-7 cell line harboring a HCV replicon. The assay comprised the following steps:

Step 1 (Compound Preparation and Serial Dilution):

Serial dilution was performed in 100% DMSO in a 384-well plate. A solution containing a compound at 225-fold concentration of the starting final serial dilution concentration was prepared in 100% DMSO and 15 μL added to the pre-specified wells in column 3 or 13 of a polypropylene 384-well plate. The rest of the 384-well plate was filled with 10 μL 100% DMSO except for columns 23 and 24, where 10 μL of 500 μM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2 (Cell Culture Plate Preparation and Compound Addition):

To each well of a black polypropylene 384-well plate, 90 μL of cell media containing 1600 suspended Huh-7 HCV replicon cells was added with a Biotek uFlow Workstation. A volume of 0.4 μL of the compound solution was transferred from the serial dilution plate to the cell culture plate on a Biomek FX Workstation. The DMSO concentration in the final assay condition was 0.44%. The plates were incubated for 3 days at 37° C. with 5% $CO_2$ and 85% humidity.

Step 3 (Detection of Cytotoxicity and Inhibition of Viral Replication):

a) Assessment of cytotoxicity: The media in the 384-well cell culture plate was aspirated with a Biotek EL405 plate-washer. A volume of 50 μL of a solution containing 400 nM Calcein AM in 100% PBS was added to each well of the plate with a Biotek uFlow Workstation. The plate was incubated for 30 minutes at RT before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 μL of Dual-Glo luciferase buffer (Promega, Dual-Glo Luciferase Assay Reagent, cat. #E298B) was added to each well of the plate with a Biotek uFlow Workstation. The plate was incubated for 10 minutes at RT. A volume of 20 μL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at RT for 10 minutes before the luminescence signal was measured with a Perkin Elmer Envision Plate Reader.

Step 4 (Calculation):

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition}=100\%/[(EC_{50}/[I])^{b}+1]$$

where b is Hill's coefficient. See, for reference, Hill, A. V., The Possible Effects of the Aggregation of the Molecules of Hæmoglobin on its Dissociation Curves, J. Physiol. 40: iv-vii. (1910). % inhibition values at a specific concentration, for example 2 μM, can also be derived from the formula above.

When tested, certain compounds of this invention were found to inhibit viral replication as listed in Table 1. In Table 1, the $EC_{50}$'s for Replicon 1a are presented as a % inhibition.

TABLE 1

| Example No. | TR-FRET | Replicon 1a % inhibition at 1 μM |
|---|---|---|
| 1 | A | 32 |
| 2 | B | 63 |
| 3 | A | 44 |
| 4 | B | 58 |
| 5 | A | 80 |
| 6 | A | 86 |
| 7 | A | 94 |
| 8 | B | 37 |
| 9 | A | 98 |
| 10 | B | 28 |
| 11 | A | 6 |
| 12 | C | 0 |
| 13 | A | 87 |
| 14 | A | 94 |
| 15 | A | 99 |
| 16 | B | 94 |
| 17 | A | 100 |
| 18 | A | 94 |
| 19 | A | 97 |
| 20 | A | 99 |
| 21 | A | 93 |
| 22 | A | 100 |
| 23 | A | 99 |
| 24 | A | 99 |
| 25 | B | 71 |
| 26 | A | 99 |
| 27 | A | 100 |
| 28 | B | 56 |
| 29 | C | 28 |
| 30 | A | 73 |
| 31 | A | 98 |
| 32 | A | 71 |
| 33 | C | 14 |
| 34 | A | 92 |
| 35 | A | 94 |
| 36 | A | 73 |

TABLE 1-continued

| Example No. | TR-FRET | Replicon 1a % inhibition at 1 μM |
|---|---|---|
| 37 | A | 76 |
| 38 | A | 98 |
| 39 | A | 98 |
| 40 | A | 96 |
| 41 | A | 96 |
| 42 | B | 16 |
| 43 | A | 97 |
| 44 | A | 78 |
| 45 | A | 80 |
| 46 | A | 90 |
| 47 | B | 9 |
| 48 | A | 40 |
| 49 | A | 85 |
| 50 | B | 12 |
| 51 | A | 83 |
| 52 | A | 98 |
| 53 | B | 89 |
| 54 | A | 98 |
| 55 | B | 76 |
| 56 | B | 47 |
| 57 | A | 100 |
| 58 | A | 99 |
| 59 | A | 100 |
| 60 | B | 65 |
| 61 | A | 72 |
| 62 | B | 25 |
| 63 | B | 80 |
| 64 | B | 35 |
| 65 | A | 92 |
| 66 | A | 80 |
| 67 | A | 97 |
| 68 | A | 91 |
| 69 | C | 19 |
| 70 | A | 95 |
| 71 | B | — |
| 72 | B | 0 |
| 73 | A | 94 |
| 74 | A | 95 |
| 75 | A | 100 |
| 76 | A | 63 |
| 77 | A | 99 |
| 78 | A | 99 |
| 79 | A | 96 |
| 80 | A | 97 |
| 81 | A | 100 |
| 82 | A | 99 |
| 83 | A | 99 |
| 84 | A | 63 |
| 85 | A | — |
| 86 | A | — |
| 87 | A | — |
| 88 | A | — |
| 89 | A | 99 |
| 90 | A | 100 |
| 91 | A | 99 |
| 92 | A | 100 |
| 93 | A | 68 |
| 94 | A | 96 |
| 95 | A | 68 |
| 96 | A | 100 |
| 97 | A | 98 |
| 98 | A | 95 |
| 99 | A | 96 |
| 100 | A | 100 |
| 101 | A | 99 |
| 102 | A | 100 |
| 103 | A | 100 |
| 104 | A | 98 |
| 106 | A | 99 |
| 107 | A | 100 |
| 108 and 109 | A | 100 |
| 110 | A | 100 |
| 111 | A | 87 |
| 112 | A | 96 |
| 113 | B | 13 |
| 114 | A | 99 |
| 115 | A | 92 |

TABLE 1-continued

| Example No. | TR-FRET | Replicon 1a % inhibition at 1 μM |
|---|---|---|
| 116 | A | 100 |
| 117 | A | 100 |
| 118 | B | 35 |
| 119 | A | 98 |
| 120 | A | 91 |
| 121 | A | 100 |
| 122 | A | 96 |
| 123 | A | 100 |
| 124 | A | 100 |
| 125 | A | 100 |
| 126 | A | 100 |
| 127 | A | 2 |
| 128 | A | — |
| 129 | A | 96 |
| 130 | A | 100 |
| 131 | A | 77 |
| 132 | A | 100 |
| 133 | A | 98 |
| 134 | A | 99 |
| 135 | A | 94 |
| 136 | A | 100 |
| 137 | A | 100 |
| 138 | A | 100 |
| 139 | A | — |
| 140 | B | 13 |
| 141 | A | 99 |
| 142 | A | 99 |
| 143 | A | 31 |
| 144 | A | 100 |
| 145 | A | — |
| 146 | A | 24 |
| 147 | A | 94 |
| 148 | A | 100 |
| 149 | A | 99 |
| 150 | A | 95 |
| 151 | C | 0 |
| 152 | A | 100 |
| 153 | A | 100 |
| 154 | A | 100 |
| 155 | A | 100 |
| 156 | A | 87 |
| 157 | — | — |
| 158 | A | 100 |
| 159 | — | — |
| 160 | A | 98 |
| 161 | A | 95 |
| 162 | C | 0 |
| 163 | A | 100 |
| 164 | A | — |
| 165 | A | 100 |
| 166 | C | 0 |
| 167 | A | 97 |
| 168 | A | 100 |
| 169 | — | — |
| 170 | A | 100 |
| 171 | A | 99 |
| 172 | A | 100 |
| 173 | A | 99 |
| 174 | A | 99 |
| 175 | A | 85 |

The specific pharmacological and biochemical responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention.

What is claimed is:

1. A compound of Formula I:

Formula I

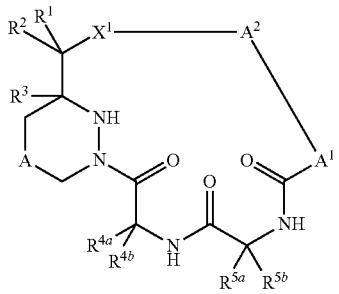

or a pharmaceutically acceptable salt, [isotope,] stereoisomer, mixture of stereoisomers, tautomer, ester or prodrug thereof, wherein:

A is a bond, —O—, —S(O)$_n$—, —NH—, —N((C$_1$-C$_4$)alkyl)- or (C$_1$-C$_2$)alkylene;

A$^1$ is

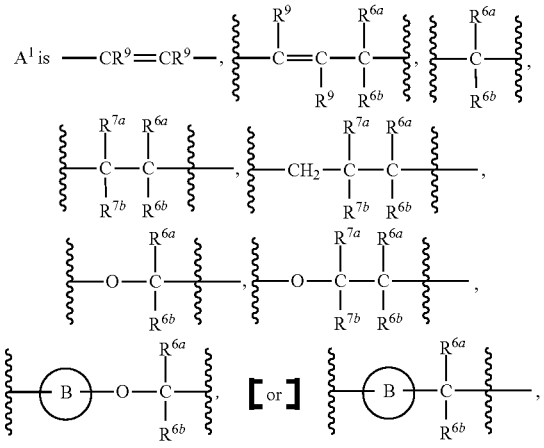

*pyrazolylene, phenylene or pyrimidinylene,* wherein B is arylene, heteroarylene, cycloalkylene or heterocycloalkylene;

A$^2$ is —CH(R$^8$)-arylene, —CH(R$^8$)-heteroarylene, —CH(R$^8$)-heterocycloalkylene, —CH(R$^8$)-cycloalkylene, arylene[, heteroarylene] or cycloalkylene, wherein A$^2$ is optionally substituted with one or more substituents selected from the group consisting of [oxo,] —OR$^9$, —SR$^9$, —S(O)R$^9$, —S(O)$_2$R$^9$, —N(R$^9$)$_2$, halo, halo(C$_1$-C$_4$)alkyl, [(C$_1$-C$_4$)alkoxy(C$_1$-C$_4$)alkyl,] halo(C$_1$-C$_4$)alkoxy, cyano and (C$_1$-C$_8$)alkyl;

X$^1$ is a bond, —O—, —NH—, —N((C$_1$-C$_4$)alkyl)- or heterocycloalkylene;

R$^1$ and R$^2$ are independently H, (C$_1$-C$_4$)alkyl, (C$_2$-C$_4$)alkenyl, (C$_2$-C$_4$)alkynyl, halo, cyano or (C$_1$-C$_4$)alkanoyl; or R$^1$ and R$^2$, when taken together with the carbon to which they are both attached, form —C(═O)—, —C(═S)— or —C(═N(C$_1$-C$_4$)alkyl)-;

R$^3$ is H or (C$_1$-C$_4$)alkyl which is optionally substituted with halo, cyano, hydroxy or (C$_1$-C$_4$)alkoxy;

R$^{4a}$ and R$^{4b}$ are independently H, (C$_1$-C$_8$)alkyl, aryl, aryl(C$_1$-C$_4$)alkyl, heterocycloalkyl, heterocycloalkyl(C$_1$-C$_4$)alkyl, cycloalkyl or cycloalkyl(C$_1$-C$_4$)alkyl, wherein each of $R^{4a}$ and $R^{4b}$ is optionally substituted with one or more substituent selected from the group consisting of cyano, [$(C_1-C_8)$alkoxy,] —COOH, [—C(O)O—$(C_1-C_8)$alkyl,] halo, hydroxyl, amino, mono$(C_1-C_8)$alkylamino, di$(C_1-C_8)$alkylamino, [—C(O)-mono$(C_1-C_8)$alkylamino, —C(O)-di$(C_1-C_8)$alkylamino, —C(O)— heterocycloalkyl, heterocycloalkyl,] aryl and heteroaryl[, wherein each substituent is optionally substituted with one or more halo, heterocycloalkyl or aryl], *or $R^{4a}$ and $R^{4b}$ are independently $(C_1-C_4)$alkoxy or halo$(C_1-C_4)$alkoxy*;

$R^{5a}$ and $R^{5b}$ are independently H, $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl$(C_1-C_4)$alkyl, cycloalkyl$(C_1-C_4)$alkyl or heterocycloalkyl$(C_1-C_4)$alkyl, wherein $R^{5a}$ and $R^{5b}$ are independently optionally substituted with one or more substituent selected from the group consisting of —$N_3$, cyano, —COOH, halo, hydroxyl, amino, mono$(C_1-C_8)$alkylamino, di$(C_1-C_8)$alkylamino, aryl and heteroaryl, or *one of $R^{5a}$ and $R^{5b}$ is heteroaryl-heteroaryl$(C_1-C_4)$alkyl; or*

$R^{5a}$ and $R^{5b}$ together form a spirocycle having Formula (a):

(a)

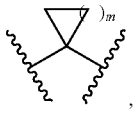

, wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, [—C(O)O—$(C_1-C_8)$alkyl, —C(O)-di$(C_1-C_8)$alkylamino, —C(O)—$(C_1-C_8)$alkyl, —C(O)-heterocycloalkyl, —$S(O)_2R^{10}$, —$OSi(R^{10})_3$,] $(C_1-C_4)$alkyl[, cyano$(C_1-C_4)$alkyl, halo$(C_1-C_4)$alkyl,] *and* $(C_1-C_4)$alkoxy[, $(C_1-C_8)$alkanoyl and aryl$(C_1-C_4)$alkyl];

$R^{6a}$, $R^{6b}$, $R^{7a}$ and $R^{7b}$ are independently H, hydroxyl, [cyano,] $(C_1-C_8)$alkyl, $(C_2-C_8)$alkenyl, $(C_2-C_8)$alkynyl, $(C_1-C_8)$alkoxy, —$CH_2CH_2CR^9$(=N$(C_1-C_4)$alkoxy), aryl, heterocycloalkyl, cycloalkyl, —$SR^9$, —$S(O)R^9$, —$S(O)_2R^9$ or —$N(R^9)_2$, wherein each of $R^{6a}$, $R^{6b}$, $R^{7a}$ and $R^{7b}$ is optionally substituted with one or more substituent selected from the group consisting of halo, hydroxyl, cyano, $(C_1-C_4)$alkyl, $(C_1-C_8)$alkoxy, aryl, cycloalkyl, heterocycloalkyl, mono$(C_1-C_8)$alkylamino, di$(C_1-C_8)$alkylamino, —$NHS(O)R^9$, —$NHC(O)R^9$[, —OC(O)—$(C_1-C_8)$alkyl —C(O)O—$(C_1-C_8)$alkyl] and $(C_1-C_8)$alkanoyl[, wherein each —OC(O)—$(C_1-C_8)$alkyl or $(C_1-C_8)$alkoxy is optionally substituted with one or more amino, —OC(O)O—$(C_1-C_8)$alkyl or —$Si(R^{10})_3$]; or $R^{6a}$ and $R^{6b}$ together form a spirocycle having Formula (a);

each $R^8$ is independently H, $(C_1-C_4)$alkyl, halo$(C_1-C_4)$alkyl, $(C_2-C_4)$alkenyl, $(C_2-C_4)$alkynyl, aryl, heteroaryl, heterocycloalkyl or cycloalkyl, wherein $R^8$ is optionally substituted with —OR, —$N(R^9)_2$, —$CON(R^9)_2$ or cyano;

each $R^9$ is independently H, $(C_1-C_4)$alkyl, $(C_2-C_4)$alkenyl or $(C_2-C_4)$alkynyl;

[each $R^{10}$ is independently H, $(C_1-C_4)$alkyl, $(C_2-C_4)$alkenyl, $(C_2-C_4)$alkynyl, cycloalkyl$(C_1-C_4)$alkyl or aryl, wherein $R^{10}$ is optionally substituted with one or more halo;]

each n is independently 0, 1 or 2; and m is 1, 2, 3, 4 or 5.

2. The compound of claim 1, wherein A is methylene.

3. The compound of claim 1, wherein $A^1$ is ethenylene, propenylene, ethylene, propylene, oxypropylene, oxypropenylene, pyrazolylene, phenylene or pyrimidinylene.

4. The compound of claim 1, wherein $A^1$ is

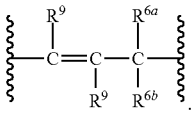

.

5. The compound of claim 1, wherein $A^2$ is —$CH(R^8)$-arylene or —$CH(R^8)$-heteroarylene.

6. The compound of claim 1, wherein $A^2$ is —$CH(R^8)$-quinolinylene, —$CH(R^8)$-isoquinolinylene, —$CH(R^8)$-naphthyridinylene, —$CH(R^8)$-cinnolinylene, —$CH(R^8)$-quinoxalinylene, —$CH(R^8)$-phenylene or —$CH(R^8)$-halophenylene.

7. The compound of claim 1, wherein $A^2$ is

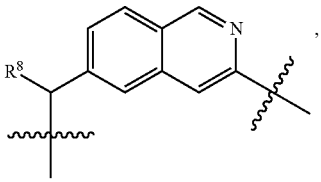

,

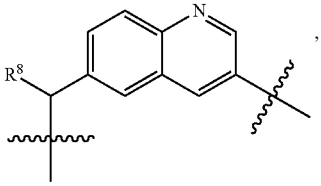

,

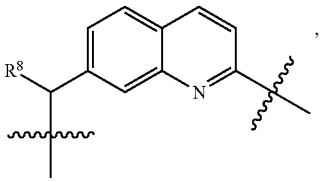

,

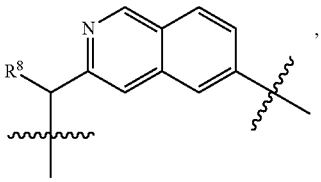

,

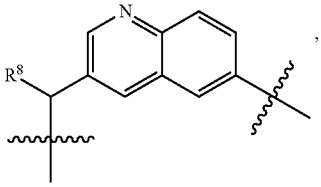

,

-continued

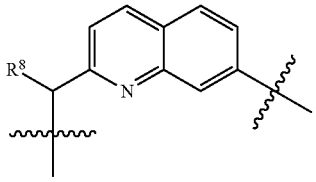

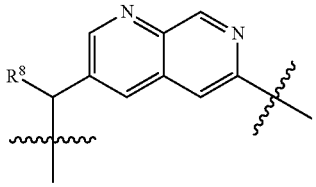

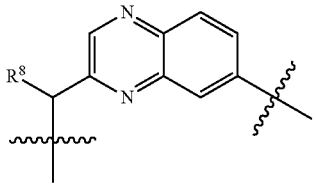

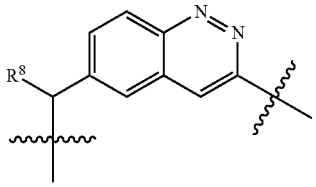

or

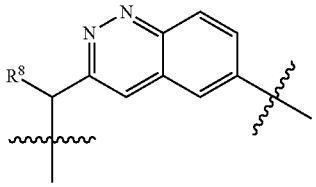

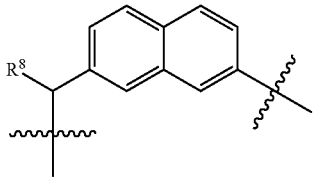

8. The compound of claim 1, wherein $X^1$ is —O— or —NH—.

9. The compound of claim 1, wherein $R^1$ and $R^2$, when taken together with the carbon to which they are both attached, form —C(═O)—.

10. The compound of claim 1, wherein $R^3$ is H.

11. The compound of claim 1, wherein $R^{6a}$ is H and $R^{6b}$ is H or $(C_1\text{-}C_4)$alkyl, or $R^{6a}$ and $R^{6b}$ together form a spirocycle having Formula (a).

12. The compound of claim 1, wherein $R^{6a}$ and $R^{6b}$ form

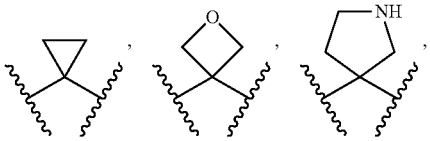

-continued

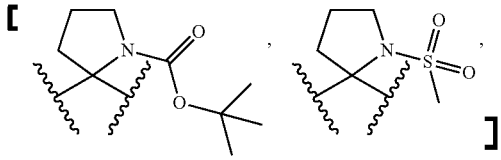

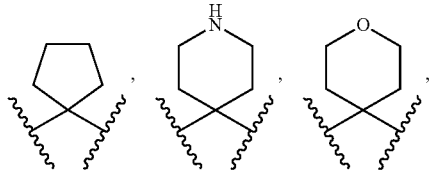

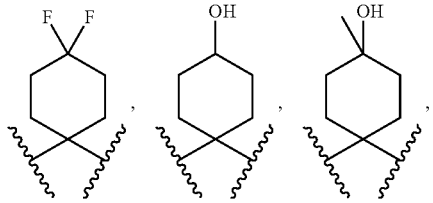

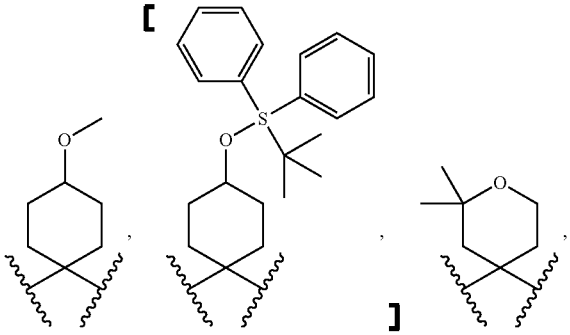

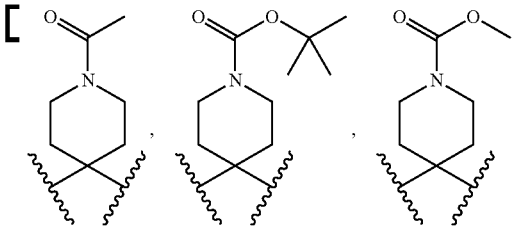

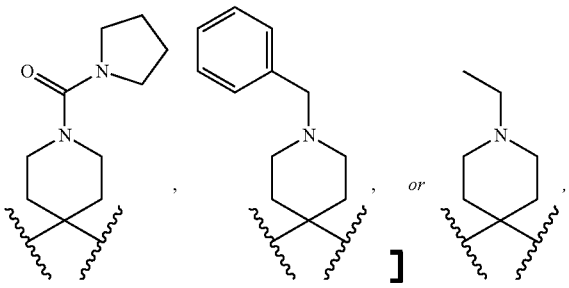

or

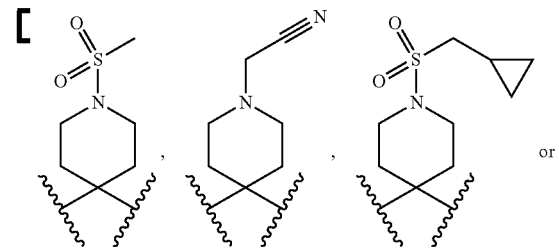

or

-continued

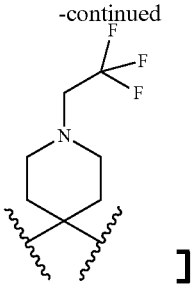

]

13. The compound of claim 1, wherein $R^3$ is H; $R^{5a}$ is H; $R^{5b}$ is H, $(C_1-C_8)$alkyl, hydroxy$(C_1-C_8)$alkyl, $(C_2-C_8)$alkenyl, $(C_2-C_8)$alkynyl, azido$(C_1-C_8)$alkyl, aryl, cycloalkyl, aryl$(C_1-C_4)$alkyl, cycloalkyl$(C_1-C_4)$alkyl, heterocycloalkyl $(C_1-C_4)$alkyl or arylheterocycloalkyl$(C_1-C_4)$alkyl; $R^{6a}$ is H; and $R^{6b}$ is H, $(C_1-C_4)$alkyl or hydroxy$(C_1-C_4)$alkyl.

14. The compound of claim 1, wherein $X^1$ is —O— or —NH—; $R^1$ and $R^2$, when taken together with the carbon to which they are both attached, form —C(═O)—; $R^3$ is H; $R^{4a}$ is H; $R^{4b}$ is methyl; $R^{5a}$ is H and $R^{5b}$ is iso-propyl, propenyl or propynyl; and $R^8$ is methyl.

15. The compound of claim 1, which is a compound of Formula II:

Formula II

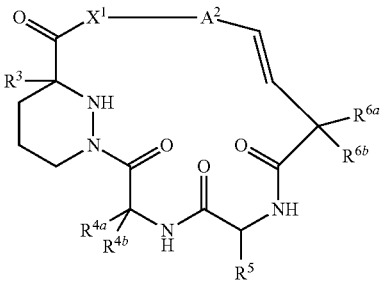

or a pharmaceutically acceptable salt, [isotope,] stereoisomer, mixture of stereoisomers, tautomer, ester or prodrug thereof, wherein:

$A^2$ is —CH($R^8$)-arylene, —CH($R^8$)-heteroarylene, —CH($R^8$)-heterocycloalkylene, —CH($R^8$)-cycloalkylene or cycloalkylene;

$X^1$ is a bond, —O—, —NH, —N($CH_3$)—,

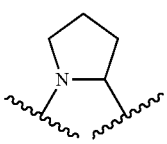

or

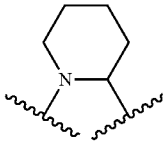

;

$R^3$ is H or $(C_1-C_4)$alkyl;

$R^{4a}$ and $R^{4b}$ are independently H, $(C_1-C_8)$alkyl, aryl, aryl$(C_1-C_4)$alkyl, heterocycloalkyl, heterocycloalkyl $(C_1-C_4)$alkyl, cycloalkyl or cycloalkyl$(C_1-C_4)$alkyl, wherein each of $R^{4a}$ and $R^{4b}$ is optionally substituted with one or more substituent selected from the group consisting of cyano, [$(C_1-C_8)$alkoxy,] —COOH, [—C(O)O—$(C_1-C_8)$alkyl,] halo, hydroxyl, amino, mono $(C_1-C_8)$alkylamino, di$(C_1-C_8)$alkylamino, [—C(O)-mono$(C_1-C_8)$alkylamino, —C(O)-di$(C_1-C_8)$alkylamino, —C(O)— heterocycloalkyl, heterocycloalkyl,] aryl and heteroaryl, [wherein each substituent is optionally substituted with one or more halo, heterocycloalkyl or aryl] *or $R^{4a}$ and $R^{4b}$ are independently $(C_1-C_4)$alkoxy or halo$(C_1-C_4)$alkoxy*;

$R^5$ is $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl$(C_1-C_4)$alkyl, cycloalkyl$(C_1-C_4)$alkyl or heterocycloalkyl $(C_1-C_4)$alkyl, wherein $R^5$ is optionally substituted with one or more substituent selected from —$N_3$, cyano, —COOH, halo, hydroxyl, amino, mono$(C_1-C_8)$alkylamino, di$(C_1-C_8)$alkylamino, aryl and heteroaryl[,];

$R^{6a}$ and $R^{6b}$ are independently H, hydroxyl, [cyano,] $(C_1-C_8)$alkyl, $(C_2-C_8)$alkenyl, $(C_2-C_8)$alkynyl, $(C_1-C_8)$alkoxy, —$CH_2CH_2CR^9$(═N$(C_1-C_4)$alkoxy), aryl, heterocycloalkyl, cycloalkyl, —$SR^9$, —S(O)$R^9$, —S(O)$_2$ $R^9$ or —N$(R^9)_2$, wherein each of $R^{6a}$ and $R^{6b}$ is optionally substituted with one or more substituent selected from the group consisting of halo, hydroxyl, cyano, $(C_1-C_4)$alkyl, $(C_1-C_8)$alkoxy, aryl, cycloalkyl, heterocycloalkyl, mono$(C_1-C_8)$alkylamino, di$(C_1-C_8)$alkylamino, —NHS(O)$R^9$, —NHC(O)$R^9$[, —OC(O)—$(C_1-C_8)$alkyl —C(O)O—$(C_1-C_8)$alkyl] and $(C_1-C_8)$alkanoyl[, wherein each —OC(O)—$(C_1-C_8)$alkyl or $(C_1-C_8)$alkoxy is optionally substituted with one or more amino, —OC(O)O—$(C_1-C_8)$alkyl or —Si$(R^{10})_3$]; or $R^{6a}$ and $R^{6b}$ together form a spirocycle having Formula (a);

(a)

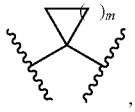

, wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, [—C(O)O—$(C_1-C_8)$alkyl, —C(O)-di$(C_1-C_8)$alkylamino, —C(O)—$(C_1-C_8)$alkyl, —C(O)-heterocycloalkyl, —S(O)$_2R^{10}$, —OSi$(R^{10})_3$,] $(C_1-C_4)$alkyl, [cyano$(C_1-C_4)$alkyl, halo$(C_1-C_4)$alkyl,] *and* $(C_1-C_4)$alkoxy[, $(C_1-C_8)$alkanoyl and aryl$(C_1-C_4)$alkyl];

$R^8$ is H or $(C_1-C_4)$alkyl; *and* each $R^9$ is independently H, $(C_1-C_4)$alkyl, $(C_2-C_4)$alkenyl or $(C_2-C_4)$alkynyl[; and each $R^{10}$ is independently H, $(C_1-C_4)$alkyl, $(C_2-C_4)$alkenyl, $(C_2-C_4)$alkynyl, cycloalkyl$(C_1-C_4)$alkyl or aryl, wherein $R^{10}$ is optionally substituted with one or more halo].

16. The compound of claim 1, which is a compound of Formula IIa:

Formula IIa

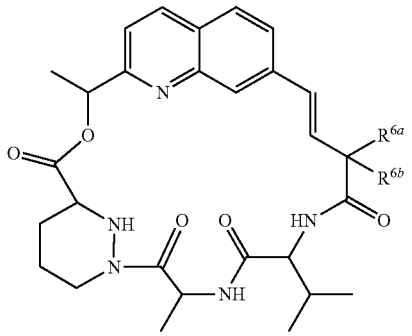

or a pharmaceutically acceptable salt, [isotope,] stereoisomer, mixture of stereoisomers, tautomer, ester or prodrug thereof, wherein:

$R^{6a}$ and $R^{6b}$ are independently H, hydroxyl, [cyano,] $(C_1-C_8)$alkyl, $(C_2-C_8)$alkenyl, $(C_2-C_8)$alkynyl, $(C_1-C_8)$alkoxy, —$CH_2CH_2CR^9$(=N$(C_1-C_4)$alkoxy), aryl, heterocycloalkyl, cycloalkyl, —$SR^9$, —$S(O)R^9$, —$S(O)_2R^9$ or —$N(R^9)_2$, wherein each of $R^{6a}$ and $R^{6b}$ is optionally substituted with one or more substituent selected from the group consisting of halo, hydroxyl, cyano, $(C_1-C_4)$alkyl, $(C_1-C_8)$alkoxy, aryl, cycloalkyl, heterocycloalkyl, mono$(C_1-C_8)$alkylamino, di$(C_1-C_8)$alkylamino, —$NHS(O)R^9$, —$NHC(O)R^9$, [—OC(O)—$(C_1-C_8)$alkyl —C(O)O—$(C_1-C_8)$alkyl] and $(C_1-C_8)$alkanoyl[, wherein each —OC(O)—$(C_1-C_8)$alkyl or $(C_1-C_8)$alkoxy is optionally substituted with one or more amino, —OC(O)O—$(C_1-C_8)$alkyl or —$Si(R^{10})_3$]; or $R^{6a}$ and $R^{6b}$ together form a spirocycle having Formula (a);

(a)

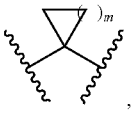

wherein one or more carbon ring atoms of Formula (a) is optionally replaced by a nitrogen, oxygen or sulfur atom, and wherein a ring atom of Formula (a) is optionally substituted with one or more substituent selected from the group consisting of halo, hydroxyl, —$NH_2$, [—C(O)O—$(C_1-C_8)$alkyl, —C(O)-di$(C_1-C_8)$alkylamino, —C(O)—$(C_1-C_8)$alkyl, —C(O)-heterocycloalkyl, —$S(O)_2R^{10}$, —$OSi(R^{10})_3$,] $(C_1-C_4)$alkyl[, cyano$(C_1-C_4)$alkyl, halo$(C_1-C_4)$alkyl,] *and* $(C_1-C_4)$alkoxy[, $(C_1-C_8)$alkanoyl and aryl$(C_1-C_4)$alkyl]; *and* each $R^9$ is independently H, $(C_1-C_4)$alkyl, $(C_2-C_4)$alkenyl or $(C_2-C_4)$alkynyl[; and each $R^{10}$ is independently H, $(C_1-C_4)$alkyl, $(C_2-C_4)$alkenyl, $(C_2-C_4)$alkynyl, cycloalkyl$(C_1-C_4)$alkyl or aryl, wherein $R^{10}$ is optionally substituted with one or more halo].

17. The compound of claim 15, wherein $R^{4a}$ and $R^{4b}$ are independently H, $(C_1-C_4)$alkoxy, halo$(C_1-C_4)$alkoxy or $(C_1-C_8)$alkyl;

$R^5$ is H, $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl $(C_1-C_4)$alkyl, cycloalkyl$(C_1-C_4)$alkyl or heterocycloalkyl$(C_1-C_4)$alkyl, wherein $R^5$ is optionally substituted with one or more substituent selected from the group consisting of —$N_3$, halo, hydroxyl, di$(C_1-C_8)$alkylamino, aryl or heteroaryl; and $R^{6a}$ and $R^{6b}$ are independently H, —OH, $(C_1-C_4)$alkoxy[, halo$(C_1-C_4)$alkoxy] or $(C_1-C_8)$alkyl, wherein each of $R^{6a}$ and $R^{6b}$ is optionally substituted with one or more substituent selected from the group consisting of halo, hydroxyl, $(C_1-C_4)$alkyl, aryl, cycloalkyl, heterocycloalkyl, di$(C_1-C_8)$alkylamino and $(C_1-C_8)$alkanoyl; or $R^{6a}$ and $R^{6b}$ together form

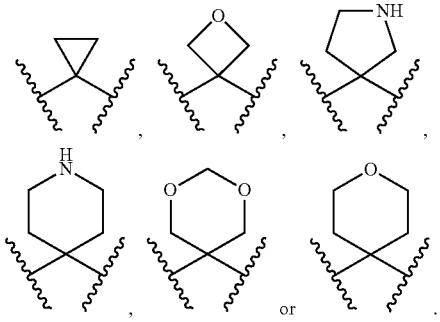

18. The compound of claim 1, which is

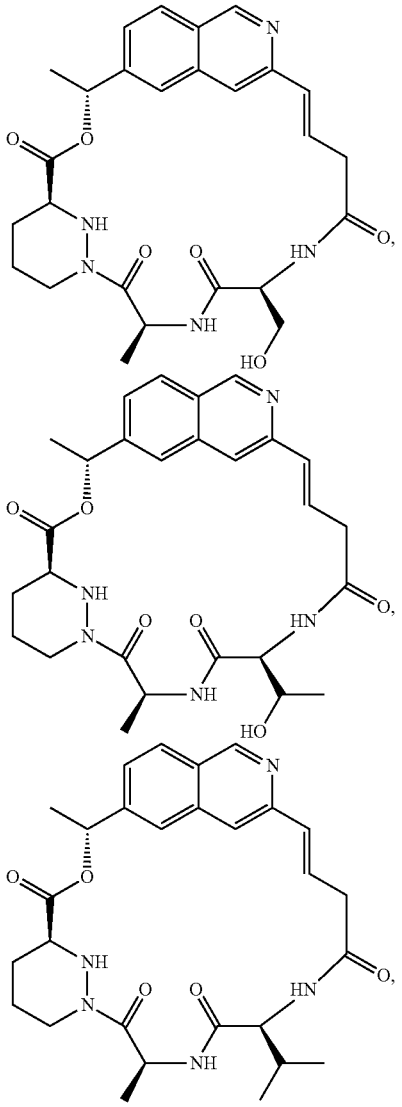

661
-continued
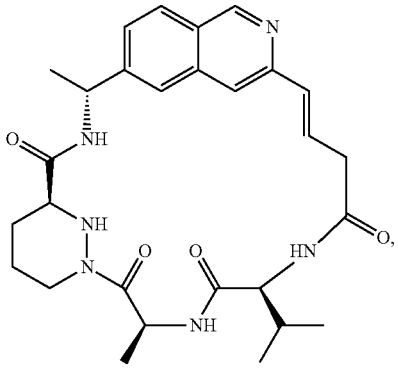
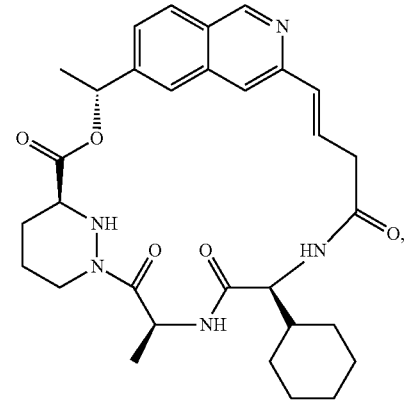
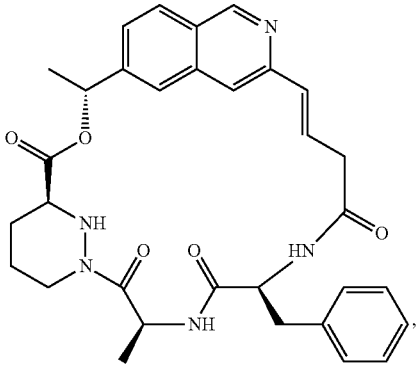
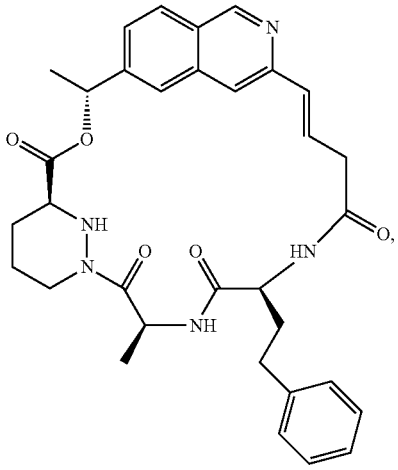
662
-continued
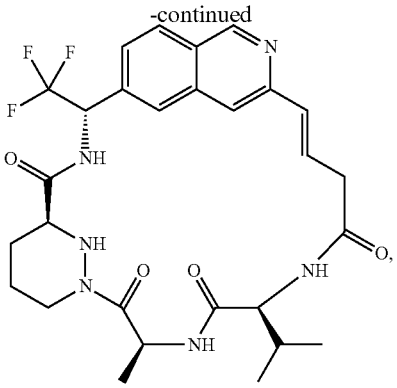
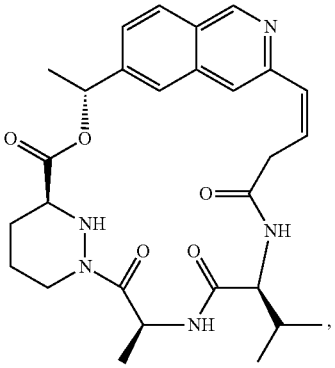
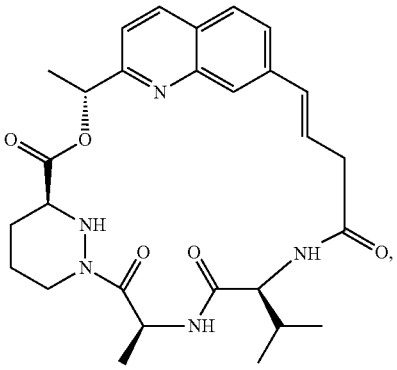
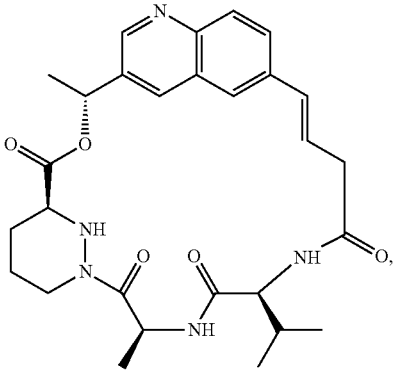

-continued
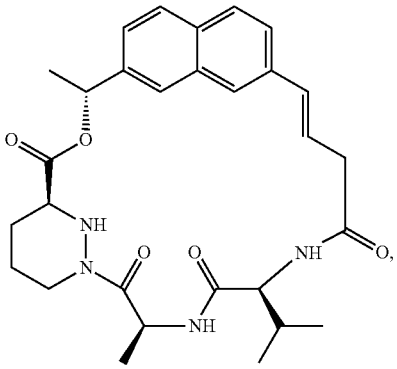
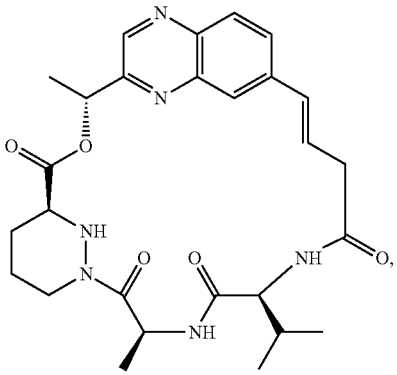
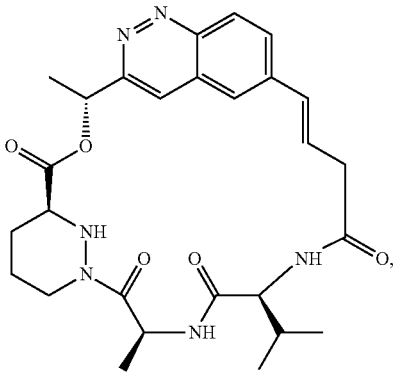
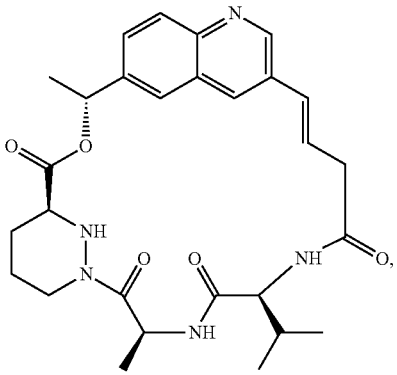
-continued
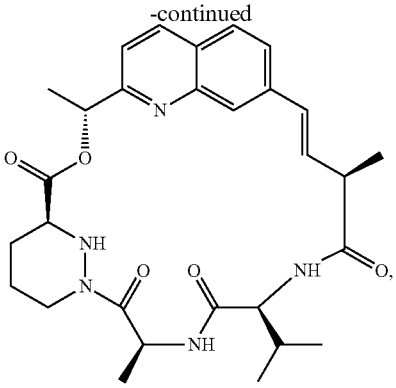
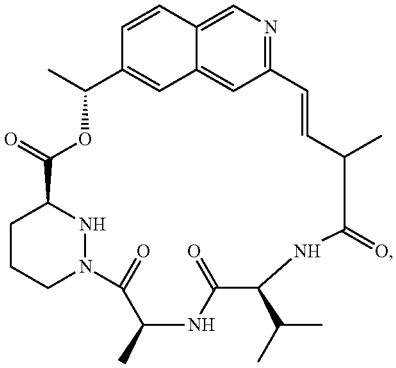
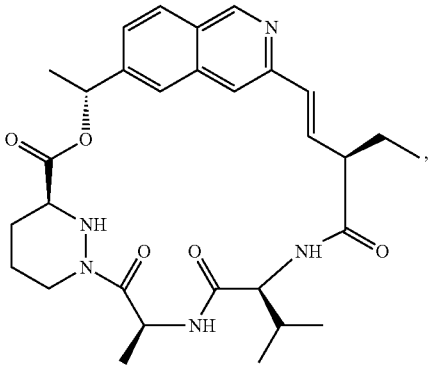
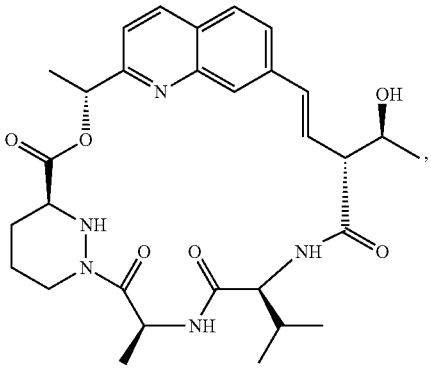

-continued
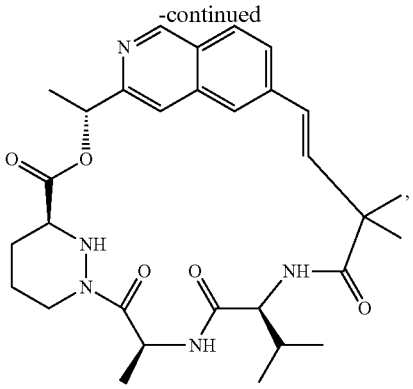
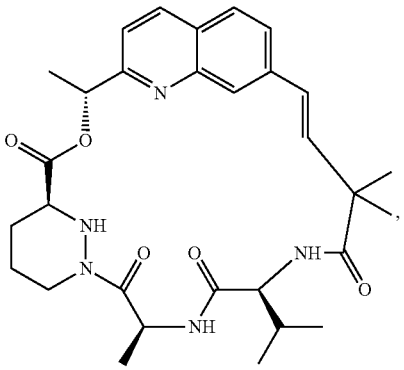
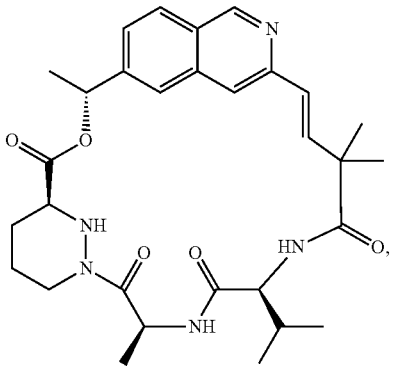
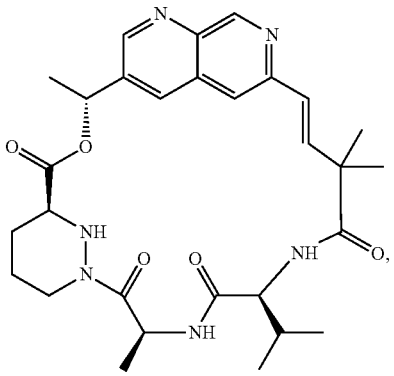
-continued
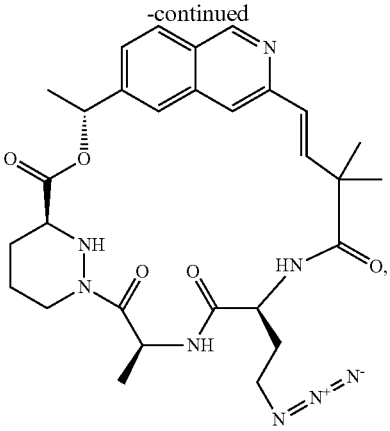
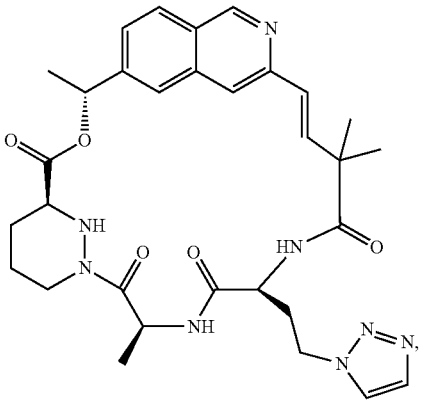
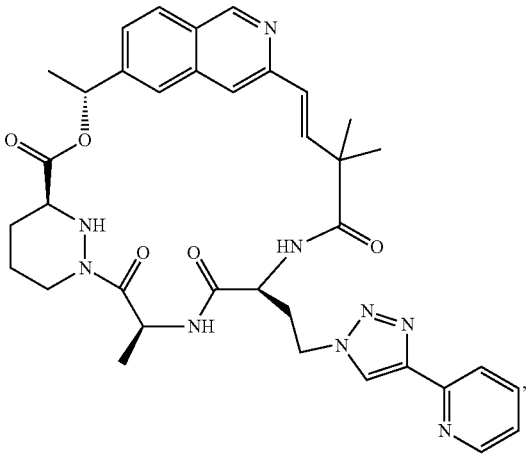
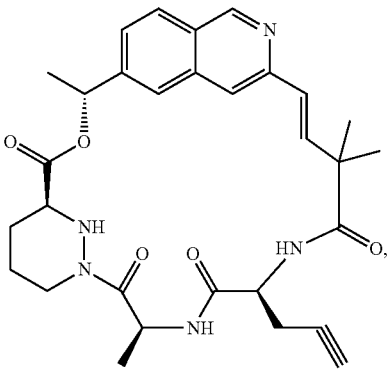

-continued
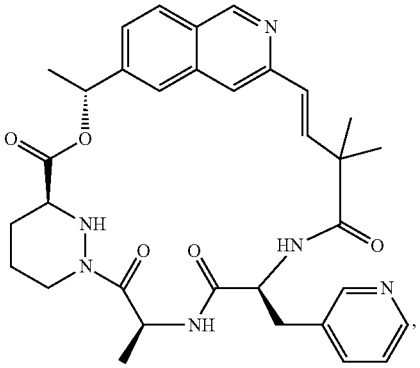
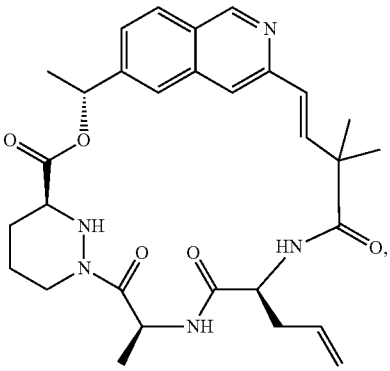
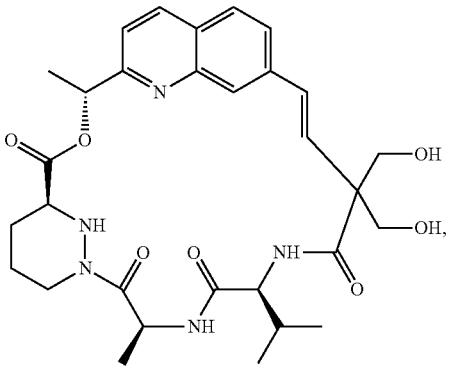
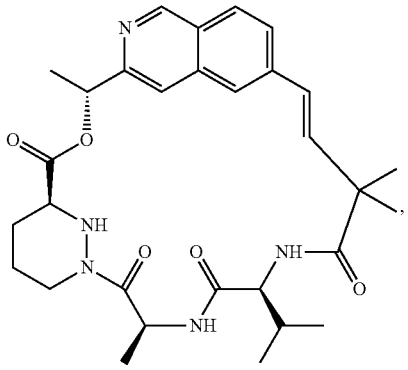
-continued
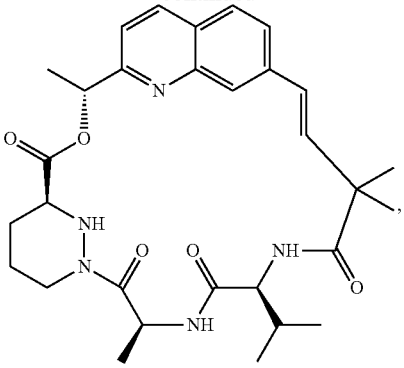
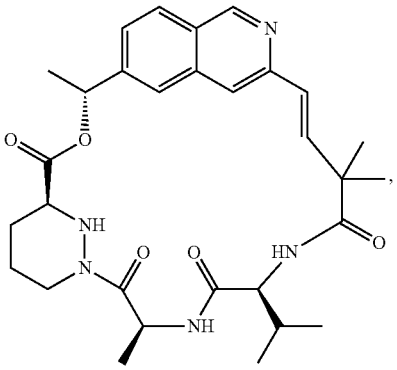
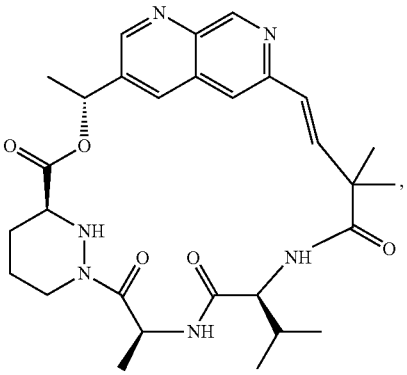
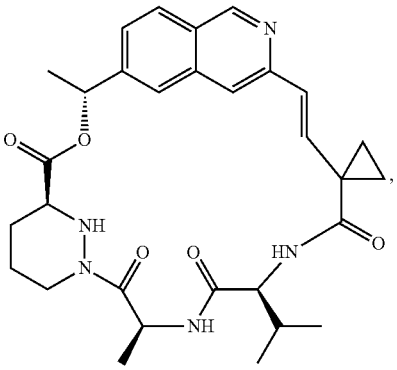

-continued
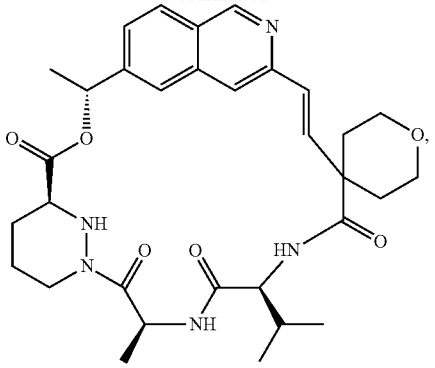
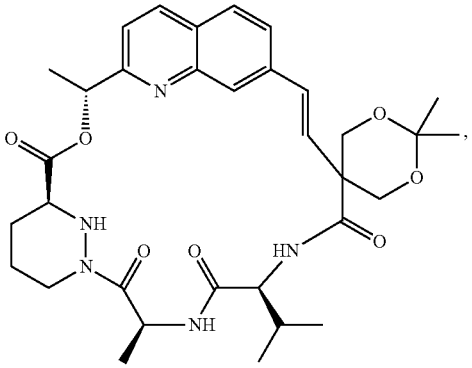
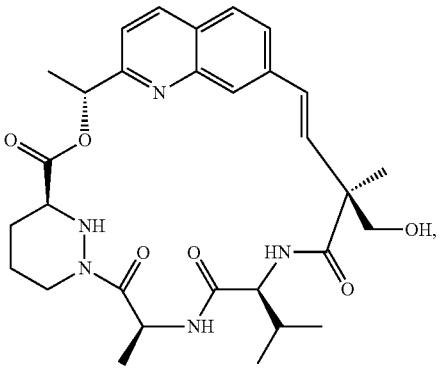
[
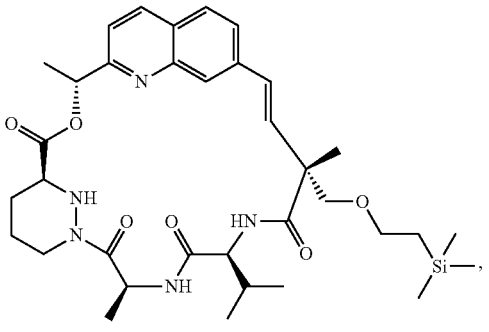
]
-continued
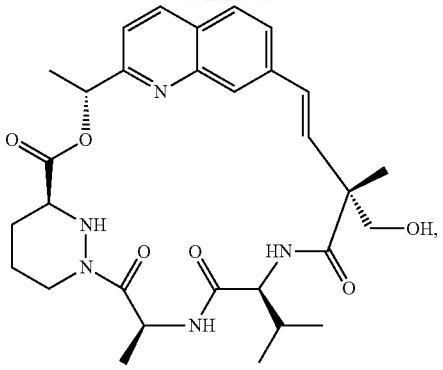
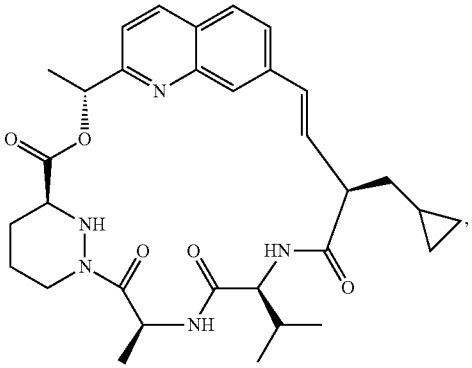
[
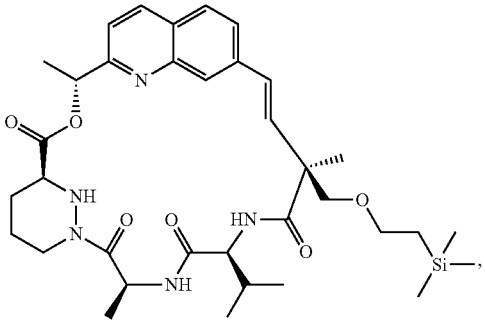
]
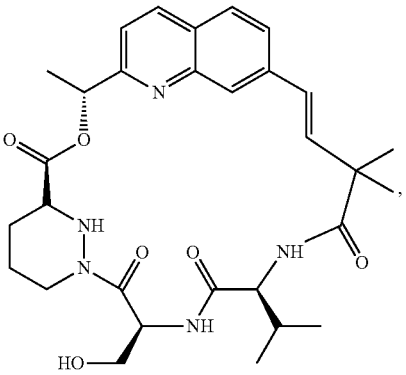

-continued
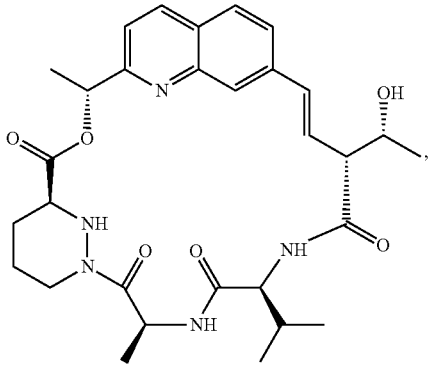
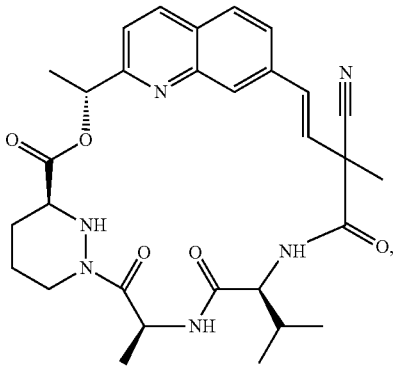
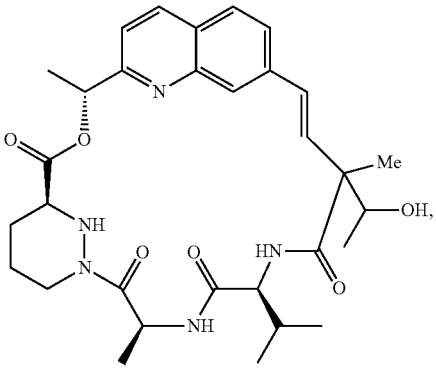
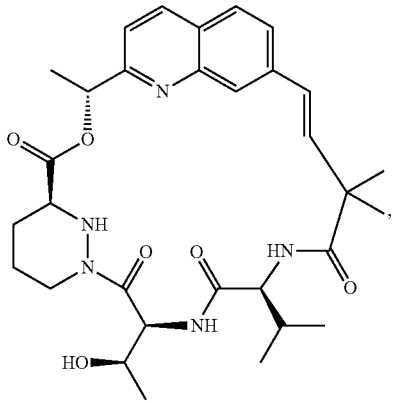
-continued
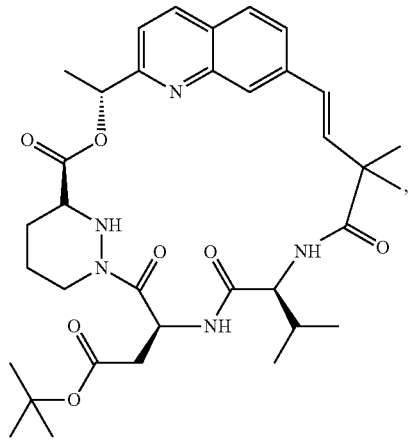
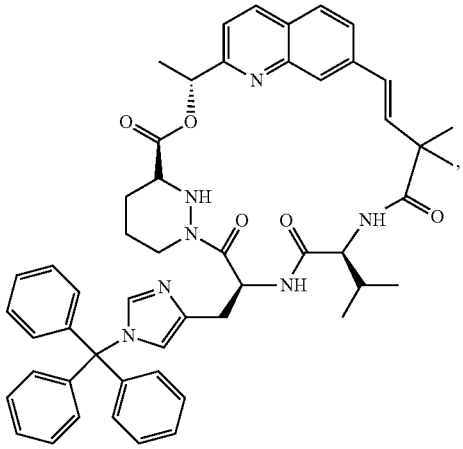
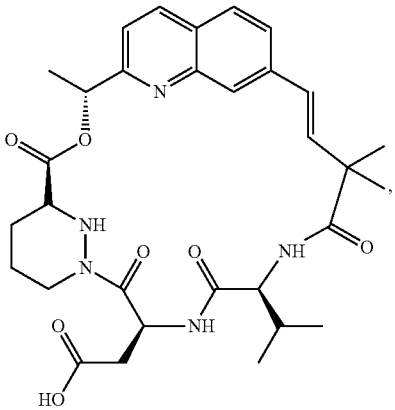
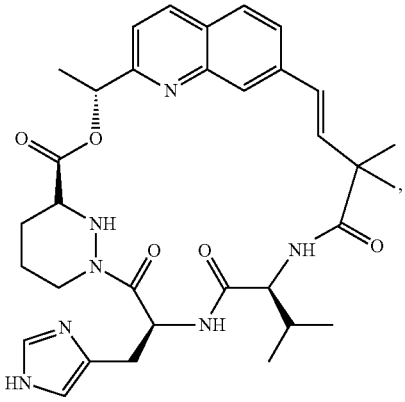

-continued
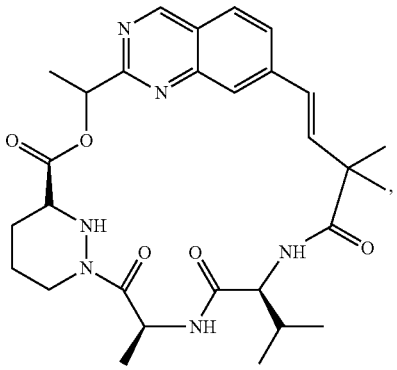
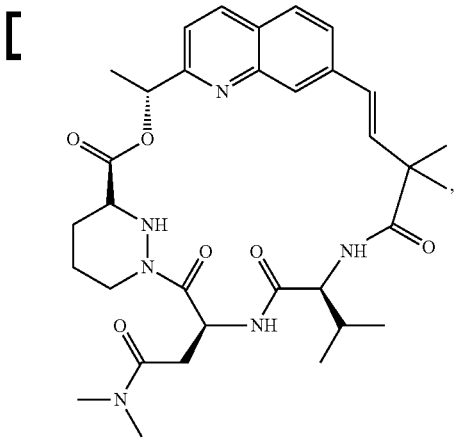
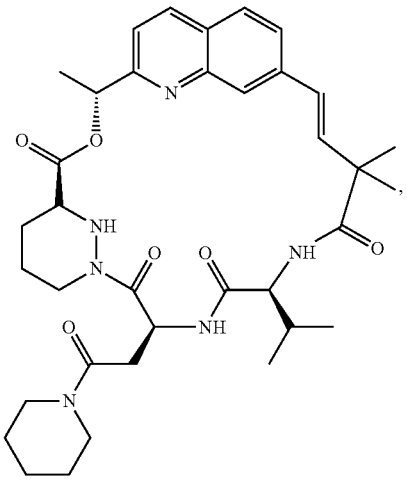
-continued
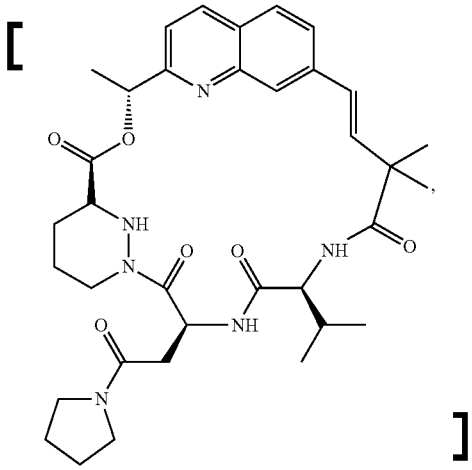
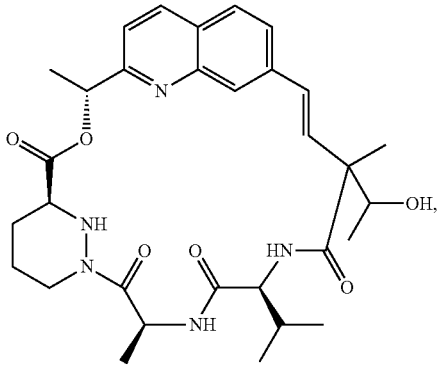
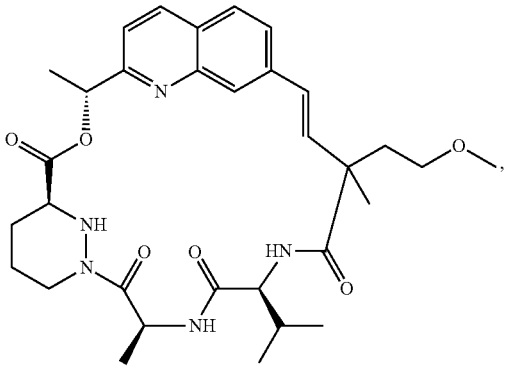
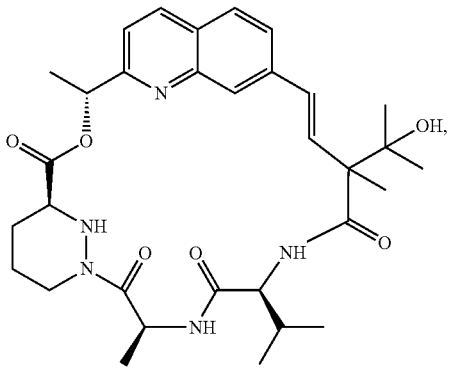

-continued
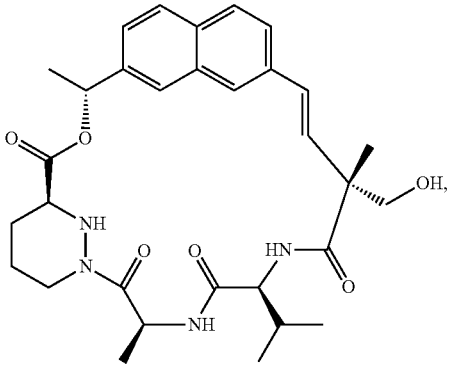
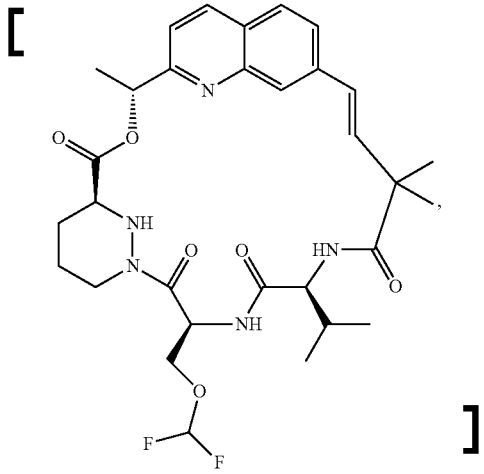
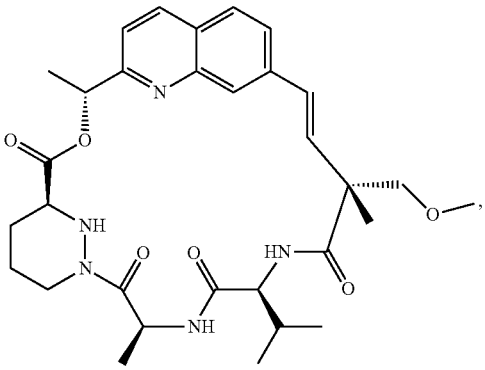
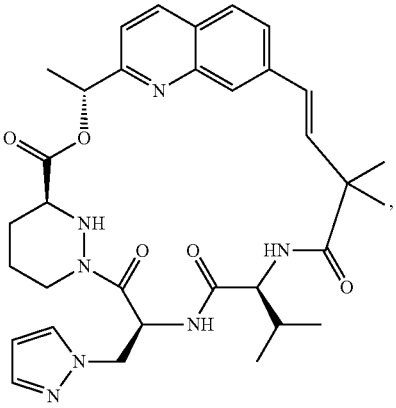
-continued
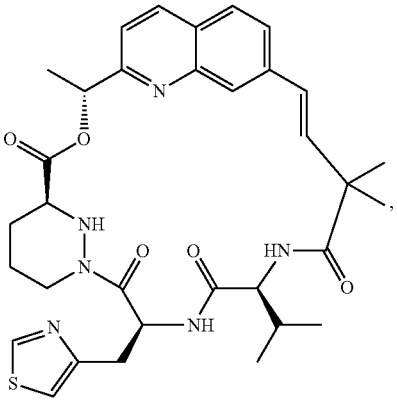
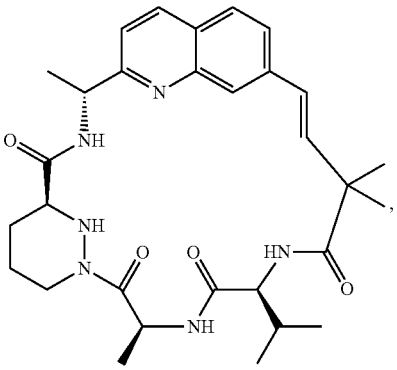
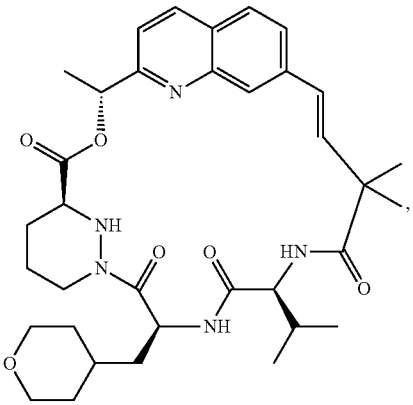
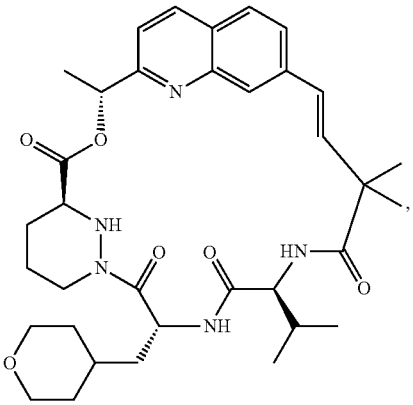

-continued
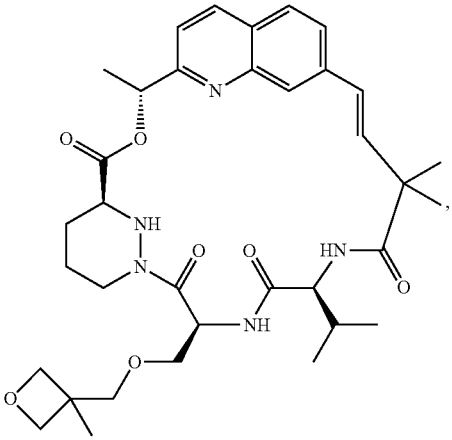
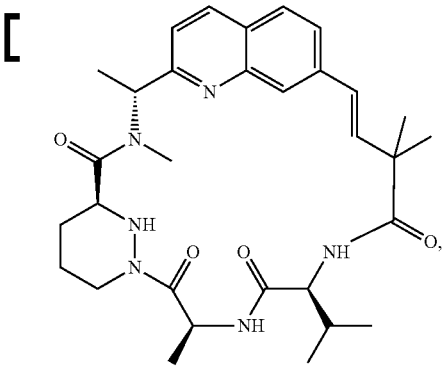
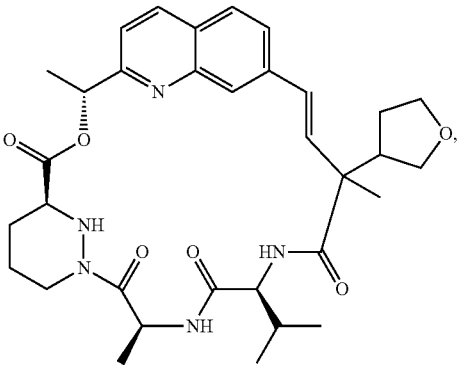
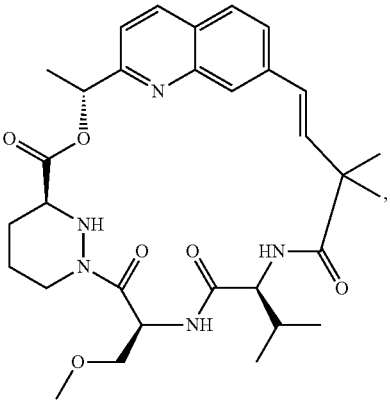
-continued
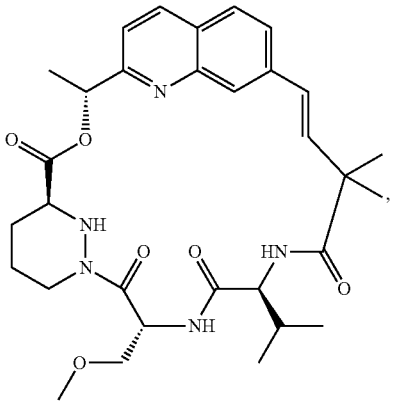
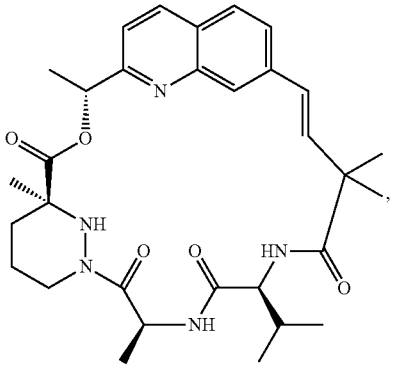
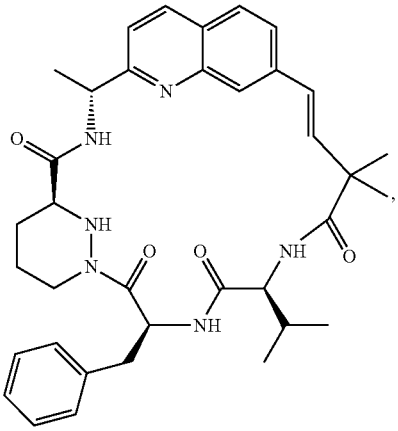
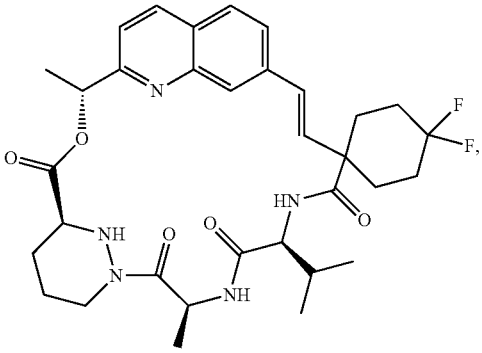

-continued
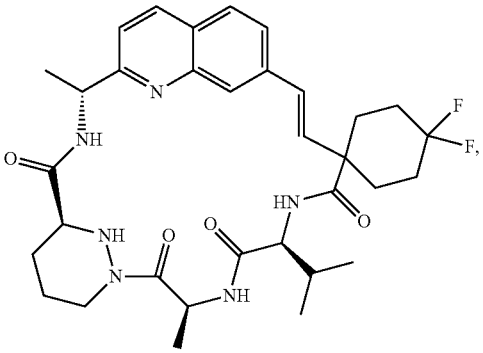
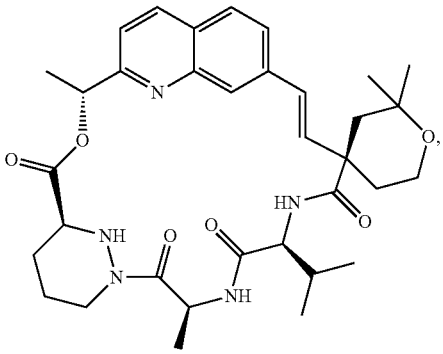
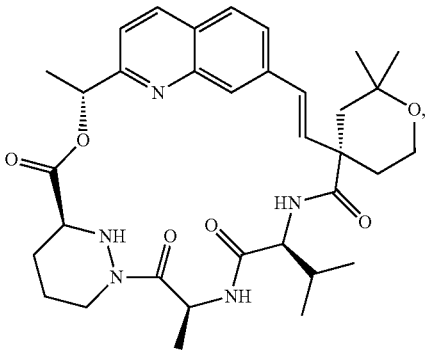
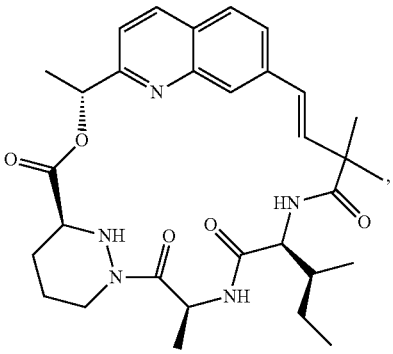
-continued
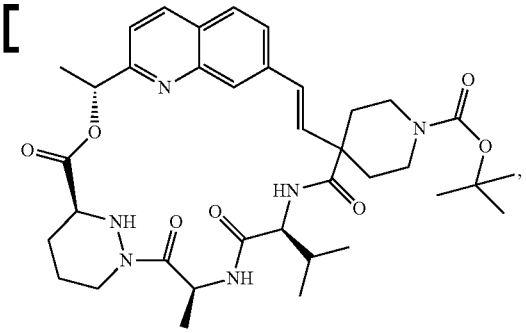
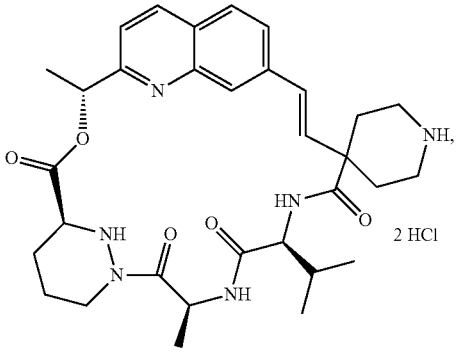
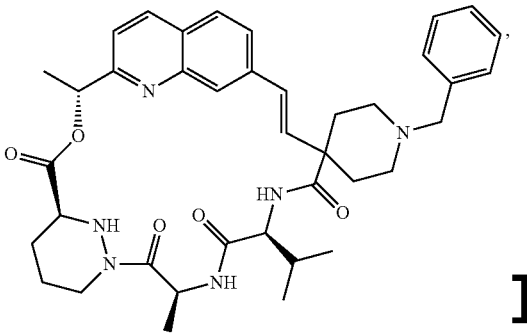
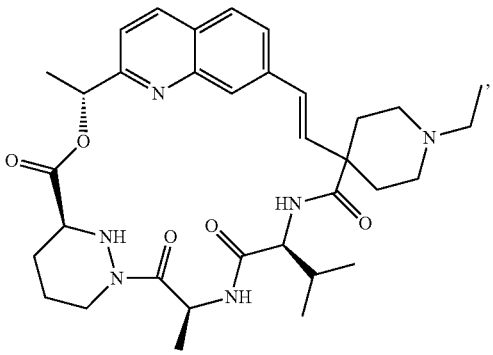

-continued
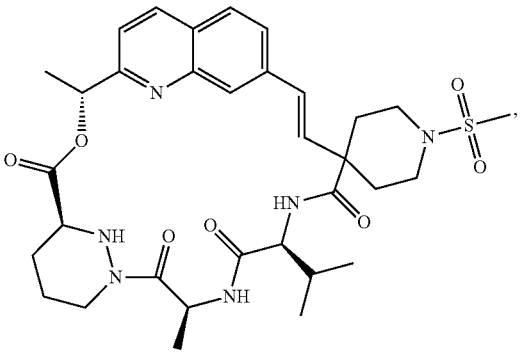
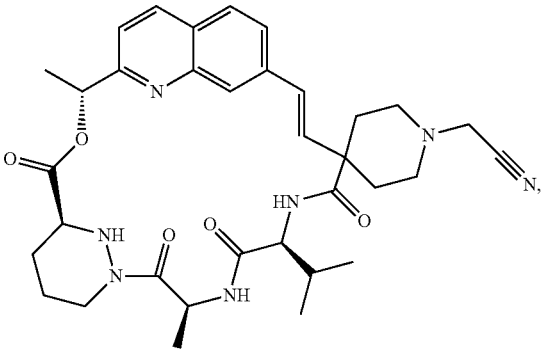
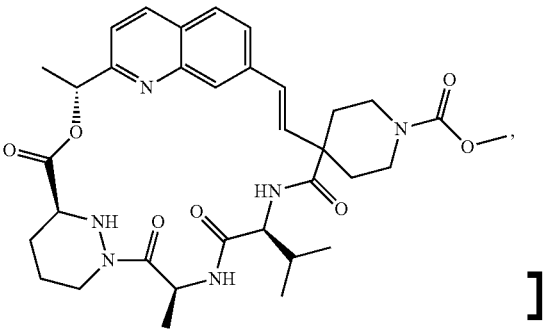
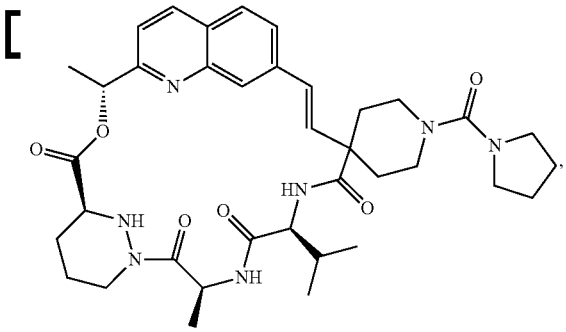
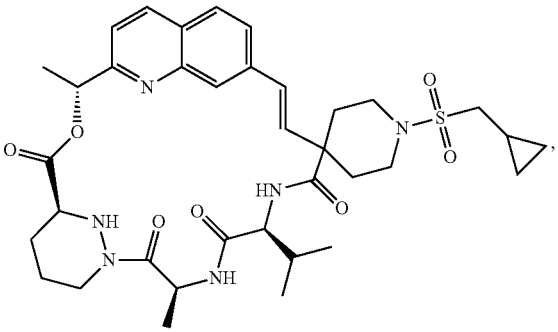
-continued
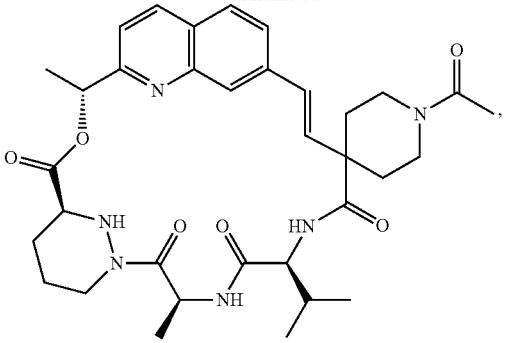
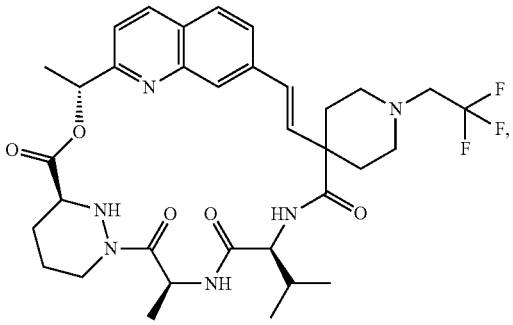
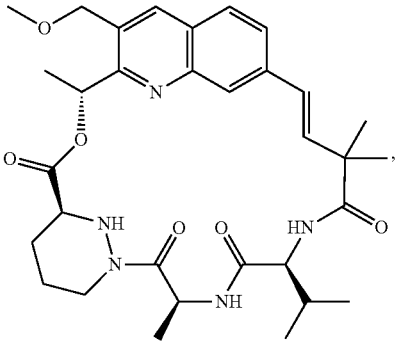
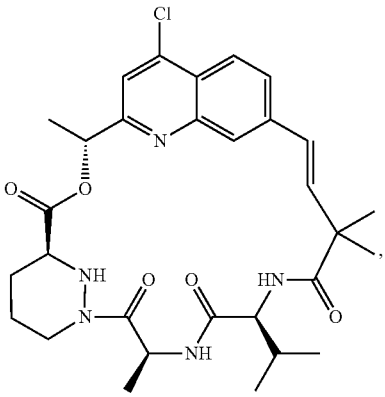

-continued
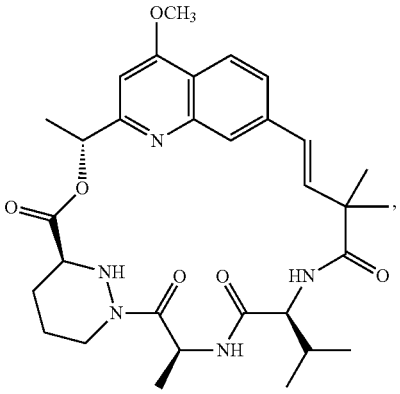
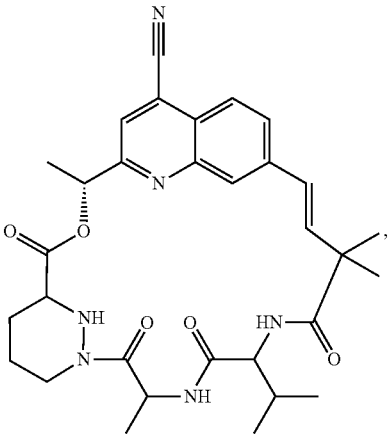
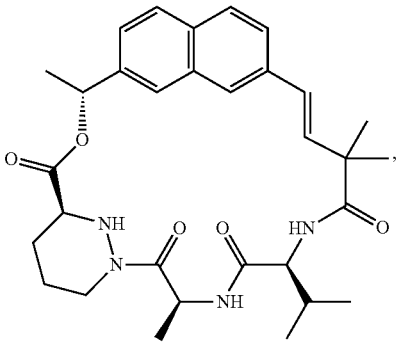
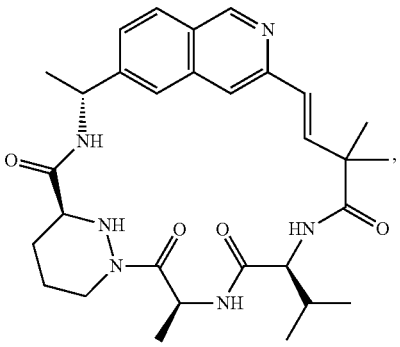
-continued
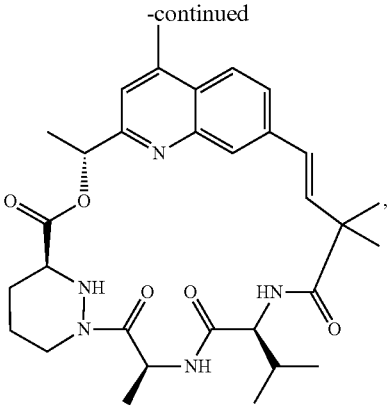
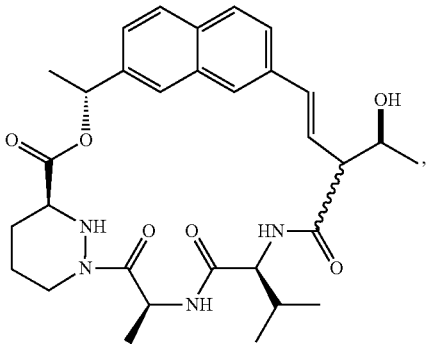
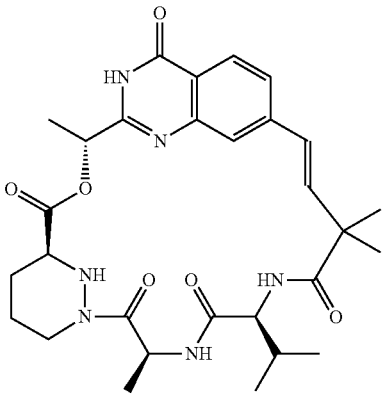
[
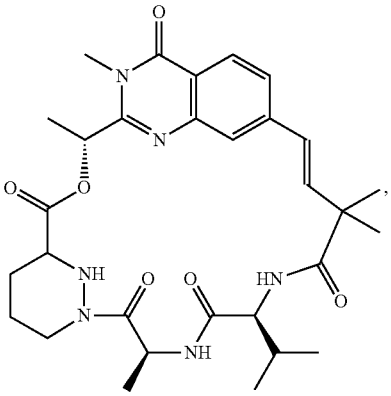
]

-continued
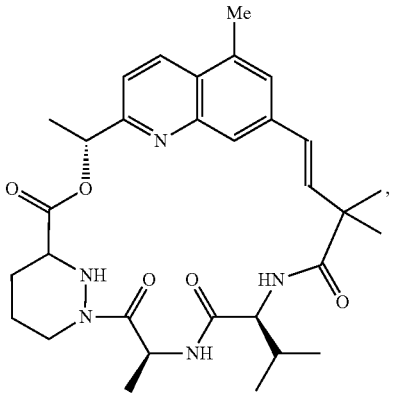
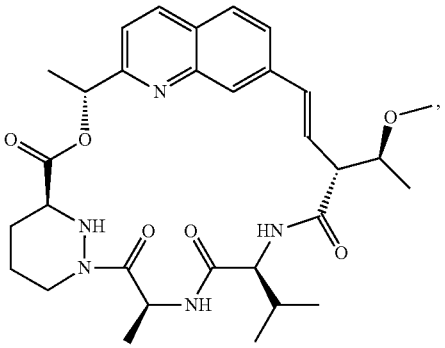
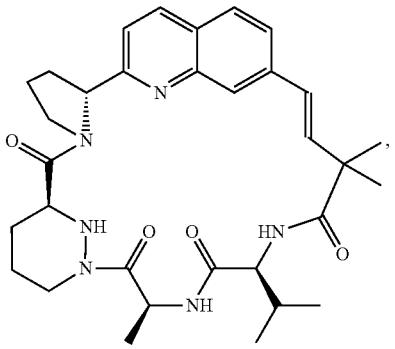
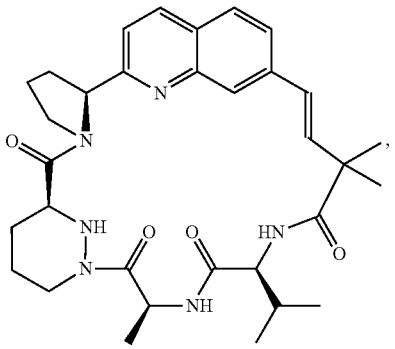
-continued
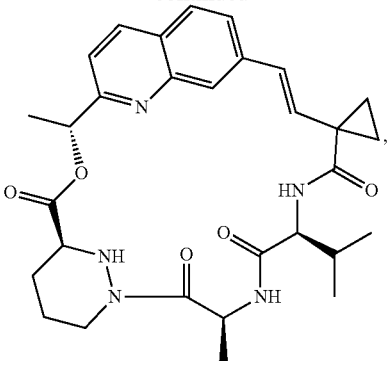
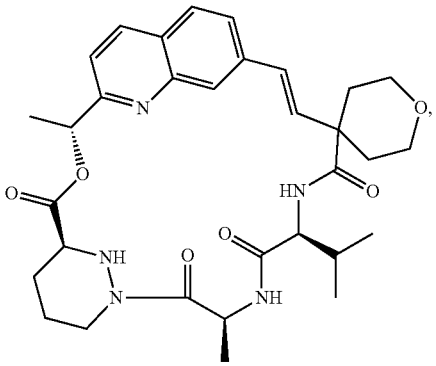
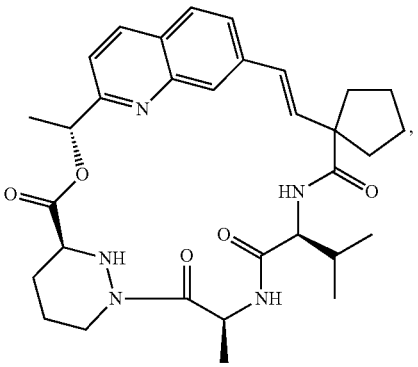
[
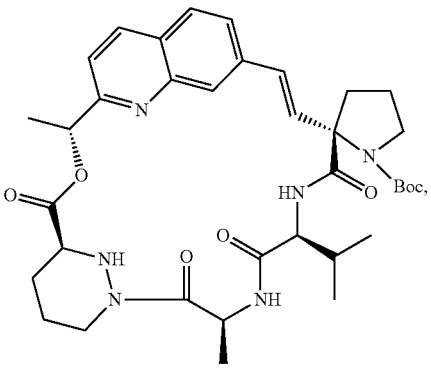

-continued
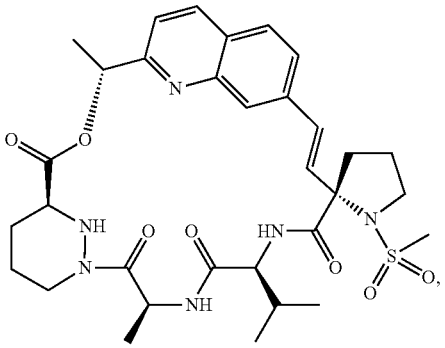
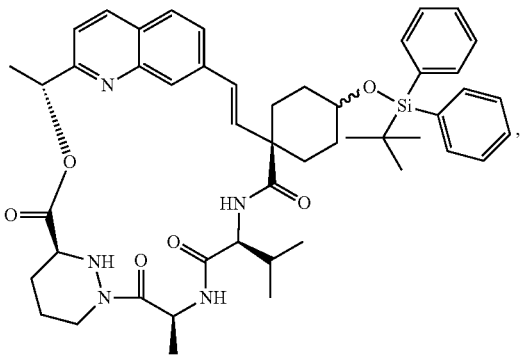
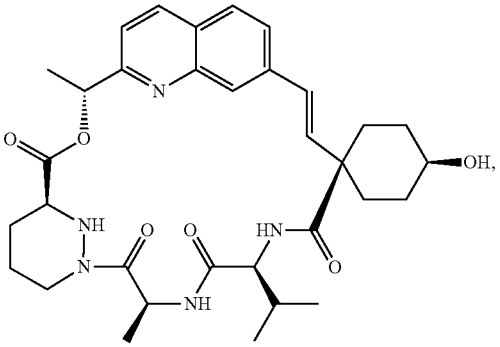
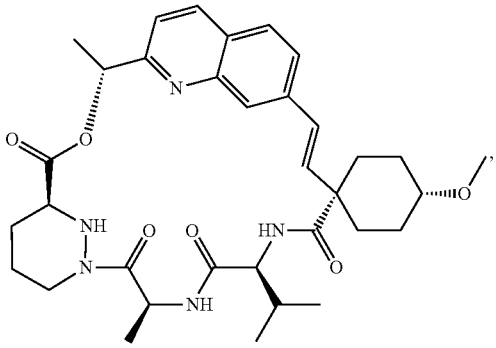
-continued
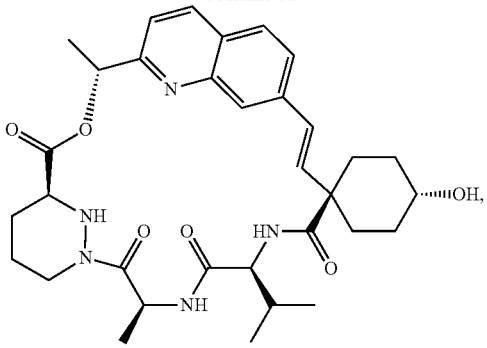
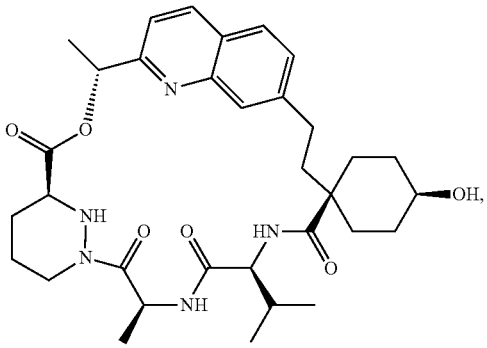
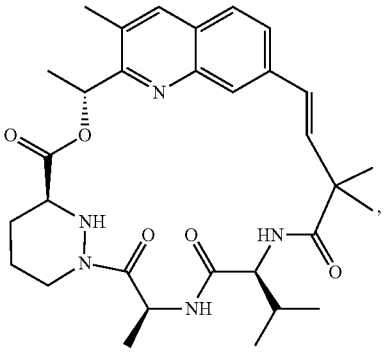
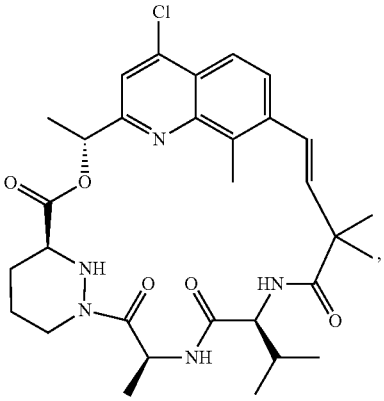

-continued
[
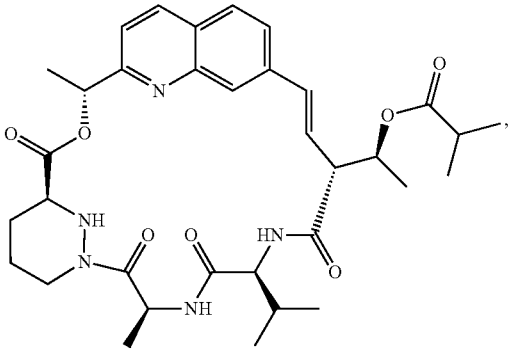
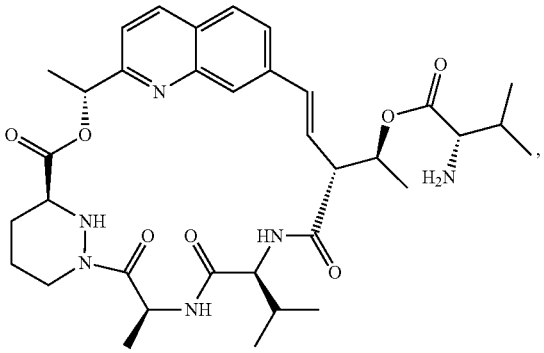
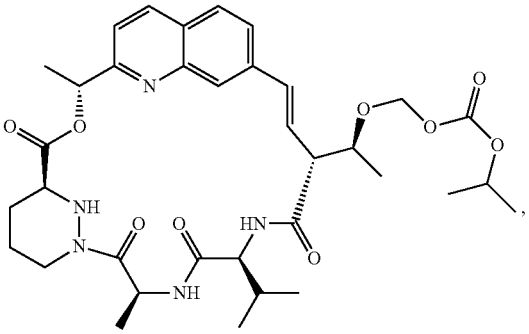
]
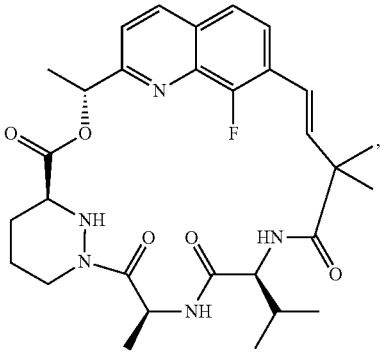
-continued
[
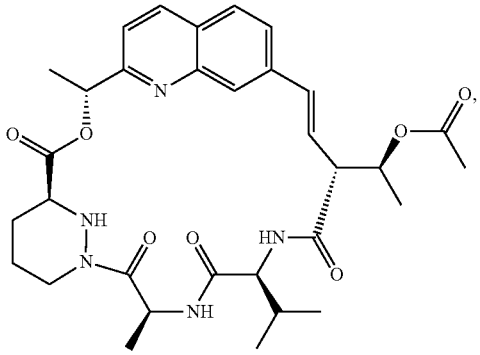
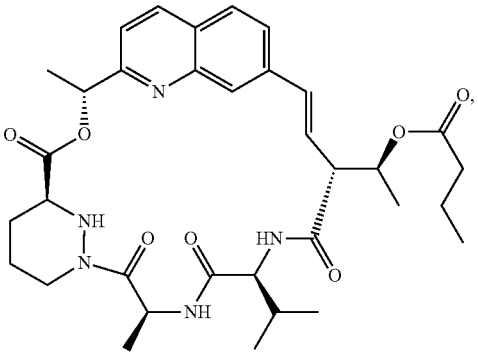
]
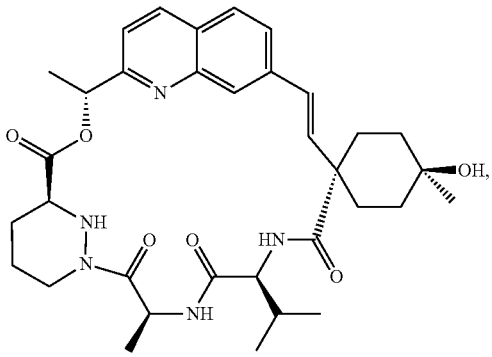
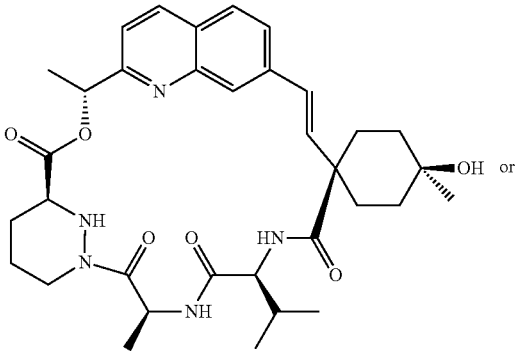
or -continued

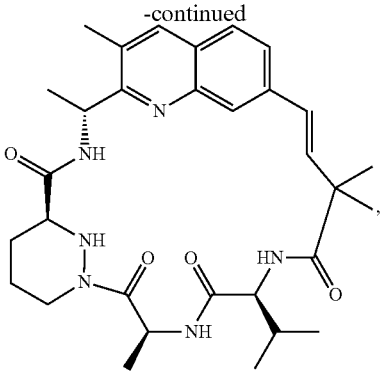

or a pharmaceutically acceptable salt, [isotope,] stereoisomer, mixture of stereoisomers, tautomer, ester or prodrug thereof.

19. The compound of claim 1, which is a compound of Formula III:

Formula III

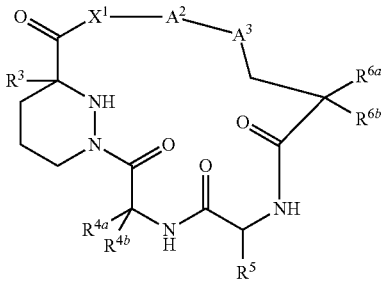

or a pharmaceutically acceptable salt, [isotope,] stereoisomer, mixture of stereoisomers, tautomer, ester or prodrug thereof, wherein $A^2$ is —CH($R^8$)-arylene, —CH($R^8$)-heteroarylene, —CH($R^8$)-heterocycloalkylene, —CH($R^8$)-cycloalkylene or cycloalkylene;

$A^3$ is —$CH_2$— or —O—;

$X^1$ is —O—, —N($CH_3$)— or —NH—;

$R^3$ is H or ($C_1$-$C_4$)alkyl;

$R^{4a}$ is H;

$R^{4b}$ is H, ($C_1$-$C_4$)alkoxy, halo($C_1$-$C_4$)alkoxy or ($C_1$-$C_8$)alkyl;

$R^5$ is H, ($C_1$-$C_8$)alkyl, hydroxy($C_1$-$C_8$)alkyl, ($C_2$-$C_8$)alkenyl, ($C_2$-$C_8$)alkynyl, azido($C_1$-$C_8$)alkyl, cycloalkyl, aryl($C_1$-$C_4$)alkyl, cycloalkyl($C_1$-$C_4$)alkyl, heterocycloalkyl($C_1$-$C_4$)alkyl or heteroarylheteroaryl($C_1$-$C_4$)alkyl;

$R^{6a}$ and $R^{6b}$ are independently H, —OH, ($C_1$-$C_4$)alkoxy, halo($C_1$-$C_4$)alkoxy or ($C_1$-$C_8$)alkyl, wherein each of $R^{6a}$ and $R^{6b}$ is optionally substituted with one or more substituent selected from the group consisting of halo, ($C_1$-$C_4$)alkyl, aryl, cycloalkyl, heterocycloalkyl, di($C_1$-$C_8$)alkylamino and ($C_1$-$C_8$)alkanoyl; or $R^{6a}$ and $R^{6b}$ together form

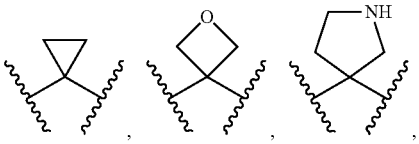

-continued

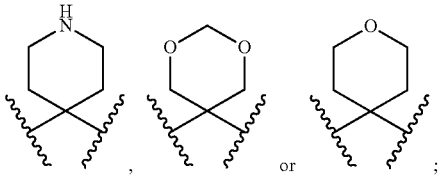

and $R^8$ is H or ($C_1$-$C_4$)alkyl.

20. The compound of claim 19, wherein $A^2$ is —CH($R^8$)-arylene or —CH($R^8$)-heteroarylene; $R^3$ is H; and $A^3$ is —$CH_2$—.

21. The compound of claim 19, wherein $A^2$ is —CH($R^8$)-arylene or —CH($R^8$)-heteroarylene; $R^3$ is H; and $A^3$ is —O—.

22. The compound of claim 19, which is

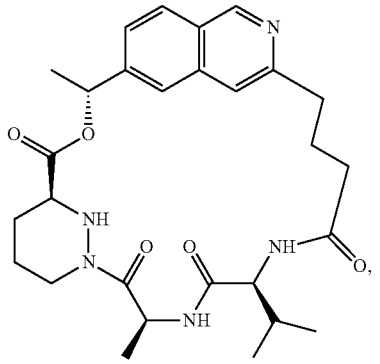

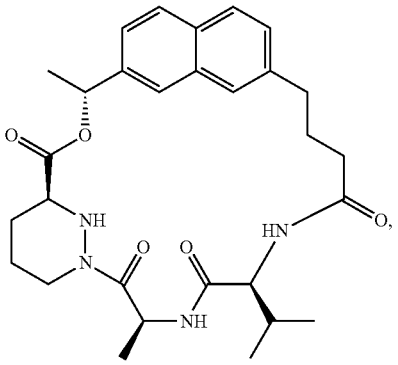

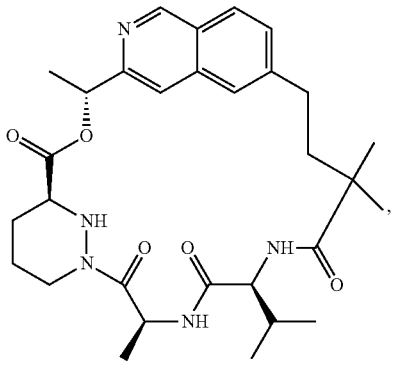

-continued

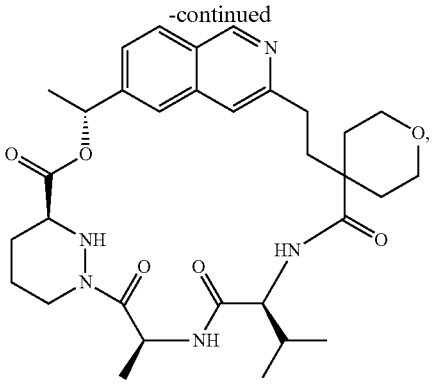

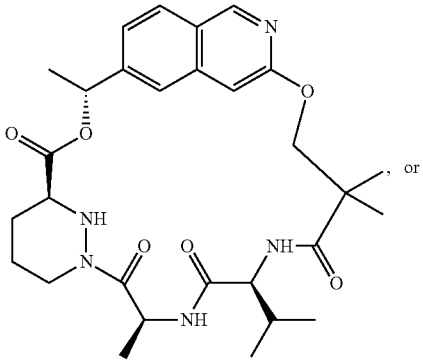

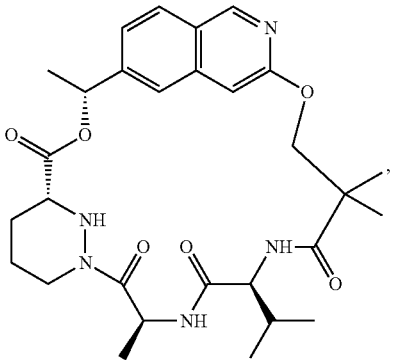

or a pharmaceutically acceptable salt, [isotope,] stereoisomer, mixture of stereoisomers, tautomer, ester or prodrug thereof.

23. The compound of claim 1, which is a compound of Formula IV:

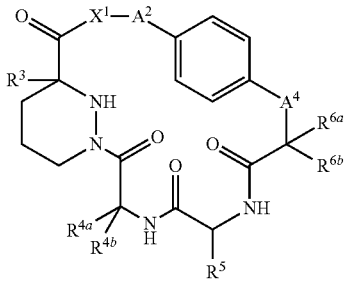

Formula IV or a pharmaceutically acceptable salt, [isotope,] stereoisomer, mixture of stereoisomers, tautomer, ester or prodrug thereof, wherein $A^2$ is —CH($R^8$)-arylene, —CH($R^8$)-heteroarylene, —CH($R^8$)-heterocycloalkylene, —CH($R^8$)-cycloalkylene or cycloalkylene;

$A^4$ is bond or —O—;

$X^1$ is —O—, —N($CH_3$)— or —NH—;

$R^3$ is H or ($C_1$-$C_4$)alkyl;

$R^{4a}$ is H;

$R^{4b}$ is H, ($C_1$-$C_4$)alkoxy, halo($C_1$-$C_4$)alkoxy or ($C_1$-$C_8$)alkyl;

$R^5$ is H, ($C_1$-$C_8$)alkyl, hydroxy($C_1$-$C_8$)alkyl, ($C_2$-$C_8$)alkenyl, ($C_2$-$C_8$)alkynyl, azido($C_1$-$C_8$)alkyl, cycloalkyl, aryl($C_1$-$C_4$)alkyl, cycloalkyl($C_1$-$C_4$)alkyl, heterocycloalkyl($C_1$-$C_4$)alkyl or heteroarylheteroaryl($C_1$-$C_4$)alkyl;

$R^{6a}$ and $R^{6b}$ are independently H, —OH, ($C_1$-$C_4$)alkoxy, halo($C_1$-$C_4$)alkoxy or ($C_1$-$C_8$)alkyl, wherein each of $R^{6a}$ and $R^{6b}$ is optionally substituted with one or more substituent selected from the group consisting of halo, ($C_1$-$C_4$)alkyl, aryl, cycloalkyl, heterocycloalkyl, di($C_1$-$C_8$)alkylamino and ($C_1$-$C_8$)alkanoyl; and $R^8$ is H or ($C_1$-$C_4$)alkyl.

24. The compound of claim 23, wherein $A^2$ is —CH($R^8$)-arylene or —CH($R^8$)-heteroarylene; $R^3$ is H; and $A^4$ is —O—.

25. The compound of claim 23, wherein $A^2$ is —CH($R^8$)-arylene or —CH($R^8$)-heteroarylene; $R^3$ is H; and $A^4$ is bond.

26. The compound of claim 23, wherein [$A^1$ is ethenylene;] $A^2$ is —CH($R^8$)-arylene, —CH($R^8$)-heteroarylene, —CH($R^8$)-heterocycloalkylene, —CH($R^8$)-cycloalkylene or cycloalkylene; $X^1$ is —O—, —NH— or —N(($C_1$-$C_4$)alkyl)-.

27. The compound of claim 23, which is

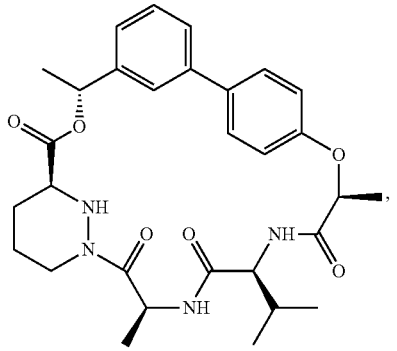

-continued

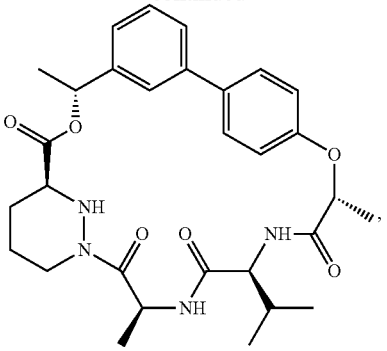

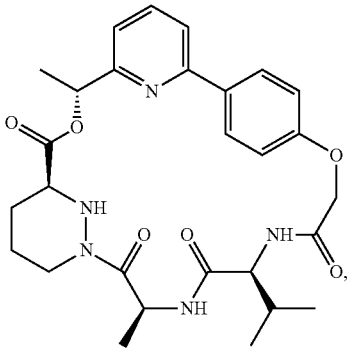

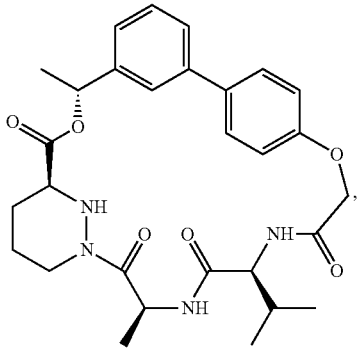

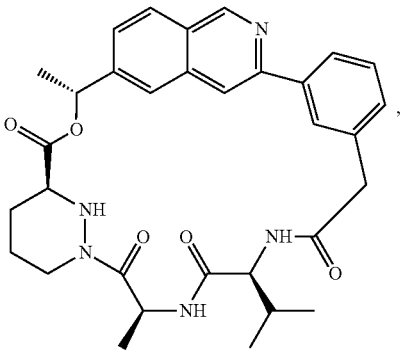

-continued

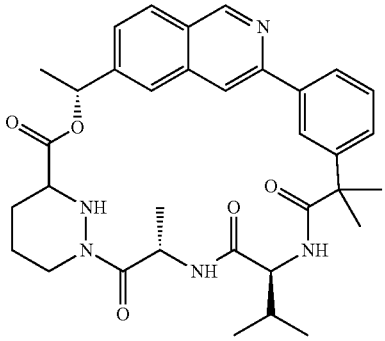

or

[

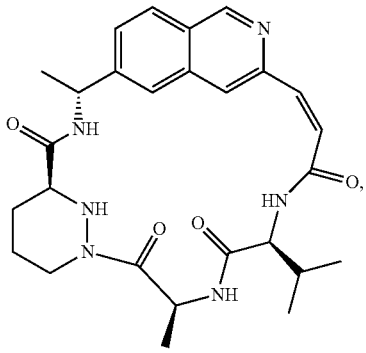

]

or a pharmaceutically acceptable salt, [isotope,] stereoisomer, mixture of stereoisomers, tautomer, ester or prodrug thereof.

28. A pharmaceutical composition comprising a therapeutically effective amount of a compound of claim 1 or a pharmaceutically acceptable salt, [isotope,] stereoisomer, mixture of stereoisomers, tautomer, ester or prodrug thereof and a pharmaceutically acceptable excipient.

29. The pharmaceutical composition of claim 28, further comprising at least one additional therapeutic agent selected from the group consisting of interferons, ribavirin, HCV NS3 protease inhibitors, HCV NS5a inhibitors, nucleoside or nucleotide inhibitors of HCV NS5B polymerase, non-nucleoside inhibitors of HCV NS5B polymerase, and TLR-7 agonists; or a mixture thereof.

30. The pharmaceutical composition of claim 29, wherein the at least one [addition] *additional* therapeutic agent is ribavirin, telaprevir, boceprevir or sofosbuvir.

* * * * *